US009315451B2

(12) United States Patent
Chen et al.

(10) Patent No.: US 9,315,451 B2
(45) Date of Patent: Apr. 19, 2016

(54) TETRACYCLINE COMPOUNDS

(75) Inventors: Chi-Li Chen, Watertown, MA (US); Roger B. Clark, Lexington, MA (US); Yonghong Deng, Watertown, MA (US); Minsheng He, Watertown, MA (US); Louis Plamondon, Belmont, MA (US); Cuixiang Sun, Watertown, MA (US); Xiao-Yi Xiao, San Diego, CA (US); Magnus Rönn, Melrose, MA (US)

(73) Assignee: TETRAPHASE PHARMACEUTICALS, INC., Watertown, MA (US)

( * ) Notice: Subject to any disclaimer, the term of this patent is extended or adjusted under 35 U.S.C. 154(b) by 340 days.

(21) Appl. No.: 13/319,298

(22) PCT Filed: May 7, 2010

(86) PCT No.: PCT/US2010/001350
§ 371 (c)(1),
(2), (4) Date: Jan. 12, 2012

(87) PCT Pub. No.: WO2010/129057
PCT Pub. Date: Nov. 11, 2010

(65) Prior Publication Data
US 2012/0135968 A1 May 31, 2012

Related U.S. Application Data

(60) Provisional application No. 61/215,757, filed on May 8, 2009.

(51) Int. Cl.

| | |
|---|---|
| ***A61K 31/65*** | (2006.01) |
| ***C07C 237/26*** | (2006.01) |
| ***C07C 275/24*** | (2006.01) |
| ***C07C 311/06*** | (2006.01) |
| ***C07C 311/19*** | (2006.01) |
| ***C07D 205/04*** | (2006.01) |
| ***C07D 207/06*** | (2006.01) |
| ***C07D 207/08*** | (2006.01) |
| ***C07D 207/10*** | (2006.01) |
| ***C07D 209/04*** | (2006.01) |
| ***C07D 209/44*** | (2006.01) |
| ***C07D 211/14*** | (2006.01) |
| ***C07D 211/34*** | (2006.01) |
| ***C07D 213/74*** | (2006.01) |

(Continued)

(52) U.S. Cl.
CPC ............. *C07C 237/26* (2013.01); *C07C 275/24* (2013.01); *C07C 311/06* (2013.01); *C07C 311/19* (2013.01); *C07D 205/04* (2013.01); *C07D 207/06* (2013.01); *C07D 207/08* (2013.01); *C07D 207/10* (2013.01); *C07D 209/04* (2013.01); *C07D 209/44* (2013.01); *C07D 211/14* (2013.01); *C07D 211/34* (2013.01); *C07D 213/74* (2013.01); *C07D 221/20* (2013.01); *C07D 223/04* (2013.01); *C07D 223/32* (2013.01); *C07D 295/13* (2013.01); *C07D 295/15* (2013.01); *C07D 295/155* (2013.01); *C07C 2101/02* (2013.01); *C07C 2101/04* (2013.01); *C07C 2101/08* (2013.01); *C07C 2101/14* (2013.01); *C07C 2102/08* (2013.01); *C07C 2102/42* (2013.01); *C07C 2103/74* (2013.01)

(58) Field of Classification Search
CPC C07C 237/26; C07C 311/16; C07C 2103/46; C07C 2103/74; C07D 205/02; C07D 205/04; C07D 205/06; C07D 205/08; C07D 211/08; C07D 211/14
USPC .......................................... 552/203; 514/152
See application file for complete search history.

(56) References Cited

U.S. PATENT DOCUMENTS 3,988,468 A 10/1976 Rogalski et al.
5,284,963 A 2/1994 Sum et al.

(Continued)

FOREIGN PATENT DOCUMENTS

CN 101027279 A 8/2007
EP 0 582 789 A1 2/1994

(Continued)

OTHER PUBLICATIONS

Notice of Allowance, U.S. Appl. No. 13/570,837, Dated: Jun. 6, 2013.

(Continued)

*Primary Examiner* — Barbara P Badio
(74) *Attorney, Agent, or Firm* — Foley Hoag LLP

(57) ABSTRACT

The present invention is directed to a compound represented by Structural Formula (I): or a pharmaceutically acceptable salt thereof. The variables for Structural Formula I are defined herein. Also described is a pharmaceutical composition comprising the compound of Structural Formula I and its therapeutic use.

(I)

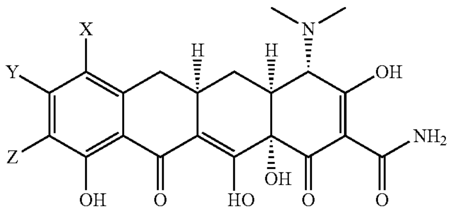

15 Claims, 161 Drawing Sheets

(51) Int. Cl.

| | |
|---|---|
| ***C07D 221/20*** | (2006.01) |
| ***C07D 223/04*** | (2006.01) |
| ***C07D 223/32*** | (2006.01) |
| ***C07D 295/13*** | (2006.01) |
| ***C07D 295/15*** | (2006.01) |
| ***C07D 295/155*** | (2006.01) |

(56) References Cited

U.S. PATENT DOCUMENTS

| | | | |
|---|---|---|---|
| 5,328,902 | A | 7/1994 | Sum et al. |
| 5,380,888 | A | 1/1995 | Sum et al. |
| 5,401,729 | A | 3/1995 | Sum et al. |
| 5,466,684 | A | 11/1995 | Sum et al. |
| 5,494,903 | A | 2/1996 | Hlavka et al. |
| 5,495,031 | A | 2/1996 | Sum et al. |
| 5,529,990 | A | 6/1996 | Hlavka et al. |
| 5,530,117 | A | 6/1996 | Hlavka et al. |
| 5,574,026 | A | 11/1996 | Backer et al. |
| 6,841,546 | B2 | 1/2005 | Draper et al. |
| 6,914,057 | B1 | 7/2005 | Ryan et al. |
| 7,045,507 | B2 | 5/2006 | Draper et al. |
| RE40,086 | E | 2/2008 | Hlavka et al. |
| RE40,183 | E | 3/2008 | Hlavka et al. |
| 7,763,735 | B2 | 7/2010 | Myers et al. |
| 7,807,842 | B2 | 10/2010 | Myers et al. |
| 7,820,641 | B2 | 10/2010 | Nelson et al. |
| 7,825,105 | B2 | 11/2010 | Bandarage et al. |
| 8,088,820 | B2 | 1/2012 | Draper et al. |
| 8,501,716 | B2 | 8/2013 | Zhou et al. |
| 8,796,245 | B2 | 8/2014 | Zhou et al. |
| 8,906,887 | B2 | 12/2014 | Zhou et al. |
| 2004/0063674 | A1 | 4/2004 | Levy et al. |
| 2004/0092490 | A1 | 5/2004 | Draper et al. |
| 2004/0214800 | A1 | 10/2004 | Levy et al. |
| 2004/0242548 | A1 | 12/2004 | Draper et al. |
| 2005/0143352 | A1 | 6/2005 | Nelson et al. |
| 2006/0166944 | A1 | 7/2006 | Berniac et al. |
| 2006/0194773 | A1 | 8/2006 | Levy et al. |
| 2006/0281717 | A1 | 12/2006 | Berniac et al. |
| 2007/0093455 | A1 | 4/2007 | Abato et al. |
| 2008/0015169 | A1 | 1/2008 | Nelson et al. |
| 2008/0070873 | A1 | 3/2008 | Alekshun et al. |
| 2008/0118979 | A1 | 5/2008 | Draper et al. |
| 2009/0118269 | A1 | 5/2009 | Berniac et al. |
| 2009/0257985 | A1 | 10/2009 | Nelson et al. |
| 2010/0022483 | A1 | 1/2010 | Berniac et al. |
| 2010/0105671 | A1 | 4/2010 | Zhou et al. |
| 2012/0208788 | A1 | 8/2012 | Deng et al. |
| 2012/0302527 | A1 | 11/2012 | Zhou et al. |
| 2013/0109657 | A1 | 5/2013 | Zhou et al. |

FOREIGN PATENT DOCUMENTS

| | | | |
|---|---|---|---|
| EP | 0 582 810 | A1 | 2/1994 |
| EP | 0536515 | | 2/1994 |
| GB | 935 384 | | 8/1963 |
| GB | 1 034 933 | | 7/1966 |
| WO | WO 00/18353 | | 4/2000 |
| WO | WO 01/98260 | A1 | 12/2001 |
| WO | WO 02/04404 | A2 | 1/2002 |
| WO | WO 02/4407 | A2 | 1/2002 |
| WO | WO 02/072022 | A2 | 9/2002 |
| WO | WO 02/072031 | A2 | 9/2002 |
| WO | WO 02/085303 | A2 | 10/2002 |
| WO | WO 03/005971 | A2 | 1/2003 |
| WO | WO 03/079984 | A2 | 10/2003 |
| WO | WO 2004/006850 | A2 | 1/2004 |
| WO | WO 2004/038000 | A2 | 5/2004 |
| WO | WO 2004/038001 | A2 | 5/2004 |
| WO | WO 2005/009943 | A2 | 2/2005 |
| WO | WO 2005/112945 | A2 | 12/2005 |
| WO | WO 2006/047671 | A2 | 5/2006 |
| WO | WO 2006/084265 | A1 | 8/2006 |
| WO | WO 2006/088720 | | 8/2006 |
| WO | WO 2007/087416 | A2 | 8/2007 |
| WO | WO 2007/117639 | A2 | 10/2007 |
| WO | WO 2007/133798 | A2 | 11/2007 |
| WO | WO 2008/045507 | A2 | 4/2008 |
| WO | WO 2008/127361 | A2 | 10/2008 |
| WO | WO 2008/127722 | A1 | 10/2008 |
| WO | WO 2009/073056 | A1 | 6/2009 |
| WO | WO 2009/128913 | A1 | 10/2009 |
| WO | WO 2010/017470 | | 2/2010 |
| WO | WO 2010/126607 | A2 | 11/2010 |
| WO | WO 2010/129055 | | 11/2010 |
| WO | WO 2010/129057 | | 11/2010 |
| WO | WO 2011/025982 | | 3/2011 |
| WO | WO 2012/021712 | | 2/2012 |
| WO | WO 2012/047907 | A1 | 4/2012 |
| WO | WO 2014/036502 | A2 | 3/2014 |

OTHER PUBLICATIONS

Notification of Transmittal of the International Search Report and the Written Opinion of the International Searching Authority, or the Declaration, International Search Report and Written Opinion in International Application No. PCT/US2010/001350, 13 pages, date of mailing Nov. 23, 2010.

Sun, C., et al., "A Robust Platform for the Synthesis of New Tetracycline Antibiotics," *J. Am. Chem. Soc.*, 130:17913-17927 (2008).

Chopra, I. and Roberts, M., "Tetracycline Antibiotics: Mode of Action, Applications, Molecular Biology, and Epidemiology of Bacterial Resistance," Microbiology and Molecular Biology Reviews, 65(2): 232-260 (2001).

Office Action, U.S. Appl. No. 13/718,909, Dated: Jul. 9, 2013.

Office Action, U.S. Appl. No. 12/462,795, Dated: Sep. 23, 2013.

Abbanat, D., et al., "New agents in development for the treatment of bacterial infections", *Current Opinion in Pharmacology*, 8(5): 582-592 (available online Sep. 18, 2008).

Charest, M.G., et al., "A Convergent Enantioselective Route to Structurally Diverse 6-Deoxytetracycline Antibiotics," Science, 308: 395-398 (2005).

Hlavka, J.J., et al., "The 6-Deoxytetracyclines. IV. A Photochemical Displacement of a Diazonium Group," *Organic Chemical Research Section*, vol. 27, pp. 3674-3675 (1962).

Podlogar, B., L., et al "Patents on tetracycline and tetracyline derivatives as antimicrobials", *Expert Opin. Ther. Patents*, 13(4): 467-478 (2003).

Sato, F., et al. "Structure-Activity Relationship Investigation of Some New Tetracyclines by Electronic Index Methodology", *Los Alamos National Laboratory*, Quantitative Biology, 1-18 (Aug. 21, 2007).

Verma, A.K., et al., "Antibiotic and non-antibiotic tetracycline patents", *Expert Opin. Ther. Patents*, vol. 18, pp. 69-82 (2008).

Written Opinion of the International Searching Authority for International Application No. PCT/US2009/053142; Date Mailed: Oct. 13, 2009.

International Search Report for International Application No. PCT/US2009/053142; Date Mailed: Oct. 13, 2009.

Notification Concerning Transmittal of International Preliminary Report on Patentability for International Application No. PCT/US2009/053142 dated Feb. 17, 2011.

Notification of Transmittal of International Search Report and the Written Opinion of the International Search Authority, or the Declaration, in International Application No. PCT/US2010/047035; Date mailed: Jul. 22, 2011.

International Preliminary Report on Patentability for International Application No. PCT/US2009/001350; Date Mailed: Nov. 9, 2011.

Notification of Transmittal of the International Search Report and the Written Opinion of the International Searching Authority, or the Declaration, in International Application No. PCT/US2011/047428, 4 pages, date of mailing Jan. 6, 2012.

International Preliminary Report on Patentability for International Application No. PCT/US2010/047035; Date Mailed: Feb. 28, 2012.

Notification Concerning Transmittal of International Preliminary Report on Patentability for International Application No. PCT/US2011/047428; Date Mailed: Feb. 21, 2013.

Office Action, U.S. Appl. No. 12/462,795, Dated: Dec. 7, 2011.

Office Action, U.S. Appl. No. 12/462,795, Dated: Jan. 24, 2012.

(56) References Cited

OTHER PUBLICATIONS

Office Action, U.S. Appl. No. 12/462,795, Dated: Jul. 24, 2012.
Office Action, U.S. Appl. No. 13/570,837, Dated: Feb. 4, 2013.
Pre Appeal Brief Conference Decision, U.S. Appl. No. 12/462,795, Dated: Feb. 19, 2013.
Office Action, U.S. Appl. No. 13/718,909, Dated: Feb. 5, 2013.
Esse, R., et al., "Tetracycloxides. II. Transformations at the C-4 Position", Journal of the American Chemical Society, 86(18): 3875-3877 (Sep. 20, 1964).
International Search Report for International Application No. PCT/US2013/057690, "Tetracycline Compounds," Date of Mailing: Feb. 24, 2014.
HCAPLUS, Accession No. 2005:99455, Document No. 142:197754 (Jun. 25, 2004).
HCAPLUS, Accession No. 2004:1036703, Document No. 141:420412 (Apr. 24, 2002).
Office Action dated Jan. 16, 2014 for U.S. Appl. No. 13/319,298, "Tetracycline Compounds".
Office Action dated Jan. 17, 2014 for U.S. Appl. No. 12/462,795, "C7-Fluoro Substituted Tetracycline Compounds."
Office Action dated Feb. 14, 2014 for U.S. Appl. No. 13/391,407, "Tetracycline Compounds."
Notice of Allowance dated Jun. 5, 2014 for U.S. Appl. No. 13/718,909, "Tetracycline Compounds."
Martin, W., et al., "Totalsynthese von d, 1-7-Chlor-6-desoxytetracyclinen und d, 1-7-Chlor-6-desmethy1-6-desoxytetracyclinen der naturlichen, der 5a-epi- und der 6-epi-Reihe", *Tetrahedron Letters*, pp. 3513-3516, (Dec. 31, 1975).
Extended Search Report for European Patent Application No. 13172357.9 dated May 16, 2014 "C7-Fluoro Substituted Tetracycline Compounds".
Notice of Allowance, U.S. Appl. No. 12/462,795, Dated: Aug. 4, 2014.
Final Office Action, U.S. Appl. No. 13/391,407, Dated: Oct. 1, 2014.

| Cmpd. No. | Lot | MIC90 values (µg/ml) | | | | | | | | | | |
|---|---|---|---|---|---|---|---|---|---|---|---|---|
| | | S. aureus MRSA | S. sapro-phyticus | E. faecalis | Efaecium | S. pneumoniae | E. coli ESBL+ | Ecloacae | K. pneumoniae ESBL+ | P. mirabilis | P. aeruginosa | A. baumannii |
| | | n=32 isolates | n=15 isolates | n=25 isolates | n=15 isolates | n=19 isolates | n=14 isolates | n=14 isolates | n=16 isolates | n=14 isolates | n=35 isolates | n=24 isolates |
| S16-10-161 | A | | (0.5) | (16) | (16) | | (1) | (4) | (1) | (16) | (>32) | |
| S24-9-21 | A | (2) | (0.5) | (4) | (4) | | (0.5) | (2) | (2) | (8) | | (2) |
| S24-9-23 | A | (4) | (0.25) | (8) | (8) | | (1) | (2) | (1) | (4) | | (1) |
| S24-9-25 | A | (4) | | (4) | | | (0.25) | (2) | (2) | (32) | | |
| S15-13-4 | A | (4) | | (4) | | | (1) | | (2) | (>32) | | |
| S24-9-17 | A | (4) | | (8) | | | (0.5) | (2) | (2) | (16) | | |
| S3-5-5 | A | (8) | | (16) | | | (1) | (2) | (2) | (2) | | |
| S15-13-194 | A | | | (4) | | | (0.5) | | (1) | (16) | | |

FIG. 1A

| Cmpd. No. | Lot | MIC90 values (μg/ml) | | | | | | | | | | |
|---|---|---|---|---|---|---|---|---|---|---|---|---|
| | | S. aureus MRSA | S. sapro-phyticus | E. faecalis | Efaecium | S. pneumoniae | E. coli ESBL+ | Ecloacae | K. pneumoniae ESBL+ | P. mirabilis | P. aeruginosa | A. baumannii |
| S25-11-1 | A | | | (8) | | | (0.5) | | (1) | (8) | | |
| S15-13-15 | A | (4) | | (4) | | | (1) | | (1) | (16) | | |
| S15-13-187 | A | | | | | | (1) | (1) | (1) | (4) | | |
| S25-11-45 | A | | | | | | (0.5) | (2) | (1) | (16) | | |
| S15-13-188 | A,B | | | | | | (0.5) | | (2) | (16) | | |
| S15-13-222 | A | | | | | | (0.25) | | (0.5) | (4) | | |
| S2-4-19 | A | | | | | | (1) | | (2) | (16) | | |
| S2-4-12 | A | | | | | | (1) | (2) | (1) | (>32) | | |
| S15-13-200 | A | | | | | | (1) | (2) | (1) | (32) | | |

FIG. 1B

| Cmpd. No. | Lot | MIC90 values (μg/ml) | | | | | | | | | | |
|---|---|---|---|---|---|---|---|---|---|---|---|---|
| | | S. aureus MRSA | S. sapro-phyticus | E. faecalis | Efaecium | S. pneumoniae | E. coli ESBL+ | Ecloacae | K. pneumoniae ESBL+ | P. mirabilis | P. aeruginosa | A. baumannii |
| S15-13-223 | A | | | | | (0.5) | (0.25) | | (2) | (32) | | |
| Tigecycline | | (0.25) | (0.25) | (0.13) | (0.063) | (≤0.016) | (0.5) | (2) | (1) | (4) | (32) | (4) |
| PTK 0796 | | (2) | | | (0.5) | (0.031) | (16) | (16) | (16) | (>64) | (32) | (8) |
| Doxycycline | | (8) | (0.5) | (16) | (16) | (8) | (>32) | | | (>64) | | (>32) |
| Tetracycline | | (>32) | (1) | (>32) | (>32) | (>32) | (>32) | (>32) | (>64) | (64) | (>32) | (>64) |
| Linezolid | | (4) | (4) | (32) | (32) | (1) | | | | | | |
| Levofloxacin | | (>32) | (0.5) | | (>32) | (1) | (32) | (32) | (64) | (32) | (32) | (32) |
| Minocycline | | (8) | | | | (8) | (32) | | | (64) | | |

FIG. 1C

| Cmpd | X | Y | Z |
|---|---|---|---|
| S1-14-115 | F | 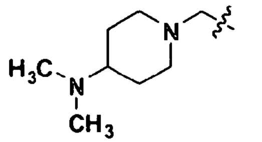 | H |
| S1-14-116 | F | 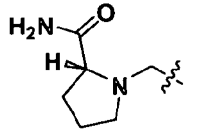 | H |
| S1-14-117 | F | 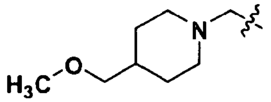 | H |
| S1-14-118 | F | 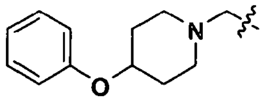 | H |
| S1-14-119 | F | 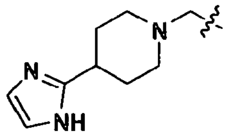 | H |
| Cmpd | X | Y | Z |
|---|---|---|---|
| S1-14-120 | F | 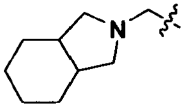 | H |
| S1-14-121 | F | 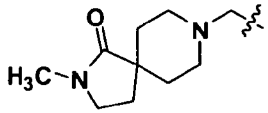 | H |
| S1-14-122 | F | 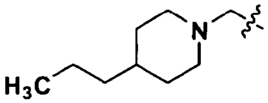 | H |
| S1-14-123 | F | 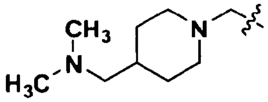 | H |
| S1-14-124 | F | 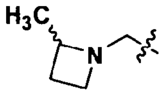 | H |
FIG. 2A

| Cmpd | X | Y | Z |
|---|---|---|---|
| S1-14-125 | F | 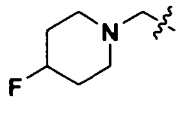 | H |
| S1-14-126 | F | 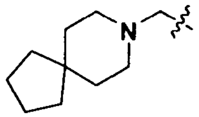 | H |
| S1-14-127 | F | 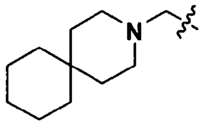 | H |
| S1-14-128 | F | 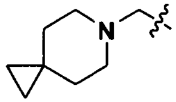 | H |
| S1-14-129 | F | 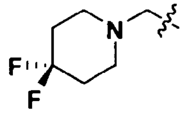 | H |
| Cmpd | X | Y | Z |
|---|---|---|---|
| S1-14-131 | F | 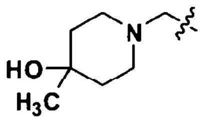 | H |
| S1-14-132 | F | 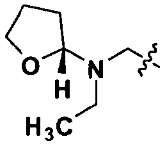 | H |
| S1-14-135 | F | 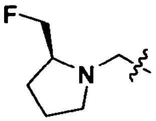 | H |
| S1-14-137 | F | 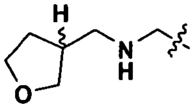 | H |
| S114-138 | F | 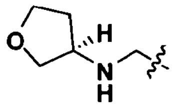 | H |
FIG. 2B

| Cmpd | X | Y | Z |
|---|---|---|---|
| S114-139 | F | 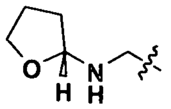 | H |
| S1-14-140 | F | 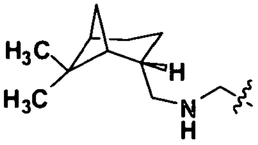 | H |
| S1-14-141 | F | 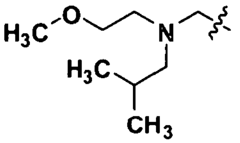 | H |
| S1-14-142 | F | 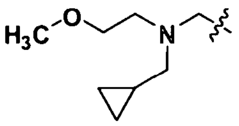 | H |
| S1-14-143 | F | 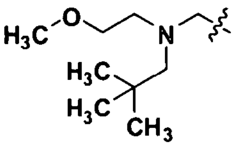 | H |
| Cmpd | X | Y | Z |
|---|---|---|---|
| S1-14-144 | F | 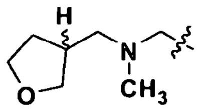 | H |
| S1-14-145 | F | 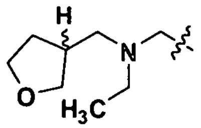 | H |
| S1-14-146 | F | 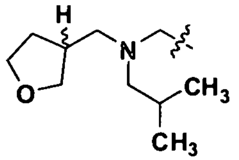 | H |
| S1-14-147 | F | 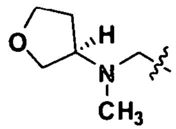 | H |
| S1-14-148 | F | 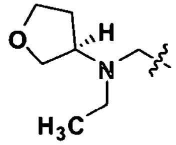 | H |
FIG. 2C

| Cmpd | X | Y | Z |
|---|---|---|---|
| S1-14-149 | F | 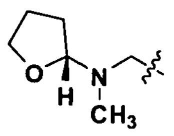 | H |
| S15-13-180 | Cl | 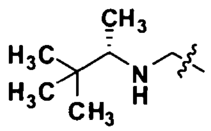 | H |
| S15-13-181 | Cl | 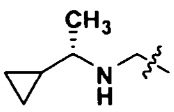 | H |
| S15-13-182 | Cl | 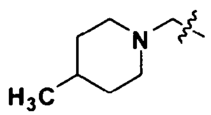 | H |
| S15-13-183 | Cl | 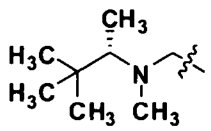 | H |
| Cmpd | X | Y | Z |
|---|---|---|---|
| S15-13-184 | Cl | 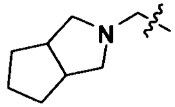 | H |
| S15-13-185 | Cl | 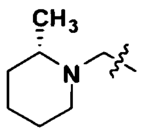 | H |
| S15-13-186 | Cl | 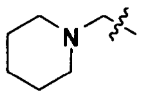 | H |
| S15-13-187 | Cl | 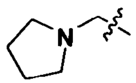 | H |
| S15-13-188 | Cl | 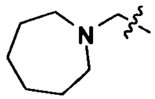 | H |
FIG. 2D

| Cmpd | X | Y | Z |
|---|---|---|---|
| S15-13-189 | Cl | 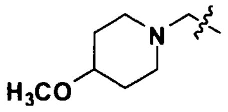 | H |
| S15-13-190 | Cl | 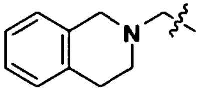 | H |
| S15-13-191 | Cl | 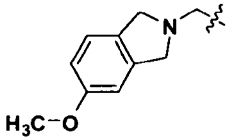 | H |
| S15-13-192 | Cl | 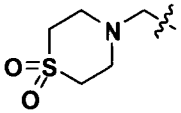 | H |
| S15-13-193 | Cl | 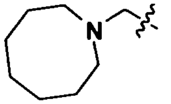 | H |
| Cmpd | X | Y | Z |
|---|---|---|---|
| S15-13-194 | Cl | 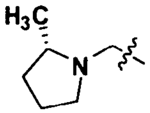 | H |
| S15-13-195 | Cl | 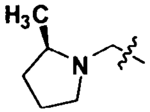 | H |
| S15-13-196 | Cl | 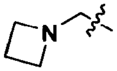 | H |
| S15-13-197 | Cl | 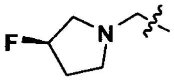 | H |
| S15-13-198 | Cl | 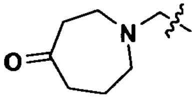 | H |
FIG. 2E

| Cmpd | X | Y | Z |
|---|---|---|---|
| S15-13-199 | Cl | 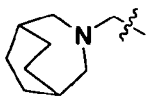 | H |
| S15-13-200 | Cl | 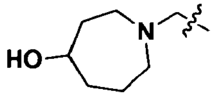 | H |
| S15-13-201 | Cl | 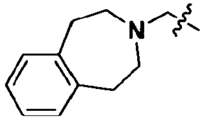 | H |
| S15-13-204 | Cl | 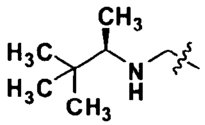 | H |
| S15-13-205 | Cl | 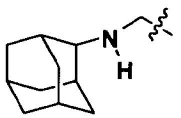 | H |
| Cmpd | X | Y | Z |
|---|---|---|---|
| S15-13-206 | Cl | 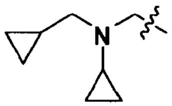 | H |
| S15-13-207 | Cl | 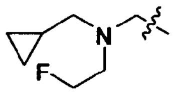 | H |
| S15-13-208 | Cl | 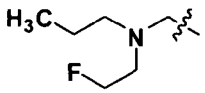 | H |
| S15-13-209 | Cl | 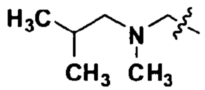 | H |
| S15-13-210 | Cl | 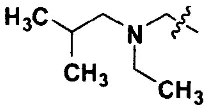 | H |
FIG. 2F

| Cmpd | X | Y | Z |
|---|---|---|---|
| S15-13-211 | Cl | 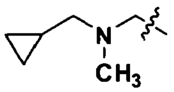 | H |
| S15-13-212 | Cl | 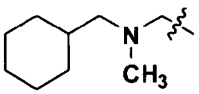 | H |
| S15-13-213 | Cl | 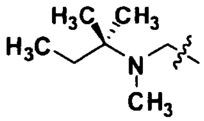 | H |
| S15-13-214 | Cl | 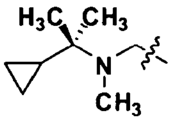 | H |
| S15-13-215 | Cl | 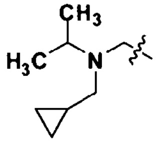 | H |
| Cmpd | X | Y | Z |
|---|---|---|---|
| S15-13-216 | Cl | 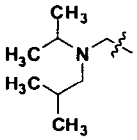 | H |
| S15-13-217 | Cl | 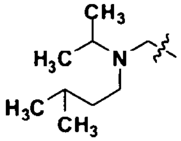 | H |
| S15-13-218 | Cl | 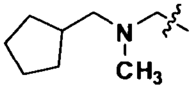 | H |
| S15-13-219 | Cl | 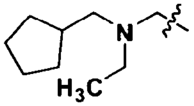 | H |
| S15-13-220 | Cl | 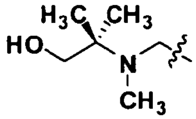 | H |
FIG. 2G

| Cmpd | X | Y | Z |
|---|---|---|---|
| S15-13-221 | Cl | 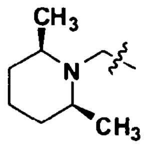 | H |
| S15-13-222 | Cl | 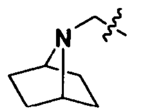 | H |
| S15-13-226 | Cl | 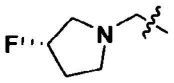 | H |
| S15-13-227 | Cl | 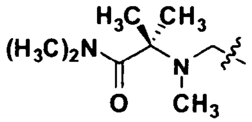 | H |
| S15-14-8 | H | 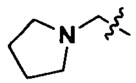 | H |
| Cmpd | X | Y | Z |
|---|---|---|---|
| S24-9-1 | $OCH_3$ | 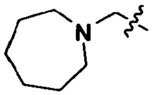 | H |
| S24-9-10 | $OCH_3$ | 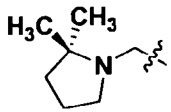 | H |
| S24-9-11 | $OCH_3$ | 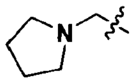 | H |
| S24-9-12 | $OCH_3$ | 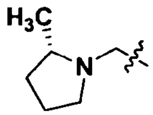 | H |
| S24-9-13 | $OCH_3$ | 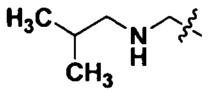 | H |
FIG. 2H

| Cmpd | X | Y | Z |
|---|---|---|---|
| S24-9-14 | $OCH_3$ | 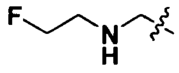 | H |
| S24-9-15 | $OCH_3$ | 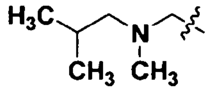 | H |
| S24-9-16 | $OCH_3$ | 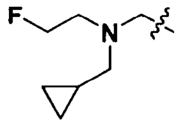 | H |
| S24-9-17 | $OCH_3$ | 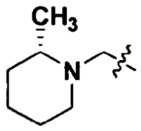 | H |
| S24-9-18 | $OCH_3$ | 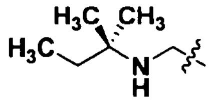 | H |
| Cmpd | X | Y | Z |
|---|---|---|---|
| S24-9-19 | $OCH_3$ | 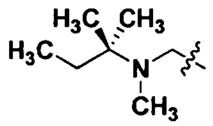 | H |
| S24-9-20 | $OCH_3$ | 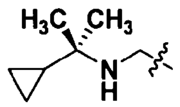 | H |
| S24-9-21 | $OCH_3$ | 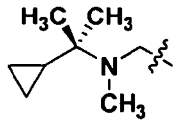 | H |
| S24-9-24 | $OCH_3$ | 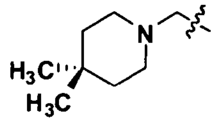 | H |
| S24-9-3 | $OCH_3$ | 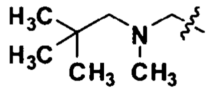 | H |
FIG. 2I

| Cmpd | X | Y | Z |
|---|---|---|---|
| S24-9-4 | $OCH_3$ | 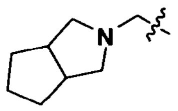 | H |
| S24-9-5 | $OCH_3$ | 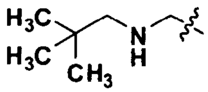 | H |
| S24-9-6 | $OCH_3$ | 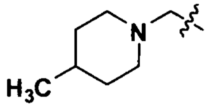 | H |
| S24-9-7 | $OCH_3$ | 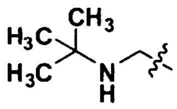 | H |
| S24-9-8 | $OCH_3$ | 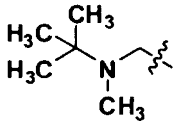 | H |
| Cmpd | X | Y | Z |
|---|---|---|---|
| S24-9-9 | $OCH_3$ | 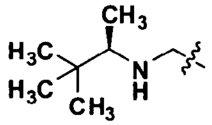 | H |
| S25-11-208 | $CF_3$ | 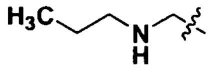 | H |
| S27-9-1 | F | 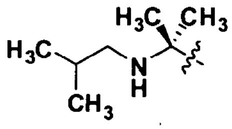 | H |
| S27-9-2 | F | 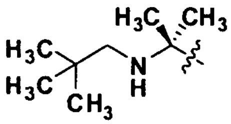 | H |
| S27-9-4 | F | 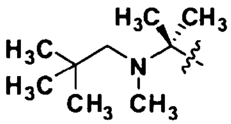 | H |
FIG. 2J

| Cmpd | X | Y | Z |
| --- | --- | --- | --- |
| S33-8-1 | H | 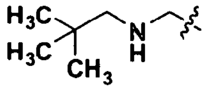 | F |
| S33-8-2 | H | 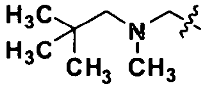 | F |
| S33-8-3 | H | 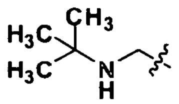 | F |
| S6-4-2 | F | 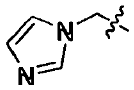 | H |
FIG. 2K

| Compound | X | Y | Z |
|---|---|---|---|
| S1-14-130 | F | 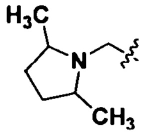 | H |
| S1-14-133 | F | 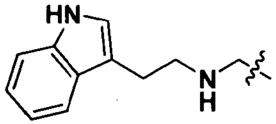 | H |
| S1-14-134 | F | 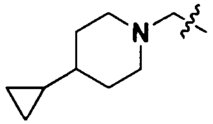 | H |
| S1-14-136 | F | 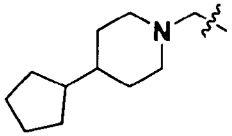 | H |
| S15-13-116 | Cl | 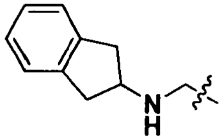 | H |
| Compound | X | Y | Z |
|---|---|---|---|
| S15-13-117 | Cl | 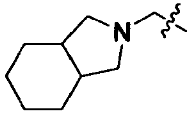 | H |
| S15-13-118 | Cl | 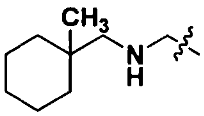 | H |
| S15-13-119 | Cl | 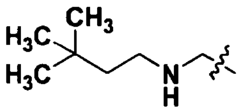 | H |
| S15-13-120 | Cl | 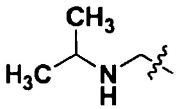 | H |
| S15-13-123 | Cl | 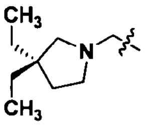 | H |
FIG. 3A

| Compound | X | Y | Z |
|---|---|---|---|
| S15-13-124 | Cl | 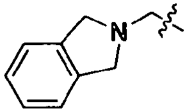 | H |
| S15-13-125 | Cl | 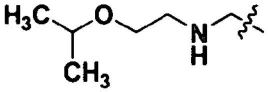 | H |
| S15-13-126 | Cl | 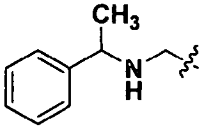 | H |
| S15-13-127 | Cl | 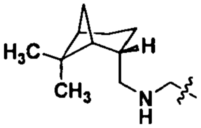 | H |
| S15-13-128 | Cl | 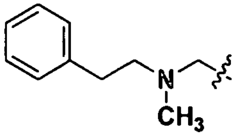 | H |
| Compound | X | Y | Z |
|---|---|---|---|
| S15-13-131 | Cl | 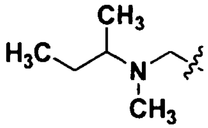 | H |
| S15-13-132 | Cl | 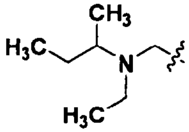 | H |
| S15-13-168 | Cl | 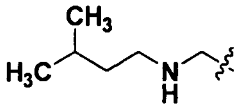 | H |
| S15-13-169 | Cl | 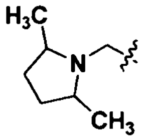 | H |
| S15-13-17 | Cl | 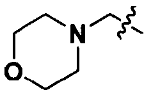 | H |
FIG. 3B

| Compound | X | Y | Z |
|---|---|---|---|
| S15-13-19 | Cl |  | H |
| S15-13-20 | Cl | 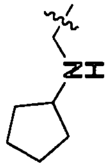 | H |
| S15-13-202 | Cl | 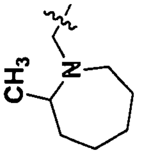 | H |
| S15-13-203 | Cl | 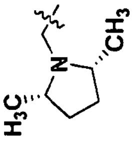 | H |
| S15-13-21 | Cl | 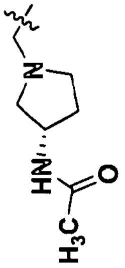 | H |
| Compound | X | Y | Z |
|---|---|---|---|
| S15-13-174 | Cl |  | H |
| S15-13-175 | Cl | 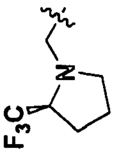 | H |
| S15-13-177 | Cl | 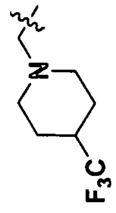 | H |
| S15-13-178 | Cl | 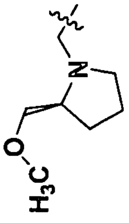 | H |
| S15-13-18 | Cl | 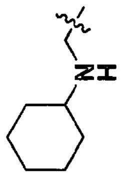 | H |
FIG. 3C

| Compound | X | Y | Z |
|---|---|---|---|
| S15-13-22 | Cl | 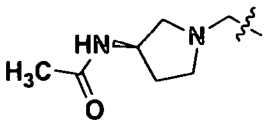 | H |
| S15-13-223 | Cl | 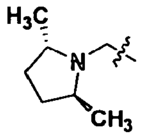 | H |
| S15-13-224 | Cl | 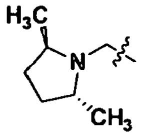 | H |
| S15-13-225 | Cl | 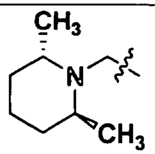 | H |
| S15-13-228 | Cl | 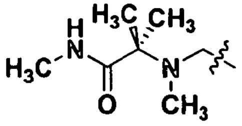 | H |
| Compound | X | Y | Z |
|---|---|---|---|
| S15-13-229 | Cl | 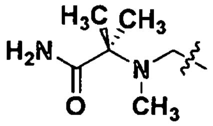 | H |
| S15-13-23 | Cl | 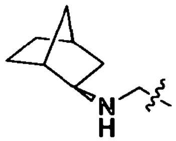 | H |
| S15-13-230 | Cl | 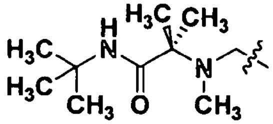 | H |
| S15-13-24 | Cl | 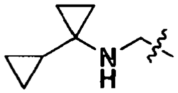 | H |
| S15-13-25 | Cl | 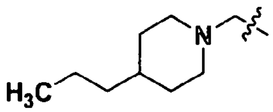 | H |
FIG. 3D

| Compound | X | Y | Z |
|---|---|---|---|
| S15-13-26 | Cl | 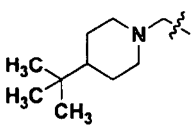 | H |
| S15-13-27 | Cl | 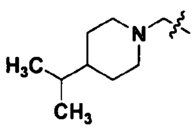 | H |
| S15-13-28 | Cl | 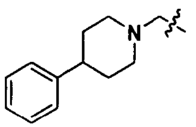 | H |
| S15-13-29 | Cl | 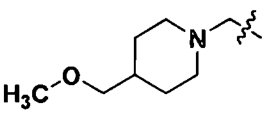 | H |
| S15-13-31 | Cl | 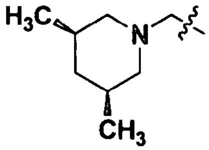 | H |
| Compound | X | Y | Z |
|---|---|---|---|
| S15-13-32 | Cl | 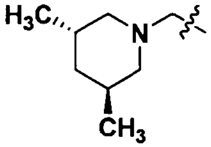 | H |
| S15-13-34 | Cl | 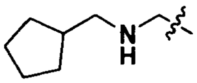 | H |
| S15-13-35 | Cl | 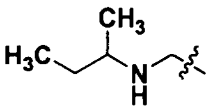 | H |
| S15-13-36 | Cl | 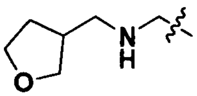 | H |
| S15-13-37 | Cl | 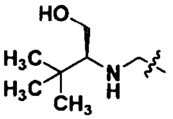 | H |
FIG. 3E

| Compound | X | Y | Z |
|---|---|---|---|
| S15-13-38 | Cl | 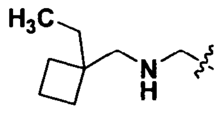 | H |
| S15-13-39 | Cl | 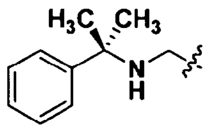 | H |
| S15-13-40 | Cl | 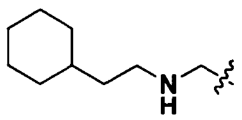 | H |
| S15-13-41 | Cl | 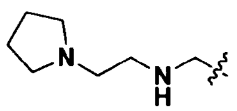 | H |
| S15-13-42 | Cl | 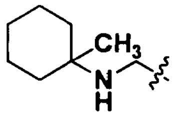 | H |
| Compound | X | Y | Z |
|---|---|---|---|
| S15-13-43 | Cl | 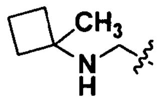 | H |
| S15-13-44 | Cl | 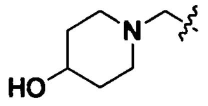 | H |
| S15-13-45 | Cl | 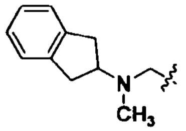 | H |
| S15-13-46 | Cl | 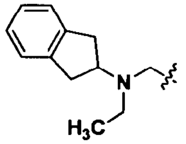 | H |
| S15-13-47 | Cl | 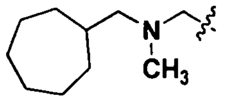 | H |
FIG. 3F

| Compound | X | Y | Z |
|---|---|---|---|
| S15-13-48 | Cl | 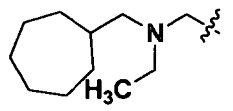 | H |
| S15-13-81 | Cl | 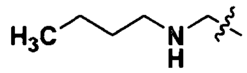 | H |
| S15-13-82 | Cl | 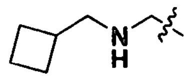 | H |
| S15-13-83 | Cl | 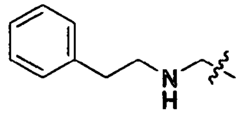 | H |
| S15-13-84 | Cl | 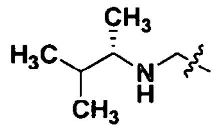 | H |
| Compound | X | Y | Z |
|---|---|---|---|
| S15-13-87 | Cl | 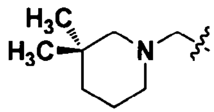 | H |
| S15-14-6 | H | 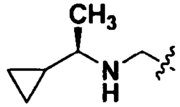 | H |
| S16-10-101 | $N(CH_3)_2$ | 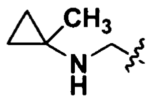 | H |
| S16-10-102 | $N(CH_3)_2$ | 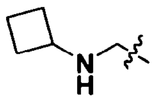 | H |
| S16-10-106 | $N(CH_3)_2$ | 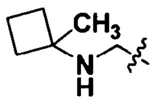 | H |
FIG. 3G

| Compound | X | Y | Z |
|---|---|---|---|
| S16-10-107 | $N(CH_3)_2$ | 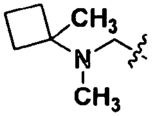 | H |
| S16-10-110 | $N(CH_3)_2$ | 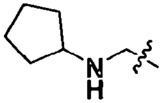 | H |
| S16-10-116 | $N(CH_3)_2$ | 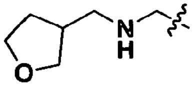 | H |
| S16-10-117 | $N(CH_3)_2$ | 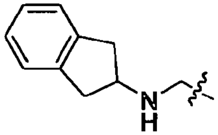 | H |
| S16-10-119 | $N(CH_3)_2$ | 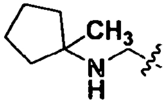 | H |
| Compound | X | Y | Z |
|---|---|---|---|
| S16-10-120 | $N(CH_3)_2$ | 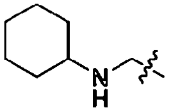 | H |
| S16-10-121 | $N(CH_3)_2$ | 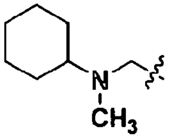 | H |
| S16-10-123 | $N(CH_3)_2$ | 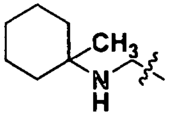 | H |
| S16-10-126 | $N(CH_3)_2$ | 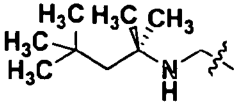 | H |
| S16-10-129 | $N(CH_3)_2$ | 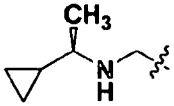 | H |
FIG. 3H

| Compound | X | Y | Z |
|---|---|---|---|
| S16-10-132 | $N(CH_3)_2$ | 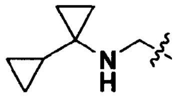 | H |
| S16-10-135 | $N(CH_3)_2$ | 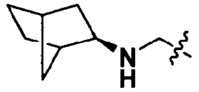 | H |
| S16-10-136 | $N(CH_3)_2$ | 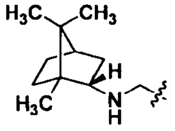 | H |
| S16-10-138 | $N(CH_3)_2$ | 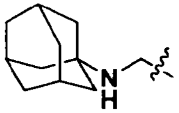 | H |
| S16-10-139 | $N(CH_3)_2$ | 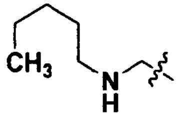 | H |
| Compound | X | Y | Z |
|---|---|---|---|
| S16-10-143 | $N(CH_3)_2$ | 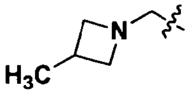 | H |
| S16-10-144 | $N(CH_3)_2$ | 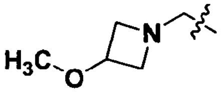 | H |
| S16-10-145 | $N(CH_3)_2$ | 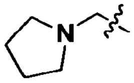 | H |
| S16-10-146 | $N(CH_3)_2$ | 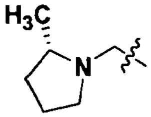 | H |
| S16-10-147 | $N(CH_3)_2$ | 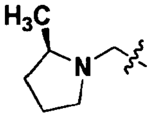 | H |
FIG. 3I

| Compound | X | Y | Z |
|---|---|---|---|
| S16-10-148 | $N(CH_3)_2$ | 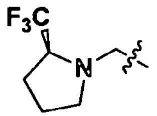 | H |
| S16-10-149 | $N(CH_3)_2$ | 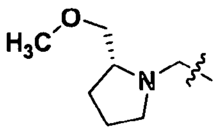 | H |
| S16-10-150 | $N(CH_3)_2$ | 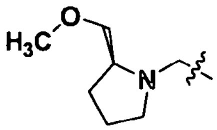 | H |
| S16-10-151 | $N(CH_3)_2$ | 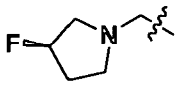 | H |
| S16-10-152 | $N(CH_3)_2$ | 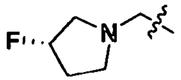 | H |
| Compound | X | Y | Z |
|---|---|---|---|
| S16-10-153 | $N(CH_3)_2$ | 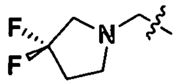 | H |
| S16-10-154 | $N(CH_3)_2$ | 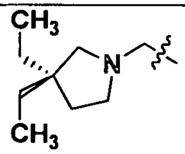 | H |
| S16-10-155 | $N(CH_3)_2$ | 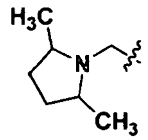 | H |
| S16-10-156 | $N(CH_3)_2$ | 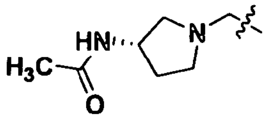 | H |
| S16-10-157 | $N(CH_3)_2$ | 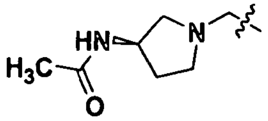 | H |
FIG. 3J

| Compound | X | Y | Z |
|---|---|---|---|
| S16-10-158 | N(CH$_3$)$_2$ | 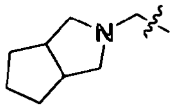 | H |
| S16-10-159 | N(CH$_3$)$_2$ | 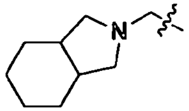 | H |
| S16-10-160 | N(CH$_3$)$_2$ | 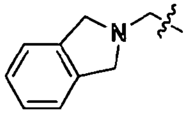 | H |
| S16-10-161 | N(CH$_3$)$_2$ | 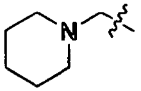 | H |
| S16-10-162 | N(CH$_3$)$_2$ | 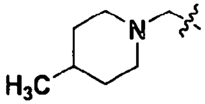 | H |
| Compound | X | Y | Z |
|---|---|---|---|
| S16-10-163 | N(CH$_3$)$_2$ | 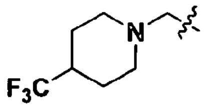 | H |
| S16-10-164 | N(CH$_3$)$_2$ | 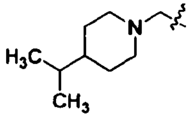 | H |
| S16-10-165 | N(CH$_3$)$_2$ | 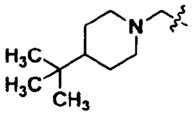 | H |
| S16-10-166 | N(CH$_3$)$_2$ | 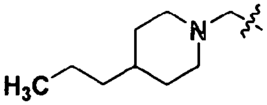 | H |
| S16-10-167 | N(CH$_3$)$_2$ | 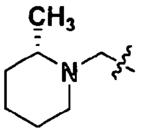 | H |
FIG. 3K

| Compound | X | Y | Z |
|---|---|---|---|
| S16-10-168 | $N(CH_3)_2$ | 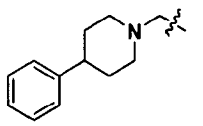 | H |
| S16-10-169 | $N(CH_3)_2$ | 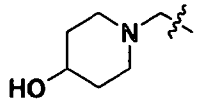 | H |
| S16-10-170 | $N(CH_3)_2$ | 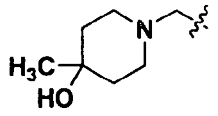 | H |
| S16-10-171 | $N(CH_3)_2$ | 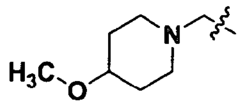 | H |
| S16-10-172 | $N(CH_3)_2$ | 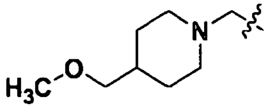 | H |
| Compound | X | Y | Z |
|---|---|---|---|
| S16-10-173 | $N(CH_3)_2$ | 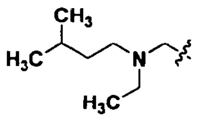 | H |
| S16-10-174 | $N(CH_3)_2$ | 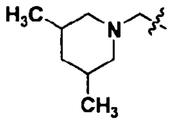 | H |
| S16-10-175 | $N(CH_3)_2$ | 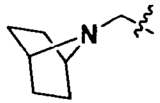 | H |
| S16-10-176 | $N(CH_3)_2$ | 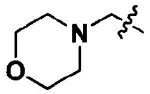 | H |
| S16-10-177 | $N(CH_3)_2$ | 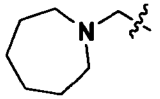 | H |
FIG. 3L

| Compound | X | Y | Z |
|---|---|---|---|
| S16-10-178 | $N(CH_3)_2$ | 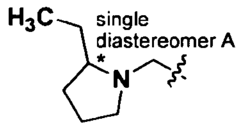 single diastereomer A | H |
| S16-10-179 | $N(CH_3)_2$ | 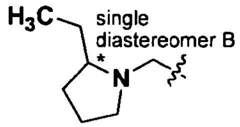 single diastereomer B | H |
| S16-10-28 | $N(CH_3)_2$ | 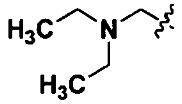 | H |
| S16-10-33 | $N(CH_3)_2$ | 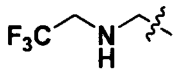 | H |
| S16-10-36 | $N(CH_3)_2$ | 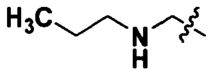 | H |
| Compound | X | Y | Z |
|---|---|---|---|
| S16-10-37 | $N(CH_3)_2$ | 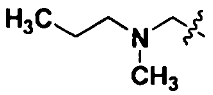 | H |
| S16-10-38 | $N(CH_3)_2$ | 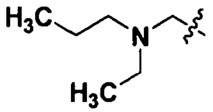 | H |
| S16-10-39 | $N(CH_3)_2$ | 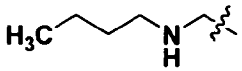 | H |
| S16-10-40 | $N(CH_3)_2$ | 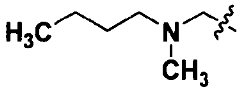 | H |
| S16-10-42 | $N(CH_3)_2$ | 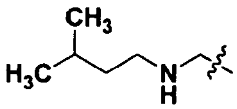 | H |
FIG. 3M

| Compound | X | Y | Z |
|---|---|---|---|
| S16-10-43 | $N(CH_3)_2$ | 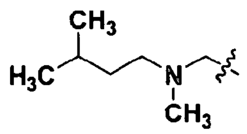 | H |
| S16-10-45 | $N(CH_3)_2$ | 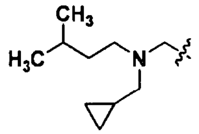 | H |
| S16-10-46 | $N(CH_3)_2$ | 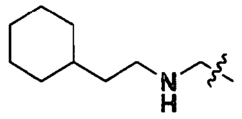 | H |
| S16-10-48 | $N(CH_3)_2$ | 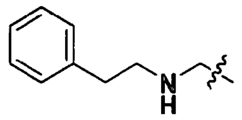 | H |
| S16-10-49 | $N(CH_3)_2$ | 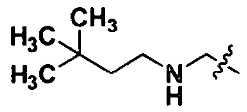 | H |
| Compound | X | Y | Z |
|---|---|---|---|
| S16-10-52 | $N(CH_3)_2$ | 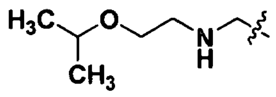 | H |
| S16-10-53 | $N(CH_3)_2$ | 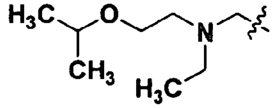 | H |
| S16-10-54 | $N(CH_3)_2$ | 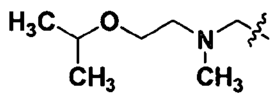 | H |
| S16-10-55 | $N(CH_3)_2$ | 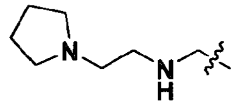 | H |
| S16-10-61 | $N(CH_3)_2$ | 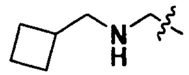 | H |
FIG. 3N

| Compound | X | Y | Z |
|---|---|---|---|
| S16-10-64 | $N(CH_3)_2$ | 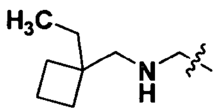 | H |
| S16-10-65 | $N(CH_3)_2$ | 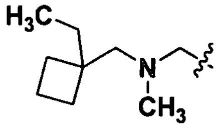 | H |
| S16-10-67 | $N(CH_3)_2$ | 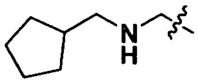 | H |
| S16-10-69 | $N(CH_3)_2$ | 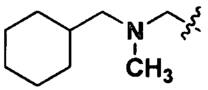 | H |
| S16-10-71 | $N(CH_3)_2$ | 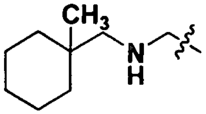 | H |
| Compound | X | Y | Z |
|---|---|---|---|
| S16-10-72 | $N(CH_3)_2$ | 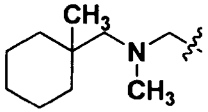 | H |
| S16-10-73 | $N(CH_3)_2$ | 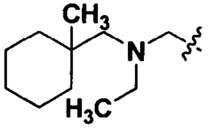 | H |
| S16-10-74 | $N(CH_3)_2$ | 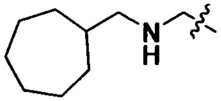 | H |
| S16-10-75 | $N(CH_3)_2$ | 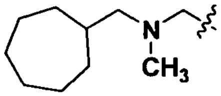 | H |
| S16-10-79 | $N(CH_3)_2$ | 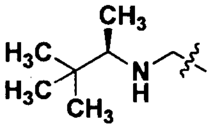 | H |
FIG. 3O

| Compound | X | Y | Z |
|---|---|---|---|
| S16-10-83 | $N(CH_3)_2$ | 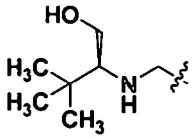 | H |
| S16-10-86 | $N(CH_3)_2$ | 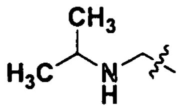 | H |
| S16-10-88 | $N(CH_3)_2$ | 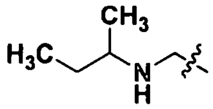 | H |
| S16-10-89 | $N(CH_3)_2$ | 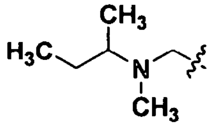 | H |
| S16-10-91 | $N(CH_3)_2$ | 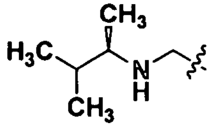 | H |
| Compound | X | Y | Z |
|---|---|---|---|
| S16-10-92 | $N(CH_3)_2$ | 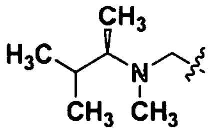 | H |
| S16-10-95 | $OCH_3$ | 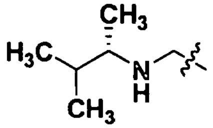 | H |
| S2-4-69 | F | 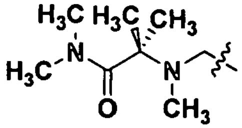 | H |
| S24-9-125 | $OCH_3$ | 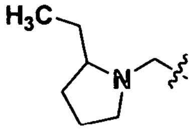 | H |
| S24-9-126 | $OCH_3$ | 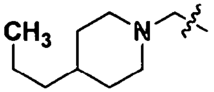 | H |
FIG. 3P

| Compound | X | Y | Z |
|---|---|---|---|
| S24-9-127 | $OCH_3$ | 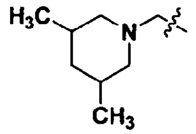 | H |
| S24-9-128 | $OCH_3$ | 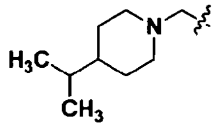 | H |
| S24-9-129 | $OCH_3$ | 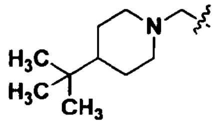 | H |
| S24-9-130 | $OCH_3$ | 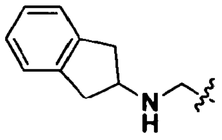 | H |
| S24-9-131 | $OCH_3$ | 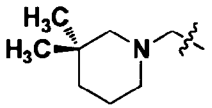 | H |
| Compound | X | Y | Z |
|---|---|---|---|
| S24-9-132 | $OCH_3$ | 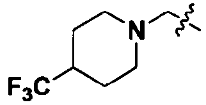 | H |
| S24-9-180 | $OCH_3$ | 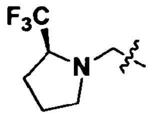 | H |
| S24-9-2 | $OCH_3$ | 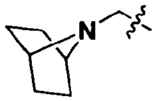 | H |
| S24-9-22 | $OCH_3$ | 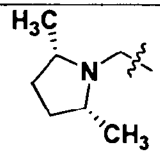 | H |
| S24-9-23 | $OCH_3$ | 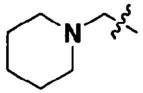 | H |
FIG. 3Q

| Compound | X | Y | Z |
|---|---|---|---|
| S24-9-25 | $OCH_3$ | 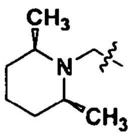 | H |
| S24-9-26 | $OCH_3$ | 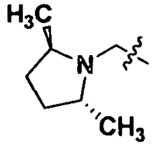 | H |
| S24-9-27 | $OCH_3$ | 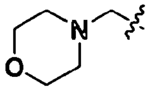 | H |
| S24-9-28 | $OCH_3$ | 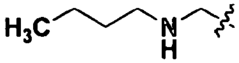 | H |
| S24-9-30 | $OCH_3$ | 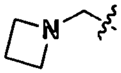 | H |
| Compound | X | Y | Z |
|---|---|---|---|
| S24-9-31 | $OCH_3$ | 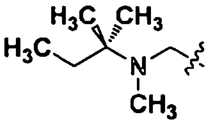 | H |
| S24-9-32 | $OCH_3$ | 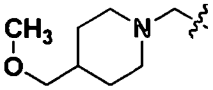 | H |
| S24-9-80 | $OCH_3$ | 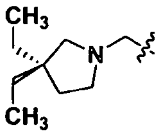 | H |
| S24-9-81 | $OCH_3$ | 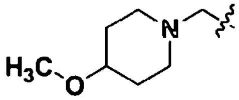 | H |
| S24-9-82 | $OCH_3$ | 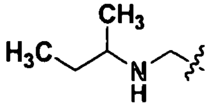 | H |
FIG. 3R

| Compound | X | Y | Z |
|---|---|---|---|
| S24-9-83 | $OCH_3$ | 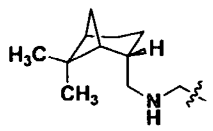 | H |
| S24-9-84 | $OCH_3$ | 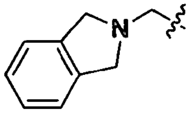 | H |
| S24-9-92 | $OCH_3$ | 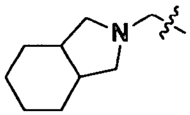 | H |
| S24-9-93 | $CF_3$ | 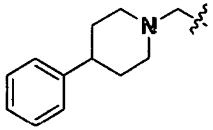 | H |
| S25-11-1 | $CF_3$ | 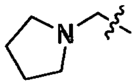 | H |
| Compound | X | Y | Z |
|---|---|---|---|
| S25-11-10 | $CF_3$ | 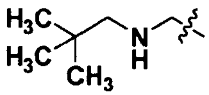 | H |
| S25-11-11 | $CF_3$ | 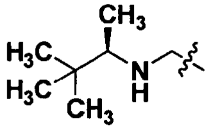 | H |
| S25-11-12 | $CF_3$ | 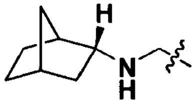 | H |
| S25-11-13 | $CF_3$ |  | H |
| S25-11-14 | $CF_3$ | 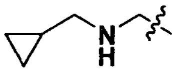 | H |
FIG. 3S

| Compound | X | Y | Z |
|---|---|---|---|
| S25-11-15 | $CF_3$ | 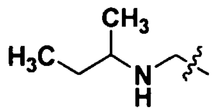 | H |
| S25-11-16 | $CF_3$ | 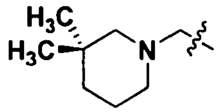 | H |
| S25-11-164 | $CF_3$ | 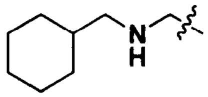 | H |
| S25-11-165 | $CF_3$ | 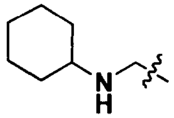 | H |
| S25-11-166 | $CF_3$ | 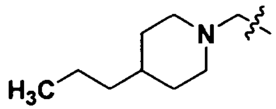 | H |
| Compound | X | Y | Z |
|---|---|---|---|
| S25-11-168 | $CF_3$ | 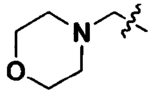 | H |
| S25-11-169 | $CF_3$ | 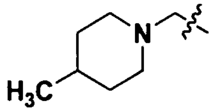 | H |
| S25-11-17 | $CF_3$ | 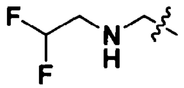 | H |
| S25-11-170 | $CF_3$ | 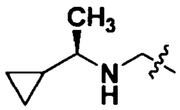 | H |
| S25-11-171 | $CF_3$ | 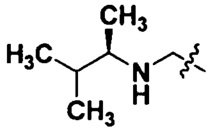 | H |
FIG. 3T

| Compound | X | Y | Z |
|---|---|---|---|
| S25-11-172 | $CF_3$ | 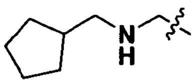 | H |
| S25-11-173 | $CF_3$ | 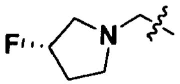 | H |
| S25-11-174 | $CF_3$ | 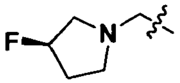 | H |
| S25-11-175 | $CF_3$ | 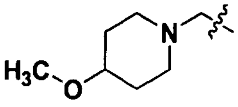 | H |
| S25-11-176 | $CF_3$ | 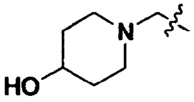 | H |
| Compound | X | Y | Z |
|---|---|---|---|
| S25-11-177 | $CF_3$ | 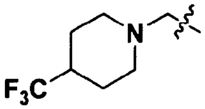 | H |
| S25-11-178 | $CF_3$ | 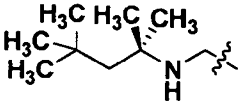 | H |
| S25-11-179 | $CF_3$ | 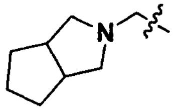 | H |
| S25-11-18 | $CF_3$ | 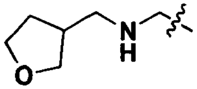 | H |
| S25-11-180 | $CF_3$ | 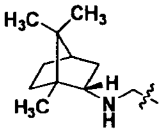 | H |
FIG. 3U

| Compound | X | Y | Z |
|---|---|---|---|
| S25-11-181 | $CF_3$ | 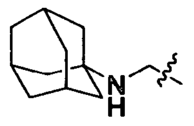 | H |
| S25-11-182 | $CF_3$ | 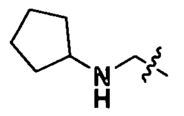 | H |
| S25-11-183 | $CF_3$ | 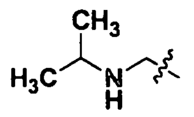 | H |
| S25-11-184 | $CF_3$ | 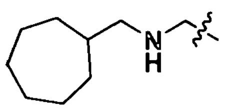 | H |
| S25-11-185 | $CF_3$ | 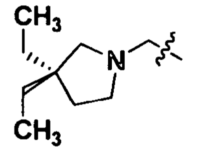 | H |
| Compound | X | Y | Z |
|---|---|---|---|
| S25-11-186 | $CF_3$ | 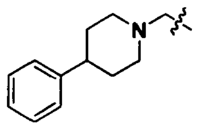 | H |
| S25-11-187 | $CF_3$ | 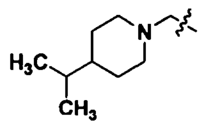 | H |
| S25-11-188 | $CF_3$ | 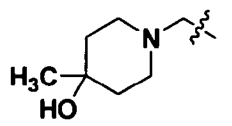 | H |
| S25-11-189 | $CF_3$ | 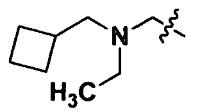 | H |
| S25-11-19 | $CF_3$ | 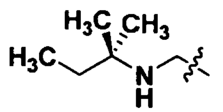 | H |
FIG. 3V

| Compound | X | Y | Z |
|---|---|---|---|
| S25-11-194 | $CF_3$ | 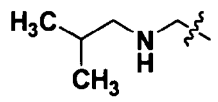 | H |
| S25-11-195 | $CF_3$ | 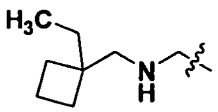 | H |
| S25-11-196 | $CF_3$ | 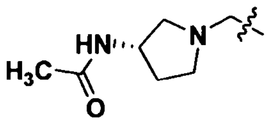 | H |
| S25-11-197 | $CF_3$ | 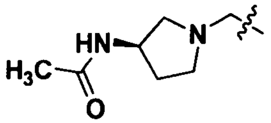 | H |
| S25-11-198 | $CF_3$ | 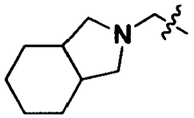 | H |
| Compound | X | Y | Z |
|---|---|---|---|
| S25-11-199 | $CF_3$ | 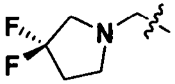 | H |
| S25-11-2 | $CF_3$ | 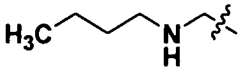 | H |
| S25-11-20 | $CF_3$ | 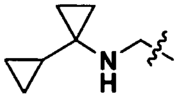 | H |
| S25-11-200 | $CF_3$ | 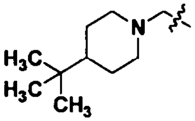 | H |
| S25-11-206 | $CF_3$ | 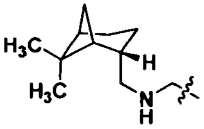 | H |
FIG. 3W

| Compound | X | Y | Z |
|---|---|---|---|
| S25-11-207 | $CF_3$ | 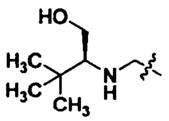 | H |
| S25-11-208 | $CF_3$ | 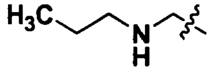 | H |
| S25-11-21 | $CF_3$ | 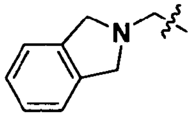 | H |
| S25-11-22 | $CF_3$ | 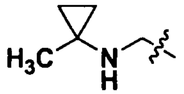 | H |
| S25-11-23 | $CF_3$ | 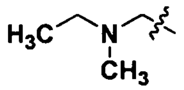 | H |
| Compound | X | Y | Z |
|---|---|---|---|
| S25-11-24 | $CF_3$ | 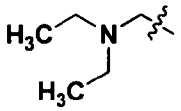 | H |
| S25-11-25 | $CF_3$ | 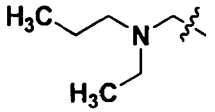 | H |
| S25-11-26 | $CF_3$ | 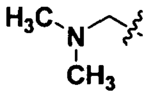 | H |
| S25-11-27 | $CF_3$ | 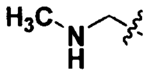 | H |
| S25-11-28 | $CF_3$ | 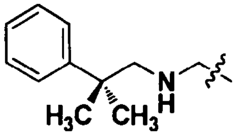 | H |
FIG. 3X

| Compound | X | Y | Z |
|---|---|---|---|
| S25-11-29 | $CF_3$ | 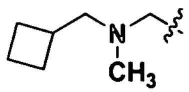 | H |
| S25-11-3 | $CF_3$ | 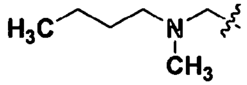 | H |
| S25-11-30 | $CF_3$ | 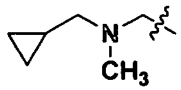 | H |
| S25-11-31 | $CF_3$ | 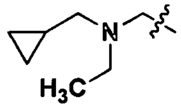 | H |
| S25-11-32 | $CF_3$ | 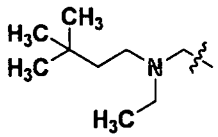 | H |
| Compound | X | Y | Z |
|---|---|---|---|
| S25-11-33 | $CF_3$ | 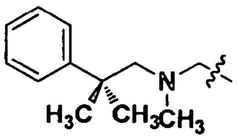 | H |
| S25-11-34 | $CF_3$ | 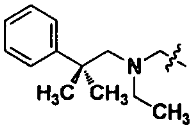 | H |
| S25-11-35 | $CF_3$ | 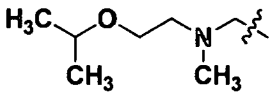 | H |
| S25-11-36 | $CF_3$ | 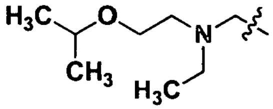 | H |
| S25-11-37 | $CF_3$ | 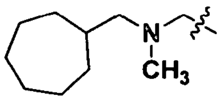 | H |
FIG. 3Y

| Compound | X | Y | Z |
|---|---|---|---|
| S25-11-4 | $CF_3$ | 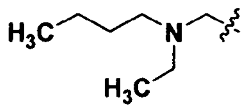 | H |
| S25-11-43 | $CF_3$ | 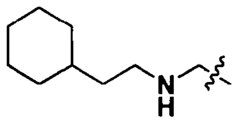 | H |
| S25-11-44 | $CF_3$ | 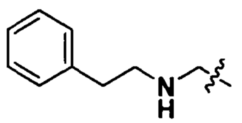 | H |
| S25-11-45 | $CF_3$ | 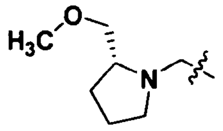 | H |
| S25-11-46 | $CF_3$ | 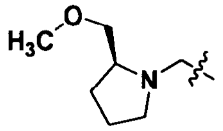 | H |
| Compound | X | Y | Z |
|---|---|---|---|
| S25-11-47 | $CF_3$ | 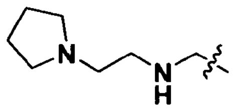 | H |
| S25-11-48 | $CF_3$ | 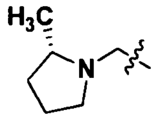 | H |
| S25-11-5 | $CF_3$ | 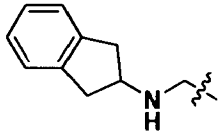 | H |
| S25-11-50 | $CF_3$ | 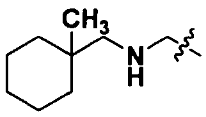 | H |
| S25-11-51 | $CF_3$ | 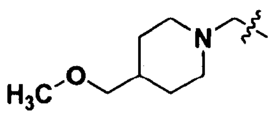 | H |
FIG. 3Z

| Compound | X | Y | Z |
|---|---|---|---|
| S25-11-52 | $CF_3$ | 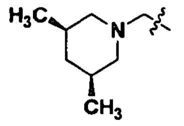 | H |
| S25-11-53 | $CF_3$ | 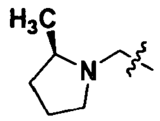 | H |
| S25-11-54 | $CF_3$ | 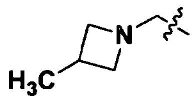 | H |
| S25-11-55 | $CF_3$ | 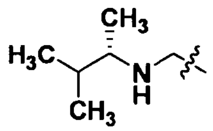 | H |
| S25-11-56 | $CF_3$ | 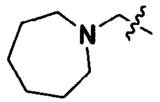 | H |
| Compound | X | Y | Z |
|---|---|---|---|
| S25-11-57 | $CF_3$ |  | H |
| S25-11-58 | $CF_3$ | 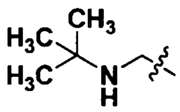 | H |
| S25-11-59 | $CF_3$ | 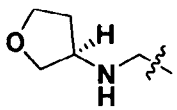 | H |
| S25-11-6 | $CF_3$ | 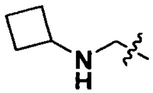 | H |
| S25-11-60 | $CF_3$ | 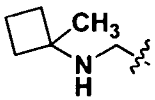 | H |
FIG. 3AA

| Compound | X | Y | Z |
|---|---|---|---|
| S25-11-61 | $CF_3$ | 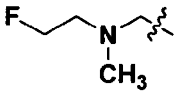 | H |
| S25-11-62 | $CF_3$ | 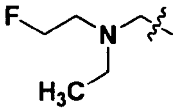 | H |
| S25-11-63 | $CF_3$ | 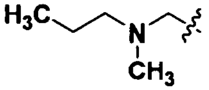 | H |
| S25-11-64 | $CF_3$ | 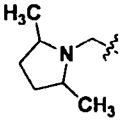 | H |
| S25-11-65 | $CF_3$ | 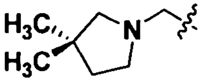 | H |
| Compound | X | Y | Z |
|---|---|---|---|
| S25-11-66 | $CF_3$ | 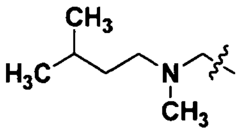 | H |
| S25-11-67 | $CF_3$ | 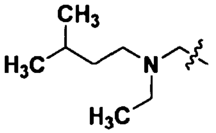 | H |
| S25-11-68 | $CF_3$ | 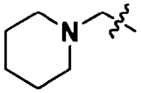 | H |
| S25-11-69 | $CF_3$ | 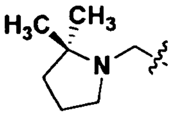 | H |
| S25-11-7 | $CF_3$ | 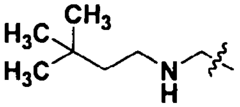 | H |
FIG. 3BB

| Compound | X | Y | Z |
|---|---|---|---|
| S25-11-70 | $CF_3$ | 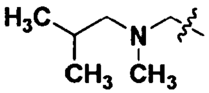 | H |
| S25-11-71 | $CF_3$ | 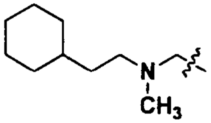 | H |
| S25-11-72 | $CF_3$ | 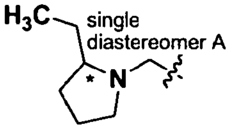 single diastereomer A | H |
| S25-11-73 | $CF_3$ | 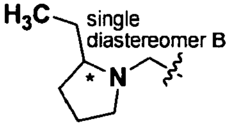 single diastereomer B | H |
| S25-11-74 | $CF_3$ | 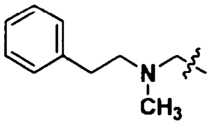 | H |
| Compound | X | Y | Z |
|---|---|---|---|
| S25-11-75 | $CF_3$ | 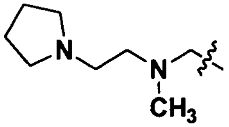 | H |
| S25-11-76 | $CF_3$ | 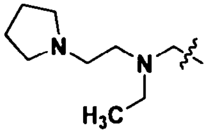 | H |
| S25-11-77 | $CF_3$ | 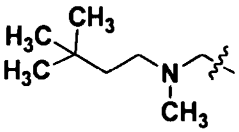 | H |
| S25-11-78 | $CF_3$ | 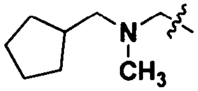 | H |
| S25-11-8 | $CF_3$ | 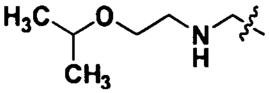 | H |
FIG. 3CC

| Compound | X | Y | Z |
|---|---|---|---|
| S25-11-9 | F | 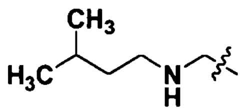 | H |
| S27-9-3 | F | 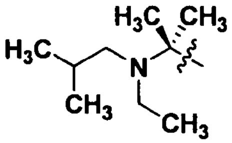 | H |
| S27-9-5 | F | 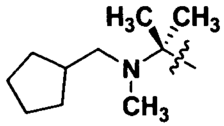 | H |
| S27-9-6 | Cl | 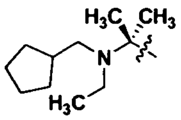 | H |
| S27-9-7 | F | 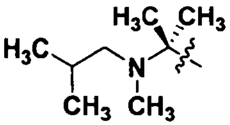 | $NH_2$ |
| Compound | X | Y | Z |
|---|---|---|---|
| S29-2-1 | F | 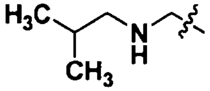 | $NH_2$ |
| S29-2-2 | F | 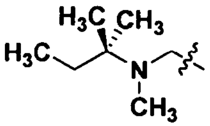 | $NH_2$ |
| S29-2-3 | Cl | 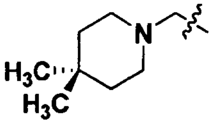 | $NH_2$ |
| S29-2-4 | F | 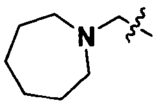 | $NHCH_3$ |
| S30-4-1 | F | 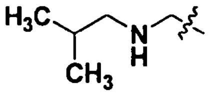 | $NHCH_3$ |
FIG. 3DD

| Compound | X | Y | Z |
|---|---|---|---|
| S30-4-2 | F | 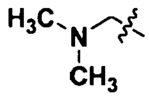 | H |
| S6-4-3 | Cl | 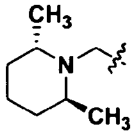 | H |
FIG. 3EE

| Cmpd | X | Y | Z |
|---|---|---|---|
| S15-13-121 | Cl | 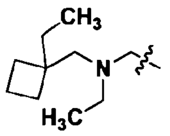 | H |
| S15-13-129 | Cl | 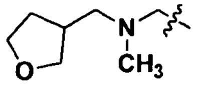 | H |
| S15-13-130 | Cl | 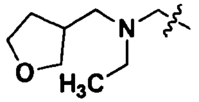 | H |
| S15-13-133 | Cl | 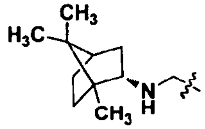 | H |
| S15-13-134 | Cl | 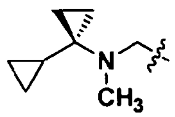 | H |
| S15-13-135 | Cl | 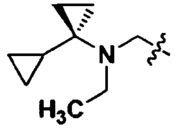 | H |
| Cmpd | X | Y | Z |
|---|---|---|---|
| S15-13-136 | Cl | 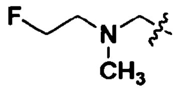 | H |
| S15-13-142 | Cl | 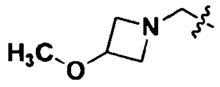 | H |
| S15-13-143 | Cl | 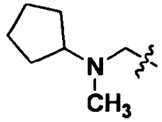 | H |
| S15-13-144 | Cl | 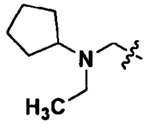 | H |
| S15-13-145 | Cl | 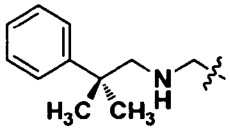 | H |
| S15-13-146 | Cl | 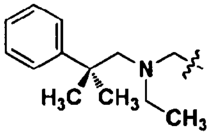 | H |
FIG. 4A

| Cmpd | X | Y | Z |
|---|---|---|---|
| S15-13-147 | Cl | 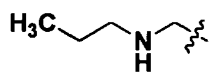 | H |
| S15-13-148 | Cl | 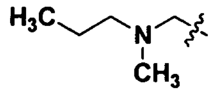 | H |
| S15-13-149 | Cl | 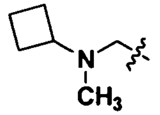 | H |
| S15-13-150 | Cl | 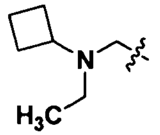 | H |
| S15-13-151 | Cl | 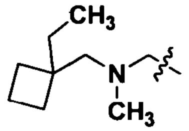 | H |
| Cmpd | X | Y | Z |
|---|---|---|---|
| S15-13-152 | Cl | 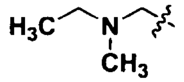 | H |
| S15-13-153 | Cl | 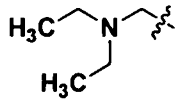 | H |
| S15-13-154 | Cl | 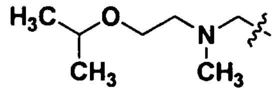 | H |
| S15-13-155 | Cl | 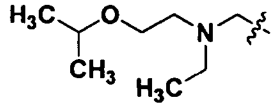 | H |
| S15-13-156 | Cl | 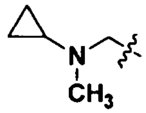 | H |
FIG. 4B

| Cmpd | X | Y | Z |
|---|---|---|---|
| S15-13-157 | Cl | 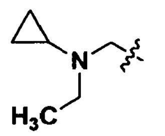 | H |
| S15-13-158 | Cl | 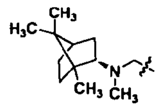 | H |
| S15-13-159 | Cl | 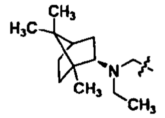 | H |
| S15-13-160 | Cl | 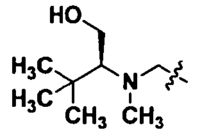 | H |
| S15-13-167 | Cl | 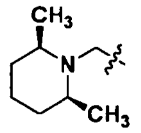 | H |
| Cmpd | X | Y | Z |
|---|---|---|---|
| S15-13-170 | Cl | 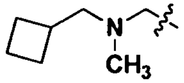 | H |
| S15-13-171 | Cl | 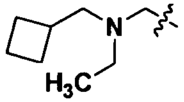 | H |
| S15-13-172 | Cl | 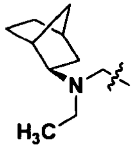 | H |
| S15-13-173 | Cl | 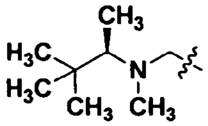 | H |
| S15-13-176 | Cl | 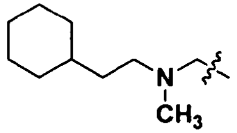 | H |
FIG. 4C

| Cmpd | X | Y | Z |
|---|---|---|---|
| S15-13-179 | Cl | 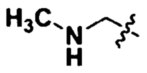 | H |
| S15-13-227 | $OCH_3$ | 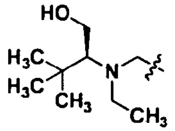 | H |
| S15-13-30 | Cl | 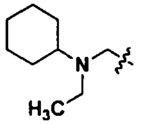 | H |
| S15-13-33 | Cl | 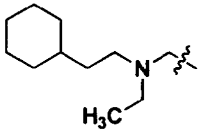 | H |
| S15-13-49 | Cl | 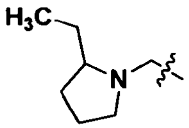 | H |
| Cmpd | X | Y | Z |
|---|---|---|---|
| S15-13-50 | Cl | 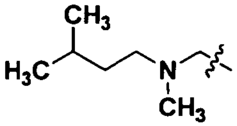 | H |
| S15-13-51 | Cl | 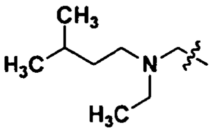 | H |
| S15-13-52 | Cl | 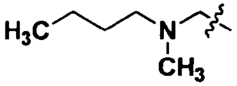 | H |
| S15-13-53 | Cl | 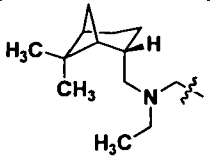 | H |
| S15-13-54 | Cl | 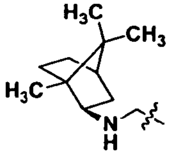 | H |
FIG. 4D

| Cmpd | X | Y | Z |
|---|---|---|---|
| S15-13-55 | Cl | 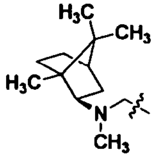 | H |
| S15-13-56 | Cl | 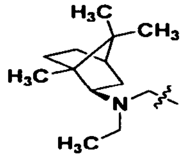 | H |
| S15-13-57 | Cl | 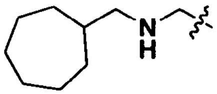 | H |
| S15-13-58 | Cl | 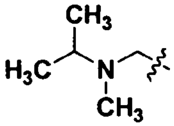 | H |
| S15-13-59 | Cl | 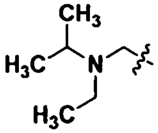 | H |
| Cmpd | X | Y | Z |
|---|---|---|---|
| S15-13-60 | Cl | 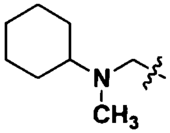 | H |
| S15-13-61 | Cl | 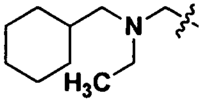 | H |
| S15-13-62 | Cl | 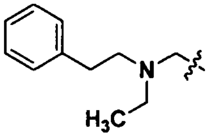 | H |
| S15-13-63 | Cl | 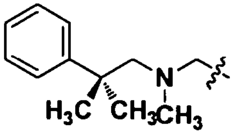 | H |
| S15-13-78 | Cl | 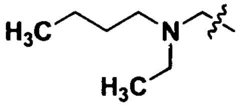 | H |
FIG. 4E

| Cmpd | X | Y | Z |
|---|---|---|---|
| S15-13-85 | Cl | 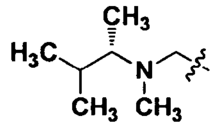 | H |
| S15-13-86 | Cl | 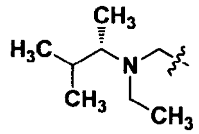 | H |
| S15-13-89 | Cl | 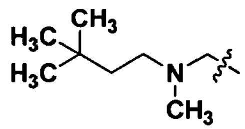 | H |
| S15-13-90 | Cl | 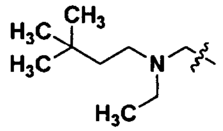 | H |
| S15-13-91 | Cl | 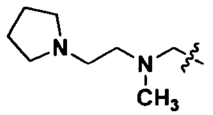 | H |
| Cmpd | X | Y | Z |
|---|---|---|---|
| S15-13-92 | Cl | 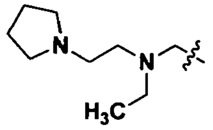 | H |
| S15-13-93 | Cl | 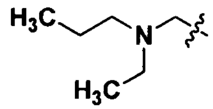 | H |
| S15-13-94 | Cl | 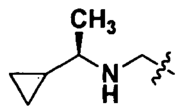 | H |
| S15-13-95 | Cl | 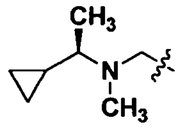 | H |
| S15-13-96 | Cl | 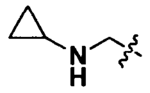 | H |
FIG. 4F

| Cmpd | X | Y | Z |
|---|---|---|---|
| S15-13-97 | Cl | 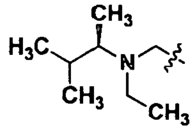 | H |
| S16-10-118 | $N(CH_3)_2$ | 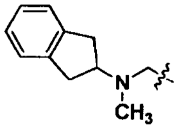 | H |
| S16-10-125 | $N(CH_3)_2$ | 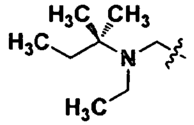 | H |
| S16-10-128 | $N(CH_3)_2$ | 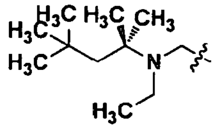 | H |
| S16-10-130 | $N(CH_3)_2$ | 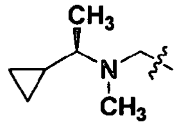 | H |
| Cmpd | X | Y | Z |
|---|---|---|---|
| S16-10-131 | $N(CH_3)_2$ | 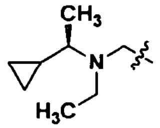 | H |
| S16-10-137 | $N(CH_3)_2$ | 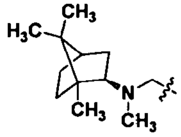 | H |
| S16-10-31 | $N(CH_3)_2$ | 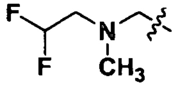 | H |
| S16-10-44 | $N(CH_3)_2$ | 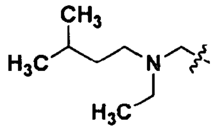 | H |
| S16-10-47 | $N(CH_3)_2$ | 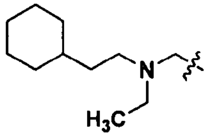 | H |
FIG. 4G

| Cmpd | X | Y | Z |
|---|---|---|---|
| S16-10-50 | $N(CH_3)_2$ | 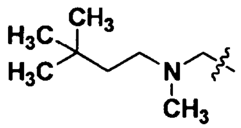 | H |
| S16-10-51 | $N(CH_3)_2$ | 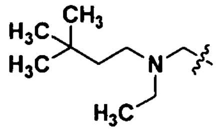 | H |
| S16-10-56 | $N(CH_3)_2$ | 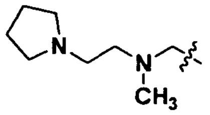 | H |
| S16-10-57 | $N(CH_3)_2$ | 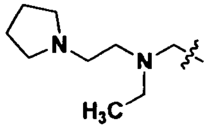 | H |
| S16-10-58 | $N(CH_3)_2$ | 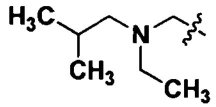 | H |
| Cmpd | X | Y | Z |
|---|---|---|---|
| S16-10-66 | $N(CH_3)_2$ | 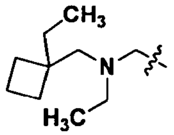 | H |
| S16-10-68 | $N(CH_3)_2$ | 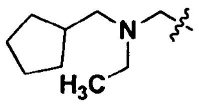 | H |
| S16-10-76 | $N(CH_3)_2$ | 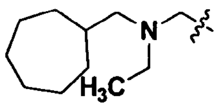 | H |
| S16-10-77 | $N(CH_3)_2$ | 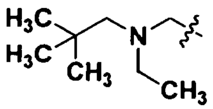 | H |
| S16-10-80 | $N(CH_3)_2$ | 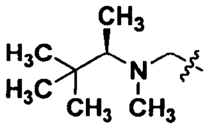 | H |
FIG. 4H

| Cmpd | X | Y | Z |
|---|---|---|---|
| S16-10-81 | $N(CH_3)_2$ | 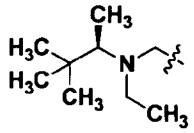 | H |
| S16-10-84 | $N(CH_3)_2$ | 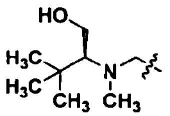 | H |
| S16-10-85 | $N(CH_3)_2$ | 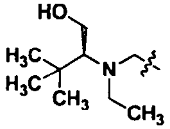 | H |
| S16-10-87 | $N(CH_3)_2$ | 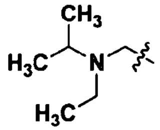 | H |
| S16-10-90 | $N(CH_3)_2$ | 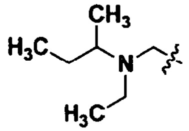 | H |
| Cmpd | X | Y | Z |
|---|---|---|---|
| S16-10-93 | $N(CH_3)_2$ | 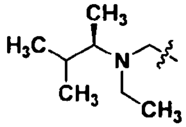 | H |
| S16-10-96 | $N(CH_3)_2$ | 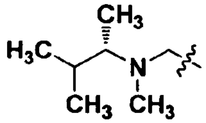 | H |
| S16-10-97 | $N(CH_3)_2$ | 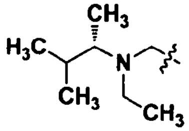 | H |
| S24-9-100 | $OCH_3$ | 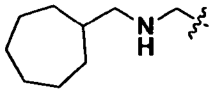 | H |
| S24-9-101 | $OCH_3$ | 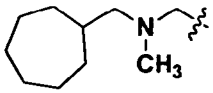 | H |
FIG. 4I

| Cmpd | X | Y | Z |
|---|---|---|---|
| S24-9-102 | $OCH_3$ | 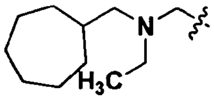 | H |
| S24-9-103 | $OCH_3$ | 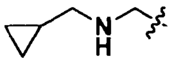 | H |
| S24-9-104 | $OCH_3$ | 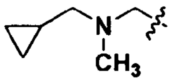 | H |
| S24-9-105 | $OCH_3$ | 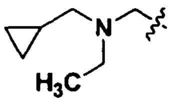 | H |
| S24-9-106 | $OCH_3$ | 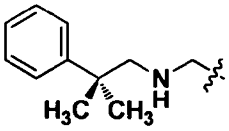 | H |
| Cmpd | X | Y | Z |
|---|---|---|---|
| S24-9-107 | $OCH_3$ | 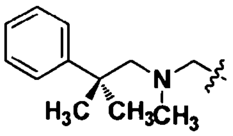 | H |
| S24-9-108 | $OCH_3$ | 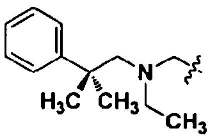 | H |
| S24-9-109 | $OCH_3$ | 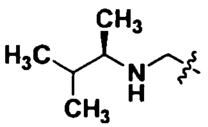 | H |
| S24-9-110 | $OCH_3$ | 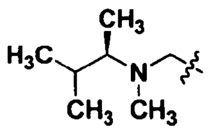 | H |
| S24-9-111 | $OCH_3$ | 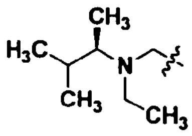 | H |
FIG. 4J

| Cmpd | X | Y | Z |
|---|---|---|---|
| S24-9-112 | $OCH_3$ | 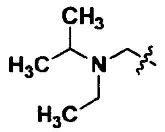 | H |
| S24-9-113 | $OCH_3$ | 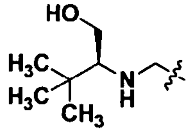 | H |
| S24-9-115 | $OCH_3$ | 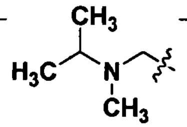 | H |
| S24-9-116 | $OCH_3$ | 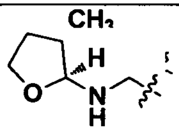 | H |
| S24-9-119 | $OCH_3$ | 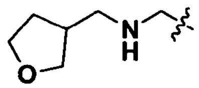 | H |
| Cmpd | X | Y | Z |
|---|---|---|---|
| S24-9-120 | $OCH_3$ | 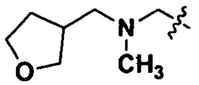 | H |
| S24-9-121 | $OCH_3$ | 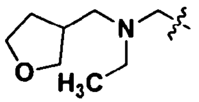 | H |
| S24-9-133 | $OCH_3$ | 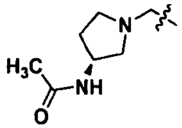 | H |
| S24-9-134 | $OCH_3$ | 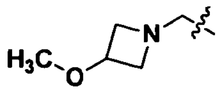 | H |
| S24-9-136 | $OCH_3$ | 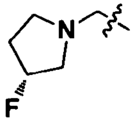 | H |
FIG. 4K

| Cmpd | X | Y | Z |
|---|---|---|---|
| S24-9-137 | $OCH_3$ | 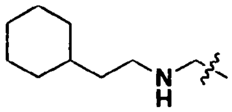 | H |
| S24-9-138 | $OCH_3$ | 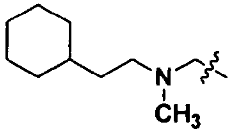 | H |
| S24-9-139 | $OCH_3$ | 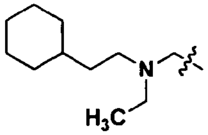 | H |
| S24-9-140 | $OCH_3$ | 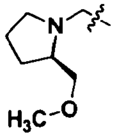 | H |
| S24-9-141 | $OCH_3$ | 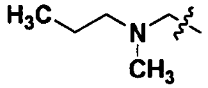 | H |
| Cmpd | X | Y | Z |
|---|---|---|---|
| S24-9-142 | $OCH_3$ | 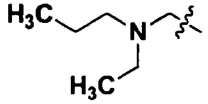 | H |
| S24-9-143 | $OCH_3$ | 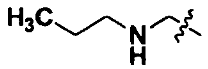 | H |
| S24-9-144 | $OCH_3$ | 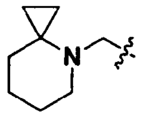 | H |
| S24-9-145 | $OCH_3$ | 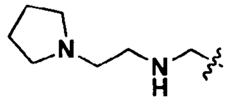 | H |
| S24-9-146 | $OCH_3$ | 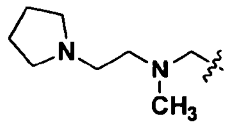 | H |
FIG. 4L

| Cmpd | X | Y | Z |
|---|---|---|---|
| S24-9-147 | $OCH_3$ | 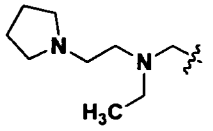 | H |
| S24-9-148 | $OCH_3$ | 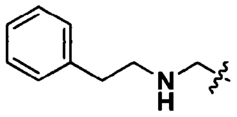 | H |
| S24-9-149 | $OCH_3$ | 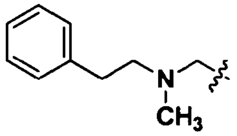 | H |
| S24-9-150 | $OCH_3$ | 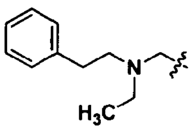 | H |
| S24-9-151 | $OCH_3$ | 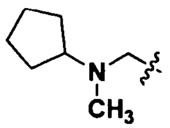 | H |
| Cmpd | X | Y | Z |
|---|---|---|---|
| S24-9-152 | $OCH_3$ | 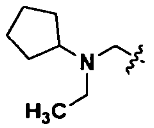 | H |
| S24-9-153 | $OCH_3$ | 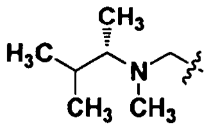 | H |
| S24-9-154 | $OCH_3$ | 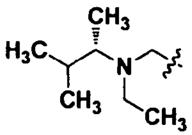 | H |
| S24-9-155 | $OCH_3$ | 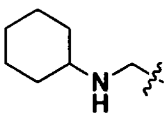 | H |
| S24-9-156 | $OCH_3$ | 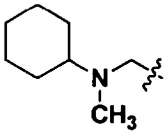 | H |
FIG. 4M

| Cmpd | X | Y | Z |
|---|---|---|---|
| S24-9-157 | $OCH_3$ | 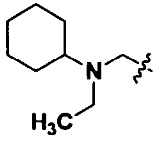 | H |
| S24-9-158 | $OCH_3$ | 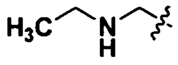 | H |
| S24-9-159 | $OCH_3$ | 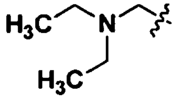 | H |
| S24-9-29 | $OCH_3$ | 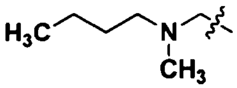 | H |
| S24-9-33 | $OCH_3$ | 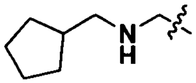 | H |
| Cmpd | X | Y | Z |
|---|---|---|---|
| S24-9-34 | $OCH_3$ | 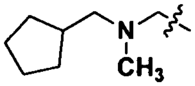 | H |
| S24-9-35 | $OCH_3$ | 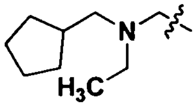 | H |
| S24-9-36 | $OCH_3$ | 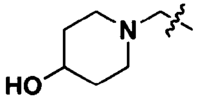 | H |
| S24-9-37 | $OCH_3$ | 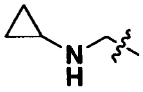 | H |
| S24-9-38 | $OCH_3$ | 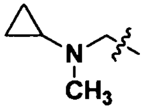 | H |
FIG. 4N

| Cmpd | X | Y | Z |
|---|---|---|---|
| S24-9-39 | $OCH_3$ | 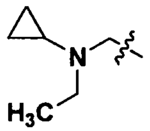 | H |
| S24-9-40 | $OCH_3$ | 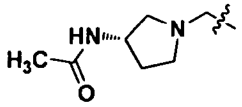 | H |
| S24-9-41 | $OCH_3$ | 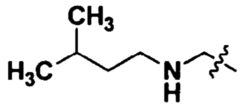 | H |
| S24-9-42 | $OCH_3$ | 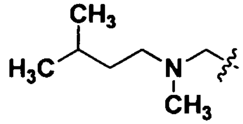 | H |
| S24-9-43 | $OCH_3$ | 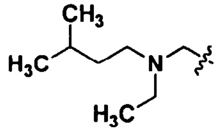 | H |
| Cmpd | X | Y | Z |
|---|---|---|---|
| S24-9-44 | $OCH_3$ | 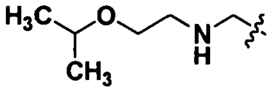 | H |
| S24-9-45 | $OCH_3$ | 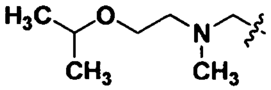 | H |
| S24-9-46 | $OCH_3$ | 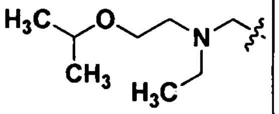 | H |
| S24-9-47 | $OCH_3$ | 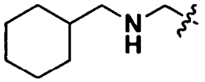 | H |
| S24-9-48 | $OCH_3$ | 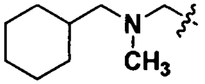 | H |
FIG. 4O

| Cmpd | X | Y | Z |
|---|---|---|---|
| S24-9-49 | $OCH_3$ | 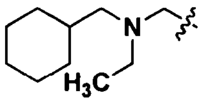 | H |
| S24-9-50 | $OCH_3$ | 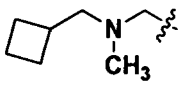 | H |
| S24-9-51 | $OCH_3$ | 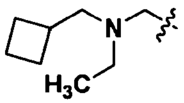 | H |
| S24-9-52 | $OCH_3$ | 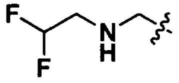 | H |
| S24-9-53 | $OCH_3$ | 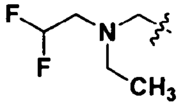 | H |
| Cmpd | X | Y | Z |
|---|---|---|---|
| S24-9-54 | $OCH_3$ | 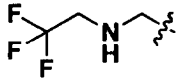 | H |
| S24-9-55 | $OCH_3$ | 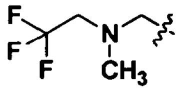 | H |
| S24-9-57 | $OCH_3$ | 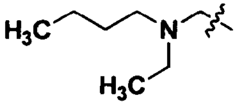 | H |
| S24-9-66 | $OCH_3$ | 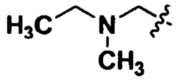 | H |
| S24-9-85 | $OCH_3$ | 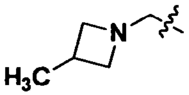 | H |
FIG. 4P

| Cmpd | X | Y | Z |
|---|---|---|---|
| S24-9-86 | $OCH_3$ | 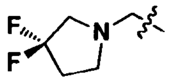 | H |
| S24-9-87 | $OCH_3$ | 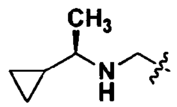 | H |
| S24-9-88 | $OCH_3$ | 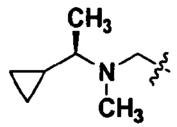 | H |
| S24-9-89 | $OCH_3$ | 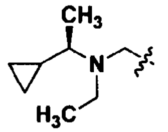 | H |
| S24-9-90 | $OCH_3$ | 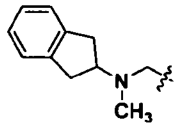 | H |
| S24-9-91 | $OCH_3$ | 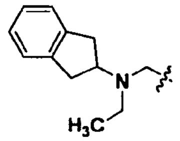 | H |
| S24-9-97 | $OCH_3$ | 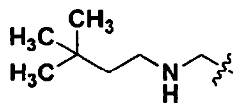 | H |
| S24-9-98 | $OCH_3$ | 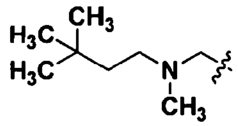 | H |
| S24-9-99 | $OCH_3$ | 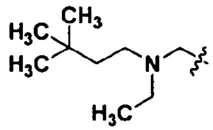 | H |
| S25-11-100 | $CF_3$ | 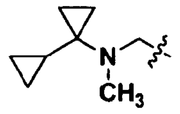 | H |
FIG. 4Q

| Cmpd | X | Y | Z |
|---|---|---|---|
| S25-11-101 | $CF_3$ | 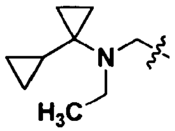 | H |
| S25-11-102 | $CF_3$ | 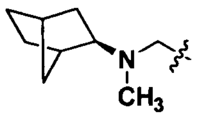 | H |
| S25-11-103 | $CF_3$ | 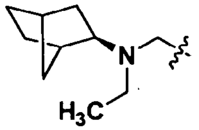 | H |
| S25-11-104 | $CF_3$ | 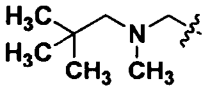 | H |
| S25-11-105 | $CF_3$ | 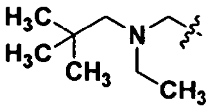 | H |
| Cmpd | X | Y | Z |
|---|---|---|---|
| S25-11-106 | $CF_3$ | 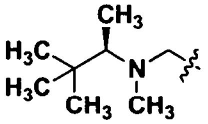 | H |
| S25-11-106 | $CF_3$ | 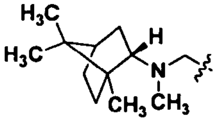 | H |
| S25-11-107 | $CF_3$ | 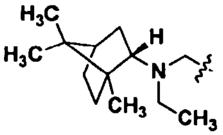 | H |
| S25-11-108 | $CF_3$ | 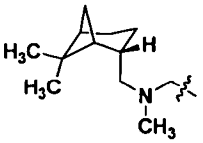 | H |
| S25-11-109 | $CF_3$ | 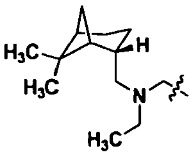 | H |
FIG. 4R

| Cmpd | X | Y | Z |
|---|---|---|---|
| S25-11-110 | $CF_3$ | 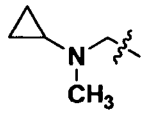 | H |
| S25-11-111 | $CF_3$ | 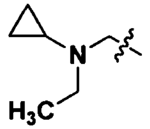 | H |
| S25-11-112 | $CF_3$ | 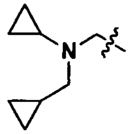 | H |
| S25-11-113 | $CF_3$ | 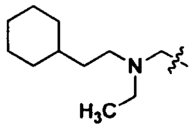 | H |
| S25-11-114 | $CF_3$ | 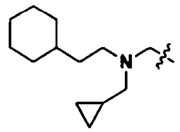 | H |
| Cmpd | X | Y | Z |
|---|---|---|---|
| S25-11-115 | $CF_3$ | 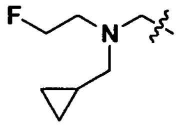 | H |
| S25-11-116 | $CF_3$ | 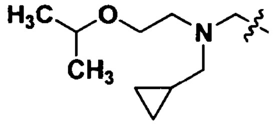 | H |
| S25-11-117 | $CF_3$ | 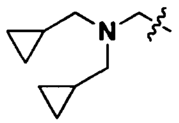 | H |
| S25-11-118 | $CF_3$ | 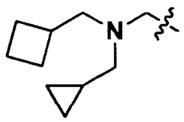 | H |
| S25-11-119 | $CF_3$ | 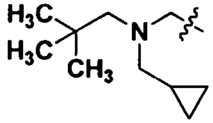 | H |
FIG. 4S

| Cmpd | X | Y | Z |
|---|---|---|---|
| S25-11-120 | $CF_3$ | 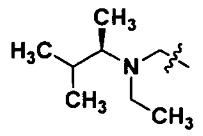 | H |
| S25-11-121 | $CF_3$ | 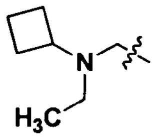 | H |
| S25-11-122 | $CF_3$ | 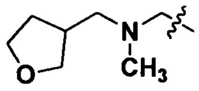 | H |
| S25-11-123 | $CF_3$ | 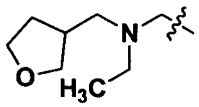 | H |
| S25-11-124 | $CF_3$ | 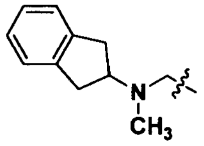 | H |
| Cmpd | X | Y | Z |
|---|---|---|---|
| S25-11-125 | $CF_3$ | 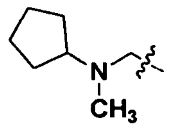 | H |
| S25-11-126 | $CF_3$ | 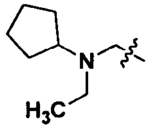 | H |
| S25-11-127 | $CF_3$ | 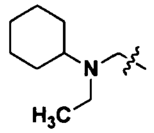 | H |
| S25-11-128 | $CF_3$ | 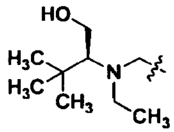 | H |
| S25-11-129 | $CF_3$ | 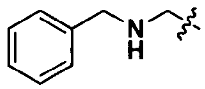 | H |
FIG. 4T

| Cmpd | X | Y | Z |
| --- | --- | --- | --- |
| S25-11-130 | $CF_3$ | 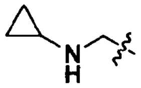 | H |
| S25-11-131 | $CF_3$ | 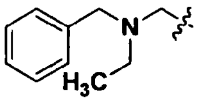 | H |
| S25-11-132 | $CF_3$ | 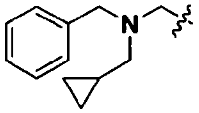 | H |
| S25-11-133 | $CF_3$ | 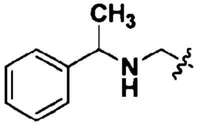 | H |
| S25-11-38 | $CF_3$ | 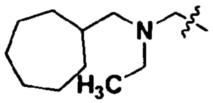 | H |
| Cmpd | X | Y | Z |
| --- | --- | --- | --- |
| S25-11-39 | $CF_3$ | 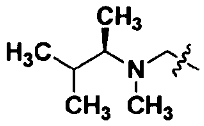 | H |
| S25-11-40 | $CF_3$ | 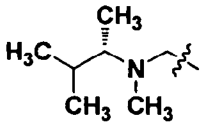 | H |
| S25-11-41 | $CF_3$ | 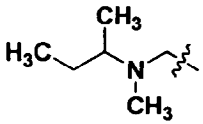 | H |
| S25-11-42 | $CF_3$ | 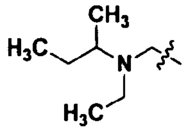 | H |
| S25-11-79 | $CF_3$ | 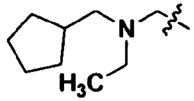 | H |
FIG. 4U

| Cmpd | X | Y | Z |
|---|---|---|---|
| S25-11-80 | $CF_3$ | 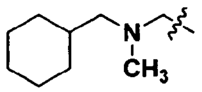 | H |
| S25-11-81 | $CF_3$ | 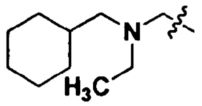 | H |
| S25-11-82 | $CF_3$ | 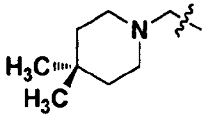 | H |
| S25-11-83 | $CF_3$ | 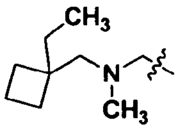 | H |
| S25-11-84 | $CF_3$ | 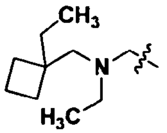 | H |
| Cmpd | X | Y | Z |
|---|---|---|---|
| S25-11-85 | $CF_3$ | 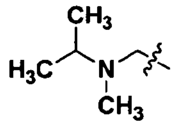 | H |
| S25-11-86 | $CF_3$ | 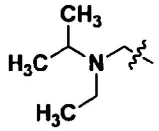 | H |
| S25-11-87 | $CF_3$ | 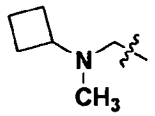 | H |
| S25-11-88 | $CF_3$ | 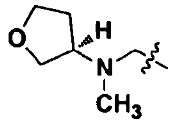 | H |
| S25-11-89 | $CF_3$ | 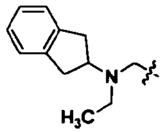 | H |
FIG. 4V

| Cmpd | X | Y | Z |
|---|---|---|---|
| S25-11-90 | $CF_3$ | 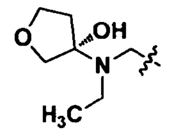 | H |
| S25-11-91 | $CF_3$ | 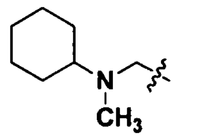 | H |
| S25-11-92 | $CF_3$ | 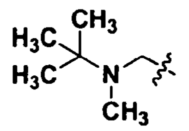 | H |
| S25-11-93 | $CF_3$ | 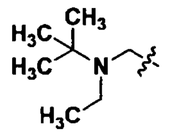 | H |
| S25-11-94 | $CF_3$ | 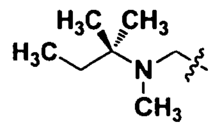 | H |
| Cmpd | X | Y | Z |
|---|---|---|---|
| S25-11-95 | $CF_3$ | 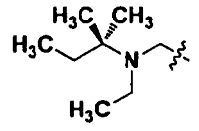 | H |
| S25-11-96 | $CF_3$ | 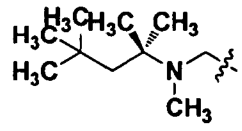 | H |
| S25-11-97 | $CF_3$ | 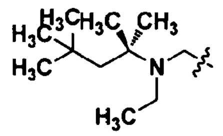 | H |
| S25-11-98 | $CF_3$ | 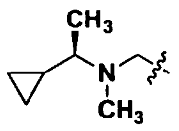 | H |
| S25-11-99 | $CF_3$ | 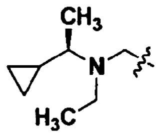 | H |
FIG. 4W

| Cmpd | X | Y | Z |
|---|---|---|---|
| S31-7-1 | 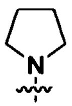 | 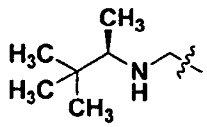 | H |
| S32-6-1-1 | $N(CH_2CH_3)_2$ | 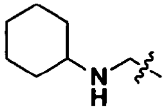 | H |
| S32-6-1-1 | $N(CH_2CH_3)_2$ | 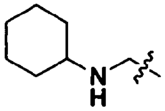 | H |
| S32-6-1-2 | $N(CH_2CH_3)_2$ | 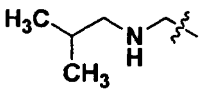 | H |
| S32-6-1-2 | $N(CH_2CH_3)_2$ | 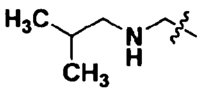 | H |
| Cmpd | X | Y | Z |
|---|---|---|---|
| S32-6-1-3 | $N(CH_2CH_3)_2$ | 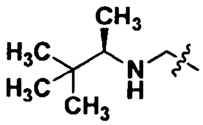 | H |
| S32-6-1-3 | $N(CH_2CH_3)_2$ | 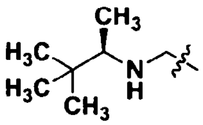 | H |
| S32-6-1-4 | $N(CH_2CH_3)_2$ | 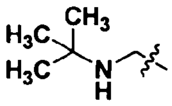 | H |
| S32-6-1-4 | $N(CH_2CH_3)_2$ | 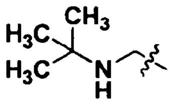 | H |
| S32-6-1-5 | $N(CH_2CH_3)_2$ | 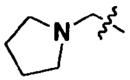 | H |
FIG. 4X

| Cmpd | X | Y | Z |
|---|---|---|---|
| S32-6-1-5 | $N(CH_2CH_3)_2$ | 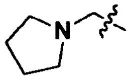 | H |
| S32-6-1-6 | $N(CH_2CH_3)_2$ | 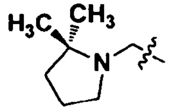 | H |
| S32-6-1-6 | $N(CH_2CH_3)_2$ | 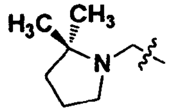 | H |
| S32-6-1-7 | $N(CH_2CH_3)_2$ | 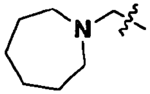 | H |
| S32-6-1-7 | $N(CH_2CH_3)_2$ | 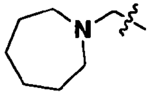 | H |
| Cmpd | X | Y | Z |
|---|---|---|---|
| S32-6-2-1 | $N(CH_3)CH(CH_3)_2$ | 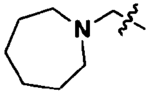 | H |
| S32-6-2-1 | $N(CH_3)CH(CH_3)_2$ | 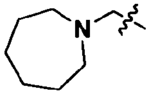 | H |
| S32-6-2-2 | $N(CH_3)CH(CH_3)_2$ | 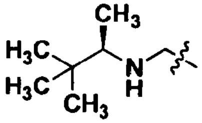 | H |
| S32-6-2-2 | $N(CH_3)CH(CH_3)_2$ | 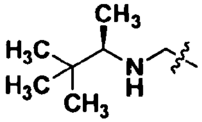 | H |
| S32-6-2-3 | $N(CH_3)CH(CH_3)_2$ | 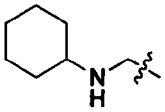 | H |
FIG. 4Y

| Cmpd | X | Y | Z |
|---|---|---|---|
| S32-6-2-3 | $N(CH_3)CH(CH_3)_2$ | 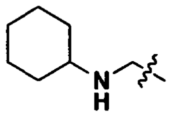 | H |
| 200 | $OCH_3$ | 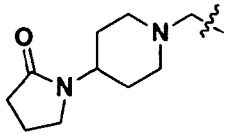 | H |
FIG. 4Z

| Cmpd # | X | Y | Z |
|---|---|---|---|
| S15-13-100 | Cl | 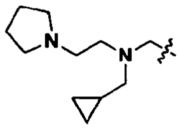 | H |
| S15-13-101 | Cl | 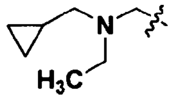 | H |
| S15-13-102 | Cl | 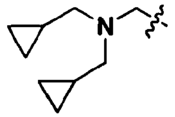 | H |
| S15-13-103 | Cl | 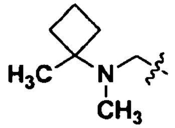 | H |
| S15-13-104 | Cl | 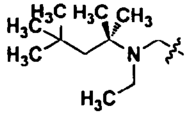 | H |
| S15-13-105 | Cl | 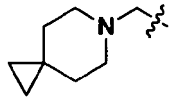 | H |
| Cmpd # | X | Y | Z |
|---|---|---|---|
| S15-13-106 | Cl | 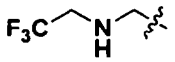 | H |
| S15-13-107 | Cl | 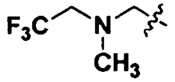 | H |
| S15-13-108 | Cl | 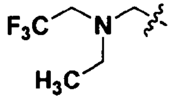 | H |
| S15-13-109 | Cl | 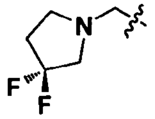 | H |
| S15-13-110 | Cl | 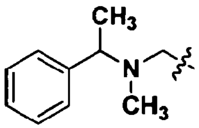 | H |
| S15-13-111 | Cl | 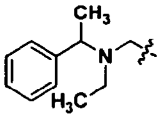 | H |
FIG. 5A

| Cmpd # | X | Y | Z |
|---|---|---|---|
| S15-13-112 | Cl | 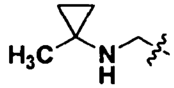 | H |
| S15-13-113 | Cl | 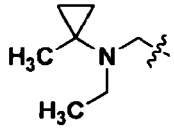 | H |
| S15-13-114 | Cl | 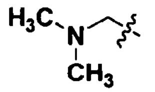 | H |
| S15-13-115 | Cl | 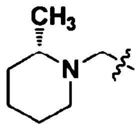 | H |
| S15-13-122 | Cl | 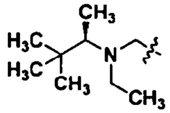 | H |
| S15-13-137 | Cl | 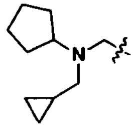 | H |
| Cmpd # | X | Y | Z |
|---|---|---|---|
| S15-13-138 | Cl | 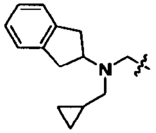 | H |
| S15-13-139 | Cl | 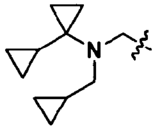 | H |
| S15-13-140 | Cl | 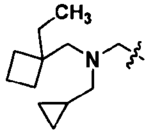 | H |
| S15-13-141 | Cl | 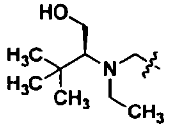 | H |
| S15-13-161 | Cl | 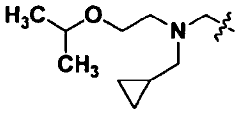 | H |
| S15-13-162 | Cl | 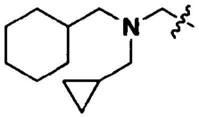 | H |
FIG. 5B

| Cmpd # | X | Y | Z |
|---|---|---|---|
| S15-13-163 | Cl | 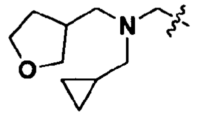 | H |
| S15-13-164 | Cl | 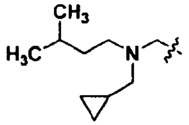 | H |
| S15-13-165 | Cl | 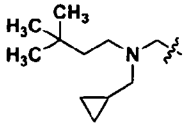 | H |
| S15-13-166 | Cl | 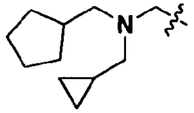 | H |
| S15-13-227 | $OCH_3$ | 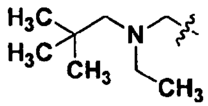 | H |
| S15-13-64 | Cl | 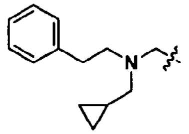 | H |
| Cmpd # | X | Y | Z |
|---|---|---|---|
| S15-13-65 | Cl | 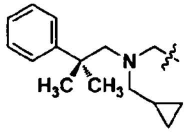 | H |
| S15-13-66 | Cl | 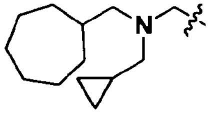 | H |
| S15-13-67 | Cl | 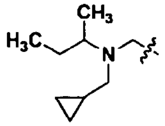 | H |
| S15-13-68 | Cl | 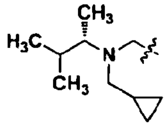 | H |
| S15-13-69 | Cl | 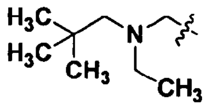 | H |
| S15-13-70 | Cl | 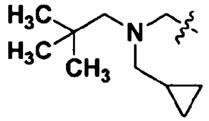 | H |
FIG. 5C

| Cmpd # | X | Y | Z |
|---|---|---|---|
| S15-13-71 | Cl | 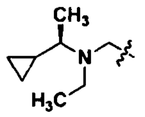 | H |
| S15-13-72 | Cl | 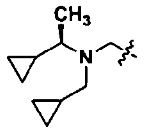 | H |
| S15-13-73 | Cl |  | H |
| S15-13-74 | Cl | 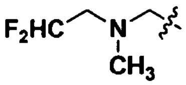 | H |
| S15-13-75 | Cl | 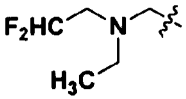 | H |
| S15-13-76 | Cl | 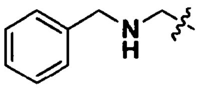 | H |
| Cmpd # | X | Y | Z |
|---|---|---|---|
| S15-13-77 | Cl | 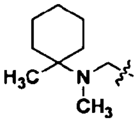 | H |
| S15-13-79 | Cl | 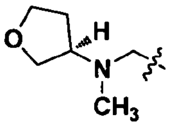 | H |
| S15-13-80 | Cl | 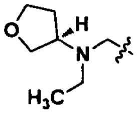 | H |
| S15-13-98 | Cl | 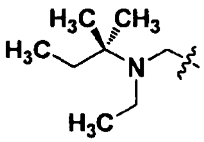 | H |
| S15-13-99 | Cl | 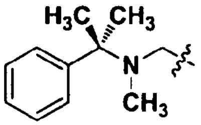 | H |
| S15-14-5 | H | 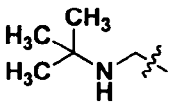 | H |
FIG. 5D

| Cmpd # | X | Y | Z |
|---|---|---|---|
| S16-10-100 | $N(CH_3)_2$ | 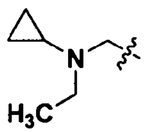 | H |
| S16-10-103 | $N(CH_3)_2$ | 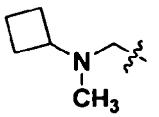 | H |
| S16-10-104 | $N(CH_3)_2$ | 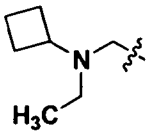 | H |
| S16-10-105 | $N(CH_3)_2$ | 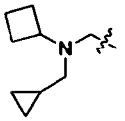 | H |
| S16-10-108 | $N(CH_3)_2$ | 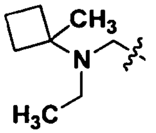 | H |
| S16-10-109 | $N(CH_3)_2$ | 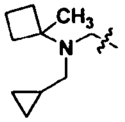 | H |
| Cmpd # | X | Y | Z |
|---|---|---|---|
| S16-10-111 | $N(CH_3)_2$ | 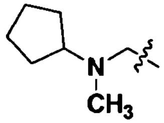 | H |
| S16-10-112 | $N(CH_3)_2$ | 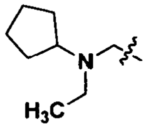 | H |
| S16-10-113 | $N(CH_3)_2$ | 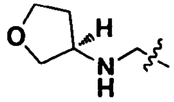 | H |
| S16-10-114 | $N(CH_3)_2$ | 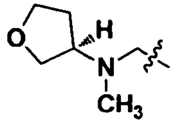 | H |
| S16-10-115 | $N(CH_3)_2$ | 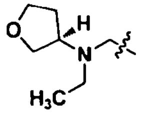 | H |
| S16-10-122 | $N(CH_3)_2$ | 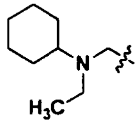 | H |
FIG. 5E

| Cmpd # | X | Y | Z |
|---|---|---|---|
| S16-10-124 | $N(CH_3)_2$ | 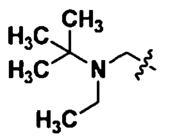 | H |
| S16-10-127 | $N(CH_3)_2$ | 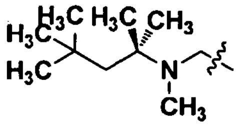 | H |
| S16-10-133 | $N(CH_3)_2$ | 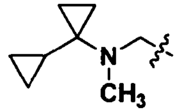 | H |
| S16-10-134 | $N(CH_3)_2$ | 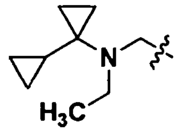 | H |
| S16-10-140 | $N(CH_3)_2$ | 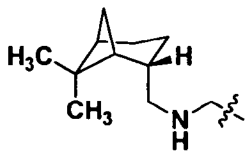 | H |
| S16-10-141 | $N(CH_3)_2$ | 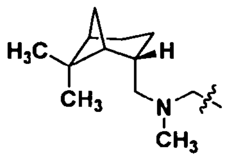 | H |
| Cmpd # | X | Y | Z |
|---|---|---|---|
| S16-10-142 | $N(CH_3)_2$ | 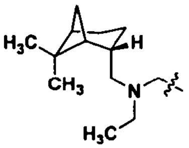 | H |
| S16-10-29 | $N(CH_3)_2$ | 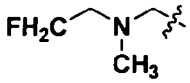 | H |
| S16-10-30 | $N(CH_3)_2$ | 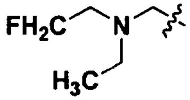 | H |
| S16-10-32 | $N(CH_3)_2$ | 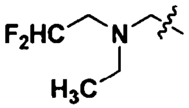 | H |
| S16-10-34 | $N(CH_3)_2$ | 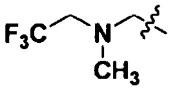 | H |
| S16-10-35 | $N(CH_3)_2$ | 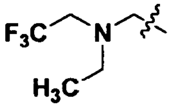 | H |
FIG. 5F

| Cmpd # | X | Y | Z |
|---|---|---|---|
| S16-10-41 | $N(CH_3)_2$ | 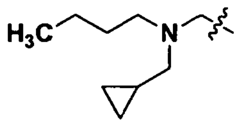 | H |
| S16-10-59 | $N(CH_3)_2$ | 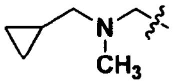 | H |
| S16-10-60 | $N(CH_3)_2$ | 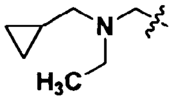 | H |
| S16-10-62 | $N(CH_3)_2$ | 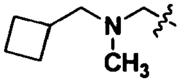 | H |
| S16-10-63 | $N(CH_3)_2$ | 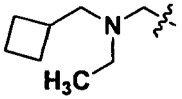 | H |
| S16-10-70 | $N(CH_3)_2$ | 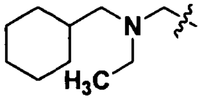 | H |
| Cmpd # | X | Y | Z |
|---|---|---|---|
| S16-10-78 | $N(CH_3)_2$ | 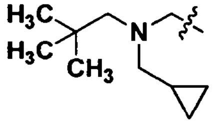 | H |
| S16-10-82 | $N(CH_3)_2$ | 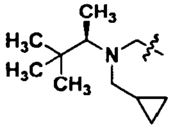 | H |
| S16-10-94 | $N(CH_3)_2$ | 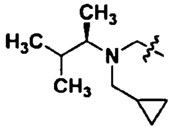 | H |
| S16-10-98 | $N(CH_3)_2$ | 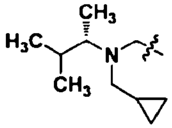 | H |
| S16-10-99 | $N(CH_3)_2$ | 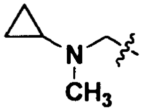 | H |
| S24-9-117 | $OCH_3$ | 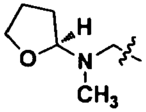 | H |
FIG. 5G

| Cmpd # | X | Y | Z |
|---|---|---|---|
| S24-9-118 | $OCH_3$ | 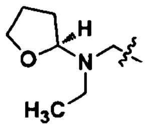 | H |
| S24-9-122 | $OCH_3$ | 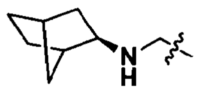 | H |
| S24-9-123 | $OCH_3$ | 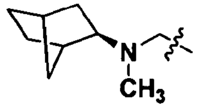 | H |
| S24-9-124 | $OCH_3$ | 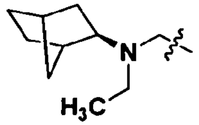 | H |
| S24-9-160 | $OCH_3$ | 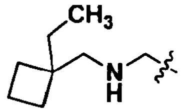 | H |
| S24-9-161 | $OCH_3$ | 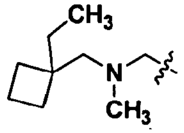 | H |
| Cmpd # | X | Y | Z |
|---|---|---|---|
| S24-9-162 | $OCH_3$ | 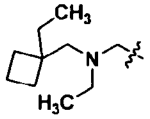 | H |
| S24-9-163 | $OCH_3$ | 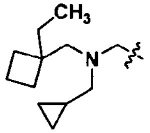 | H |
| S24-9-164 | $OCH_3$ | 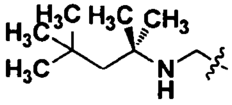 | H |
| S24-9-165 | $OCH_3$ | 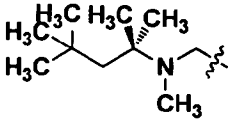 | H |
| S24-9-166 | $OCH_3$ | 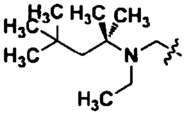 | H |
| S24-9-167 | $OCH_3$ | 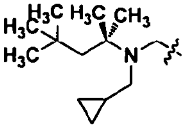 | H |
FIG. 5H

| Cmpd # | X | Y | Z |
|---|---|---|---|
| S24-9-168 | $OCH_3$ | 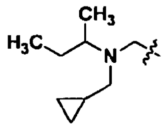 | H |
| S24-9-169 | $OCH_3$ | 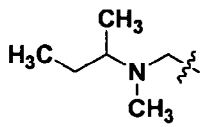 | H |
| S24-9-170 | $OCH_3$ | 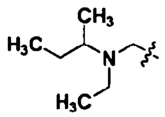 | H |
| S24-9-171 | $OCH_3$ | 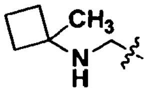 | H |
| S24-9-172 | $OCH_3$ | 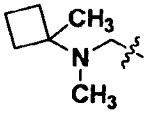 | H |
| S24-9-173 | $OCH_3$ | 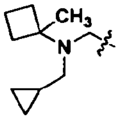 | H |
| Cmpd # | X | Y | Z |
|---|---|---|---|
| S24-9-174 | $OCH_3$ | 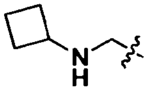 | H |
| S24-9-175 | $OCH_3$ | 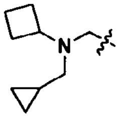 | H |
| S24-9-179 | $OCH_3$ | 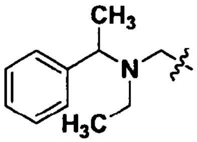 | H |
| S24-9-182 | $OCH_3$ | 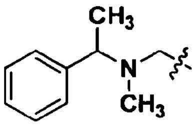 | H |
| S24-9-56 | $OCH_3$ | 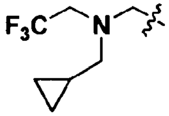 | H |
| S24-9-58 | $OCH_3$ | 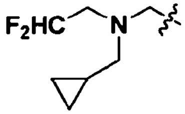 | H |
FIG. 5I

| Cmpd # | X | Y | Z |
|---|---|---|---|
| S24-9-59 | $OCH_3$ |  | H |
| S24-9-60 | $OCH_3$ | 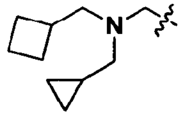 | H |
| S24-9-61 | $OCH_3$ | 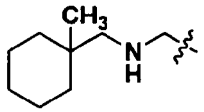 | H |
| S24-9-62 | $OCH_3$ | 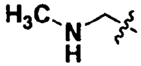 | H |
| S24-9-63 | $OCH_3$ | 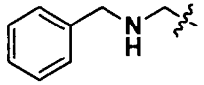 | H |
| S24-9-64 | $OCH_3$ | 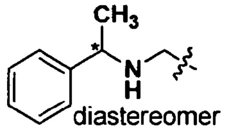 diastereomer A | H |
| Cmpd # | X | Y | Z |
|---|---|---|---|
| S24-9-65 | $OCH_3$ | 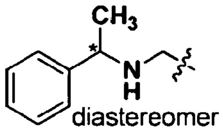 diastereomer B | H |
| S24-9-67 | $OCH_3$ | 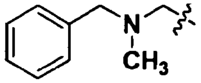 | H |
| S24-9-68 | $OCH_3$ | 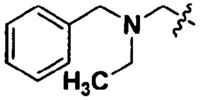 | H |
| S24-9-69 | $OCH_3$ | 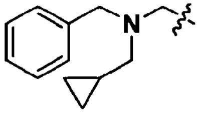 | H |
| S24-9-70 | $OCH_3$ | 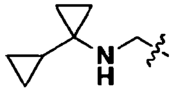 | H |
| S24-9-71 | $OCH_3$ | 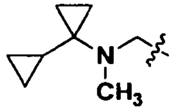 | H |
FIG. 5J

| Cmpd # | X | Y | Z |
|---|---|---|---|
| S24-9-72 | $OCH_3$ | 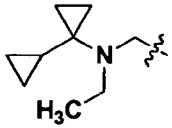 | H |
| S24-9-73 | $OCH_3$ | 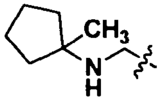 | H |
| S24-9-74 | $OCH_3$ | 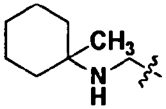 | H |
| S24-9-75 | $OCH_3$ | 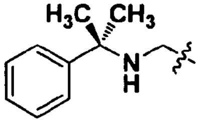 | H |
| S24-9-76 | $OCH_3$ | 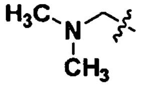 | H |
| S24-9-77 | $OCH_3$ | 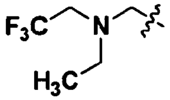 | H |
| Cmpd # | X | Y | Z |
|---|---|---|---|
| S24-9-78 | $OCH_3$ | 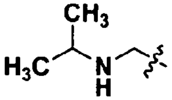 | H |
| S24-9-79 | $OCH_3$ | 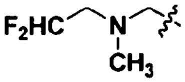 | H |
| S24-9-94 | $OCH_3$ | 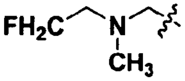 | H |
| S24-9-95 | $OCH_3$ | 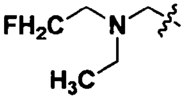 | H |
| S24-9-96 | $OCH_3$ | 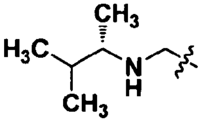 | H |
| S25-11-134 | $CF_3$ | 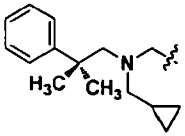 | H |
FIG. 5K

| Cmpd # | X | Y | Z |
|---|---|---|---|
| S25-11-135 | $CF_3$ | 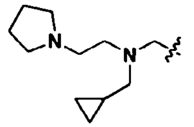 | H |
| S25-11-136 | $CF_3$ | 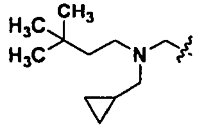 | H |
| S25-11-137 | $CF_3$ | 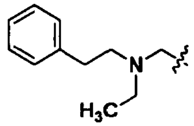 | H |
| S25-11-138 | $CF_3$ | 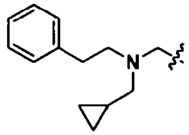 | H |
| S25-11-139 | $CF_3$ | 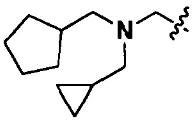 | H |
| S25-11-140 | $CF_3$ | 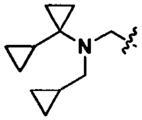 | H |
| Cmpd # | X | Y | Z |
|---|---|---|---|
| S25-11-141 | $CF_3$ | 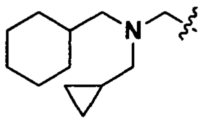 | H |
| S25-11-142 | $CF_3$ | 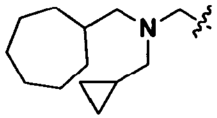 | H |
| S25-11-143 | $CF_3$ | 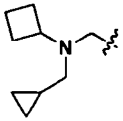 | H |
| S25-11-144 | $CF_3$ | 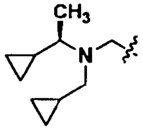 | H |
| S25-11-145 | $CF_3$ | 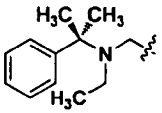 | H |
| S25-11-146 | $CF_3$ | 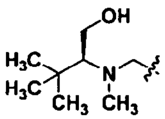 | H |
FIG. 5L

| Cmpd # | X | Y | Z |
|---|---|---|---|
| S25-11-147 | $CF_3$ | 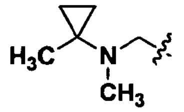 | H |
| S25-11-148 | $CF_3$ | 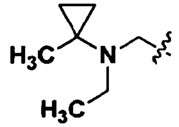 | H |
| S25-11-149 | $CF_3$ | 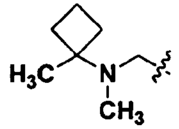 | H |
| S25-11-150 | $CF_3$ | 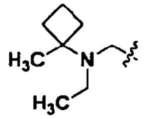 | H |
| S25-11-151 | $CF_3$ | 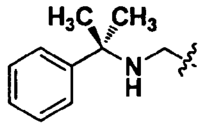 | H |
| S25-11-152 | $CF_3$ | 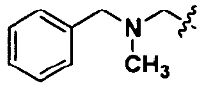 | H |
| Cmpd # | X | Y | Z |
|---|---|---|---|
| S25-11-153 | $CF_3$ | 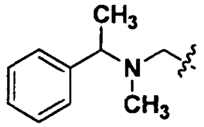 | H |
| S25-11-154 | $CF_3$ | 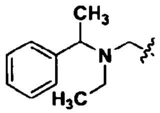 | H |
| S25-11-155 | $CF_3$ |  | H |
| S25-11-156 | $CF_3$ | 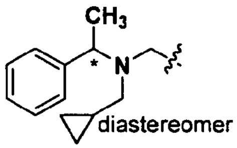 diastereomer A | H |
| S25-11-157 | $CF_3$ | 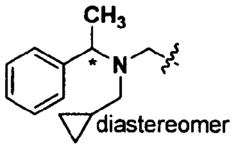 diastereomer B | H |
| S25-11-158 | $CF_3$ | 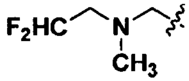 | H |
FIG. 5M

| Cmpd # | X | Y | Z |
|---|---|---|---|
| S25-11-159 | $CF_3$ | 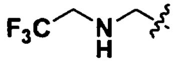 | H |
| S25-11-160 | $CF_3$ | 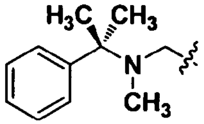 | H |
| S25-11-161 | $CF_3$ | 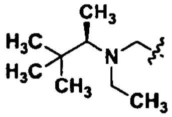 | H |
| S25-11-162 | $CF_3$ | 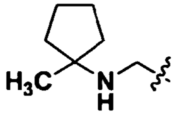 | H |
| S25-11-163 | $CF_3$ | 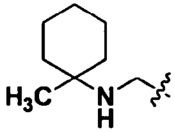 | H |
| S25-11-167 | $CF_3$ | 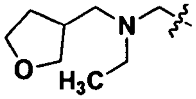 | H |
| Cmpd # | X | Y | Z |
|---|---|---|---|
| S25-11-190 | $CF_3$ | 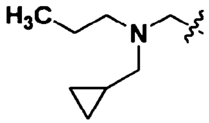 | H |
| S25-11-191 | $CF_3$ | 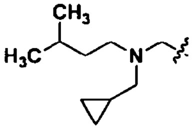 | H |
| S25-11-192 | $CF_3$ | 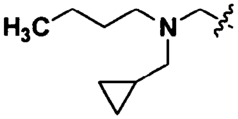 | H |
| S25-11-193 | $CF_3$ | 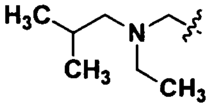 | H |
| S25-11-201 | $CF_3$ | 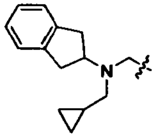 | H |
| S25-11-202 | $CF_3$ | 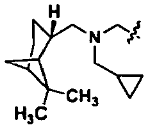 | H |
FIG. 5N

| Cmpd # | X | Y | Z |
|---|---|---|---|
| S25-11-203 | $CF_3$ | 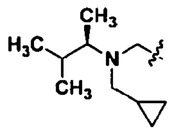 | H |
| S25-11-204 | $CF_3$ | 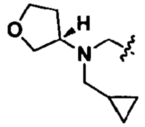 | H |
| S25-11-205 | $CF_3$ | 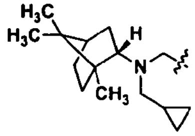 | H |
| S25-11-209 | $CF_3$ | 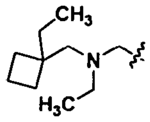 | H |
| S26-7-1 | $OCH(CH_3)_2$ | 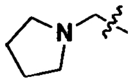 | H |
| S26-7-2 | $OCH(CH_3)_2$ | 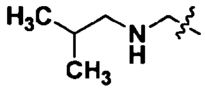 | H |
| Cmpd # | X | Y | Z |
|---|---|---|---|
| S26-7-3 | $OCH(CH_3)_2$ | 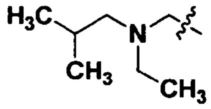 | H |
| S26-7-4 | $OCH(CH_3)_2$ | 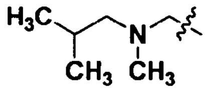 | H |
FIG. 5O

| Cmpd | X | Y | Z |
|---|---|---|---|
| S1-14-4 | F | 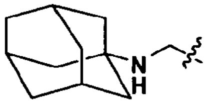 | H |
| S1-14-65 | F | 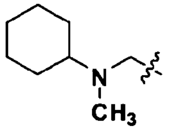 | H |
| S1-14-9 | F | 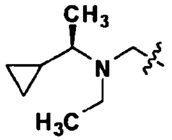 | H |
| S2-4-1 | F | 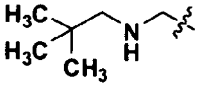 | H |
| S2-4-14 | F | 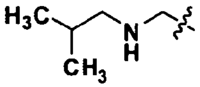 | H |
| Cmpd | X | Y | Z |
|---|---|---|---|
| S2-4-19 | F | 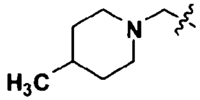 | H |
| S2-4-22 | F | 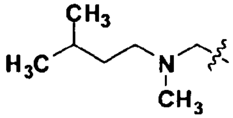 | H |
| S2-4-23 | F | 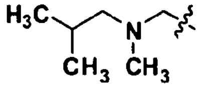 | H |
| S2-4-27 | F | 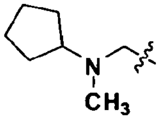 | H |
| S2-4-28 | F | 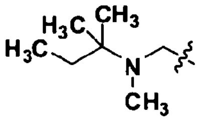 | H |
FIG. 6A

| Cmpd | X | Y | Z |
|---|---|---|---|
| S2-4-29 | F | 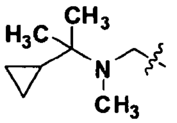 | H |
| S2-4-32 | F | 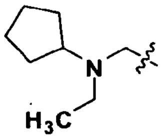 | H |
| S2-4-33 | F | 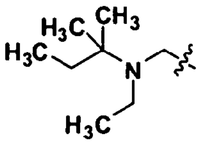 | H |
| S2-4-50 | F | 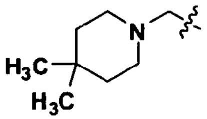 | H |
| S2-4-51 | F | 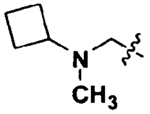 | H |
| Cmpd | X | Y | Z |
|---|---|---|---|
| S2-4-52 | F | 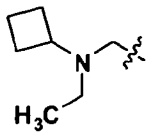 | H |
| S2-4-7 | F | 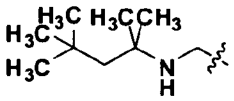 | H |
| S2-4-8 | F | 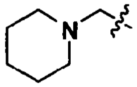 | H |
| S-15-13-1 | Cl | 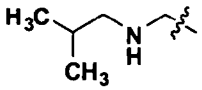 | H |
| S15-13-15 | Cl | 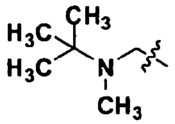 | H |
FIG. 6B

| Cmpd | X | Y | Z |
|---|---|---|---|
| S15-13-2 | Cl | 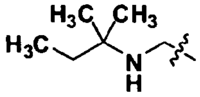 | H |
| S15-13-3 | Cl | 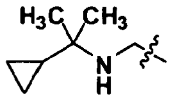 | H |
| S15-13-4 | Cl | 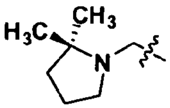 | H |
| S15-13-8 | Cl | 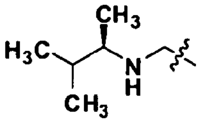 | H |
| S16-10-13 | $N(CH_3)_2$ | 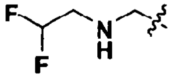 | H |
| Cmpd | X | Y | Z |
|---|---|---|---|
| S19-7-2 | $N(CH_3)_2$ | F | H |
| S1-14-1 | F | 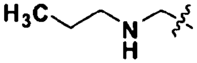 | H |
| S1-14-10 | F | 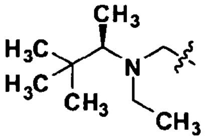 | H |
| S1-14-100 | F | 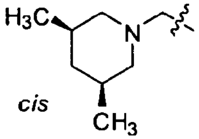 | H |
| S1-14-101 | F | 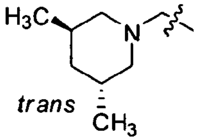 | H |
FIG. 6C

| Cmpd | X | Y | Z |
|---|---|---|---|
| S1-14-102 | F | 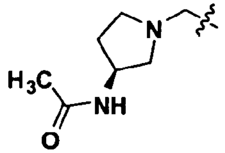 | H |
| S1-14-103 | F | 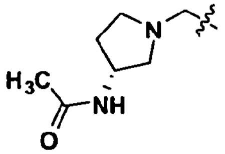 | H |
| S1-14-104 | F | 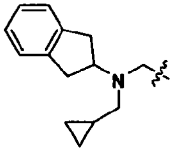 | H |
| S1-14-105 | F | 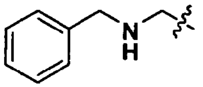 | H |
| S1-14-106 | F | 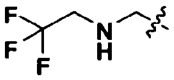 | H |
| Cmpd | X | Y | Z |
|---|---|---|---|
| S1-14-107 | F | 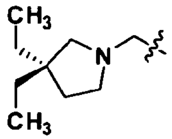 | H |
| S1-14-108 | F | 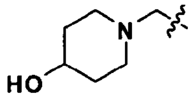 | H |
| S1-14-109 | F | 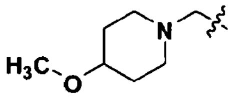 | H |
| S1-14-11 | F | 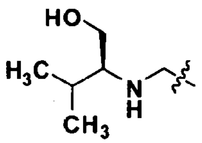 | H |
| S1-14-110 | F | 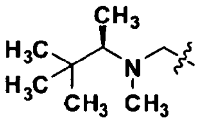 | H |
FIG. 6D

| Cmpd | X | Y | Z |
|---|---|---|---|
| S1-14-111 | F | 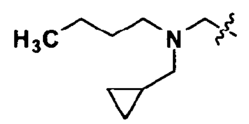 | H |
| S1-14-112 | F | 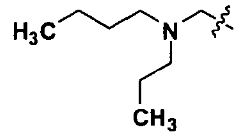 | H |
| S1-14-113 | F | 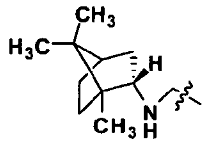 | H |
| S1-14-114 | F | 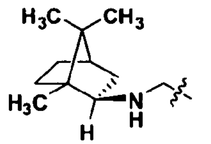 | H |
| S1-14-12 | F | 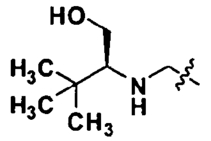 | H |
| Cmpd | X | Y | Z |
|---|---|---|---|
| S1-14-13 | F | 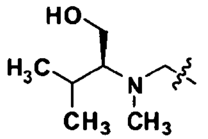 | H |
| S1-14-14 | F | 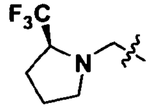 | H |
| S1-14-15 | F | 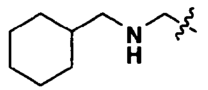 | H |
| S1-14-16 | F | 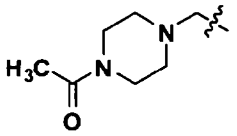 | H |
| S1-14-17 | F | 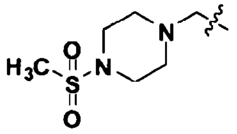 | H |
FIG. 6E

| Cmpd | X | Y | Z |
|---|---|---|---|
| S1-14-18 | F | 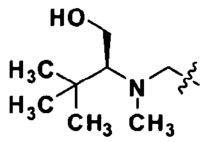 | H |
| S1-14-19 | F | 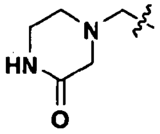 | H |
| S1-14-2 | F | 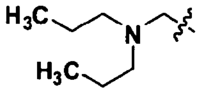 | H |
| S1-14-22 | F | 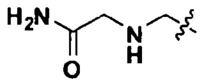 | H |
| S1-14-24 | F | 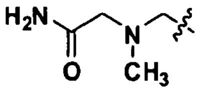 | H |
| Cmpd | X | Y | Z |
|---|---|---|---|
| S1-14-25 | F | 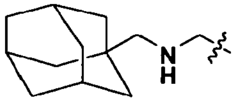 | H |
| S1-14-26 | F | 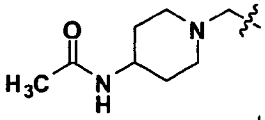 | H |
| S1-14-27 | F | 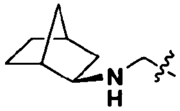 | H |
| S1-14-28 | F | 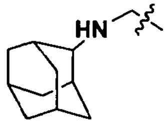 | H |
| S1-14-29 | F | 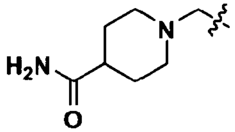 | H |
FIG. 6F

| Cmpd | X | Y | Z |
|---|---|---|---|
| S1-14-3 | F | 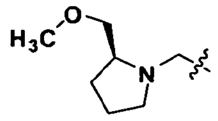 | H |
| S1-14-30 | F | 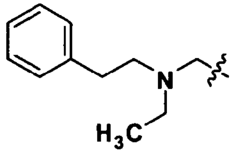 | H |
| S1-14-31 | F | 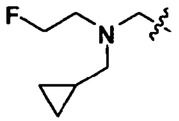 | H |
| S1-14-32 | F | 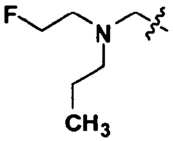 | H |
| S1-14-33 | F | 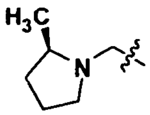 | H |
| Cmpd | X | Y | Z |
|---|---|---|---|
| S1-14-34 | F | 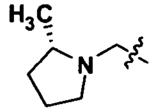 | H |
| S1-14-35 | F | 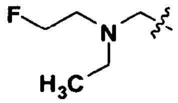 | H |
| S1-14-36 | F | 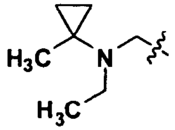 | H |
| S1-14-37 | F | 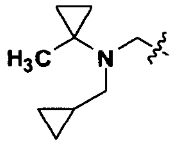 | H |
| S1-14-38 | F | 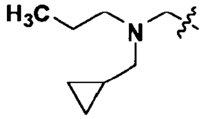 | H |
FIG. 6G

| Cmpd | X | Y | Z |
| --- | --- | --- | --- |
| S1-14-39 | F | 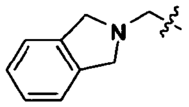 | H |
| S1-14-40 | F | 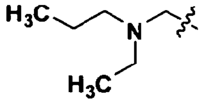 | H |
| S1-14-41 | F | 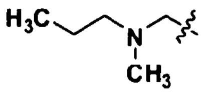 | H |
| S1-14-42 | F | 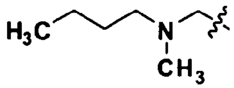 | H |
| S1-14-43 | F | 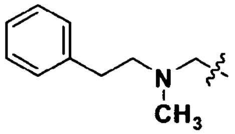 | H |
| Cmpd | X | Y | Z |
| --- | --- | --- | --- |
| S1-14-44 | F | 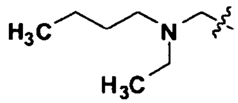 | H |
| S1-14-45 | F | 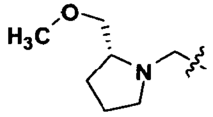 | H |
| S1-14-46 | F | 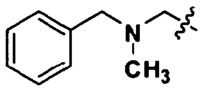 | H |
| S1-14-47 | F | 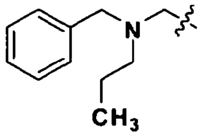 | H |
| S1-14-48 | F | 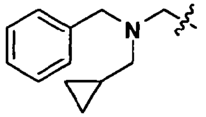 | H |
FIG. 6H

| Cmpd | X | Y | Z |
|---|---|---|---|
| S1-14-49 | F | 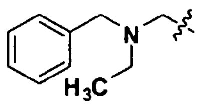 | H |
| S1-14-5 | F | 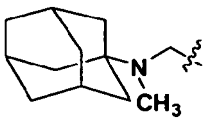 | H |
| S1-14-50 | F | 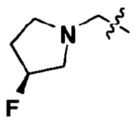 | H |
| S1-14-51 | F | 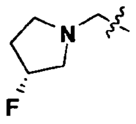 | H |
| S1-14-52 | F | 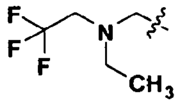 | H |
| Cmpd | X | Y | Z |
|---|---|---|---|
| S1-14-53 | F | 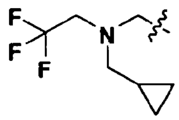 | H |
| S1-14-54 | F | 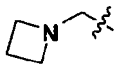 | H |
| S1-14-55 | F | 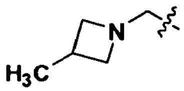 | H |
| S1-14-56 | F | 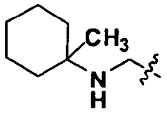 | H |
| S1-14-57 | F | 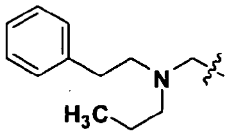 | H |
FIG. 6I

| Cmpd | X | Y | Z |
|---|---|---|---|
| S1-14-58 | F | 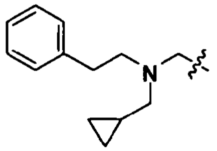 | H |
| S1-14-59 | F | 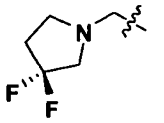 | H |
| S1-14-6 | F | 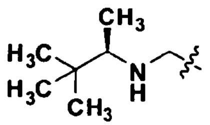 | H |
| S1-14-60 | F | 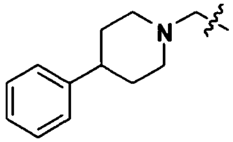 | H |
| S1-14-61 | F | 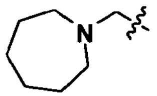 | H |
| Cmpd | X | Y | Z |
|---|---|---|---|
| S1-14-66 | F | 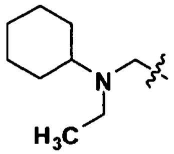 | H |
| S1-14-67 | F | 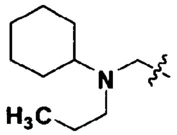 | H |
| S1-14-68 | F | 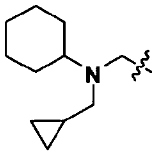 | H |
| S1-14-69 | F | 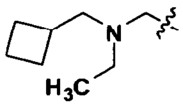 | H |
| S1-14-7 | F | 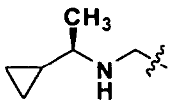 | H |
FIG. 6J

| Cmpd | X | Y | Z |
|---|---|---|---|
| S1-14-70 | F | 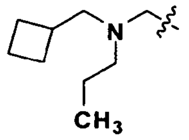 | H |
| S1-14-71 | F | 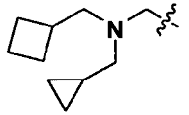 | H |
| S1-14-72 | F | 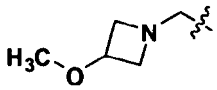 | H |
| S1-14-73 | F | 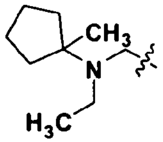 | H |
| S1-14-74 | F |  | H |
| Cmpd | X | Y | Z |
|---|---|---|---|
| S1-14-75 | F | 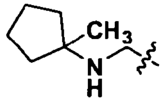 | H |
| S1-14-76 | F | 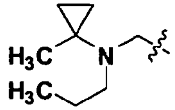 | H |
| S1-14-77 | F |  | H |
| S1-14-78 | F | 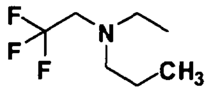 | H |
| S1-14-79 | F | 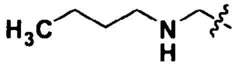 | H |
FIG. 6K

| Cmpd | X | Y | Z |
|---|---|---|---|
| S1-14-8 | F | 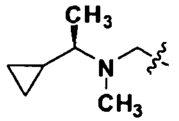 | H |
| S1-14-80 | F | 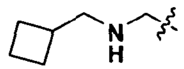 | H |
| S1-14-81 | F | 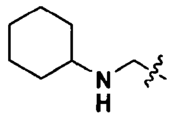 | H |
| S1-14-82 | F | 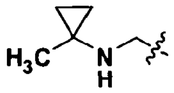 | H |
| S1-14-83 | F | 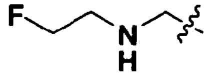 | H |
| Cmpd | X | Y | Z |
|---|---|---|---|
| S1-14-84 | F | 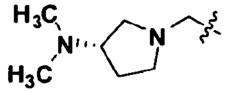 | H |
| S1-14-85 | F | 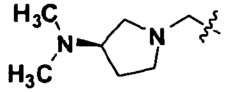 | H |
| S1-14-86 | F | 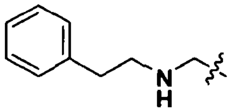 | H |
| S1-14-87 | F | 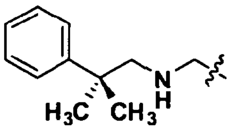 | H |
| S1-14-88 | F | 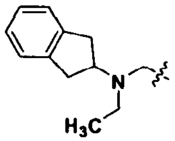 | H |
FIG. 6L

| Cmpd | X | Y | Z |
|---|---|---|---|
| S1-14-89 | F | 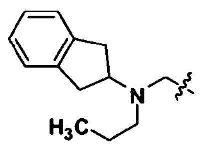 | H |
| S1-14-90 | F | 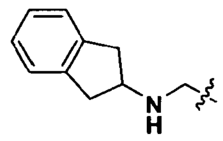 | H |
| S1-14-91 | F | 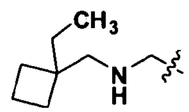 | H |
| S1-14-92 | F | 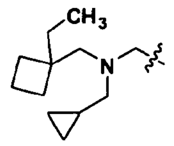 | H |
| S1-14-93 | F | 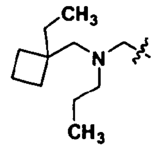 | H |
| Cmpd | X | Y | Z |
|---|---|---|---|
| S1-14-94 | F | 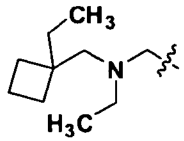 | H |
| S1-14-95 | F | 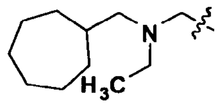 | H |
| S1-14-96 | F | 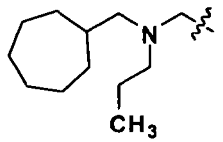 | H |
| S1-14-97 | F | 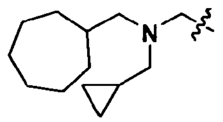 | H |
| S1-14-98 | F | 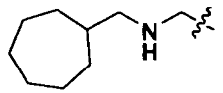 | H |
FIG. 6M

| Cmpd | X | Y | Z |
|---|---|---|---|
| S1-14-99 | F | 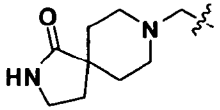 | H |
| S2-4-10 | F | 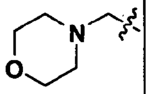 | Br |
| S2-4-11 | F | 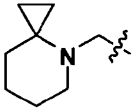 | H |
| S2-4-12 | F | 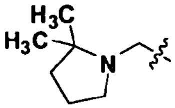 | H |
| S2-4-13 | F | 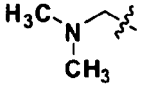 | H |
| Cmpd | X | Y | Z |
|---|---|---|---|
| S2-4-15 | F | 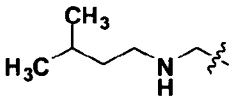 | H |
| S2-4-16 | F | 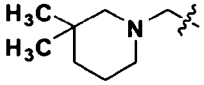 | H |
| S2-4-17 | F | 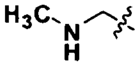 | H |
| S2-4-18 | F | 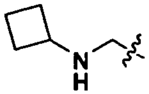 | H |
| S2-4-2 | F | 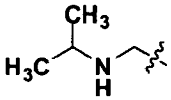 | H |
FIG. 6N

| Cmpd | X | Y | Z |
|---|---|---|---|
| S2-4-21 | F | 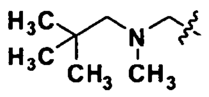 | H |
| S2-4-24 | F | 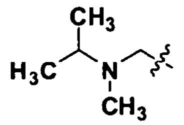 | H |
| S2-4-25 | F | 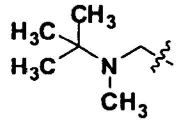 | H |
| S2-4-26 | F | 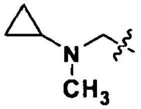 | H |
| S2-4-3 | F | 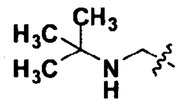 | H |
| Cmpd | X | Y | Z |
|---|---|---|---|
| S2-4-30 | F | 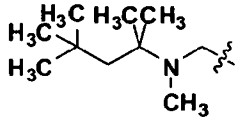 | H |
| S2-4-31 | F | 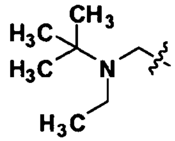 | H |
| S2-4-34 | F | 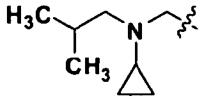 | H |
| S2-4-35 | F | 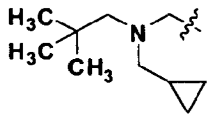 | H |
| S2-4-36 | F | 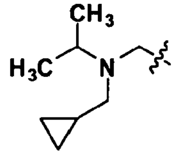 | H |
FIG. 6O

| Cmpd | X | Y | Z |
|---|---|---|---|
| S2-4-37 | F | 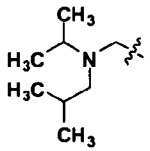 | H |
| S2-4-38 | F | 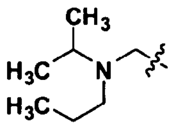 | H |
| S2-4-39 | F | 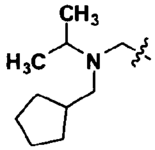 | H |
| S2-4-4 | F | 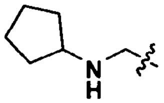 | H |
| S2-4-40 | F | 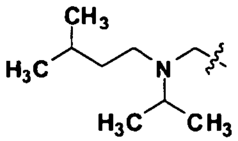 | H |
| Cmpd | X | Y | Z |
|---|---|---|---|
| S2-4-41 | F | 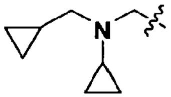 | H |
| S2-4-42 | F | 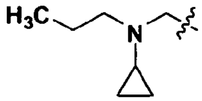 | H |
| S2-4-43 | F | 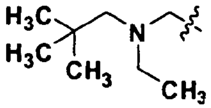 | H |
| S2-4-44 | F | 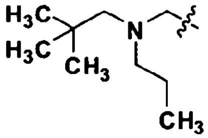 | H |
| S2-4-45 | F | 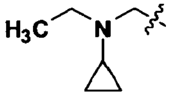 | H |
FIG. 6P

| Cmpd | X | Y | Z |
|---|---|---|---|
| S2-4-46 | F | 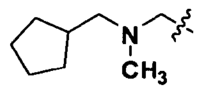 | H |
| S2-4-47 | F | 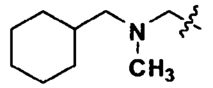 | H |
| S2-4-48 | F | 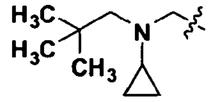 | H |
| S2-4-49 | F | 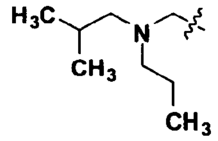 | H |
| S2-4-5 | F | 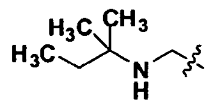 | H |
| Cmpd | X | Y | Z |
|---|---|---|---|
| S2-4-50 | F | 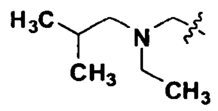 | H |
| S2-4-53 | F | 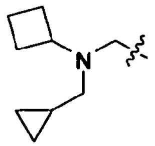 | H |
| S2-4-54 | F | 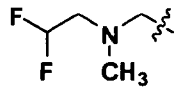 | H |
| S2-4-55 | F | 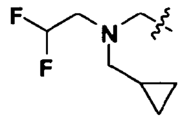 | H |
| S2-4-56 | F | 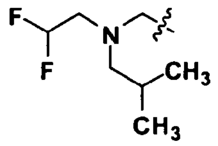 | H |
FIG. 6Q

| Cmpd | X | Y | Z |
|---|---|---|---|
| S2-4-57 | F | 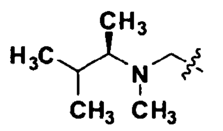 | H |
| S2-4-58 | F | 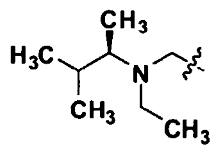 | H |
| S2-4-59 | F | 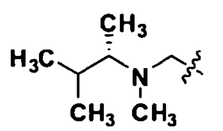 | H |
| S2-4-6 | F | 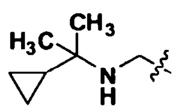 | H |
| S2-4-60 | F | 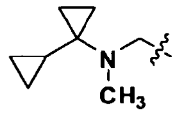 | H |
| Cmpd | X | Y | Z |
|---|---|---|---|
| S2-4-61 | F | 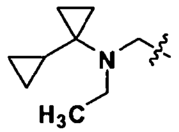 | H |
| S2-4-62 | F | 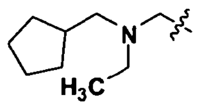 | H |
| S2-4-63 | F | 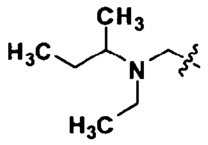 | H |
| S2-4-64 | F | 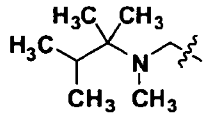 | H |
| S2-4-65 | F | 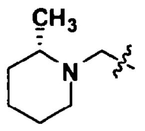 | H |
FIG. 6R

| Cmpd | X | Y | Z |
|---|---|---|---|
| S2-4-66 | F | 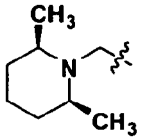 | H |
| S2-4-67 | F | 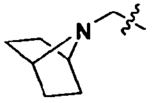 | H |
| S2-4-68 | F | 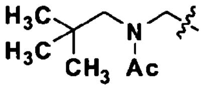 | H |
| S2-4-9 | F | 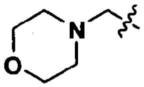 | H |
| S3-5-1 | F | CH2OH | H |
| Cmpd | X | Y | Z |
|---|---|---|---|
| S3-5-2 | F | 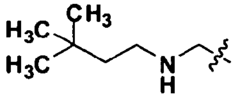 | H |
| S3-53 | F | 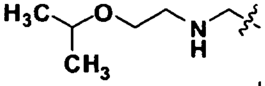 | H |
| S3-5-4 | F | 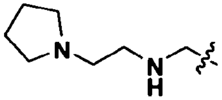 | H |
| S3-5-5 | F | 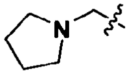 | H |
| S3-5-6 | F | 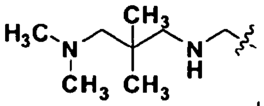 | H |
FIG. 6S

| Cmpd | X | Y | Z |
|---|---|---|---|
| S4-5-1 | F | 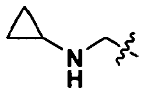 | H |
| S4-5-2 | F | 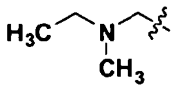 | H |
| S4-5-3 | F | 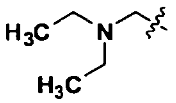 | H |
| S4-5-4 | F | 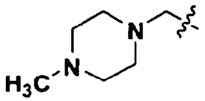 | H |
| S4-5-5 | F | 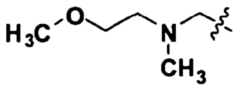 | H |
| Cmpd | X | Y | Z |
|---|---|---|---|
| S4-5-6 | F | 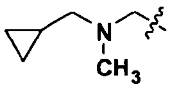 | H |
| S5-5-1 | F | 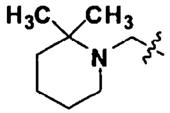 | H |
| S6-4-1 | F | 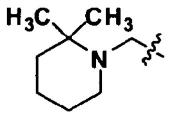 | H |
| S7-4-1 | F | 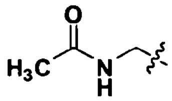 | H |
| S7-4-10 | F | 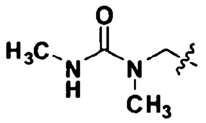 | H |
FIG. 6T

| Cmpd | X | Y | Z |
|---|---|---|---|
| S7-4-11 | F | 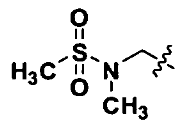 | H |
| S7-4-12 | F | 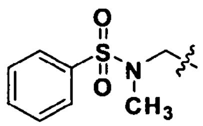 | H |
| S7-4-2 | F | 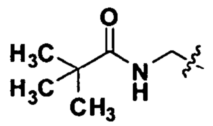 | H |
| S7-4-4 | F | 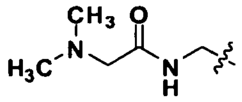 | H |
| S7-4-5 | F | 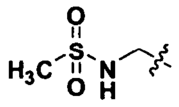 | H |
| Cmpd | X | Y | Z |
|---|---|---|---|
| S7-4-6 | F | 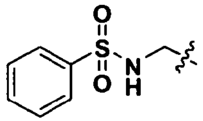 | H |
| S7-4-7 | F | 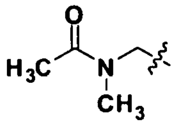 | H |
| S7-4-8 | F | 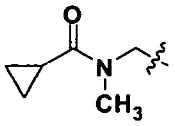 | H |
| S7-4-9 | F | 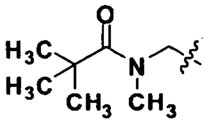 | H |
| S8-4-1 | F | 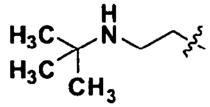 | H |
FIG. 6U

| Cmpd | X | Y | Z |
|---|---|---|---|
| S9-4-1 | F | 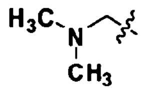 | $CH_3$ |
| S10-10-5 | F | 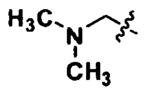 | $NHCH_2C(CH_3)_2$ |
| S10-10-6 | F | 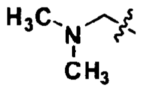 | $NH_2$ |
| S12-5-1 | F | 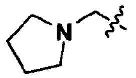 | F |
| S12-5-2 | F | 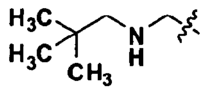 | F |
| Cmpd | X | Y | Z |
|---|---|---|---|
| S12-5-3 | F | 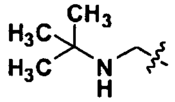 | F |
| S12-5-4 | F | 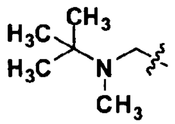 | F |
| S14-10 | F | CH3 | $NH_2$ |
| S14-8 | F | CH3 | H |
| S14-9 | F | CH3 | $NO_2$ |
FIG. 6V

| Cmpd | X | Y | Z |
| --- | --- | --- | --- |
| S15-13-10 | Cl | 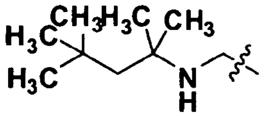 | H |
| S15-13-11 | Cl | 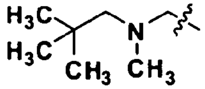 | H |
| S15-13-13 | Cl | 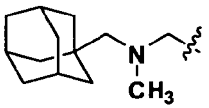 | H |
| S15-13-14 | Cl | 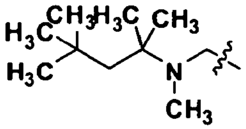 | H |
| S15-13-16 | Cl | 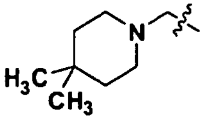 | H |
| Cmpd | X | Y | Z |
| --- | --- | --- | --- |
| S15-13-5 | Cl | 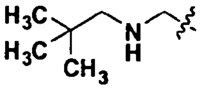 | H |
| S15-13-6 | Cl |  | H |
| S15-13-7 | Cl | 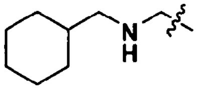 | H |
| S15-13-9 | Cl | 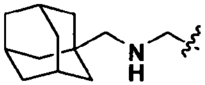 | H |
| S15-14-1 | H | 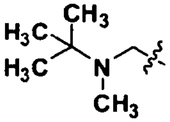 | H |
FIG. 6W

| Cmpd | X | Y | Z |
|---|---|---|---|
| S15-14-2 | H | 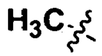 | H |
| S15-14-3 | H | 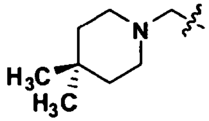 | H |
| S15-14-4 | H | 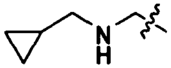 | H |
| S16-10-10 | $N(CH_3)_2$ | 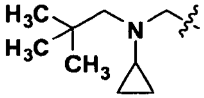 | H |
| S16-10-12 | $N(CH_3)_2$ |  | H |
| Cmpd | X | Y | Z |
|---|---|---|---|
| S16-10-14 | $N(CH_3)_2$ |  | H |
| S16-10-15 | $N(CH_3)_2$ | 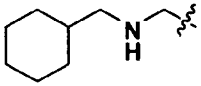 | H |
| S16-10-16 | $N(CH_3)_2$ | 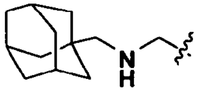 | H |
| S16-10-17 | $N(CH_3)_2$ | 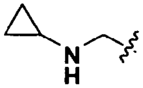 | H |
| S16-10-18 | $N(CH_3)_2$ | 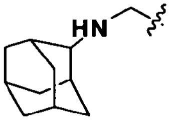 | H |
FIG. 6X

| Cmpd | X | Y | Z |
|---|---|---|---|
| S16-10-19 | $N(CH_3)_2$ | 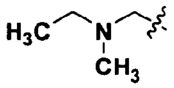 | H |
| S16-10-2 | $N(CH_3)_2$ | 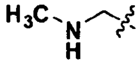 | H |
| S16-10-20 | $N(CH_3)_2$ | 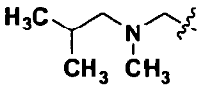 | H |
| S16-10-21 | $N(CH_3)_2$ | 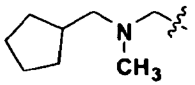 | H |
| S16-10-22 | $N(CH_3)_2$ | 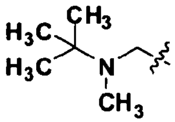 | H |
| Cmpd | X | Y | Z |
|---|---|---|---|
| S16-10-23 | $N(CH_3)_2$ | 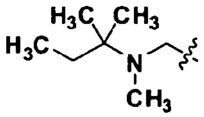 | H |
| S16-10-24 | $N(CH_3)_2$ | 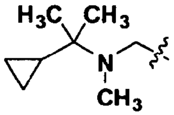 | H |
| S16-10-25 | $N(CH_3)_2$ | 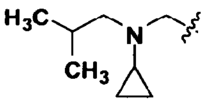 | H |
| S16-10-26 | $N(CH_3)_2$ | 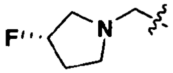 | H |
| S16-10-3 | $N(CH_3)_2$ | 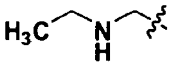 | H |
FIG. 6Y

| Cmpd | X | Y | Z |
|---|---|---|---|
| S16-10-5 | $N(CH_3)_2$ | 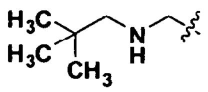 | H |
| S16-10-6 | $N(CH_3)_2$ | 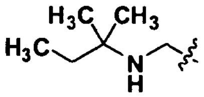 | H |
| S16-10-7 | $N(CH_3)_2$ | 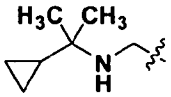 | H |
| S16-10-9 | $N(CH_3)_2$ | 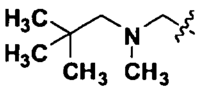 | H |
| S17-9-1 | CN | 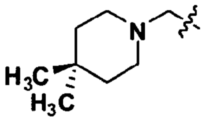 | H |
| Cmpd | X | Y | Z |
|---|---|---|---|
| S17-9-2 | CN | 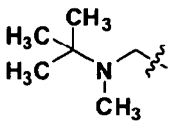 | H |
| S19-3 | H | F | H |
| S19-4 | $NH_2$ | F | H |
| S19-5 | H | F | $NH_2$ |
| S21-11 | H | N(CH3)2 | H |
FIG. 6Z

| Cmpd | X | Y | Z |
|---|---|---|---|
| S21-12-1 | H | 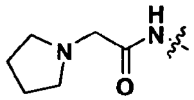 | H |
| S21-12-2 | H | 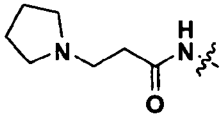 | H |
| S21-12-3 | H | 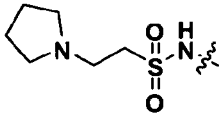 | H |
| S21-12-4 | H | 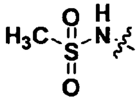 | H |
| S21-12-5 | H | 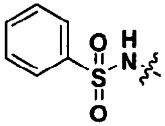 | H |
| Cmpd | X | Y | Z |
|---|---|---|---|
| S21-12-6 | H | 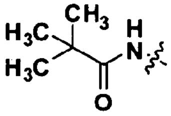 | H |
| S22-6 | H | 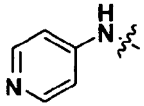 | H |
| S22-8-1 | H | 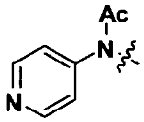 | H |
| S23-5-1 | F | 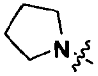 | H |
| S7-4-3 | F | 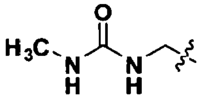 | H |
FIG. 6AA

| Cmpd | X | Y | Z |
| --- | --- | --- | --- |
| S11-4-1 | F | 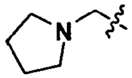 | CN |
| S21-10 | H | NH2 | H |
| S1-14-20 | F | 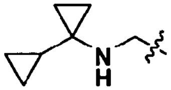 | H |
| S1-14-21 | F | 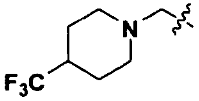 | H |
| S1-14-23 | F | 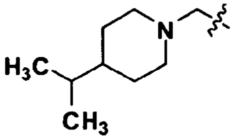 | H |
| Cmpd | X | Y | Z |
| --- | --- | --- | --- |
| S1-14-62 | F | 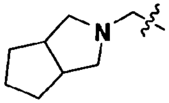 | H |
| S1-14-63 | F | 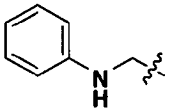 | H |
| S1-14-64 | F | 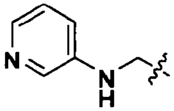 | H |
| S16-10-1 | $N(CH_3)_2$ | 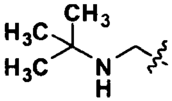 | H |
| S16-10-11 | $N(CH_3)_2$ | 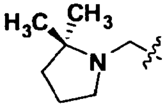 | H |
FIG. 6BB

| Cmpd | X | Y | Z |
|---|---|---|---|
| S16-10-27 | $N(CH_3)_2$ | 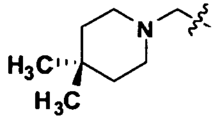 | H |
| S16-10-4 | $N(CH_3)_2$ | 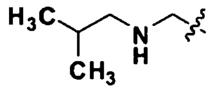 | H |
| Cmpd | X | Y | Z |
|---|---|---|---|
| S19-7-1 | 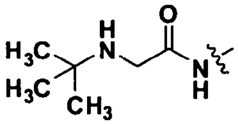 | F | H |
FIG. 6CC

| Cmpd | X | Y | Z |
|---|---|---|---|
| S10-10-1 | F | $CH_2N(CH_3)_2$ | 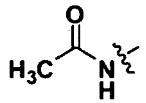 |
| S10-10-2 | F | $CH_2N(CH_3)_2$ | 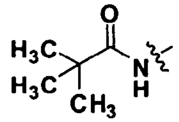 |
| S10-10-4 | F | $CH_2N(CH_3)_2$ | 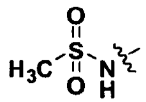 |
| S14-11 | F | $CH_3$ | 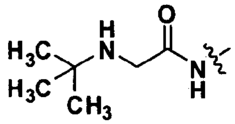 |
| S18-9-1 | H | F | 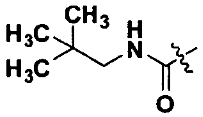 |
| Cmpd | X | Y | Z |
|---|---|---|---|
| S18-9-2 | H | F | 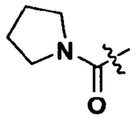 |
| S18-9-3 | H | F | 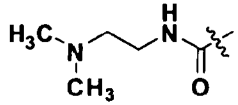 |
| S18-9-4 | H | F | 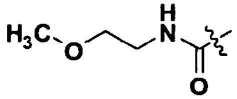 |
| S20-10-9 | H | $NHCH_2CH(CH_3)_2$ | 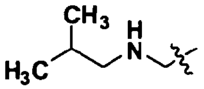 |
| S10-10-3 | F | $CH_2N(CH_3)_2$ | 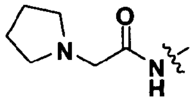 |
FIG. 6DD

| Cmpd | X | Y | Z |
|---|---|---|---|
| S19-6-1 | H | F | 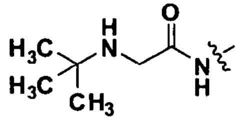 |
| S19-8-1 | H | F | 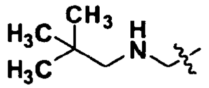 |
| S20-10-2 | H | F | 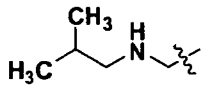 |
| S20-10-3 | H | F | 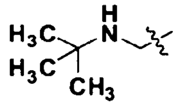 |
| S20-10-4 | H | F | 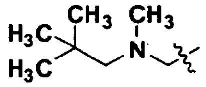 |
| Cmpd | X | Y | Z |
|---|---|---|---|
| S20-10-5 | H | F | 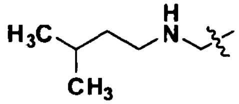 |
| S20-10-6 | H | F | 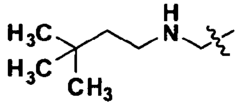 |
| S20-10-7 | H | F | 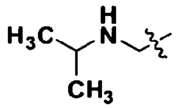 |
| S20-10-8 | H | F | 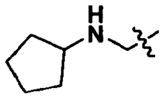 |
| S18-7-1 | H | F | 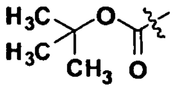 |
FIG. 6EE

| Cmpd | X | Y | Z |
|---|---|---|---|
| S13-9-1 | F | F | 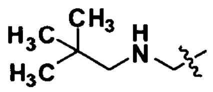 |
| S13-9-2 | F | F | 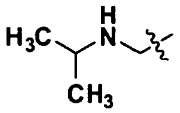 |
FIG. 6FF

| Compound | SA101 29213 | SA100 13709 | SA161 MRSA, tetM | SA158 tetK | EF103 29212 | EF159 tetM | SP106 49619 | SP160 tetM | EC107 25922 | EC155 tetA | AB110 19606 | PA111 27853 | EC108 13047 | KP109 13883 | KP153 tetA |
|---|---|---|---|---|---|---|---|---|---|---|---|---|---|---|---|
| S1-14-1 | B | B | C | B | B | B | A | B | B | B | C | A | A | B | B |
| S1-14-10 | B | B | A | B | B | B | C | C | B | C | C | B | C | B | C |
| S1-14-100 | B | B | B | B | B | B | B | B | B | B | A | B | B | B | B |
| S1-14-101 | B | B | B | B | B | B | B | B | B | B | A | B | B | B | B |
| S1-14-102 | C | C | C | B | C | C | B | C | B | C | C | B | C | C | C |
| S1-14-103 | C | C | C | B | C | C | B | B | B | C | C | B | C | C | C |
| S1-14-104 | C | B | B | B | B | B | C | C | C | C | C | B | C | C | C |
| S1-14-105 | B | B | B | B | B | B | A | B | B | B | A | B | B | B | B |
| S1-14-106 | B | B | B | B | B | B | A | B | B | B | B | B | C | C | C |
| S1-14-107 | B | B | B | B | B | B | B | B | B | B | B | B | B | B | B |
| S1-14-108 | C | B | C | B | B | C | B | B | B | B | C | B | B | B | B |
| S1-14-109 | C | B | C | B | B | C | B | B | B | B | B | B | B | B | B |
| S1-14-11 | B | B | C | B | B | C | B | B | B | B | C | B | B | B | B |
| S1-14-110 | B | B | B | B | B | B | B | B | B | B | A | B | B | B | B |
| S1-14-111 | B | B | B | B | B | B | B | B | B | B | B | B | B | B | B |
| S1-14-112 | C | B | B | B | B | B | B | B | B | B | B | B | B | B | B |
| S1-14-113 | B | B | B | B | B | B | B | B | B | B | B | B | C | B | B |
| S1-14-114 | A | B | A | B | B | B | C | C | B | C | C | B | C | B | C |
| S1-14-12 | B | B | C | B | B | B | B | B | B | B | B | B | B | B | B |
| S1-14-13 | B | B | B | B | B | B | B | B | B | B | A | B | B | B | B |
| S1-14-14 | B | B | A | B | B | B | C | B | C | C | C | B | C | C | C |
| S1-14-15 | B | B | B | B | B | B | A | B | B | B | A | B | B | B | B |
| S1-14-16 | B | B | C | B | C | C | B | B | B | C | C | B | C | C | C |
| S1-14-17 | C | B | C | B | B | C | B | B | B | C | C | B | C | C | C |
| S1-14-18 | B | B | B | B | B | B | B | B | B | B | B | B | B | B | B |
| S1-14-19 | C | C | C | B | C | C | B | C | C | C | C | B | C | C | C |
| S1-14-2 | B | B | B | B | B | B | B | B | B | B | A | B | B | B | B |
| S1-14-20 | B | B | B | NT | B | B | A | B | B | B | A | B | B | B | B |
| S1-14-21 | B | B | B | NT | B | B | B | B | B | B | B | B | B | B | B |
| S1-14-22 | C | C | C | B | C | C | C | C | B | C | C | B | C | C | C |
| S1-14-23 | B | B | B | NT | B | B | B | B | B | B | B | B | B | B | B |

FIG. 7A

| Compound | SA101 29213 | SA100 13709 | SA161 MRSA, tetM | SA158 tetK | EF103 29212 | EF159 tetM | SP106 49619 | SP160 tetM | EC107 25922 | EC155 tetA | AB110 19606 | PA111 27853 | EC108 13047 | KP109 13883 | KP153 tetA |
|---|---|---|---|---|---|---|---|---|---|---|---|---|---|---|---|
| S1-14-24 | C | B | C | B | C | C | B | C | C | C | C | B | C | C | C |
| S1-14-25 | B | B | B | B | B | B | B | B | B | B | B | B | B | B | B |
| S1-14-26 | C | B | C | B | B | C | B | B | B | B | C | B | B | B | B |
| S1-14-27 | B | B | B | B | B | B | A | B | B | B | A | B | B | B | A |
| S1-14-28 | B | B | B | B | B | B | B | B | B | B | A | B | B | B | B |
| S1-14-29 | C | C | C | B | C | C | B | B | B | B | C | B | C | C | B |
| S1-14-3 | B | B | C | B | B | B | B | B | B | B | A | B | B | B | B |
| S1-14-30 | B | B | B | B | B | B | B | B | B | B | B | B | C | B | B |
| S1-14-31 | B | B | B | B | B | B | B | B | B | B | B | B | C | B | B |
| S1-14-32 | B | B | B | B | B | B | B | B | B | B | B | B | B | B | B |
| S1-14-33 | B | B | C | B | B | B | A | B | B | B | A | B | A | B | A |
| S1-14-34 | B | B | C | B | B | B | A | B | B | B | A | B | A | B | A |
| S1-14-35 | B | B | B | B | B | B | B | B | B | B | A | B | B | B | B |
| S1-14-36 | B | B | B | B | B | B | B | B | B | B | B | B | B | B | B |
| S1-14-37 | B | B | A | B | B | B | C | B | B | C | C | B | C | B | C |
| S1-14-38 | C | C | B | B | B | B | B | B | B | B | A | B | B | B | B |
| S1-14-39 | B | B | B | B | B | B | C | B | B | B | B | B | B | B | B |
| S1-14-4 | B | B | B | A | B | B | A | B | B | B | A | B | B | B | A |
| S1-14-40 | B | B | C | B | B | B | B | B | B | B | A | B | B | B | B |
| S1-14-41 | B | B | C | B | B | B | A | B | B | B | A | B | B | B | B |
| S1-14-42 | B | B | C | B | B | B | A | B | B | B | A | B | B | B | B |
| S1-14-43 | B | B | B | B | B | B | B | B | B | B | A | B | B | B | B |
| S1-14-44 | B | B | B | B | B | B | A | B | B | B | A | B | B | B | B |
| S1-14-45 | B | B | C | B | B | B | B | B | B | B | A | B | B | B | B |
| S1-14-46 | B | B | B | B | B | B | B | B | B | B | B | B | B | B | B |
| S1-14-47 | B | B | A | B | B | B | C | C | C | C | C | B | C | C | C |
| S1-14-48 | B | B | B | B | B | B | C | C | C | C | C | B | C | C | C |
| S1-14-49 | B | B | B | B | B | B | C | C | B | B | C | B | C | B | C |
| S1-14-5 | B | B | B | B | B | B | B | B | B | B | B | B | B | B | B |
| S1-14-50 | B | B | B | B | B | B | A | B | B | B | A | B | B | B | B |
| S1-14-51 | B | B | B | B | B | B | A | B | B | B | A | B | B | B | B |

FIG. 7B

| Compound | SA101 29213 | SA100 13709 | SA161 MRSA, tetM | SA158 tetK | EF103 29212 | EF159 tetM | SP106 49619 | SP160 tetM | EC107 25922 | EC155 tetA | AB110 19606 | PA111 27853 | EC108 13047 | KP109 13883 | KP153 tetA |
|---|---|---|---|---|---|---|---|---|---|---|---|---|---|---|---|
| S1-14-52 | C | B | B | B | B | B | C | C | C | C | C | B | C | C | C |
| S1-14-53 | C | C | B | B | B | B | C | B | C | C | C | B | C | C | C |
| S1-14-54 | B | B | C | B | B | C | B | B | B | B | C | A | B | B | B |
| S1-14-55 | B | B | C | B | B | B | A | B | B | B | B | B | A | B | B |
| S1-14-56 | B | B | B | B | B | B | A | B | B | B | A | B | B | B | B |
| S1-14-57 | B | B | B | B | B | B | C | C | C | C | C | B | C | C | C |
| S1-14-58 | B | B | B | B | B | B | C | C | C | C | C | B | C | C | C |
| S1-14-59 | B | B | B | B | B | B | B | B | C | B | C | B | C | C | C |
| S1-14-6 | B | B | B | B | B | B | B | B | B | B | A | B | B | B | B |
| S1-14-60 | B | B | B | B | B | B | B | B | B | B | B | B | C | B | B |
| S1-14-61 | B | B | B | B | B | B | A | B | B | B | A | B | A | A | A |
| S1-14-62 | B | B | B | NT | B | B | A | B | B | B | A | B | B | B | A |
| S1-14-63 | B | B | A | NT | B | B | C | B | C | C | C | B | C | C | C |
| S1-14-64 | C | B | B | NT | C | B | B | B | B | C | C | B | C | B | C |
| S1-14-65 | B | B | B | A | B | B | A | B | B | B | A | B | B | B | B |
| S1-14-66 | C | B | B | B | B | B | B | B | B | B | B | B | B | B | B |
| S1-14-67 | B | B | B | B | B | B | B | B | B | B | C | B | C | B | B |
| S1-14-68 | B | B | B | B | B | B | B | B | B | B | C | B | C | B | B |
| S1-14-69 | B | B | B | B | B | B | B | B | B | B | A | B | B | B | B |
| S1-14-7 | B | B | B | B | B | B | A | B | B | B | B | B | A | B | B |
| S1-14-70 | B | B | B | B | B | B | B | B | B | B | B | B | B | B | B |
| S1-14-71 | B | B | B | B | B | B | C | B | B | B | C | B | C | B | B |
| S1-14-72 | B | B | C | B | B | B | A | B | B | B | B | B | B | B | B |
| S1-14-73 | B | B | A | B | B | B | A | B | B | B | A | B | B | B | B |
| S1-14-74 | B | B | C | B | B | C | B | B | B | B | C | A | A | B | B |
| S1-14-75 | B | B | B | B | B | B | B | B | B | B | B | B | B | B | B |
| S1-14-76 | B | B | A | B | B | B | C | B | B | B | C | B | C | B | C |
| S1-14-77 | B | B | C | B | B | C | B | B | B | B | C | B | B | B | B |
| S1-14-78 | B | B | B | B | B | B | C | C | C | C | C | B | C | C | NT |
| S1-14-79 | B | B | C | B | B | B | A | B | B | B | B | B | A | B | B |
| S1-14-8 | B | B | C | B | B | B | A | B | B | B | A | B | B | B | B |

FIG. 7C

| Compound | SA101 29213 | SA100 13709 | SA161 MRSA, tetM | SA158 tetK | EF103 29212 | EF159 tetM | SP106 49619 | SP160 tetM | EC107 25922 | EC155 tetA | AB110 19606 | PA111 27853 | EC108 13047 | KP109 13883 | KP153 tetA |
|---|---|---|---|---|---|---|---|---|---|---|---|---|---|---|---|
| S1-14-80 | B | B | C | B | B | B | A | B | B | B | A | B | A | B | B |
| S1-14-81 | B | B | B | B | B | B | A | B | B | B | A | B | A | B | B |
| S1-14-82 | B | B | B | B | B | B | B | B | B | B | A | B | B | B | B |
| S1-14-83 | B | B | C | B | B | C | B | B | B | B | B | B | B | B | B |
| S1-14-84 | C | B | C | B | B | C | C | B | B | B | C | B | B | B | B |
| S1-14-85 | C | C | C | B | C | C | B | B | B | B | C | B | B | B | B |
| S1-14-86 | B | B | B | B | B | B | B | B | B | B | A | B | B | B | B |
| S1-14-87 | B | B | B | B | B | B | B | B | B | B | B | B | C | B | B |
| S1-14-88 | B | B | B | B | B | B | C | C | B | C | C | B | C | C | C |
| S1-14-89 | B | B | A | B | B | B | C | C | C | C | C | B | C | C | C |
| S1-14-9 | A | B | B | A | B | B | A | B | B | B | A | B | B | B | A |
| S1-14-90 | B | B | B | B | B | B | B | B | B | B | A | B | B | B | B |
| S1-14-91 | B | B | B | B | B | B | B | B | B | B | A | B | B | B | B |
| S1-14-92 | B | B | B | B | B | B | C | C | C | C | C | B | C | C | C |
| S1-14-93 | B | B | A | B | B | B | C | C | C | C | C | B | C | C | C |
| S1-14-94 | B | B | B | B | B | B | C | C | C | C | C | B | C | C | C |
| S1-14-95 | B | B | B | B | B | B | C | C | C | C | C | B | C | C | C |
| S1-14-96 | C | B | B | B | B | B | C | C | C | C | C | B | C | C | C |
| S1-14-97 | B | B | B | B | B | B | C | C | C | C | C | B | C | C | C |
| S1-14-98 | B | B | B | B | B | B | B | B | B | B | A | B | B | B | B |
| S1-14-99 | C | B | C | B | B | C | B | B | B | B | C | B | B | B | B |
| S2-4-1 | B | B | B | A | B | B | A | B | B | B | A | B | B | B | A |
| S2-4-10 | C | C | B | B | B | B | C | B | C | C | C | B | C | C | C |
| S2-4-11 | B | B | B | B | B | B | B | B | B | B | A | B | B | B | B |
| S2-4-12 | A | B | B | B | B | B | A | B | B | A | A | B | B | B | A |
| S2-4-13 | B | B | C | B | B | B | B | B | B | B | B | A | A | B | B |
| S2-4-14 | B | B | C | A | B | B | A | B | B | B | A | B | A | B | B |
| S2-4-15 | B | B | C | B | B | B | A | B | B | B | A | B | B | B | B |
| S2-4-16 | B | B | B | B | B | B | B | B | B | B | A | B | B | B | B |
| S2-4-17 | C | B | C | B | B | C | B | B | B | C | C | B | B | B | B |
| S2-4-18 | B | B | C | B | B | B | B | B | B | B | B | A | A | B | B |

FIG. 7D

| Compound | SA101 29213 | SA100 13709 | SA161 MRSA, tetM | SA158 tetK | EF103 29212 | EF159 tetM | SP106 49619 | SP160 tetM | EC107 25922 | EC155 tetA | AB110 19606 | PA111 27853 | EC108 13047 | KP109 13883 | KP153 tetA |
|---|---|---|---|---|---|---|---|---|---|---|---|---|---|---|---|
| S2-4-19 | B | A | B | A | B | B | B | B | B | B | A | B | B | B | A |
| S2-4-2 | B | B | C | B | B | C | B | B | B | B | C | A | B | B | B |
| S2-4-21 | B | A | A | B | B | B | B | B | B | B | A | B | B | B | B |
| S2-4-22 | A | A | B | A | B | B | B | B | B | B | A | B | B | B | B |
| S2-4-23 | A | A | B | A | B | B | B | B | B | B | A | B | B | B | B |
| S2-4-24 | B | B | C | B | B | B | B | B | B | B | A | B | A | B | A |
| S2-4-25 | B | B | B | B | B | B | A | B | B | A | A | B | A | B | A |
| S2-4-26 | B | B | B | B | B | B | B | B | B | B | A | B | B | B | B |
| S2-4-27 | A | A | B | A | B | B | B | B | B | B | A | B | B | B | B |
| S2-4-28 | B | A | B | A | B | B | B | B | B | A | A | B | B | B | A |
| S2-4-29 | A | A | B | A | B | B | A | B | B | B | A | B | B | B | A |
| S2-4-3 | B | B | B | B | B | B | B | B | B | B | C | B | B | B | B |
| S2-4-30 | B | B | B | B | B | B | B | B | B | B | B | B | B | B | B |
| S2-4-31 | B, | B | B | B | B | B | B | B | B | B | A | B | B | B | A |
| S2-4-32 | B | B | B | A | B | B | B | B | B | B | A | B | B | B | B |
| S2-4-33 | B | A | B | A | B | B | B | B | B | B | A | B | B | B | B |
| S2-4-34 | B | B | B | B | B | B | C | C | B | C | C | B | C | B | C |
| S2-4-35 | B | B | B | B | B | B | C | C | C | C | C | B | C | C | C |
| S2-4-36 | B | B | B | B | B | B | A | B | B | B | A | B | B | B | B |
| S2-4-37 | B | B | B | B | B | B | B | B | B | B | B | B | B | B | B |
| S2-4-38 | B | B | B | B | B | B | A | B | B | B | A | B | B | B | B |
| S2-4-39 | B | B | B | B | B | B | C | B | B | B | C | B | C | B | B |
| S2-4-4 | B | B | B | B | B | B | B | B | B | B | B | B | A | B | B |
| S2-4-40 | B | B | B | B | B | B | B | B | B | B | C | B | B | B | B |
| S2-4-41 | B | B | B | B | B | B | C | B | B | B | B | B | B | B | B |
| S2-4-42 | B | B | B | B | B | B | C | B | B | B | B | B | B | B | B |
| S2-4-43 | B | B | B | B | B | B | C | B | B | B | C | B | C | B | B |
| S2-4-44 | B | B | B | B | B | B | C | C | C | C | C | B | C | C | C |
| S2-4-45 | B | B | B | B | B | B | B | B | B | B | A | B | B | B | B |
| S2-4-46 | B | B | B | B | B | B | B | B | B | B | B | B | B | B | B |
| S2-4-47 | B | B | B | B | B | B | C | B | B | B | B | B | B | B | B |

FIG. 7E

| Compound | SA101 29213 | SA100 13709 | SA161 MRSA, tetM | SA158 tetK | EF103 29212 | EF159 tetM | SP106 49619 | SP160 tetM | EC107 25922 | EC155 tetA | AB110 19606 | PA111 27853 | EC108 13047 | KP109 13883 | KP153 tetA |
|---|---|---|---|---|---|---|---|---|---|---|---|---|---|---|---|
| S2-4-48 | C | B | B | B | B | B | C | C | B | B | C | B | C | C | C |
| S2-4-49 | B | B | B | B | B | B | C | B | B | B | C | B | C | B | B |
| S2-4-5 | B | B | B | B | B | B | B | B | B | B | B | B | B | B | B |
| S2-4-50 | A | A | B | A | B | B | B | B | A | B | A | B | B | B | A |
| S2-4-50 | B | B | B | B | B | B | B | B | B | B | A | B | B | B | B |
| S2-4-51 | B | A | B | A | B | B | B | B | B | B | A | B | B | B | B |
| S2-4-52 | B | B | B | A | B | B | B | B | B | B | A | B | B | B | B |
| S2-4-53 | B | B | B | B | B | B | B | B | B | B | A | B | B | B | B |
| S2-4-54 | B | B | B | B | B | B | B | B | B | B | C | B | C | C | C |
| S2-4-55 | B | B | A | B | B | B | C | B | C | C | C | B | C | C | C |
| S2-4-56 | B | B | B | B | B | B | C | C | C | C | C | B | C | C | C |
| S2-4-57 | B | B | B | B | B | B | B | B | B | B | A | B | B | B | B |
| S2-4-58 | B | B | B | B | B | B | C | B | B | B | B | B | C | B | B |
| S2-4-59 | C | B | B | B | B | B | B | B | B | B | A | B | B | B | B |
| S2-4-6 | B | B | B | B | B | B | B | B | B | B | C | B | B | B | B |
| S2-4-60 | B | B | A | B | B | B | C | B | B | B | B | B | B | B | B |
| S2-4-61 | B | B | A | B | B | B | C | B | B | B | B | B | C | B | B |
| S2-4-62 | B | B | B | B | B | B | B | B | B | B | B | B | B | B | B |
| S2-4-63 | B | B | B | B | B | B | A | B | B | B | A | B | B | B | B |
| S2-4-64 | C | C | B | B | B | B | C | B | B | B | C | B | C | B | B |
| S2-4-65 | B | B | B | B | B | B | A | B | B | B | A | B | A | A | A |
| S2-4-66 | B | A | B | B | B | B | A | B | B | B | A | B | B | B | A |
| S2-4-67 | B | B | B | B | B | B | B | B | B | B | C | B | B | B | A |
| S2-4-68 | C | B | B | B | B | B | B | B | C | C | C | B | C | C | C |
| S2-4-7 | B | B | B | A | B | B | B | B | B | B | A | B | B | B | B |
| S2-4-8 | B | B | B | A | B | B | B | B | B | B | A | B | A | A | A |
| S2-4-9 | B | B | B | B | B | B | B | B | B | B | A | B | B | B | B |
| S3-5-1 | B | B | B | B | B | B | B | B | B | C | B | B | B | B | C |
| S3-5-2 | B | B | B | B | B | B | B | B | B | B | A | B | B | B | B |
| S3-53 | B | B | C | B | B | C | A | B | B | B | B | B | B | B | B |
| S3-5-4 | C | C | C | B | C | C | B | C | B | C | C | B | B | B | C |

FIG. 7F

| Compound | SA101 29213 | SA100 13709 | SA161 MRSA, tetM | SA158 tetK | EF103 29212 | EF159 tetM | SP106 49619 | SP160 tetM | EC107 25922 | EC155 tetA | AB110 19606 | PA111 27853 | EC108 13047 | KP109 13883 | KP153 tetA |
|---|---|---|---|---|---|---|---|---|---|---|---|---|---|---|---|
| S3-5-5 | B | B | C | B | B | B | A | B | B | B | B | A | A | B | B |
| S3-5-6 | C | C | C | B | C | C | C | C | B | B | C | B | B | C | B |
| S4-5-1 | B | B | B | B | B | B | A | B | B | B | A | B | A | B | B |
| S4-5-2 | B | B | C | B | B | B | B | B | B | B | B | A | A | B | B |
| S4-5-3 | B | B | C | B | B | B | B | B | B | B | B | B | B | B | B |
| S4-5-4 | B | B | C | B | B | C | B | B | B | B | C | B | B | B | B |
| S4-5-5 | B | B | C | B | B | C | B | B | B | B | B | B | B | B | B |
| S4-5-6 | B | B | C | B | B | B | A | B | B | B | A | B | A | B | B |
| S5-5-1 | B | B | B | B | B | B | B | B | B | B | A | B | B | B | A |
| S6-4-1 | A | B | B | B | B | B | A | B | B | A | A | B | B | B | A |
| S7-4-1 | B | B | C | B | C | C | B | C | B | C | C | B | C | C | C |
| S7-4-10 | C | B | C | B | C | C | B | C | C | C | C | B | C | C | C |
| S7-4-11 | B | B | C | B | C | C | B | B | B | C | C | B | C | C | C |
| S7-4-12 | B | B | B | B | B | B | B | B | C | C | C | B | C | C | C |
| S7-4-2 | C | B | B | B | C | C | B | B | C | C | C | B | C | C | C |
| S7-4-3 | C | C | C | C | C | C | C | C | C | C | C | B | C | C | C |
| S7-4-4 | C | C | C | B | C | C | B | C | B | B | C | B | B | C | C |
| S7-4-5 | B | B | C | B | C | C | B | C | B | C | C | B | C | C | C |
| S7-4-6 | C | B | B | B | C | C | B | B | B | C | C | B | C | C | C |
| S7-4-7 | B | B | C | B | C | C | B | C | B | C | C | B | C | C | C |
| S7-4-8 | C | B | B | B | B | B | B | B | C | C | C | B | C | C | C |
| S7-4-9 | C | B | B | B | B | B | C | B | C | C | C | B | C | C | C |
| S8-4-1 | C | B | C | B | B | C | B | B | B | B | C | B | B | B | B |
| S9-4-1 | C | C | C | B | B | B | C | B | B | B | C | B | B | B | C |
| S10-10-1 | C | C | C | NT | C | C | C | C | C | C | C | B | C | C | C |
| S10-10-2 | C | C | C | NT | C | C | C | C | C | C | C | B | C | C | C |
| S10-10-3 | C | C | C | C | C | C | C | C | C | C | C | B | C | C | C |
| S10-10-4 | C | C | C | NT | C | C | C | C | C | C | C | B | C | C | C |
| S10-10-5 | C | C | C | B | B | B | C | B | B | B | C | B | C | C | B |
| S10-10-6 | B | B | B | B | B | B | A | B | B | B | B | A | B | B | A |
| S11-4-1 | C | C | C | C | C | C | C | C | C | C | C | B | C | C | C |

FIG. 7G

| Compound | SA101 29213 | SA100 13709 | SA161 MRSA, tetM | SA158 tetK | EF103 29212 | EF159 tetM | SP106 49619 | SP160 tetM | EC107 25922 | EC155 tetA | AB110 19606 | PA111 27853 | EC108 13047 | KP109 13883 | KP153 tetA |
|---|---|---|---|---|---|---|---|---|---|---|---|---|---|---|---|
| S12-5-1 | C | B | C | B | B | C | B | B | B | B | C | B | B | B | B |
| S12-5-2 | C | C | B | B | B | B | C | B | B | B | C | B | C | B | B |
| S12-5-3 | C | B | C | B | B | C | B | B | B | B | C | B | B | B | B |
| S12-5-4 | C | B | C | B | B | C | B | B | B | B | C | B | B | B | B |
| S13-9-1 | B | B | B | B | B | A | B | B | B | B | B | B | B | B | B |
| S13-9-2 | C | B | B | B | B | B | B | B | B | C | C | B | B | B | C |
| S14-10 | A | B | B | B | B | B | B | B | B | B | C | B | B | B | B |
| S14-11 | C | C | C | C | B | B | C | B | C | C | C | B | C | C | C |
| S14-8 | B | B | B | B | B | B | C | B | B | B | C | B | C | C | B |
| S14-9 | C | C | B | B | B | B | C | C | C | B | C | B | C | C | C |
| S-15-13-1 | B | B | B | A | B | B | A | B | B | B | A | B | B | B | B |
| S15-13-10 | B | B | B | B | B | B | B | B | B | B | B | B | B | B | B |
| S15-13-11 | B | B | A | B | B | B | C | B | B | B | C | B | C | B | B |
| S15-13-13 | C | B | B | B | B | B | C | C | C | C | C | B | C | C | C |
| S15-13-14 | B | B | B | B | B | B | B | C | B | B | C | B | B | B | B |
| S15-13-15 | A | A | B | A | B | B | A | B | A | A | A | B | A | A | A |
| S15-13-16 | B | B | B | B | B | B | B | B | B | B | A | B | B | B | B |
| S15-13-2 | B | B | B | A | B | B | A | B | B | B | A | B | B | B | A |
| S15-13-3 | B | B | B | A | B | B | A | B | B | B | A | B | B | B | A |
| S15-13-4 | A | A | B | A | B | B | A | B | B | A | A | B | B | A | A |
| S15-13-5 | B | B | B | B | B | B | B | B | B | B | A | B | B | B | B |
| S15-13-6 | B | B | C | B | B | B | B | B | B | B | B | B | A | B | B |
| S15-13-7 | B | B | B | B | B | B | B | B | B | B | A | B | B | B | B |
| S15-13-8 | A | A | B | A | B | B | A | B | A | B | A | B | A | A | A |
| S15-13-9 | B | B | A | B | B | A | C | C | B | B | C | B | C | B | C |
| S15-14-1 | B | B | C | B | B | C | B | B | B | B | B | B | B | B | A |
| S15-14-2 | B | B | B | B | B | B | B | B | B | B | C | B | C | C | B |
| S15-14-3 | B | B | C | B | B | B | B | B | B | B | A | B | B | B | B |
| S15-14-4 | C | B | C | B | B | C | B | B | B | B | C | B | B | B | B |
| S16-10-1 | C | C | C | NT | C | C | B | C | C | C | C | B | C | C | C |
| S16-10-10 | B | B | B | B | B | B | B | B | B | B | C | B | B | B | B |

FIG. 7H

| Compound | SA101 29213 | SA100 13709 | SA161 MRSA, tetM | SA158 tetK | EF103 29212 | EF159 tetM | SP106 49619 | SP160 tetM | EC107 25922 | EC155 tetA | AB110 19606 | PA111 27853 | EC108 13047 | KP109 13883 | KP153 tetA |
|---|---|---|---|---|---|---|---|---|---|---|---|---|---|---|---|
| S16-10-11 | B | B | B | NT | B | B | B | B | B | A | B | B | B | B | A |
| S16-10-12 | B | B | C | B | B | C | B | B | B | B | C | B | B | B | B |
| S16-10-13 | A | B | C | A | B | B | A | B | B | B | A | B | B | B | B |
| S16-10-14 | B | B | C | B | B | C | B | B | B | B | C | B | B | B | B |
| S16-10-15 | B | B | B | B | B | B | A | B | B | B | B | B | B | B | B |
| S16-10-16 | B | B | B | B | B | B | B | B | B | B | C | B | B | B | B |
| S16-10-17 | B | B | B | B | B | B | B | B | B | B | A | B | B | B | B |
| S16-10-18 | A | B | B | B | B | B | A | B | B | B | B | B | B | B | B |
| S16-10-19 | B | B | C | B | B | C | B | B | B | B | C | B | B | B | B |
| S16-10-2 | C | B | C | B | B | C | B | B | B | B | C | B | B | B | B |
| S16-10-20 | B | B | C | B | B | C | A | B | B | B | A | B | B | B | B |
| S16-10-21 | B | B | C | B | B | C | A | B | B | B | B | B | B | B | B |
| S16-10-22 | B | B | C | B | B | C | B | B | B | B | C | B | B | B | A |
| S16-10-23 | B | B | C | B | B | C | B | B | B | B | B | B | B | B | A |
| S16-10-24 | B | B | C | B | B | C | B | B | B | B | C | B | B | B | B |
| S16-10-25 | B | B | B | B | B | B | C | B | B | B | C | B | C | B | B |
| S16-10-26 | B | B | C | B | B | C | A | B | B | B | A | B | B | B | B |
| S16-10-27 | B | B | B | NT | B | B | C | B | B | B | B | B | B | B | B |
| S16-10-3 | C | B | C | B | B | C | B | B | B | B | C | B | B | B | B |
| S16-10-4 | C | C | C | NT | C | C | B | C | C | C | C | C | C | C | C |
| S16-10-5 | B | B | B | B | B | B | B | B | B | B | B | B | B | B | B |
| S16-10-6 | B | B | B | B | B | B | B | B | B | B | C | B | B | B | B |
| S16-10-7 | B | B | C | B | B | B | B | B | B | B | C | B | B | B | B |
| S16-10-9 | A | B | B | B | B | B | A | B | B | B | A | B | B | B | B |
| S17-9-1 | C | B | B | B | B | B | B | B | B | B | B | B | B | B | B |
| S17-9-2 | B | B | C | B | B | B | A | B | B | B | B | B | B | B | B |
| S18-7-1 | C | C | B | B | B | B | C | B | C | C | C | B | C | C | C |
| S18-9-1 | C | C | C | C | C | C | C | C | C | C | C | B | C | C | C |
| S18-9-2 | C | C | C | C | C | C | C | C | C | C | C | B | C | C | C |
| S18-9-3 | C | C | C | C | C | C | C | C | C | C | C | B | C | C | C |
| S18-9-4 | C | C | C | C | C | C | C | C | C | C | C | B | C | C | C |

FIG. 7I

| Compound | SA101 29213 | SA100 13709 | SA161 MRSA, tetM | SA158 tetK | EF103 29212 | EF159 tetM | SP106 49619 | SP160 tetM | EC107 25922 | EC155 tetA | AB110 19606 | PA111 27853 | EC108 13047 | KP109 13883 | KP153 tetA |
|---|---|---|---|---|---|---|---|---|---|---|---|---|---|---|---|
| S19-3 | A | B | B | B | B | B | B | B | B | B | A | B | B | B | B |
| S19-4 | B | B | B | B | B | B | B | B | B | C | B | B | B | B | C |
| S19-5 | A | B | B | B | B | B | B | B | B | B | A | B | B | B | C |
| S19-6-1 | C | C | C | B | B | B | C | B | B | C | C | B | B | B | C |
| S19-7-1 | C | C | C | B | B | C | C | B | B | C | C | B | C | C | C |
| S19-7-2 | A | A | B | A | B | B | B | B | B | B | A | B | B | B | B |
| S19-8-1 | B | B | B | B | B | B | B | B | B | B | C | B | B | B | B |
| S20-10-2 | B | B | B | B | B | B | B | B | B | B | C | B | B | B | B |
| S20-10-3 | C | C | B | B | B | B | C | B | B | B | C | B | B | B | B |
| S20-10-4 | C | C | B | B | B | B | C | B | B | B | C | B | C | B | B |
| S20-10-5 | C | C | B | B | B | B | B | B | B | B | C | B | B | B | B |
| S20-10-6 | C | C | B | B | B | B | B | B | B | B | C | B | B | B | B |
| S20-10-7 | C | C | B | B | B | B | C | B | B | B | C | B | B | B | B |
| S20-10-8 | C | B | B | B | B | B | B | B | B | B | C | B | B | B | B |
| S20-10-9 | C | C | B | C | B | B | C | B | C | C | C | B | C | C | C |
| S21-10 | C | C | C | C | C | C | C | C | B | C | C | B | C | C | C |
| S21-11 | C | C | B | B | B | B | C | C | C | C | C | B | C | C | C |
| S21-12-1 | B | B | B | B | B | B | B | B | B | B | C | B | B | B | B |
| S21-12-2 | C | C | C | B | B | C | C | B | B | B | C | B | B | C | B |
| S21-12-3 | C | C | C | B | C | C | C | C | C | C | C | B | C | C | C |
| S21-12-4 | C | B | C | B | C | C | C | C | C | C | C | B | C | C | C |
| S21-12-5 | C | B | B | B | B | B | C | B | C | C | C | B | C | C | C |
| S21-12-6 | B | B | B | B | B | B | B | B | C | B | C | B | C | C | C |
| S22-6 | B | B | C | B | C | C | B | B | B | C | C | B | B | B | C |
| S22-8-1 | C | C | C | B | C | C | C | C | C | C | C | B | C | C | C |
| S23-5-1 | C | B | B | B | B | B | C | C | C | C | C | B | C | C | C |
| Minocycline | 0.0625 | 0.0625 | 8 | 0.0312 | 1 | 16 | 0.0156 | 2 | 0.5 | 8 | 0.0625 | 16 | 2 | 1 | 8 |
| Sancycline | 0.5 | 1 | | 4 | 8 | 8 | 0.25 | 8 | 8 | 32 | 0.25 | 33 | 8 | 8 | 32 |
| Tigecycline | 0.0625 | 0.0625 | 0.125 | 0.0625 | 0.0312 | 0.0625 | 0.0156 | 0.0156 | 0.0312 | 0.5 | 0.25 | 8 | 0.25 | 0.125 | 1 |

FIG. 7J

| Compound | SA101 29213 | SA100 13709 | SA161 MRSA, tetM | SA158 tetK | EF103 29212 | EF159 tetM | SP106 49619 | SP160 tetM | EC107 25922 | EC155 tetA | AB110 19606 | PA111 27853 | EC108 13047 | KP109 13883 | KP153 tetA |
|---|---|---|---|---|---|---|---|---|---|---|---|---|---|---|---|
| S15-13-181 | B | A | C | A | B | B | A | B | B | B | A | B | A | A | B |
| S15-13-182 | B | A | B | A | B | B | A | B | B | A | A | C | B | A | A |
| S15-13-183 | A | B | A | B | B | B | C | C | B | C | C | C | C | C | C |
| S15-13-184 | B | B | B | A | B | B | A | B | B | A | A | B | B | B | A |
| S15-13-185 | B | B | B | A | B | B | A | B | B | A | A | B | B | B | A |
| S15-13-186 | A | A | B | A | B | B | A | B | A | A | A | B | A | A | A |
| S15-13-187 | A | A | C | A | B | B | A | B | B | B | A | A | A | A | A |
| S15-13-188 | A | A | B | A | B | B | A | B | A | A | A | B | A | A | A |
| S15-13-189 | A | A | B | A | B | B | A | B | B | B | A | B | B | A | B |
| S15-13-190 | C | B | B | B | B | B | C | C | C | C | C | C | C | C | C |
| S15-13-191 | B | B | B | B | B | B | C | C | C | C | C | C | C | C | C |
| S15-13-192 | C | B | C | B | C | B | A | B | B | C | C | C | C | C | C |
| S15-13-193 | B | A | B | B | B | B | B | B | B | B | A | C | B | B | B |
| S15-13-194 | A | B | B | A | B | B | A | B | A | B | A | B | A | A | A |
| S15-13-195 | B | B | C | A | B | B | A | B | B | B | A | B | A | B | A |
| S15-13-196 | B | A | C | A | B | B | A | B | B | B | A | A | A | A | B |
| S15-13-197 | B | B | B | B | B | B | A | B | B | B | A | B | B | B | B |
| S15-13-198 | C | B | C | B | B | B | B | B | B | C | C | C | C | C | C |
| S15-13-199 | A | A | A | B | B | A | C | C | B | B | B | C | C | B | B |
| S15-13-200 | B | B | C | B | B | C | A | B | B | B | C | B | A | B | A |
| S15-13-201 | B | B | A | B | B | B | C | C | B | C | C | C | C | C | C |
| S15-13-204 | B | B | B | A | B | B | A | B | B | B | A | B | B | B | B |
| S15-13-205 | B | B | B | B | B | B | B | C | B | B | B | C | B | B | B |
| S15-13-206 | B | B | A | B | B | B | C | B | B | C | C | C | C | C | C |
| S15-13-207 | B | B | A | B | B | B | C | B | B | C | C | C | C | C | C |
| S15-13-208 | B | B | A | B | B | B | C | B | B | C | C | C | C | C | C |
| S15-13-209 | B | B | B | B | B | B | B | B | B | B | A | B | B | B | B |
| S15-13-210 | B | B | B | B | B | B | B | B | B | B | A | C | B | B | B |
| S15-13-211 | A | B | C | A | B | B | A | B | B | B | A | B | B | B | B |
| S15-13-212 | B | B | B | B | B | B | C | C | B | B | C | C | C | C | B |
| S15-13-213 | A | B | B | A | B | B | A | B | B | B | A | C | B | B | B |
| S15-13-214 | B | B | B | A | B | B | A | B | B | B | A | C | B | B | A |
| S15-13-215 | B | B | B | B | B | B | B | B | B | B | A | C | B | B | B |

FIG. 8A

| Compound | SA101 29213 | SA100 13709 | SA161 MRSA, tetM | SA158 tetK | EF103 29212 | EF159 tetM | SP106 49619 | SP160 tetM | EC107 25922 | EC155 tetA | AB110 19606 | PA111 27853 | EC108 13047 | KP109 13883 | KP153 tetA |
|---|---|---|---|---|---|---|---|---|---|---|---|---|---|---|---|
| S15-13-216 | C | B | A | B | B | B | C | C | C | C | C | C | C | C | C |
| S15-13-217 | B | B | B | B | B | B | C | B | B | B | C | C | C | C | C |
| S15-13-218 | B | B | B | B | B | B | C | B | B | B | A | C | B | B | B |
| S15-13-219 | B | B | B | B | B | B | C | C | B | B | C | C | C | B | C |
| S15-13-220 | B | A | C | A | B | C | A | B | B | B | C | B | A | A | A |
| S15-13-221 | B | B | B | B | B | B | B | B | B | B | A | C | B | B | B |
| S15-13-222 | B | A | C | A | B | B | A | B | A | A | A | B | A | A | A |
| S15-13-226 | B | B | B | A | B | B | A | B | B | B | A | B | B | B | B |
| S15-13-227 | B | B | B | B | B | B | B | B | C | C | C | C | C | C | C |
| S15-14-8 | C | B | C | B | NT | C | NT | B | B | B | NT | NT | NT | NT | A |
| S24-9-1 | B | B | C | B | B | C | A | B | B | B | B | B | A | B | B |
| S24-9-10 | B | B | B | B | B | B | A | B | B | A | B | B | A | B | A |
| S24-9-11 | B | B | C | B | B | C | B | B | B | B | C | A | B | B | B |
| S24-9-12 | B | B | B | B | B | B | B | B | B | B | C | B | B | B | B |
| S24-9-13 | B | B | C | B | B | B | B | B | B | B | C | B | B | B | B |
| S24-9-14 | B | B | C | B | B | C | B | B | B | C | C | A | B | A | C |
| S24-9-15 | A | B | C | A | B | C | A | B | B | B | A | B | B | B | B |
| S24-9-16 | B | B | C | B | B | B | A | B | B | B | A | C | B | B | B |
| S24-9-17 | B | B | B | B | B | B | B | B | B | B | C | B | B | B | A |
| S24-9-18 | B | B | B | B | B | B | B | B | B | B | C | B | B | B | B |
| S24-9-19 | B | B | B | B | B | B | A | B | B | A | A | B | B | B | A |
| S24-9-20 | B | B | C | B | B | C | B | B | B | B | C | B | B | B | B |
| S24-9-21 | B | B | B | B | B | B | A | B | B | A | B | B | B | B | A |
| S24-9-24 | B | B | C | B | B | C | A | B | B | B | A | C | B | B | B |
| S24-9-3 | C | B | C | A | B | B | A | B | B | B | A | C | B | B | B |
| S24-9-4 | C | B | C | B | B | C | A | B | B | B | A | C | B | B | B |
| S24-9-5 | B | B | B | B | B | B | A | B | B | B | A | B | B | B | B |
| S24-9-6 | B | B | C | B | B | C | A | B | B | B | A | B | A | B | B |
| S24-9-7 | C | B | C | B | B | C | B | B | B | B | C | B | B | B | C |
| S24-9-8 | B | B | C | B | B | B | B | B | B | B | C | B | B | B | A |
| S24-9-9 | B | B | B | B | B | B | A | B | B | B | A | C | B | B | B |
| S25-11-208 | A | A | C | A | B | C | A | B | B | B | A | B | A | A | B |
| S27-9-1 | C | C | C | B | B | C | B | B | B | B | A | C | B | B | B |

FIG. 8B

| Compound | SA101 29213 | SA100 13709 | SA161 MRSA, tetM | SA158 tetK | EF103 29212 | EF159 tetM | SP106 49619 | SP160 tetM | EC107 25922 | EC155 tetA | AB110 19606 | PA111 27853 | EC108 13047 | KP109 13883 | KP153 tetA |
|---|---|---|---|---|---|---|---|---|---|---|---|---|---|---|---|
| **S27-9-2** | C | B | C | B | B | B | A | B | B | B | A | C | B | B | B |
| **S27-9-4** | C | B | B | B | B | B | B | B | B | B | A | C | B | B | B |
| **S33-8-1** | C | B | C | B | B | B | A | B | B | B | C | C | B | B | B |
| **S33-8-2** | C | C | B | B | B | B | C | C | C | C | C | C | C | C | C |
| **S33-8-3** | C | B | C | B | B | C | B | B | B | B | C | C | B | B | B |
| **S6-4-2** | C | B | C | B | C | C | B | C | B | C | C | C | C | C | C |
| **Sancycline** | 0.5 | 1 | | 4 | 8 | 8 | 0.25 | 8 | 8 | 32 | 0.25 | 33 | 8 | 8 | 32 |
| **Minocycline** | 0.063 | 0.063 | 8 | 0.031 | 1 | 16 | 0.016 | 2 | 0.5 | 8 | 0.063 | 16 | 2 | 1 | 8 |
| **Tigecycline** | 0.063 | 0.063 | 0.125 | 0.063 | 0.03 | 0.063 | 0.016 | 0.016 | 0.03 | 0.5 | 0.25 | 8 | 0.25 | 0.125 | 1 |

FIG. 8C

| Compound | SA101 29213 | SA100 13709 | SA161 MRSA, tetM | SA158 tetK | EF103 29212 | EF159 tetM | SP106 49619 | SP160 tetM | EC107 25922 | EC155 tetA | AB110 19606 | PA111 27853 | EC108 13047 | KP109 13883 | KP153 tetA |
|---|---|---|---|---|---|---|---|---|---|---|---|---|---|---|---|
| S1-14-115 | C | C | C | B | C | C | C | C | B | B | C | C | C | C | B |
| S1-14-116 | C | C | C | B | C | C | B | C | C | C | C | C | C | C | C |
| S1-14-117 | B | B | C | B | B | C | A | B | B | B | A | B | B | B | B |
| S1-14-118 | C | B | B | B | B | B | C | C | B | B | C | C | C | B | B |
| S1-14-119 | C | C | C | B | C | C | C | C | C | B | C | C | C | C | C |
| S1-14-120 | C | B | C | A | B | B | A | B | B | B | A | B | B | B | A |
| S1-14-121 | C | B | C | B | B | C | B | B | B | B | C | C | B | B | B |
| S1-14-122 | C | B | B | B | B | B | B | B | B | B | B | B | B | B | B |
| S1-14-123 | C | B | C | B | B | C | B | B | B | B | C | B | B | B | B |
| S1-14-124 | C | B | C | B | B | C | A | B | B | B | C | B | A | B | B |
| S1-14-125 | C | B | B | A | B | B | A | B | B | B | A | C | B | B | B |
| S1-14-126 | C | B | B | B | B | B | B | B | B | B | C | C | B | B | B |
| S1-14-127 | B | B | B | B | B | B | B | B | B | B | B | C | B | B | B |
| S1-14-128 | C | A | B | A | B | B | A | B | B | B | A | B | B | B | A |
| S1-14-129 | C | B | B | B | B | B | B | C | C | C | C | C | C | C | C |
| S1-14-131 | C | B | C | B | B | C | B | B | B | B | C | B | B | B | B |
| S1-14-132 | C | B | C | B | B | B | A | B | B | B | A | C | B | B | B |
| S1-14-135 | B | B | B | B | B | B | B | B | B | B | A | C | B | B | B |
| S1-14-137 | C | B | C | B | B | C | B | B | B | B | C | C | B | B | B |
| S114-138 | B | B | C | B | B | C | A | B | B | C | C | B | B | B | C |
| S114-139 | B | B | C | B | B | C | A | B | B | B | C | B | B | B | B |
| S1-14-140 | C | B | B | B | B | B | B | B | B | B | C | C | C | B | B |
| S1-14-141 | C | B | B | B | B | B | C | B | B | B | C | C | C | C | C |
| S1-14-142 | C | B | B | B | B | B | B | B | B | B | B | C | C | B | B |
| S1-14-143 | C | B | B | B | B | B | C | B | C | C | C | C | C | C | C |
| S1-14-144 | C | B | C | B | B | C | A | B | B | B | A | C | B | B | B |
| S1-14-145 | C | B | C | B | B | B | A | B | B | B | A | C | B | B | B |
| S1-14-146 | C | B | B | B | B | B | C | C | C | C | C | C | C | C | C |
| S1-14-147 | B | B | C | B | B | C | A | B | B | C | A | C | B | B | B |
| S1-14-148 | B | B | C | B | B | B | A | B | B | B | A | C | B | B | B |
| S1-14-149 | C | B | C | B | B | C | A | B | B | B | A | C | B | B | B |
| S15-13-180 | B | B | B | B | B | B | B | B | B | B | A | C | B | B | B |

FIG. 8D

| Cmpd | SA1 01 292 13 | SA1 00 137 09 | SA1 61 tetM | SA1 58 tetK | SE1 64 122 28 | EF1 59 tetM | SP1 06 496 19 | SP1 60 tetM | SP1 93 866 8 | HI2 62 339 29 | MC 205 817 6 | EC1 07 259 22 | EC1 55 tetA | KP1 53 tetA | KP1 94 700 603 | PM1 12 356 59 | PA1 69 | PA1 73 | AB2 50 | SM2 56 | BC2 40 |
|---|---|---|---|---|---|---|---|---|---|---|---|---|---|---|---|---|---|---|---|---|---|
| S1-14-130 | C | B | C | B | A | C | A | B | B | A | B | B | B | B | B | B | C | A | A | C | C |
| S1-14-133 | B | B | C | B | A | B | NT | C | B | NT | B | B | B | C | NT | B | A | A | A | C | C |
| S1-14-134 | B | B | B | B | A | B | NT | B | B | A | B | B | B | B | NT | B | B | A | C | A | A |
| S1-14-136 | C | C | B | B | B | B | C | C | C | C | C | C | C | C | C | C | C | C | C | C | C |
| S15-13-116 | C | B | B | B | A | B | B | C | B | C | C | B | B | C | C | B | C | C | C | C | A |
| S15-13-117 | B | B | B | B | A | B | A | B | A | A | A | B | B | B | B | B | C | B | A | C | A |
| S15-13-118 | C | B | B | B | B | B | C | C | C | C | C | C | B | C | C | C | C | C | C | C | C |
| S15-13-119 | C | B | B | B | A | B | A | B | A | A | A | B | B | B | A | B | C | A | A | C | A |
| S15-13-120 | B | B | C | B | A | C | A | B | A | A | A | B | B | B | A | A | B | A | A | C | B |
| S15-13-123 | C | C | B | B | B | B | B | B | B | C | C | B | B | C | C | C | C | C | C | C | C |
| S15-13-124 | C | B | B | B | B | B | C | C | C | C | C | C | C | C | C | C | C | C | C | C | C |
| S15-13-125 | C | B | C | B | A | C | A | B | A | A | B | B | C | B | C | B | C | A | C | C | C |
| S15-13-126 | C | C | C | B | B | B | C | C | C | C | C | B | B | C | C | C | C | C | C | C | C |
| S15-13-127 | C | C | B | B | B | B | C | C | C | C | C | C | B | C | C | C | C | C | C | C | C |
| S15-13-128 | C | NT | B | B | B | B | B | C | NT | C | C | C | C | C | C | C | NT | NT | C | C | C |
| S15-13-131 | C | B | B | B | A | B | A | B | A | A | A | B | B | B | B | B | C | A | A | C | C |
| S15-13-132 | C | C | B | B | A | B | B | C | B | C | C | B | B | B | C | C | C | C | A | C | C |
| S15-13-168 | C | B | C | B | A | B | A | B | A | A | A | B | B | B | B | B | C | A | A | C | A |
| S15-13-169 | C | B | C | B | A | B | A | B | B | A | C | B | B | B | C | C | C | A | A | C | C |
| S15-13-17 | B | B | B | A | A | B | B | B | B | C | B | B | B | C | NT | B | C | A | A | C | C |
| S15-13-174 | C | B | C | B | B | C | A | B | B | A | B | B | C | C | C | B | C | A | C | C | C |
| S15-13-175 | C | C | C | C | C | B | C | C | C | C | C | C | C | C | C | C | C | C | C | C | C |
| S15-13-177 | C | C | B | B | B | B | C | C | C | C | C | C | C | C | C | C | C | C | C | C | C |
| S15-13-178 | C | B | C | B | A | B | A | B | A | C | B | B | B | B | C | C | C | B | A | C | C |

FIG. 9A

| Cmpd | SA1 01 292 13 | SA1 00 137 09 | SA1 61 tetM | SA1 58 tetK | SE1 64 122 28 | EF1 59 tetM | SP1 06 496 19 | SP1 60 tetM | SP1 93 866 8 | HI2 62 339 29 | MC 205 817 6 | EC1 07 259 22 | EC1 55 tetA | KP1 53 tetA | KP1 94 700 603 | PM1 12 356 59 | PA1 69 | PA1 73 | AB2 50 | SM2 56 | BC2 40 |
|---|---|---|---|---|---|---|---|---|---|---|---|---|---|---|---|---|---|---|---|---|---|
| S15-13-18 | B | B | B | B | A | B | B | B | A | A | B | B | B | B | A | A | B | A | A | NT | A |
| S15-13-19 | B | B | C | C | A | B | B | B | A | A | B | B | B | B | A | A | A | A | A | NT | B |
| S15-13-20 | B | B | C | B | A | B | B | B | A | A | B | B | B | B | A | A | A | A | A | NT | B |
| S15-13-202 | B | B | B | B | A | B | B | B | B | C | B | B | B | B | B | C | C | A | A | C | C |
| S15-13-203 | B | B | B | B | A | B | B | B | B | A | B | B | B | A | NT | A | C | A | A | A | A |
| S15-13-21 | C | C | C | B | B | C | A | C | B | A | C | B | C | C | C | C | C | A | C | C | C |
| S15-13-22 | C | C | C | B | B | C | A | C | B | A | C | B | C | C | C | C | C | A | C | C | C |
| S15-13-223 | B | B | B | A | A | B | B | B | A | A | B | A | A | A | A | B | B | A | A | A | C |
| S15-13-224 | B | B | B | B | A | B | B | B | B | A | B | B | B | A | B | B | C | A | A | C | C |
| S15-13-225 | B | B | B | B | A | B | B | B | A | A | B | B | B | A | B | B | C | A | A | NT | C |
| S15-13-228 | C | C | B | B | B | C | B | C | C | C | C | C | C | C | C | C | C | C | C | C | C |
| S15-13-229 | C | C | C | B | C | C | B | C | B | C | C | C | C | C | C | C | C | C | C | C | C |
| S15-13-23 | B | B | B | A | A | B | A | B | B | C | A | B | B | B | B | B | C | A | A | C | A |
| S15-13-230 | C | C | B | B | B | B | C | C | C | C | C | C | C | C | C | C | C | C | C | NT | C |
| S15-13-24 | C | B | B | B | A | B | A | B | B | A | C | B | B | B | C | C | C | A | A | C | C |
| S15-13-25 | C | B | B | B | B | B | B | B | B | C | C | C | B | C | C | C | C | C | C | C | B |
| S15-13-26 | C | C | B | B | B | B | C | C | C | C | C | C | C | C | C | C | C | C | C | C | NT |
| S15-13-27 | C | C | B | B | B | B | B | B | B | C | C | C | C | C | C | C | C | C | C | C | C |
| S15-13-28 | C | C | B | B | B | B | C | C | C | C | C | C | C | C | C | C | C | C | C | C | C |
| S15-13-29 | B | B | B | A | A | B | A | B | A | A | A | B | B | B | C | B | C | A | A | C | B |
| S15-13-31 | C | C | B | B | B | B | B | B | C | C | C | B | B | B | C | C | C | C | C | C | C |
| S15-13-32 | C | C | B | B | B | B | C | C | C | C | C | B | B | B | C | C | C | C | C | C | C |
| S15-13-34 | C | B | B | B | A | B | B | B | B | A | B | B | B | B | B | B | C | A | A | C | B |
| S15-13-35 | C | B | C | A | A | B | A | B | B | A | A | B | B | B | A | A | C | A | A | C | A |

FIG. 9B

| Cmpd | SA1 01 292 13 | SA1 00 137 09 | SA1 61 tetM | SA1 58 tetK | SE1 64 122 28 | EF1 59 tetM | SP1 06 496 19 | SP1 60 tetM | SP1 93 866 8 | HI2 62 339 29 | MC 205 817 6 | EC1 07 259 22 | EC1 55 tetA | KP1 53 tetA | KP1 94 700 603 | PM1 12 356 59 | PA1 69 | PA1 73 | AB2 50 | SM2 56 | BC2 40 |
|---|---|---|---|---|---|---|---|---|---|---|---|---|---|---|---|---|---|---|---|---|---|
| S15-13-36 | C | B | C | B | A | C | A | B | A | A | A | B | C | B | B | A | C | A | A | C | C |
| S15-13-37 | C | B | C | B | A | B | A | B | B | A | B | B | B | B | C | C | C | B | A | C | C |
| S15-13-38 | C | B | B | B | B | B | B | C | C | C | C | B | B | B | C | C | C | C | A | C | C |
| S15-13-39 | C | B | B | B | B | B | B | C | C | C | C | B | B | C | C | C | C | C | C | C | C |
| S15-13-40 | C | NT | B | B | B | B | B | B | NT | C | C | B | B | B | C | B | NT | NT | C | C | A |
| S15-13-41 | C | NT | C | B | B | C | B | C | NT | A | C | B | C | C | C | B | NT | NT | C | C | C |
| S15-13-42 | B | NT | B | A | A | B | A | B | NT | A | A | B | B | B | B | B | NT | NT | A | C | B |
| S15-13-43 | C | NT | C | A | A | B | A | B | NT | A | A | B | B | B | A | B | NT | NT | A | C | B |
| S15-13-44 | B | NT | C | B | A | C | A | B | NT | A | A | B | B | B | B | A | NT | NT | A | C | C |
| S15-13-45 | C | NT | B | B | B | B | C | C | NT | C | C | C | C | C | C | C | NT | NT | C | C | C |
| S15-13-46 | C | NT | C | C | B | B | C | C | NT | C | C | C | C | C | C | C | NT | NT | C | C | C |
| S15-13-47 | C | NT | B | B | B | B | C | C | NT | C | C | C | C | C | C | C | NT | NT | C | C | C |
| S15-13-48 | C | NT | C | C | B | B | C | C | NT | C | C | C | C | C | C | C | NT | NT | C | C | C |
| S15-13-81 | B | B | C | A | A | B | A | B | A | A | A | B | B | B | A | A | B | A | A | C | A |
| S15-13-82 | B | A | C | A | A | B | A | B | A | A | A | A | B | B | A | B | B | A | A | C | A |
| S15-13-83 | C | C | C | B | A | B | B | B | B | C | C | B | B | B | C | C | C | C | C | C | B |
| S15-13-84 | C | C | C | B | A | C | A | B | B | C | B | B | B | B | C | C | C | A | A | C | C |
| S15-13-87 | C | C | B | B | B | B | C | C | C | C | C | C | C | C | C | C | C | C | C | C | C |
| S15-14-6 | C | B | C | B | A | C | A | B | B | A | C | B | B | B | A | A | C | A | C | C | C |
| S16-10-101 | B | B | C | B | A | C | A | B | A | A | C | B | B | B | B | B | C | A | A | C | C |
| S16-10-102 | B | B | C | B | A | C | B | B | B | A | B | B | B | B | NT | B | C | A | C | C | C |
| S16-10-106 | C | B | C | B | A | C | A | B | B | A | B | B | B | B | B | B | C | A | C | C | C |
| S16-10-107 | C | B | C | B | A | C | A | B | B | A | B | B | A | A | B | B | C | A | A | C | C |
| S16-10-110 | C | B | C | B | A | C | B | B | B | A | B | B | B | B | B | B | C | A | C | C | C |

FIG. 9C

| Cmpd | SA1 01 292 13 | SA1 00 137 09 | SA1 61 tetM | SA1 58 tetK | SE1 64 122 28 | EF1 59 tetM | SP1 06 496 19 | SP1 60 tetM | SP1 93 866 8 | HI2 62 339 29 | MC 205 817 6 | EC1 07 259 22 | EC1 55 tetA | KP1 53 tetA | KP1 94 700 603 | PM1 12 356 59 | PA1 69 | PA1 73 | AB2 50 | SM2 56 | BC2 40 |
|---|---|---|---|---|---|---|---|---|---|---|---|---|---|---|---|---|---|---|---|---|---|
| S16-10-116 | C | B | C | B | A | C | A | B | B | A | C | B | C | C | B | B | C | A | A | C | C |
| S16-10-117 | B | B | B | B | A | B | NT | B | B | NT | B | B | B | B | NT | B | B | A | C | C | B |
| S16-10-119 | C | B | C | B | A | B | A | B | B | C | B | B | B | B | B | B | C | A | C | C | C |
| S16-10-120 | B | B | C | B | A | B | NT | B | B | NT | B | B | B | B | NT | B | C | A | C | C | C |
| S16-10-121 | C | B | C | B | A | C | A | B | B | C | C | B | B | B | C | C | C | A | A | C | C |
| S16-10-123 | C | B | B | B | A | B | A | B | B | C | B | B | B | B | C | C | C | A | C | C | C |
| S16-10-126 | B | B | B | B | A | B | A | B | A | C | A | B | B | B | C | C | C | A | C | C | C |
| S16-10-129 | C | B | C | B | A | C | A | B | B | A | B | B | B | B | B | B | C | A | C | C | C |
| S16-10-132 | B | B | B | A | A | C | A | B | A | A | B | B | B | B | B | B | C | A | A | C | B |
| S16-10-135 | B | B | B | B | A | B | A | B | B | C | B | B | B | B | C | C | C | A | A | C | C |
| S16-10-136 | C | B | B | B | A | B | A | B | B | C | B | B | B | B | C | C | C | B | C | C | C |
| S16-10-138 | C | B | B | B | A | B | A | B | A | C | C | B | B | B | C | C | C | A | C | C | C |
| S16-10-139 | B | B | C | B | A | C | NT | B | B | NT | B | B | B | B | NT | B | C | A | C | C | C |
| S16-10-143 | C | B | C | B | A | C | A | B | B | A | B | B | B | B | B | A | C | A | A | C | C |
| S16-10-144 | B | B | C | NT | A | C | B | B | B | A | B | B | B | B | NT | B | C | A | A | C | C |
| S16-10-145 | B | B | C | B | A | C | NT | B | B | NT | B | B | B | B | NT | A | B | A | A | C | C |
| S16-10-146 | C | B | C | B | B | C | B | B | B | C | C | B | B | B | NT | C | C | A | C | C | C |
| S16-10-147 | C | B | C | B | A | C | B | B | B | A | C | B | B | B | B | B | C | A | C | C | C |
| S16-10-148 | C | C | B | B | B | B | C | C | C | C | C | C | C | C | C | C | C | C | C | C | C |
| S16-10-149 | B | B | C | B | A | C | NT | B | B | A | B | B | B | B | NT | B | C | A | C | C | C |
| S16-10-150 | C | B | C | B | A | C | NT | B | B | NT | C | B | B | B | NT | C | C | A | C | C | C |
| S16-10-151 | B | A | C | A | A | C | A | B | A | A | A | B | B | B | B | B | C | A | A | A | C |
| S16-10-152 | B | B | C | B | A | C | A | B | A | A | A | B | B | B | B | B | C | A | A | A | C |
| S16-10-153 | C | C | B | B | B | B | B | C | B | C | C | C | C | C | C | C | C | C | A | C | C |

FIG. 9D

| Cmpd | SA1 01 292 13 | SA1 00 137 09 | SA1 61 tetM | SA1 58 tetK | SE1 64 122 28 | EF1 59 tetM | SP1 06 496 19 | SP1 60 tetM | SP1 93 866 8 | HI2 62 339 29 | MC 205 817 6 | EC1 07 259 22 | EC1 55 tetA | KP1 53 tetA | KP1 94 700 603 | PM1 12 356 59 | PA1 69 | PA1 73 | AB2 50 | SM2 56 | BC2 40 |
|---|---|---|---|---|---|---|---|---|---|---|---|---|---|---|---|---|---|---|---|---|---|
| S16-10-154 | C | B | C | B | A | B | B | B | B | C | B | B | B | B | C | C | C | A | C | C | C |
| S16-10-155 | C | B | C | B | A | C | B | B | B | C | C | B | B | B | C | C | C | A | C | C | C |
| S16-10-156 | C | B | C | B | B | C | B | B | B | C | C | B | C | B | C | C | C | A | C | C | C |
| S16-10-157 | C | B | C | B | B | C | B | B | B | C | C | B | C | C | C | C | C | A | C | C | C |
| S16-10-158 | B | B | C | B | A | C | A | B | A | A | A | B | B | A | C | B | C | A | A | C | C |
| S16-10-159 | B | B | C | B | A | C | B | B | B | C | B | B | B | B | NT | B | C | A | A | C | C |
| S16-10-160 | C | B | B | B | A | B | B | B | B | C | B | B | B | B | C | C | C | A | A | C | NT |
| S16-10-161 | B | B | C | NT | A | C | B | B | B | A | B | B | B | B | NT | B | C | A | A | C | C |
| S16-10-162 | B | B | C | B | A | C | A | B | B | A | B | B | B | B | B | B | C | A | A | C | C |
| S16-10-163 | C | C | C | B | A | B | B | B | B | C | C | B | B | B | C | C | C | B | C | C | C |
| S16-10-164 | B | B | C | B | A | C | A | B | A | C | A | B | B | B | C | C | C | A | C | C | C |
| S16-10-165 | C | B | C | B | A | B | C | B | B | C | C | B | B | B | C | C | C | A | C | C | C |
| S16-10-166 | C | B | C | B | A | C | A | B | B | C | B | B | B | B | C | C | C | A | C | C | C |
| S16-10-167 | C | B | C | B | A | C | B | B | B | C | C | B | B | A | C | C | C | A | C | C | C |
| S16-10-168 | C | C | C | B | A | B | B | B | B | C | C | B | B | B | C | C | C | B | C | C | C |
| S16-10-169 | C | C | C | B | B | C | B | B | B | C | C | B | B | B | B | B | C | A | C | C | C |
| S16-10-170 | C | B | C | B | B | C | B | B | B | A | C | B | B | B | C | B | C | A | C | C | C |
| S16-10-171 | C | B | C | B | A | C | B | B | B | A | B | B | B | B | NT | B | C | A | A | C | C |
| S16-10-172 | C | B | C | B | A | C | A | B | B | C | B | B | B | B | C | C | C | A | A | C | NT |
| S16-10-173 | C | C | C | B | A | C | A | B | B | C | C | B | B | B | C | C | C | B | A | C | C |
| S16-10-174 | C | B | C | B | A | C | A | B | B | C | B | B | B | B | C | C | C | A | C | C | C |
| S16-10-175 | B | B | C | B | A | C | A | B | B | A | B | B | B | B | B | B | C | A | C | C | C |
| S16-10-176 | B | B | C | NT | A | C | B | B | B | C | B | B | B | B | NT | C | C | A | A | C | C |
| S16-10-177 | B | B | C | B | A | C | A | B | B | A | B | B | B | A | B | B | C | A | A | C | C |

FIG. 9E

| Cmpd | SA1 01 292 13 | SA1 00 137 09 | SA1 61 tetM | SA1 58 tetK | SE1 64 122 28 | EF1 59 tetM | SP1 06 496 19 | SP1 60 tetM | SP1 93 866 8 | HI2 62 339 29 | MC 205 817 6 | EC1 07 259 22 | EC1 55 tetA | KP1 53 tetA | KP1 94 700 603 | PM1 12 356 59 | PA1 69 | PA1 73 | AB2 50 | SM2 56 | BC2 40 |
|---|---|---|---|---|---|---|---|---|---|---|---|---|---|---|---|---|---|---|---|---|---|
| S16-10-178 | C | C | C | B | B | C | B | B | B | C | C | B | B | B | C | B | B | A | C | C | C |
| S16-10-179 | C | B | C | B | A | C | A | B | B | A | B | B | B | B | C | C | C | A | A | C | C |
| S16-10-28 | C | B | C | B | A | C | B | B | B | A | C | B | B | B | B | B | C | A | C | C | C |
| S16-10-33 | C | B | C | B | A | B | A | C | B | C | C | C | C | C | C | C | C | C | C | C | C |
| S16-10-36 | C | B | C | B | B | C | NT | C | B | NT | C | B | C | C | NT | B | C | A | C | C | C |
| S16-10-37 | B | B | C | B | A | C | A | B | B | A | B | B | B | B | A | B | C | A | A | C | C |
| S16-10-38 | C | B | C | B | B | C | B | B | B | C | C | B | B | B | C | B | C | A | C | C | C |
| S16-10-39 | C | B | C | B | B | C | NT | B | B | NT | C | B | C | C | NT | B | C | A | C | C | C |
| S16-10-40 | B | B | C | B | A | C | A | B | A | A | B | B | B | B | C | B | C | A | A | C | C |
| S16-10-42 | B | B | C | B | A | C | NT | B | B | NT | B | B | B | B | NT | B | C | A | C | C | C |
| S16-10-43 | C | B | C | B | A | C | A | B | A | C | B | B | B | B | C | C | C | A | A | C | C |
| S16-10-45 | C | B | C | B | A | C | A | B | B | C | C | B | B | B | C | C | C | A | A | C | C |
| S16-10-46 | C | B | B | B | A | B | A | B | B | C | B | B | B | B | B | B | C | A | A | C | B |
| S16-10-48 | B | B | B | NT | A | B | B | B | A | C | B | B | B | B | NT | B | C | A | A | C | C |
| S16-10-49 | B | B | C | B | A | B | NT | B | B | NT | B | B | B | B | NT | C | C | A | C | C | C |
| S16-10-52 | C | B | C | B | A | C | A | B | B | A | C | B | C | C | C | B | C | A | C | C | C |
| S16-10-53 | C | B | C | B | A | C | A | B | B | C | B | B | B | B | C | C | C | A | C | C | C |
| S16-10-54 | B | B | C | B | A | C | A | B | B | C | B | B | B | B | C | C | C | A | A | C | C |
| S16-10-55 | C | B | C | B | B | C | B | B | B | C | C | B | C | B | C | C | C | A | C | C | C |
| S16-10-61 | C | B | C | NT | A | C | B | B | B | C | B | B | B | B | NT | B | C | A | C | C | C |
| S16-10-64 | B | B | B | A | A | B | B | B | A | C | B | B | B | B | NT | C | C | A | A | C | C |
| S16-10-65 | C | B | B | B | A | B | A | B | B | C | B | B | B | B | C | C | C | B | C | C | C |
| S16-10-67 | B | B | C | B | A | C | B | B | B | C | B | B | B | B | NT | B | C | A | A | C | C |
| S16-10-69 | C | B | C | A | A | B | A | B | A | C | B | B | B | B | C | C | C | A | A | C | C |

FIG. 9F

| Cmpd | SA1 01 292 13 | SA1 00 137 09 | SA1 61 tetM | SA1 58 tetK | SE1 64 122 28 | EF1 59 tetM | SP1 06 496 19 | SP1 60 tetM | SP1 93 866 8 | HI2 62 339 29 | MC 205 817 6 | EC1 07 259 22 | EC1 55 tetA | KP1 53 tetA | KP1 94 700 603 | PM1 12 356 59 | PA1 69 | PA1 73 | AB2 50 | SM2 56 | BC2 40 |
|---|---|---|---|---|---|---|---|---|---|---|---|---|---|---|---|---|---|---|---|---|---|
| S16-10-71 | C | B | B | B | A | B | A | B | B | C | B | B | B | B | C | C | C | A | C | C | C |
| S16-10-72 | C | C | B | B | A | B | A | B | B | C | C | B | B | B | C | C | C | C | A | C | C |
| S16-10-73 | C | C | B | B | B | B | B | B | B | C | C | B | B | B | C | C | C | C | C | C | C |
| S16-10-74 | B | B | B | NT | A | B | B | B | B | C | B | B | B | B | NT | C | C | A | A | C | C |
| S16-10-75 | C | B | B | B | A | B | A | B | B | C | B | B | B | B | C | C | C | C | C | C | C |
| S16-10-79 | B | B | B | NT | A | B | B | B | B | C | B | B | B | B | NT | C | C | A | A | C | C |
| S16-10-83 | C | B | C | B | A | B | A | B | B | C | C | B | B | B | C | C | C | A | C | C | C |
| S16-10-86 | C | B | C | B | A | C | B | B | B | A | C | B | B | B | B | B | C | A | C | C | C |
| S16-10-88 | C | B | C | B | A | C | NT | B | B | NT | C | B | B | B | NT | B | C | A | C | C | C |
| S16-10-89 | C | B | C | B | A | C | A | B | B | A | C | B | B | B | C | C | C | A | C | C | C |
| S16-10-91 | C | B | C | B | A | C | A | B | B | A | C | B | B | B | C | C | C | A | C | C | C |
| S16-10-92 | B | B | C | B | A | C | A | B | A | A | B | B | B | A | B | C | C | A | A | C | C |
| S16-10-95 | B | B | C | NT | A | C | B | B | B | C | B | B | B | B | NT | B | C | A | C | C | C |
| S2-4-69 | C | C | B | B | B | B | C | B | C | C | C | C | C | C | NT | C | C | C | C | C | C |
| S24-9-125 | B | B | C | B | A | B | A | B | B | A | B | B | B | A | A | B | B | A | A | C | C |
| S24-9-126 | B | NT | C | B | A | B | A | B | NT | A | A | B | B | B | C | C | NT | NT | A | C | C |
| S24-9-127 | B | NT | C | B | A | B | A | B | NT | A | B | B | B | B | B | B | NT | NT | A | C | C |
| S24-9-128 | B | NT | C | B | A | B | A | B | NT | A | A | B | B | B | C | C | NT | NT | A | A | B |
| S24-9-129 | C | NT | B | A | A | B | A | B | NT | C | A | B | B | B | C | C | NT | NT | A | C | B |
| S24-9-130 | B | NT | C | A | A | B | A | B | NT | A | B | B | B | B | B | C | NT | NT | A | A | A |
| S24-9-131 | B | NT | C | B | A | B | A | B | NT | A | A | B | B | B | B | C | NT | NT | A | C | C |
| S24-9-132 | C | NT | B | B | A | B | A | B | NT | C | B | B | B | B | C | C | NT | NT | A | C | C |
| S24-9-180 | C | NT | B | B | B | B | C | C | NT | C | C | C | C | C | C | C | NT | NT | C | C | C |
| S24-9-2 | B | B | C | B | A | C | B | B | B | A | C | B | B | B | NT | B | C | A | C | C | C |

FIG. 9G

| Cmpd | SA1 01 292 13 | SA1 00 137 09 | SA1 61 tetM | SA1 58 tetK | SE1 64 122 28 | EF1 59 tetM | SP1 06 496 19 | SP1 60 tetM | SP1 93 866 8 | HI2 62 339 29 | MC 205 817 6 | EC1 07 259 22 | EC1 55 tetA | KP1 53 tetA | KP1 94 700 603 | PM1 12 356 59 | PA1 69 | PA1 73 | AB2 50 | SM2 56 | BC2 40 |
|---|---|---|---|---|---|---|---|---|---|---|---|---|---|---|---|---|---|---|---|---|---|
| S24-9-22 | B | B | C | B | A | B | NT | B | B | NT | B | B | B | B | NT | B | C | A | A | C | C |
| S24-9-23 | B | B | C | B | A | B | NT | B | B | NT | B | B | B | A | NT | A | A | A | A | C | C |
| S24-9-25 | B | B | B | B | A | B | B | B | A | A | B | A | A | A | A | B | B | A | A | A | C |
| S24-9-26 | C | B | C | B | A | C | B | B | B | A | B | B | B | A | A | B | C | A | A | C | C |
| S24-9-27 | B | B | C | B | A | C | A | B | B | C | B | B | C | C | C | C | C | A | A | C | C |
| S24-9-28 | C | NT | C | B | A | C | B | B | NT | A | B | B | C | B | A | A | NT | NT | C | C | C |
| S24-9-30 | C | NT | C | B | A | C | A | B | NT | A | B | B | C | B | A | A | NT | NT | C | C | C |
| S24-9-31 | B | NT | B | B | A | B | A | B | NT | A | B | B | A | A | A | B | NT | NT | A | C | B |
| S24-9-32 | C | NT | C | B | A | C | A | B | NT | A | B | B | B | B | B | B | NT | NT | A | C | C |
| S24-9-80 | B | B | C | A | A | B | A | B | A | C | A | B | B | B | B | B | C | A | A | C | C |
| S24-9-81 | B | B | C | B | A | B | A | B | B | A | B | B | B | B | B | B | C | A | A | C | C |
| S24-9-82 | C | B | C | B | A | C | A | B | B | A | B | B | B | B | A | A | A | A | C | C | C |
| S24-9-83 | C | NT | B | B | A | B | A | B | NT | C | C | B | B | B | C | C | NT | NT | A | C | C |
| S24-9-84 | B | NT | B | B | A | B | A | B | NT | A | B | B | B | B | C | B | NT | NT | A | C | B |
| S24-9-92 | B | NT | C | B | A | B | A | B | NT | A | B | B | B | A | B | A | NT | NT | A | C | C |
| S24-9-93 | C | B | B | B | A | B | A | B | A | C | B | B | B | B | C | C | C | C | A | C | B |
| S25-11-1 | A | A | C | A | A | B | A | B | A | A | A | A | B | A | A | A | A | A | A | A | B |
| S25-11-10 | C | C | B | B | B | B | B | B | B | C | C | B | B | C | C | C | C | C | A | C | C |
| S25-11-11 | C | B | B | B | B | B | B | B | B | C | C | C | B | C | C | C | C | C | A | C | C |
| S25-11-12 | C | B | B | B | A | B | A | B | B | C | B | B | B | B | C | C | C | A | A | C | B |
| S25-11-13 | B | A | B | A | A | B | A | B | A | A | A | B | B | B | A | B | B | A | A | C | NT |
| S25-11-14 | B | B | C | B | A | C | A | B | A | A | A | B | B | B | A | A | B | A | A | C | A |
| S25-11-15 | B | B | C | B | A | C | A | B | A | A | A | B | B | B | B | B | B | A | A | C | A |
| S25-11-16 | C | C | B | B | B | B | C | C | C | C | C | C | C | C | C | C | C | C | C | C | C |

FIG. 9H

| Cmpd | SA1 01 292 13 | SA1 00 137 09 | SA1 61 tetM | SA1 58 tetK | SE1 64 122 28 | EF1 59 tetM | SP1 06 496 19 | SP1 60 tetM | SP1 93 866 8 | HI2 62 339 29 | MC 205 817 6 | EC1 07 259 22 | EC1 55 tetA | KP1 53 tetA | KP1 94 700 603 | PM1 12 356 59 | PA1 69 | PA1 73 | AB2 50 | SM2 56 | BC2 40 |
|---|---|---|---|---|---|---|---|---|---|---|---|---|---|---|---|---|---|---|---|---|---|
| S25-11-164 | C | B | B | B | A | B | A | B | B | C | B | B | B | B | C | C | C | B | C | C | A |
| S25-11-165 | A | B | C | A | A | B | A | B | A | C | B | B | B | B | C | C | C | A | A | C | B |
| S25-11-166 | C | C | C | C | B | B | C | C | C | C | C | C | C | C | C | C | C | C | C | C | C |
| S25-11-168 | C | B | B | B | A | B | B | B | B | C | B | B | C | C | C | C | C | C | A | C | NT |
| S25-11-169 | C | B | B | B | B | B | B | B | B | C | B | B | B | B | C | C | C | C | A | C | NT |
| S25-11-17 | C | B | C | B | B | B | A | C | B | C | B | B | C | C | C | C | C | C | C | C | C |
| S25-11-170 | B | A | C | A | A | B | A | B | A | A | A | B | B | B | A | B | C | A | A | C | A |
| S25-11-171 | B | A | B | A | A | B | A | B | A | A | A | B | B | B | B | C | C | B | A | C | B |
| S25-11-172 | B | B | B | B | A | B | A | B | A | C | B | B | B | B | B | B | C | A | A | C | A |
| S25-11-173 | B | B | B | B | A | B | A | B | B | C | B | B | B | B | C | C | C | C | A | C | B |
| S25-11-174 | C | B | B | B | A | B | A | B | B | C | B | B | B | C | C | C | C | C | A | C | B |
| S25-11-175 | B | B | B | B | A | B | A | B | B | C | B | B | B | B | C | C | C | B | A | C | C |
| S25-11-176 | A | B | C | A | A | C | A | B | A | A | A | B | B | B | C | B | C | A | A | C | C |
| S25-11-177 | C | C | C | C | C | B | C | C | C | C | C | C | C | C | C | C | C | C | C | C | C |
| S25-11-178 | C | C | B | B | B | B | B | B | B | C | C | C | C | C | C | C | C | C | C | C | C |
| S25-11-179 | C | B | B | B | A | B | B | B | B | C | C | B | B | C | C | C | C | C | C | C | B |
| S25-11-18 | B | B | C | B | A | C | A | B | A | A | A | B | C | C | C | C | C | A | A | C | C |
| S25-11-180 | C | C | B | C | C | B | C | C | C | C | C | C | C | C | C | C | C | C | C | C | C |
| S25-11-181 | C | C | B | B | B | B | C | C | C | C | C | C | C | C | C | C | C | C | C | C | C |
| S25-11-182 | B | B | B | A | A | B | A | B | A | A | A | A | B | B | A | B | B | A | A | C | A |
| S25-11-183 | B | B | C | A | A | C | A | B | A | A | A | B | B | B | A | A | B | A | A | C | B |
| S25-11-184 | C | B | B | B | B | B | C | C | C | C | C | B | C | C | C | C | C | C | C | C | B |
| S25-11-185 | C | C | B | B | B | B | C | C | C | C | C | C | C | C | C | C | C | C | C | C | C |
| S25-11-186 | C | C | C | B | C | B | C | C | C | C | C | C | C | C | C | C | C | C | C | C | C |

FIG. 9I

| Cmpd | SA1 01 292 13 | SA1 00 137 09 | SA1 61 tetM | SA1 58 tetK | SE1 64 122 28 | EF1 59 tetM | SP1 06 496 19 | SP1 60 tetM | SP1 93 866 8 | HI2 62 339 29 | MC 205 817 6 | EC1 07 259 22 | EC1 55 tetA | KP1 53 tetA | KP1 94 700 603 | PM1 12 356 59 | PA1 69 | PA1 73 | AB2 50 | SM2 56 | BC2 40 |
|---|---|---|---|---|---|---|---|---|---|---|---|---|---|---|---|---|---|---|---|---|---|
| S25-11-187 | C | C | B | B | B | B | C | C | C | C | C | C | C | C | C | C | C | C | C | C | C |
| S25-11-188 | C | B | C | B | A | C | A | B | A | A | B | B | B | B | C | B | C | A | C | C | C |
| S25-11-189 | C | C | B | B | B | B | C | C | C | C | C | C | C | C | C | C | C | C | C | C | C |
| S25-11-19 | B | A | B | A | A | B | A | B | A | A | A | B | B | B | B | B | C | A | A | C | B |
| S25-11-194 | B | A | B | A | A | B | B | B | A | A | B | A | B | B | B | B | C | A | A | A | B |
| S25-11-195 | C | B | B | B | B | B | C | C | C | C | C | C | C | C | C | C | C | C | C | C | C |
| S25-11-196 | C | C | C | B | C | C | B | C | B | A | C | B | C | C | C | C | C | B | C | C | C |
| S25-11-197 | C | C | C | B | B | C | A | C | B | C | C | B | C | C | C | C | C | B | C | C | C |
| S25-11-198 | C | B | B | B | A | B | B | B | C | C | C | B | B | B | C | C | C | C | A | C | B |
| S25-11-199 | C | C | B | B | B | B | C | B | C | C | C | C | C | C | C | C | C | C | C | C | NT |
| S25-11-2 | A | A | C | NT | A | B | B | B | A | A | B | A | B | B | NT | A | B | A | A | A | B |
| S25-11-20 | C | B | B | B | A | B | B | C | B | C | C | B | B | C | C | C | C | C | A | C | C |
| S25-11-200 | C | C | C | C | B | B | C | C | C | C | C | C | C | C | C | C | C | C | C | C | NT |
| S25-11-206 | C | C | B | B | B | B | C | C | C | C | C | C | C | C | C | C | C | C | A | C | C |
| S25-11-207 | C | B | B | B | A | B | A | B | A | C | C | B | B | B | C | C | C | B | A | C | B |
| S25-11-208 | A | A | C | B | NT | C | B | B | NT | NT | NT | B | B | B | NT | NT | NT | NT | NT | NT | NT |
| S25-11-21 | C | C | C | C | B | B | C | C | C | C | C | C | C | C | C | C | C | C | C | C | C |
| S25-11-22 | C | B | B | B | A | B | A | B | B | A | A | B | B | B | C | C | C | B | A | C | B |
| S25-11-23 | B | B | C | A | A | B | A | B | A | A | A | A | B | B | A | A | B | A | A | A | C |
| S25-11-24 | C | B | B | A | A | B | A | B | A | A | A | B | B | B | B | B | C | A | A | A | C |
| S25-11-25 | C | C | B | B | A | B | B | B | B | A | C | B | B | B | C | C | C | C | A | C | C |
| S25-11-26 | B | B | C | B | A | C | A | B | A | A | A | B | B | B | A | A | B | A | A | A | B |
| S25-11-27 | B | B | C | B | B | C | A | B | B | A | A | B | B | B | A | A | A | A | C | C | C |
| S25-11-28 | C | C | B | B | B | B | C | C | C | C | C | C | C | C | C | C | C | C | C | C | C |

FIG. 9J

| Cmpd | SA1 01 292 13 | SA1 00 137 09 | SA1 61 tetM | SA1 58 tetK | SE1 64 122 28 | EF1 59 tetM | SP1 06 496 19 | SP1 60 tetM | SP1 93 866 8 | HI2 62 339 29 | MC 205 817 6 | EC1 07 259 22 | EC1 55 tetA | KP1 53 tetA | KP1 94 700 603 | PM1 12 356 59 | PA1 69 | PA1 73 | AB2 50 | SM2 56 | BC2 40 |
|---|---|---|---|---|---|---|---|---|---|---|---|---|---|---|---|---|---|---|---|---|---|
| S25-11-29 | C | B | B | B | B | B | C | C | C | C | C | C | B | C | C | C | C | C | C | C | C |
| S25-11-3 | C | B | B | B | B | B | B | B | B | C | C | B | B | B | C | C | C | C | A | C | B |
| S25-11-30 | C | A | B | A | A | B | A | B | A | A | A | B | B | B | C | C | C | A | A | C | A |
| S25-11-31 | C | C | B | B | B | B | B | B | B | C | C | B | B | B | C | C | C | C | C | C | C |
| S25-11-32 | C | C | C | B | B | B | C | C | C | C | C | C | C | C | C | C | C | C | C | C | C |
| S25-11-33 | C | C | C | C | C | C | C | C | C | C | C | C | C | C | C | C | C | C | C | C | C |
| S25-11-34 | C | C | C | C | C | C | C | C | C | C | C | C | C | C | C | C | C | C | C | C | C |
| S25-11-35 | C | C | B | B | B | B | B | B | B | C | C | B | B | C | C | C | C | C | A | C | C |
| S25-11-36 | C | C | B | B | B | B | C | C | C | C | C | C | C | C | C | C | C | C | C | C | C |
| S25-11-37 | C | C | C | C | C | C | C | C | C | C | C | C | C | C | C | C | C | C | C | C | C |
| S25-11-4 | C | C | B | B | B | B | C | C | B | C | C | B | B | C | C | C | C | C | C | C | C |
| S25-11-43 | B | B | B | NT | A | B | B | B | B | C | B | B | B | B | NT | B | C | C | A | C | A |
| S25-11-44 | C | B | B | B | A | B | B | B | B | C | B | B | B | B | C | C | C | A | A | C | A |
| S25-11-45 | B | B | B | A | A | B | A | B | A | C | B | B | B | B | C | C | C | A | A | C | C |
| S25-11-46 | C | C | B | B | A | B | B | B | B | C | C | B | B | B | C | C | C | B | A | C | C |
| S25-11-47 | C | B | C | B | B | C | B | B | B | A | C | B | C | C | C | C | C | A | C | C | C |
| S25-11-48 | A | A | B | A | A | B | A | B | A | A | A | B | B | B | B | B | B | A | A | A | C |
| S25-11-5 | C | B | B | B | B | B | B | C | B | C | C | B | C | C | C | C | C | C | C | C | A |
| S25-11-50 | C | C | B | B | B | B | C | C | C | C | C | C | C | C | C | C | C | C | C | C | C |
| S25-11-51 | C | B | B | B | A | B | B | B | B | C | B | B | B | B | C | C | C | B | A | C | NT |
| S25-11-52 | C | C | B | B | B | B | C | C | C | C | C | C | C | C | C | C | C | C | C | C | C |
| S25-11-53 | B | B | B | B | A | B | A | B | A | A | A | B | B | B | B | B | C | A | A | A | C |
| S25-11-54 | B | B | C | B | A | B | A | B | A | A | A | B | B | B | A | A | B | A | A | A | B |
| S25-11-55 | B | A | B | A | A | B | A | B | A | A | A | A | B | B | B | B | C | A | A | C | A |

FIG. 9K

| Cmpd | SA1 01 292 13 | SA1 00 137 09 | SA1 61 tetM | SA1 58 tetK | SE1 64 122 28 | EF1 59 tetM | SP1 06 496 19 | SP1 60 tetM | SP1 93 866 8 | HI2 62 339 29 | MC 205 817 6 | EC1 07 259 22 | EC1 55 tetA | KP1 53 tetA | KP1 94 700 603 | PM1 12 356 59 | PA1 69 | PA1 73 | AB2 50 | SM2 56 | BC2 40 |
|---|---|---|---|---|---|---|---|---|---|---|---|---|---|---|---|---|---|---|---|---|---|
| S25-11-56 | B | B | B | B | A | B | A | B | B | A | A | B | B | B | B | C | C | B | C | C | B |
| S25-11-57 | B | A | C | B | B | C | A | B | A | A | A | B | B | B | B | B | B | A | A | A | A |
| S25-11-58 | B | B | C | A | A | B | A | B | A | A | A | B | B | B | A | B | C | A | A | C | B |
| S25-11-59 | B | A | C | A | A | C | A | B | A | A | A | B | C | C | C | C | C | A | C | C | C |
| S25-11-6 | B | A | C | B | A | B | B | B | A | A | B | B | B | B | A | B | B | A | A | A | B |
| S25-11-60 | B | B | B | A | A | B | A | B | A | A | A | B | B | B | B | B | C | A | A | C | A |
| S25-11-61 | C | B | B | B | B | B | B | C | B | A | B | B | B | C | C | C | C | C | A | C | C |
| S25-11-62 | C | C | B | B | B | B | C | C | C | C | C | C | C | C | C | C | C | C | C | C | C |
| S25-11-63 | B | B | B | A | A | B | A | B | A | A | A | B | B | B | B | B | C | A | A | C | B |
| S25-11-64 | C | B | B | B | A | B | A | B | B | A | B | B | B | B | C | C | C | B | A | C | C |
| S25-11-65 | C | B | B | B | A | B | B | B | B | C | C | B | B | B | C | C | C | C | C | C | C |
| S25-11-66 | C | NT | B | B | B | B | C | B | NT | C | C | C | B | C | C | C | NT | NT | C | C | C |
| S25-11-67 | C | NT | C | B | B | B | C | C | NT | C | C | C | C | C | C | C | NT | NT | C | C | C |
| S25-11-68 | B | B | B | A | A | B | A | B | A | A | A | B | B | B | B | B | C | A | A | A | C |
| S25-11-69 | B | B | B | B | A | B | A | B | A | A | B | B | B | B | C | C | C | B | A | C | C |
| S25-11-7 | C | B | B | A | A | B | A | B | A | A | A | B | B | B | C | C | C | A | A | C | A |
| S25-11-70 | C | NT | B | B | B | B | C | C | NT | C | C | C | C | C | C | C | NT | NT | C | C | C |
| S25-11-71 | C | NT | C | C | C | B | C | C | NT | C | C | C | C | C | C | C | NT | NT | C | C | C |
| S25-11-72 | C | B | B | B | A | B | A | B | B | A | C | B | B | B | C | C | C | B | A | C | C |
| S25-11-73 | C | B | B | B | A | B | A | B | A | A | B | B | B | B | C | C | C | B | A | C | C |
| S25-11-74 | C | C | B | B | B | B | C | C | C | C | C | C | C | C | C | C | C | C | C | C | C |
| S25-11-75 | C | B | C | B | A | C | B | C | B | A | C | B | C | C | C | C | C | C | C | C | C |
| S25-11-76 | C | C | C | B | B | C | A | B | B | C | C | B | B | C | C | C | C | B | C | C | C |
| S25-11-77 | C | NT | B | B | B | B | B | B | NT | C | C | C | C | C | C | C | NT | NT | C | C | C |

FIG. 9L

| Cmpd | SA1 01 292 13 | SA1 00 137 09 | SA1 61 tetM | SA1 58 tetK | SE1 64 122 28 | EF1 59 tetM | SP1 06 496 19 | SP1 60 tetM | SP1 93 866 8 | HI2 62 339 29 | MC 205 817 6 | EC1 07 259 22 | EC1 55 tetA | KP1 53 tetA | KP1 94 700 603 | PM1 12 356 59 | PA1 69 | PA1 73 | AB2 50 | SM2 56 | BC2 40 |
|---|---|---|---|---|---|---|---|---|---|---|---|---|---|---|---|---|---|---|---|---|---|
| S25-11-78 | C | NT | B | B | B | B | C | C | NT | C | C | C | C | C | C | C | NT | NT | C | C | C |
| S25-11-8 | B | B | C | A | A | C | A | B | A | A | A | B | B | B | C | C | C | A | A | C | B |
| S25-11-9 | B | B | B | NT | A | B | B | B | A | A | B | B | B | B | NT | B | B | A | A | A | A |
| S27-9-3 | C | C | B | B | B | B | B | B | B | C | C | B | B | B | C | C | C | C | C | NT | C |
| S27-9-5 | B | B | B | B | B | B | NT | B | B | A | B | B | B | B | NT | B | C | A | A | A | C |
| S27-9-6 | C | C | B | B | B | B | B | B | B | C | C | B | B | B | C | C | C | B | C | C | C |
| S27-9-7 | B | B | B | B | A | B | A | B | B | A | A | B | B | B | B | A | C | A | A | C | C |
| S29-2-1 | B | B | B | B | A | B | A | B | B | C | C | B | B | B | A | B | B | A | A | C | C |
| S29-2-2 | B | A | B | A | A | B | A | B | A | C | B | B | B | A | B | B | B | A | A | A | C |
| S29-2-3 | B | B | B | B | A | B | A | B | A | C | B | B | B | B | B | C | C | A | A | C | B |
| S29-2-4 | A | A | B | A | A | B | A | B | A | C | A | B | B | B | B | B | B | A | A | A | C |
| S30-4-1 | C | C | B | B | B | B | C | B | C | C | C | C | C | B | C | C | C | A | C | C | NT |
| S30-4-2 | C | C | C | B | B | C | C | B | B | C | C | B | C | B | C | B | C | A | C | C | NT |
| S6-4-3 | C | B | C | B | A | B | A | B | B | A | C | B | B | A | B | B | C | NT | A | C | C |
| Sancycline | 0.5 | 1 | 2 | 4 | 4 | 8 | 0.25 | 8 | 1 | 0.5 | 0.12 5 | 8 | 32 | 32 | 32 | 4 | 32 | 33 | 16 | 1 | 4 |
| Minocycline | 0.06 | 0.06 | 8 | 0.03 | 0.12 5 | 16 | 0.01 55 | 2 | 0.01 56 | 1 | 0.01 55 | 0.5 | 8 | 8 | 32 | 8 | 32 | 16 | 8 | 0.5 | 8 |
| Tigecycline | 0.06 | 0.06 | 0.12 5 | 0.06 | 0.12 5 | 0.06 | 0.01 56 | 0.01 56 | 0.01 56 | 1 | 0.01 55 | 0.03 | 0.5 | 1 | 8 | 1 | 15 | 16 | 8 | 1 | 16 |

FIG. 9M

| Compound | SA1 01 292 13 | SA1 91 | SA1 61 tetM | SA1 58 tetK | SE1 64 122 28 | EF1 59 tetM | SP1 06 496 19 | SP1 60 tetM | SP3 12 tetM | HI26 2 339 29 | MC2 05 817 6 | EC1 07 259 22 | EC1 55 tetA | KP1 53 tetA | KP4 57 | PM1 12 356 59 | PA5 55 | PA5 56 | AB2 50 | SM2 56 | BC2 40 |
|---|---|---|---|---|---|---|---|---|---|---|---|---|---|---|---|---|---|---|---|---|---|
| S15-13-121 | C | C | C | C | C | C | C | B | B | C | C | C | C | C | C | C | C | C | C | C | C |
| S15-13-129 | C | B | C | B | A | B | A | B | B | A | B | B | B | B | NT | C | C | C | A | C | C |
| S15-13-130 | C | B | B | B | B | B | B | B | B | C | C | B | B | B | NT | C | C | C | A | C | C |
| S15-13-133 | C | B | C | C | B | B | C | B | B | C | C | C | C | C | NT | C | C | C | C | C | C |
| S15-13-134 | C | B | B | B | B | B | C | B | B | C | C | C | C | C | C | C | C | C | C | C | C |
| S15-13-135 | C | C | C | C | B | B | C | B | B | C | C | C | C | C | C | C | C | C | C | C | C |
| S15-13-136 | C | B | B | B | A | B | A | B | B | A | B | B | B | C | B | C | C | C | A | C | C |
| S15-13-142 | C | C | C | B | A | C | A | B | B | A | B | B | C | C | A | B | C | C | A | C | C |
| S15-13-143 | C | B | B | B | A | B | A | B | B | A | B | B | B | B | A | B | C | C | A | C | B |
| S15-13-144 | C | B | B | B | A | B | A | B | B | C | B | B | B | B | A | C | C | C | A | C | C |
| S15-13-145 | C | C | C | B | B | B | C | C | C | C | C | C | C | C | C | C | C | C | C | C | C |
| S15-13-146 | C | C | C | C | C | C | C | C | C | C | C | C | C | C | C | C | C | C | C | C | C |
| S15-13-147 | C | C | C | B | A | C | A | B | B | A | A | B | B | B | A | A | A | A | A | C | B |
| S15-13-148 | C | B | B | A | A | B | A | B | B | A | A | B | B | B | A | A | C | C | A | A | B |
| S15-13-149 | B | B | B | A | A | B | A | B | B | A | A | B | B | B | A | B | C | C | A | C | C |
| S15-13-150 | C | B | B | B | A | B | A | B | B | A | A | B | B | B | A | C | C | C | A | C | C |
| S15-13-151 | C | B | B | B | B | B | C | B | B | C | C | C | C | C | C | C | C | C | C | C | C |
| S15-13-152 | C | C | C | B | A | C | A | B | B | A | B | B | B | B | A | A | A | A | A | A | B |
| S15-13-153 | B | B | C | B | A | B | A | B | B | A | A | B | B | A | A | A | C | B | A | A | C |
| S15-13-154 | C | B | B | B | A | B | A | B | B | C | B | B | B | B | B | C | C | C | C | C | C |
| S15-13-155 | C | B | B | B | B | B | B | B | B | C | C | B | C | B | C | C | C | C | C | C | C |
| S15-13-156 | C | B | B | B | A | B | B | B | B | A | C | B | B | B | A | C | C | C | A | C | C |
| S15-13-157 | C | B | B | B | B | B | B | B | B | A | C | B | B | B | B | C | C | C | A | C | C |
| S15-13-158 | C | B | C | B | C | C | C | B | B | C | C | C | C | C | C | C | C | C | C | C | C |
| S15-13-159 | C | C | C | C | C | C | C | C | C | C | C | C | C | C | C | C | C | C | C | C | C |
| S15-13-160 | C | B | B | B | B | B | B | B | B | C | C | B | C | C | C | C | C | C | C | C | C |
| S15-13-167 | B | A | B | B | A | B | A | B | B | C | C | B | B | B | B | C | C | C | A | C | B |
| S15-13-170 | C | B | B | B | A | B | A | B | B | A | B | B | B | B | NT | C | C | C | A | C | C |
| S15-13-171 | C | B | B | B | A | B | B | B | B | C | C | B | B | B | NT | C | C | C | C | C | C |

FIG. 10A

| Compound | SA1 01 292 13 | SA1 91 | SA1 61 tetM | SA1 58 tetK | SE1 64 122 28 | EF1 59 tetM | SP1 06 496 19 | SP1 60 tetM | SP3 12 tetM | HI26 2 339 29 | MC2 05 817 6 | EC1 07 259 22 | EC1 55 tetA | KP1 53 tetA | KP4 57 | PM1 12 356 59 | PA5 55 | PA5 56 | AB2 50 | SM2 56 | BC2 40 |
|---|---|---|---|---|---|---|---|---|---|---|---|---|---|---|---|---|---|---|---|---|---|
| S15-13-172 | C | B | B | B | B | B | C | B | B | C | C | C | C | C | NT | C | C | C | C | C | C |
| **S15-13-173** | C | B | B | B | B | B | C | B | B | C | C | C | C | C | NT | C | C | C | C | C | C |
| **S15-13-176** | C | B | B | B | B | B | C | B | B | C | C | C | C | C | C | C | C | C | C | C | C |
| **S15-13-179** | C | C | C | B | B | C | A | B | B | A | B | B | B | B | A | A | A | A | C | C | C |
| **S15-13-227** | C | C | C | B | A | B | B | B | B | C | C | B | B | B | C | C | C | C | C | C | C |
| **S15-13-30** | C | B | B | B | A | B | B | B | B | C | C | B | C | C | C | C | C | C | C | C | C |
| **S15-13-33** | C | C | C | C | C | B | C | C | B | C | C | C | C | C | C | C | C | C | C | C | C |
| **S15-13-49** | C | B | B | B | A | B | A | B | B | A | B | B | B | B | NT | B | C | C | A | C | C |
| **S15-13-50** | C | B | B | B | A | B | A | B | B | C | C | B | B | B | NT | C | C | C | C | C | C |
| **S15-13-51** | C | B | B | B | B | B | B | B | B | C | C | B | B | C | NT | C | C | C | C | C | C |
| **S15-13-52** | C | B | B | B | A | B | A | B | B | A | A | B | B | B | NT | B | C | C | A | C | C |
| **S15-13-53** | C | C | C | C | B | B | C | C | C | C | C | C | C | C | NT | C | C | C | C | C | C |
| S15-13-54 | C | B | B | B | B | B | C | C | C | C | C | C | C | C | NT | C | C | C | C | C | C |
| S15-13-55 | C | C | C | C | C | C | C | C | C | C | C | C | C | C | NT | C | C | C | C | C | C |
| S15-13-56 | C | C | C | C | C | C | C | C | C | C | C | C | C | C | NT | C | C | C | C | C | C |
| **S15-13-57** | C | B | B | B | B | B | C | C | C | C | C | C | C | C | C | B | C | C | C | C | C |
| **S15-13-58** | C | C | C | B | A | B | A | B | B | A | A | B | B | B | A | A | C | B | A | C | C |
| **S15-13-59** | C | B | B | B | A | B | A | B | B | A | A | B | B | B | A | B | C | C | A | C | C |
| **S15-13-60** | C | B | B | B | A | B | A | B | B | A | B | B | B | B | A | B | C | C | A | C | C |
| **S15-13-61** | C | B | B | C | B | B | C | C | C | C | C | C | C | C | C | C | C | C | C | C | C |
| **S15-13-62** | C | B | C | B | B | B | C | B | B | C | C | C | C | C | C | C | C | C | C | C | C |
| **S15-13-63** | C | C | C | C | C | C | C | B | B | C | C | C | C | C | C | C | C | C | C | C | C |
| **S15-13-78** | C | B | B | B | A | B | B | B | B | C | C | B | B | B | A | C | C | C | A | C | C |
| **S15-13-85** | C | B | B | B | B | B | C | B | B | C | C | C | B | C | C | C | C | C | C | C | C |
| **S15-13-86** | C | B | B | B | B | B | C | B | B | C | C | C | C | C | C | C | C | C | C | C | C |
| **S15-13-89** | C | B | B | B | B | B | B | B | B | C | C | B | B | B | NT | C | C | C | C | C | C |
| **S15-13-90** | C | B | C | B | B | B | C | C | B | C | C | C | C | C | NT | C | C | C | C | C | C |
| **S15-13-91** | C | C | C | B | B | C | B | C | C | A | C | B | C | C | NT | C | C | C | C | C | C |
| **S15-13-92** | C | C | C | B | B | C | B | C | C | C | C | B | C | C | NT | C | C | C | C | C | C |

FIG. 10B

| Compound | SA1 01 292 13 | SA1 91 | SA1 61 tetM | SA1 58 tetK | SE1 64 122 28 | EF1 59 tetM | SP1 06 496 19 | SP1 60 tetM | SP3 12 tetM | HI26 2 339 29 | MC2 05 817 6 | EC1 07 259 22 | EC1 55 tetA | KP1 53 tetA | KP4 57 | PM1 12 356 59 | PA5 55 | PA5 56 | AB2 50 | SM2 56 | BC2 40 |
|---|---|---|---|---|---|---|---|---|---|---|---|---|---|---|---|---|---|---|---|---|---|
| S15-13-93 | C | B | B | B | A | B | A | B | B | A | A | B | B | B | A | B | C | C | A | A | C |
| S15-13-94 | C | C | C | B | A | C | A | B | B | A | B | B | B | B | A | B | C | B | A | C | C |
| S15-13-95 | C | C | C | B | A | C | A | B | B | A | B | B | B | B | A | C | C | C | A | C | C |
| S15-13-96 | C | C | C | B | A | B | A | B | B | A | A | B | B | B | A | B | C | C | A | C | B |
| S15-13-97 | C | B | B | B | B | B | C | B | B | C | C | C | C | C | C | C | C | C | C | C | C |
| S16-10-118 | C | B | C | B | A | B | A | B | B | C | C | C | B | B | NT | C | C | C | C | C | C |
| S16-10-125 | C | C | C | B | A | C | A | B | B | C | C | B | B | B | A | C | C | C | C | C | C |
| S16-10-128 | C | C | C | B | B | C | A | B | B | C | C | B | B | B | C | C | C | C | C | C | C |
| S16-10-130 | C | C | C | B | A | C | A | B | B | A | B | B | B | A | A | B | C | B | A | C | C |
| S16-10-131 | C | C | C | B | A | C | B | B | B | A | C | B | B | B | A | C | C | B | C | C | C |
| S16-10-137 | C | B | B | B | A | B | A | B | B | C | A | C | B | C | C | C | C | C | C | C | C |
| S16-10-31 | C | B | C | B | A | B | A | B | B | C | C | B | B | B | NT | C | C | C | A | C | C |
| S16-10-44 | C | C | C | B | B | C | B | B | C | C | C | B | B | B | C | C | C | C | C | C | C |
| S16-10-47 | C | C | C | B | B | C | B | C | C | C | C | C | B | C | C | C | C | C | C | C | C |
| S16-10-50 | C | C | C | B | A | C | A | B | B | C | B | B | B | B | B | C | C | C | A | C | C |
| S15-13-227 | C | C | C | B | A | C | A | B | B | C | B | B | B | B | C | C | C | C | C | C | C |
| S16-10-56 | C | C | C | B | B | C | B | C | C | C | C | B | C | C | B | C | C | B | C | C | C |
| S16-10-57 | C | C | C | B | B | C | B | C | C | C | C | B | B | B | C | C | C | C | C | C | C |
| S16-10-58 | C | C | C | B | A | C | B | B | C | C | C | B | B | B | B | C | C | C | C | C | C |
| S16-10-66 | C | B | C | B | B | B | B | C | C | C | C | C | B | B | C | C | C | C | C | C | C |
| S16-10-68 | C | C | C | B | B | C | B | B | C | C | C | B | B | B | A | C | C | C | C | C | C |
| S16-10-76 | C | C | C | B | B | C | B | C | C | C | C | C | B | C | C | C | C | C | C | C | C |
| S16-10-77 | C | C | C | B | A | C | A | B | B | C | B | B | B | B | A | C | C | C | C | C | C |
| S16-10-80 | C | B | C | B | A | B | A | B | B | C | A | B | B | B | A | C | C | C | A | C | C |
| S16-10-81 | C | B | B | B | B | B | B | B | B | C | C | B | B | B | B | C | C | C | C | C | C |
| S16-10-84 | B | C | C | B | A | C | A | B | B | A | B | B | A | B | NT | C | C | C | C | C | C |
| S16-10-85 | C | C | C | B | A | C | A | B | B | C | C | B | B | B | NT | C | C | C | C | C | C |
| S16-10-87 | C | C | C | B | A | C | B | B | B | A | C | B | B | A | A | B | C | B | C | C | C |
| S16-10-90 | C | C | C | B | A | C | A | B | B | C | B | B | B | B | B | C | C | C | C | C | C |
| S16-10-93 | C | C | C | B | A | C | A | B | B | A | B | B | B | B | A | C | C | C | A | C | C |

FIG. 10C

| Compound | SA1 01 292 13 | SA1 91 | SA1 61 tetM | SA1 58 tetK | SE1 64 122 28 | EF1 59 tetM | SP1 06 496 19 | SP1 60 tetM | SP3 12 tetM | HI26 2 339 29 | MC2 05 817 6 | EC1 07 259 22 | EC1 55 tetA | KP1 53 tetA | KP4 57 | PM1 12 356 59 | PA5 55 | PA5 56 | AB2 50 | SM2 56 | BC2 40 |
|---|---|---|---|---|---|---|---|---|---|---|---|---|---|---|---|---|---|---|---|---|---|
| S16-10-96 | C | C | C | B | A | C | A | B | B | A | B | B | B | B | NT | C | C | C | A | C | C |
| S16-10-97 | C | B | C | B | A | B | A | B | B | C | C | B | B | B | B | C | C | C | C | C | C |
| S24-9-100 | C | B | B | B | A | B | A | B | B | A | B | B | B | B | A | B | C | C | A | C | B |
| S24-9-101 | C | B | B | B | A | B | A | B | B | A | B | B | B | B | A | B | C | C | A | C | B |
| S24-9-102 | C | B | B | B | A | B | B | B | B | C | C | B | B | B | C | C | C | C | C | C | C |
| S24-9-103 | C | C | C | B | B | C | B | B | B | A | C | B | C | C | A | A | C | B | C | C | C |
| S24-9-104 | B | C | C | B | A | C | A | B | B | A | B | B | B | B | A | A | A | B | A | C | C |
| S24-9-105 | C | C | C | B | A | C | A | B | B | A | B | B | B | B | A | B | C | B | A | C | C |
| S24-9-106 | C | B | C | B | A | B | A | B | B | C | C | B | B | B | B | C | C | C | A | C | C |
| S24-9-107 | C | B | C | B | B | B | C | C | B | C | C | C | C | C | C | C | C | C | C | C | C |
| S24-9-108 | C | B | C | B | B | B | C | C | B | C | C | C | C | C | C | C | C | C | C | C | C |
| S24-9-109 | C | B | B | B | A | B | A | B | B | A | B | B | B | B | A | A | C | B | A | C | C |
| S24-9-110 | C | B | C | B | A | B | A | B | B | A | A | B | B | B | A | B | C | C | A | C | C |
| S24-9-111 | C | B | C | B | A | B | A | B | B | A | B | B | B | B | A | B | C | C | A | C | C |
| S24-9-112 | C | B | C | B | A | C | B | B | B | A | B | B | B | B | A | A | C | B | A | C | C |
| S24-9-113 | C | B | C | B | A | C | A | B | B | A | C | B | C | C | A | C | C | B | C | C | C |
| S24-9-115 | B | B | C | B | A | C | C | B | B | A | B | B | B | B | A | A | A | B | A | C | C |
| S24-9-116 | C | C | C | B | B | C | B | B | B | A | C | B | C | C | A | B | C | B | C | C | C |
| S24-9-119 | C | C | C | B | B | C | B | B | B | A | C | B | C | C | A | A | A | B | C | C | C |
| S24-9-120 | C | C | C | B | A | C | A | B | B | A | B | B | C | B | A | B | C | B | A | C | C |
| S24-9-121 | C | B | C | B | A | C | A | B | B | A | B | B | B | B | A | B | C | B | A | C | C |
| S24-9-133 | C | C | C | B | B | C | C | C | B | A | C | C | C | C | NT | C | C | C | C | C | C |
| S24-9-134 | C | C | C | B | A | C | A | B | B | A | B | B | C | C | NT | A | C | B | A | C | C |
| S24-9-136 | B | C | C | B | A | C | A | B | B | A | B | B | B | B | NT | B | C | A | A | C | C |
| S24-9-137 | C | B | C | B | A | B | A | B | B | A | B | B | B | B | NT | B | C | C | A | C | B |
| S24-9-138 | C | B | B | B | A | B | A | B | B | C | B | B | B | B | NT | C | C | C | A | C | C |
| S24-9-139 | C | B | B | B | A | B | A | B | B | C | B | B | B | B | NT | C | C | C | A | C | C |
| S24-9-140 | C | B | C | B | A | B | A | B | B | A | B | B | B | B | NT | B | C | B | A | C | C |
| S24-9-141 | B | C | C | B | A | C | A | B | B | A | B | B | B | B | NT | A | A | A | A | C | C |

FIG. 10D

| Compound | SA1 01 292 13 | SA1 91 | SA1 61 tetM | SA1 58 tetK | SE1 64 122 28 | EF1 59 tetM | SP1 06 496 19 | SP1 60 tetM | SP3 12 tetM | HI26 2 339 29 | MC2 05 817 6 | EC1 07 259 22 | EC1 55 tetA | KP1 53 tetA | KP4 57 | PM1 12 356 59 | PA5 55 | PA5 56 | AB2 50 | SM2 56 | BC2 40 |
|---|---|---|---|---|---|---|---|---|---|---|---|---|---|---|---|---|---|---|---|---|---|
| S24-9-142 | B | C | C | B | A | C | A | B | B | A | B | B | B | B | NT | B | C | B | A | C | C |
| S24-9-143 | C | C | C | B | B | C | B | B | B | A | C | B | C | C | NT | A | A | C | C | C | C |
| S24-9-144 | C | C | C | B | A | C | A | B | B | C | B | B | B | B | B | C | C | C | A | C | C |
| S24-9-145 | C | C | C | C | C | C | C | C | C | C | C | C | C | C | C | C | C | C | C | C | C |
| S24-9-146 | C | C | C | B | B | C | C | C | C | C | C | C | C | C | C | C | C | B | C | C | C |
| S24-9-147 | C | C | C | B | B | C | B | C | C | C | C | C | C | C | C | C | C | C | C | C | C |
| S24-9-148 | C | C | C | B | A | C | B | B | C | A | C | B | C | C | A | B | C | B | C | C | C |
| S24-9-149 | C | B | C | B | A | B | A | B | B | A | B | B | B | B | A | C | C | C | A | C | C |
| S24-9-150 | C | B | C | B | A | B | A | B | B | C | C | B | B | B | B | C | C | C | A | C | C |
| S24-9-151 | C | B | C | B | A | C | A | B | B | A | A | B | B | B | A | A | C | A | A | C | C |
| S24-9-152 | C | C | C | B | A | C | A | B | B | A | C | B | B | B | A | B | C | C | A | C | C |
| S24-9-153 | C | C | C | B | A | C | A | B | B | A | C | B | B | B | A | C | C | C | A | C | C |
| S24-9-154 | C | B | B | B | A | B | A | B | B | A | A | B | B | B | A | C | C | C | A | C | C |
| S24-9-155 | C | B | C | B | A | B | A | B | B | A | C | B | B | B | A | B | C | B | C | C | C |
| S24-9-156 | C | B | C | B | A | B | A | B | B | A | B | B | B | B | A | B | C | B | A | A | C |
| S24-9-157 | C | C | C | B | A | B | A | B | B | A | B | B | B | B | A | C | C | C | A | A | C |
| S24-9-158 | C | C | C | B | B | C | C | C | B | A | C | B | C | C | A | A | C | B | C | C | C |
| S24-9-159 | C | C | C | B | A | C | B | B | B | A | B | B | B | B | A | A | C | B | A | C | C |
| S24-9-29 | B | B | C | B | A | C | A | B | B | A | A | B | B | B | NT | A | C | B | A | A | B |
| S24-9-33 | C | B | C | B | A | C | A | B | B | A | B | B | B | B | NT | B | C | B | C | C | C |
| S24-9-34 | C | C | C | B | A | C | A | B | B | A | B | B | B | B | NT | C | C | C | A | C | C |
| S24-9-35 | B | B | C | B | A | B | A | B | B | A | A | B | B | B | NT | C | C | C | A | C | C |
| S24-9-36 | C | C | C | B | B | C | B | B | B | A | C | B | B | B | NT | A | C | C | C | C | C |
| S24-9-37 | B | C | C | B | A | C | A | B | B | A | B | B | B | B | NT | A | A | A | A | C | B |
| S24-9-38 | B | C | C | B | A | C | A | B | B | A | A | B | B | B | NT | B | C | B | A | C | C |
| S24-9-39 | B | C | C | A | A | C | A | B | B | C | A | B | B | B | NT | C | C | C | A | C | C |
| S24-9-40 | C | C | C | B | B | C | C | C | B | A | C | C | C | C | NT | C | C | C | C | C | C |
| S24-9-41 | C | B | C | B | A | C | A | B | B | A | B | B | B | B | NT | A | A | A | A | C | C |
| S24-9-42 | B | B | C | B | A | C | A | B | B | A | A | B | B | B | A | B | C | B | A | A | B |
| S24-9-43 | B | B | C | B | A | C | A | B | B | A | A | B | B | B | A | C | C | C | A | C | C |

FIG. 10E

| Compound | SA1 01 292 13 | SA1 91 | SA1 61 tetM | SA1 58 tetK | SE1 64 122 28 | EF1 59 tetM | SP1 06 496 19 | SP1 60 tetM | SP3 12 tetM | HI26 2 339 29 | MC2 05 817 6 | EC1 07 259 22 | EC1 55 tetA | KP1 53 tetA | KP4 57 | PM1 12 356 59 | PA5 55 | PA5 56 | AB2 50 | SM2 56 | BC2 40 |
|---|---|---|---|---|---|---|---|---|---|---|---|---|---|---|---|---|---|---|---|---|---|
| S24-9-44 | C | C | C | B | A | C | A | B | B | A | B | B | C | C | A | B | C | A | C | C | C |
| S24-9-45 | C | C | C | B | A | C | A | B | B | A | B | B | B | B | A | B | C | B | A | C | C |
| S24-9-46 | B | C | C | B | A | C | A | B | B | A | B | B | B | B | A | C | C | B | A | C | C |
| S24-9-47 | B | B | C | B | A | B | A | B | B | A | A | B | B | B | A | B | C | B | A | C | B |
| S24-9-48 | C | B | C | B | A | B | A | B | B | A | A | B | B | B | A | B | C | C | A | C | C |
| S24-9-49 | C | B | B | B | A | B | A | B | C | C | B | B | B | B | B | C | C | C | A | C | C |
| S24-9-50 | C | B | C | B | A | C | A | B | B | A | A | B | B | B | A | A | C | B | A | A | C |
| S24-9-51 | C | C | C | B | A | C | A | B | B | A | B | B | B | B | A | B | C | C | A | A | C |
| S24-9-52 | C | C | C | B | B | C | A | C | C | A | C | B | C | C | C | C | C | C | A | C | C |
| S24-9-53 | C | B | B | B | B | B | C | C | B | C | C | C | C | C | C | C | C | C | C | C | C |
| S24-9-54 | C | C | C | B | B | C | B | C | C | C | C | C | C | C | C | C | C | C | A | C | C |
| S24-9-55 | C | B | B | B | B | B | C | C | B | C | C | C | C | C | C | C | C | C | C | C | C |
| S24-9-57 | B | B | C | B | A | C | A | B | B | A | A | B | B | B | NT | B | C | B | A | A | C |
| S24-9-66 | C | C | C | B | B | C | B | B | B | A | B | B | B | B | A | A | A | A | A | C | C |
| S24-9-85 | C | B | C | B | A | C | A | B | B | A | B | B | B | B | NT | A | A | A | C | C | C |
| S24-9-86 | C | C | C | B | A | B | A | C | B | C | C | C | C | C | NT | C | C | C | C | C | C |
| S24-9-87 | C | C | C | B | B | C | B | B | B | A | C | B | C | C | A | B | C | B | C | C | C |
| S24-9-88 | C | B | C | B | A | C | A | B | B | A | B | B | B | B | A | B | C | B | A | C | C |
| S24-9-89 | C | C | C | B | A | C | A | B | B | A | C | B | B | B | A | C | C | C | A | C | C |
| S24-9-90 | C | B | B | B | A | B | A | B | B | C | C | B | B | B | A | C | C | C | A | C | B |
| S24-9-91 | C | B | B | B | A | B | B | B | B | C | C | B | B | C | C | C | C | C | C | C | C |
| S24-9-97 | B | B | B | B | A | B | A | B | B | A | B | B | B | B | A | B | C | B | A | C | B |
| S24-9-98 | B | B | C | B | A | B | A | B | B | A | A | B | B | B | A | C | C | C | A | A | C |
| S24-9-99 | C | B | C | A | A | C | A | B | B | A | A | B | B | B | A | C | C | C | A | C | C |
| S25-11-100 | C | C | C | B | B | C | C | B | B | C | C | C | C | C | C | C | C | C | C | C | C |
| S25-11-101 | C | C | C | C | C | C | C | B | C | C | C | C | C | C | C | C | C | C | C | C | C |
| S25-11-102 | C | B | B | B | B | B | C | B | B | C | C | C | C | C | C | C | C | C | C | C | C |
| S25-11-103 | C | C | C | C | C | C | C | B | C | C | C | C | C | C | C | C | C | C | C | C | C |
| S25-11-104 | C | C | C | B | C | C | C | B | B | C | C | C | C | C | C | C | C | C | C | C | C |
| S25-11-105 | C | C | C | C | C | C | C | C | C | C | C | C | C | C | C | C | C | C | C | C | C |

FIG. 10F

| Compound | SA1 01 292 13 | SA1 91 | SA1 61 tetM | SA1 58 tetK | SE1 64 122 28 | EF1 59 tetM | SP1 06 496 19 | SP1 60 tetM | SP3 12 tetM | HI26 2 339 29 | MC2 05 817 6 | EC1 07 259 22 | EC1 55 tetA | KP1 53 tetA | KP4 57 | PM1 12 356 59 | PA5 55 | PA5 56 | AB2 50 | SM2 56 | BC2 40 |
|---|---|---|---|---|---|---|---|---|---|---|---|---|---|---|---|---|---|---|---|---|---|
| S25-11-106 | C | C | C | C | C | B | C | B | C | C | C | C | C | C | C | C | C | C | C | C | C |
| S25-11-106 | C | C | C | C | C | C | C | C | C | C | C | C | C | C | C | C | C | C | C | C | C |
| S25-11-107 | C | C | C | C | C | C | C | C | C | C | C | C | C | C | C | C | C | C | C | C | C |
| S25-11-108 | C | C | C | C | C | C | C | C | C | C | C | C | C | C | C | C | C | C | C | C | C |
| S25-11-109 | C | C | C | C | C | C | C | C | C | C | C | C | C | C | C | C | C | C | C | C | C |
| S25-11-110 | C | B | B | B | B | B | C | C | B | C | C | C | C | C | C | C | C | C | C | C | C |
| S25-11-111 | C | B | B | B | B | B | C | B | B | C | C | C | C | C | C | C | C | C | C | C | C |
| S25-11-112 | C | C | C | C | C | C | C | B | B | C | C | C | C | C | C | C | C | C | C | C | C |
| S25-11-113 | C | C | C | C | C | C | C | B | B | C | C | C | C | C | C | C | C | C | C | C | C |
| S25-11-114 | C | C | C | C | C | C | C | B | C | C | C | C | C | C | C | C | C | C | C | C | C |
| S25-11-115 | C | B | C | B | B | B | C | B | B | C | C | C | C | C | C | C | C | C | C | C | C |
| S25-11-116 | C | C | C | C | C | B | C | B | B | C | C | C | C | C | C | C | C | C | C | C | C |
| S25-11-117 | C | B | B | B | B | B | B | B | B | C | C | C | C | C | C | C | C | C | C | C | C |
| S25-11-118 | C | B | B | B | B | B | C | B | B | C | C | C | C | C | C | C | C | C | C | C | C |
| S25-11-119 | C | C | C | C | C | C | C | C | C | C | C | C | C | C | C | C | C | C | C | C | C |
| S25-11-120 | C | C | C | C | C | B | C | C | C | C | C | C | C | C | NT | C | C | C | C | C | C |
| S25-11-121 | C | B | B | B | A | B | B | B | B | A | C | B | B | B | NT | C | C | C | A | C | C |
| S25-11-122 | C | B | B | B | B | B | B | B | B | A | C | B | C | C | NT | C | C | C | A | C | C |
| S25-11-123 | C | B | B | B | B | B | B | B | B | C | C | C | C | C | NT | C | C | C | C | C | C |
| S25-11-124 | C | C | C | C | B | C | C | C | C | C | C | C | C | C | C | C | C | C | C | C | C |
| S25-11-125 | C | B | B | B | A | B | B | C | B | A | C | B | B | B | A | C | C | C | A | C | C |
| S25-11-126 | C | B | B | B | B | B | B | B | B | C | C | B | C | C | C | C | C | C | C | C | C |
| S25-11-127 | C | B | B | B | B | B | C | B | B | C | C | C | C | C | C | C | C | C | C | C | C |
| S25-11-128 | C | C | B | C | C | B | C | C | C | C | C | C | C | C | C | C | C | C | C | C | C |
| S25-11-129 | C | B | B | B | A | B | B | B | B | A | B | B | C | B | B | C | C | C | A | C | A |
| S25-11-130 | B | C | C | B | A | B | A | B | B | A | A | B | B | B | A | C | C | C | A | C | B |
| S25-11-131 | C | C | C | C | C | C | C | B | B | C | C | C | C | C | C | C | C | C | C | C | C |
| S25-11-132 | C | C | C | C | C | C | C | C | C | C | C | C | C | C | C | C | C | C | C | C | C |
| S25-11-133 | C | C | C | B | B | B | B | B | B | C | C | C | C | C | C | C | C | C | C | C | C |
| S25-11-38 | C | C | C | C | C | C | C | C | C | C | C | C | C | C | NT | C | C | C | C | C | C |

FIG. 10G

| Compound | SA1 01 292 13 | SA1 91 | SA1 61 tetM | SA1 58 tetK | SE1 64 122 28 | EF1 59 tetM | SP1 06 496 19 | SP1 60 tetM | SP3 12 tetM | HI26 2 339 29 | MC2 05 817 6 | EC1 07 259 22 | EC1 55 tetA | KP1 53 tetA | KP4 57 | PM1 12 356 59 | PA5 55 | PA5 56 | AB2 50 | SM2 56 | BC2 40 |
|---|---|---|---|---|---|---|---|---|---|---|---|---|---|---|---|---|---|---|---|---|---|
| **S25-11-39** | C | B | B | B | B | B | C | B | B | C | C | B | C | C | NT | C | C | C | C | C | C |
| **S25-11-40** | C | B | B | B | B | B | C | C | C | C | C | C | C | C | NT | C | C | C | C | C | C |
| **S25-11-41** | C | B | B | B | A | B | A | B | B | A | C | B | B | B | NT | C | C | C | A | C | C |
| **S25-11-42** | C | B | B | B | B | B | C | C | B | C | C | C | C | C | NT | C | C | C | C | C | C |
| **S25-11-79** | C | C | C | C | C | C | C | C | C | C | C | C | C | C | NT | C | C | C | C | C | C |
| **S25-11-80** | C | B | C | B | B | B | C | C | C | C | C | C | C | C | NT | C | C | C | C | C | C |
| **S25-11-81** | C | C | C | C | C | C | C | C | C | C | C | C | C | C | NT | C | C | C | C | C | C |
| **S25-11-82** | C | B | C | B | B | B | B | C | B | C | C | C | B | C | NT | C | C | C | C | C | C |
| **S25-11-83** | C | C | C | C | C | C | C | B | B | C | C | C | C | C | NT | C | C | C | C | C | C |
| **S25-11-84** | C | C | C | C | C | C | C | C | C | C | C | C | C | C | NT | C | C | C | C | C | C |
| **S25-11-85** | B | B | B | A | A | B | A | B | B | A | A | B | B | B | NT | B | A | C | A | A | C |
| **S25-11-86** | C | B | B | B | A | B | A | B | B | A | C | B | B | B | NT | C | C | C | A | C | C |
| **S25-11-87** | C | B | B | B | A | B | A | B | B | A | B | B | B | B | NT | C | C | C | A | C | C |
| **S25-11-88** | C | B | B | B | A | B | B | B | B | C | C | B | C | C | NT | C | C | C | A | C | C |
| **S25-11-89** | C | C | C | C | C | C | C | C | C | C | C | C | C | C | C | C | C | C | C | C | C |
| **S25-11-90** | C | B | C | B | B | B | C | B | B | C | C | C | C | C | C | C | C | C | C | C | C |
| **S25-11-91** | C | B | B | B | A | B | B | B | B | C | B | B | B | B | C | C | C | C | C | C | C |
| **S25-11-92** | C | B | B | B | A | B | A | B | B | A | A | B | B | B | A | C | C | C | A | A | C |
| **S25-11-93** | C | B | B | B | B | B | B | B | B | C | C | B | C | C | C | C | C | C | C | C | C |
| **S25-11-94** | C | B | B | B | B | B | B | B | B | C | C | B | B | C | C | C | C | C | C | C | C |
| **S25-11-95** | C | C | B | B | B | B | C | B | B | C | C | C | C | C | C | C | C | C | C | C | C |
| **S25-11-96** | C | C | B | C | C | B | C | B | B | C | C | C | C | C | C | C | C | C | C | C | C |
| **S25-11-97** | C | C | C | C | C | C | C | C | C | C | C | C | C | C | C | C | C | C | C | C | C |
| **S25-11-98** | C | B | B | B | A | B | A | B | B | A | A | B | B | B | A | C | C | C | A | C | C |
| **S25-11-99** | C | B | B | B | B | B | B | B | B | C | C | B | B | C | C | C | C | C | C | C | C |
| **S31-7-1** | C | B | B | B | A | B | A | B | B | C | A | B | B | B | B | C | C | C | C | C | C |
| **S32-6-1-1** | C | B | B | B | A | B | A | B | B | C | C | B | B | B | NT | C | C | C | C | C | C |
| **S32-6-1-1** | C | B | B | B | A | B | A | B | B | C | C | B | B | B | NT | C | C | C | C | C | C |
| **S32-6-1-2** | C | B | C | B | A | C | A | B | B | A | C | B | B | B | NT | C | C | C | A | C | C |
| **S32-6-1-2** | C | B | C | B | A | C | A | B | B | A | C | B | B | B | NT | C | C | C | A | C | C |

FIG. 10H

| Compound | SA1 01 292 13 | SA1 91 | SA1 61 tetM | SA1 58 tetK | SE1 64 122 28 | EF1 59 tetM | SP1 06 496 19 | SP1 60 tetM | SP3 12 tetM | HI26 2 339 29 | MC2 05 817 6 | EC1 07 259 22 | EC1 55 tetA | KP1 53 tetA | KP4 57 | PM1 12 356 59 | PA5 55 | PA5 56 | AB2 50 | SM2 56 | BC2 40 |
|---|---|---|---|---|---|---|---|---|---|---|---|---|---|---|---|---|---|---|---|---|---|
| **S32-6-1-3** | C | B | B | B | A | B | A | B | A | C | A | B | B | B | NT | C | NT | NT | C | C | C |
| **S32-6-1-3** | C | B | B | B | A | B | A | B | A | C | A | B | B | B | NT | C | NT | NT | C | C | C |
| **S32-6-1-4** | C | B | C | B | A | C | A | B | B | A | C | B | B | B | NT | C | C | C | C | C | C |
| **S32-6-1-4** | C | B | C | B | A | C | A | B | B | A | C | B | B | B | NT | C | C | C | C | C | C |
| **S32-6-1-5** | C | B | C | B | A | C | A | B | B | A | B | B | B | B | NT | B | C | B | A | C | C |
| **S32-6-1-5** | C | B | C | B | A | C | A | B | B | A | B | B | B | B | NT | B | C | B | A | C | C |
| **S32-6-1-6** | B | B | C | B | A | C | A | B | B | C | B | B | B | B | NT | C | C | C | C | C | C |
| **S32-6-1-6** | B | B | C | B | A | C | A | B | B | C | B | B | B | B | NT | C | C | C | C | C | C |
| **S32-6-1-7** | C | A | C | B | A | C | A | B | A | A | A | B | B | B | NT | C | NT | NT | C | C | C |
| **S32-6-1-7** | C | A | C | B | A | C | A | B | A | A | A | B | B | B | NT | C | NT | NT | C | C | C |
| **S32-6-2-1** | B | C | C | B | A | B | A | B | B | A | A | B | B | B | NT | C | C | C | A | C | C |
| **S32-6-2-1** | B | C | C | B | A | B | A | B | B | A | A | B | B | B | NT | C | C | C | A | C | C |
| **S32-6-2-2** | C | C | B | B | A | B | A | B | B | C | B | B | B | B | NT | C | C | C | C | C | C |
| **S32-6-2-2** | C | C | B | B | A | B | A | B | B | C | B | B | B | B | NT | C | C | C | C | C | C |
| **S32-6-2-3** | C | B | C | B | A | B | A | B | B | C | C | B | B | B | NT | C | C | C | C | C | C |
| **S32-6-2-3** | C | B | C | B | A | B | A | B | B | C | C | B | B | B | NT | C | C | C | C | C | C |
| **200** | C | C | C | B | B | C | B | B | B | A | C | B | B | B | NT | C | C | C | C | C | C |
| **Sancycline** | 0.5 | 8 | 2 | 4 | 4 | 8 | 0.25 | 8 | 4 | 0.5 | 0.12 5 | 8 | 32 | 32 | 32 | 4 | 32 | 1 | 16 | 1 | 4 |
| **Minocycline** | 0.06 | 8 | 8 | 0.03 | 0.12 5 | 16 | 0.01 55 | 2 | 16 | 1 | 0.01 55 | 0.5 | 8 | 8 | 32 | 8 | 16 | 0.12 5 | 8 | 0.5 | 8 |
| **Tigecycline** | 0.06 | 0.5 | 0.12 5 | 0.06 | 0.12 5 | 0.06 | 0.01 56 | 0.01 56 | 0.01 55 | 1 | 0.01 55 | 0.03 | 0.5 | 1 | 8 | 1 | 16 | 0.25 | 8 | 1 | 16 |

FIG. 10I

| Compound | SA1 01 292 13 | SA1 61 tetM | SA1 58 tetK | EF3 27 tetM | EF4 04 tetM | SP1 60 tetM | SP3 12 tetM | EC1 07 259 22 | EC1 55 tetA | EC8 78 tolC | EC8 80 ipxC | EC8 82 imp | KP4 57 CTX-M-15 | PM 385 | PA5 55 BAA -47 | PA5 56 | PA8 84 351 51 | PA6 89 | EC6 03 tetA | AB2 50 | SM 256 | BC2 40 |
|---|---|---|---|---|---|---|---|---|---|---|---|---|---|---|---|---|---|---|---|---|---|---|
| S15-13-100 | C | C | B | B | C | B | B | B | B | C | C | C | C | C | C | C | C | C | C | C | C | C |
| S15-13-101 | C | B | B | B | B | B | B | B | B | C | B | B | C | C | C | C | C | C | B | A | C | C |
| S15-13-102 | C | B | B | B | B | B | B | C | C | C | C | C | C | C | C | C | C | C | C | C | C | C |
| S15-13-103 | B | B | B | B | B | B | B | B | B | C | A | A | C | B | C | C | C | B | B | A | A | C |
| S15-13-104 | C | C | C | B | B | B | B | C | C | C | C | C | C | C | C | C | C | C | C | C | C | C |
| S15-13-105 | C | B | B | B | B | B | B | B | B | C | B | B | C | B | C | C | C | C | B | A | C | B |
| S15-13-106 | C | B | B | B | B | B | B | C | C | C | C | C | C | C | C | C | C | C | C | C | C | C |
| S15-13-107 | C | B | C | B | B | B | B | C | C | C | C | C | C | C | C | C | C | C | C | C | C | C |
| S15-13-108 | C | C | C | B | B | B | B | C | C | C | C | C | C | C | C | C | C | C | C | C | C | C |
| S15-13-109 | C | B | B | B | B | B | B | C | C | C | C | C | C | C | C | C | C | C | C | C | C | C |
| S15-13-110 | C | B | B | B | B | B | B | C | C | C | C | C | C | C | C | C | C | C | C | C | C | C |
| S15-13-111 | C | C | C | B | B | B | B | C | C | C | C | C | C | C | C | C | C | C | C | C | C | C |
| S15-13-112 | C | C | B | B | B | B | B | B | B | B | B | B | C | B | C | C | C | B | B | A | C | B |
| S15-13-113 | C | C | B | B | B | B | B | C | C | C | C | C | C | C | C | C | C | C | C | C | C | C |
| S15-13-114 | B | C | B | B | B | B | B | B | B | B | B | B | A | A | A | A | B | A | B | A | A | B |
| S15-13-115 | C | B | B | B | B | B | B | B | B | C | A | B | C | B | C | C | B | B | B | A | C | C |
| S15-13-122 | C | C | C | C | B | C | C | C | C | C | C | C | C | C | C | C | C | C | C | C | C | C |
| S15-13-137 | C | B | B | B | B | B | B | C | C | C | C | C | C | C | C | C | C | C | C | C | C | C |
| S15-13-138 | C | C | C | C | B | C | B | C | C | C | C | C | C | C | C | C | C | C | C | C | C | C |
| S15-13-139 | C | C | C | C | B | C | B | C | C | C | C | C | C | C | C | C | C | C | C | C | C | C |
| S15-13-140 | C | C | C | C | B | C | B | C | C | C | C | C | C | C | C | C | C | C | C | C | C | C |
| S15-13-141 | C | B | B | B | B | B | B | C | C | C | C | C | C | C | C | C | C | C | C | C | C | C |
| S15-13-161 | C | B | B | B | B | B | B | C | C | C | C | C | C | C | C | C | C | C | C | C | C | C |
| S15-13-162 | C | C | C | C | B | B | B | C | C | C | C | C | C | C | C | C | C | C | C | C | C | C |
| S15-13-163 | C | B | B | B | B | B | B | C | C | C | C | C | C | C | C | C | C | C | C | C | C | C |
| S15-13-164 | C | B | B | B | B | B | B | C | C | C | C | C | C | C | C | C | C | C | C | C | C | C |
| S15-13-165 | C | B | B | B | B | B | B | C | C | C | C | C | C | C | C | C | C | C | C | C | C | C |
| S15-13-166 | C | C | C | B | B | B | B | C | C | C | C | C | C | C | C | C | C | C | C | C | C | C |
| S15-13-227 | C | C | B | B | C | B | B | B | B | C | B | B | C | C | C | C | C | C | B | C | C | C |
| S15-13-64 | C | C | B | B | B | B | B | C | C | C | C | C | C | C | C | C | C | C | C | C | C | C |

FIG. 11A

| Compound | SA1 01 292 13 | SA1 61 tetM | SA1 58 tetK | EF3 27 tetM | EF4 04 tetM | SP1 60 tetM | SP3 12 tetM | EC1 07 259 22 | EC1 55 tetA | EC8 78 tolC | EC8 80 ipxC | EC8 82 imp | KP4 57 CTX-M-15 | PM 385 | PA5 55 BAA -47 | PA5 56 | PA8 84 351 51 | PA6 89 | EC6 03 tetA | AB2 50 | SM 256 | BC2 40 |
|---|---|---|---|---|---|---|---|---|---|---|---|---|---|---|---|---|---|---|---|---|---|---|
| S15-13-65 | C | C | C | C | C | C | C | C | C | C | C | C | C | C | C | C | C | C | C | C | C | C |
| S15-13-66 | C | C | C | C | B | C | B | C | C | C | C | C | C | C | C | C | C | C | C | C | C | C |
| S15-13-67 | C | B | B | B | B | B | B | C | C | C | C | C | C | C | C | C | C | C | C | C | C | C |
| S15-13-68 | C | B | C | B | B | B | B | C | C | C | C | C | C | C | C | C | C | C | C | A | C | C |
| S15-13-69 | C | C | C | B | B | B | B | C | C | C | C | C | C | C | C | C | C | C | C | C | C | C |
| S15-13-70 | C | C | C | C | B | C | C | C | C | C | C | C | C | C | C | C | C | C | C | C | C | C |
| S15-13-71 | C | B | B | B | B | B | B | B | B | C | B | B | C | C | C | C | C | C | B | A | C | C |
| S15-13-72 | C | B | B | B | B | B | B | B | C | C | C | C | C | C | C | C | C | C | C | C | C | C |
| S15-13-73 | C | C | B | B | C | C | B | C | C | C | C | C | C | C | C | C | C | C | C | C | C | C |
| S15-13-74 | C | B | B | B | B | B | B | C | C | C | C | C | C | C | C | C | C | C | C | C | C | C |
| S15-13-75 | C | B | B | B | B | B | B | C | C | C | C | C | C | C | C | C | C | C | C | C | C | C |
| S15-13-76 | NT | NT | NT | NT | NT | NT | NT | NT | NT | NT | NT | NT | NT | NT | NT | NT | NT | NT | NT | NT | NT | NT |
| S15-13-77 | NT | NT | NT | NT | NT | NT | NT | NT | NT | NT | NT | NT | NT | NT | NT | NT | NT | NT | NT | NT | NT | NT |
| S15-13-79 | C | C | B | B | C | C | B | B | C | C | C | C | C | C | C | C | C | C | C | C | C | C |
| S15-13-80 | C | B | B | B | B | B | B | C | C | C | C | C | C | C | C | C | C | C | C | C | C | C |
| S15-13-98 | C | B | B | B | B | B | B | B | B | C | C | C | C | C | C | C | C | C | C | C | C | C |
| S15-13-99 | C | C | C | C | B | B | B | C | C | C | C | C | C | C | C | C | C | C | C | C | C | C |
| S15-14-5 | C | C | B | C | C | B | B | B | B | C | C | C | B | A | C | B | B | A | B | C | C | C |
| S16-10-100 | C | C | B | B | C | B | B | B | B | B | A | A | C | C | C | C | C | C | B | A | C | C |
| S16-10-103 | C | C | B | C | C | B | B | B | B | B | A | A | B | B | C | B | B | B | B | A | C | C |
| S16-10-104 | C | C | B | C | C | B | B | B | B | B | B | B | B | C | C | B | B | B | B | A | C | C |
| S16-10-105 | C | C | B | C | C | B | C | B | B | C | B | B | C | C | C | C | B | C | B | C | C | C |
| S16-10-108 | C | C | B | B | C | B | B | B | B | B | A | A | B | C | C | B | B | B | B | A | C | C |
| S16-10-109 | C | C | B | C | C | B | C | B | B | C | B | B | C | C | C | C | B | C | B | C | C | C |
| S16-10-111 | C | C | B | B | C | B | B | B | B | B | A | B | B | B | C | B | B | B | B | A | C | C |
| S16-10-112 | C | C | B | B | C | B | B | B | B | B | B | B | B | C | C | C | B | B | B | C | C | C |
| S16-10-113 | C | C | B | C | C | B | B | B | C | B | C | C | C | C | C | B | B | B | C | C | C | B |
| S16-10-114 | C | C | B | C | C | B | B | B | B | B | B | B | C | C | C | B | B | B | B | A | C | C |
| S16-10-115 | C | C | B | C | C | B | B | B | B | B | B | B | C | C | C | C | B | C | B | A | C | C |
| S16-10-122 | C | C | B | C | C | B | B | B | B | C | B | B | C | C | C | C | B | C | B | C | C | C |

FIG. 11B

| Compound | SA1 01 292 13 | SA1 61 tetM | SA1 58 tetK | EF3 27 tetM | EF4 04 tetM | SP1 60 tetM | SP3 12 tetM | EC1 07 259 22 | EC1 55 tetA | EC8 78 tolC | EC8 80 ipxC | EC8 82 imp | KP4 57 CTX-M-15 | PM 385 | PA5 55 BAA -47 | PA5 56 | PA8 84 351 51 | PA6 89 | EC6 03 tetA | AB2 50 | SM 256 | BC2 40 |
|---|---|---|---|---|---|---|---|---|---|---|---|---|---|---|---|---|---|---|---|---|---|---|
| S16-10-124 | C | C | B | C | C | B | C | B | B | C | B | B | B | C | C | C | B | B | B | C | C | C |
| S16-10-127 | B | C | A | B | B | B | B | B | B | C | A | A | C | C | C | C | B | B | B | C | C | C |
| S16-10-133 | C | C | B | B | C | B | B | B | B | C | A | A | C | C | C | C | C | C | B | A | C | C |
| S16-10-134 | C | C | B | B | C | C | B | B | B | C | B | B | C | C | C | C | C | C | B | C | C | C |
| S16-10-140 | C | B | B | B | B | B | B | B | B | C | C | C | C | C | C | C | C | C | C | C | C | C |
| S16-10-141 | C | B | B | B | B | B | B | C | B | C | C | C | C | C | C | C | C | C | C | C | C | C |
| S16-10-142 | C | B | B | B | B | B | C | C | C | C | C | C | C | C | C | C | C | C | C | C | C | C |
| S16-10-29 | B | C | B | B | C | B | B | B | B | B | A | A | A | B | C | A | B | B | B | A | C | C |
| S16-10-30 | C | C | B | C | C | B | B | B | B | B | A | A | B | B | C | B | B | B | B | A | C | C |
| S16-10-32 | C | B | B | B | B | C | B | B | B | C | C | C | C | C | C | C | C | C | C | A | C | C |
| S16-10-34 | C | B | B | B | B | C | B | C | C | C | C | C | C | C | C | C | C | C | C | C | C | C |
| S16-10-35 | C | B | B | B | B | C | B | C | C | C | C | C | C | C | C | C | C | C | C | C | C | C |
| S16-10-41 | C | C | B | C | C | B | C | B | B | C | B | B | C | C | C | C | B | C | C | C | C | C |
| S15-13-227 | C | C | B | C | C | B | B | B | B | B | B | B | B | B | C | B | B | B | B | A | C | C |
| S16-10-60 | C | C | B | C | C | B | B | B | B | B | B | B | B | B | C | B | B | B | B | A | C | C |
| S16-10-62 | C | C | B | C | C | B | B | B | B | B | B | A | C | C | C | C | B | B | B | A | C | C |
| S16-10-63 | C | C | B | C | C | B | B | B | B | C | B | B | C | C | C | C | B | C | B | C | C | C |
| S16-10-70 | C | C | B | B | C | B | B | B | B | C | A | A | C | C | C | C | C | C | B | C | C | C |
| S16-10-78 | C | B | B | B | B | C | C | B | B | C | C | C | C | C | C | C | C | C | C | C | C | C |
| S16-10-82 | C | B | B | B | B | C | B | C | B | C | C | C | C | C | C | C | C | C | C | C | C | C |
| S16-10-94 | C | C | B | B | C | B | C | B | B | C | B | B | C | C | C | C | B | C | C | C | C | C |
| S16-10-98 | C | C | B | B | C | B | C | B | B | C | B | B | C | C | C | C | B | C | B | C | C | C |
| S16-10-99 | B | C | B | B | C | B | B | B | B | B | A | A | C | C | C | C | B | B | B | A | C | C |
| S24-9-117 | B | C | B | C | C | B | C | B | C | B | B | B | C | C | C | B | C | C | C | A | C | C |
| S24-9-118 | C | C | B | C | C | B | C | B | C | B | B | B | C | C | C | B | C | C | C | A | C | C |
| S24-9-122 | C | C | B | C | C | B | B | B | B | B | C | C | C | C | C | B | B | B | B | C | C | C |
| S24-9-123 | C | C | B | B | C | B | B | B | B | C | A | B | C | C | C | C | B | C | B | C | C | C |
| S24-9-124 | C | C | B | B | B | B | B | B | B | C | A | A | C | C | C | C | B | C | B | C | C | C |
| S24-9-160 | C | C | B | B | B | B | B | B | B | B | A | A | C | C | C | C | C | B | B | A | C | C |
| S24-9-161 | C | B | B | B | B | B | B | B | B | C | A | A | C | C | C | C | C | C | B | A | C | C |

FIG. 11C

| Compound | SA1 01 292 13 | SA1 61 tetM | SA1 58 tetK | EF3 27 tetM | EF4 04 tetM | SP1 60 tetM | SP3 12 tetM | EC1 07 259 22 | EC1 55 tetA | EC8 78 tolC | EC8 80 ipxC | EC8 82 imp | KP4 57 CTX-M-15 | PM 385 | PA5 55 BAA -47 | PA5 56 | PA8 84 351 51 | PA6 89 | EC6 03 tetA | AB2 50 | SM 256 | BC2 40 |
|---|---|---|---|---|---|---|---|---|---|---|---|---|---|---|---|---|---|---|---|---|---|---|
| S24-9-162 | C | B | B | B | B | B | B | B | B | C | B | B | C | C | C | C | C | C | B | A | C | C |
| S24-9-163 | C | B | B | B | B | C | B | C | C | C | C | C | C | C | C | C | C | C | C | C | C | C |
| S24-9-164 | B | B | A | B | B | B | B | B | B | B | A | A | C | C | C | C | B | B | B | A | C | C |
| S24-9-165 | C | B | A | B | B | B | B | C | B | B | A | A | C | C | C | C | B | B | B | A | C | C |
| S24-9-166 | C | B | B | B | B | B | B | B | B | C | A | A | C | C | C | C | C | C | B | A | C | C |
| S24-9-167 | C | B | B | B | B | B | B | C | B | C | C | B | C | C | C | C | C | C | C | A | C | C |
| S24-9-168 | C | C | A | B | B | B | B | B | A | B | A | A | C | B | C | C | B | B | B | C | A | C |
| S24-9-169 | B | C | B | B | B | B | B | B | B | B | A | A | A | A | C | B | B | A | A | C | A | C |
| S24-9-170 | B | C | B | B | B | B | B | B | B | B | A | A | B | A | C | B | B | B | A | C | A | C |
| S24-9-171 | C | B | B | B | B | B | B | B | B | B | B | A | A | A | A | A | B | A | B | C | C | C |
| S24-9-172 | B | B | B | B | B | B | B | B | A | B | A | A | A | A | C | B | B | A | A | A | A | B |
| S24-9-173 | B | C | B | B | B | B | B | B | B | B | A | A | C | C | C | C | B | B | B | C | A | C |
| S24-9-174 | C | C | B | B | B | B | B | B | B | B | B | B | A | A | A | A | B | A | B | C | C | C |
| S24-9-175 | C | C | B | B | B | B | B | B | B | B | A | A | C | C | C | C | B | B | B | A | C | C |
| S24-9-179 | NT | NT | NT | NT | NT | NT | NT | NT | NT | NT | NT | NT | NT | NT | NT | NT | NT | NT | NT | NT | NT | NT |
| S24-9-182 | NT | NT | NT | NT | NT | NT | NT | NT | NT | NT | NT | NT | NT | NT | NT | NT | NT | NT | NT | NT | NT | NT |
| S24-9-56 | C | B | B | B | B | B | B | C | C | C | C | C | C | C | C | C | C | C | C | C | C | C |
| S24-9-58 | C | B | B | B | B | B | B | C | C | C | C | C | C | C | C | C | C | C | C | C | C | C |
| S24-9-59 | C | C | B | B | B | B | B | B | B | B | B | B | A | A | A | A | B | A | C | A | C | C |
| S24-9-60 | C | C | A | B | B | B | B | B | B | B | A | A | C | C | C | C | B | B | B | A | C | C |
| S24-9-61 | C | C | B | B | B | B | B | B | B | B | A | A | C | C | C | C | C | C | B | A | C | C |
| S24-9-62 | C | C | B | C | C | C | B | B | C | B | C | C | B | A | C | B | B | A | C | C | C | C |
| S24-9-63 | B | C | A | B | B | B | B | B | B | A | A | A | B | A | A | A | B | B | B | A | A | A |
| S24-9-64 | B | C | A | B | B | B | B | B | B | A | A | A | C | B | C | B | C | B | B | A | C | B |
| S24-9-65 | B | B | A | B | B | B | B | B | B | A | A | A | C | B | C | B | C | B | B | A | C | B |
| S24-9-67 | C | C | B | B | C | B | B | B | B | B | A | A | C | C | C | C | C | C | B | A | C | C |
| S24-9-68 | C | C | B | B | C | B | B | B | B | C | B | B | C | C | C | C | C | C | C | A | C | C |
| S24-9-69 | C | B | B | B | B | B | B | C | C | C | C | C | C | C | C | C | C | C | C | C | C | C |
| S24-9-70 | B | C | A | B | B | B | B | B | B | B | A | A | B | B | C | B | B | B | B | A | C | B |
| S24-9-71 | C | B | B | B | B | B | B | B | B | C | A | A | C | C | C | C | C | C | B | A | C | C |

FIG. 11D

| Compound | SA1 01 292 13 | SA1 61 tetM | SA1 58 tetK | EF3 27 tetM | EF4 04 tetM | SP1 60 tetM | SP3 12 tetM | EC1 07 259 22 | EC1 55 tetA | EC8 78 tolC | EC8 80 ipxC | EC8 82 imp | KP4 57 CTX-M-15 | PM 385 | PA5 55 BAA -47 | PA5 56 | PA8 84 351 51 | PA6 89 | EC6 03 tetA | AB2 50 | SM 256 | BC2 40 |
|---|---|---|---|---|---|---|---|---|---|---|---|---|---|---|---|---|---|---|---|---|---|---|
| S24-9-72 | C | B | B | B | B | B | B | B | B | C | B | B | C | C | C | C | C | C | B | C | C | C |
| S24-9-73 | C | C | B | B | B | B | B | B | B | B | B | B | B | A | C | B | B | A | B | C | C | C |
| S24-9-74 | C | B | B | B | B | B | B | B | B | B | B | B | B | A | C | B | B | B | B | A | C | C |
| S24-9-75 | B | B | A | B | B | B | B | B | B | B | A | A | C | B | C | C | B | B | B | A | C | B |
| S24-9-76 | C | C | B | C | C | B | C | B | B | B | B | B | B | A | A | A | B | A | B | C | C | C |
| S24-9-77 | C | B | B | B | B | C | B | C | C | C | C | C | C | C | C | C | C | C | C | C | C | C |
| S24-9-78 | C | C | B | C | C | B | B | B | C | B | C | B | B | A | A | A | B | A | B | C | C | C |
| S24-9-79 | NT | NT | NT | NT | NT | NT | NT | NT | NT | NT | NT | NT | NT | NT | NT | NT | NT | NT | NT | NT | NT | NT |
| S24-9-94 | C | C | B | C | C | B | C | B | C | B | B | B | C | C | C | B | C | B | C | A | C | C |
| S24-9-95 | C | C | B | C | C | B | C | B | C | B | B | B | C | C | C | B | C | C | C | A | C | C |
| S24-9-96 | NT | NT | NT | NT | NT | NT | NT | NT | NT | NT | NT | NT | NT | NT | NT | NT | NT | NT | NT | NT | NT | NT |
| S25-11-134 | C | C | C | C | C | C | C | C | C | C | C | C | C | C | C | C | C | C | C | C | C | C |
| S25-11-135 | C | C | B | B | C | B | B | B | B | C | C | C | C | C | C | C | C | C | B | C | C | C |
| S25-11-136 | C | C | C | B | C | B | B | C | C | C | C | C | C | C | C | C | C | C | C | C | C | C |
| S25-11-137 | C | C | C | C | C | B | B | C | C | C | C | C | C | C | C | C | C | C | C | C | C | C |
| S25-11-138 | C | C | C | C | C | B | B | C | C | C | C | C | C | C | C | C | C | C | C | A | C | C |
| S25-11-139 | C | C | C | B | B | C | C | C | C | C | C | C | C | C | C | C | C | C | C | C | C | C |
| S25-11-140 | C | C | C | C | C | C | C | C | C | C | C | C | C | C | C | C | C | C | C | C | C | C |
| S25-11-141 | C | C | C | C | C | C | C | C | C | C | C | C | C | C | C | C | C | C | C | C | C | C |
| S25-11-142 | C | C | C | C | C | C | C | C | C | C | C | C | C | C | C | C | C | C | C | C | C | C |
| S25-11-143 | C | B | B | B | B | B | B | C | C | C | C | C | C | C | C | C | C | C | C | C | C | C |
| S25-11-144 | C | C | B | B | B | B | B | C | C | C | C | C | C | C | C | C | C | C | C | C | C | C |
| S25-11-145 | C | C | B | C | B | C | C | B | C | C | C | C | C | C | C | C | B | B | C | C | C | C |
| S25-11-146 | C | B | B | B | B | C | B | C | C | C | C | C | C | C | C | C | C | C | C | C | C | C |
| S25-11-147 | C | B | B | B | B | B | B | C | C | C | C | C | C | C | C | C | C | C | C | C | C | C |
| S25-11-148 | C | C | B | B | B | B | B | C | C | C | C | C | C | C | C | C | C | C | C | C | C | C |
| S25-11-149 | C | B | B | B | B | B | B | B | B | C | C | B | C | C | C | C | C | C | B | A | C | C |
| S25-11-150 | C | B | B | B | B | B | B | B | C | C | C | C | C | C | C | C | C | C | C | C | C | C |
| S25-11-151 | C | B | B | B | B | B | B | C | C | C | C | C | C | C | C | C | C | C | C | C | C | C |
| S25-11-152 | C | C | B | B | B | B | B | C | C | C | C | C | C | C | C | C | C | C | C | C | C | C |

FIG. 11E

| Compound | SA1 01 292 13 | SA1 61 tetM | SA1 58 tetK | EF3 27 tetM | EF4 04 tetM | SP1 60 tetM | SP3 12 tetM | EC1 07 259 22 | EC1 55 tetA | EC8 78 tolC | EC8 80 ipxC | EC8 82 imp | KP4 57 CTX-M-15 | PM 385 | PA5 55 BAA -47 | PA5 56 | PA8 84 351 51 | PA6 89 | EC6 03 tetA | AB2 50 | SM 256 | BC2 40 |
|---|---|---|---|---|---|---|---|---|---|---|---|---|---|---|---|---|---|---|---|---|---|---|
| S25-11-153 | C | C | C | C | B | C | B | C | C | C | C | C | C | C | C | C | C | C | C | C | C | C |
| S25-11-154 | C | C | C | C | B | C | C | C | C | C | C | C | C | C | C | C | C | C | C | C | C | C |
| S25-11-155 | C | C | B | B | B | B | B | B | C | B | B | A | A | A | A | A | B | A | C | C | C | C |
| S25-11-156 | C | C | C | C | C | C | C | C | C | C | C | C | C | C | C | C | C | C | C | C | C | C |
| S25-11-157 | C | C | C | C | C | C | C | C | C | C | C | C | C | C | C | C | C | C | C | C | C | C |
| S25-11-158 | C | B | B | B | B | B | B | C | C | C | C | C | C | C | C | C | C | C | C | C | C | C |
| S25-11-159 | C | B | B | B | B | B | B | C | C | C | C | C | C | C | A | C | C | C | C | C | C | B |
| S25-11-160 | C | C | C | C | B | B | C | C | C | C | C | C | C | C | C | C | C | C | C | C | C | C |
| S25-11-161 | C | C | C | C | B | C | C | C | C | C | C | C | C | C | C | C | C | C | C | C | C | C |
| S25-11-162 | C | B | A | B | B | B | B | B | B | B | A | A | C | B | A | C | B | B | B | A | C | B |
| S25-11-163 | C | B | B | B | B | B | B | B | B | C | B | B | C | C | C | C | C | C | B | A | C | B |
| S25-11-167 | C | C | C | B | B | B | B | C | C | C | C | C | C | C | C | C | C | C | C | C | C | C |
| S25-11-190 | C | B | B | B | B | B | B | C | C | C | C | C | C | C | C | C | C | C | C | C | C | C |
| S25-11-191 | C | C | B | B | B | B | B | C | C | C | C | C | C | C | C | C | C | C | C | C | C | C |
| S25-11-192 | C | B | B | B | B | B | B | C | C | C | C | C | C | C | C | C | C | C | C | C | C | C |
| S25-11-193 | C | B | B | B | B | B | B | C | C | C | C | C | C | C | C | C | C | C | C | A | C | C |
| S25-11-201 | C | C | C | C | C | C | C | C | C | C | C | C | C | C | C | C | C | C | C | C | C | C |
| S25-11-202 | C | C | C | C | C | C | C | C | C | C | C | C | C | C | C | C | C | C | C | C | C | C |
| S25-11-203 | C | C | C | C | C | C | C | C | C | C | C | C | C | C | C | C | C | C | C | C | C | C |
| S25-11-204 | C | B | B | B | B | B | B | C | C | C | C | C | C | C | C | C | C | C | C | C | C | C |
| S25-11-205 | C | C | C | C | C | C | C | C | C | C | C | C | C | C | C | C | C | C | C | C | C | C |
| S25-11-209 | C | C | C | C | C | C | C | C | C | C | C | C | C | C | C | C | C | C | C | A | C | C |
| S26-7-1 | C | C | B | B | B | B | B | B | B | B | B | B | B | A | C | B | B | A | B | A | C | C |
| S26-7-2 | C | C | B | B | B | B | B | B | B | B | B | B | B | B | C | B | B | B | B | A | C | C |
| S26-7-3 | C | C | B | B | B | B | B | B | B | C | A | A | C | C | C | C | C | C | B | C | C | C |
| S26-7-4 | C | C | B | B | B | B | B | B | B | C | A | A | C | C | C | C | C | C | B | A | C | C |
| Sancycline | 0.5 | 2 | 4 | 4 | 4 | 8 | 4 | 8 | 32 | 1 | 0.25 | 0.25 | 8 | 8 | 32 | 1 | 4 | 16 | 32 | 16 | 1 | 4 |
| Minocycline | 0.06 | 8 | 0.03 | 32 | 8 | 2 | 16 | 0.5 | 8 | 0.25 | 0.01 55 | 0.01 55 | 8 | 16 | 16 | 0.12 5 | 1 | 8 | 33 | 8 | 0.5 | 8 |
| Tigecycline | 0.06 | 0.12 | 0.06 | 0.06 | 0.03 | 0.01 | 0.01 | 0.03 | 0.5 | 0.03 | 0.01 | 0.01 | 1 | 4 | 16 | 0.25 | 0.06 | 1 | 2 | 8 | 1 | 16 |

FIG. 11F

| Compound | SA1 01 292 13 | SA1 61 tetM | SA1 58 tetK | EF3 27 tetM | EF4 04 tetM | SP1 60 tetM | SP3 12 tetM | EC1 07 259 22 | EC1 55 tetA | EC8 78 tolC | EC8 80 ipxC | EC8 82 imp | KP4 57 CTX-M-15 | PM 385 | PA5 55 BAA -47 | PA5 56 | PA8 84 351 51 | PA6 89 | EC6 03 tetA | AB2 50 | SM 256 | BC2 40 |
|---|---|---|---|---|---|---|---|---|---|---|---|---|---|---|---|---|---|---|---|---|---|---|
| | | 5 | | 25 | 12 | 55 | 55 | | | 12 | 55 | 55 | | | | | 25 | | | | | |

FIG. 11G

TETRACYCLINE COMPOUNDS

RELATED APPLICATIONS

This application is the U.S. National Stage of International Application No. PCT/US2010/001350, filed May 7, 2010, which designates the U.S., published in English, and claims the benefit of U.S. Provisional Application No. 61/215,757, filed on May 8, 2009. The entire teachings of the above application are incorporated herein by reference.

BACKGROUND OF THE INVENTION

The tetracyclines are broad spectrum anti-microbial agents that are widely used in human and veterinary medicine. The total production of tetracyclines by fermentation or semi-synthesis is measured in the thousands of metric tons per year.

The widespread use of tetracyclines for therapeutic purposes has led to the emergence of resistclance to these antibiotics, even among highly susceptible bacterial species. Therefore, there is need for new tetracycline analogs with improved antibacterial activities and efficacies against other tetracycline responsive diseases or disorders.

SUMMARY OF THE INVENTION

Compounds of Formula I are new tetracycline analogs with improved antibacterial activities and efficacies against other tetracycline responsive diseases or disorders:

I

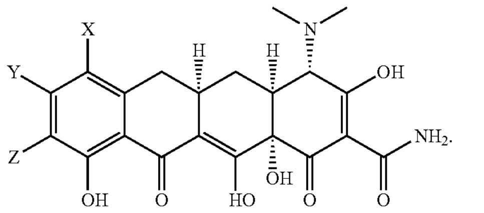

Pharmaceutically acceptable salts of the compound of Formula I are also included. Values for the variables in Formula I are provided below:

X is selected from hydrogen, bromo, fluoro, chloro, $C_1$-$C_6$ alkyl, —O—$C_1$-$C_6$ alkyl, —$S(O)_m$—$C_1$-$C_6$ alkyl, $C_3$-$C_7$ cycloalkyl, —O—$C_3$-$C_7$ cycloalkyl, —$S(O)_m$—$C_3$-$C_7$ cycloalkyl, —CN, —$N(R^4)(R^5)$, and —NH—C(O)—($C_1$-$C_6$ alkylene)-$N(R^4)(R^5)$, wherein each alkyl, alkylene or cycloalkyl in the group represented by X is optionally substituted with fluoro;

Y is selected from fluoro, —$C_1$-$C_6$ alkyl, and —$[C(R^{1a})(R^{1b})]_m$—$N(R^2)(R^3)$;

Z is selected from hydrogen, fluoro, bromo, —CN, —$[C(R^{1a})(R^{1b})]_n$—$N(R^2)(R^3)$, —$N(R^4)(R^5)$, $NO_2$, —NH—C(O)—$C_1$-$C_4$ alkylene-$N(R^4)(R^5)$, $C_1$-$C_6$ alkyl, —NH—C(O)—$C_1$-$C_6$ alkyl, —NH—$S(O)_m$—$C_1$-$C_6$ alkyl, —NH—$S(O)_m$—$C_3$-$C_{10}$ carbocyclyl, —NH—$S(O)_m$-(4-13 membered) heterocyclyl;

each $R^{1a}$ and $R^{1b}$ is independently selected from hydrogen, $C_1$-$C_4$ alkyl, and $C_3$-$C_{10}$ carbocyclyl;

$R^2$ is selected from hydrogen, $C_1$-$C_{12}$ alkyl, —$C_0$-$C_6$ alkylene-$C_3$-$C_{10}$ carbocyclyl, and —$C_0$-$C_6$ alkylene-(4-13 membered) heterocyclyl;

$R^3$ is selected from hydrogen, $C_1$-$C_8$ alkyl, —$C_0$-$C_6$ alkylene-$C_3$-$C_{10}$ carbocyclyl, —$C_0$-$C_6$ alkylene-(4-13 membered) heterocyclyl, —C(O)—$C_1$-$C_6$ alkyl, —$C_0$-$C_6$ alkylene-C(O)$N(R^4)(R^5)$, —C(O)—$C_1$-$C_6$ alkylene-$N(R^4)(R^5)$, —$C_2$-$C_6$ alkylene-$N(R^4)(R^5)$, —$S(O)_m$—$C_1$-$C_6$ alkyl, —$S(O)_m$—$C_3$-$C_{10}$ carbocyclyl, and —$S(O)_m$-(4-13 membered) heterocyclyl, wherein each alkyl, carbocyclyl, alkylene or heterocyclyl in the group represented by $R^2$ or $R^3$ is optionally and independently substituted with one or more substituents independently selected from fluoro, chloro, —OH, —O—$C_1$-$C_4$ alkyl, $C_1$-$C_4$ alkyl, fluoro-substituted-$C_1$-$C_4$ alkyl, —$N(R^4)(R^5)$, $C_3$-$C_{10}$ carbocyclyl or a (4-13 membered) heterocyclyl; or $R^2$ and $R^3$ taken together with the nitrogen atom to which they are bound form a (4-7 membered) monocyclic heterocylic ring, or a (6-13 membered) bicyclic, spirocyclic or bridged heterocylic ring, wherein the (4-7 membered) monocyclic heterocylic ring, or the (6-13 membered) bicyclic, spirocyclic or bridged heterocyclic ring optionally comprises 1 to 4 additional heteroatoms independently selected from N, S and O; and wherein the (4-7 membered) monocyclic heterocylic ring, or the (6-13 membered) bicyclic, spirocyclic or bridged heterocyclic ring is optionally substituted with one or more substituents independently selected from $C_3$-$C_{10}$ carbocyclyl, (4-13 membered) heterocyclyl, fluoro, chloro, —OH, $C_1$-$C_4$ fluoroalkyl, $C_1$-$C_4$ alkyl, —O—$C_3$-$C_{10}$ carbocyclyl, —O-(4-13 membered) heterocyclyl, —$C_0$-$C_4$ alkyl-O—$C_1$-$C_4$ alkyl, —$C_0$-$C_4$ alkyl-O—$C_1$-$C_4$ fluoroalkyl, =O, —C(O)—$C_1$-$C_4$ alkyl, —C(O)$N(R^4)(R^5)$, —$N(R^4)$—C(O)—$C_1$-$C_4$ alkyl, and —$C_0$-$C_4$ alkylene-$N(R^4)(R^5)$, and wherein each carbocyclyl or heterocyclyl substituent is optionally substituted with fluoro, chloro, —OH, $C_1$-$C_4$ fluoroalkyl, $C_1$-$C_4$ alkyl, —O—$C_1$-$C_4$ alkyl, —O—$C_1$-$C_4$ fluoroalkyl, —$NH_2$, —NH($C_1$-$C_4$ alkyl), or —N($C_1$-$C_4$ alkyl$)_2$;

each of $R^4$ and $R^5$ is independently selected from hydrogen and $C_1$-$C_4$ alkyl; or $R^4$ and $R^5$ taken together with the nitrogen atom to which they are bound form a (4-7 membered) heterocylic ring optionally comprising one additional heteroatom selected from N, S and O, wherein the (4-7 membered) heterocylic ring is optionally substituted with fluoro, chloro, —OH, fluoro-substituted $C_1$-$C_4$ alkyl, —$C_1$-$C_4$ alkyl, or —$C_1$-$C_4$ alkylene-O—$C_1$-$C_4$ alkyl, and is optionally benzofused;

m is 0, 1 or 2; and n is 1 or 2, with the proviso that when Z is —NH—C(O)—$C_1$-$C_4$ alkyl-$N(R^4)(R^5)$, X is other than fluoro.

Another embodiment of the present invention is directed to a pharmaceutical composition comprising a pharmaceutically acceptable carrier or diluent and a compound disclosed herein or a pharmaceutically acceptable salt thereof. The pharmaceutical composition is used in therapy, such as treating an infection in a subject.

Another embodiment of the present invention is a method of treating an infection in a subject comprising administering to the subject an effective amount of a compound disclosed herein or a pharmaceutically acceptable salt thereof.

Another embodiment of the present invention is the use of a compound disclosed herein or a pharmaceutically acceptable salt thereof for the manufacture of a medicament for treating an infection in a subject.

Another embodiment of the present invention is the use of a compound disclosed herein or a pharmaceutically acceptable salt thereof for therapy, such as treating an infection in a subject.

BRIEF DESCRIPTION OF THE DRAWINGS

FIGS. 1A-1C provide MIC values for the indicated compound.

FIGS. 2A-2K provide compounds in accordance with Structure Formula I.

FIGS. 3A-3EE provide compounds in accordance with Structure Formula I.

FIGS. 4A-4Z provide compounds in accordance with Structure Formula I.

FIGS. 5A-5O provide compounds in accordance with Structure Formula I.

FIGS. 6A-6FF provide compounds in accordance with Structure Formula I.

FIGS. 7A-7J provide MIC values for compounds of the invention.

FIGS. 8A-8D provide MIC values for compounds of the invention.

FIGS. 9A-9M provide MIC values for compounds of the invention.

FIGS. 10A-10I provide MIC values for compounds of the invention.

FIGS. 11A-11G provide MIC values for compounds of the invention.

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

DETAILED DESCRIPTION OF THE INVENTION

The present invention is directed to a compound represented by Structural Formula I or a pharmaceutically acceptable salt thereof. Values and alternative values for the variables in Structural Formula I are defined as the following:

X is hydrogen, bromo, fluoro, chloro, $C_1$-$C_6$ alkyl, —O—$C_1$-$C_6$ alkyl, —$S(O)_m$—$C_1$-$C_6$ alkyl, $C_3$-$C_7$ cycloalkyl, —O—$C_3$-$C_7$ cycloalkyl, —$S(O)_m$—$C_3$-$C_7$ cycloalkyl, —CN, —$N(R^4)(R^5)$ or —NH—C(O)—($C_1$-$C_6$ alkylene)-$N(R^4)(R^5)$. Each alkyl, alkylene or cycloalkyl in the group represented by X is optionally substituted with fluoro. In another embodiment, X is fluoro, chloro, —CN or —$N(CH_3)_2$. Alternatively, X is fluoro, chloro or —$N(CH_3)_2$. In another alternative, X is fluoro. In yet another alternative, X is chloro. In yet another alternative, X is —$N(CH_3)_2$. In yet another embodiment, X is hydrogen. In still another embodiment when Z is —NH—C(O)—$C_1$-$C_4$ alkyl-$N(R^4)(R^5)$, X is other than fluoro.

Y is fluoro, —$C_1$-$C_6$ alkyl, or —$[C(R^{1a})(R^{1b})]_m$—$N(R^2)(R^3)$. In another embodiment, Y is fluoro, methyl, —$CH(R^{1a})$—$N(R^2)(R^3)$, —$(CH_2)_2$—$N(R^2)(R^3)$, —NH(pyridyl), —NH($C_1$-$C_8$ alkyl), —NHC(O)—$C_1$-$C_3$ alkylene-piperidine, —NHC(O)—$C_1$-$C_3$ alkylene-pyrrolidine or —$NHS(O)_2$-phenyl, wherein each piperidine and each pyrrolidine in the group represented by Y is optionally substituted with one or more —$C_1$-$C_6$ alkyl. In another embodiment, Y is fluoro, methyl or —$CH(R^{1a})$—$N(R^2)(R^3)$. Alternatively, Y is —$CH(R^{1a})$—$N(R^2)(R^3)$. In another alternative, Y is fluoro. In yet another alternative, Y is —$NHR^3$.

Z is hydrogen, fluoro, bromo, —CN, —$[C(R^{1a})(R^{1b})]_n$—$N(R^2)(R^3)$, —$N(R^4)(R^5)$, $NO_2$, —NH—C(O)—$C_1$-$C_4$ alkylene-$N(R^4)(R^5)$, $C_1$-$C_6$ alkyl, —NH—C(O)—$C_1$-$C_6$ alkyl, —NH—$S(O)_m$—$C_1$-$C_6$ alkyl, —NH—$S(O)_m$—$C_3$-$C_{10}$ carbocyclyl or —NH—$S(O)_m$-(4-13 membered) heterocyclyl. In another embodiment, Z is hydrogen, $NH_2$ or —$CH_2$—NH—$CH_2$—$C(CH_3)_3$. In another embodiment, Z is hydrogen. Alternatively, Z is —$[C(R^{1a})(R^{1b})]_n$—$N(R^2)(R^3)$ or —$N(R^4)(R^5)$.

Each $R^{1a}$ and $R^{1b}$ is independently hydrogen, $C_1$-$C_4$ alkyl or $C_3$-$C_{10}$ carbocyclyl. In another alternative, $R^{1a}$ is hydrogen or methyl.

$R^2$ is hydrogen, $C_1$-$C_{12}$ alkyl, —$C_0$-$C_6$ alkylene-$C_3$-$C_{10}$ carbocyclyl, and —$C_0$-$C_6$ alkylene-(4-13 membered) heterocyclyl. Each alkyl, carbocyclyl, alkylene or heterocyclyl in the group represented by $R^2$ is optionally and independently substituted with one or more substituents independently selected from fluoro, chloro, —OH, —O—$C_1$-$C_4$ alkyl, $C_1$-$C_4$ alkyl, fluoro-substituted-$C_1$-$C_4$ alkyl, —$N(R^4)(R^5)$, $C_3$-$C_{10}$ carbocyclyl and a (4-13 membered) heterocyclyl. In another alternative, $R^2$ is hydrogen, $C_1$-$C_3$ straight chained alkyl, $C_1$-$C_3$ straight chained fluoroalkyl, cyclopropyl or —$CH_2$-cyclopropyl. Alternatively, $R^2$ is hydrogen, $C_1$-$C_3$ straight chained alkyl or —$CH_2$-cyclopropyl.

$R^3$ is hydrogen, $C_1$-$C_8$ alkyl, —$C_0$-$C_6$ alkylene-$C_3$-$C_{10}$ carbocyclyl, —$C_0$-$C_6$ alkylene-(4-13 membered) heterocyclyl, —C(O)—$C_1$-$C_6$ alkyl, —$C_0$-$C_6$ alkylene-C(O)N$(R^4)(R^5)$, —C(O)—$C_1$-$C_6$ alkylene-$N(R^4)(R^5)$, —$C_2$-$C_6$ alkylene-$N(R^4)(R^5)$, —$S(O)_m$—$C_1$-$C_6$ alkyl, —$S(O)_m$—$C_3$-$C_{10}$ carbocyclyl or —$S(O)_m$-(4-13 membered) heterocyclyl. When $R^2$ is hydrogen or $C_1$-$C_2$ alkyl, $R^3$ is additionally benzyl. Each alkyl, carbocyclyl, alkylene or heterocyclyl in the group represented by $R^3$ is optionally and independently substituted with one or more substituents independently selected from fluoro, chloro, —OH, —O—$C_1$-$C_4$ alkyl, $C_1$-$C_4$ alkyl, fluoro-substituted-$C_1$-$C_4$ alkyl, —$N(R^4)(R^5)$, $C_3$-$C_{10}$ carbocyclyl and a (4-13 membered) heterocyclyl. In another alternative, $R^3$ is hydrogen, $C_1$-$C_8$ alkyl, —$CH_2$—$CHF_2$, —$C_2$-$C_6$ alkylene-O—$C_1$-$C_3$ alkyl, —$C_3$-$C_{10}$ cycloalkyl, —$C_3$-$C_{10}$cycloalkyl-substituted $C_1$-$C_3$ alkyl, cyclopropyl-substituted cyclopropyl, —$(CH_2)_2$-phenyl or —$S(O)_2$-phenyl. Alternatively, $R^3$ is hydrogen, $C_1$-$C_8$ alkyl, —$CH_2$—$CHF_2$, —$C_1$-$C_6$ alkylene-O—$C_1$-$C_3$ alkyl, $C_3$-$C_{10}$ cycloalkyl, $C_3$-$C_{10}$ cycloalkyl-substituted $C_1$-$C_3$ alkyl, —$(CH_2)_2$-phenyl, and when $R^2$ is hydrogen or —$C_1$-$C_2$ alkyl, $R^3$ is additionally benzyl. In another embodiment, $R^3$ is selected from hydrogen, $C_1$-$C_8$ alkyl, —$CH_2$—$CHF_2$, —$C_1$-$C_6$ alkylene-O—$C_1$-$C_3$ alkyl, $C_3$-$C_{10}$ cycloalkyl, —$(CH_2)_2$-phenyl and $C_3$-$C_{10}$ cycloalkyl-substituted $C_1$-$C_3$ alkyl, wherein each cycloalkyl in the group represented by $R^3$ is optionally substituted with —$C_1$-$C_3$ alkyl or optionally benzo-fused.

Alternatively, $R^2$ and $R^3$ taken together with the nitrogen atom to which they are bound form a (4-7 membered) monocyclic heterocylic ring, or a (6-13 membered) bicyclic, spirocyclic or bridged heterocylic ring, wherein the (4-7 membered) monocyclic heterocylic ring, or the (6-13 membered) bicyclic, spirocyclic or bridged heterocyclic ring optionally comprises 1 to 4 additional heteroatoms independently selected from N, S and O. The (4-7 membered) monocyclic heterocylic ring, or the (6-13 membered) bicyclic, spirocyclic or bridged heterocyclic ring is optionally substituted with one or more substituents independently selected from $C_3$-$C_{10}$ carbocyclyl, (4-13 membered) heterocyclyl, fluoro, chloro, —OH, $C_1$-$C_4$ fluoroalkyl, $C_1$-$C_4$ alkyl, —O—$C_3$-$C_{10}$ carbocyclyl, —O-(4-13 membered) heterocyclyl, —$C_0$-$C_4$ alkyl-O—$C_1$-$C_4$ alkyl, —$C_0$-$C_4$ alkyl-O—$C_1$-$C_4$ fluoroalkyl, =O, —C(O)—$C_1$-$C_4$ alkyl, —C(O)$N(R^4)(R^5)$, —$N(R^4)$—C(O)—$C_1$-$C_4$ alkyl, and —$C_0$-$C_4$ alkylene-$N(R^4)(R^5)$, and wherein each carbocyclyl or heterocyclyl substituent is optionally substituted with fluoro, chloro, —OH, $C_1$-$C_4$ fluoroalkyl, $C_1$-$C_4$ alkyl, —O—$C_1$-$C_4$ alkyl, —O—$C_1$-$C_4$ fluoroalkyl, —$NH_2$, —NH($C_1$-$C_4$ alkyl), or —$N(C_1$-$C_4$ alkyl$)_2$.

In another embodiment, $R^2$ and $R^3$ taken together with the nitrogen atom to which they are bound form a ring selected from pyrrolidine, piperidine, piperazine or morpholine, wherein the ring is optionally substituted with one or more substituents independently selected from —OH, —$C_1$-$C_3$ alkyl and —$C_1$-$C_3$ alkylene-O—$C_1$-$C_3$ alkyl, and wherein the ring is optionally benzofused or spirofused to cyclopropyl. Alternatively, $R^2$ and $R^3$ taken together with the nitrogen atom to which they are bound form a ring selected from pyrrolidine and piperidine, wherein the ring is optionally substituted with one or more substituents independently selected from fluoro, $C_1$-$C_3$ alkyl and —$C_1$-$C_3$ alkylene-O—$C_1$-$C_3$ alkyl, and wherein the ring is optionally benzofused or spirofused to cyclopropyl.

Each of $R^4$ and $R^5$ is independently hydrogen or $C_1$-$C_4$ alkyl.

Alternatively, $R^4$ and $R^5$ taken together with the nitrogen atom to which they are bound form a (4-7 membered) heterocylic ring optionally comprising one additional heteroatom selected from N, S and O, wherein the (4-7 membered) heterocylic ring is optionally substituted with fluoro, chloro, —OH, fluoro-substituted $C_1$-$C_4$ alkyl, —$C_1$-$C_4$ alkyl, or —$C_1$-$C_4$ alkylene-O—$C_1$-$C_4$ alkyl, and is optionally benzofused.

Each m is independently 0, 1 or 2.

n is 1 or 2.

In a second embodiment, the compound of the present invention is represented by Structural Formula I or a pharmaceutically acceptable salt thereof wherein, Y is fluoro, methyl, —CH($R^{1a}$)—N($R^2$)($R^3$), —$(CH_2)_2$—N($R^2$)($R^3$), —NH(pyridyl), —NH($C_1$-$C_8$ alkyl), —NHC(O)—$C_1$-$C_3$ alkylene-piperidine, —NHC(O)—$C_1$-$C_3$ alkylene-pyrrolidine or —NHS$(O)_2$-phenyl, and each piperidine and each pyrrolidine in the group represented by Y is optionally substituted with one or more —$C_1$-$C_6$ alkyl; $R^{1a}$ is hydrogen or methyl; $R^2$ is hydrogen, $C_1$-$C_3$ straight chained alkyl, $C_1$-$C_3$ straight chained fluoroalkyl, cyclopropyl or —$CH_2$-cyclopropyl; $R^3$ is hydrogen, $C_1$-$C_8$ alkyl, —$CH_2$—$CHF_2$, —$C_2$-$C_6$ alkylene-O—$C_1$-$C_3$ alkyl, —$C_3$-$C_{10}$ cycloalkyl, —$C_3$-$C_{10}$cycloalkyl-substituted $C_1$-$C_3$ alkyl, cyclopropyl-substituted cyclopropyl, —$(CH_2)_2$-phenyl or —S$(O)_2$-phenyl, and when $R^2$ is hydrogen or $C_1$-$C_2$ alkyl, $R^3$ is additionally benzyl; or $R^2$ and $R^3$ taken together with the nitrogen atom to which they are bound form a ring selected from pyrrolidine, piperidine, piperazine or morpholine, wherein the ring is optionally substituted with one or more substituents independently selected from —OH, —$C_1$-$C_3$ alkyl and —$C_1$-$C_3$ alkylene-O—$C_1$-$C_3$ alkyl, and wherein the ring is optionally benzofused or spirofused to cyclopropyl; and values and alternative values for the remainder of the variables are as described above.

In a third embodiment, the compound of the present invention is represented by Structural Formula I or a pharmaceutically acceptable salt thereof wherein, Y is fluoro, methyl or —CH($R^{1a}$)—N($R^2$)($R^3$); $R^{1a}$ is hydrogen or methyl; $R^2$ is hydrogen, $C_1$-$C_3$ straight chained alkyl or —$CH_2$-cyclopropyl; $R^3$ is hydrogen, $C_1$-$C_8$ alkyl, —$CH_2$—$CHF_2$, —$C_1$-$C_6$ alkylene-O—$C_1$-$C_3$ alkyl, $C_3$-$C_{10}$ cycloalkyl, $C_3$-$C_{10}$ cycloalkyl-substituted $C_1$-$C_3$ alkyl, wherein each cycloalkyl in the group represented by $R^3$ is optionally substituted with —$C_1$-$C_3$ alkyl or optionally benzofused, or —$(CH_2)_2$-phenyl, and when $R^2$ is hydrogen or —$C_1$-$C_2$ alkyl, $R^3$ is additionally benzyl; or $R^2$ and $R^3$ taken together with the nitrogen atom to which they are bound form a ring selected from pyrrolidine and piperidine, wherein the ring is optionally substituted with one or more substituents independently selected from fluoro, —$C_1$-$C_3$ alkyl and —$C_1$-$C_3$ alkylene-O—$C_1$-$C_3$ alkyl, and wherein the ring is optionally benzofused or spirofused to cyclopropyl; and values and alternative values for the remainder of the variables are as described above.

In a fourth embodiment the compound of the present invention is represented by Structural Formula I or a pharmaceutically acceptable salt thereof wherein, X is fluoro, chloro, —CN or —N$(CH_3)_2$; Z is hydrogen, $NH_2$ or —$CH_2$—NH—$CH_2$—C$(CH_3)_3$; and values and alternative values for the remainder of the variables are as described above for Structural Formula I or for the second or third embodiment.

In another embodiment of a compound of Formula I:

X is selected from OCH3, CF3, Cl, F, and N(CH3)2;

Z is hydrogen and when X is F, Z is additionally selected from NH2, NH(C1 C2 alkyl), and N(C1 C2 alkyl)2; and Y is CH2 NR2R3; wherein R2 is selected from hydrogen, and C1-C3 alkyl; and R3 is selected from hydrogen, C1-C8 alkyl, C0-C6 alkylene C3-C10 carbocyclyl, C0-C6 alkylene (4-13 membered) heterocyclyl, and C2 C6 alkylene N(R4)(R5), wherein each carbocyclyl or heterocyclyl in the group represented by R3 is optionally and independently substituted with one or more substituents independently selected from fluoro, OH, O C1 C3 alkyl, C1-C3 alkyl, fluoro-substituted C1-C3 alkyl, N(R4)(R5), C3-C10 carbocyclyl or a (4-13 membered) heterocyclyl; or R2 and R3 taken together with the nitrogen atom to which they are bound form a (4 7 membered) saturated monocyclic heterocylic ring, or a (6-13 membered) saturated bicyclic, spirocyclic or bridged heterocylic ring, wherein the (4 7 membered) monocyclic heterocylic ring, or the (6-13 membered) bicyclic, spirocyclic or bridged heterocyclic ring is optionally substituted with one or more substituents independently selected from C3-C10 carbocyclyl, (4-13 membered) heterocyclyl, fluoro, OH, —C1 C3 fluoroalkyl, —C1 C3 alkyl, O C3-C10 carbocyclyl, O (4-13 membered) heterocyclyl, C0 C2 alkylene O C1-C3 alkyl, C0 C2 alkylene O C1-C3 fluoroalkyl, =O, and C0-C4 alkylene N(R4)(R5), and wherein each carbocyclyl or heterocyclyl substituent is optionally substituted with fluoro, OH, C1 C3 fluoroalkyl, C1 C3 alkyl, O C1 C3 alkyl, O C1 C3 fluoroalkyl, NH2, NH(C1 C4 alkyl), or N(C1 C4 alkyl)2; and each of R4 and R5 is independently selected from hydrogen and C1-C4 alkyl.

In one specific aspect of this embodiment X is OCH3. In another specific aspect, X is CF3. In still another specific aspect, X is Cl. In another specific aspect, X is F and Z is hydrogen. In another specific aspect, X is F and Z is selected from NH2, NH(C1 C2 alkyl), and N(C1 C2 alkyl)2. In still another specific aspect X is N(CH3)2.

A fifth embodiment is a compound of Structural Formulas II, III, IIIa or IV or a pharmaceutically acceptable salt thereof:

II

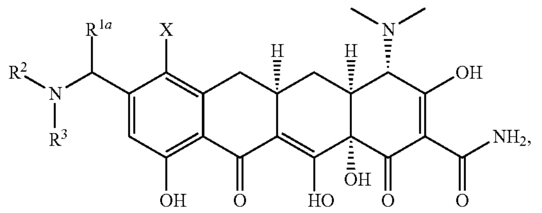

-continued

III

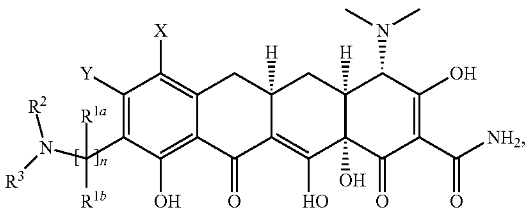

IIIa

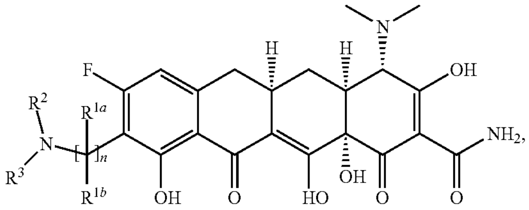

or

IV

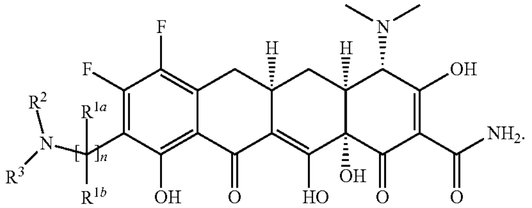

Values and alternative values for the variables in Structural Formulas II, III, IIIa and IV are as defined for Structural Formula I or in the second or in the third embodiment. Alternatively, values for the variables in Structural Formula II are as defined in the fourth embodiment. In Structural Formula II, X is preferably fluoro, chloro or —$N(CH_3)_2$.

In a sixth embodiment, the compound of the present invention is represented by Structural Formula I or a pharmaceutically acceptable salt thereof wherein, Y is —$NHR^3$; $R^3$ is pyridyl, $C_1$-$C_8$ alkyl, —C(O)—$C_1$-$C_3$ alkylene-piperidine or —C(O)—$C_1$-$C_3$ alkylene-pyrrolidine. Each piperidine or pyrrolidine in the group represented by $R^3$ is optionally substituted with one or more $C_1$-$C_3$ alkyl. Values and alternative values for the remainder of the variables are as defined for Structural Formula I above or in the second or in the third embodiment.

A seventh embodiment is a compound of Structural Formula V or a pharmaceutically acceptable salt thereof:

V

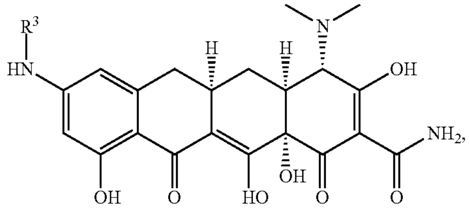

and values and alternative values for the remainder of the variables are as defined in the preceding paragraph.

Specific examples of compounds of the invention are represented by Structural Formula II, wherein:

X is fluoro and —$CH(R^{1a})$—$NR^2R^3$ is

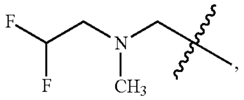

Cmpd. # S2-4-54;
X is fluoro and —$CH(R^{1a})$—$NR^2R^3$ is

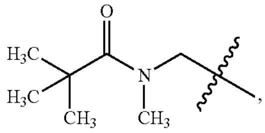

Cmpd. # S7-4-9;
X is fluoro and —$CH(R^{1a})$—$NR^2R^3$ is

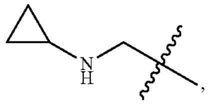 [SMILES: *CNC1CC1]

Cmpd. # S4-5-1;
X is fluoro and —$CH(R^{1a})$—$NR^2R^3$ is

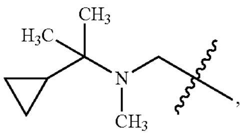

Cmpd. # S2-4-29;
X is fluoro and —$CH(R^{1a})$—$NR^2R^3$ is

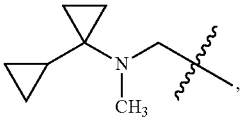

Cmpd. # S2-4-60;
X is fluoro and —$CH(R^{1a})$—$NR^2R^3$ is

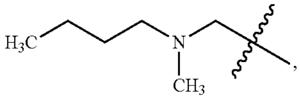 [SMILES: *CN(C)CCCC]

Cmpd. # S1-14-42;
X is fluoro and —$CH(R^{1a})$—$NR^2R^3$ is

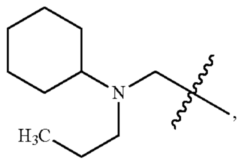 [SMILES: *CN(CCC)C1CCCCC1]

Cmpd. # S1-14-67;

X is fluoro and —CH($R^{1a}$)—$NR^2R^3$ is

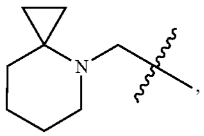 [SMILES: *CN1CCCCC12CC2]

Cmpd. # S2-4-11;

X is fluoro and —CH($R^{1a}$)—$NR^2R^3$ is

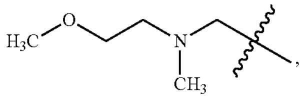

Cmpd. # S4-5-5;

X is fluoro and —CH($R^{1a}$)—$NR^2R^3$ is

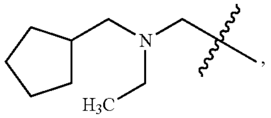

Cmpd. # S2-4-62;

X is fluoro and —CH($R^{1a}$)—$NR^2R^3$ is

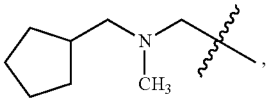 [SMILES: *CN(C)CC1CCCC1]

Cmpd. # S2-4-46;

X is fluoro and —CH($R^{1a}$)—$NR^2R^3$ is

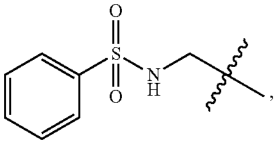 [SMILES: *CNS(=O)(=O)c1ccccc1]

Cmpd. # S7-4-6;

X is fluoro and —CH($R^{1a}$)—$NR^2R^3$ is

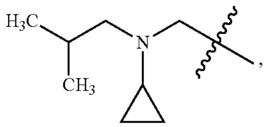

Cmpd. # S2-4-34;

X is fluoro and —CH($R^{1a}$)—$NR^2R^3$ is

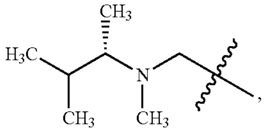

Cmpd. # S2-4-59

X is fluoro and —CH($R^{1a}$)—$NR^2R^3$ is

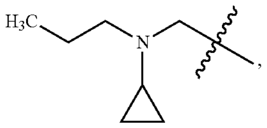 [SMILES: *CN(CCC)C1CC1]

Cmpd. # S2-4-42;

X is fluoro and —CH($R^{1a}$)—$NR^2R^3$ is

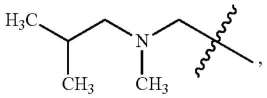

Cmpd. # S2-4-23;

X is fluoro and —CH($R^{1a}$)—$NR^2R^3$ is

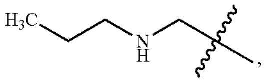 [SMILES: *CNCCC]

Cmpd. # S1-14-1;

X is fluoro and —CH($R^{1a}$)—$NR^2R^3$ is

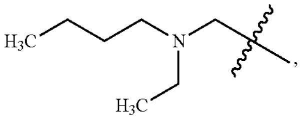

Cmpd. # S1-14-44;

X is fluoro and —CH($R^{1a}$)—$NR^2R^3$ is

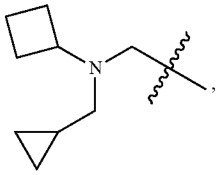 [SMILES: *CN(CC1CC1)C1CCC1]

Cmpd. # S2-4-53;

X is fluoro and —CH($R^{1a}$)—$NR^2R^3$ is

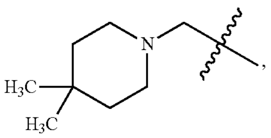

Cmpd. # S2-4-16;

X is fluoro and —CH($R^{1a}$)—$NR^2R^3$ is

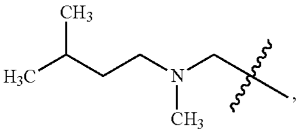 [SMILES: *CN(C)CCC(C)C]

Cmpd. # S2-4-22;

X is fluoro and —CH($R^{1a}$)—$NR^2R^3$ is

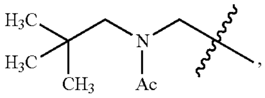

Cmpd. # S2-4-68;

X is fluoro and —CH($R^{1a}$)—$NR^2R^3$ is

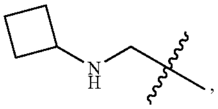 [SMILES: *CNC1CCC1]

Cmpd. # S2-4-18;

X is fluoro and —CH($R^{1a}$)—$NR^2R^3$ is

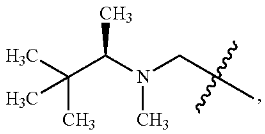

Cmpd. # S1-14-110;

X is fluoro and —CH($R^{1a}$)—$NR^2R^3$ is

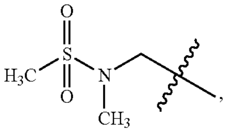

Cmpd. # S7-4-11;

X is fluoro and —CH($R^{1a}$)—$NR^2R^3$ is

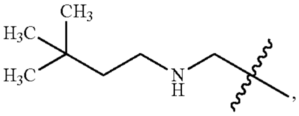 [SMILES: *CNCCC(C)(C)C]

Cmpd. # S3-5-2;

X is fluoro and —CH($R^{1a}$)—$NR^2R^3$ is

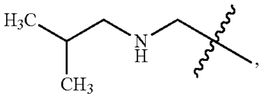

Cmpd. # S2-4-14;

X is fluoro and —CH($R^{1a}$)—$NR^2R^3$ is

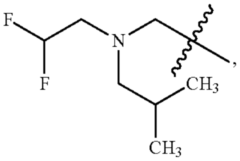

Cmpd. # S2-4-56;

X is fluoro and —CH($R^{1a}$)—$NR^2R^3$ is

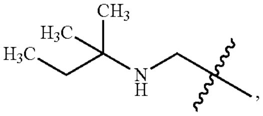 [SMILES: *CNC(C)(C)CC]

Cmpd. # S2-4-5;

X is fluoro and —CH($R^{1a}$)—$NR^2R^3$ is

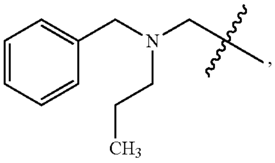

Cmpd. # S1-14-47;

X is fluoro and —CH($R^{1a}$)—$NR^2R^3$ is

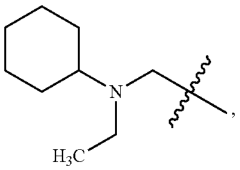 [SMILES: *CN(CC)C1CCCCC1]

Cmpd. # S1-14-66;

X is fluoro and —CH($R^{1a}$)—$NR^2R^3$ is

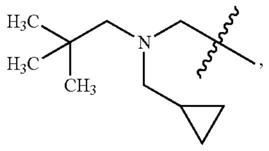 [SMILES: *CN(CC1CC1)CC(C)(C)C]

Cmpd. # S2-4-35;

X is fluoro and —CH($R^{1a}$)—$NR^2R^3$ is

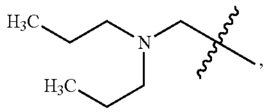 [SMILES: *CN(CCC)CCC]

Cmpd. # S1-14-2;

X is fluoro and —CH($R^{1a}$)—$NR^2R^3$ is

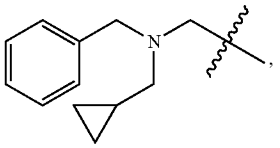 [SMILES: *CN(Cc1ccccc1)CC1CC1]

Cmpd. # S1-14-48;

X is fluoro and —CH($R^{1a}$)—$NR^2R^3$ is

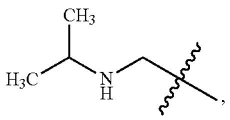 [SMILES: *CNC(C)C]

Cmpd. # S2-4-2;

X is fluoro and —CH($R^{1a}$)—$NR^2R^3$ is

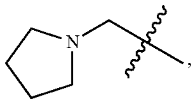 [SMILES: *CN1CCCC1]

Cmpd. # S3-5-5;

X is fluoro and —CH($R^{1a}$)—$NR^2R^3$ is

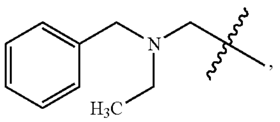 [SMILES: *CN(CC)Cc1ccccc1]

Cmpd. # S1-14-49;

X is fluoro and —CH($R^{1a}$)—$NR^2R^3$ is

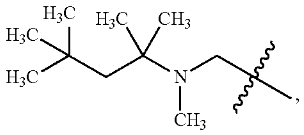 [SMILES: *CN(C)C(C)(C)CC(C)(C)C]

Cmpd. # S2-4-30;

X is fluoro and —CH($R^{1a}$)—$NR^2R^3$ is

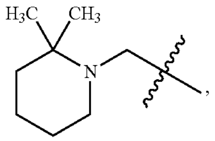

Cmpd. # S6-4-1;

X is fluoro and —CH($R^{1a}$)—$NR^2R^3$ is

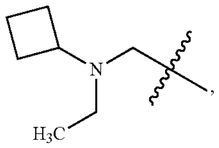

Cmpd. # S2-4-52;

X is fluoro and —CH($R^{1a}$)—$NR^2R^3$ is

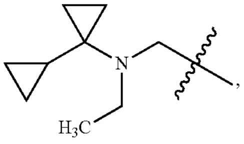 [SMILES: *CN(CC)C1(C2CC2)CC1]

Cmpd. # S2-4-61;

X is fluoro and —CH($R^{1a}$)—$NR^2R^3$ is

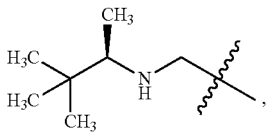

Cmpd. # S1-14-6;

X is fluoro and —CH($R^{1a}$)—$NR^2R^3$ is

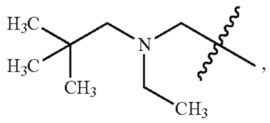

Cmpd. # S2-4-43;

X is fluoro and —$CH(R^{1a})$—$NR^2R^3$ is

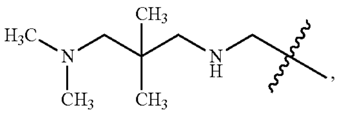

Cmpd. # S3-5-6;

X is fluoro and —$CH(R^{1a})$—$NR^2R^3$ is

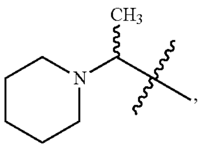 [SMILES: *C(C)N1CCCCC1]

Cmpd. # S5-5-1;

X is fluoro and —$CH(R^{1a})$—$NR^2R^3$ is

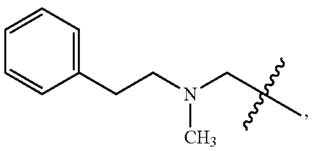 [SMILES: *CN(C)CCc1ccccc1]

Cmpd. # S1-14-43;

X is fluoro and —$CH(R^{1a})$—$NR^2R^3$ is

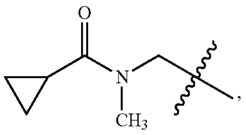

Cmpd. # S7-4-8;

X is fluoro and —$CH(R^{1a})$—$NR^2R^3$ is

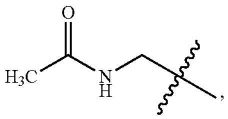 [SMILES: *CNC(C)=O]

Cmpd. # S7-4-1;

X is fluoro and —$CH(R^{1a})$—$NR^2R^3$ is

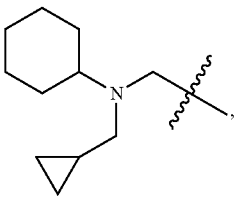 [SMILES: *CN(CC1CC1)C1CCCCC1]

Cmpd. # S1-14-68;

X is fluoro and —$CH(R^{1a})$—$NR^2R^3$ is

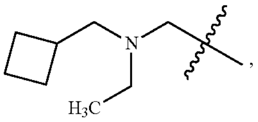

Cmpd. # S1-14-69;

X is fluoro and —$CH(R^{1a})$—$NR^2R^3$ is

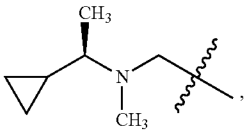

Cmpd. # S1-14-8;

X is fluoro and —$CH(R^{1a})$—$NR^2R^3$ is

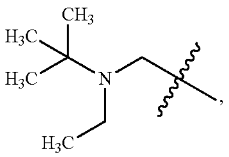

Cmpd. # S2-4-31;

X is fluoro and —$CH(R^{1a})$—$NR^2R^3$ is

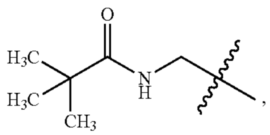

Cmpd. # S7-4-2;

X is fluoro and —$CH(R^{1a})$—$NR^2R^3$ is

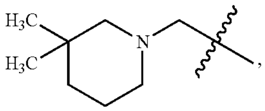 [SMILES: *CN1CCCC(C)(C)C1]

Cmpd. # S2-4-16;

X is fluoro and —$CH(R^{1a})$—$NR^2R^3$ is

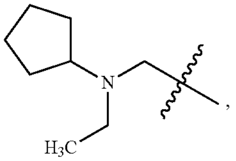 [SMILES: *CN(CC)C1CCCC1]

Cmpd. # S2-4-32;

X is fluoro and —CH($R^{1a}$)—$NR^2R^3$ is

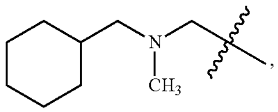 [SMILES: *CN(C)CC1CCCCC1]

Cmpd. # S2-4-47;

X is fluoro and —CH($R^{1a}$)—$NR^2R^3$ is

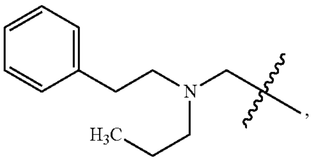 [SMILES: *CN(CCC)CCc1ccccc1]

Cmpd. # S1-14-57;

X is fluoro and —CH($R^{1a}$)—$NR^2R^3$ is

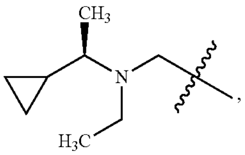 [SMILES: *CN(CC)[C@H](C)C1CC1]

Cmpd. # S1-14-9;

X is fluoro and —CH($R^{1a}$)—$NR^2R^3$ is

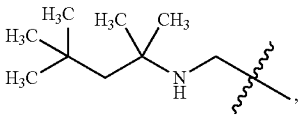 [SMILES: *CNC(C)(C)CC(C)(C)C]

Cmpd. # S2-4-7;

X is fluoro and —CH($R^{1a}$)—$NR^2R^3$ is

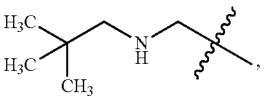

Cmpd. # S2-4-1;

X is fluoro and —CH($R^{1a}$)—$NR^2R^3$ is

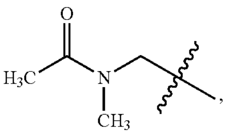

Cmpd. # S7-4-7;

X is fluoro and —CH($R^{1a}$)—$NR^2R^3$ is

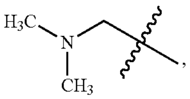

Cmpd. # S2-4-13;

X is fluoro and —CH($R^{1a}$)—$NR^2R^3$ is

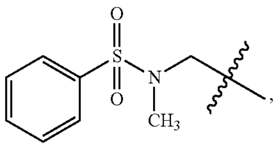 [SMILES: *CN(C)S(=O)(=O)c1ccccc1]

Cmpd. # S7-4-12;

X is fluoro and —CH($R^{1a}$)—$NR^2R^3$ is

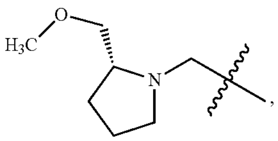

Cmpd. # S1-14-45;

X is fluoro and —CH($R^{1a}$)—$NR^2R^3$ is

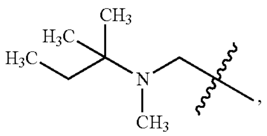

Cmpd. # S2-4-28;

X is fluoro and —CH($R^{1a}$)—$NR^2R^3$ is

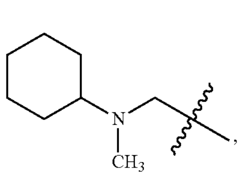

Cmpd. # S1-14-65;

X is fluoro and —CH($R^{1a}$)—$NR^2R^3$ is

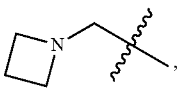 [SMILES: *CN1CCC1]

Cmpd. # S1-14-54;

X is fluoro and —CH($R^{1a}$)—$NR^2R^3$ is

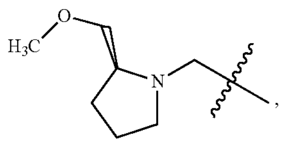 [SMILES: *CN1CCC[C@H]1COC]

Cmpd. # S1-14-3;

X is fluoro and —CH($R^{1a}$)—$NR^2R^3$ is

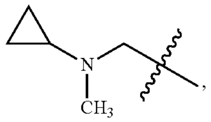 [SMILES: *CN(C)C1CC1]

Cmpd. # S2-4-26;

X is fluoro and —CH($R^{1a}$)—$NR^2R^3$ is

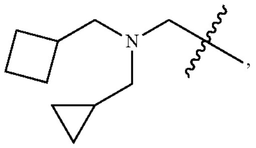 [SMILES: *CN(CC1CCC1)CC1CC1]

Cmpd. # S1-14-71;

X is fluoro and —CH($R^{1a}$)—$NR^2R^3$ is

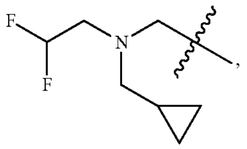 [SMILES: *CN(CC(F)F)CC1CC1]

Cmpd. # S2-4-55;

X is fluoro and —CH($R^{1a}$)—$NR^2R^3$ is

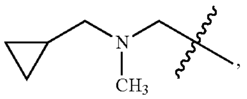

Cmpd. # S4-5-6;

X is fluoro and —CH($R^{1a}$)—$NR^2R^3$ is

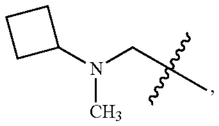

Cmpd. # S2-4-51;

X is fluoro and —CH($R^{1a}$)—$NR^2R^3$ is

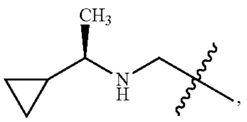 [SMILES: *CN[C@H](C)C1CC1]

Cmpd. # S1-14-17;

X is fluoro and —CH($R^{1a}$)—$NR^2R^3$ is

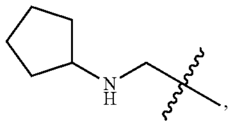

Cmpd. # S2-4-4;

X is fluoro and —CH($R^{1a}$)—$NR^2R^3$ is

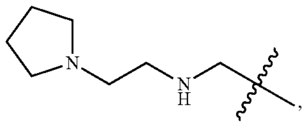 [SMILES: *CNCCN1CCCC1]

Cmpd. #3-5-4;

X is fluoro and —CH($R^{1a}$)—$NR^2R^3$ is

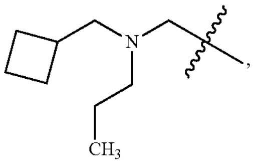 [SMILES: *CN(CCC)CC1CCC1]

Cmpd. # S1-14-70;

X is fluoro and —CH($R^{1a}$)—$NR^2R^3$ is

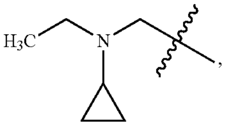

Cmpd. # S2-4-45;

X is fluoro and —CH($R^{1a}$)—$NR^2R^3$ is

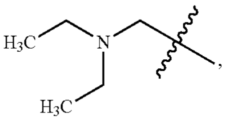

Cmpd. # S4-5-3;

X is fluoro and —CH($R^{1a}$)—$NR^2R^3$ is

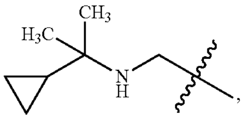 [SMILES: *CNC(C)(C)C1CC1]

Cmpd. # S2-4-6;

X is fluoro and —CH($R^{1a}$)—$NR^2R^3$ is

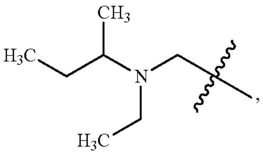 [SMILES: *CN(CC)C(C)CC]

Cmpd. # S2-4-63;

X is fluoro and —CH($R^{1a}$)—$NR^2R^3$ is

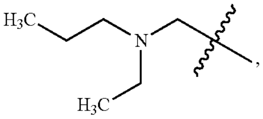

Cmpd. # S1-14-40;

X is fluoro and —CH($R^{1a}$)—$NR^2R^3$ is

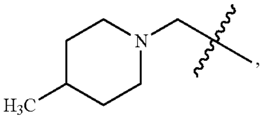 [SMILES: *CN1CCC(C)CC1]

Cmpd. # S2-4-19;

X is fluoro and —CH($R^{1a}$)—$NR^2R^3$ is

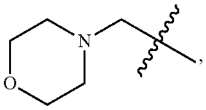 [SMILES: *CN1CCOCC1]

Cmpd. # S2-4-9;

X is fluoro and —CH($R^{1a}$)—$NR^2R^3$ is

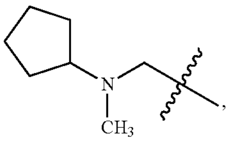 [SMILES: *CN(C)C1CCCC1]

Cmpd. # S2-4-27;

X is fluoro and —CH($R^{1a}$)—$NR^2R^3$ is

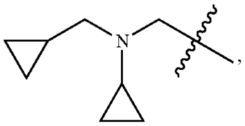 [SMILES: *CN(CC1CC1)C1CC1]

Cmpd. # S2-4-14;

X is fluoro and —CH($R^{1a}$)—$NR^2R^3$ is

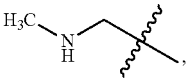

Cmpd. # S2-4-17;

X is fluoro and —CH($R^{1a}$)—$NR^2R^3$ is

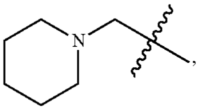 [SMILES: *CN1CCCCC1]

Cmpd. # S2-4-8;

X is fluoro and —CH($R^{1a}$)—$NR^2R^3$ is

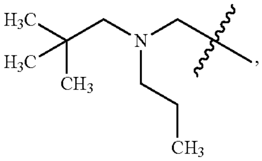

Cmpd. #2-4-44;

X is fluoro and —CH($R^{1a}$)—$NR^2R^3$ is

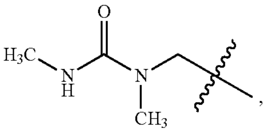

Cmpd. # S7-4-10;

X is fluoro and —CH($R^{1a}$)—$NR^2R^3$ is

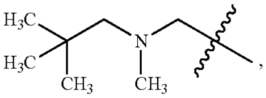

Cmpd. # S2-4-21;

X is fluoro and —CH($R^{1a}$)—$NR^2R^3$ is

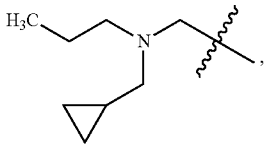 [SMILES: *CN(CCC)CC1CC1]

Cmpd. # S1-14-38;

X is fluoro and —CH($R^{1a}$)—$NR^2R^3$ is

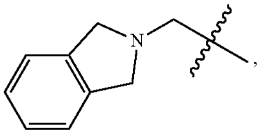 [SMILES: *CN1Cc2ccccc2C1]

Cmpd. # S1-14-39;

X is fluoro and —CH($R^{1a}$)—$NR^2R^3$ is

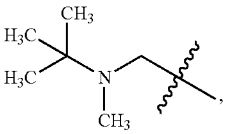

Cmpd. # S2-4-25;

X is fluoro and —CH($R^{1a}$)—$NR^2R^3$ is

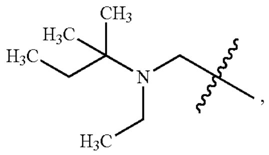

Cmpd. # S2-4-33;

X is fluoro and —CH($R^{1a}$)—$NR^2R^3$ is

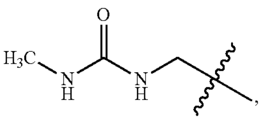 [SMILES: *CNC(=O)NC]

Cmpd. # S7-4-3;

X is fluoro and —CH($R^{1a}$)—$NR^2R^3$ is

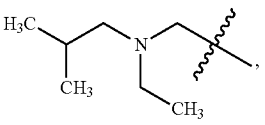

Cmpd. # S2-4-50;

X is fluoro and —CH($R^{1a}$)—$NR^2R^3$ is

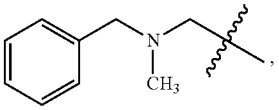 [SMILES: *CN(C)Cc1ccccc1]

Cmpd. # S1-14-46;

X is fluoro and —CH($R^{1a}$)—$NR^2R^3$ is

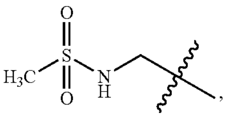 [SMILES: *CNS(C)(=O)=O]

Cmpd. # S7-4-5;

X is fluoro and —CH($R^{1a}$)—$NR^2R^3$ is

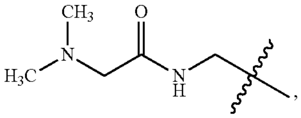 [SMILES: *CNC(=O)CN(C)C]

Cmpd. # S7-4-4;

X is fluoro and —CH($R^{1a}$)—$NR^2R^3$ is

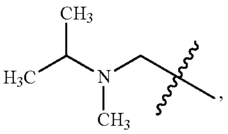

Cmpd. # S2-4-24;

X is fluoro and —CH($R^{1a}$)—$NR^2R^3$ is

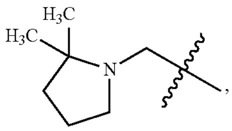

Cmpd. # S2-4-12;

X is fluoro and —CH($R^{1a}$)—$NR^2R^3$ is

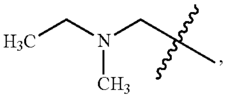

Cmpd. # S4-5-2;

X is fluoro and —CH($R^{1a}$)—$NR^2R^3$ is

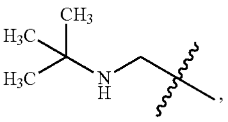

Cmpd. # S2-4-3;

X is fluoro and —CH($R^{1a}$)—$NR^2R^3$ is

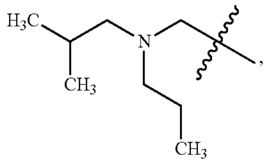

Cmpd. # S2-4-49;

X is fluoro and —CH($R^{1a}$)—$NR^2R^3$ is

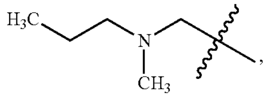 [SMILES: *CN(C)CCC]

Cmpd. # S1-14-41;

X is fluoro and —CH($R^{1a}$)—$NR^2R^3$ is

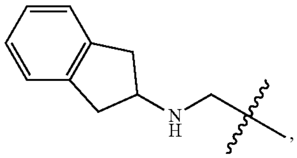 [SMILES: *CNC1Cc2ccccc2C1]

Cmpd. # S1-14-90;

X is fluoro and —CH($R^{1a}$)—$NR^2R^3$ is

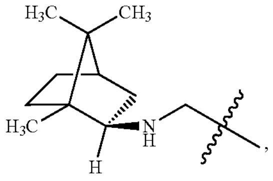 [SMILES: *CN[C@@H]1CC2CCC1(C)C2(C)C]

Cmpd. # S1-14-114;

X is fluoro and —CH($R^{1a}$)—$NR^2R^3$ is

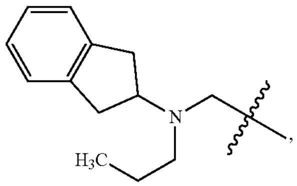 [SMILES: *CN(CCC)C1Cc2ccccc2C1]

Cmpd. # S1-14-88;

X is fluoro and —CH($R^{1a}$)—$NR^2R^3$ is

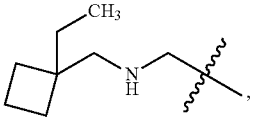 [SMILES: *CNCC1(CC)CCC1]

Cmpd. # S1-14-91;

X is fluoro and —CH($R^{1a}$)—$NR^2R^3$ is

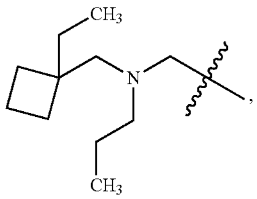 [SMILES: *CN(CCC)CC1(CC)CCC1]

Cmpd. # S1-14-94;

X is fluoro and —CH($R^{1a}$)—$NR^2R^3$ is

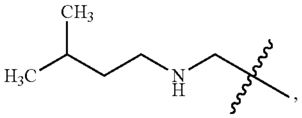 [SMILES: *CNCCC(C)C]

Cmpd. # S2-4-15;

X is fluoro and —CH($R^{1a}$)—$NR^2R^3$ is

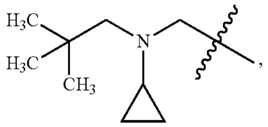 [SMILES: *CN(CC(C)(C)C)C1CC1]

Cmpd. # S2-4-48;

X is fluoro and —CH($R^{1a}$)—$NR^2R^3$ is

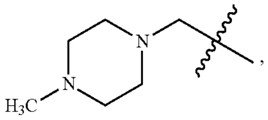

Cmpd. # S4-5-4;

X is fluoro and —CH($R^{1a}$)—$NR^2R^3$ is

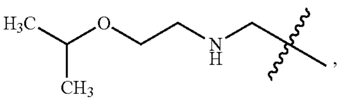

Cmpd. # S3-53;

X is fluoro and —CH($R^{1a}$)—$NR^2R^3$ is

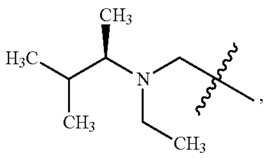

Cmpd. # S2-4-58;

X is chloro and —CH($R^{1a}$)—$NR^2R^3$ is

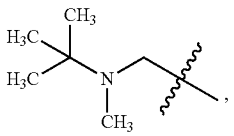

Cmpd. # S15-13-11;
X is chloro and —CH($R^{1a}$)—$NR^2R^3$ is

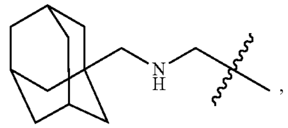 [SMILES: *CNCC12CC3CC(CC(C3)C1)C2]

Cmpd. # S15-13-9;
X is chloro and —CH($R^{1a}$)—$NR^2R^3$ is

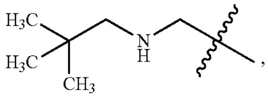

Cmpd. # S15-13-5;
X is chloro and —CH($R^{1a}$)—$NR^2R^3$ is

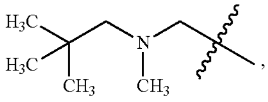

Cmpd. # S15-13-11;
X is chloro and —CH($R^{1a}$)—$NR^2R^3$ is

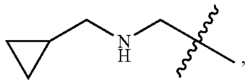 [SMILES: *CNCC1CC1]

Cmpd. # S15-13-6;
X is chloro and —CH($R^{1a}$)—$NR^2R^3$ is

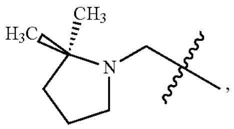

Cmpd. # S15-13-4;
X is chloro and —CH($R^{1a}$)—$NR^2R^3$ is

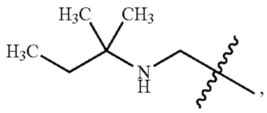 [SMILES: *CNC(C)(C)CC]

Cmpd. # S15-13-2;

X is chloro and —CH($R^{1a}$)—$NR^2R^3$ is

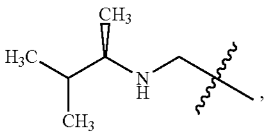

Cmpd. # S15-13-8;
X is chloro and —CH($R^{1a}$)—$NR^2R^3$ is

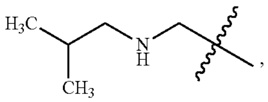 [SMILES: *CNCC(C)C]

Cmpd. # S15-13-1;
X is chloro and —CH($R^{1a}$)—$NR^2R^3$ is

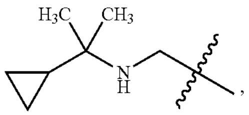 [SMILES: *CNC(C)(C)C1CC1]

Cmpd. # S15-13-3;
X is chloro and —CH($R^{1a}$)—$NR^2R^3$ is

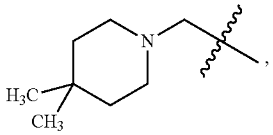

Cmpd. # S15-13-16;
X is —$N(CH_3)_2$ and —CH($R^{1a}$)—$NR^2R^3$ is

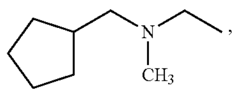

Cmpd. # S16-10-21;
X is —$N(CH_3)_2$ and —CH($R^{1a}$)—$NR^2R^3$ is

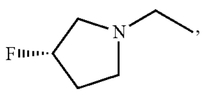

Cmpd. # S16-10-26;
X is —$N(CH_3)_2$ and —CH($R^{1a}$)—$NR^2R^3$ is

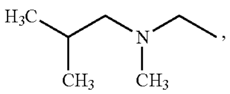

Cmpd. # S16-10-20;

X is $-N(CH_3)_2$ and $-CH(R^{1a})-NR^2R^3$ is

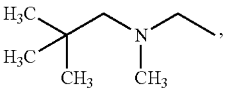

Cmpd. # S16-10-9;

X is $-N(CH_3)_2$ and $-CH(R^{1a})-NR^2R^3$ is

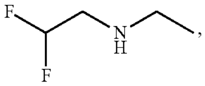

Cmpd. # S16-10-13;

X is $-N(CH_3)_2$ and $-CH(R^{1a})-NR^2R^3$ is

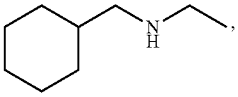

Cmpd. # S16-10-15;

X is $-N(CH_3)_2$ and $-CH(R^{1a})-NR^2R^3$ is

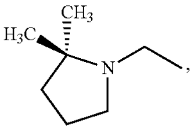

Cmpd. # S16-10-15;

X is $-N(CH_3)_2$ and $-CH(R^{1a})-NR^2R^3$ is

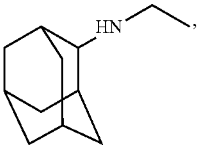

Cmpd. # S16-10-18; or

X is $-N(CH_3)_2$ and $-CH(R^{1a})-NR^2R^3$ is

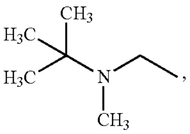

Cmpd. # S1-14-54.

Other specific examples of compounds of the invention are represented by Structural Formulas IIIa, wherein:

$-[C(R^{1a})(R^{1b})]_n-N(R^2)(R^3)$ is

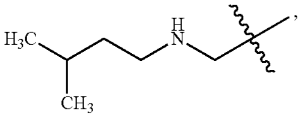 [SMILES: *CNCCC(C)C]

Cmpd. #S20-10-5;

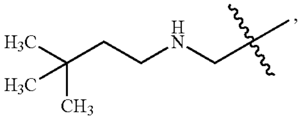

Cmpd. #S20-10-6;

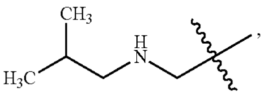 [SMILES: *CNCC(C)C]

Cmpd. #S20-10-2;

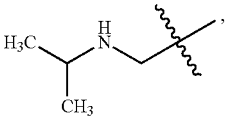

Cmpd. # S20-10-7;

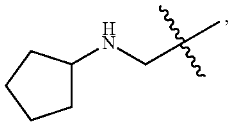 [SMILES: *CNC1CCCC1]

Cmpd. # S20-10-8;

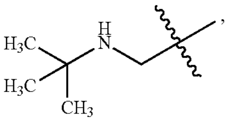

Cmpd. # S20-10-3; or

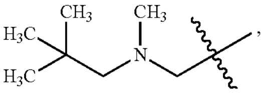 [SMILES: *CN(C)CC(C)(C)C]

Cmpd. # S20-10-4.

Additional specific examples of compounds of the invention are represented by Structural Formula V, wherein:

$R^3$ is

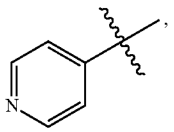 [SMILES: *c1ccncc1]

Cmpd. # S22-6;

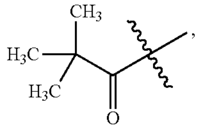 [SMILES: *C(=O)C(C)(C)C]

Cmpd. # S21-12-6;

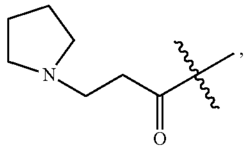 [SMILES: *C(=O)CCN1CCCC1]

Cmpd. # S21-12-2; or

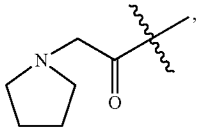 [SMILES: *C(=O)CN1CCCC1]

Cmpd. # S21-12-1.

Additional specific examples of the compounds of the present invention are represented by Structural Formula IVa and IVb, or a pharmaceutically acceptable salt thereof:

IVa

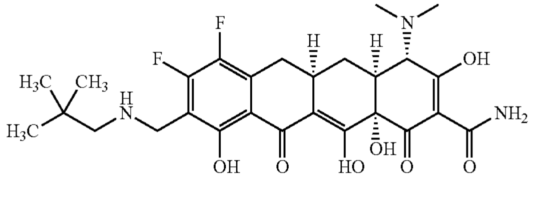

and

IVb

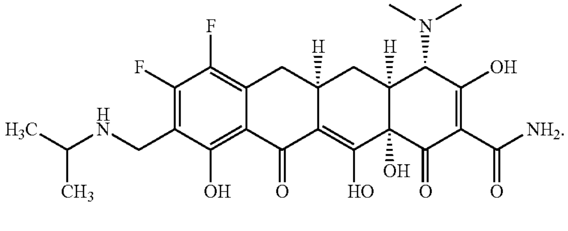

Methods of preparation of the exemplified compounds are provided in Exemplification section.

DEFINITIONS

"Alkyl" means a saturated aliphatic branched or straight-chain monovalent hydrocarbon radical having the specified number of carbon atoms. Thus, "($C_1$-$C_{12}$) alkyl" means a radical having from 1-12 carbon atoms in a linear or branched arrangement. "($C_1$-$C_{12}$)alkyl" includes methyl, ethyl, propyl, butyl, pentyl, hexyl, heptyl, octyl, nonyl, decyl, undecyl and dodecyl. Unless otherwise specified, suitable substitutions for a "substituted alkyl" include halogen, —OH, —O—$C_1$-$C_4$ alkyl, $C_1$-$C_4$ alkyl, fluoro-substituted-$C_1$-$C_4$ alkyl, —O—$C_1$-$C_4$ fluoroalkyl, —$NH_2$, —NH($C_1$-$C_4$ alkyl), —N($C_1$-$C_4$ alkyl)$_2$, $C_3$-$C_{10}$ carbocyclyl (e.g., cyclopropyl, cyclobutyl, cyclopentyl, cyclohexyl, phenyl or naphthalenyl), a (4-13 membered) heterocyclyl (e.g., pyrrolidine, piperidine, piperazine, tetrahydrofuran, tetrahydropyran or morpholine) or —N($R^4$)($R^5$), wherein $R^4$ and $R^5$ are as described above.

As used here, the term "alkylene" refers to a divalent alkyl group that has two points of attachment to the rest of the compound. An alkyl moiety of an alkylene group, alone or as a part of a larger moiety (alkoxy, alkylammonium, and the like) is preferably a straight chained or branched saturated aliphatic group with 1 to about 12 carbon atoms, e.g., methyl, ethyl, n-propyl, iso-propyl, n-butyl, sec-butyl, tert-butyl, pentyl, hexyl, heptyl or octyl, or a saturated cycloaliphatic group with 3 to about 12 carbon atoms. Non-limiting examples of alkylene groups include a divalent C1-6 groups such as methylene (—$CH_2$—), ethylene (—$CH_2CH_2$—), n-propylene (—$CH_2CH_2CH_2$—), isopropylene (—$CH_2CH(CH_3)$—), and the like. Examples of a divalent C1-6 alkyl group include, for example, a methylene group, an ethylene group, an ethylidene group, an n-propylene group, an isopropylene group, an isobutylene group, an s-butylene group, an n-butylene group, and a t-butylene group.

"Cycloalkyl" means a saturated aliphatic cyclic hydrocarbon radical having the specified number of carbon atoms. ($C_3$-$C_6$)cycloalkyl includes cyclopropyl, cyclobutyl, cyclopentyl, and cyclohexyl. The cycloalkyl can be (3-7 membered) monocyclic, (6-13 membered) fused bicyclic, (4-13 membered) bridged bicyclic, (6-13 membered) spiro bicyclic or bridged tricyclic (e.g., adamantyl). Suitable substituents for a "substituted cycloalkyl" include, but are not limited to halogen, —OH, —O—$C_1$-$C_4$ alkyl, $C_1$-$C_4$ alkyl, fluoro-substituted-$C_1$-$C_4$ alkyl, $C_3$-$C_{10}$ carbocyclyl (e.g., cyclopropyl, cyclobutyl, cyclopentyl, cyclohexyl, phenyl or naphthalenyl), a (4-13 membered) heterocyclyl (e.g., pyrrolidine, piperidine, piperazine, tetrahydrofuran, tetrahydropyran or morpholine), or —N($R^4$)($R^5$), wherein $R^4$ and $R^5$ are as described above.

"Heterocycle" means a saturated or partially unsaturated (4-13 membered) heterocyclic ring containing 1, 2, 3 or 4 heteroatoms independently selected from N, O or S, and includes for example heteroaryl. When one heteroatom is S, it can be optionally mono- or di-oxygenated (i.e. —S(O)— or —S(O)$_2$—). The heterocycle can be (4-7 membered) monocyclic, (6-13 membered) fused bicyclic, (6-13 membered) bridged bicyclic, or (6-13 membered) spiro bicyclic.

Examples of monocyclic heterocycle include, but not limited to, azetidine, pyrrolidine, piperidine, piperazine, hexahydropyrimidine, tetrahydrofuran, tetrahydropyran, morpholine, thiomorpholine, thiomorpholine 1,1-dioxide, tetrahydro-2H-1,2-thiazine, tetrahydro-2H-1,2-thiazine 1,1-dioxide, isothiazolidine, or isothiazolidine 1,1-dioxide.

A fused bicyclic heterocycle has two rings which have two adjacent ring atoms in common. The first ring is a monocyclic heterocycle and the second ring is a cycloalkyl, partially unsaturated carbocycle, phenyl or heteroaryl (e.g., pyrrole, imidazole, pyrazole, oxazole, isoxazole, thiazole, isothiazole, 1,2,3-triazole, 1,2,4-triazole, 1,3,4-oxadiazole, 1,2,5-thiadiazole, 1,2,5-thiadiazole 1-oxide, 1,2,5-thiadiazole 1,1-dioxide, 1,3,4-thiadiazole, pyridine, pyrazine, pyrimidine, pyridazine, 1,2,4-triazine, 1,3,5-triazine, and tetrazole).

A spiro bicyclic heterocycle has two rings which have only one ring atom in common. The first ring is a monocyclic heterocycle and the second ring is a cycloalkyl, partially unsaturated carbocycle or a monocyclic heterocycle. For example, the second ring is a ($C_3$-$C_6$)cycloalkyl. Example of spiro bicyclic heterocycle includes, but not limited to, azaspiro[4.4]nonane, 7-azaspiro[4.4]nonane, azaspiro[4.5]decane, 8-azaspiro[4.5]decane, azaspiro[5.5]undecane, 3-azaspiro[5.5]undecane and 3,9-diazaspiro[5.5]undecane.

A bridged bicyclic heterocycle has two rings which have three or more adjacent ring atoms in common. The first ring is a monocyclic heterocycle and the other ring is a cycloalkyl (such as ($C_3$-$C_6$)cycloalkyl), partially unsaturated carbocycle or a monocyclic heterocycle. Examples of bridged bicyclic heterocycles include, but are not limited to, azabicyclo[3.3.1]nonane, 3-azabicyclo[3.3.1]nonane, azabicyclo[3.2.1]octane, 3-azabicyclo[3.2.1]octane, 6-azabicyclo[3.2.1]octane and azabicyclo[2.2.2]octane, 2-azabicyclo[2.2.2]octane.

"Heteroaryl" means a (5-12 membered) monovalent heteroaromatic monocyclic or bicyclic ring radical. A heteroaryl contains 1, 2, 3 or 4 heteroatoms independently selected from N, O, and S. Heteroaryls include, but are not limited to pyrrole, imidazole, pyrazole, oxazole, isoxazole, thiazole, isothiazole, 1,2,3-triazole, 1,2,4-triazole, 1,3,4-oxadiazole, 1,2,5-thiadiazole, 1,2,5-thiadiazole 1-oxide, 1,2,5-thiadiazole 1,1-dioxide, 1,3,4-thiadiazole, pyridine, pyrazine, pyrimidine, pyridazine, 1,2,4-triazine, 1,3,5-triazine, and tetrazole. Bicyclic heteroaryl rings include, but are not limited to, bicyclo[4.4.0] and bicyclo[4.3.0] fused ring systems such as indolizine, indole, isoindole, indazole, benzimidazole, benzthiazole, purine, quinoline, isoquinoline, cinnoline, phthalazine, quinazoline, quinoxaline, 1,8-naphthyridine, and pteridine.

"Carbocyclyl" and "carbocycle" both mean (3-10 membered) saturated, partially saturated or unsaturated aliphatic cyclic hydrocarbon ring and includes for example aryl. "Carbocyclyl" includes, but are not limited to $C_3$-$C_6$ cycloalkyl and aryl. $C_3$-$C_6$cycloalkyl includes, but is not limited to optionally substituted cyclopropyl, cyclobutyl, cyclopentyl and cyclohexyl.

"Aryl" means an aromatic monocyclic or polycyclic (e.g. bicyclic or tricyclic) carbocyclic ring system. Aryl systems include, but not limited to, phenyl, naphthalenyl, fluorenyl, indenyl, azulenyl, and anthracenyl.

"Alkoxy" means an alkyl radical attached through an oxygen linking atom. "($C_1$-$C_4$)-alkoxy" includes methoxy, ethoxy, propoxy, and butoxy.

"Alkylthio" means an alkyl radical attached through a sulfur linking atom. "($C_1$-$C_4$)alkylthio" include methylthio, ethylthio, propylthio and butylthio.

"Alkylsulfinyl" means an alkyl radical attached through a —S(O)— linking group. "($C_1$-$C_4$)alkylsulfinyl" include methylsulfinyl, ethylsulfinyl, propylsulfinyl and butylsulfinyl.

"Alkylsulfonyl" means an alkyl radical attached through a —$S(O)_2$— linking group. "($C_1$-$C_4$)alkylsulfonyl" include methylsulfonyl, ethylsulfonyl, propylsulfonyl and butylsulfonyl.

Haloalkyl and halocycloalkyl include mono, poly, and perhaloalkyl groups where each halogen is independently selected from fluorine, chlorine, and bromine.

"Cycloalkoxy" means a cycloalkyl radical attached through an oxygen linking atom. "($C_3$-$C_6$)cycloalkoxy" includes cyclopropyloxy, cyclobutyloxy, cyclopentyloxy and cyclohexyloxy.

"Aryloxy" means an aryl moiety attached through an oxygen linking atom. Aryloxy includes, but not limited to, phenoxy.

"Arylthio" means an aryl moiety attached through a sulfur linking atom. Arylthio includes, but not limited to, phenylthio.

"Arylsulfinyl" means an aryl moiety attached through a —S(O)— linking group. Arylsulfinyl includes, but not limited to, phenylsulfinyl.

"Arylsulfonyl" means an aryl moiety attached through a —$S(O)_2$— linking group. Arylsulfonyl includes, but not limited to, phenylsulfonyl.

"Hetero" refers to the replacement of at least one carbon atom member in a ring system with at least one heteroatom selected from N, S, and O. A hetero ring system may have 1, 2, or 3 carbon atom members replaced by a heteroatom.

"Halogen" and "halo" are interchangeably used herein and each refers to fluorine, chlorine, bromine, or iodine.

Another embodiment of the present invention is a pharmaceutical composition comprising one or more pharmaceutically acceptable carrier and/or diluent and a compound disclosed herein or a pharmaceutically acceptable salt thereof.

"Pharmaceutically acceptable carrier" means non-therapeutic components that are of sufficient purity and quality for use in the formulation of a composition of the invention that, when appropriately administered to an animal or human, typically do not produce an adverse reaction, and that are used as a vehicle for a drug substance (i.e. a compound of the present invention).

"Pharmaceutically acceptable diluent" means non-therapeutic components that are of sufficient purity and quality for use in the formulation of a composition of the invention that, when appropriately administered to an animal or human, typically do not produce an adverse reaction, and that are used as a diluting agent for a drug substance (i.e. a compound of the present invention).

Pharmaceutically acceptable salts of the compounds of the present invention are also included. For example, an acid salt of a compound of the present invention containing an amine or other basic group can be obtained by reacting the compound with a suitable organic or inorganic acid, resulting in pharmaceutically acceptable anionic salt forms. Examples of anionic salts include the acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrobromide, hydrochloride, hydroxynaphthoate, iodide, isethionate, lactate, lactobionate, malate, maleate, mandelate, mesylate, methylsulfate, mucate, napsylate, nitrate, pamoate, pantothenate, phosphate/diphosphate, polygalacturonate, salicylate, stearate, subacetate, succinate, sulfate, tannate, tartrate, teoclate, tosylate, and triethiodide salts.

Salts of the compounds of the present invention containing a carboxylic acid or other acidic functional group can be prepared by reacting with a suitable base. Such a pharmaceutically acceptable salt may be made with a base which affords a pharmaceutically acceptable cation, which includes alkali metal salts (especially sodium and potassium), alkaline earth metal salts (especially calcium and magnesium), aluminum salts and ammonium salts, as well as salts made from physiologically acceptable organic bases such as trimethylamine, triethylamine, morpholine, pyridine, piperidine, picoline, dicyclohexylamine, N,N'-dibenzylethylenediamine, 2-hydroxyethylamine, bis-(2-hydroxyethyl)amine, tri-(2-hydroxyethyl)amine, procaine, dibenzylpiperidine, dehydroabietylamine, N,N'-bisdehydroabietylamine, glucamine, N-methylglucamine, collidine, quinine, quinoline, and basic amino acids such as lysine and arginine.

The invention also includes various isomers and mixtures thereof. Certain of the compounds of the present invention may exist in various stereoisomeric forms. Stereoisomers are compounds which differ only in their spatial arrangement. Enantiomers are pairs of stereoisomers whose mirror images are not superimposable, most commonly because they contain an asymmetrically substituted carbon atom that acts as a chiral center. "Enantiomer" means one of a pair of molecules that are mirror images of each other and are not superimposable. Diastereomers are stereoisomers that are not related as mirror images, most commonly because they contain two or more asymmetrically substituted carbon atoms. "R" and "S" represent the configuration of substituents around one or more chiral carbon atoms. When a chiral center is not defined as R or S, a mixture of both configurations is present.

"Racemate" or "racemic mixture" means a compound of equimolar quantities of two enantiomers, wherein such mixtures exhibit no optical activity; i.e., they do not rotate the plane of polarized light.

The compounds of the invention may be prepared as individual isomers by either isomer-specific synthesis or resolved from an isomeric mixture. Conventional resolution techniques include forming the salt of a free base of each isomer of an isomeric pair using an optically active acid (followed by fractional crystallization and regeneration of the free base), forming the salt of the acid form of each isomer of an isomeric pair using an optically active amine (followed by fractional crystallization and regeneration of the free acid), forming an ester or amide of each of the isomers of an isomeric pair using an optically pure acid, amine or alcohol (followed by chromatographic separation and removal of the chiral auxiliary), or resolving an isomeric mixture of either a starting material or a final product using various well known chromatographic methods.

When the stereochemistry of a disclosed compound is named or depicted by structure, the named or depicted stereoisomer is at least 60%, 70%, 80%, 90%, 99% or 99.9% by weight pure relative to the other stereoisomers. When a single enantiomer is named or depicted by structure, the depicted or named enantiomer is at least 60%, 70%, 80%, 90%, 99% or 99.9% by weight optically pure. Percent optical purity by weight is the ratio of the weight of the enantiomer over the weight of the enantiomer plus the weight of its optical isomer.

The present invention also provides a method of treating a subject with a tetracycline-responsive disease or disorder comprising administering to the subject an effective amount of a compound of the present invention or a pharmaceutically acceptable salt thereof.

"Tetracycline-responsive disease or disorder" refers to a disease or disorder that can be treated, prevented, or otherwise ameliorated by the administration of a tetracycline compound of the present invention. Tetracycline-responsive disease or disorder includes infections, cancer, inflammatory disorders, autoimmune disease, arteriosclerosis, corneal ulceration, emphysema, arthritis, osteoporosis, osteoarthritis, multiple sclerosis, osteosarcoma, osteomyelitis, bronchiectasis, chronic pulmonary obstructive disease, skin and eye diseases, periodontitis, osteoporosis, rheumatoid arthritis, ulcerative colitis, inflammatory disorders, tumor growth and invasion, metastasis, acute lung injury, stroke, ischemia, diabetes, aortic or vascular aneurysms, skin tissue wounds, dry eye, bone, cartilage degradation, malaria, senescence, diabetes, vascular stroke, neurodegenerative disorders, cardiac disease, juvenile diabetes, acute and chronic bronchitis, sinusitis, and respiratory infections, including the common cold; acute and chronic gastroenteritis and colitis; acute and chronic cystitis and urethritis; acute and chronic dermatitis; acute and chronic conjunctivitis; acute and chronic serositis; uremic pericarditis; acute and chronic cholecystis; cystic fibrosis, acute and chronic vaginitis; acute and chronic uveitis; drug reactions; insect bites; burns and sunburn, bone mass disorder, acute lung injury, chronic lung disorders, ischemia, stroke or ischemic stroke, skin wound, aortic or vascular aneurysm, diabetic retinopathy, hemorrhagic stroke, angiogenesis, and other states for which tetracycline compounds have been found to be active (see, for example, U.S. Pat. Nos. 5,789,395; 5,834,450; 6,277,061 and 5,532,227, each of which is expressly incorporated herein by reference). Compounds of the invention can be used to prevent or control important mammalian and veterinary diseases such as diarrhea, urinary tract infections, infections of skin and skin structure, ear, nose and throat infections, wound infection, mastitis and the like. In addition, methods for treating neoplasms using tetracycline compounds of the invention are also included (van der Bozert et al., Cancer Res., 48: 6686-6690 (1988)).

Infections that can be treated using compounds of the invention (i.e. compound of Structural Formula (I)) or a pharmaceutically acceptable salt thereof include, but are not limited to, skin infections, GI infections, urinary tract infections, genito-urinary infections, respiratory tract infections, sinuses infections, middle ear infections, systemic infections, cholera, influenza, bronchitis, acne, malaria, sexually transmitted disease including syphilis and gonorrhea, Legionnaires' disease, Lyme disease, Rocky Mountain spotted fever, Q fever, typhus, bubonic plague, gas gangrene, hospital acquired infections, leptospirosis, whooping cough, anthrax and infections caused by the agents responsible for lymphogranuloma venereum, inclusion conjunctivitis, or psittacosis. Infections can be bacterial, fungal, parasitic and viral infections (including those which are resistant to other tetracycline compounds).

In one embodiment, the infection can be caused bacteria. In another embodiment, the infection is caused by a Gram-positive bacteria. In a specific aspect of this embodiment, the infection is caused by a Gram-positive bacteria selected from *S. aureus, S. pneumoniae, P. granulosum* and *P. acnes.*

In another embodiment, the infection is caused by a Gram-negative bacteria. In a specific aspect of this embodiment, the infection is caused by a Gram-negative bacteria selected from *E. coli* or *B. thetaiotaomicron.*

In another embodiment, the infection is caused by an organism selected from the group consisting of *K. pneumoniae, Salmonella, E. hirae, A. baumanii, B. catarrhalis, H. influenzae, P. aeruginosa, E. faecium, E. coli, S. aureus*, and *E. faecalis*. In another embodiment, the infection is caused by an organism selected from the group consisting of rickettsiae, chlamydiae, and *Mycoplasma pneumoniae*. In another embodiment, the infection is caused by an organism resistant to tetracycline. In another embodiment, the infection is caused by an organism resistant to methicillin. In another embodiment, the infection is caused by an organism resistant to vancomycin. In another embodiment the infection is a *Bacillus anthracis* infection. "*Bacillus anthracis* infection" includes any state, diseases, or disorders caused or which result from exposure or alleged exposure to *Bacillus anthracis* or another member of the *Bacillus cereus* group of bacteria.

In a further embodiment, the tetracycline responsive disease or disorder is not a bacterial infection. In another embodiment, the tetracycline compounds of the invention are essentially non-antibacterial. For example, non-antibacterial compounds of the invention may have MIC values greater than about 4 μg/ml (as measured by assays known in the art and/or the assay given in Example 22). Tetracycline responsive disease or disorder also includes diseases or disorders associated with inflammatory process associated states (IPAS). The term "inflammatory process associated state" includes states in which inflammation or inflammatory factors (e.g., matrix metalloproteinases (MMPs), nitric oxide (NO), TNF, interleukins, plasma proteins, cellular defense systems, cytokines, lipid metabolites, proteases, toxic radicals, adhesion molecules, etc.) are involved or are present in an area in aberrant amounts, e.g., in amounts which may be advantageous to alter, e.g., to benefit the subject. The inflammatory process is the response of living tissue to damage. The cause of inflammation may be due to physical damage, chemical substances, micro-organisms, tissue necrosis, cancer or other agents. Acute inflammation is short-lasting, lasting only a few days. If it is longer lasting however, then it may be referred to as chronic inflammation.

IPASs include inflammatory disorders. Inflammatory disorders are generally characterized by heat, redness, swelling, pain and loss of function. Examples of causes of inflammatory disorders include, but are not limited to, microbial infections (e.g., bacterial and fungal infections), physical agents (e.g., burns, radiation, and trauma), chemical agents (e.g., toxins and caustic substances), tissue necrosis and various types of immunologic reactions.

Examples of inflammatory disorders can be treated using the compounds of the invention (i.e. compound of Structural Formula (I)) or a pharmaceutically acceptable salt thereof include, but are not limited to, osteoarthritis, rheumatoid arthritis, acute and chronic infections (bacterial and fungal, including diphtheria and pertussis); acute and chronic bronchitis, sinusitis, and upper respiratory infections, including the common cold; acute and chronic gastroenteritis and colitis; inflammatory bowel disorder; acute and chronic cystitis and urethritis; vasculitis; sepsis; nephritis; pancreatitis; hepatitis; lupus; inflammatory skin disorders including, for example, eczema, dermatitis, psoriasis, pyoderma gangrenosum, acne rosacea, and acute and chronic dermatitis; acute and chronic conjunctivitis; acute and chronic serositis (pericarditis, peritonitis, synovitis, pleuritis and tendinitis); uremic pericarditis; acute and chronic cholecystis; acute and chronic vaginitis; acute and chronic uveitis; drug reactions; insect bites; burns (thermal, chemical, and electrical); and sunburn.

IPASs also include matrix metalloproteinase associated states (MMPAS). MMPAS include states characterized by aberrant amounts of MMPs or MMP activity. Examples of matrix metalloproteinase associated states ("MMPAS's") can be treated using compounds of the invention or a pharmaceutically acceptable salt thereof, include, but are not limited to, arteriosclerosis, corneal ulceration, emphysema, osteoarthritis, multiple sclerosis (Liedtke et al., Ann. Neurol. 1998, 44: 35-46; Chandler et al., J. Neuroimmunol. 1997, 72: 155-71), osteosarcoma, osteomyelitis, bronchiectasis, chronic pulmonary obstructive disease, skin and eye diseases, periodontitis, osteoporosis, rheumatoid arthritis, ulcerative colitis, inflammatory disorders, tumor growth and invasion (Stetler-Stevenson et al., Annu. Rev. Cell Biol. 1993, 9: 541-73; Tryggvason et al., Biochim. Biophys. Acta 1987, 907: 191-217; Li et al., Mol. Carcillog. 1998, 22: 84-89)), metastasis, acute lung injury, stroke, ischemia, diabetes, aortic or vascular aneurysms, skin tissue wounds, dry eye, bone and cartilage degradation (Greenwald et al., Bone 1998, 22: 33-38; Ryan et al., Curr. Op. Rheumatol. 1996, 8: 238-247). Other MMPAS include those described in U.S. Pat. Nos. 5,459,135; 5,321,017; 5,308,839; 5,258,371; 4,935,412; 4,704,383, 4,666,897, and RE 34,656, incorporated herein by reference in their entirety.

In a further embodiment, the IPAS includes disorders described in U.S. Pat. Nos. 5,929,055; and 5,532,227, incorporated herein by reference in their entirety.

Tetracycline responsive disease or disorder also includes diseases or disorders associated with NO associated states. The term "NO associated states" includes states which involve or are associated with nitric oxide (NO) or inducible nitric oxide synthase (iNOS). NO associated state includes states which are characterized by aberrant amounts of NO and/or iNOS. Preferably, the NO associated state can be treated by administering tetracycline compounds of the invention. The disorders, diseases and states described in U.S. Pat. Nos. 6,231,894; 6,015,804; 5,919,774; and 5,789,395 are also included as NO associated states. The entire contents of each of these patents are hereby incorporated herein by reference.

Examples of diseases or disorders associated with NO associated states can be treated using the compounds of the present invention (i.e. compound of Structural Formula (I)) or a pharmaceutically acceptable salt thereof include, but are not limited to, malaria, senescence, diabetes, vascular stroke, neurodegenerative disorders (Alzheimer's disease and Huntington's disease), cardiac disease (reperfusion-associated injury following infarction), juvenile diabetes, inflammatory disorders, osteoarthritis, rheumatoid arthritis, acute, recurrent and chronic infections (bacterial, viral and fungal); acute and chronic bronchitis, sinusitis, and respiratory infections, including the common cold; acute and chronic gastroenteritis and colitis; acute and chronic cystitis and urethritis; acute and chronic dermatitis; acute and chronic conjunctivitis; acute and chronic serositis (pericarditis, peritonitis, synovitis, pleuritis and tendonitis); uremic pericarditis; acute and chronic cholecystis; cystic fibrosis, acute and chronic vaginitis; acute and chronic uveitis; drug reactions; insect bites; burns (thermal, chemical, and electrical); and sunburn.

In another embodiment, the tetracycline responsive disease or disorder is cancer. Examples of cancers that can be treated using the compounds of the invention (i.e. compound of Structural Formula (I)) or a pharmaceutically acceptable salt thereof include all solid tumors, i.e., carcinomas e.g., adenocarcinomas, and sarcomas. Adenocarcinomas are carcinomas derived from glandular tissue or in which the tumor cells form recognizable glandular structures. Sarcomas broadly include tumors whose cells are embedded in a fibrillar or homogeneous substance like embryonic connective tissue. Examples of carcinomas which may be treated using the methods of the invention include, but are not limited to, carcinomas of the prostate, breast, ovary, testis, lung, colon, and breast. The methods of the invention are not limited to the treatment of these tumor types, but extend to any solid tumor derived from any organ system. Examples of treatable cancers include, but are not limited to, colon cancer, bladder cancer, breast cancer, melanoma, ovarian carcinoma, prostate carcinoma, lung cancer, and a variety of other cancers as well. The methods of the invention also cause the inhibition of cancer growth in adenocarcinomas, such as, for example, those of the prostate, breast, kidney, ovary, testes, and colon. In one embodiment, the cancers treated by methods of the invention include those described in U.S. Pat. Nos. 6,100,248; 5,843,925; 5,837,696; or 5,668,122, incorporated herein by reference in their entirety.

Alternatively, the tetracycline compounds may be useful for preventing or reducing the likelihood of cancer recurrence, for example, to treat residual cancer following surgical resection or radiation therapy. The tetracycline compounds useful according to the invention are especially advantageous as they are substantially non-toxic compared to other cancer treatments.

In a further embodiment, the compounds of the invention are administered in combination with standard cancer therapy, such as, but not limited to, chemotherapy.

Examples of tetracycline responsive states can be treated using the compounds of the invention (i.e. compound of Structural Formula (I)) or a pharmaceutically acceptable salt thereof also include neurological disorders which include both neuropsychiatric and neurodegenerative disorders, but are not limited to, such as Alzheimer's disease, dementias related to Alzheimer's disease (such as Pick's disease), Parkinson's and other Lewy diffuse body diseases, senile dementia, Huntington's disease, Gilles de la Tourette's syndrome, multiple sclerosis, amyotrophic lateral sclerosis (ALS), progressive supranuclear palsy, epilepsy, and Creutzfeldt-Jakob disease; autonomic function disorders such as hypertension and sleep disorders, and neuropsychiatric disorders, such as depression, schizophrenia, schizoaffective disorder, Korsakoff's psychosis, mania, anxiety disorders, or phobic disorders; learning or memory disorders, e.g., amnesia or age-related memory loss, attention deficit disorder, dysthymic disorder, major depressive disorder, mania, obsessive-compulsive disorder, psychoactive substance use disorders, anxiety, phobias, panic disorder, as well as bipolar affective disorder, e.g., severe bipolar affective (mood) disorder (BP-1), bipolar affective neurological disorders, e.g., migraine and obesity.

Further neurological disorders include, for example, those listed in the American Psychiatric Association's Diagnostic and Statistical manual of Mental Disorders (DSM), the most current version of which is incorporated herein by reference in its entirety.

In another embodiment, the tetracycline responsive disease or disorder is diabetes. Diabetes that can be treated using the compounds of the invention or a pharmaceutically acceptable salt thereof include, but are not limited to, juvenile diabetes, diabetes mellitus, diabetes type I, or diabetes type II. In a further embodiment, protein glycosylation is not affected by the administration of the tetracycline compounds of the invention. In another embodiment, the tetracycline compound of the invention is administered in combination with standard diabetic therapies, such as, but not limited to insulin therapy.

In another embodiment, the tetracycline responsive disease or disorder is a bone mass disorder. Bone mass disorders that can be treated using the compounds of the invention or a pharmaceutically acceptable salt thereof include disorders where a subjects bones are disorders and states where the formation, repair or remodeling of bone is advantageous. For examples bone mass disorders include osteoporosis (e.g., a decrease in bone strength and density), bone fractures, bone formation associated with surgical procedures (e.g., facial reconstruction), osteogenesis imperfecta (brittle bone disease), hypophosphatasia, Paget's disease, fibrous dysplasia, osteopetrosis, myeloma bone disease, and the depletion of calcium in bone, such as that which is related to primary hyperparathyroidism. Bone mass disorders include all states in which the formation, repair or remodeling of bone is advantageous to the subject as well as all other disorders associated with the bones or skeletal system of a subject which can be treated with the tetracycline compounds of the invention. In a further embodiment, the bone mass disorders include those described in U.S. Pat. Nos. 5,459,135; 5,231,017; 5,998,390; 5,770,588; RE 34,656; 5,308,839; 4,925,833; 3,304,227; and 4,666,897, each of which is hereby incorporated herein by reference in its entirety.

In another embodiment, the tetracycline responsive disease or disorder is acute lung injury. Acute lung injuries that can be treated using the compounds of the invention or a pharmaceutically acceptable salt thereof include adult respiratory distress syndrome (ARDS), post-pump syndrome (PPS), and trauma. Trauma includes any injury to living tissue caused by an extrinsic agent or event. Examples of trauma include, but are not limited to, crush injuries, contact with a hard surface, or cutting or other damage to the lungs.

The tetracycline responsive disease or disorder of the invention also includes chronic lung disorders. Examples of chronic lung disorders that can be treated using the compounds of the invention or a pharmaceutically acceptable salt thereof include, but are not limited, to asthma, cystic fibrosis, chronic obstructive pulmonary disease (COPD), and emphysema. In a further embodiment, the acute and/or chronic lung disorders that can be treated using the compounds of the invention or a pharmaceutically acceptable salt thereof include those described in U.S. Pat. Nos. 5,977,091; 6,043,231; 5,523,297; and 5,773,430, each of which is hereby incorporated herein by reference in its entirety.

In yet another embodiment, the tetracycline responsive disease or disorder is ischemia, stroke, or ischemic stroke.

In a further embodiment, the tetracycline compounds of the invention or a pharmaceutically acceptable salt thereof can be used to treat such disorders as described above and in U.S. Pat. Nos. 6,231,894; 5,773,430; 5,919,775 and 5,789,395, incorporated herein by reference.

In another embodiment, the tetracycline responsive disease or disorder is a skin wound. The invention also provides a method for improving the healing response of the epithelialized tissue (e.g., skin, mucosae) to acute traumatic injury (e.g., cut, burn, scrape, etc.). The method includes using a tetracycline compound of the invention or a pharmaceutically acceptable salt thereof to improve the capacity of the epithelialized tissue to heal acute wounds. The method may increase the rate of collagen accumulation of the healing tissue. The method may also decrease the proteolytic activity in the epithelialized tissue by decreasing the collagenolytic and/or gellatinolytic activity of MMPs. In a further embodiment, the tetracycline compound of the invention or a pharmaceutically acceptable salt thereof is administered to the surface of the skin (e.g., topically). In a further embodiment, the tetracycline compound of the invention or a pharmaceutically acceptable salt thereof is used to treat a skin wound, and other such disorders as described in, for example, U.S. Pat. Nos. 5,827,840; 4,704,383; 4,935,412; 5,258,371; 5,308,839, 5,459,135; 5,532,227; and 6,015,804; each of which is incorporated herein by reference in its entirety.

In yet another embodiment, the tetracycline responsive disease or disorder is an aortic or vascular aneurysm in vascular tissue of a subject (e.g., a subject having or at risk of having an aortic or vascular aneurysm, etc.). The tetracycline compound or a pharmaceutically acceptable salt thereof may be effective to reduce the size of the vascular aneurysm or it may be administered to the subject prior to the onset of the vascular aneurysm such that the aneurysm is prevented. In one embodiment, the vascular tissue is an artery, e.g., the aorta, e.g., the abdominal aorta. In a further embodiment, the tetracycline compounds of the invention are used to treat disorders described in U.S. Pat. Nos. 6,043,225 and 5,834,449, incorporated herein by reference in their entirety.

The compounds of the invention or a pharmaceutically acceptable salt thereof can be used alone or in combination with one or more therapeutic agent in the methods of the invention disclosed herein.

The language "in combination with" another therapeutic agent or treatment includes co-administration of the tetracycline compound and with the other therapeutic agent or treatment as either a single combination dosage form or as multiple, separate dosage forms, administration of the tetracycline compound first, followed by the other therapeutic agent or treatment and administration of the other therapeutic agent or treatment first, followed by the tetracycline compound.

The other therapeutic agent may be any agent that is known in the art to treat, prevent, or reduce the symptoms of a tetracycline-responsive disease or disorder. The choice of additional therapeutic agent(s) is based upon the particular tetracycline-responsive disease or disorder being treated. Such choice is within the knowledge of a treating physician. Furthermore, the other therapeutic agent may be any agent of benefit to the patient when administered in combination with the administration of a tetracycline compound.

As used herein, the term "subject" means a mammal in need of treatment, e.g., companion animals (e.g., dogs, cats, and the like), farm animals (e.g., cows, pigs, horses, sheep, goats and the like) and laboratory animals (e.g., rats, mice, guinea pigs and the like). Typically, the subject is a human in need of the specified treatment.

As used herein, the term "treating" or 'treatment" refers to obtaining desired pharmacological and/or physiological effect. The effect can be prophylactic or therapeutic, which includes achieving, partially or substantially, one or more of the following results: partially or totally reducing the extent of the disease, disorder or syndrome; ameliorating or improving a clinical symptom or indicator associated with the disorder; delaying, inhibiting or decreasing the likelihood of the progression of the disease, disorder or syndrome; or partially or totally delaying, inhibiting or reducing the likelihood of the onset or development of disease, disorder or syndrome.

"Effective amount" means that amount of active compound agent that elicits the desired biological response in a subject. Such response includes alleviation of the symptoms of the disease or disorder being treated. In one embodiment, the effective amount of a compound of the invention is from about 0.01 mg/kg/day to about 1000 mg/kg/day, from about 0.1 mg/kg/day to about 100 mg/kg/day, or from about 0.5 mg/kg/day to about 50 mg/kg/day.

The invention further includes the process for making the composition comprising mixing one or more of the present compounds and an optional pharmaceutically acceptable carrier; and includes those compositions resulting from such a process, which process includes conventional pharmaceutical techniques.

The compositions of the invention include ocular, oral, nasal, transdermal, topical with or without occlusion, intravenous (both bolus and infusion), and injection (intraperitoneally, subcutaneously, intramuscularly, intratumorally, or parenterally). The composition may be in a dosage unit such as a tablet, pill, capsule, powder, granule, liposome, ion exchange resin, sterile ocular solution, or ocular delivery device (such as a contact lens and the like facilitating immediate release, timed release, or sustained release), parenteral solution or suspension, metered aerosol or liquid spray, drop, ampoule, auto-injector device, or suppository; for administration ocularly, orally, intranasally, sublingually, parenterally, or rectally, or by inhalation or insufflation.

Compositions of the invention suitable for oral administration include solid forms such as pills, tablets, caplets, capsules (each including immediate release, timed release, and sustained release formulations), granules and powders; and, liquid forms such as solutions, syrups, elixirs, emulsions, and suspensions. Forms useful for ocular administration include sterile solutions or ocular delivery devices. Forms useful for parenteral administration include sterile solutions, emulsions, and suspensions.

The compositions of the invention may be administered in a form suitable for once-weekly or once-monthly administration. For example, an insoluble salt of the active compound may be adapted to provide a depot preparation for intramuscular injection (e.g., a decanoate salt) or to provide a solution for ophthalmic administration.

The dosage form containing the composition of the invention contains an effective amount of the active ingredient necessary to provide a therapeutic effect. The composition may contain from about 5,000 mg to about 0.5 mg (preferably, from about 1,000 mg to about 0.5 mg) of a compound of the invention or salt form thereof and may be constituted into any form suitable for the selected mode of administration. The composition may be administered about 1 to about 5 times per day. Daily administration or post-periodic dosing may be employed.

For oral administration, the composition is preferably in the form of a tablet or capsule containing, e.g., 500 to 0.5 milligrams of the active compound. Dosages will vary depending on factors associated with the particular patient being treated (e.g., age, weight, diet, and time of administration), the severity of the condition being treated, the compound being employed, the mode of administration, and the strength of the preparation.

The oral composition is preferably formulated as a homogeneous composition, wherein the active ingredient is dispersed evenly throughout the mixture, which may be readily subdivided into dosage units containing equal amounts of a compound of the invention. Preferably, the compositions are prepared by mixing a compound of the invention (or pharmaceutically acceptable salt thereof) with one or more optionally present pharmaceutical carriers (such as a starch, sugar, diluent, granulating agent, lubricant, glidant, binding agent, and disintegrating agent), one or more optionally present inert pharmaceutical excipients (such as water, glycols, oils, alcohols, flavoring agents, preservatives, coloring agents, and syrup), one or more optionally present conventional tableting ingredients (such as corn starch, lactose, sucrose, sorbitol, talc, stearic acid, magnesium stearate, dicalcium phosphate, and any of a variety of gums), and an optional diluent (such as water).

Binder agents include starch, gelatin, natural sugars (e.g., glucose and beta-lactose), corn sweeteners and natural and synthetic gums (e.g., acacia and tragacanth). Disintegrating agents include starch, methyl cellulose, agar, and bentonite.

Tablets and capsules represent an advantageous oral dosage unit form. Tablets may be sugarcoated or filmcoated using standard techniques. Tablets may also be coated or otherwise compounded to provide a prolonged, control-release therapeutic effect. The dosage form may comprise an inner dosage and an outer dosage component, wherein the outer component is in the form of an envelope over the inner component. The two components may further be separated by a layer which resists disintegration in the stomach (such as an enteric layer) and permits the inner component to pass intact into the duodenum or a layer which delays or sustains release. A variety of enteric and non-enteric layer or coating materials (such as polymeric acids, shellacs, acetyl alcohol, and cellulose acetate or combinations thereof) may be used.

Compounds of the invention may also be administered via a slow release composition; wherein the composition includes a compound of the invention and a biodegradable slow release carrier (e.g., a polymeric carrier) or a pharmaceutically acceptable non-biodegradable slow release carrier (e.g., an ion exchange carrier).

Biodegradable and non-biodegradable slow release carriers are well known in the art. Biodegradable carriers are used to form particles or matrices which retain an active agent(s) and which slowly degrade/dissolve in a suitable environment (e.g., aqueous, acidic, basic and the like) to release the agent. Such particles degrade/dissolve in body fluids to release the active compound(s) therein. The particles are preferably nanoparticles (e.g., in the range of about 1 to 500 nm in diameter, preferably about 50-200 nm in diameter, and most preferably about 100 nm in diameter). In a process for preparing a slow release composition, a slow release carrier and a compound of the invention are first dissolved or dispersed in an organic solvent. The resulting mixture is added into an aqueous solution containing an optional surface-active agent(s) to produce an emulsion. The organic solvent is then evaporated from the emulsion to provide a colloidal suspension of particles containing the slow release carrier and the compound of the invention.

The compound disclosed herein may be incorporated for administration orally or by injection in a liquid form such as aqueous solutions, suitably flavored syrups, aqueous or oil suspensions, flavored emulsions with edible oils such as cottonseed oil, sesame oil, coconut oil or peanut oil and the like, or in elixirs or similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone, and gelatin. The liquid forms in suitably flavored suspending or dispersing agents may also include synthetic and natural gums. For parenteral administration, sterile suspensions and solutions are desired. Isotonic preparations, which generally contain suitable preservatives, are employed when intravenous administration is desired.

The compounds may be administered parenterally via injection. A parenteral formulation may consist of the active ingredient dissolved in or mixed with an appropriate inert liquid carrier. Acceptable liquid carriers usually comprise aqueous solvents and other optional ingredients for aiding solubility or preservation. Such aqueous solvents include sterile water, Ringer's solution, or an isotonic aqueous saline solution. Other optional ingredients include vegetable oils (such as peanut oil, cottonseed oil, and sesame oil), and organic solvents (such as solketal, glycerol, and formyl). A sterile, non-volatile oil may be employed as a solvent or suspending agent. The parenteral formulation is prepared by dissolving or suspending the active ingredient in the liquid carrier whereby the final dosage unit contains from 0.005 to 10% by weight of the active ingredient. Other additives include preservatives, isotonizers, solubilizers, stabilizers, and pain-soothing agents. Injectable suspensions may also be prepared, in which case appropriate liquid carriers, suspending agents and the like may be employed.

Compounds of the invention may be administered intranasally using a suitable intranasal vehicle.

Compounds of the invention may also be administered topically using a suitable topical transdermal vehicle or a transdermal patch.

For ocular administration, the composition is preferably in the form of an ophthalmic composition. The ophthalmic compositions are preferably formulated as eye-drop formulations and filled in appropriate containers to facilitate administration to the eye, for example a dropper fitted with a suitable pipette. Preferably, the compositions are sterile and aqueous based, using purified water. In addition to the compound of the invention, an ophthalmic composition may contain one or more of: a) a surfactant such as a polyoxyethylene fatty acid ester; b) a thickening agents such as cellulose, cellulose derivatives, carboxyvinyl polymers, polyvinyl polymers, and polyvinylpyrrolidones, typically at a concentration n the range of about 0.05 to about 5.0% (wt/vol); c) (as an alternative to or in addition to storing the composition in a container containing nitrogen and optionally including a free oxygen absorber such as Fe), an anti-oxidant such as butylated hydroxyanisol, ascorbic acid, sodium thiosulfate, or butylated hydroxytoluene at a concentration of about 0.00005 to about 0.1% (wt/vol); d) ethanol at a concentration of about 0.01 to 0.5% (wt/vol); and e) other excipients such as an isotonic agent, buffer, preservative, and/or pH-controlling agent. The pH of the ophthalmic composition is desirably within the range of 4 to 8.

In certain embodiments, the composition of this invention includes one or more additional agents. The other therapeutic agent may be any agent that is capable of treating, preventing or reducing the symptoms of a tetracycline-responsive disease or disorder. Alternatively, the other therapeutic agent may be any agent of benefit to a patient when administered in combination with the tetracycline compound in this invention.

The following abbreviations are used in the synthesis examples below.

ABBREVIATIONS

Ac acetyl
AIBN 2,2'-azobis(2-methylpropionitrile)
aq aqueous
Bn benzyl
Boc tert-butoxycarbonyl
Bu butyl
Cbz benzyloxycarbonyl
Cy tricyclohexylphosphine
dba dibenzylideneacetone
DIBAL-H diisobutylaluminum hydride
DIEA N,N-diisopropylethylamine
DMAP 4-(dimethylamino)pyridine
DME 1,2-dimethoxyethane
DMF N,N-dimethylformamide
DMPU 1,3-dimethyl-3,4-5,6-tetrahydro-2(1H)-pyrimidone
DMSO dimethyl sulfoxide
EDC N-(3-dimethylaminopropyl)-N'-ethylcarbodiimide
ESI electrospray ionization
Et ethyl
EtOAc ethyl acetate
HPLC high performance liquid chromatography
HOBt 1-hydroxybenzotriazole
i iso
IBX 2-iodoxybenzoic acid
LDA lithium diisopropylamide
LHMDS lithium bis(trimethylsilyl)amide
LTMP lithium 2,2,6,6-tetramethylpiperidide
MeOH methanol
Ms methanesulfonyl
MS mass spectrometry
MTBE methyl tert-butyl ether NBS N-bromosuccinimide
NCS N-chlorosuccinimide
NMR nuclear magnetic resonance spectrometry
Ph phenyl
Pr propyl
s secondary
t tertiary
TMEDA N,N,N'N'-tetramethylethylenediamine
TBS tert-butyldimethylsilyl
TEA triethylamine
Tf trifluoromathanesulfonyl
TFA trifluoroacetic acid
TFAA trifluoroacetic anhydride
THF tetrahydrofuran
TLC thin layer chromatography
Ts para-toluenesulfonyl
TsOH para-toluenesulfonic acid
Xantphos 4,5-bis(diphenylphosphino)-9,9-dimethylxanthene

EXAMPLE 1

Synthesis of Compounds Via Scheme 1

Scheme 1

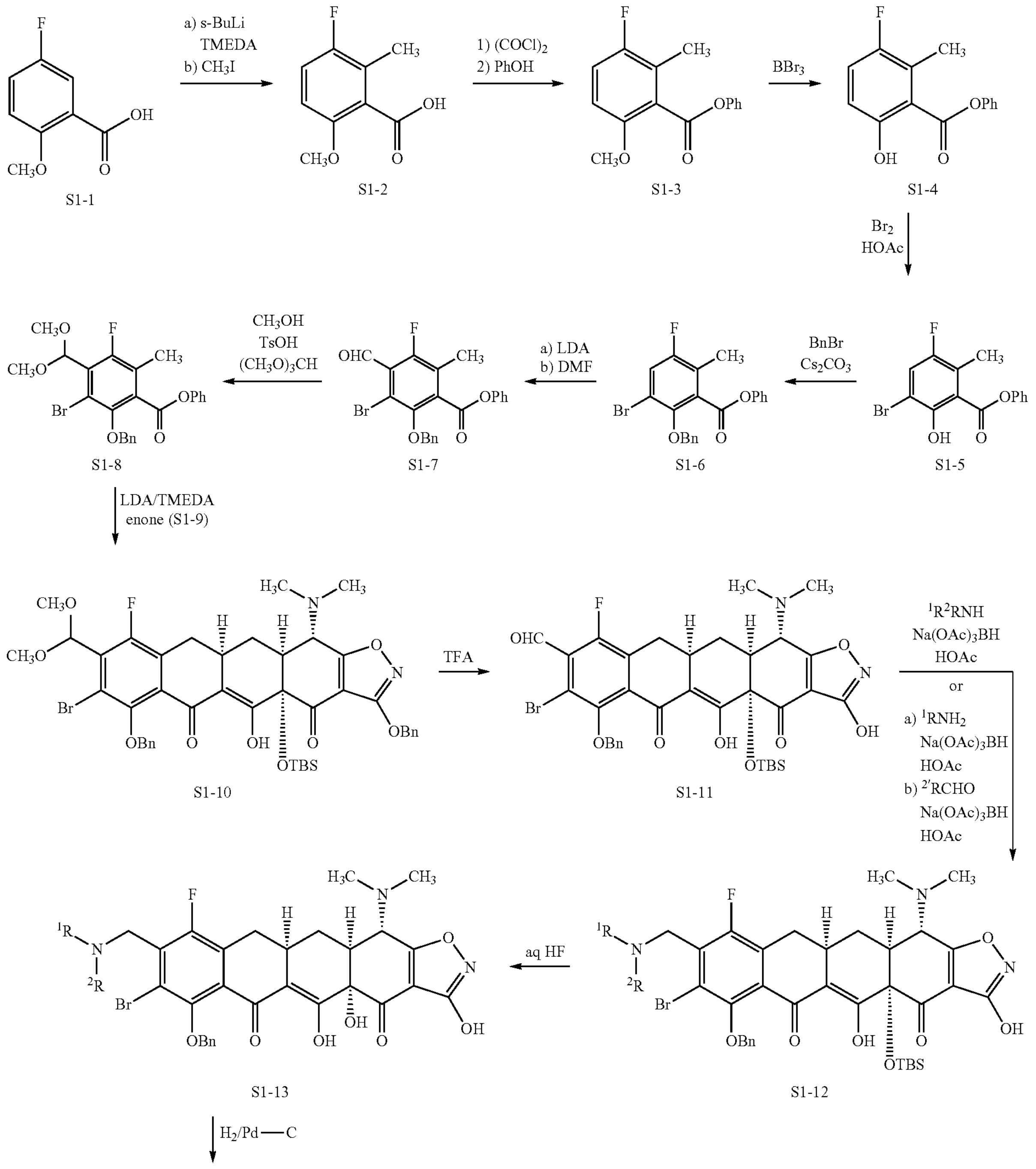

-continued

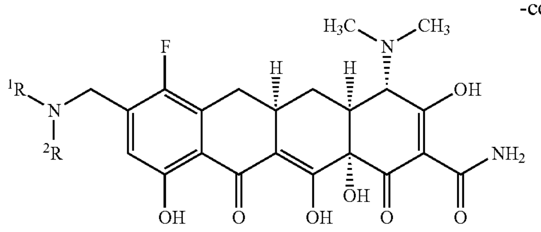

S1-14

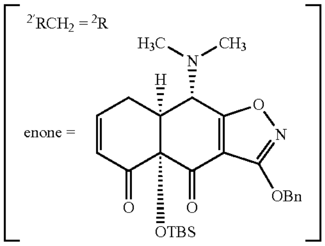

S1-9

The following compounds were prepared according to Scheme 1.

S1-2

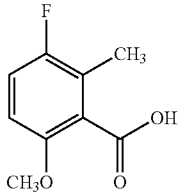

To a THF solution of 5-fluoro-2-methoxybenzoic acid (S1-1, 0.50 g, 2.94 mmol, 1.0 equiv, Aldrich 523097) cooled at −78° C. was added a THF solution of s-BuLi (4.60 mL, 1.40 M/cyclohexane, 6.44 mmol, 2.2 equiv) and TMEDA (0.97 mL, 6.47 mmol, 2.2 equiv). The reaction was stirred at −78° C. for 2 hrs. Iodomethane (1.10 mL, 17.64 mmol, 6.0 equiv) was added to the reaction mixture dropwise. The reaction was allowed to warm to 25° C. over 1 h and stirred at 25° C. for 1 h. Aqueous NaOH (6 N, 20 mL) was added. The resulting mixture was extracted with t-butylmethyl ether (20 mL×2). The aqueous layer was acidified with hydrochloric acid (6 N) to pH 1 and extracted with EtOAc (20 mL×4). The combined EtOAc extracts were dried over sodium sulfate and concentrated to give 0.51 g of crude S1-2: $^1$H NMR (400 MHz, $CDCl_3$) δ 7.06 (dd, J=9.8, 8.5 Hz, 1 H), 6.75 (dd, J=9.8, 3.7 Hz, 1 H), 3.86 (s, 3 H), 2.34 (d, J=2.4 Hz, 3 H); MS (ESI) m/z 185.12 (M+H).

S1-3

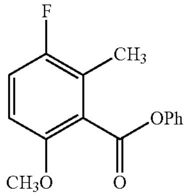

Oxalyl chloride (0.95 mL, 11.10 mmol, 5.5 equiv) was added to a dichloromethane solution (15 mL, anhydrous) of S1-2 (0.51 g, 2.00 mmol, 1.0 equiv). DMF (0.1 mL) was added to the resulting mixture. The reaction was stirred at 25° C. for 1 h and concentrated. The resulting solid was redissolved in 15 mL of anhydrous dichloromethane. Phenol (0.52 g, 5.50 mmol, 2.8 equiv), DMAP (0.67 g, 5.60 mmol, 2.8 equiv), and triethylamine (1.90 mL, 13.90 mmol, 7.0 equiv) were added to the reaction mixture. The reaction was stirred at 25° C. for 12 hrs and concentrated. EtOAc and $H_2O$ were added to the residue. The organic layer was washed with aqueous NaOH (1 N), $H_2O$, and brine, dried over sodium sulfate, and concentrated. Flash chromatography on silica gel (40:1 hexanes/EtOAc) yielded 0.40 g of compound S1-3 (52%, 2 steps): $^1$H NMR (400 MHz, $CDCl_3$) δ 7.47-7.41 (m, 2 H), 7.31-7.24 (m, 3 H), 7.08 (dd, J=9.2, 9.2 Hz, 1 H), 6.77 (dd, J=9.2, 3.7 Hz, 1 H), 3.88 (s, 3 H), 2.36 (d, J=2.3 Hz, 3 H); MS (ESI) m/z 261.12 (M+H).

S1-4

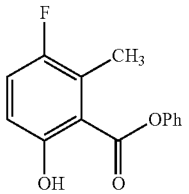

$BBr_3$ (1.85 mL, 1 M/dichloromethane, 1.85 mmol, 1.2 equiv) was added to a dichloromethane solution (8 mL) of S1-3 (0.40 g, 1.54 mmol, 1.0 equiv) at −78° C. The reaction was stirred from −78° C. to 25° C. for 1.5 hrs, quenched by saturated aqueous $NaHCO_3$, and concentrated. EtOAc and $H_2O$ were added to the reaction mixture. The aqueous layer was extracted with EtOAc. The combined EtOAc extracts were dried over sodium sulfate and concentrated under reduced pressure to yield 0.36 g of crude S1-4: $^1$H NMR (400 MHz, $CDCl_3$) δ 10.66 (s, 1 H), 7.50-7.44 (m, 2 H), 7.36-7.31 (m, 1 H), 7.26-7.18 (m, 3 H), 6.86 (dd, J=9.3, 4.9 Hz, 1 H), 2.60 (d, J=2.4 Hz, 3 H); MS (ESI) m/z 245.11 (M−H).

S1-5

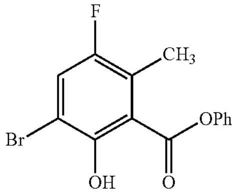

Compound S1-4 (4.92 g, 95% purity, 20.00 mmol, 1.0 equiv) was dissolved in acetic acid (50 mL). Bromine (1.54 mL, 30.00 mmol, 1.5 equiv) was added via syringe at rt. After stirring at rt for 2 hrs, LC/MS indicated that the starting material was consumed. The reaction mixture was diluted with EtOAc, washed with water (3×100 mL) and brine, dried over sodium sulfate, filtered, and concentrated under reduced pressure to give 7.06 g of compound S1-5 as a light yellow solid: $^1$H NMR (400 MHz, $CDCl_3$) δ 11.14 (s, 1 H), 7.52 (d, J=9.2 Hz, 1 H), 7.49-7.43 (m, 2 H), 7.36-7.30 (m, 1 H), 7.21-7.16 (m, 2 H), 2.55 (d, J=2.3 Hz, 3 H).

S1-6

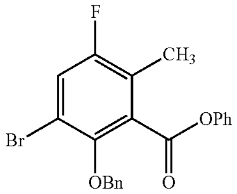

Compound S1-5 (crude, 1.06 g, 2.97 mmol, 1.0 equiv) was dissolve in acetone (20 mL), added with potassium carbonate (0.82 g, 5.94 mmol, 2.0 equiv), and cooled to 0° C. in an ice-bath. Benzyl bromide (540 μL, 4.45 mmol, 1.5 equiv) was added dropwise. After 2 hrs, LC/MS indicated that 40% of the starting material was consumed. The reaction mixture was heated to 50° C. for another hour and the starting material was completely consumed. The reaction mixture was diluted with EtOAc (100 mL), washed with water and brine, dried over sodium sulfate, filtered, and concentrated under reduced pressure to give 2.2 g of crude S1-6, which was purified by column chromatography (Biotage 10 g column, 2 to 5% EtOAc in hexanes gradient), yielding 1.03 g (84%, two steps) of the pure compound S1-6 as an colorless oil: $^1$H NMR (400 MHz, $CDCl_3$) δ 7.50-7.47 (m, 2 H), 7.40-7.33 (m, 6 H), 7.25 (t, J=7.3 Hz, 1 H), 7.04 (d, J=8.6 Hz, 2 H), 5.09 (s, 2 H), 2.32 (d, J=1.8 Hz, 3 H).

S1-7

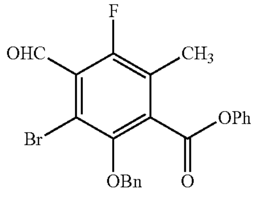

An LDA/THF solution was prepared by adding n-BuLi (1.6 M/hexanes, 5.10 mL, 8.16 mmol, 1.5 equiv) to diisopropylamine (1.15 mL, 8.16 mmol, 1.5 equiv) in THF (15 mL) at −78° C. The reaction mixture was warmed to −20° C. and stirred for 15 min. After the LDA solution was cooled to −78° C., compound S1-6 (2.26 g, 5.44 mmol, 1.0 equiv) in THF (5 mL) was added dropwise. An orange-red solution was formed. After 10 min, DMF (1.26 mL, 16.30 mmol, 3.0 equiv) was added dropwise. The reaction solution was allowed to warm to −20° C. in 1 h and quenched by saturated aqueous $NH_4Cl$. LC/MS indicated that the starting material was consumed. The reaction mixture was diluted with EtOAc (100 mL), washed with water and brine, dried over sodium sulfate, filtered, and concentrated under reduced pressure. This gave 2.42 g of crude S1-7, which was purified by column chromatography (Biotage 24 g column, 5 to 10% EtOAc in hexanes gradient), yielding 2.23 g (92%) of the pure compound S1-7 as a light yellow solid: $^1$H NMR (400 MHz, $CDCl_3$) δ 10.37 (s, 1 H), 7.51-7.47 (m, 2 H), 7.40-7.33 (m, 5 H), 7.27 (t, J=7.3 Hz, 1 H), 7.06-7.02 (m, 2 H), 5.12 (s, 2 H), 2.37 (d, J=2.3 Hz, 3 H).

S1-8

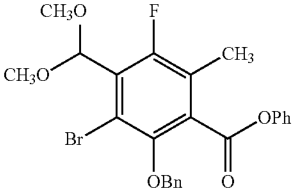

To a solution of compound S1-7 (10 g, 22.60 mmol, 1.0 equiv) in MeOH was added trimethylorthoformate (4.8 g, 45.20 mmol, 2.0 equiv) and TsOH.$H_2O$ (0.13 g, 0.68 mmol, 0.03 equiv) at rt. The reaction mixture was heated to reflux overnight and concentrated under reduced pressure. The residue was diluted with $H_2O$ and extracted with EtOAc. The organic layer was dried over sodium sulfate and evaporated to dryness. The crude product was purified by column chromatography on silica gel (petroleum ether:EtOAc from 100:1 to 30:1) to afford compound S1-8 as a light yellow solid (10 g, 91%): $^1$H NMR (400 MHz, $CDCl_3$) δ 7.41-7.45 (m, 2 H), 7.25-7.35 (m, 5 H), 7.16-7.21 (m, 1 H), 6.98 (d, J=8.0 Hz, 2 H), 5.71 (s, 1 H), 5.04 (s, 2 H), 3.46 (s, 6 H), 2.29 (d, J=2.4 Hz, 3 H).

S1-10

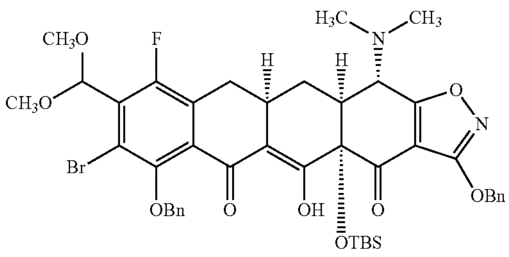

Compound S1-8 (1.37 g, 2.80 mmol, 3.0 equiv) and enone S1-9 (0.45 g, 0.93 mmol, 1.0 equiv) were dissolved in dry THF (5 mL) under $N_2$. Freshly prepared LDA/TMEDA/THF (0.71 M/THF, 7.9 mL, 5.60 mmol, 2.0 equiv) was added to the solution at −78° C. The solution was stirred at −78° C. for about 10 min, and then the temperature was slowly increased from −78° C. to −10° C. over 20 min. The reaction mixture was quenched by saturated aqueous $NH_4Cl$ (50 mL) and extracted with EtOAc (50 ml×3). The organic phase was dried over sodium sulfate and evaporated under reduced pressure to afford the crude product. The crude product was purified by column chromatography on silica gel (petroleum ether:EtOAc: from 50:1 to 15:1) to give the desired compound S1-10 (0.60 g, 0.68 mmol, 74%): $^1$H NMR (400 MHz, $CD_3OD$) δ 15.97 (s, 1 H), 7.61-7.59 (m, 2 H), 7.55-7.53 (m, 2 H)□7.42-7.40 (m, 6 H), 5.83 (s, 1 H), 5.40 (s, 2 H), 5.02-4.97 (m, 2 H)□3.96 (d, J=10.8 Hz, 1 H), 3.57 (s, 6 H), 3.35-3.26 (m, 1 H), 3.09-2.95 (m, 1 H), 2.67-2.58 (m, 1 H), 2.53 (s, 6 H), 2.50-2.39 (m, 1 H), 2.21-2.10 (m, 1 H), 1.58 (s, 9 H), 0.31 (s, 3 H), 0.16 (s, 3 H); MS (ESI) m/z 877.3 (M+H).

Preparation of LDA/TMEDA/THF: To diisopropylamine (1.1 g, 10.90 mmol, 1.0 equiv) and TMEDA (5 mL) in dry THF (5 mL) at −78° C. was added n-BuLi (4.8 mL, 2.5 M/hexanes, 12.00 mmol, 1.1 equiv) dropwise under $N_2$. The solution was stirred at −78° C. for 1 h. The prepared LDA/TMEDA/THF solution was about 0.71 M and was used immediately.

S1-11

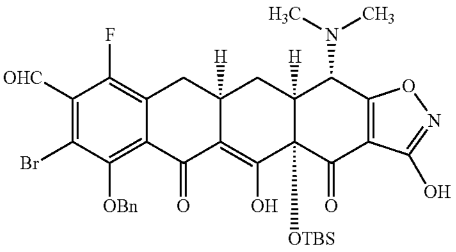

Compound S1-10 (50 mg, 0.057 mmol, 1.0 equiv) was dissolved in dry dichloromethane (1 mL). TFA (0.5 mL) was added. The solution was stirred at 10° C. for 1 h. LC-MS analysis showed the complete consumption of starting material. The reaction mixture was washed with $H_2O$ (10 mL×3) and concentrated under reduced pressure to give crude S1-11, which was used for the next step without further purification: MS (ESI) m/z 741.1 (M+H).

S1-12-1

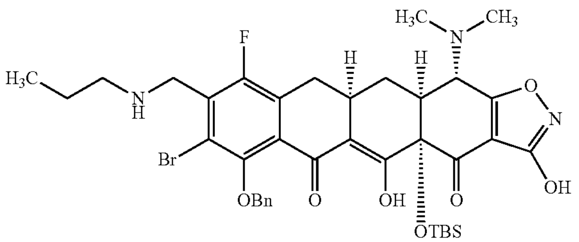

Compound S1-11 (crude, 0.057 mmol, 1.0 equiv) was dissolved in 1,2-dichloroethane (2 mL). HOAc (20 μL) and n-propylamine (49 mg, 0.34 mmol, 6.0 equiv) were added. The mixture was stirred for 1 h. $Na(OAc)_3BH$ (73 mg, 0.34 mmol, 6.0 equiv) was added and the resulting mixture was stirred for another hour. The mixture was washed with $H_2O$ (10 mL) and concentrated to give crude S1-12-1, which was used for the next step without further purification: MS (ESI) m/z 786.2 (M+H).

S1-12-2

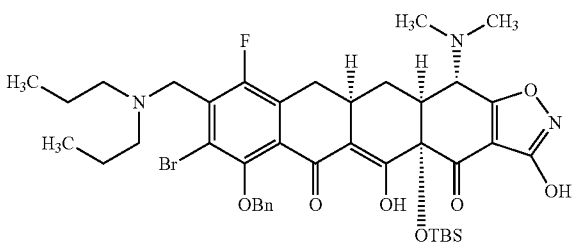

Compound S1-12-1 (crude, 0.057 mmol, 1.0 equiv) was dissolved in 1,2-dichloroethane (2 mL). HOAc (20 μL) and propionaldehyde (49 mg, 0.34 mmol, 6.0 equiv) were added. The mixture was stirred for 1 h. $Na(OAc)_3BH$ (73 mg, 0.34 mmol, 6.0 equiv) was added and the resulting mixture was stirred for another hour. The mixture was washed with $H_2O$ (10 mL) and concentrated to give crude S1-12-2, which was used for the next step without further purification: MS (ESI) m/z 828.2 (M+H).

S1-13-2

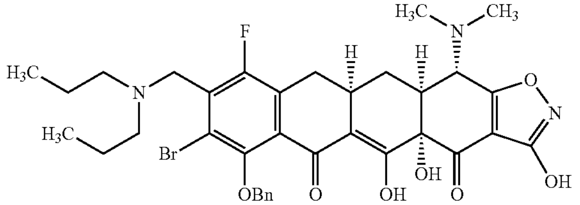

Compound S1-12-2 (crude, 0.057 mmol, 1.0 equiv) was dissolved in THF (5 mL) in a polypropylene tube at rt. Aqueous HF (2 mL, 48-50%) was added. The reaction mixture was stirred at rt for 1 h. The resulting mixture was carefully poured into an aqueous solution of $K_2HPO_4$. The pH of the mixture was adjusted to 7-8 by adding more aqueous $K_2HPO_4$. The mixture was extracted with EtOAc (20 mL), and the EtOAc extract was concentrated to give crude S1-13-2, which was used for the next step without further purification: MS (ESI) m/z 714.0 (M+H).

S1-14-2

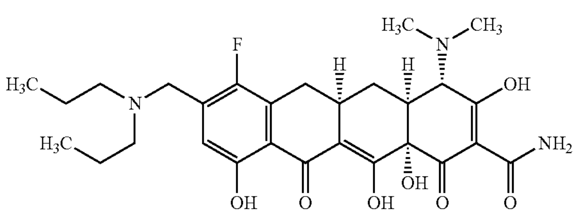

Compound S1-13-2 (crude, 0.057 mmol, 1.0 equiv) was dissolved in MeOH (5 mL). HCl/MeOH (1 mL, 4 M) and 10% Pd—C (15 mg) was added. The reaction mixture was purged with hydrogen and stirred under $H_2$ (balloon) at rt for 1 h. The mixture was filtered and concentrated. The crude compound was purified by preparative HPLC using similar conditions for S2-4-1 to afford the desired compound S1-14-2 as a yellow solid (10 mg, 32%, 5 steps): $^1$H NMR (400 MHz, $CD_3OD$) δ 7.06 (d, J=6.0 Hz, 1 H), 4.41 (s, 2 H), 4.10 (s, 1 H), 3.18-2.91 (m, 13 H), 2.37-2.23 (m, 2 H), 1.83-1.73 (m, 4 H), 1.67-1.58 (m, 1 H), 0.96 (t, J=7.2 Hz, 3 H); MS (ESI) m/z 546.2 (M+H).

S1-14-1

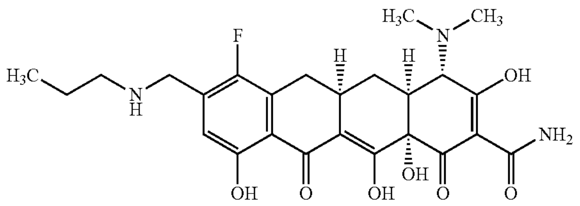

Similarly, compound S1-14-1 was prepared directly from S1-12-1 via HF treatment followed by hydrogenation: $^1$H NMR (400 MHz, $CD_3OD$) δ 7.03 (d, J=6.0 Hz, 1 H), 4.27 (s, 2 H), 4.12 (s, 1 H), 3.21 (dd, J=15.1, 4.6 Hz, 1 H), 3.05 (s, 3 H), 2.97 (s, 3 H), 2.94 (d, J=6.9 Hz, 2 H), 3.14-2.98 (m, 2 H), 2.21-2.39 (m, 2 H), 1.82-1.71 (m, 2 H), 1.70-1.58 (m, 1 H), 1.02 (t, J=7.6 Hz, 3 H); MS (ESI) m/z 504.44 (M+H).

S1-12-3

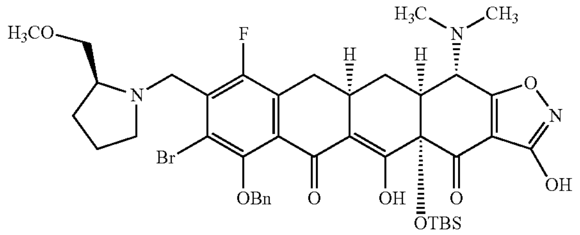

Compound S1-11 (crude, 0.057 mmol, 1.0 equiv) was dissolved in 1,2-dichloroethane (2 mL). HOAc (20 μL) and (S)-(+)-2-(methyoxymethyl)pyrrolidine (49 mg, 0.34 mmol, 6.0 equiv) were added. The mixture was stirred at rt for 1 h. $Na(OAc)_3BH$ (73 mg, 0.34 mmol, 6.0 equiv) was added and the resulting mixture was stirred for another hour. The mixture was washed with $H_2O$ (10 mL) and concentrated to give crude S1-12-3, which was used for the next step without further purification: MS (ESI) m/z 842.3 (M+H).

S1-13-3

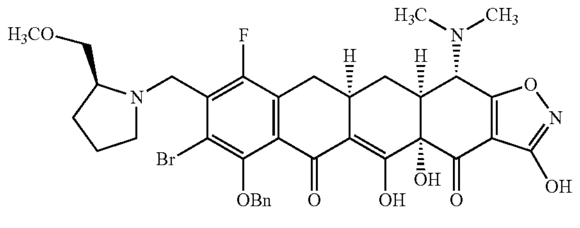

Compound S1-12-3 (crude, 0.057 mmol, 1.0 equiv) was dissolved in THF (5 mL) in a polypropylene tube at rt. Aqueous HF (2 mL, 48-50%) was added. The reaction mixture was stirred at rt for 1 h. The resulting mixture was poured into an aqueous solution of $K_2HPO_4$. The pH of the mixture was adjusted to 7-8 with more aqueous $K_2HPO_4$. The mixture was extracted with EtOAc (20 mL), and the EtOAc extract was concentrated to give crude S1-13-3, which was used for the next step without further purification: MS (ESI) m/z 728.2 (M+H).

S1-14-3

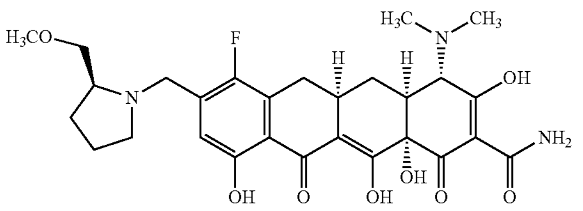

Compound S1-13-3 (crude, 0.057 mmol, 1.0 equiv) was dissolved in MeOH (5 mL). HCl/MeOH (1 mL, 4 M) and 10% Pd—C (15 mg) was added. The reaction mixture was purged with hydrogen and stirred under $H_2$ (balloon) at rt for 1 h. The mixture was filtered and concentrated. The crude product was purified by preparative HPLC using similar conditions for S2-4-1 to afford the desired compound S1-14-3 as a yellow solid (10 mg, 31%, 4 steps): $^1$H NMR (400 MHz, $CD_3OD$) δ 7.03 (d, J=5.6 Hz, 1 H), 4.68 (d, J=13.2 Hz, 1 H), 4.29 (d, J=13.2 Hz, 1 H), 4.10 (s, 1 H), 3.85-3.82 (m, 1 H), 3.71-3.59 (m, 2 H), 3.46-3.41 (m, 1 H), 3.39 (s, 3 H), 3.26-2.93 (m, 10 H), 2.33-2.24 (m, 3 H), 2.22-2.09 (m, 1 H), 1.95-1.81 (m, 2 H), 1.63-1.55 (m, 1 H); MS (ESI) m/z 560.1 (M+H).

The following compounds were prepared similarly to S1-14-1, S1-14-2, or S1-14-3.

S1-14-4

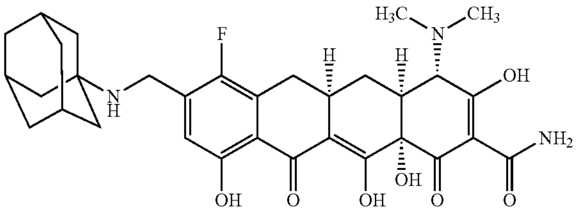

S1-14-4: $^1$H NMR (400 MHz, $CD_3OD$ with DCl) δ 7.09 (d, J=5.96 Hz, 1 H), 4.23 (s, 2 H), 4.16 (s, 1 H), 3.26-2.94 (m, 9 H), 2.38-2.20 (m, 5 H), 2.12-2.00 (m, 6 H), 1.84-1.71 (m, 6 H), 1.70-1.56 (m, 1 H); MS (ESI) m/z 596.18 (M+H).

S1-14-5

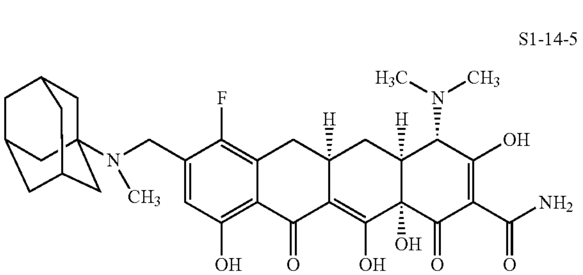 [SMILES: CN(C)[C@@H]1C(O)=C(C(N)=O)C(=O)[C@@]2(O)C(O)=C3C(=O)c4c(O)cc(CN(C)C56CC7CC(CC(C7)C5)C6)c(F)c4C[C@H]3C[C@@H]12]

S1-14-5: $^1$H NMR (400 MHz, $CD_3OD$ with DCl) δ 7.09 (d, J=5.5 Hz, 1 H), 4.89-4.79 (m, 1 H), 4.17 (s, 1 H), 3.98-3.89 (m, 1 H), 3.26-2.94 (m, 9 H), 2.74 (s, 3 H), 2.38-2.05 (m, 11 H), 1.84-1.71 (m, 6 H), 1.70-1.56 (m, 1 H); MS (ESI) m/z 610.19 (M+H).

S1-14-6

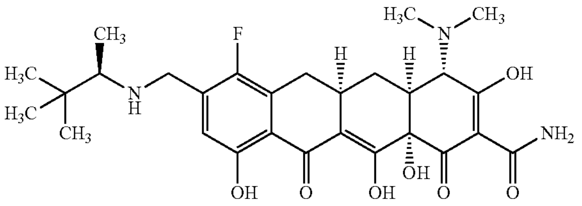

S1-14-6: $^1$H NMR (400 MHz, $CD_3OD$) δ 7.08 (d, J=6.0 Hz, 1 H), 4.40 (d, J=14.2 Hz, 1 H), 4.34 (d, J=14.2 Hz, 1 H), 4.10 (s, 1 H), 3.21 (dd, J=15.5, 4.6 Hz, 1 H), 3.04 (s, 3 H), 2.95 (s, 3 H), 3.17-2.97 (m, 2 H), 2.34 (t, J=14.7 Hz, 1 H), 2.28-2.20 (m, 1 H), 1.69-1.59 (m, 1 H), 1.34 (d, J=6.9 Hz, 3 H), 1.00 (s, 9 H); MS (ESI) m/z 546.30 (M+H).

S1-14-7

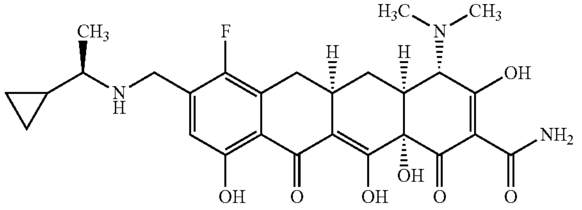

S1-14-7: $^1$H NMR (400 MHz, $CD_3OD$) δ 7.04 (d, J=6.0 Hz, 1 H), 4.40 (d, J=14.2 Hz, 1 H), 4.29 (d, J=14.2 Hz, 1 H), 4.10 (s, 1 H), 3.21 (dd, J=15.5, 4.6 Hz, 1 H), 3.04 (s, 3 H), 2.96 (s, 3 H), 3.17-2.97 (m, 2 H), 2.73 (m, 1 H), 2.34 (t, J=14.7 Hz, 1 H), 2.23 (m, 1 H), 1.69-1.59 (m, 1 H), 1.46 (d, J=6.9 Hz, 3 H), 1.00 (s, 9 H), 1.07-0.99 (m, 1 H), 0.79-0.72 (m, 2 H), 0.63-0.55 (m, 1 H), 0.41-0.32 (m, 1 H); MS (ESI) m/z 530.25 (M+H).

S1-14-8

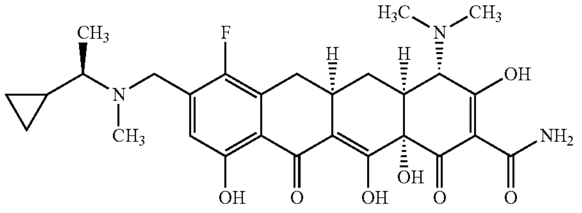

S1-14-8: $^1$H NMR (400 MHz, $CD_3OD$) δ 7.09 (d, J=6.0 Hz, 1 H), 4.69 (dd, J=30.2, 13.3 Hz, 1 H), 4.20 (dd, J=30.2, 13.3 Hz, 1 H), 4.11 (s, 1 H), 3.05 (s, 3 H), 2.97 (s, 3 H), 3.26-2.97 (m, 3 H), 2.85 (d, J=21.1 Hz, 3 H), 2.36 (t, J=14.6 Hz, 1 H), 2.29-2.21 (m, 1 H), 1.69-1.60 (m, 1 H), 1.52 (t, J=5.0 Hz, 3 H), 1.30-1.12 (m, 1 H), 0.90-0.74 (m, 2 H), 0.72-0.64 (m, 1 H), 0.59-0.51 (m, 1 H), 0.49-0.37 (m, 1 H); MS (ESI) m/z 544.28 (M+H).

S1-14-9

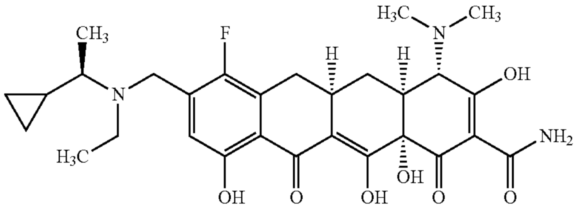

S1-14-9: $^1$H NMR (400 MHz, $CD_3OD$) δ 7.08 (d, J=6.0 Hz, 1 H), 4.73 (dd, J=29.8, 13.3 Hz, 1 H), 4.25 (dd, J=30.2, 13.3 Hz, 1 H), 4.10 (s, 1 H), 3.05 (s, 3 H), 2.97 (s, 3 H), 3.50-2.97 (m, 5 H), 2.36 (t, J=14.6 Hz, 1 H), 2.28-2.20 (m, 1 H), 1.70-1.60 (m, 1 H), 1.48 (dd, J=18.3, 6.4 Hz, 3 H), 1.29 (dt, J=30.7, 6.4 Hz, 1 H), 0.90-0.73 (m, 2 H), 0.65-0.49 (m, 2 H), 0.46-0.37 (m, 1 H); MS (ESI) m/z 558.29 (M+H).

S1-14-10

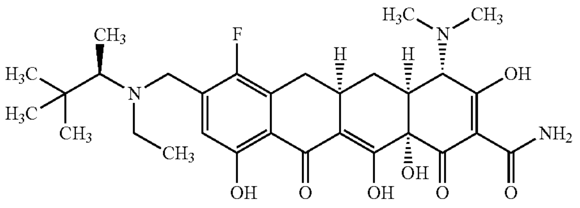

S1-14-10: $^1$H NMR (400 MHz, $CD_3OD$) δ 7.06 (d, J=6.0 Hz, 1 H), 4.58 (d, J=13.2 Hz, 1 H), 4.17 (d, J=13.2 Hz, 1 H), 4.11 (s, 1 H), 3.63-3.55 (m, 1 H), 3.05 (s, 3 H), 2.97 (s, 3 H), 3.25-2.97 (m, 5 H), 2.36 (t, J=14.7 Hz, 1 H), 2.30-2.22 (m, 1 H), 1.71-1.61 (m, 1 H), 1.36 (d, J=6.9 Hz, 3 H), 1.21 (s, 9 H); MS (ESI) m/z 574.32 (M+H).

S1-14-11

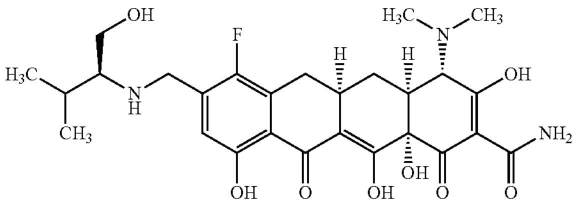

S1-14-11: $^1$H NMR (400 MHz, $CD_3OD$) δ 7.08 (d, J=6.0 Hz, 1 H), 4.39 (t, J=13.3 Hz, 2 H), 4.13 (s, 1 H), 3.93 (dd, J=12.3, 2.7 Hz, 1 H), 3.80 (dd, J=12.4, 6.9 Hz, 1 H), 3.06 (s, 3 H), 2.97 (s, 3 H), 3.23-2.97 (m, 4 H), 2.37-2.23 (m, 2 H), 2.22-2.16 (m, 1 H), 2.13 (d, J=1.4 Hz, 1 H), 1.68-1.58 (m, 1 H), 1.06 (dd, J=23.4, 6.4 Hz, 6 H); MS (ESI) m/z 548.25 (M+H).

S1-14-12

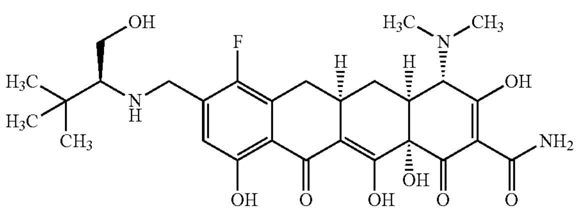

S1-14-12: $^1$H NMR (400 MHz, $CD_3OD$) δ 7.10 (d, J=6.0 Hz, 1 H), 4.48 (m, 2 H), 4.13 (s, 1 H), 3.98 (dd, J=12.4, 2.7 Hz, 1 H), 3.85 (dd, J=11.0, 7.8 Hz, 1 H), 3.06 (s, 3 H), 2.98 (s, 3 H), 3.23-2.97 (m, 4 H), 2.40-2.23 (m, 2 H), 2.10 (d, J=1.4 Hz, 1 H), 1.69-1.59 (m, 1 H), 1.06 (s, 9 H); MS (ESI) m/z 562.26 (M+H).

S1-14-13

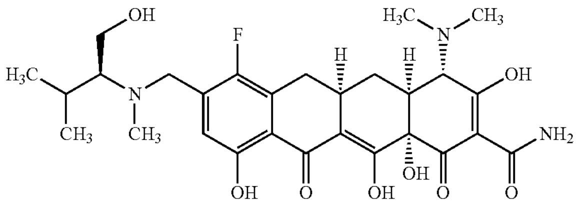

S1-14-13: $^1$H NMR (400 MHz, $CD_3OD$) δ 7.11 (br, s, 1 H), 4.71 (d, J=13.3 Hz, 1 H), 4.39 (d, J=13.3 Hz, 1 H), 4.13 (s, 1 H), 4.04-3.88 (m, 2 H), 3.80 (dd, J=12.4, 6.9 Hz, 1 H), 3.06 (s, 3 H), 2.97 (s, 3 H), 3.23-2.92 (m, 7 H), 2.47-2.23 (m, 3 H), 1.69-1.59 (m, 1 H), 1.18-1.02 (m, 6 H); MS (ESI) m/z 562.27 (M+H).

S1-14-14

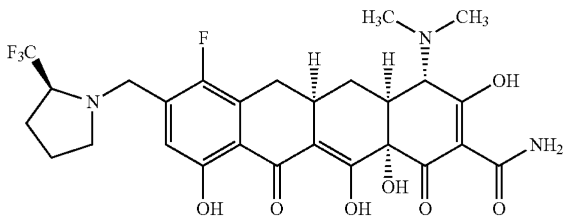

S1-14-14: $^1$H NMR (400 MHz, $CD_3OD$) δ 6.98 (d, J=5.5 Hz, 1 H), 4.25 (d, J=14.7 Hz, 1 H), 4.05 (d, J=14.7 Hz, 1 H), 4.08 (s, 1 H), 3.81-3.73 (m, 1 H), 3.04 (s, 3 H), 2.96 (s, 3 H), 3.27-2.97 (m, 4 H), 2.76 (m, 1 H), 2.35-2.17 (m, 3 H), 2.09-1.99 (m, 1 H), 1.99-1.87 (m, 2 H), 1.69-1.59 (m, 1 H); MS (ESI) m/z 584.26 (M+H).

S1-14-15

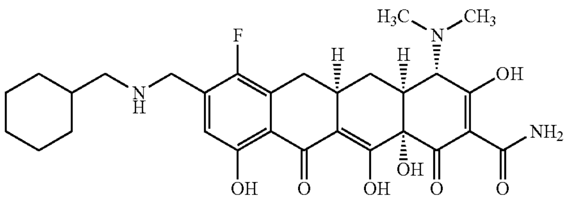

S1-14-15: $^1$H NMR (400 MHz, $CD_3OD$) δ 7.06 (d, J=5.9 Hz, 1 H), 4.27 (s, 2 H), 4.12 (s, 1 H), 3.02 (s, 3 H), 3.27-2.96 (m, 8 H), 2.40-2.24 (m, 2 H), 1.87-1.58 (m, 7 H), 1.40-1.19 (m, 3 H), 1.11-0.98 (m, 2 H); MS (ESI) m/z 558.31 (M+H).

S1-14-16

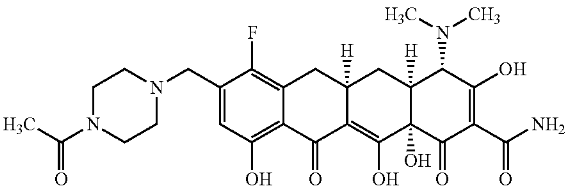

S1-14-16: $^1$H NMR (400 MHz, $CD_3OD$) δ 7.10 (d, J=5.5 Hz, 1 H), 4.45 (s, 2 H), 4.10 (s, 1 H), 3.27-2.98 (m, 7 H), 3.04 (s, 3 H), 2.97 (s, 3 H), 2.37 (t, J=15.1 Hz, 1 H), 2.27-2.17 (m, 1 H), 2.14 (s, 3 H), 1.70-1.60 (m, 1 H); MS (ESI) m/z 573.26 (M+H).

S1-14-17

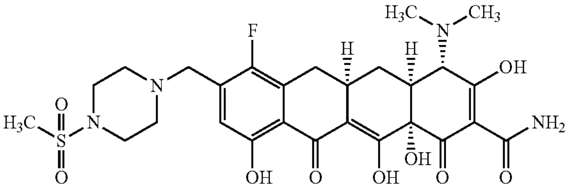

S1-14-17: $^1$H NMR (400 MHz, $CD_3OD$) δ 7.11 (d, J=5.5 Hz, 1 H), 4.47 (s, 2 H), 4.09 (s, 1 H), 3.27-2.98 (m, 7 H), 3.04 (s, 3 H), 2.97 (s, 3 H), 2.96 (s, 3 H), 2.36 (t, J=15.1 Hz, 1 H), 2.26-2.18 (m, 1 H), 1.70-1.60 (m, 1 H); MS (ESI) m/z 609.20 (M+H).

S1-14-18

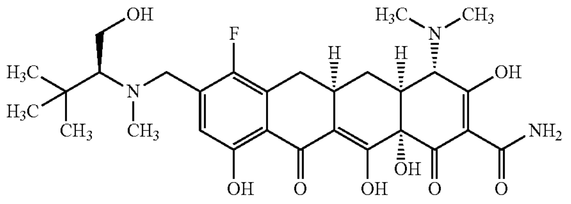

S1-14-18: $^1$H NMR (400 MHz, $CD_3OD$) δ 7.09 (d, J=6.0 Hz, 1 H), 4.77 (d, J=13.3 Hz, 1 H), 4.55 (d, J=13.3 Hz, 1 H), 4.12-4.06 (m, 3 H), 3.14 (s, 3 H), 3.04 (s, 3 H), 2.96 (s, 3 H), 3.23-2.97 (m, 4 H), 2.42-3.34 (m, 1 H), 2.23 (m, 1 H), 1.70-1.60 (m, 1 H), 1.02 (s, 9 H); MS (ESI) m/z 576.27 (M+H).

S1-14-19

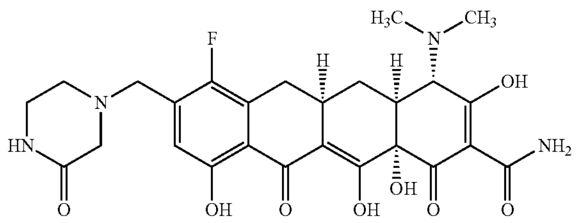

S1-14-19: $^1$H NMR (400 MHz, $CD_3OD$) δ 7.09 (d, J=5.5 Hz, 1 H), 4.53 (s, 2 H), 4.08 (s, 1 H), 3.90 (s, 2 H), 3.67-3.55 (m, 4 H), 3.27-2.98 (m, 3 H), 3.04 (s, 3 H), 2.96 (s, 3 H), 2.38 (t, J=15.1 Hz, 1 H), 2.27-2.19 (m, 1 H), 1.70-1.60 (m, 1 H); MS (ESI) m/z 545.19 (M+H).

S1-14-20

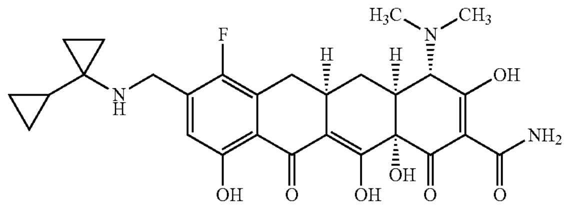

S1-14-20: $^1$H NMR (400 MHz, $CD_3OD$) δ 7.03 (d, J=5.9 Hz, 1 H), 4.51 (d, J=4.1 Hz, 2 H), 4.07 (s, 1 H), 3.03 (s, 3 H), 2.95 (s, 3 H), 3.25-2.96 (m, 3 H), 2.35 (t, J=15.1 Hz, 1 H), 2.26-2.18 (m, 1 H), 1.70-1.60 (m, 1 H), 1.59-1.51 (m, 1 H), 1.02-0.94 (m, 2 H), 0.86-0.78 (m, 2 H), 0.76-0.68 (m, 2 H), 0.43-0.35 (m, 2 H); MS (ESI) m/z 542.29 (M+H).

S1-14-21

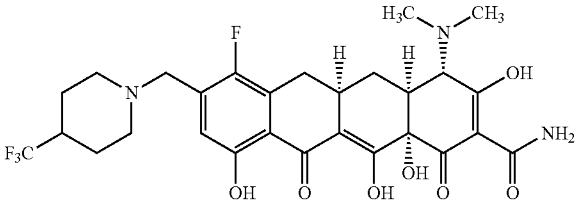

S1-14-21: $^1$H NMR (400 MHz, $CD_3OD$) δ 7.07 (d, J=5.5 Hz, 1 H), 4.41 (s, 2 H), 4.08 (s, 1 H), 3.72-3.64 (m, 2 H), 3.24-2.98 (m, 5 H), 3.04 (s, 3 H), 2.96 (s, 3 H), 2.65-2.55 (m, 1 H), 2.37 (t, J=15.1 Hz, 1 H), 2.24-2.10 (m, 3 H), 1.90-1.77 (m, 2 H), 1.71-1.61 (m, 1 H); MS (ESI) m/z 598.30 (M+H).

S1-14-22

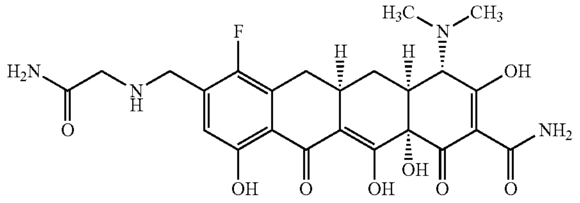

S1-14-22: $^1$H NMR (400 MHz, $CD_3OD$) δ 7.01 (d, J=6.0 Hz, 1 H), 4.32 (s, 2 H), 4.09 (s, 1 H), 3.87 (s, 2 H), 3.24-2.98 (m, 3 H), 3.04 (s, 3 H), 2.96 (s, 3 H), 2.35 (t, J=15.1 Hz, 1 H), 1.98, (s, 1.5 H), 1.70-1.60 (m, 1 H); MS (ESI) m/z 519.23 (M+H).

S1-14-23

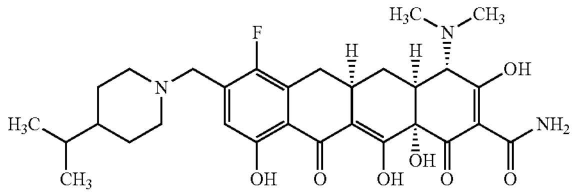

S1-14-23: $^1$H NMR (400 MHz, $CD_3OD$) δ 7.06 (d, J=5.5 Hz, 1 H), 4.34 (s, 2 H), 4.08 (s, 1 H), 3.58-3.50 (m, 2 H), 3.24-2.98 (m, 5 H), 3.03 (s, 3 H), 2.96 (s, 3 H), 2.36 (t, J=15.1 Hz, 1 H), 2.23 (m, 1 H), 2.02-1.92 (m, 2 H), 1.69-1.59 (m, 1 H), 1.54-1.40 (m, 3 H), 1.40-1.32 (m, 1 H), 0.91 (d, J=6.4 Hz, 6 H); MS (ESI) m/z 572.27 (M+H).

S1-14-24

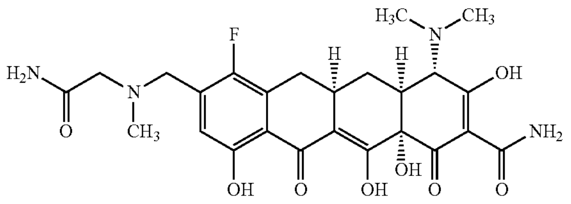

S1-14-24: $^1$H NMR (400 MHz, $CD_3OD$) δ 7.07 (d, J=6.0 Hz, 1 H), 4.51-2.43 (m, 2 H), 4.08 (s, 1 H), 4.04 (s, 2 H), 3.24-2.98 (m, 3 H), 3.03 (s, 3 H), 2.96 (s, 3 H), 2.92 (s, 3 H), 2.35 (t, J=15.1 Hz, 1 H), 2.28-2.18 (m, 1 H), 1.69-1.59 (m, 1 H); MS (ESI) m/z 533.29 (M+H).

S1-14-25

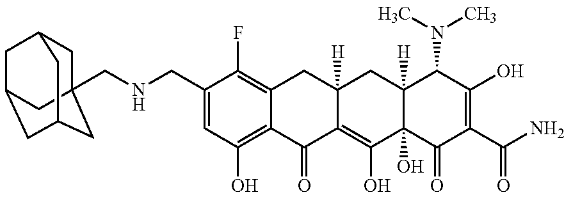

S1-14-25: $^1$H NMR (400 MHz, $CD_3OD$) δ 7.07 (d, J=5.5 Hz, 1 H), 4.31 (s, 2 H), 4.10 (s, 1 H), 3.05 (s, 3 H), 2.97 (s, 3 H), 3.27-2.96 (m, 3 H), 2.77 (s, 2 H), 2.61 (s, 1 H), 2.36 (t, J=15.1 Hz, 1 H), 2.28-2.20 (m, 1 H), 1.84-1.76 (m, 4 H), 1.75-1.66 (m, 5 H), 1.63 (br, s, 5 H), 1.59 (br, s, 2 H); MS (ESI) m/z 610.28 (M+H).

S1-14-26

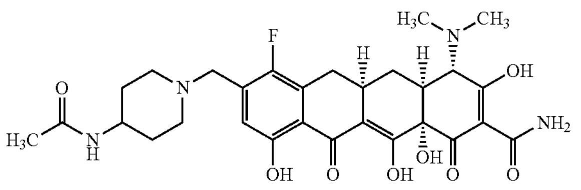

S1-14-26: $^1$H NMR (400 MHz, $CD_3OD$) δ 7.07 (br, s, 1 H), 4.37 (s, 2 H), 4.07 (s, 1 H), 3.92-2.84 (m, 1 H), 3.61-3.54 (m, 2 H), 3.24-2.98 (m, 5 H), 3.03 (s, 3 H), 2.96 (s, 3 H), 2.36 (t, J=15.1 Hz, 1 H), 2.24-2.10 (m, 2 H), 2.18-1.96 (m, 1 H), 1.91 (s, 3 H), 1.80-1.59 (m, 3 H); MS (ESI) m/z 587.24 (M+H).

S1-14-27

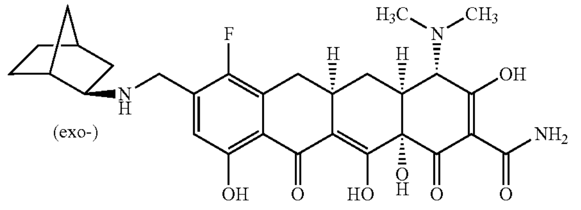

S1-14-27: $^1$H NMR (400 MHz, $CD_3OD$) δ 7.03 (d, J=5.5 Hz, 1 H), 4.24 (s, 2 H), 4.09 (s, 1 H), 3.04 (s, 3 H), 2.96 (s, 3 H), 3.27-2.96 (m, 4 H), 2.57 (d, J=4.2 Hz, 1 H), 2.43 (s, 1 H), 2.34 (t, J=15.1 Hz, 1 H), 2.27-2.19 (m, 1 H), 1.87 (dd, J=13.7, 7.8 Hz, 1 H), 1.73-1.52 (m, 5 H), 1.35 (d, J=11.0 Hz, 1 H), 1.28-1.20 (m, 2 H); MS (ESI) m/z 556.30 (M+H).

S1-14-28

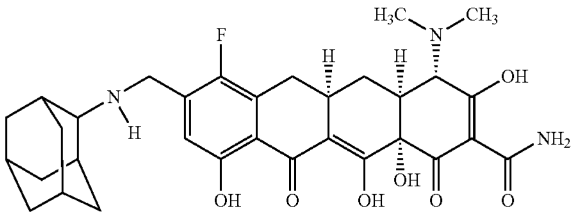

S1-14-28: $^1$H NMR (400 MHz, $CD_3OD$) δ 7.07 (d, J=5.9 Hz, 1 H), 4.31 (s, 2 H), 4.09 (s, 1 H), 3.47 (s, 1 H), 3.04 (s, 3 H), 2.96 (s, 3 H), 3.27-2.96 (m, 3 H), 2.57 (d, J=4.2 Hz, 1 H), 2.43 (s, 1 H), 2.35 (t, J=15.5 Hz, 1 H), 2.26 (s, 2 H), 2.29-2.20 (m, 1 H), 2.04-1.89 (m, 6 H), 1.87-1.73 (m, 6 H), 1.70-1.60 (m, 1 H); MS (ESI) m/z 596.36 (M+H).

S1-14-29

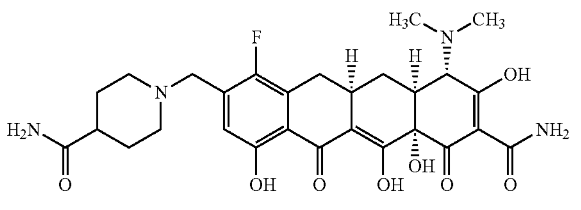

S1-14-29: $^1$H NMR (400 MHz, $CD_3OD$) δ 7.07 (d, J=5.9 Hz, 1 H), 4.39 (s, 2 H), 4.10 (s, 1 H), 3.65-3.56 (m, 2 H), 3.24-2.98 (m, 5 H), 3.04 (s, 3 H), 2.97 (s, 3 H), 2.60-2.52 (m, 1 H), 2.37 (t, J=15.1 Hz, 1 H), 2.28-2.20 (m, 1 H), 2.13-2.02 (m, 2 H), 1.97-1.88 (m, 2 H), 1.70-1.60 (m, 1 H); MS (ESI) m/z 573.28 (M+H).

S1-14-30

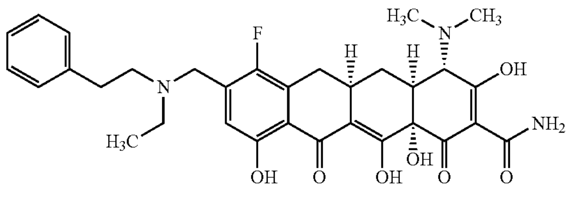

S1-14-30: $^1$H NMR (400 MHz, $CD_3OD$) δ 7.25-7.19 (m, 5 H), 7.02 (d, J=5.6 Hz, 1 H), 4.42 (s, 2 H), 3.98 (s, 1 H), 3.34-3.21 (m, 4 H), 3.15-2.85 (m, 11 H), 2.30-2.18 (m, 2 H), 1.62-1.52 (m, 1 H), 1.33 (t, J=7.2 Hz, 3 H); MS (ESI) m/z 594.1 (M+H).

S1-14-31

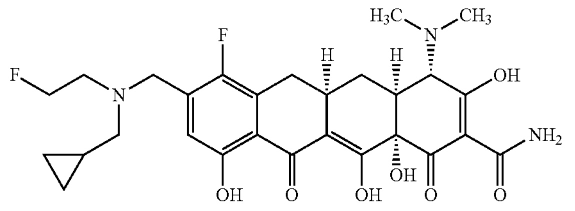

S1-14-31: $^1$H NMR (400 MHz, $CD_3OD$) δ 7.00 (d, J=5.6 Hz, 1 H), 4.88 (t, J=4.4 Hz, 1 H), 4.55 (t, J=4.4 Hz, 1 H), 4.01 (s, 1 H), 3.70-3.50 (m, 2 H), 3.17 (d, J=7.2 Hz, 2 H), 3.10-2.87 (m, 11 H), 2.31-2.12 (m, 2 H), 1.57-1.54 (m, 1 H), 1.13-1.08 (m, 1 H), 0.74-0.72 (m, 2 H), 0.41-0.37 (m, 2 H); MS (ESI) m/z 562.1 (M+H).

S1-14-32

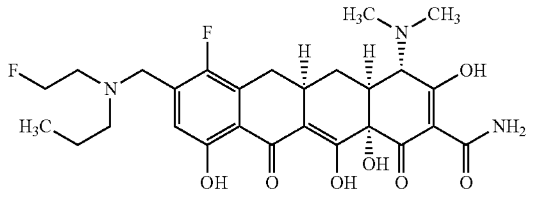

S1-14-32: $^1$H NMR (400 MHz, $CD_3OD$) δ 7.00 (d, J=5.6 Hz, 1 H), 4.87 (t, J=4.0 Hz, 1 H), 4.74 (t, J=4.0 Hz 1 H), 4.43 (s, 2 H), 4.02 (s, 1 H), 3.60-3.51 (m, 2 H), 3.20-2.88 (m, 11 H), 2.31-2.15 (m, 2 H), 1.78-1.7 (m, 2 H), 1.58-1.55 (m, 1 H), 0.93 (t, J=7.2 Hz, 3 H); MS (ESI) m/z 550.1 (M+H).

S1-14-33

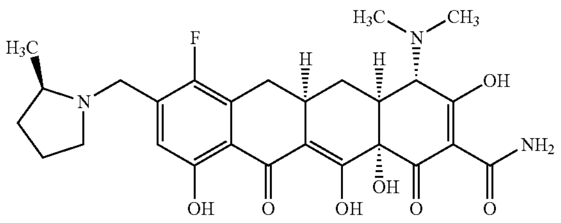

S1-14-33: $^{1}$H NMR (400 MHz, $CD_3OD$) δ 7.01 (d, J=5.6 Hz, 1 H), 4.56 (d, J=13.2 Hz, 1 H), 4.13 (d, J=13.2 Hz, 1 H), 4.01 (s, 1 H), 3.56-3.36 (m, 2 H), 3.16-2.86 (m, 10 H), 2.33-2.16 (m, 3 H), 2.07-1.91 (m, 2 H), 1.73-1.67 (m, 1 H), 1.61-1.52 (m, 1 H), 1.42 (d, J=6.4 Hz, 3 H); MS (ESI) m/z 575.2 (M+H).

S1-14-34

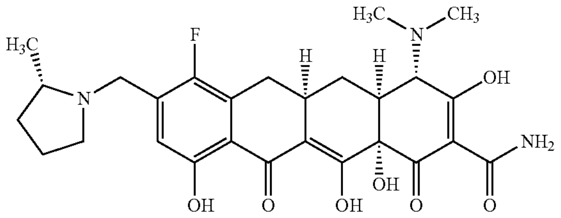

S1-14-34: $^{1}$H NMR (400 MHz, $CD_3OD$) δ 7.01 (d, J=5.6 Hz, 1 H), 4.56 (d, J=13.2 Hz, 1 H), 4.13 (d, J=13.2 Hz, 1 H), 4.01 (s, 1 H), 3.56-3.36 (m, 2 H), 3.16-2.86 (m, 10 H), 2.33-2.16 (m, 3 H), 2.07-1.91 (m, 2 H), 1.73-1.67 (m, 1 H), 1.61-1.52 (m, 1 H), 1.42 (d, J=6.4 Hz, 3 H); MS (ESI) m/z 575.2 (M+H).

S1-14-35

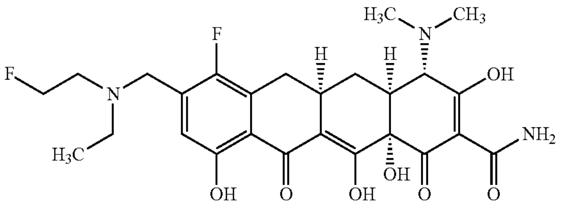

S1-14-35: $^{1}$H NMR (400 MHz, $CD_3OD$) δ 7.09 (d, J=6.0 Hz, 1 H), 4.96 (t, J=6.0 Hz, 1 H), 4.78 (t, J=6.0 Hz, 1 H), 4.51 (s, 2 H), 4.11 (s, 1 H), 3.72-3.59 (m, 2 H), 3.40 (q, J=6.8 Hz, 2 H), 3.24-2.97 (m, 9 H), 2.39-2.24 (m, 2 H), 1.69-1.60 (m, 1 H), 1.41 (t, J=7.2 Hz, 3 H); MS (ESI) m/z 536.1 (M+H).

S1-14-36

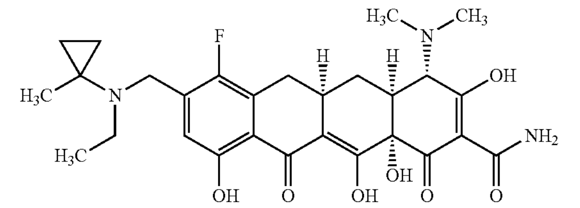

S1-14-36: $^{1}$H NMR (400 MHz, $CD_3OD$) δ 7.10 (d, J=6.0 Hz, 1 H), 4.62-4.47 (m, 2 H), 4.12 (s, 1 H), 3.50-3.44 (m, 2 H), 3.23-2.98 (m, 9 H), 2.38-2.25 (m, 2 H), 1.69-1.66 (m, 1 H), 1.55 (s, 3 H), 1.42-1.39 (t, J=7.2 Hz, 3 H), 1.39-1.35 (m, 3 H), 094-0.86 (m, 3 H); MS (ESI) m/z 544.2 (M+H).

S1-14-37

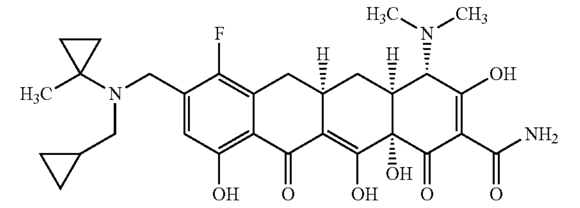

S1-14-37: $^{1}$H NMR (400 MHz, $CD_3OD$) δ 7.09 (d, J=6.0 Hz, 1 H), 4.59 (s, 2 H), 4.10 (s, 1 H), 3.24-2.97 (m, 11 H), 2.40-2.24 (m, 2 H), 1.70-1.59 (m, 1 H), 1.56 (s, 3 H), 1.21-1.15 (m, 1 H), 0.93-0.89 (m, 2 H), 0.79-0.77 (m, 2 H), 0.69-0.66 (m, 1 H), 0.59-0.56 (m, 1 H), 0.47-0.46 (m, 2 H); MS (ESI) m/z 570.1 (M+H).

S1-14-38

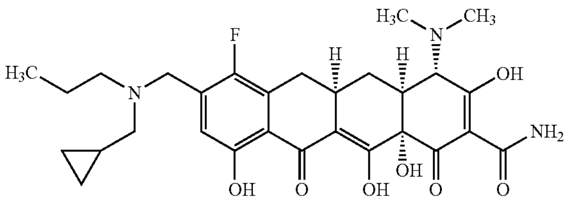

S1-14-38: $^{1}$H NMR (400 MHz, $CD_3OD$) δ 7.09 (d, J=6.0 Hz, 1 H), 4.63-4.60 (m, 1 H), 4.50-4.47 (m, 1 H), 4.11 (s, 1 H), 3.13-2.98 (m, 11 H), 2.39-2.24 (m, 2 H), 1.94-1.92 (m, 1 H), 1.75-1.70 (m, 1 H); 1.66-1.63 (m, 1 H), 1.58 (s, 3 H), 1.38-1.29 (m, 1 H), 1.02 (t, J=7.2 Hz, 3 H), 0.92-0.87 (m, 3 H); MS (ESI) m/z 558.1 (M+H).

S1-14-39

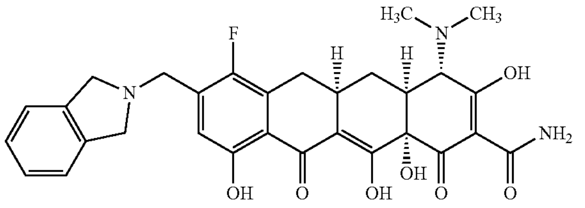

S1-14-39: $^1$H NMR (400 MHz, $CD_3OD$) δ 7.34 (s, 4 H), 7.04 (d, J=5.2 Hz, 1 H), 4.71-4.63 (m, 4 H), 4.63 (s, 2 H) 3.99 (s, 1 H), 3.17-2.87 (m, 9 H), 2.28-2.15 (m, 2 H) 1.61-1.51 (m, 1 H); MS (ESI) m/z 564.2 (M+H).

S1-14-40

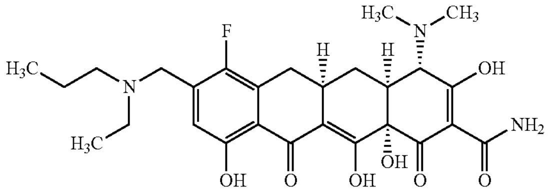

S1-14-40: $^1$H NMR (400 MHz, $CD_3OD$) δ 7.08 (d, J=5.6 Hz, 1 H), 4.42 (d, J=4.0 Hz, 2 H), 4.12 (s, 1 H), 3.29-2.90 (m, 13 H), 2.41-2.22 (m, 2 H), 1.90-1.75 (m, 2 H), 1.71-1.60 (M, 1 H); 1.38 (t, J=7.2 Hz, 3 H), 1.05 (t, J=7.2 Hz, 3 H), MS (ESI) m/z 530.2 (M+H).

S1-14-41

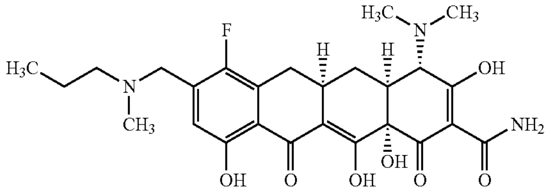

S1-14-41: $^1$H NMR (400 MHz, $CD_3OD$) δ 7.05 (d, J=5.2 Hz, 1 H), 4.48 (d, J=13.2 Hz, 1 H), 4.27 (d, J=13.2 Hz, 1 H), 4.09 (d, J=4.4 Hz, 1 H), 3.22-2.92 (m, 11 H), 2.84 (s, 3 H), 2.38-2.22 (m, 2 H), 1.87-1.70 (m, 2 H), 1.68-1.62 (m, 1 H), 1.03 (t, J=7.2 Hz, 3 H); MS (ESI) m/z 518.0 (M+H).

S1-14-42

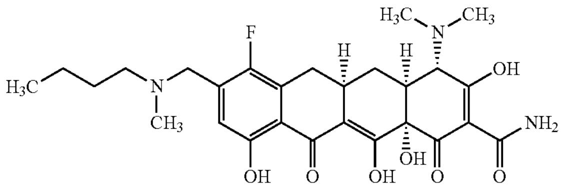

S1-14-42: $^1$H NMR (400 MHz, $CD_3OD$) δ 7.05 (d, J=5.6 Hz, 1 H), 4.51 (d, J=13.6 Hz, 1 H), 4.28 (d, J=13.6 Hz, 1 H), 4.09 (s, 1 H), 3.20-2.95 (m, 11 H), 2.83 (s, 3 H), 2.40-2.13 (m, 2 H), 1.79-1.71 (m, 2 H), 1.69-1.57 (m, 1 H), 1.46-1.35 (m, 2 H), 0.98 (t, J=7.2 Hz, 3 H); MS (ESI) m/z 532.1 (M+H).

S1-14-43

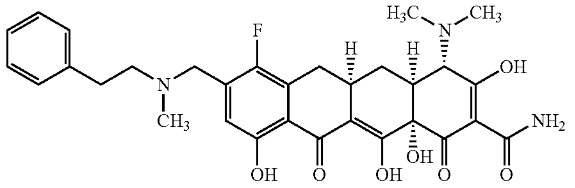

S1-14-43: $^1$H NMR (400 MHz, $CD_3OD$) δ 7.27-7.16 (m, 5 H), 7.01 (d, J=5.6 Hz, 1 H), 4.52-4.48 (m, 1 H), 4.29-4.25 (m, 1 H), 4.03 (s, 1 H), 3.45-3.25 (m, 2 H), 3.15-2.88 (m, 11 H), 2.84 (s, 3 H), 2.30-2.16 (m, 2 H), 1.60-1.54 (m, 1 H), MS (ESI) m/z 580.1 (M+H).

S1-14-44

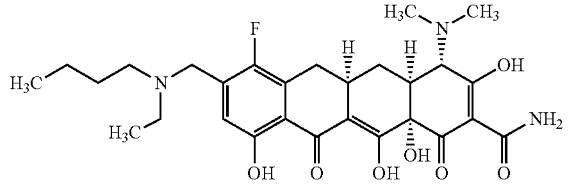

S1-14-44: $^1$H NMR (400 MHz, $CD_3OD$) δ 7.07 (d, J=4.8 Hz, 1 H), 4.40 (s, 2 H), 4.11 (s, 1 H), 3.29-2.95 (m, 13 H), 2.37-2.23 (m, 2 H), 1.79-1.71 (m, 2 H), 1.67-1.58 (m, 1 H), 1.45-1.38 (m, 2 H), 1.37 (t, J=7.2 Hz, 3 H), 0.95 (t, J=7.2 Hz, 3 H); MS (ESI) m/z 546.2 (M+H).

S1-14-45

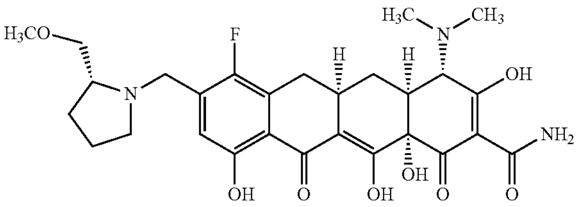

S1-14-45: $^1$H NMR (400 MHz, $CD_3OD$) δ 7.03 (d, J=5.6 Hz, 1 H), 4.70 (d, J=13.2 Hz, 1 H), 4.29 (d, J=13.2 Hz, 1 H), 4.09 (s, 1 H), 3.86-3.83 (m, 1 H), 3.73-3.60 (m, 2 H), 3.49-3.41 (m, 1 H), 3.40 (s, 3 H), 3.22-2.95 (m, 10 H), 2.37-2.26 (m, 3 H), 2.22-1.84 (m, 3 H), 1.68-1.57 (m, 1 H), MS (ESI) m/z 560.1 (M+H).

S1-14-46

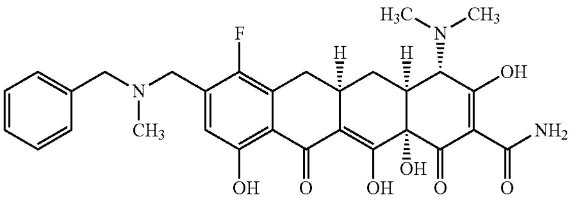

S1-14-46: $^1$H NMR (400 MHz, $CD_3OD$) δ 7.47-7.41 (m, 5 H), 6.95 (d, J=6.0 Hz, 1 H), 4.41-4.36 (m, 2 H), 4.34-4.18 (m, 2 H), 4.02 (s, 1 H), 3.12-2.88 (m, 9 H), 2.72 (s, 3 H), 2.28-2.12 (m, 2 H), 1.60-1.50 (m, 1 H); MS (ESI) m/z 565.2 (M+H).

S1-14-47

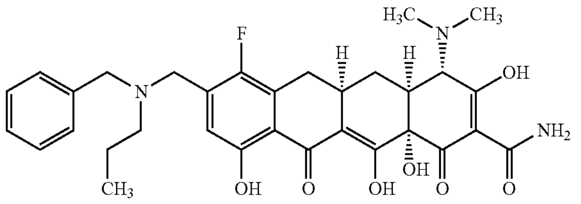

S1-14-47: $^1$H NMR (400 MHz, $CD_3OD$) δ 7.58-7.49 (m, 5 H), 6.99 (d, J=5.6 Hz, 1 H), 4.49-4.42 (m, 4 H), 4.13 (s, 1 H), 3.18-2.97 (m, 11 H), 2.35-2.23 (m, 2 H), 1.91-1.88 (m, 2 H), 1.68-1.47 (m, 1 H), 0.97 (t, J=7.2 Hz, 3 H); MS (ESI) m/z 594.2 (M+H).

S1-14-48

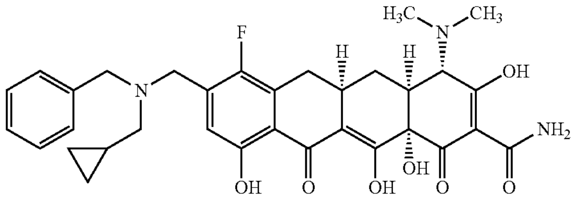

S1-14-48: $^1$H NMR (400 MHz, $CD_3OD$) δ 7.53-7.49 (m, 5 H), 6.96 (d, J=5.2 Hz, 1 H), 4.62-4.35 (m, 4 H), 4.09 (s, 1 H), 3.20-2.96 (m, 11 H), 2.35-2.21 (m, 2 H), 1.67-1.48 (m, 1 H), 1.26-1.13 (m, 1 H), 0.86-0.74 (m, 2 H), 0.44-0.33 (m, 2 H); MS (ESI) m/z 606.1 (M+H).

S1-14-49

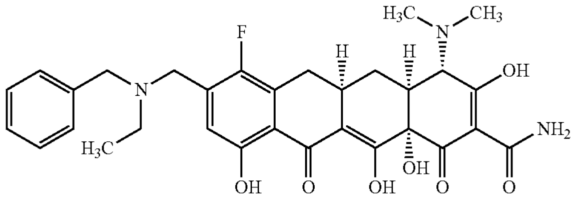

S1-14-49: $^1$H NMR (400 MHz, $CD_3OD$) δ 7.53-7.48 (m, 5 H), 6.96 (d, J=5.6 Hz, 1 H), 4.48-4.34 (m, 4 H), 4.09 (s, 1 H), 3.26-2.87 (m, 11 H), 2.35-2.20 (m, 2 H), 1.62-1.56 (m, 1 H), 1.44 (t, J=7.2 Hz, 3 H); MS (ESI) m/z 580.1 (M+H).

S1-14-50

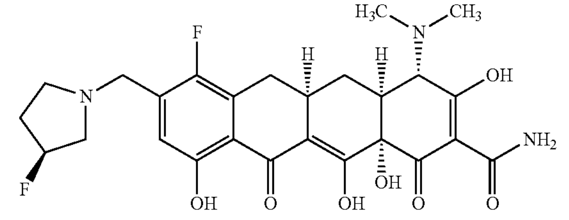

S1-14-50: $^1$H NMR (400 MHz, $CD_3OD$) δ 7.11 (d, J=5.6 Hz, 1 H), 5.47 (d, J=52 Hz, 1 H), 4.55 (s, 2 H), 4.12 (s, 1 H), 3.95-3.47 (m, 4 H), 3.24-2.98 (m, 9 H), 2.70-2.62 (m, 1 H), 2.39-2.25 (m, 3 H), 1.69-1.61 (m, 1 H); MS (ESI) m/z 534.1 (M+H).

S1-14-51

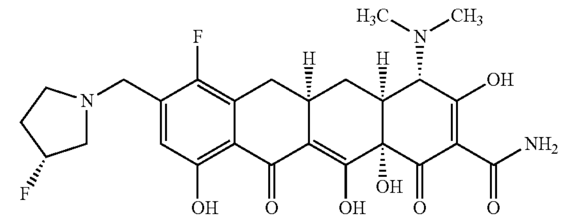

S1-14-51: $^1$H NMR (400 MHz, $CD_3OD$) δ 7.10 (d, J=6 Hz, 1 H), 5.47 (d, J=52.4 Hz, 1 H), 4.54 (s, 2 H), 4.11 (s, 1 H), 3.92-3.39 (m, 4 H), 3.26-2.98 (m, 9 H), 2.70-2.62 (m, 1 H), 2.40-2.23 (m, 3 H), 1.71-1.62 (m, 1 H); MS (ESI) m/z 534.1 (M+H).

S1-14-52

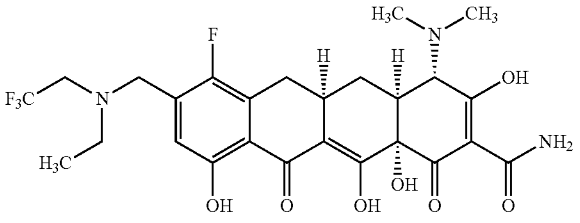

S1-14-52: $^1$H NMR (400 MHz, $CD_3OD$) δ 6.98 (d, J=5.6 Hz, 1 H), 4.07 (s, 1 H), 3.93 (s, 2 H), 3.31 (q, J=9.2 Hz, 2 H), 3.19-2.89 (m, 9 H), 2.77 (q, J=7.2 Hz, 2 H), 2.34-2.15 (m, 2 H), 1.68-1.57 (m, 1 H), 1.11 (t, J=7.2 Hz, 3 H); MS (ESI) m/z 572.1 (M+H).

S1-14-53

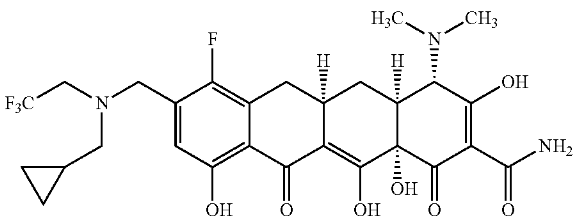

S1-14-53: $^1$H NMR (400 MHz, $CD_3OD$) δ 7.04 (d, J=6.0 Hz, 1 H), 4.20 (s, 2 H), 4.09 (s, 1 H), 3.76-3.65 (m, 2 H), 3.74 (q, J=7.2 Hz, 2 H), 3.20-2.96 (m, 9 H), 2.81 (d, J=6.8 Hz, 2 H), 2.34-2.21 (m, 2 H), 1.68-1.56 (m, 1 H), 1.07-0.98 (m, 1 H), 0.65-0.58 (m, 2 H), 0.27-0.23 (m, 2 H); MS (ESI) m/z 598.1 (M+H).

S1-14-54

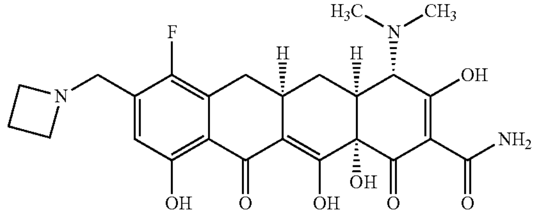

S1-14-54: $^1$H NMR (400 MHz, $CD_3OD$) δ 6.97 (d, J=6.0 Hz, 1 H), 4.45 (s, 2 H), 4.25-4.17 (m, 4 H), 4.09 (s, 1 H), 3.21-2.95 (m, 9 H), 2.61-2.51 (m, 1 H), 2.49-2.38 (s, 1 H), 2.32-2.18 (m, 2 H), 1.65-1.53 (m, 1 H); MS (ESI) m/z 502.1 (M+H).

S1-14-55

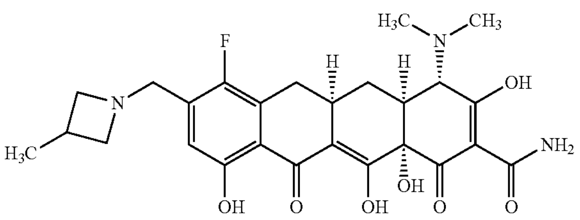

S1-14-55: $^1$H NMR (400 MHz, $CD_3OD$) δ 6.98 (d, J=6.0 Hz, 1 H), 4.50-4.42 (m□2H), 4.29-4.21 (m, 2 H), 4.09 (s, 1 H), 3.92-3.85 (m□2H), 3.22-2.97 (m, 9 H), 2.28-2.33 (m, 2 H), 1.66 (ddd, J=11.6, 11.2, 11.6 Hz, 1 H), 1.33 (d, J=6.8 Hz, 1 H), 1.28 (d, J=6.8 Hz, 2 H); MS (ESI) m/z 516.1 (M+H).

S1-14-56

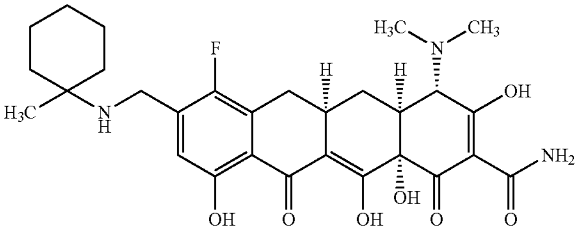

S1-14-56: $^1$H NMR (400 MHz, $CD_3OD$) δ 7.05 (d, J=5.2 Hz, 1 H), 4.24 (s, 2 H), 4.10 (s, 1 H), 3.24-2.97 (m, 9 H), 2.28-2.23 (m, 2 H), 1.98-1.56 (m, 10 H), 1.55 (s, 3 H); MS (ESI) m/z 558.1 (M+H).

S1-14-57

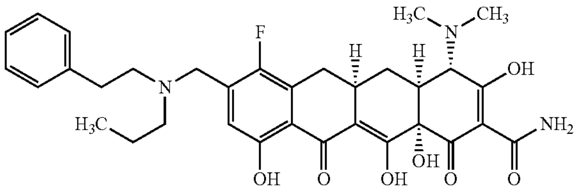

S1-14-57: $^1$H NMR (400 MHz, $CD_3OD$) δ 7.36-7.32 (m, 2 H), 7.29-7.27 (m, 3 H), 7.12 (d, J=5.6 Hz, 1 H), 4.53 (s, 2 H), 4.11 (s, 1 H), 3.40 (t, 2 H), 3.28-2.94 (m, 13 H), 2.43-2.22 (m, 2 H), 1.92-1.61 (m, 3 H), 1.02 (t, J=7.2 Hz, 3 H); MS (ESI) m/z 607.3 (M+H).

S1-14-58

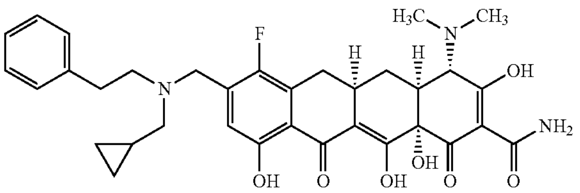

S1-14-58: $^1$H NMR (400 MHz, $CD_3OD$) δ 7.26-7.19 (m, 5 H), 7.05 (d, J=5.6 Hz, 1 H), 4.61-4.42 (m, 2 H), 4.03 (s, 1 H), 3.47-3.33 (m, 2 H), 3.17 (d, J=7.2 Hz, 1 H), 3.11-2.88 (m, 11 H), 2.32-2.14 (m, 2 H), 1.61-1.51 (m, 1 H), 1.21-1.11 (m, 1 H), 0.74-0.72 (m, 2 H), 0.41-0.38 (m, 2 H); MS (ESI) m/z 620.3 (M+H).

S1-14-59

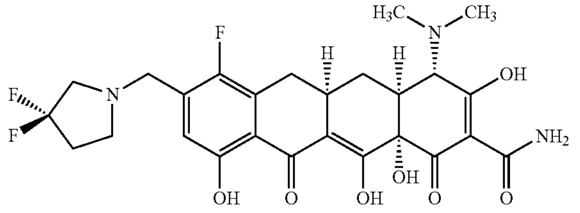

S1-14-59: $^1$H NMR (400 MHz, $CD_3OD$) δ 7.00 (d, J=5.6 Hz, 1 H), 4.48 (s, 2 H), 4.01 (s, 1 H), 3.87 (t, J=11.6 Hz, 2 H), 3.87 (t, J=7.6 Hz, 2 H), 3.18-2.88 (m, 9 H), 2.18-2.07 (m, 2 H), 2.33-2.11 (m, 2 H), 1.56-1.51 (m, 1 H); MS (ESI) m/z 552.2 (M+H).

S1-14-60

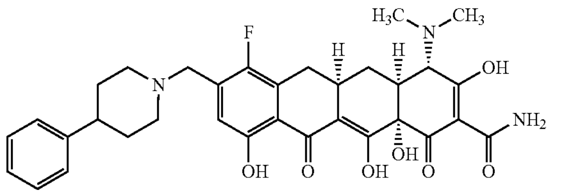

S1-14-60: $^1$H NMR (400 MHz, $CD_3OD$) δ 7.24-7.11 (m, 5 H), 7.07 (d, J=4.8 Hz, 1 H), 4.35 (s, 2 H), 4.04 (s, 1 H), 3.60-3.57 (m, 3 H), 3.16-2.80 (m, 11 H), 2.31-2.17 (m, 2 H), 2.06-1.96 (s, 4 H), 1.63-1.52 (m, 1 H); MS (ESI) m/z 606.2 (M+H).

S1-14-61

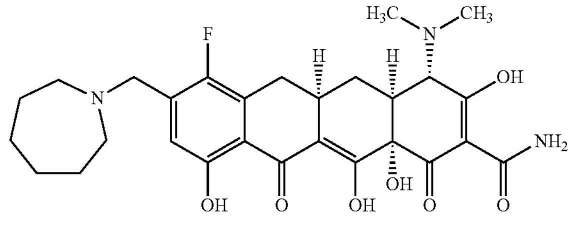

S1-14-61: $^{1}$H NMR (400 MHz, $CD_3OD$) δ 7.04 (d, J=5.6 Hz, 1 H), 4.35 (s, 2 H), 4.03 (s, 1 H), 3.45-3.40 (m, 2 H), 3.23-2.90 (m, 11 H), 2.32-2.16 (m, 2 H), 2.07-1.81 (m, 4 H), 1.79-1.65 (m, 4 H), 1.63-1.53 (m, 1 H); MS (ESI) m/z 544.2 (M+H).

S1-14-62

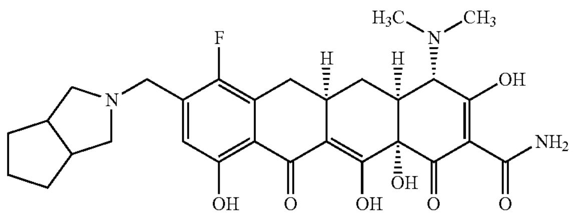

S1-14-62: $^{1}$H NMR (400 MHz, $CD_3OD$) δ 7.00 (d, J=6.0 Hz, 1 H), 4.37 (s, 2 H), 4.03 (s, 1 H), 3.72-3.65 (m, 2 H), 3.19-2.84 (m, 11 H), 2.82-2.65 (m, 2 H), 2.32-2.16 (m, 2 H), 1.70-1.41 (m, 7 H); MS (ESI) m/z 556.2 (M+H).

S1-14-63

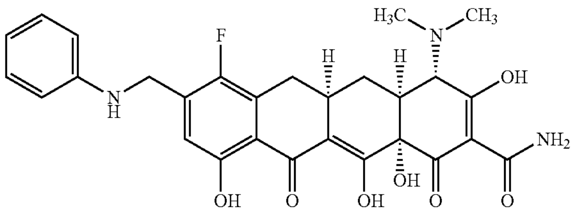

S1-14-63: $^{1}$H NMR (400 MHz, $CD_3OD$) δ 7.59-7.34 (m, 5 H), 6.94 (d, J=5.6 Hz, 1 H), 4.63 (s, 2 H), 4.10 (s, 1 H), 3.19-2.97 (m, 9 H), 2.34-2.23 (m, 2 H), 1.68 (ddd, J=13.2, 13.2, 13.2 Hz, 1 H); MS (ESI) m/z 538.2 (M+H).

S1-14-64

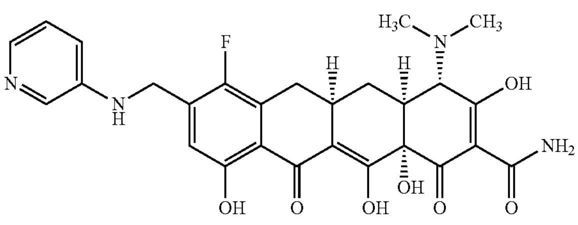

S1-14-64: $^{1}$H NMR (400 MHz, $CD_3OD$) δ 7.97 (s, 1 H), 7.91 (t, J=2.8 Hz, 1 H), 7.66-7.65 (m, 2 H), 6.74 (d, J=5.6 Hz, 1 H), 4.46 (s, 2 H), 4.00 (s, 1 H), 3.25-2.88 (m, 9 H), 2.27-2.12 (m, 2 H), 1.56 (ddd, J=13.6, 13.6, 13.6 Hz, 1 H); MS (ESI) m/z 539.2 (M+H).

S1-14-65

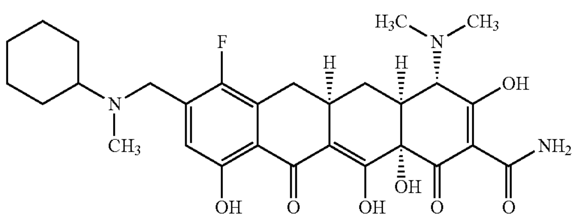

S1-14-65: $^{1}$H NMR (400 MHz, $CD_3OD$) δ 7.10 (d, J=5.6 Hz, 1 H), 4.62 (d, J=13.2 Hz, 1 H), 4.19 (d, J=13.2 Hz, 1 H), 4.17 (s, 1 H), 3.41-2.35 (m, 1 H), 3.25-2.99 (m, 9 H), 2.71 (s, 3 H), 2.41-2.27 (m, 2 H), 2.24-2.17 (m, 2 H); 2.05-1.92 (m, 2 H), 1.78-1.558 (m, 4 H), 1.50-1.37 (M, 2 H), 1.35-1.20 (m, 1 H); MS (ESI) m/z 558.2 (M+H).

S1-14-66

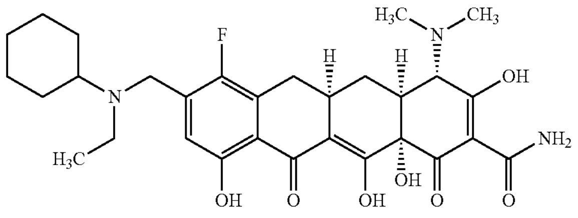

S1-14-66: $^{1}$H NMR (400 MHz, $CD_3OD$) δ 7.07 (d, J=6.0 Hz, 1 H), 4.57 (d, J=13.6 Hz, 1 H), 4.21 (d, J=13.6 Hz, 1 H), 4.10 (s, 1 H), 3.44-3.35 (m, 1 H), 3.30-2.95 (m, 11 H), 2.38-2.20 (m, 2 H), 2.15-2.05 (m, 2 H), 2.00-1.90 (m, 2 H), 1.75-1.55 (m, 4 H), 1.50-1.35 (m, 2 H), 1.35-1.20 (m, 1 H), 1.32 (t, J=7.2 Hz, 3 H); MS (ESI) m/z 572.2 (M+H).

S1-14-67

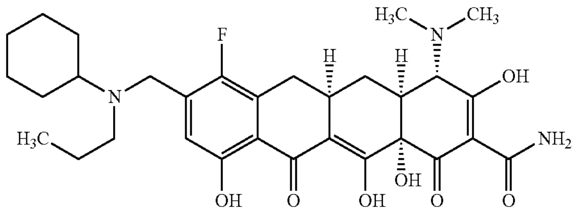

S1-14-67: $^{1}$H NMR (400 MHz, $CD_3OD$) δ 7.07 (d, J=5.6 Hz, 1 H), 4.56 (d, J=13.6 Hz, 1 H), 4.25 (d, J=13.6 Hz, 1 H), 4.11 (s, 1 H), 3.40-3.32 (m, 1 H), 3.25-2.95 (m, 11 H), 2.40-2.21 (m, 2 H), 2.17-2.06 (m, 2 H), 1.99-1.90 (m, 2 H), 1.85-1.56 (m, 6 H), 1.47-1.20 (m, 3 H), 0.96 (t, J=7.2 Hz, 3 H); MS (ESI) m/z 586.2 (M+H).

S1-14-68

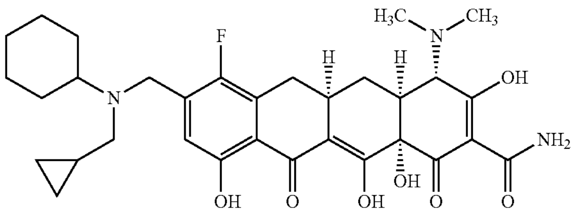

S1-14-68: $^1$H NMR (400 MHz, $CD_3OD$) δ 7.08 (d, J=5.9 Hz, 1 H), 4.56 (d, J=12.0 Hz, 1 H), 4.32 (d, J=12.0 Hz, 1 H), 4.11 (s, 1 H), 3.56-3.48 (m, 1 H), 3.21-2.93 (m, 11 H), 2.39-2.21 (m, 2 H), 2.18-2.04 (m, 2 H), 2.0-1.9 (m, 2 H), 1.81-1.56 (m, 4 H), 1.46-1.20 (m, 3 H), 1.15-1.03 (s, 1 H), 0.78-0.69 (m, 2 H), 0.45-0.35 (m, 2 H); MS (ESI) m/z 598.2 (M+H).

S1-14-69

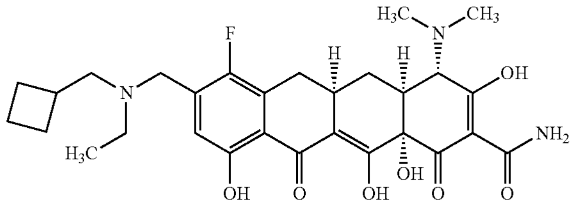

S1-14-69: $^1$H NMR (400 MHz, $CD_3OD$) δ 7.07 (d, J=5.6 Hz, 1 H), 4.30 (s, 2 H), 4.11 (s, 1 H), 3.28-2.95 (m, 13 H), 2.90-2.79 (m, 1 H), 2.40-2.15 (m, 4 H), 2.07-1.81 (m, 4 H), 1.57-1.29 (m, 1 H), 1.39-1.33 (t, J=7.2 Hz, 3 H); MS (ESI) m/z 557.2 (M+H).

S1-14-70

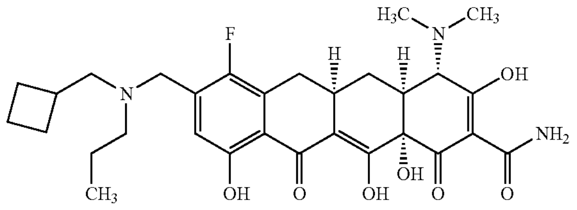

S1-14-70: $^1$H NMR (400 MHz, $CD_3OD$) δ 7.05 (d, J=5.6 Hz, 1 H), 4.36 (s, 2 H), 4.10 (s, 1 H), 3.28-2.96 (m, 13 H), 2.90-2.80 (m, 1 H), 2.40-2.14 (m, 4 H), 2.06-1.72 (m, 6 H), 1.67-1.55 (m, 1 H), 1.02-0.96 (t, J=7.2 Hz, 3 H); MS (ESI) m/z 572.2 (M+H).

S1-14-71

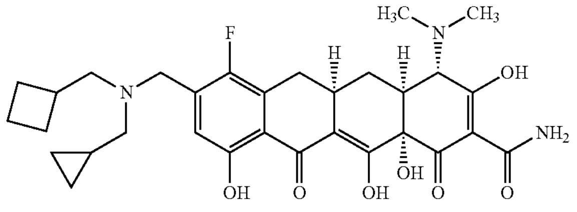

S1-14-71: $^1$H NMR (400 MHz, $CD_3OD$) δ 7.08 (d, J=5.6 Hz, 1 H), 4.55-4.36 (m, 2 H), 4.12 (s, 1 H), 3.43-2.80 (m, 13 H), 2.39-2.12 (m, 4 H), 2.08-1.80 (m, 5 H), 1.70-1.56 (m, 1 H), 1.21-1.12 (m, 1 H), 0.82-0.72 (m, 2 H), 0.49-0.39 (m, 2 H); MS (ESI) m/z 584.2 (M+H).

S1-14-72

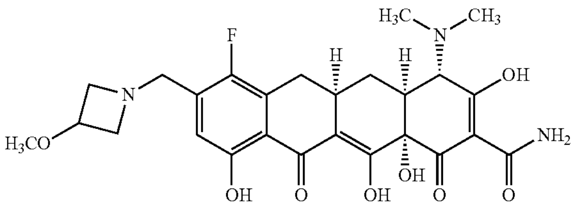

S1-14-72: $^1$H NMR (400 MHz, $CD_3OD$) δ 6.98 (dd, J=2.0, 6.0 Hz, 1 H), 4.55-4.45 (m, 3 H), 4.45-3.38 (m, 2 H), 4.18-4.02 (m, 3 H), 3.33 (s, 3 H), 3.22-2.95 (m, 9 H), 2.37-2.22 (m, 2 H), 1.68-1.58 (m, 1 H); MS (ESI) m/z 532.1 (M+H).

S1-14-73

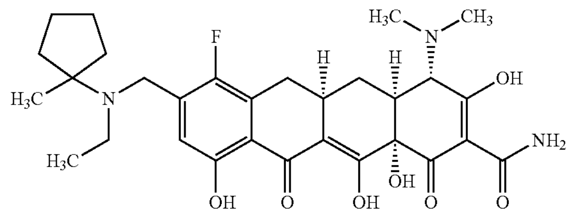

S1-14-73: $^1$H NMR (400 MHz, $CD_3OD$) δ 7.14 (d, J=5.6 Hz, 1 H), 4.60-4.51 (m, 1 H), 4.52-4.45 (m, 1 H), 4.11 (s, 1 H), 3.25-2.92 (m, 11 H), 2.41-2.20 (m, 2 H), 2.08-1.75 (m, 8 H), 1.68-1.59 (m, 1 H), 1.50 (s, 3 H), 1.14 (t, J=7.2 Hz, 3 H); MS (ESI) m/z 572.2 (M+H).

S1-14-74

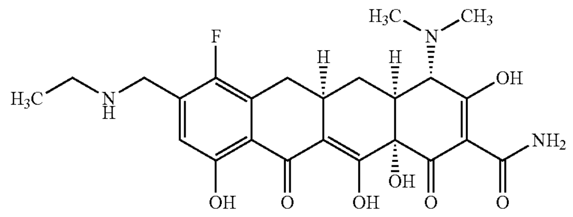

S1-14-74: $^1$H NMR (400 MHz, $CD_3OD$) δ 7.02 (d, J=5.6 Hz, 1 H), 4.25 (s, 2 H), 4.11 (s, 1 H), 3.22-2.98 (m, 11 H), 2.36-2.23 (m, 2 H), 1.68-1.58 (m, 1 H), 1.33 (t, J=7.2 Hz, 3 H); MS (ESI) m/z 490.4 (M+H).

S1-14-75

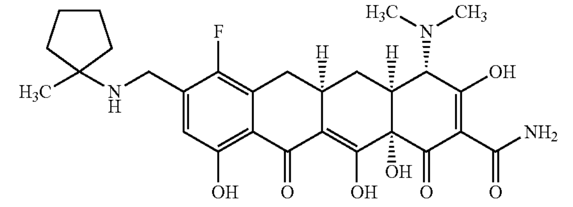

S1-14-75: $^1$H NMR (400 MHz, $CD_3OD$) δ 7.08 (d, J=5.6 Hz, 1 H), 4.23 (s, 2 H), 4.11 (s, 1 H), 3.25-2.91 (m, 9 H), 2.39-2.20 (m, 2 H), 2.00-1.75 (m, 8 H), 1.68-1.59 (m, 1 H), 1.49 (s, 3 H); MS (ESI) m/z 544.3 (M+H).

S1-14-76

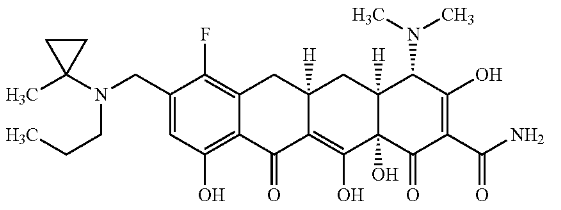

S1-14-76: $^1$H NMR (400 MHz, $CD_3OD$) δ 7.10 (d, J=6.0 Hz, 1 H), 4.64-4.47 (m, 2 H), 4.11 (s, 1 H), 3.25-2.98 (m, 11 H), 2.39-2.24 (m, 2 H), 1.98-1.90 (m, 1 H), 1.80-1.70 (m, 1 H), 1.68-1.60 (m, 1 H), 1.55 (s, 3 H), 1.38-1.29 (m, 1 H), 1.02 (t, J=7.2 Hz, 3 H), 0.98-0.82 (m, 3 H); MS (ESI) m/z 558.1 (M+H).

S1-14-77

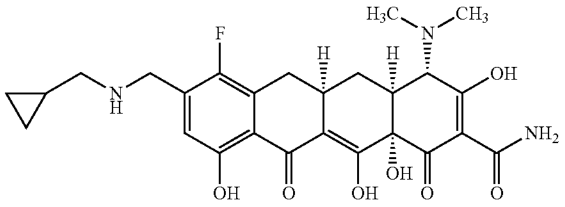

S1-14-77: $^1$H NMR (400 MHz, $CD_3OD$) δ 7.06 (d, J=5.6 Hz, 1 H), 4.30 (s, 2 H), 4.12 (s, 1 H), 3.24-2.98 (m, 11 H), 2.37-2.25 (m, 2 H), 1.69-1.60 (m, 1 H), 1.19-1.14 (m, 1 H), 0.79-0.73 (m, 2 H), 0.48-0.42 (m, 2 H); MS (ESI) m/z 516.0 (M+H).

S1-14-78

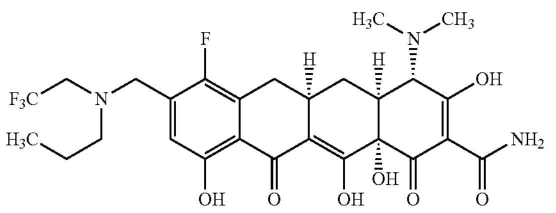

S1-14-78: $^1$H NMR (400 MHz, $CD_3OD$) δ 6.97 (d, J=5.6 Hz, 1 H), 4.07 (s, 1 H), 3.96 (s, 2 H), 3.38 (t, J=9.6 Hz, 2 H), 3.20-2.94 (m, 9 H), 2.68 (t, J=7.6 Hz, 2 H), 2.35-2.25 (m, 2 H), 1.58-1.50 (m, 3 H), 0.88 (t, J=7.2 Hz, 3 H); MS (ESI) m/z 586.1 (M+H).

S1-14-79

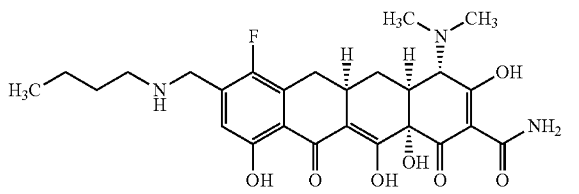

S1-14-79: $^1$H NMR (400 MHz, $CD_3OD$) δ 6.94 (d, J=6.0 Hz, 1 H), 4.18 (s, 2 H), 4.02 (s, 1 H), 3.15-2.82 (m, 11 H), 2.28-2.15 (m, 2 H), 1.66-1.51 (m, 3 H), 1.40-1.30 (m, 2 H), 0.90 (t, J=7.2 Hz, 3 H); MS (ESI) m/z 518.1 (M+H).

S1-14-80

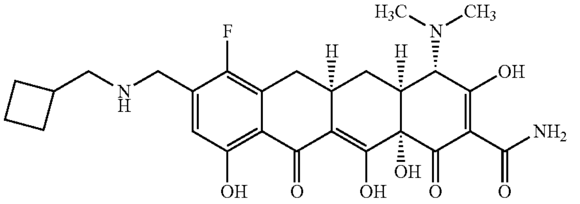

S1-14-80: $^1$H NMR (400 MHz, $CD_3OD$) δ 6.91 (d, J=5.6 Hz, 1 H), 4.12 (s, 2 H), 4.00 (s, 1 H), 3.10-2.84 (m, 11 H), 2.62-2.54 (m, 1 H), 2.24-2.05 (m, 4 H), 1.89-1.71 (m, 4 H), 1.56-1.47 (m, 1 H); MS (ESI) m/z 530.1 (M+H).

S1-14-81

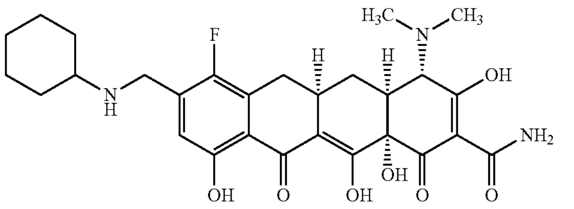

S1-14-81: $^1$H NMR (400 MHz, $CD_3OD$) δ 6.92 (d, J=5.2 Hz, 1 H), 4.16 (s, 2 H), 4.00 (s, 1 H), 3.10-2.84 (m, 10 H), 2.23-2.06 (m, 4 H), 1.79-1.76 (m, 2 H), 1.61-1.50 (m, 2 H), 1.32-1.10 (m, 5 H); MS (ESI) m/z 530.1 (M+H).

S1-14-82

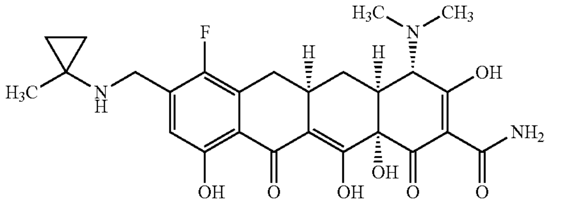

S1-14-82: $^1$H NMR (400 MHz, $CD_3OD$) δ 7.01 (d, J=6.0 Hz, 1 H), 4.36 (s, 2 H), 4.10 (s, 1 H), 3.22-2.95 (m, 9 H), 2.32-2.23 (m, 2 H), 1.67-1.59 (m, 1 H), 1.56 (s, 3 H), 1.12-1.09 (m, 2 H), 0.86-0.83 (m, 2 H); MS (ESI) m/z 516.0 (M+H).

S1-14-83

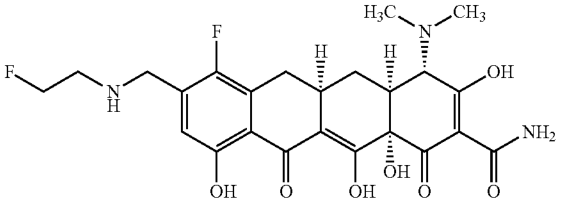

S1-14-83: $^1$H NMR (400 MHz, $CD_3OD$) δ 7.04 (d, J=5.2 Hz, 1 H), 4.86 (d, J=4.4 Hz, 1 H), 4.72 (d, J=4.4 Hz, 1 H), 4.35 (s, 2 H), 4.11 (s, 1 H), 3.52 (d, J=4.0 Hz, 1 H), 3.45 (d, J=4.0 Hz, 1 H), 3.23-2.95 (m, 9 H), 2.36-2.24 (m, 2 H), 1.68-1.58 (m, 1 H); MS (ESI) m/z 508.0 (M+H).

S1-14-84

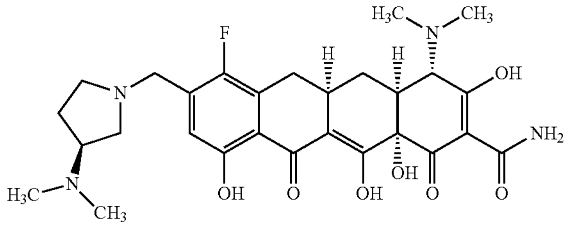

S1-14-84: $^1$H NMR (400 MHz, $CD_3OD$) δ 7.15 (d, J=5.6 Hz, 1 H), 4.61-4.55 (m, 2 H), 4.30-4.19 (m, 1 H), 4.11 (s, 1 H), 4.05-3.50 (m, 4 H), 3.23-2.90 (m, 15 H), 2.70-2.60 (m, 1 H), 2.55-2.45 (m, 1 H), 2.35-2.20 (m, 2 H), 1.68-1.57 (m, 1 H); MS (ESI) m/z 559.1 (M+H).

S1-14-85

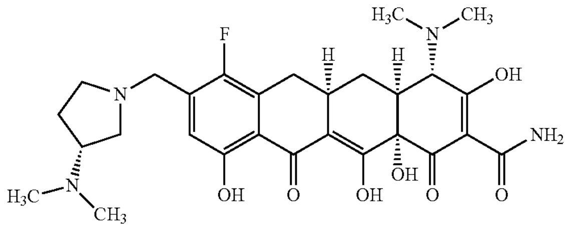

S1-14-85: $^1$H NMR (400 MHz, $CD_3OD$) δ 7.13 (d, J=6.06 Hz, 1 H), 4.55 (s, 2 H), 4.25-4.18 (m, 1 H), 4.09 (s, 1 H), 3.95-3.48 (m, 4 H), 3.23-2.95 (m, 15 H), 2.65-2.58 (m, 1 H), 2.45-2.39 (m, 1 H), 2.38-2.19 (m, 2 H), 1.70-1.58 (m, 1 H); MS (ESI) m/z 559.1 (M+H).

S1-14-86

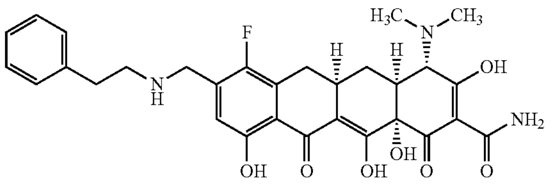

S1-14-86: $^1$H NMR (400 MHz, $CD_3OD$) δ 7.28-7.16 (m, 5 H), 6.93 (d, J=6.0 Hz, 1 H), 4.23 (s, 2 H), 4.00 (s, 1 H), 3.25 (t, J=7.6 Hz, 2 H), 3.21-2.88 (m, 11 H), 2.28-2.14 (m, 2 H), 1.61-1.50 (m, 1 H); MS (ESI) m/z 566.1 (M+H).

S1-14-87

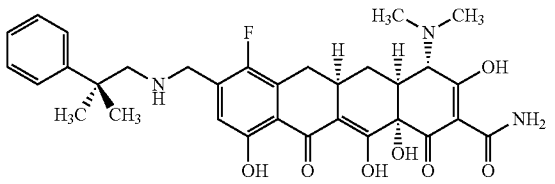

S1-14-87: $^1$H NMR (400 MHz, $CD_3OD$) δ 7.38-7.27 (m, 5 H), 6.90 (d, J=6.0 Hz, 1 H), 4.20 (s, 2 H), 4.10 (s, 1 H), 3.20-2.98 (m, 11 H), 2.29-2.20 (m, 2 H), 1.69-1.60 (m, 1 H), 1.44 (s, 6 H); MS (ESI) m/z 594.0 (M+H).

S1-14-88

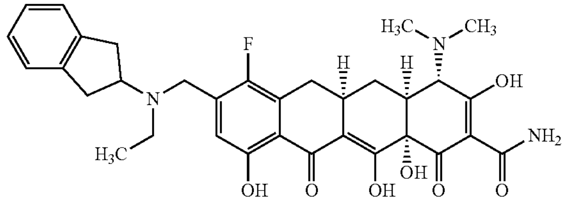

S1-14-88: $^1$H NMR (400 MHz, $CD_3OD$) δ 7.29-7.23 (m, 4 H), 7.11 (d, J=6.0 Hz, 1 H), 4.49-4.43 (m, 3 H), 4.10 (s, 1 H), 3.57-3.48 (m, 4 H), 3.24-2.98 (m, 11 H), 2.40-2.25 (m, 2 H), 1.66-1.58 (m, 1 H), 1.41 (t, J=7.2 Hz, 3 H); MS (ESI) m/z 605.9 (M+H).

S1-14-89

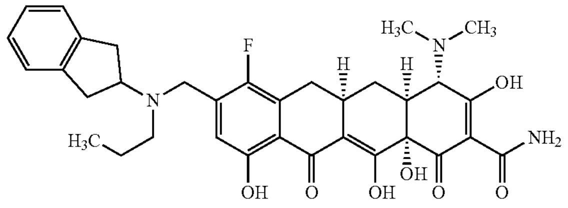

S1-14-89: $^1$H NMR (400 MHz, $CD_3OD$) δ 7.22-7.16 (m, 4 H), 7.05 (d, J=6.0 Hz, 1 H), 4.48-4.41 (m, 3 H), 4.05 (s, 1 H), 3.60-3.46 (m, 4 H), 3.18-2.95 (m, 11 H), 2.35-2.17 (m, 2 H), 1.82-1.68 (m, 2 H), 1.62-1.52 (m, 1 H), 0.90 (t, J=7.2 Hz, 3 H); MS (ESI) m/z 620.3 (M+H).

S1-14-90

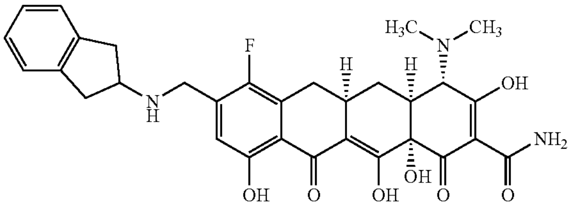

S1-14-90: $^1$H NMR (400 MHz, $CD_3OD$) δ 7.18-7.10 (m, 4 H), 6.95 (d, J=6.0 Hz, 1 H), 4.25 (s, 2 H), 4.11-4.04 (m, 1 H), 4.00 (s, 1 H), 3.40-3.34 (m, 2 H), 3.19-2.85 (m, 11 H), 2.26-2.12 (m, 2 H), 1.57-1.51 (m, 1 H); MS (ESI) m/z 578.4 (M+H).

S1-14-91

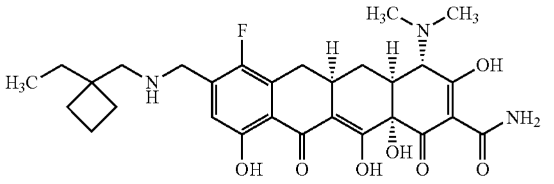

S1-14-91: $^1$H NMR (400 MHz, $CD_3OD$) δ 7.10 (d, J=5.6 Hz, 1 H), 4.34 (s, 2 H), 4.13 (s, 1 H), 3.20-2.89 (m, 11 H), 2.31-2.25 (m, 2 H), 1.90-1.73 (m, 6 H), 1.60-1.48 (m, 3 H), 0.86 (t, J=7.2 Hz, 3 H); MS (ESI) m/z 558.1 (M+H).

S1-14-92

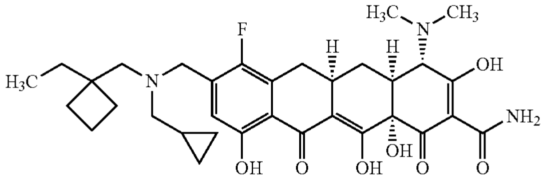

S1-14-92: $^1$H NMR (400 MHz, $CD_3OD$) δ 7.04 (d, J=5.6 Hz, 1 H), 4.38 (s, 2 H), 4.03 (s, 1 H), 3.18-2.85 (m, 13 H), 2.30-2.15 (m, 2 H), 1.90-1.75 (m, 6 H), 1.70-1.518 (m, 3 H), 1.20-1.11 (m, 1 H), 0.81 (t, J=7.2 Hz, 3 H), 0.78-0.69 (m, 2 H), 0.45-0.36 (m, 2 H); MS (ESI) m/z 612.1 (M+H).

S1-14-93

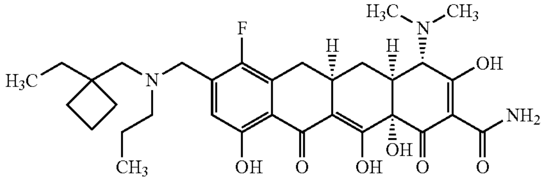

S1-14-93: $^1$H NMR (400 MHz, $CD_3OD$) δ 7.10 (d, J=5.6 Hz, 1 H), 4.38-4.34 (m, 2 H), 4.03 (s, 1 H), 3.36-3.29 (m, 1 H), 3.19-2.88 (m, 12 H), 2.36-2.25 (m, 2 H), 2.00-1.81 (m, 8 H), 1.72-1.50 (m, 3 H), 0.91 (t, J=7.2 Hz, 3 H), 0.82 (t, J=7.2 Hz, 3 H); MS (ESI) m/z 600.2 (M+H).

S1-14-94

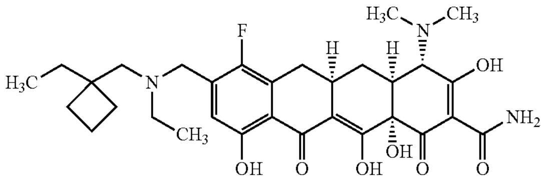

S1-14-94: $^1$H NMR (400 MHz, $CD_3OD$) δ 7.08 (d, J=5.6 Hz, 1 H), 4.38-4.34 (m, 2 H), 4.11 (s, 1 H), 3.38-3.30 (m, 1 H), 3.25-2.95 (m, 12 H), 2.36-2.25 (m, 2 H), 2.05-1.85 (m, 6 H), 1.78-1.61 (m, 3 H), 1.45 (t, J=7.2 Hz, 3 H), 0.90 (t, J=7.2 Hz, 3 H); MS (ESI) m/z 586.0 (M+H).

S1-14-95

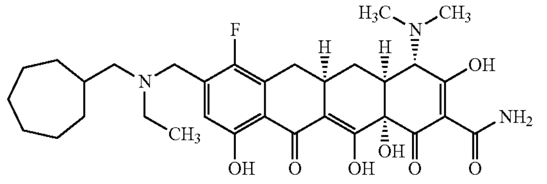

S1-14-95: $^1$H NMR (400 MHz, $CD_3OD$) δ 7.01 (d, J=5.2 Hz, 1 H), 4.40 (d, J=13.2 Hz, 1 H), 4.28 (d, J=13.6 Hz, 1 H), 4.04 (s, 1 H), 3.22-2.81 (m, 13 H), 2.31-2.17 (m, 2 H), 2.06-1.93 (m, 2 H), 1.82-1.43 (m, 9 H), 1.31 (t, J=7.2 Hz, 3 H), 1.25-1.14 (m, 3 H); MS (ESI) m/z 600.3 (M+H).

S1-14-96

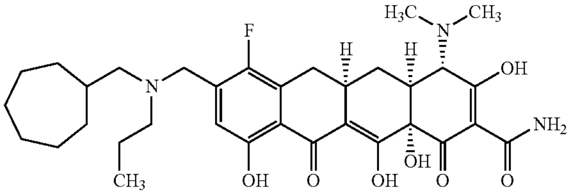

S1-14-96: $^1$H NMR (400 MHz, $CD_3OD$) δ 7.02 (d, J=6 Hz, 1 H), 4.42-4.29 (m, 2 H), 4.05 (s, 1 H), 3.22-2.81 (m, 13 H), 2.31-2.17 (m, 2 H), 2.06-1.93 (m, 2 H), 1.82-1.43 (m, 11 H), 1.31 (t, J=7.2 Hz, 3 H), 1.25-1.14 (m, 3 H), MS (ESI) m/z 600.3 (M+H).

S1-14-97

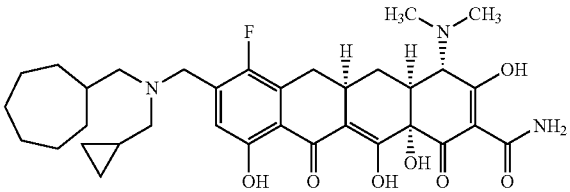

S1-14-97: $^1$H NMR (400 MHz, $CD_3OD$) δ 7.15 (d, J=5.2 Hz, 1 H), 4.54 (s, 2 H), 4.16 (s, 1 H), 3.23-3.01 (m, 13 H), 2.42-2.29 (m, 2 H), 2.14-2.05 (m, 1 H), 1.92-1.83 (m, 1 H), 1.79-1.45 (m, 9 H), 1.48-1.21 (m, 4 H), 0.86-0.75 (m, 2 H), 0.55-0.47 (m, 2 H); MS (ESI) m/z 626.2 (M+H).

S1-14-98

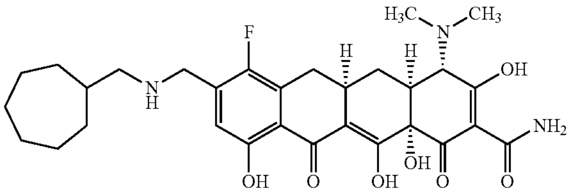

S1-14-98: $^1$H NMR (400 MHz, $CD_3OD$) δ 7.07 (d, J=5.6 Hz, 1 H), 4.29 (s, 2 H), 4.13 (s, 1 H), 3.21-2.96 (m, 11 H), 2.38-2.25 (m, 2 H), 2.02-1.91 (m, 1 H), 1.85-1.47 (m, 11 H), 1.37-1.26 (m, 2 H); MS (ESI) m/z 572.2 (M+H).

S1-14-99

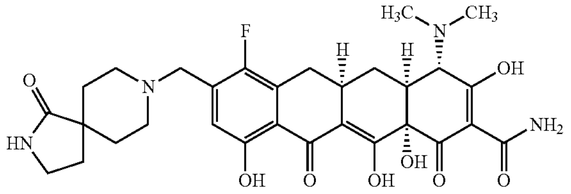

S1-14-99: $^{1}$H NMR (400 MHz, $CD_3OD$) δ 6.97 (d, J=5.6 Hz, 1 H), 4.31 (s, 2 H), 4.00 (s, 1 H), 3.57-3.44 (m, 3 H), 3.27-3.22 (m, 2 H), 3.13-2.85 (m, 10 H), 2.28-2.21 (m, 1 H), 2.15-2.08 (m, 2 H), 2.04-1.89 (m, 3 H), 1.85-1.77 (m, 1 H), 1.70-1.66 (m, 1 H), 1.60-1.48 (m, 1 H); MS (ESI) m/z 599.2 (M+H).

S1-14-100

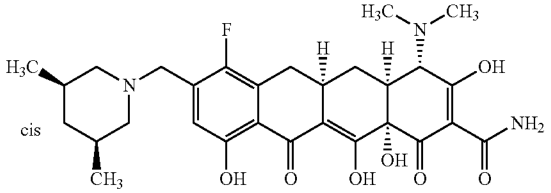

S1-14-100: $^{1}$H NMR (400 MHz, $CD_3OD$) δ 7.03 (d, J=6.0 Hz, 1 H), 4.29 (s, 2 H), 4.03 (s, 1 H), 3.40-3.29 (m, 1 H), 3.23-2.81 (m, 10 H), 2.63-2.56 (m, 1 H), 2.32-2.07 (m, 4 H), 1.62-1.49 (m, 2 H), 1.35-1.25 (m, 1 H), 1.10 (d, J=7.6 Hz, 3 H), 0.90 (d, J=7.6 Hz, 3 H), 0.89-0.78 (m, 1 H); MS (ESI) m/z 558.3 (M+H).

S1-14-101

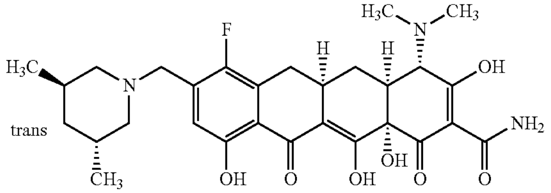

S1-14-101: $^{1}$H NMR (400 MHz, $CD_3OD$) δ7.10 (d, J=5.6 Hz, 1 H), 4.37 (s, 2 H), 4.11 (s, 1 H), 3.43-3.37 (m, 2 H), 3.23-2.97 (m, 9 H), 2.68-2.60 (m, 2 H), 2.42-2.24 (m, 2 H), 1.98-1.81 (m, 3 H), 1.71-1.58 (m, 1 H), 0.99 (d, J=7.6 Hz, 6 H), 0.95-0.85 (m, 1 H); MS (ESI) m/z 558.6 (M+H).

S1-14-102

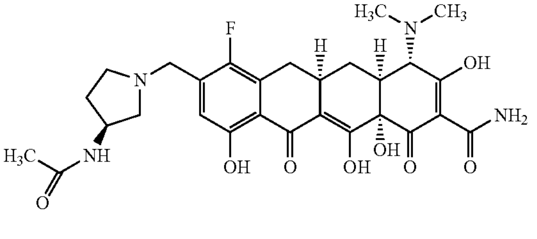

S1-14-102: $^{1}$H NMR (400 MHz, $CD_3OD$) δ 7.10 (d, J=6.0 Hz, 1 H), 4.53-4.48 (m, 2 H), 4.42-4.38 (m, 1 H), 4.10 (s, 1 H), 3.92-3.62 (m, 2 H), 3.55-3.50 (m, 2 H), 3.25-2.96 (m, 9 H), 2.62-2.51 (m, 1 H), 2.40-2.21 (m, 2 H), 2.19-2.02 (m, 2 H), 1.96 (d, J=7.2 Hz, 3 H), 1.71-1.60 (m, 1 H); MS (ESI) m/z 573.3 (M+H).

S1-14-103

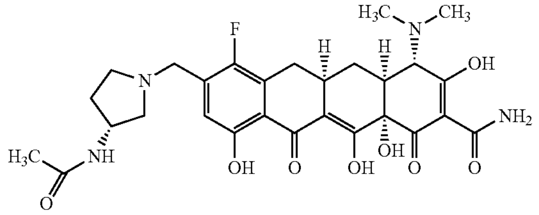

S1-14-103: $^{1}$H NMR (400 MHz, $CD_3OD$) δ 7.12 (d, J=6.0 Hz, 1 H), 4.57-4.46 (m, 3 H), 4.15 (s, 1 H), 3.90-3.83 (m, 1 H), 3.68-3.51 (m, 3 H), 3.24-2.98 (m, 9 H), 2.62-2.55 (m, 1 H), 2.39-2.25 (m, 2 H), 2.21-2.05 (m, 2 H), 1.98 (d, J=10 Hz, 3 H), 1.67-1.60 (m, 1 H); MS (ESI) m/z 572.9 (M+H).

S1-14-104

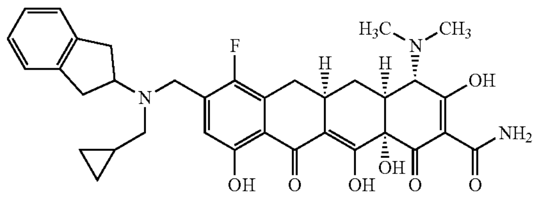

S1-14-104: $^{1}$H NMR (400 MHz, $CD_3OD$) δ 7.22-7.16 (m, 4 H), 7.02 (d, J=6.0 Hz, 1 H), 4.52-4.38 (m, 3 H), 4.05 (s, 1 H), 3.45-3.32 (m, 4 H), 3.18-2.95 (m, 11 H), 2.32-2.15 (m, 2 H), 1.61-1.52 (m, 1 H), 1.15-1.08 (m, 1 H), 0.73-0.67 (m, 2 H), 0.39-0.33 (m, 2 H); MS (ESI) m/z 632.0 (M+H).

S1-14-105

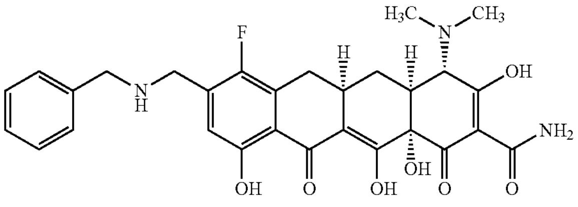

S1-14-105: $^{1}$H NMR (400 MHz, $CD_3OD$) δ 7.44-7.37 (m, 5 H), 6.93 (d, J=5.6 Hz, 1 H), 4.23 (s, 2 H), 4.21 (s, 2 H), 4.03 (s, 1 H), 3.25-2.88 (m, 9 H), 2.27-2.15 (m, 2 H), 1.59-1.50 (m, 1 H); MS (ESI) m/z 552.0 (M+H).

S1-14-106

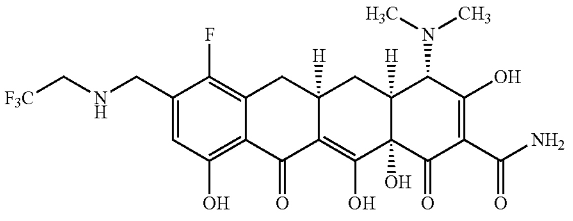

S1-14-106: $^1$H NMR (400 MHz, $CD_3OD$) δ 6.97 (d, J=5.6 Hz, 1 H), 4.34 (s, 2 H), 4.05 (d, J=8.8 Hz, 2 H), 4.02 (s, 1 H), 3.25-2.88 (m, 9 H), 2.30-2.15 (m, 2 H), 1.61-1.51 (m, 1 H); MS (ESI) m/z 544.1 (M+H).

S1-14-107

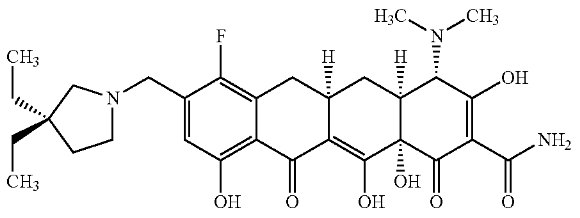

S1-14-107: $^1$H NMR (400 MHz, $CD_3OD$) δ 7.03 (d, J=5.2 Hz, 1 H), 4.39 (s, 2 H), 4.04 (s, 1 H), 3.58-3.49 (m, 1 H), 3.48-3.44 (m, 1 H), 3.18-2.88 (m, 11 H), 2.32-2.15 (m, 2 H), 1.98-1.88 (m, 1 H), 1.82-1.73 (m, 1 H), 1.62-1.41 (m, 5 H), 0.82 (m, J=7.2 Hz, 3 H), 0.78 (m, J=7.2 Hz, 3 H); MS (ESI) m/z 572.1 (M+H).

S1-14-108

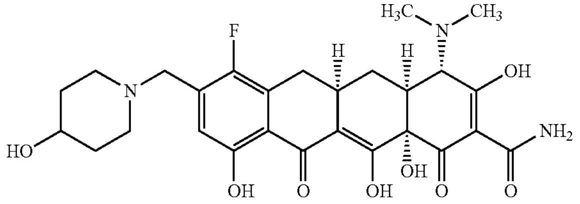

S1-14-108: $^1$H NMR (400 MHz, $CD_3OD$) δ 6.99 (t, J=6.0 Hz, 1 H), 4.29-4.28 (m, 2 H), 4.01 (s, 1 H), 4.00-3.98 (m, 1 H), 3.33-3.29 (m, 2 H), 3.18-2.95 (m, 11 H), 2.31-2.27 (m, 2 H), 2.17-2.04 (m, 2 H), 1.95-1.84 (m, 2 H), 1.57-1.49 (m, 1 H); MS (ESI) m/z 546.9 (M+H).

S1-14-109

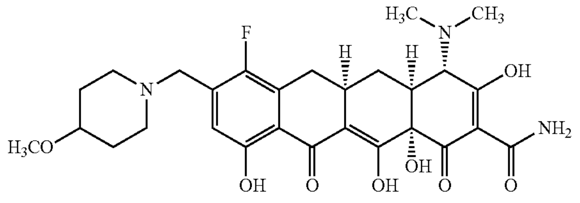

S1-14-109: $^1$H NMR (400 MHz, $CD_3OD$) δ 6.98 (t, J=5.6 Hz, 1 H), 4.30-4.28 (m, 2 H), 4.01 (s, 1 H), 4.00-3.98 (m, 1 H), 3.55-3.48 (m, 2 H), 3.39-3.37 (m, 1 H), 3.26 (s, 3 H), 3.18-2.95 (m, 11 H), 2.32-2.16 (m, 3 H), 2.06-2.02 (m, 1 H), 1.85-1.78 (m, 2 H), 1.62-1.50 (m, 1 H); MS (ESI) m/z 560.0 (M+H).

S1-14-110

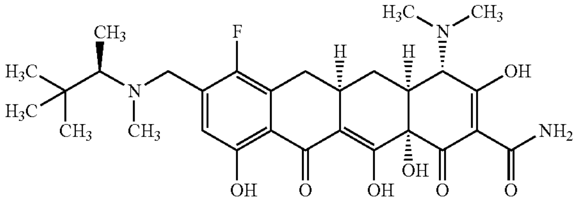

S1-14-110: $^1$H NMR (400 MHz, $CD_3OD$) δ 7.16 (d, J=6.0 Hz, 1 H), 4.55 (d, J=13.2 Hz, 1 H), 4.39 (d, J=13.2 Hz, 1 H), 4.10 (s, 1 H), 3.51-3.43 (m, 1 H), 3.04 (s, 3 H), 2.96 (s, 3 H), 2.89 (s, 3 H), 3.25-2.97 (m, 3 H), 2.35 (t, J=14.7 Hz, 1 H), 2.29-2.21 (m, 1 H), 1.69-1.59 (m, 1 H), 1.38 (d, J=6.9 Hz, 3 H), 1.00 (s, 9 H); MS (ESI) m/z 560.25 (M+H).

S1-14-111

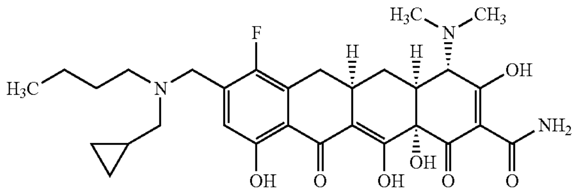

S1-14-111: $^1$H NMR (400 MHz, $CD_3OD$) δ 7.10 (d, J=6.5 Hz, 1 H), 4.55 (d, J=12.2 Hz, 1 H), 4.44 (d, J=12.2 Hz, 1 H), 4.12 (s, 1 H), 2.95-3.05 (m, 13 H), 2.22-2.40 (m, 2 H), 1.59-1.75 (m, 3 H), 1.35-1.45 (m, 2 H), 1.12-1.25 (m, 1 H), 0.95 (t, J–7.7 Hz, 3 H), 0.75-0.85 (m, 2 H), 0.40-0.50 (m, 2 H); MS (ESI) m/z 572.2 (M+H).

S1-14-112

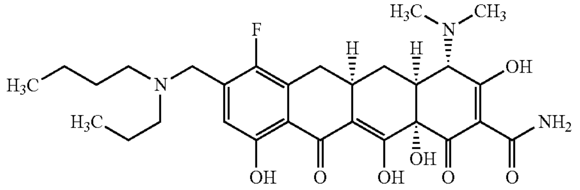

S1-14-112: $^1$H NMR (400 MHz, $CD_3OD$) δ 7.00 (d, J=5.6 Hz, 1 H), 4.35 (s, 2 H), 4.00 (s, 1 H), 2.70-3.20 (m, 12 H), 2.12-2.31 (m, 2 H), 1.50-1.80 (m, 6 H), 1.15-1.40 (m, 2 H), 0.85-0.95 (m, 6 H); MS (ESI) m/z 560.1.

S1-14-113

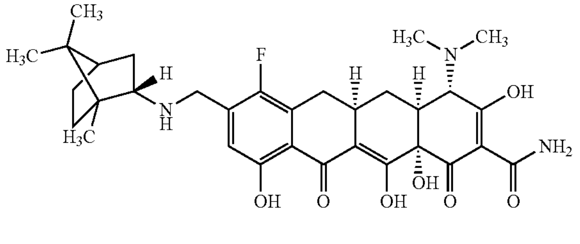

S1-14-113: $^1$H NMR (400 MHz, $CD_3OD$) δ 7.07 (d, J=6.0 Hz, 1 H), 4.30 (s, 2 H), 4.06 (s, 1 H), 3.23-3.16 (m, 1 H), 3.17-2.95 (m, 9 H), 2.39-2.30 (m, 2 H), 2.26-2.19 (m, 1 H), 1.90-1.81 (m, 1 H), 1.78 (t, J=4.6, 1 H), 1.67-1.54 (m, 4 H), 1.42-1.33 (m, 1 H), 1.21 (dd, J=13.7, 4.1 Hz, 1 H), 1.01 (s, 3 H), 0.93 (s, 3 H), 0.89 (s, 3 H); MS (ESI) m/z 598.33 (M+H).

S1-14-114

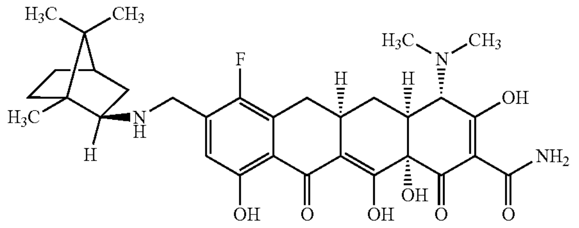

S1-14-114: $^1$H NMR (400 MHz, $CD_3OD$) δ 7.07 (d, J=6.0 Hz, 1 H), 4.37 (d, J=13.3 Hz, 1 H), 4.20 (d, J=13.3 Hz, 1 H), 4.09 (s, 1 H), 3.23-3.16 (m, 1 H), 3.17-2.96 (m, 9 H), 2.35 (t, J=14.7 Hz, 1 H), 2.28-2.21 (m, 1 H), 2.13-2.06 (m, 1 H), 1.92-1.77 (m, 4 H), 1.74-1.60 (m, 2 H), 1.24-1.17 (m, 1 H), 1.08 (s, 3 H), 0.98 (s, 3 H), 0.92 (s, 3 H); MS (ESI) m/z 598.28 (M+H).

S1-14-115

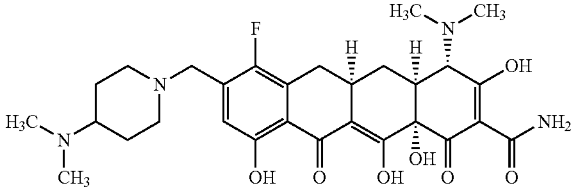

$^1$H NMR (400 MHz, $CD_3OD$) δ 7.11 (d, J=5.2 Hz, 1 H), 4.37 (s, 2 H), 4.07 (s, 1 H)□3.66-3.55 (m, 3 H), 3.19-2.92 (m, 11 H), 2.84 (s, 6 H), 2.40-1.98 (m, 6H), 1.63-1.53 (m, 1H); MS (ESI) m/z 573.1 (M+H)

S1-14-116

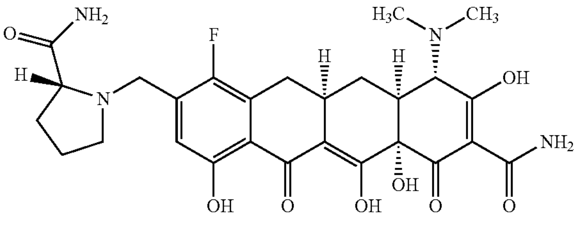

$^1$H NMR (400 MHz, $CD_3OD$) δ 6.96 (d, J=5.6 Hz, 1 H), 4.44-4.33 (m, 2 H), 4.19 (t, J=8.4 Hz, 1 H), 4.02 (s, 1H), 3.59-3.57 (m, 1H), 3.40-3.30 (m, 1 H), 3.14-3.11 (m, 2 H), 3.03-2.88 (m, 7 H), 2.56-2.50 (m, 1 H), 2.28-2.20 (m, 1 H), 2.17-2.13 (m, 2 H), 1.97-1.90 (m, 2 H), 1.60-1.51 (m, 1 H); MS (ESI) m/z 559.2 (M+H).

S1-14-117

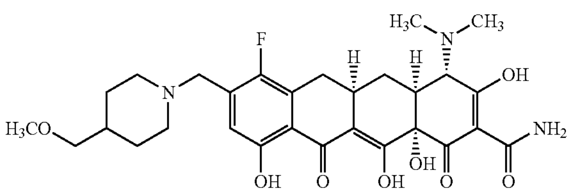

$^1$H NMR (400 MHz, $CD_3OD$) δ 7.11 (d, J=5.2 Hz, 1 H), 4.36 (s, 2 H), 4.13 (s, 1 H), 3.56 (d, J=11.6 Hz, 2 H), 3.28 (s, 3 H), 3.26 (d, J=5.6 Hz, 2 H), 3.22-2.97 (m, 11 H), 2.35-2.25 (m, 2 H), 1.98-1.90 (m, 3 H), 1.67-1.56 (m, 3 H); MS (ESI) m/z 574.2 (M+H).

S1-14-118

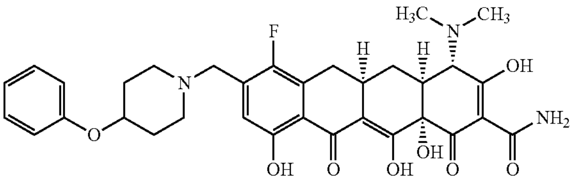

$^1$H NMR (400 MHz, $CD_3OD$) δ 7.30-7.23 (m, 2 H), 7.14 (d, J=4.4 Hz, 1 H), 7.01-6.91 (m, 3 H), 4.44 (s, 2 H), 4.11 (s, 1 H), 3.64 (d, J=12 Hz, 1 H), 3.45 (s, 3 H), 3.23-3.18 (m, 1 H), 3.11-2.96 (m, 9 H), 2.36-2.16 (m, 6 H), 1.68-1.61 (m, 1 H); MS (ESI) m/z 622.2 (M+H).

S1-14-119

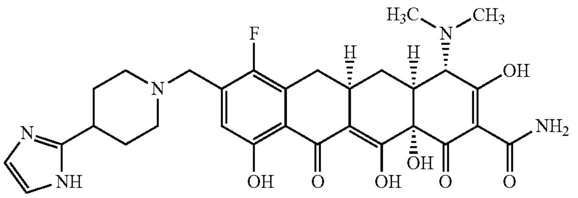

$^1$H NMR (400 MHz, $CD_3OD$) δ 7.49 (s, 2 H), 7.19 (d, J=5.6 Hz, 1 H), 4.46 (s, 2 H), 4.13 (s, 1 H), 3.72 (d, J=12 Hz, 2 H), 3.53-3.49 (m, 1 H), 3.41-3.35 (m, 2 H), 3.23-2.98 (m, 9 H), 2.39-2.24 (m, 6 H), 1.68-1.58 (m, 1 H); MS (ESI) m/z 596.2 (M+H).

S1-14-120

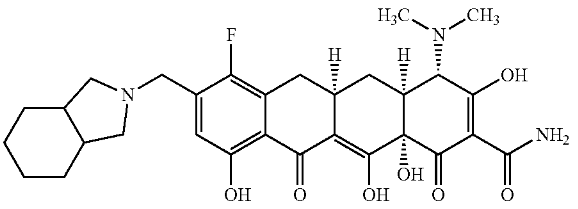

$^1$H NMR (400 MHz, $CD_3OD$) δ 7.15-7.11 (m, 1 H), 4.49 (d, J=9.2 Hz, 2 H), 4.11 (s, 1 H), 3.64-3.60 (m, 1 H), 3.49-3.34 (m, 1 H), 3.34-3.33 (m, 1 H), 3.22-2.96 (m, 10 H), 2.60-2.51 (m, 1 H), 2.43-2.20 (m, 3 H), 1.78-1.50 (m, 7 H), 1.42-1.40 (m, 2 H); MS (ESI) m/z 570.2 (M+H).

S1-14-121

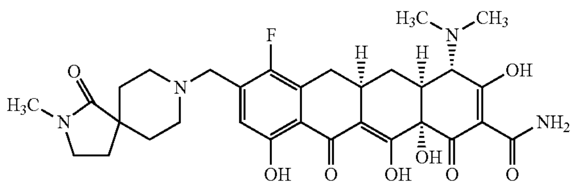

$^1$H NMR (400 MHz, $CD_3OD$) δ 7.13-7.12 (m, 1 H), 4.48 (s, 2 H), 4.15 (s, 1 H), 3.74-3.56 (m, 2 H), 3.46-3.37 (m, 3 H), 3.28-3.17 (m, 2 H), 3.11-2.97 (m, 8 H), 2.82 (d, J=12.8 Hz, 3 H), 2.33-2.26 (m, 2 H), 2.17-1.92 (m, 5 H), 1.75 (d, J=14.4 Hz, 1 H), 1.67-1.68 (m, 1 H); MS (ESI) m/z 613.3 (M+H).

S1-14-122

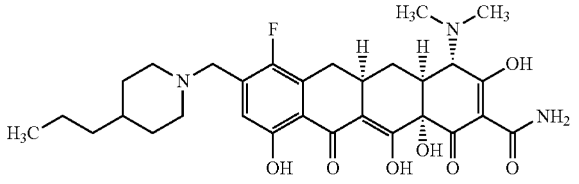

$^1$H NMR (400 MHz, $CD_3OD$) δ 7.13 (s, 1 H), 4.36 (s, 2 H), 4.15 (s, 1 H), 3.53 (d, J=11.2 Hz, 2 H), 3.25-2.98 (m, 11 H), 2.29 (d, J=13.2 Hz, 2 H), 1.94 (d, J=14 Hz, 2 H), 1.75-1.51 (m, 4 H), 1.37-1.23 (m, 4 H), 091-0.88 (t, J=6.8 Hz, 3 H); MS (ESI) m/z 572.3 (M+H).

S1-14-123

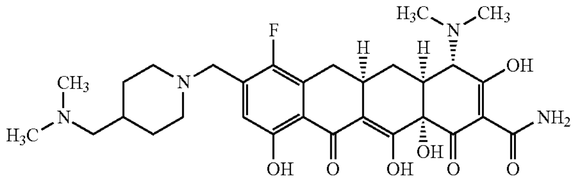

$^1$H NMR (400 MHz, $CD_3OD$) δ 7.16 (d, J=5.6 Hz, 1 H), 4.42 (s, 2 H), 4.14 (s, 1 H), 3.63 (d, J=11.2 Hz, 2 H), 3.25-3.12 (m, 6 H), 3.07-2.93 (m, 13 H), 2.40-2.30 (m, 3 H), 2.11 (d, J=14 Hz, 2 H), 1.74-1.65 (m, 3 H); MS (ESI) m/z 587.3 (M+H).

S1-14-124

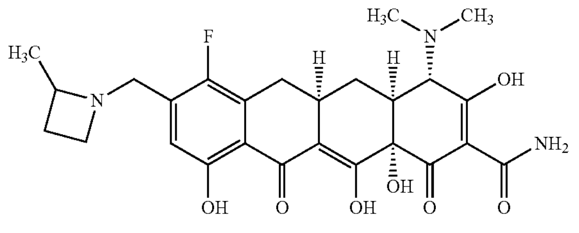

$^1$H NMR (400 MHz, $CD_3OD$) δ 6.96 (d, J=4.8 Hz, 1 H), 4.59-4.57 (m, 1 H), 4.41-4.31 (m, 2 H), 4.04-3.93 (m, 3 H), 3.13-2.88 (m, 9 H), 2.50-2.46 (m, 1 H), 2.28-2.16 (m, 3 H), 1.61-1.50 (m, 1 H), 1.34 (d, J=4.8 Hz, 3 H); MS (ESI) m/z 516.2 (M+H).

S1-14-125

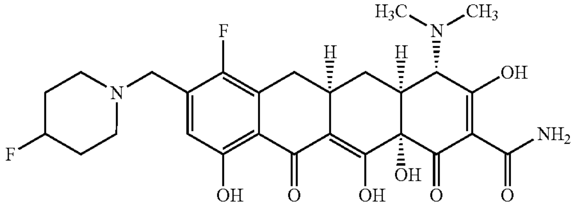

$^1$H NMR (400 MHz, $CD_3OD$) δ 7.14 (d, J=5.6 Hz, 1 H), 5.04-5.02 (m, 0.5 H), 4.90-4.88 (m, 0.5 H), 4.41 (s, 2 H), 4.12 (s, 1 H), 3.65-3.33 (m, 4 H), 3.25-2.97 (m, 9 H), 2.37-2.03 (m, 6 H), 1.67-1.58 (m, 1 H); MS (ESI) m/z 548.2 (M+H).

S1-14-126

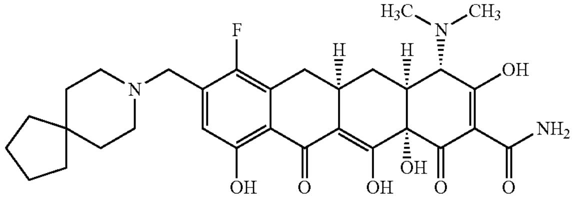

$^1$H NMR (400 MHz, $CD_3OD$) δ 7.11 (d, J=5.6 Hz, 1 H), 4.38 (s, 2 H), 4.11 (s, 1 H)□3.45-3.42 (m, 2 H), 3.22-2.97 (m, 11 H), 2.36-2.24 (m, 2 H), 1.85-1.54 (m, 11 H), 1.50-1.45 (m, 2 H); MS (ESI) m/z 584.3 (M+H)

S1-14-127

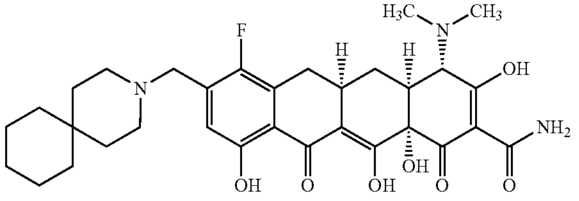

$^1$H NMR (400 MHz, $CD_3OD$) δ 7.10 (d, J=5.6 Hz, 1 H), 4.38 (s, 2 H), 4.11 (s, 1 H), 3.40-3.30 (m, 2 H), 3.23-2.97 (m, 11 H), 2.36-2.24 (m, 2 H), 1.90-1.87 (m, 2 H), 1.64-1.32 (m, 13 H); MS (ESI) m/z 597.9 (M+H).

S1-14-128

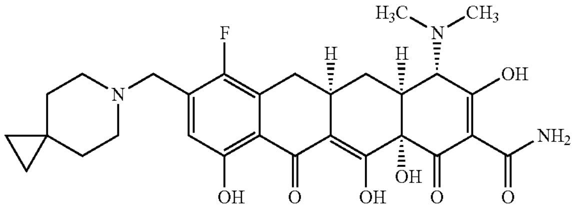

$^1$H NMR (400 MHz, $CD_3OD$) δ 7.11 (d, J=5.6 Hz, 1 H), 4.41 (s, 2 H), 4.11 (s, 1 H), 3.54-3.51 (m, 2 H), 3.22-2.97 (m, 11 H), 2.37-2.18 (m, 4 H), 1.68-1.62 (m, 1 H), 1.22-1.19 (m, 2 H), 0.53-0.50 (m, 4 H); MS (ESI) m/z 556.2 (M+H).

S1-14-129

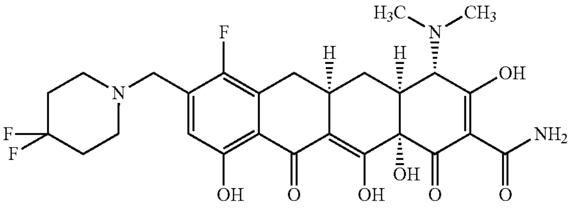

$^1$H NMR (400 MHz, $CD_3OD$) δ 7.15 (d, J=5.6 Hz, 1 H), 4.47 (s, 2 H), 4.11 (s, 1 H), 3.66-3.50 (m, 2 H), 3.46-3.32 (m, 2 H), 3.22-2.97 (m, 9 H), 2.38-2.24 (m, 6 H), 1.68-1.58 (m, 1 H); MS (ESI) m/z 566.2 (M+H).

S1-14-130

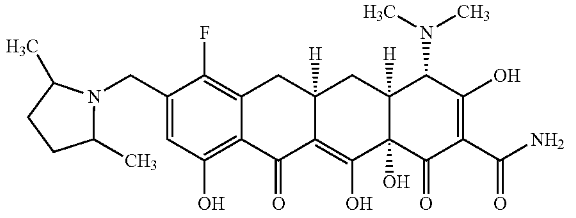

$^1$H NMR (400 MHz, MeOD) δ 7.11 and 7.10 (each s, total 1 H), 4.50 (s, 2 H), 4.13 (s, 1 H), 3.73-3.64 (m, 2 H), 3.27-2.95 (m, 9 H), 2.40-2.25 (m, 4 H), 1.79-1.75 (m, 2 H), 1.70-1.60 (m, 1 H), 1.42 (d, J=7.2 Hz, 6 H); MS (ESI) m/z 544.1 (M+H).

S1-14-131

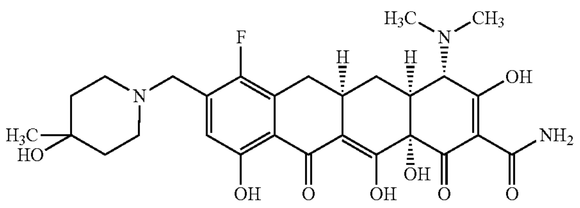

$^1$H NMR (400 MHz, $CD_3OD$) δ 7.04 (d, J=5.6 Hz, 1 H), 4.30 (s, 2 H), 4.05 (s, 1 H), 3.29-3.22 (m, 4 H), 3.13-2.89 (m, 9 H), 2.27-2.17 (m, 2 H), 1.85-1.80 (m, 2 H), 1.72-1.68 (m, 2 H), 1.60-1.51 (m, 1 H), 1.19 (s, 3 H); MS (ESI) m/z 560.0 (M+H).

S1-14-132

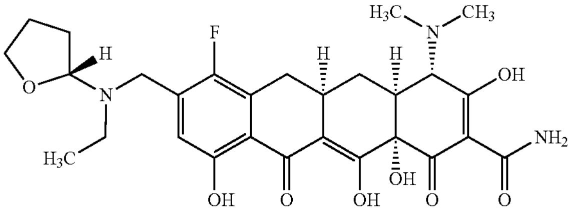

$^1$H NMR (400 MHz, $CD_3OD$) δ 7.08 (dd, J=11.0, 5.5 Hz, 1 H), 4.61 (dd, J=26.7, 14.2 Hz, 1 H), 4.47-4.27 (m, 2 H), 4.10 (s, 1 H), 4.00-3.82 (m, 2 H), 3.43-3.30 (m, 2 H), 3.25-2.94 (m, 11 H), 2.42-2.32 (m, 1 H), 2.29-2.11 (m, 2 H), 2.03-1.90 (m, 2 H), 1.71-1.56 (m, 2 H), 1.38 (t, J=7.3 Hz, 3 H); MS (ESI) m/z 574.20 (M+H).

S1-14-133

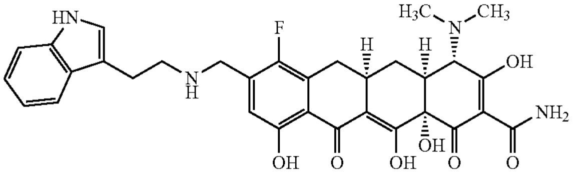

$^1$H NMR (400 MHz, $CD_3OD$) δ 7.53 (d, J=7.6 Hz, 1 H), 7.36 (d, J=8.0 Hz, 1 H), 7.19 (s, 1 H), 7.11 (t, J=7.6 Hz, 1 H), 7.04-7.00 (m, 2 H), 4.33-4.26 (m, 2 H), 4.11 (s, 1 H), 3.42-3.37 (m, 2 H), 3.26-2.95 (m, 11 H), 2.33-2.23 (m, 2 H), 1.68-1.59 (m, 1 H); MS (ESI) m/z 605.0 (M+H).

S1-14-134

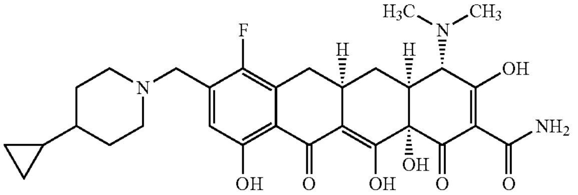

$^1$H NMR (400 MHz, $CD_3OD$) δ 7.00 (d, J=5.6 Hz, 1 H), 4.24 (s, 2 H), 4.02 (s, 1 H), 3.45-3.42 (m, 2 H), 3.11-2.87 (m, 11 H), 2.26-2.15 (m, 3 H), 1.93-1.89 (m, 2 H), 1.60-1.48 (m, 3 H), 0.80-0.69 (m, 1 H), 0.50-0.40 (m, 1 H), 0.35-0.33 (m, 2 H), 0.07-0.02 (m, 2 H); MS (ESI) m/z 570.0 (M+H).

S1-14-135

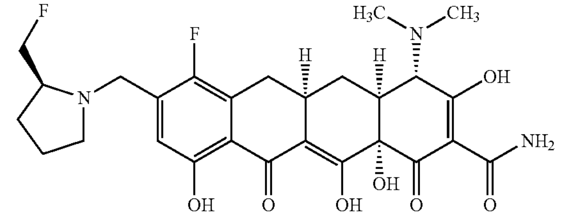

$^1$H NMR (400 MHz, $CD_3OD$) δ 7.03 (d, J=5.6 Hz, 1 H), 4.41 (s, 2 H), 4.09 (s, 1 H), 3.79-3.66 (m, 1 H), 3.61-3.52 (m, 1 H), 3.46-3.37 (m, 2 H), 3.26-2.93 (m, 10 H), 2.43-2.33 (m, 1 H), 2.27-2.20 (m, 1 H), 2.18-2.05 (m, 2 H), 1.95-1.72 (m, 2 H), 1.72-1.60 (m, 1 H); MS (ESI) m/z 548.14 (M+H).

S1-14-136

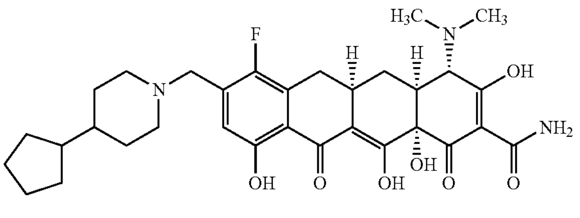

$^1$H NMR (400 MHz, $CD_3OD$) δ 6.98 (d, J=5.6 Hz, 1 H), 4.26 (s, 2 H), 4.00 (s, 1 H), 3.47-3.44 (m, 2 H), 3.15-2.89 (m, 11 H), 2.32-2.25 (m, 1 H), 2.17-2.14 (m, 1 H), 1.95-1.92 (m, 3 H), 1.76-1.66 (m, 2 H), 1.64-1.02 (m, 10 H); MS (ESI) m/z 598.1 (M+H).

S1-14-137

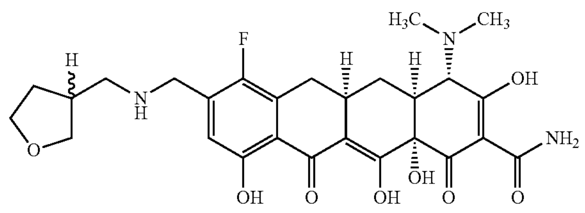

$^1H$ NMR (400 MHz, $CD_3OD$) δ 7.05 (d, J=5.9 Hz, 1 H), 4.31 (s, 2 H), 4.09 (s, 1 H), 3.95-3.85 (m, 2 H), 3.75 (t, J=7.3 Hz, 1 H), 3.54 (dd, J=8.7, 5.5 Hz, 1 H), 3.20-2.90 (m, 11 H), 2.70-2.59 (m, 1 H), 2.40-2.30 (m, 1 H), 2.28-2.13 (m, 2 H), 1.75-1.59 (m, 2 H); MS (ESI) m/z 546.16 (M+H).

S1-14-138

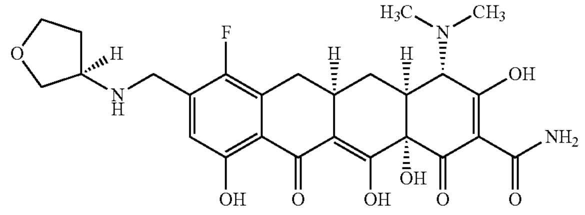

$^1H$ NMR (400 MHz, $CD_3OD$) δ 7.04 (d, J=5.9 Hz, 1 H), 4.30 (s, 2 H), 4.18-3.94 (m, 4 H), 3.90-3.80 (m, 1 H), 3.80-3.65 (m, 1 H), 3.24-2.85 (m, 9 H), 2.50-2.20 (m, 3 H), 2.18-2.00 (m, 1 H), 1.70-1.57 (m, 1 H); MS (ESI) m/z 532.11 (M+H).

S1-14-139

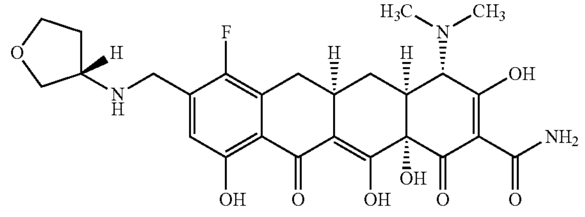

$^1H$ NMR (400 MHz, $CD_3OD$) δ 7.01 (d, J=5.9 Hz, 1 H), 4.31 (d, J=5.0 Hz, 2 H), 4.23-4.15 (m, 1 H), 4.08 (s, 1 H), 3.95-3.88 (m, 1 H), 3.85-3.78 (m, 1 H), 3.25-3.16 (m, 1 H), 3.15-2.93 (m, 9 H), 2.39-2.29 (m, 1 H), 2.27-2.19 (m, 1 H), 2.17-2.07 (m, 1 H), 2.00-1.91 (m, 2 H), 1.70-1.56 (m, 2 H); MS (ESI) m/z 546.13 (M+H).

S1-14-140

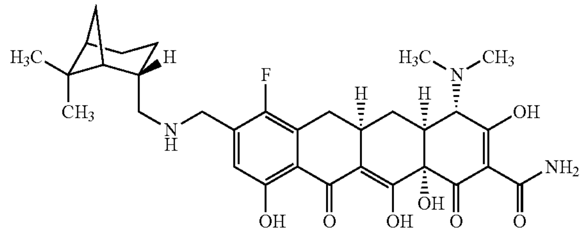

$^1H$ NMR (400 MHz, $CD_3OD$) δ 7.05 (d, J=5.5 Hz, 1 H), 4.28 (s, 2 H), 4.10 (s, 1 H), 3.24-2.83 (m, 11 H), 2.54-2.40 (m, 3 H), 2.39-2.30 (m, 1 H), 2.28-2.21 (m, 1 H), 2.11-1.90 (m, 5 H), 1.70-1.50 (m, 2 H), 1.23 (s, 3 H), 1.01 (s, 3 H); MS (ESI) m/z 598.19 (M+H).

S1-14-141

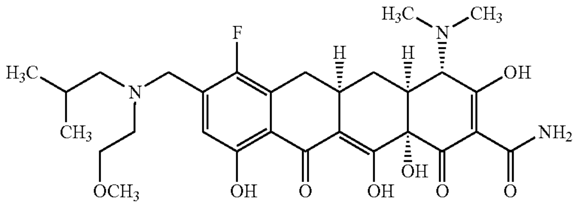

$^1H$ NMR (400 MHz, $CD_3OD$) δ 7.09 (d, J=6.0 Hz, 1 H), 4.51 (d, J=1.7 Hz, 2 H), 4.09 (s, 1 H), 3.78 (t, J=4.8 Hz, 2 H), 3.46-3.40 (m, 5 H), 3.24-2.94 (m, 11 H), 2.37 (t, J=14.7 Hz, 1 H), 2.28-2.17 (m, 2 H), 1.72-1.60 (m, 1 H), 1.09-1.01 (m, 6 H); MS (ESI) m/z 576.24 (M+H).

S1-14-142

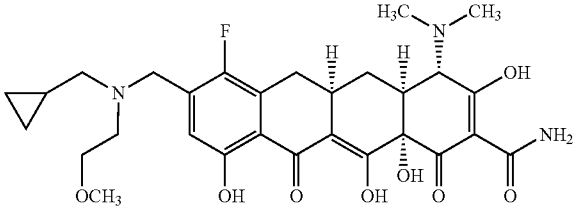

$^1H$ NMR (400 MHz, $CD_3OD$) δ 7.09 (d, J=5.9 Hz, 1 H), 4.55 (d, J=3.7 Hz, 2 H), 4.07 (s, 1 H), 3.77 (t, J=4.8 Hz, 2 H), 3.66-3.54 (m, 1 H), 3.41 (s, 3 H), 3.48-3.37 (m, 1 H), 3.25-2.90 (m, 11 H), 2.43-2.33 (m, 1 H), 2.28-2.20 (m, 1 H), 1.71-1.60 (m, 1 H), 1.25-1.15 (m, 1 H), 1.85-1.75 (m, 2 H), 0.50-0.42 (m, 2 H); MS (ESI) m/z 574.21 (M+H).

S1-14-143

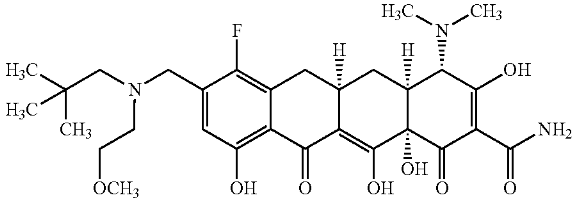

$^1H$ NMR (400 MHz, $CD_3OD$) δ 7.14 (d, J=6.0 Hz, 1 H), 4.56 (br, 2 H), 4.09 (s, 1 H), 3.80 (br, 2 H), 3.55-3.46 (m, 2 H), 3.42 (s, 3 H), 3.44-3.39 (m, 1 H), 3.22-2.92 (m, 10 H), 2.42-2.33 (m, 1 H), 2.27-2.20 (m, 1 H), 1.72-1.60 (m, 1 H), 1.09 (s, 9 H); MS (ESI) m/z 590.21 (M+H).

S1-14-144

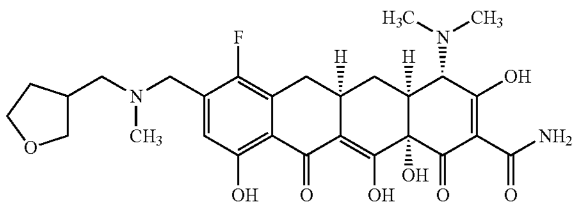

$^1$H NMR (400 MHz, $CD_3OD$) δ 7.08 (d, J=5.9 Hz, 1 H), 4.64-4.52 (m, 1 H), 4.38-4.22 (m, 1 H), 4.10 (s, 1 H), 3.98-3.82 (m, 2 H), 3.76 (t, J=7.3 Hz, 1 H), 3.55-3.45 (m, 1 H), 3.27-2.88 (m, 14 H), 2.85-2.73 (m, 1 H), 2.42-2.32 (m, 1 H), 2.28-2.19 (m, 2 H), 1.77-1.59 (m, 2 H); MS (ESI) m/z 560.21 (M+H).

S1-14-145

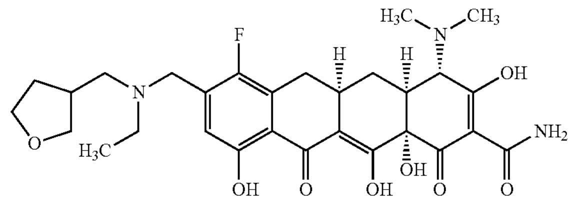

$^1$H NMR (400 MHz, $CD_3OD$) δ 7.08 (d, J=5.9 Hz, 1 H), 4.55-4.39 (m, 2 H), 4.08 (s, 1 H), 3.98-3.82 (m, 2 H), 3.75 (t, J=7.3 Hz, 1 H), 3.53-3.40 (m, 1 H), 3.36-2.92 (m, 13 H), 2.80-2.71 (m, 1 H), 2.43-2.33 (m, 1 H), 2.28-2.18 (m, 2 H), 1.73-1.59 (m, 2 H), 1.40 (t, J=7.3 Hz, 3 H); MS (ESI) m/z 574.28 (M+H).

S1-14-146

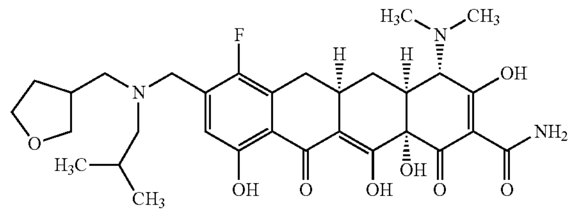

$^1$H NMR (400 MHz, $CD_3OD$) δ 7.08 (d, J=5.9 Hz, 1 H), 4.60-4.40 (m, 2 H), 4.09 (s, 1 H), 4.02-3.94 (m, 1 H), 3.92-3.84 (m, 1 H), 3.83-3.73 (m, 1 H), 3.52-3.43 (m, 1 H), 3.36-2.92 (m, 13 H), 2.83-2.71 (m, 1 H), 2.43-2.34 (m, 1 H), 2.33-2.18 (m, 3 H), 1.75-1.60 (m, 2 H), 1.06 (dd, J=13.7, 6.9 Hz, 6 H); MS (ESI) m/z 602.30 (M+H).

S1-14-147

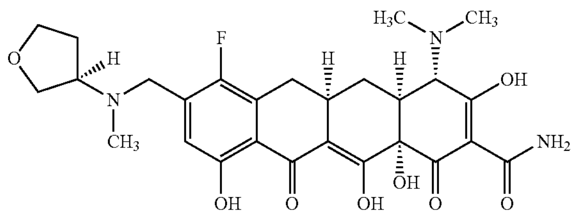

$^1$H NMR (400 MHz, $CD_3OD$) δ 7.09 (d, J=6.0 Hz, 1 H), 4.60-4.42 (m, 1 H), 4.36-4.22 (m, 2 H), 4.22-4.09 (m, 2 H), 4.10 (s, 1 H), 3.84 (dd, J=11.4, 6.0 Hz, 1 H), 3.78-3.67 (m, 1 H), 3.24-3.17 (m, 1 H), 3.17-2.92 (m, 8 H), 2.83 (s, 3 H), 2.54-2.20 (m, 4 H), 1.70-1.59 (m, 1 H); MS (ESI) m/z 546.14 (M+H).

S1-14-148

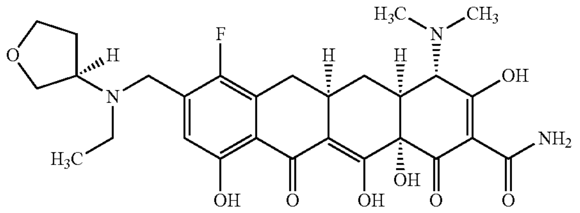

$^1$H NMR (400 MHz, $CD_3OD$) δ 7.08 (d, J=6.0 Hz, 1 H), 4.48 (d, J=13.7 Hz, 1 H), 4.43-4.11 (m, 4 H), 4.09 (s, 1 H), 3.90-3.78 (m, 1 H), 3.76-3.64 (m, 1 H), 3.40-3.27 (m, 2 H), 3.24-3.18 (m, 1 H), 3.17-2.92 (m, 8 H), 2.50-2.20 (m, 4 H), 1.71-1.59 (m, 1 H), 1.45-1.32 (m, 3 H); MS (ESI) m/z 560.19 (M+H).

S1-14-149

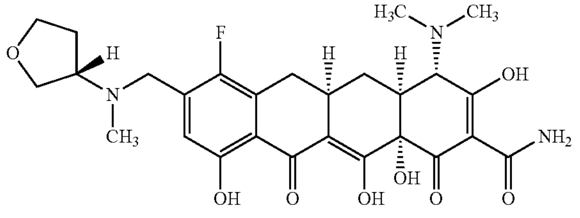

$^1$H NMR (400 MHz, $CD_3OD$) δ 7.06 (dd, J=11.9, 5.9 Hz, 1 H), 4.63 (t, J=11.7 Hz, 1 H), 4.44-4.25 (m, 2 H), 4.09 (s, 1 H), 4.00-3.82 (m, 2 H), 3.47-3.39 (m, 1 H), 3.25-2.87 (m, 11 H), 2.42-2.31 (m, 1 H), 2.27-2.10 (m, 2 H), 2.02-1.90 (m, 2 H), 1.71-1.56 (m, 2 H); MS (ESI) m/z 560.18 (M+H).

EXAMPLE 2

Synthesis of Compounds Via Scheme 2

Scheme 2

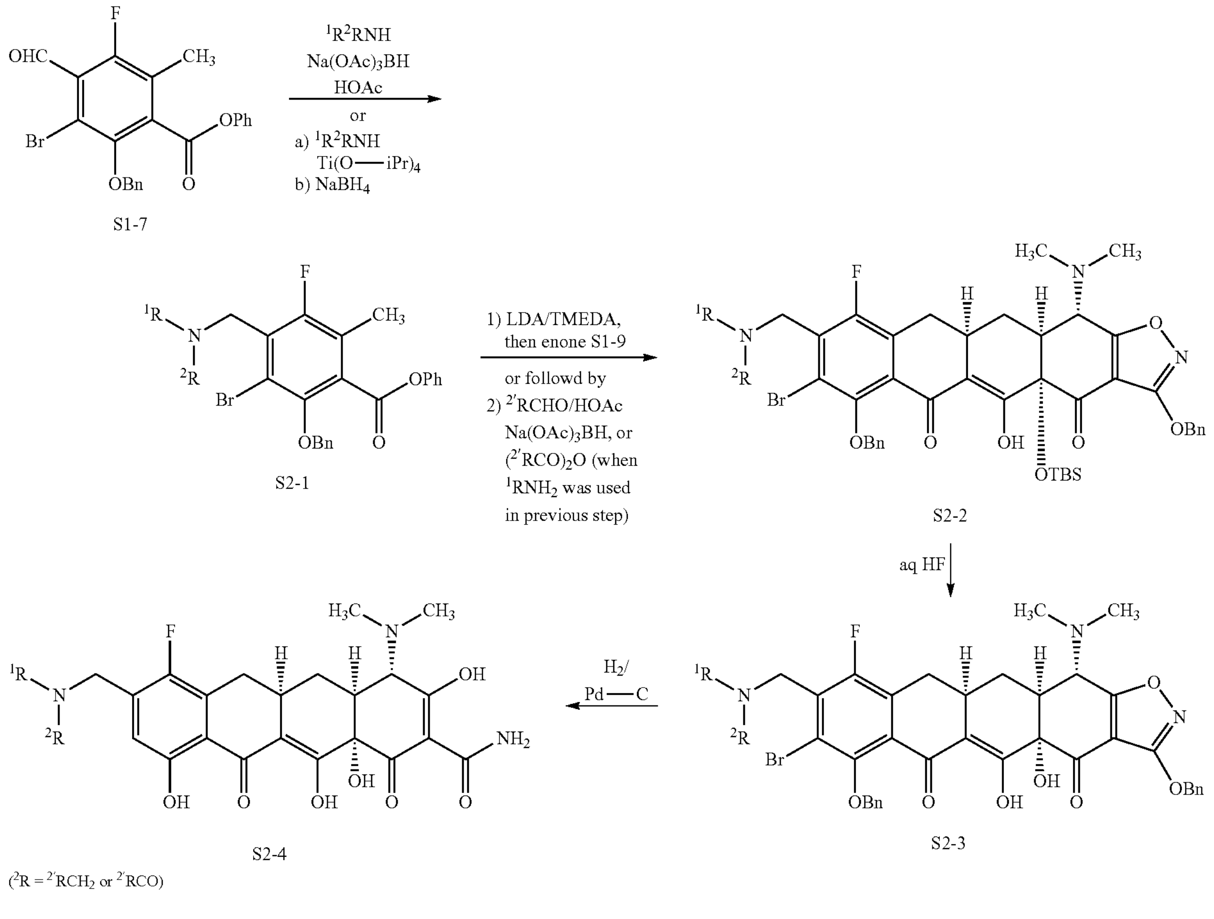

The following compounds were prepared according to Scheme 2.

S2-1-1

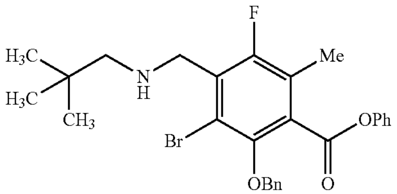

Compound S1-7 (0.25 g, 0.56 mmol, 1.0 equiv) was dissolved in 1,2-dichloroethane (4 mL). Neopentylamine (98 mg, 0.11 mmol, 2.0 equiv) was added via a syringe, followed by the addition of acetic acid (64 μL, 0.11 mmol) under a nitrogen atmosphere. After stirring at rt for 1 h, sodium triacetoxyborohydride (0.36 g, 1.68 mmol, 3.0 equiv) was added to the reaction mixture. LC/MS indicated that the starting material was consumed after overnight. The reaction mixture was diluted with dichloromethane, washed with saturated aqueous $NaHCO_3$ (3×20 mL) and brine, dried over sodium sulfate, filtered, and concentrated under reduced pressure to give the crude product, which was purified by column chromatography (Biotage 10 g column, 10% to 20% EtOAc in hexanes gradient), yielding pure compound S2-1-1 as a colorless oil (0.25 g, 86%): $^1$H NMR (400 MHz, $CDCl_3$) δ 7.52-7.47 (m, 2 H), 7.40-7.33 (m, 6 H), 7.25 (t, J=6.9 Hz, 1 H), 7.04 (d, J=8.2 Hz, 2 H), 5.10 (s, 2 H), 4.04 (d, J=2.3 Hz, 2 H), 2.35 (d, J=1.8 Hz, 3 H), 2.30 (s, 2 H), 0.89 (s, 9 H).

S2-2-1

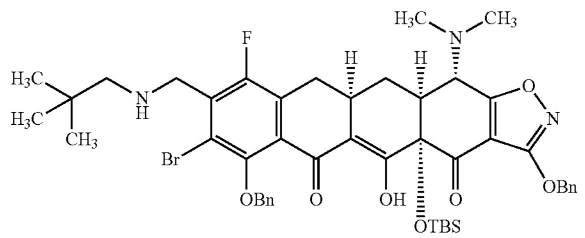

LDA/THF was prepared by adding n-BuLi (0.29 mL, 1.6 M/hexanes, 0.46 mmol, 3.0 equiv) to diisopropylamine (65 μL, 0.46 mmol, 3.0 equiv) in 3 mL dry THF under a nitrogen atmosphere in a flame dried schenck flask at −78° C. The resulting solution was warmed to −20° C. and stirred for another 15 min. After the LDA solution was cooled down to −78° C., TMEDA (69 μL, 0.46 mmol, 3.0 equiv) was added slowly via a syringe. Compound S2-1-1 (0.10 g, 0.20 mmol, 1.3 equiv) was dissolved in 1 mL dry THF and added into the LDA solution slowly via a syringe. A dark-red color appeared as soon as addition started. After stirring for 10 min, enone S1-9 (74 mg, 0.15 mmol, 1.0 equiv) in 1 mL dry THF was added slowly a via syringe. After 10 min, LC/MS indicated that the enone was consumed and the product present. The reaction mixture was allowed to slowly warm to −20° C. in 1 h. A phosphate buffer solution (pH 7, 10 mL) was added, followed by the addition of 20 mL saturated aqueous ammonium chloride. The resulting mixture was extracted with dichloromethane (3×15 mL). The combined extracts were dried over sodium sulfate, filtered and concentrated under reduced pressure. The resulting orange-red oil was purified by column chromatography (Biotage 10 g column, 10% to 30% EtOAc in hexanes gradient) to yield the desired compound S2-2-1 (90 mg, 65%).

S2-4-1

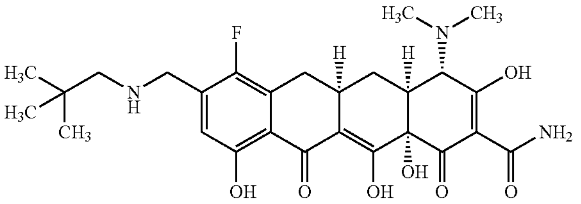

Aqueous HF (0.3 mL, 48-50%) was added to a $CH_3CN$ solution (1.0 mL) of 7 (20 mg) in a plastic vial at 25° C. The reaction was stirred at 25° C. for 18 hrs. The resulting mixture was poured into an aqueous solution (10 mL) of $K_2HPO_4$ (2 g). The solution was extracted with EtOAc (3×15 mL). The combined EtOAc extracts were dried over sodium sulfate and concentrated to give the crude intermediate.

10% Pd—C (5 mg) was added to a MeOH solution (2 mL) of the above crude intermediate. HCl/MeOH (0.5 mL, 0.5 N) was also added. The reaction mixture was stirred under $H_2$ (balloon) at 25° C. for 2 hrs and filtered through a pad of Celite. The filtrate was concentrated to give the crude product. The crude product was purified by HPLC on a Polymerx 10μ RP-γ 100 R column [30×21.20 mm, 10 micron, solvent A: 0.05 N HCl, solvent B: $CH_3CN$, sample in 2.0 mL (0.05 N HCl), gradient elution with 0→70% B over 15 min, mass-directed fraction collection] to yield the desired product S2-4-1 as a yellow solid (8 mg, 66%, 2 steps): $^1$H NMR (400 MHz, $CD_3OD$) δ 7.09 (d, J=6.0 Hz, 1 H), 4.42 (s, 2 H), 4.14 (s, 1 H), 3.21 (dd, J=15.5, 4.6 Hz, 1 H), 3.05 (s, 3 H), 2.97 (s, 3 H), 2.92 (s, 2 H), 3.17-2.97 (m, 2 H), 2.39-2.22 (m, 2 H), 1.70-1.58 (m, 1 H), 1.06 (s, 9 H); MS (ESI) m/z 532.49 (M+H).

The following compounds were prepared according to the methods for S2-4-1, substituting the appropriate amine for isobutylamine.

S2-4-2

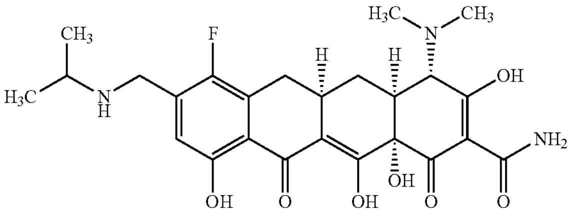

S2-4-2: $^1$H NMR (400 MHz, $CD_3OD$/DCl) δ 7.08 (d, J=5.96 Hz, 1 H), 4.27 (s, 2 H), 4.16 (s, 1 H), 3.51 (hept, J=6.9 Hz, 1 H), 3.28-2.94 (m, 9 H), 2.38-2.26 (m, 2 H), 1.60 (dd, J=13.3, 11.0 Hz, 1 H), 1.41 (d, J=6.9 Hz, 6 H); MS (ESI) m/z 504.28 (M+H).

S2-4-3

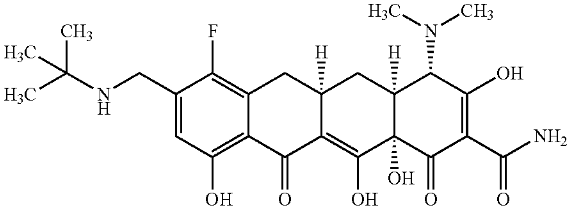

S2-4-3: $^1$H NMR (400 MHz, $CD_3OD$/DCl) δ 7.09 (d, J=5.92 Hz, 1 H), 4.22 (s, 2 H), 4.16 (s, 1 H), 3.28-2.94 (m, 9 H), 2.38-2.26 (m, 2 H), 1.60 (dd, J=14.0, 11.0 Hz, 1 H), 1.47 (s, 9 H); MS (ESI) m/z 518.28 (M+H).

S2-4-4

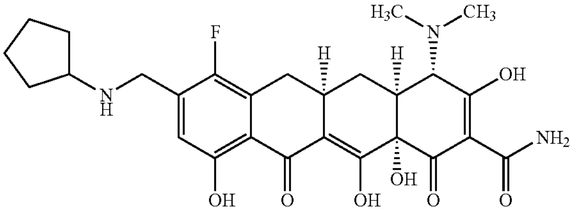

S2-4-4: $^1$H NMR (400 MHz, $CD_3OD$/DCl) δ 7.07 (d, J=5.96 Hz, 1 H), 4.26 (s, 2 H), 4.16 (s, 1 H), 3.66 (quint, J=6.9 Hz, 1 H), 3.34-2.94 (m, 11 H), 2.36-2.24 (m, 2 H), 2.23-2.12 (m, 2 H), 1.90-1.54 (m, 5 H); MS (ESI) m/z 530.23 (M+H).

S2-4-5

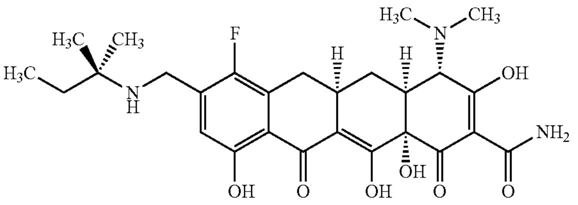

S2-4-5: $^1$H NMR (400 MHz, $CD_3OD$/DCl) δ 7.08 (d, J=5.96 Hz, 1 H), 4.21 (s, 2 H), 4.15 (s, 1 H), 3.26-2.96 (m, 9

H), 2.36-2.24 (m, 2 H), 1.82 (q, J=7.32 Hz, 2 H), 1.69-1.55 (m, 1 H), 1.42 (s, 6 H), 1.02 (d, J=7.32 Hz, 3 H); MS (ESI) m/z 532.24 (M+H).

S2-4-6

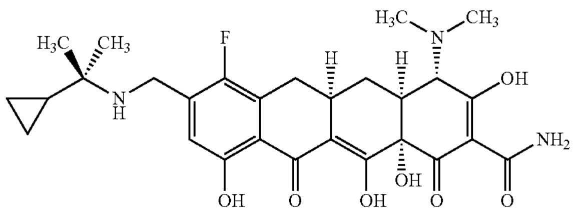

S2-4-6: $^{1}$H NMR (400 MHz, $CD_3OD$/DCl) δ 7.11 (d, J=5.96 Hz, 1 H), 4.33 (s, 2 H), 4.16 (s, 1 H), 3.26-2.94 (m, 9 H), 2.36-2.25 (m, 2 H), 1.69-1.55 (m, 1 H), 1.33 (s, 6 H), 1.29-1.20 (m, 1 H), 0.72-0.64 (m, 2 H), 0.63-0.56 (m, 2 H); MS (ESI) m/z 544.24 (M+H).

S2-4-7

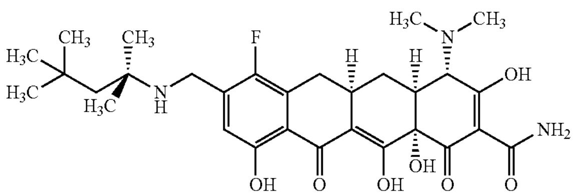

S2-4-7: $^{1}$H NMR (400 MHz, $CD_3OD$/DCl) δ 7.11 (d, J=5.48 Hz, 1 H), 4.24 (s, 2 H), 4.18 (s, 1 H), 3.28-2.96 (m, 9 H), 2.37-2.26 (m, 2 H), 1.84 (s, 2 H), 1.69-1.54 (m, 7 H), 1.10 (s, 9 H); MS (ESI) m/z 574.28 (M+H).

S2-4-8

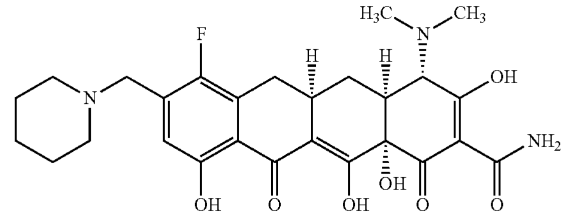

S2-4-8: $^{1}$H NMR (400 MHz, $CD_3OD$/DCl) δ 7.15 (d, J=5.96 Hz, 1 H), 4.37 (s, 2 H), 4.17 (s, 1 H), 3.56-3.48 (m, 2 H), 3.40-2.94 (m, 11 H), 2.38-2.26 (m, 2 H), 1.99-1.78 (m, 5 H), 1.70-1.48 (m, 2 H); MS (ESI) m/z 530.29 (M+H).

S2-4-9

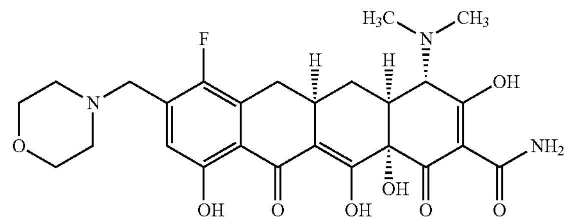

S2-4-9: $^{1}$H NMR (400 MHz, $CD_3OD$/DCl) δ 7.17 (d, J=5.96 Hz, 1 H), 4.45 (s, 2 H), 4.16 (s, 1 H), 4.08-3.98 (m, 2 H), 3.92-3.80 (m, 2 H), 3.52-3.42 (m, 2 H), 3.38-2.94 (m, 11 H), 2.38-2.25 (m, 2 H), 1.70-1.55 (m, 1 H); MS (ESI) m/z 532.27 (M+H).

S2-4-10

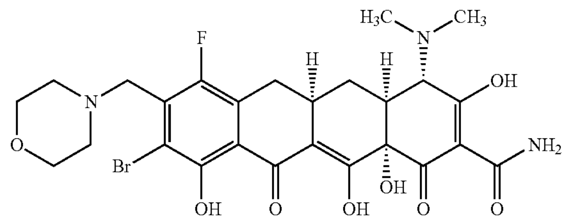

S2-4-10: $^{1}$H NMR (400 MHz, $CD_3OD$/DCl) δ 4.69 (s, 2 H), 4.17 (s, 1 H), 4.10-3.98 (m, 2 H), 3.95-3.84 (m, 2 H), 3.34-2.94 (m, 13 H), 2.38-2.25 (m, 2 H), 1.71-1.57 (m, 1 H); MS (ESI) m/z 610.2, 612.19 (M+H).

S2-4-11

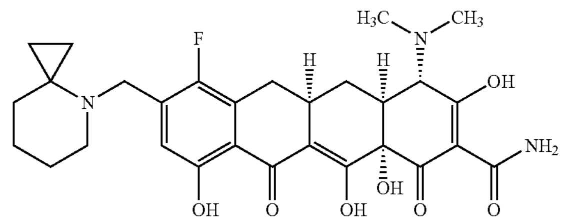

S2-4-11: $^{1}$H NMR (400 MHz, CD3OD/DCl) δ 7.15 (br s, 1 H), 4.76-4.58 (m, 2 H), 4.17 (s, 1 H), 3.40-2.92 (m, 11 H), 2.60-2.48 (m, 1 H), 2.38-2.15 (m, 3 H), 1.99-1.82 (m, 2 H), 1.82-1.55 (m, 2 H), 1.45-1.36 (m, 1 H), 1.22-1.14 (m, 1 H), 1.10-0.99 (m, 1 H), 0.99-0.80 (m, 2 H); MS (ESI) m/z 556.20 (M+H).

S2-4-12

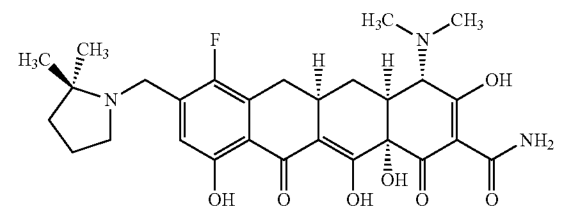

S2-4-12: $^{1}$H NMR (400 MHz, CD3OD/DCl) δ 7.12 (d, J=5.96 Hz, 1 H), 4.56 (d, J=3.2 Hz, 1 H), 4.17 (s, 1 H), 4.10 (d, J=3.2 Hz, 1 H), 3.54-3.45 (m, 2 H), 3.26-2.96 (m, 9 H), 2.39-2.26 (m, 2 H), 2.23-1.95 (m, 4 H), 1.70-1.56 (m, 4 H), 1.44 (s, 3 H); MS (ESI) m/z 544.22 (M+H).

S2-4-13

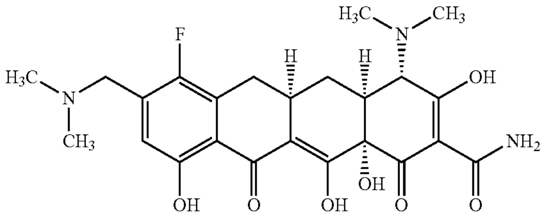

S2-4-13: $^1H$ NMR (400 MHz, $CD_3OD$) δ 7.08 (d, J=6.0 Hz, 1 H), 4.42 (s, 2 H), 4.14 (s, 1 H), 3.06 (s, 3 H), 2.98 (s, 3 H), 2.92 (s, 6 H), 3.24-2.97 (m, 3 H), 2.37-2.25 (m, 2 H), 1.70-1.57 (m, 1 H); MS (ESI) m/z 490.43 (M+H).

S2-4-14

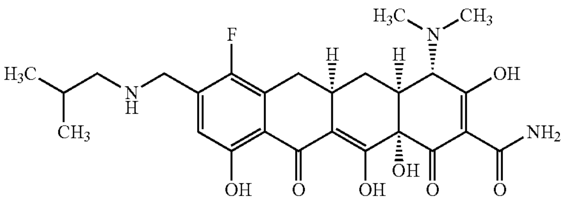

S2-4-14: $^1H$ NMR (400 MHz, $CD_3OD$) δ 7.08 (d, J=6.0 Hz, 1 H), 4.28 (s, 2 H), 4.14 (s, 1 H), 3.21 (dd, J=15.5, 4.6 Hz, 1 H), 3.06 (s, 3 H), 2.97 (s, 3 H), 2.94 (d, J=6.9 Hz, 2 H), 3.17-2.97 (m, 2 H), 2.35-2.25 (m, 2 H), 2.12-2.02 (m, 1 H), 1.70-1.58 (m, 1 H), 1.04 (d, J=6.9 Hz, 6 H); MS (ESI) m/z 518.47 (M+H).

S2-4-15

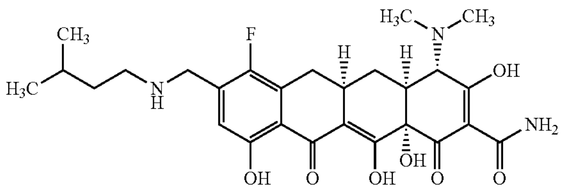

S2-4-15: $^1H$ NMR (400 MHz, $CD_3OD$) δ 7.03 (d, J=6.0 Hz, 1 H), 4.28 (s, 2 H), 4.12 (s, 1 H), 3.21 (dd, J=15.1, 4.6 Hz, 1 H), 3.05 (s, 3 H), 2.97 (s, 3 H), 2.94 (d, J=6.9 Hz, 2 H), 3.16-2.98 (m, 4 H), 2.38-2.22 (m, 2 H), 1.72-1.58 (m, 4 H), 0.97 (d, J=6.4 Hz, 6 H); MS (ESI) m/z 532.50 (M+H).

S2-4-16

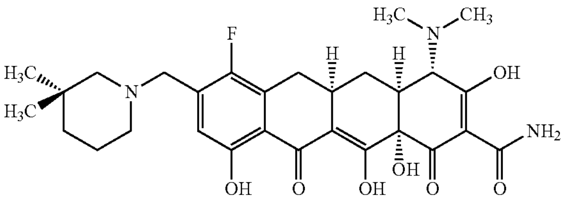

S2-4-16: $^1H$ NMR (400 MHz, $CD_3OD$) δ 7.10 (d, J=5.5 Hz, 1 H), 4.37 (s, 2 H), 4.10 (s, 1 H), 3.50 (m, 1 H), 3.27-2.93 (m, 5 H), 3.05 (s, 3 H), 2.97 (s, 3 H), 2.85 (m, 1 H), 2.36 (t, J=15.1 Hz, 1 H), 2.29-2.21 (m, 1 H), 1.99-1.81 (m, 2 H), 1.72-1.53 (m, 2 H), 1.49-1.38 (m, 1 H), 1.12 (s, 3 H), 1.02 (s, 3 H); MS (ESI) m/z 558.49 (M+H).

S2-4-17

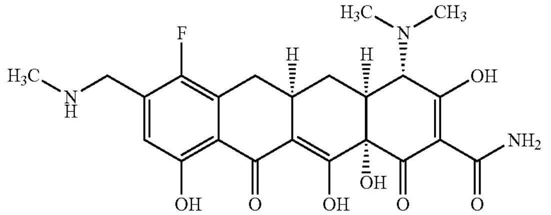

S2-4-17: $^1H$ NMR (400 MHz, $CD_3OD$) δ 7.01 (d, J=6.0 Hz, 1 H), 4.17 (s, 2 H), 4.10 (s, 1 H), 3.21 (dd, J=15.1, 4.6 Hz, 1 H), 3.05 (s, 3 H), 2.97 (s, 3 H), 2.84 (s, 3 H), 3.14-2.98 (m, 2 H), 2.21-2.39 (m, 2 H), 1.70-1.60 (m, 1 H); MS (ESI) m/z 476.31 (M+H).

S2-4-18

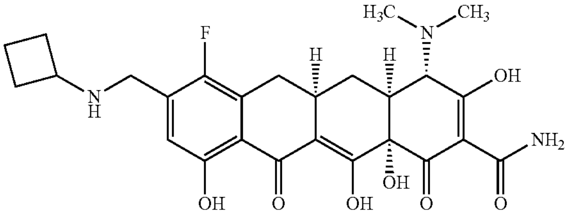

S2-4-18: $^1H$ NMR (400 MHz, $CD_3OD$) δ 7.00 (d, J=6.0 Hz, 1 H), 4.14 (s, 2 H), 4.10 (s, 1 H), 3.84 (m, 1 H), 3.21 (dd, J=15.5, 4.6 Hz, 1 H), 3.04 (s, 3 H), 2.96 (s, 3 H), 3.14-2.97 (m, 2 H), 2.36 (t, J=14.7 Hz, 1 H), 2.40-2.30 (m, 3 H), 2.28-2.17 (m, 3 H), 1.93 (m, 2 H), 1.68-1.58 (m, 1 H); MS (ESI) m/z 516.34 (M+H).

S2-4-19

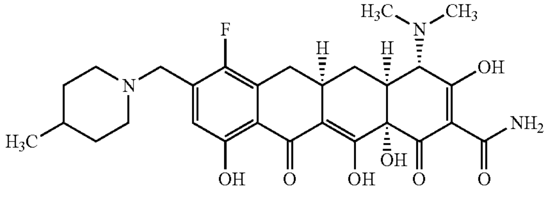

S2-4-19: $^1H$ NMR (400 MHz, $CD_3OD$) δ 7.10 (d, J=5.5 Hz, 1 H), 4.35 (s, 2 H), 4.12 (s, 1 H), 3.51 (m, 2 H), 3.24-2.98 (m, 5 H), 3.05 (s, 3 H), 2.97 (s, 3 H), 234 (t, J=15.1 Hz, 1 H), 2.29-2.21 (m, 1 H), 1.96-1.85 (m, 2 H), 1.79-1.56 (m, 2 H), 1.54-1.40 (m, 2 H), 0.99 (d, J=6.4 Hz, 3 H); MS (ESI) m/z 544.25 (M+H).

S2-4-20

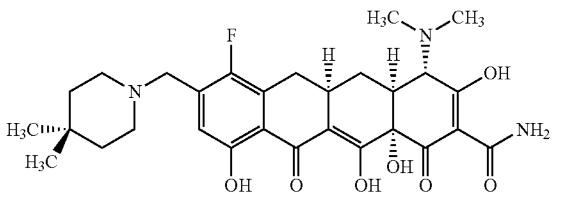

S2-4-20: $^1H$ NMR (400 MHz, $CD_3OD$) δ 7.07 (d, J=5.5 Hz, 1 H), 4.39 (s, 2 H), 4.09 (s, 1 H), 3.38 (m, 2 H), 3.24-2.98 (m, 5 H), 3.04 (s, 3 H), 2.96 (s, 3 H), 2.35 (t, J=15.1 Hz, 1 H), 2.27-2.19 (m, 1 H), 1.77-1.58 (m, 5 H), 1.09 (s, 3 H), 1.03 (s, 3 H); MS (ESI) m/z 558.29 (M+H).

S2-2-2

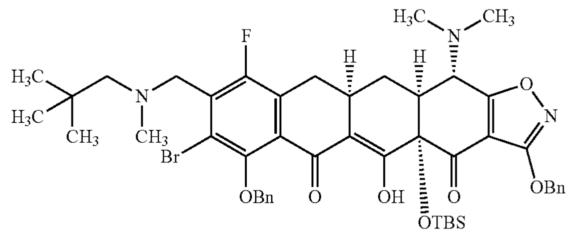

Compound S2-2-1 (30 mg, 0.033 mmol) was dissolved in 1,2-dichloroethane (2 mL). Formaldehyde solution-(12 μL, 0.16 mmol, 5.0 equiv) and acetic acid (9 μL, 0.17 mmol) were added via a syringe under a nitrogen atmosphere. After stirring at rt for 1 h, sodium triacetoxyborohydride (21 mg, 0.16 mmol) was added to the reaction mixture. LC/MS indicated that the starting material was consumed after 2 hrs. The reaction mixture was diluted with dichloromethane, washed with $NaHCO_3$ (saturated aqueous solution, 3×20 mL) and brine, dried over sodium sulfate, filtered, and concentrated under reduced pressure, yielding 26 mg of crude compound S2-2-2, which was used without further purification.

S2-4-21

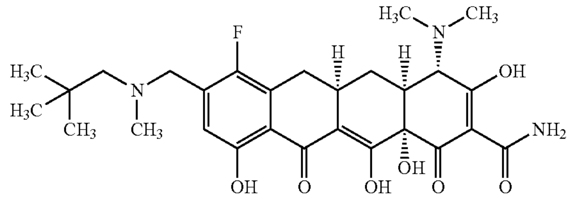

Aqueous HF (0.3 mL, 48-50%) solution was added to a $CH_3CN$ solution (1.0 mL) of S2-2-2 (crude, 26 mg) in a plastic vial at 25° C. The reaction was stirred at 25° C. for 18 hrs. The resulting mixture was poured into an aqueous solution (10 mL) of $K_2HPO_4$ (2 g). The solution was extracted with EtOAc (3×15 mL). The combined EtOAc extracts were dried over sodium sulfate and concentrated to give the crude intermediate.

Pd—C (5 mg, 10 wt %) was added to MeOH solution (2 mL) of the crude intermediate. HCl in MeOH (0.5 N, 0.5 mL) was added. The reaction was stirred under $H_2$ (balloon) at 25° C. for 2 hrs and filtered through a pad of Celite. The filtrate was concentrated, and the crude product was purified by HPLC on a Polymerx 10μ RP-γ 100 R column [30×21.20 mm, 10 micron, solvent A: 0.05 N HCl, solvent B: $CH_3CN$, sample in 2.0 mL (0.05 N HCl), gradient elution with 0→70% B over 15 min, mass-directed fraction collection]. Fractions containing the desired product were collected and freeze-dried, yielding product S2-4-21 as a yellow solid 19 mg (>95% for 3 steps): $^1H$ NMR (400 MHz, $CD_3OD$) δ 7.12 (d, J=5.8 Hz, 1 H), 4.58 (d, J=13.3 Hz, 1 H), 4.36 (d, J=13.3 Hz, 1 H), 4.11 (s, 1 H), 3.05 (s, 3 H), 2.97 (s, 3 H), 2.95 (s, 5 H), 3.26-3.01 (m, 3 H), 2.37 (t, J=14.6 Hz, 1 H), 2.29-2.22 (m, 1 H), 1.71-1.61 (m, 1 H), 1.08 (s, 9 H); MS (ESI) m/z 546.37 (M+H).

The following compounds were prepared according to the methods for S2-4-21 above, using either formaldehyde or substituting the appropriate aldehyde for formaldehyde.

S2-4-22

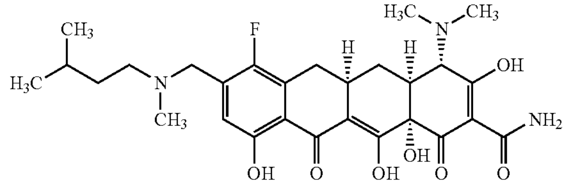

S2-4-22: $^1H$ NMR (400 MHz, $CD_3OD/DCl$) δ 7.13 (d, J=5.48 Hz, 1 H), 4.60-4.48 (m, 1 H), 4.36-4.26 (m, 1 H), 4.17 (s, 1 H), 3.40-2.94 (m, 11 H), 2.85 (s, 3 H), 2.38-2.26 (m, 2 H), 1.78-1.56 (m, 4 H), 1.00-0.92 (m, 6 H); MS (ESI) m/z 546.30 (M+H).

S2-4-23

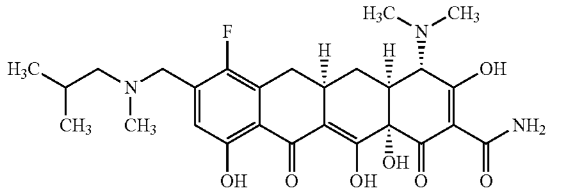

S2-4-23: $^1H$ NMR (400 MHz, $CD_3OD/DCl$) δ 7.11 (d, J=5.96 Hz, 1 H), 4.63-4.52 (m, 1 H), 4.33-4.24 (m, 1 H), 4.16 (s, 1 H), 3.26-2.94 (m, 11 H), 2.87 (s, 3 H), 2.38-2.26 (m, 3 H), 1.70-1.56 (m, 1 H), 1.10-1.02 (m, 6 H); MS (ESI) m/z 532.31 (M+H).

S2-4-24

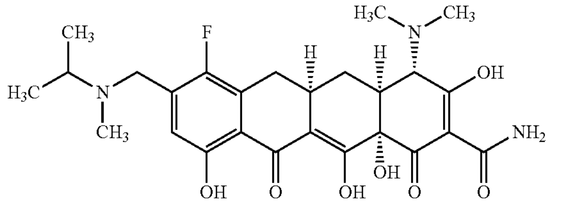

S2-4-24: $^1H$ NMR (400 MHz, $CD_3OD/DCl$) δ 7.13 (d, J=5.92 Hz, 1 H), 4.60-4.50 (m, 1 H), 4.24-4.14 (m, 2 H), 3.76-3.66 (m, 1 H), 3.26-2.94 (m, 9 H), 2.79 (s, 3 H), 2.40-2.26 (m, 2 H), 1.70-1.58 (m, 1 H), 1.50-1.40 (m, 6 H); MS (ESI) m/z 518.31 (M+H).

S2-4-25

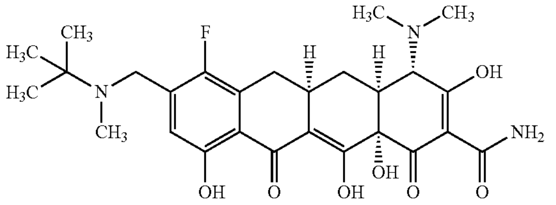

S2-4-25: $^1$H NMR (400 MHz, $CD_3OD/DCl$) δ 7.10 (d, J=4.1 Hz, 1 H), 4.80-4.72 (m, 1 H), 4.15 (s, 1 H), 4.04-3.96 (m, 1 H), 3.26-2.94 (m, 9 H), 2.78-2.74 (m, 3 H), 2.39-2.25 (m, 2 H), 1.72-1.53 (m, 10 H); MS (ESI) m/z 532.30 (M+H).

S2-4-26

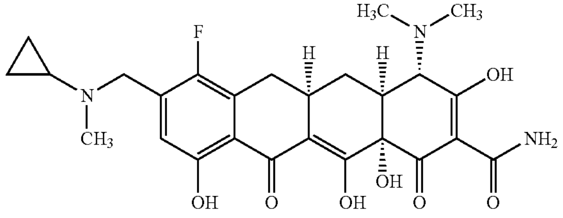

S2-4-26: $^1$H NMR (400 MHz, $CD_3OD/DCl$) δ 7.13 (d, J=5.5 Hz, 1 H), 4.64-4.46 (m, 2 H), 4.17 (s, 1 H), 3.26-2.94 (m, 12 H), 2.39-2.25 (m, 2 H), 1.70-1.56 (m, 1 H), 1.14-1.04 (m, 1 H), 0.98-0.85 (m, 4 H); MS (ESI) m/z 516.22 (M+H).

S2-4-27

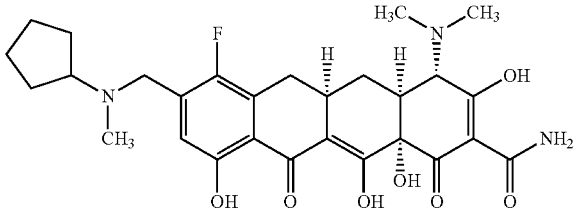

S2-4-27: $^1$H NMR (400 MHz, $CD_3OD/DCl$) δ 7.12 (d, J=5.5 Hz, 1 H), 4.62-4.53 (m, 1 H), 4.28-4.20 (m, 1 H), 4.17 (s, 1 H), 3.84-3.74 (m, 1 H), 3.26-2.94 (m, 9 H), 2.79 (s, 3 H), 2.39-2.25 (m, 3 H), 2.23-2.13 (m, 1 H), 1.97-1.81 (m, 4 H), 1.80-1.55 (m, 3 H); MS (ESI) m/z 544.27 (M+H).

S2-4-28

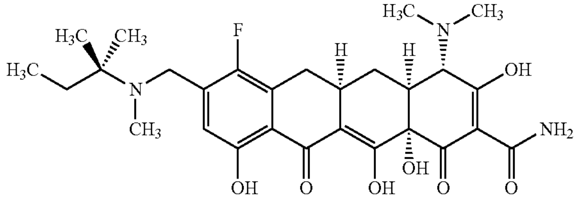

S2-4-28: $^1$H NMR (400 MHz, $CD_3OD/DCl$) δ 7.10 (d, J=5.96 Hz, 1 H), 4.80-4.71 (m, 1 H), 4.18 (s, 1 H), 4.06-198 (m, 1 H), 3.26-2.95 (m, 9 H), 2.76 (s, 3 H), 2.37-2.25 (m, 2 H), 2.01-1.89 (m, 2 H), 1.69-1.54 (m, 1 H), 1.51 (s, 3 H), 1.48 (s, 3 H), 1.07 (t, J=6.4 Hz, 3 H); MS (ESI) m/z 546.27 (M+H).

S2-4-29

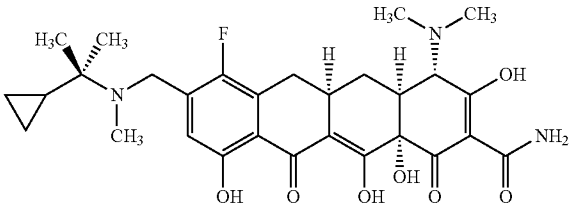

S2-4-29: $^1$H NMR (400 MHz, $CD_3OD/DCl$) δ 7.11 (d, J=5.0 Hz, 1 H), 4.96-4.88 (m, 1 H), 4.16 (s, 1 H), 4.10-4.01 (m, 1 H), 3.26-2.95 (m, 9 H), 2.82 (s, 3 H), 2.39-2.25 (m, 2 H), 1.70-1.58 (m, 1 H), 1.50-1.28 (m, 7 H), 0.82-0.59 (m, 4 H); MS (ESI) m/z 558.28 (M+H).

S2-4-30

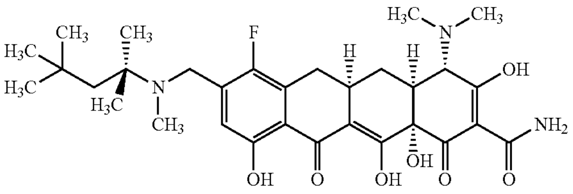

S2-4-30: $^1$H NMR (400 MHz, $CD_3OD/DCl$) δ 7.10 (d, J=5.5 Hz, 1 H), 4.82-4.74 (m, 1 H), 4.17 (s, 1 H), 4.05-3.97 (m, 1 H), 3.28-2.95 (m, 9 H), 2.76 (s, 3 H), 2.38-2.26 (m, 2 H), 2.01-1.80 (m, 2 H), 1.76-1.56 (m, 7 H), 1.12 (s, 9 H); MS (ESI) m/z 588.29 (M+H).

S2-4-31

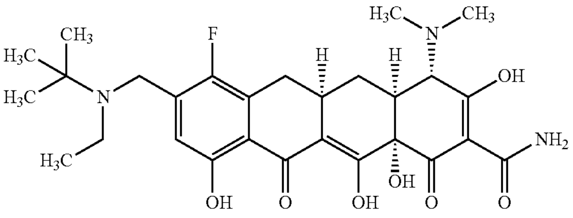

S2-4-31: $^1$H NMR (400 MHz, $CD_3OD/DCl$) δ 7.21 (d, J=5.0 Hz, 1 H), 4.70-4.61 (m, 1 H), 4.32-4.26 (m, 1 H), 4.19 (s, 1 H), 3.56-3.45 (m, 1 H), 3.34-2.95 (m, 10 H), 2.40-2.26 (m, 2 H), 1.72-1.55 (m, 10 H), 1.19 (t, J=7.3 Hz, 3 H); MS (ESI) m/z 546.26 (M+H).

S2-4-32

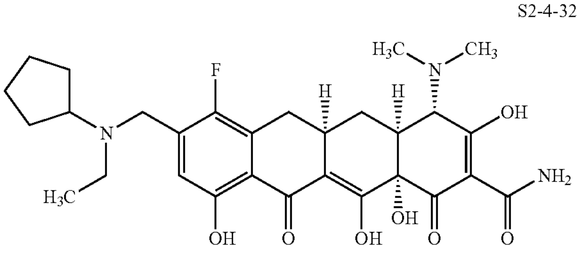 [SMILES: CCN(Cc1cc(O)c2c(c1F)C[C@H]1C[C@H]3[C@H](N(C)C)C(O)=C(C(N)=O)C(=O)[C@@]3(O)C(O)=C1C2=O)C1CCCC1]

S2-4-32: $^1$H NMR (400 MHz, $CD_3OD/DCl$) δ 7.12 (d, J=4.1 Hz, 1 H), 4.51-4.34 (m, 2 H), 4.16 (s, 1 H), 3.92-3.82

(m, 1 H), 3.34-2.94 (m, 11 H), 2.40-2.08 (m, 4 H), 1.98-1.79 (m, 4 H), 1.78-1.55 (m, 3 H), 1.36 (t, J=7.4 Hz, 3 H); MS (ESI) m/z 558.29 (M+H).

S2-4-33

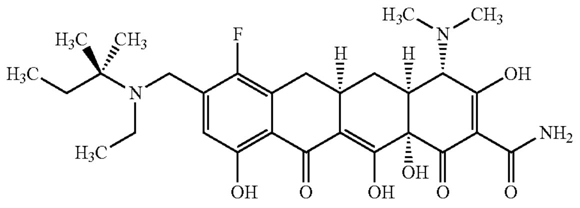

S2-4-33: $^{1}$H NMR (400 MHz, $CD_3OD/DCl$) δ 7.19 (d, J=5.5 Hz, 1 H), 4.72-4.63 (m, 1 H), 4.34-4.24 (m, 1 H), 4.17 (s, 1 H), 3.59-3.50 (m, 1 H), 3.26-2.96 (m, 10 H), 2.40-2.26 (m, 2 H), 2.04-1.93 (m, 2 H), 1.70-1.50 (m, 7 H), 1.18 (t, J=7.3 Hz, 3 H), 1.06 (t, J=7.6 Hz, 3 H); MS (ESI) m/z 560.35 (M+H).

S2-4-34

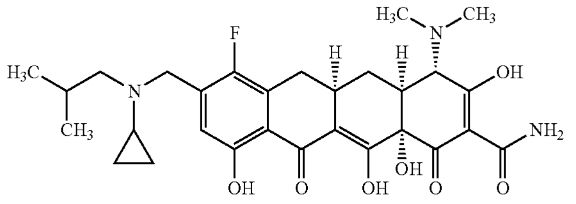

S2-4-34: $^{1}$H NMR (400 MHz, $CD_3OD/DCl$) δ 7.15 (d, J=5.5 Hz, 1 H), 4.64-4.44 (m, 2 H), 4.16 (s, 1 H), 3.26-2.94 (m, 11 H), 2.93-2.82 (m, 1 H), 2.41-2.25 (m, 3 H), 1.70-1.56 (m, 1 H), 1.20-1.05 (m, 7 H), 1.05-0.84 (m, 3 H); MS (ESI) m/z 558.27 (M+H).

S2-4-35

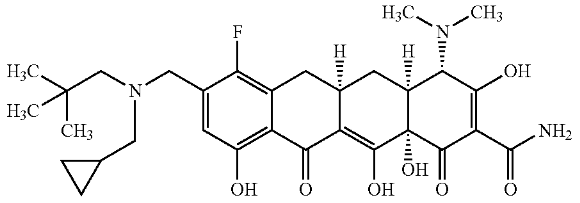

S2-4-35: $^{1}$H NMR (400 MHz, $CD_3OD/DCl$) δ 7.20 (d, J=3.2 Hz, 1 H), 4.60-4.49 (m, 2 H), 4.16 (s, 1 H), 3.45-3.36 (m, 1 H), 3.34-2.94 (m, 12 H), 2.40-2.26 (m, 2 H), 1.70-1.56 (m, 1 H), 1.36-1.26 (m, 1 H), 1.07 (s, 9 H), 0.86-0.74 (m, 2 H), 0.57-0.49 (m, 2 H); MS (ESI) m/z 586.33 (M+H).

S2-4-36

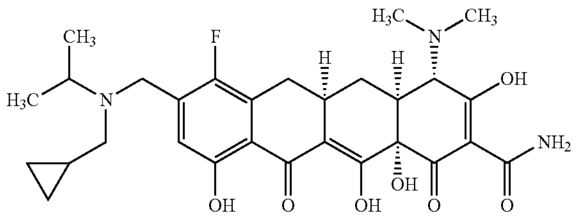

S2-4-36: $^{1}$H NMR (400 MHz, $CD_3OD/DCl$) δ 7.13 (d, J=5.5 Hz, 1 H), 4.54-4.33 (m, 2 H), 4.16 (s, 1 H), 3.98-3.86 (m, 1 H), 3.26-2.94 (m, 11 H), 2.40-2.24 (m, 2 H), 1.70-1.56 (m, 1 H), 1.52-1.35 (m, 6 H), 1.20-1.08 (m, 1 H), 0.80-0.70 (m, 2 H), 0.50-0.40 (m, 2 H); MS (ESI) m/z 558.21 (M+H).

S2-4-37

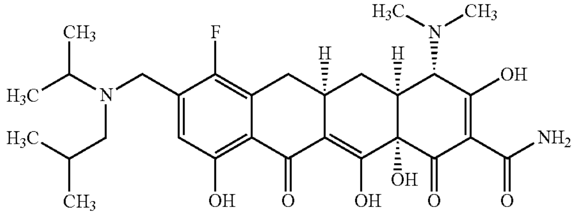

S2-4-37: $^{1}$H NMR (400 MHz, $CD_3OD/DCl$) δ 7.18 (d, J=5.96 Hz, 1 H), 4.52-4.35 (m, 2 H), 4.17 (s, 1 H), 3.82-3.70 (m, 1 H), 3.26-2.94 (m, 11 H), 2.41-2.28 (m, 2 H), 2.04-1.93 (m, 1 H), 1.71-1.58 (m, 1 H), 1.52-1.38 (m, 6 H), 1.08-1.02 (d, J=6.9 Hz, 3 H), 1.00-0.94 (d, J=6.4 Hz, 3 H); MS (ESI) m/z 560.20 (M+H).

S2-4-38

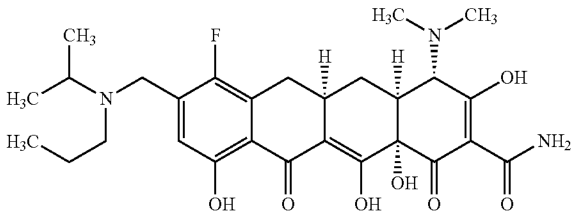

S2-4-38: $^{1}$H NMR (400 MHz, $CD_3OD/DCl$) δ 7.11 (d, J=5.5 Hz, 1 H), 4.54-4.44 (m, 1 H), 4.28-4.22 (m, 1 H), 4.15 (s, 1 H), 3.80-3.72 (m, 1 H), 3.36-2.94 (m, 11 H), 2.40-2.26 (m, 2 H), 1.88-1.54 (m, 3 H), 1.50-1.38 (m, 6 H), 1.03-0.94 (m, 3 H); MS (ESI) m/z 546.20 (M+H).

S2-4-39

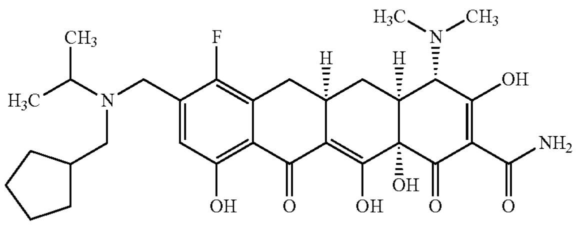

S2-4-39: $^1$H NMR (400 MHz, $CD_3OD$/DCl) δ 7.17 (d, J=5.5 Hz, 1 H), 4.52-4.33 (m, 2 H), 4.17 (s, 1 H), 3.84-3.72 (m, 1 H), 3.36-2.94 (m, 11 H), 2.40-2.16 (m, 3 H), 1.99-1.83 (m, 2 H), 1.75-1.53 (m, 5 H), 1.52-1.42 (m, 6 H), 1.34-1.15 (m, 2 H); MS (ESI) m/z 586.26 (M+H).

S2-4-40

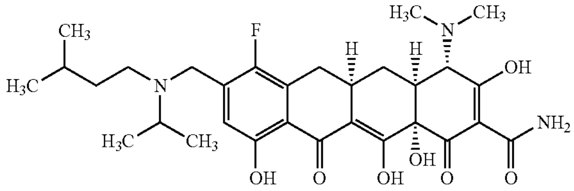

S2-4-40: $^1$H NMR (400 MHz, $CD_3OD$/DCl) δ 7.14 (d, J=5.5 Hz, 1 H), 4.56-4.47 (m, 1 H), 4.33-4.24 (m, 1 H), 4.17 (s, 1 H), 3.84-3.72 (m, 1 H), 3.36-2.94 (m, 11 H), 2.40-2.25 (m, 2 H), 1.75-1.54 (m, 4 H), 1.52-1.40 (m, 6 H), 1.02-0.88 (m, 6 H); MS (ESI) m/z 574.26 (M+H).

S2-4-41

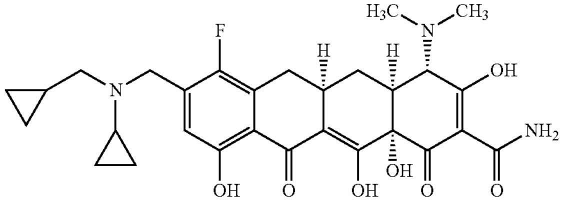

S2-4-41: $^1$H NMR (400 MHz, $CD_3OD$) δ 7.10 (d, J=5.9 Hz, 1 H), 4.64 (br, s, 1 H), 4.57 (br, s, 1 H), 4.10 (s, 1 H), 3.21 (dd, J=15.1, 4.6 Hz, 1 H), 3.05 (s, 3 H), 2.97 (s, 3 H), 3.15-2.89 (m, 5 H), 2.36 (m, 1 H), 2.29-2.21 (m, 1 H), 1.70-1.60 (m, 1 H), 1.33-1.23 (m, 1 H), 1.10-0.85 (m, 3 H), 0.85-0.79 (m, 2 H), 0.78-0.67 (m, 1 H), 0.53-0.47 (m, 2 H); MS (ESI) m/z 556.33 (M+H).

S2-4-42

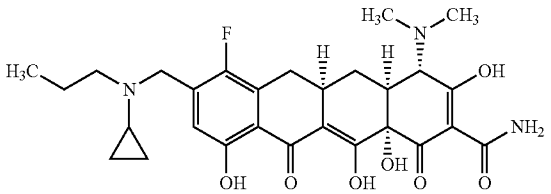

S2-4-42: $^1$H NMR (400 MHz, $CD_3OD$) δ 7.10 (d, J=5.5 Hz, 1 H), 4.54 (d, J=6.4 Hz, 2 H), 4.12 (s, 1 H), 3.21 (dd, J=15.1, 4.6 Hz, 1 H), 3.17-2.95 (m, 4 H), 3.05 (s, 3 H), 2.97 (s, 3 H), 2.92-2.87 (m, 1 H), 2.36 (t, J=13.8 Hz, 1 H), 2.29-2.21 (m, 1 H), 1.9-1.84 (m, 2 H), 1.70-1.60 (m, 1 H), 1.03 (t, J=7.3 Hz, 3 H), 1.10-0.85 (m, 3 H), 0.82-0.68 (m, 1 H); MS (ESI) m/z 544.33 (M+H).

S2-4-43

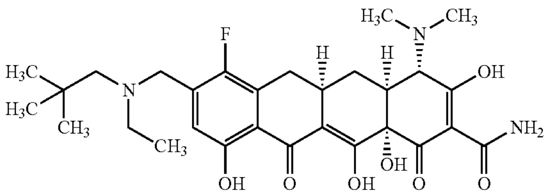

S2-4-43: $^1$H NMR (400 MHz, $CD_3OD$) δ 7.09 (d, J=5.5 Hz, 1 H), 4.51 (d, J=13.3 Hz, 1 H), 4.39 (d, J=13.3 Hz, 1 H), 4.07 (s, 1 H), 3.03 (s, 3 H), 2.95 (s, 3 H), 3.25-2.96 (m, 7 H), 2.42-2.33 (m, 1 H), 2.26-2.18 (m, 1 H), 1.70-1.60 (m, 1 H), 1.43 (t, J=7.3 Hz, 3 H), 1.06 (s, 9 H); MS (ESI) m/z 560.50 (M+H).

S2-4-44

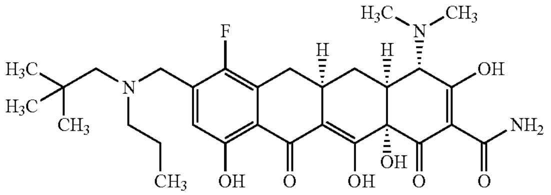

S2-4-44: $^1$H NMR (400 MHz, $CD_3OD$) δ 7.09 (d, J=5.5 Hz, 1 H), 4.52 (d, J=13.3 Hz, 1 H), 4.41 (d, J=13.3 Hz, 1 H), 4.07 (s, 1 H), 3.03 (s, 3 H), 2.96 (s, 3 H), 3.25-2.96 (m, 7 H), 2.43-2.33 (m, 1 H), 2.27-2.19 (m, 1 H), 1.98-1.88 (m, 1 H), 1.86-1.74 (m, 1 H), 1.71-1.61 (m, 1 H), 1.08 (s, 9 H), 1.01 (t, J=6.9 Hz, 3 H); MS (ESI) m/z 574.52 (M+H).

S2-4-45

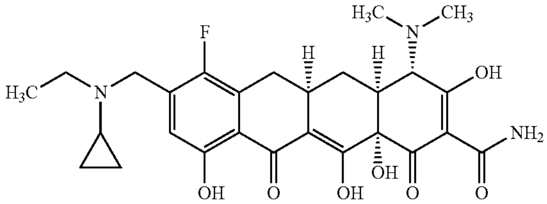

S2-4-45: $^1$H NMR (400 MHz, $CD_3OD$) δ 7.08 (d, J=5.5 Hz, 1 H), 4.53 (d, J=6.8 Hz, 2 H), 4.10 (s, 1 H), 3.41 (q, J=7.3 Hz, 2 H), 3.21 (dd, J=15.1, 4.6 Hz, 1 H), 3.17-2.95 (m, 2 H), 3.04 (s, 3 H), 2.96 (s, 3 H), 2.93-2.85 (m, 1 H), 2.36 (t, J=13.8 Hz, 1 H), 2.29-2.20 (m, 1 H), 1.69-1.59 (m, 1 H), 1.46 (t, J=7.3 Hz, 3 H), 1.10-0.84 (m, 3 H), 0.79-0.69 (m, 1 H); MS (ESI) m/z 530.38 (M+H).

S2-4-46

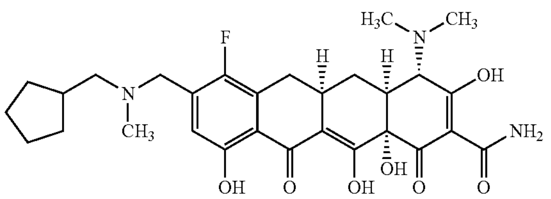

S2-4-46: $^1$H NMR (400 MHz, $CD_3OD$) δ 7.07 (d, J=5.9 Hz, 1 H), 4.58 (d, J=13.3 Hz, 1 H), 4.26 (d, J=13.3 Hz, 1 H), 4.10 (s, 1 H), 3.05 (s, 3 H), 2.97 (s, 3 H), 2.87 (s, 5 H), 3.27-2.96 (m, 3 H), 2.43-2.32 (m, 2 H), 2.28-2.20 (m, 1 H), 2.03-1.91 (m, 2 H), 1.78-1.60 (m, 5 H), 1.36-1.20 (m, 2 H); MS (ESI) m/z 558.40 (M+H).

S2-4-47

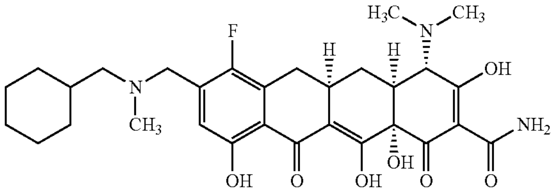

S-2-4-47: $^1$H NMR (400 MHz, $CD_3OD$) δ 7.06 (d, J=5.9 Hz, 1 H), 4.56 (d, J=13.3 Hz, 1 H), 4.23 (d, J=13.3 Hz, 1 H), 4.09 (s, 1 H), 3.04 (s, 3 H), 2.97 (s, 3 H), 2.86 (s, 5 H), 3.27-2.96 (m, 3 H), 2.37 (t, J=13.8 Hz, 1 H), 2.28-2.20 (m, 1 H), 1.96-1.59 (m, 7 H), 1.44-1.30 (m, 2 H), 1.29-1.19 (m, 1 H), 1.13-0.95 (m, 2 H); MS (ESI) m/z 572.41 (M+H).

S2-4-48

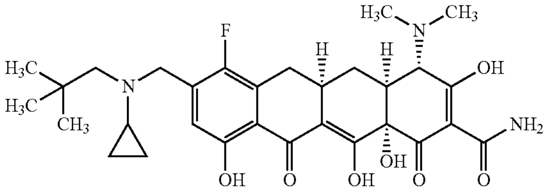

S2-4-48: $^1$H NMR (400 MHz, $CD_3OD$) δ 7.09 (d, J=5.5 Hz, 1 H), 4.52 (d, J=13.3 Hz, 1 H), 4.41 (d, J=13.3 Hz, 1 H), 4.07 (s, 1 H), 3.03 (s, 3 H), 2.96 (s, 3 H), 3.25-2.96 (m, 6 H), 2.43-2.33 (m, 1 H), 2.27-2.19 (m, 1 H), 1.66 (m, 1 H), 1.08 (s, 9 H), 1.10-0.85 (m, 3 H), 0.81-0.71 (m, 1 H); MS (ESI) m/z 572.43 (M+H).

S2-4-49

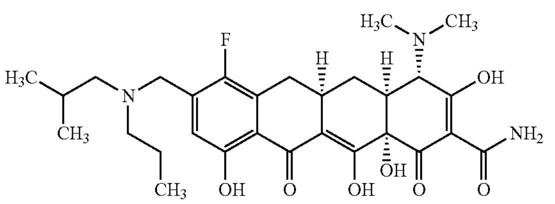

S2-4-49: $^1$H NMR (400 MHz, $CD_3OD$) δ 7.08 (d, J=6.0 Hz, 1 H), 4.50 (d, J=13.7 Hz, 1 H), 4.37 (d, J=13.7 Hz, 1 H), 4.28 (s, 2 H), 4.10 (s, 1 H), 3.21 (dd, J=15.5, 4.6 Hz, 1 H), 3.05 (s, 3 H), 2.97 (s, 3 H), 3.17-2.98 (m, 6 H), 2.37 (t, J=14.7 Hz, 1 H), 2.29-2.12 (m, 2 H), 1.93-1.73 (m, 2 H), 1.71-1.61 (m, 1 H), 1.09-0.98 (m, 9 H); MS (ESI) m/z 560.35 (M+H).

S2-4-50

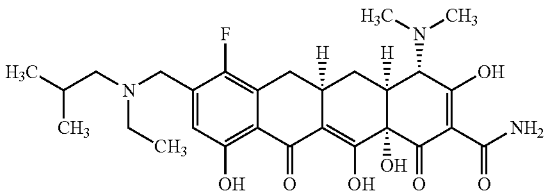

S-2-4-50: $^1$H NMR (400 MHz, $CD_3OD$) δ 7.08 (d, J=6.0 Hz, 1 H), 4.50 (d, J=13.5 Hz, 1 H), 4.34 (d, J=13.5 Hz, 1 H), 4.28 (s, 2 H), 4.10 (s, 1 H), 3.04 (s, 3 H), 2.96 (s, 3 H), 3.27-2.97 (m, 7 H), 2.36 (t, J=14.7 Hz, 1 H), 2.28-2.12 (m, 2 H), 1.70-1.60 (m, 1 H), 1.39 (t, J=6.9 Hz, 3 H), 1.05 (dd, J=15.1, 6.4 Hz, 6 H); MS (ESI) m/z 546.39 (M+H).

S2-4-51

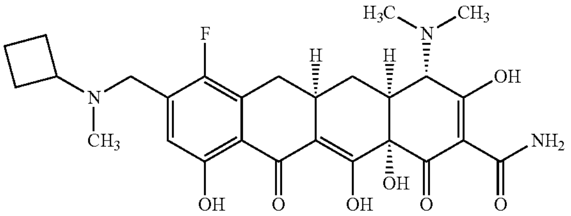

S2-4-51: $^1$H NMR (400 MHz, $CD_3OD$) δ 7.07 (d, J=6.0 Hz, 1 H), 4.41 (d, J=12.4 Hz, 1 H), 4.14 (d, J=12.4 Hz, 1 H), 4.12 (s, 1 H), 3.88 (m, 1 H), 3.05 (s, 3 H), 2.97 (s, 3 H), 3.25-2.97 (m, 3 H), 2.70 (s, 3 H), 2.43-2.22 (m, 6 H), 1.96-1.77 (m, 2 H), 1.69-1.59 (m, 1 H); MS (ESI) m/z 530.34 (M+H).

S2-4-52

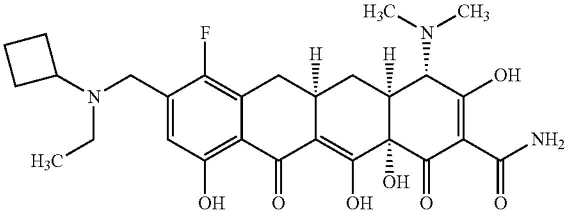

S2-4-52: $^1$H NMR (400 MHz, $CD_3OD$) δ 7.09 (d, J=6.0 Hz, 1 H), 4.31 (br, s, 2 H), 4.14 (s, 1 H), 4.00-3.92 (m, 1 H), 3.06 (s, 3 H), 2.97 (s, 3 H), 3.26-2.97 (m, 5 H), 2.42-2.22 (m, 6 H), 1.92-1.77 (m, 2 H), 1.69-1.59 (m, 1 H), 1.35 (t, J=6.8 Hz, 3 H); MS (ESI) m/z 544.35 (M+H).

S2-4-53

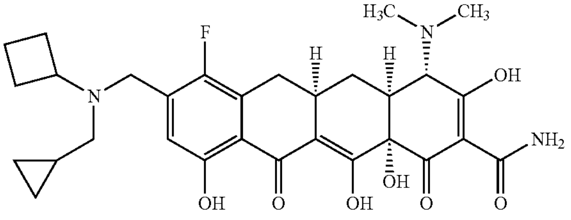

S2-4-53: $^1$H NMR (400 MHz, $CD_3OD$) δ 7.11 (d, J=6.0 Hz, 1 H), 4.48 (m, 1 H), 4.37 (m, 1 H), 4.13 (s, 1 H), 4.04 (m,

1 H), 3.05 (s, 3 H), 2.97 (s, 3 H), 3.25-2.95 (m, 5 H), 2.45-2.13 (m, 6 H), 1.89-1.74 (m, 2 H), 1.69-1.59 (m, 1 H), 1.19-1.11 (m, 1 H), 0.81-0.72 (m, 2 H), 0.46-0.36 (m, 2 H); MS (ESI) m/z 570.39 (M+H).

S2-4-54

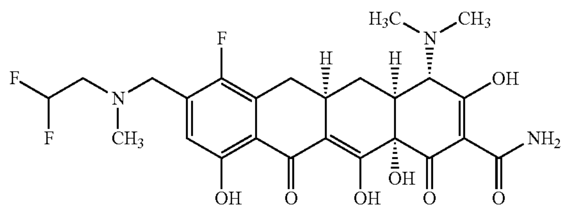

S2-4-54: $^{1}$H NMR (400 MHz, $CD_3OD$) δ 7.09 (d, J=5.0 Hz, 1 H), 6.48 (t, J=53.6 Hz, 1 H), 4.55 (s, 2 H), 4.11 (s, 1 H), 3.83 (t, J=14.2 Hz, 2 H), 3.05 (s, 3 H), 3.01 (s, 3 H), 2.97 (s, 3 H), 3.25-2.98 (m, 5 H), 2.37 (t, J=14.7 Hz, 1 H), 2.29-2.21 (m, 1 H), 1.70-1.60 (m, 1 H); MS (ESI) m/z 540.31 (M+H).

S2-4-55

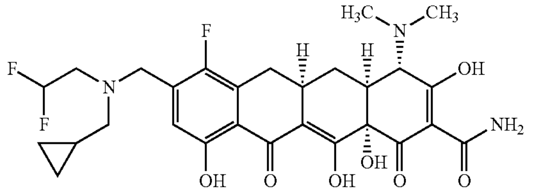

S2-4-55: $^{1}$H NMR (400 MHz, $CD_3OD$) δ 7.11 (br, s, 1 H), 6.51 (t, J=53.6 Hz, 1 H), 4.64 (s, 2 H), 4.12 (s, 1 H), 3.87 (t, J=14.2 Hz, 2 H), 3.05 (s, 3 H), 2.97 (s, 3 H), 3.25-2.98 (m, 7 H), 2.44-2.22 (m, 2 H), 1.70-1.61 (m, 1 H), 1.27-1.19 (m, 1 H), 0.88-0.80 (m, 2 H), 0.55-0.45 (m, 2 H); MS (ESI) m/z 580.34 (M+H).

S2-4-56

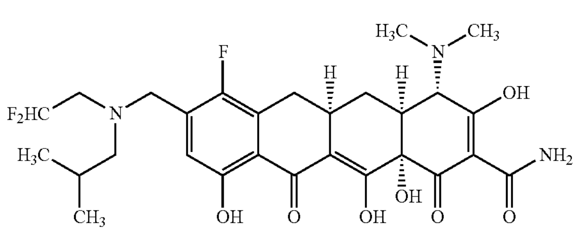

S2-4-56: $^{1}$H NMR (400 MHz, $CD_3OD$) δ 7.07 (d, J=5.0 Hz, 1 H), 6.38 (t, J=53.6 Hz, 1 H), 4.40 (br, s, 2 H), 4.09 (s, 1 H), 3.56 (m, 2 H), 3.03 (s, 3 H), 2.96 (s, 3 H), 3.22-2.98 (m, 5 H), 2.35 (t, J=14.2 Hz, 1 H), 2.28-2.08 (m, 2 H), 1.69-1.59 (m, 1 H), 1.02 (d, J=6.9 Hz, 6 H); MS (ESI) m/z 582.34 (M+H).

S2-4-57

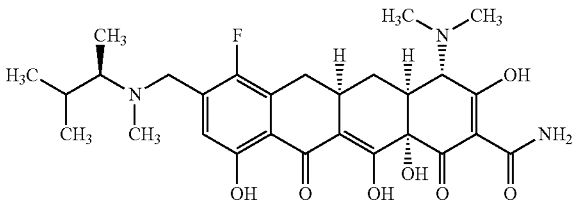

S2-4-57: $^{1}$H NMR (400 MHz, $CD_3OD$) δ 7.08 (t, J=6.0 Hz, 1 H), 4.61 (dd, J=18.3, 13.7 Hz, 1 H), 4.18 (dd, J=78.3, 13.7 Hz, 1 H), 4.10 (s, 1 H), 3.87 (t, J=14.2 Hz, 1 H), 3.05 (s, 3 H), 2.97 (s, 3 H), 2.84 (s, 3 H), 3.25-2.98 (m, 3 H), 2.42-2.20 (m, 3 H), 1.70-1.60 (m, 1 H), 1.41 (dd, J=30.2, 6.9 Hz, 3 H), 1.13 (dd, J=30.2, 6.9 Hz, 3 H), 1.04 (dd, J=15.6, 6.9 Hz, 3 H); MS (ESI) m/z 546.30 (M+H).

S2-4-58

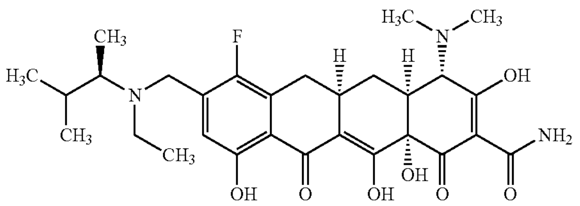

S2-4-58: $^{1}$H NMR (400 MHz, $CD_3OD$) δ 7.07 (m, 1 H), 4.08 (s, 1 H), 4.61 (dd, J=18.3, 13.7 Hz, 1 H), 4.18 (dd, J=78.3, 13.7 Hz, 1 H), 3.47 (m, 1 H), 3.03 (s, 3 H), 2.96 (s, 3 H), 3.41-2.97 (m, 5 H), 2.42-2.20 (m, 3 H), 1.70-1.60 (m, 1 H), 1.37 (dd, J=30.2, 6.9 Hz, 3 H), 1.29 (t, J=6.9 Hz, 3 H), 1.13 (dd, J=30.2, 6.9 Hz, 3 H), 1.03 (dd, J=15.6, 6.9 Hz, 3 H); MS (ESI) m/z 560.33 (M+H).

S2-4-59

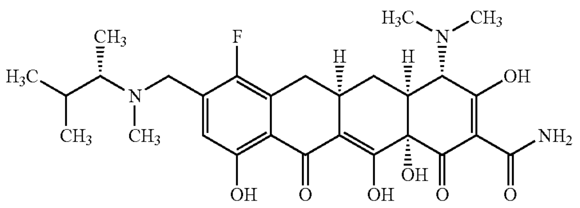

S2-4-59: $^{1}$H NMR (400 MHz, $CD_3OD$) δ 7.08 (t, J=6.0 Hz, 1 H), 4.61 (dd, J=18.3, 13.7 Hz, 1 H), 4.18 (dd, J=78.3, 13.7 Hz, 1 H), 4.10 (s, 1 H), 3.05 (s, 3 H), 2.97 (s, 3 H), 3.27-2.98 (m, 4 H), 2.83 (s, 3 H), 2.42-2.20 (m, 3 H), 1.70-1.60 (m, 1 H), 1.41 (dd, J=30.2, 6.9 Hz, 3 H), 1.13 (dd, J=30.2, 6.9 Hz, 3 H), 1.04 (dd, J=15.6, 6.9 Hz, 3 H); MS (ESI) m/z 546.32 (M+H).

S2-4-60

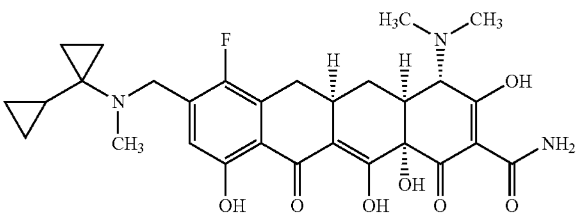

S2-4-60: $^1H$ NMR (400 MHz, $CD_3OD$) δ 7.10 (d, J=5.9 Hz, 1 H), 4.75 (d, J=13.3 Hz, 1 H), 4.60 (d, J=13.3, 1 H), 4.10 (s, 1 H), 3.04 (s, 3 H), 3.02 (s, 3 H), 2.96 (s, 3 H), 3.25-2.96 (m, 3 H), 2.41-2-20 (m, 2 H), 1.70-1.59 (m, 2 H), 1.19-1.01 (m, 2 H), 0.96-0.88 (m, 1 H), 0.86-0.70 (m, 3 H), 0.43-0.31 (m, 2 H); MS (ESI) m/z 556.31 (M+H).

S2-4-61

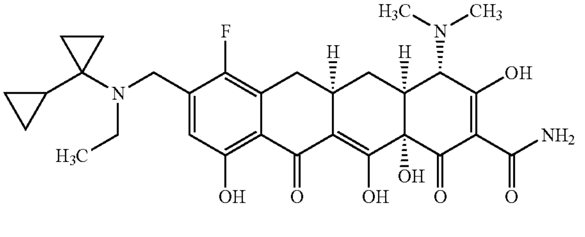

S2-4-61: $^1H$ NMR (400 MHz, $CD_3OD$) δ 7.10 (d, J=5.9 Hz, 1 H), 4.75 (d, J=13.3 Hz, 1 H), 4.60 (d, J=13.3, 1 H), 4.10 (s, 1 H), 3.05 (s, 3 H), 2.96 (s, 3 H), 3.25-2.96 (m, 5 H), 2.41-2-20 (m, 2 H), 1.70-1.59 (m, 2 H), 1.35 (t, J=6.8 Hz, 3 H), 1.19-1.01 (m, 2 H), 0.96-0.88 (m, 1 H), 0.86-0.70 (m, 3 H), 0.43-0.31 (m, 2 H); MS (ESI) m/z 570.32 (M+H).

S2-4-62

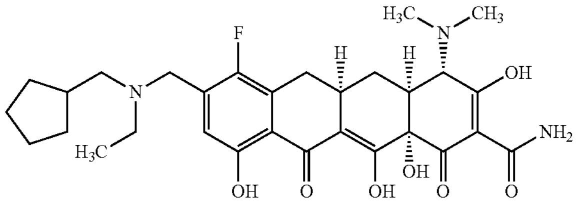

S2-4-62: $^1H$ NMR (400 MHz, $CD_3OD$) δ 7.17 (d, J=6.0 Hz, 1 H), 4.51-4.33 (m, 2 H), 4.17 (s, 1 H), 3.27-3.19 (m, 1 H), 3.08 (s, 3 H), 2.99 (s, 3 H), 3.17-2.97 (m, 4 H), 2.38-2.27 (m, 2 H), 2.27-2.18 (m, 1 H), 1.99-1.83 (m, 2 H), 1.74-1.55 (m, 5 H), 1.43 (t, J=7.3 Hz, 3 H), 1.32-1.14 (m, 2 H); MS (ESI) m/z 572.39 (M+H).

S2-4-63

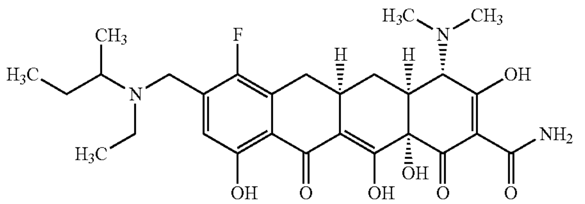

S2-4-63: $^1H$ NMR (400 MHz, $CD_3OD$) δ 7.11-7.07 (m, 1 H), 4.61 (dd, J=18.3, 13.7 Hz, 1 H), 4.29, 4.09 (ABq, J=13.7 Hz, 1 H), 4.11 (s, 1 H), 3.51-3.43 (m, 1 H), 3.03 (s, 3 H), 2.96 (s, 3 H), 3.41-2.97 (m, 5 H), 2.34 (t, J=6.9 Hz, 1 H), 2.27-2.20 (m, 1 H), 2.06-1.95 (m, 1 H), 1.74-1.59 (m, 2 H), 1.44 (d, J=6.1 Hz, 3 H), 1.29 (t, J=6.9 Hz, 3 H), 1.08 (t, J=7.6 Hz, 3 H); MS (ESI) m/z 546.38 (M+H).

S2-4-64

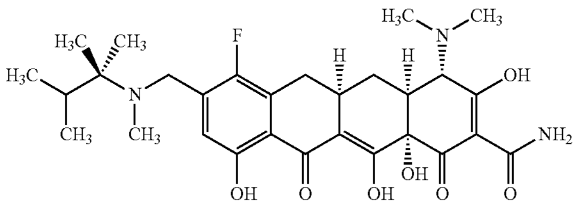

S2-4-64: $^1H$ NMR (400 MHz, $CD_3OD$) δ 7.11 (d, J=6.0 Hz, 1 H), 4.80-4.71 (m, 1 H), 4.18 (s, 1 H), 4.06-3.98 (m, 1 H), 3.26-2.95 (m, 9 H), 2.76 (s, 3 H), 2.42-2.30 (m, 2 H), 2.01-1.89 (m, 1 H), 1.69-1.54 (m, 1 H), 1.51 (s, 3 H), 1.48 (s, 3 H), 1.02 (d, J=6.4 Hz, 6 H); MS (ESI) m/z 560.23 (M+H).

S2-1-3

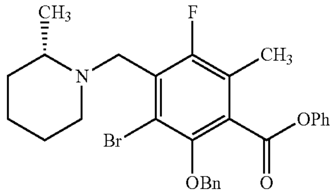

Compound S1-7 (89 mg, 0.20 mmol, 1.0 equiv) and (S)-2-methylpiperidine (60 μL, 0.50 mmol, 2.5 equiv) were dissolved in 1,2-dichloroethane (2 mL). Titanium(IV) isopropoxide (0.18 mL, 0.60 mmol, 3.0 equiv) was added at rt. After stirring at rt overnight, LC/MS indicated that most of the starting material was consumed and the intermediate formed. MeOH (1 mL) and sodium borohydride (40 mg, 1.1 mmol, 5.5 equiv, added in 4 equal portions) were added until the intermediate was completely converted to the product. The reaction mixture was diluted with dichloromethane, washed with saturated aqueous sodium bicarbonate, water (2×20 mL) and brine, dried over sodium sulfate, filtered, and concentrated under reduced pressure. The crude product was purified by column chromatography (Biotage 10 g column, 10% to 50% EtOAc in hexanes gradient), yielding 86 mg (82%) of the desired compound S2-1-3 as a colorless oil.

S2-2-3

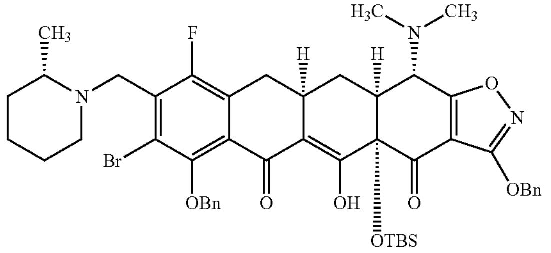

LDA was prepared by adding n-BuLi (0.24 mL, 1.6 M/hexanes, 0.38 mmol, 3.0 equiv) to diisopropylamine (53 μL, 0.38 mmol, 3.0 equiv) in 2 mL dry THF under a nitrogen atmosphere in a flame dried schenck flask cooled at −78° C. The resulting solution was warmed to −20° C. and stirred for 15 min. After the LDA solution was cooled down to −78° C., TMEDA (57 μL, 0.38 mmol, 3.0 equiv) was added slowly via a syringe, followed by the dropwise addition of compound S2-1-3 (86 mg, 0.16 mmol, 1.3 equiv) in 1 mL dry THF (a dark-red color appeared as soon as addition started). After stirring for 10 min, enone S1-9 (54 mg, 0.13 mmol, 1.0 equiv) in 1 mL dry THF was added slowly via a syringe. After 10 min, LC/MS indicated that the enone was consumed and the product present. The reaction mixture was allowed to slowly warm to −30° C. in 1 h, added with a phosphate buffer (pH 7, 10 mL) and saturated aqueous ammonium chloride (20 mL), and extracted with dichloromethane (3×15 mL). The combined extracts were dried over sodium sulfate, filtered, and concentrated under reduced pressure. The resulting orange-red oil was purified by preparative reverse phase HPLC on a Waters Autopurification system using a Sunfire Prep C18 OBD column [5 μm, 19×50 mm; flow rate, 20 mL/min; Solvent A: $H_2O$ with 0.1% $HCO_2H$; Solvent B: $CH_3CN$ with 0.1% $HCO_2H$; injection volume: 4.0 mL ($CH_3CN$); gradient: 20→100% B over 15 min; mass-directed fraction collection]. Fractions containing the desired product were collected and concentrated at rt to remove most of the acetonitrile. The resulting mostly aqueous solution was extracted with EtOAc. The EtOAc extract was dried (sodium sulfate) and concentrated to give 26 mg (23%) of the desired compound S2-2-3: $^1$H NMR (400 MHz, $CDCl_3$) δ 16.00 (br, s, 1 H), 7.58-7.54 (m, 2 H), 7.51-7.47 (m, 2 H), 7.40-7.31 (m, 6 H), 5.35 (s, 2 H), 4.98 (q, J=11.0 Hz, 2 H), 4.13-4.07 (m, 1 H), 3.93 (d, J=11.0 Hz, 1 H), 3.42 (d, J=12.2 Hz, 1 H), 3.24 (dd, J=15.9, 4.9 Hz, 1 H), 3.03-2.93 (m, 1 H), 2.69-2.62 (m, 1 H), 2.58-2.51 (m, 1 H), 2.48 (s, 6 H), 2.50-2.40 (m, 3 H), 2.19-2.10 (m, 2 H), 1.66-1.58 (m, 2 H), 1.48-1.26 (m, 4 H), 1.22 (d, J=6.1 Hz, 3 H), 0.81 (s, 9 H), 0.26 (s, 3 H), 0.12 (s, 3 H).

S2-4-65

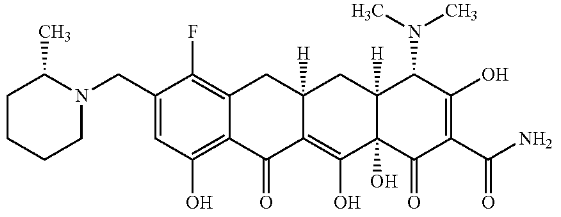

Aqueous HF (0.3 mL, 48-50%) was added to a $CH_3CN$ solution (1.0 mL) of S2-2-3 (26 mg) in a plastic vial at 25° C. The reaction was stirred at 25° C. for 18 hrs. The resulting mixture was poured into an aqueous solution (10 mL) of $K_2HPO_4$ (2 g). The solution was extracted with EtOAc (3×15 mL). The combined EtOAc extracts were dried over sodium sulfate and concentrated to give the crude intermediate (18 mg).

Pd—C (10 mg, 10 wt %) was added to a MeOH solution (2 mL) of the above crude intermediate. HCl/MeOH (0.5 mL, 0.5 N) was also added. The reaction was stirred under $H_2$ (balloon) at 25° C. for 2 hrs and filtered through a pad of Celite. The filtrate was concentrated, and the crude product was purified by HPLC on a Polymerx 10μ RP-γ 100 R column [30×21.20 mm, 10 micron, solvent A: 0.05 N HCl, solvent B: $CH_3CN$, sample in 2.0 mL (0.05 N HCl), gradient elution with 0→70% B over 15 min, mass-directed fraction collection] to yield the desired product S2-4-65 as a yellow solid (9 mg, 59%, two steps): $^1$H NMR (400 MHz, $CD_3OD$) δ 7.07 (d, J=6.0 Hz, 1 H), 4.76 (d, J=13.7 Hz, 1 H), 4.15 (d, J=13.7 Hz, 1 H), 4.10 (s, 1 H), 3.40-3.32 (m, 2 H), 3.05 (s, 3 H), 2.97 (s, 3 H), 3.27-2.96 (m, 4 H), 2.42-2.32 (m, 1 H), 2.27-2.21 (m, 1 H), 1.92-1.80 (m, 2 H), 1.73-1.58 (m, 3 H), 1.56 (d, J=6.4 Hz, 3 H); MS (ESI) m/z 544.26 (M+H).

The following compounds were prepared according to the methods of S2-4-65, substituting the appropriate amine for 2-methylpiperidine.

S2-4-66

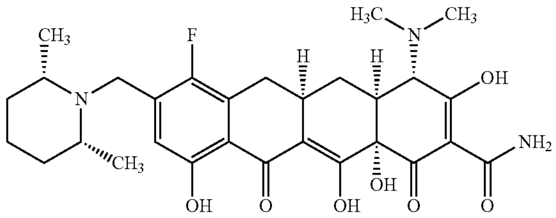

S2-4-66: $^1$H NMR (400 MHz, $CD_3OD$) δ 7.06 (dd, J=8.2, 6.0 Hz, 1 H), 4.40 (s, 2 H), 4.09 (s, 1 H), 3.68-3.57 (m, 2 H), 3.24-2.98 (m, 3 H), 3.04 (s, 3 H), 2.96 (s, 3 H), 2.40-2.32 (m, 1 H), 2.29-2.21 (m, 1 H), 2.05-1.58 (m, 7 H), 1.54 (d, J=6.0 Hz, 3 H), 1.35 (d, J=6.0 Hz, 3 H); MS (ESI) m/z 558.31 (M+H).

S2-4-67

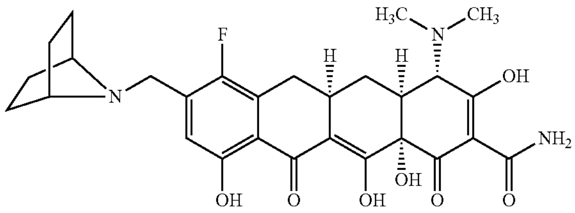

S2-4-67: $^1$H NMR (400 MHz, $CD_3OD$) δ 7.08 (d, J=6.0 Hz, 1 H), 4.33 (s, 2 H), 4.15 (br, s, 2 H), 4.09 (s, 1 H), 3.04 (s, 3 H), 2.97 (s, 3 H), 3.23-2.96 (m, 3 H), 2.38-2.29 (m, 3 H), 2.27-2.20 (m, 1 H), 2.08-2.01 (m, 2 H), 1.86-1.80 (m, 2 H), 1.71-1.61 (m, 1 H); MS (ESI) m/z 542.26 (M+H).

S2-2-4

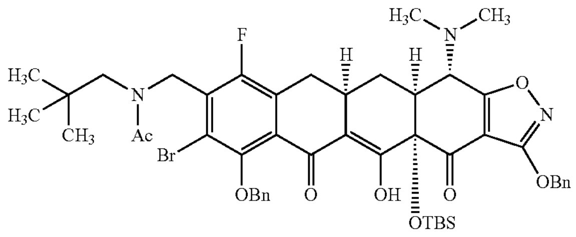

Acetic anhydride (3.6 μL, 0.038 mmol, 2.0 equiv) was added to a solution of S2-2-1 (17 mg, 0.019 mmol, 1.0 equiv) in dichloromethane (1 mL). After 2 hrs, the reaction mixture was concentrated under reduced pressure. The crude product was purified by preparative reverse phase HPLC on a Waters Autopurification system using a Sunfire Prep C18 OBD column [5 μm, 19×50 mm; flow rate, 20 mL/min; Solvent A: $H_2O$ with 0.1% $HCO_2H$; Solvent B: $CH_3CN$ with 0.1% $HCO_2H$; gradient: 90→100% B over 15 min; mass-directed fraction collection]. Fractions containing the desired product, eluting at 5.0-6.0 min, were collected and concentrated under reduced pressure to give 12 mg (66%) of the desired compound S2-2-4: $^1H$ NMR (400 MHz, $CDCl_3$) δ 16.02-15.88 (m, 1 H), 7.58-7.44 (m, 4 H), 7.40-7.28 (m, 6 H), 5.36 (s, 2 H), 5.03-4.70 (m, 4 H), 3.94 (br s, 1 H), 3.30-3.14 (m, 3 H), 3.04-2.93 (m, 1 H), 2.64-2.32 (m, 9 H), 2.16-2.06 (m, 4 H), 1.04-0.94 (m, 9 H), 0.81 (s, 9 H), 0.24 (s, 3 H), 0.12 (s, 3 H); MS (ESI) m/z 944.61, 946.61 (M+H).

S2-4-68

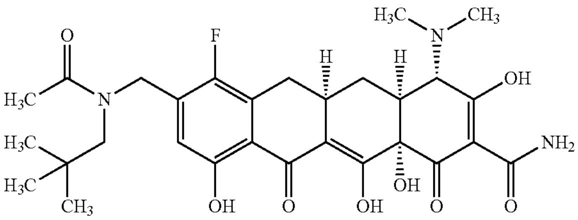

A solution of compound S2-2-4 (12 mg, 0.013 mmol) in 1,4-dioxane (0.80 mL) was treated with HF (0.40 mL, 48-50% aqueous solution) at rt. After stirring overnight, the mixture was poured into a solution of $K_2HPO_4$ (4.8 g) in water (20 mL). This mixture was extracted with EtOAc (3 times), and the combined extracts were dried over sodium sulfate, filtered, and concentrated under reduced pressure to yield the crude intermediate.

The above crude intermediate was dissolved in MeOH (1 mL)/1,4-dioxane (1 mL). HCl/MeOH (0.5 mL, 0.5 N) and 10% Pd—C (Degussa, 2 mg) were added, and an atmosphere of hydrogen was introduced. After 2 hrs, the reaction mixture was filtered through Celite and concentrated under reduced pressure. The crude product was purified by preparative reverse phase HPLC on a Waters Autopurification system using a Polymerx 10μ RP-γ 100 R column [30×21.20 mm, 10 micron, solvent A: 0.05 N HCl, solvent B: $CH_3CN$, gradient elution with 0→70% B over 10 min; mass-directed fraction collection]. Fractions containing the desired product, eluting at 9.8-11.4 min, were collected and freeze-dried to yield the desired compound S2-4-68 (5 mg, 69%): $^1H$ NMR (400 MHz, $CD_3OD/DCl$) δ 7.14 (d, J=5.5 Hz, 1 H), 4.40 (s, 2 H), 4.15 (s, 1 H), 3.82-3.56 (m, 5 H), 3.26-2.94 (m, 9 H), 2.36-2.24 (m, 2 H), 2.24-1.98 (br m, 9 H), 1.70-1.55 (m, 1 H); MS (ESI) m/z 574.33 (M+H).

S2-1-2

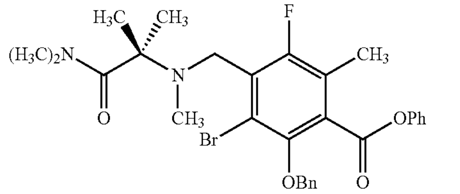

Compound S2-1-2 was prepared from S1-7 using similar procedures to that of S15-15-2. A colorless oil: $^1H$ NMR (400 MHz, $CDCl_3$) δ 7.49 (dd, J=2.3, 7.8 Hz, 2 H), 7.33-7.38 (m, 5 H), 7.25 (t, J=7.8 Hz, 1 H), 7.05 (d, J=7.8 Hz, 2 H), 5.10 (s, 2 H), 3.81 (s, 2 H), 3.43 (s, 3 H), 2.93 (s, 3 H), 2.34 (s, 3 H), 2.07 (s, 3 H), 1.45 (s, 6 H); MS (ESI) m/z 571.2 (M+H), calcd for $C_{29}H_{32}BrFN_2O_4$ 571.15.

S2-4-69

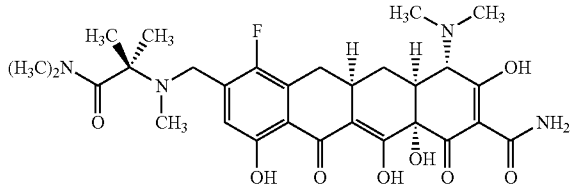

Compound S2-4-69 was prepared from S2-1-2 using similar procedures to that of S2-4-1. The crude product was purified by HPLC on a Waters Autopurification system using a Phenomenex Polymerx 10μ RP-γ 100 R column [30×21.20 mm, 10 micron; flow rate, 20 mL/min; Solvent A: 0.05 N HCl/water; Solvent B: MeOH; injection volume: 4.0 mL (0.05 N HCl/water); gradient: 10→100% B over 20 min; mass-directed fraction collection]. Fractions containing the desired product, eluting at 10.20-10.80 min, were collected and freeze-dried to give the desired product S2-4-69 as a yellow solid: $^1H$ NMR (400 MHz, $CD_3OD$) δ 7.39 (d, J=5.8 Hz, 1 H), 4.23 (d, J=12.4 Hz, 1 H), 4.15 (d, J=12.4 Hz, 1 H), 4.10 (s, 1 H), 2.97-3.16 (m, 15 H), 2.71 (s, 3 H), 2.35 (dd, J=15.1 Hz, 1 H), 2.23-2.26 (m, 1 H), 1.86 (s, 3 H), 1.66 (s, 3 H), 1.60-1.70 (m, 1 H); MS (ESI) m/z 589.5 (M+H), calcd for $C_{29}H_{38}FN_4O_8$ 589.26.

EXAMPLE 3

Synthesis of Compounds Via Scheme 3

Scheme 3

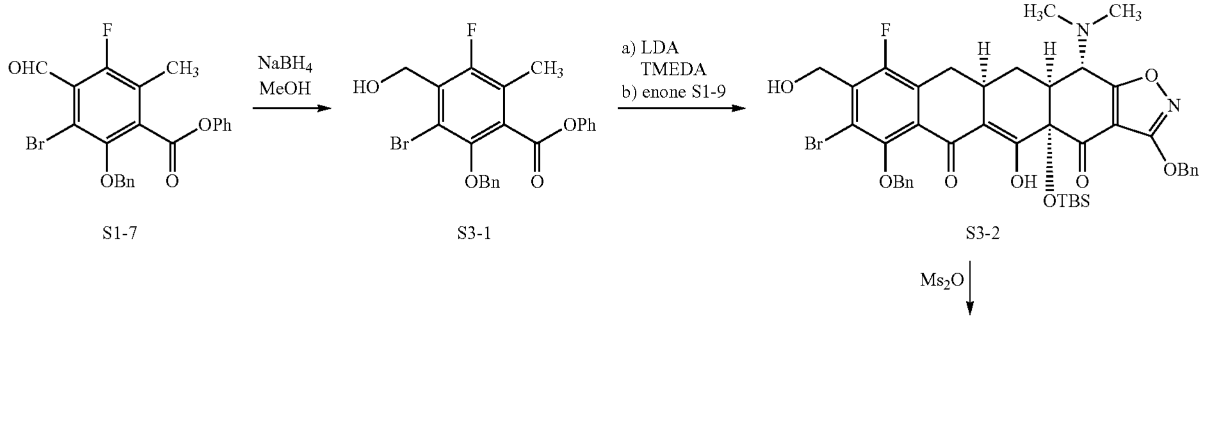

S1-7 S3-1 S3-2

-continued

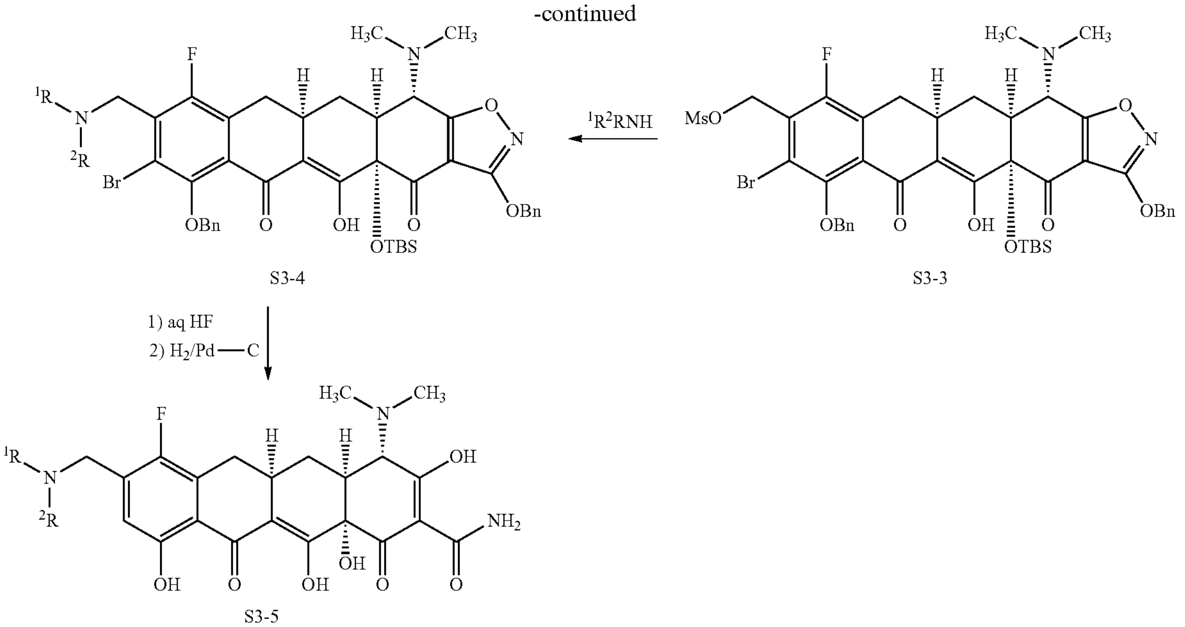

S3-4

S3-3

S3-5

The following compounds were prepared according to Scheme 3.

S3-1

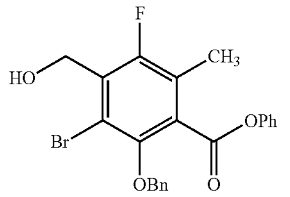

Compound S1-7 (0.42 g, 0.94 mmol, 1.0 equiv) was dissolved in MeOH (5 mL). Sodium borohydride (76 mg, 2.00 mmol, 2.1 equiv) was added in several portions. During the addition, gas evolution was observed. After stirring at rt for 30 min, LC/MS indicated that the starting material was consumed. The reaction mixture was diluted with EtOAc, washed with water (2×20 mL) and brine, dried over sodium sulfate, filtered, and concentrated under reduced pressure. The crude material was purified by column chromatography (Biotage 10 g column, 5% to 20% EtOAc in hexanes gradient), yielding 0.37 g (88%) of the desired compound S3-1 as a colorless oil: $^1$H NMR (400 MHz, $CDCl_3$) δ 10.37 (s, 1 H), 7.49 (dd, J=7.8, 2.3 Hz, 2 H), 7.40-7.33 (m, 5 H), 7.25 (t, J=7.8 Hz, 1 H), 7.07-7.02 (m, 2 H), 5.10 (s, 2 H), 4.91 (dd, J=6.9, 2.3 Hz, 2 H), 2.35 (d, J=2.3 Hz, 3 H).

LDA was freshly prepared by adding n-BuLi (1.6 M/hexanes, 1.59 mmol, 3.0 equiv) to diisopropylamine (0.22 mL, 1.59 mmol, 3.0 equiv) in 10 mL dry THF under a nitrogen atmosphere in a flame dried schenck flask at −78° C. The pale solution was warmed to −20° C. and stirred for 15 min. After the LDA solution was cooled down to −78° C. with a dry ice/acetone bath, TMEDA (0.24 mL, 1.59 mmol, 3.0 equiv) was added slowly via a syringe. Compound S3-1 (0.28 g, 0.64 mmol, 1.2 equiv) in 2 mL dry THF was added to slowly via a syringe. A dark-red color appeared as soon as the addition started. After stirring at −78° C. for 10 min, enone S1-9 (0.26 g, 0.53 mmol, 1.0 equiv) 2 mL dry THF was added slowly via a syringe. After 10 min, LC/MS indicated that the enone was consumed and the product present. The reaction mixture was allowed to slowly warm to −20° C. in 1 h. Phosphate buffer (pH 7, 10 mL) was added, followed by the addition of 20 mL saturated aqueous ammonium chloride. The resulting mixture was extract with dichloromethane (3×15 mL). The combined extracts were dried over sodium sulfate, filtered, and concentrated under reduced pressure. The resulting orange-red oil was purified by column chromatography (Biotage 24 g column, 10% to 30% EtOAc in hexanes gradient) yielding 0.22 g of compound S3-2 (50%): $^1$H NMR (400 MHz, $CDCl_3$) δ 16.1 (br, s, 1 H), 7.58-7.54 (m, 2 H), 7.51-7.47 (m, 2 H), 7.41-7.32 (m, 6 H), 5.36 (s, 2 H), 4.95 (dd, J=26.6, 9.6 Hz, 2 H), 4.89 (d, J=7.8 Hz, 2 H), 3.92 (d, J=10.6 Hz, 1 H), 3.25 (dd, J=15.6, 4.1 Hz, 1 H), 3.04-2.94 (m, 1 H), 2.59-2.53 (m, 1 H), 2.49 (s, 6 H), 2.40 (t, J=15.6 Hz, 1 H), 2.20-2.10 (m, 2 H), 0.81 (s, 9 H), 0.26 (s, 3 H), 0.12 (s, 3 H).

S3-2

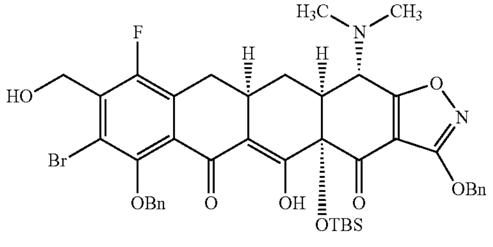

S3-5-1

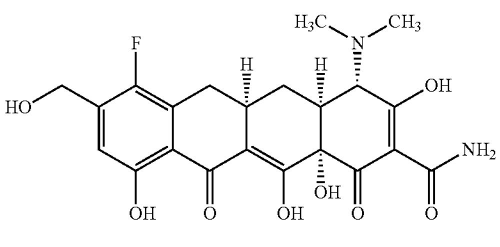

Aqueous HF (0.3 mL, 48-50%) solution was added to a $CH_3CN$ solution (1.0 mL) of S3-2 (5 mg, 0.06 mmol) in a plastic vial at 25° C. The reaction was stirred at 25° C. for 18 hrs. The reaction mixture was poured into an aqueous solution (10 mL) of $K_2HPO_4$ (2 g). The solution was extracted with EtOAc (3×15 mL). The combined EtOAc extracts were dried over sodium sulfate and concentrated to give the crude intermediate.

Pd—C (5 mg, 10 wt %) was added to a MeOH solution (2 mL) of the crude intermediate. HCl in MeOH (0.5 mL, 0.5 N) was added and the reaction was stirred under $H_2$ (balloon) at 25° C. for 2 hrs. The catalyst was filtered off with a pad of Celite. The filtrate was concentrated to afford the crude product, which was purified by HPLC on a Polymerx 10μ RP-γ 100 R column [30×21.20 mm, 10 micron, solvent A: 0.05 N HCl, solvent B: $CH_3CN$, sample in 2.0 mL (0.05 N HCl), gradient elution with 0→70% B over 15 min, mass-directed fraction collection], yielding 2 mg of the desired product S3-5-1 as a yellow solid (54%, two steps): $^1H$ NMR (400 MHz, $CD_3OD$) δ 6.94 (d, J=6.0 Hz, 1 H), 4.33 (s, 2 H), 4.12 (s, 1 H), 3.03 (s, 3 H), 2.96 (s, 3 H), 3.18-2.95 (m, 3 H), 2.27 (t, J=16.4 Hz, 1 H), 2.24-2.17 (m, 1 H), 1.67-1.57 (m, 1 H); MS (ESI) m/z 463.37 (M+H).

S3-3

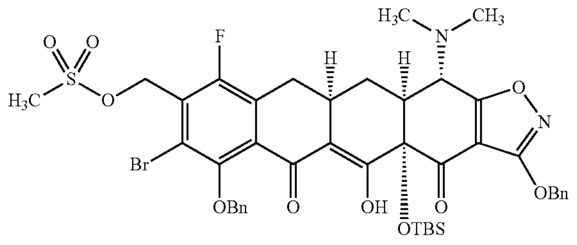

Methanesulfonic anhydride (99 mg, 0.57 mmol, 3.0 equiv) was added to a solution of S3-2 (0.16 g, 0.19 mmol, 1.0 equiv) in THF (4 mL). After 1 h, triethylamine (0.079 mL, 0.57 mmol, 3.0 equiv) was added. After 1 h, additional methanesulfonic anhydride (0.16 g, 0.95 mmol, 5.0 equiv) was added. After 1 h, the reaction mixture was used without concentration in subsequent reactions: MS (ESI) m/z 911.45, 913.44 (M+H).

S3-4-2

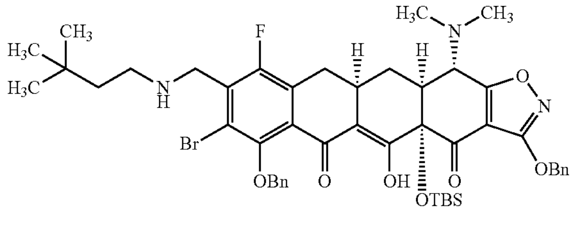

3,3-Dimethylbutylamine (0.063 mL, 0.47 mmol, 10 equiv) was added to a solution of S3-3 in THF (1 mL, 0.047 mmol, 1.0 equiv). After 1 h, additional 3,3-dimethylbutylamine (0.13 mL, 0.95 mmol, 20 equiv) was added. After 30 minutes, the reaction mixture was concentrated under reduced pressure. The crude product was purified by preparative reverse phase HPLC on a Waters Autopurification system using a Sunfire Prep C18 OBD-column [5 μm, 19×50 mm; flow rate, 20 mL/min; Solvent A: $H_2O$ with 0.1% $HCO_2H$; Solvent B: $CH_3CN$ with 0.1% $HCO_2H$; gradient: 20→100% B over 15 min; mass-directed fraction collection]. Fractions containing the desired product, eluting at 8.2-9.0 min, were collected and freeze-dried to yield 10 mg (22%) of compound S3-4-2: $^1H$ NMR (400 MHz, $CDCl_3$) δ 16.10-15.79 (br s, 1 H), 7.60-7.45 (m, 4 H), 7.43-7.28 (m, 6 H), 5.35 (s, 2 H), 5.04-4.84 (m, 2 H), 3.90 (d, J=11.0 Hz, 1 H), 3.32-3.19 (m, 1 H), 3.06-2.93 (m, 1 H), 2.86-2.76 (m, 1 H), 2.60-2.34 (m, 10 H), 2.18-2.10 (m, 1 H), 1.70-1.58 (m, 4 H), 0.99-0.76 (m, 18 H), 0.26 (s, 3 H), 0.11 (s, 3 H); MS (ESI) m/z 916.54, 918.49 (M+H).

S3-5-2

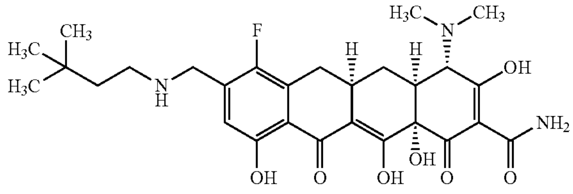

A solution of compound S3-4-2 (10 mg, 0.011 mmol) in 1,4-dioxane (0.80 mL) was treated with HF (0.40 mL, 48-50% aqueous solution). After stirring overnight, the mixture was poured into a solution of $K_2HPO_4$ (4.8 g) in water (20 mL). This mixture was extracted with EtOAc (3 times). The combined extracts were dried over sodium sulfate, filtered, and concentrated under reduced pressure to yield the crude intermediate.

The above crude intermediate was dissolved in MeOH (1 mL), 1,4-dioxane (1 mL), and 0.5 N HCl/MeOH (0.4 mL). 10% Pd—C (Degussa, 2 mg) was added, and an atmosphere of hydrogen was introduced. After 2 hrs, the reaction mixture was filtered through Celite and concentrated under reduced pressure. The crude product was purified by preparative reverse phase HPLC on a Waters Autopurification system using a Polymerx 10μ RP-γ100 R column [30×21.20 mm, 10 micron, solvent A: 0.05 N HCl, solvent B: $CH_3CN$, gradient elution with 0→70% B over 10 min; mass-directed fraction collection]. Fractions containing the desired product, eluting at 8.2-9.6 min, were collected and freeze-dried to yield 5 mg (69%) of compound S3-5-2: $^1H$ NMR (400 MHz, $CD_3OD$/DCl) δ 7.08 (d, J=5.48 Hz, 1 H), 4.29 (s, 2 H), 4.16 (s, 1 H), 3.34-2.96 (m, 11 H), 2.36-2.25 (m, 2 H), 1.71-1.58 (m, 3 H), 0.97 (s, 9 H); MS (ESI) m/z 546.32 (M+H).

The following compounds were prepared according to the methods of S3-5-2, substituting the appropriate amine for 3,3-dimethylbutylamine:

S3-5-3

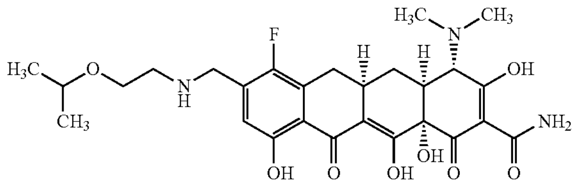

S3-5-3: $^1H$ NMR (400 MHz, $CD_3OD$/DCl) δ 7.07 (d, J=5.96 Hz, 1 H), 4.32 (s, 2 H), 4.17 (s, 1 H), 3.80-3.65 (m, 3 H), 3.36-2.96 (m, 11 H), 2.38-2.25 (m, 2 H), 1.62 (dd, J=14.0, 11.4 Hz, 1 H), 1.18 (d, J=6.4 Hz, 6 H); MS (ESI) m/z 548.30 (M+H).

S3-5-4
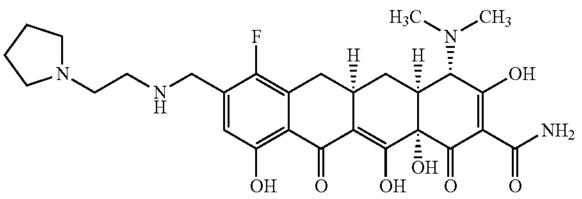
S3-5-4: $^1$H NMR (400 MHz, $CD_3OD/DCl$) δ 6.55 (d, J=5.60 Hz, 0.45 H), 6.45 (d, J=5.52 Hz, 0.55 H), 4.78 (s, 1.1 H), 4.67 (s, 0.9 H), 4.15 (s, 1 H), 3.40-2.96 (m, 16 H), 2.32-2.20 (m, 4 H), 2.10 (s, 2 H), 1.62 (m, 1 H), 1.02 (s, 4 H); MS (ESI) m/z 559.33 (M+H).
S3-5-5
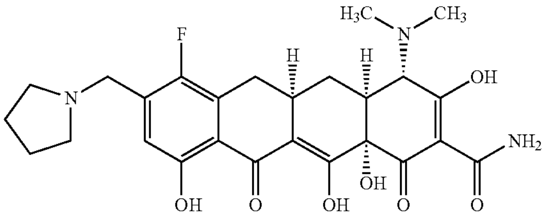
S3-5-5: $^1$H NMR (400 MHz, $CD_3OD$) δ 7.06 (d, J=6.0 Hz, 1 H), 4.46 (s, 2 H), 4.09 (s, 1 H), 3.04 (s, 3 H), 2.97 (s, 3 H), 3.27-2.97 (m, 3 H), 2.37 (m, 1 H), 2.28-2.14 (m, 3 H), 2.08-2.00 (m, 2 H), 1.72-1.62 (m, 1 H); MS (ESI) m/z 516.40 (M+H).
S3-5-6
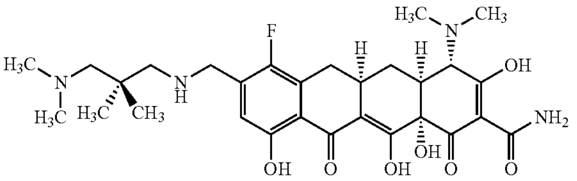
S3-5-6: $^1$H NMR (400 MHz, $CD_3OD/DCl$) δ 7.22 (d, J=5.96 Hz, 1 H), 4.39 (s, 2 H), 4.17 (s, 1 H), 3.40 (s, 2 H), 3.26-2.90 (m, 17 H), 2.40-2.25 (m, 2 H), 1.70-1.57 (m, 1 H), 1.32 (s, 6 H); MS (ESI) m/z 575.37 (M+H).
EXAMPLE 4
Synthesis of Compounds Via Scheme 4
Scheme 4
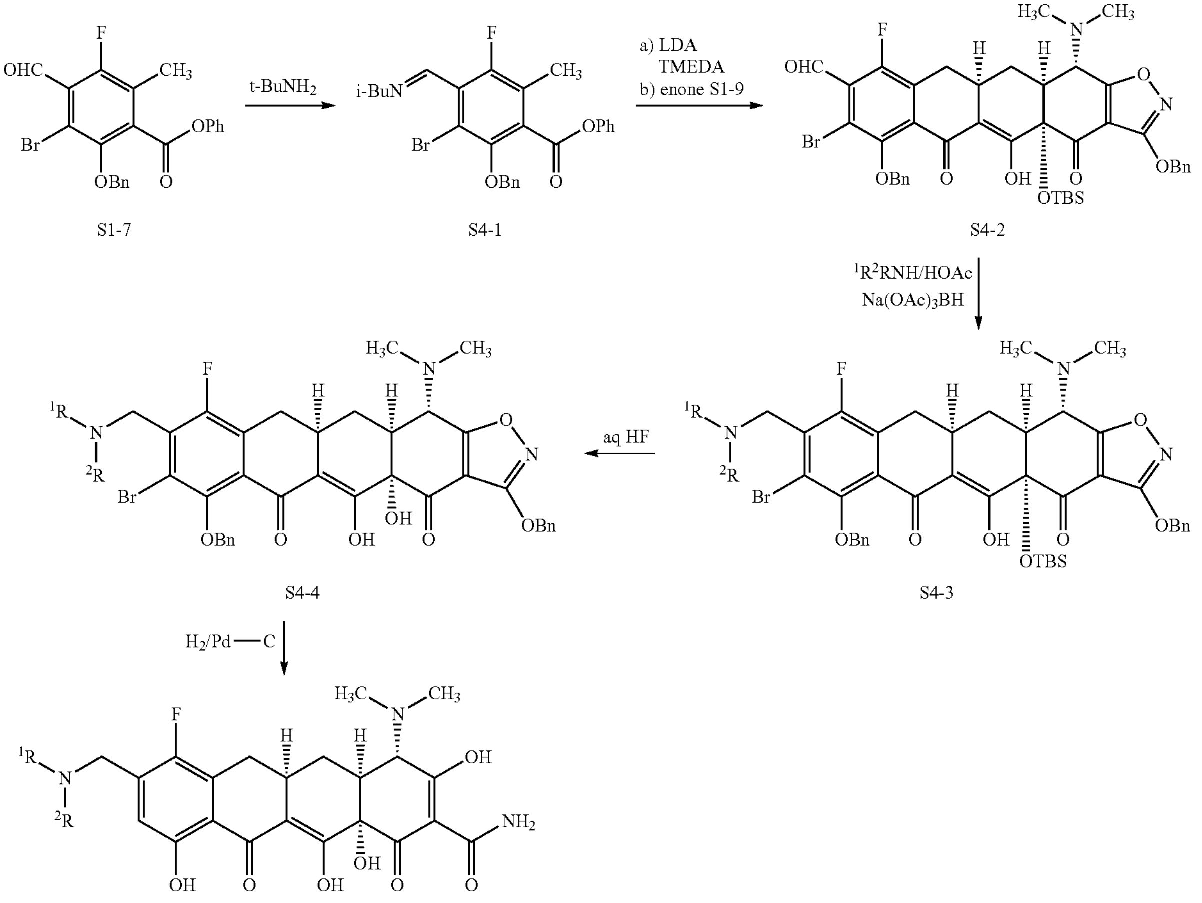
S1-7 S4-1 S4-2 S4-3 S4-4 S4-5

The following compounds were prepared according to Scheme 4.

S4-1

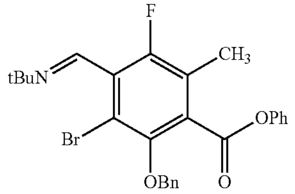

Compound S1-7 (0.50 g, 1.14 mmol, 1.0 equiv) and t-butylamine (0.60 mL, 5.68 mmol, 5.0 equiv) were stirred at rt in toluene (5 mL) overnight. The reaction mixture was concentrated under reduced pressure. $^1$H NMR indicated a 4:1 mixture of S4-1:S1-7. The material was redissolved in toluene (5 mL). t-Butylamine (0.60 mL, 5.68 mmol, 5.0 equiv) and 4 Å molecular sieves (0.50 g) were added. After stirring at rt overnight, the reaction mixture was filtered through Celite and concentrated to give crude S4-1 (with ~10% S1-7): $^1$H NMR (400 MHz, $CDCl_3$) δ 8.32 (s, 1 H), 7.38 (d, J=6.0 Hz, 2 H), 7.45-7.32 (m, 5 H), 7.31-7.14 (m, 3 H), 5.11 (s, 2 H), 2.35 (s, 3 H), 1.38 (s, 9 H).

S4-2

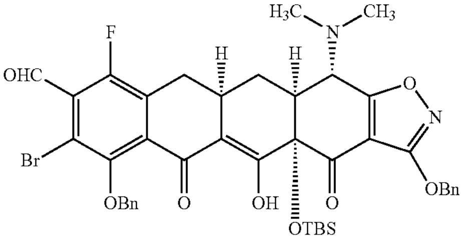

A solution of S4-1 (0.56 g, 1.13 mmol, 1.2 equiv) in THF (5 mL) was added to a solution of LHMDS (1.4 mL, 1.0 M/THF, 1.40 mmol, 1.5 equiv) and TMEDA (1.02 mL, 6.78 mmol, 6.0 equiv) in THF (10 mL) at −78° C. No color change was observed. Additional LDA (1.22 mL, 1.2 M/THF, 1.47 mmol, 1.3 equiv) was added dropwise, immediately producing a red colored solution. The reaction was stirred at −78° C. for 5 min. A solution of enone S1-9 (0.45 g, 0.94 mmol, 1.0 equiv) in THF (3 mL) was added dropwise to the reaction mixture. The reaction was stirred from −78° C. to −20° C. for 1 h, quenched by saturated aqueous $NH_4Cl$, and extracted with EtOAc. The combined EtOAc extracts were dried (sodium sulfate) and concentrated to yield the crude product, which was purified by preparative reverse phase HPLC on a Waters Autopurification system using a Sunfire Prep C18 OBD column [5 μm, 19×50 mm; flow rate, 20 mL/min; Solvent A: $H_2O$ with 0.1% $HCO_2H$; Solvent B: $CH_3CN$ with 0.1% $HCO_2H$; gradient: 90→100% B over 15 min; mass-directed fraction collection]. Fractions containing the desired product, eluting at 5.8-7.4 min, were collected and concentrated under reduced pressure to give 0.23 g (29%) of pure S4-2 (The imine hydrolyzed to the aldehyde on concentration): $^1$H NMR (400 MHz, $CDCl_3$) δ 15.79 (s, 1 H), 10.33 (s, 1 H), 7.60-7.45 (m, 4 H), 7.45-7.30 (m, 6 H), 5.28 (s, 2 H), 4.98 (q, J=9.2 Hz, 2 H), 3.89 (d, J=10.4 Hz, 1 H), 3.30-3.22 (m, 1 H), 3.08-2.95 (m, 1 H), 2.62-2.57 (m, 1 H), 2.52-2.32 (m, 8 H), 2.20-2.12 (m, 1 H), 0.81 (s, 9 H), 0.26 (s, 3 H), 0.12 (s, 3 H); MS (ESI) m/z 831.56, 833.55 (M+H).

S4-3-1

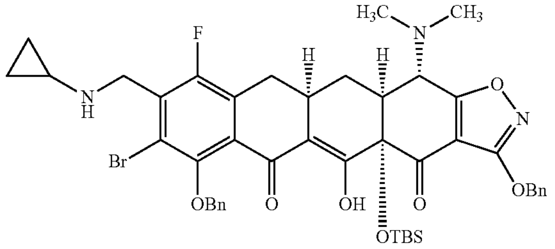

Cyclopropylamine (0.030 mL, 0.42 mmol, 7.0 equiv) was added to a solution of S4-2 (50 mg, 0.060 mmol, 1.0 equiv) and acetic acid (0.024 mL, 0.42 mmol, 7.0 equiv) in dichloromethane (1 mL). After 30 min., sodium triacetoxyborohydride (64 mg, 0.30 mmol, 5.0 equiv) was added. After an additional 3 hrs, the mixture was quenched by $NaHCO_3$ (saturated, aqueous solution) and pH 7 phosphate buffer. The mixture was extracted with dichloromethane, and the combined extracts were dried over sodium sulfate, filtered, and concentrated under reduced pressure. The crude product was purified by preparative reverse phase HPLC on a Waters Autopurification system using a Sunfire Prep C18 OBD column [5 μm, 19×50 mm; flow rate, 20 mL/min; Solvent A: $H_2O$ with 0.1% $HCO_2H$; Solvent B: $CH_3CN$ with 0.1% $HCO_2H$; gradient: 20→100% B over 15 min; mass-directed fraction collection]. Fractions containing the desired product, eluting at 8.6-10.4 min, were collected and freeze-dried to yield 8 mg of compound S4-3-1 (16%, ~90% pure by $^1$H NMR): $^1$H NMR (400 MHz, $CDCl_3$) δ 16.00-15.79 (br s, 1 H), 7.60-7.45 (m, 4 H), 7.43-7.26 (m, 6 H), 4.97 (q, J=9.4 Hz, 2 H), 4.37 (br s, 2 H), 3.90 (d, J=10.4 Hz, 1 H), 3.30-3.22 (m, 1 H), 3.08-2.95 (m, 1 H), 2.62-2.27 (m, 12 H), 2.18-2.10 (m, 1 H), 0.88-0.74 (m, 11 H), 0.70-0.62 (m, 2 H), 0.26 (s, 3 H), 0.12 (s, 3 H); MS (ESI) m/z 872.43, 874.41 (M+H).

S4-5-1

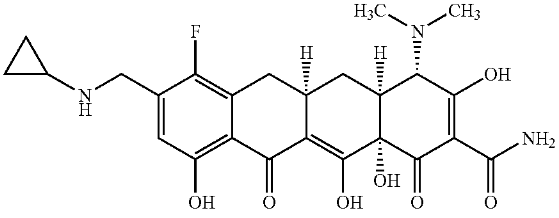

A solution of compound S4-3-1 (8 mg, 0.0094 mmol) in 1,4-dioxane (1 mL) was treated with HF (0.40 mL, 48-50% aqueous solution). After stirring at rt overnight, the mixture was poured into a solution of $K_2HPO_4$ (4.8 g) in water (20 mL). This mixture was extracted with EtOAc (3 times), and the combined extracts were dried over sodium sulfate, filtered, and concentrated under reduced pressure to yield the crude product.

The above crude product was dissolved in MeOH (1 mL), 1,4-dioxane (1 mL), and 0.5 N HCl/MeOH (0.5 mL). 10% Pd—C (Degussa, 2 mg) was added, and an atmosphere of hydrogen was introduced. After 2 hrs, the reaction mixture was filtered through Celite and concentrated under reduced pressure. The crude product was purified by preparative reverse phase HPLC on a Waters Autopurification system using a Polymerx 10μ RP-γ100 R column [30×21.20 mm, 10 micron, solvent A: 0.05 N HCl, solvent B: $CH_3CN$, gradient elution with 0→70% B over 10 min; mass-directed fraction collection]. Fractions containing the desired product, eluting at 6.8-7.6 min, were collected and freeze-dried to yield 3 mg (56%) of compound S4-5-1: $^1$H NMR (400 MHz, $CD_3OD$/DCl) δ 7.08 (d, J=5.96 Hz, 1 H), 4.38 (s, 2 H), 4.18 (s, 1 H), 3.34-2.96 (m, 9 H), 2.86-2.79 (m, 1 H), 2.36-2.25 (m, 2 H), 1.62 (dd, J=14.0, 11.0 Hz, 1 H), 1.02-0.86 (m, 4 H); MS (ESI) m/z 502.22 (M+H).

The following compounds were prepared according to the methods of S4-5-1, substituting the appropriate amines for cyclopropylamine.

S4-5-2

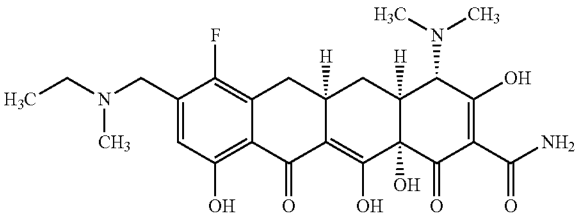

S4-5-2: $^1$H NMR (400 MHz, $CD_3OD$/DCl) δ 7.11 (d, J=5.48 Hz, 1 H), 4.51 (dd, J=13.3, 6.4 Hz, 1 H), 4.31 (dd, J=13.3, 6.4 Hz, 1 H), 4.16 (s, 1 H), 3.42-3.10 (m, 4 H), 3.10-2.97 (m, 7 H), 2.85 (s, 3 H), 2.39-2.25 (m, 2 H), 1.62 (dd, J=14.0, 11.0 Hz, 1 H), 1.41 (t, J=7.3 Hz, 3 H); MS (ESI) m/z 504.22 (M+H).

S4-5-3

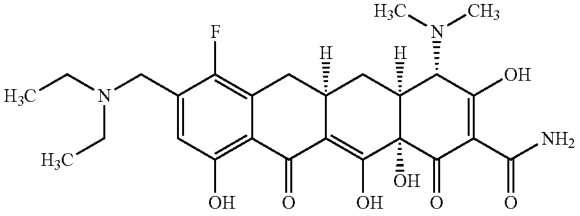

S4-5-3: $^1$H NMR (400 MHz, $CD_3OD$/DCl) δ 7.10 (d, J=5.96 Hz, 1 H), 4.23 (s, 2 H), 4.17 (s, 1 H), 3.35-2.96 (m, 13 H), 2.40-2.25 (m, 2 H), 1.63 (dd, J=14.0, 11.0 Hz, 1 H), 1.39 (t, J=7.1 Hz, 6 H); MS (ESI) m/z 518.24 (M+H).

S4-5-4

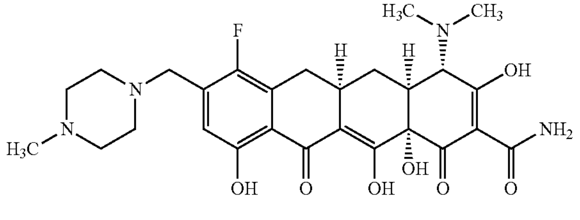

S4-5-4: $^1$H NMR (400 MHz, $CD_3OD$/DCl) δ 7.22 (d, J=5.48 Hz, 1 H), 4.60 (s, 2 H), 4.16 (s, 1 H), 3.98-3.60 (br m, 8 H), 3.24-2.94 (m, 12 H), 2.40-2.24 (m, 2 H), 1.64 (dd, J=14.0, 11.0 Hz, 1 H); MS (ESI) m/z 545.26 (M+H).

S4-3-2

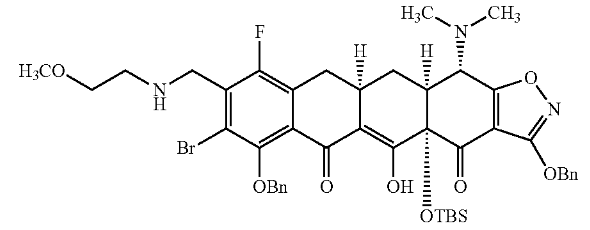

Prepared according to the method of compound S4-3-1 above, substituting 2-methoxyethylamine for cyclopropylamine: $^1$H NMR (400 MHz, $CDCl_3$) δ 16.00-15.79 (br s, 1 H), 7.58-7.45 (m, 4 H), 7.42-7.30 (m, 6 H), 5.36 (s, 2 H), 5.02-4.88 (m, 2 H), 4.35-4.20 (m, 2 H), 3.95-3.88 (m, 1 H), 3.75-58 (m, 2 H), 3.35 (s, 3 H), 3.30-3.19 (m, 1 H), 3.08-2.95 (br m, 3 H), 2.62-2.36 (m, 9 H), 2.18-2.10 (m, 1 H), 0.81 (s, 9 H), 0.26 (s, 3 H), 0.12 (s, 3 H); MS (ESI) m/z 890.55, 892.53 (M+H).

S4-5-5

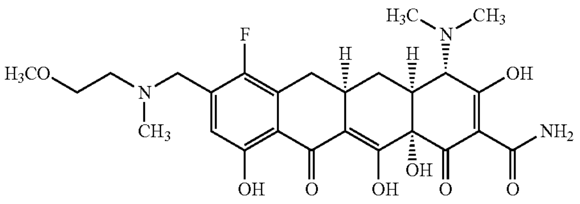

Formaldehyde (37% aqueous solution, 0.0092 mL, 0.12 mmol, 5.0 equiv) was added to a solution of compound S4-3-2 (22 mg, 0.025 mmol) in dichloromethane (1 mL) and HOAc (0.0071 mL, 0.12 mmol, 5.0 equiv). After 30 minutes, $Na(OAc)_3BH$ (16 mg, 0.074 mmol, 3.0 equiv) was added. After 2 hrs, the mixture was quenched by $NaHCO_3$ (saturated, aqueous solution) and pH 7 phosphate buffer. This mixture was extracted with dichloromethane, and the combined extracts were dried over sodium sulfate, filtered, and concentrated under reduced pressure.

The above crude intermediate was dissolved in 1,4-dioxane (0.80 mL) and treated with HF (0.40 mL, 48-50% aqueous solution) at rt. After stirring overnight, the mixture was poured into a solution of $K_2HPO_4$ (4.8 g) in water (20 mL) and extracted with EtOAc (3 times). The combined extracts were dried over sodium sulfate, filtered, and concentrated under reduced pressure.

The above crude intermediate was dissolved in MeOH (1 mL), 1,4-dioxane (1 mL), and 0.5 N HCl/MeOH (0.5 mL). 10% Pd—C (Degussa, 2 mg) was added, and an atmosphere of hydrogen was introduced. After 2 hrs, the reaction mixture was filtered through Celite and concentrated under reduced pressure to afford the crude product, which was purified by preparative reverse phase HPLC on a Waters Autopurification system using a Polymerx 10μ RP-γ100 R column [30×21.20 mm, 10 micron, solvent A: 0.05 N HCl, solvent B: $CH_3CN$, gradient elution with 0→70% B over 10 min; mass-directed fraction collection]. Fractions containing the desired product, eluting at 6.5-7.6 min, were collected and freeze-dried to yield 11 mg of compound S4-5-5 (75%, 3 steps): $^1$H NMR (400 MHz, $CD_3OD$/DCl) δ 7.10 (d, J=5.52 Hz, 1 H), 4.59 (dd, J=13.3, 7.8 Hz, 1 H), 4.34 (dd, J=13.3, 7.8 Hz, 1 H), 4.17 (s, 1 H), 3.84-3.72 (m, 2 H), 3.54-3.35 (m, 5 H), 3.34-2.96 (m, 9 H), 2.91 (s, 3 H), 2.38-2.25 (m, 2 H), 1.70-1.55 (m, 1 H); MS (ESI) m/z 534.25 (M+H).
S4-5-6
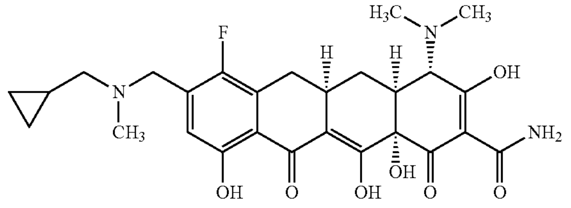
Prepared according to the methods of S4-5-5, substituting cyclopropanemethylamine for 2-methoxyethylamine: $^1H$ NMR (400 MHz, $CD_3OD$/DCl) δ 7.12 (d, J=5.52 Hz, 1 H), 4.62 (dd, J=13.3, 7.8 Hz, 1 H), 4.32 (dd, J=13.3, 7.8 Hz, 1 H), 4.16 (s, 1 H), 3.35-2.96 (m, 11 H), 2.90 (s, 3 H), 2.40-2.26 (m, 2 H), 1.63 (dd, J=14.0, 11.4 Hz, 1 H), 1.30-1.17 (m, 1 H), 0.86-0.74 (m, 2 H), 0.56-0.43 (m, 2 H); MS (ESI) m/z 530.25 (M+H).
EXAMPLE 5
Synthesis of Compounds Via Scheme 5
Scheme 5
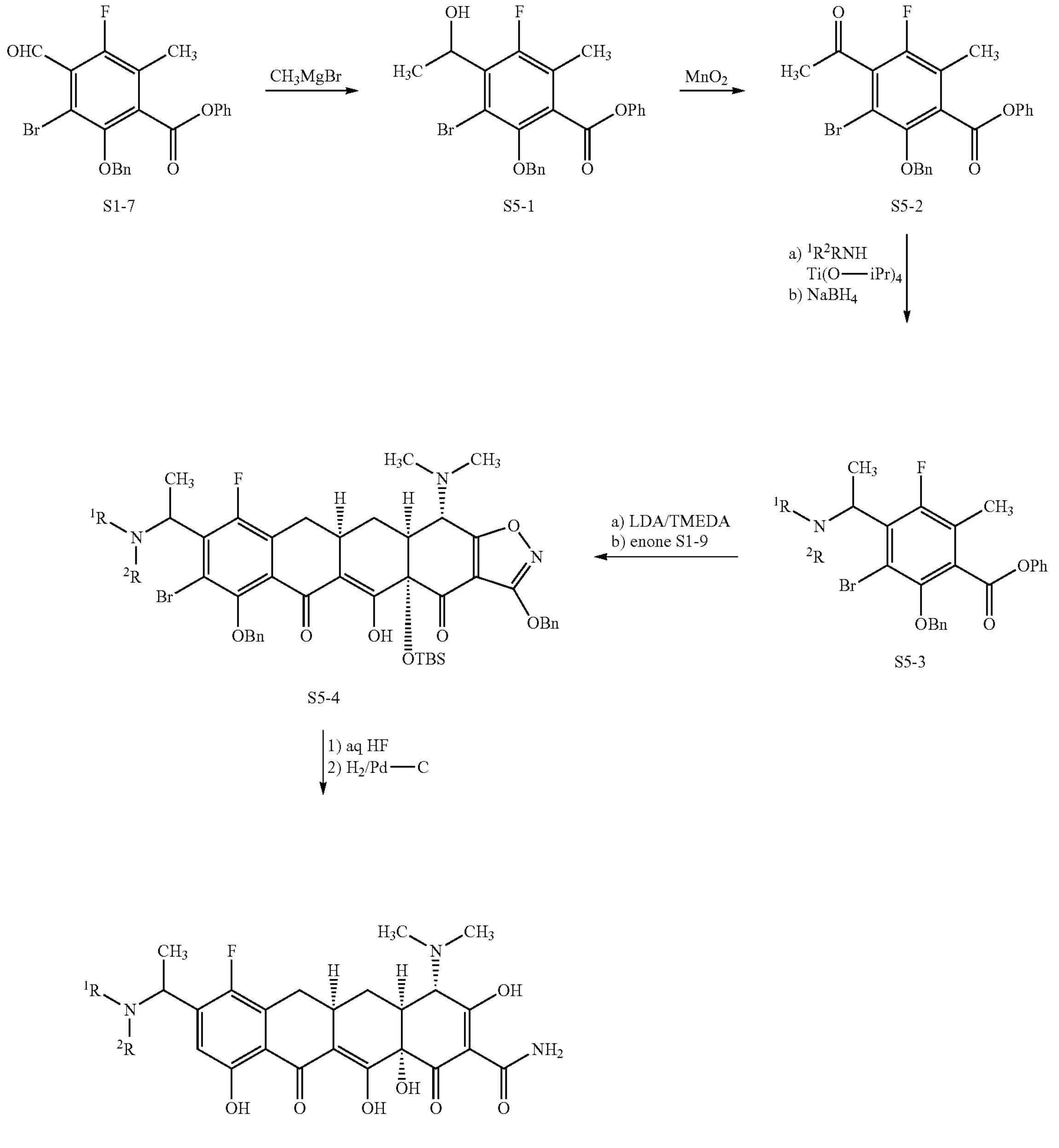
S1-7 S5-1 S5-2 S5-3 S5-4 S5-5

The following compounds were prepared according to Scheme 5.

S5-1

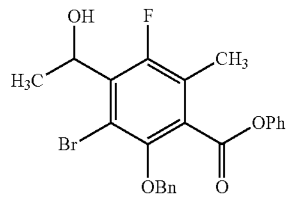

Methylmagnesium bromide (0.51 mL, 3.0 M/$Et_2O$, 1.53 mmol, 1.0 equiv) was added to a solution of compound S1-7 (0.67 g, 1.52 mmol, 1.0 equiv) in THF (8 mL) at −78° C. After 30 minutes, the reaction mixture was quenched by $NH_4Cl$ (saturated, aqueous solution) and extracted with EtOAc. The extracts were washed with brine, dried over sodium sulfate, filtered, and concentrated under reduced pressure. The material was purified by column chromatography on silica (Biotage 10 g prepacked column, 0% to 25% EtOAc in hexanes gradient), yielding 0.50 g (72%) of compound S5-1: $R_f$ 0.35 (30% EtOAc/hexanes); $^1H$ NMR (400 MHz, $CDCl_3$) δ 7.52-7.46 (m, 2 H), 7.40-7.32 (m, 5 H), 7.28-7.20 (m, 1 H), 7.08-7.00 (m, 2 H), 5.41 (q, J=6.9 Hz, 1 H), 5.09 (s, 2 H), 2.34 (s, 1 H), 1.63 (d, J=6.9 Hz, 3 H); MS (ESI) m/z 481.14, 483.1 (M+Na).

S5-2

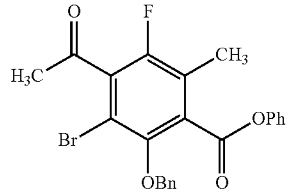

Manganese dioxide (activated, 0.20 g, 2.07 mmol, 5.0 equiv) was added to a solution of compound S5-1 (0.19 g, 0.41 mmol, 1.0 equiv) in dichloromethane (5 mL). After stirring overnight, the reaction was ~30% complete. Additional manganese dioxide (activated, 0.20 g, 2.07 mmol, 5.0 equiv) was added. After stirring overnight, the reaction mixture was diluted with EtOAc (20 mL) and filtered through Celite. The filtrate was concentrated under reduced pressure, yielding 0.16 g (83%) of compound S5-2: $R_f$ 0.24 (10% EtOAc/hexanes); MS (ESI) m/z 479.10, 481.10 (M+Na).

S5-3-1

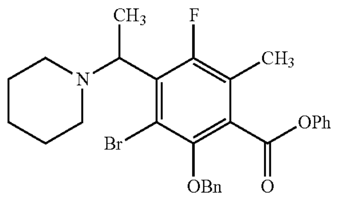

Compound S5-2 (55 mg, 0.12 mmol, 1.0 equiv), piperidine (0.059 mL, 0.60 mmol, 5.0 equiv), and titanium(IV) isopropoxide (0.18 mL, 0.60 mmol, 5.0 equiv) were stirred in dichloromethane (0.20 mL) overnight. Additional piperidine (0.20 mL, 2.00 mmol, 1.7 equiv) and titanium(IV) isopropoxide (0.20 mL, 0.67 mmol, 5.6 equiv) were added, and the reaction mixture was heated to 50° C. overnight. The reaction mixture was diluted with MeOH (2 mL) and $NaBH_4$ (15 mg, 0.40 mmol, 3.3 equiv) was added. Additional $NaBH_4$ (10 mg portions, 0.26 mmol, 2.2 equiv) was added every 30 minutes for 4 hrs, resulting in ~75% conversion. More MeOH (10 mL) and $NaBH_4$ (0.10 g, 2.64 mmol, 22 equiv) were added. After bubbling ceased, the reaction mixture was concentrated under reduced pressure. The resulting solids were dissolved in EtOAc, washed with $NaHCO_3$ (saturated, aqueous solution, 3 times) and brine, dried over sodium sulfate, filtered, and concentrated under reduced pressure, yielding 55 mg (87% crude) of compound S5-3-1. The material was concentrated from toluene (2 times) and used without further purification: $R_f$ 0.35 (30% EtOAc/hexanes; MS (ESI) m/z 526.18, 528.17 (M+H).

S5-4-1

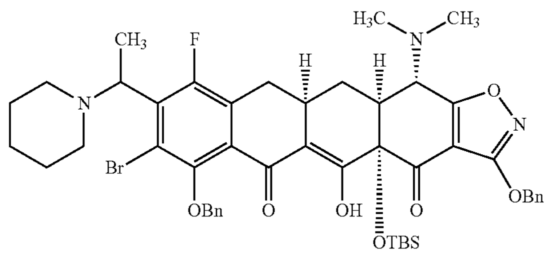

n-Butyllithium (0.074 mL, 2.5 M/hexanes, 0.18 mmol, 2.25 equiv) was added to diisopropylamine (0.026 mL, 0.18 mmol, 2.25 equiv) in THF (2 mL) at −40° C. The reaction mixture was cooled to −78° C., and TMEDA (0.072 mL, 0.48 mmol, 6.0 equiv) was added. A solution of compound S5-3-1 (55 mg, 0.10 mmol, 1.25 equiv) in THF (1 mL) was added dropwise. The reaction was stirred at −78° C. for 5 min. A solution of enone S1-9 (39 mg, 0.080 mmol, 1.0 equiv) in THF (0.5 mL) was added dropwise to the reaction mixture. Additional LDA (20.050 mL, 2.0 M/heptane/THF/ethylbenzene, 0.10 mmol, 1.25 equiv) was added. The reaction was stirred from −78° C. to −20° C. for 45 minutes, quenched by saturated aqueous $NH_4Cl$, and extracted with EtOAc (2 times). The combined EtOAc extracts were dried (sodium sulfate) and concentrated to yield the crude product, which was purified by preparative reverse phase HPLC on a Waters Autopurification system using a Sunfire Prep C18 OBD column [5 μm, 19×50 mm; flow rate, 20 mL/min; Solvent A: $H_2O$ with 0.1% $HCO_2H$; Solvent B: $CH_3CN$ with 0.1% $HCO_2H$; gradient: 20→100% B over 15 min; mass-directed fraction collection]. Fractions containing the desired product, eluting at 7.2-8.6 min, were collected and freeze-dried to give 26 mg of compound S5-4-1 (36%): $^1$H NMR (400 MHz, $CDCl_3$) δ 16.0-15.9 (m, 1 H), 7.58-7.45 (m, 4 H), 7.40-7.28 (m, 6 H), 5.35 (s, 2 H), 5.03-4.89 (m, 2 H), 4.52-4.34 (br s, 1 H), 3.92 (d, J=10.4 Hz, 1 H), 3.29-3.19 (m, 1 H), 3.06-2.93 (m, 1 H), 2.78-2.58 (m, 1 H), 2.58-2.34 (m, 11 H), 2.22-1.76 (br m, 2 H), 1.72-1.36 (br m, 9 H), 0.88-0.76 (m, 9 H), 0.26 (s, 3 H), 0.12 (s, 3 H); MS (ESI) m/z 914.30, 916.32 (M+H).

S5-5-1

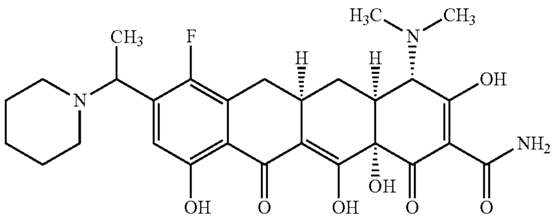

A solution of compound S5-4-1 (26 mg, 0.028 mmol) in 1,4-dioxane (1 mL) was treated with HF (0.40 mL, 48-50% aqueous solution). After stirring overnight, the mixture was poured into a solution of $K_2HPO_4$ (4.8 g) in water (20 mL). This mixture was extracted with EtOAc (3 times). The combined extracts were dried over sodium sulfate, filtered, and concentrated under reduced pressure.

The above material was dissolved in MeOH (2 mL), 1,4-dioxane (2 mL), and 0.5 N HCl/MeOH (0.5 mL). 10% Pd—C (Degussa, 5 mg) was added, and an atmosphere of hydrogen was introduced. After 2 hrs, the reaction mixture was filtered through Celite and concentrated under reduced pressure. The crude product was purified by preparative reverse phase HPLC on a Waters Autopurification system using a Polymerx 10μ RP-γ100 R column [30×21.20 mm, 10 micron, solvent A: 0.05 N HCl, solvent B: $CH_3CN$, gradient elution with 0→70% B over 10 min; mass-directed fraction collection]. Fractions containing the desired product, eluting at 6.8-8.2 min, were collected and freeze-dried to yield 12 mg (68%) of compound S5-5-1: $^1$H NMR (400 MHz, $CD_3OD/DCl$) δ 7.17 (d, J=5.0 Hz, 1 H), 4.80-4.68 (m, 1 H), 4.15 (s, 1 H), 3.80-3.72 (m, 1 H), 3.42-3.30 (m, 1 H), 3.26-2.78 (m, 11 H), 2.40-2.25 (m, 2 H), 2.05-1.71 (m, 8 H), 1.70-1.40 (m, 2 H); MS (ESI) m/z 544.15 (M+H).

EXAMPLE 6

Synthesis of Compounds Via Scheme 6

Scheme 6

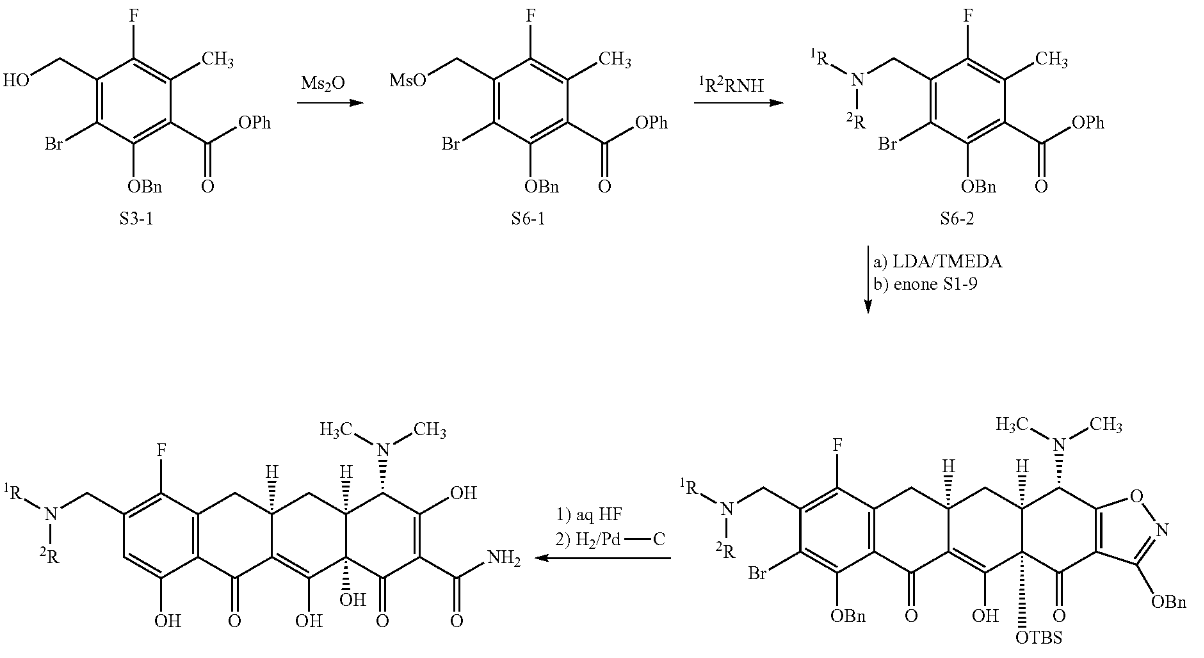

S3-1 S6-1 S6-2 S6-3 S6-4

The following compounds were prepared according to Scheme 6.

S6-2-1

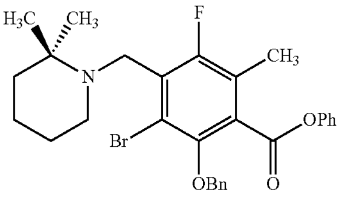

Compound S3-1 (0.36 g, 0.81 mmol, 1.0 equiv) was dissolved in 1,2-dichloroethane (15 mL) with triethylamine (0.57 mL, 4.07 mmol, 5.0 equiv). Methanesulfonic anhydride (0.71 g, 4.07 mmol, 5.0 equiv) was added in one portion at 0° C. During the addition, color change was observed. After stirring at rt for one hour, LC/MS indicated that the starting material was consumed. The reaction mixture was diluted with dichloromethane, quenched by pH 7 phosphate buffer, washed with water (2×20 mL) and brine, dried over sodium sulfate, filtered, and concentrated under reduced pressure. The crude intermediate was used without further purification.

The above crude intermediate (0.16 g, 0.30 mmol, 1.0 equiv) was dissolved in 1,2-dichloroethane (2 mL) with diisopropylethylamine (0.13 mL, 0.72 mmol, 2.4 equiv). 2,2-Dimethyl piperidine hydrochloric salt (54 mg, 0.36 mmol, 1.2 equiv) was first neutralized with sodium hydroxide solution and then was added to reaction mixture in one portion at rt: After stirring at 60° C. for four days, LC/MS indicated that most of the starting material was consumed. The reaction mixture was diluted with dichloromethane, washed with water (2×20 mL) and brine, dried over sodium sulfate, filtered, and concentrated under reduced pressure to afford the desired product S6-2-1, which was used without further purification.

S6-3-1

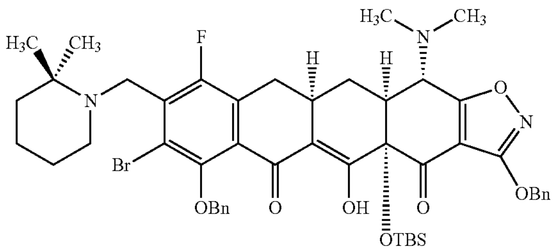

A solution of LDA was prepared by adding n-BuLi (0.31 mL, 1.6 M/hexanes, 0.50 mmol, 2.5 equiv) to diisopropylamine (71 μL, 0.50 mmol, 2.5 equiv) in 2 mL dry THF under a nitrogen atmosphere in a flame dried schenck flask at −78° C. The pale solution was warmed to −20° C., stirred for 15 min, and cooled down to −78° C. TMEDA (75 μL, 0.50 mmol, 2.5 equiv) was added slowly via a syringe, followed by the dropwise addition of compound S6-2-1 (crude, 0.30 mmol, 1.5 equiv)/THF (1 mL). A dark-red color appeared as soon as addition started. After stirring for 10 min, enone S1-9 (96 mg, 0.20 mmol, 1.0 equiv) in 1 mL dry THF was added slowly via a syringe. After 10 min, LC/MS indicated that the enone was consumed and the product present. The reaction mixture was allowed to slowly warm to −20° C. in 1 h. Phosphate buffer (pH 7, 10 mL) and saturated aqueous ammonium chloride (20 mL) were added. The resulting mixture was extracted with dichloromethane (3×15 mL), and the combined extracts were dried over sodium sulfate, filtered, and concentrated under reduced pressure to yield crude S6-3-1 as a red-orange oil (97 mg).

S6-4-1

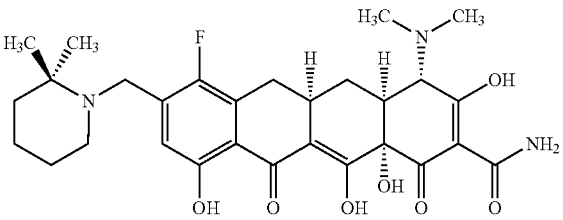

Aqueous HF (0.3 mL, 48-50%) was added to a $CH_3CN$ solution (1.0 mL) of S6-3-1 (97 mg) in a plastic vial at 25° C. The reaction was stirred at 25° C. for 18 hrs. The reaction mixture was poured into an aqueous solution (10 mL) of $K_2HPO_4$ (2 g). The solution was extracted with EtOAc (3×15 mL). The combined EtOAc extracts were dried over sodium sulfate and concentrated to give the crude intermediate (18 mg).

Pd—C (5 mg, 10 wt %) was added to a MeOH solution (2 mL) of the above crude intermediate. HCl in MeOH (0.5 N, 0.5 mL) was added. The reaction was stirred under $H_2$ (balloon) at 25° C. for 2 hrs and filtered through a pad of Celite. The filtrate was concentrated, and the crude product was purified by HPLC on a Polymerx 10μ RP-γ100 R column [30×21.20 mm, 10 micron, solvent A: 0.05 N HCl, solvent B: $CH_3CN$, sample in 2.0 mL (0.05 N HCl), gradient elution with 0→70% B over 15 min, mass-directed fraction collection]. Fractions containing the desired product were collected and freeze-dried, yielding 9 mg of the desired product S6-4-1 as a yellow solid (5%, five steps): $^1$H NMR (400 MHz, $CD_3OD$) δ 7.04 (d, J=5.5 Hz, 1 H), 4.75 (dd, J=13.7, 7.3 Hz, 1 H), 4.08 (s, 1 H), 3.92 (dd, J=13.7, 7.3 Hz, 1 H), 3.32 (m, 2 H), 3.24-2.98 (m, 3 H), 3.03 (s, 3 H), 2.96 (s, 3 H), 2.37 (t, J=15.1 Hz, 1 H), 2.27-2.20 (m, 1 H), 1.91-1.82 (m, 2 H), 1.80-1.63 (m, 5 H), 1.63 (s, 3 H), 1.50 (s, 3 H); MS (ESI) m/z 558.30 (M+H).

The following compounds were prepared similarly to S6-4-1.

S6-4-2

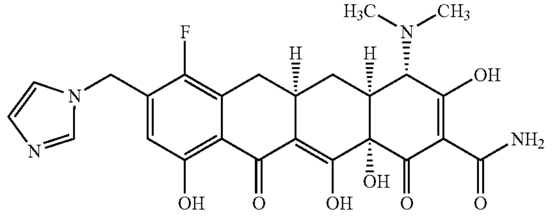

$^1$H NMR (400 MHz, $CD_3OD$) δ 9.11 (s, 1 H), 7.68 (m, 1 H), 7.62 (m, 1 H), 6.86 (d, J=5.9 Hz, 1 H), 5.54 (s, 2 H), 4.07 (s, 1 H), 3.22-2.93 (m, 9 H), 2.37-2.27 (m, 1 H), 2.24-2.17 (m, 1 H), 1.70-1.57 (m, 1 H); MS (ESI) m/z 513.17 (M+H).

S6-4-3

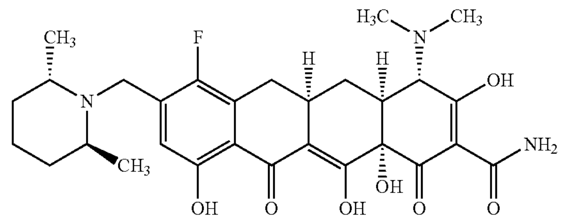

$^1$H NMR (400 MHz, $CD_3OD$) δ 7.06 (dd, J=8.2, 6.0 Hz, 1 H), 4.39 (s, 2 H), 4.10 (s, 1 H), 3.65-3.54 (m, 2 H), 3.24-92 (m, 9 H), 2.43-2.32 (m, 1 H), 2.28-2.17 (m, 1 H), 2.07-1.58 (m, 7 H), 1.51 (d, J=6.0 Hz, 3 H), 1.39 (d, J=6.0 Hz, 3 H); MS (ESI) m/z 558.61 (M+H).

EXAMPLE 7

Synthesis of Compounds Via Scheme 7

To a solution of sodium bicarbonate (0.21 g, 2.48 mmol, 1.1 equiv) in water (10 mL) was added O-benzylhydroxylamine hydrochloride (0.40 g, 2.48 mmol, 1.1 equiv). The solution was heated until all solid dissolved. Compound S1-7 (1.00 g, 2.26 mmol, 1.0 equiv) in EtOH (6 mL) and 1,4-dioxane (6 mL) were added. The solution was heated until all solid dissolved, and then stirred at rt for 2 hrs. The mixture was diluted with EtOAc (100 mL), washed with brine (20 mL×3), dried (sodium sulfate), and concentrated. The residue was purified by flash chromatography on silica gel, eluting with hexanes/EtOAc (30:1 to 5:1) to afford 1.10 g (89%) of compound S7-1: $^1$H NMR (400 MHz, $CDCl_3$) δ 8.33 (s, 1 H), 7.48-7.24 (comp, 13 H), 7.03-6.96 (comp, 2 H), 5.22 (s, 2 H), 5.03 (s, 2 H), 2.30 (d, J=2.4 Hz, 3 H); MS (ESI) m/z 548.16 (M+H).

Scheme 7

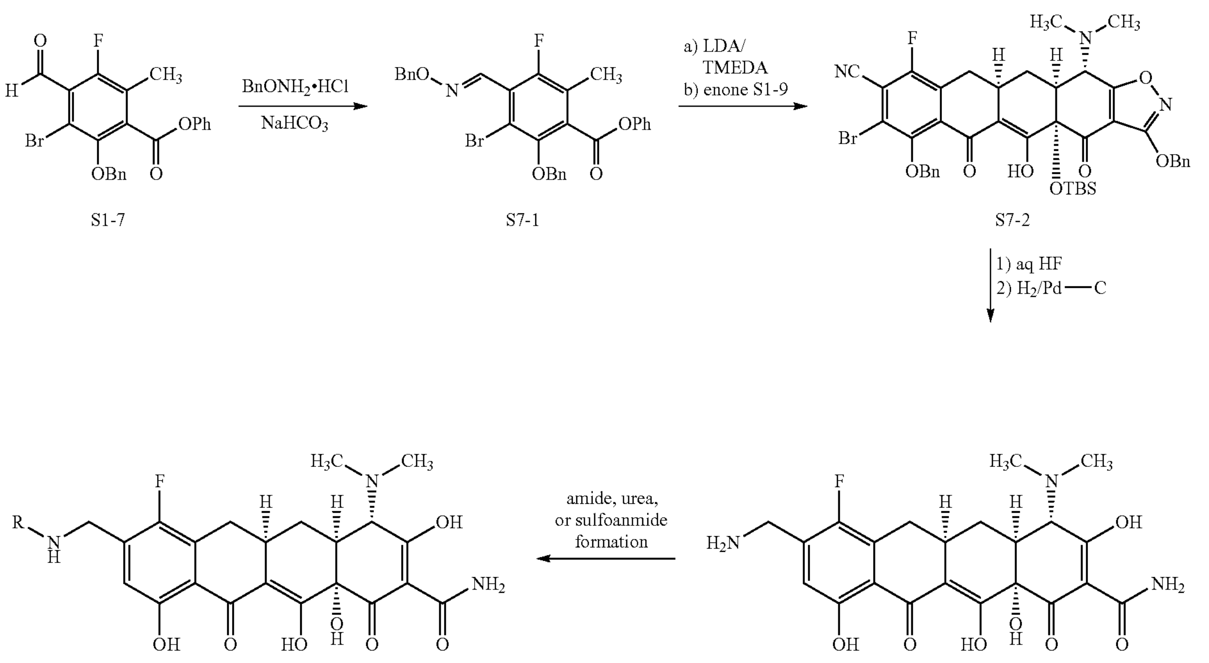

S1-7, S7-1, S7-2, S7-3, S7-4

The following compounds were prepared according to Scheme 7.

S7-1

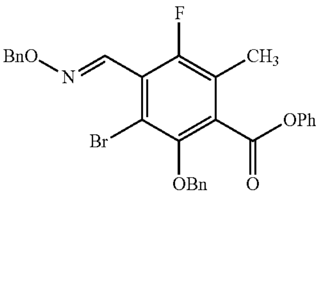

S7-2

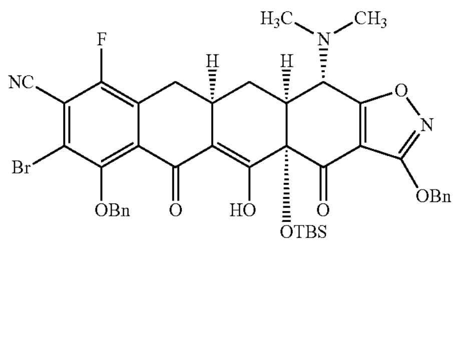

To a solution of LDA (0.38 mL, 1.0 M/THF, 0.38 mmol, 2.9 equiv) in THF (1 mL) was added TMEDA (57 μL, 0.38 mmol, 2.9 equiv) at −78° C. After stirring for 5 min, a solution of compound S7-1 (89 mg, 0.16 mmol, 1.2 equiv) in THF (0.3 mL) was added dropwise to the LDA solution. After complete addition, the reaction mixture was stirred at −78° C. for 10 min. A solution of enone S1-9 (60 mg, 0.13 mmol, 1.0 equiv) in THF (0.3 mL) was added dropwise. The mixture was slowly warmed to −20° C. over 30 min. The mixture was quenched by phosphate buffer (pH 8, 1.5 mL) and saturated ammonium chloride solution (0.5 mL). The aqueous layer was extracted with EtOAc (3 mL×4). All organic layers were combined, dried (sodium sulfate), and concentrated. The crude product was purified by preparative reverse phase HPLC on a Waters Autopurification system using a Sunfire Prep C18 OBD column [5 μm, 19×50 mm; flow rate, 20 mL/min; Solvent A: $H_2O$ with 0.1% $HCO_2H$; Solvent B: $CH_3CN$ with 0.1% $HCO_2H$; injection volume: 2.0 mL ($CH_3CN$); gradient: 80→100% B over 15 min; mass-directed fraction collection]. Fractions containing the desired product, eluting at 6.1-8.3 min, were collected and freeze-dried to give 33 mg of S7-2 (32%): $^1H$ NMR (400 MHz, $CDCl_3$) δ 15.71 (s, 1 H), 7.55-7.24 (comp, 10 H), 5.35 (s, 2 H), 4.99 (d, J=9.8 Hz, 1 H), 4.95 (d, J=9.8 Hz, 1 H), 3.87 (d, J=10.4 Hz, 1 H), 3.24 (dd, J=16.5, 4.6 Hz, 1 H), 3.07-2.97 (m, 1 H), 2.49 (s, 6 H), 2.64-2.33 (comp, 3 H), 2.20-2.12 (m, 1 H), 0.80 (s, 9 H), 0.26 (s, 3 H), 0.12 (s, 3 H); MS (ESI) m/z 828.16 (M+H).

S7-3

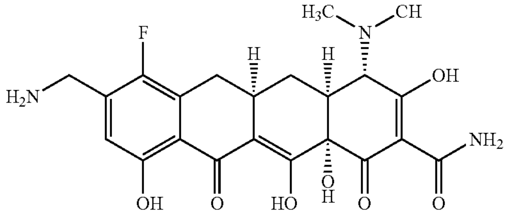

To a solution of S7-2 (33 mg, 0.040 mmol) in acetonitrile (1 mL) was added HF (0.3 mL, 48-50% solution in water). The mixture was stirred at 0° C. for 63 hrs and rt for 3 hrs. The mixture was quenched by potassium phosphate dibasic solution (prepared from 8 g $K_2HPO_4$ and 8 mL water). The aqueous layer was extracted with EtOAc (8 mL×5). All organic layers were combined, dried (sodium sulfate) and concentrated to afford the crude intermediate.

To the above crude intermediate in MeOH/dioxane solution (1:1, 1.4 mL) was added Pd—C (15 mg, 10 wt %) and HCl/MeOH (0.5 N, 0.25 mL). The reaction was bubbled with $H_2$ (balloon) at 25° C. for 90 min. The mixture was filtered through a small Celite plug and flashed with MeOH. The filtrate was concentrated to yield the crude product, which was purified by preparative reverse phase HPLC on a Waters Autopurification system using a Phenomenex Polymerx 10μ RP-$_1$ 100A column [10 μm, 150×21.20 mm; flow rate, 20 mL/min; Solvent. A: 0.05 N HCl/water; Solvent B: $CH_3CN$; injection volume: 4.5 mL (0.05 N HCl/water); gradient: 0→50% B over 10 min; mass-directed fraction collection]. Fractions containing the desired product, eluting at 6.9-8.1 min, were collected and freeze-dried to yield 10 mg of primary S7-3 (55% for 2 steps): $^1H$ NMR (400 MHz, $CD_3OD$) δ 6.95 (d, J=6.1 Hz, 1 H), 4.18 (s, 2 H), 4.09 (s, 1 H), 3.04 (s, 3 H), 2.96 (s, 3 H), 3.22-2.90 (comp, 3 H), 2.39-2.28 (m, 1 H), 2.28-2.18 (m, 1 H), 1.70-1.57 (m, 1 H); MS (ESI) m/z 462.12 (M+H).

S7-4-1

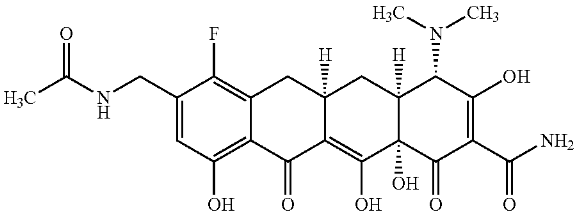

To a solution of compound S7-3 (10 mg, 0.020 mmol, 1.0 equiv) and $Ac_2O$ (diluted 20 times in dichloromethane, 45 μL, 0.020 mmol, 1.0 equiv) in DMF (1.5 mL) was added $Et_3N$ (15 μL, 0.11 mmol, 5.5 equiv) at 0° C. The mixture was stirred for 30 min and then submitted to preparative reverse phase HPLC purification on a Waters Autopurification system using a Phenomenex Polymerx 10μ RP-γ 100A column [10 μm, 150×21.20 mm; flow rate, 20 mL/min; Solvent A: 0.05 N HCl/water; Solvent B: $CH_3CN$; injection volume: 3.0 mL (0.05 N HCl/water); gradient: 0→70% B over 20 min; mass-directed fraction collection]. Fractions containing the desired product, eluting at 9.4-10.6 min, were collected and freeze-dried to yield 4 mg of S7-4-1 (40%): $^1H$ NMR (400 MHz, $CD_3OD$) δ 6.73 (d, J=5.5 Hz, 1 H), 4.38 (d, J=1.8 Hz, 2 H), 4.07 (s, 1 H), 3.15 (dd, J=15.3, 4.3 Hz, 1 H), 3.03 (s, 3 H), 2.95 (s, 3 H), 3.10-2.92 (comp, 2 H), 2.32-2.23 (m, 1 H), 2.22-2.15 (m, 1 H), 2.01 (s, 3 H), 1.68-1.56 (m, 1 H); MS (ESI) m/z 504.10 (M+H).

S7-4-2

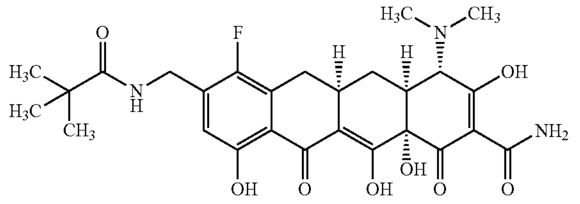

S7-4-2 was prepared according to the procedure for the preparation of S7-4-1: $^1H$ NMR (400 MHz, $CD_3OD$) δ 6.65 (d, J=6.1 Hz, 1 H), 4.41 (d, J=16.5 Hz, 1 H), 4.35 (d, J=16.5 Hz, 1 H), 4.06 (s, 1 H), 3.15 (dd, J=15.3, 4.6 Hz, 1 H), 3.03 (s, 3 H), 2.95 (s, 3 H), 3.10-2.91 (comp, 2 H), 2.33-2.22 (m, 1 H), 2.22-2.14 (m, 1 H), 1.68-1.56 (m, 1 H), 1.22 (s, 9 H); MS (ESI) m/z 546.27 (M+H).

S7-4-3

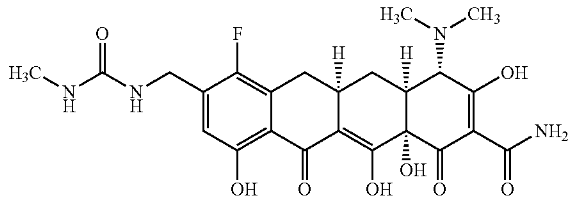

To a solution of compound S7-3 (11 mg, 0.020 mmol, 1.0 equiv) and methyl isocyanate (1.4 mg, 0.020 mmol, 1.0 equiv) in DMF (1.5 mL) was added $Et_3N$ (18 μL, 0.13 mmol, 6.5 equiv) at 0° C. The mixture was stirred for 10 min and then submitted to preparative reverse phase HPLC purification on a Waters Autopurification system using a Phenomenex Polymerx 10µ RP-γ 100A column [10 µm, 150×21.20 mm; flow rate, 20 mL/min; Solvent A: 0.05 N HCl/water; Solvent B: $CH_3CN$; injection volume: 3.3 mL (0.05 N HCl/water); gradient: 0→70% B over 20 min; mass-directed fraction collection]. Fractions containing the desired product, eluting at 9.3-10.6 min, were collected and freeze-dried to yield 4 mg of S7-4-3 (31%): $^1H$ NMR (400 MHz, $CD_3OD$) δ 6.74 (d, J=6.1 Hz, 1 H), 4.37 (d, J=17.3 Hz, 1 H), 4.32 (d, J=17.3 Hz, 1 H), 4.06 (s, 1 H), 3.15 (dd, J=15.9, 4.6 Hz, 1 H), 3.03 (s, 3 H), 2.95 (s, 3 H), 3.10-2.92 (comp, 2 H), 2.72 (s, 3 H), 2.32-2.22 (m, 1 H), 2.22-2.15 (m, 1 H), 1.67-1.56 (m, 1 H); MS (ESI) m/z 519.08 (M+H).

S7-4-4

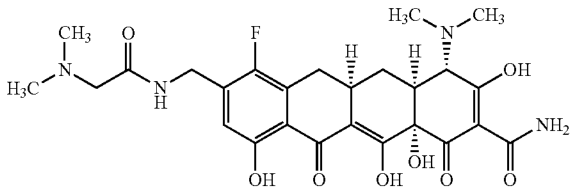

S7-4-4 was prepared from S7-3 according to the procedure for the preparation of S7-4-1: $^1H$ NMR (400 MHz, $CD_3OD$) δ 6.79 (d, J=6.1 Hz, 1 H), 4.49 (d, J=5.5 Hz, 2 H), 4.07 (s, 1 H), 4.03 (s, 2 H), 3.15 (dd, J=15.2, 4.3 Hz, 1 H), 3.03 (s, 3 H), 2.95 (s, 3 H), 2.94 (s, 6 H), 3.10-2.92 (comp, 2 H), 2.33-2.23 (m, 1 H), 2.22-2.17 (m, 1 H), 1.68-1.56 (m, 1 H); MS (ESI) m/z 547.11 (M+H).

S7-4-5

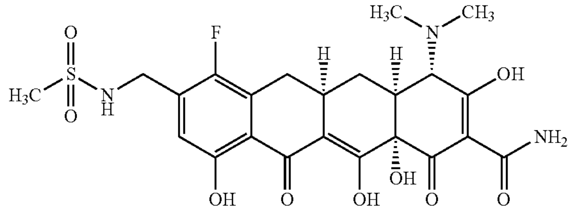

To a solution of compound S7-3 (11 mg, 0.020 mmol, 1.0 equiv) and methanesulfonic anhydride (5 mg, 0.030 mmol, 1.5 equiv) in DMF (1.5 mL) was added $Et_3N$ (18 µL, 0.13 mmol, 6.5 equiv) at 0° C. The mixture was stirred for 50 min and then submitted to preparative reverse phase HPLC purification on a Waters Autopurification system using a Phenomenex Polymerx 10µ RP-γ 100A column [10 µm, 150×21.20 mm; flow rate, 20 mL/min; Solvent A: 0.05 N HCl/water; Solvent B: $CH_3CN$; injection volume: 3 mL (0.05 N HCl/water); gradient: 0→70% B over 20 min; mass-directed fraction collection]. Fractions containing the desired product, eluting at 10.3-11.6 min, were collected and freeze-dried to yield 3 mg of S7-4-5 (22%): $^1H$ NMR (400 MHz, $CD_3OD$) δ 6.93 (d, J=6.1 Hz, 1 H), 4.29 (s, 2 H), 4.06 (s, 1 H), 3.16 (dd, J=15.9, 4.6 Hz, 1 H), 3.03 (s, 3 H), 2.94 (s, 3 H), 2.93 (s, 3 H), 3.10-2.92 (comp, 2 H), 2.34-2.23 (m, 1 H), 2.23-2.16 (m, 1 H), 1.68-1.57 (m, 1 H); MS (ESI) m/z 540.04 (M+H).

S7-4-6

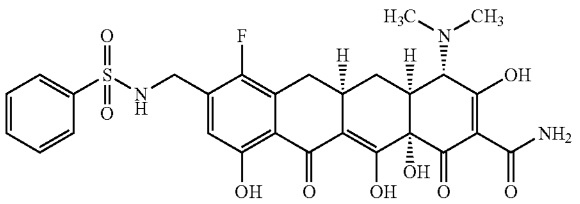

S7-4-6 was prepared according to the procedure for the preparation of S7-4-5: $^1H$ NMR (400 MHz, $CD_3OD$) δ 7.79 (d, J=7.4 Hz, 2 H), 7.59-7.48 (comp, 3 H), 6.76 (d, J=6.1 Hz, 1 H), 4.12 (s, 2 H), 4.06 (s, 1 H), 3.03 (s, 3 H), 2.95 (s, 3 H), 3.15-2.91 (comp, 3 H), 2.24-2.13 (comp, 2 H), 1.67-1.54 (m, 1 H); MS (ESI) m/z 602.22 (M+H).

The following compounds were prepared from S2-4-17 using similar amide, urea, or sulfonamide formation conditions.

S7-4-7

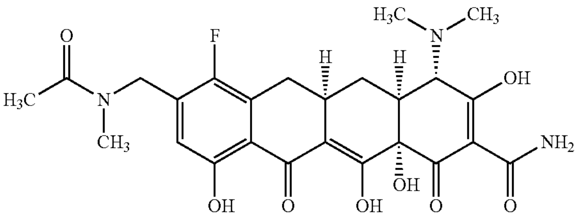

To a solution of S2-4-17 (8 mg, 0.020 mmol, 1.0 equiv) and $Ac_2O$ (diluted 20 times in dichloromethane, 38 µL, 0.020 mmol, 1.0 equiv) in DMF/acetonitrile (1:1, 2 mL) was added $Et_3N$ (9 µL, 0.070 mmol, 3.5 equiv) at rt. The mixture was stirred for 30 min and then submitted to preparative reverse phase HPLC purification on a Waters Autopurification system using a Phenomenex Polymerx 10µ RP-γ 100A column [10 µm, 150×21.20 mm; flow rate, 20 mL/min; Solvent A: 0.05 N HCl/water; Solvent B: $CH_3CN$; injection volume: 1.5 mL (0.05 N HCl/water); gradient: 0→100% B over 10 min; mass-directed fraction collection]. Fractions containing the desired product, eluting at 8.1-9.0 min, were collected and freeze-dried to yield 5 mg of S7-4-7 (52%): $^1H$ NMR (400 MHz, $CD_3OD$) δ 6.62 (d, J=6.1 Hz, 1 H), 4.67-4.60 (m, 2 H), 4.07 (s, 1 H), 3.09 (s, 3 H), 3.03 (s, 3 H), 2.95 (s, 3 H), 3.21-2.90 (comp, 3 H), 2.36-2.12 (comp, 5 H), 1.68-1.58 (m, 1 H); MS (ESI) m/z 518.12 (M+H).

S7-4-8

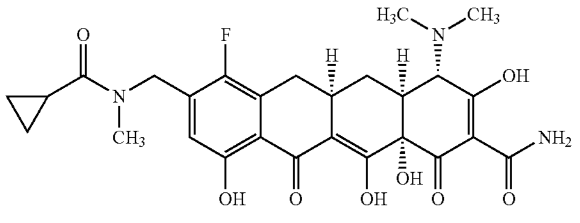

S7-4-8: $^1H$ NMR (400 MHz, $CD_3OD$) δ 6.64-6.56 (m, 1 H), 4.63 (br s, 2 H), 4.07 (s, 1 H), 3.25 (s, 3 H), 3.03 (s, 3 H), 2.95 (s, 3 H), 3.21-2.92 (comp, 3 H), 2.35-2.16 (comp, 2 H), 2.07-1.99 (m, 1 H), 1.70-1.57 (m, 1 H), 0.94-0.76 (comp, 4 H); MS (ESI) m/z 544.25 (M+H).

S7-4-9

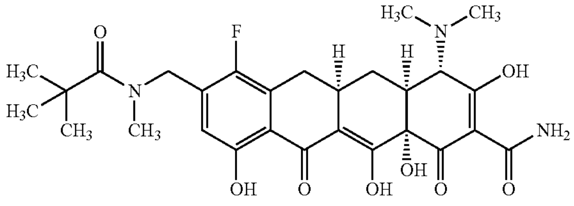

S7-4-9: $^1$H NMR (400 MHz, $CD_3OD$) δ 6.53 (d, J=6.1 Hz, 1 H), 4.63 (d, J=4.3 Hz, 2 H), 4.06 (s, 1 H), 3.17 (s, 3 H), 3.03 (s, 3 H), 2.95 (s, 3 H), 3.20-2.92 (comp, 3 H), 2.37-2.16 (comp, 2 H), 1.68-1.58 (m, 1 H), 1.32 (s, 9 H); MS (ESI) m/z 560.30 (M+H).

S7-4-10

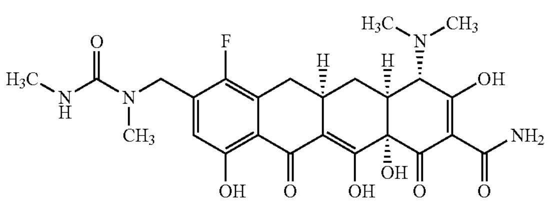

To a solution of S2-4-17 (15 mg, 0.030 mmol, 1.0 equiv) and methyl isocyanate (2 mg, 0.030 mmol, 1.0 equiv) in DMF (1.5 mL) was added $Et_3N$ (22 μL, 0.16 mmol, 5.3 equiv) at 0° C. The mixture was stirred for 30 min and then submitted to preparative reverse phase HPLC purification on a Waters Autopurification system using a Phenomenex Polymerx 10μ RP-γ 100A column [10 μm, 150×21.20 min; flow rate, 20 mL/min; Solvent A: 0.05 N HCl/water; Solvent B: $CH_3CN$; injection volume: 2.6 mL (0.05 N HCl/water); gradient: 0→100% B over 20 min; mass-directed fraction collection]. Fractions containing the desired product, eluting at 8.4-10.2 min, were collected and freeze-dried to yield 14 mg of S7-4-10 (83%): $^1$H NMR (400 MHz, $CD_3OD$) δ 6.59 (d, J=6.1 Hz, 1 H), 4.55 (s, 2 H), 4.07 (s, 1 H), 3.03 (s, 3 H), 2.95 (s, 3 H), 2.91 (s, 3 H), 3.19-2.89 (comp, 3 H), 2.75 (s, 3 H), 2.32-2.16 (comp, 2 H), 1.68-1.57 (m, 1 H); MS (ESI) m/z 533.11 (M+H).

S7-4-11

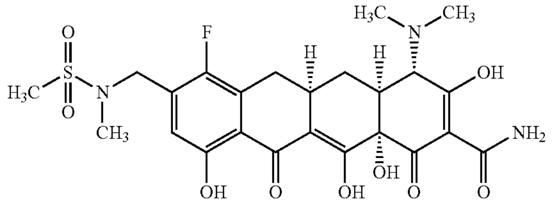

To a solution of S2-4-17 (15 mg, 0.030 mmol, 1.0 equiv) and methanesulfonic anhydride (6 mg, 0.030 mmol, 1.0 equiv) in DMF (1.5 mL) was added $Et_3N$ (22 μL, 0.16 mmol, 5.3 equiv) at 0° C. The mixture was stirred at 0° C. for 30 min and rt for 20 min. The mixture was submitted to preparative reverse phase HPLC purification on a Waters Autopurification system using a Phenomenex Polymerx 10μ RP-γ 100A column [10 μm, 150×21.20 mm; flow rate, 20 mL/min; Solvent A: 0.05 N HCl/water; Solvent B: $CH_3CN$; injection volume: 3 mL (0.05 N HCl/water); gradient: 0→100% B over 20 min; mass-directed fraction collection]. Fractions containing the desired product, eluting at 9.8-11.6 min, were collected and freeze-dried to yield 7 mg of S7-4-11 (38%): $^1$H NMR (400 MHz, $CD_3OD$) δ 6.90 (d, J=5.5 Hz, 1 H), 4.38 (s, 2 H), 4.07 (s, 1 H), 3.03 (s, 3 H), 2.95 (s, 3 H), 2.94 (s, 3 H), 3.19-2.93 (comp, 3 H), 2.83 (s, 3 H), 2.34-2.16 (comp, 2 H), 1.69-1.58 (m, 1 H); MS (ESI) m/z 554.06 (M+H).

S7-4-12

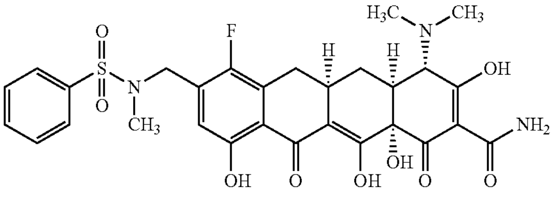

S7-4-12 was prepared according to the procedure for the preparation of S7-4-11: $^1$H NMR (400 MHz, $CD_3OD$) δ 7.85 (dd, J=7.4, 1.8 Hz, 2 H), 7.72-7.60 (comp, 3 H), 6.87 (d, J=6.1 Hz, 1 H), 4.25 (d, J=1.8 Hz, 2 H), 4.06 (s, 1 H), 3.03 (s, 3 H), 2.95 (s, 3 H), 3.15-2.92 (comp, 3 H), 2.71 (s, 3 H), 2.32-2.16 (comp, 2 H), 1.68-1.57 (m, 1 H); MS (ESI) m/z 616.20 (M+H).

EXAMPLE 8

Synthesis of Compounds Via Scheme 8

Scheme 8

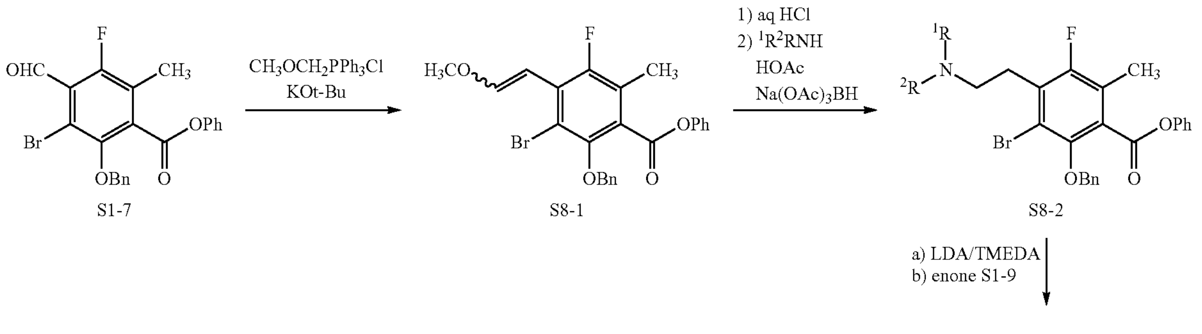

S1-7 S8-1 S8-2

-continued

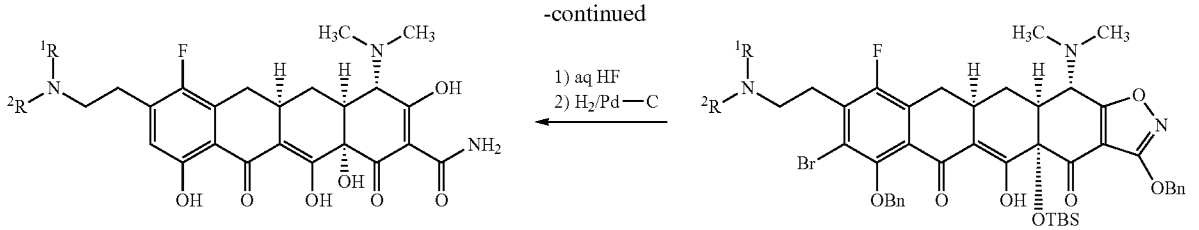

S8-4 S8-3

The following compounds were prepared according to Scheme 8.

S8-1

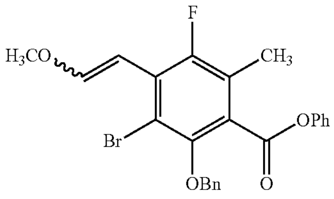

(Methoxymethyl)triphenylphosphonium chloride (0.46 g, 1.35 mmol, 2.0 equiv) was added to a suspension of potassium t-butoxide (0.15 g, 1.35 mmol, 2.0 equiv) in THF (3 mL), resulting in a red colored mixture. After 15 minutes, a solution of compound S1-7 (0.30 g, 0.68 mmol, 1.0 equiv) in THF (2 mL) was added, resulting in a yellowish orange mixture. After 1 h, the reaction mixture was quenched by water (15 mL) and extracted with EtOAc (2×20 mL). The combined extracts were dried over sodium sulfate, filtered, and concentrated under reduced pressure. The material was purified by column chromatography on silica (Biotage 10 g prepacked column, 0% to 6% EtOAc in hexanes gradient). The two regioisomeric compounds mostly co-eluted and were combined, yielding 0.23 g (73%) of compound S8-1 ($^1$H NMR indicated a 2:1 mixture of cis and trans isomers): $R_f$ 0.40, 0.34 (10% EtOAc/hexanes); $^1$H NMR (400 MHz, $CDCl_3$) δ 7.52-7.46 (m, 2 H), 7.40-7.32 (m, 5.66 H), 7.28-7.20 (m, 1 H), 7.04 (d, J=8.2 Hz, 2 H), 6.31 (d, J=6.8 Hz, 0.34 H), 5.93 (d, J=12.8 Hz, 0.66 H), 5.22 (d, J=6.8 Hz, 0.34 H), 5.08 (s, 2 H), 3.77 (s, 2 H), 3.73 (s, 1 H), 2.36-2.31 (m, 3 H); MS (ESI) m/z 493.26, 495.26 (M+Na).

S8-2-1

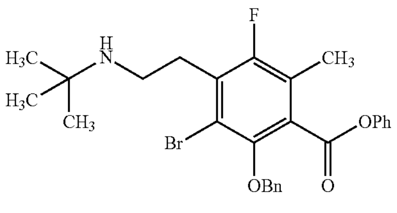

A solution of S8-1 (0.35 g, 0.74 mmol) in 6 N HCl in water (2 mL) and THF (6 mL) was heated to 70° C. After 4 hrs, the reaction mixture was cooled to room temperature and diluted with EtOAc (25 mL). The layers were separated, and the EtOAc layer was dried over sodium sulfate, filtered, and concentrated under reduced pressure, yielding 0.32 g (95%) of crude aldehyde intermediate: MS (ESI) m/z 479.19, 481.15 (M+Na).

The aldehyde intermediate (0.10 g, 0.13 mmol, 1.0 equiv) was dissolved in 1,2-dichloroethane (2 mL) and HOAc (0.054 mL, 0.94 mmol, 7.2 equiv) and t-butylamine (0.099 mL, 0.94 mmol, 7.2 equiv) were added. After 15 minutes, Na$(OAc)_3$BH (0.14 g, 0.67 mmol, 5.2 equiv) was added. After stirring overnight, the reaction mixture was quenched by $NaHCO_3$ (saturated, aqueous solution), diluted with dichloromethane (20 mL), washed with $NaHCO_3$ (saturated, aqueous solution, 10 mL), dried over sodium sulfate, filtered, and concentrated under reduced pressure. The material was purified by column chromatography on silica (Biotage 5 g prepacked column, 0% to 60% EtOAc in hexanes gradient), yielding 20 mg (28%) of compound S8-2-1: $^1$H NMR (400 MHz, $CDCl_3$) δ 7.52-7.46 (m, 2 H), 7.40-7.32 (m, 5 H), 7.28-7.20 (m, 1 H), 7.04 (d, J=8.2 Hz, 2 H), 5.10 (s, 2 H), 3.25-2.98 (m, 2 H), 2.90-2.70 (m, 2 H), 2.35 (s, 3 H), 1.17 (br s, 9 H); MS (ESI) m/z 514.31, 516.3 (M+H).

S8-3-1

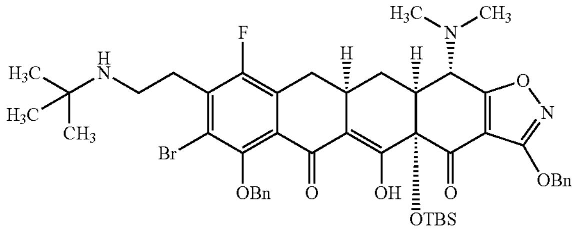

A solution of S8-2-1 (20 mg, 0.038 mmol, 1.2 equiv) in THF (1 mL) was added to a solution of LDA (1.2 M/THF/heptane/ethylbenzene, 0.058 mL, 0.070 mmol, 2.2 equiv) and TMEDA (0.028 mL, 0.19 mmol, 6.0 equiv) in THF (2 mL) at −78° C., giving a red colored solution. The reaction was stirred at −78° C. for 5 min. A solution of enone S1-9 (15 mg, 0.032 mmol, 1.0 equiv) in THF (0.5 mL) was added dropwise to the reaction mixture. The reaction was stirred from −78° C. to −20° C. for 1 h, quenched by saturated aqueous $NH_4Cl$, and extracted with EtOAc (2 times). The combined EtOAc extracts were dried (sodium sulfate) and concentrated to yield the crude product. The crude product was purified by preparative reverse phase HPLC on a Waters Autopurification system using a Sunfire Prep C18 OBD column [5 μm, 19×50 mm; flow rate, 20 mL/min; Solvent A: $H_2O$ with 0.1% $HCO_2H$; Solvent B: $CH_3CN$ with 0.1% $HCO_2H$; gradient: 20→100% B over 15 min; mass-directed fraction collection]. Fractions containing the desired product, eluting at 7.0-8.0 min, were collected and freeze-dried to give 18 mg of pure compound S8-3-1 (62%): $^1$H NMR (400 MHz, $CDCl_3$) δ 7.58-7.45 (m, 4 H), 7.40-7.28 (m, 6 H), 5.35 (s, 2 H), 5.00-4.87 (m, 2 H), 3.91 (d, J=10.4 Hz, 1 H), 3.54-3.15 (m, 3 H), 3.02-2.88 (m, 3 H), 2.58-2.32 (m, 9 H), 2.17-2.08 (m, 1 H), 1.48-1.20 (br s, 9 H), 0.80 (s, 9 H), 0.26 (s, 3 H), 0.11 (s, 3 H); MS (ESI) m/z 902.48, 904.45 (M+H).

S8-4-1

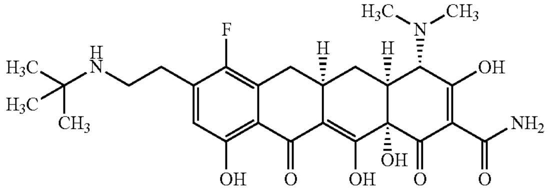

A solution of compound S8-3-1 (18 mg, 0.020 mmol) in 1,4-dioxane (0.80 mL) was treated with HF (0.40 mL, 48-50% aqueous solution). After stirring overnight, the mixture was poured into a solution of $K_2HPO_4$ (4.8 g) in water (20 mL). This mixture was extracted with EtOAc (3 times), and the combined extracts were dried over sodium sulfate, filtered, and concentrated under reduced pressure.

The above material was dissolved in MeOH (1 mL), 1,4-dioxane (1 mL), and 0.5 N HCl/MeOH (0.4 mL). 10% Pd—C (Degussa, 2 mg) was added, and an atmosphere of hydrogen was introduced. After 2 hrs, the reaction mixture was filtered through Celite and concentrated under reduced pressure. The crude product was purified by preparative reverse phase HPLC on a Waters Autopurification system using a Polymerx 10μ RP-γ 100 R column [30×21.20 mm, 10 micron, solvent A: 0.05 N HCl, solvent B: $CH_3CN$, gradient elution with 0→70% B over 10 min; mass-directed fraction collection]. Fractions containing the desired product, eluting at 7.0-8.4 min, were collected and freeze-dried to yield 8 mg of compound S8-4-1 (64%): $^1H$ NMR (400 MHz, $CD_3OD/DCl$) δ 6.86 (d, J=5.5 Hz, 1 H), 4.14 (s, 1 H), 3.34-2.94 (m, 13 H), 2.33-2.21 (m, 2 H), 1.70-1.55 (m, 1 H), 1.49 (s, 9 H); MS (ESI) m/z 532.31 (M+H).

EXAMPLE 9

Synthesis of Compounds Via Scheme 9

The following compounds were prepared according to Scheme 9.

S9-1-1

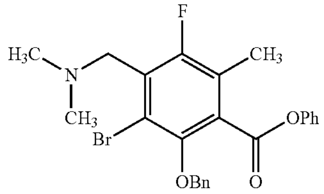

Compound S1-7 (0.25 g, 0.56 mmol, 1.0 equiv) was dissolved in 1,2-dichloroethane (4 mL). Dimethylamine (0.56 mL, 2.0 M/THF, 1.12 mmol, 2.0 equiv) and acetic acid (64 μL, 1.12 mmol, 2.0 equiv) were added under a nitrogen atmosphere. After stirring at rt for 1 h, sodium triacetoxyborohydride (0.36 g, 1.68 mmol, 3.0 equiv) was added to reaction mixture. After overnight, LC/MS indicated that the starting material was consumed. The reaction mixture was diluted with dichloromethane, washed with $NaHCO_3$ (saturated aqueous solution, 3×10 mL) and brine, dried over sodium sulfate, filtered, and concentrated under reduced pressure. The crude product was purified by flash column chromatography (Biotage 10 g column, 10% to 30% EtOAc in hexanes gradient), yielding 0.21 g (78%) of the pure compound S9-1-1 as a colorless oil: $^1H$ NMR (400 MHz, $CDCl_3$) δ 7.52-7.47 (m, 2 H), 7.40-7.33 (m, 5 H), 7.26 (t, J=7.8 Hz, 1 H), 7.07-7.03 (m, 2 H), 5.11 (s, 2 H), 3.66 (d, J=2.3 Hz, 2 H), 2.37 (d, J=2.3 Hz, 3 H), 2.35 (s, 6 H).

Scheme 9

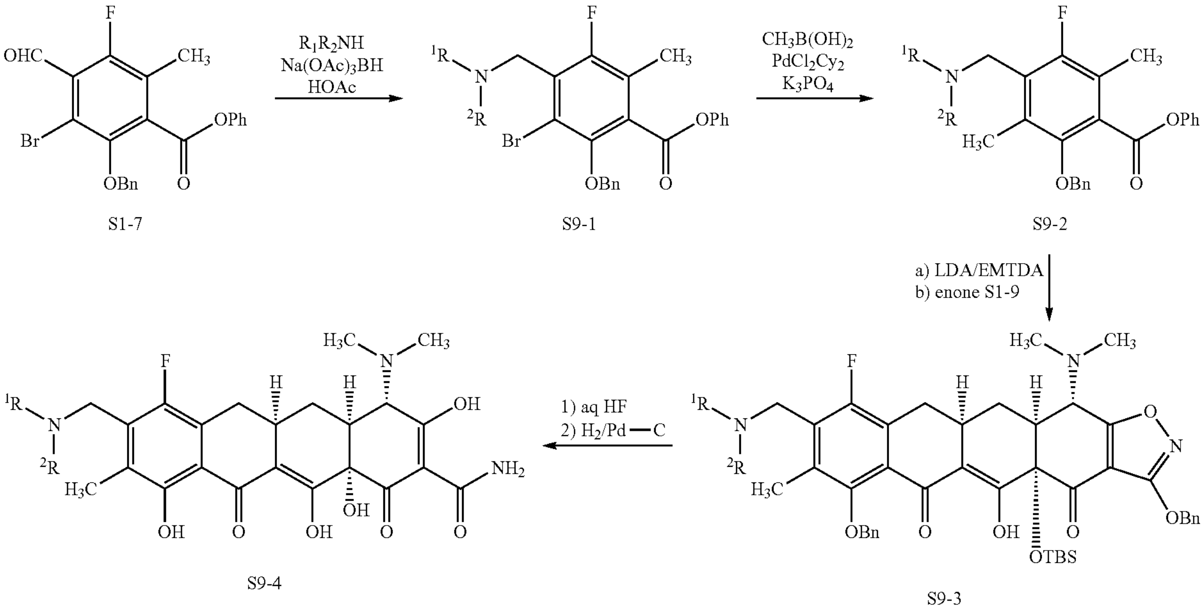

S1-7

S9-1

S9-2

S9-4

S9-3

S9-2-1

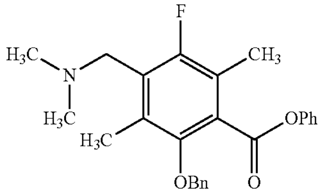

Compound S9-1-1 (0.10 g, 0.21 mmol), methylboronic acid (38 mg, 0.64 mmol), dichlorobis(tricyclohexylphosphine)palladium(II) (4 mg, 0.011 mmol) and $K_3PO_4$ (0.14 g, 0.64 mmol) were heated to 80° C. in toluene (2 mL) and water (5 drops). After 5 hrs, additional $K_3PO_4$ (0.14 g, 0.64 mmol) and methylboronic acid (38 mg, 0.64 mmol) were added. The reaction mixture was heated to 100° C. After one hour, the reaction mixture was cooled to rt and let stand for 3 days. Additional dichlorobis-(tricyclohexylphosphine)palladium (II) (5 mg, 0.015 mmol) and methylboronic acid (38 mg, 0.64 mmol) were added, followed by enough $K_3PO_4$ to give a saturated aqueous layer. This was heated to 110° C. After 2 hrs, the reaction was complete. Upon cooling to rt, the reaction mixture was diluted with EtOAc, washed with water (2 times) and brine (1 time), dried over sodium sulfate, filtered, and concentrated under reduced pressure. The material was purified by column chromatography on silica (Biotage 5 g prepacked column, 0% to 6% MeOH in dichloromethane gradient), yielding 81 mg (93%) of compound S9-2-1. The compound was ~80-90% pure and contaminated with phosphine ligand: $R_f$ 0.49 (10% MeOH/dichloromethane); $^1H$ NMR (400 MHz, $CDCl_3$) δ 7.50-7.30 (m, 7 H), 7.30-7.20 (m, 1 H), 7.12-7.04 (m, 2 H), 4.96 (s, 2 H), 2.80-2.20 (m, 9 H), 1.56 (s, 3 H); MS (ESI) m/z 408.34 (M+H).

S9-3-1

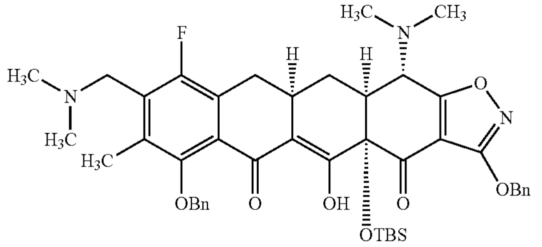

n-Butyllithium (2.5 M/hexanes, 0.14 mL, 0.35 mmol, 2.3 equiv) was added to a −40° C. solution of diisopropylamine (0.050 mL, 0.35 mmol, 2.3 equiv) in THF (5 mL). The reaction mixture was cooled to −78° C., and TMEDA (0.14 mL, 0.92 mmol, 6.1 equiv) was added. A solution of S9-2-1 (81 mg, 0.20 mmol, 1.3 equiv) in THF (2 mL) was added dropwise. A solution of enone S1-9 (74 mg, 0.15 mmol, 1.0 equiv) in THF (1 mL) was added dropwise to the reaction mixture. The reaction was stirred from −78° C. to −20° C. for 1 h, quenched by saturated aqueous $NH_4Cl$, and extracted with EtOAc (2 times). The combined EtOAc extracts were dried (sodium sulfate) and concentrated to yield the crude product. The crude product was purified by preparative reverse phase HPLC on a Waters Autopurification system using a Sunfire Prep C18 OBD column [5 μm, 19×50 mm; flow rate, 20 mL/min; Solvent A: $H_2O$ with 0.1% $HCO_2H$; Solvent B: $CH_3CN$ with 0.1% $HCO_2H$; gradient: 50→100% B over 15 min; mass-directed fraction collection]. Fractions containing the desired product, eluting at 2.5-3.6 min, were collected and freeze-dried to give 34 mg of compound S9-3-1 (28%, contaminated with the phosphine ligand): MS (ESI) m/z 796.53 (M+H).

S9-4-1

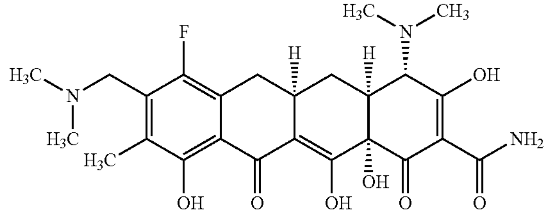

A solution of compound S9-3-1 (34 mg, 0.043 mmol) in 1,4-dioxane (0.9 mL) was treated with HF (0.40 mL, 48-50% aqueous solution). After stirring overnight, the mixture was poured into a solution of $K_2HPO_4$ (4.8 g) in water (20 mL). This mixture was extracted with EtOAc (3 times), and the combined extracts were dried over sodium sulfate, filtered, and concentrated under reduced pressure.

The above crude material was dissolved in MeOH (2 mL), 1,4-dioxane (2 mL), and 0.5 N HCl/MeOH (0.5 mL). 10% Pd—C (Degussa, 10 mg) was added, and an atmosphere of hydrogen was introduced. Upon completion, the reaction mixture was filtered through Celite and concentrated under reduced pressure. The crude product was purified by preparative reverse phase HPLC on a Waters Autopurification system using a Polymerx 10μ RP-γ 100 R column [30×21.20 mm, 10 micron, solvent A: 0.05 N HCl, solvent B: $CH_3CN$, gradient elution with 0→70% B over 10 min; mass-directed fraction collection]. Fractions containing the desired product, eluting at 6.6-7.6 min, were collected and freeze-dried to yield 10 mg of compound S9-4-1 (41%): $^1H$ NMR (400 MHz, $CD_3OD$/DCl) δ 4.52 (s, 2 H), 4.15 (s, 1 H), 3.24-2.92 (m, 15 H), 2.36 (s, 3 H), 2.34-2.24 (m, 2 H), 1.70-1.56 (m, 1 H); MS (ESI) m/z 504 (M+H).

EXAMPLE 10

Synthesis of Compounds Via Scheme 10

Scheme 10

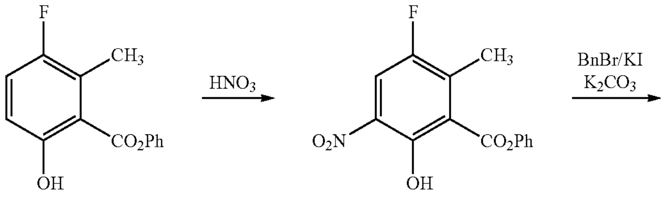

S1-4 S10-1

-continued
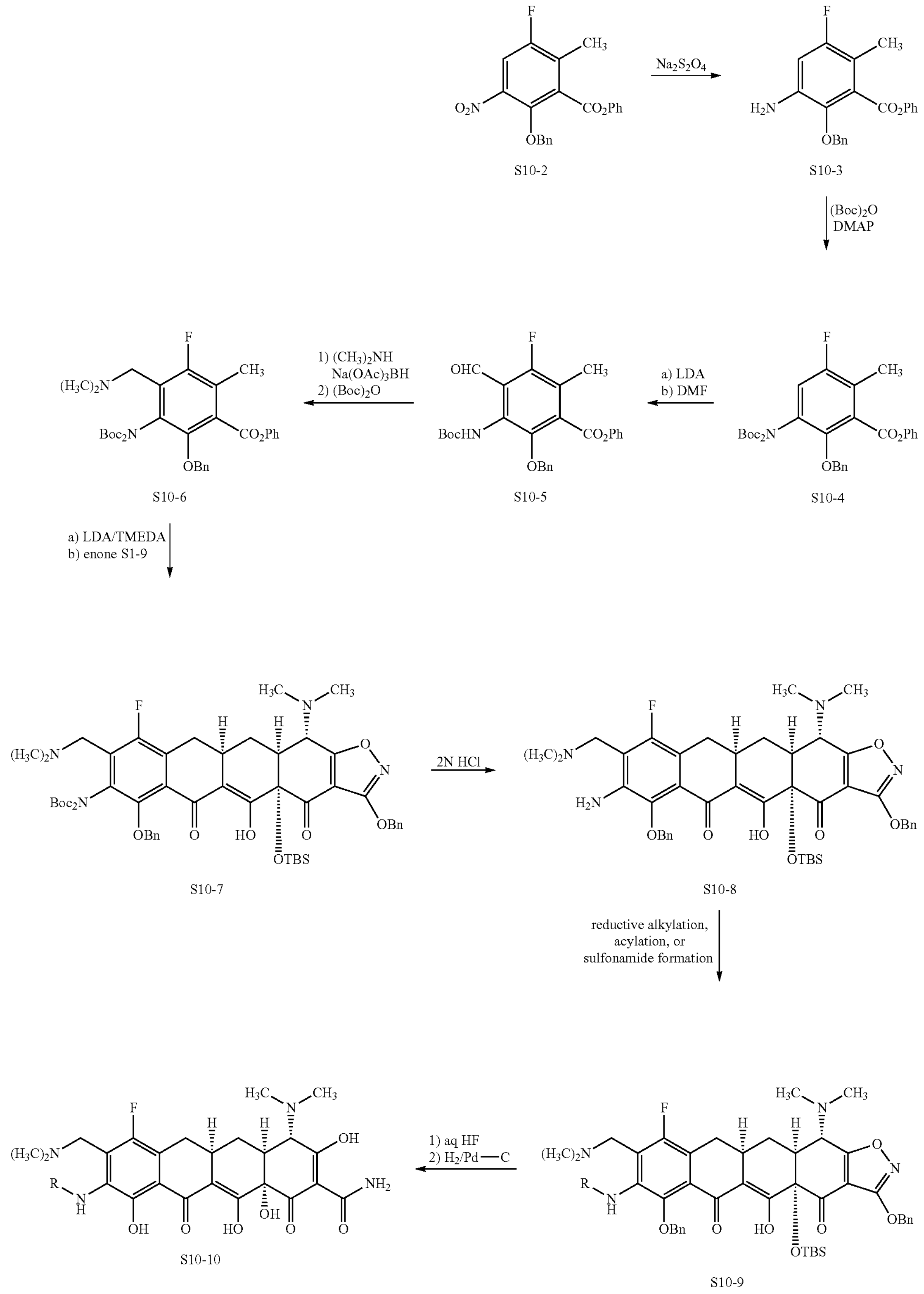
S10-2 S10-3 S10-4 S10-5 S10-6 S10-7 S10-8 S10-9 S10-10

The following compounds were prepared according to Scheme 10.

S10-1

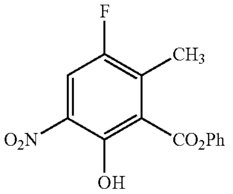

To a 250 mL round bottom flask was added compound S1-4 (14.47 g, 56.30 mmol, 1.0 equiv, crude), tetrabutylammonium bromide (0.90 g, 2.80 mmol, 0.05 equiv), 1,2-dichloroethane (60 mL), and water (60 mL). The clear bi-layer was cooled in a 20° C. water bath. Nitric acid (7.2 mL, 70 wt %, 112.60 mmol, 2.0 equiv) was added. After the addition, the reaction temperature slowly rose to 26° C. The reaction was stirred at room temperature overnight (19 hrs). TLC (heptane/EtOAc=9.5/0.5) showed the reaction was complete. The organic layer was separated, washed with water (60 mL×2) and brine, and dried over anhydrous sodium sulfate. The solvent was removed to give compound S10-1 as a brown oil, which solidified on standing (17.71 g, quantitative). The crude product was used directly for the next step.

S10-2

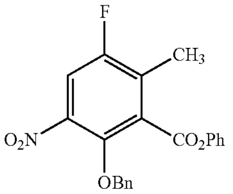

To a 250 mL round bottom flask was added compound S10-1 (17.7 g, 56.30 mmol 1.0 equiv), acetone (177 mL), anhydrous potassium carbonate (15.6 g, 113.00 mmol, 2.0 equiv), and potassium iodide (0.47 g, 2.80 mmol, 0.05 equiv). To the stirred suspension at room temperature was added benzyl bromide (7.03 mL, 59.10 mmol, 1.05 equiv). The suspension was then heated to 56° C. for 4 hrs. TLC (heptane/EtOAc=9/1) showed the reaction was complete. The solid was removed by filtration and washed with acetone (30 mL). The filtrated was concentrated to give a paste. The paste was partitioned between methyl t-butyl ether (MTBE, 120 mL) and water (80 mL). The organic layer was washed with water (80 mL) and brine, dried over anhydrous sodium sulfate, and concentrated to give compound S10-2 as a brown oil (21.09 g, 98%). The crude product was used directly for the next step.

S10-3

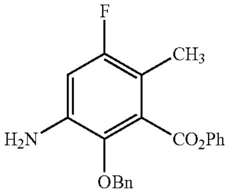

To a 1 L round bottom flask was added compound S10-2 (21.08 g, 55.40 mmol, 1.0 equiv) and THF (230 mL). The solution was cooled in a cold water bath to 10° C. To another 500 mL round bottom flask containing water (230 mL), sodium hydrosulfite ($Na_2S_2O_4$, 56.7 g, 276.80 mmol, 5.0 equiv) was added slowly with stirring. The aqueous solution of sodium hydrosulfite was added to the THF solution of compound S10-2. The temperature quickly rose from 10° C. to 20.4° C. after the addition. The yellow suspension was stirred while the cold water bath slowly warmed up to room temperature overnight to give an orange cloudy solution. The reaction temperature during this period was between 15° C. to 19° C. TLC (heptane/EtOAc=9/1) showed the reaction was complete. The orange cloudy solution was diluted with EtOAc (460 mL). The organic layer was washed with water (150 mL×2) and brine, dried over anhydrous sodium sulfate, and concentrated under reduced pressure to give the crude product as a brown oil. The crude product was purified by flash silica gel column eluted with heptane/EtOAc 9/1 to yield the desired product S10-3 (15.83 g, 80%, 3 steps).

S10-4

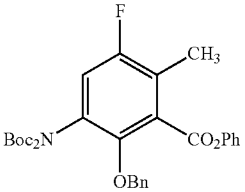

Di-t-butyl dicarbonate (10.56 g, 48.40 mmol, 2.5 equiv) and DMAP (0.12 g, 0.97 mmol, 0.05 equiv) were added to the solution of S10-3 (6.80 g, 19.40 mmol, 1.0 equiv) in anhydrous DMF (39 mL). The resulting mixture was stirred at rt for 20 hrs and diluted with EtOAc. The solution was washed with $H_2O$ (three times) and brine, dried over sodium sulfate, filtered and concentrated. Further purification of the residue by flash chromatography (silica gel, 95:5 hexanes/EtOAc) yielded compound S10-4 as a white solid (8.70 g, 81%): $^1H$ NMR (400 MHz, $CDCl_3$) δ 1.39 (s, 18H), 2.36 (d, J=1.8 Hz, 3 H), 4.92 (s, 2 H), 6.96-7.02 (m, 3 H), 7.22-7.38 (m, 8 H); MS (ESI) m/z 574.3 (M+Na), calcd for $C_{31}H_{34}FNO_3Na$ 574.2.

S10-5

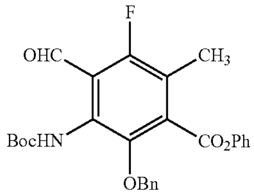

To compound S10-4 (4.80 g, 8.70 mmol, 1.0 equiv) in anhydrous THF (50 mL) at −78° C. was added LDA (7.25 mL, 1.8 M/heptane/ethylbenzene/THF, 13.05 mmol, 1.5 equiv) dropwise over a period of 2 min. The resulting deep red-brown solution was stirred at −78° C. for 30 min. Anhydrous DMF (1.35 mL, 17.44 mmol, 2.0 equiv) was added. The resulting light brown solution was stirred at −78° C. for 30 min. The reaction was quenched at −78° C. with HOAc (0.90 mL), warmed up to rt, diluted with EtOAc (200 mL), washed with water (500 mL×1), saturated aqueous sodium bicarbonate (100 mL×1), and brine (100 mL×1). The EtOAc solution was dried over sodium sulfate and concentrated under reduced pressure. Flash column chromatography on silica gel with 0%-15% EtOAc/hexanes yielded the desired product S10-5 as an orange solid (2.55 g, 61%): $R_f$ 0.50 (20% EtOAc/hexanes): $^1$H NMR (400 MHz, $CDCl_3$) δ 10.26 (s, 1 H), 7.39 (br s, 1 H), 7.30-7.42 (m, 7 H), 7.23-7.30 (m, 1 H), 7.07 (d, J=7.3 Hz, 2 H), 4.96 (s, 2 H), 2.36 (d, J=2.4 Hz, 3 H), 1.44 (s, 9 H); MS (ESI) m/z 480.1 (M+H), calcd for $C_{27}H_{26}FNO_6$ 479.2.

S10-6

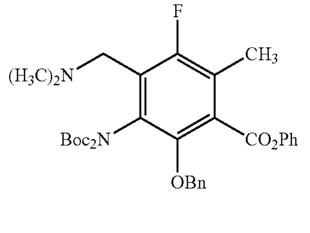

To a solution of S10-5 (0.40 g, 0.83 mmol, 1.0 equiv) in 1,2-dichloroethane (8.4 mL) was added dimethylamine (33% in EtOH, 0.57 mL, 4.18 mmol, 5.0 equiv) and acetic acid (0.14 mL, 2.50 mmol, 3.0 equiv). The mixture was stirred at rt for 2 hrs. $Na(OAc)_3BH$ (0.53 g, 2.50 mmol, 3.0 equiv) was added, and the reaction was stirred for 15 hrs. The mixture was diluted with EtOAc (15 mL). The organic layer was washed two times with potassium phosphate dibasic solution (prepared from 2 g $K_2HPO_4$ and 5 mL water), dried (sodium sulfate) and concentrated.

To the above residue in DMF (8 mL) was added $Boc_2O$ (0.24 g, 1.08 mmol, 1.3 equiv), DMAP (10 mg, 0.080 mmol, equiv) and $Et_3N$ (0.58 mL, 4.20 mmol, 5.1 equiv). The reaction was stirred at rt for 2 hrs. Sodium hydride (60% dispersion in mineral oil, 0.18 g, 4.40 mmol, 5.3 equiv) was added, and the mixture was stirred for 2 hrs. The mixture was quenched by brine (2 mL) and diluted with EtOAc (100 mL). The organic layer was washed with brine (30 mL×5), dried (sodium sulfate) and concentrated. The residue was purified by flash chromatography on silica gel, eluting with hexanes/EtOAc (5:1) to afford 0.52 g of compound 60 (quant. yield): $^1$H NMR (400 MHz, $CDCl_3$) δ 7.40-7.18 (comp, 8 H), 7.02-6.96 (comp, 2 H), 4.96 (s, 2 H), 3.37 (s, 2 H), 2.37 (d, J=2.4 Hz, 3 H), 2.22 (s, 6 H), 1.36 (s, 18 H); MS (ESI) m/z 609.33 (M+H).

S10-7

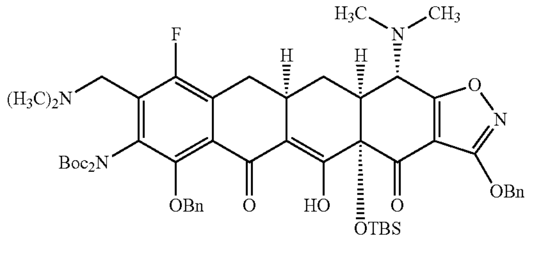

To a solution of i-$Pr_2NH$ (0.27 mL, 1.93 mmol, 3.0 equiv) in THF (7 mL) was added a solution of n-BuLi (0.89 mL, 2.17 M/hexanes, 1.93 mmol, 3.0 equiv) dropwise at −78° C. The reaction was allowed to warm to 0° C., stirred at 0° C. for 25 min, and then cooled to −78° C. TMEDA (0.29 mL, 1.93 mmol, 3.0 equiv) was added, and the mixture was stirred at −78° C. for 5 min. A solution of compound S10-6 (0.51 g, 0.83 mmol, 1.3 equiv) in THF (0.5 mL) was added dropwise to the LDA solution over 5 min. Once addition was complete, the reaction mixture was stirred at −78° C. for 30 min. A solution of enone S1-9 (0.31 g, 0.64 mmol, 1.0 equiv) in THF (0.5 mL) was added dropwise over 2 min. The mixture was slowly warmed to −20° C. over 40 min and quenched by phosphate buffer (pH 7, 10 mL). The aqueous layer was extracted with EtOAc (20 mL×3). All organic layers were combined, dried (sodium sulfate), and concentrated. The residue was purified by flash chromatography on silica gel, eluting with hexanes/EtOAc (20:1 to 3:1) to afford 0.56 g of compound S10-7 (87%): $^1$H NMR (400 MHz, $CDCl_3$) δ 15.96 (s, 1 H), 7.50-7.24 (comp, 10 H), 5.35 (s, 2 H), 4.93 (d, J=9.8 Hz, 1 H), 4.83 (d, J=9.8 Hz, 1 H), 3.94 (d, J=12.2 Hz, 1 H), 3.35 (s, 2 H), 3.31-3.23 (m, 1 H), 3.05-2.94 (m, 1 H), 2.49 (s, 6 H), 2.59-2.36 (comp, 3 H), 2.21 (s, 6 H), 2.20-2.10 (m, 1 H), 1.37 (s, 9 H), 1.32 (s, 9 H), 0.81 (s, 9 H), 0.27 (s, 3 H), 0.12 (s, 3 H); MS (ESI) m/z 997.42 (M+H).

S10-8

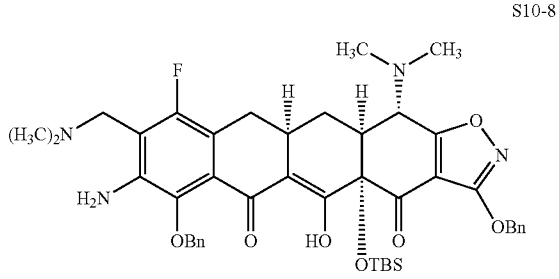

To a solution of compound S10-7 in 1,4-dioxane (4 mL) was added HCl in 1,4-dioxane (4 N, 4 mL). The mixture was stirred for 3 hrs and then concentrated under reduced pressure. Potassium phosphate dibasic solution (prepared from 2 g $K_2HPO_4$ and 5 mL water) was added. The mixture was extracted with EtOAc (10 mL×3). All organic layers were combined, dried (sodium sulfate) and concentrated to afford 0.45 g (quant. yield) of compound S10-8: $^1$H NMR (400 MHz, $CDCl_3$) δ 16.15 (s, 1 H), 7.57-7.24 (comp, 10 H), 5.35 (s, 2 H), 4.90 (d, J=11.9 Hz, 1 H), 4.82 (d, J=11.9 Hz, 1 H), 3.97 (d, J=10.4 Hz, 1 H), 3.50 (s, 2 H), 3.17-3.09 (m, 1 H), 3.03-2.93 (m, 1 H), 2.48 (s, 6 H), 2.18 (s, 6 H), 2.57-2.08 (comp, 4 H), 0.82 (s, 9 H), 0.27 (s, 3 H), 0.13 (s, 3 H); MS (ESI) m/z 797.36 (M+H).

S10-9-1

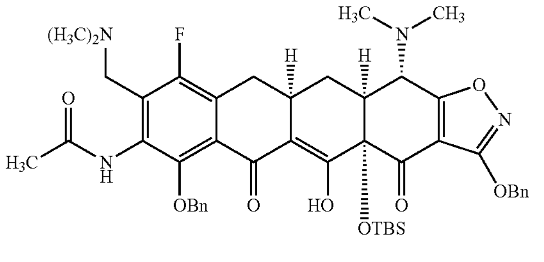

To a solution of compound S10-8 (14 mg, 0.020 mmol, 1.0 equiv) and $Et_3N$ (37 μL, 0.26 mmol, 13 equiv) in dichloromethane (2 mL) was added a solution of AcCl (2.2 μL 0.030 mmol, 1.5 equiv) in dichloromethane (0.4 mL). The reaction was stirred at rt for 1 h, quenched by MeOH (0.3 mL), and then concentrated under reduced pressure. The crude product was purified by preparative reverse phase HPLC on a Waters Autopurification system using a Sunfire Prep C18 OBD column [5 μm, 19×50 mm; flow rate, 20 mL/min; Solvent A: $H_2O$ with 0.1% $HCO_2H$; Solvent B: $CH_3CN$ with 0.1% $HCO_2H$; injection volume: 2.0 mL ($CH_3CN$); gradient: 30→70% B over 10 min; mass-directed fraction collection]. Fractions containing the desired product, eluting at 6.2-7.0 min, were collected and freeze-dried to give 14 mg of S10-9-1 (96%): $^1$H NMR (400 MHz, $CDCl_3$) δ 15.98 (s, 1 H), 7.54-7.24 (comp, 10 H), 5.35 (s, 2 H), 4.96-4.83 (m, 2 H), 3.94 (d, J=9.8 Hz, 1 H), 3.47 (s, 2 H), 3.26-3.18 (m, 1 H), 3.05-2.95 (m, 1 H), 2.49 (s, 6 H), 2.23 (s, 6 H), 2.60-2.10 (comp, 4 H), 2.00 (s, 3 H), 0.82 (s, 9 H), 0.27 (s, 3 H), 0.13 (s, 3 H); MS (ESI) m/z 839.34 (M+H).

S10-10-1

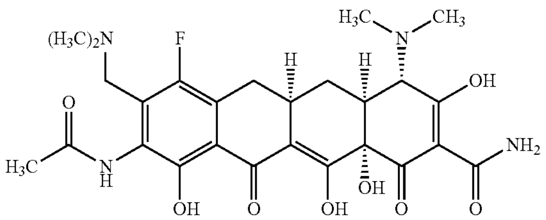

To a solution of S10-9-1 (14 mg, 0.020 mmol) in 1,4-dioxane (3 mL) was added a solution of HF (0.3 mL of 48-50% solution in water). The mixture was stirred for 4 hrs and then quenched by potassium phosphate dibasic solution (prepared from 2 g $K_2HPO_4$ and 5 mL water). The mixture was extracted with EtOAc (5 mL×3). All organic layers were combined, dried (sodium sulfate) and concentrated.

To the above residue in MeOH/dioxane solution (1:1, 4 mL) was added Pd—C (10 mg, 10 wt %) and HCl in MeOH (0.5 N, 0.3 mL). The reaction was bubbled with $H_2$ (balloon) at 25° C. for 30 min. The mixture was filtered through a small Celite plug. The filtrate was concentrated to yield the crude product. The crude product was purified by preparative reverse phase HPLC on a Waters Autopurification system using a Phenomenex Polymerx 10μ RP-$_1$ 100A column [10 μm, 150×21.20 mm; flow rate, 20 mL/min; Solvent A: 0.05 N HCl/water; Solvent B: $CH_3CN$; injection volume: 2.1 mL (0.05 N HCl/water); gradient: 0→100% B over 10 min; mass-directed fraction collection]. Fractions containing the desired product, eluting at 5.1-5.3 min, were collected and freeze-dried to yield 1 mg of S10-10-1 (11% for 2 steps): $^1$H NMR (400 MHz, $CD_3OD$) δ 4.36 (s, 2 H), 4.10 (s, 1 H), 3.05 (s, 3 H), 2.96 (s, 3 H), 2.94 (s, 6 H), 3.22-2.88 (comp, 3 H), 2.45-2.34 (m, 1 H), 2.28 (s, 3 H), 2.28-2.21 (m, 1 H), 1.73-1.61 (m, 1 H); MS (ESI) m/z 547.22 (M+H).

S10-10-2

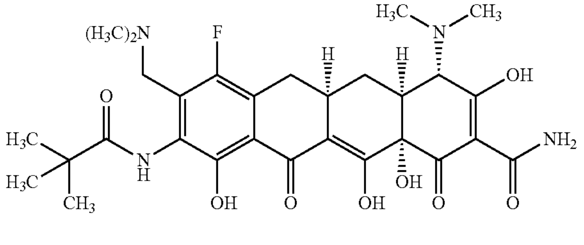

S10-10-2 was prepared according to the procedure for the preparation of S10-10-1: $^1$H NMR (400 MHz, $CD_3OD$) δ 4.30 (s, 2 H), 4.09 (s, 1 H), 3.05 (s, 3 H), 2.96 (s, 3 H), 2.94 (s, 6 H), 3.22-2.90 (comp, 3 H), 2.46-2.36 (m, 1 H), 2.29-2.20 (comp, 1 H), 1.74-1.62 (m, 1 H), 1.39 (s, 9 H); MS (ESI) m/z 589.18 (M+H).

S10-10-3

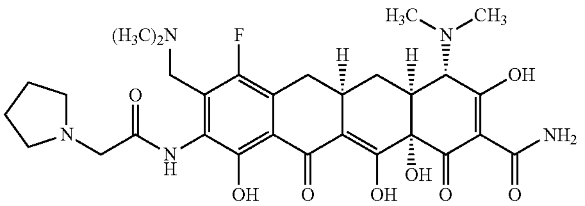

S10-10-3 was prepared according to the procedure for the preparation of S10-10-1: $^1$H NMR (400 MHz, $CD_3OD$) δ 4.49 (s, 2 H), 4.47 (s, 2 H), 4.11 (s, 1 H), 3.86-3.76 (m, 2 H), 3.38-3.32 (m, 2 H), 3.04 (s, 3 H), 2.99 (s, 3 H), 2.96 (s, 6 H), 3.24-2.90 (comp, 3 H), 2.45-2.36 (m, 1 H), 2.30-2.00 (comp, 5 H), 1.72-1.60 (m, 1 H); MS (ESI) m/z 616.25 (M+H).

S10-9-2

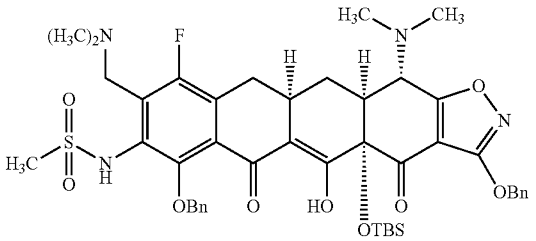

To a solution of compound S10-8 (59 mg, 0.070 mmol, 1.0 equiv) and $Et_3N$ (0.15 mL, 1.11 mmol, 16 equiv) in dichloromethane (2 mL) was added methanesulfonic anhydride (28 mg, 0.30 mmol, 4.3 equiv). The reaction was stirred at rt for 1 h. The mixture was purified by flash chromatography on silica gel, eluting with hexanes/EtOAc (20:1 to 2:1) to afford 10 mg of compound S10-9-2 (15%): $^1$H NMR (400 MHz, $CDCl_3$) δ 16.01 (s, 1 H), 7.54-7.24 (comp, 10 H), 5.35 (s, 2 H), 4.96 (s, 2 H), 3.93 (d, J=10.4 Hz, 1 H), 3.68 (d, J=13.7 Hz, 1 H), 3.62 (d, J=13.7 Hz, 1 H), 3.24-3.17 (m, 1 H), 3.00 (s, 3 H), 3.06-2.98 (m, 1 H), 2.48 (s, 6 H), 2.27 (s, 6 H), 2.59-2.11 (comp, 4 H), 0.83 (s, 9 H), 0.27 (s, 3 H), 0.14 (s, 3 H); MS (ESI) m/z 875.38 (M+H).

S10-10-4

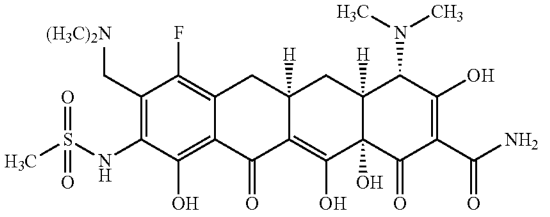

S10-10-4 was prepared from S10-9-2 according to the procedure for the preparation of S10-10-1: $^1$H NMR (400 MHz, $CD_3OD$) δ 4.67 (d, J=13.4 Hz, 1 H), 4.63 (d, J=13.4 Hz, 1 H), 4.10 (s, 1 H), 3.11 (s, 3 H), 3.04 (s, 3 H), 2.99 (s, 3 H), 2.96 (s, 6 H), 3.24-2.90 (comp, 3 H), 2.46-2.35 (m, 1 H), 2.29-2.22 (comp, 1 H), 1.72-1.61 (m, 1 H); MS (ESI) m/z 583.10 (M+H).

S10-9-3

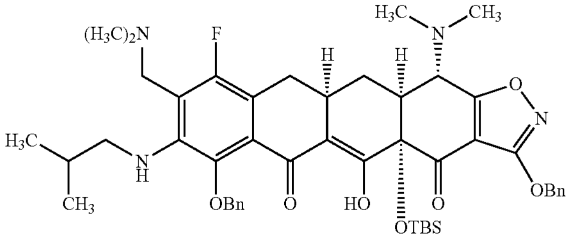

To a solution of compound S10-8 (27 mg, 0.030 mmol, 1.0 equiv) and acetic acid (6 μL, 0.10 mmol, 3.3 equiv) in 1,2-dichloroethane (1 mL) was added isobutyraldehyde (16 μL, 0.17 mmol, 5.6 equiv). The mixture was stirred at rt for 2 hrs. $Na(OAc)_3BH$ (22 mg, 0.10 mmol, 3.3 equiv) was added, and the reaction was stirred for 3 hrs. Another portion of $Na(OAc)_3BH$ (22 mg, 0.10 mmol, 3.3 equiv) was added, and the reaction was stirred for another 3 hrs. The mixture was diluted with EtOAc (10 mL). The organic layer was washed four times with potassium phosphate dibasic solution (prepared from 0.5 g $K_2HPO_4$ and 1 mL water), dried (sodium sulfate) and concentrated. The residue was purified by flash chromatography on silica gel, eluting with hexanes/EtOAc (20:1 to 10:1) to afford 23 mg of compound S10-9-3 (80%): $^1$H NMR (400 MHz, $CDCl_3$) δ 16.27 (s, 1 H), 7.55-7.24 (comp, 10 H), 5.83-5.56 (br, 1 H), 5.35 (s, 2 H), 4.89 (d, J=10.4 Hz, 1 H), 4.81 (d, J=10.4 Hz, 1 H), 3.97 (d, J=10.4 Hz, 1 H), 3.48 (s, 2 H), 3.22-3.07 (comp, 3 H), 2.97-2.87 (m, 1 H), 2.48 (s, 6 H), 2.55-2.30 (comp, 3 H), 2.23 (s, 6 H), 2.14-2.06 (m, 1 H), 1.78-1.66 (m, 1 H), 0.89 (d, J=1.8 Hz, 3 H), 0.87 (d, J=1.8 Hz, 3 H), 0.82 (s, 9 H), 0.26 (s, 3 H), 0.13 (s, 3 H); MS (ESI) m/z 853.39 (M+H).

S10-10-5

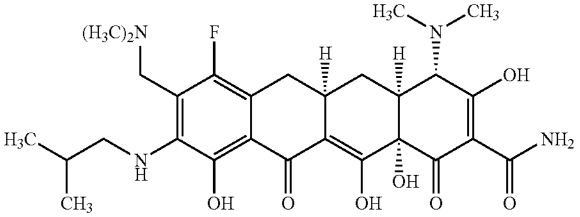

S10-10-5 was prepared from S10-9-3 according to the procedure for the preparation of S10-10-1: $^1$H NMR (400 MHz, $CD_3OD$) δ 4.51 (s, 2 H), 4.08 (s, 1 H), 3.03 (s, 3 H), 2.96 (s, 3 H), 2.90 (s, 6 H), 3.21-2.82 (comp, 5 H), 2.36-2.25 (m, 1 H), 2.25-2.17 (m, 1 H), 1.93-1.81 (m, 1 H), 1.69-1.58 (m, 1 H), 1.04 (d, J=2.4 Hz, 3 H), 1.02 (d, J=2.4 Hz, 3 H); MS (ESI) m/z 561.18 (M+H).

S10-10-6

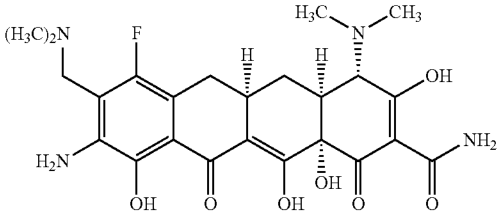

S10-10-6 was prepared from S10-8 via HF treatment followed by hydrogenation according to the procedure for the preparation of S10-10-1: $^1$H NMR (400 MHz, $CD_3OD$) δ 4.42 (s, 2 H), 4.08 (s, 1 H), 3.14 (dd, J=21.4, 4.9 Hz, 1 H), 3.03 (s, 3 H), 2.96 (s, 3 H), 2.92 (s, 6 H), 3.09-2.88 (comp, 2 H), 2.26-2.17 (comp, 2 H), 1.66-1.54 (m, 1 H); MS (ESI) m/z 505.12 (M+H).

EXAMPLE 11

Synthesis of Compounds Via Scheme 11

Scheme 11

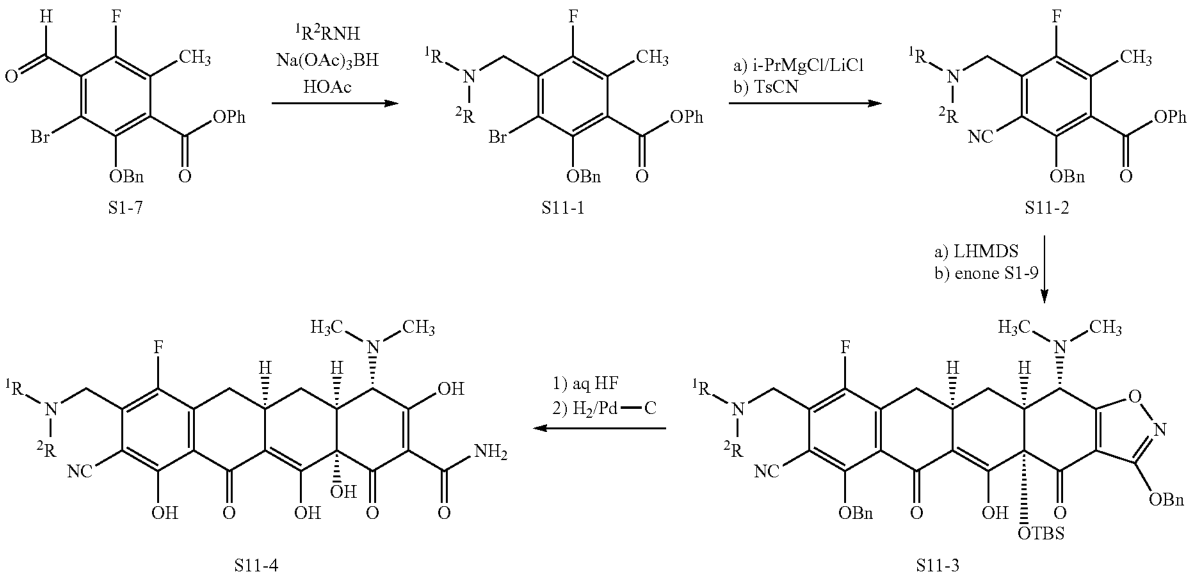

S1-7
S11-1
S11-2
S11-3
S11-4

The following compounds were prepared according to Scheme 11.

S11-1-1

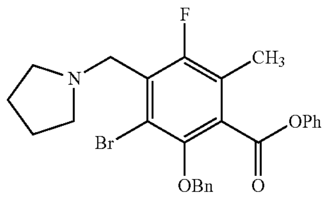

Compound S1-7 (0.44 g, 1.00 mmol, 1.0 equiv) was dissolved in 1,2-dichloroethane (5 mL) and pyrrolidine (0.25 mL, 3.00 mmol, 3.0 equiv) was added via a syringe followed by acetic acid (0.17 mL, 3.00 mmol, 3.0 equiv) under a nitrogen atmosphere. After stirring at rt for 1 h, sodium triacetoxyborohydride (0.32 g, 1.50 mmol, 1.5 equiv) was added to reaction mixture. The reaction was stirred at rt overnight. Another 1.0 equiv of reagents were added. LC/MS indicated that the starting material was consumed after stirring for another 2 hrs. The reaction mixture was diluted with dichloromethane, washed with $NaHCO_3$ (saturated aqueous solution, 3×20 mL) and brine, dried over sodium sulfate, filtered, and concentrated under reduced pressure to give crude compound S11-1-1 (0.53 g), which was used without further purification: $^1H$ NMR (400 MHz, $CDCl_3$) δ 10.37 (s, 1 H), 7.53-7.49 (m, 2 H), 7.40-7.33 (m, 5 H), 7.26 (t, J=7.8 Hz, 1 H), 7.09-7.05 (m, 2 H), 5.13 (s, 2 H), 3.94 (d, J=2.7 Hz, 2 H), 2.66 (br, s, 2 H), 2.35 (d, J=2.3 Hz, 3 H), 1.82-1.76 (m, 2 H).

S11-2-1

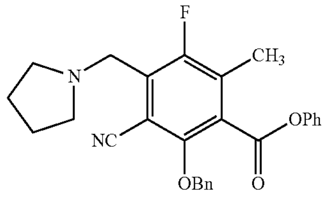

Isopropylmagnesium chloride/lithium chloride (0.30 mL, 1.2 M/THF, 0.36 mmol, 1.8 equiv) was added to compound S11-1-1 (0.10 g, 0.20 mmol, 1.0 equiv) in THF (2 mL) under a nitrogen atmosphere at −78° C. The resulting solution was warmed up to rt and stirred for another 45 min. After the solution was cooled down to −78° C., $TsN_3$ (91 mg, 0.50 mmol, 2.5 equiv) in THF (1 mL) was added slowly via a syringe. The reaction was warmed to −40° C. and stirred for another 45 min. LC/MS indicated that the starting materials was consumed and the product present. The reaction mixture was allowed to slowly warm to −20° C. Saturated aqueous sodium bicarbonate (10 mL) was added. The resulting mixture was extracted with dichloromethane (3×15 mL), and the combined extracts were dried over sodium sulfate, filtered, and concentrated under reduced pressure to yield crude S11-2-1 (0.15 g) as a pale yellow oil.

S11-3-1

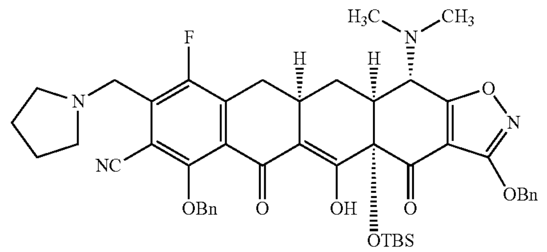

Compound S11-2-1 (crude, 0.15 g, 0.20 mmol, 1.5 equiv) and enone S1-9 (64 mg, 0.13 mmol, 1.0 equiv) were dissolved in 2 mL dry THF under a nitrogen atmosphere in a flame dried schenck flask at −78° C. LHMDS (0.40 mL, 1.0 M/THF, 0.40 mmol, 3.1 equiv) was added slowly via a syringe. A red-orange color appeared. The reaction was warmed to −30° C. and stirred for another 15 min. Phosphate buffer (pH 7, 10 mL) was added, followed by the addition of 20 mL saturated aqueous ammonium chloride. The resulting mixture was extracted with dichloromethane (3×15 mL), and the combined extracts were dried over sodium sulfate, filtered, and concentrated under reduced pressure. The red-orange oil was purified by preparative reverse phase HPLC purification on a Waters Autopurification system using a Sunfire Prep C18 OBD column [5 μm, 19×50 mm; flow rate, 20 mL/min; Solvent A: $H_2O$ with 0.1% $HCO_2H$; Solvent B: $CH_3CN$ with 0.1% $HCO_2H$; injection volume: 4.0 mL ($CH_3CN$); gradient: 0→50% B over 15 min; mass-directed fraction collection]. Fractions containing the desired product were collected and concentrated at rt to remove most of the acetonitrile. The resulting mostly aqueous solution was extracted with EtOAc. The EtOAc extract was dried (sodium sulfate), and concentrated to give 20 mg of compound S11-3-1 (12% for 3 steps).

S11-4-1

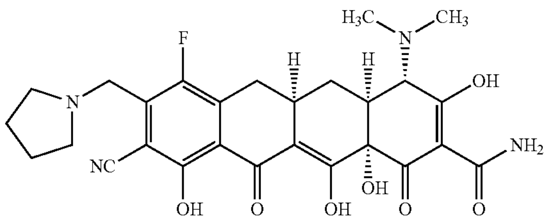

Aqueous HF (0.3 mL, 48-50%) was added to a $CH_3CN$ solution (1.0 mL) of S11-3-1 (20 mg) in a plastic vial at 25° C. The reaction was stirred at 25° C. for 18 hrs. The reaction solution was poured into an aqueous solution (10 mL) of $K_2HPO_4$ (2 g). The mixture was extracted with EtOAc (3×15 mL). The combined EtOAc extracts were dried over sodium sulfate and concentrated to give the crude intermediate (18 mg).

Pd—C (5 mg, 10 wt %) was added to a MeOH solution (2 mL) of the above crude intermediate. HCl in MeOH (0.5 N, 0.5 mL) was added. The reaction was stirred under $H_2$ (balloon) at 25° C. for 45 min and filtered through a pad of Celite. The filtrate was concentrated to afford the crude product, which was purified by reverse phase HPLC on a Polymerx 10μ RP-γ100 R column [30×21.20 mm, 10 micron, solvent A: 0.05 N HCl, solvent B: $CH_3CN$, sample in 2.0 mL (0.05 N HCl), gradient elution with 0→70% B over 15 min, mass-directed fraction collection]. Fractions containing the desired product were collected and freeze-dried, yielding 8 mg of the desired product S11-4-1 as a yellow solid (65% for two steps): $^{1}H$ NMR (400 MHz, $CD_3OD$) δ 4.64 (s, 2 H), 4.12 (s, 1 H), 3.68 (m, 2 H), 3.32 (m, 2 H), 3.05 (s, 3 H), 2.96 (s, 3 H), 3.27-2.97 (m, 3 H), 2.45 (m, 1 H), 2.30-2.13 (m, 3 H), 2.13-2.00 (m, 2 H), 1.69-1.59 (m, 1 H); MS (ESI) m/z 541.27 (M+H).

EXAMPLE 12

Synthesis of Compounds Via Scheme 12 iPrMgCl.LiCl (4.00 mL, 1.2 M/THF, 4.80 mmol, 2.0 equiv) was added to a THF solution (12 mL) of S1-6 (1.00 g, 2.40 mmol,) at 0° C. The reaction was stirred at 0° C. for 30 min. $(PhSO_2)_2NF$ (1.50 g, 4.80 mmol, 2.0 equiv) was added to the reaction mixture. The reaction was stirred at 0° C. for 30 min and allowed to warm to 25° C. over 1 h, quenched by saturated aqueous $NH_4Cl$, and extracted with EtOAc. The EtOAc extract was dried (sodium sulfate) and concentrated to give the crude product. Flash chromatography on silica gel (30:1 hexanes/EtOAc) yielded 0.50 g of compound S12-1 (59%).

Scheme 12

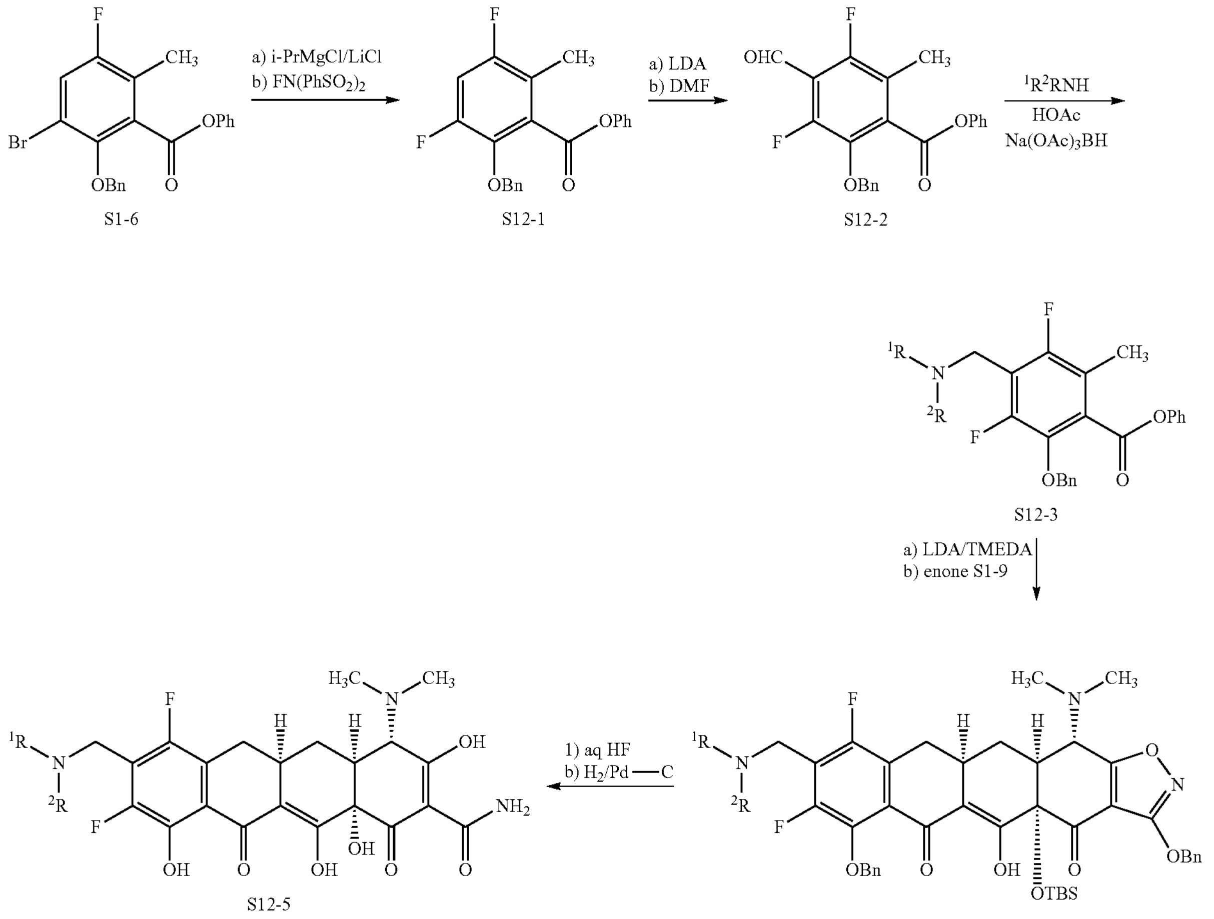

S1-6 S12-1 S12-2 S12-3 S12-4 S12-5

The following compounds were prepared according to Scheme 12.

S12-1

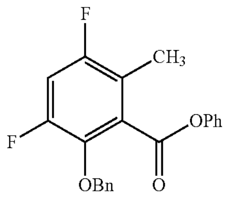

S12-2

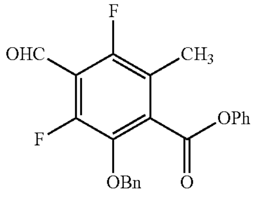

n-BuLi (6.50 mL, 1.6 M/hexanes, 10.40 mmol, 1.5 equiv) was added to a THF solution (15 mL) of diisopropylamine (1.50 mL, 10.40 mmol, 1.5 equiv) at 0° C. The reaction was stirred at 0° C. for 30 min and cooled to −78° C. To the mixture was added a THF solution (15 mL) of S12-1 (2.29 g, 6.47 mmol, 1.0 equiv). The reaction was stirred at −78° C. for 20 min and DMF (1.50 mL, 19.40 mmol, 3.0 equiv) was added. The reaction was allowed to warm to 25° C. over 1 h and quenched by saturated aqueous $NH_4Cl$. The resulting mixture was extracted with EtOAc. The EtOAc extract was dried over sodium sulfate and concentrated. Flash chromatography on silica gel (10:1 hexanes/EtOAc) yielded 1.70 g of compound S12-2 (69%).

S12-3-1

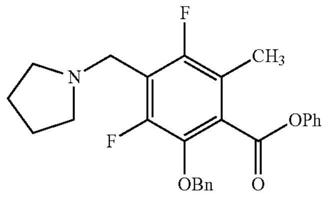

Pyrrolidine (65 μL, 0.79 mmol, 5.0 equiv), $Na(OAc)_3BH$ (68 mg, 0.32 mmol, 2.0 equiv), and HOAc (47 μL) were added to a dichloromethane solution (3 mL) of S12-2 (60 mg, 0.16 mmol, 1.0 equiv). The reaction was stirred at 25° C. for 1 h and quenched by $H_2O$. The resulting mixture was extracted with dichloromethane. The dichloromethane extract was dried (sodium sulfate) and concentrated to give crude S12-3-1.

S12-4-1

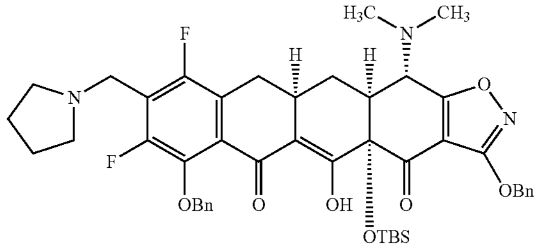

A THF solution (1 mL) of crude S12-3-1 (0.14 mmol, 1.7 equiv) was added to a THF solution (1 mL) of LDA (0.17 mL, 1.8 M/THF/heptane/ethylbenzene, 0.31 mmol, 3.7 equiv) and TMEDA (84 μL, 0.56 mmol, 6.7 equiv). The reaction was stirred at −78° C. for 10 min. A THF solution (1 mL) of enone S1-9 (40 mg, 0.084 mmol, 1.0 equiv) was added to the reaction at −78° C. The reaction was stirred at −78° C. for 30 min and allowed to warm to 25° C. over 1 h, quenched by saturated aqueous $NH_4Cl$, and extracted with EtOAc. The EtOAc extract was dried (sodium sulfate) and concentrated. The crude product was purified by preparative reverse phase HPLC on a Waters Autopurification system using a Sunfire Prep C18 OBD column [5 μm, 19×50 mm; flow rate, 20 mL/min; Solvent A: $H_2O$ with 0.1% $HCO_2H$; Solvent B: $CH_3CN$ with 0.1% $HCO_2H$; injection volume: 4.0 mL ($CH_3CN$); gradient: 50→100% B over 15 min; mass-directed fraction collection]. Fractions containing the desired product were collected and concentrated at 25° C. to remove most of the acetonitrile. The resulting aqueous solution was extracted with EtOAc, and the EtOAc extract was dried (sodium sulfate) and concentrated to give 16 mg of S12-4-1 (23%).

S12-5-1

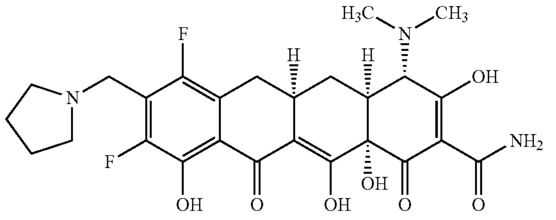

Aqueous HF (0.5 mL, 48-50%) was added to a $CH_3CN$ solution (2 mL) of S12-4-1 (16 mg, 0.019 mmol) in a polypropylene tube at 25° C. The reaction was stirred at 25° C. for 18 hrs. The resulting mixture was poured into an aqueous solution of $K_2HPO_4$ (4 g, dissolved in 30 mL water). The mixture was extracted with EtOAc, and the EtOAc extract was dried (sodium sulfate) and concentrated to yield the crude intermediate.

Pd—C (8 mg, 10 wt %) was added to a HCl/MeOH solution (0.5N, 2 mL) of the above crude product. The reaction was purged with hydrogen and stirred under $H_2$ (balloon) at 25° C. for 4 hrs. The reaction mixture was filtered through a small Celite plug. The filtrate was concentrated to yield the crude product, which was purified by preparative reverse phase HPLC on a Waters Autopurification system using a Phenomenex Polymerx 10μ RP-γ 100A column [10 μm, 150×21.20 mm; flow rate, 20 mL/min; Solvent A: 0.05 N HCl/water; Solvent B: $CH_3CN$; injection volume: 4.0 mL (0.05 N HCl/water); gradient: 0→70% B over 7 min, 70→100% over 3 min, and 100% over 5 min; mass-directed fraction collection]. Fractions containing the desired product were collected and freeze-dried to yield 2 mg of compound S12-5-1: $^1$H NMR (400 MHz, $CD_3OD$) δ 4.58 (s, 2 H), 4.10 (s, 1 H), 3.71-3.67 (m, 2 H), 3.30-2.92 (m, 5 H), 3.05 (s, 3 H), 2.97 (s, 3 H), 2.41-2.32 (m, 1 H), 2.29-2.15 (m, 3 H), 2.10-1.98 (m, 2 H), 1.72-1.60 (m, 1 H); MS (ESI) m/z 534.23 (M+H).

The following compounds were prepared similarly to S12-5-1.

S12-5-2

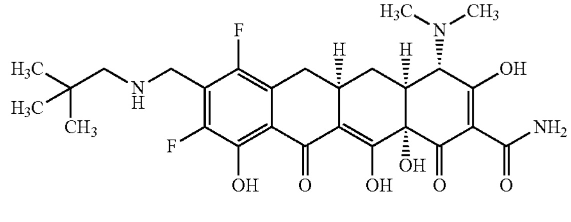

S12-5-2: $^1$H NMR (400 MHz, $CD_3OD$) δ 4.43 (s, 2 H), 4.08 (s, 1 H), 3.29-2.92 (m, 3 H), 3.04 (s, 3 H), 3.00 (s, 2 H), 2.96 (s, 3 H), 2.39-2.28 (m, 1 H), 2.26-2.19 (m, 1 H), 1.70-1.59 (m, 1 H), 1.06 (s, 9 H); MS (ESI) m/z 550.16 (M+H).

S12-5-3
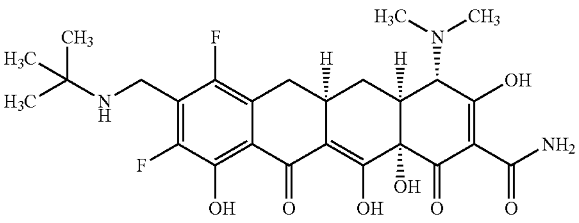
S12-5-3: $^{1}H$ NMR (400 MHz, $CD_3OD$) δ 4.32 (s, 2 H), 4.10 (s, 1 H), 3.24-2.93 (m, 3 H), 3.04 (s, 3 H), 2.95 (s, 3 H), 2.39-2.20 (m, 2 H), 1.70-1.58 (m, 1 H), 1.48 (s, 9 H); MS (ESI) m/z 536.24 (M+H).
S12-5-4
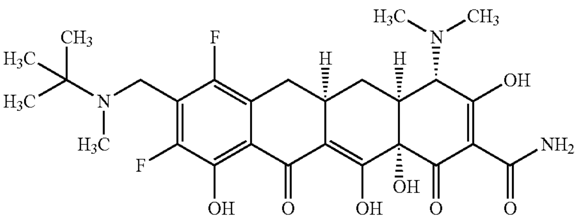
S12-5-4: $^{1}H$ NMR (400 MHz, $CD_3OD$) δ 4.19 (s, 2 H), 4.11 (s, 1 H), 3.25-2.95 (m, 3 H), 3.06 (s, 3 H), 2.96 (s, 3 H), 2.80 (s, 3 H), 2.42-2.21 (m, 2 H), 1.71-1.58 (m, 1 H), 1.58 (s, 9 H); MS (ESI) m/z 550.26 (M+H).
EXAMPLE 13
Synthesis of Compounds Via Scheme 13
Scheme 13
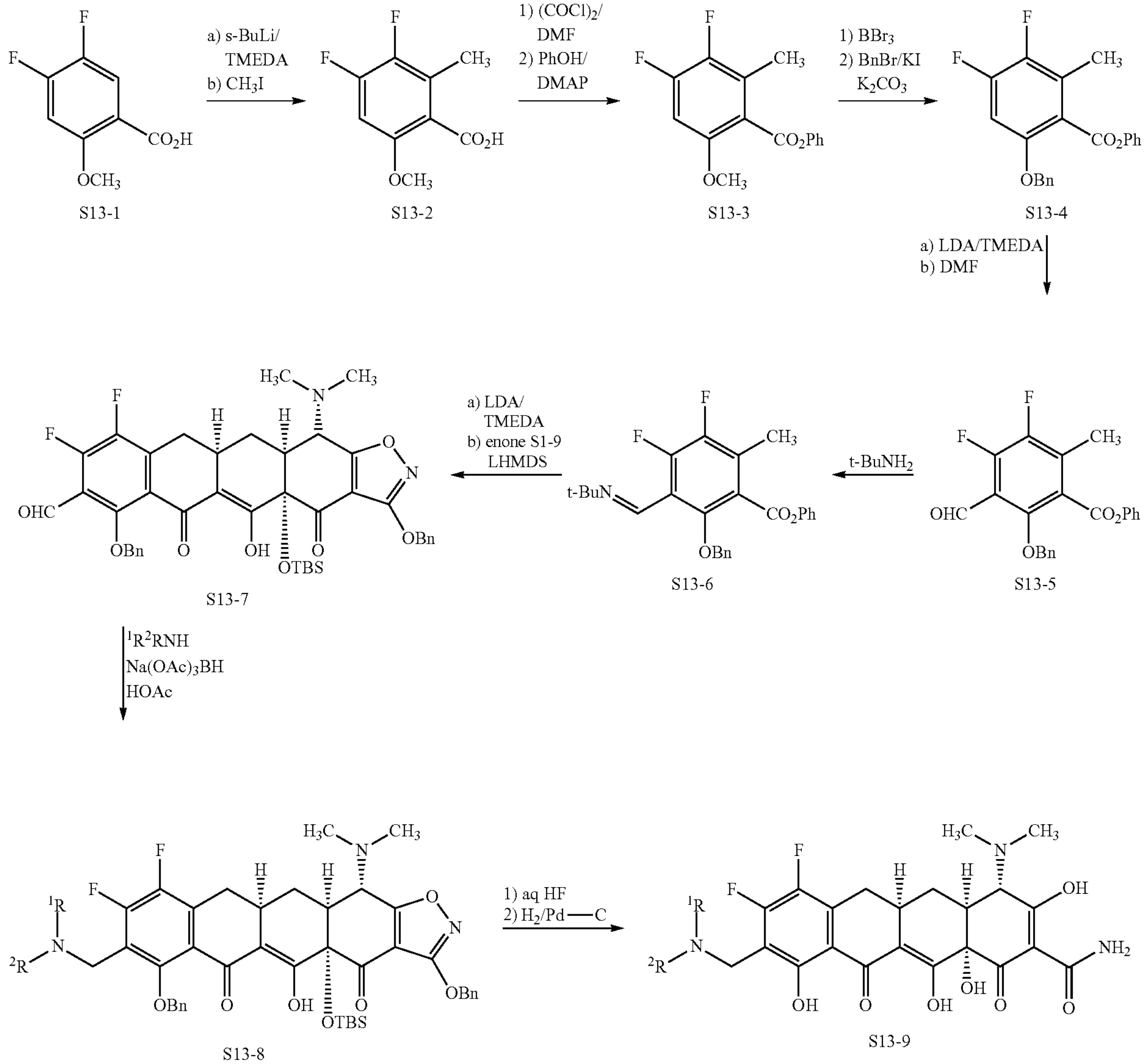
S13-1 S13-2 S13-3 S13-4 S13-5 S13-6 S13-7 S13-8 S13-9

The following compounds were prepared according to Scheme 13

S13-2

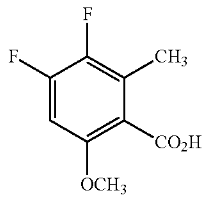

A solution of benzoic acid S13-1 (5.00 g, 26.60 mmol, 1.0 equiv) in THF (40 mL) was added dropwise to a solution of s-BuLi (41.76 mL, 1.4 M/cyclohexane, 58.50 mmol, 2.2 equiv) and TMEDA (8.77 mL, 58.50 mmol, 2.2 equiv) in THF (40 mL) at −78° C. via a cannula over 30 min. The resulting red-orange thick reaction mixture was stirred at −78° C. for 2 hrs, slowly changing to a yellow brownish suspension. Iodomethane (8.30 mL, 133.00 mmol, 5.0 equiv) was added at −78° C. slowly. The resulting yellow suspension was then stirred at rt for 30 min. Water (50 mL) was added, and the resulting mixture was concentrated to remove most of the THF. Aqueous NaOH (40 mL, 6 N) was added, and the resulting mixture was extracted with methyl t-butyl ether (2×60 mL). The combined organic phases were extracted with aqueous NaOH (40 mL, 3 N). The combined aqueous layers were acidified with 6 N HCl (~65 mL) to pH 1, and extracted with EtOAc (120 mL, then 80 mL). The combined EtOAc extracts were dried over magnesium sulfate, filtered and concentrated to afford crude S13-2 as an orange solid (S13-2:region-isomer:S13-1=~1.2:0.8:1 by $^1$H NMR).

S13-3

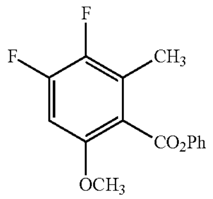

The above crude product was dissolved in dry dichloromethane (100 mL). Oxalyl chloride (2.78 mL, 31.89 mmol, 1.2 equiv) was added, followed by a few drops of DMF. The reaction mixture was stirred at rt for 1 h, concentrated and further dried under high vacuum. The residue was re-dissolved in dry dichloromethane (100 mL). Phenol (2.75 g, 29.26 mmol, 1.1 equiv), triethylamine (7.40 mL, 53.20 mmol, 2.0 equiv), and DMAP (0.10 g, 0.82 mmol, 0.03 equiv) were added. The reaction mixture was stirred at rt for 1 h. The solvent was evaporated and the residue was dissolved in EtOAc (200 mL). The organic layer was washed with 1 N HCl (60 mL), 1 N NaOH (70 mL), water (50 mL) and brine (60 mL), dried over anhydrous magnesium sulfate, filtered, and concentrated. The residue was purified by flash column chromatography (1-4% EtOAc/hexanes) to afford the desired product S13-3 as a white solid (1.39 g, 19% over two steps): $^1$H NMR (400 MHz, $CDCl_3$) δ 7.47-7.43 (m, 2 H), 7.31-7.29 (m, 1 H), 7.26-7.24 (m, 2 H), 6.67 (dd, J=6.0, 11.4 Hz, 1 H), 3.84 (s, 3 H), 2.41 (s, 3 H); MS (ESI) m/z 277.22 (M−H).

S13-4

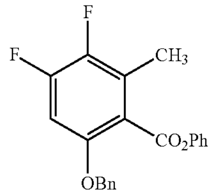

A solution of $BBr_3$ in dichloromethane (6.00 mL, 1.0 M, 6.00 mmol, 1.2 equiv) was added slowly to compound S13-3 (1.39 g, 5.00 mmol, 1.0 equiv) in dichloromethane (25 mL) at −78° C. The resulting orange solution was allowed to warm to 0° C. in 30 min and kept at that temperature for 10 min [monitored by LC-MS or TLC (product is slightly more polar)]. Saturated aqueous $NaHCO_3$ was added. The mixture was stirred at rt for 5 min and dichloromethane was evaporated. The residue was extracted with EtOAc (60 mL, then 20 mL). The organic extracts were combined, dried over anhydrous magnesium sulfate, filtered, and concentrated to give the crude intermediate (1.27 g) as a waxy solid: $^1$H NMR (400 MHz, $CDCl_3$) δ 11.07 (s, 1 H), 7.47-7.44 (m, 2 H), 7.34-7.30 (m, 1 H), 7.19-7.17 (m, 2 H), 6.69 (dd, J=6.7, 11.0 Hz, 1 H), 2.63 (d, J=3.0 Hz, 3 H); MS (ESI) m/z 263.20 (M−H).

Benzylbromide (0.24 mL, 2.04 mmol, 1.2 equiv), $K_2CO_3$ powder (0.47 g, 3.41 mmol, 2.0 equiv) and KI (14 mg, 0.085 mmol, 0.05 equiv) were added to the above crude intermediate (0.45 g, 1.70 mmol, 1.0 equiv) in acetone (3.4 mL). The mixture was heated at reflux for 4.5 hrs, cooled to rt, and diluted with EtOAc (50 mL) and water (30 mL). The organic phase was separated, washed with brine, dried over magnesium sulfate, and concentrated. The residue was purified by flash column chromatography (1-4% EtOAc/hexanes) to afford the desired product S13-4 as a crystalline white solid (0.50 g, 79% over 2 steps): $^1$H NMR (400 MHz, $CDCl_3$) δ 7.45-7.31 (m, 7 H), 7.28-7.24 (m, 1 H), 7.10-7.08 (m, 2 H), 6.71 (dd, J=6.1, 11.6 Hz, 1 H), 5.10 (s, 2 H), 2.41 (d, J=1.8 Hz, 3 H); MS (ESI) m/z 353.21 (M−H).

S13-5

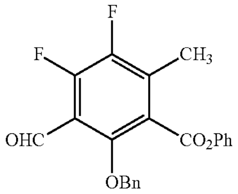

A solution of compound S13-4 (0.38 g, 1.08 mmol, 1.0 equiv) in THF (4 mL) was added via a cannula dropwise to a solution of LDA (1.01 mL, 1.62 mmol, 1.5 equiv) and TMEDA (0.24 mL, 1.62 mmol, 1.5 equiv) in THF (6 mL) at −78° C. The resulting red orange solution was stirred at −78° C. for 5 min. DMF (0.17 mL, 2.16 mmol, 2.0 equiv) was added. The reaction was stirred at −78° C. for 1 h. Saturated aqueous $NH_4Cl$ (30 mL) was added dropwise to the reaction mixture at −78° C. The resulting mixture was then warmed up to rt and extracted with EtOAc (60 mL, then 20 mL). The combined EtOAc extracts were dried (sodium sulfate), filtered and concentrated. The residue was purified by flash column chromatography (1-20% EtOAc/hexanes) to afford the desired product S13-5 as a colorless oil (0.26 g, 62%): $^1$H NMR (400 MHz, $CDCl_3$) δ 7.42-7.35 (m, 7 H), 7.29-7.25 (m, 1 H), 7.06-7.04 (m, 2 H), 5.10 (s, 2 H), 2.48 (d, J=2.4 Hz, 3 H); MS (ESI) m/z 381.24 (M−H).

S13-7

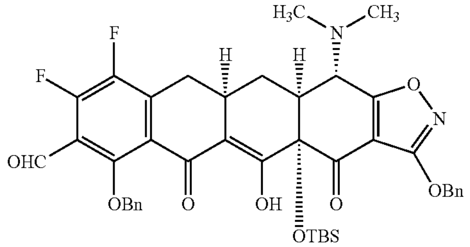

t-$BuNH_2$ (96 μL, 0.91 mmol, 5.0 equiv) was added to a mixture of aldehyde S13-5 (69 mg, 0.18 mmol, 1.0 equiv) and sodium sulfate in toluene (1 mL). The resulting light greenish reaction mixture was stirred at rt overnight. The solids were filtered off. The filtrate was concentrated under reduced pressure to afford the crude imine, which was used directly in the next step.

A solution of the above imine (0.18 mmol, 1.0 equiv) in THF (1.5 mL) was added via a cannula dropwise to a solution of LDA (0.16 mL, 0.26 mmol, 1.4 equiv) and TMEDA (38 μL, 0.26 mmol, 1.4 equiv) in THF (4 mL) at −78° C. The resulting red-purple reaction mixture was then stirred at −78° C. for 5 min. A solution of enone S1-9 (70 mg, 0.15 mmol, 0.8 equiv) in THF (1.5 mL) was added via a cannula. The resulting dark purple solution was stirred at −78° C. for 8 min, and LHMDS solution (0.18 mL, 1.0 M/THF, 0.18 mmol, 1.0 equiv) was added. The reaction mixture was warmed to −10° C. over 1 h 25 min, quenched by saturated aqueous NH4Cl (20 mL), and extracted with EtOAc (50 mL, then 20 mL). The combined EtOAc extracts were dried (sodium sulfate), filtered and concentrated. The residue was purified by a preparative reverse phase HPLC on a Waters Autopurification system using a Sunfire Prep C18 OBD column [5 μm, 19×50 mm; flow rate, 20 mL/min; Solvent A: $H_2O$ with 0.1% $HCO_2H$; Solvent B: $CH_3CN$ with 0.1% $HCO_2H$; injection volume: 4.0 mL ($CH_3CN$); gradient: 80→100% B in A over 10 min; mass-directed fraction collection]. Fractions containing the desired product were collected and concentrated at rt to yield the desired product S13-7 (23 mg, 20%): $^1H$ NMR (400 MHz, $CDCl_3$) δ 15.85 (br s, 1 H), 10.10 (s, 1 H), 7.70-7.68 (m, 1 H), 7.52-7.49 (m, 3 H), 7.40-7.31 (m, 6 H), 5.36 (s, 2 H), 5.06, 4.98 (ABq, J=10.4 Hz, 2 H), 3.91 (d, J=11.0 Hz, 1 H), 3.34 (dd, J=4.3, 15.9 Hz, 1 H), 3.07-3.00 (m, 1 H), 2.61-2.58 (m, 1 H), 2.54-2.34 (m, 2 H), 2.50 (s, 6 H), 2.20-2.16 (m, 1 H), 0.82 (s, 9 H), 0.28 (s, 3 H), 0.14 (s, 3 H); MS (ESI) m/z 771.53 (M+H).

S13-8-1

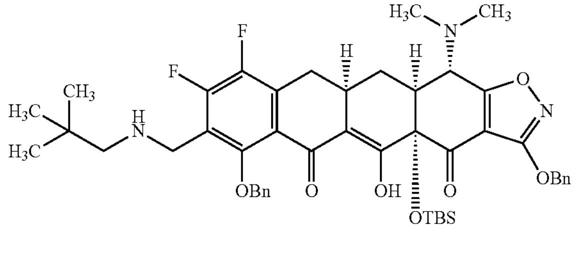

Neopentylamine (17 μL, 0.15 mmol, 5.0 equiv), acetic acid (8 μL, 0.15 mmol, 5.0 equiv) and sodium triacetoxyborohydride (12 mg, 0.058 mmol, 2.0 equiv) were added sequentially to a solution of aldehyde S13-7 (23 mg, 0.029 mmol, 1.0 equiv) in 1,2-dichloroethane (1 mL) at 23° C. After stirring for 1 h, the reaction mixture was quenched by the addition of saturated aqueous sodium bicarbonate and pH 7 phosphate buffer (1:1, 15 mL) and extracted with dichloromethane (50 mL). The organic phase was dried over anhydrous sodium sulfate, filtered, and concentrated to afford crude S13-8-1, which was used directly in the next step.

S13-9-1

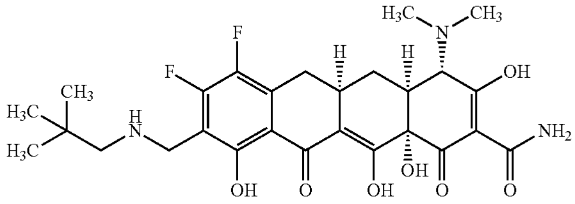

Aqueous HF (48-50%, 0.3 mL) was added to a solution of compound S13-8-1 in acetonitrile (0.7 mL) in a polypropylene reaction vessel at 23° C. The reaction was stirred vigorously at 23° C. overnight and poured into aqueous $K_2HPO_4$ (3.6 g dissolved in 20 mL water). The mixture was extracted with EtOAc (2×25 mL). The combined organic extracts were dried over anhydrous sodium sulfate, filtered, and concentrated. The residue was used directly in the next step without further purification.

Pd—C (10 wt %, 7 mg) was added into a solution of the above crude product in a mixture of HCl/MeOH (0.5 N, 0.12 mL, 2.0 equiv) and MeOH (2 mL) at 23° C. The reaction vessel was sealed and purged with hydrogen by briefly evacuating the flask followed by flushing with hydrogen gas (1 atm). The reaction was stirred at 23° C. for 30 min. The reaction mixture was then filtered through a small Celite pad. The filtrate was concentrated. The residue was purified by a preparative reverse phase HPLC on a Waters Autopurification system using a Phenomenex Polymerx 10μ RP-$_1$ 100A column [10 μm, 150×21.20 mm; flow rate, 20 mL/min; Solvent A: 0.05 N HCl/water; Solvent B: $CH_3CN$; injection volume: 3.0 mL (0.05 N HCl/water); gradient: 5→40% B over 15 min; mass-directed fraction collection]. Fractions containing the desired product, eluting at 12.6-13.1 min, were collected and freeze-dried to yield compound S13-9-1 (4 mg, 23% for 3 steps): $^1H$ NMR (400 MHz, $CD_3OD$) δ 4.38 (s, 2 H), 4.10 (s, 1 H), 3.11-2.96 (m, 11 H), 2.39 (t, J=15.1 Hz, 1 H), 2.26-2.23 (m, 1 H), 1.70-1.60 (m, 1 H), 1.07 (s, 9 H); MS (ESI) m/z 550.40 (M+H).

S13-9-2

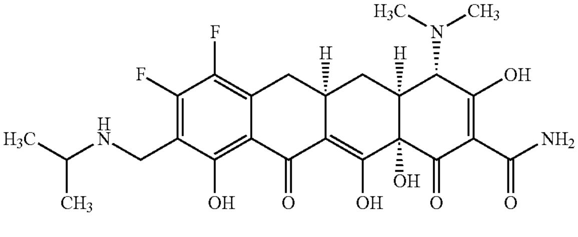

S13-9-2 was prepared similarly: $^1H$ NMR (400 MHz, $CD_3OD$) δ 4.31 (s, 2 H), 4.11 (s, 1 H), 3.57-2.50 (hept, J=6.4 Hz, 1 H), 3.04-2.96 (m, 9 H), 2.39 (t, J=15.1 Hz, 1 H), 2.27-2.24 (m, 1 H), 1.70-1.60 (m, 1 H), 1.43 (t, J=6.4 Hz, 6 H); MS (ESI) m/z 522.41 (M+H).

EXAMPLE 14
Synthesis of Compounds Via Scheme 14
Scheme 14
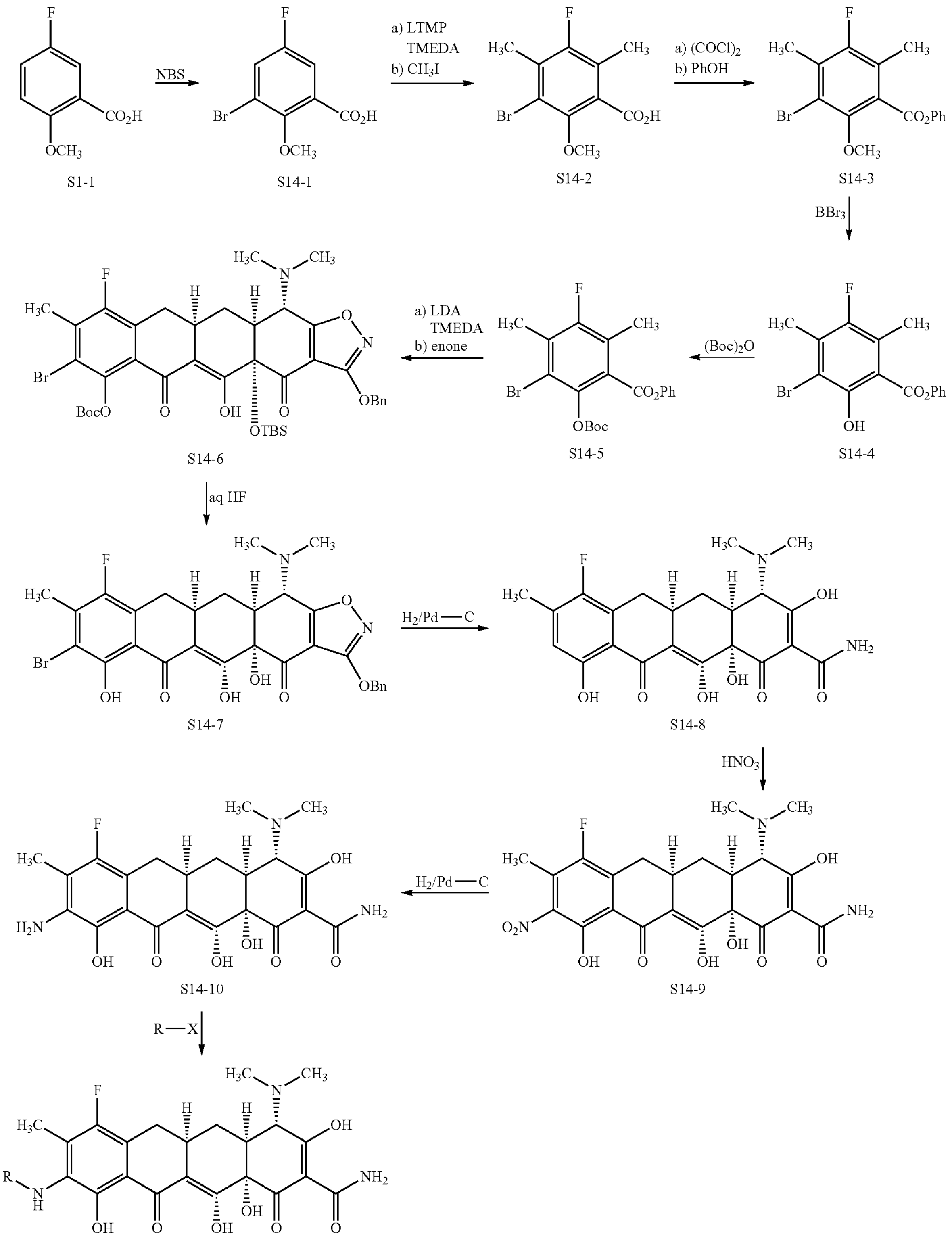
S14-11

The following compounds were prepared according to Scheme 14.

S14-1

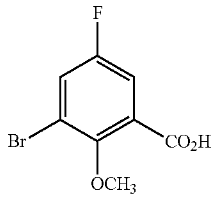

To compound S1-1 (5.00 g, 29.38 mmol, 1.0 equiv) in sulfuric acid (10 mL) and trifluoroacetic acid (20 mL) at rt was added NBS (5.75 g, 32.30 mmol, 1.1 equiv). The pale solution was stirred at rt for 3 hrs. The resulting pale suspension was carefully poured onto 500 g crushed ice. The mixture was extracted with EtOAc (200 mL×1, 100 mL×3). The EtOAc extracts were combined, dried over sodium sulfate, and concentrated under reduced pressure. The light yellow residue was suspended in minimum dichloromethane. The solid was collected, washed with cold dichloromethane (5 mL×3), and dried under vacuum overnight to yield the desired product S14-1 as a white crystalline solid (5.49 g, 75%): $R_f$ 0.55 (0.5% HOAc/EtOAc); $^1$H NMR (400 MHz, $CDCl_3$) δ 7.74-7.77 (m, 1 H), 7.24-7.55 (m, 1 H), 4.01 (s, 3 H); MS (ESI) m/z 247.1 (M−H), calcd for $C_8H_6BrFO_3$ 248.0.

S14-2

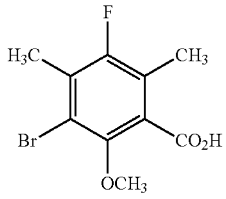

To compound S14-1 (0.25 g, 1.00 mmol, 1.0 equiv) in anhydrous THF (5 mL) at −78° C. was added TMEDA (0.75 mL, 5.00 mmol, 5.0 equiv) and LTMP (4.00 mmol, freshly prepared, in 4 mL THF) dropwise. The cloudy deep red solution was stirred at −78° C. for 30 min. Iodomethane (0.31 mL, 5.00 mmol, 5.0 equiv) was added dropwise at −78° C. The resulting pale suspension was allowed to warm to rt and was stirred overnight. Aqueous HCl (1 N) was added to the reaction until pH 1-2. The mixture was extracted with EtOAc (100 mL×1, 20 mL×3). The EtOAc extracts were combined, dried over sodium sulfate, and concentrated under reduced pressure to afford crude S14-2 as an orange solid (0.30 g).

S14-3

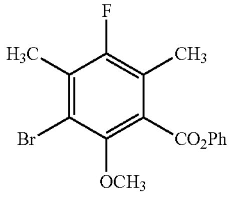

The compound S14-2 was dissolved in dry dichloromethane (10 mL). Anhydrous DMF (2 drops) and oxalyl chloride (0.43 mL, 5.00 mmol, 5.0 equiv) were added dropwise at rt. The yellow solution was stirred at rt for 30 min and concentrated under reduced pressure. The residue was redissolved in dry dichloromethane (10 mL). Phenol (0.14 g, 1.50 mmol, 1.5 equiv), DIEA (0.70 mL, 4.00 mmol, 4.0 equiv), and DMAP (12 mg, 0.10 mmol, 0.1 equiv) were added. The reaction was stirred at rt overnight, diluted with saturated aqueous sodium bicarbonate (50 mL), and extracted with dichloromethane (50 mL×3). The dichloromethane extracts were combined, dried over sodium sulfate, and concentrated under reduced pressure. Flash column chromatography on silica gel using 0% to 5% EtOAc/hexanes yielded the desired product S14-3 as a pale oil (0.13 g, 37%, 2 steps): $R_f$ 0.70 (10% EtOAc/hexanes); $^1$H NMR (400 MHz, $CDCl_3$) δ 7.40-7.50 (m, 2 H), 7.16-7.23 (m, 3 H), 3.94 (s, 3 H), 2.38 (s, 3 H), 2.32 (s, 3 H); MS (ESI) m/z 351.1 (M−H), calcd for $C_{16}H_{14}BrFO_3$ 352.0.

S14-4

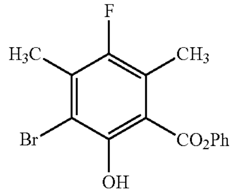

Compound S14-3 (0.13 g, 0.37 mmol, 1.0 equiv) was dissolved in anhydrous dichloromethane (4 mL) and the solution was cooled to −78° C. $BBr_3$ (0.93 mL, 1.0 M/dichloromethane, 0.93 mmol, 2.5 equiv) was added dropwise. The orange-brown solution was warmed to −10° C. with stirring over a period of 2 hrs. The reaction was quenched by saturated aqueous sodium bicarbonate (20 mL) and extracted with EtOAc (20 mL×3). The extracts were combined, dried over sodium sulfate, and concentrated under reduced pressure to yield crude S14-4 as a pale solid (0.13 g).

S14-5

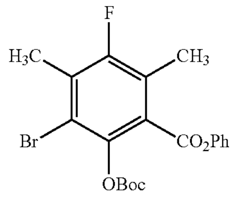

Phenol S14-4 was dissolved in dichloromethane. Di-t-butyl dicarbonate (0.12 g, 0.56 mmol, 1.5 equiv), DIEA (0.13 mL, 0.74 mmol, 2.0 equiv), and DMAP (5 mg, 0.040 mmol, 0.1 equiv) were added. The reaction was stirred at rt overnight and concentrated under reduced pressure. Flash column chromatography on silica gel using 0% to 2% EtOAc/hexanes yielded the desired compound S14-5 as a white solid (0.14 g, 88%, 2 steps): $R_f$ 0.25 (3% EtOAc/hexanes); $^1$H NMR (400 MHz, $CDCl_3$) δ 77.40-7.49 (m, 2 H), 7.18-7.32 (m, 3 H), 2.42 (d, J=3.0 Hz, 3 H), 2.38 (d, J=2.5 Hz, 3 H), 1.45 (s, 9 H); MS (ESI) m/z 437.1 (M−H), calcd for $C_{20}H_{20}BrFO_3$ 438.0.

S14-6

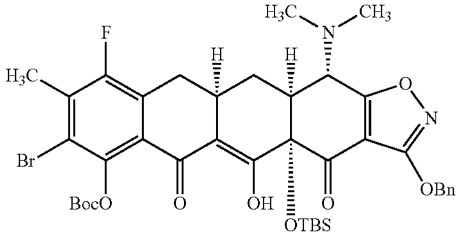

To diisopropylamine (0.090 mL, 0.64 mmol, 5.0 equiv) in anhydrous THF at −78° C. was added n-BuLi (0.40 mL, 1.6 M/hexanes, 0.64 mmol, 5.0 equiv). The colorless solution was stirred at 0° C. for 10 min and cooled to −78° C. TMEDA (0.29 mL, 1.92 mmol, 15 equiv) was added, followed by the dropwise addition of compound S14-5 (0.14 g, 0.32 mmol, 2.5 equiv, in 3 mL THF) over a period of 5 min. The deep red solution was stirred at −78° C. for 15 min. Enone S1-9 (62 mg, 0.13 mmol, 1.0 equiv, in 3 mL THF) was added. The reaction was warmed from −78° C. to −10° C. with stirring over a period of 30 min, quenched by HOAc (0.12 mL) and saturated aqueous ammonium chloride (50 mL), and extracted with EtOAc (100 mL×1, 50 mL×2). The EtOAc extracts were combined, dried over sodium sulfate, and concentrated under reduced pressure. Reverse phase HPLC purification yielded the desired product S14-6 as a light-yellow solid (36 mg, 34%): $R_f$ 0.45 (20% EtOAc/hexanes); $^1H$ NMR (400 MHz, $CDCl_3$) δ 15.69 (br s, 1 H), 7.45-7.50 (m, 2 H), 7.30-7.40 (m, 3 H), 5.34 (s, 2 H), 3.97 (br s, 1 H), 3.20-3.30 (br m, 1 H), 2.98-3.07 (br m, 1 H), 2.1-2.7 (m, 11 H), 1.5-1.6 (m, 11 H), 0.80 (s, 9 H), 0.23 (s, 3 H), 0.11 (s, 3 H); MS (ESI) m/z 827.3 (M+H), calcd for $C_{40}H_{48}BrFN_3O_9Si$ 826.2.

S14-8

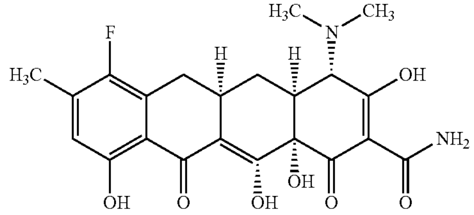

Compound S14-6 (36 mg, 0.044 mmol) was dissolved in acetonitrile (1.5 mL). Aqueous HF (0.75 mL, 48-50%) was added. The yellow solution was stirred at rt overnight, diluted with aqueous $K_2HPO_4$ (3.2 g in 16 mL water), and extracted with dichloromethane (20 mL×3). The dichloromethane extracts were combined, dried over sodium sulfate, and concentrated under reduced pressure to yield crude S14-7 as a bright-yellow solid (31 mg): MS (ESI) m/z 613.2 (M+H), calcd for $C_{29}H_{26}BrFN_2O_7$ 612.1.

The above crude product S14-7 was dissolved in MeOH (4 mL) and dioxane (2 mL). 10% Pd—C (19 mg, 0.0090 mmol, 0.2 equiv) was added. The mixture was purged with hydrogen and stirred under 1 atm hydrogen atmosphere at rt for 1 h. The catalyst was filtered off with a small Celite pad and washed with MeOH (5 mL×3). The yellow filtrate was concentrated under reduced pressure to yield crude S14-8 as a yellow solid (27 mg). 10% of the crude product was purified with reverse phase HPLC using similar conditions for S2-4-1 to yield compound S14-8 as a yellow solid (2 mg, 71%, 2 steps, HCl salt): $^1H$ NMR (400 MHz, $CD_3OD$) δ 6.69 (d, J=6.1 Hz, 1 H), 4.06 (s, 1 H), 2.80-3.50 (m, 3 H), 3.03 (s, 3 H), 2.95 (s, 3 H), 2.10-2.40 (m, 2 H), 2.27 (s, 3 H), 1.56-1.68 (m, 1 H); MS (ESI) m/z 447.1 (M+H), calcd for $C_{22}H_{23}FN_2O_7$ 446.2.

S14-9

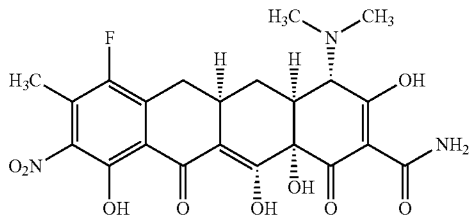

Compound S14-8 (90% of crude from above, 0.40 mmol) was dissolved in cold sulfuric acid (2 mL, 0° C.). Nitric acid (0.12 mL, 0.5 M in sulfuric acid, 0.060 mmol, 1.5 equiv) was added. The deep brown solution was stirred at 0° C. for 1 h. The resulting deep red solution was added dropwise into ether (100 mL) with stirring. The yellow solid was collected onto a small Celite pad, washed with ether (5 mL×4, discarded), and eluted with MeOH (5 mL×3). The yellow MeOH solution was collected and concentrated under reduced pressure to yield the desired compound S14-9 as a yellow solid (27 mg): MS (ESI) m/z 492.3 (M+H), calcd for $C_{22}H_{22}FN_3O_9$ 491.1.

S14-10

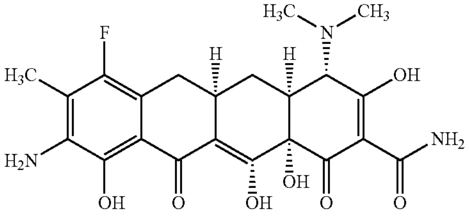

Compound S14-9 (25 mg, 0.036 mmol) was dissolved in MeOH (4 mL). 10% Pd—C (15 mg, 0.0070 mmol, 0.2 equiv) was added. The mixture was purged with hydrogen and stirred at rt under 1 atm hydrogen atmosphere for 4 hrs. The catalyst was filtered off with a small Celite pad and washed with MeOH (5 mL×3). The yellow filtrate was concentrated under reduced pressure. HPLC purification using similar conditions for S2-4-1 yielded the desired product S14-10 as a deep red solid (6 mg, 31%, 3 steps; bis-HCl salt): $^1H$ NMR (400 MHz, $CD_3OD$) δ 4.09 (s, 1 H), 2.80-3.50 (m, 3 H), 3.03 (s, 3 H), 2.95 (s, 3 H), 2.30-2.40 (m, 1 H), 2.34 (s, 3 H), 2.19-2.27 (m, 1 H), 1.60-1.62 (m, 1 H); MS (ESI) m/z 462.1 (M+H), calcd $C_{22}H_{24}FN_3O_7$ 461.2.

S14-11-1

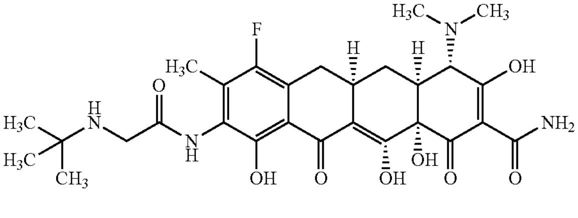

Compound S14-10 (4 mg, 0.0075 mmol, 1.0 equiv) was dissolved in acetonitrile/DMPU (0.1 mL, 1:1 v/v). t-Butylaminoacetyl chloride (2 mg, HCl salt, 0.011 mmol, 1.5 equiv, prepared by treating t-butylaminoacetic acid with excess thionyl chloride followed by concentration under reduced pressure) was added. The deep red solution was stirred at rt for 3 hrs and quenched by aqueous HCl (2 mL, 0.1 N). HPLC purification using similar conditions for S2-4-1 yielded the desired product S14-11 as a yellow solid (2 mg, 41%, bis-HCl salt): $^1H$ NMR (400 MHz, $CD_3OD$) δ 4.08 (br s, 3 H), 2.78-3.50 (m 3 H), 3.04 (s, 3 H), 2.95 (s, 3 H), 2.18-2.37 (m, 2 H), 2.21 (s, 3 H), 1.60-1.62 (m, 1 H), 1.42 (s, 9 H); MS (ESI) m/z 575.4 (M+H), calcd for $C_{28}H_{35}FN_4O_8$ 574.2.

EXAMPLE 15

Synthesis of Compounds Via Scheme 15

Scheme 15

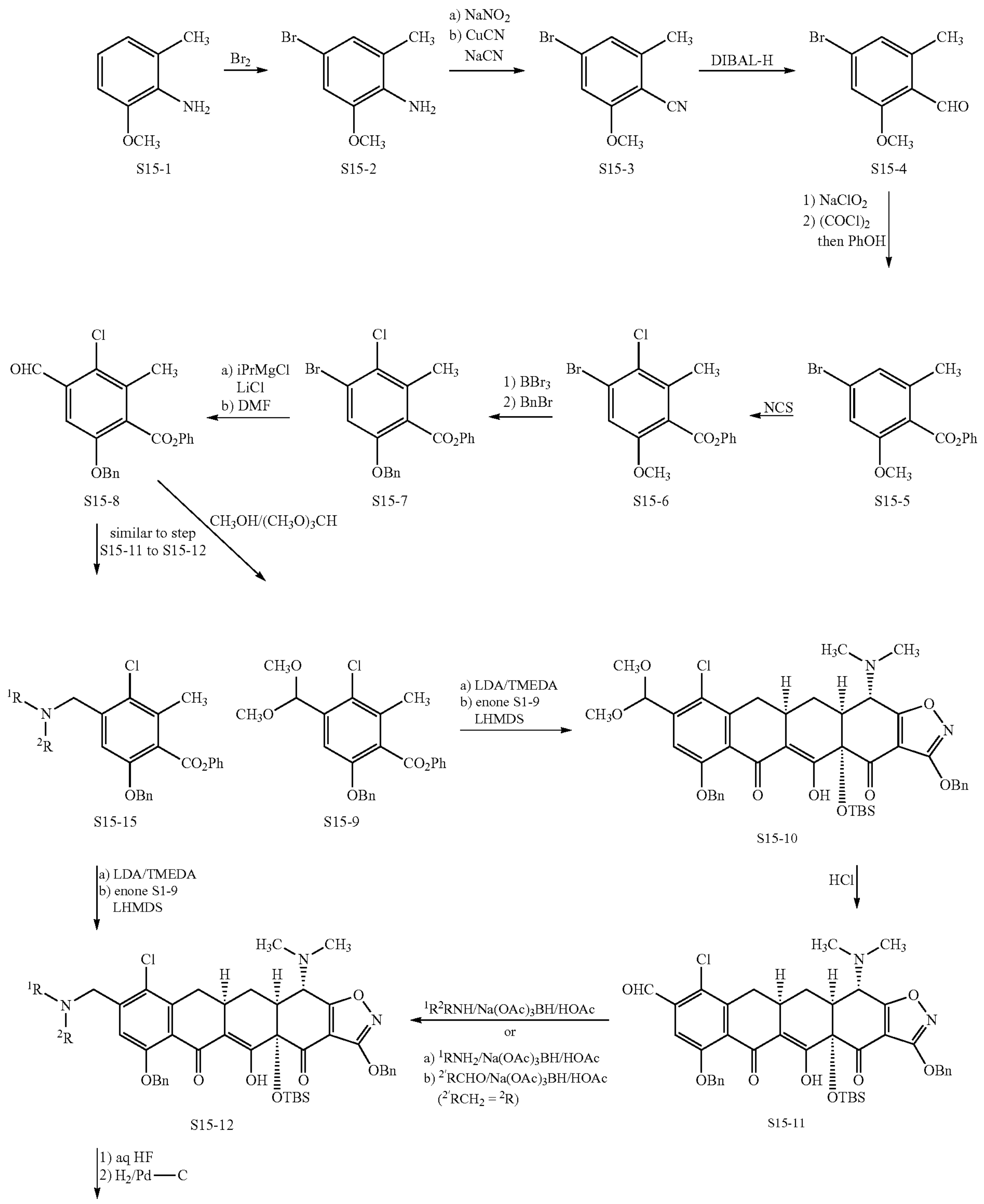

-continued

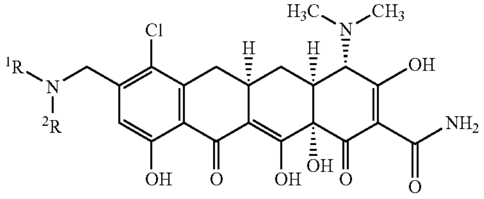

S15-13 and/or

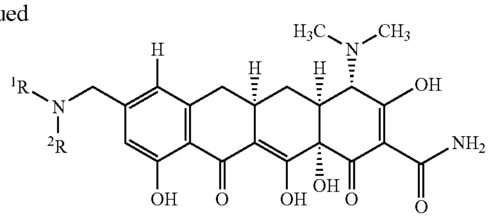

S15-14

The following compounds were prepared according to Scheme 15.

S15-2

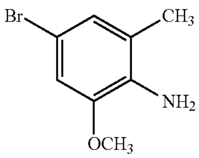

To an ice-cooled solution of 2-methoxy-6-methylaniline (S15-1, 25.12 g, 183.10 mmol, 1 equiv) in MeOH (79 mL) and HOAc (25 mL) was added a solution of bromine (9.41 mL, 183.10 mmol) in HOAc (79 mL) dropwise via an addition funnel. The reaction mixture was allowed to warm to rt and stirred for 2 hrs after complete addition. EtOAc (150 mL) was added, and the solid was collected by filtration and washed with more EtOAc, yielding 37.20 g of compound S15-2 as an off-white solid (HBr salt).

S15-3

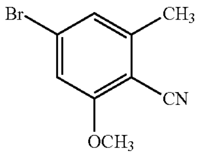

4-Bromo-2-methoxy-6-methylaniline (S15-2, HBr salt, 20.00 g, 92.70 mmol, 1.0 equiv) was suspended in concentrated HCl (22 mL) and crushed ice (76 g) cooled in an ice-bath. A solution of $NaNO_2$ (6.52 g, 94.60 mmol, 1.02 equiv) in $H_2O$ (22 mL) was added dropwise. The resulting mixture was stirred at 0° C. for 30 min and neutralized with aqueous $Na_2CO_3$. A suspension of CuCN (10.4 g, 115.90 mmol, 1.25 equiv) in $H_2O$ (44 mL) was mixed with a solution of NaCN (14.4 g, 294.80 mmol, 3.18 equiv) in 22 mL of $H_2O$, and cooled in an ice-bath. The initial diazonium salt mixture was then added to the CuCN and NaCN mixture with vigorous stirring while maintaining the temperature at 0° C. (toluene (180 mL) was also added in portions during the addition). The reaction mixture was stirred at 0° C. for 1 h, rt for 2 hrs, and 50° C. for another 1 h. After cooling to rt, the layers were separated. The aqueous layer was extracted with toluene. The combined organic layers were washed with brine, dried over magnesium sulfate, and concentrated. The residue was passed through a silica gel plug, washed with toluene, and concentrated to yield 14.50 g of compound S15-3 as a light yellow solid.

S15-4

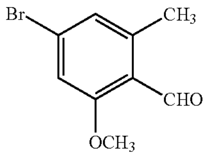

To a solution of S15-3 (11.34 g, 50.20 mmol, 1.0 equiv) in THF (100 mL) was added 1.5 M DIBAL-H in toluene (40.10 mL, 60.20 mmol, 1.2 equiv) slowly at −78° C. The reaction was allowed to warm to rt gradually and stirred overnight. After re-cooled to 0° C., the reaction was carefully quenched by 1 N HCl. The resulting mixture was stirred at rt for 1 h and extracted three times with EtOAc. The combined EtOAc layers were washed with $H_2O$, saturated aqueous $NaHCO_3$ and brine, dried over magnesium sulfate, and concentrated to provide compound S15-4 as a yellow solid, which was used directly in the next step.

S15-5

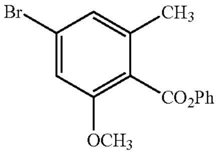

To a suspension of S15-4 (50.20 mmol, 1.0 equiv) in t-BuOH (200 mL) was added a solution of $NaClO_2$ (11.34 g, 100.30 mmol, 2.0 equiv) and $NaH_2PO_4$ (34.6 g, 250.80 mmol, 5.0 equiv) in $H_2O$ (100 mL) via an addition funnel. After complete addition, 2-methyl-2-butene (42.40 mL, 0.40 mol, 8 equiv)) was added. The resulting homogenous solution was stirred at rt for 30 min, and volatiles were removed. The residue was suspended in 150 mL of $H_2O$. The solution was acidified to pH ~1 with 1 N HCl and extracted three times with t-butyl methyl ether. The combined organic solution was extracted three times with 1 N NaOH. The combined aqueous solution was acidified with 6 N HCl, and extracted three times with EtOAc. The combined EtOAc extracts were washed with brine, dried over magnesium sulfate, and concentrated to provide 8.64 g of the benzoic acid intermediate (15-4-a) as an off-white solid, which was used directly in the next step.

To a solution of the above benzoic acid (8.64 g, 35.20 mmol, 1.0 equiv) in dichloromethane (70 mL) was added oxalyl chloride (3.76 mL, 42.30 mmol, 1.2 equiv), followed by a couple of drops of DMF (caution: gas evolution). The mixture was stirred at rt for 30 min and the volatiles were evaporated under reduce pressure. The residue was further dried under high vacuum to afford the crude benzoyl chloride. The crude benzoyl chloride was re-dissolved in dichloromethane (70 mL). Triethylamine (12.3 mL, 88.10 mmol, 2.5 equiv), phenol (3.98 g, 42.30 mmol, 1.2 equiv) and DMAP (0.43 g, 3.52 mmol, 0.1 equiv) were added. The mixture was stirred at rt for 1 h. The solvent was evaporated. The residue was suspended in EtOAc, and the precipitate was filtered off. The organic solution was then washed with 1 N HCl (three times), $H_2O$, saturated aqueous $NaHCO_3$, and brine, dried over sodium sulfate, filtered and concentrated. Purification of the residue by flash chromatography gave compound S15-5 (10.05 g, 89%) as an off-white solid: $^1H$ NMR (400 MHz, $CDCl_3$) δ 7.41-7.45 (m, 2 H), 7.22-7.27 (m, 3 H), 7.04 (d, J=0.9 Hz, 1 H), 6.97 (d, J=0.9 Hz, 1 H), 3.87 (s, 3 H), 2.42 (s, 3 H); MS (ESI) m/z 319.0 (M−H), calcd for $C_{15}H_{12}BrO_3$ 319.0.

S15-6

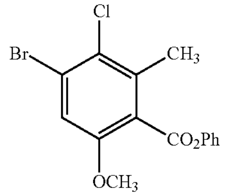

To a solution of compound S15-5 (2.52 g, 7.87 mmol, 1.0 equiv) in acetonitrile (16 mL) was added NCS (1.10 g, 8.27 mmol, 1.05 equiv) in one portion. The resulting mixture was heated in a 60° C. oil bath for 45 hrs. The solvent was evaporated. The residue was redissolved in $Et_2O$ (400 mL), washed with 1 N NaOH, $H_2O$ and brine, dried over sodium sulfate, and concentrated to provide 2.76 g of compound S15-6 as a white solid. This material was used directly in the next step without further purification: $^1H$ NMR (400 MHz, $CDCl_3$) δ 7.44 (dd, J=7.8, 7.8 Hz, 2 H), 7.22-7.28 (m, 3 H), 7.13 (s, 1 H), 3.87 (s, 3 H), 2.51 (s, 3 H); MS (ESI) m/z 353.0 (M−H), calcd for $C_{15}H_{11}BrClO_3$ 352.97.

S15-7

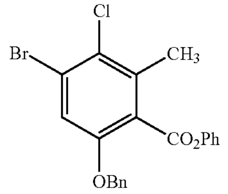

Compound S15-6 (2.76 g, 7.76 mmol, 1.0 equiv) was dissolved in anhydrous dichloromethane (78 mL) and cooled to −78° C. A solution of boron tribromide (1.0 M in dichloromethane, 7.76 mL, 7.76 mmol, 1.0 equiv) was added dropwise at −78° C. The resulting yellow solution was stirred at −78° C. for 15 min, and at 0° C. for 30 min. Saturated aqueous $NaHCO_3$ was added. The mixture was stirred at rt for 10 min., and extracted with EtOAc three times. The combined organic layers were washed with brine, dried over sodium sulfate, and concentrated to provide 2.69 g of the phenol intermediate as an off-white solid. This material was used directly in the next step without further purification: $^1H$ NMR (400 MHz, $CDCl_3$) δ 7.46 (dd, J=7.8, 7.8 Hz, 2 H), 7.32 (dd, J=7.8, 7.8 Hz, 1 H), 7.27 (s, 1 H), 7.19 (d, J=7.8 Hz, 2 H), 2.83 (s, 3 H); MS (ESI) m/z 339.0 (M−H), calcd for $C_{14}H_9BrClO_3$ 338.95.

The above phenol (2.65 g, 7.76 mmol, 1.0 equiv) was dissolved in acetone (40 mL), and added with $K_2CO_3$ (2.14 g, 15.5 mmol, 2.0 equiv) and benzylbromide (0.97 mL, 8.15 mmol, 1.05 equiv) at rt. After stirring overnight at rt, the solution was filtered through a bed of Celite. The solid cake was further washed with three portions of EtOAc. The combined organic solution was concentrated. The residue was purified by flash chromatography to yield 2.97 g (89%) of compound S15-7 as a white solid: $^1H$ NMR (400 MHz, $CDCl_3$) δ 7.33-7.43 (m, 7 H), 7.19-7.26 (m, 2 H), 7.05 (d, J=7.8 Hz, 2 H), 5.11 (s, 2 H), 2.51 (s, 3 H); MS (ESI) m/z 429.0 (M−H), calcd for $C_{21}H_{15}BrClO_3$ 429.00.

S15-8

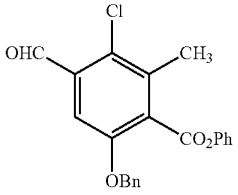

To a solution of compound S15-7 (1.98 g, 4.59 mmol, 1.0 equiv) in anhydrous THF (23 mL) was added i-PrMgCl.LiCl (7.65 mL, 1.2 M/THF, 9.18 mmol, 2.0 equiv) dropwise at −78° C. under a $N_2$ atmosphere. After 10 min, the temperature was raised to 0° C. and the reaction was stirred for 1 h at 0° C. DMF (1.80 mL, 22.90 mmol, 5.0 equiv) was then added. The reaction was warmed to rt, stirred for 30 min at rt, and quenched by saturated aqueous $NH_4Cl$. The layers were separated and the aqueous layer was further extracted twice with EtOAc. The combined organic layers were washed with brine, dried over sodium sulfate, filtered, and concentrated. Purification of the residue by flash chromatography gave compound S15-8 (1.45 g, 83%) as a white solid: $^1H$ NMR (400 MHz, $CDCl_3$) δ 10.51 (s, 1 H), 7.33-7.44 (m, 8 H), 7.25-7.27 (m, 1 H), 7.05 (d, J=7.8 Hz, 2 H), 5.19 (s, 2 H), 2.51 (s, 3 H); MS (ESI) m/z 379.1 (M−H), calcd for $C_{22}H_{16}ClO_4$ 379.08.

S15-9

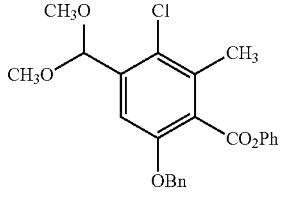

To a solution of aldehyde S15-8 (1.66 g, 4.37 mmol, 1.0 equiv) in MeOH (22 mL) was added trimethylorthoformate (2.40 mL, 21.90 mmol, 5.0 equiv) and TsOH (83 mg, 0.44 mmol, 0.1 equiv). The reaction was heated to 65° C. for 4 hrs. The solvent was evaporated. The residue was redissolved in EtOAc (200 mL), washed with saturated aqueous $NaHCO_3$ and brine, dried over sodium sulfate, and concentrated. Purification of the residue by flash chromatography gave compound S15-9 (1.75 g, 94%) as a white solid: $^1H$ NMR (400 MHz, $CDCl_3$) δ 7.43 (d, J=7.8 Hz, 2 H), 7.34-7.37 (m, 5 H), 7.20-7.25 (m, 2 H), 7.07 (d, J=7.8 Hz, 2 H), 5.62 (s, 1 H), 5.19 (s, 2 H), 3.36 (s, 6 H), 2.48 (s, 3 H); MS (ESI) m/z 425.10 (M−H), calcd for $C_{24}H_{22}ClO_5$ 425.12.

S15-10

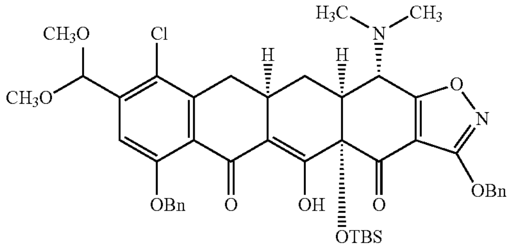

A solution of n-BuLi in hexanes (2.37 mL, 2.2 M, 5.23 mmol, 1.2 equiv) was added dropwise to a solution of i-$Pr_2NH$ (0.77 mL, 5.45 mmol, 1.25 equiv) in THF (27 mL) at −78° C. under a $N_2$ atmosphere. The resulting solution was stirred at −78° C. for 20 min and 0° C. for 5 min, and then re-cooled to −78° C. N,N,N',N'-Tetramethylethylenediamine (TMEDA, 0.85 mL, 5.67 mmol, 1.30 equiv) was added, followed by the dropwise addition of S15-9 (2.05 g, 4.80 mmol, 1.1 equiv) in THF (30 mL) via a cannula. After complete addition, the resulting dark-red mixture was stirred for another hour at −78° C. and then cooled to −100° C. A solution of enone S1-9 (2.10 g, 4.36 mmol, 1.0 equiv) in THF (30 mL) was added dropwise via a cannula. The resulting red mixture was slowly warmed to −78° C. LHMDS (4.36 mL, 1.0 M/THF, 4.36 mmol, 1.0 equiv) was then added and the reaction was slowly warmed to −5° C. Saturated aqueous $NH_4Cl$ was added. The resulting mixture was extracted three times with EtOAc. The combined EtOAc extracts were washed with brine, dried (sodium sulfate), and concentrated. Purification of the residue by flash chromatography gave compound S15-10 (3.20 g, 90%) as a light yellow foam: $^1H$ NMR (400 MHz, $CDCl_3$) δ 0.16 (s, 3 H), 7.22-7.52 (m, 11 H), 5.55 (s, 1 H), 5.38 (s, 2 H), 5.29 (d, J=11.4 Hz, 1 H), 5.24 (d, J=11.4 Hz, 1 H), 3.97 (d, J=10.4 Hz, 1 H), 3.46 (dd, J=4.9, 15.9 Hz, 1 H), 3.38 (s, 3 H), 3.29 (s, 3 H), 2.96-3.04 (m, 1 H), 2.45-2.58 (m, 9 H), 2.15 (d, J=14.6 Hz, 1 H), 0.84 (s, 9 H), 0.28 (s, 3 H); MS (ESI) m/z 815.30 (M+H), calcd for $C_{44}H_{52}ClN_2O_9Si$ 815.31.

S15-11

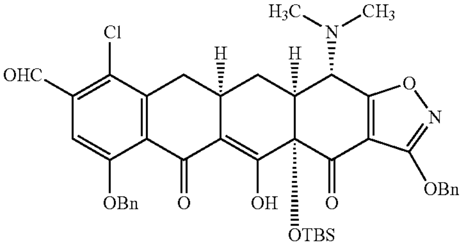

To a solution of compound S15-10 (1.48 g, 1.82 mmol, 1.0 equiv) in THF (15 mL) was added 3 N HCl (3 mL) at 0° C. The resulting mixture was stirred at rt for 4 hrs, diluted with EtOAc, washed with saturated aqueous $NaHCO_3$ and brine, dried over sodium sulfate, and concentrated. Purification of the residue by flash chromatography gave aldehyde S15-11 (1.05 g, 75%) as a light yellow foam: $^1H$ NMR (400 MHz, $CDCl_3$) δ 15.8 (s, 1 H), 10.5 (s, 1 H), 7.28-7.50 (m, 11 H), 5.36 (s, 2 H), 5.28 (d, J=11.4 Hz, 1 H), 5.23 (d, J=11.4 Hz, 1 H), 3.94 (d, J=10.4 Hz, 1 H), 3.48 (dd, J=4.9, 15.9 Hz, 1 H), 2.96-3.06 (m, 1 H), 2.44-2.60 (m, 9 H), 2.16 (d, J=14.6 Hz, 1 H), 0.82 (s, 9 H), 0.26 (s, 3 H), 0.14 (s, 3 H); MS (ESI) m/z 769.30 (M+H), calcd for $C_{42}H_{46}ClN_2O_8Si$ 769.26.

S15-13-1

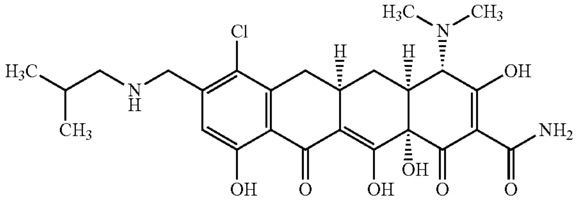

Compound S15-11 (30 mg, 0.039 mmol, 1.0 equiv) was dissolved in 1,2-dichloroethane (1.0 mL). Isobutylamine (14 μL, 0.12 mmol, 3.0 equiv) and acetic acid (7 μL, 0.12 mmol, 3.0 equiv) were added. After stirring at rt for 1 h, sodium triacetoxyborohydride (17 mg, 0.078 mmol, 2.0 equiv) was added. Stirring was continued overnight. The reaction mixture was poured into saturated aqueous $NaHCO_3$ and extracted three times with dichloromethane. The combined organic extracts were washed with brine, dried over sodium sulfate, and concentrated to give the crude intermediate, which was used directly in the next step without further purification.

In a plastic vial, the above amine intermediate was dissolved in $CH_3CN$ (1 mL). Aqueous HF (48-50%, 0.25 mL) was added. After stirring at rt for 16 hrs, the reaction mixture was poured into aqueous solution (12.5 mL) of $K_2HPO_4$ (1.75 g) and extracted three times with dichloromethane. The combined organic phases were washed with brine, dried, and concentrated to yield the crude intermediate.

The above crude intermediate was dissolved in EtOAc (2.0 mL). Pd—C (10 wt %, 8 mg, 30% w/w) was added. The reaction flask was briefly evacuated and re-filled with hydrogen. The reaction mixture was stirred at rt and monitored by LC-MS. After the reaction was complete, MeOH (5 mL) and 0.5 N HCl/MeOH (0.5 mL) were added. The mixture was stirred for 30 min, and filtered through a small pad of Celite. The filtrate was concentrated to give the crude product, which was purified by HPLC on a Waters Autopurification system using a Phenomenex Polymerx 10μ RP-γ 100 R column [30×21.20 mm, 10 micron; flow rate, 20 mL/min; Solvent A: 0.05 N HCl/water; Solvent B: MeOH; injection volume: 4.0 mL (0.05 N HCl/water); gradient: 20→100% B over 10 min; mass-directed fraction collection]. Fractions containing the desired product, eluting at 7.85-8.95 min, were collected and freeze-dried to give the desired product S15-13-1 as a yellow solid: $^1H$ NMR (400 MHz, $CD_3OD$) δ 7.16 (s, 1 H), 7.16 (s, 1 H), 4.38 (s, 2 H), 4.12 (s, 1 H), 3.40 (dd, J=4.6, 16.0 Hz, 1 H), 2.96-3.11 (m, 10 H), 2.41 (dd, J=14.0, 14.0 Hz, 1 H), 2.24-2.28 (m, 1 H), 2.08-2.13 (m, 1 H), 1.60-1.70 (m, 1 H), 1.06 (d, J=6.4 Hz, 6 H); MS (ESI) m/z 534.2 (M+H), calcd for $C_{26}H_{33}ClN_3O_7$ 534.19.

The following compounds were prepared similarly to S15-13-1.

S15-13-2

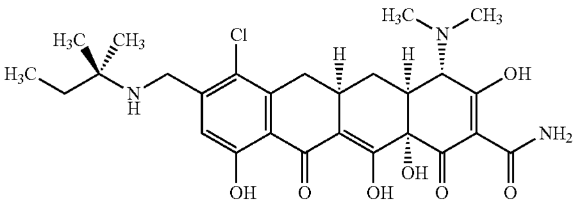

The crude product was purified by HPLC on a Waters Autopurification system using a Phenomenex Polymerx 10μ RP-γ 100 R column [30×21.20 mm, 10 micron; flow rate, 20 mL/min; Solvent A: 0.05 N HCl/water; Solvent B: MeOH; injection volume: 4.0 mL (0.05 N HCl/water); gradient: 20→100% B over 10 min; mass-directed fraction collection]. Fractions containing the desired product, eluting at 8.00-9.50 min, were collected and freeze-dried to give the desired product S15-13-2 as a yellow solid: $^1$H NMR (400 MHz, $CD_3OD$) δ 7.19 (s, 1 H), 4.33 (s, 2 H), 4.13 (s, 1 H), 3.41 (dd, J=4.6, 16.0 Hz, 1 H), 2.96-3.10 (m, 8 H), 2.40 (dd, J=15.0, 15.0 Hz, 1 H), 2.25-2.28 (m, 1 H), 1.84 (q, J=7.3 Hz, 2 H), 1.60-1.70 (m, 1 H), 1.44 (s, 6 H), 1.04 (t, J=7.3 Hz, 3 H); MS (ESI) m/z 548.3 (M+H), calcd for $C_{27}H_{35}ClN_3O_7$ 548.21.

S15-13-3

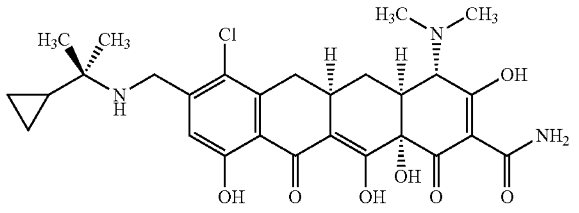

The crude product was purified by HPLC on a Waters Autopurification system using a Phenomenex Polymerx 10μ RP-γ 100 R column [30×21.20 mm, 10 micron; flow rate, 20 mL/min; Solvent A: 0.05 N HCl/water; Solvent B: MeOH; injection volume: 4.0 mL (0.05 N HCl/water); gradient: 20→100% B over 10 min; mass-directed fraction collection]: Fractions containing the desired product, eluting at 8.35-9.80 min, were collected and freeze-dried to give the desired product S15-13-3 as a yellow solid: $^1$H NMR (400 MHz, $CD_3OD$) δ 7.19 (s, 1 H), 4.44 (s, 2 H), 4.13 (s, 1 H), 3.41 (dd, J=4.6, 16.0 Hz, 1 H), 2.96-3.10 (m, 8 H), 2.41 (dd, J=15.0, 15.0 Hz, 1 H), 2.23-2.28 (m, 1 H), 1.60-1.70 (m, 1 H), 1.34 (s, 6 H), 1.21-1.26 (m, 1 H), 0.69-0.72 (m, 2 H), 0.60-0.63 (m, 2 H); MS (ESI) m/z 560.3 (M+H), calcd for $C_{28}H_{35}ClN_3O_7$ 560.21.

S15-13-4

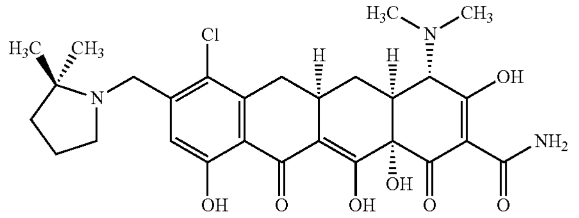

The crude product was purified by HPLC on a Waters Autopurification system using a Phenomenex Polymerx 10μ RP-γ 100 R column [30×21.20 mm, 10 micron; flow rate, 20 mL/min; Solvent A: 0.05 N HCl/water; Solvent B: MeOH; injection volume: 4.0 mL (0.05 N HCl/water); gradient: 20→100% B over 10 min; mass-directed fraction collection]. Fractions containing the desired product, eluting at 7.15-8.50 min, were collected and freeze-dried to give the desired product S15-13-4 as a yellow solid: $^1$H NMR (400 MHz, $CD_3OD$) δ 7.21 (s, 1 H), 4.72 (t, J=13.2 Hz, 1 H), 4.10-4.15 (m, 2 H), 3.38-3.55 (m, 2 H), 2.95-3.10 (m, 8 H), 2.41 (dd, J=15.0, 15.0 Hz, 1 H), 1.96-2.28 (m, 5 H), 1.96-2.28 (m, 5 H), 1.66 (s, 3 H), 1.63-1.66 (m, 1 H), 1.45 (s, 3 H); MS (ESI) m/z 560.3 (M+H), calcd for $C_{28}H_{35}ClN_3O_7$ 560.21.

S15-13-5

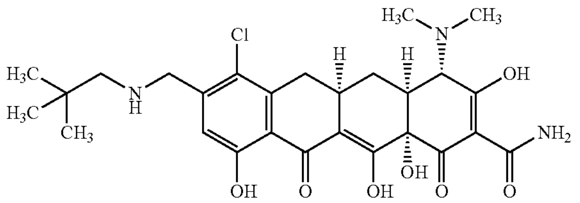

The crude product was purified by HPLC on a Waters Autopurification system using a Phenomenex Polymerx 10μ RP-γ 100 R column [30×21.20 mm, 10 micron; flow rate, 20 mL/min; Solvent A: 0.05 N HCl/water; Solvent B: MeOH; injection volume: 4.0 mL (0.05 N HCl/water); gradient: 20→100% B over 10 min; mass-directed fraction collection]. Fractions containing the desired product, eluting at 7.65-8.50 min, were collected and freeze-dried to give the desired product S15-13-5 as a yellow solid: $^1$H NMR (400 MHz, $CD_3OD$) δ 7.20 (s, 1 H), 4.24 (s, 2 H), 4.13 (s, 1 H), 3.41 (dd, J=4.6, 16.0 Hz, 1 H), 2.94-3.14 (m, 10 H), 2.41 (dd, J=15.0, 15.0 Hz, 1 H), 2.24-2.30 (m, 1 H), 1.60-1.70 (m, 1 H), 1.08 (s, 9 H); MS (ESI) m/z 548.3 (M+H), calcd for $C_{27}H_{35}ClN_3O_7$ 548.21.

S15-13-6

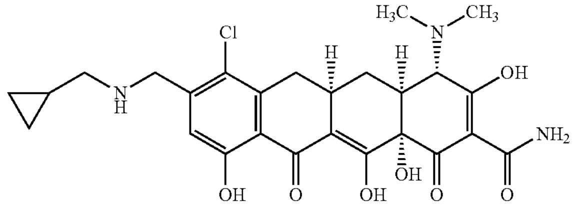

The crude product was purified by HPLC on a Waters Autopurification system using a Phenomenex Polymerx 10μ RP-γ 100 R column [30×21.20 mm, 10 micron; flow rate, 20 mL/min; Solvent A: 0.05 N HCl/water; Solvent B: MeOH; injection volume: 4.0 mL (0.05 N HCl/water); gradient: 0→100% B over 20 min; mass-directed fraction collection]. Fractions containing the desired product, eluting at 13.80-14.90 min, were collected and freeze-dried to give the desired product S15-13-6 as a yellow solid: $^1$H NMR (400 MHz, $CD_3OD$) δ 7.14 (s, 1 H), 4.40 (s, 2 H), 4.13 (s, 1 H), 3.40 (dd, J=4.6, 16.0 Hz, 1 H), 2.94-3.14 (m, 10 H), 2.40 (dd, J=15.0, 15.0 Hz, 1 H), 2.25-2.28 (m, 1 H), 1.60-1.70 (m, 1 H), 1.16-1.21 (m, 1 H), 0.72-0.77 (m, 2 H), 0.43-0.47 (m, 2 H); MS (ESI) m/z 532.2 (M+H), calcd for $C_{26}H_{31}ClN_3O_7$ 532.18.

S15-13-7

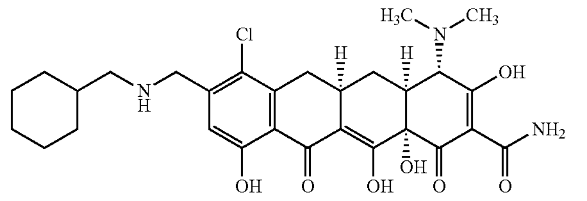

The crude product was purified by HPLC on a Waters Autopurification system using a Phenomenex Polymerx 10μ RP-γ 100 R column [30×21.20 mm, 10 micron; flow rate, 20 mL/min; Solvent A: 0.05 N HCl/water; Solvent B: MeOH; injection volume: 4.0 mL (0.05 N HCl/water); gradient: 0->100% B over 20 min; mass-directed fraction collection]. Fractions containing the desired product, eluting at 15.55-16.00 min, were collected and freeze-dried to give the desired product S15-13-7 as a yellow solid: $^1$H NMR (400 MHz, $CD_3OD$) δ 7.15 (s, 1 H), 4.37 (s, 2 H), 4.12 (s, 1 H), 3.40 (dd, J=4.6, 16.0 Hz, 1 H), 2.94-3.14 (m, 10 H), 2.40 (dd, J=15.0, 15.0 Hz, 1 H), 2.24-2.28 (m, 1 H), 1.60-1.88 (m, 7 H), 1.21-1.35 (m, 3 H), 1.01-1.09 (m, 2 H); MS (ESI) m/z 574.3 (M+H), calcd for $C_{29}H_{37}ClN_3O_7$ 574.22.

S15-13-8

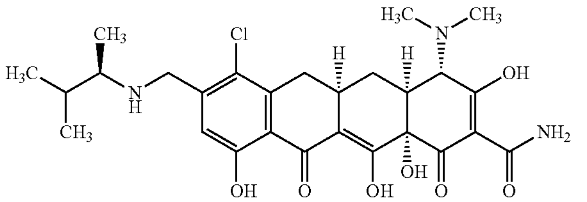

The crude product was purified by HPLC on a Waters Autopurification system using a Phenomenex Polymerx 10μ RP-γ 100 R column [30×21.20 mm, 10 micron; flow rate, 20 mL/min; Solvent A: 0.05 N HCl/water; Solvent B: MeOH; injection volume: 4.0 mL (0.05 N HCl/water); gradient: 0→100% B over 20 min; mass-directed fraction collection]. Fractions containing the desired product, eluting at 13.85-14.90 min, were collected and freeze-dried to give the desired product S15-13-8 as a yellow solid: $^1$H NMR (400 MHz, $CD_3OD$) δ 7.18 (s, 1 H), 4.40 (s, 2 H), 4.13 (s, 1 H), 3.41 (dd, J=4.6, 16.0 Hz, 1 H), 3.32-3.36 (m, 1 H), 2.94-3.11 (m, 8 H), 2.40 (dd, J=15.0, 15.0 Hz, 1 H), 2.20-228 (m, 2 H), 1.60-1.70 (m, 1 H), 1.34 (d, J=6.8 Hz, 3 H), 1.06 (d, J=6.8 Hz, 3 H), 1.01 (d, J=6.8 Hz, 3 H); MS (ESI) m/z 548.2 (M+H), calcd for $C_{27}H_{35}ClN_3O_7$ 548.21.

S15-13-9

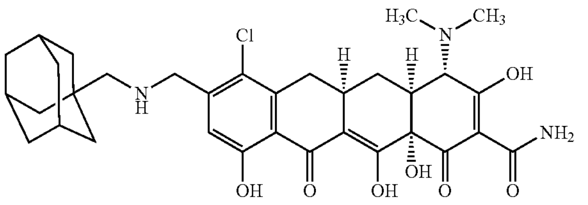

The crude product was purified by HPLC on a Waters Autopurification system using a Phenomenex Polymerx 10μ RP-γ 100 R column [30×21.20 mm, 10 micron; flow rate, 20 mL/min; Solvent A: 0.05 N HCl/water; Solvent B: MeOH; injection volume: 4.0 mL (0.05 N HCl/water); gradient: 20→100% B over 10 min; mass-directed fraction collection]. Fractions containing the desired product, eluting at 9.60-10.85 min, were collected and freeze-dried to give the desired product S15-13-9 as a yellow solid: $^1$H NMR (400 MHz, $CD_3OD$) δ 7.20 (s, 1 H), 4.41 (s, 2 H), 4.15 (s, 1 H), 3.40 (dd, J=4.6, 16.0 Hz, 1 H), 2.83-3.15 (m, 10 H), 2.39 (dd, J=15.0, 15.0 Hz, 1 H), 2.26-2.32 (m, 1 H), 2.03 (br. s, 3 H), 1.59-1.81 (m, 13 H); MS (ESI) m/z 626.3 (M+H), calcd for $C_{33}H_{41}ClN_3O_7$ 626.26.

S15-13-10

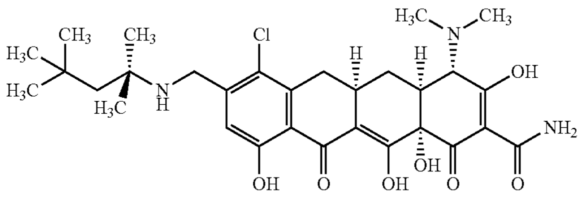

The crude product was purified by HPLC on a Waters Autopurification system using a Phenomenex Polymerx 10μ RP-γ 100 R column [30×21.20 mm, 10 micron; flow rate, 20 mL/min; Solvent A: 0.05 N HCl/water; Solvent B: MeOH; injection volume: 4.0 mL (0.05 N HCl/water); gradient: 10→100% B over 20 min; mass-directed fraction collection]. Fractions containing the desired product, eluting at 15.15-16.45 min, were collected and freeze-dried to give the desired product S15-13-10 as a yellow solid: $^1$H NMR (400 MHz, $CD_3OD$) δ 7.17 (s, 1 H), 4.34 (s, 2 H), 4.13 (s, 1 H), 3.41 (dd, J=4.6, 16.0 Hz, 1 H), 2.94-3.15 (m, 8 H), 2.40 (dd, J=15.0, 15.0 Hz, 1 H), 2.24-2.28 (m, 1 H), 1.83 (s, 2 H), 1.60-1.70 (m, 1 H), 1.58 (s, 6 H), 1.11 (s, 9 H); MS (ESI) m/z 590.3 (M+H), calcd for $C_{30}H_{41}ClN_3O_7$ 590.26.

S15-13-11

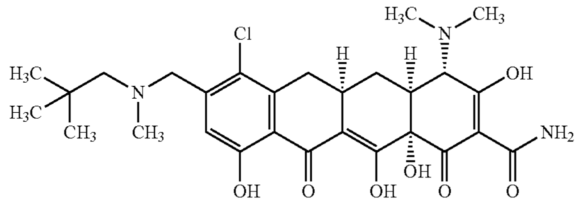

To a solution of compound S15-13-5 (12 mg, 0.022 mmol, 1.0 equiv) in DMF (0.5 mL) was added sequentially triethylamine (6 μL, 0.045 mmol, 2.0 equiv), HCHO (37 wt % in $H_2O$, 5 μL, 0.067 mmol, 3.0 equiv) and $InCl_3$ (0.5 mg, 0.0022 mmol, 0.1 equiv) at rt. After stirring for 5 min, $Na(OAc)_3BH$ (10 mg, 0.045 mmol, 2.0 equiv) was added. Stirring was continued for another hour. HCl/MeOH (0.20 mL, 0.5 N) was added. The resulting mixture was added dropwise to vigorously stirring diethyl ether (100 mL). The precipitate was collected onto a small Celite pad and washed three times with more diethyl ether. The Celite pad was then eluted several times with MeOH. The MeOH solution was collected and concentrated to provide the crude product, which was purified by HPLC on a Waters Autopurification system using a Phenomenex Polymerx 10μ RP-γ 100 R column [30×21.20 mm, 10 micron; flow rate, 20 mL/min; Solvent A: 0.05 N HCl/ water; Solvent B: MeOH; injection volume: 4.0 mL (0.05 N HCl/water); gradient: 0→100% B over 20 min; mass-directed fraction collection]. Fractions containing the desired product, eluting at 13.90-15.40 min, were collected and freeze-dried to give the desired product S15-13-11 as a yellow solid: $^1$H NMR (400 MHz, $CD_3OD$) δ 7.28 (s, 1 H), 4.71-4.78 (m, 1 H), 4.43-4.48 (m, 1 H), 4.13 (s, 1 H), 3.41 (dd, J=4.6, 16.0 Hz, 1 H), 2.94-3.15 (m, 13 H), 2.44 (dd, J=15.0, 15.0 Hz, 1 H), 2.24-2.28 (m, 1 H), 1.60-1.70 (m, 1 H), 1.09 (s, 9 H); MS (ESI) m/z 562.2 (M+H), calcd for $C_{28}H_{37}ClN_3O_7$ 562.22.

S15-13-12

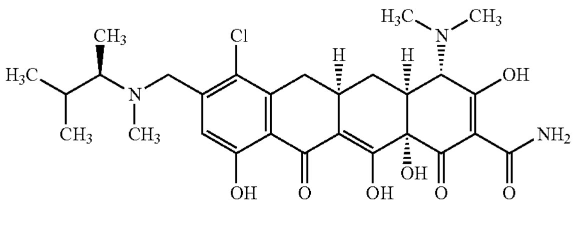

Compound S15-13-12 was prepared similarly from S15-13-8. The crude product was purified by HPLC on a Waters Autopurification system using a Phenomenex Polymerx 10μ RP-γ 100 R column [30×21.20 mm, 10 micron; flow rate, 20 mL/min; Solvent A: 0.05 N HCl/water; Solvent B: MeOH; injection volume: 4.0 mL (0.05 N HCl/water); gradient: 0→100% B over 20 min; mass-directed fraction collection]. Fractions containing the desired product, eluting at 14.15-15.25 min, were collected and freeze-dried to give the desired product S15-13-12 as a yellow solid: $^1$H NMR (400 MHz, $CD_3OD$) δ 7.22 (s, 1 H), 4.26-4.76 (m, 2 H), 4.12 (s, 1 H), 3.34-3.44 (m, 2 H), 2.82-3.11 (m, 11 H), 2.18-2.47 (m, 3 H), 1.60-1.70 (m, 1 H), 1.39-1.46 (m, 3 H), 1.03-1.08 (m, 6 H); MS (ESI) m/z 562.2 (M+H), calcd for $C_{28}H_{37}ClN_3O_7$ 562.22.

S15-13-13

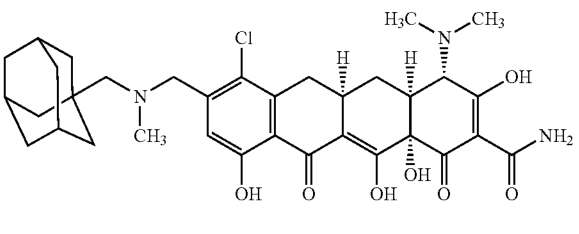

Compound S15-13-13 was prepared similarly from S15-13-9. The crude product was purified by HPLC on a Waters Autopurification system using a Phenomenex Polymerx 10μ RP-γ 100 R column [30×21.20 mm, 10 micron; flow rate, 20 mL/min; Solvent A: 0.05 N HCl/water; Solvent B: MeOH; injection volume: 4.0 mL (0.05 N HCl/water); gradient: 20→100% B over 20 min; mass-directed fraction collection]. Fractions containing the desired product, eluting at 17.00-18.85 min, were collected and freeze-dried to give the desired product S15-13-13 as a yellow solid: $^1$H NMR (400 MHz, $CD_3OD$) δ 7.26 (s, 1 H), 4.68-4.74 (m, 1 H), 4.43-4.47 (m, 1 H), 4.12 (s, 1 H), 3.42 (dd, J=4.6, 16.0 Hz, 1 H), 2.94-3.12 (m, 13 H), 2.45 (dd, J=15.0, 15.0 Hz, 1 H), 2.24-2.29 (m, 1 H), 2.02 (br. s, 3 H), 1.57-1.81 (m, 13 H); MS (ESI) m/z 640.2 (M+H), calcd for $C_{34}H_{43}ClN_3O_7$ 640.27.

S15-13-14

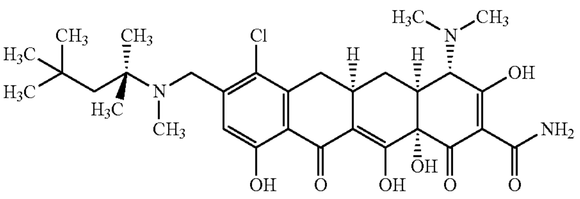

Compound S15-13-14 was prepared similarly from S15-13-10. The crude product was purified by HPLC on a Waters Autopurification system using a Phenomenex Polymerx 10μ RP-γ 100 R column [30×21.20 mm, 10 micron; flow rate, 20 mL/min; Solvent A: 0.05 N HCl/water; Solvent B: MeOH; injection volume: 4.0 mL (0.05 N HCl/water); gradient: 10→100% B over 20 min; mass-directed fraction collection]. Fractions containing the desired product, eluting at 16.35-17.65 min, were collected and freeze-dried to give the desired product S15-13-14 as a yellow solid: $^1$H NMR (400 MHz, $CD_3OD$) δ 7.17 (s, 1 H), 4.12-4.18 (m, 1 H), 4.11 (s, 1 H), 3.40-3.50 (m, 2 H), 2.94-3.15 (m, 8 H), 2.75 (s, 3 H), 2.39-2.48 (m, 1 H), 2.24-2.28 (m, 1 H), 1.83-2.00 (m, 2 H), 1.73 (s, 3 H), 1.60-1.70 (m, 1 H), 1.63 (s, 3 H), 1.14 (s, 9 H); MS (ESI) m/z 604.3 (M+H), calcd for $C_{31}H_{43}ClN_3O_7$ 604.27.

S15-15-1

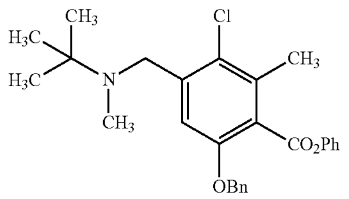

To a solution of compound S15-8 (0.39 g, 1.02 mmol, 1.0 equiv) in 1,2-dichloroethane (10 mL) was added t-butylamine (0.13 mL, 1.22 mmol, 1.2 equiv) and acetic acid (0.18 mL, 3.05 mmol, 3.0 equiv). After stirring at rt for 2.5 hrs, sodium triacetoxyborohydride (0.43 g, 2.03 mmol, 2.0 equiv) was added. Stirring was continued overnight. The reaction mixture was poured into saturated aqueous $NaHCO_3$ and extracted three times with dichloromethane. The combined organic extracts were washed with brine, dried over sodium sulfate, and concentrated to give the crude intermediate as an off-white oil. The crude intermediate was redissolved in 1,2-dichloroethane (10 mL). Formaldehyde (37 wt % in $H_2O$, 0.76 mL, 10.20 mmol, 10 equiv) and acetic acid (0.18 mL, 3.05 mmol, 3.0 equiv) were added After stirring at rt for 1 h, sodium triacetoxyborohydride (0.43 g, 2.03 mmol, 2.0 equiv) was added. Stirring was continued for another hour. The reaction mixture was poured into saturated aqueous $NaHCO_3$ and extracted three times with dichloromethane. The combined organic extracts were washed with brine, dried over sodium sulfate, and concentrated. Purification of the residue by flash chromatography gave compound S15-15-1 (0.35 g) as a white solid: $^1$H NMR (400 MHz, $CDCl_3$) δ 7.43 (d, J=7.8 Hz, 2 H), 7.20-7.40 (m, 7 H), 7.12 (d, J=7.8 Hz, 2 H), 5.18 (s, 2 H), 3.59 (s, 2 H), 2.44 (s, 3 H), 2.09 (s, 3 H), 1.10 (s, 9 H); MS (ESI) m/z 452.3 (M+H), calcd for $C_{27}H_{31}ClNO_3$ 452.19.

S15-12-1

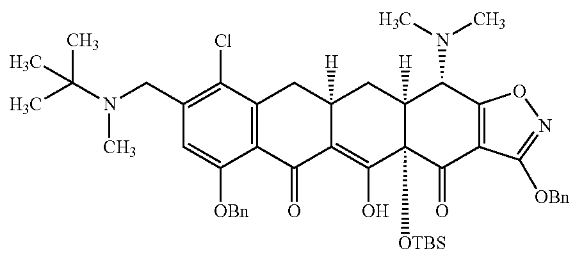

Compound S15-12-1 was prepared by the procedure of S15-10 employing compound S15-15-1: $^1$H NMR (400 MHz, $CDCl_3$) δ 16.0 (s, 1 H), 7.22-7.52 (m, 11 H), 5.36 (s, 2 H), 5.27 (s, 2 H), 3.97 (d, J=10.4 Hz, 1 H), 3.55 (s, 2 H), 3.42 (dd, J=4.9, 15.9 Hz, 1 H), 2.93-3.04 (m, 1 H), 2.43-2.53 (m, 9 H), 2.13 (d, J=14.6 Hz, 1 H), 2.01 (s, 3 H), 1.07 (s, 9 H), 0.84 (s, 9 H), 0.28 (s, 3 H), 0.13 (s, 3 H); MS (ESI) m/z 840.4 (M+H), calcd for $C_{47}H_{59}ClN_3O_7Si$ 840.37.

S15-13-15

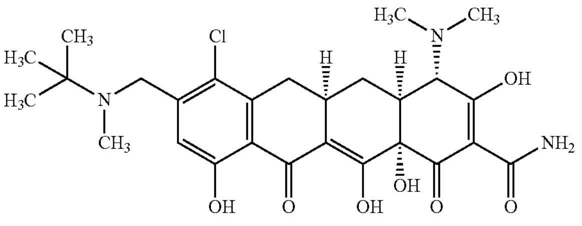

In a plastic vial, compound S15-12-1 (85 mg, 0.10 mmol) was dissolved in $CH_3CN$ (2 mL). Aqueous HF (48-50%, 0.5 mL) was added. After stirring at rt for 7 hrs, the reaction mixture was poured into an aqueous solution (25 mL) of $K_2HPO_4$ (3.5 g). The resulting mixture was extracted three times with dichloromethane. The combined organic phases were washed with brine, dried, and concentrated under reduced pressure to yield the crude desilylated product.

The above crude intermediate was dissolved in EtOAc (6 mL). Pd—C (10 wt %, 22 mg) was added. The reaction flask was briefly evacuated and re-filled with hydrogen. The reaction mixture was stirred at rt and monitored by LC-MS. After the reaction was complete, MeOH (5 mL) and 0.5 N HCl/MeOH (0.5 mL) were added. The mixture was stirred for 30 min and filtered through a small pad of Celite. The filtrate was concentrated to give the crude product, which was purified by HPLC on a Waters Autopurification system using a Phenomenex Polymerx 10μ RP-γ 100 R column [30×21.20 mm, 10 micron; flow rate, 20 mL/min; Solvent A: 0.05 N HCl/water; Solvent B: MeOH; injection volume: 4.0 mL (0.05 N HCl/water); gradient: 20→100% B over 10 min; mass-directed fraction collection]. Fractions containing the desired product, eluting at 6.30-8.85 min, were collected and freeze-dried to give the desired product S15-13-15 as a yellow solid: $^1$H NMR (400 MHz, $CD_3OD$) δ 7.20 (s, 1 H), 4.80-4.87 (m, 1 H), 4.12-4.20 (m, 1 H), 4.12 (s, 1 H), 3.38-3.40 (m, 1 H), 2.96-3.11 (m, 8 H), 2.75 (s, 3 H), 2.38-2.40 (m, 1 H), 2.24-2.28 (m, 1 H), 1.60-1.70 (m, 1 H), 1.57 (s, 9 H); MS (ESI) m/z 548.2 (M+H), calcd for $C_{27}H_{35}ClN_3O_7$ 548.21.

S15-14-1

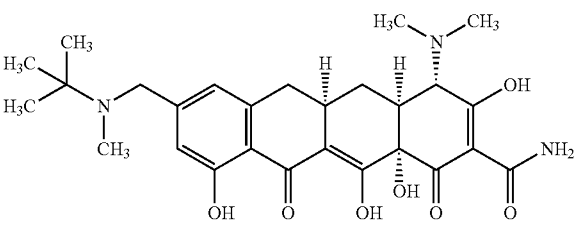

S15-14-2

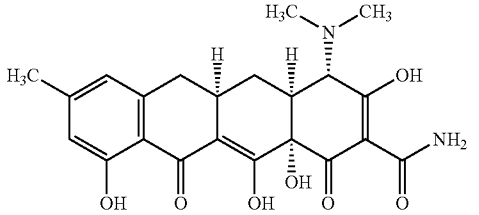

Alternatively, the crude desilylated product of S15-12-1 (13 mg) was dissolved in 0.5 N HCl/MeOH (0.07 mL). The volatiles were evaporated. The residue was redissolved in MeOH (2 mL) and added with Pd—C (10 wt %, 7 mg). The reaction flask was briefly evacuated and re-filled with hydrogen. The reaction mixture was stirred at rt and monitored by LC-MS. After all the reaction was complete, the reaction mixture was filtered through a small pad of Celite. The filtrate was concentrated to yield the crude product, which was purified by HPLC on a Waters Autopurification system using a Phenomenex Polymerx 10μ RP-γ 100 R column [30×21.20 mm, 10 micron; flow rate, 20 mL/min; Solvent A: 0.05 N HCl/water; Solvent B: $CH_3CN$; injection volume: 4.0 mL (0.05 N HCl/water); gradient: 10→50% B over 15 min; mass-directed fraction collection]. Fractions containing the desired product, eluting at 6.08-8.75 min, were collected and freeze-dried to give the following two products.

S15-14-1, a yellow solid: $^1$H NMR (400 MHz, $CD_3OD$) δ 7.01 (s, 1 H), 6.93 (s, 1 H), 4.65 (d, J=12.8 Hz, 1 H), 4.08 (s, 1 H), 3.90 (d, J=12.8 Hz, 1 H), 2.96-3.11 (m, 9 H), 2.70 (s, 3 H), 2.58-2.68 (m, 1 H), 2.19-2.22 (m, 1 H), 1.60-1.70 (m, 1 H), 1.53 (s, 9 H); MS (ESI) m/z 514.3 (M+H), calcd for $C_{27}H_{36}N_3O_7$ 514.25.

S15-14-2, a yellow solid: $^1$H NMR (400 MHz, $CD_3OD$) δ 6.62 (s, 1 H), 6.59 (s, 1 H), 4.06 (s, 1 H), 2.77-3.11 (m, 9 H), 2.51 (dd, J=14.2, 14.2 Hz, 1 H), 2.30 (s, 3 H), 2.14-2.17 (m, 1 H), 1.52-1.62 (m, 1 H); MS (ESI) m/z 429.3 (M+H), calcd for $C_{22}H_{25}N_2O_7$ 429.16.

The following compounds were prepared using similar procedures to that of S15-13-1, S15-13-11, S15-13-15 or S15-14-1.

S15-13-16

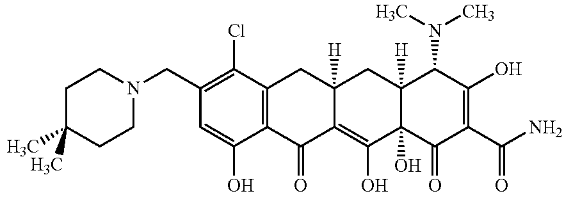

S15-13-16, a yellow solid: $^1$H NMR (400 MHz, $CD_3OD$) δ 7.26 (s, 1 H), 4.53 (s, 2 H), 4.13 (s, 1 H), 3.30-3.45 (m, 5 H), 2.96-3.15 (m, 8 H), 2.40 (dd, J=15.9, 15.9 Hz, 1 H), 2.25-2.29 (m, 1 H), 1.61-1.79 (m, 5 H), 1.09 (s, 3 H), 1.03 (s, 3 H); MS (ESI) m/z 574.3 (M+H), calcd for $C_{29}H_{37}ClN_3O_7$ 574.22.

S15-14-3

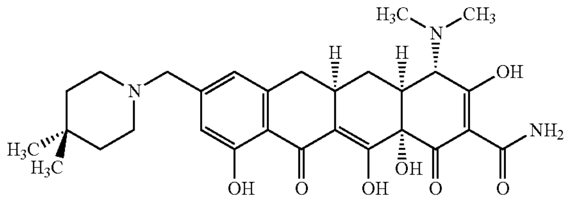

S15-14-3, a yellow solid: $^1$H NMR (400 MHz, $CD_3OD$) δ 7.00 (s, 1 H), 6.95 (s, 1 H), 4.28 (s, 2 H), 4.09 (s, 1 H), 2.96-3.15 (m, 13 H), 2.61 (dd, J=15.9, 15.9 Hz, 1 H), 2.18-2.22 (m, 1 H), 1.59-1.75 (m, 5 H), 1.09 (s, 3 H), 1.04 (s, 3 H); MS (ESI) m/z 540.3 (M+H), calcd for $C_{29}H_{38}N_3O_7$ 540.26.

S15-14-4

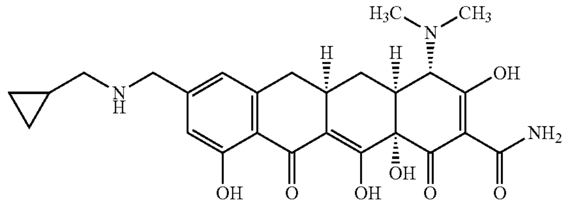

S15-14-4, a yellow solid: $^1$H NMR (400 MHz, $CD_3OD$) δ 6.97 (s, 1 H), 6.90 (s, 1 H), 4.18 (s, 2 H), 4.09 (s, 1 H), 2.94-3.14 (m, 11 H), 2.60 (dd; J=15.0, 15.0 Hz, 1 H), 2.19-2.22 (m, 1 H), 1.59-1.65 (m, 1 H), 1.10-1.15 (m, 1 H), 0.71-0.74 (m, 2 H), 0.40-0.43 (m, 2 H); MS (ESI) m/z 497.2 (M+H), calcd for $C_{26}H_{32}N_3O_7$ 497.22.

S15-13-17

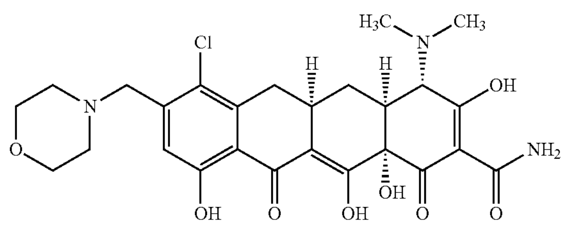

$^1$H NMR (400 MHz, $CD_3OD$) δ 7.31 (s, 1 H), 4.56 (dd, J=19.2 Hz, 13.6 Hz, 2 H), 4.15 (s, 1 H), 4.08-3.98 (m, 2 H), 3.90-3.79 (m, 2 H), 3.53-3.33 (m, 5 H), 3.20-2.90 (m, 8 H), 2.45-2.36 (m, 1 H), 2.32-2.25 (m, 1 H), 1.71-160 (m, 1 H); MS (ESI) m/z 548.1 (M+H).

S15-13-18

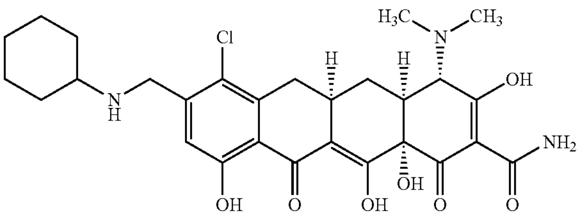

$^1$H NMR (400 MHz, $CD_3OD$) δ 7.16 (s, 1 H), 4.40 (s, 2 H), 4.14 (s, 1 H), 3.50-136 (m, 1 H), 3.32-3.21 (m, 1 H), 3.18-2.90 (m, 8 H), 2.48-2.36 (m, 1 H), 2.31-2.20 (m, 3 H), 1.98-1.88 (m, 2 H), 1.80-1.60 (m, 2 H), 1.50-1.35 (m, 4 H), 1.34-1.20 (m, 1 H); MS (ESI) m/z 560.1 (M+H).

S15-13-19

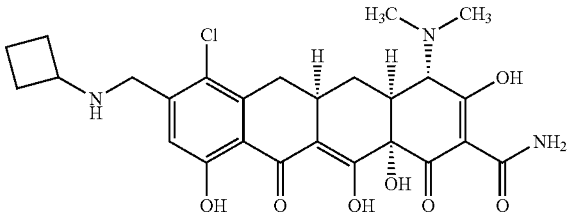

$^1$H NMR (400 MHz, $CD_3OD$) δ 7.13 (s, 1 H), 4.26 (s, 2 H), 4.13 (s, 1 H), 3.95-3.86 (m, 1 H), 3.45-3.37 (m, 1 H), 3.18-2.95 (m, 8 H), 2.45-2.33 (m, 3 H), 2.32-2.20 (m, 3 H), 2.02-1.90 (m, 2 H), 1.72-1.60 (m, 1 H); MS (ESI) m/z 532.1 (M+H).

S15-13-20

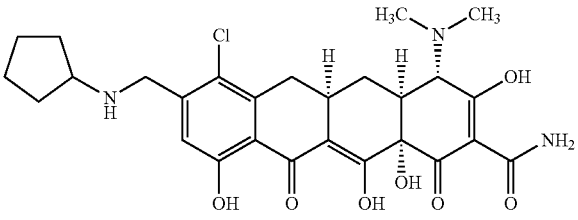

$^1$H NMR (400 MHz, $CD_3OD$) δ 7.16 (s, 1 H), 4.38 (s, 2 H), 4.13 (s, 1 H), 3.79-3.65 (m, 1 H), 3.45-3.38 (m, 1 H), 3.17-2.95 (m, 8 H), 2.48-2.38 (m, 1 H), 2.30-2.15 (m, 3 H), 1.91-1.78 (m, 2 H), 1.80-1.67 (m, 5 H); MS (ESI) m/z 546.1 (M+H).

S15-13-21

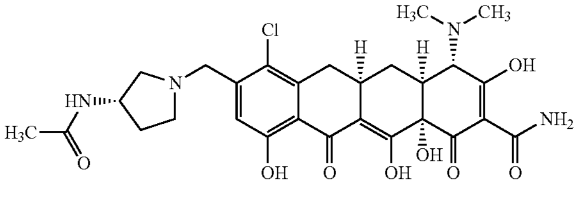

$^1$H NMR (400 MHz, $CD_3OD$) δ 7.24 (s, 1 H), 4.72-4.56 (m, 2 H), 4.50-4.32 (m, 1 H), 4.14 (s, 1 H), 3.97-3.78 (m, 1 H), 3.75-3.50 (m, 2 H), 3.46-3.38 (m, 1 H), 3.20-2.90 (m, 9 H), 2.70-2.52 (m, 1 H), 2.50-2.38 (m, 1 H), 2.32-2.24 (m, 1 H), 2.20-2.05 (m, 1 H), 1.97 (s, 3 H), 1.73-1.61 (m, 1 H); MS (ESI) m/z 589.0 (M+H).

S15-13-22

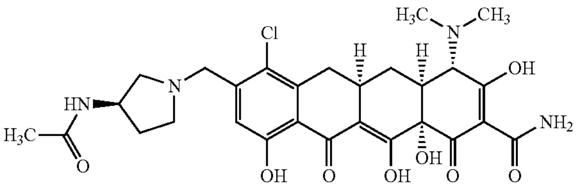

$^1$H NMR (400 MHz, $CD_3OD$) δ 7.24 (s, 1 H), 4.72-4.56 (m, 2 H), 4.48-4.33 (m, 1 H), 4.14 (s, 1 H), 3.98-3.79 (m, 1 H), 3.75-3.50 (m, 2 H), 3.45-3.38 (m, 1 H), 3.18-2.90 (m, 9 H), 2.70-2.51 (m, 1 H), 2.50-2.38 (m, 1 H), 2.32-2.24 (m, 1 H), 2.20-2.05 (m, 1 H), 1.97 (s, 3 H), 1.73-1.61 (m, 1 H); MS (ESI) m/z 589.0 (M+H).

S15-13-23

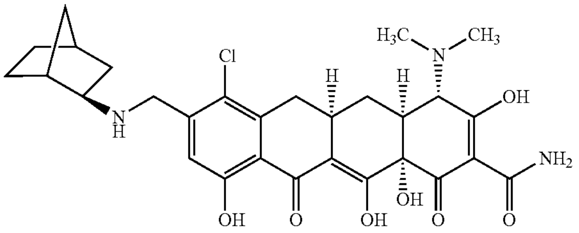

$^1$H NMR (400 MHz, $CD_3OD$) δ 7.20 (s, 1 H), 4.42-4.32 (m, 2 H), 4.16 (s, 1 H), 3.71-3.60 (m, 1 H), 3.46-3.41 (m, 1 H), 3.20-2.95 (m, 8 H), 2.71 (br s, 1 H), 2.46-2.25 (m, 4 H), 2.20-2.18 (m, 1 H), 1.75-1.52 (m, 4 H), 1.60-1.50 (m, 2 H), 1.50-1.41 (m, 1 H), 1.24-1.16 (m, 1 H); MS (ESI) m/z 572.2 (M+H).

S15-13-24

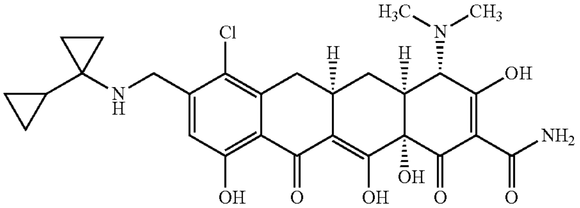

$^1$H NMR (400 MHz, $CD_3OD$) δ 7.19 (s, 1 H), 4.64 (s, 2 H), 4.14 (s, 1 H), 3.48-3.39 (m, 1 H), 3.10-2.95 (m, 8 H), 2.48-2.38 (m, 1 H), 2.32-2.25 (m, 1 H), 1.68-1.59 (m, 1 H), 1.50-1.39 (m, 1 H), 1.05-0.97 (m, 2 H), 0.88-0.82 (m, 2 H), 0.78-0.73 (m, 2 H), 0.45-0.38 (m, 2 H); MS (ESI) m/z 558.1 (M+H).

S15-13-25

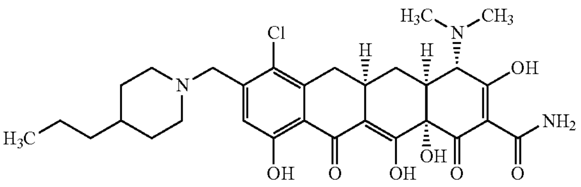

$^1$H NMR (400 MHz, $CD_3OD$) δ 7.27 (s, 1 H), 4.51 (s, 2 H), 4.15 (s, 1 H), 3.62-3.53 (m, 2 H), 3.47-3.38 (m, 1 H), 3.24-2.90 (m, 10 H), 2.49-2.37 (m, 1 H), 2.32-2.25 (m, 1 H), 2.02-1.93 (m, 2 H), 1.70-1.58 (m, 2 H), 1.57-1.24 (m, 6 H), 1.00-0.89 (m, 3 H); MS (ESI) m/z 588.2 (M+H).

S15-13-26

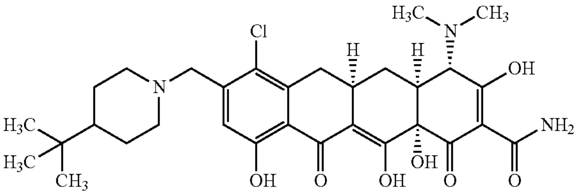

$^1$H NMR (400 MHz, $CD_3OD$) δ 7.25 (s, 1 H), 4.49 (s, 2 H), 4.13 (s, 1 H), 3.65-3.58 (m, 2 H), 3.49-3.38 (m, 1 H), 3.20-2.95 (m, 10 H), 2.49-2.38 (m, 1 H), 2.31-2.24 (m, 1 H), 2.02-1.93 (m, 2 H), 1.71-1.55 (m, 3 H), 1.48-1.38 (m, 1 H), 0.91 (s, 9 H); MS (ESI) m/z 602.2 (M+H).

S15-13-27

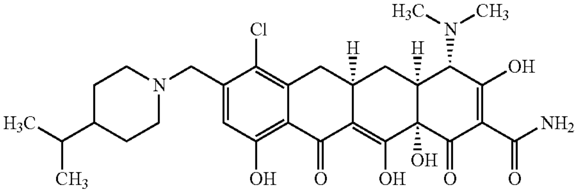

$^1$H NMR (400 MHz, $CD_3OD$) δ 7.27 (s, 1 H), 4.51 (s, 2 H), 4.15 (s, 1 H), 3.65-3.56 (m, 2 H), 3.48-3.38 (m, 1 H), 3.23-2.95 (m, 10 H), 2.48-3.38 (m, 1 H), 2.32-2.26 (m, 1 H), 2.02-1.93 (m, 2 H), 1.72-1.38 (m, 5 H), 0.95 (d, J=6.4 Hz, 6 H); MS (ESI) m/z 588.3 (M+H).

S15-13-28

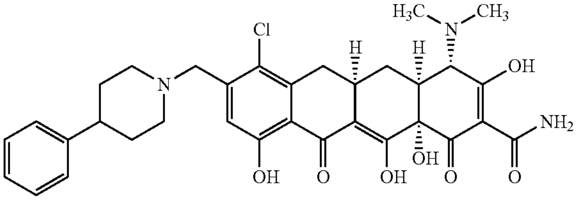

$^1$H NMR (400 MHz, $CD_3OD$) δ 7.47-7.20 (m, 6 H), 4.58 (s, 2 H), 4.14 (s, 1 H), 3.75-3.65 (m, 1 H), 3.57-3.35 (m, 2 H), 3.20-2.85 (m, 9 H), 2.61-2.40 (m, 2 H), 2.31-2.19 (m, 1 H), 2.18-2.00 (m, 4 H), 1.73-1.60 (m, 1 H); MS (ESI) m/z 622.0 (M+H).

S15-13-29

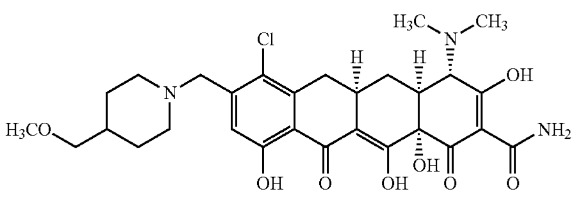

$^1$H NMR (400 MHz, $CD_3OD$) δ 7.26 (s, 1 H), 4.51 (s, 2 H), 4.14 (s, 1 H), 3.64-3.57 (m, 2 H), 3.46-3.37 (m, 1 H), 3.32 (s, 3 H), 3.30-2.25 (m, 2 H), 3.25-2.95 (m, 10 H), 2.48-2.38 (m, 1 H), 2.31-2.24 (m, 1 H), 2.02-1.98 (m, 3 H), 1.71-1.52 (m, 3 H); MS (ESI) m/z 590.0 (M+H).

S15-13-232

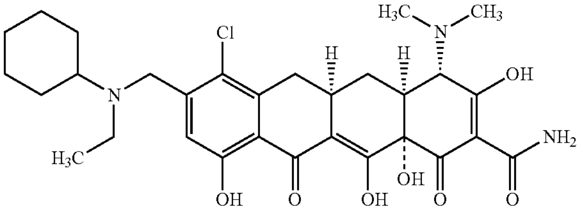

MS (ESI) m/z 588.1.4 (M+H), calcd for $C_{30}H_{39}ClN_3O_9$ 588.24.

S15-13-31

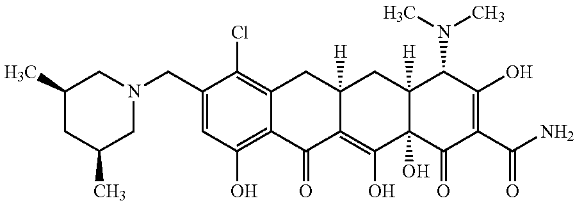

$^1$H NMR (400 MHz, $CD_3OD$) δ 7.30 (s, 1 H), 4.53 (dd, J=18.4 Hz, 13.6 Hz, 2 H), 4.15 (s, 1 H), 3.48-3.38 (m, 3 H), 3.20-2.95 (m, 8 H), 2.80-2.70 (m, 2 H), 2.48-2.38 (m, 1 H), 2.34-2.26 (m, 1 H), 2.10-1.95 (m, 2 H), 1.91-1.82 (m, 1 H), 1.72-1.61 (m, 1 H), 1.00 (d, J=6.4 Hz, 6 H); MS (ESI) m/z 574.5 (M+H).

S15-13-32

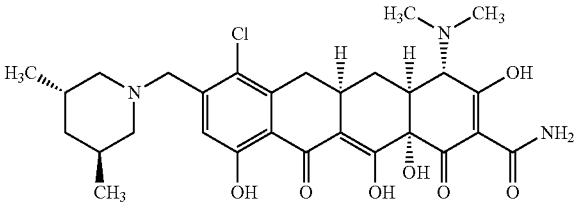

$^1$H NMR (400 MHz, $CD_3OD$) δ 7.32 (s, 1 H), 4.60-4.32 (m, 2 H), 4.15 (s, 1 H), 3.50-3.38 (m, 2 H), 3.20-2.94 (m, 9 H), 2.83-2.70 (m, 1 H), 2.48-2.38 (m, 1 H), 2.35-2.10 (m, 3 H), 2.08-1.95 (m, 1 H), 1.72-1.53 (m, 2 H), 1.50-1.40 (m, 1 H), 1.19 (d, J=6.8 Hz, 3 H), 0.99 (d, J=6.8 Hz, 3 H); MS (ESI) m/z 574.3 (M+H).

S15-13-33

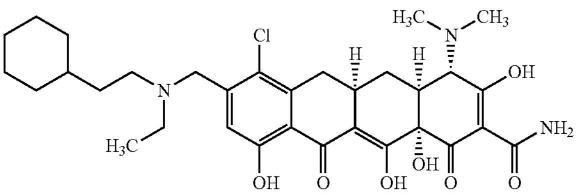

$^1$H NMR (400 MHz, $CD_3OD$) δ 7.22 (s, 1 H), 4.56-4.48 (m, 2 H), 4.13 (s, 1 H), 2.43-3.39 (m, 1 H), 3.20-2.95 (m, 12 H), 2.45-2.38 (m, 1 H), 2.29-2.26 (m, 1 H), 1.80-1.59 (m, 8 H), 1.42-1.12 (m, 7 H), 1.08-0.93 (m, 2 H); MS (ESI) m/z 616.1 (M+H).

S15-13-34

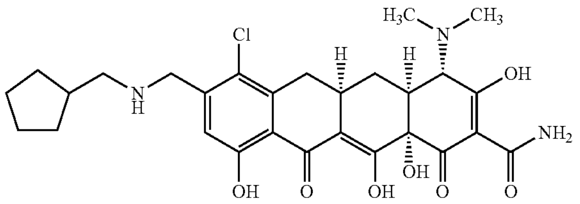

$^1$H NMR (400 MHz, $CD_3OD$) δ 7.06 (s, 1 H), 4.30 (s, 2 H), 4.02 (s, 1 H), 3.35-3.28 (m, 1 H), 3.08-2.85 (m, 10 H), 2.38-2.28 (m, 1 H), 2.21-2.10 (m, 2 H), 1.90-1.78 (m, 2 H), 1.68-1.49 (m, 5 H), 1.28-1.12 (m, 2 H); MS (ESI) m/z 560.3 (M+H).

S15-13-35

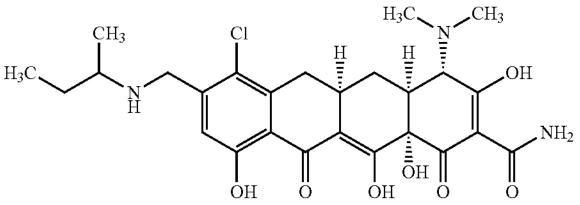

$^1$H NMR (400 MHz, $CD_3OD$) δ 7.17 (s, 1 H), 4.38 (s, 2 H), 4.13 (s, 1 H), 3.44-3.30 (m, 2 H), 3.18-2.88 (m, 8 H), 2.45-2.35 (m, 1 H), 2.31-2.24 (m, 1 H), 2.03-1.90 (m, 1 H), 1.70-1.58 (m, 2 H), 1.43 (d, J=7.0 Hz, 3 H), 1.05 (t, J=7.2 Hz, 3 H); MS (ESI) m/z 534.0 (M+H).

S15-13-36

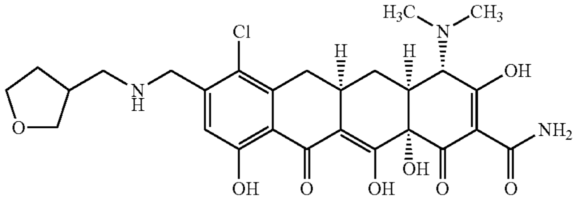

$^1$H NMR (400 MHz, $CD_3OD$) δ 7.16 (s, 1 H), 4.40 (s, 2 H), 4.11 (s, 1 H), 3.92-3.86 (m, 2 H), 3.80-3.70 (m, 1 H), 3.57-3.54 (m, 1 H), 3.42-3.34 (m, 1 H), 3.22-3.19 (m, 1 H), 3.15-2.85 (m, 8 H), 2.72-2.60 (m, 1 H), 2.43-2.35 (m, 2.28-2.13 (m, 2 H), 1.76-1.58 (m, 2 H); MS (ESI) m/z 562.1 (M+H).

S15-13-37

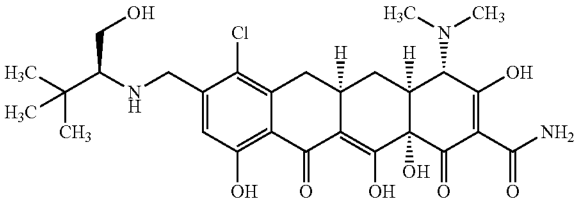

$^1$H NMR (400 MHz, $CD_3OD$) δ 7.20 (s, 1 H), 4.57 (s, 2 H), 4.10 (s, 1 H), 3.97 (dd, J=12.0 Hz and 8.0 Hz, 1 H), 3.86 (dd, J=12.0 Hz and 7.6 Hz, 1 H), 3.41 (dd, J=16.4 Hz and 4.8 Hz, 1 H), 3.13-2.94 (m, 9 H), 2.44-2.37 (m, 1 H), 2.28-2.20 (m, 1 H), 1.69-1.59 (m, 1 H), 1.08 (s, 9 H); MS (ESI) m/z 578.1 (M+H).

S15-13-38

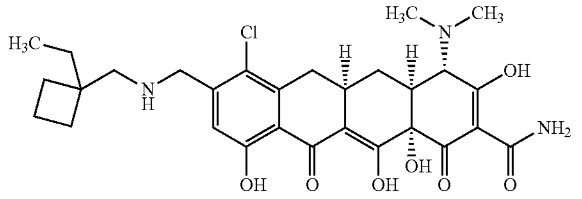

$^1$H NMR (400 MHz, $CD_3OD$) δ 7.21 (s, 1 H), 4.44 (s, 2 H), 4.14 (s, 1 H), 3.42 (dd, J=12.0 Hz and 4.8 Hz, 1 H), 3.22-2.87 (m, 10 H), 2.48-2.38 (m, 1 H), 2.31-2.25 (m, 1 H), 2.00-1.80 (m, 6 H), 1.70-1.58 (m, 3 H), 0.89 (t, J=7.6 Hz, 3 H); MS (ESI) m/z 574.2 (M+H).

S15-13-39

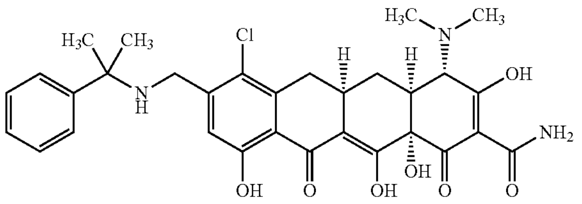

$^1$H NMR (400 MHz, $CD_3OD$) δ 7.75-7.65 (m, 2 H), 7.60-7.48 (m, 3 H), 6.97 (s, 1 H), 4.12 (s, 1 H), 4.00 (s, 2 H), 3.37-3.32 (m, 1 H), 3.10-2.95 (m, 8 H), 2.41-2.32 (m, 1 H), 2.30-2.20 (m, 1 H), 1.89 (s, 6 H), 1.70-1.59 (m, 1 H); MS (ESI) m/z 596.3 (M+H).

S15-13-40

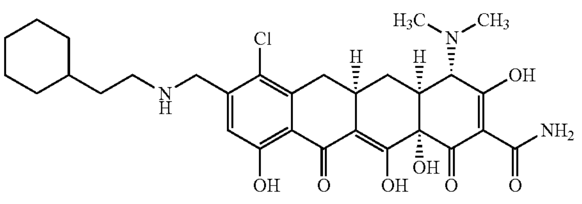

$^1$H NMR (400 MHz, $CD_3OD$) δ 7.15 (s, 1 H), 4.38 (s, 2 H), 4.14 (s, 1 H), 3.42 (dd, J=16.0 Hz and 4.4 Hz, 1 H), 3.23-2.96 (m, 10 H), 2.47-2.38 (m, 1 H), 2.32-2.25 (m, 1 H), 1.81-1.60 (m, 8 H), 1.45-1.17 (m, 4 H), 1.08-0.96 (m, 2 H); MS (ESI) m/z 588.2 (M+H).

S15-13-41

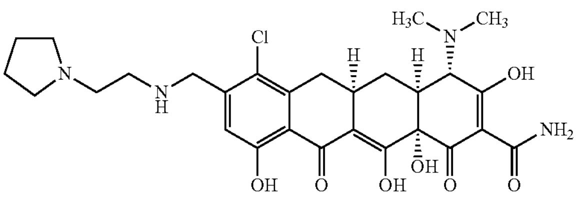

$^1$H NMR (400 MHz, $CD_3OD$) δ 7.25 (s, 1 H), 4.50 (s, 2 H), 4.14 (s, 1 H), 3.90-3.65 (m, 6 H), 3.43 (dd, J=16.0 Hz and 4.4 Hz, 1 H), 3.20-2.90 (m, 10 H), 2.46-2.35 (m, 1 H), 2.31-2.22 (m, 1 H), 2.20-2.00 (m, 4 H), 1.71-1.60 (m, 1 H); MS (ESI) m/z 575.3 (M+H).

S15-13-42

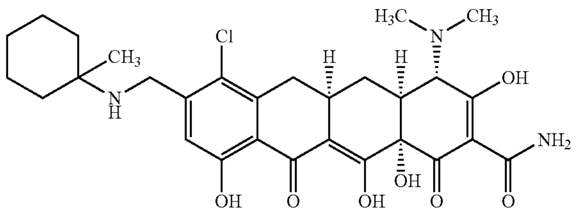

$^1$H NMR (400 MHz, $CD_3OD$) δ 7.17 (s, 1 H), 4.35 (s, 2 H), 4.11 (s, 1 H), 3.41 (dd, J=16.0 Hz and 4.4 Hz, 1 H), 3.15-2.95 (m, 8 H), 2.46-2.38 (m, 1 H), 2.28-2.22 (m, 1 H), 2.00-1.93 (m, 2 H), 1.83-1.62 (m, 6 H), 1.61-1.49 (m, 6 H); MS (ESI) m/z 574.0 (M+H).

S15-13-43

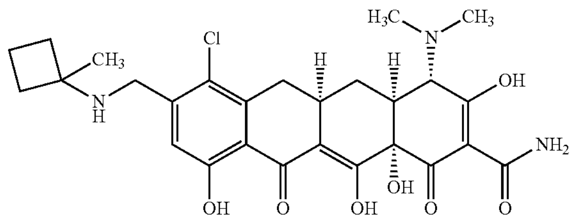

$^1$H NMR (400 MHz, $CD_3OD$) δ 7.16 (s, 1 H), 4.22 (s, 2 H), 4.14 (s, 1 H), 3.41 (dd, J=16.4 Hz and 4.4 Hz, 1 H), 3.18-2.32 (m, 8 H), 2.55-2.35 (m, 3 H), 2.31-2.22 (m, 1 H), 2.18-2.08 (m, 2 H), 2.05-1.93 (m, 2 H), 1.66 (s, 3 H); MS (ESI) m/z 546.0 (M+H).

S15-13-44

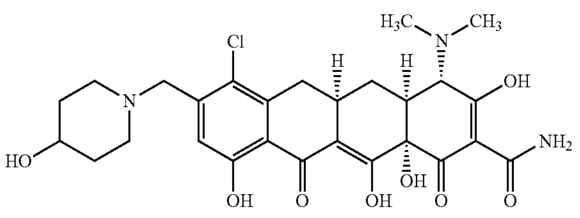

$^1$H NMR (400 MHz, $CD_3OD$) δ 7.27 (s, 1 H), 4.55-4.47 (m, 2 H), 4.13 (s, 1 H), 3.86 (m, 1 H), 3.61-3.52 (m, 1 H), 3.50-3.35 (m, 3 H), 3.30-2.94 (m, 9 H), 2.45-2.35 (m, 1 H), 2.31-2.22 (m, 1 H), 2.18-1.98 (m, 2 H), 1.95-1.87 (m, 1 H), 1.85-1.70 (m, 1 H), 1.70-1.56 (m, 1 H); MS (ESI) m/z 562.1 (M+H).

S15-13-45

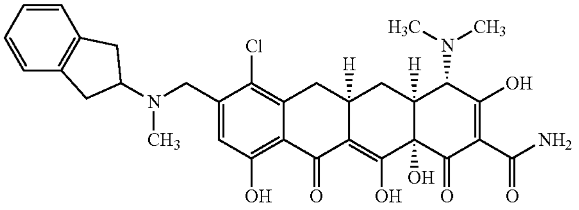

$^1$H NMR (400 MHz, $CD_3OD$) δ 7.32-7.23 (m, 5 H), 2.48-2.38 (m, 2 H), 4.13 (s, 1 H), 3.65-3.38 (m, 6 H), 3.20-2.95 (m, 8 H), 2.84 (s, 3 H), 2.50-2.38 (m, 1 H), 2.32-2.25 (m, 1 H), 1.72-1.60 (m, 1 H); MS (ESI) m/z 608.0 (M+H).

S15-13-46

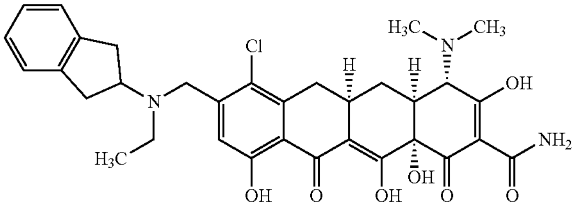

$^1$H NMR (400 MHz, $CD_3OD$) δ 7.20-7.35 (m, 5 H), 4.65-4.40 (m, 3 H), 4.14 (s, 1 H), 3.60-3.38 (m, 6 H), 3.20-2.95 (m, 9 H), 2.50-2.39 (m, 1 H), 2.33-2.26 (m, 1 H), 1.73-1.61 (m, 1 H), 1.43 (t, J=7.6 Hz, 3 H); MS (ESI) m/z 622.1 (M+H).

S15-13-47

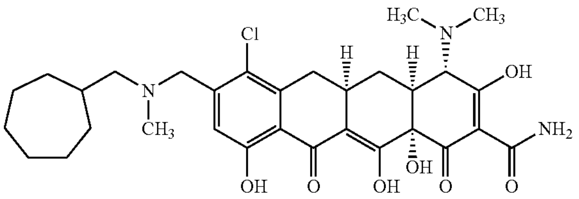

$^1$H NMR (400 MHz, $CD_3OD$) δ 7.25 (s, 1 H), 4.74 (t, J=13.6 Hz, 1 H), 4.32 (t, J=11.6 Hz, 1 H), 4.16 (s, 1 H), 3.43 (dd, J=16.0 Hz and 3.6 Hz, 1 H), 3.26-2.85 (m, 13 H), 2.47-2.40 (m, 1 H), 2.32-2.90 (m, 1 H), 2.20-2.08 (m, 1 H), 1.95-1.50 (m, 11 H), 1.40-1.25 (m, 2 H); MS (ESI) m/z 602.0 (M+H).

S15-13-48

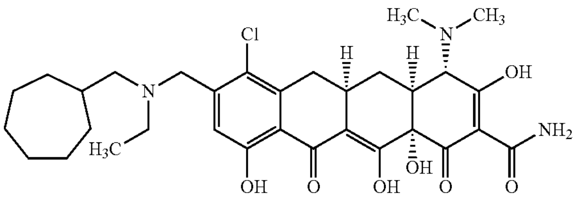

$^1$H NMR (400 MHz, $CD_3OD$) δ 7.26 (s, 1 H), 4.64 (t, J=13.6 Hz, 1 H), 4.49 (t, J=11.6 Hz, 1 H), 4.15 (s, 1 H), 3.44 (dd, J=16.0 Hz and 3.6 Hz, 1 H), 3.22-2.98 (m, 12 H), 2.50-2.40 (m, 1 H), 2.34-2.26 (m, 1 H), 2.10-2.00 (m, 1 H), 1.91-1.80 (m, 1 H), 1.80-1.50 (m, 9 H), 1.44 (t, J=7.6 Hz, 3 H), 1.40-1.23 (m, 3 H); MS (ESI) m/z 616.1 (M+H).

S15-13-49

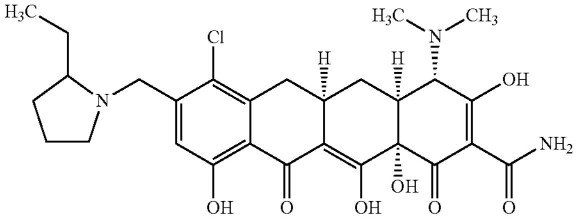

$^1$H NMR (400 MHz, $CD_3OD$) δ 7.24 (s, 1 H), 4.79 (d, J=13.6 Hz, 1 H), 4.35 (d, J=13.2 Hz, 1 H), 4.13 (s, 1 H), 3.60-3.37 (m, 4 H), 3.16-2.94 (m, 8 H), 2.48-2.34 (m, 2 H), 2.30-2.22 (m, 1 H), 2.20-2.08 (m, 2 H), 2.08-1.98 (m, 1 H), 1.85-1.71 (m, 1 H), 1.70-1.57 (m, 2 H), 1.06 (t, J=7.6 Hz, 3 H); MS (ESI) m/z 560.4 (M+H).

S15-13-50

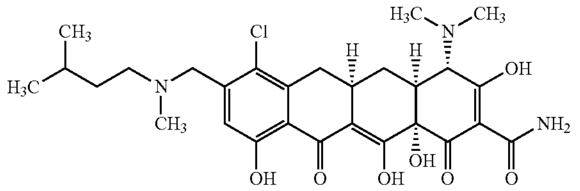

$^1$H NMR (400 MHz, $CD_3OD$) δ 7.23 (s, 1 H), 4.68 (t, J=13.6 Hz, 1 H), 4.39 (t, J=14.0 Hz, 1 H), 4.15 (s, 1 H), 3.43-3.36 (m, 1 H), 3.18-2.72 (m, 13 H), 2.46-2.38 (m, 1 H), 2.30-2.25 (m, 1 H), 1.80-1.60 (m, 4 H), 0.99 (d, J=7.6 Hz, 6 H); MS (ESI) m/z 562.1 (M+H).

S15-13-51

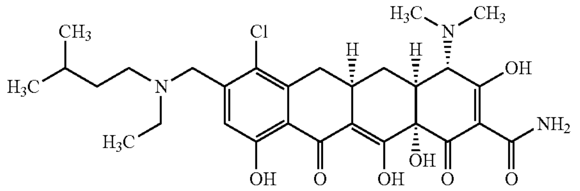

$^1$H NMR (400 MHz, $CD_3OD$) δ 7.22 (s, 1 H), 4.54 (s, 2 H), 4.23 (s, 1 H), 3.42 (dd, J=16.0 Hz and 4.4 Hz, 1 H), 3.26-2.97 (m, 12 H), 2.48-2.38 (m, 1 H), 2.30-2.23 (m, 1 H), 1.75-1.60 (m, 4 H), 1.40 (t, J=7.6 Hz, 3 H), 0.96 (t, J=7.2 Hz, 6 H); MS (ESI) m/z 576.0 (M+H).

S15-13-52

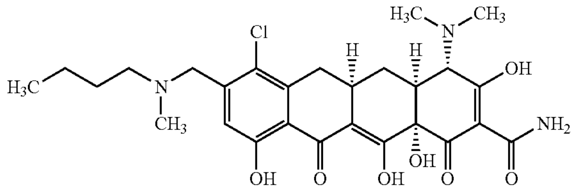

$^1H$ NMR (400 MHz, $CD_3OD$) δ 7.22 (s, 1 H), 4.68 (t, J=13.6 Hz, 1 H), 4.39 (t, J=14.0 Hz, 1 H), 4.13 (s, 1 H), 3.40 (dd, J=16.0 Hz and 4.4 Hz, 1 H), 3.19-2.83 (m, 13 H), 2.49-2.39 (m, 1 H), 2.31-2.25 (m, 1 H), 1.88-1.78 (m, 2 H), 1.71-1.60 (m, 1 H), 1.50-1.39 (m, 2 H), 1.01 (t, J=7.6 Hz, 3 H); MS (ESI) m/z 548.0 (M+H).

S15-13-53

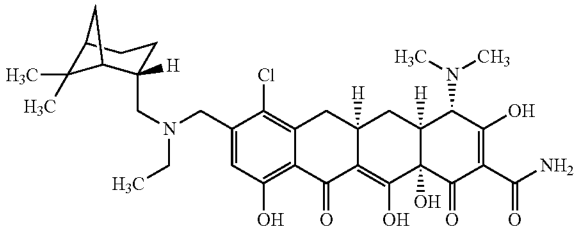

$^1H$ NMR (400 MHz, $CD_3OD$) δ 7.17 (s, 1 H), 4.46 (s, 2 H), 4.06 (s, 1 H), 3.38-3.28 (m, 1 H), 3.20-2.88 (m, 12 H), 2.60-2.28 (m, 3 H), 2.25-2.17 (m, 1 H), 2.11-2.00 (m, 1 H), 1.98-1.90 (m, 1 H), 1.90-1.78 (m, 3 H), 1.64-1.50 (m, 1 H), 1.40-1.28 (m, 2 H), 1.28-1.12 (m, 3 H), 1.03-0.93 (m, 3 H), 0.71 (s, 3 H); MS (ESI) m/z 642.2 (M+H).

S15-13-54

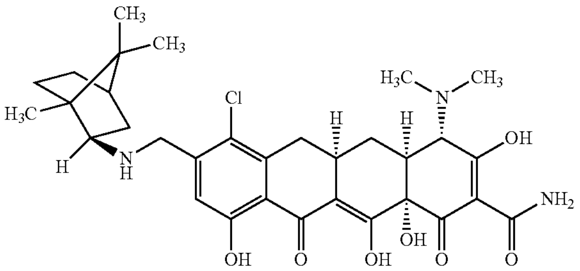

$^1H$ NMR (400 MHz, $CD_3OD$) δ 7.25 (s, 1 H), 4.48 (d, J=13.6 Hz, 1 H), 4.29 (d, J=13.6 Hz, 1 H), 4.15 (s, 1 H), 3.42 (dd, J=16.4 Hz and 4.4 Hz, 1 H), 3.18-2.87 (m, 9 H), 2.47-2.35 (m, 1 H), 2.32-2.16 (m, 2 H), 1.99-1.60 (m, 5 H), 1.32-1.20 (m, 2 H), 1.13 (s, 3 H), 1.02 (s, 3 H), 0.94 (s, 3 H); MS (ESI) m/z 614.0 (M+H).

S15-13-55

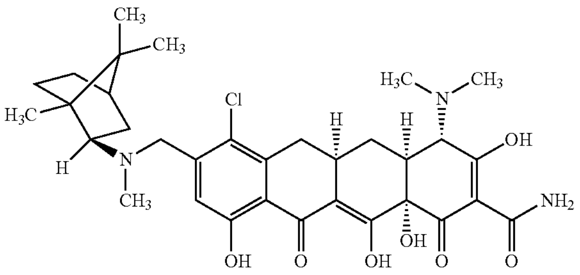

$^1H$ NMR (400 MHz, $CD_3OD$) δ 7.22 (s, 1 H), 4.14 (s, 1 H), 3.62-3.50 (m, 1 H), 3.48-3.38 (m, 1 H), 3.20-2.78 (m, 12 H), 2.60-2.49 (m, 1 H), 2.48-2.35 (m, 1 H), 2.32-2.18 (m, 2 H), 2.10-2.02 (m, 1 H), 1.98-1.80 (m, 3 H), 1.80-1.59 (m, 2 H), 1.28 (s, 3 H), 1.05 (s, 3 H), 0.95 (s, 3 H); MS (ESI) m/z 628.0 (M+H).

S15-13-56

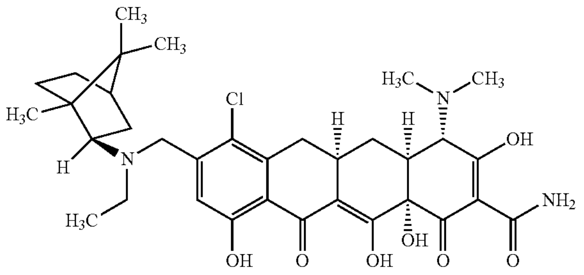

$^1H$ NMR (400 MHz, $CD_3OD$) δ 7.19 (s, 1 H), 4.55 (d, J=13.6 Hz, 1 H), 4.29 (d, J=13.6 Hz, 1 H), 4.14 (s, 1 H), 3.71-3.52 (m, 2 H), 3.50-3.38 (m, 2 H), 3.25-2.94 (m, 9 H), 2.58-2.37 (m, 2 H), 2.38-2.24 (m, 2 H), 2.09-1.82 (m, 4 H), 1.80-1.62 (m, 2 H), 1.42 (s, 3 H), 1.28 (s, 3 H), 1.07 (s, 3 H), 0.96 (t, J=8.0 Hz, 3 H); MS (ESI) m/z 642.0 (M+H).

S15-13-57

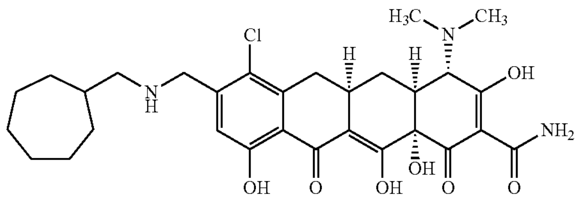

$^1H$ NMR (400 MHz, $CD_3OD$) δ 7.16 (s, 1 H), 4.38 (s, 2 H), 4.13 (s, 1 H), 3.41 (dd, J=16.0 Hz and 4.4 Hz, 1 H), 3.15-2.97 (m, 10 H), 2.44-2.37 (m, 1 H), 2.30-2.22 (m, 1 H), 2.04-1.92 (m, 1 H), 1.88-1.78 (m, 2 H), 1.78-1.48 (m, 9 H), 1.39-1.27 (m, 2 H); MS (ESI) m/z 588.1 (M+H).

S15-13-58

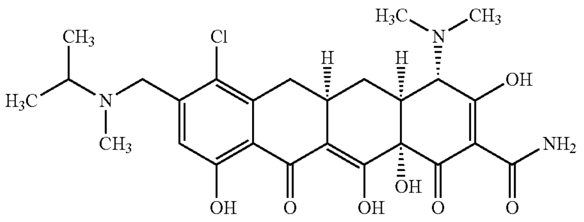

$^1H$ NMR (400 MHz, $CD_3OD$) δ 7.25 (s, 1 H), 4.68 (t, J=13.2 Hz, 1 H), 4.29 (t, J=13.2 Hz, 1 H), 4.16 (s, 1 H), 3.80 (m, 1 H), 3.44 (m, 1 H), 3.20-2.90 (m, 8 H), 2.81 (s, 3 H), 2.50-2.38 (m, 1 H), 2.34-2.26 (m, 1 H), 1.73-1.60 (m, 1 H), 1.52 (d, J=5.6 Hz, 3 H), 1.47 (d, J=6.4 Hz, 1 H); MS (ESI) m/z 534.0 (M+H).

S15-13-59

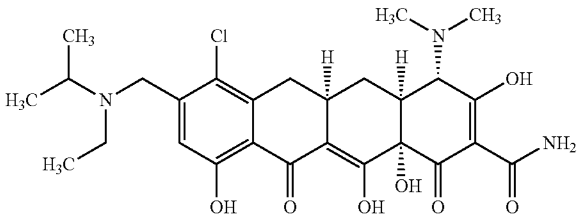

$^1H$ NMR (400 MHz, $CD_3OD$) δ 7.25 (s, 1 H), 4.65 (t, J=13.2 Hz, 1 H), 4.39 (t, J=13.2 Hz, 1 H), 4.16 (s, 1 H), 3.91-3.82 (m, 1 H), 3.45 (m, 1 H), 3.28-2.90 (m, 10 H), 2.51-2.40 (m, 1 H), 2.34-2.26 (m, 1 H), 1.75-1.62 (m, 1 H), 1.61 (d, J=7.6 Hz, 3 H), 1.45 (d, J=6.8 Hz, 3 H), 1.37 (t, J=7.2 Hz, 3 H); MS (ESI) m/z 547.9 (M+H).

S15-13-60

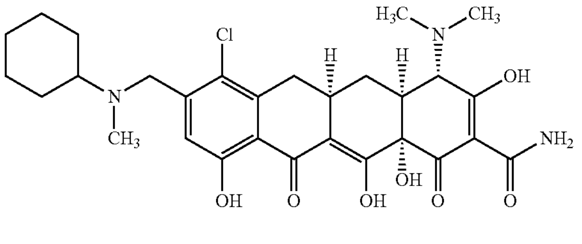

$^1H$ NMR (400 MHz, $CD_3OD$) δ 7.25 (s, 1 H), 4.74 (t, J=13.6 Hz, 1 H), 4.29 (t, J=13.2 Hz, 1 H), 4.16 (s, 1 H), 3.50-3.39 (m, 2 H), 3.20-2.97 (m, 8 H), 2.82 (s, 3 H), 2.49-2.38 (m, 1 H), 2.34-2.26 (m, 1 H), 2.20 (m, 2 H), 2.00 (m, 2 H), 1.80-1.55 (m, 4 H), 1.52-1.38 (m, 2 H), 1.35-1.25 (m, 1 H); MS (ESI) m/z 574.0 (M+H).

S15-13-61

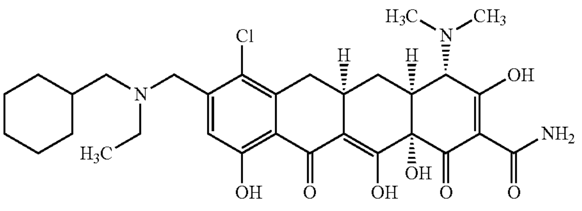

$^1H$ NMR (400 MHz, $CD_3OD$) δ 7.25 (s, 1 H), 4.64 (t, J=13.2 Hz, 1 H), 4.51 (t, J=13.2 Hz, 1 H), 4.16 (s, 1 H), 3.45 (dd, J=16.0 Hz and 4.4 Hz, 1 H), 3.22-2.90 (m, 12 H), 2.51-2.42 (m, 1 H), 2.35-2.26 (m, 1 H), 1.96-1.64 (m, 7 H), 1.43 (t, J=7.2 Hz, 3 H), 1.40-1.20 (m, 3 H), 1.15-0.95 (m, 2 H); MS (ESI) m/z 601.9 (M+H).

S15-13-62

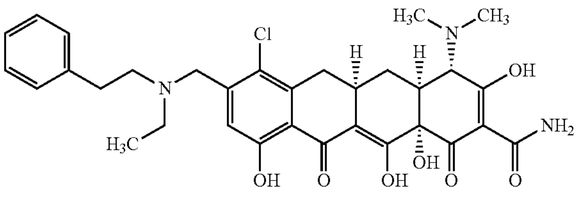

$^1H$ NMR (400 MHz, $CD_3OD$) δ 7.40-7.26 (m, 6 H), 4.72-4.58 (m, 2 H), 4.16 (s, 1 H), 3.52-2.39 (m, 5 H), 3.21-2.88 (m, 10 H), 2.50-2.39 (m, 1 H), 2.35-2.26 (m, 1 H), 1.74-1.62 (m, 1 H), 1.46 (t, J=7.2 Hz, 3 H); MS (ESI) m/z 610.1 (M+H).

S15-13-63

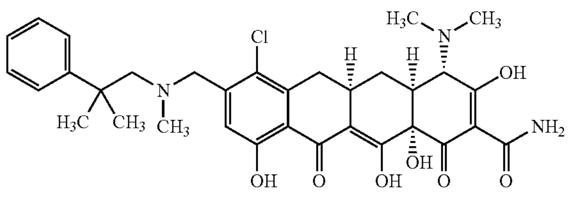

$^1H$ NMR (400 MHz, $CD_3OD$) δ 7.51 (d, J=7.8 Hz, 2 H), 7.41 (t, J=7.8 Hz, 2 H), 7.30 (br s, 1 H), 7.05 (s, 1 H), 4.41 (t, J=12.4 Hz, 1 H), 4.23 (t, J=12.4 Hz, 1 H), 3.75 (dd, J=31.2 Hz and 13.6 Hz, 2 H), 3.40-3.30 (m, 1 H), 3.20-2.88 (m, 8 H), 2.75 (s, 3 H), 2.45-2.36 (m, 1 H), 2.32-2.25 (m, 1 H), 1.72-1.60 (m, 1 H), 1.58 (s, 3 H), 1.49 (s, 3 H); MS (ESI) m/z 624.1 (M+H).

S15-13-64

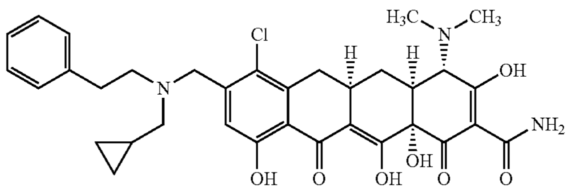

$^1H$ NMR (400 MHz, $CD_3OD$) δ 7.38 (m, 2 H), 7.31-7.28 (m, 4 H), 4.81 (t, J=14.0 Hz, 1 H), 4.68 (t, J=14.0 Hz, 1 H), 4.16 (s, 1 H), 3.60-3.49 (m, 2 H), 3.43 (dd, J=16.0 Hz and 4.4 Hz, 1 H), 3.36-3.30 (m, 2 H), 3.26-2.97 (m, 10 H), 2.49-2.39 (m, 1 H), 2.34-2.26 (m, 1 H), 1.73-1.62 (m, 1 H), 1.33-1.24 (m, 1 H), 0.87-0.83 (m, 2 H), 0.54-0.51 (m, 2 H); MS (ESI) m/z 636.0 (M+H).

S15-13-65

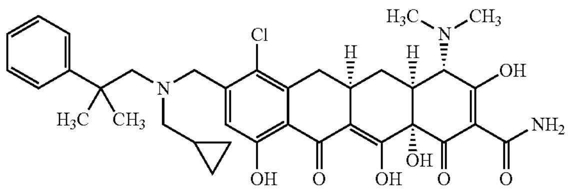

$^1H$ NMR (400 MHz, $CD_3OD$) δ 7.48-7.42 (m, 2 H), 7.42-7.33 (m, 2 H), 7.33-7.25 (m, 1 H), 7.12-7.08 (m, 1 H), 4.57-4.49 (m, 1 H), 4.44-4.34 (m, 1 H), 4.16 (s, 1 H), 3.91-3.82 (m, 1 H), 3.66-3.58 (m, 1 H), 3.36-3.28 (m, 1 H), 3.24-2.97 (m, 10 H), 2.46-2.32 (m, 1 H), 2.32-2.25 (m, 1 H), 1.73-1.60 (m, 1 H), 1.55 (s, 3 H), 1.44 and 1.42 (each s, total 3 H), 1.30-1.18 (m, 1 H), 0.83-0.73 (m, 2 H), 0.40-0.31 (m, 2 H); MS (ESI) m/z 664.1 (M+H).

S15-13-66

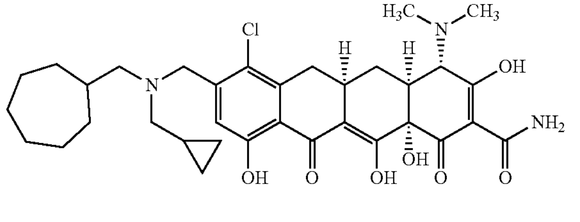

$^1$H NMR (400 MHz, $CD_3OD$) δ 7.30 (s, 1 H), 4.74-4.62 (m, 2 H), 4.16 (s, 1 H), 3.45 (dd, J=12.4 Hz and 4.4 Hz, 1 H), 3.39-3.31 (m, 1 H), 3.28-3.22 (m, 2 H), 3.20-2.98 (m, 9 H), 2.53-2.43 (m, 1 H), 2.35-2.26 (m, 1 H), 2.12-2.02 (m, 1 H), 1.92-1.82 (m, 1 H), 1.80-1.45 (m, 10 H), 1.40-1.18 (m, 3 H), 0.90-0.82 (m, 2 H), 0.55-0.48 (m, 2 H); MS (ESI) m/z 642.0 (M+H).

S15-13-67

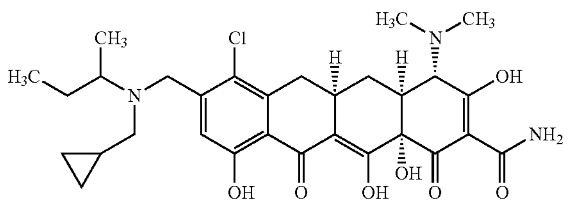

$^1$H NMR (400 MHz, $CD_3OD$) δ 7.26 and 7.24 (each s, total 1 H), 4.68-4.59 (m, 1 H), 4.58-4.46 (m, 1 H), 4.15 (s, 1 H), 3.75-3.63 (m, 1 H), 3.48-3.37 (m, 1 H), 3.25-2.98 (m, 11 H), 2.50-2.40 (m, 1 H), 2.33-2.26 (m, 1 H), 2.12-1.92 (m, 1 H), 1.85-1.60 (m, 2 H), 1.54 and 1.44 (each d, J=6.8 Hz, total 3 H), 1.18-1.02 (m, 4 H), 0.82-0.73 (m, 2 H), 0.50-0.38 (m, 2 H); MS (ESI) m/z 588.1 (M+H).

S15-13-68

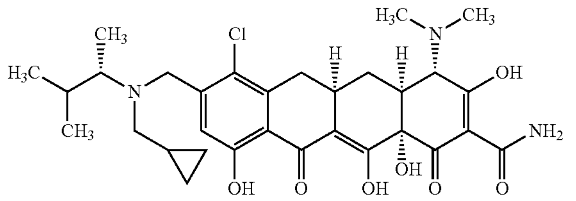

$^1$H NMR (400 MHz, $CD_3OD$) δ 7.31 and 7.24 (each s, total 1 H), 4.75-4.64 (m, 1 H), 4.39-4.30 (m, 1 H), 4.16 (s, 1 H), 3.85-3.76 (m, 1 H), 3.48-3.39 (m, 1 H), 3.26-2.98 (m, 10 H), 2.50-2.12 (m, 3 H), 1.73-1.62 (m, 1 H), 1.44 (d, J=6.4 Hz, 3 H), 1.30-1.00 (m, 7 H), 0.88-0.68 (m, 2 H), 0.60-0.38 (m, 2 H); MS (ESI) m/z 602.1 (M+H).

S15-13-69

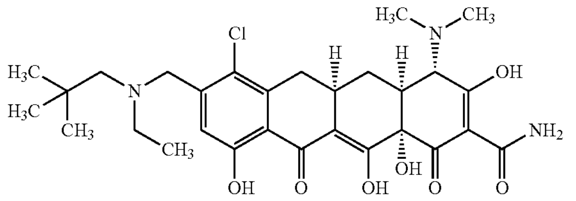

$^1$H NMR (400 MHz, $CD_3OD$) δ 7.30 (s, 1 H), 4.70-4.50 (m, 2 H), 4.14 (s, 1 H), 3.48-3.35 (m, 3 H), 3.18-2.86 (m, 10 H), 2.48-2.37 (m, 1 H), 2.31-2.22 (m, 1 H), 1.71-1.58 (m, 1)□1.47 (t, J=6.4 Hz, 3 H), 1.06 (s, 9 H); MS (ESI) m/z 576.1 (M+H).

S15-13-70

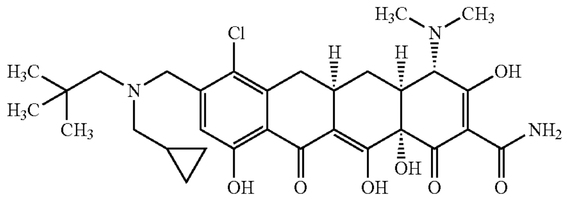

$^1$H NMR (400 MHz, $CD_3OD$) δ 7.34 (s, 1 H), 4.77-4.66 (m, 2 H), 4.14 (s, 1 H), 3.49-3.38 (m, 2 H), 3.32-3.18 (m, 1 H), 3.18-2.94 (m, 10 H), 2.50-2.37 (m, 1 H), 2.30-2.22 (m, 1 H), 1.71-1.60 (m, 1 H), 1.38-1.28 (m, 1 H), 1.03 (s, 9 H), 0.90-0.74 (m, 2 H), 0.55-0.44 (m, 2 H); MS (ESI) m/z 602.1 (M+H).

S15-13-71

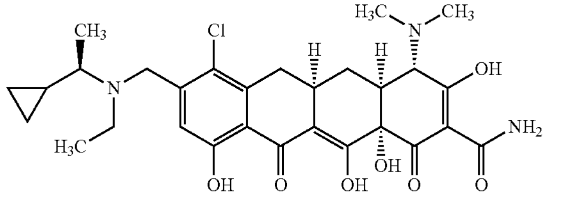

$^1$H NMR (400 MHz, $CD_3OD$) δ 7.26 (s, 1 H), 4.50 and 4.38 (each d, J=13.6 Hz, total 1 H), 4.16 (s, 1 H), 3.52-3.35 (m, 4 H), 3.20-2.98 (m, 9 H), 2.50-2.40 (m, 1 H), 2.34-2.26 (m, 1 H), 1.75-1.62 (m, 1 H), 1.58 and 1.53 (each d, J=6.4 Hz, total 3 H), 1.38 and 1.29 (each t, J=7.2 Hz, total 3 H), 0.96-0.78 (m, 2 H), 0.72-0.40 (m, 2); MS (ESI) m/z 574.1 (M+H).

S15-13-72

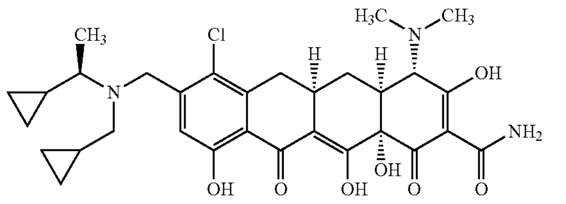

$^1$H NMR (400 MHz, $CD_3OD$) δ 7.28 and 7.25 (each s, total 1 H), 4.76-4.72 (m, 1 H), 4.47-4.40 (m, 1 H), 4.14 (s, 1 H), 3.57-3.35 (m, 3 H), 3.20-2.98 (m, 10 H), 2.50-2.40 (m, 1 H), 2.33-2.26 (m, 1 H), 1.74-1.62 (m, 1 H), 1.51 (t, J=7.2 Hz, 3 H), 1.45-1.22 (m, 1 H), 1.22-1.16 and 1.05-0.95 (each m, total 1 H), 0.90-0.60 (m, 5 H), 0.60-0.34 (m, 3 H); MS (ESI) m/z 600.1 (M+H).

S15-13-73

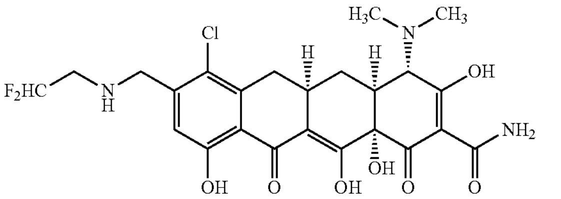

$^1$H NMR (400 MHz, $CD_3OD$) δ 7.15 (s, 1 H), 6.36 (tt, J=53.6 Hz and 3.2 Hz, 1 H), 4.50 (s, 2 H), 4.12 (s, 1 H), 3.71

(dt, J=15.2 Hz and 3.2 Hz, 2 H), 3.41 (dd, J=16.0 Hz and 4.8 Hz, 1 H), 3.15-2.95 (m, 8 H), 2.46-2.38 (m, 1 H), 2.30-2.22 (m, 1 H), 1.72-1.61 (m, 1 H); MS (ESI) m/z 542.0 (M+H).

S15-13-74

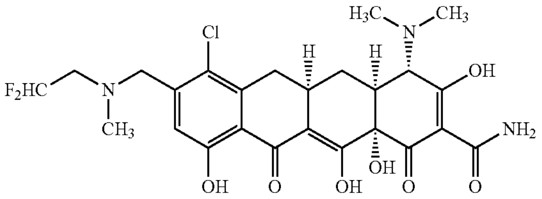

$^1$H NMR (400 MHz, $CD_3OD$) δ 7.23 (s, 1 H), 6.50 (tt, J=53.6 Hz and 3.2 Hz, 1 H), 4.65 (s, 2 H), 4.12 (s, 1 H), 3.90-3.80 (m, 2 H), 3.44-3.38 (m, 1 H), 3.16-2.95 (m, 11 H), 2.47-2.40 (m, 1 H), 2.30-2.23 (m, 1 H), 1.71-1.61 (m, 1 H); MS (ESI) m/z 556.0 (M+H).

S15-13-75

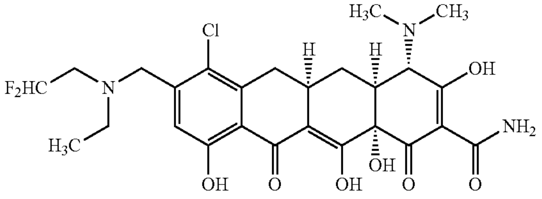

$^1$H NMR (400 MHz, $CD_3OD$) δ 7.24 (s, 1 H), 6.51 (br t, J=55.2 Hz, 1 H), 4.68 (dd, J=16.8 Hz and 14.8 Hz, 2 H), 4.13 (s, 1 H), 3.86-3.76 (m, 2 H), 3.48-3.39 (m, 3 H), 3.18-2.95 (m, 8 H), 2.47-2.39 (m, 1 H), 2.30-2.24 (m, 1 H), 1.71-1.60 (m, 1 H), 1.44 (t, J=7.2 Hz, 3 H); MS (ESI) m/z 570.0 (M+H).

S15-13-76

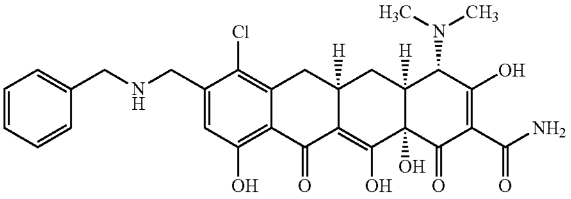

$^1$H NMR (400 MHz, $CD_3OD$) δ 7.56-7.48 (m, 5 H), 7.10 (s, 1 H), 4.37 (br s, 4 H), 4.12 (s, 1 H), 3.38 (dd, J=16.0 Hz and 4.4 Hz, 1 H), 3.14-2.95 (m, 8 H), 2.43-2.35 (m, 1 H), 2.27-2.22 (m, 1 H), 1.70-1.69 (m, 1 H); MS (ESI) m/z 568.3 (M+H).

S15-13-77

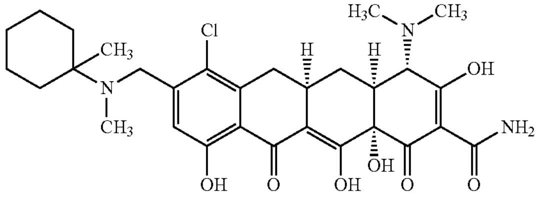

$^1$H NMR (400 MHz, $CD_3OD$) δ 7.22 (s, 1 H), 4.89-4.83 (m, 1 H), 4.17-4.10 (m, 2 H), 3.47-3.37 (m, 1 H), 3.18-2.95 (m, 8 H), 2.76-2.72 (m, 3 H), 2.48-2.22 (m, 3 H), 2.04-1.95 (m, 1 H), 1.91-1.70 (m, 5 H), 1.70-1.50 (m, 6 H), 1.33-1.20 (m, 1 H); MS (ESI) m/z 588.4 (M+H).

S15-13-78

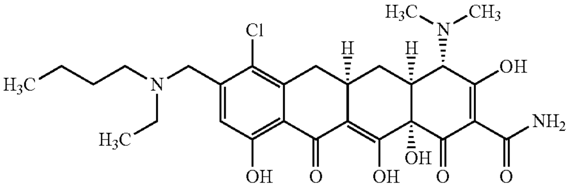

$^1$H NMR (400 MHz, $CD_3OD$) δ 7.21 (s, 1 H), 4.58-4.48 (m, 2 H), 4.13 (s, 1 H), 3.42 (dd, J=16.0 Hz and 4.0 Hz, 1 H), 3.23-2.95 (m, 12 H), 2.46-2.39 (m, 1 H), 2.30-2.27 (m, 1 H), 1.88-1.78 (m, 2 H), 1.70-1.60 (m, 1 H), 1.47-1.36 (m, 5 H), 0.98 (t, J=6.8 Hz, 3 H); MS (ESI) m/z 562.1 (M+H).

S15-13-79

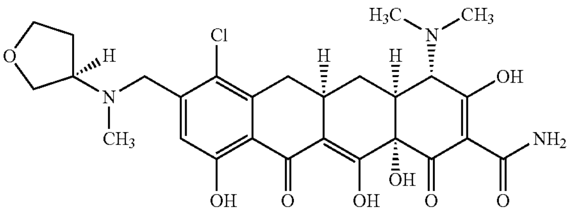

$^1$H NMR (400 MHz, $CD_3OD$) δ 7.27 (s, 1 H), 4.44-4.15 (m, 5 H), 3.90-3.76 (m, 2 H), 3.16-2.88 (m, 10 H), 3.00 (s, 3 H), 2.51-2.28 (m, 4 H), 1.75-1.65 (m, 1 H); MS (ESI) m/z 562.3 (M+H).

S15-13-80

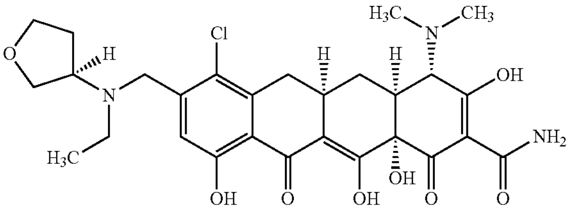

$^1$H NMR (400 MHz, $CD_3OD$) δ 7.25 (s, 1 H), 4.65-4.15 (m, 7 H), 3.86 (s, 1 H), 3.78-3.71 (m, 1 H), 3.16-3.00 (m, 10 H), 2.52-2.28 (m, 4 H), 1.75-1.65 (m, 1 H), 1.44 (s, 3 H); MS (ESI) m/z 576.3 (M+H).

S15-13-81

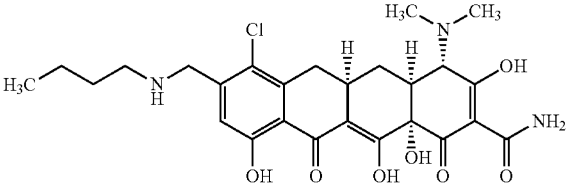

$^1$H NMR (400 MHz, $CD_3OD$) δ 7.14 (s, 1 H), 4.37 (s, 2 H), 4.13 (s, 1 H), 3.40 (dd, J=16.0 Hz and 4.0 Hz, 1 H), 3.17-2.97

(m, 10 H), 2.45-2.35 (m, 1 H), 2.30-2.23 (m, 1 H), 1.77-1.64 (m, 3 H), 1.48-1.43 (m, 2 H), 1.00 (t, J=7.2 Hz, 3 H); MS (ESI) m/z 534.0 (M+H).

S15-13-82

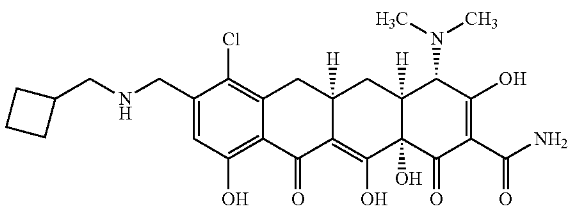

$^1$H NMR (400 MHz, $CD_3OD$) δ 7.13 (s, 1 H), 4.34 (s, 2 H), 4.13 (s, 1 H), 3.40 (dd, J=16.0 Hz and 4.4 Hz, 1 H), 3.19-2.97 (m, 10 H), 2.46-2.36 (m, 1 H), 2.28-2.18 (m, 3 H), 2.05-1.94 (m, 1 H), 1.92-1.86 (m, 4 H), 1.74-1.59 (m, 1 H); MS (ESI) m/z 546.0 (M+H).

S15-13-83

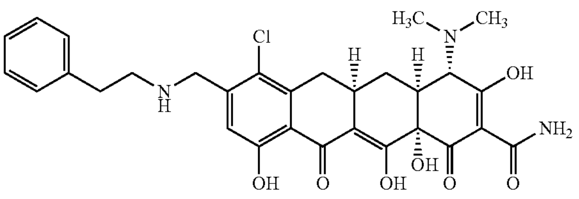

$^1$H NMR (400 MHz, $CD_3OD$) δ 7.32-7.15 (m, 5 H), 7.07 (s, 1 H), 4.35 (s, 2 H), 4.04 (s, 1 H), 3.35-3.25 (m, 3 H), 3.08-2.88 (m, 10 H), 2.40-2.30 (m, 1 H), 2.24-2.14 (m, 1 H), 1.65-1.54 (m, 1 H); MS (ESI) m/z 582.0 (M+H).

S15-13-84

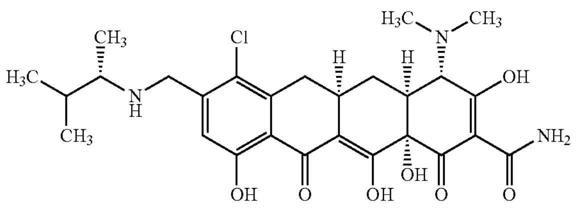

$^1$H NMR (400 MHz, $CD_3OD$) δ 7.20 (s, 1 H), 4.42 (s, 2 H), 4.14 (s, 1 H), 3.47-3.40 (m, 1 H), 3.18-2.97 (m, 9 H), 2.49-2.39 (m, 1 H), 2.32-2.20 (m, 2 H), 1.74-1.63 (m, 1 H), 1.37 (d, J=6.8 Hz, 3 H), 1.09 (d, J=6.8 Hz, 3 H), 1.04 (d, J=6.8 Hz, 3 H); MS (ESI) m/z 547.9 (M+H).

S15-13-85

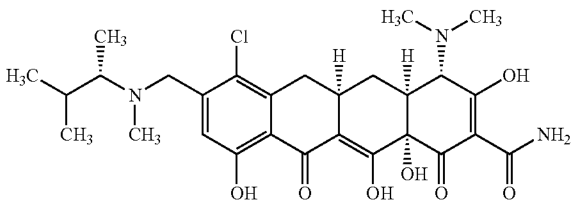

$^1$H NMR (400 MHz, $CD_3OD$) δ 7.27 and 7.24 (each s, total 1 H), 4.76-4.70 (m, 1 H), 4.46-4.41 and 4.27-4.15 (each m, total 1 H), 4.15 (s, 1 H), 3.47-3.33 (m, 2 H), 3.20-2.97 (m, 8 H), 2.85 (s, 3 H), 2.49-2.41 (m, 1 H), 2.38-2.26 (m, 1 H), 2.25-2.12 (m, 1 H), 1.72-1.63 (m, 1 H), 1.47 and 1.42 (each d, J=6.8 Hz, total 3 H), 1.20 and 1.06 (each d, J=6.4 Hz, total 3 H), 1.13-1.09 (m, 3 H); MS (ESI) m/z 562.1 (M+H).

S15-13-86

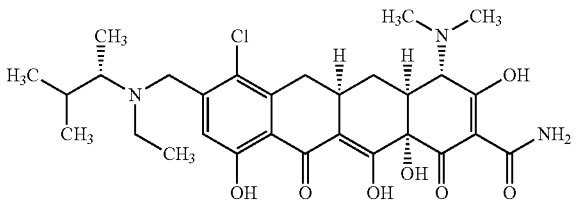

$^1$H NMR (400 MHz, $CD_3OD$) δ 7.26 and 7.23 (each s, total 1 H), 4.72-4.67 (m, 1 H), 4.55 and 4.31 (each d, J=14.0 Hz, total 1 H), 4.15 (s, 1 H), 3.46-3.30 (m, 3 H), 3.20-2.97 (m, 9 H), 2.48-2.40 (m, 1 H), 2.38-2.26 (m, 2 H), 1.72-1.62 (m, 1 H), 1.44-1.31 (m, 6 H), 1.19-1.13 (m, 3 H), 1.09-1.05 (m, 3 H); MS (ESI) m/z 576.2 (M+H).

S15-13-87

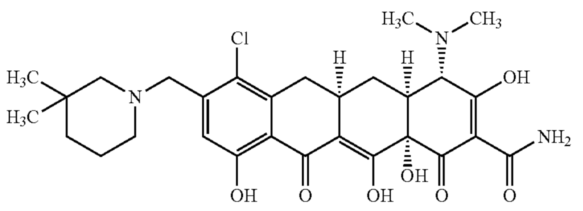

$^1$H NMR (400 MHz, $CD_3OD$) δ 7.29 (s, 1 H), 4.60-4.42 (m, 2 H), 4.13 (s, 1 H), 3.60-3.51 (m, 1 H), 3.46-3.38 (m, 1 H), 3.25-2.86 (m, 11 H), 2.48-2.38 (m, 1 H), 2.32-2.24 (m, 1 H), 2.06-1.94 (m, 1 H), 1.90-1.80 (m, 1 H), 1.70-1.53 (m, 2 H), 1.53-1.43 (m, 1 H), 1.13 (s, 3 H), 1.03 (s, 3 H); MS (ESI) m/z 574.0 (M+H).

S15-13-88

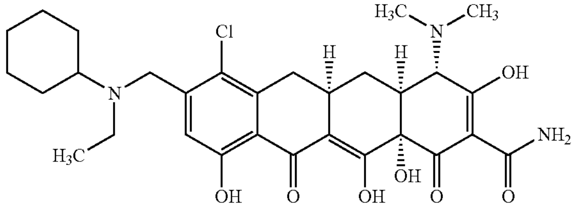

$^1$H NMR (400 MHz, $CD_3OD$) δ 7.21 (s, 1 H), 4.69 (t, J=13.2 Hz, 1 H), 4.35 (t, J=13.2 Hz, 1 H), 4.13 (s, 1 H), 3.47-3.36 (m, 2 H), 3.20-2.95 (m, 10 H), 2.46-2.39 (m, 1 H), 2.29-2.26 (m, 1 H), 2.20-2.10 (m, 2 H), 2.01-1.92 (m, 2 H), 1.82-1.58 (m, 4 H), 1.50-1.37 (m, 2 H), 1.34 (t, J=7.2 Hz, 3 H), 1.34-1.25 (m, 1 H); MS (ESI) m/z 588.2 (M+H).

S15-13-89

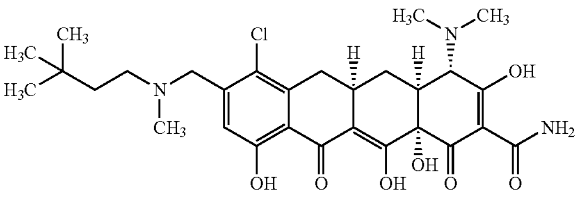

$^1$H NMR (400 MHz, $CD_3OD$) δ 7.24 (s, 1 H), 4.70 (t, J=13.2 Hz, 1 H), 4.39 (t, J=13.2 Hz, 1 H), 4.15 (s, 1 H), 3.47-3.30 (m, 2 H), 3.20-2.95 (m, 9 H), 2.88 (s, 3 H), 2.48-2.40 (m, 1 H), 2.31-2.26 (m, 1 H), 1.77 (t, J=8.4 Hz, 2 H), 1.73-1.61 (m, 1 H), 1.01 (s, 9 H); MS (ESI) m/z 576.3 (M+H).

S15-13-90

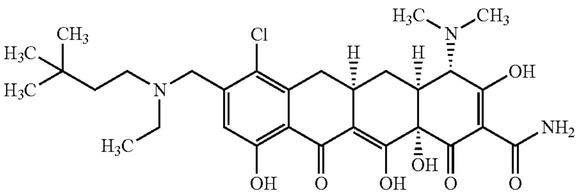

$^1$H NMR (400 MHz, $CD_3OD$) δ 7.24 (s, 1 H), 4.60-4.55 (m, 2 H), 4.14 (s, 1 H), 3.47-3.42 (m, 1 H), 3.20-2.96 (m, 12 H), 2.52-2.43 (m, 1 H), 2.33-2.26 (m, 1 H), 1.77-1.65 (m, 3 H), 1.42 (t, J=6.8 Hz, 3 H), 1.00 (s, 9 H); MS (ESI) m/z 590.3 (M+H).

S15-13-91

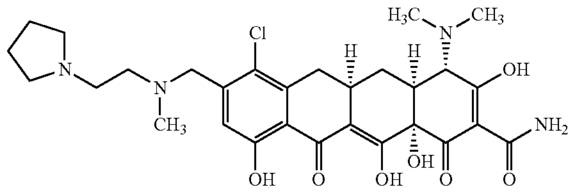

$^1$H NMR (400 MHz, $CD_3OD$) δ 7.33 (s, 1 H), 4.60-4.50 (m, 2 H), 4.11 (s, 1 H), 3.80-3.64 (m, 4 H), 3.45-3.36 (m, 1 H), 3.15-2.88 (m, 9 H), 2.65 (s, 6 H), 2.48-2.38 (m, 1 H), 2.28-2.21 (m, 1 H), 2.12 (br s, 4 H), 1.71-1.60 (m, 1 H); MS (ESI) m/z 589.2 (M+H).

S15-13-92

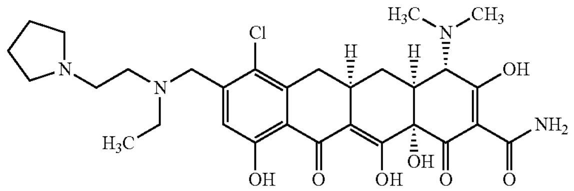

$^1$H NMR (400 MHz, $CD_3OD$) δ 7.36 (s, 1 H), 4.60-4.52 (m, 1 H), 4.14 (s, 1 H), 3.82-3.60 (m, 4 H), 3.46-3.38 (m, 1 H), 3.20-2.96 (m, 9 H), 2.68 (s, 6 H), 2.52-2.40 (m, 1 H), 2.30-2.24 (m, 1 H), 2.20-2.09 (m, 4 H), 1.48-1.40 (m, 3 H); MS (ESI) m/z 603.4 (M+H).

S15-13-93

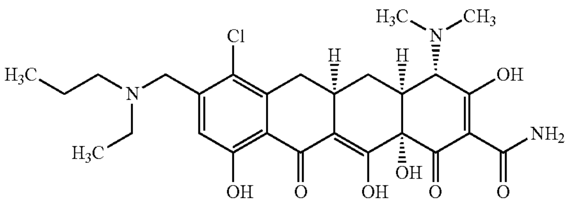

$^1$H NMR (400 MHz, $CD_3OD$) δ 7.21 (s, 1 H), 4.58-4.48 (m, 2 H), 4.13 (s, 1 H), 3.42 (dd, J=16.4 Hz and 4.4 Hz, 2 H), 3.20-2.96 (m, 11 H), 2.48-2.38 (m, 1 H), 2.31-2.23 (m, 1 H), 1.90-1.77 (m, 2 H), 1.72-1.60 (m, 1 H), 1.39 (t, J=7.2 Hz, 3 H), 1.02 (t, J=7.2 Hz, 3 H); MS (ESI) m/z 548.3 (M+H).

S15-13-94

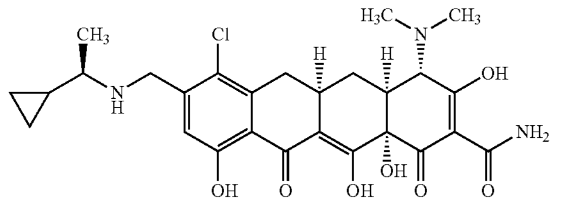

$^1$H NMR (400 MHz, $CD_3OD$) δ 7.17 (s, 1 H), 4.58-4.50 (m, 1 H), 4.43-4.36 (m, 1 H), 4.13 (s, 1 H), 3.42 (dd, J=16.0 Hz and 4.4 Hz, 1 H), 3.20-2.93 (m, 9 H), 2.85-2.77 (m, 1 H), 2.46-2.36 (m, 1 H), 2.30-2.26 (m, 1 H), 1.70-1.60 (m, 1 H), 1.50 (d, J=6.8 Hz, 3 H), 1.13-1.04 (m, 1 H), 0.88-0.70 (m, 2 H), 0.68-0.59 (m, 1 H), 0.43-0.36 (m, 1 H); MS (ESI) m/z 546.1 (M+H).

S15-13-95

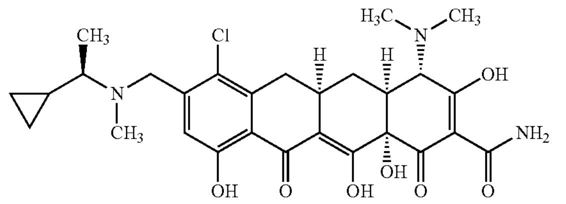

$^1$H NMR (400 MHz, $CD_3OD$) δ 7.20 (s, 1 H), 4.36-4.24 (m, 2 H), 4.10 (s, 1 H), 3.42-3.35 (m, 1 H), 3.12-2.77 (m, 12 H), 2.47-2.38 (m, 1 H), 2.27-2.23 (m, 1 H), 1.69-1.59 (m, 1 H), 1.57-1.49 (br s, 3 H), 1.33-1.25 and 1.20-1.10 (each m, total 1 H), 0.88-0.73 (m, 2 H), 0.72-0.66 and 0.60-0.52 (each m, total 1 H), 0.48-0.35 (m, 1 H); MS (ESI) m/z 560.4 (M+H).

S15-13-96

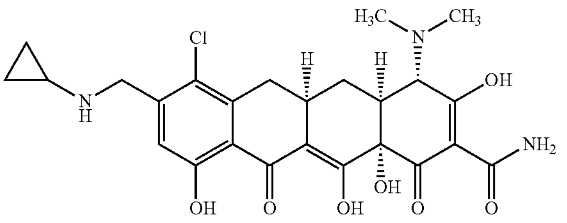

$^1$H NMR (400 MHz, $CD_3OD$) δ 7.13 (s, 1 H), 4.49 (s, 2 H), 4.13 (s, 1 H), 3.41 (dd, J=16.0 Hz and 4.4 Hz, 1 H), 3.16-2.84

(m, 9 H), 2.44-2.37 (m, 1 H), 2.28-2.25 (m, 1 H), 1.70-1.60 (m, 1 H), 0.97-0.93 (m, 4 H); MS (ESI) m/z 518.2 (M+H).

S15-13-97

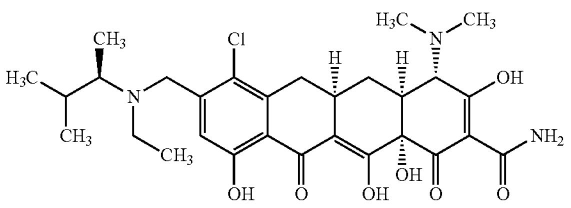

$^1$H NMR (400 MHz, $CD_3OD$) δ 7.17 and 7.24 (each s, total 1 H), 4.74, 4.67, 4.53 and 4.35 (each d, J=13.6 Hz, total 2 H), 4.15 (s, 1 H), 3.49-3.36 (m, 3 H), 3.20-2.90 (m, 9 H), 2.50-2.40 (m, 1 H), 2.40-2.28 (m, 2 H), 1.73-1.64 (m, 1 H), 1.47-1.30 (m, 6 H), 1.20-1.12 (m, 3 H), 1.10-1.05 (m, 3 H); MS (ESI) m/z 576.2 (M+H).

S15-13-98

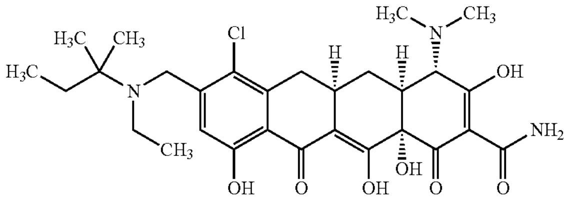

$^1$H NMR (400 MHz, $CD_3OD$) δ 7.28 (s, 1 H), 4.77-4.70 (m, 1 H), 4.51-4.44 (m, 1 H), 4.12 (s, 1 H), 3.54-3.38 (m, 2 H), 3.18-2.85 (m, 9 H), 2.48-2.38 (m, 1 H), 2.27-2.24 (m, 1 H), 2.02-1.90 (m, 2 H), 1.70-1.60 (m, 1 H), 1.54 (s, 3 H), 1.53 (s, 3 H), 1.13-1.05 (m, 6 H); MS (ESI) m/z 576.2 (M+H).

S15-13-99

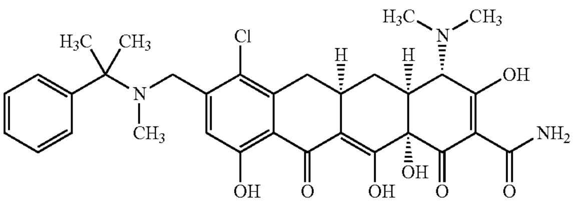

$^1$H NMR (400 MHz, $CD_3OD$) δ 7.80-7.76 (m, 2 H), 7.58-7.48 (m, 3 H), 6.97-6.96 (m, 1 H), 4.41-4.35 (m, 1 H), 4.09-4.03 (m, 2 H), 3.15-2.90 (m, 9 H), 2.90-2.80 (m, 3 H), 2.36-2.28 (m, 1 H), 2.25-2.18 (m, 1 H), 1.98 (s, 3 H), 1.95 (s, 3 H), 1.65-1.55 (m, 1 H); MS (ESI) m/z 610.1 (M+H).

S15-13-100

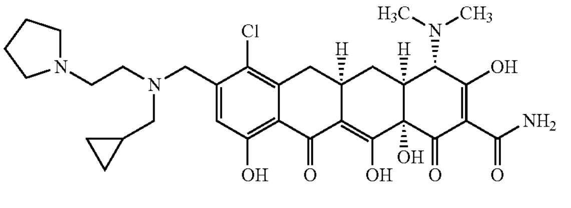

$^1$H NMR (400 MHz, $CD_3OD$) δ 7.41 (s, 1 H), 4.85-4.58 (m, 2 H), 4.13 (s, 1 H), 3.87-3.60 (m, 7 H), 3.42 (dd, J=16.0 Hz and 4.0 Hz, 1 H), 3.20-3.10 (m, 3 H), 3.09-2.95 (m, 8 H), 2.47-2.39 (m, 1 H), 2.28-2.24 (m, 1 H), 2.20-2.00 (m, 4 H), 1.71-1.60 (m, 1 H), 1.35-1.23 (m, 1 H), 0.87-0.80 (m, 2 H), 0.57-0.49 (m, 2 H); MS (ESI) m/z 629.2 (M+H).

S15-13-101

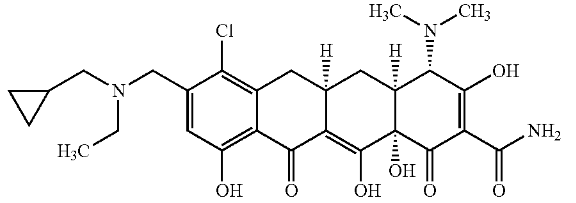

$^1$H NMR (400 MHz, $CD_3OD$) δ 7.21 (s, 1 H), 4.73-4.64 (m, 1 H), 4.57-4.48 (m, 1 H), 4.12 (s, 1 H), 3.44-3.34 (m, 2 H), 3.25-2.95 (m, 11 H), 2.50-2.38 (m, 1 H), 2.30-2.21 (m, 1 H), 1.71-1.60 (m, 1 H), 1.42-1.36 (m, 3 H), 1.25-1.15 (m, 1 H), 0.84-0.77 (m, 2 H), 0.50-0.42 (m, 2 H); MS (ESI) m/z 560.3 (M+H).

S15-13-102

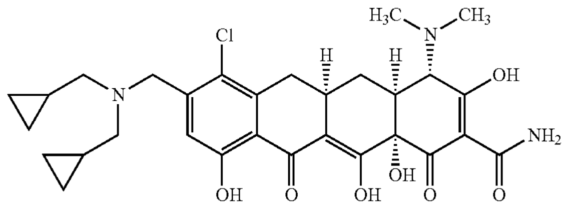

$^1$H NMR (400 MHz, $CD_3OD$) δ 7.29 and 7.22 (each s, total 1 H), 4.73-4.68 (m, 2 H), 4.11 (s, 1 H), 3.45-3.35 (m, 1 H), 3.20-2.90 (m, 12 H), 2.49-2.40 (m, 1 H), 2.30-2.21 (m, 1 H), 1.71-1.60 (m, 1 H), 0.82-0.77 (m, 4 H), 0.50-0.39 (m, 4 H); MS (ESI) m/z 586.1 (M+H).

S15-13-103

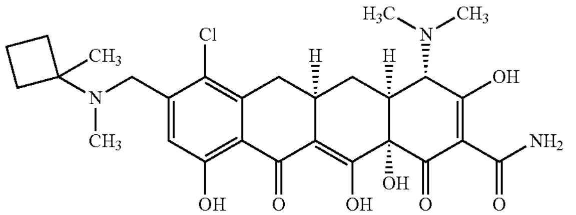

$^1$H NMR (400 MHz, $CD_3OD$) δ 7.23 (s, 1 H), 4.51-4.44 (m, 1 H), 4.20-4.13 (m, 2 H), 3.46-3.39 (m, 1 H), 3.18-2.95 (m, 8 H), 2.71-2.58 (m, 4 H), 2.58-2.37 (m, 2 H), 2.30-2.22 (m, 2 H), 2.10-2.02 (m, 1 H), 2.00-1.87 (m, 2 H), 1.70-1.59 (m, 4 H); MS (ESI) m/z 560.1 (M+H).

S15-13-104

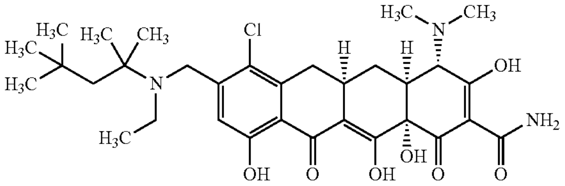

$^1$H NMR (400 MHz, $CD_3OD$) δ 7.32 (s, 1 H), 4.78-4.71 (m, 1 H), 4.51-4.44 (m, 1 H), 4.14 (s, 1 H), 3.62-3.50 (m, 1 H), 3.48-3.37 (m, 1 H), 3.30-2.95 (m, 9 H), 2.49-2.36 (m, 1 H), 2.30-2.26 (m, 1 H), 1.99-1.90 (m, 2 H), 1.77-1.58 (m, 7 H), 1.17-1.07 (m, 12 H); MS (ESI) m/z 618.1 (M+H).

S15-13-105

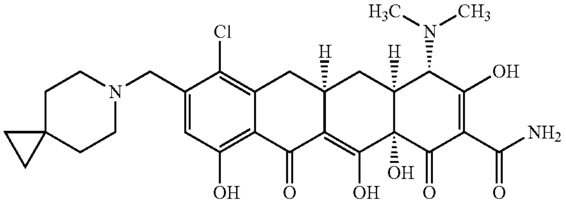

$^1$H NMR (400 MHz, $CD_3OD$) δ 7.21 (s, 1 H), 4.54-4.47 (m, 2 H), 4.08 (s, 1 H), 3.55-3.47 (m, 2 H), 3.37 (dd, J=16.4 Hz and 4.8 Hz, 1 H), 3.11-2.89 (m, 10 H), 2.41-2.34 (m, 1 H), 2.20-2.13 (m, 3 H), 1.65-1.54 (m, 1 H), 1.20-1.16 (m, 2 H), 0.50-0.41 (m, 4 H); MS (ESI) m/z 572.2 (M+H).

S15-13-106

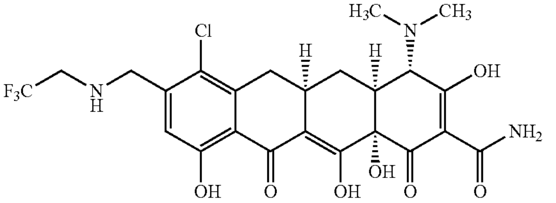

$^1$H NMR (400 MHz, $CD_3OD$) δ 7.11 (s, 1 H), 4.46 (s, 2 H), 4.15-4.07 (m, 2 H), 3.35 (dd, J=16.4 Hz and 4.8 Hz, 1 H), 3.10-2.89 (m, 9 H), 2.40-2.32 (m, 1 H), 2.27-2.17 (m, 1 H), 1.65-1.55 (m, 1 H); MS (ESI) m/z 560.1 (M+H).

S15-13-107

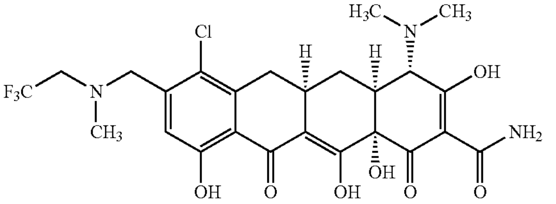

$^1$H NMR (400 MHz, $CD_3OD$) δ 7.13 (s, 1 H), 4.10 (s, 3 H), 3.62-3.55 (m, 2 H), 3.40 (dd, J=16.0 Hz and 4.4 Hz, 1 H), 3.10-2.95 (m, 8 H), 2.62 (s, 3 H), 2.41-2.32 (m, 1 H), 2.27-2.20 (m, 1 H), 1.69-1.59 (m, 1 H); MS (ESI) m/z 574.0 (M+H).

S15-13-108

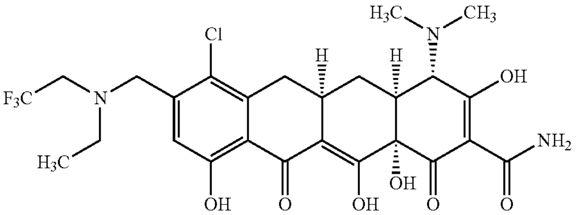

$^1$H NMR (400 MHz, $CD_3OD$) δ 7.10 (s, 1 H), 4.09 (s, 2 H), 4.05 (s, 1 H), 3.58-3.50 (m, 2 H), 3.33 (dd, J=16.4 Hz and 4.8 Hz, 1 H), 3.05-2.85 (m, 10 H), 2.33-2.25 (m, 1 H), 2.20-2.14 (m, 1 H), 1.63-1.53 (m, 1 H), 1.13 (t, J=6.8 Hz, 3 H); MS (ESI) m/z 588.1 (M+H).

S15-13-109

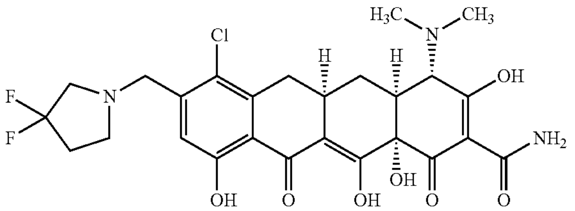

$^1$H NMR (400 MHz, $CD_3OD$) δ 7.27 (s, 1 H), 4.78-4.69 (m, 2 H), 4.15 (s, 1 H), 4.07-4.01 (m, 2 H), 3.85-3.81 (m, 2 H), 3.41 (dd, J=16.0 Hz and 4.4 Hz, 1 H), 3.17-2.95 (m, 8 H), 2.76-2.66 (m, 2 H), 2.43-2.36 (m, 1 H), 2.31-2.27 (m, 1 H), 1.70-1.60 (m, 1 H); MS (ESI) m/z 568.0 (M+H).

S15-13-110

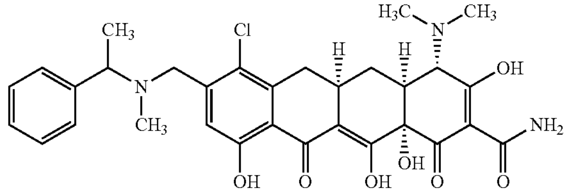

$^1$H NMR (400 MHz, $CD_3OD$) δ 7.61-7.51 (m, 5 H), 7.15 and 7.07 (each s, total 1 H), 4.71-4.58 (m, 1 H), 4.18-4.00 (m, 2 H), 3.12-2.70 (m, 13 H), 2.40-2.18 (m, 2 H), 1.86 (br s, 3 H), 1.66-1.52 (m, 1 H); MS (ESI) m/z 596.1 (M+H).

S15-13-111

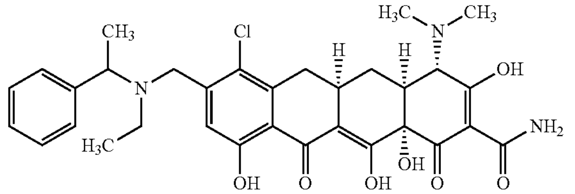

$^1$H NMR (400 MHz, $CD_3OD$) δ 7.61-7.50 (m, 5 H), 7.03, 6.99 and 6.97 (each s, total 1 H), 5.02-4.96 (m, 1 H), 4.78-4.70 (m, 1 H), 4.45-4.35 (m, 1 H), 4.34-4.20 (m, 1 H), 4.10 (s, 1 H), 3.49-3.38 (m, 1 H), 3.20-2.91 (m, 8 H), 2.37-2.30 (m, 1 H), 2.23-2.20 (m, 1 H), 1.81 (d, J=6.0 Hz, 3 H), 1.65-1.52 (m, 1 H), 1.48-1.35 (m, 3 H); MS (ESI) m/z 610.2 (M+H).

S15-13-112

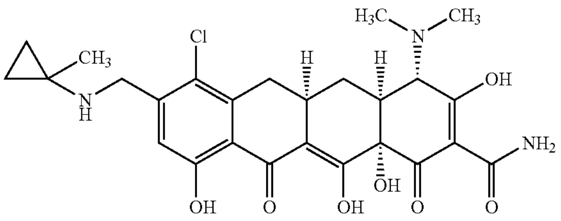

$^1$H NMR (400 MHz, $CD_3OD$) δ 7.11 (s, 1 H), 4.45 (s, 2 H), 4.09 (s, 1 H), 3.42-3.35 (m, 1 H), 3.12-2.93 (m, 8 H), 2.43-2.36 (m, 1 H), 2.25-2.22 (m, 1 H), 1.68-1.55 (m, 4 H), 1.15-1.12 (m, 2 H), 0.90-0.87 (m, 2 H); MS (ESI) m/z 532.1 (M+H).

S15-13-113

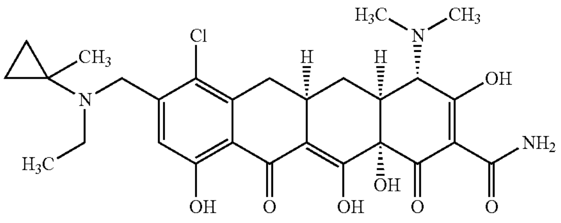

$^1$H NMR (400 MHz, $CD_3OD$) δ 7.23 (s, 1 H), 4.73-4.64 (m, 2 H), 4.12 (s, 1 H), 3.54-3.38 (m, 2 H), 3.18-2.85 (m, 9 H), 2.49-2.38 (m, 1 H), 2.28-2.24 (m, 1 H), 1.70-1.57 (m, 4 H), 1.39 (t, J=7.2 Hz, 3 H), 1.05-0.89 (m, 4 H); MS (ESI) m/z 560.1 (M+H).

S15-13-114

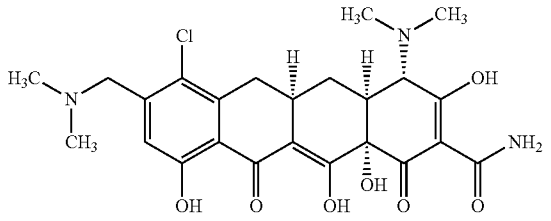

$^1$H NMR (400 MHz, $CD_3OD$) δ 7.21 (s, 1 H), 4.54-4.47 (m, 2 H), 4.12 (s, 1 H), 3.39 (dd, J=16.0 Hz and 4.4 Hz, 1 H), 3.15-2.85 (m, 14 H), 2.44-2.37 (m, 1 H), 2.28-2.22 (m, 1 H), 1.70-1.59 (m, 1 H); MS (ESI) m/z 506.1 (M+H).

S15-13-115

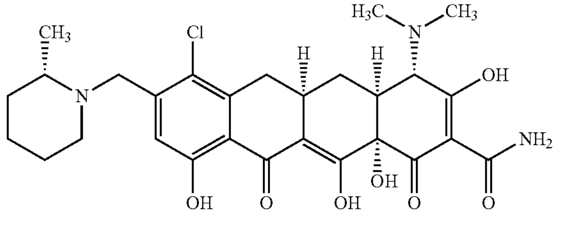

$^1$H NMR (400 MHz, $CD_3OD$) δ 7.25-7.20 (m, 1 H), 4.55-4.40 (m, 1 H), 4.29-4.25 (m, 1 H), 4.13 (s, 1 H), 3.50-3.42 (m, 2 H), 3.20-2.88 (m, 10 H), 2.48-2.40 (m, 1 H), 2.30-2.24 (m, 1 H), 2.10-2.00 (m, 1 H), 1.91-1.62 (m, 6 H), 1.59 and 1.52 (each d, J=6.4 Hz, total 3 H); MS (ESI) m/z 560.1 (M+H).

S15-13-116

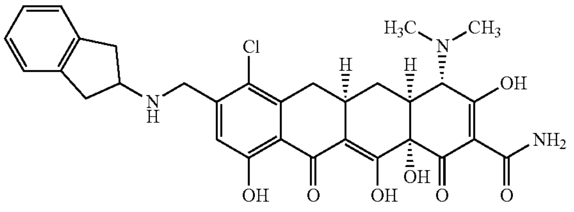

$^1$H NMR (400 MHz, $CD_3OD$) δ 7.31-7.18 (m, 5 H), 4.45 (s, 2 H), 4.26 (m, 1 H), 4.12 (s, 1 H), 3.50 (dd, J=16.4 Hz and 7.6 Hz, 2 H), 3.23 (dd, J=16.8 Hz and 6.4 Hz, 2 H), 3.05-2.97 (m, 9 H), 2.45-2.25 (m, 2 H), 1.70-1.60 (m, 1 H); MS (ESI) m/z 594.2 (M+H).

S15-13-117

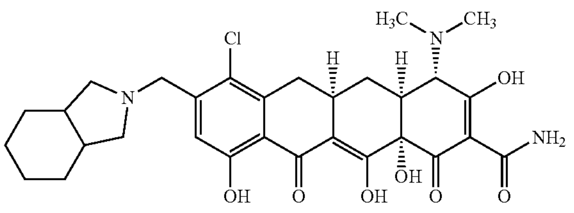

$^1$H NMR (400 MHz, $CD_3OD$) δ 7.28 (s, 1 H), 4.63 (d, J=11.2 Hz, 2 H), 4.13 (s, 1 H), 3.68-3.64 (m, 1 H), 3.52-3.51 (m, 1 H), 3.43-3.42 (m, 2 H), 3.12-2.89 (m, 9 H), 2.59 (s, 1 H), 2.43-2→2.37 (m, 2 H), 2.28-2.26 (m. 1 H) 1.76-1.43 (m, 9 H); MS (ESI) m/z 586.2 (M+H).

S15-13-118

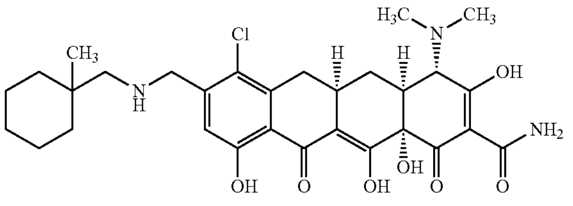

$^1$H NMR (400 MHz, $CD_3OD$) δ 7.19 (s, 1 H), 4.43 (s, 2 H), 4.14 (s, 1 H), 3.11-2.97 (m, 11 H), 2.44-2.41 (m, 1 H), 2.29-2.26 (m, 1 H), 1.70-1.64 (m, 1 H), 1.51-1.41 (m, 10 H), 1.08 (s, 3 H); MS (ESI) m/z 558.3 (M+H).

S15-13-119

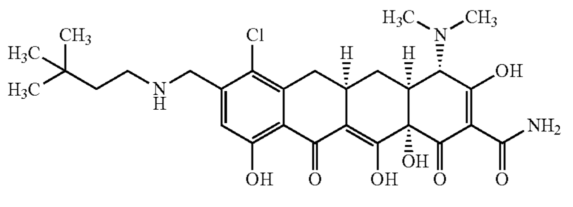

$^1H$ NMR (400 MHz, $CD_3OD$) δ 7.14 (s, 1 H), 4.39 (s, 2 H), 4.12 (s, 1 H), 3.21-2.97 (m, 11 H), 2.45-2.41 (m, 1 H), 2.28-2.25 (m, 1 H), 1.69-1.66 (m, 3 H), 0.99 (s, 9 H); MS (ESI) m/z 562.3 (M+H).

S15-13-120

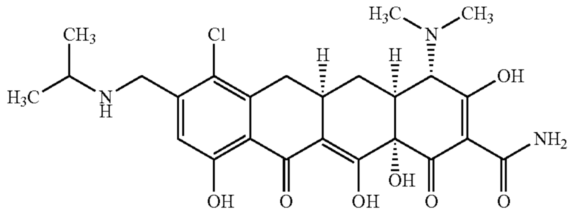

$^1H$ NMR (400 MHz, $CD_3OD$) δ 7.14 (s, 1 H), 4.36 (s, 2 H), 4.11 (s, 1 H), 3.54-3.51 (m, 1 H) 3.12-2.97 (m, 9 H), 2.45-2.38 (m, 1 H), 2.28-2.25 (m, 1 H), 1.67-1.64 (m, 1 H), 1.43 (d, J=6.4 Hz, 6 H); MS (ESI) m/z 519.9 (M+H).

S15-13-121

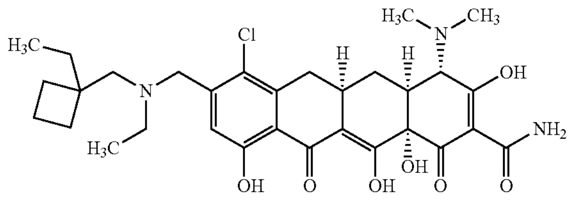

$^1H$ NMR (400 MHz, $CD_3OD$) δ 7.26 (s, 1 H), 4.57-4.47 (m, 2 H), 4.14 (s, 1 H), 3.43-3.39 (m, 2 H), 3.21-2.95 (m, 11 H), 2.46-2.38 (m, 1 H), 2.29-2.26 (m, 1 H), 2.05-1.85 (m, 6 H), 1.82-1.72 (m, 2 H), 1.70-1.60 (m, 1 H), 1.46 (t, J=7.2 Hz, 3 H), 0.87 (t, J=6.8 Hz, 3 H); MS (ESI) m/z 602.1 (M+H).

S15-13-122

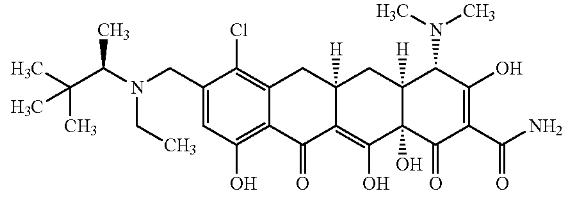

$^1H$ NMR (400 MHz, $CD_3OD$) δ 7.24 and 7.12 (each s, total 1 H), 4.75-4.70, 4.54-4.44 and 4.34-4.27 (each m, total 2 H), 4.03 (s, 1 H), 3.55-3.46 (m, 1 H), 3.40-3.26 (m, 1 H), 3.18-2.85 (m, 10 H), 2.40-2.30 (m, 1 H), 2.20-2.14 (m, 1 H), 1.61-1.52 (m, 1 H), 1.49 and 1.25 (each t, J=6.8 Hz, total 3 H), 1.40 and 1.35 (each d, J=7.2 Hz, total 3 H), 1.16 (s, 3 H), 0.99 (s, 3 H), 0.85 (s, 3 H); MS (ESI) m/z 590.4 (M+H).

S15-13-123

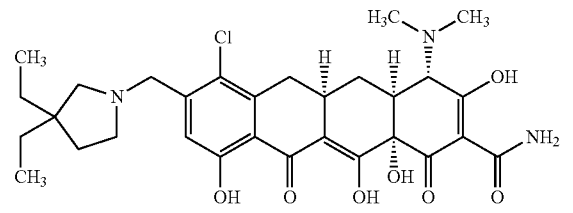

$^1H$ NMR (400 MHz, $CD_3OD$) δ 7.15 (s, 1 H), 4.52 (br s, 2 H), 4.03 (s, 1 H), 3.55 (s, 1 H), 3.35-3.30 (m, 3 H), 3.03-2.88 (m, 9 H), 2.38-2.30 (m, 1 H), 2.19-2.15 (m, 1 H), 1.93-1.77 (m, 2 H)□1.54-1.47 (m, 5 H), 0.83-0.79 (m, 6 H); MS (ESI) m/z 588.0 (M+H).

S15-13-124

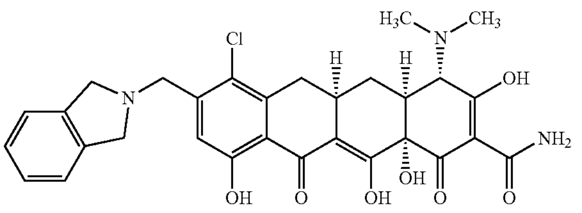

$^1H$ NMR (400 MHz, $CD_3OD$) δ 7.32 (s, 4 H), 7.12 (s, 1 H), 4.74-4.72 (m, 6 H), 4.03 (s, 1 H), 3.39-3.31 (m, 1 H), 3.05-2.90 (m, 8 H), 2.19-2.16 (m, 1 H), 1.61-1.53 (m, 1 H); MS (ESI) m/z 580.0 (M+H).

S15-13-125

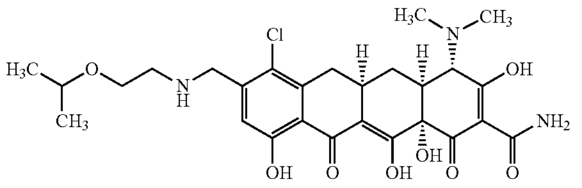

$^1H$ NMR (400 MHz, $CD_3OD$) δ 7.05 (s, 1 H), 4.35 (s, 2 H), 4.04 (s, 1 H), 3.69-3.61 (m, 3 H), 3.36-3.24 (m, 3 H), 3.03-2.81 (m, 8 H), 2.38-2.30 (m, 1 H), 2.17-2.16 (m, 1 H), 1.63-1.53 (m, 1 H), 1.14-1.12 (m, 6 H); MS (ESI) m/z 564.1 (M+H).

S15-13-126

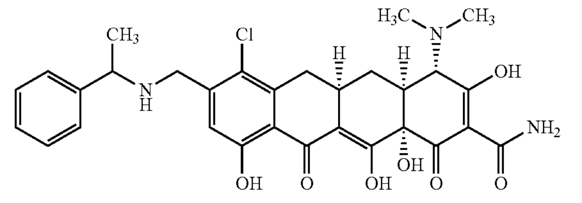

$^1H$ NMR (400 MHz, $CD_3OD$) δ 7.46-7.42 (m, 5 H), 6.97 (s, 1 H), 4.49-4.47 (m, 1 H), 4.16-3.97 (m, 2 H), 2.99-2.88 (m, 10 H), 2.32-2.25 (m, 2 H), 1.95-1.94 (m, 1 H), 1.69-1.67 (m, 3 H), 1.57-1.52 (m, 1 H); MS (ESI) m/z 582.4 (M+H).

S15-13-127

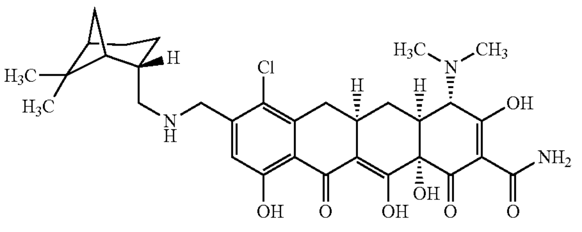

$^1$H NMR (400 MHz, $CD_3OD$) δ 7.08 (s, 1 H), 4.31 (s, 2 H), 4.05 (s, 1 H), 3.36-3.31 (m, 2 H), 3.12-2.91 (m, 9 H), 2.47-2.36 (m, 3 H), 2.33-2.29 (m, 1 H), 2.08-1.86 (m, 5 H), 1.60-1.53 (m, 2 H), 1.25-1.14 (s, 3 H), 1.05-0.91 (s, 3 H); MS (ESI) m/z 614.1 (M+H).

S15-13-128

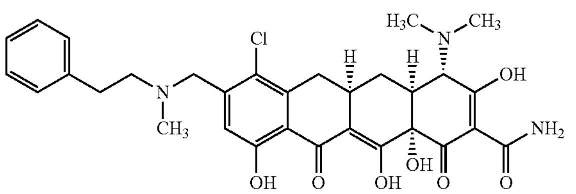

$^1$H NMR (400 MHz, $CD_3OD$) δ 7.27-7.16 (m, 6 H), 4.70-4.63 (m, 1 H), 4.41-4.34 (m, 1 H), 4.06 (s, 1 H), 3.48-3.41 (m, 2 H), 3.33-3.29 (m, 1 H), 3.12-2.80 (m, 13 H), 2.35-2.28 (m, 1 H), 2.20-2.17 (m, 1 H), 1.61-1.51 (m, 1 H); MS (ESI) m/z 596.0 (M+H).

S15-13-129

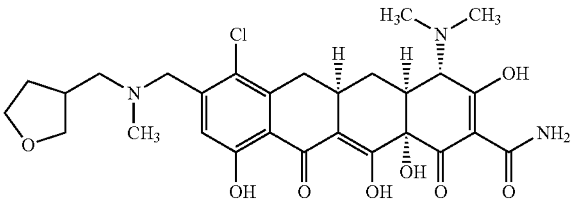

$^1$H NMR (400 MHz, $CD_3OD$) δ 7.26 (s, 1 H), 4.74 (m, 1 H), 4.42 (m, 1 H), 4.15 (s, 1 H), 3.97-3.89 (m, 2 H), 3.80-3.77 (m, 1 H), 3.53 (m, 1 H), 3.39 (s, 3 H), 3.13-2.88 (m, 12 H), 2.46-2.38 (m, 1 H), 2.29-2.26 (m, 2 H), 1.71-1.64 (m, 2 H); MS (ESI) m/z 576.1 (M+H).

S15-13-130

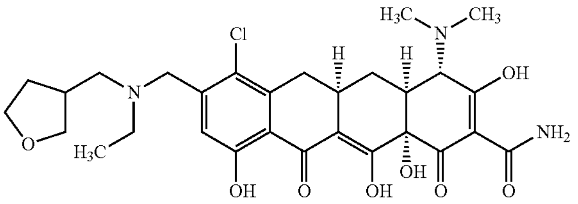

$^1$H NMR (400 MHz, $CD_3OD$) δ 7.24 (s, 1 H), 4.64-4.53 (m, 2 H), 4.13 (s, 1 H), 3.96-3.87 (m, 2 H), 3.77-3.75 (m, 1 H), 3.52-3.34 (m, 5 H), 3.22-2.79 (m, 10 H), 2.48-2.40 (m, 1 H), 2.28-2.26 (m, 2 H), 1.71-1.65 (m, 2 H), 1.44-1.41 (m, 3 H); MS (ESI) m/z 590.1 (M+H).

S15-13-131

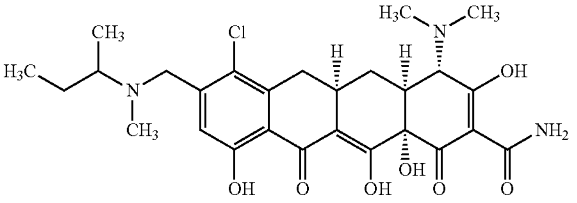

$^1$H NMR (400 MHz, $CD_3OD$) δ 7.15 and 7.14 (each s, total 1 H), 4.59-4.54 (m, 1 H), 4.24-4.15 (m, 1 H), 4.05 (s, 1 H), 3.39-3.30 (m, 2 H), 3.03-2.88 (m, 8 H), 2.70 (s, 3 H), 2.37-2.29 (m, 1 H), 2.20-2.17 (m, 1 H), 1.95-1.88 (m, 1 H), 1.70-1.52 (m, 2 H), 1.40-1.34 (m, 3 H), 0.01-0.95 (m, 3 H); MS (ESI) m/z 548.0 (M+H).

S15-13-132

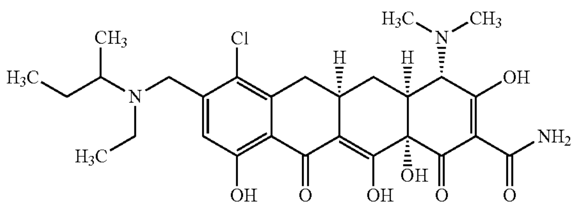

$^1$H NMR (400 MHz, $CD_3OD$) δ 7.12 and 7.10 (each s, total 1 H), 4.53 (m, 1 H), 4.28-4.26 (m, 1 H), 4.03 (s, 1 H), 3.41-3.35 (m, 3 H), 3.03-2.87 (m, 9 H), 2.39-2.31 (m, 1 H), 2.18-2.15 (m, 1 H), 1.91 (m, 1 H), 1.71-1.52 (m, 2 H), 1.43-1.23 (m, 6 H); 0.99-0.95 (m, 3 H); MS (ESI) m/z 562.1 (M+H) □

S15-13-133

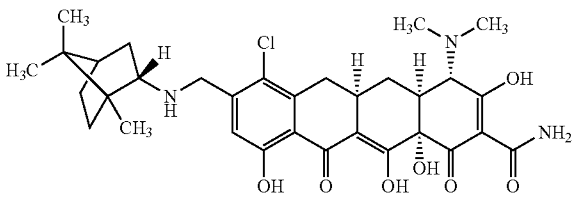

$^1$H NMR (400 MHz, $CD_3OD$) δ 7.13 (s, 1 H), 4.33 (s, 2 H), 4.04 (s, 1 H), 3.40-3.30 (m, 2 H), 3.12-2.88 (m, 9 H), 2.32-2.18 (m, 2 H), 1.77-1.71 (m, 2 H), 1.53-1.50 (m, 2 H), 1.33-1.20 (m, 3 H), 0.95 (s, 3 H), 0.84 (d, J=9.6 Hz, 6 H); MS (ESI) m/z 614.4 (M+H) □

S15-13-134

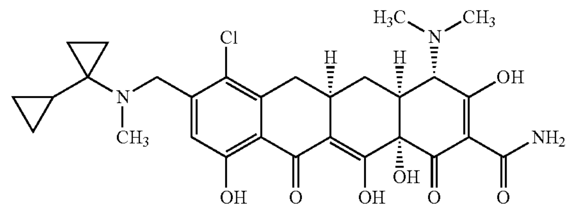

$^1$H NMR (400 MHz, $CD_3OD$) δ 7.17 (s, 1 H), 4.80-4.61 (m, 2 H), 4.04 (s, 1 H), 3.37-3.27 (m, 1 H), 3.09-2.85 (m, 11 H), 2.38-2.27 (m, 1 H), 2.22-2.15 (m, 1 H), 1.66-1.50 (m, 2 H), 1.22-1.04 (m, 4 H), 0.92-0.81 (m, 1 H), 0.78-0.65 (m, 3 H); MS (ESI) m/z 572.2 (M+H).

S15-13-135

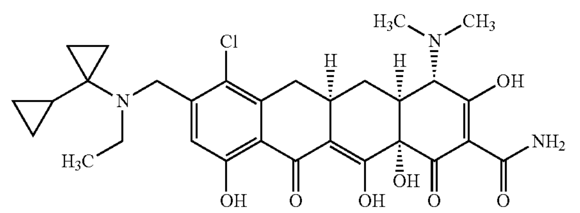

$^1H$ NMR (400 MHz, $CD_3OD$) δ 7.19 (s, 1 H), 4.80-4.62 (m, 2 H), 4.05 (s, 1 H), 3.73-3.60 (m, 1 H), 3.42-3.28 (m, 2 H), 3.10-2.85 (m, 8 H), 2.40-2.27 (m, 1 H), 2.22-2.15 (m, 1 H), 1.62-1.50 (m, 2 H), 1.35-1.15 (m, 4 H), 0.97-0.78 (m, 2 H), 0.78-0.60 (m, 3 H), 0.35-0.27 (m, 2 H); MS (ESI) m/z 586.2 (M+H).

S15-13-136

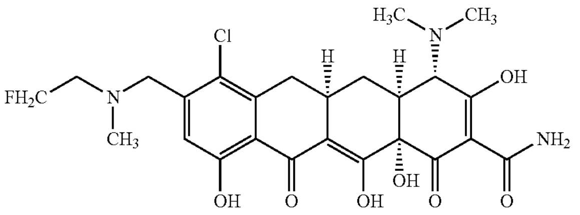

$^1H$ NMR (400 MHz, $CD_3OD$) δ 7.17 (s, 1 H), 4.93 (br s, 2 H), 4.74-4.39 (m, 2 H), 3.65 (br d, J=27.2 Hz, 2 H), 3.36 (dd, J=16.4 Hz and 4.4 Hz, 1 H), 3.10-2.89 (m, 11 H), 2.43-2.35 (m, 1 H), 2.25-2.17 (m, 1 H), 1.66-1.55 (m, 1 H); MS (ESI) m/z 537.9 (M+H).

S15-13-137

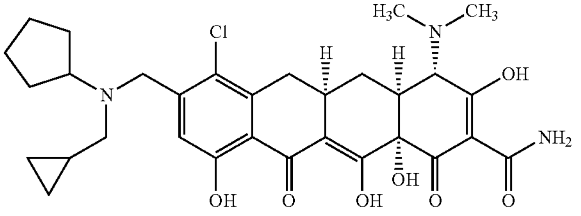

$^1H$ NMR (400 MHz, $CD_3OD$) δ 7.24 (s, 1 H), 4.74-4.68 (m, 1 H), 4.59-4.54 (m, 1 H), 4.13 (s, 1 H), 4.08-4.04 (m, 1 H), 3.42 (dd, J=16.4 Hz and 4.4 Hz, 1 H), 3.18-2.94 (m, 10 H), 2.47-2.40 (m, 1 H), 2.31-2.08 (m, 3 H), 2.05-1.92 (m, 1 H), 1.90-1.79 (m, 3 H), 1.78-1.60 (m, 3 H), 1.20-1.09 (m, 1 H), 0.82-0.70 (m, 2 H), 0.45-0.36 (m, 2 H); MS (ESI) m/z 600.0 (M+H).

S15-13-138

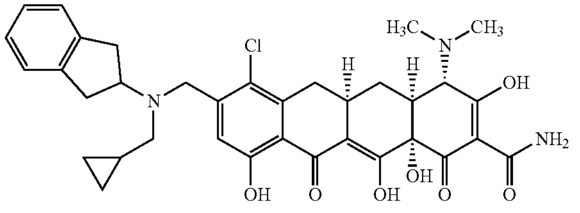

$^1H$ NMR (400 MHz, $CD_3OD$) δ 7.31-7.18 (m, 5 H), 4.70-4.48 (m, 3 H), 4.12 (s, 1 H), 3.55-3.35 (m, 5 H), 3.18-2.93 (m, 10 H), 2.45-2.37 (m, 1 H), 2.30-2.20 (m, 1 H), 1.70-1.58 (m, 1 H), 1.23-1.10 (m, 1 H), 0.82-0.70 (m, 2 H), 0.43-0.36 (m, 2 H); MS (ESI) m/z 648.1 (M+H).

S15-13-139

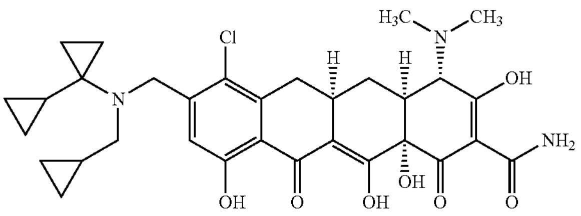

$^1H$ NMR (400 MHz, $CD_3OD$) δ 7.29 and 7.26 (each s, total 1 H), 4.85-4.73 (m, 1 H), 4.14 (s, 1 H), 3.80-3.73 (m, 1 H), 3.62-3.52 (m, 1 H), 3.48-3.38 (m, 1 H), 3.25-2.86 (m, 9 H), 2.50-2.36 (m, 1 H), 2.30-2.22 (m, 1 H), 1.78-1.60 (m, 2 H), 1.55-1.36 (m, 1 H), 1.27-1.13 (m, 1 H), 1.05-0.68 (m, 8 H), 0.52-0.28 (m, 4 H); MS (ESI) m/z 612.1 (M+H).

S15-13-140

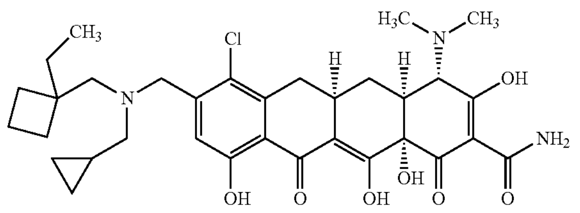

$^1H$ NMR (400 MHz, $CD_3OD$) δ 7.30 (s, 1 H), 4.70-4.57 (m, 2 H), 4.13 (s, 1 H), 3.58-3.55 (m, 1 H), 3.44-3.39 (m, 1 H), 3.26-2.95 (m, 11 H), 2.48-2.37 (m, 1 H), 2.31-2.24 (m, 1 H), 2.15-1.72 (m, 7 H), 1.71-1.59 (m, 1 H), 1.35-1.24 (m, 3 H), 0.90-0.79 (m, 4 H), 0.55-0.44 (m, 2 H); MS (ESI) m/z 627.9 (M+H).

S15-13-141

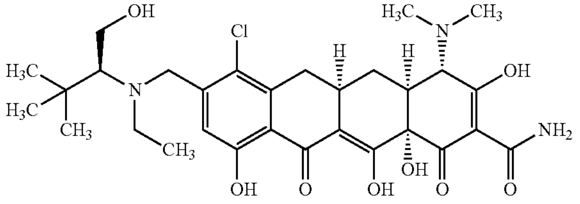

$^1H$ NMR (400 MHz, $CD_3OD$) δ 7.29 and 7.24 (each s, total 1 H), 4.20-4.08 (m, 3 H), 3.93-3.57 (m, 3 H), 3.48-3.38 (m, 2 H), 3.21-2.89 (m, 9 H), 2.50-2.40 (m, 1 H), 2.32-2.26 (m, 1 H), 1.75-1.60 (m, 1 H), 1.68-1.58 and 1.44-1.36 (each m, total 3 H), 1.31 and 1.01 (each s, total 9 H); MS (ESI) m/z 606.1 (M+H).

S15-13-142

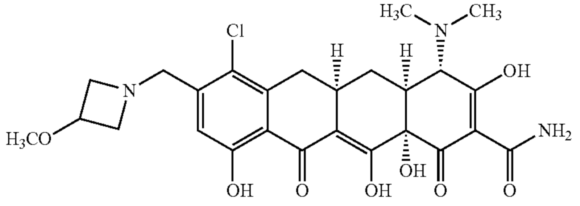

$^1H$ NMR (400 MHz, $CD_3OD$) δ 7.07 (s, 1 H), 4.64 (s, 2 H), 4.57-4.09 (m, 6 H), 3.39 (dd, J=16.0 Hz and 4.4 Hz, 1 H), 3.35

(s, 3 H), 3.15-2.95 (m, 8 H), 2.47-2.37 (m, 1 H), 2.28-2.22 (m, 1 H), 1.70-1.57 (m, 1 H); MS (ESI) m/z 548.4 (M+H).

S15-13-143

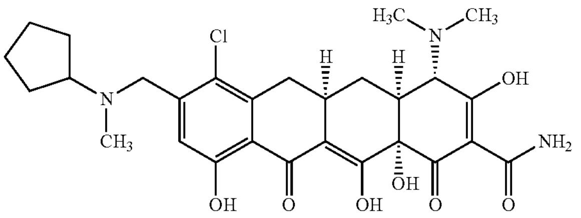

$^1$H NMR (400 MHz, $CD_3OD$) δ 7.22 (s, 1 H), 4.72 (t, J=12.8 Hz, 1 H), 4.33 (t, J=12.4 Hz, 1 H), 4.13 (s, 1 H), 3.88-3.79 (m, 1 H), 3.45-3.37 (m, 1 H), 3.18-2.73 (m, 11 H), 2.48-2.36 (m, 1 H), 2.36-2.14 (m, 3 H), 1.98-1.82 (m, 4 H), 1.78-1.60 (m, 3 H); MS (ESI) m/z 560.0 (M+H).

S15-13-144

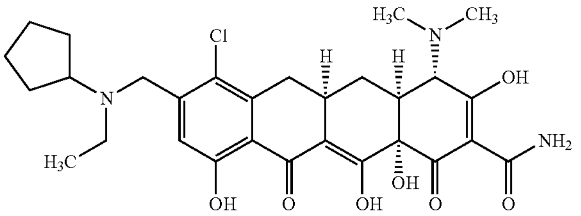

$^1$H NMR (400 MHz, $CD_3OD$) δ 7.22 (s, 1 H), 4.62-4.46 (m, 2 H), 4.23 (s, 1 H), 4.42-4.35 (m, 1 H), 3.43-3.37 (m, 1 H), 3.25-2.95 (m, 10 H), 2.45-2.37 (m, 1 H), 2.31-2.14 (m, 3 H), 2.00-1.80 (m, 4 H), 1.79-1.60 (m, 3 H), 1.36 (t, J=6.8 Hz, 3 H); MS (ESI) m/z 574.1 (M+H).

S15-13-145

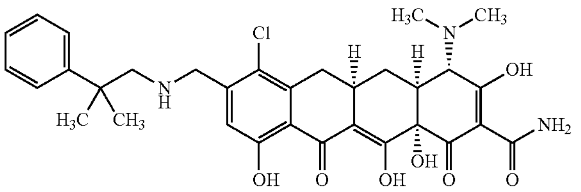

$^1$H NMR (400 MHz, $CD_3OD$) δ 7.43-7.28 (m, 5 H), 7.00 (s, 1H), 7.28 (s, 2 H), 7.11 (s, 1 H), 3.41 (s, 2 H), 3.15-2.95 (m, 9 H), 2.41-2.33 (m, 1 H), 2.26-2.23 (m, 1 H), 1.60-1.59 (m, 1 H), 1.46 (s, 6 H); MS (ESI) m/z 610.0 (M+H).

S15-13-146

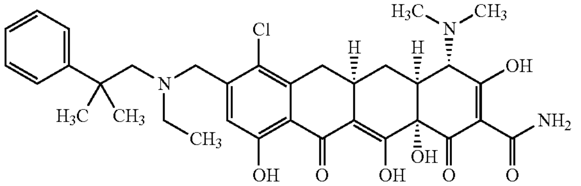

$^1$H NMR (400 MHz, $CD_3OD$) δ 7.55-7.27 (m, 5 H), 6.96 and 6.94 (each s, total 1 H), 4.30-4.18 (m, 2 H), 4.12 (s, 1 H), 3.75-3.69 (m, 1 H), 3.63-3.56 (m, 1 H), 3.34 (s, 2 H), 3.24-2.86 (m, 9 H), 2.42-2.30 (m, 1 H), 2.27-2.23 (m, 1 H), 1.69-1.59 (m, 1 H), 1.54 (s, 3 H), 1.45 (s, 3 H), 1.38-1.32 (m, 3 H); MS (ESI) m/z 638.1 (M+H).

S15-13-147

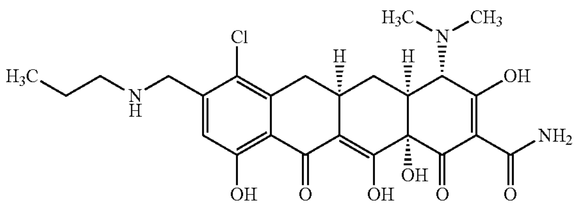

$^1$H NMR (400 MHz, $CD_3OD$) δ 7.13 (s, 1 H), 4.37 (s, 2 H), 4.11 (s, 1 H), 3.41 (dd, J=16.4 Hz and 4.4 Hz, 1 H), 3.15-2.95 (m, 10 H), 2.45-2.37 (m, 1 H), 2.29-2.24 (m, 1 H), 1.84-1.74 (m, 2 H), 1.70-1.60 (m, 1 H), 1.05 (t, J=6.8 Hz, 3 H); MS (ESI) m/z 519.9 (M+H).

S15-13-148

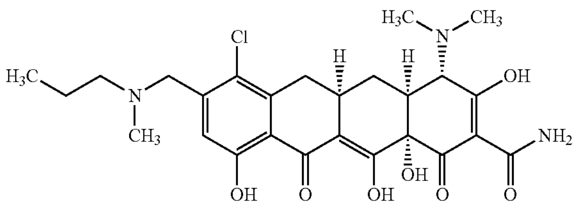

$^1$H NMR (400 MHz, $CD_3OD$) δ 7.22 (s, 1 H), 4.66 (t, J=13.6 Hz, 1 H), 4.38 (t, J=12.8 Hz, 1 H), 4.13 (s, 1 H), 3.41 (dd, J=16.0 Hz and 4.0 Hz, 1 H), 3.30-2.95 (m, 10 H), 2.86 (s, 3 H), 2.45-2.38 (m, 1 H), 2.30-2.24 (m, 1 H), 1.91-1.80 (m, 2 H), 1.70-1.60 (m, 1 H), 1.03 (t, J=7.2 Hz, 3 H); MS (ESI) m/z 534.0 (M+H).

S15-13-149

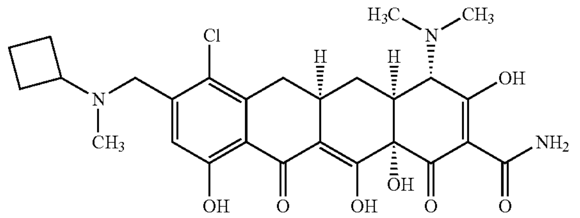

$^1$H NMR (400 MHz, $CD_3OD$) δ 7.23 (s, 1 H), 4.55 (t, J=14.4 Hz, 1 H), 4.38 (t, J=14.4 Hz, 1 H), 4.14 (s, 1 H), 3.99-3.93 (m, 1 H), 3.43-3.38 (m, 1 H), 3.17-2.87 (m, 8 H), 2.74 (s, 3 H), 2.46-2.23 (m, 6 H), 1.93-135 (m, 2 H), 1.70-1.60 (m, 1 H); MS (ESI) m/z 546.0 (M+H).

S15-13-150

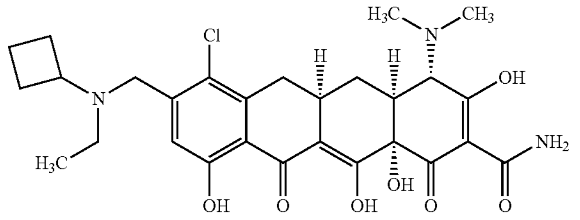

$^1H$ NMR (400 MHz, $CD_3OD$) δ 7.22 (s, 1 H), 4.49-4.37 (m, 2 H), 4.13 (s, 1 H), 4.08-3.98 (m, 1 H), 3.41 (dd, J=16.0 Hz and 4.0 Hz, 1 H), 3.25-2.95 (m, 10 H), 2.47-2.12 (m, 6 H), 1.90-1.75 (m, 2 H), 1.70-1.60 (m, 1 H), 1.38 (t, J=6.8 Hz, 3 H); MS (ESI) m/z 560.0 (M+H).

S15-13-151

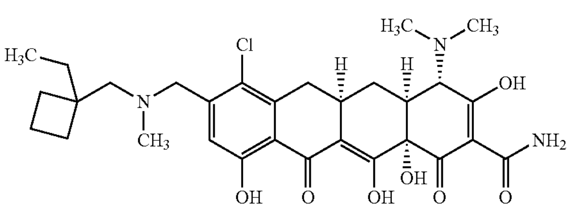

$^1H$ NMR (400 MHz, $CD_3OD$) δ 7.26 (s, 1 H), 4.68-4.61 (M, 1 H), 4.44-4.39 (m, 1 H), 4.14 (s, 1 H), 3.44-3.35 (m, 2 H), 3.18-2.88 (m, 11 H), 2.46-2.39 (m, 1 H), 2.30-2.26 (m, 1 H), 2.15-1.60 (m, 8 H), 0.89 (t, J=6.8 Hz, 3 H); MS (ESI) m/z 588.1 (M+H).

S15-13-152

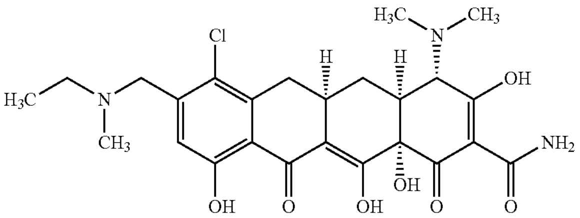

$^1H$ NMR (400 MHz, $CD_3OD$) δ 7.22 (s, 1 H), 4.64 (t, J=13.6 Hz, 1 H), 4.38 (t, J=12.8 Hz, 1 H), 4.14 (s, 1 H), 3.45-3.36 (m, 2 H), 3.18-2.95 (m, 9 H), 2.86 (s, 3 H), 2.46-2.38 (m, 1 H), 2.29-2.26 (m, 1 H), 1.70-1.60 (m, 1 H), 1.45 (t, J=6.8 Hz, 3 H); MS (ESI) m/z 520.0 (M+H).

S15-13-153

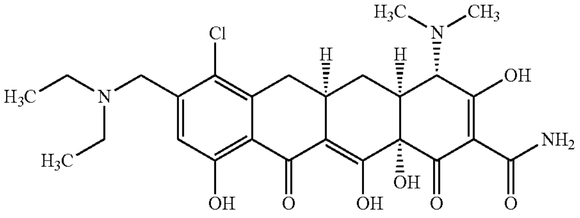

$^1H$ NMR (400 MHz, $CD_3OD$) δ 7.21 (s, 1 H), 4.55-4.48 (m, 2 H), 4.13 (s, 1 H), 3.44-3.39 (m, 1 H), 3.18-2.86 (m, 12 H), 2.46-2.39 (m, 1 H), 2.28-2.25 (m, 1 H), 1.70-1.60 (m, 1 H), 1.44-1.37 (m, 6 H); MS (ESI) m/z 534.0 (M+H).

S15-13-154

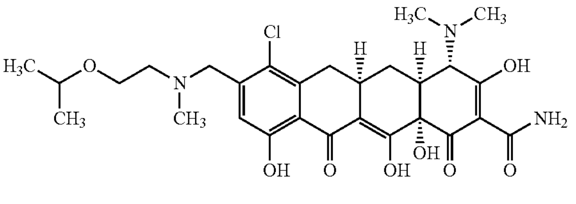

$^1H$ NMR (400 MHz, $CD_3OD$) δ 7.21 (s, 1 H); 4.81-4.74 (m, 1 H), 4.44-4.39 (m, 1 H), 4.13 (s, 1 H), 3.84 (br s, 2 H), 3.76-3.68 (m, 1 H), 3.49 (br s, 2 H), 3.41 (dd, J=16.4 Hz and 4.4 Hz, 1 H), 3.18-2.85 (m, 11 H), 2.46-2.39 (m, 1 H), 2.29-2.26 (m, 1 H), 1.70-1.60 (m, 1 H), 1.22-1.18 (m, 6 H); MS (ESI) m/z 578.0 (M+H).

S15-13-155

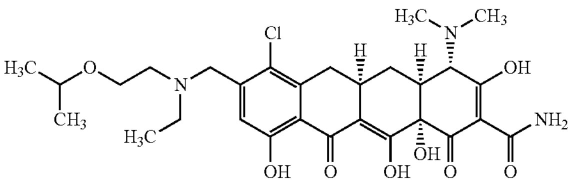

$^1H$ NMR (400 MHz, $CD_3OD$) δ 7.23 (s, 1 H), 4.72-4.66 (m, 1 H), 4.57-4.52 (m, 1 H), 4.11 (s, 1 H), 3.83-3.81 (m, 2 H), 3.72-3.66 (m, 1 H), 3.53-3.47 (m, 1 H), 3.45-3.34 (m, 4 H), 3.17-2.95 (m, 9 H), 2.47-2.39 (m, 1 H), 2.28-2.24 (m, 1 H), 1.70-1.60 (m, 1 H), 1.50 (t, J=6.8 Hz, 3 H), 1.21-1.13 (m, 6); MS (ESI) m/z 592.0 (M+H).

S15-13-156

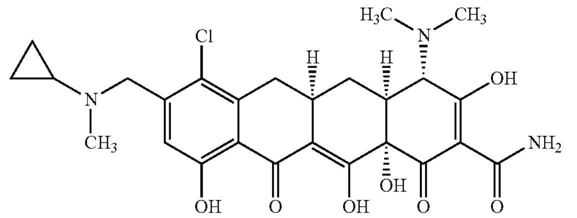

$^1H$ NMR (400 MHz, $CD_3OD$) δ 7.23 (s, 1 H), 4.80-4.70 (m, 2 H), 4.13 (s, 1 H), 3.41 (dd, J=16.0 Hz and 4.4 Hz, 1 H), 3.18-2.96 (m, 12 H), 2.46-2.39 (m, 1 H), 2.29-2.25 (m, 1 H), 1.70-1.60 (m, 1 H), 1.10-0.82 (m, 4 H); MS (ESI) m/z 532.0 (M+H).

S15-13-157

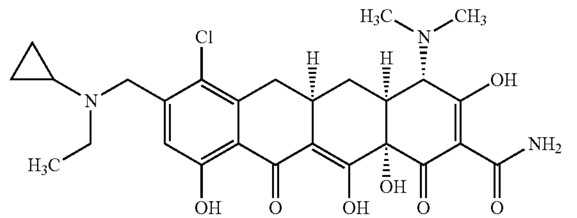

$^1H$ NMR (400 MHz, $CD_3OD$) δ 7.24 (s, 1 H), 4.76-4.60 (m, 2 H), 4.13 (s, 1 H), 3.49-3.39 (m, 3 H), 3.18-2.95 (m, 9 H), 2.47-2.39 (m, 1 H), 2.28-2.25 (m, 1 H), 1.70-1.61 (m, 1 H), 1.49 (t, J=7.6 Hz, 3 H), 1.10-0.80 (m, 3 H), 0.75-0.60 (m, 1 H); MS (ESI) m/z 546.0 (M+H).

S15-13-158

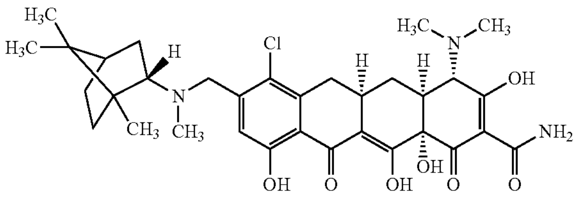

$^1$H NMR (400 MHz, $CD_3OD$) δ 7.22 (s, 1 H), 4.82-4.76 (m, 1 H), 4.33-4.27 (m, 1 H), 4.13 (s, 1 H), 3.75-3.65 (m, 1 H), 3.47-3.39 (m, 1 H), 3.18-2.75 (m, 11 H), 2.51-2.39 (m, 1 H), 2.29-2.25 (m, 1 H), 2.20-1.76 (m, 4 H), 1.70-1.40 (m, 4 H), 1.30 (s, 3 H), 0.99-0.96 (m, 6 H); MS (ESI) m/z 628.1 (M+H).

S15-13-159

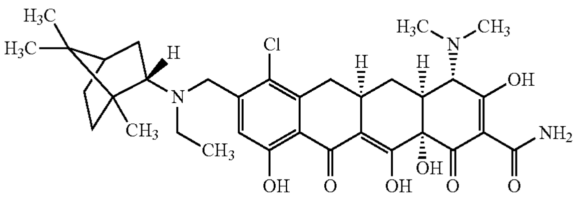

$^1$H NMR (400 MHz, $CD_3OD$) δ 7.25 and 7.24 (each s, total 1 H), 4.82-4.73 (m, 1 H), 4.53-4.44 (m, 1 H), 4.13 (s, 1 H), 3.88-3.71 (m, 1 H), 3.48-3.32 (m, 3 H), 3.18-2.95 (m, 8 H), 2.54-2.36 (m, 2 H), 2.29-2.25 (m, 1 H), 1.98-1.85 (m, 2 H), 1.84-1.75 (m, 1 H), 1.70-1.60 (m, 1 H), 1.59-1.40 (m, 3 H), 1.38-1.27 (m, 6 H), 1.00-0.93 (m, 6 H); MS (ESI) m/z 642.1 (M+H).

S15-13-160

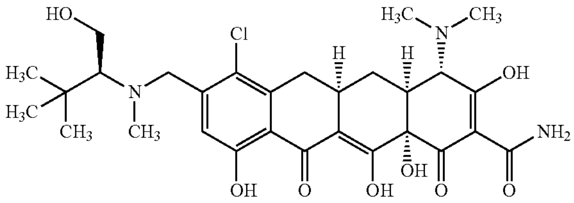

$^1$H NMR (400 MHz, $CD_3OD$) δ 7.29 (s, 1 H), 4.97-4.94 (m, 1 H), 4.68-4.65 (m, 1 H), 4.17-4.06 (m, 3 H), 3.45-3.40 (m, 2 H), 3.18-2.95 (m, 11 H), 2.45-2.38 (m, 1 H), 2.30-2.26 (m, 1 H), 1.70-1.61 (m, 1 H), 1.05 (s, 9 H); MS (ESI) m/z 592.1 (M+H).

S15-13-161

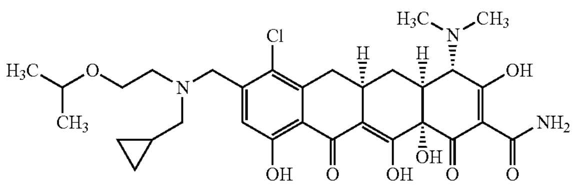

$^1$H NMR (400 MHz, $CD_3OD$) δ 7.26 (s, 1 H), 4.75-4.67 (m, 2 H), 4.12 (s, 1 H), 3.88-3.76 (m, 2 H), 3.75-3.56 (m, 2 H), 3.55-3.37 (m, 2 H), 3.28-2.95 (m, 10 H), 2.46-2.39 (m, 1 H), 2.29-2.25 (m, 1 H), 1.71-1.61 (m, 1 H), 1.30-1.10 (m, 7 H), 0.85-0.74 (m, 2 H), 0.51-0.42 (m, 2 H); MS (ESI) m/z 618.1 (M+H).

S15-13-162

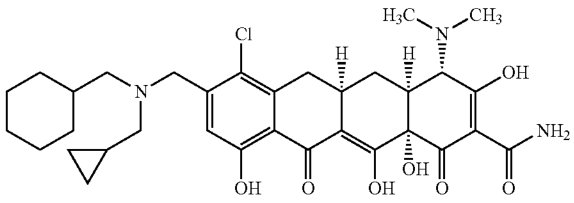

$^1$H NMR (400 MHz, $CD_3OD$) δ 7.24 (s, 1 H), 4.70-4.59 (m, 2 H), 4.12 (s, 1 H), 3.42 (dd, J=16.4 Hz and 4.4 Hz, 1 H), 3.25-2.95 (m, 12 H), 2.47-2.40 (m, 1 H), 2.29-2.25 (m, 1 H), 1.92-1.60 (m, 7 H), 1.40-1.12 (m, 4 H), 1.10-0.90 (m, 2 H), 0.89-0.78 (m, 2 H), 0.52-0.45 (m, 2 H); MS (ESI) m/z 628.1 (M+H).

S15-13-163

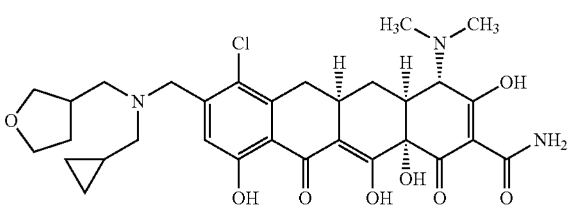

$^1$H NMR (400 MHz, $CD_3OD$) 7.26 (s, 1 H), 4.75-4.60 (m, 2 H), 4.13 (s, 1 H), 3.97-3.70 (m, 2 H), 3.69-3.61 (m, 1 H), 3.55-3.38 (m, 3 H), 3.28-2.95 (m, 11 H), 2.86-2.76 (m, 1 H), 2.48-2.40 (m, 1 H), 2.31-2.19 (m, 2 H), 1.76-1.57 (m, 2 H), 1.30-1.20 (m, 1 H), 0.84-0.82 (m, 2 H), 0.50-0.49 (m, 2 H); MS (ESI) m/z 616.1 (M+H).

S15-13-164

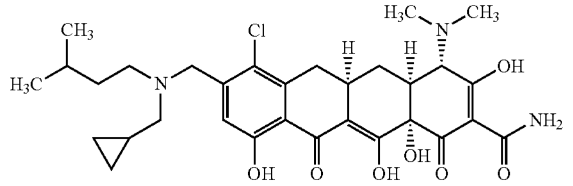

$^1$H NMR (400 MHz, $CD_3OD$) δ 7.23 (s, 1 H), 4.72-4.66 (m, 1 H), 4.58-4.55 (m, 1 H), 4.13 (s, 1 H), 3.42 (dd, J=16.0 Hz and 4.4 Hz, 1 H), 3.28-2.95 (m, 12 H), 2.48-2.40 (m, 1 H), 2.30-2.25 (m, 1 H), 1.78-1.60 (m, 4 H), 1.25-1.16 (m, 1 H), 0.98-0.95 (m, 6 H), 0.83-0.79 (m, 2 H), 0.48-0.46 (m, 2 H); MS (ESI) m/z 602.1 (M+H).

S15-13-165

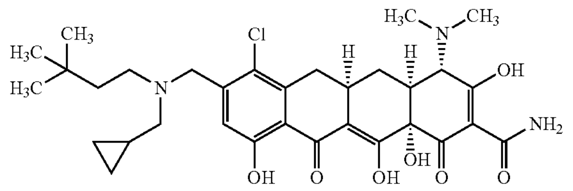

$^1$H NMR (400 MHz, $CD_3OD$) δ 7.23 (s, 1 H), 4.75-4.66 (m, 1 H), 4.60-4.52 (m, 1 H), 4.12 (s, 1 H), 3.47-3.38 (m, 1 H), 3.25-2.95 (m, 12 H), 2.48-2.40 (m, 1 H), 2.30-2.25 (m, 1 H), 1.78-1.61 (m, 3 H), 1.25-1.16 (m, 1 H), 0.94 (s, 9 H), 0.83-0.80 (m, 2 H), 0.49-0.47 (m, 2 H); MS (ESI) m/z 616.0 (M+H).

S15-13-166

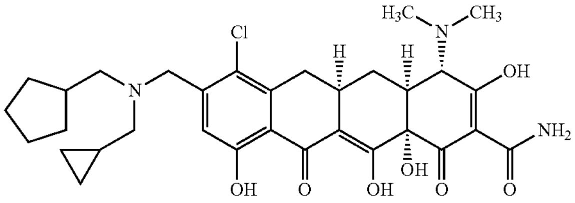

$^1$H NMR (400 MHz, $CD_3OD$) δ 7.24 (s, 1 H), 4.74-4.61 (m, 2 H), 4.13 (s, 1 H), 3.44-3.40 (m, 2 H), 3.28-2.95 (m, 11 H), 2.47-2.35 (m, 2 H), 2.29-2.26 (m, 1 H), 2.00-1.90 (m, 1 H), 1.75-1.59 (m, 5 H), 1.38-1.16 (m, 3 H), 0.85-0.78 (m, 2 H), 0.51-0.46 (m, 2 H); MS (ESI) m/z 614.1 (M+H).

S15-13-167

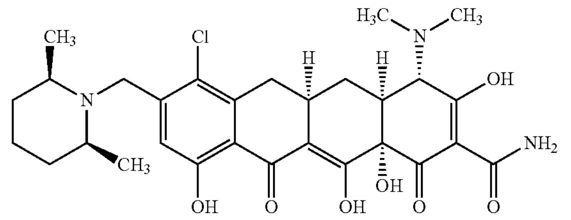

$^1$H NMR (400 MHz, $CD_3OD$) δ 7.16 (s, 1 H), 4.73 (br s, 1 H), 4.48 (dd, J=27.6 Hz and 16.0 Hz, 2 H), 4.10 (br s, 1 H), 3.69-3.46 (m, 2 H), 3.40-3.29 (m, 1 H), 3.10-2.88 (m, 7 H), 2.38-2.20 (m, 2 H), 1.98-1.72 (m, 5 H), 1.71-1.50 (m, 2 H), 1.40-1.18 (m, 6 H); MS (ESI) m/z 574.1 (M+H).

S15-13-168

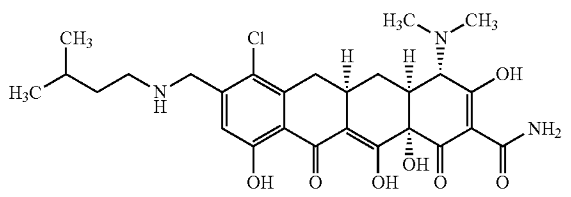

$^1$H NMR (400 MHz, $CD_3OD$) δ 7.13 (s, 1 H), 4.38 (s, 2 H), 4.11 (s, 1 H), 3.41 (dd, J=16.0 Hz and 4.4 Hz, 1 H), 3.22-2.87 (m, 10 H), 2.45-2.37 (m, 1 H), 2.28-2.25 (m, 1 H), 1.73-1.64 (m, 4 H), 1.01-0.97 (m, 6 H); MS (ESI) m/z 548.0 (M+H).

S15-13-169

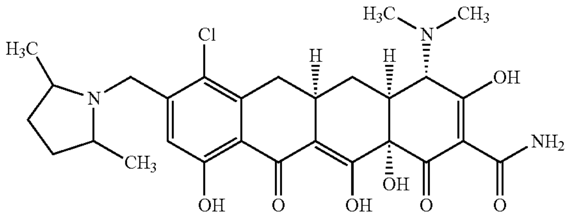

$^1$H NMR (400 MHz, $CD_3OD$) δ 7.25 (s, 1 H), 4.62 (dd, J=18.4 Hz and 13.6 Hz, 2 H), 4.11 (s, 1 H), 3.86-3.81 (m, 2 H), 3.42 (dd, J=16.0 Hz and 4.8 Hz, 1 H), 3.18-2.95 (m, 8 H), 2.49-2.41 (m, 1 H), 2.37-2.24 (m, 3 H), 1.83-1.76 (m, 2 H), 1.72-1.62 (m, 1 H), 1.37-1.33 (m, 6 H); MS (ESI) m/z 560.0 (M+H).

S15-13-170

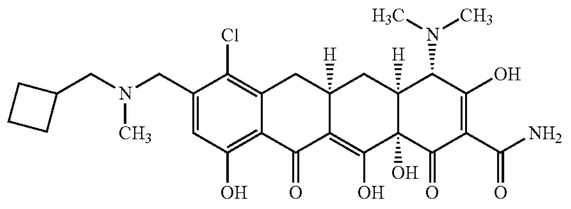

$^1$H NMR (400 MHz, $CD_3OD$) δ 7.20 (s, 1 H), 4.61 (t, J=12.8 Hz, 1 H), 4.33 (t, J=12.8 Hz, 1 H), 4.13 (s, 1 H), 3.41 (dd, J=16.4 Hz and 4.4 Hz, 1 H), 3.36-3.30 (m, 1 H), 3.18-2.80 (m, 12 H), 2.46-2.38 (m, 1 H), 2.29-1.18 (m, 3 H), 2.10-2.00 (m, 1), 2.00-1.85 (m, 4 H), 1.70-1.60 (m, 1 H); MS (ESI) m/z 560.2 (M+H).

S15-13-171

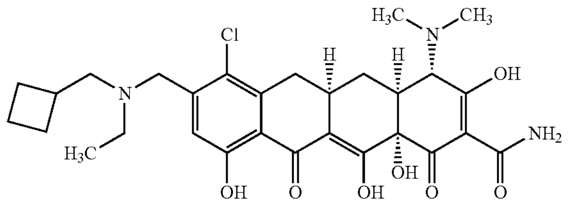

$^1$H NMR (400 MHz, $CD_3OD$) δ 7.19 (s, 1 H), 4.52-4.42 (m, 2 H), 4.12 (s, 1 H), 3.45-3.38 (m, 1 H), 3.28-2.80 (m, 12 H), 2.49-2.40 (m, 1 H), 2.30-2.13 (m, 3 H), 2.08-1.97 (m, 1 H), 1.96-1.80 (m, 4 H), 1.70-1.60 (m, 1 H), 1.38 (t, J=7.2 Hz, 3 H); MS (ESI) m/z 574.2 (M+H).

S15-13-172

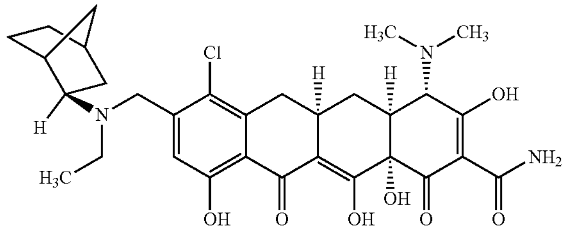

$^1$H NMR (400 MHz, $CD_3OD$) δ 7.23 and 7.20 (each s, total 1 H), 4.68-4.42 (m, 2 H), 4.13 (s, 1 H), 3.85-3.75 (m, 1 H), 3.47-3.38 (m, 1 H), 3.18-2.85 (m, 10 H), 2.46-2.01 (m, 3 H), 1.73-1.49 (m, 10 H); MS (ESI) m/z 600.1 (M+H).

S15-13-173

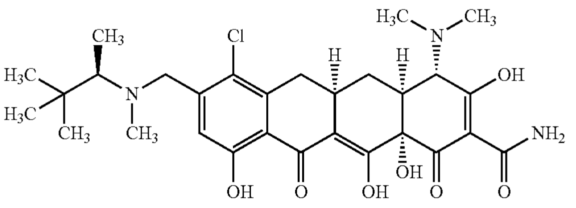

$^1$H NMR (400 MHz, $CD_3OD$) δ 7.25 (s, 1 H), 4.70 (d, J=13.2 Hz, 1 H), 4.42 (d, J=13.2 Hz, 1 H), 4.06 (s, 1 H), 3.40 (dd, J=16.4 Hz and 4.8 Hz, 1 H), 3.12-2.80 (m, 12 H), 2.44-2.36 (m, 1 H), 2.23-2.20 (m, 1 H), 1.67-1.57 (m, 1 H), 0.97 (s, 9 H); MS (ESI) m/z 576.0 (M+H).

S15-13-174

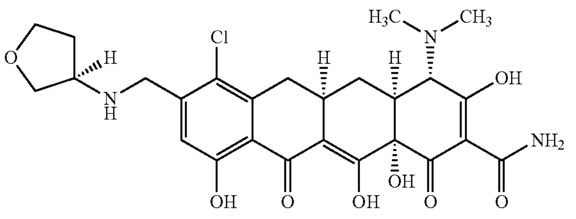

$^1$H NMR (400 MHz, $CD_3OD$) δ 7.16 (s, 1 H), 4.40 (s, 2 H), 4.12-4.05 (m, 4 H), 3.90-3.84 (m, 1 H), 3.78-3.71 (m, 1 H), 3.44-3.37 (m, 1 H), 3.15-2.95 (m, 8 H), 2.50-2.40 (m, 2 H), 2.28-2.23 (m, 1 H), 2.20-2.09 (m, 1 H), 1.71-1.60 (m, 1 H); MS (ESI) m/z 548.1 (M+H).

S15-13-175

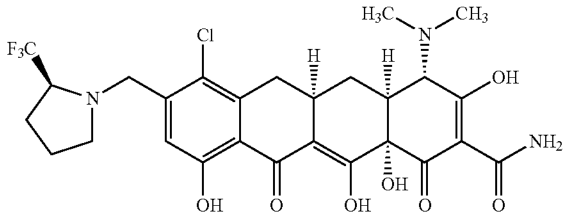

$^1$H NMR (400 MHz, $CD_3OD$) δ 7.16 (s, 1 H), 4.32 (t, J=15.6 Hz, 1 H), 4.17 (t, J=15.6 Hz, 1 H), 4.11 (s, 1 H), 3.90-3.80 (m, 1 H), 3.40 (dd, J=16.0 Hz and 4.4 Hz, 1 H), 3.29-3.20 (m, 1 H), 3.10-2.95 (m, 8 H), 2.83-2.74 (m, 1 H), 2.41-2.20 (m, 3 H), 2.12-1.90 (m, 3 H), 1.70-1.60 (m, 1 H); MS (ESI) m/z 599.9 (M+H).

S15-13-176

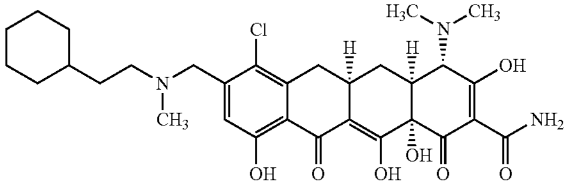

$^1$H NMR (400 MHz, $CD_3OD$) δ 7.21 (s, 1 H), 4.66 (t, J=12.8 Hz, 1 H), 4.37 (t, J=12.8 Hz, 1 H), 4.13 (s, 1 H), 3.43-3.39 (m, 1 H), 3.20-2.95 (m, 9 H), 2.86 (s, 3 H), 2.46-2.39 (m, 1 H), 2.28-2.25 (m, 1 H), 1.80-1.60 (m, 8 H), 1.44-1.12 (m, 4 H), 1.08-0.96 (m, 2 H); MS (ESI) m/z 602.1 (M+H).

S15-13-177

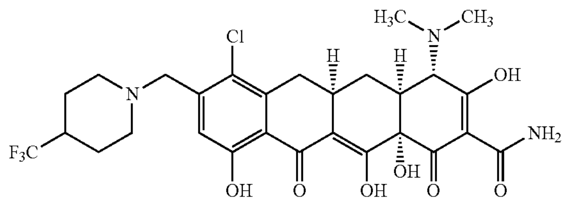

$^1$H NMR (400 MHz, $CD_3OD$) δ 7.26 (s, 1 H), 4.53 (s, 2 H), 4.11 (s, 1 H), 3.71-3.62 (m, 2 H), 3.40 (dd, J=16.4 Hz and 4.8 Hz, 1 H), 3.16-2.95 (m, 10 H), 2.70-2.60 (m, 1 H), 2.45-2.38 (m, 1 H), 2.27-2.23 (m, 1 H), 2.17-2.14 (m, 2 H), 1.96-1.83 (m, 2 H), 1.70-1.59 (m, 1 H); MS (ESI) m/z 614.1 (M+H).

S15-13-178

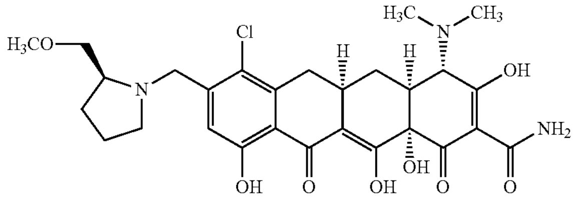

$^1$H NMR (400 MHz, $CD_3OD$) δ 7.19 (s, 1 H), 4.82-4.77 (m, 1 H), 4.39-4.36 (m, 1 H), 4.10 (s, 1 H), 3.92-3.85 (m, 1 H), 3.76-3.72 (m, 1 H), 3.68-3.60 (m, 1 H), 3.51-3.32 (m, 5 H), 3.17-2.95 (m, 9 H), 2.45-2.37 (m, 1), 2.24-2.31 (m, 2 H), 2.20-2.10 (m, 1 H), 2.05-1.87 (m, 2 H), 1.70-1.59 (m, 1 H); MS (ESI) m/z 576.1 (M+H).

S15-13-179

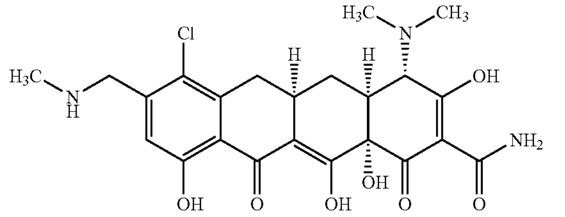

$^1$H NMR (400 MHz, $CD_3OD$) δ 7.10 (s, 1 H), 4.36 (s, 2 H), 4.11 (s, 1 H), 3.40 (dd, J=16.0 Hz and 4.4 Hz, 1 H), 3.16-2.95 (m, 8 H), 2.81 (s, 3 H), 2.45-2.37 (m, 1 H), 2.27-2.24 (m, 1 H), 1.70-1.60 (m, 1 H); MS (ESI) m/z 492.1 (M+H).

S15-13-180

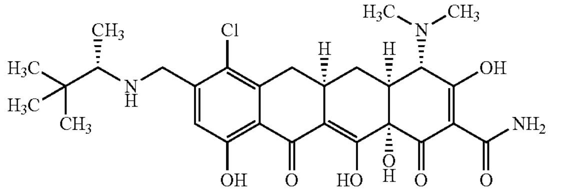

$^1$H NMR (400 MHz, $CD_3OD$) δ 7.21 (s, 1 H), 4.50 (d, J=13.7 Hz, 1 H), 4.43 (d, J=13.7 Hz, 1 H), 4.12 (s, 1 H), 3.48-3.38 (m, 1 H), 3.05 (s, 3 H), 2.97 (s, 3 H), 3.16=2.94 (comp, 3 H), 2.49-2.39 (m, 1 H), 2.30-2.23 (m, 1 H), 1.72-1.61 (m, 1 H), 1.40 (d, J=7.3 Hz, 3 H), 1.05 (s, 9 H); MS (ESI) m/z 562.22 (M+H).

S15-13-181

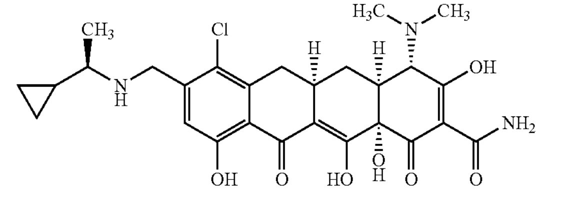

$^1$H NMR (400 MHz, $CD_3OD$) δ 7.16 (s, 1 H), 4.52 (d, J=13.4 Hz, 1 H), 4.39 (d, J=13.4 Hz, 1 H), 4.11 (s, 1 H), 3.49-3.36 (m, 1 H), 3.05 (s, 3 H), 2.96 (s, 3 H), 3.14-2.94 (comp, 3 H), 2.48-2.38 (m, 1 H), 2.29-2.22 (m, 1 H), 1.73-1.62 (m, 1 H), 1.50 (d, J=6.7 Hz, 3 H), 1.12-1.03 (m, 1 H), 0.87-0.73 (m, 2 H), 0.67-0.59 (m, 1 H), 0.44-0.36 (m, 1 H); MS (ESI) m/z 546.16 (M+H).

S15-13-182

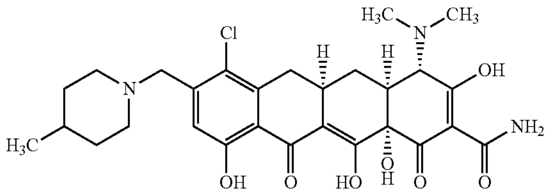

$^1$H NMR (400 MHz, $CD_3OD$) δ 7.22 (s, 1 H), 4.49 (s, 2 H), 4.11 (s, 1 H), 3.60-3.37 (comp, 4 H), 3.05 (s, 3 H), 2.97 (s, 3 H), 3.23-2.94 (comp, 3 H), 2.48-2.39 (m, 1 H), 2.28-2.21 (m, 1 H), 1.97-1.88 (m, 2 H), 1.80-1.61 (m, 2 H), 1.53-1.38 (m, 2 H), 1.01 (d, J=6.1 Hz, 3 H); MS (ESI) m/z 560.19 (M+H).

S15-13-183

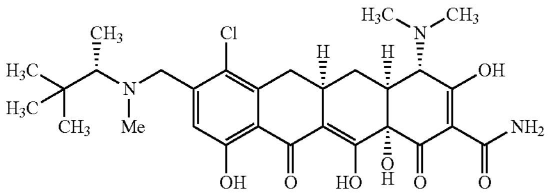

$^1$H NMR (400 MHz, $CD_3OD$) δ 7.31 (s, 1 H), 4.71 (d, J=13.4 Hz, 1 H), 4.47 (d, J=13.4 Hz, 1 H), 4.11 (s, 1 H), 3.48-3.38 (m, 1 H), 3.04 (s, 3 H), 2.96 (s, 3 H), 2.90 (s, 3 H), 3.16-2.86 (comp, 3 H), 2.50-2.40 (m, 1 H), 2.29-2.22 (m, 1 H), 1.72-1.60 (m, 1 H), 1.43 (d, J=6.7 Hz, 3 H), 1.02 (s, 9 H); MS (ESI) m/z 576.20 (M+H).

S15-13-184

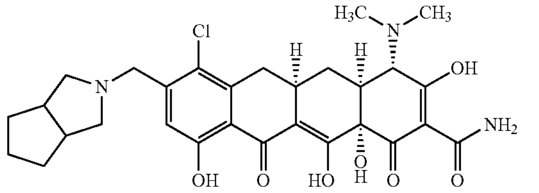

$^1$H NMR (400 MHz, $CD_3OD$) δ 7.19 (s, 1 H), 4.57 (s, 2 H), 4.11 (s, 1 H), 3.85-3.76 (m, 2 H), 3.57-3.38 (m, 1 H), 3.05 (s, 3 H), 2.97 (s, 3 H), 3.15-2.81 (comp, 4 H), 2.49-2.39 (m, 1 H), 2.29-2.21 (m, 1 H), 1.95-1.47 (comp, 9 H); MS (ESI) m/z 572.14 (M+H).

S15-13-185

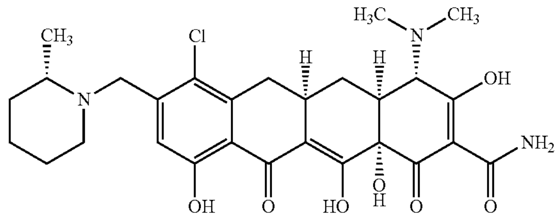

$^1$H NMR (400 MHz, $CD_3OD$) δ 7.21-7.18 (m, 1 H), 4.54-4.24 (m, 2 H), 4.10 (s, 1 H), 3.49-3.35 (comp, 3 H), 3.04 (s, 3 H), 2.96 (s, 3 H), 3.14-2.93 (comp, 3 H), 2.49-2.38 (m, 1 H), 2.28-2.21 (m, 1 H), 2.07-2.00 (m, 1 H), 1.91-1.49 (comp, 9 H); MS (ESI) m/z 560.15 (M+H).

S15-13-186

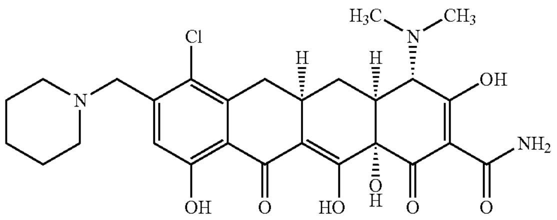

$^1$H NMR (400 MHz, $CD_3OD$) δ 7.24 (s, 1 H), 4.50 (d, J=13.7 Hz, 1 H), 4.46 (d, J=13.7 Hz, 1 H), 4.12 (s, 1 H), 3.57-3.36 (comp, 3 H), 3.05 (s, 3 H), 2.96 (s, 3 H), 3.20-2.94 (comp, 4 H), 2.47-2.37 (m, 1 H), 2.30-2.21 (m, 1 H), 1.99-1.47 (comp, 7 H); MS (ESI) m/z 546.10 (M+H).

S15-13-187

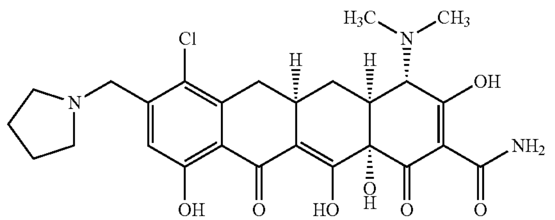

$^1$H NMR (400 MHz, $CD_3OD$) δ 7.20 (s, 1 H), 4.58 (s, 2 H), 4.11 (s, 1 H), 3.69-3.56 (m, 2 H), 3.48-3.36 (m, 2 H), 3.04 (s, 3 H), 2.96 (s, 3 H), 3.16-2.93 (comp, 3 H), 2.46-2.37 (m, 1 H), 2.29-1.98 (comp, 5 H), 1.71-1.59 (m, 1 H); MS (ESI) m/z 532.09 (M+H).

S15-13-188

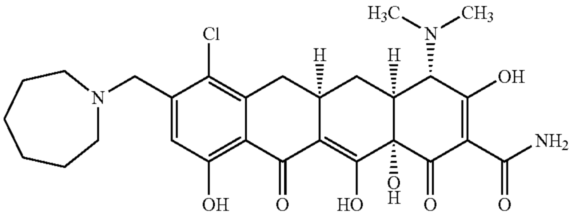

$^1$H NMR (400 MHz, $CD_3OD$) δ 7.24 (s, 1 H), 4.53 (s, 2 H), 4.11 (s, 1 H), 3.54-3.33 (comp, 5 H), 3.04 (s, 3 H), 2.96 (s, 3 H), 3.14-2.93 (comp, 2 H), 2.47-2.38 (m, 1 H), 2.28-2.21 (m, 1 H), 2.06-1.60 (comp, 9 H); MS (ESI) m/z 560.15 (M+H).

S15-13-189

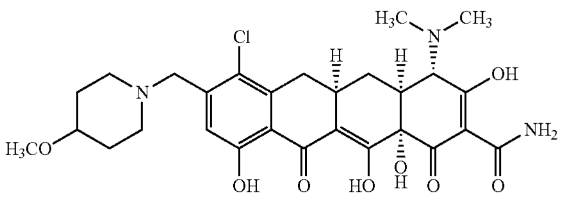

$^1$H NMR (400 MHz, $CD_3OD$) δ 7.25-7.23 (m, 1 H), 4.53-4.47 (m, 2 H), 4.12 (s, 1 H), 3.63-3.34 (comp, 8 H), 3.04 (s, 3 H), 2.96 (s, 3 H), 3.14-2.94 (comp, 3 H), 2.47-2.37 (m, 1 H), 2.31-1.60 (comp, 6 H); MS (ESI) m/z 576.15 (M+H).

S15-13-190

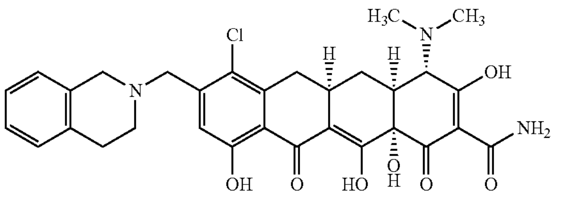

$^1$H NMR (400 MHz, $CD_3OD$) δ 7.34-7.24 (comp, 4 H), 7.21-7.17 (m, 1 H), 4.69 (s, 2 H), 4.54 (s, 2 H), 4.11 (s, 1 H), 3.90-3.53 (m, 2 H), 3.47-3.39 (m, 2 H), 3.04 (s, 3 H), 2.96 (s, 3 H), 3.28-2.94 (comp, 3 H), 2.50-2.40 (m, 1 H), 2.29-2.22 (m, 1 H), 1.72-1.61 (m, 1 H); MS (ESI) m/z 594.15 (M+H).

S15-13-191

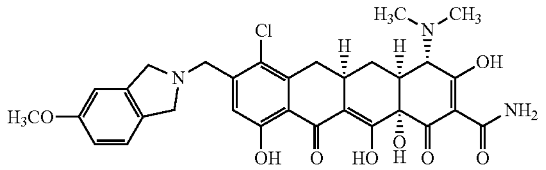

$^1$H NMR (400 MHz, $CD_3OD$) δ 7.32-7.26 (m, 2 H), 6.99-6.94 (m, 2 H), 4.93-4.64 (comp, 6 H), 4.13 (s, 1 H), 3.81 (s, 3 H), 3.46-3.33 (m, 1 H), 3.05 (s, 3 H), 2.97 (s, 3 H), 3.18-2.95 (comp, 2 H), 2.50-2.39 (m, 1 H), 2.30-2.23 (m, 1 H), 1.73-1.61 (m, 1 H); MS (ESI) m/z 610.15 (M+H).

S15-13-192

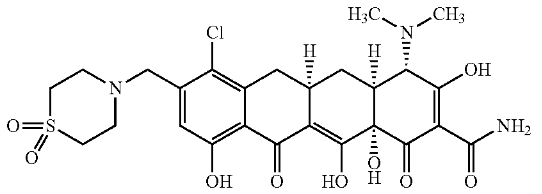

$^1$H NMR (400 MHz, $CD_3OD$) δ 7.25 (s, 1 H), 4.44 (s, 2 H), 4.10 (s, 1 H), 3.71 (s, 4 H), 3.47 (s, 4 H), 3.44-3.33 (m, 1 H), 3.04 (s, 3 H), 2.95 (s, 3 H), 3.15-2.93 (comp, 2 H), 2.45-2.36 (m, 1 H), 2.27-2.20 (m, 1 H), 1.71-1.59 (m, 1 H); MS (ESI) m/z 596.08 (M+H).

S15-13-193

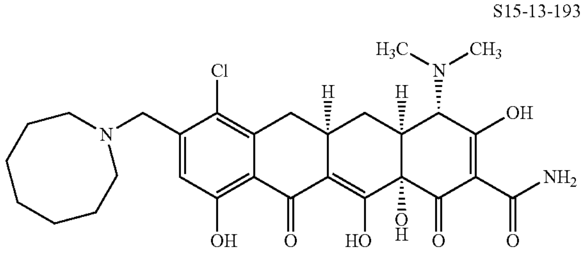 [SMILES: CN(C)[C@@H]1C(O)=C(C(N)=O)C(=O)[C@@]2(O)C(O)=C3C(=O)c4c(O)cc(CN5CCCCCCC5)c(Cl)c4C[C@H]3C[C@@H]12]

$^1$H NMR (400 MHz, $CD_3OD$) δ 7.25 (s, 1 H), 4.55 (d, J=13.7 Hz, 1 H), 4.51 (d, J=13.7 Hz, 1 H), 4.12 (s, 1 H), 3.56-3.31 (comp, 5 H), 3.05 (s, 3 H), 2.96 (s, 3 H), 3.16-2.94 (comp, 2 H), 2.48-2.36 (m, 1 H), 2.30-2.22 (m, 1 H), 2.14-1.59 (comp, 11 H); MS (ESI) m/z 574.18 (M+H).

S15-13-194

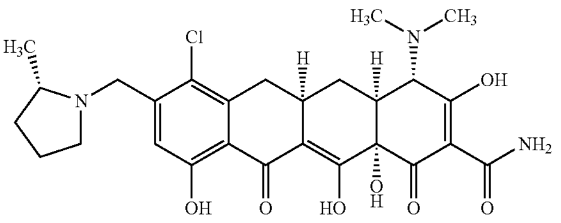

$^1$H NMR (400 MHz, $CD_3OD$) δ 7.22 (s, 1 H), 4.81 (d, J=13.4 Hz, 1 H), 4.31 (d, J=13.4 Hz, 1 H), 4.12 (s, 1 H), 3.75-3.33 (comp, 4 H), 3.06 (s, 3 H), 2.97 (s, 3 H), 3.18-2.94 (comp, 2 H), 2.50-1.61 (comp, 7 H), 1.53 (d, J=6.1 Hz, 3 H); MS (ESI) m/z 546.20 (M+H).

S15-13-195

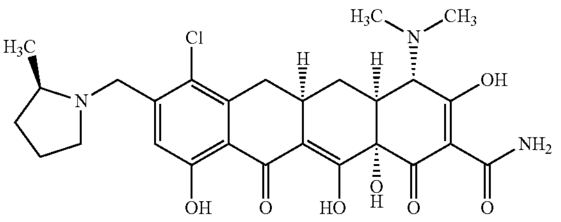

$^1$H NMR (400 MHz, $CD_3OD$) δ 7.23 (s, 1 H), 4.77 (d, J=13.4 Hz, 1 H), 4.33 (d, J=13.4 Hz, 1 H), 4.13 (s, 1 H), 3.75-3.32 (comp, 4 H), 3.05 (s, 3 H), 2.96 (s, 3 H), 3.17-2.94 (comp, 2 H), 2.46-1.97 (comp, 5 H), 1.84-1.60 (comp, 2 H), 1.53 (d, J=6.1 Hz, 3 H); MS (ESI) m/z 546.16 (M+H).

S15-13-196

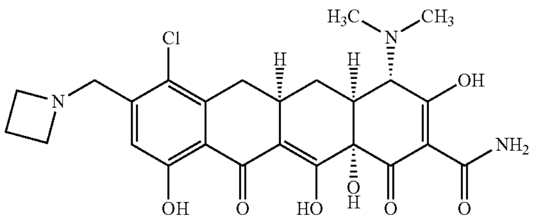

$^1$H NMR (400 MHz, $CD_3OD$) δ 7.07 (s, 1 H), 4.59 (s, 2 H), 4.35-4.20 (m, 4 H), 4.11 (s, 1 H), 3.43-3.37 (m, 1 H), 3.05 (s, 3 H), 2.97 (s, 3 H), 3.15-2.95 (comp, 2 H), 2.67-2.20 (comp, 4 H), 1.72-1.61 (m, 1 H); MS (ESI) m/z 518.11 (M+H).

S15-13-197

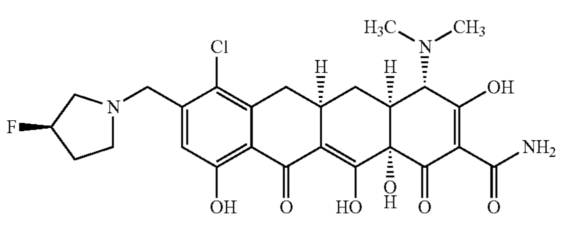

$^{1}$H NMR (400 MHz, $CD_3OD$) δ 7.24 (s, 1 H), 5.58-5.39 (m, 1 H), 4.68 (s, 2 H), 4.12 (s, 1 H), 4.03-3.38 (comp, 5 H), 3.05 (s, 3 H), 2.97 (s, 3 H), 3.17-2.95 (comp, 2 H), 2.83-2.20 (comp, 4 H), 1.73-1.61 (m, 1 H); MS (ESI) m/z 550.16 (M+H).

S15-13-198

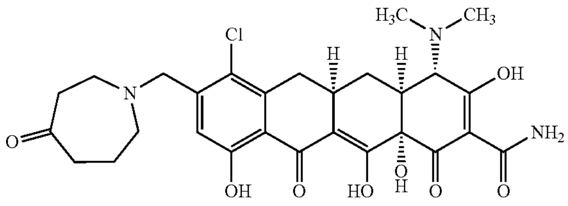

$^{1}$H NMR (400 MHz, $CD_3OD$) δ 7.30-7.21 (m, 1 H), 4.66-4.51 (m, 2 H), 4.11 (s, 1 H), 3.84-3.31 (comp, 5 H), 3.05 (s, 3 H), 2.97 (s, 3 H), 3.16-2.95 (comp, 2 H), 2.87-2.61 (m, 2 H), 2.50-2.40 (m, 1 H), 2.33-1.83 (comp, 5 H), 1.73-1.61 (m, 1 H); MS (ESI) m/z 574.18 (M+H).

S15-13-199

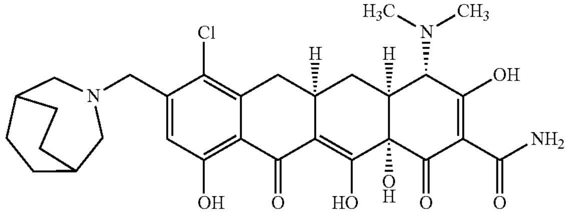

$^{1}$H NMR (400 MHz, $CD_3OD$) δ 7.37 (s, 1 H), 4.62 (d, J=14.0 Hz, 1 H), 4.57 (d, J=14.0 Hz, 1 H), 4.12 (s, 1 H), 3.75-3.66 (m, 2 H), 3.48-3.32 (comp, 3 H), 3.04 (s, 3 H), 2.96 (s, 3 H), 3.17-2.94 (comp, 2 H), 2.48-2.37 (m, 1 H), 2.29-2.22 (m, 1 H), 2.22-2.13 (br, 2 H), 1.98-1.60 (comp, 9 H); MS (ESI) m/z 586.24 (M+H).

S15-13-200

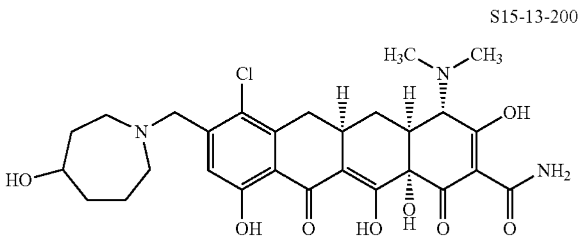 [SMILES: CN(C)[C@@H]1C(O)=C(C(N)=O)C(=O)[C@@]2(O)C(O)=C3C(=O)c4c(O)cc(CN5CCCC(O)CC5)c(Cl)c4C[C@H]3C[C@@H]12]

$^{1}$H NMR (400 MHz, $CD_3OD$) δ 7.26-7.22 (m, 1 H), 4.60-4.48 (m, 2 H), 4.12 (s, 1 H), 4.12-4.01 (m, 1 H), 3.73-3.33 (comp, 4 H), 3.05 (s, 3 H), 2.97 (s, 3 H), 3.29-2.95 (comp, 3 H), 2.49-2.39 (m, 1 H), 2.30-1.61 (comp, 8 H); MS (ESI) m/z 576.22 (M+H).

S15-13-201

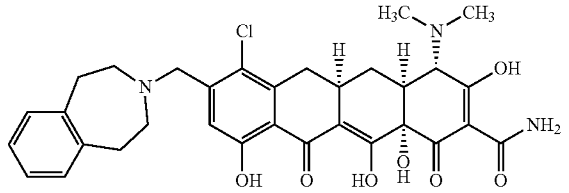

$^{1}$H NMR (400 MHz, $CD_3OD$) δ 7.31 (s, 1 H), 7.23 (s, 4 H), 4.62 (d, J=14.3 Hz, 1 H), 4.58 (d, J=14.3 Hz, 1 H), 4.12 (s, 1 H), 3.85-3.75 (m, 2 H), 3.06 (s, 3 H), 2.97 (s, 3 H), 3.63-2.94 (comp, 9 H), 2.50-2.41 (m, 1 H), 2.30-2.23 (m, 1 H), 1.73-1.62 (m, 1 H); MS (ESI) m/z 608.21 (M+H).

S15-13-202

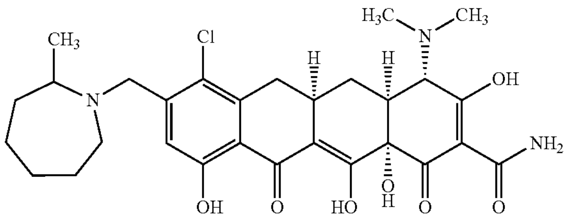

$^{1}$H NMR (400 MHz, $CD_3OD$) δ 7.23-7.15 (m, 1 H), 4.74-4.61 (m, 1 H), 4.55-4.33 (m, 1 H), 4.11 (s, 1 H), 3.98-3.37 (comp, 3 H), 3.04 (s, 3 H), 2.96 (s, 3 H), 3.16-2.94 (comp, 3 H), 2.50-2.37 (m, 1 H), 2.30-2.21 (m, 1 H), 2.10-1.50 (comp, 12 H); MS (ESI) m/z 574.32 (M+H).

S15-13-203

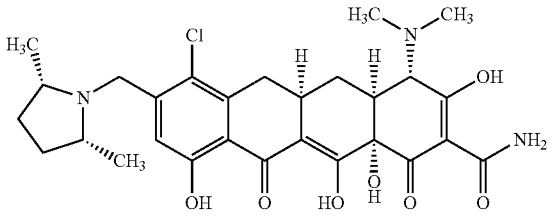

$^{1}$H NMR (400 MHz, $CD_3OD$) δ 7.24 (s, 1 H), 4.64 (d, J=13.2 Hz, 1 H), 4.58 (d, J=13.2 Hz, 1 H), 4.11 (s, 1 H), 3.88-3.78 (m, 2 H), 3.49-3.38 (m, 1 H), 3.04 (s, 3 H), 2.96 (s, 3 H), 3.16-2.93 (comp, 2 H), 2.49-2.21 (comp, 4 H), 1.84-1.61 (m, 3 H), 1.38-1.32 (m, 6 H); MS (ESI) m/z 560.27 (M+H).

S15-13-204

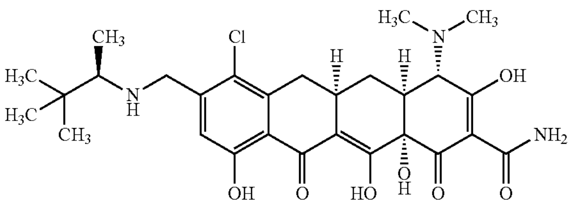

$^{1}$H NMR (400 MHz, $CD_3OD$) δ 7.22 (s, 1 H), 4.50 (d, J=13.7 Hz, 1 H), 4.46 (d, J=13.7 Hz, 1 H), 4.14 (s, 1 H), 3.48-3.36 (m, 1 H), 3.06 (s, 3 H), 2.97 (s, 3 H), 3.16-2.95 (comp, 3 H), 2.48-2.37 (m, 1 H), 2.32-2.23 (m, 1 H), 1.72-1.60 (m, 1 H), 1.40 (d, J=6.7 Hz, 3 H), 1.05 (s, 9 H); MS (ESI) m/z 562.23 (M+H).

S15-13-205

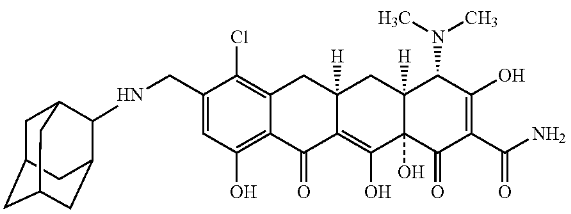

$^1$H NMR (400 MHz, $CD_3OD$) δ 7.23 (s, 1 H), 4.42 (s, 2 H), 4.14 (s, 1 H), 3.31 (br s, 1 H), 3.39-3.45 (m, 1 H), 2.97-3.14 (m, 8 H), 2.26-2.44 (m, 3 H), 1.61-2.06 (m, 14 H); MS (ESI) m/z 612.3 (M+H), calcd for $C_{32}H_{39}ClN_3O_7$ 612.24.

S15-13-206

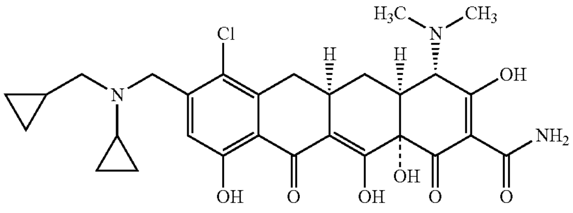

$^1$H NMR (400 MHz, $CD_3OD$) δ 7.27 (s, 1 H), 4.71-4.87 (m, 2 H), 4.14 (s, 1 H), 3.37-3.46 (m, 2 H), 2.94-3.28 (m, 10 H), 2.42 (dd, J=14.0, 14.0 Hz, 1 H), 2.24-2.32 (m, 1 H), 1.60-1.70 (m, 1 H), 1.27-1.36 (m, 1 H), 0.51-1.14 (m, 8 H); MS (ESI) m/z 572.3 (M+H), calcd for $C_{29}H_{35}ClN_3O_7$ 572.21.

S15-13-207

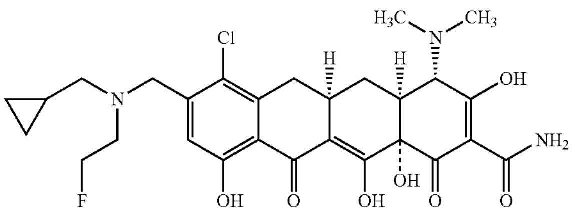

$^1$H NMR (400 MHz, $CD_3OD$) δ 7.24 (s, 1 H), 4.60-5.00 (m, 4 H), 4.14 (s, 1 H), 3.64-3.82 (m, 2 H), 3.20-3.46 (m, 3 H), 2.94-3.20 (m, 8 H), 2.41 (dd, J=14.0, 14.0 Hz, 1 H), 2.25-2.29 (m, 1 H), 1.60-1.70 (m, 1 H), 1.24-1.28 (m, 1 H), 0.78-0.86 (m, 2 H), 0.46-0.52 (m, 2 H); MS (ESI) m/z 578.3 (M+H), calcd for $C_{28}H_{34}ClFN_3O_7$ 578.20.

S15-13-208

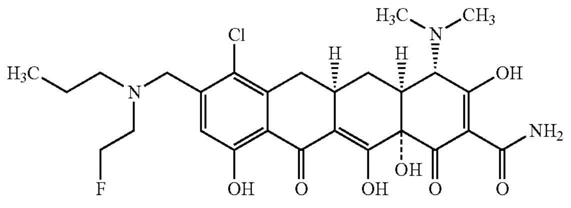

$^1$H NMR (400 MHz, $CD_3OD$) δ 7.23 (s, 1 H), 4.63-5.00 (m, 4 H), 4.13 (s, 1 H), 3.61-3.72 (m, 2 H), 3.20-3.43 (m, 3 H), 2.94-3.20 (m, 8 H), 2.42 (dd, J=14.0, 14.0 Hz, 1 H), 2.25-2.29 (m, 1 H), 1.85-1.88 (m, 2 H), 1.60-1.70 (m, 1 H), 1.01 (t, J=7.3 Hz, 3 H); MS (ESI) m/z 566.3 (M+H), calcd for $C_{27}H_{34}ClFN_3O_7$ 566.20.

S15-13-209

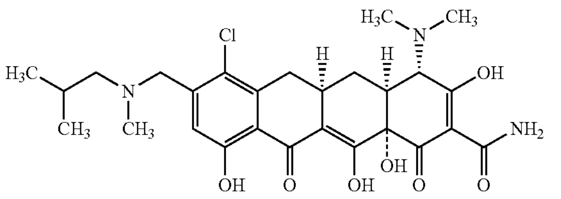

$^1$H NMR (400 MHz, $CD_3OD$) δ 7.22 (s, 1 H), 4.72 (dd, J=13.7, 13.7 Hz, 1 H), 4.34 (dd, J=10.2, 10.2 Hz, 1 H), 4.14 (s, 1 H), 3.38-3.44 (m, 1 H), 2.87-3.21 (m, 13 H), 2.42 (dd, J=14.0, 14.0 Hz, 1 H), 2.23-2.31 (m, 2 H), 1.60-1.70 (m, 1 H), 1.09 (d, J=6.5 Hz, 3 H), 1.05 (d, J=6.5 Hz, 3 H); MS (ESI) m/z 548.3 (M+H), calcd for $C_{27}H_{35}ClFN_3O_7$ 548.21.

S15-13-210

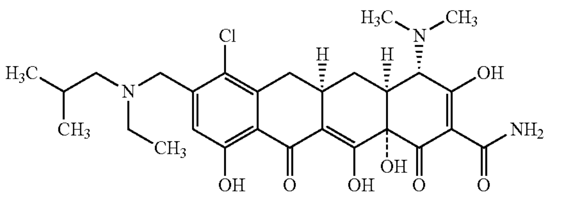

$^1$H NMR (400 MHz, $CD_3OD$) δ 7.23 (s, 1 H), 4.63 (dd, J=13.7, 13.7 Hz, 1 H), 4.47 (dd, J=10.2, 10.2 Hz, 1 H), 4.14 (s, 1 H), 3.29-3.44 (m, 3 H), 2.94-3.21 (m, 10 H), 2.43 (dd, J=14.0, 14.0 Hz, 1 H), 2.18-2.29 (m, 2 H), 1.60-1.70 (m, 1 H), 1.40 (t, J=7.3 Hz, 3 H), 1.09 (d, J=6.5 Hz, 3 H), 1.03 (d, J=6.5 Hz, 3 H); MS (ESI) m/z 562.3 (M+H), calcd for $C_{28}H_{37}ClN_3O_7$ 562.22.

S15-13-211

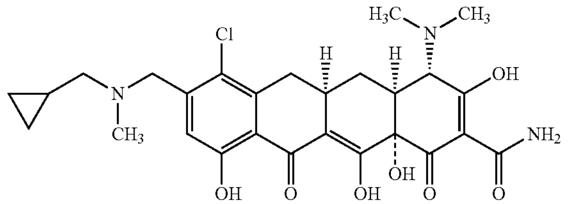

$^1$H NMR (400 MHz, $CD_3OD$) δ 7.20 (s, 1 H), 4.75-4.80 (m, 1 H), 4.33-4.37 (m, 1 H), 4.11 (s, 1 H), 2.88-3.49 (m, 16 H), 2.43 (dd, J=15.0, 15.0 Hz, 1 H), 2.23-2.26 (m, 1 H), 1.60-1.70 (m, 1 H), 1.19-1.28 (m, 1 H), 0.80-0.82 (m, 2 H), 0.46-0.50 (m, 2 H); MS (ESI) m/z 546.2 (M+H), calcd for $C_{27}H_{33}ClN_3O_7$ 546.19.

S15-13-212

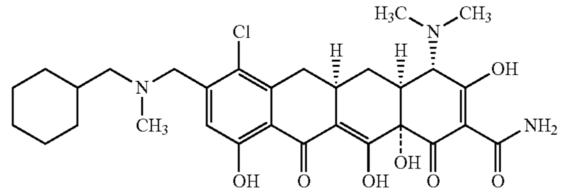

$^1$H NMR (400 MHz, $CD_3OD$) δ 7.20 (s, 1 H), 4.72 (dd, J=12.8, 12.8 Hz, 1 H), 4.32 (dd, J=4.4, 12.8 Hz, 1 H), 4.12 (s, 1 H), 3.40 (dd, J=4.6, 16.0 Hz, 1 H), 2.87-3.14 (m, 13 H), 2.43 (dd, J=15.0, 15.0 Hz, 1 H), 2.24-2.28 (m, 1 H), 1.60-1.98 (m, 7 H), 1.21-1.42 (m, 3 H), 1.01-1.12 (m, 2 H); MS (ESI) m/z 588.3 (M+H), calcd for $C_{30}H_{39}ClN_3O_7$ 588.24.

S15-13-213

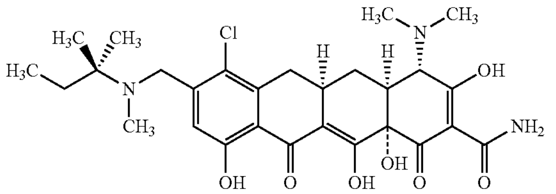

$^1$H NMR (400 MHz, $CD_3OD$) δ 7.20 (s, 1 H), 4.83-4.95 (m, 1 H), 4.14-4.19 (m, 1 H), 4.10 (s, 1 H), 2.74-3.50 (m, 12 H), 2.42 (dd, J=15.0, 15.0 Hz, 1 H), 2.22-2.28 (m, 1 H), 1.90-2.20 (m, 2 H), 1.60-1.70 (m, 1 H), 1.53 (s, 3 H), 1.50 (s, 3 H), 1.08 (t, J=7.3 Hz, 3 H); MS (ESI) m/z 562.3 (M+H), calcd for $C_{28}H_{37}ClN_3O_7$ 562.22.

S15-13-214

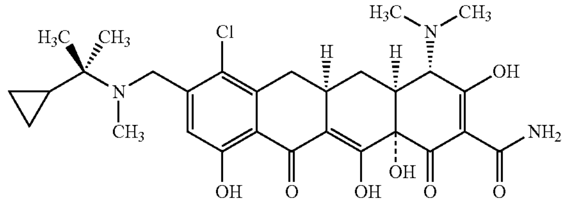

$^1$H NMR (400 MHz, $CD_3OD$) δ 7.22 (s, 1 H), 4.91-4.99 (m, 1 H), 4.18-4.22 (m, 1 H), 4.12 (s, 1 H), 3.41 (dd, J=4.6, 16.0 Hz, 1 H), 2.96-3.10 (m, 11 H), 2.45 (dd, J=15.0, 15.0 Hz, 1 H), 2.24-2.30 (m, 1 H), 1.61-1.71 (m, 1 H), 1.42 (s, 6 H), 1.28-1.36 (m, 1 H), 0.76-0.81 (m, 2 H), 0.64-0.72 (m, 2 H); MS (ESI) m/z 574.2 (M+H), calcd for $C_{29}H_{37}ClN_3O_7$ 574.22.

S15-13-215

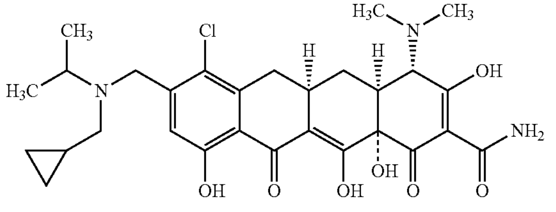

$^1$H NMR (400 MHz, $CD_3OD$) δ 7.23 (s, 1 H), 4.46-4.63 (m, 2 H), 4.14 (s, 1 H), 3.95-4.02 (m, 1 H), 3.40 (dd, J=4.6, 16.0 Hz, 1 H), 2.96-3.21 (m, 10 H), 2.41 (dd, J=15.0, 15.0 Hz, 1 H), 2.26-2.29 (m, 1 H), 1.60-1.70 (m, 1 H), 1.50 (d, J=6.4 Hz, 3 H), 1.41 (d, J=6.4 Hz, 3 H), 1.06-1.17 (m, 1 H), 0.72-0.78 (m, 2 H), 0.42-0.44 (m, 2 H); MS (ESI) m/z 574.2 (M+H), calcd for $C_{29}H_{37}ClN_3O_7$ 574.22.

S15-13-216

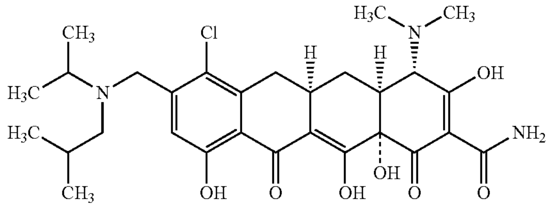

$^1$H NMR (400 MHz, $CD_3OD$) δ 7.30 (s, 1 H), 4.50-4.60 (m, 2 H), 4.14 (s, 1 H), 3.78-3.84 (m, 1 H), 3.42 (dd, J=4.6, 16.0 Hz, 1 H), 2.94-3.21 (m, 10 H), 2.42 (dd, J=15.0, 15.0 Hz, 1 H), 2.26-2.30 (m, 1 H), 1.96-2.02 (m, 1 H), 1.60-1.70 (m, 1 H), 1.50 (d, J=6.4 Hz, 3 H), 1.44 (d, J=6.4 Hz, 3 H), 1.03 (d, J=6.4 Hz, 3 H), 0.94 (d, J=6.4 Hz, 3 H); MS (ESI) m/z 576.3 (M+H), calcd for $C_{29}H_{39}ClN_3O_7$ 576.24.

S15-13-217

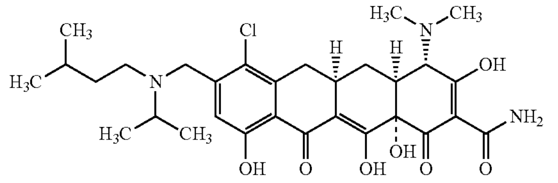

$^1$H NMR (400 MHz, $CD_3OD$) δ 7.24 (s, 1 H), 4.63 (dd, J=14.2, 14.2 Hz, 1 H), 4.40 (dd, J=14.2, 14.2 Hz, 1 H), 4.14 (s, 1 H), 3.78-3.84 (m, 1 H), 3.42 (dd, J=4.6, 16.0 Hz, 1 H), 2.96-3.28 (m, 10 H), 2.42 (dd, J=15.0, 15.0 Hz, 1 H), 2.26-2.29 (m, 1 H), 1.54-1.70 (m, 4 H), 1.51 (d, J=6.4 Hz, 3 H), 1.43 (d, J=6.4 Hz, 3 H), 0.89-0.94 (m, 6 H); MS (ESI) m/z 590.3 (M+H), calcd for $C_{30}H_{41}ClN_3O_7$ 590.26.

S15-13-218

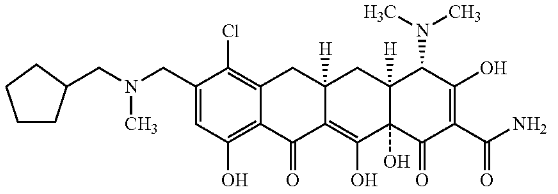

$^1$H NMR (400 MHz, $CD_3OD$) δ 7.22 (s, 1 H), 4.74 (dd, J=14.2, 14.2 Hz, 1 H), 4.34 (dd, J=8.7, 14.2 Hz, 1 H), 4.13 (s, 1 H), 3.41 (dd, J=4.6, 16.0 Hz, 1 H), 2.88-3.34 (m, 13 H), 2.39-2.46 (m, 2 H), 2.26-2.28 (m, 1 H), 1.96-2.01 (m, 2 H), 1.61-1.74 (m, 5 H), 1.23-1.35 (m, 2 H); MS (ESI) m/z 574.2 (M+H), calcd for $C_{29}H_{37}ClN_3O_7$ 574.22.

S15-13-219

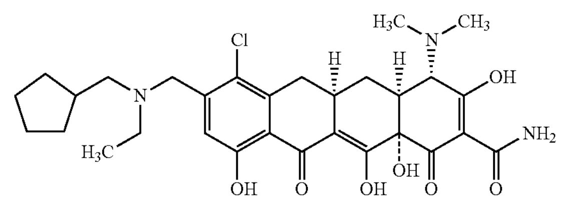

$^1$H NMR (400 MHz, $CD_3OD$) δ 7.22 (s, 1 H), 4.62 (dd, J=14.2, 14.2 Hz, 1 H), 4.48 (dd, J=8.7, 14.2 Hz, 1 H), 4.14 (s, 1 H), 3.41 (dd, J=4.6, 16.0 Hz, 1 H), 2.96-3.34 (m, 12 H), 2.26-2.41 (m, 3 H), 1.96-2.01 (m, 2 H), 1.61-1.74 (m, 5 H), 1.40 (t, J=7.3 Hz, 3 H), 1.22-1.32 (m, 2 H); MS (ESI) m/z 588.3 (M+H), calcd for $C_{30}H_{39}ClN_3O_7$ 588.24.

S15-13-220

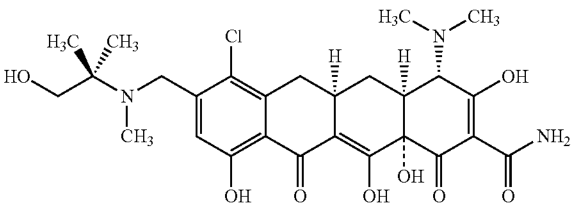

$^1$H NMR (400 MHz, $CD_3OD$) δ 7.23 (s, 1 H), 4.75 (dd, J=9.6, 12.8 Hz, 1 H), 4.28 (dd, J=9.6, 12.8 Hz, 1 H), 4.12 (s, 1 H), 3.92 (d, J=12.1 Hz, 1 H), 3.71 (d, J=12.1 Hz, 1 H), 3.38-3.47 (m, 1 H), 2.97-3.16 (m, 8 H), 2.72 (s, 3 H), 2.38-2.47 (m, 1 H), 2.25-2.28 (m, 1 H), 1.60-1.70 (m, 1 H), 1.51 (s, 3 H), 1.46 (s, 3 H); MS (ESI) m/z 564.3 (M+H), calcd for $C_{27}H_{35}ClN_3O_8$ 564.20.

S15-13-221

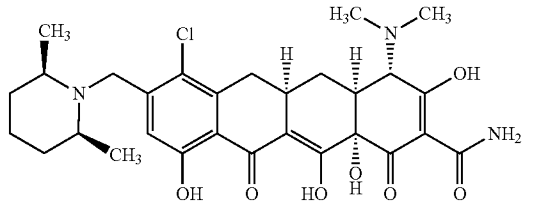

$^1$H NMR (400 MHz, $CD_3OD$) δ 7.21-7.16 (m, 1 H), 4.78-4.49 (m, 2 H), 4.12 (s, 1 H), 3.71-3.32 (comp, 3 H), 3.16-2.95 (comp, 2 H), 3.04 (s, 3 H), 2.96 (s, 3 H), 2.46-2.36 (m, 1 H), 2.30-2.22 (m, 1 H), 2.14-1.58 (comp, 7 H), 1.45-1.26 (comp, 6 H); MS (ESI) m/z 574.18 (M+H).

S15-13-222

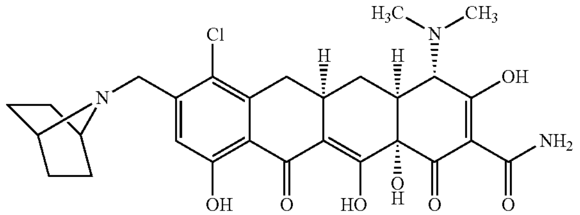

$^1$H NMR (400 MHz, $CD_3OD$) δ 7.23 (s, 1 H), 4.44 (s, 2 H), 4.23 (s, 2 H), 4.10 (s, 1 H), 3.48-3.36 (comp, 1 H), 3.04 (s, 3 H), 2.96 (s, 3 H), 3.14-2.94 (comp, 2 H), 2.49-2.02 (comp, 6 H), 1.98-1.81 (m, 4 H), 1.72-1.61 (m, 1 H); MS (ESI) m/z 558.21 (M+H).

S15-13-223

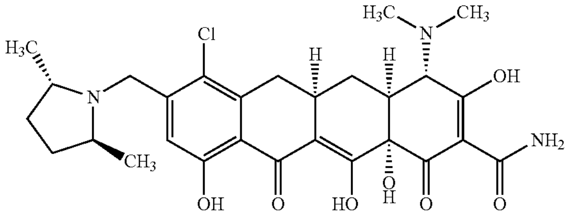

$^1$H NMR (400 MHz, $CD_3OD$) δ 7.28 (s, 1 H), 4.68-4.48 (m, 2 H), 4.13 (s, 1 H), 4.12-4.02 (m, 1 H), 3.90-3.80 (m, 1 H), 3.49-3.38 (m, 1 H), 3.05 (s, 3 H), 2.97 (s, 3 H), 3.17-2.95 (comp, 2 H), 2.52-2.23 (comp, 4 H), 1.98-1.60 (comp, 3 H), 1.48-1.34 (m, 6 H); MS (ESI) m/z 560.28 (M+H).

S15-13-224

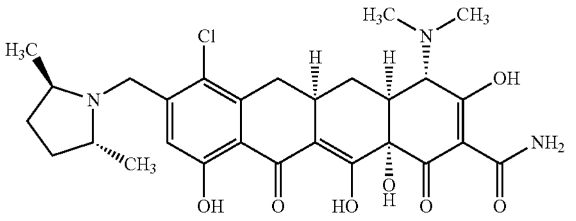

$^1$H NMR (400 MHz, $CD_3OD$) δ 7.26 (s, 1 H), 4.52 (s, 2 H), 4.11 (s, 1 H), 4.10-4.00 (m, 1 H), 3.90-3.80 (m, 1 H), 3.46-3.37 (m, 1 H), 3.05 (s, 3 H), 2.96 (s, 3 H), 3.16-2.90 (comp, 2 H), 2.52-2.12 (m, 4 H), 1.98-1.58 (m, 3 H), 1.48-1.33 (comp, 6 H); MS (ESI) m/z 560.27 (M+H).

S15-13-225

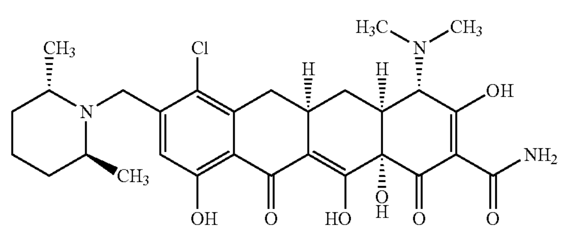

$^1$H NMR (400 MHz, $CD_3OD$) δ 7.25 (s, 1 H), 4.68 (d, J=14.4 Hz, 1 H), 4.51 (d, J=14.4 Hz, 1 H), 4.11 (s, 1 H), 3.88-3.66 (m, 2 H), 3.45-3.37 (m, 1 H), 3.04 (s, 3 H), 2.96 (s, 3 H), 3.15-2.94 (comp, 2 H), 2.49-2.38 (m, 1 H), 2.29-2.21 (m, 1 H), 2.19-2.08 (m, 1 H), 1.95-1.59 (comp, 6 H), 1.48 (d, J=6.7 Hz, 3 H), 1.44 (d, J=6.7 Hz, 3 H); MS (ESI) m/z 574.30 (M+H).

S15-13-226

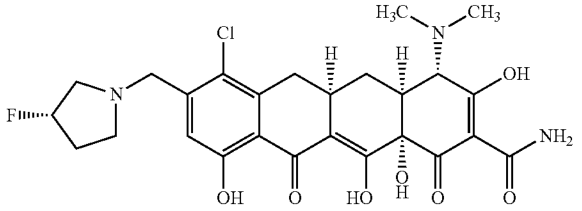

$^1$H NMR (400 MHz, $CD_3OD$) δ 7.23 (s, 1 H), 5.58-5.38 (m, 1 H), 4.67 (s, 2 H), 4.11 (s, 1 H), 4.03-3.30 (comp, 5 H), 3.04 (s, 3 H), 2.96 (s, 3 H), 3.22-2.94 (comp, 2 H), 2.76-2.10 (comp, 4 H), 1.72-1.59 (m, 1 H); MS (ESI) m/z 550.18 (M+H).

S15-14-5

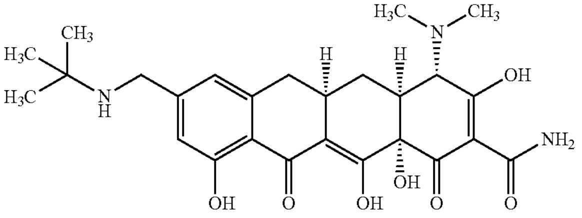

$^1$H NMR (400 MHz, $CD_3OD$) δ 6.99 (s, 1 H), 6.94 (s, 1 H), 4.14 (s, 2 H), 4.11 (s, 1 H), 3.16-2.90 (m, 9 H), 2.62-2.55 (m, 1 H), 2.25-2.20 (m, 1 H), 1.65-1.56 (m, 1 H), 1.46 (s, 9 H); MS (ESI) m/z 500.1 (M+H).

S15-14-6

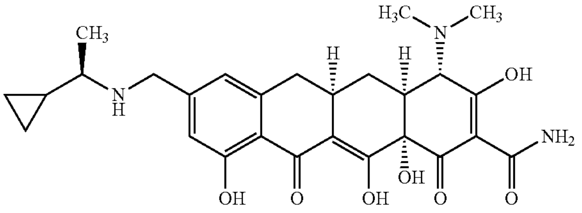

$^1$H NMR (400 MHz, $CD_3OD$) δ 6.92 (s, 1 H), 6.86 (s, 1 H), 4.18 (dd, J=43.6 Hz and 13.2 Hz, 2 H), 4.04 (s, 1 H), 2.97-2.83 (m, 10 H), 2.56-2.46 (m, 1 H), 2.18-1.14 (m, 1 H), 1.57-1.47 (m, 1 H), 1.39-1.38 (m, 3 H), 0.99-0.97 (m, 1 H), 0.72-0.64 (m, 2 H), 0.51-0.49 (m, 1 H), 0.28-0.26 (m, 1 H); MS (ESI) m/z 512.0 (M+H).

S15-14-7

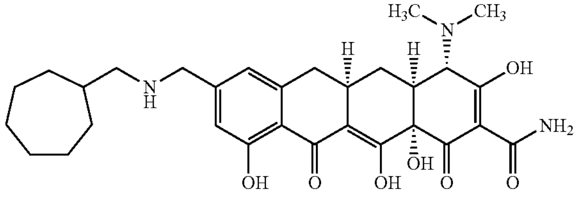

$^1$H NMR (400 MHz, $CD_3OD$) δ 6.97 (s, 1 H), 6.91 (s, 1 H), 4.15 (s, 2 H), 4.10 (s, 1 H), 3.15-2.87 (m, 11 H), 2.67-2.52 (m, 2 H), 2.24-2.16 (m, 1 H), 1.98-1.88 (m, 2 H), 1.81-1.43 (m, 9 H), 1.34-1.20 (m, 2 H); MS (ESI) m/z 554.0 (M+H).

S15-14-8

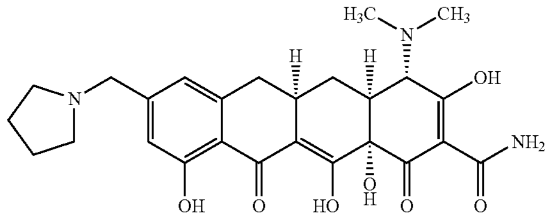

$^1$H NMR (400 MHz, $CD_3OD$) δ 6.99 (s, 1 H), 6.94 (s, 1 H), 4.33 (s, 2 H), 4.09 (s, 1 H), 3.57-3.47 (m, 2 H), 3.03 (s, 3 H), 2.96 (s, 3 H), 3.23-2.87 (comp, 5 H), 2.64-2.55 (m, 1 H), 2.24-1.94 (comp, 5 H), 1.66-1.54 (comp, 1 H); MS (ESI) m/z 498.19 (M+H).

S15-15-2

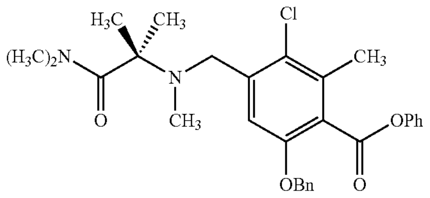

To a suspension of□-(Boc-amino)isobutyric acid (3.0 g, 14.8 mmol, 1.0 equiv) in 4:1 dichloromethane-dimethylformamide (30 mL) was added hydroxybenzotriazole (2.19 g, 16.2 mmol, 1.1 equiv) and dicyclohexycarbodiimide (3.26 g, 15.8 mmol, 1.07 equiv). After stirring at rt for 30 min, solution of dimethylamine in THF (2.0 M, 11 mL, 22.1 mmol, 1.5 equiv) was added. The reaction mixture was stirred at rt for another 16 h and then diluted with dichloromethane (100 mL). The reaction solution was washed sequentially with saturated $NaHCO_3$ (2×30 mL), $H_2O$ (30 mL), citric acid (10% w/v, 2×30 mL), and brine (30 mL). The organic solution was dried over sodium sulfate, and concentrated to give the crude product, which was purified by Biotage to provide the desired dimethylamide as white solid.

The dimethylamide prepared above was dissolved in a solution of HCl in dioxane (4.0 M, 25 mL). The reaction mixture was stirred at rt for an overnight. After evaporating volatiles, the white solid residue was washed with diethylether, and further dried under high vacuum. The formed amine hydrochloric acid salt was used directly for the next step.

To a solution of compound S15-8 (0.10 g, 0.26 mmol, 1.0 equiv) in 1,2-dichloroethane (10 mL) was added amine hydrochloric acid salt (0.131 mg, 0.79 mmol, 3.0 equiv) and triethylamine (0.11 mL, 0.79 mmol, 3.0 equiv). After stirring at rt for 30 min, acetic acid (0.045 mL, 0.79 mmol, 3.0 equiv) was added. After another 24 hrs, sodium triacetoxyborohydride (0.111 g, 0.53 mmol, 2.0 equiv) was added. Stirring was continued for 36 hrs. The reaction mixture was poured into saturated aqueous $NaHCO_3$ and extracted three times with dichloromethane. The combined organic extracts were washed with brine, dried over sodium sulfate, and concentrated to give the crude intermediate as off-white oil. The crude intermediate was redissolved in 1,2-dichloroethane (2 mL). Formaldehyde (37 wt % in $H_2O$, 0.044 mL, 0.59 mmol) and acetic acid (0.034 mL, 0.059 mmol) were added. After stirring at rt for 1 h, sodium triacetoxyborohydride (0.083 g, 0.39 mmol) was added. Stirring was continued for another hour. The reaction mixture was poured into saturated aqueous $NaHCO_3$ and extracted three times with dichloromethane. The combined organic extracts were washed with brine, dried over sodium sulfate, and concentrated. Purification of the residue by Biotage gave compound S15-15-2 as a colorless oil: $^1H$ NMR (400 MHz, $CDCl_3$) δ 7.20-7.44 (m, 8 H), 7.12 (d, J=7.8 Hz, 2 H), 6.98 (s, 1 H), 5.14 (s, 2 H), 3.61 (s, 2 H), 3.41 (s, 3 H), 2.89 (s, 3 H), 2.46 (s, 3 H), 2.04 (s, 3 H), 1.38 (s, 6 H); MS (ESI) m/z 509.2 (M+H), calcd for $C_{29}H_{34}ClN_2O_4$ 509.21.

S15-13-227

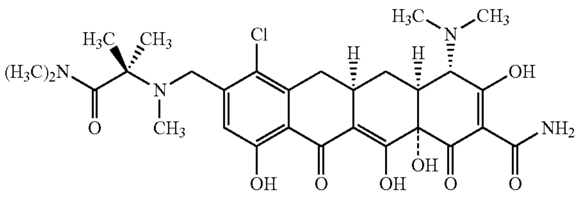

Compound S15-13-227 was prepared from S15-15-2 using similar procedures to that of S15-13-15. The crude product was purified by HPLC on a Waters Autopurification system using a Phenomenex Polymerx 10μ RP-γ 100 R column [30×21.20 mm, 10 micron; flow rate, 20 mL/min; Solvent A: 0.05 N HCl/water; Solvent B: MeOH; injection volume: 4.0 mL (0.05 N HCl/water); gradient: 10→100% B over 20 min; mass-directed fraction collection]. Fractions containing the desired product, eluting at 11.30-14.05 min, were collected and freeze-dried to give the desired product S15-13-227 as a yellow solid: $^1H$ NMR (400 MHz, $CD_3OD$) δ 7.61 and 7.59 (s, 1 H), 4.36 (br s, 2 H), 4.13 (s, 1 H), 3.42 (dd, J=4.6, 16.0 Hz, 1 H), 2.97-3.16 (m, 14 H), 2.71 (s, 3 H), 2.43 (dd, J=15.1 Hz, 1 H), 2.25-2.28 (m, 1 H), 1.89 (s, 3 H), 1.69 (s, 3 H), 1.60-1.70 (m, 1 H); MS (ESI) m/z 605.4 (M+H), calcd for $C_{29}H_{38}ClN_4O_8$ 605.23.

S15-13-228

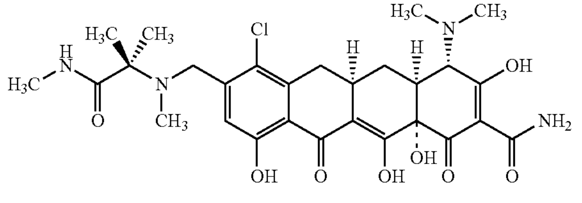

Compound S15-13-228 was prepared using similar procedures to that of S15-13-227, a yellow solid: $^1H$ NMR (400 MHz, $CD_3OD$) δ 7.44 (s, 1 H), 4.31-4.45 (m, 2 H), 4.13 (s, 1 H), 3.42 (dd, J=4.6, 16.0 Hz, 1 H), 2.97-3.16 (m, 11 H), 2.73 (s, 3 H), 2.43 (dd, J=15.1 Hz, 1 H), 2.25-2.28 (m, 1 H), 1.75 (s, 3 H), 1.63 (s, 3 H), 1.60-1.70 (m, 1 H); MS (ESI) m/z 591.5 (M+H), calcd for $C_{28}H_{36}ClN_4O_8$ 591.21.

S15-13-229

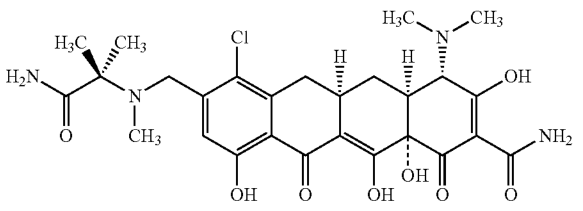

Compound S15-13-229 was prepared using similar procedures to that of S15-13-227, a yellow solid: $^1H$ NMR (400 MHz, $CD_3OD$) δ 7.46 (s, 1 H), 4.35-4.38 (m, 2 H), 4.12 (s, 1 H), 3.42 (dd, J=4.6, 16.0 Hz, 1 H), 2.97-3.16 (m, 8 H), 2.73 (s, 3 H), 2.43 (dd, J=15.1 Hz, 1 H), 2.25-2.28 (m, 1 H), 1.78 (s, 3 H), 1.66 (s, 3 H), 1.60-1.70 (m, 1 H); MS (ESI) m/z 577.5 (M+H), calcd for $C_{27}H_{34}ClN_4O_8$ 577.20.

S15-13-230

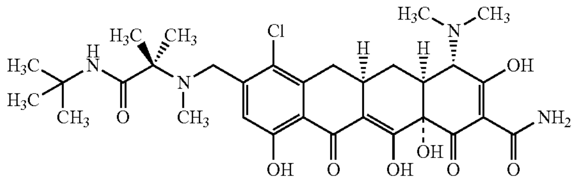

Compound S15-13-230 was prepared using similar procedures to that of S15-13-227, a yellow solid: $^1H$ NMR (400 MHz, $CD_3OD$) δ 7.39 (s, 1 H), 4.39 (dd, J=9.6, 12.8 Hz, 1 H), 4.23 (dd, J=9.6, 12.8 Hz, 1 H), 4.13 (s, 1 H), 3.41 (dd, J=4.6, 16.0 Hz, 1 H), 2.97-3.16 (m, 8 H), 2.71 (s, 3 H), 2.40 (dd, J=15.1 Hz, 1 H), 2.25-2.28 (m, 1 H), 1.78 (s, 3 H), 1.62 (s, 3 H), 1.60-1.70 (m, 1 H), 1.44 (s, 9 H); MS (ESI) m/z 633.6 (M+H), calcd for $C_{31}H_{42}ClN_4O_8$ 633.26.

S15-13-231

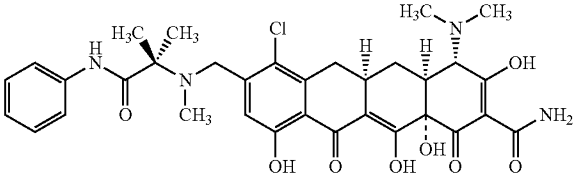

Compound S15-13-231 was prepared using similar procedures to that of S15-13-227, a yellow solid: $^1H$ NMR (400 MHz, $CD_3OD$) δ 7.67 (d, J=7.8 Hz, 2 H), 7.53 (s, 1 H), 7.38 (t, J=7.8 Hz, 2 H), 7.20 (d, J=7.8 Hz, 1 H), 4.46 (s, 2 H), 4.13 (s, 1 H), 3.42 (dd, J=4.6, 16.0 Hz, 1 H), 2.97-3.16 (m, 8 H), 2.80 (s, 3 H), 2.42 (dd, J=15.1 Hz, 1 H), 2.25-2.28 (m, 1 H), 1.94 (s, 3 H), 1.78 (s, 3 H), 1.60-1.70 (m, 1 H); MS (ESI) m/z 653.5 (M+H), calcd for $C_{33}H_{38}ClN_4O_8$ 653.23.

EXAMPLE 16
Synthesis of Compounds Via Scheme 16
Scheme 16
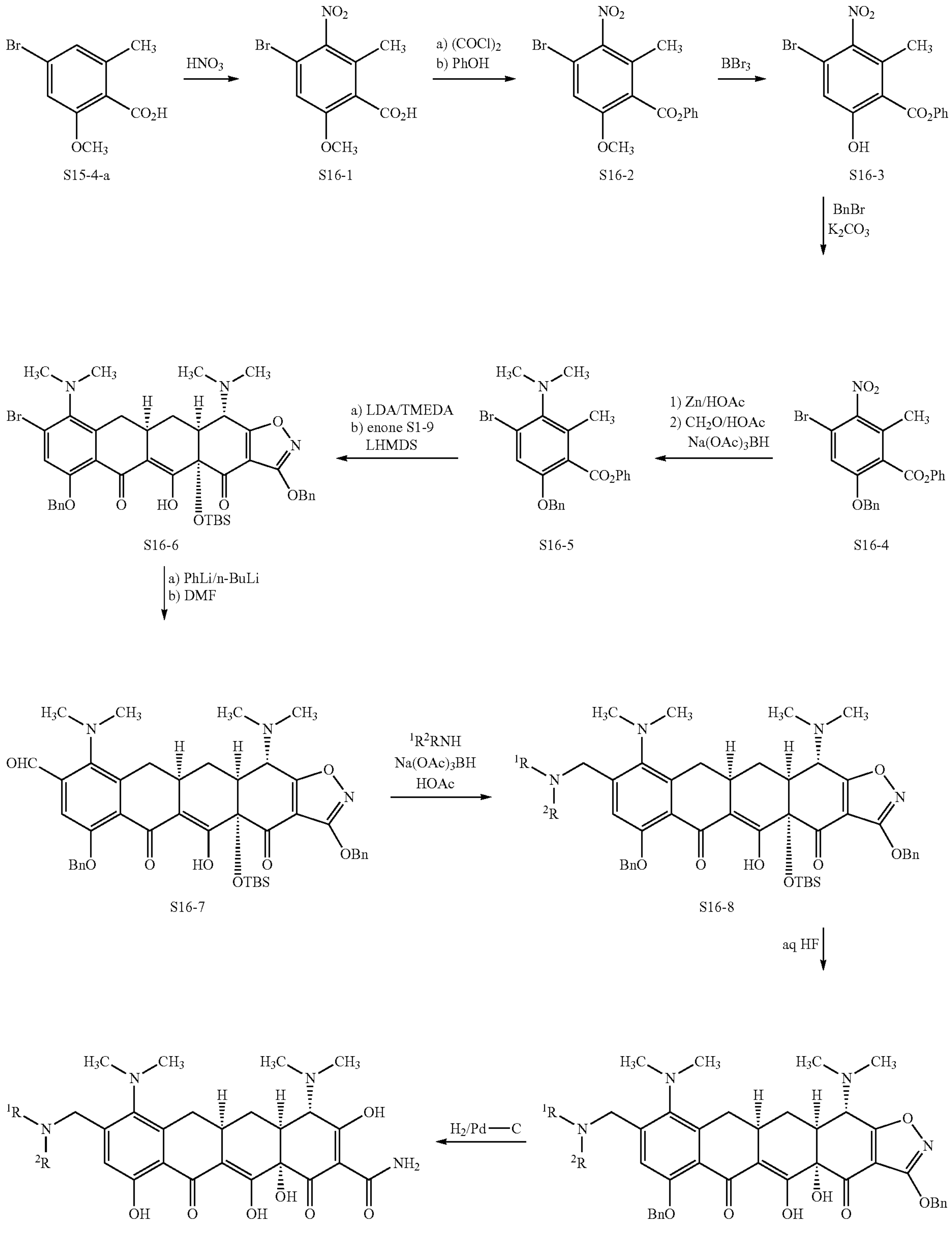

The following compounds were prepared according to Scheme 16.

S16-1

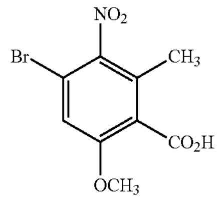

A solution of $HNO_3$ (68-70%, 0.56 mL, 8.57 mmol, 1.05 equiv) in concentrated $H_2SO_4$ (2 mL) was added dropwise to a solution of compound S15-4-a (2.00 g, 8.16 mmol, 1.0 equiv) in concentrated $H_2SO_4$ (20 mL) at 0° C. The reaction mixture was stirred at 0° C. for 10 min and poured onto ice (~200 mL). The mixture was extracted with EtOAc (150 mL). The organic phase was separated, washed with brine (2×50 mL), dried over magnesium sulfate, filtered, and concentrated to give crude S16-1 as an orange solid: $^1H$ NMR (400 MHz, $CDCl_3$) δ 11.5 (br s, 1 H), 7.06 (s, 1 H), 3.90 (s, 3 H), 2.32 (s, 3 H); MS (ESI) m/z 288.01, 289.99 (M−H).

S16-2

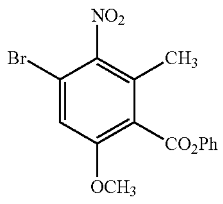

Compound S16-1 was dissolved in dichloromethane (16 mL). Oxalyl chloride (0.85 mL, 9.79 mmol, 1.2 equiv) was added, followed by a few drops of DMF. The reaction mixture was stirred at rt for 30 min, concentrated, and further dried under high vacuum. The residue was redissolved in dichloromethane (16 mL). Phenol (0.92 g, 9.79 mmol, 1.2 equiv), triethylamine (2.84 mL, 20.40 mmol, 2.5 equiv), and DMAP (100 mg, 0.82 mmol, equiv) were added. The reaction was stirred at rt for 1 h and concentrated under reduced pressure. The residue was dissolved in EtOAc (150 mL), washed with 1 N aqueous HCl (50 mL), brine (50 mL), 1 N aqueous NaOH (50 mL), and then brine (50 mL), dried over anhydrous magnesium sulfate, filtered, and concentrated to afford the desired product S16-2 as a light yellow solid: $^1H$ NMR (400 MHz, $CDCl_3$) δ 7.45-7.41 (m, 2 H), 7.30-7.26 (m, 1 H), 7.21-7.16 (m, 2 H), 7.09 (s, 1 H), 3.94 (s, 3 H), 2.38 (s, 3 H); MS (ESI) m/z 364.05, 366.06 (M−H).

S16-3

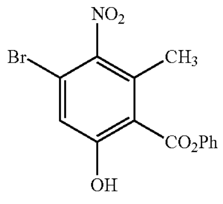

A solution of $BBr_3$ in dichloromethane (1.0 M, 8.16 mL, 8.16 mmol, 1.0 equiv) was added slowly to a solution of compound S16-2 in dichloromethane (32 mL) at −78° C. The reaction was stirred at −78° C. for 15 min and then allowed to warm to 0° C. in 50 min and kept at that temperature for 10 min. The reaction mixture was poured into saturated aqueous $NaHCO_3$ solution (50 mL) and stirred at rt for 10 min. The dichloromethane was evaporated. The residue was extracted with EtOAc (100 mL, then 30 mL). The organic extracts were combined and dried over anhydrous magnesium sulfate. The dried solution was filtered, and the filtrate was concentrated to give crude S16-3 (2.20 g): $^1H$ NMR (400 MHz, $CDCl_3$) δ 11.2 (br s, 1 H), 7.48-7.44 (m, 2 H), 7.36-7.32 (m, 1 H), 7.25 (s, 1 H), 7.18-7.16 (m, 2 H), 2.63 (s, 3 H); MS (ESI) m/z 350.01, 352.03 (M−H).

S16-4

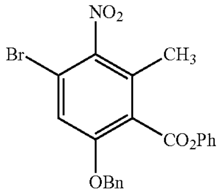

Benzylbromide (0.78 mL, 6.56 mmol, 1.05 equiv) and $K_2CO_3$ powder (1.73 g, 12.50 mmol, 2.0 equiv) were added to a solution of compound S16-3 (2.20 g, 6.25 mmol, 1.0 equiv) in acetone (12 mL). The mixture was stirred at rt overnight. The solid was filtered off and further washed with EtOAc (30 mL). The filtrate was concentrated. The residue was purified by flash column chromatography (2-20% EtOAc/hexanes) to afford the desired product S16-4 as a white solid (1.68 g, 47% over four steps): $^1H$ NMR (400 MHz, $CDCl_3$) δ 7.40-7.32 (m, 8 H), 7.15 (s, 1 H), 7.03-7.01 (m, 2 H), 5.18 (s, 2 H), 2.39 (s, 3 H); MS (ESI) m/z 440.09, 442.06 (M−H).

S16-5

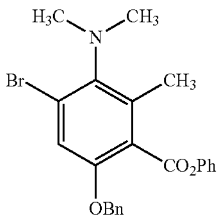

Zn dust (2.33 g, 35.70 mmol, 10.0 equiv) was added portionwise to a solution of compound S16-4 (1.58 g, 3.57 mmol, 1.0 equiv) in a mixture of THF (5 mL) and HOAc (1 mL) (caution: exothermic!). The reaction mixture was stirred at rt for 3.5 hrs, diluted with EtOAc, and filtered through a pad of Celite. The cake was washed thoroughly with EtOAc. The filtrate was washed with saturated aqueous $NaHCO_3$ (60 mL). The aqueous layer was extracted with EtOAc (40 mL). The combined extracts were dried over sodium sulfate, filtered and concentrated to yield the crude aniline intermediate S16-4a, which was used directly in the next step.

HCHO (1.59 mL, 37% aqueous solution, 21.42 mmol, 6.0 equiv), HOAc (0.62 mL, 10.71 mmol, 3.0 equiv) and $Na(OAc)_3BH$ (2.27 g, 10.71 mmol, 3.0 equiv) were added to a solution of the above crude product S16-4a in acetonitrile (30 mL). The reaction mixture was then stirred at rt for 2 h.

Then $Na(OAc)_3BH$ (0.38 g, 1.78 mmol, 0.5 equiv) was added. The reaction mixture was stirred at rt overnight. Saturated aqueous $NaHCO_3$ (70 mL) was added slowly (bubbling). The resulting mixture was then stirred at rt for 5 min and extracted with EtOAc (100 mL, then 50 mL). The combined extracts were dried over sodium sulfate, filtered and concentrated. The residue was purified by flash column chromatography (2-5% EtOAc/hexanes) to afford the desired product S16-5 as a white solid (1.43 g, 91% over 2 steps): $^1$H NMR (400 MHz, $CDCl_3$) δ 7.44-7.35 (m, 7 H), 7.26-7.22 (m, 1 H), 7.09-7.07 (m, 3 H), 5.10 (s, 2 H), 2.83 (s, 6 H), 2.42 (s, 3 H); MS (ESI) m/z 440.12, 442.13 (M+H).

S16-6

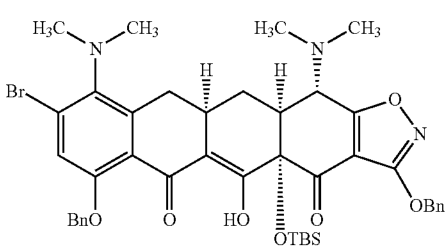

n-BuLi (1.46 mL, 2.17 M/hexanes, 3.16 mmol, 1.10 equiv) was added dropwise to a solution of diisopropylamine (0.45 mL, 3.16 mmol, 1.10 equiv) in THF (6 mL) at −78° C. The reaction solution was warmed to −20° C. and then re-cooled to −78° C. TMEDA (0.47 mL, 3.16 mmol, 1.10 equiv) was added and the reaction mixture was stirred at −78° C. for 15 min. A solution of ester S16-5 (1.27 g, 2.88 mmol, 1.05 equiv) in THF (3 mL) was added via a cannula. The resulting deep red solution was stirred at −78° C. for 55 min and was then cooled to −100° C. A solution of enone S1-9 (1.33 g, 2.75 mmol, 1.0 equiv) in THF (3 mL) was added to the reaction mixture via a cannula. The reaction mixture was allowed to warm to −70° C. over 30 min. LHMDS (3.02 mL, 1.0 M/THF, 3.02 mmol, 1.1 equiv) was added. The reaction mixture was warmed to −5° C. slowly over 1 h 20 min, quenched by a mixture of saturated aqueous $NH_4Cl$ and pH 7 phosphate buffer (100 mL, 1:1, v/v), and extracted with EtOAc (75 mL, then 25 mL). The combined EtOAc extracts were dried (sodium sulfate), filtered and concentrated. The residue was purified by a preparative reverse phase HPLC on a Waters Autopurification system using a Sunfire Prep C18 OBD column [5 μm, 19×50 mm; flow rate, 20 mL/min; Solvent A: $H_2O$ with 0.1% $HCO_2H$; Solvent B: $CH_3CN$ with 0.1% $HCO_2H$; injection volume: 4.0 mL ($CH_3CN$); gradient: 80→100% B in A over 10 min; mass-directed fraction collection]. Fractions containing the desired product, eluting at 7.6-11 min, were collected and concentrated at rt to remove most of the acetonitrile. The resulting mostly aqueous solution was freeze-dried to yield the desired product S16-6 (1.71 g, 75%): $^1$H NMR (400 MHz, $CDCl_3$) δ 16.00 (br s, 1 H), 7.50-7.46 (m, 4 H), 7.39-7.27 (m, 6 H), 7.10 (s, 1 H), 5.36 (s, 2 H), 5.18, 5.12 (ABq, J=12.8 Hz, 2 H), 4.10 (d, J=10.4 Hz, 1 H), 3.37 (dd, J=4.3, 15.9 Hz, 1 H), 2.88-2.74 (m, 7 H), 2.55-2.40 (m, 9 H), 2.12 (d, J=14.0 Hz, 1 H), 0.84 (s, 9 H), 0.28 (s, 3 H), 0.14 (s, 3 H); MS (ESI) m/z 828.27, 830.30 (M+H).

S16-7

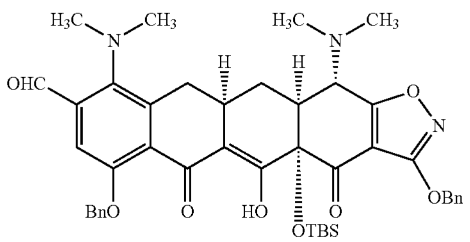

A solution of phenyllithium in di-n-butyl ether (0.10 mL, 1.8 M, 0.18 mmol, 1.5 equiv) was added dropwise to a solution of compound S16-6 (0.10 g, 0.12 mmol, 1.0 equiv) in THF (3 mL) at −78° C., forming an orange solution. After 5 min, a solution of n-butyllithium in hexanes (68 μL, 2.2 M, 0.15 mmol, 1.2 equiv) was added dropwise at −78° C., followed 2 min later by the addition of N,N-dimethylformamide (47 μL, 0.61 mmol, 5.0 equiv). The resulting dark red reaction mixture was stirred at −78° C. for 65 min. Saturated aqueous ammonium chloride (10 mL) was added dropwise at −78° C. The reaction mixture was allowed to warm to 23° C., diluted with saturated aqueous ammonium chloride (~20 mL), and extracted with EtOAc (2×15 mL). The organic extracts were combined, dried over anhydrous sodium sulfate, filtered, and concentrated, affording compound S16-7 as an orange oil, which was used directly in the next reactions: $^1$H NMR (400 MHz, $CDCl_3$) δ 15.85 (s, 1 H), 10.32 (s, 1 H), 7.50-7.46 (m, 4 H), 7.39-7.26 (m, 7 H), 5.36 (s, 2 H), 5.25, 5.18 (ABq, J=12.8 Hz, 2 H), 4.02 (d, J=11.0 Hz, 1 H), 3.13 (dd, J=4.9, 15.9 Hz, 1 H), 2.98-2.90 (m, 7 H), 2.58-2.46 (m, 9 H), 2.15 (d, J=14.0 Hz, 1 H), 0.83 (s, 9 H), 0.27 (s, 3 H), 0.15 (s, 3 H); MS (ESI) m/z 778.34 (M+H).

S16-8-1

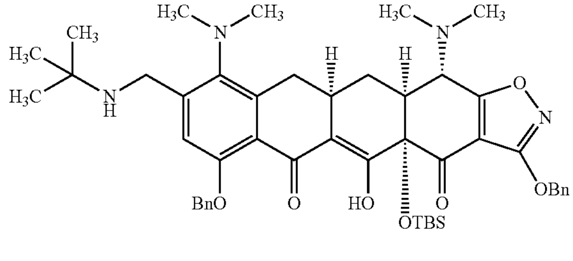

t-Butylamine (19 μL, 0.18 mmol, 3.0 equiv), acetic acid (10 μL, 0.18 mmol, 3.0 equiv) and sodium triacetoxyborohydride (26 mg, 0.12 mmol, 2.0 equiv) were added sequentially to a solution of compound S16-7 (half of the above crude product, 0.061 mmol, 1.0 equiv) in 1,2-dichloroethane (2 mL) at 23° C. After stirring for 1 h 45 min, the reaction mixture was quenched by the addition of saturated aqueous sodium bicarbonate and brine (1:1, 15 mL) and extracted with dichloromethane (2×15 mL). The combined organic extracts were dried over anhydrous sodium sulfate, filtered, and concentrated. The residue was purified by preparative reverse phase HPLC on a Waters Autopurification system using a Sunfire Prep C18 OBD column [5 μm, 19×50 mm; flow rate, 20 mL/min; Solvent A: $H_2O$ with 0.1% $HCO_2H$; Solvent B: $CH_3CN$ with 0.1% $HCO_2H$; injection volume: 3.0 mL ($CH_3CN$); gradient: 20→100% B in A over 10 min; mass-directed fraction collection]. Fractions containing the desired product, eluting at 5.6-6.5 min, were collected and freeze-dried to yield compound S16-8-1 (19 mg, 37% for 2 steps):

$^1$H NMR (400 MHz, $CDCl_3$) δ 7.50-7.48 (m, 4 H), 7.39-7.26 (m, 6 H), 7.06 (s, 1 H), 5.35 (s, 2 H), 5.23, 5.17 (ABq, J=12.8 Hz, 2 H), 4.04 (d, J=10.4 Hz, 1 H), 3.81, 3.63 (ABq, J=13.4 Hz, 2 H), 3.09 (dd, J=4.3, 15.3 Hz, 1 H), 2.88-2.76 (m, 7 H), 2.53-2.46 (m, 9 H), 2.11 (d, J=13.4 Hz, 1 H), 1.14 (s, 9 H), 0.83 (s, 9 H), 0.27 (s, 3 H), 0.14 (s, 3 H); MS (ESI) m/z 835.48 (M+H).

S16-10-1

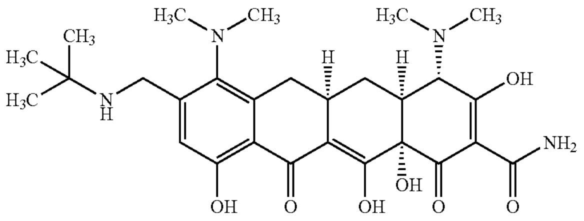

Aqueous HF (48-50%, 0.2 mL) was added to a solution of compound S16-9-1 (19 mg, 0.024 mmol, 1.0 equiv) in acetonitrile (0.6 mL) in a polypropylene reaction vessel at 23° C. The mixture was stirred vigorously at 23° C. overnight and poured into aqueous $K_2HPO_4$ (2.5 g dissolved in 20 mL water). The mixture was extracted with EtOAc (2×25 mL). The combined organic extracts were dried over anhydrous sodium sulfate, filtered, and concentrated. The residue was used directly in the next step without further purification.

Pd—C (10 wt %, 9 mg) was added in one portion into the yellow solution of the above crude product in a mixture of HCl/MeOH (0.5 N, 0.14 mL, 3.0 equiv) and MeOH (2 mL) at 23° C. The reaction vessel was sealed and purged with hydrogen by briefly evacuating the flask followed by flushing with hydrogen gas (1 atm). The resulting mixture was stirred at 23° C. for 30 min. The reaction mixture was then filtered through a small Celite pad. The filtrate was concentrated. The residue was purified by preparative reverse phase HPLC on a Waters Autopurification system using a Phenomenex Polymerx 10μ RP-γ 100A column [10 μm, 150×21.20 mm; flow rate, 20 mL/min; Solvent A: 0.05 N HCl/water; Solvent B: $CH_3CN$; injection volume: 3.0 mL (0.05 N HCl/water); gradient: 15→60% B over 10 min; mass-directed fraction collection]. Fractions containing the desired product, eluting at 5.8-8.0 min, were collected and freeze-dried to yield compound S16-10-1 (11 mg, 67% for 2 steps): $^1$H NMR (400 MHz, $CD_3OD$) δ 7.01 (s, 1 H), 4.36 (d, J=12.8 Hz, 1 H), 4.14 (d, J=12.8 Hz, 1 H), 4.12 (s, 1 H), 3.11-2.83 (m, 15 H), 2.45 (t, J=14.2 Hz, 1 H), 2.29-2.26 (m, 1 H), 1.70-1.60 (m, 1 H), 1.47 (s, 9 H); MS (ESI) m/z 543.31 (M+H).

The following compounds were prepared similarly to S16-8-1 or S16-10-1.

S16-8-2

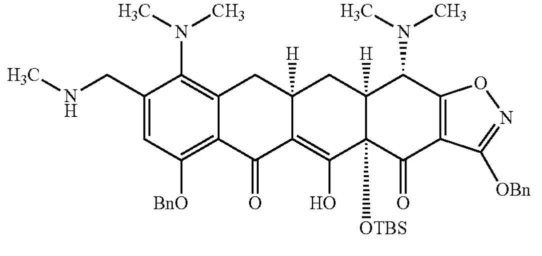

S16-8-2: $^1$H NMR (400 MHz, $CDCl_3$) δ 7.44-7.41 (m, 4 H), 7.33-7.23 (m, 6 H), 7.11 (s, 1 H), 5.29 (s, 2 H), 5.23, 5.15 (ABq, J=12.8 Hz, 2 H), 4.07 (d, J=14.0 Hz, 1 H), 3.96 (d, J=10.4 Hz, 1 H), 3.80 (d, J=14.0 Hz, 1 H), 2.96 (dd, J=4.3, 15.9 Hz, 1 H), 2.83-2.71 (m, 8 H), 2.51-2.36 (m, 11 H), 2.05 (d, J=14.6 Hz, 1 H), 0.77 (s, 9 H), 0.21 (s, 3 H), 0.08 (s, 3 H); MS (ESI) m/z 793.35 (M+H).

S16-8-3

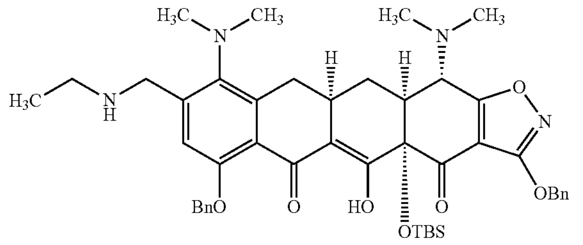

S16-8-3: $^1$H NMR (400 MHz, $CDCl_3$) δ 7.50-7.47 (m, 4 H), 7.39-7.28 (m, 6 H), 7.15 (s, 1 H), 5.35 (s, 2 H), 5.28, 5.21 (ABq, J=12.8 Hz, 2 H), 4.11 (d, J=14.0 Hz, 1 H), 4.02 (d, J=10.4 Hz, 1 H), 3.84 (d, J=14.0 Hz, 1 H), 3.02 (dd, J=4.9, 15.9 Hz, 1 H), 2.88-2.76 (m, 8 H), 2.66 (q, J=7.3 Hz, 2 H), 2.56-2.44 (m, 8 H), 2.11 (d, J=14.0 Hz, 1 H), 1.19 (t, J=7.3 Hz, 3 H), 0.83 (s, 9 H), 0.27 (s, 3 H), 0.14 (s, 3 H); MS (ESI) m/z 807.37 (M+H).

S16-8-4

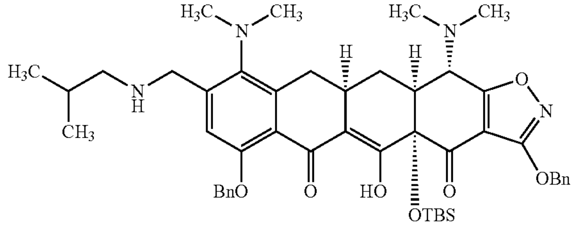

S16-8-4: $^1$H NMR (400 MHz, $CDCl_3$) δ 7.50-7.47 (m, 4 H), 7.39-7.31 (m, 5 H), 7.28-7.24 (m, 1 H), 7.00 (s, 1 H), 5.35 (s, 2 H), 5.23, 5.18 (ABq, J=12.2 Hz, 2 H), 4.05 (d, J=10.4 Hz, 1 H), 3.88, 3.65 (ABq, J=14.6 Hz, 2 H), 3.10 (dd, J=4.3, 15.9 Hz, 1 H), 2.93-2.74 (m, 7 H), 2.54-2.44 (m, 9 H), 2.33 (d, J=6.7 Hz, 2 H), 2.12 (d, J=14.0 Hz, 1 H), 1.76-1.69 (m, 1 H), 0.88 (d, J=6.7 Hz, 6 H), 0.84 (s, 9 H), 0.28 (s, 3 H), 0.15 (s, 3 H); MS (ESI) m/z 835.50 (M+H).

S16-8-5

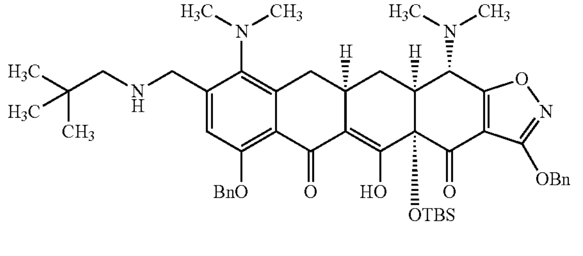

S16-8-5: $^1$H NMR (400 MHz, $CDCl_3$) δ 7.50-7.47 (m, 4 H), 7.39-7.24 (m, 6 H), 7.21 (s, 1 H), 5.35 (s, 2 H), 5.24, 5.19 (ABq, J=12.8 Hz, 2 H), 4.06-3.99 (m, 2 H), 3.76-3.73 (m, 1

H), 3.08 (dd, J=4.3, 15.3 Hz, 1 H), 2.89-2.71 (m, 8 H), 2.55-2.46 (m, 8 H), 2.31-2.26 (m, 2 H), 2.11 (d, J=13.4 Hz, 1 H), 0.92 (s, 9 H), 0.83 (s, 9 H), 0.27 (s, 3 H), 0.14 (s, 3 H); MS (ESI) m/z 849.40 (M+H).

S16-8-6

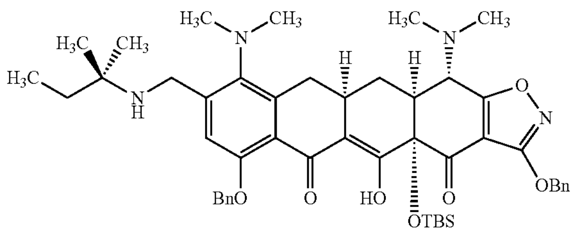

S16-8-6: $^1$H NMR (400 MHz, $CDCl_3$) δ 7.50-7.48 (m, 4 H), 7.39-7.31 (m, 5 H), 7.28-7.24 (m, 1 H), 7.08 (s, 1 H), 5.35 (s, 2 H), 5.23, 5.19 (ABq, J=12.8 Hz, 2 H), 4.05 (d, J=10.4 Hz, 1 H), 3.73, 3.57 (ABq, J=13.4 Hz, 2 H), 3.10 (dd, J=4.3, 15.3 Hz, 1 H), 2.92-2.76 (m, 7 H), 2.53-2.45 (m, 9 H), 2.11 (d, J=13.4 Hz, 1 H), 1.44 (q, J=7.3 Hz, 2 H), 1.06 (s, 6 H), 0.86 (t, J=7.3 Hz, 3 H), 0.84 (s, 9 H), 0.28 (s, 3 H), 0.14 (s, 3 H); MS (ESI) m/z 849.43 (M+H).

S16-8-7

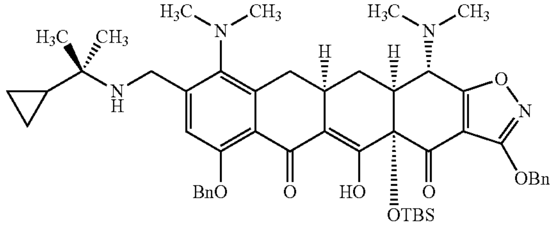

S16-8-7: $^1$H NMR (400 MHz, $CDCl_3$) δ 7.50-7.48 (m, 4 H), 7.39-7.31 (m, 5 H), 7.28-7.26 (m, 1 H), 7.08 (s, 1 H), 5.35 (s, 2 H), 5.24, 5.18 (ABq, J=12.8 Hz, 2 H), 4.05 (d, J=10.4 Hz, 1 H), 3.90, 3.71 (ABq, J=13.4 Hz, 2 H), 3.11 (dd, J=4.3, 15.9 Hz, 1 H), 2.92-2.76 (m, 7 H), 2.54-2.43 (m, 9 H), 2.11 (d, J=14.0 Hz, 1 H), 0.98 (d, J=2.4 Hz, 6 H), 0.83 (s, 9 H), 0.39-0.34 (m, 2 H), 0.27 (s, 3 H), 0.25-0.22 (m, 2 H), 0.14 (s, 3 H); MS (ESI) m/z 861.39 (M+H).

S16-8-8

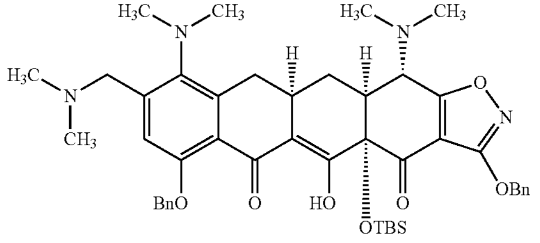

S16-8-8: $^1$H NMR (400 MHz, $CDCl_3$) δ 16.11 (br s, 1 H), 7.51-7.48 (m, 4 H), 7.39-7.30 (m, 6 H), 7.26 (s, 1 H), 5.35 (s, 2 H), 5.28, 5.21 (ABq, J=12.8 Hz, 2 H), 4.04 (d, J=10.4 Hz, 1 H), 3.57 (br s, 2 H), 3.12 (dd, J=3.7, 15.3 Hz, 1 H), 2.92-2.72 (m, 7 H), 2.54-2.43 (m, 9 H), 2.26 (s, 6 H), 2.11 (d, J=1.34 Hz, 1 H), 0.83 (s, 9 H), 0.27 (s, 3 H), 0.14 (s, 3 H); MS (ESI) m/z 807.32 (M+H).

S16-8-9

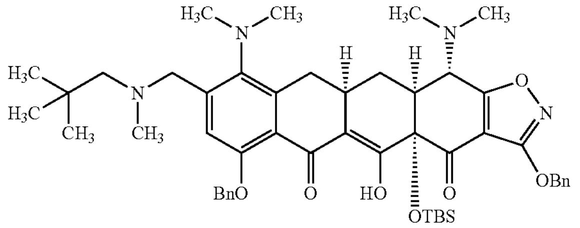

S16-8-9: $^1$H NMR (400 MHz, $CDCl_3$) δ 16.12 (br s, 1 H), 7.50-7.46 (m, 4 H), 7.39-7.28 (m, 6 H), 7.23 (s, 1 H), 5.35 (s, 2 H), 5.26 (s, 2 H), 4.05 (d, J=10.4 Hz, 1 H), 3.58 (br s, 2 H), 3.15-3.12 (m, 1 H), 2.92-2.85 (m, 1 H), 2.77-2.70 (m, 7 H), 2.53-2.43 (m, 9 H), 2.31-2.27 (m, 2 H), 2.12-2.04 (m, 3 H), 0.88 (s, 9 H), 0.84 (s, 9 H), 0.28 (s, 3 H), 0.15 (s, 3 H); MS (ESI) m/z 863.44 (M+H).

S16-8-10

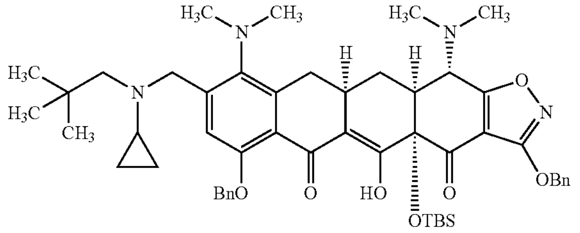

S16-8-10: $^1$H NMR (400 MHz, $CDCl_3$) δ 16.04 (br s, 1 H), 7.40-7.38 (m, 2 H), 7.34-7.32 (m, 2 H), 7.29-7.19 (m, 5 H), 7.15-7.14 (m, 1 H), 7.11 (s, 1 H), 5.26 (s, 2 H), 5.12 (s, 2 H), 3.97 (d, J=10.4 Hz, 1 H), 3.76 (d, J=15.9 Hz, 1 H), 3.58 (d, J=15.9 Hz, 1 H), 3.04 (dd, J=4.3, 15.9 Hz, 1 H), 2.84-2.78 (m, 1 H), 2.69 (s, 3 H), 2.62 (s, 3 H), 2.43-2.28 (m, 11 H), 2.02 (d, J=14.0 Hz, 1 H), 1.76-1.75 (m, 1 H), 0.75 (s, 9 H), 0.73 (s, 9 H), 0.18 (s, 3 H), 0.06 (s, 3 H), 0.03-0.09 (m, 4 H); MS (ESI) m/z 899.48 (M+H).

S16-8-11

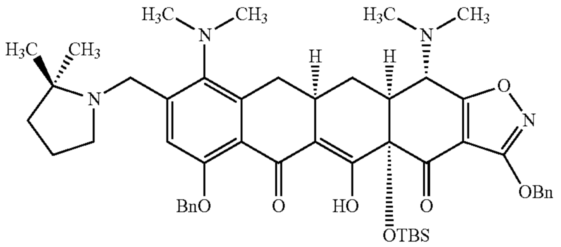

S16-8-11: $^1$H NMR (400 MHz, $CDCl_3$) δ 16.14 (br s, 1 H), 7.50-7.45 (m, 4 H), 7.39-7.31 (m, 5 H), 7.25-7.21 (m, 2 H), 5.36 (s, 2 H), 5.22 (s, 2 H), 4.05 (d, J=10.4 Hz, 1 H), 3.53, 3.46 (ABq, J=15.3 Hz, 2 H), 3.18 (dd, J=3.7, 15.3 Hz, 1 H), 2.92-2.86 (m, 1 H), 2.81-2.71 (m, 6 H), 2.53-2.31 (m, 11 H), 2.11 (d, J=13.4 Hz, 1 H), 1.64 (br s, 4 H), 1.62 (s, 3 H), 0.98 (s, 3 H), 0.84 (s, 9 H), 0.28 (s, 3 H), 0.15 (s, 3 H); MS (ESI) m/z 861.49 (M+H).

S16-10-2

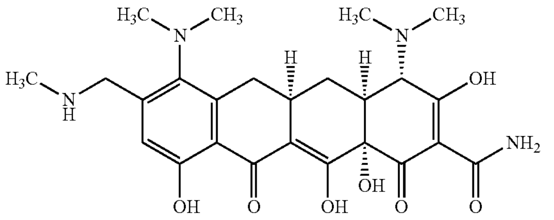

S16-10-2: $^1$H NMR (400 MHz, $CD_3OD$) δ 6.89 (s, 1 H), 4.37 (d, J=13.7 Hz, 1 H), 4.12 (d, J=13.7 Hz, 1 H), 4.10 (s, 1 H), 3.10-2.78 (m, 18 H), 2.43 (t, J=14.6 Hz, 1 H), 2.27-2.24 (m, 1 H), 1.70-1.60 (m, 1 H); MS (ESI) m/z 501.29 (M+H).

S16-10-3

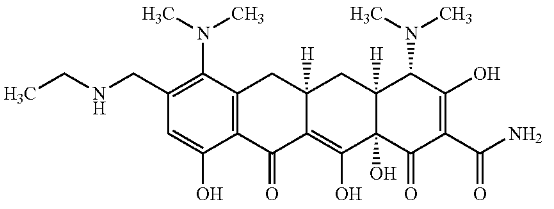

S16-10-3: $^1$H NMR (400 MHz, $CD_3OD$) δ 6.94 (s, 1 H), 4.38 (d, J=13.7 Hz, 1 H), 4.15 (d, J=14.2 Hz, 1 H), 4.11 (s, 1 H), 3.16 (q, J=7.3 Hz, 2 H), 3.12-2.81 (m, 15 H), 2.44 (t, J=14.2 Hz, 1 H), 2.28-2.25 (m, 1 H), 1.69-1.60 (m, 1 H), 1.37 (t, J=7.3 Hz, 3 H); MS (ESI) m/z 515.30 (M+H).

S16-10-4

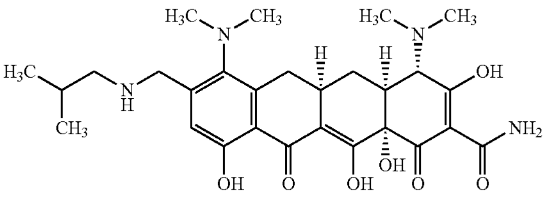

S16-10-4: $^1$H NMR (400 MHz, $CD_3OD$) δ 7.05 (s, 1 H), 4.50 (d, J=13.3 Hz, 1 H), 4.26 (d, J=13.7 Hz, 1 H), 4.15 (s, 1 H), 3.18-2.89 (m, 17 H), 2.52 (t, J=12.8 Hz, 1 H), 2.34-2.31 (m, 1 H), 2.15-2.08 (m, 1 H), 1.70-1.61 (m, 1 H), 1.06 (d, J=6.4 Hz, 6 H); MS (ESI) m/z 543.32 (M+H).

S16-10-5

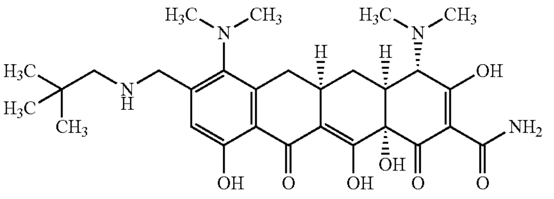

S16-10-5: $^1$H NMR (400 MHz, $CD_3OD$) δ 6.93 (s, 1 H), 4.42 (d, J=13.7 Hz, 1 H), 4.17 (d, J=13.7 Hz, 1 H), 4.10 (s, 1 H), 3.04-2.83 (m, 17 H), 2.47 (t, J=14.6 Hz, 1 H), 2.28-2.24 (m, 1 H), 1.70-1.60 (m, 1 H), 1.08 (s, 9 H); MS (ESI) m/z 557.31 (M+H).

S16-10-6

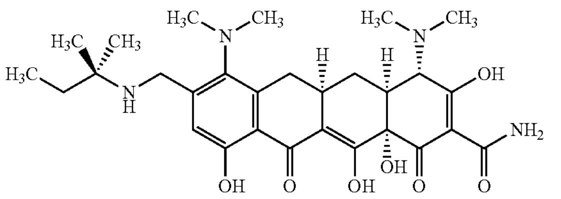

S16-10-6: $^1$H NMR (400 MHz, $CD_3OD$) δ 7.03 (s, 1 H), 4.38 (d, J=12.8 Hz, 1 H), 4.16 (d, J=12.8 Hz, 1 H), 4.14 (s, 1 H), 3.13-2.87 (m, 15 H), 2.47 (t, J=14.6 Hz, 1 H), 2.31-2.28 (m, 1 H), 1.82 (q, J=7.3 Hz, 2 H), 1.70-1.61 (m, 1 H), 1.44 (s, 6 H), 1.05 (t, J=7.3 Hz, 3 H); MS (ESI) m/z 557.32 (M+H).

S16-10-7

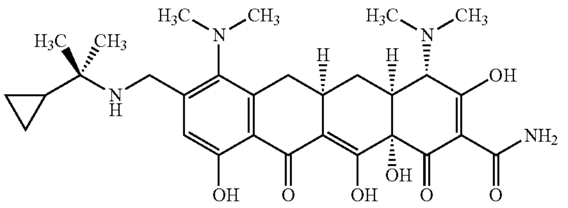

S16-10-7: $^1$H NMR (400 MHz, $CD_3OD$) δ 7.04 (s, 1 H), 4.50 (d, J=13.3 Hz, 1 H), 4.26 (d, J=13.3 Hz, 1 H), 4.14 (s, 1 H), 3.12-2.86 (m, 15 H), 2.46 (t, J=14.2 Hz, 1 H), 2.31-2.27 (m, 1 H), 1.70-1.61 (m, 1 H), 1.34 (s, 6 H), 1.25-1.19 (m, 1 H), 0.72-0.59 (m, 4 H); MS (ESI) m/z 569.30 (M+H).

S16-10-8

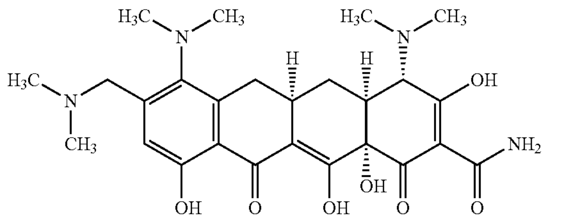

S16-10-8: $^1$H NMR (400 MHz, $CD_3OD$) δ 6.96 (s, 1 H), 4.55 (d, J=13.3 Hz, 1 H), 4.23 (d, J=13.3 Hz, 1 H), 4.12 (s, 1 H), 3.09-2.82 (m, 21 H), 2.47 (t, J=15.1 Hz, 1 H), 2.28-2.25 (m, 1 H), 1.70-1.60 (m, 1 H); MS (ESI) m/z 515.28 (M+H).

S16-10-9

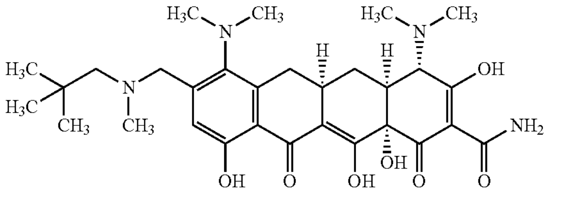

S16-10-9: $^1H$ NMR (400 MHz, $CD_3OD$) δ 6.99 (s, 1 H), 4.74 (d, J=12.8 Hz, 0.7 H), 4.54 (br d, J=12.8 Hz, 0.3 H), 4.38 (br d, J=12.8 Hz, 0.3 H), 4.17 (d, J=12.8 Hz, 0.3 H), 4.11 (s, 1 H), 3.20-2.80 (m, 20 H), 2.55-2.48 (m, 1 H), 2.29-2.26 (m, 1 H), 1.70-1.61 (m, 1 H), 1.10 (s, 9 H); MS (ESI) m/z 571.38 (M+H).

S16-10-10

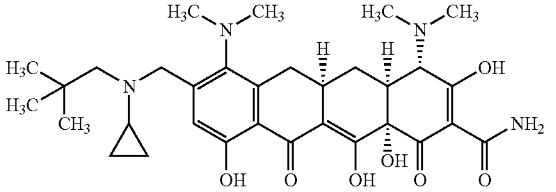

S16-10-10: $^1H$ NMR (400 MHz, $CD_3OD$) δ 7.08 (s, 1 H), 4.72 (d, J=12.8 Hz, 1 H), 4.42 (d, J=12.8 Hz, 1 H), 4.10 (s, 1 H), 3.09-2.85 (m, 18 H), 2.51 (t, J=15.6 Hz, 1 H), 2.28-2.24 (m, 1 H), 1.71-1.62 (m, 1 H), 1.13 (s, 9 H), 1.08-1.06 (m, 4 H); MS (ESI) m/z 597.38 (M+H).

S16-10-11

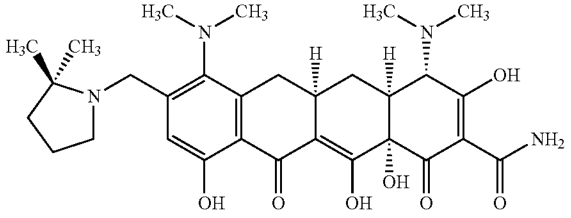

S16-10-11: $^1H$ NMR (400 MHz, $CD_3OD$) δ 6.99 (s, 0.4 H), 6.97 (s, 0.6 H), 4.68 (d, J=12.8 Hz, 0.6 H), 4.43 (d, J=12.8 Hz, 0.4 H), 4.19 (d, J=12.8 Hz, 0.4 H), 4.10 (s, 1 H), 3.93 (d, J=12.8 Hz, 0.6 H), 3.08-2.80 (m, 17 H), 2.48 (t, J=16.0 Hz, 1 H), 2.28-2.24 (m, 1 H), 2.16-2.14 (m, 2 H), 2.04-1.99 (m, 2 H), 1.71-1.61 (m, 1 H), 1.61 (s, 3 H), 1.44 (s, 3 H); MS (ESI) m/z 569.32 (M+H).

S16-10-12

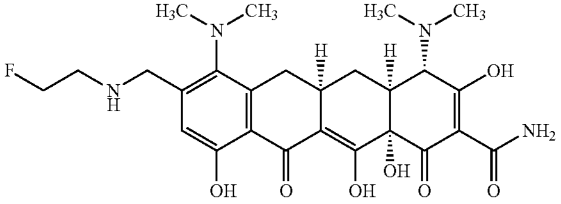

S16-10-12: $^1H$ NMR (400 MHz, $CD_3OD$) δ 6.96 (s, 1 H), 4.81 (dt, J=47.2, 4.1 Hz, 2 H), 4.49 (d, J=14.2 Hz, 1 H), 4.26 (d, J=14.2 Hz, 1 H), 4.13 (s, 1 H), 3.49 (dt, J=26.6, 3.7 Hz, 2 H), 3.12-2.85 (m, 15 H), 2.46 (t, J=14.2 Hz, 1 H), 2.30-2.27 (m, 1 H), 1.70-1.60 (m, 1 H); MS (ESI) m/z 533.31 (M+H).

S16-10-13

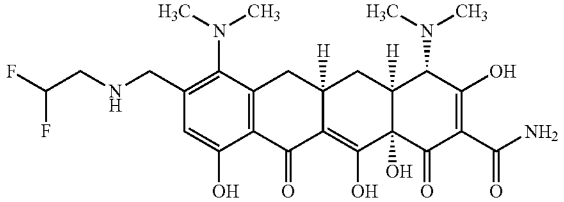

S16-10-13: $^1H$ NMR (400 MHz, $CD_3OD$) δ 6.94 (s, 1 H), 6.37 (tt, J=2.8, 53.6 Hz, 1 H), 4.52 (d, J=14.2 Hz, 1 H), 4.29 (d, J=14.2 Hz, 1 H), 4.13 (s, 1 H), 3.64 (t, J=15.6 Hz, 2 H), 3.12-2.85 (m, 15 H), 2.47 (t, J=14.2 Hz, 1 H), 2.31-2.27 (m, 1 H), 1.70-1.60 (m, 1 H); MS (ESI) m/z 551.27 (M+H).

S16-10-14

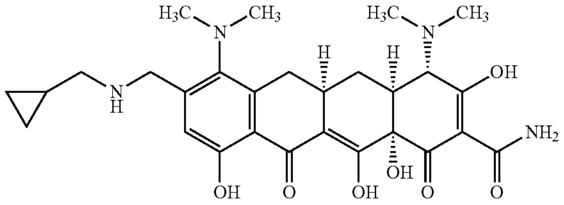

S16-10-14: $^1H$ NMR (400 MHz, $CD_3OD$) δ 6.95 (s, 1 H), 4.42 (d, J=14.2 Hz, 1 H), 4.19 (d, J=14.2 Hz, 1 H), 4.12 (s, 1 H), 3.07-2.97 (m, 17 H), 2.44 (t, J=14.2 Hz, 1 H), 2.28-2.25 (m, 1 H), 1.70-1.60 (m, 1 H), 1.21-1.14 (m, 1 H), 0.77-0.73 (m, 2 H), 0.46-0.42 (m, 2 H); MS (ESI) m/z 541.29 (M+H).

S16-10-15

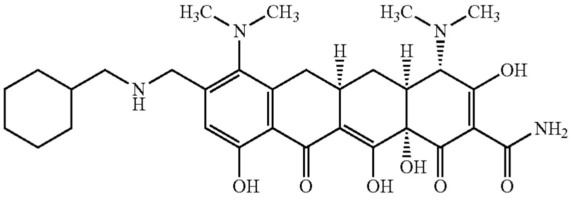

S16-10-15: $^1H$ NMR (400 MHz, $CD_3OD$) δ 6.93 (s, 1 H), 4.39 (d, J=13.7 Hz, 1 H), 4.14 (d, J=13.7 Hz, 1 H), 4.10 (s, 1 H), 3.10-2.81 (m, 17 H), 2.45 (t, J=14.6 Hz, 1 H), 2.28-2.24 (m, 1 H), 1.84-1.64 (m, 6 H), 1.39-1.21 (m, 4 H), 1.10-1.04 (m, 2 H); MS (ESI) m/z 583.34 (M+H).

S16-10-16

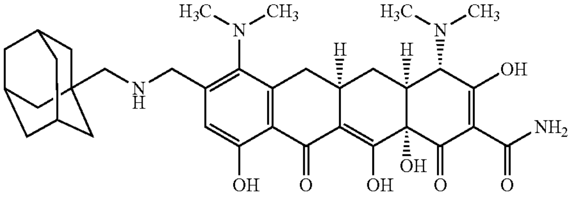

S16-10-16: $^1H$ NMR (400 MHz, $CD_3OD$) δ 6.93 (s, 1 H), 4.40 (d, J=13.7 Hz, 1 H), 4.16 (d, J=13.7 Hz, 1 H), 4.12 (s, 1 H), 3.10-2.77 (m, 17 H), 2.47 (t, J=14.6 Hz, 1 H), 2.29-2.26 (m, 1 H), 2.04 (br s, 3 H), 1.82-1.70 (m, 7 H), 1.66-1.64 (m, 6 H); MS (ESI) m/z 635.34 (M+H).

S16-10-17

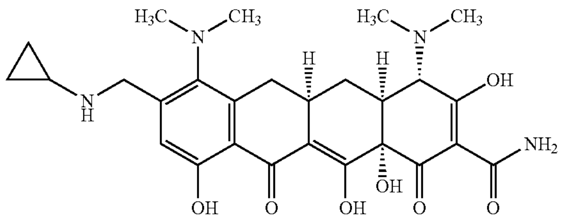

S16-10-17: $^1$H NMR (400 MHz, $CD_3OD$) δ 6.93 (s, 1 H), 4.49 (d, J=13.7 Hz, 1 H), 4.27 (d, J=13.7 Hz, 1 H), 4.10 (s, 1 H), 3.10-2.81 (m, 16 H), 2.43 (t, J=14.2 Hz, 1 H), 2.27-2.24 (m, 1 H), 1.69-1.60 (m, 1 H), 0.95-0.94 (m, 4 H); MS (ESI) m/z 527.35 (M+H).

S16-10-18

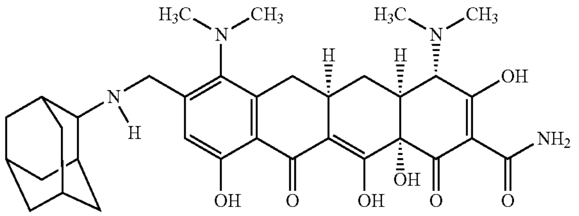

S16-10-18: $^1$H NMR (400 MHz, $CD_3OD$) δ 6.98 (s, 1 H), 4.44 (d, J=13.3 Hz, 1 H), 4.16 (d, J=13.7 Hz, 1 H), 4.12 (s, 1 H), 3.45 (s, 1 H), 3.08-2.85 (m, 15 H), 2.48 (t, J=14.6 Hz, 1 H), 2.30-2.23 (m, 3 H), 2.06-1.94 (m, 6 H), 1.85-1.79 (m, 6 H), 1.73-1.61 (m, 1 H); MS (ESI) m/z 621.35 (M+H).

S16-10-19

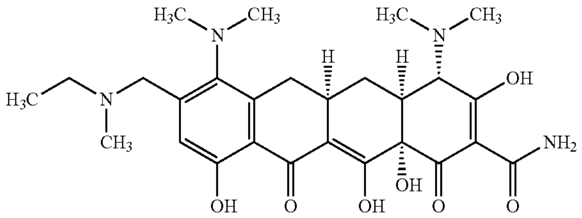

S16-10-19: $^1$H NMR (400 MHz, $CD_3OD$) δ 6.97 (s, 1 H), 4.64 (d, J=13.3 Hz, 0.5 H), 4.48 (d, J=13.3 Hz, 0.5 H), 4.32 (d, J=13.3 Hz, 0.5 H), 4.12 (s, 1 H), 4.11 (d, J=12.8 Hz, 0.5 H), 3.22-2.82 (m, 20 H), 2.47 (t, J=14.6 Hz, 1 H), 2.29-2.25 (m, 1 H), 1.70-1.61 (m, 1 H), 1.44-1.37 (m, 3 H); MS (ESI) m/z 529.30 (M+H).

S16-10-20

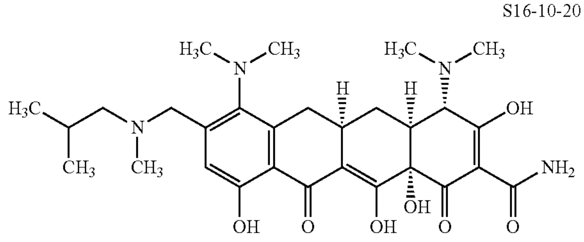 [SMILES: CC(C)CN(C)Cc1cc(O)c2c(c1N(C)C)C[C@H]1C[C@H]3[C@H](N(C)C)C(O)=C(C(N)=O)C(=O)[C@@]3(O)C(O)=C1C2=O]

S16-10-20: $^1$H NMR (400 MHz, $CD_3OD$) δ 6.98 (s, 0.4 H), 6.96 (s, 0.6 H), 4.86 (br s, 0.4 H), 4.72 (d, J=13.3 Hz, 0.6 H), 4.43 (br s, 0.6 H), 4.13-4.60 (m, 1.4 H), 3.25-2.87 (m, 20 H), 2.51-2.47 (m, 1 H), 2.27 (br s, 2 H), 1.66 (br s, 1 H), 1.08 (d, J=4.1 Hz, 6 H); MS (ESI) m/z 557.32 (M+H).

S16-10-21

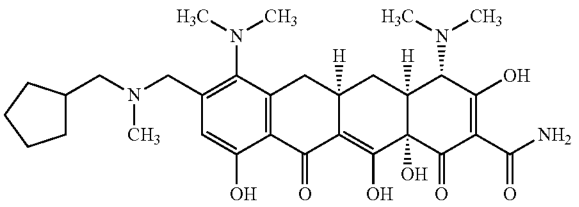

S16-10-21: $^1$H NMR (400 MHz, $CD_3OD$) δ 6.96 (s, 0.4 H), 6.94 (s, 0.6 H), 4.72 (d, J=13.3 Hz, 0.4 H), 4.42 (s, 0.6 H), 4.09 (s, 1 H), 4.09 (d, J=13.3 Hz, 0.4 H), 3.08-2.81 (m, 20 H), 2.50-2.38 (m, 1 H), 2.27-2.24 (m, 1 H), 1.71-1.57 (m, 5 H), 1.38-1.28 (m, 4 H); MS (ESI) m/z 583.38 (M+H).

S16-10-22

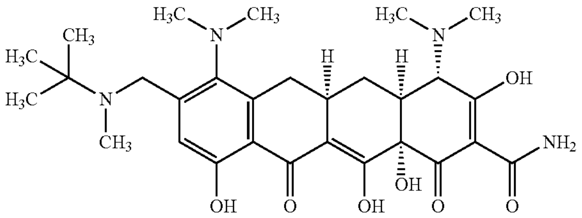

S16-10-22: $^1$H NMR (400 MHz, $CD_3OD$) δ 6.99 (s, 0.4 H), 6.69 (s, 0.6 H), 4.81 (d, J=13.3 Hz, 0.6 H), 4.54 (d, J=12.8 Hz, 0.4 H), 4.24 (d, J=12.8 Hz, 0.4 H), 4.12 (s, 1 H), 3.96 (d, J=13.3 Hz, 0.6 H), 3.05-2.72 (m, 18 H), 2.54-2.47 (m, 1 H), 2.30-2.26 (m, 1 H), 1.71-1.62 (m, 1 H), 1.55 (s, 9 H); MS (ESI) m/z 557.31 (M+H).

S16-10-23

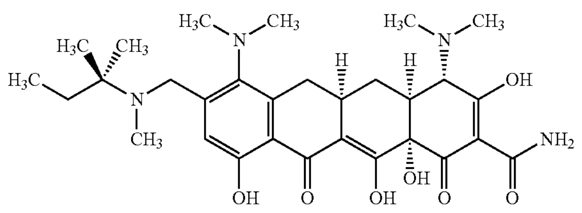

S16-10-23: $^1$H NMR (400 MHz, $CD_3OD$) δ 6.98 (s, 0.35 H), 6.95 (s, 0.75 H), 4.92 (d, J=13.3 Hz, 0.75 H), 4.56 (d, J=12.8 Hz, 0.35 H), 4.24 (d, J=12.8 Hz, 0.35 H), 4.13 (s, 1 H), 4.00 (d, J=13.3 Hz, 0.75 H), 3.12-2.73 (m, 18 H), 2.55-2.46 (m, 1 H), 2.31-2.28 (m, 1 H), 2.02-1.82 (m, 2 H), 1.71-1.61 (m, 1 H), 1.53-1.49 (m, 6 H), 1.09 (t, J=7.3 Hz, 3 H); MS (ESI) m/z 571.31 (M+H).

S16-10-24

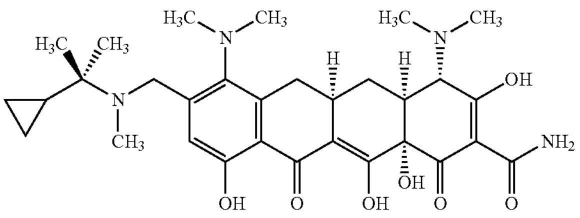

S16-10-24: $^1$H NMR (400 MHz, $CD_3OD$) δ 7.01 (s, 0.4 H), 6.96 (s, 0.6 H), 4.68 (d, J=12.8 Hz, 0.4 H), 4.32 (d, J=12.8 Hz, 0.4 H), 4.13 (s, 1 H), 4.05 (d, J=13.3 Hz, 0.6 H), 3.25-2.80 (m, 18 H), 2.55-2.43 (m, 1 H), 2.32-2.28 (m, 1 H), 1.71-1.62 (m, 1 H), 1.42-1.38 (m, 6 H), 1.31-1.28 (m, 1 H), 0.80-078 (m, 2 H), 0.68-0.64 (m, 2 H); MS (ESI) m/z 583.32 (M+H).

S16-10-25

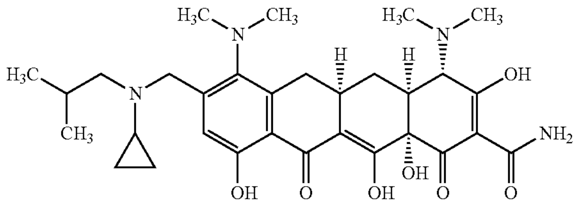

S16-10-25: $^1$H NMR (400 MHz, $CD_3OD$) δ 7.02 (s, 1 H), 4.71 (d, J=13.3 Hz, 1 H), 4.42 (d, J=13.3 Hz, 1 H), 4.12 (s, 1 H), 3.14-2.82 (m, 18 H), 2.49 (t, J=15.6 Hz, 1 H), 2.40-2.33 (m, 1 H), 2.29-2.26 (m, 1 H), 1.70-1.61 (m, 1 H), 1.07-0.99 (m, 10 H); MS (ESI) m/z 583.36 (M+H).

S16-10-26

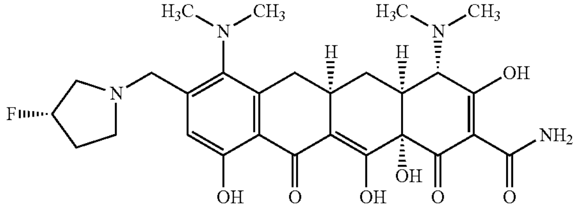

S16-10-26: $^1$H NMR (400 MHz, $CD_3OD$) δ 7.01 (s, 1 H), 5.46 (br d, J=52.2 Hz, 1 H), 4.72 (d, J=13.3 Hz, 1 H), 4.39 (br s, 1 H), 4.12 (s, 1 H), 3.85 (br s, 2 H), 3.55-3.46 (m, 2 H), 3.12-2.84 (m, 15 H), 2.51-2.43 (m, 3 H), 2.30-2.26 (m, 1 H), 1.70-1.60 (m, 1 H); MS (ESI) m/z 559.26 (M+H).

S16-10-27

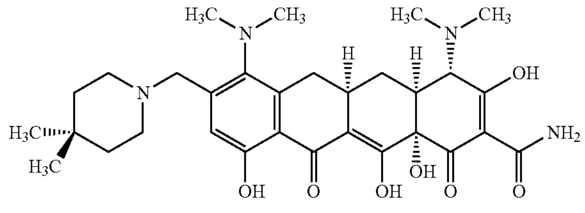

S16-10-27: $^1$H NMR (400 MHz, $CD_3OD$) δ 7.04 (s, 1 H), 4.56 (d, J=12.8 Hz, 1 H), 4.30 (d, J=12.8 Hz, 1 H), 4.12 (s, 1 H), 3.36-2.83 (m, 19 H), 2.47 (t, J=14.2 Hz, 1 H), 2.29-2.26 (m, 1 H), 1.77-1.61 (m, 5 H), 1.11 (s, 3 H), 1.05 (s, 3 H); MS (ESI) m/z 583.36 (M+H).

S16-10-28

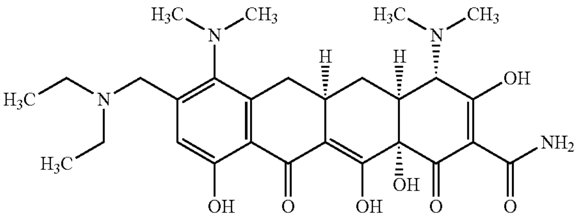

S16-10-28: $^1$H NMR (400 MHz, $CD_3OD$) δ 7.00 (s, 1 H), 4.58 (d, J=14.0 Hz, 1 H), 4.24 (d, J=13.2 Hz, 1 H), 4.13 (s, 1 H), 3.28-124 (m, 4 H), 3.09-2.80 (m, 15 H), 2.60-2.48 (m, 1 H), 2.32-2.28 (m, 1 H), 1.68-1.63 (m, 1 H), 0.93-0.85 (m, 6 H); MS (ESI) m/z 543.1 (M+H).

S16-10-29

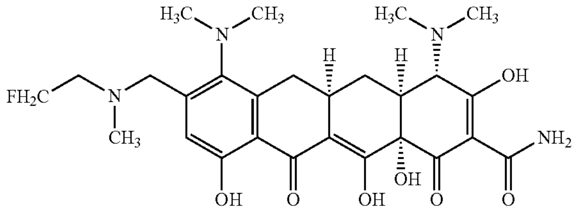

S16-10-29: $^1$H NMR (400 MHz, $CD_3OD$) δ 6.97 (s, 1 H), 5.00-4.95 (m, 1 H), 4.85-4.800 (m, 1 H), 4.78-4.58 (m, 1 H), 4.48-4.24 (m, 1 H), 4.14 (s, 1 H), 3.68-3.49 (m, 2 H), 3.12-2.87 (m, 18 H), 2.61-2.49 (m, 1 H), 2.32-2.29 (m, 1 H), 1.69-1.63 (m, 1 H); MS (ESI) m/z 547.0 (M+H).

S16-10-30

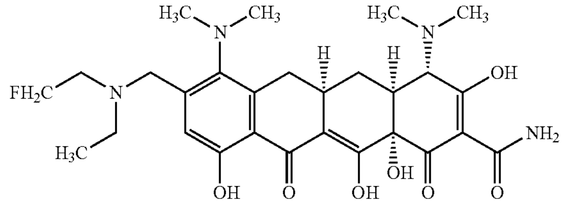

S16-10-30: $^1$H NMR (400 MHz, $CD_3OD$) δ 7.00 (s, 1 H), 5.08-5.02 (m, 1 H), 4.90-4.85 (m, 1 H), 4.76-4.72 (m, 1 H), 4.39-4.36 (m, 1 H), 4.15 (s, 1 H), 3.67-3.60 (m, 2 H), 3.16-2.91 (m, 17 H), 2.62-2.48 (m, 1 H), 2.34-2.31 (m, 1 H), 1.72-1.69 (m, 1 H), 1.49-1.38 (m, 3 H); MS (ESI) m/z 561.1 (M+H).

S16-10-31

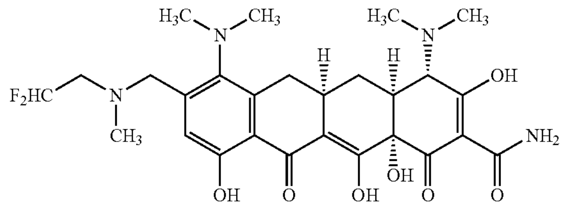

S16-10-31: $^1$H NMR (400 MHz, $CD_3OD$) δ 6.92 (s, 1 H), 6.40 (t, J=54.0 Hz, 1 H), 4.56 (d, J=13.2 Hz, 1 H), 4.21 (d, J=13.6 Hz, 1 H), 4.12 (s, 1 H), 3.40-3.57 (m, 3 H), 3.21-2.90 (m, 16 H), 2.70-2.62 (m, 1 H), 2.39-2.27 (m, 1 H), 1.76-1.58 (m, 1 H); MS (ESI) m/z 565.1 (M+H).

S16-10-32

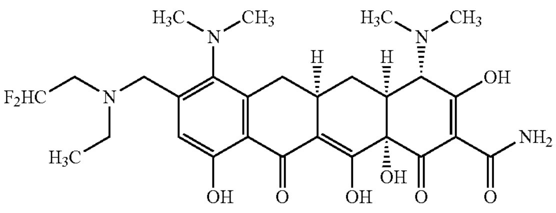

S16-10-32: $^1$H NMR (400 MHz, $CD_3OD$) δ 6.97 (s, 1 H), 6.42 (t, J=54.0 Hz, 1 H), 4.60 (d, J=15.2 Hz, 1 H), 4.30 (d, J=15.2 Hz, 1 H), 4.16 (s, 1 H), 3.63-3.52 (m, 2 H), 3.24-3.00 (m, 17 H), 2.66-2.52 (m, 1 H), 2.39-2.36 (m, 1 H), 1.71-1.65 (m, 1 H), 1.31 (t, J=6.8 Hz, 3 H); MS (ESI) m/z 579.1 (M+H).

S16-10-33

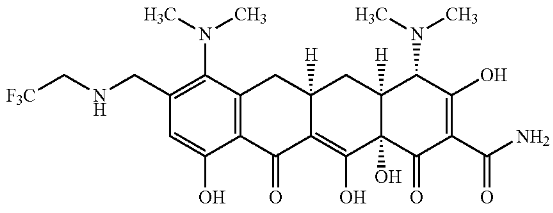

S16-10-33: $^1$H NMR (400 MHz, $CD_3OD$) δ 6.90 (s, 1 H), 4.45 (d, J=15.2 Hz, 1 H), 4.26 (d, J=15.2 Hz, 1 H), 4.12 (s, 1 H), 3.81 (m, 2 H), 3.20-2.96 (m, 15 H), 2.64-2.52 (m, 1 H), 2.36-2.31 (m, 1 H), 1.69-1.55 (m, 1 H); MS (ESI) m/z 569.2 (M+H).

S16-10-34

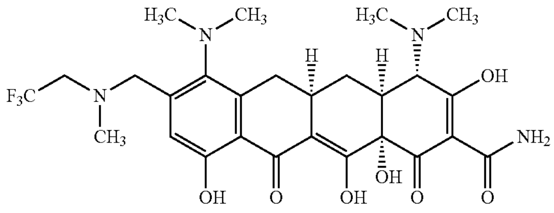

S16-10-34: $^1$H NMR (400 MHz, $CD_3OD$) δ 6.89 (s, 1 H), 4.43 (d, J=15.2 Hz, 1 H), 4.14 (s, 1 H), 4.07 (d, J=15.2 Hz, 1 H), 3.64-3.54 (m, 2 H), 3.42 (s, 3 H), 3.31 (s, 3 H), 3.19-2.94 (m, 9 H), 2.63 (t, J=28.8, 14.4 Hz, 1 H), 2.60 (s, 3 H), 2.41-2.37 (m, 1 H), 1.69-1.59 (m, 1 H); MS (ESI) m/z 583.1 (M+H).

S16-10-35

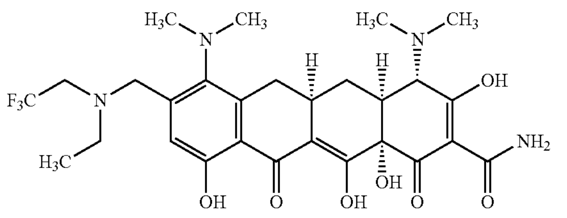

S16-10-35: $^1$H NMR (400 MHz, $CD_3OD$) δ 6.95 (s, 1 H), 4.43 (d, J=15.6 Hz, 1 H), 4.18 (d, J=15.6 Hz, 1 H), 4.16 (s, 1 H), 3.66-3.53 (m, 2 H), 3.47 (s, 3 H), 3.35 (s, 3 H), 3.19-2.82 (m, 11 H), 2.68-2.55 (m, 1 H), 2.42-2.39 (m, 1 H), 1.70-1.62 (m, 1 H), 1.17 (t, J=7.2 Hz, 3 H); MS (ESI) m/z 597.1 (M+H).

S16-10-36

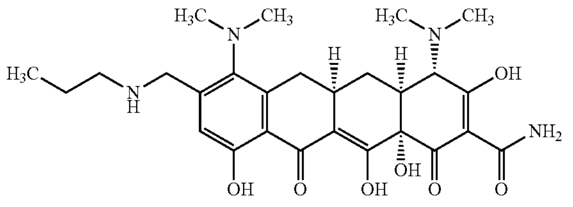

S16-10-36: $^1$H NMR (400 MHz, $CD_3OD$) δ 6.90 (s, 1 H), 4.35 (d, J=14.0 Hz, 1 H), 4.12 (d, J=14.0 Hz, 1 H), 4.08 (s, 1 H), 3.08-2.75 (m, 17 H), 2.48-2.38 (m, 1 H), 2.28-2.23 (m, 1 H), 1.78-1.73 (m, 2 H), 1.63-1.58 (m, 1 H), 1.03-0.98 (m, 3 H); MS (ESI) m/z 529.3 (M+H).

S16-10-37

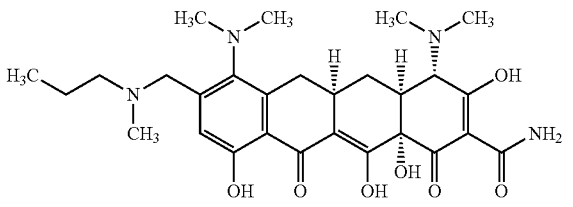

S16-10-37: $^1$H NMR (400 MHz, $CD_3OD$) δ 6.89, 6.88 (s, 1 H total), 4.58, 4.39 (d, J=13.6 Hz, 1 H, total), 4.26, 4.03 (d, J=13.6 Hz, 1 H, total), 4.03 (s, 1 H), 3.12-2.72 (m, 20H), 2.43-2.34 (m, 1 H), 2.21-2.18 (m, 1 H), 1.78-1.75 (m, 2 H), 1.61-1.51 (m, 1 H), 0.97-0.90 (m, 3 H); MS (ESI) m/z 543 (M+H).

S16-10-38

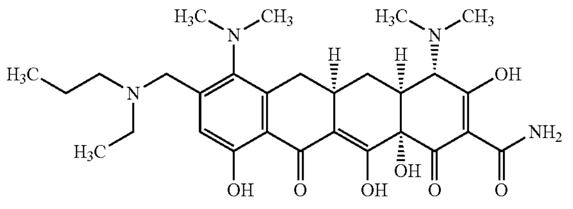

S16-10-38: $^1$H NMR (400 MHz, $CD_3OD$) δ 6.85 (s, 1 H), 4.52-4.47 (m, 1 H), 4.18-4.15 (m, 1 H), 4.07 (s, 1 H), 3.16-

2.75 (m, 19 H), 2.41-2.34 (m, 1 H), 2.28-2.25 (m, 1 H), 1.74-1.73 (m, 2 H), 1.60-1.50 (m, 1 H), 1.30-1.25 (m, 3 H), 0.96-0.92 (m, 3 H); MS (ESI) m/z 557.1 (M+H).

S16-10-39

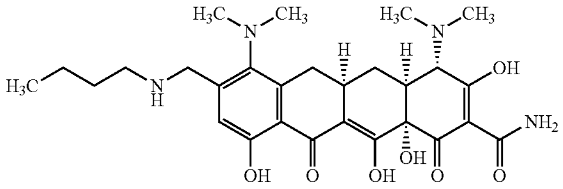

S16-10-39: $^1$H NMR (400 MHz, $CD_3OD$) δ 6.91 (s, 1 H), 4.46 (d, J=14.4 Hz, 1 H), 4.13 (d, J=14.4 Hz, 1 H), 4.08 (s, 1 H), 3.08-2.63 (m, 17 H), 2.47-2.38 (m, 1 H), 2.27-2.22 (m, 1 H), 1.75-1.68 (m, 2 H), 1.67-1.62 (m, 1 H), 1.44-1.42 (m, 2 H), 0.98 (t, J=7.2 Hz, 3 H); MS (ESI) m/z 543.0 (M+H).

S16-10-40

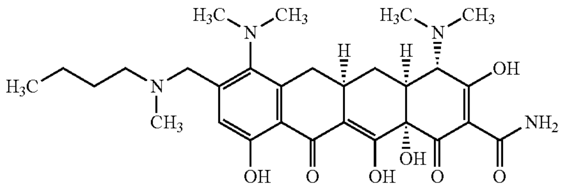

S16-10-40: $^1$H NMR (400 MHz, $CD_3OD$) δ 6.96, 6.95 (s, 1 H total), 4.66, 4.46 (d, J=13.6 Hz, 1 H total), 4.34, 4.11 (d, J=13.6 Hz, 1 H total), 4.11 (s, 1 H), 3.20-2.79 (m, 20 H), 2.50-2.41 (m, 1 H), 2.28-2.24 (m, 1 H), 1.81-1.75 (m, 2 H), 1.68-1.59 (m, 1 H), 1.45-1.38 (m, 2 H), 0.97 (m, 3 H); MS (ESI) m/z 557.3 (M+H).

S16-10-41

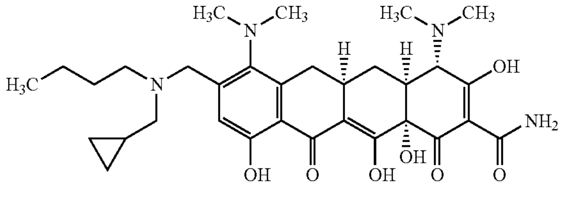

S16-10-41: $^1$H NMR (400 MHz, $CD_3OD$) δ 6.99, 6.98 (s, 1 H, total), 4.82, 4.67 (d, J=13.6 Hz, 1 H, total), 4.43, 4.30 (d, J=13.6 Hz, 1 H, total), 4.15 (s, 1H), 3.22-2.88 (m, 19 H), 2.58-2.51 (m, 1 H), 2.35-2.30 (m, 1 H), 1.87-1.79 (m, 1 H), 1.75-1.65 (m, 1 H), 1.49-1.38 (m, 2 H), 1.35-1.145 (m, 2 H), 1.03-0.95 (m, 3 H), 0.88-0.81 (m, 2 H), 0.51-0.40 (m, 2 H); MS (ESI) m/z 597.1 (M+H).

S16-10-42

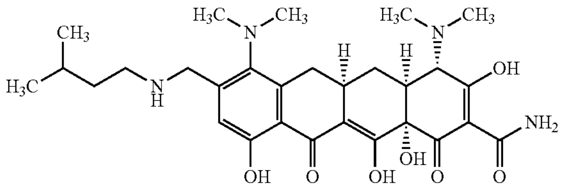

S16-10-42: $^1$H NMR (400 MHz, $CD_3OD$) δ 6.96 (s, 1 H), 4.42 (d, J=14.4 Hz, 1 H), 4.18 (d, J=14.4 Hz, 1 H), 4.13 (s, 1 H), 3.14-2.84 (m, 17 H), 2.51-2.39 (m, 1 H), 2.31-2.25 (m, 1 H), 1.68-1.64 (m, 4 H), 0.99-0.96 (m, 6 H); MS (ESI) m/z 557.3 (M+H).

S16-10-43

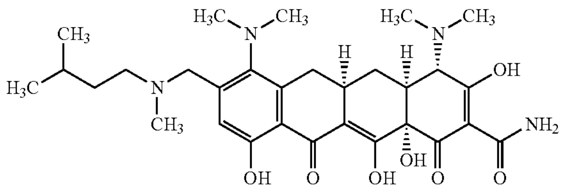

S16-10-43: $^1$H NMR (400 MHz, $CD_3OD$) δ 6.99, 6.97 (s, 1 H, total), 4.69, 4.50 (d, J=13.2 Hz, 1 H, total), 4.37, 4.14 (d, J=13.2 Hz, 1 H, total), 4.12 (s, 1 H), 3.09, 2.82 (m, 20 H), 2.54-2.45 (m, 1 H), 2.30-2.26 (m, 1 H), 1.76-1.62 (m, 4 H), 1.01-0.97 (m, 6 H); MS (ESI) m/z 571.3 (M+H).

S16-10-44

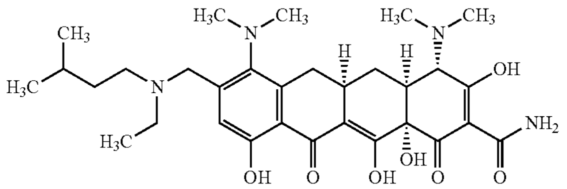

S16-10-44: $^1$H NMR (400 MHz, $CD_3OD$) δ 6.97, 6.96 (s, 1 H, total), 4.60 (d, J=13.2 Hz, 1 H), 4.24 (d, J=13.2 Hz, 1 H), 4.12 (s, 1 H), 3.23-3.15 (m, 4 H), 3.13-2.84 (m, 15 H), 2.56-2.41 (m, 1 H), 2.30-2.26 (m, 1 H), 1.68-1.64 (m, 4 H), 1.39-1.34 (m, 3 H), 0.97 (d, J=6.4 Hz, 6 H); MS (ESI) m/z 585.1 (M+H).

S16-10-45

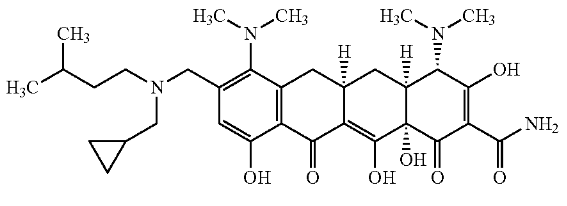

S16-10-45: $^1$H NMR (400 MHz, $CD_3OD$) δ 6.96 (s, 1 H), 4.62-4.56 (m, 1 H), 4.25-4.22 (m, 1 H), 4.12-4.11 (m, 1 H), 3.26-2.83 (m, 19 H), 2.55-2.41 (m, 1 H), 2.29-2.26 (m, 1 H), 1.76-1.63 (m, 4 H), 1.45-1.37 (m, 7 H), 1.00-0.95 (m, 4 H); MS (ESI) m/z 611.1 (M+H).

S16-10-46

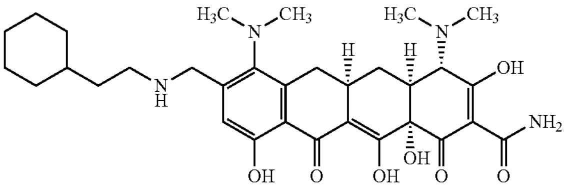

S16-10-46: $^{1}$H NMR (400 MHz, $CD_3OD$) δ 6.85 (s, 1 H), 4.28 (d, J=14.8 Hz, 1 H), 4.05 (d, J=14.4 Hz, 1 H), 4.03 (s, 1 H), 3.05-2.72 (m, 17 H), 2.38-2.31 (m, 1 H), 2.20-2.17 (m, 1H), 1.67-1.53 (m, 8 H), 1.31-1.06 (m, 4 H), 0.95-0.85 (m, 2H); MS (ESI) m/z 597.1 (M+H).

S16-10-47

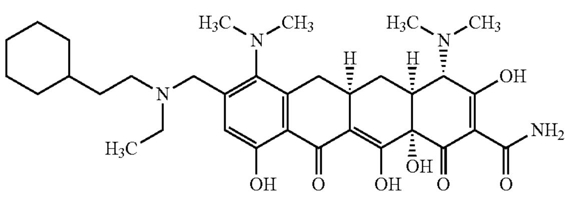

S16-10-47: $^{1}$H NMR (400 MHz, $CD_3OD$) δ 6.85, 6.85 (s, 1 H, total), 4.48 (d, J=13.6 Hz, 1 H), 4.12 (d, J=13.6 Hz, 1 H), 4.01 (s, 1 H), 3.25-2.70 (m, 19 H), 2.44-2.30 (m, 1 H), 2.18-2.13 (m, 1 H), 1.68-1.52 (m, 6 H), 1.79-1.11 (m, 8 H), 0.93-0.85 (m, 3 H); MS (ESI) m/z 625.1 (M+H).

S16-10-48

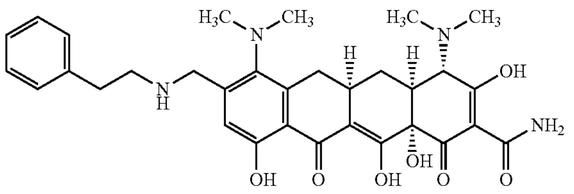

S16-10-48: $^{1}$H NMR (400 MHz, $CD_3OD$) δ 7.39-7.27 (m, 5 H), 6.91 (s, 1H), 4.40 (d, J=14.8 Hz, 1 H), 4.18 (d, J=14.6 Hz, 1 H), 4.11 (s, 1 H), 3.42-3.38 (m, 2 H), 3.15-2.97 (m, 9 H), 2.88-2.58 (m, 6H), 2.44-2.36 (m, 1 H), 2.27-2.24 (m, 1 H), 1.64-1.58 (m, 1H); MS (ESI) m/z 591.1 (M+H).

S16-10-49

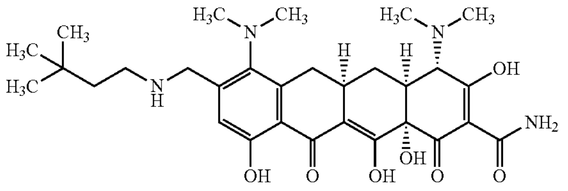

S16-10-49: $^{1}$H NMR (400 MHz, $CD_3OD$) δ 6.83 (s, 1 H), 4.30 (d, J=14.4 Hz, 1 H), 4.07 (d, J=14.4 Hz, 1 H), 3.99 (s, 1 H), 3.05-2.77 (m, 17 H), 2.45-2.31 m, 1 H), 2.17-2.18 (m, 1 H), 1.59-1.54 (m, 3 H), 0.89 (s, 9 H); MS (ESI) m/z 571.1 (M+H).

S16-10-50

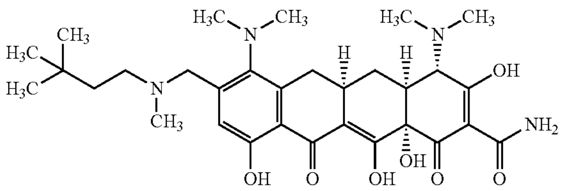

S16-10-50: $^{1}$H NMR (400 MHz, $CD_3OD$) δ 7.02, 6.99 (s, 1 H, total), 4.71, 4.54 (d, J=13.2 Hz, 1 H, total), 4.40, 4.17 (d, J=13.2 Hz, 1 H, total), 4.14 (s, 1 H), 3.11-2.84 (m, 20 H), 2.60-2.48 (m, 1 H), 2.32-2.29 (m, 1 H), 1.77-1.63 (m, 3 H), 1.02, 0.99 (s, 9 H, total); MS (ESI) m/z 585.1 (M+H).

S16-10-51

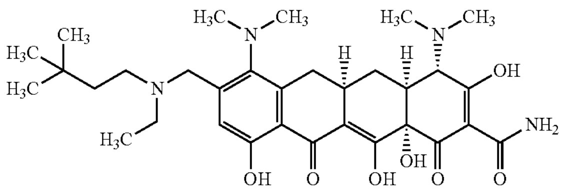

S16-10-51: $^{1}$H NMR (400 MHz, $CD_3OD$) δ 6.96, 6.95 (s, 1 H, total), 4.62-4.56 (m, 1 H), 4.28-4.22 (m, 1 H), 4.10 (s, 1 H), 3.25-2.81 (m, 19 H), 2.53-2.40 (m, 1 H), 2.28-2.23 (m, 1 H), 1.69-1.62 (m, 3 H), 1.40-1.35 (m, 3 H), 0.99, 0.97 (s, 9 H total); MS (ESI) m/z 599.1 (M+H).

S16-10-52

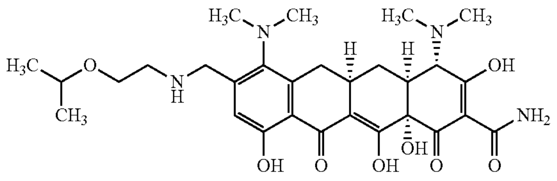

S16-10-52: $^{1}$H NMR (400 MHz, $CD_3OD$) δ 6.81 (s, 1 H), 4.32 (d, J=14.0 Hz, 1 H), 4.08 (d, J=14.0 Hz, 1 H), 4.03 (s, 1 H), 3.68-3.60 (m, 3 H), 3.05-2.73 (m, 17 H), 2.45-2.33 (m, 1 H), 2.21-2.15 (m, 1 H), 1.58-1.50 (m, 1 H), 1.15-1.10 (m, 6 H); MS (ESI) m/z 573.1 (M+H).

S16-10-53

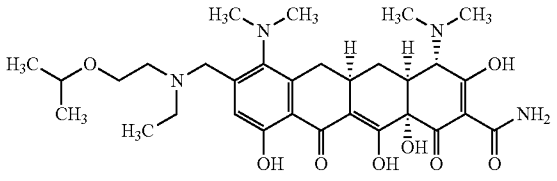

S16-10-53: $^{1}$H NMR (400 MHz, $CD_3OD$) δ 6.93, 6.91 (s, 1 H total), 4.66-4.63 (m, 1 H), 4.31-4.25 (m, 1 H), 4.11 (s, 1 H), 3.82-3.70 (m, 3 H), 3.55-3.51 (m, 1 H, 3.42-3.37 (m, 2 H), 3.18-2.84 (m, 16 H), 2.50-2.46 (m, 1 H), 2.30-2.27 (m, 1 H), 1.66-1.63 (m, 1 H), 1.43-1.12 (m, 9 H); MS (ESI) m/z 601.1 (M+H).

S16-10-54

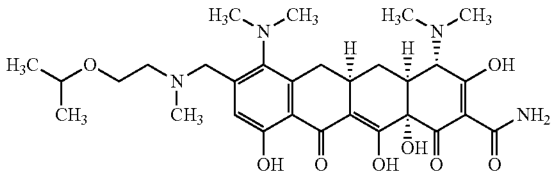

S16-10-54: $^{1}$H NMR (400 MHz, $CD_3OD$) δ 6.91, 6.89 (s, 1 H total), 4.72-4.69 (m, 1 H), 4.48-4.39 (m, 1 H), 4.11 (s, 1 H), 3.89-3.70 (m, 3 H), 3.56-3.39 (m, 4 H), 3.05-2.83 (m, 16

H), 2.53-2.45 (m, 1 H), 2.29-2.26 (m, 1 H), 1.66-1.63 (m, 1 H), 1.27-1.20 (m, 6 H); MS (ESI) m/z 586.9 (M+H).

S16-10-55

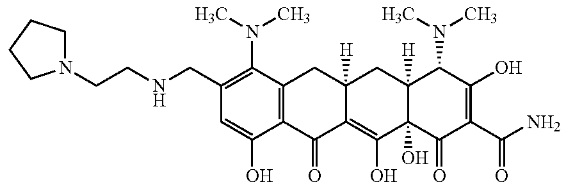

S16-10-55: $^{1}$H NMR (400 MHz, $CD_3OD$) δ 7.01 (s, 1 H), 4.50-4.46 (m, 1H), 4.29-4.25 (m, 1H), 4.09 (s, 1 H), 3.83-3.59 (m, 6 H), 3.21-2.79 (m, 17H), 2.46-2.26 (m, 1H), 2.36-2.31 (m, 1H), 2.39-2.06 (m, 4 H), 1.68-1.62 (m, 1 H); MS (ESI) m/z 584.3 (M+H).

S16-10-56

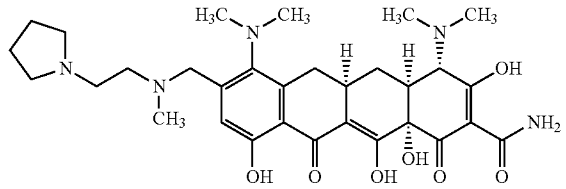

S16-10-56: $^{1}$H NMR (400 MHz, $CD_3OD$) δ 7.12 (s, 1 H), 4.66-4.62 (m, 1 H), 4.36-4.34 (m, 1 H), 4.13 (s, 1 H), 3.81-3.60 (m, 6 H), 3.07-2.87 (m, 20 H), 2.56-2.41 (m, 1 H), 2.32-2.29 (m, 1 H), 2.25-2.08 (m, 4 H), 1.73-1.58 (m, 1 H); MS (ESI) m/z 598.1 (M+H).

S16-10-57

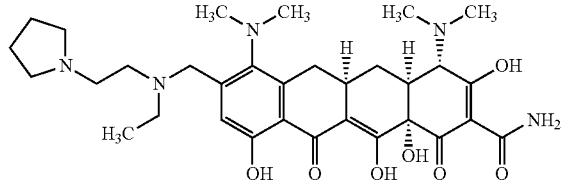

S16-10-57: $^{1}$H NMR (400 MHz, $CD_3OD$) δ 7.10 (s, 1 H), 4.67-4.64 (m, 1 H), 4.35-4.32 (m, 1 H), 4.13 (s, 1 H), 3.82-3.60 (m, 6 H), 3.14-2.89 (m, 19 H), 2.556-2.42 (m, 1 H), 2.31-2.29 (m, 1 H), 2.22-2.02 (m, 4 H), 1.61-1.72 (m, 1 H), 1.45-1.38 (m, 3 H); MS (ESI) m/z 612.3 (M+H).

S16-10-58

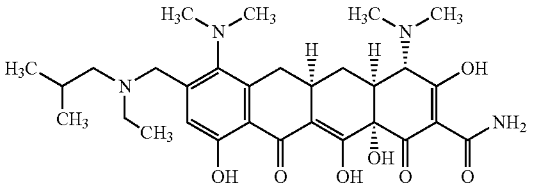

S16-10-58: $^{1}$H NMR (400 MHz, $CD_3OD$) δ 6.94 (s, 1 H), 4.67, 4.54 (d, J=13.6 Hz, 1 H, total), 4.53, 4.23 (d, J=13.6 Hz, 1 H, total), 4.10 (s, 1 H), 3.19-2.83 (m, 19 H), 2.55-2.42 (m, 1 H), 2.29-2.26 (m, 1 H), 2.20-2.16 (m, 1 H), 1.66-1.64 (m, 1 H), 1.41-1.28 (m, 3 H), 1.11-1.01 (m, 6 H); MS (ESI) m/z 571.1 (M+H).

S16-10-59

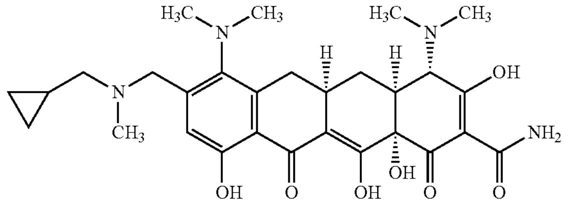

S16-10-59: $^{1}$H NMR (400 MHz, $CD_3OD$) δ 7.01, 6.98 (s, 1 H, total), 4.81 (s, 1 H), 4.48 (s, 1 H), 4.14 (s, 1 H), 3.25-2.85 (m, 20 H), 2.55-2.43 (m, 1 H), 2.32-2.29 (m, 1 H), 1.69-1.63 (m, 1 H), 1.30-1.20 (m, 1 H), 0.89-0.81 (m, 2 H), 0.54-0.48 (m, 2 H); MS (ESI) m/z 555.0 (M+H).

S16-10-60

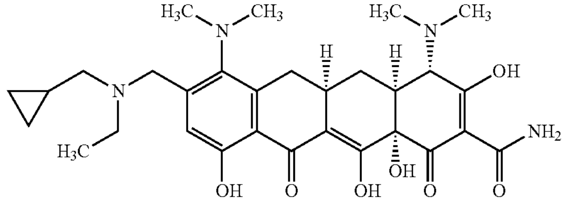

S16-10-60: $^{1}$H NMR (400 MHz, $CD_3OD$) δ 6.93, 6.92 (s, 1 H, total), 4.76, 4.57 (d, J=13.6 Hz, 1 H, total), 4.36, 4.21 (d, J=13.6 Hz, 1 H, total), 4.08 (s, 1 H), 3.20-2.81 (m, 19 H), 2.50-2.45 (m, 1 H), 2.26-2.23 (m, 1 H), 1.64-1.61 (m, 1 H), 1.37, 1.31 (t, J=6.8 Hz, 3 H, total), 1.29-1.22 (m, 1 H), 0.79-0.74 (m, 2 H), 0.48-0.38 (m, 2 H); MS (ESI) m/z 569.1 (M+H).

S16-10-61

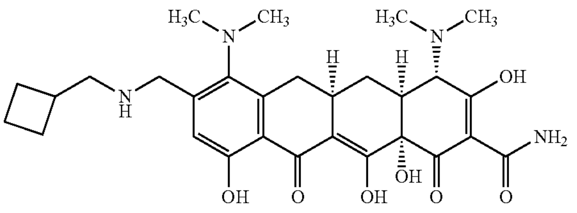

S16-10-61: $^{1}$H NMR (400 MHz, $CD_3OD$) δ 6.90 (s, 1 H), 4.33 (d, J=14.0 Hz, 1 H), 4.09 (d, J=14.0 Hz, 1 H), 4.08 (s, 1 H), 3.12-2.94 (m, 11 H), 2.87-2.75 (m, 6 H), 2.78-2.63 (m, 1 H), 2.45-2.38 (m, 1H), 2.25-2.15 (m, 3H), 2.03-1.82 (m, 4H), 1.69-1.53 (m, 1H); MS (ESI) m/z 555.2 (M+H).

S16-10-62

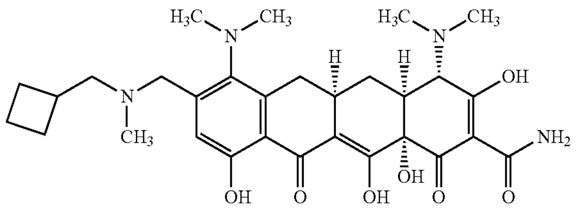

S16-10-62: $^1$H NMR (400 MHz, $CD_3OD$) δ 6.96, 6.94 (s, 1 H, total), 4.60, 4.41 (d, J=13.2 Hz, total), 4.35, 4.08 (d, J=13.2 Hz, 1 H, total), 4.11 (s, 1 H), 3.09-2.80 (m, 20 H), 2.52-2.45 (m, 1 H), 2.30-2.20 (m, 3 H), 2.08-2.02 (m, 1 H), 1.98-1.85 (m, 4 H), 1.68-1.62 (m, 1 H); MS (ESI) m/z 569.1 (M+H).

S16-10-63

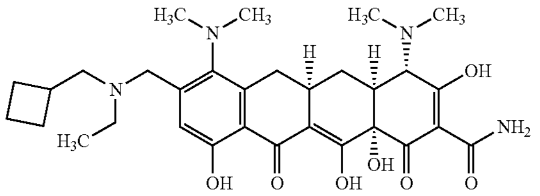

S16-10-63: $^1$H NMR (400 MHz, $CD_3OD$) δ 6.96 (s, 1 H), 4.57-4.55 (m, 1 H), 4.25-4.23 (m, 1 H), 4.12 (s, 1 H), 3.25-2.82 (m, 19 H), 2.57-2.42 (m, 1 H), 2.27-2.23 (m, 3 H), 2.10-2.05 (m, 1 H), 2.00-1.91 (m, 4 H), 1.72-1.68 (m, 1 H), 1.39-1.35 (m, 3 H); MS (ESI) m/z 583.1 (M+H).

S16-10-64

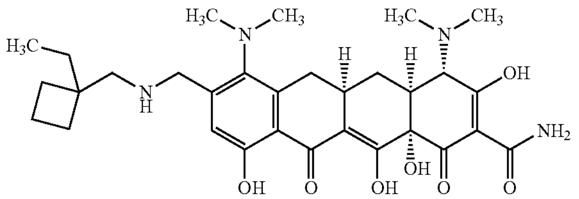

S16-10-64: $^1$H NMR (400 MHz, $CD_3OD$) δ 6.99 (s, 1 H), 4.46 (d, J=13.6 Hz, 1 H), 4.24 (d, J=13.6 Hz, 1 H), 4.15 (s, 1 H), 3.27-2.87 (m, 17 H), 2.56-2.46 (m, 1 H), 2.32-2.29 (m, 1 H), 1.96-1.94 (m, 6 H), 1.70-1.65 (m, 3 H), 0.94 (t, J=7.6 Hz, 3 H); MS (ESI) m/z 583.1 (M+H).

S16-10-65

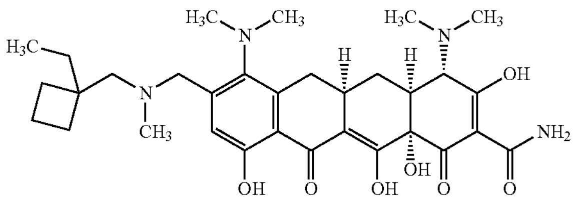

S16-10-65: $^1$H NMR (400 MHz, $CD_3OD$) δ 6.98, 6.96 (s, 1 H, total), 4.68, 4.45 (d, J=13.2 Hz, 1 H, total), 4.34, 4.11 (d, J=13.2 Hz, 1 H, total), 4.11 (s, 1 H), 3.08-2.78 (m, 20 H), 2.55-2.42 (m, 1 H), 2.29-2.25 (m, 1 H), 2.16-2.12 (m, 1 H), 2.01-1.92 (m, 5 H), 1.92-1.81 (m, 1 H), 1.71-1.60 (m, 2 H), 0.97 (t, J=7.6 Hz, 3 H); MS (ESI) m/z 597.1 (M+H).

S16-10-66

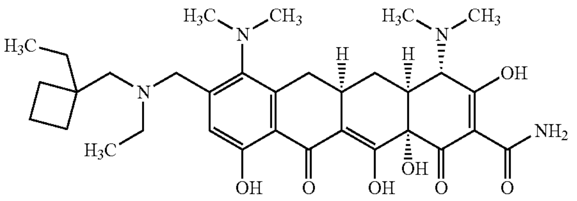

S16-10-66: $^1$H NMR (400 MHz, $CD_3OD$) δ 6.99 (s, 1 H), 4.60, 4.47 (d, J=13.2 Hz, 1 H, total), 4.35, 4.24 (d, J=13.2 Hz, 1 H, total), 4.13 (s, 1 H), 3.47-3.41 (m, 1 H), 3.20-2.84 (m, 18 H), 2.60-2.50 (m, 1 H), 2.31-2.29 (m, 1 H), 2.11-1.96 (m, 6 H), 1.85-1.61 (m, 3 H), 1.45-1.36 (m, 3 H), 1.03-0.95 (m, 3 H); MS (ESI) m/z 611.1 (M+H).

S16-10-67

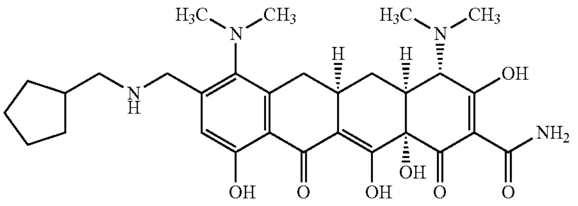

S16-10-67: $^1$H NMR (400 MHz, $CD_3OD$) δ 6.98 (s, 1 H), 4.43 (d, J=13.2 Hz, 1 H), 4.19 (d, J=13.2 Hz, 1 H), 4.14 (s, 1 H), 3.01-2.85 (m, 17 H), 2.50-2.43 (m, 1H), 2.32-2.25 (m, 2 H), 1.99-1.89 (m, 2H), 1.74-1.66 (m, 5 H), 1.33-1.30 (m, 2H); MS (ESI) m/z 569.3 (M+H).

S16-10-68

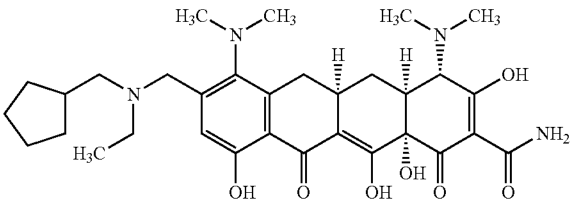

S-16-10-68: $^1$H NMR (400 MHz, $CD_3OD$) δ 6.94 (s, 1 H), 4.61, 4.58, 4.50, 4.47 (s, 1 H, total), 4.26, 4.23, 4.20, 4.17 (s, 1 H, total), 4.11 (s, 1 H), 3.55-3.45 (m, 2 H), 3.10-2.85 (m, 17 H), 2.51-2.48 (m, 1 H), 2.31-2.28 (m, 1 H), 2.05-1.75 (m, 2 H), 1.66-1.62 (m, 2 H), 1.46-1.30 (m, 6 H), 1.12-1.01 (m, 3 H); MS (ESI) m/z 597.0 (M+H).

S16-10-69

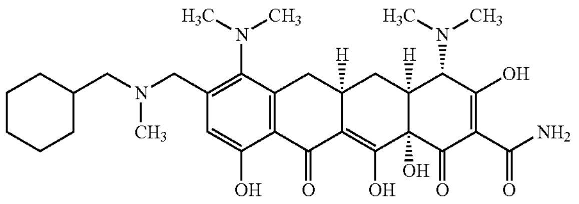

S16-10-69: $^{1}H$ NMR (400 MHz, $CD_3OD$) δ 6.93 (s, 1 H), 4.71 (d, J=13.2 Hz, 1 H), 4.38 (s, 1 H), 4.11 (s, 1 H), 3.09-2.79 (m, 20 H), 2.52-2.42 (m, 1 H), 2.27-2.25 (m, 1 H), 1.95-1.92 (m, 1 H), 1.81-1.62 (m, 6 H), 1.37-1.25 (m, 3 H), 1.08-1.03 (m, 2 H); MS (ESI) m/z 597.1 (M+H).

S16-10-70

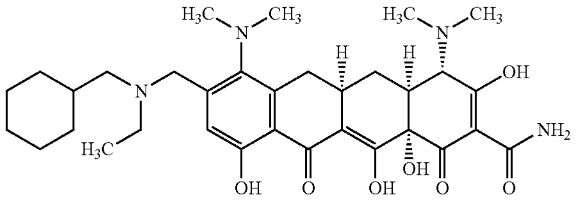

S16-10-70: $^{1}H$ NMR (400 MHz, $CD_3OD$) δ 6.97 (s, 1 H), 4.71, 4.57 (d, J=13.6 Hz, 1 H, total), 4.37, 4.24 (d, J=13.6 Hz, 1 H, total), 4.14 (s, 1 H), 3.22-2.86 (m, 19 H), 2.58-2.52 (m, 1 H), 2.32-2.29 (m, 1 H), 1.98-1.62 (m, 7 H), 1.45-1.33 (m, 5 H), 1.33-1.25 (m, 1 H), 1.20-1.05 (m, 2 H); MS (ESI) m/z 611.1 (M+H).

S16-10-71

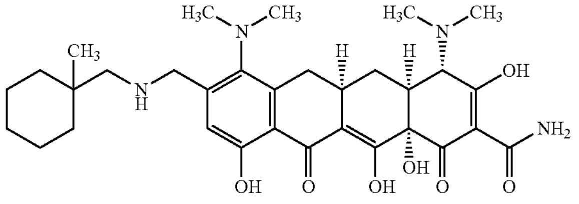

S16-10-71: $^{1}H$ NMR (400 MHz, $CD_3OD$) δ 6.93 (s, 1 H), 4.42-4.39 (m, 1H), 4.19-4.16 (m, 1H), 4.11 (s, 1 H), 3.10-2.82 (m, 17 H), 2.49-2.42 (m, 1H), 2.28-2.20 (m, 1 H), 1.68-1.25 (m, 11 H), 1.09 (s, 3H); MS (ESI) m/z 597.3 (M+H).

S16-10-72

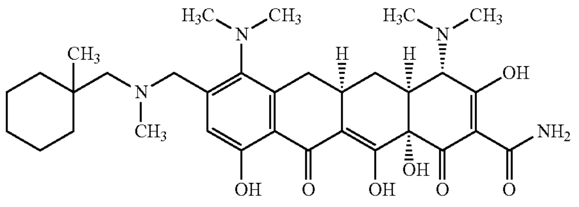

S16-10-72: $^{1}H$ NMR (400 MHz, $CD_3OD$) δ 7.00 (s, 1 H), 4.73, 4.72, 4.58, 4.55 (m, 1 H, total), 4.39, 4.36, 4.19, 4.16 (m, 1 H, total), 4.10 (s, 1 H), 3.28 (s, 2 H), 3.13-2.78 (m, 18 H), 2.52-2.40 (m, 1 H), 2.29-2.26 (m, 1 H), 1.70-1.60 (m, 1 H), 1.67-1.35 (m, 10 H), 1.10 (s, 3 H); MS (ESI) m/z 611.4 (M+H).

S16-10-73

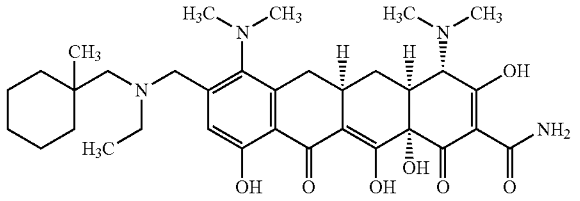

S16-10-73: $^{1}H$ NMR (400 MHz, $CD_3OD$) δ 6.99 (s, 1 H), 4.93, 4.90, 4.62, 4.59 (s, 1 H, total), 4.49, 4.46, 4.32, 4.29 (s, 1 H, total), 4.15 (s, 1 H), 3.17-2.85 (m, 19 H), 2.55 (m, 1 H), 2.36-2.30 (m, 1 H), 1.73-1.65 (m, 1 H), 1.55-1.35 (m, 13 H), 1.17-1.15 (m, 3 H); MS (ESI) m/z 625.1 (M+H).

S16-10-74

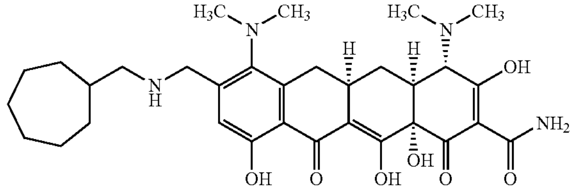

S16-10-74: $^{1}H$ NMR (400 MHz, $CD_3OD$) δ 6.96 (s, 1 H), 4.40 (d, J=14.0 Hz, 1 H), 4.17 (d, J=14.0 Hz, 1 H), 4.14 (s, 1 H), 3.06-2.84 (m, 17 H), 2.55-2.42 (m, 1 H), 2.31-2.20 (m, 1 H), 2.01-1.96 (m, 1 H), 1.83-1.57 (m, 11 H), 1.38-1.28 (m, 2 H); MS (ESI) m/z 597.1 (M+H).

S16-10-75

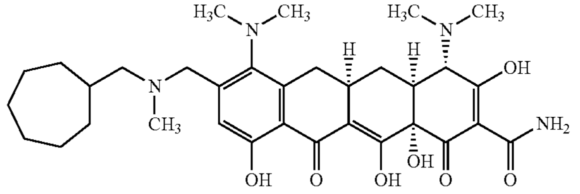

S16-10-75: $^{1}H$ NMR (400 MHz, $CD_3OD$) δ 6.93 (s, 1 H), 4.71, 4.68, 4.43, 4.40 (m, 1 H, total), 4.37, 4.68, 4.06, 4.03, (m, 1 H, total), 4.11 (s, 1 H), 3.11-2.78 (m, 20 H), 2.51-2.40 (m, 1 H), 2.28-2.25 (m, 1 H), 2.10 (s, 1 H), 1.77-1.54 (m, 11 H), 1.31-1.26 (m, 2 H); MS (ESI) m/z 611.1 (M+H).

S16-10-76

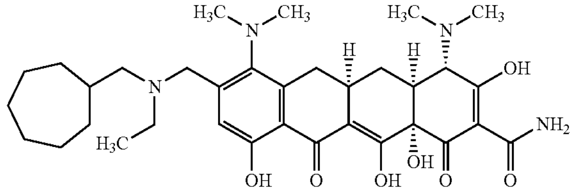

S16-10-76: $^{1}$H NMR (400 MHz, $CD_3OD$) δ 6.94 (s, 1 H), 4.68, 4.65, 4.51, 4.47 (s, 1 H, total), 4.33, 4.30, 4.17, 4.13 (s, 1 H, total), 4.10 (s, 1 H), 3.16-2.82 (m, 19 H), 2.53-2.41 (m, 1 H), 2.38-2.33 (m, 1 H), 2.13-2.10 (m, 1 H), 1.77-1.58 (m, 11 H), 1.39-1.30 (m, 2 H), 1.28-1.21 (m, 3 H); MS (ESI) m/z 625.3 (M+H).

S16-10-77

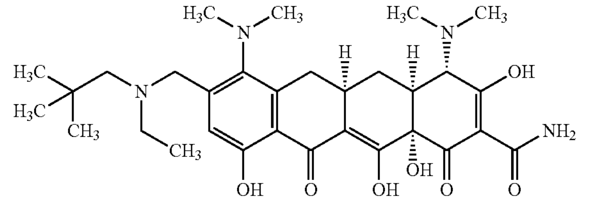

S16-10-77: $^{1}$H NMR (400 MHz, $CD_3OD$) δ 6.97, 6.93 (s, 1 H, total), 4.65, 4.62, 4.36, 4.33 (s, 1 H, total), 4.39 (s, 1 H), 4.10 (s, 1 H), 3.28-3.31 (m, 4 H), 3.13-2.80 (m, 15 H), 2.53-2.41 (m, 1 H), 2.29-2.26 (m, 1 H), 1.64-1.62 (m, 1 H), 1.41-1.34 (m, 3 H), 2.24 (t, J=6.8 Hz, 2 H), 1.09-1.04 (m, 6 H); MS (ESI) m/z 585.1 (M+H).

S16-10-78

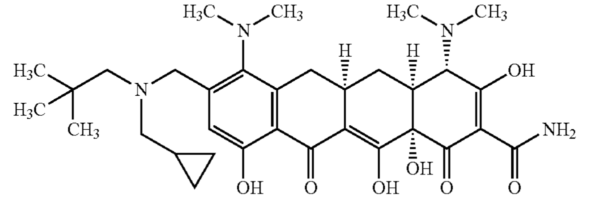

S16-10-78: $^{1}$H NMR (400 MHz, $CD_3OD$) δ 7.01 (s, 1 H), 4.79, 4.76, 4.65, 4.62 (s, 1 H, total), 4.47, 4.43, 4.41, 4.37 (s, 1 H, total), 4.13 (s, 1H), 3.53-3.51 (m, 1 H), 3.19-2.89 (m, 18 H), 2.53-2.41 (m, 1 H), 2.32-2.29 (m, 1 H), 1.68-1.63 (m, 1 H), 1.31-1.25 (m, 1 H), 1.15 (s, 9 H), 0.86-0.80 (m, 2 H), 0.50-0.39 (m, 2H); MS (ESI) m/z 611.1 (M+H).

S16-10-79

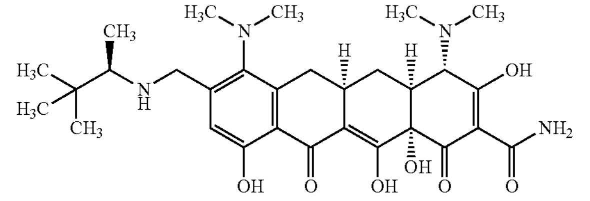

S16-10-79: $^{1}$H NMR (400 MHz, $CD_3OD$) δ 6.98 (s, 1 H), 4.45-4.42 (m, 1 H), 4.31-4.27 (m, 1 H), 4.12 (s, 1 H), 3.12-2.82 (m, 16 H), 2.49-2.42 (m, 1 H), 2.31-2.28 (m, 1 H), 1.68-1.62 (m, 1 H), 1.40 (d, J=7.2 Hz, 3 H), 1.08 (s, 9 H); MS (ESI) m/z 571.3 (M+H).

S16-10-80

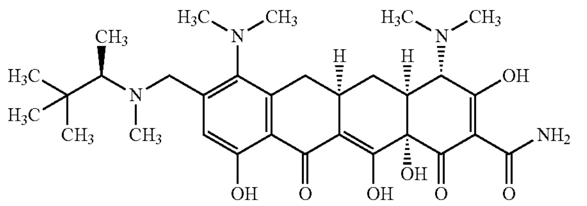

S16-10-80: $^{1}$H NMR (400 MHz, $CD_3OD$) δ 7.07, 6.97 (s, 1 H, total), 4.66 (d, J=11.6 Hz, 1 H), 4.33 (d, J=13.2 Hz, 1 H), 4.15 (s, 1 H), 3.53-3.50 (m, 1 H), 3.23-2.82 (m, 18 H), 2.55-2.46 (m, 1 H), 2.33-2.30 (m, 1 H), 1.71-1.62 (m, 1 H), 1.52, 1.43 (s, 3 H, total), 1.24 (s, 3 H), 1.10 (s, 6 H); MS (ESI) m/z 585.1 (M+H).

S16-10-81

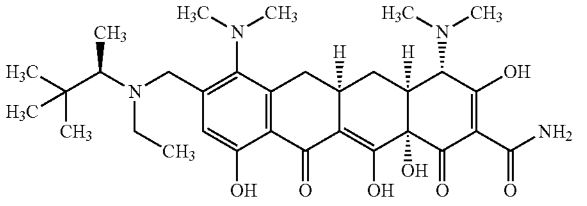

S16-10-81: $^{1}$H NMR (400 MHz, $CD_3OD$) δ 7.01, 6.94 (s, 1 H, total), 4.60 (d, J=13.6 Hz, 1 H), 4.19 (d, J=13.6 Hz, 1 H), 4.11 (s, 1 H), 3.61-3.59 (m, 1 H), 3.19-2.89 (m, 17 H), 2.55-3.42 (m, 1 H), 2.29-2.26 (m, 1 H), 1.64-1.59 (m, 1 H), 1.49-1.41 (m, 4 H), 1.30 (t, J=6.8 Hz, 2 H), 1.28, 0.95 (s, 9 H, total); MS (ESI) m/z 599.2 (M+H).

S16-10-82

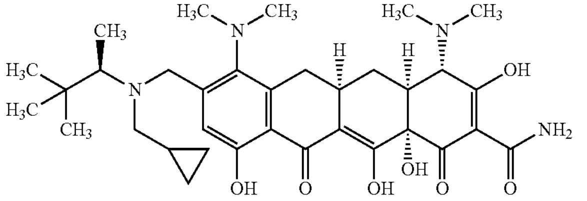

S16-10-82: $^{1}$H NMR (400 MHz, $CD_3OD$) δ 7.01, 6.94 (s, 1 H, total), 4.63, 4.60, 4.17, 4.14 (s, 1 H, total), 4.12 (s, 1H), 3.88-3.86 (m, 1 H), 3.19-2.90 (m, 18 H), 2.55-2.42 (m, 1 H), 2.31-2.28 (m, 1 H), 1.68-1.63 (m, 1 H), 1.55-1.52 (m, 2 H), 1.45-1.41 (m, 1 H), 1.22 (s, 6H), 1.06-1.02 (m, 1 H), 0.96 (s, 3H), 0.82-0.75 (m, 1 H), 0.71-0.63 (m, 1 H), 0.42-0.36 (m, 1 H), 0.25-0.20 (m, 1 H); MS (ESI) m/z 625.3 (M+H).

S16-10-83

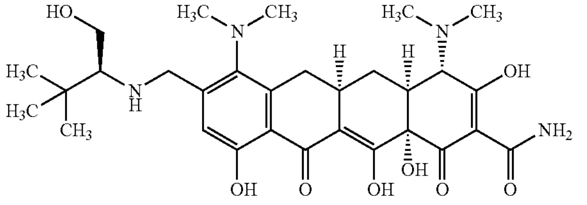

S16-10-83: $^{1}$H NMR (400 MHz, $CD_3OD$) δ 6.84 (s, 1 H), 4.46 (d, J=14.0 Hz, 1 H), 4.14 (d, J=14.0 Hz, 1 H), 4.05 (s, 1

H), 3.96-3.92 (m, 1 H), 3.82-3.77 (m, 1 H), 3.06-2.84 (m, 16 H), 2.43-2.37 (m, 1 H), 2.24-2.20 (m, 1 H), 1.62-1.53 (m, 1 H), 1.06 (s, 9 H); MS (ESI) m/z 587.1 (M+H)

S16-10-84

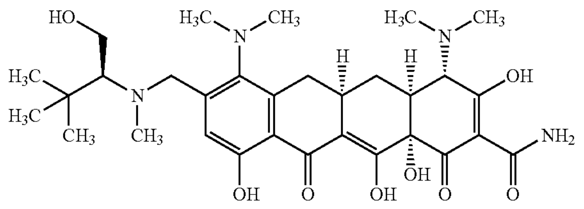

S16-10-84 $^1$H NMR (400 MHz, $CD_3OD$) δ 6.94 (s, 1 H), 4.79-4.76 (m, 1 H), 4.58-4.52 (m, 1 H), 4.13 (s, 1 H), 4.08-4.05 (m, 1 H), 3.99-3.94 (m, 1 H), 3.49-3.47 (m, 1 H), 3.12-2.80 (m, 18 H), 2.52-2.48 (m, 1 H), 2.30-2.28 (m, 1 H), 1.68-1.63 (m, 1 H), 1.28-1.10 (m, 9 H); MS (ESI) m/z 601.1 (M+H).

S16-10-85

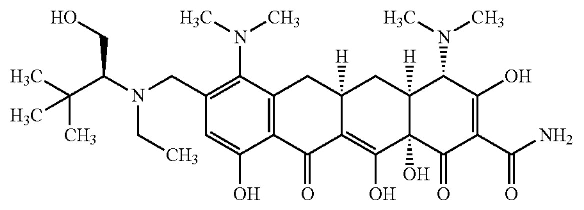

S16-10-85: $^1$H NMR (400 MHz, $CD_3OD$) δ 7.01, 6.92 (s, 1 H total), 4.56-4.54 (m, 1 H), 4.13 (s, 3 H), 3.60-3.48 (m, 2 H), 3.21-2.91 (m, 17 H), 2.58-2.51 (m, 1 H), 2.31-2.28 (m, 1 H), 1.71-1.61 (m, 1 H), 1.29, 1.25 (s, 9H total), 1.09-1.07 (m, 3H); MS (ESI) m/z 615.4 (M+H)

S16-10-86

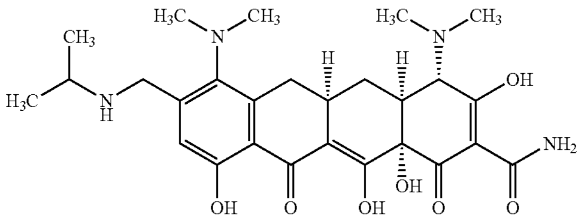

S16-10-86: $^1$H NMR (400 MHz, $CD_3OD$) δ 6.93 (s, 1 H), 4.32 (d, J=14.0 Hz, 1 H), 4.11 (d, J=14.0 Hz, 1 H), 4.07 (s, 1 H), 3.44-3.41 (m, 1 H), 3.02-2.77 (m, 15 H), 2.48-2.37 (m, 1 H), 2.25-2.22 (m, 1H), 1.66-1.56 (m, 1 H), 1.38-1.36 (m, 6 H); MS (ESI) m/z 529.0 (M+H).

S16-10-87

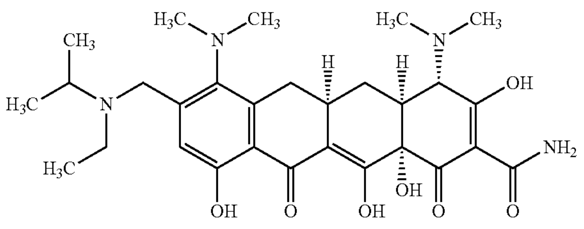

S16-10-87: $^1$H NMR (400 MHz, $CD_3OD$) δ 6.95 (s, 1 H), 4.62-4.56 (m, 1 H), 4.28-4.25 (m, 1 H), 4.10 (s, 1 H), 3.08-2.82 (m, 18 H), 2.53-2.49 (m, 1 H), 2.28-2.23 (m, 1 H), 1.68-1.62 (m, 1 H), 1.48-1.43 (m, 2 H), 1.42-1.31 (m, 7 H); MS (ESI) m/z 557.1 (M+H).

S16-10-88

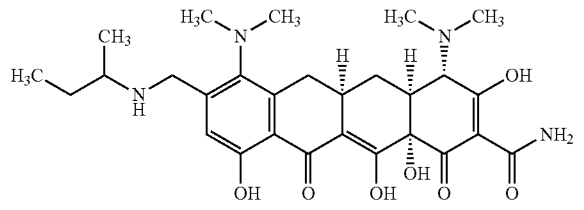

S16-10-88: $^1$H NMR (400 MHz, $CD_3OD$) δ 6.89 (s, 1 H), 4.33-4.29 (m, 1 H), 4.12-4.07 (m, 1 H), 4.04 (s, 1 H), 3.05-2.74 (m, 16 H), 2.42-2.31 (m, 1 H), 2.21-2.18 (m, 1 H), 1.89-1.81 (m, 1 H), 1.59-1.53 (m, 2 H), 1.32 (d, J=6.4 Hz, 3 H), 0.97 (t, J=6.4 Hz, 3 H); MS (ESI) m/z 543.1 (M+H).

S16-10-89

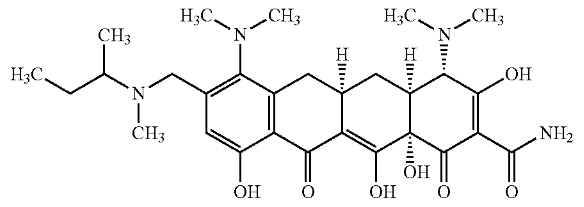

S16-10-89: $^1$H NMR (400 MHz, $CD_3OD$) δ 6.97, 6.96 (s, 1 H, total), 4.68-4.63 (m, 1 H), 4.42-4.38 (m, 1 H), 4.11 (s, 1 H), 3.48-3.43 (m, 1 H), 3.10-2.80 (m, 18 H), 2.51-2.45 (m, 1 H), 2.31-2.28 (m, 1 H), 1.91-1.85 (m, 1 H), 1.71-1.60 (m, 2 H), 1.43-1.43 (m, 3 H), 1.09-1.01 (m, 3 H); MS (ESI) m/z 557.1 (M+H).

S16-10-90

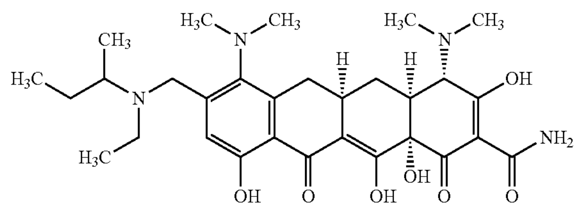

S16-10-90: $^1$H NMR (400 MHz, $CD_3OD$) δ 6.94 (s, 1 H), 4.68, 4.64, 4.54, 4.51 (s, 1 H, total), 4.34, 4.31, 4.23, 4.20 (s, 1 H, total), 4.10 (s, 1 H), 3.18-2.83 (m, 18 H), 2.55-2.42 (m, 1 H), 2.37-2.34 (m, 1 H), 2.29-2.26 (m, 1 H), 2.02-1.95 (m, 2 H), 1.67 (s, 3 H), 1.39-1.28 (m, 6 H); MS (ESI) m/z 571.1 (M+H).

S16-10-91

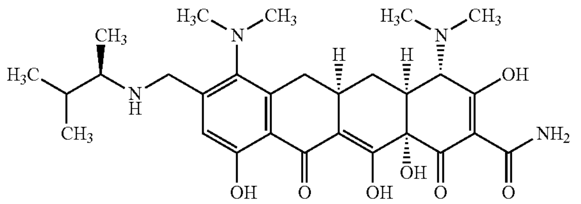

S16-10-91: $^1H$ NMR (400 MHz, $CD_3OD$) δ 7.01 (s, 1 H), 4.44 (d, J=13.6 Hz, 1 H), 4.20 (d, J=13.2 Hz, 1 H), 4.14 (s, 1 H), 3.21-2.88 (m, 16 H), 2.54-2.42 (m, 1 H), 2.33-2.29 (m, 1 H), 2.21-2.13 (m, 1 H), 1.68-1.63 (m, 1 H), 1.39-1.31 (m, 3 H), 1.10-1.03 (m, 6 H); MS (ESI) m/z 557.1 (M+H).

S16-10-92

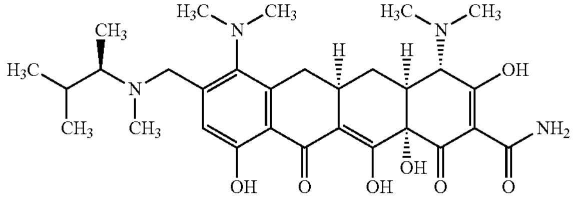

S16-10-92: $^1H$ NMR (400 MHz, $CD_3OD$) δ 7.01, 6.99 (s, 1 H, total), 4.70, 4.67, 4.56, 4.53 (s, 1 H, total), 4.44, 4.41, 4.02, 3.99 (s, 1 H, total), 4.17 (s, 1 H), 3.19-2.86 (m, 19 H), 2.53-2.48 (m, 1 H), 2.35-2.27 (m, 1 H), 2.16-2.12 (m, 1 H), 1.72-1.62 (m, 1 H), 1.47, 1.45, 1.41, 1.40 (s, 3 H, total), 1.22-1.06 (m, 6 H); MS (ESI) m/z 571.3 (M+H).

S16-10-93

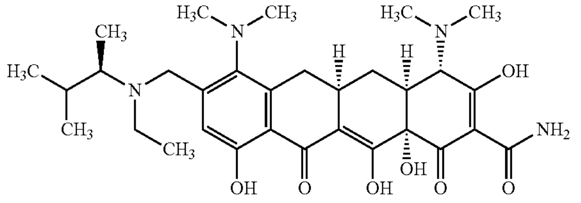

S16-10-93: $^1H$ NMR (400 MHz, $CD_3OD$) δ 7.00, 6.98 (s, 1 H, total), 4.69 (t, J=28.8, 14.0 Hz, 1 H), 4.34, 4.30, 4.14, 4.10 (s, 1 H, total), 4.16 (s, 1 H), 3.52-3.43 (m, 1 H), 3.23-2.92 (m, 17 H), 2.60-2.50 (m, 1 H), 2.34-2.31 (m, 1 H), 2.28-2.13 (m, 1 H), 1.75-1.62 (m, 1 H), 1.51, 1.33 (t, J=7.2 Hz, 3 H, total), 1.43-1.38 (m, 3 H), 1.20, 1.14, 1.05 (d, J=6.4 Hz, 6 H, total); MS (ESI) m/z 585.1 (M+H).

S16-10-94

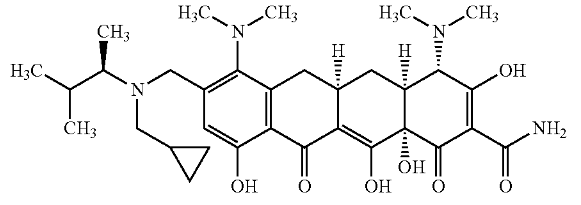

S16-10-94: $^1H$ NMR (400 MHz, $CD_3OD$) δ 7.03, 7.01 (s, 1 H, total), 5.49, 5.45, 4.74, 4.70 (s, 1 H, total), 4.34, 4.31, 4.17, 4.13 (s, 1 H, total), 4.17 (s, 1 H), 3.21-2.93 (m, 18 H), 2.60-2.49 (m, 1 H), 2.37-2.33 (m, 1 H), 2.28-2.16 (m, 1 H, total), 1.73-1.68 (m, 1 H), 1.49, 1.44 (d, J=6.8 Hz, 3 H, total), 1.28, 1.22 (d, J=6.4 Hz, 3 H, total), 1.09-1.05 (m, 3 H), 0.98-0.92 (m, 1 H), 0.88-0.83 (m, 1 H), 0.77-0.54 (m, 1 H), 0.55-0.48 (m, 1 H), 0.28-0.23 (m, 1 H); MS (ESI) m/z 611.3 (M+H).

S16-10-95

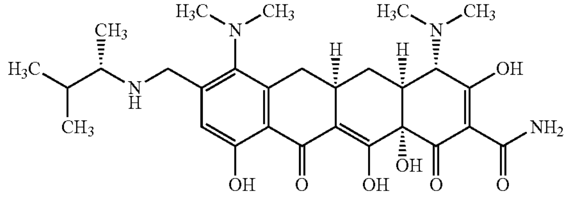

S16-10-95: $^1H$ NMR (400 MHz, $CD_3OD$) δ 7.02 (s, 1 H), 4.43 (d, J=14.0 Hz, 1 H), 4.23 (d, J=13.6 Hz, 1 H), 4.15 (s, 1 H), 3.14-2.87 (m, 16 H), 2.48-2.40 (m, 1 H), 2.34-2.29 (m, 1 H), 2.18-2.16 (m, 1 H), 1.73-1.53 (m, 1 H), 1.35 (d, J=6.8 Hz, 3 H), 1.07 (d, J=6.8 Hz, 3 H), 1.05 (d, J=6.8 Hz, 3 H); MS (ESI) m/z 557.3 (M+H).

S16-10-96

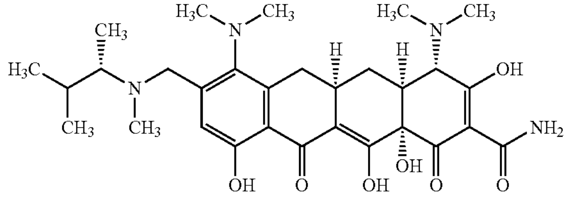

S16-10-96: $^1H$ NMR (400 MHz, $CD_3OD$) δ 6.88 (s, 1 H), 4.60-4.57 (m, 1 H), 4.20-4.16 (m, 1 H), 4.02 (s, 1 H), 2.97-2.58 (m, 19 H), 2.52-2.36 (m, 1H), 2.20-2.18 (m, 1H), 2.05-1.90 (m, 1 H), 1.60-1.48 (m, 1 H), 1.33 (d, J=6.4 Hz, 3 H), 1.07 (d, J=6.4 Hz, 3 H), 1.02 (d, J=6.4 Hz, 3 H); MS (ESI) m/z 571.1 (M+H)

S16-10-97

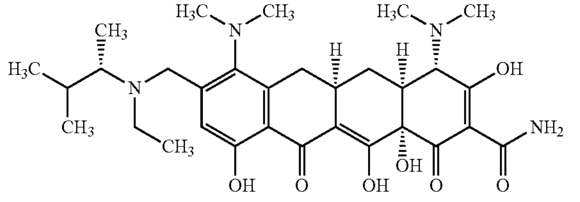

S16-10-97: $^1H$ NMR (400 MHz, $CD_3OD$) δ 6.98 (s, 1 H), 4.70, 4.67, 4.28, 4.25 (s, 1 H, total), 4.85, 4.46 (s, 1 H, total), 4.13 (s, 1 H), 3.16-2.83 (m, 18 H), 2.54-2.45 (m, 1 H), 2.32-2.23 (m, 1 H), 2.02-1.95 (m, 1 H), 1.67-1.64 (m, 1 H), 1.45-1.33 (m, 3 H), 1.28-1.26 (m, 1 H), 1.18-1.13 (m, 9 H); MS (ESI) m/z 585.3 (M+H).

S16-10-98

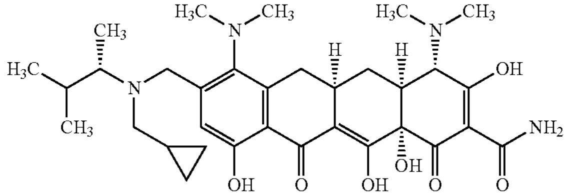

S16-10-98: $^{1}$H NMR (400 MHz, $CD_3OD$) δ 6.99, 6.93 (s, 1 H, total), 4.63, 4.61, 4.59, 4.58 (s, 1 H, total), 4.50, 4.47, 4.43, 4.40 (s, 1 H, total), 4.11 (s, 1 H), 3.14-2.85 (m, 18 H), 2.56-2.45 (m, 1 H), 2.32-2.25 (m, 1 H), 2.15-2.08 (m, 1 H), 1.69-1.60 (m, 1 H), 1.41, 1.34 (d, J=8.0 Hz, 3 H, total), 1.15 (d, J=6.8 Hz, 3 H), 1.07 (d, J=7.2 Hz, 3 H), 0.83-0.79 (m, 2 H), 0.65-0.58 (m, 1 H), 0.48-0.43 (m, 1 H), 0.38-0.21 (m, 1 H); MS (ESI) m/z 611.2 (M+H).

S16-10-99

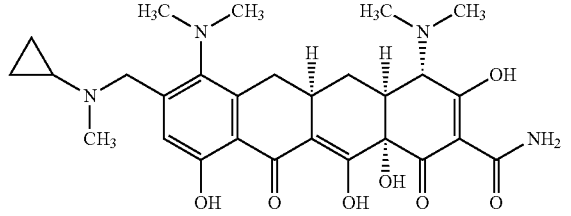

S16-10-99: $^{1}$H NMR (400 MHz, $CD_3OD$) δ 7.05, 7.03 (s, 1 H, total), 4.73 (s, 1 H), 4.45 (s, 1 H), 4.14 (s, 1 H), 3.10-2.85 (m, 19 H), 2.50-2.40 (m, 1 H), 2.31-2.28 (m, 1 H), 1.72-1.63 (m, 1 H), 1.00-0.95 (m, 4 H); MS (ESI) m/z 541.1 (M+H).

S16-10-100

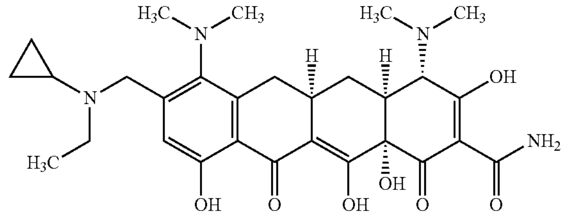

S16-10-100: $^{1}$H NMR (400 MHz, $CD_3OD$) δ 7.08 (s, 1 H), 4.81, 4.77 (s, 1 H, total), 4.52, 4.48 (s, 1 H, total), 4.18 (s, 1 H), 3.16-2.90 (m, 18 H), 2.57-2.43 (m, 1 H), 2.36-2.33 (m, 1 H), 1.76-1.73 (m, 1 H), 1.53 (t, J=7.2 Hz, 3 H), 1.20-1.03 (m, 3 H), 0.95-0.82 (m, 1 H); MS (ESI) m/z 555.1 (M+H).

S16-10-101

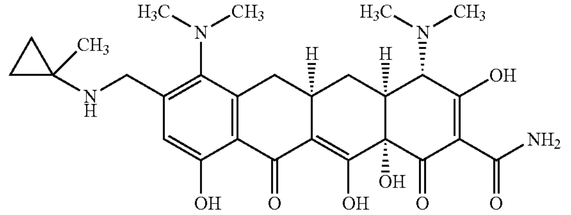

S16-10-101: $^{1}$H NMR (400 MHz, $CD_3OD$) δ 6.95 (s, 1 H), 4.48 (d, J=13.6 Hz, 1 H), 4.25 (d, J=12.8 Hz, 1 H), 4.12 (s, 1 H), 3.08-2.80 (m, 15 H), 2.48-2.38 (m, 1 H), 2.28-2.25 (m, 1 H), 1.68-1.63 (m, 1 H), 1.58 (s, 3 H), 1.15 (s, 2 H), 0.88 (s, 2 H); MS (ESI) m/z 541.1 (M+H).

S16-10-102

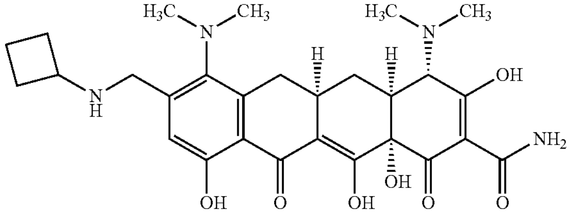

S16-10-102: $^{1}$H NMR (400 MHz, $CD_3OD$) δ 6.95 (s, 1 H), 4.46 (d, J=14 Hz, 1 H), 4.14 (s, 1 H), 4.11 (d, J=14 Hz, 1 H), 3.88-3.84 (m, 1 H), 3.07-2.45 (m, 15 H), 2.45-2.27 (m, 6H), 1.99-1.92 (m, 2 H), 1.71-1.62 (m, 1 H); MS (ESI) m/z 541.1 (M+H).

S16-10-103

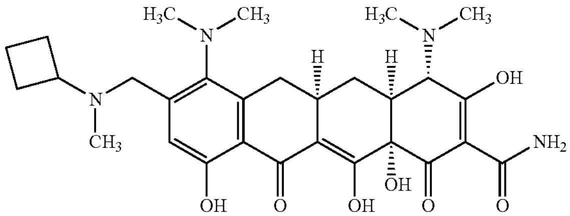

S16-10-103: $^{1}$H NMR (400 MHz, $CD_3OD$) δ 7.08, 7.04 (s, 1 H, total), 4.52, 4.48, 4.32, 4.29 (s, 1 H, total), 4.11 (s, 1 H), 4.24, 4.21, 4.02, 3.99 (s, 1 H, total), 3.90-3.86 (m, 1 H), 3.10-2.81 (m, 15 H), 2.65 (s, 3 H), 2.48-2.37 (m, 1 H), 2.35-2.24 (m, 5 H), 1.89-1.81 (m, 2 H), 1.68-1.62 (m, 1 H); MS (ESI) m/z 555.1 (M+H).

S16-10-104

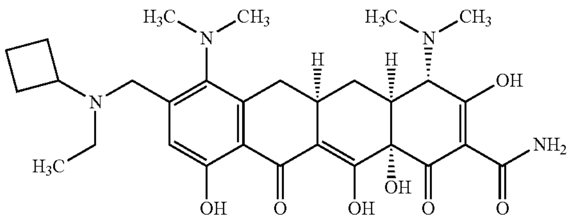

S16-10-104: $^{1}$H NMR (400 MHz, $CD_3OD$) δ 7.01, 6.97 (s, 1 H, total), 4.52, 4.49, 4.45, 4.41 (s, 1 H, total), 4.12 (s, 1 H), 4.20, 4.17, 4.12, 4.09 (s, 1 H, total), 4.00-3.97 (m, 1 H), 3.18-2.84 (m, 17 H), 2.49-2.38 (m, 1 H), 2.39-2.20 (m, 5 H), 1.88-1.82 (m, 2 H), 1.68-1.62 (m, 1 H), 1.35-1.28 (m, 3 H); MS (ESI) m/z 569.1 (M+H).

S16-10-105

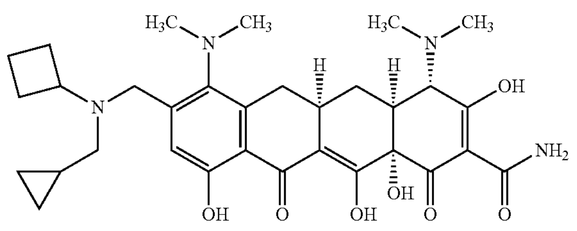

S16-10-105: $^1$H NMR (400 MHz, $CD_3OD$) δ 7.01, 6.99 (s, 1 H, total), 4.68, 4.65, 4.52, 4.49 (s, 1 H, total), 4.35, 4.31, 4.11, 4.08 (s, 1 H, total), 4.11 (s, 1H), 4.19-4.16 (m, 1 H), 3.10-2.85 (m, 17 H), 2.50-2.40 (m, 1 H), 2.38-2.33 (m, 2 H), 2.30-2.15 (m, 3 H), 1.90-1.78 (m, 2 H), 1.68-1.62 (m, 1 H), 1.15-1.08 (m, 1 H), 0.76-0.74 (m, 2 H), 0.48-0.42 (m, 2 H); MS (ESI) m/z 595.1 (M+H).

S16-10-106

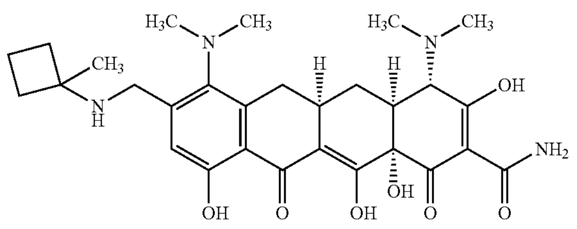

S16-10-106: $^1$H NMR (400 MHz, $CD_3OD$) δ 6.98 (s, 1 H), 4.22, 4.20 (s, 1 H, total), 4.13 (s, 1 H), 4.06, 4.04 (s, 1 H, total), 3.03-2.83 (m, 15 H), 2.50-2.40 (m, 3 H), 2.23-2.29 (m, 1 H), 2.16-2.14 (m, 2 H), 2.04-1.99 (m, 2 H), 1.72-1.65 (m, 1 H), 1.65 (s, 3 H); MS (ESI) m/z 555.1 (M+H).

S16-10-107

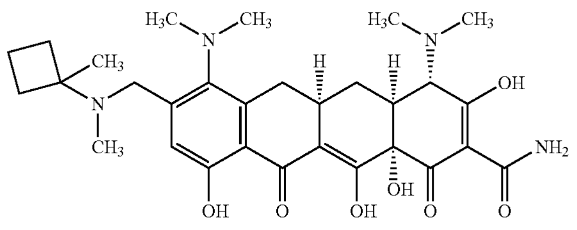

S16-10-107: $^1$H NMR (400 MHz, $CD_3OD$) δ 7.01, 6.97 (s, 1 H, total), 4.43, 4.40, 4.22, 4.19 (s, 1 H, total), 4.17, 4.14, 3.95, 3.92 (s, 1 H, total), 4.12 (s, 1 H), 3.08-2.79 (m, 15 H), 2.67, 2.59 (s, 3 H, total), 2.47-2.41 (m, 3 H), 2.28-2.20 (m, 2 H), 2.11-2.04 (m, 1 H), 1.92-1.88 (m, 2 H), 1.64-1.60 (m, 1 H), 1.60 (s, 3 H); MS (ESI) m/z 569.3 (M+H).

S16-10-108

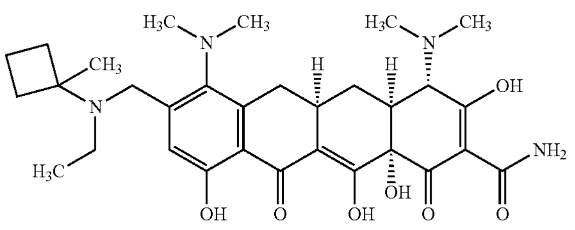

S16-10-108: $^1$H NMR (400 MHz, $CD_3OD$) δ 7.05, 7.04, 7.01, 7.00 (s, 1 H, total), 4.49-4.38 (m, 1 H), 4.17-4.12 (m, 2 H), 3.22-2.85 (m, 17 H), 2.65-2.21 (m, 4 H), 2.20-2.05 (m, 2 H), 1.98-1.89 (m, 2 H), 1.68-1.61 (m, 4 H), 1.23-1.15 (m, 3 H); MS (ESI) m/z 583.2 (M+H).

S16-10-109

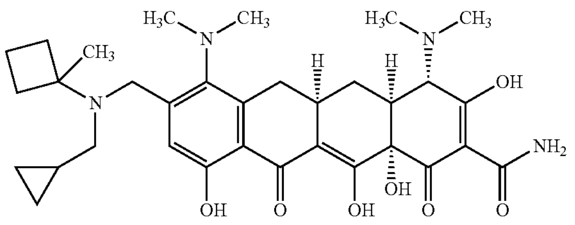

S16-10-109: $^1$H NMR (400 MHz, $CD_3OD$) δ 7.07, 7.05 (s, 1 H, total), 4.57, 4.54, 4.48, 4.45 (s, 1 H, total), 4.23, 4.20, 4.18, 4.15 (s, 1 H, total), 4.13 (s, 1 H), 3.14-2.93 (m, 17 H), 2.54-2.51 (m, 2 H), 2.45-2.41 (m, 1 H), 2.35-2.18 (m, 3 H), 1.99-1.89 (m, 3 H), 1.68-1.65 (m, 4 H), 0.95-0.60 (m, 2 H), 0.40-0.20 (m, 2 H); MS (ESI) m/z 609.1 (M+H).

S16-10-110

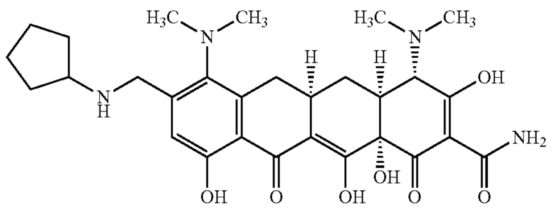

S16-10-110: $^1$H NMR (400 MHz, $CD_3OD$) δ 6.97 (s, 1 H), 4.38 (d, J=14.0 Hz, 1 H), 4.17 (d, J=13.6 Hz, 1 H), 4.12 (s, 1 H), 3.69-3.62 (m, 1 H), 3.06-2.82 (m, 15 H), 2.49-2.38 (m, 1 H), 2.29-2.22 (m, 1 H), 2.18-2.04 (m, 2 H), 1.85-1.82 (m, 2 H), 1.78-1.61 (m, 5 H); MS (ESI) m/z 555.3 (M+H).

S16-10-111

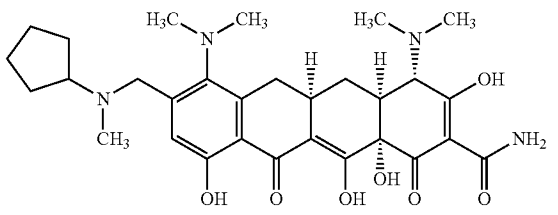

S16-10-111: $^{1}$H NMR (400 MHz, $CD_3OD$) δ 7.03 (d, J=6.8 Hz, 1 H), 4.68 (d, J=13.2 Hz, 1 H), 4.51-4.39 (m, 1 H), 4.16 (s, 1 H), 3.84-3.78 (m, 1 H), 3.09-2.86 (m, 19 H), 2.55-2.48 (m, 1 H), 2.34-2.30 (m, 2H), 1.91 (s, 5 H), 1.77-1.68 (m,3 H); MS (ESI) m/z 569.1 (M+H).

S16-10-112

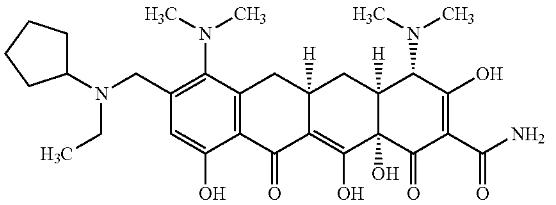

S16-10-112: $^{1}$H NMR (400 MHz, $CD_3OD$) δ 7.00 (m, J=7.6 Hz, 1 H), 4.71-4.59 (m, 1 H), 4.34-4. 25 (m, 1 H), 4.15 (s, 1 H), 3.27-2.87 (m, 18 H), 2.56-2.48 (m, 1 H), 2.34-2.20 (m, 2 H), 1.89 (s, 5 H), 1.75-1.67 (m, 3 H), 1.43-1.37 (m, 3 H); MS (ESI) m/z 583.1 (M+H).

S16-10-113

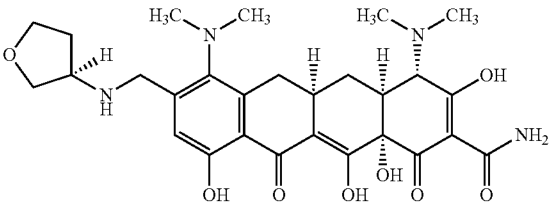

S16-10-113: $^{1}$H NMR (400 MHz, $CD_3OD$) δ 6.97 (s, 1 H), 4.40 (d, J=14 Hz, 1 H), 4.19 (d, J=13.6 Hz, 1 H), 4.11-4.05 (m, 3 H), 4.01-3.98 (m, 1 H), 3.75-3.71 (m, 1 H), 3.09-2.80 (m, 16 H), 2.49-2.41 (m, 2 H), 2.29-2.26 (m, 1 H), 2.15-2.09 (m, 1 H), 1.68-1.63 (m, 1 H); MS (ESI) m/z 557.1 (M+H).

S16-10-114

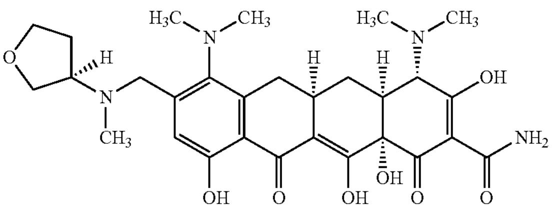

S16-10-114: $^{1}$H NMR (400 MHz, $CD_3OD$) δ 7.48 (s, 1 H), 4.65-4.62, 4.49-4.46 (m, 1 H, total), 4.33-4.28 (m, 2 H), 4.18-4.10 (m, 3 H), 3.75-3.68 (m, 1H), 3.09-2.82 (m, 19 H), 2.50-2.41 (m, 2 H), 2.35-2.25 (m, 2 H), 1.68-1.63 (m, 1 H); MS (ESI) m/z 571.1 (M+H).

S16-10-115

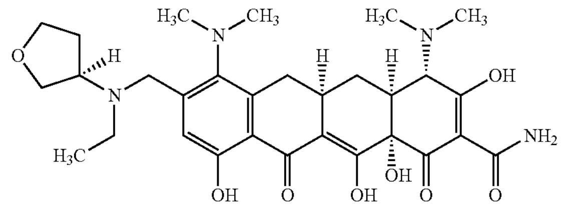

S16-10-115: $^{1}$H NMR (400 MHz, $CD_3OD$) δ 6.96 (s, 1 H), 4.71-4.55 (m, 1 H), 4.28-4.23 (m, 2 H), 4.19-4.13 (m, 2 H), 4.11 (s, 1 H), 3.68-3.63 (m, 1 H), 3.09-2.81 (m, 18 H), 2.53-2.14 (m, 4 H), 1.68-1.59 (m, 1 H), 1.41-1.33 (m, 3 H); MS (ESI) m/z 585.1 (M+H).

S16-10-116

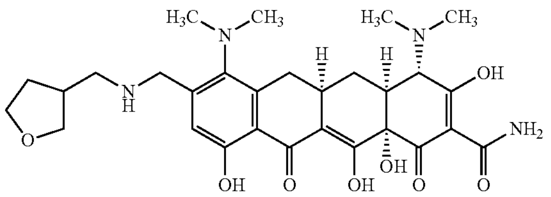

S16-10-116: $^{1}$H NMR (400 MHz, $CD_3OD$) δ 6.97 (s, 1 H), 4.45, 4.42 (s, 1 H, total), 4.22, 4.18 (s, 1 H, total), 4.13 (s, 1 H), 3.93-3.88 (m, 2 H), 3.80-3.73 (m, 1 H), 3.59-3.55 (m, 1 H), 3.17-2.83 (m, 17 H), 2.69-2.66 (m, 1 H), 2.51-2.40 (m, 1 H), 2.30-2.17 (m, 2 H), 1.75-1.60 (m, 2 H); MS (ESI) m/z 571.1 (M+H).

S16-10-117

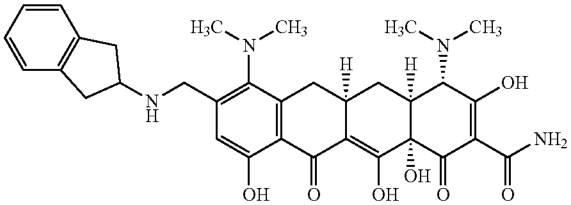

S16-10-117: $^{1}$H NMR (400 MHz, $CD_3OD$) δ 7.25-7.16 (m, 4 H), 6.90 (s, 1H), 4.37 (d, J=14 Hz, 1 H), 4.13-4.04 (m, 2 H), 4.04 (s, 1 H), 3.61-3.39 (m, 3 H), 3.17-2.58 (m, 16 H), 2.39-2.31 (m, 1 H), 2.21-2.18 (m, 1 H), 1.61-1.52 (m, 1 H); MS (ESI) m/z 603.0 (M+H).

S16-10-118

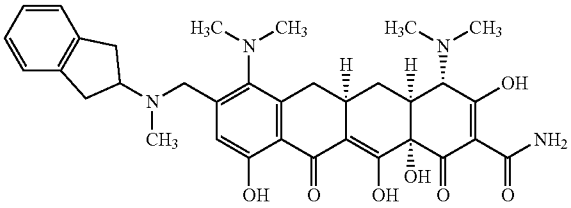

S16-10-118: $^{1}$H NMR (400 MHz, $CD_3OD$) δ 7.25-7.18 (m, 4 H), 6.95, 6.93 (s, 1 H, total), 4.58, 4.54, 4.45, 4.42 (s, 1 H, total), 4.36, 4.33, 4.06, 4.03 (s, 1 H, total), 4.28-4.23 (m, 2 H), 4.04 (s, 1 H), 3.52-3.27 (m, 6 H), 2.98-2.71 (m, 15 H), 2.45-2.38 (m, 1 H), 2.21-2.18 (m, 1 H), 1.63-1.54 (m, 1 H); MS (ESI) m/z 617.1 (M+H)

S16-10-119

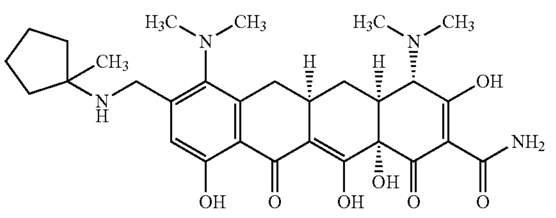

S16-10-119: $^1$H NMR (400 MHz, $CD_3OD$) δ 6.89 (s, 1 H), 4.22 (d, J=14.2 Hz, 1 H), 4.03 (d, J=14.4 Hz, 1 H), 4.01 (s, 1 H), 2.93-2.70 (m, 15 H), 2.48-2.38 (m, 1 H), 2.18-2.14 (m, 1 H), 1.85-1.69 (m, 8 H), 1.56-1.47 (m, 1 H), 1.38 (s, 3 H); MS (ESI) m/z 569.0 (M+H).

S16-10-120

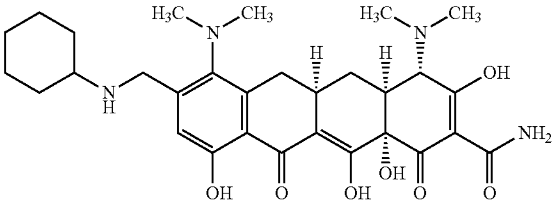

S16-10-120: $^1$H NMR (400 MHz, $CD_3OD$) δ 6.99 (s, 1 H), 4.43-4.39 (m, 1 H), 4.22-4.19 (m, 1 H), 4.14 (s, 1 H), 3.23-2.91 (m, 9 H), 2.96-2.83 (m, 6 H), 2.52-2.42 (m, 1 H), 2.31-2.28 (m, 1 H), 2.25-2.15 (m, 2 H), 1.93-1.87 (m, 2 H), 1.75-1.61 (m, 2 H), 1.49-1.25 (m, 6 H); MS (ESI) m/z 569.3 (M+H).

S16-10-121

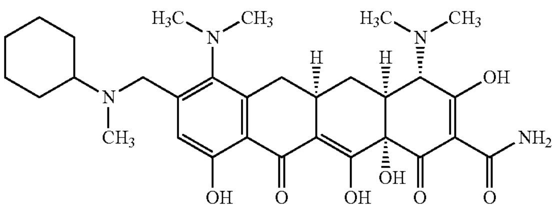

S16-10-121: $^1$H NMR (400 MHz, $CD_3OD$) δ 6.97, 6.96 (s, 1 H total), 4.69, 4.66, 4.41, 4.39 (s, 1 H total), 4.38, 4.37, 4.04, 4.01 (s, 1 H total), 4.11 (s, 1 H), 3.21-2.73 (m, 19 H), 2.54-2.47 (m, 1 H), 2.30-2.26 (m, 1 H), 2.13-2.10 (m, 2 H), 2.00-1.92 (m, 1 H), 1.76-1.57 (m, 4 H), 1.44-1.20 (m, 4 H); MS (ESI) m/z 583.4 (M+H).

S16-10-122

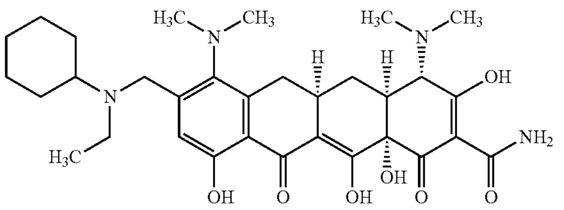

S16-10-122: $^1$H NMR (400 MHz, $CD_3OD$) δ 6.98 (s, 1 H), 4.74, 4.71, 4.57, 4.54 (s, 1 H, total), 4.40, 4.37, 4.19, 4.15 (s, 1 H, total), 4.15 (s, 1 H), 3.50-3.47 (m, 1 H), 3.26-2.86 (m, 17 H), 2.54-2.45 (m, 1 H), 2.37-2.32 (m, 1 H), 2.18-1.95 (m, 4 H), 1.85-1.61 (m, 4 H), 1.51-1.28 (m, 6 H); MS (ESI) m/z 597.1 (M+H).

S16-10-123

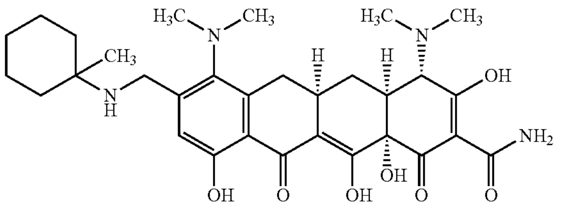

S16-10-123: $^1$H NMR (400 MHz, $CD_3OD$) δ 7.00 (s, 1 H), 4.37, 4.34 (s, 1 H, total), 4.14, 4.11 (s, 1 H, total), 4.11 (s, 1 H), 3.09-2.82 (m, 15 H), 2.48-2.38 (m, 1 H), 2.30-2.25 (m, 1 H), 1.96-1.84 (m, 3 H), 1.75-1.54 (m, 8 H), 1.47 (s, 3 H); MS (ESI) m/z 583.1 (M+H).

S16-10-124

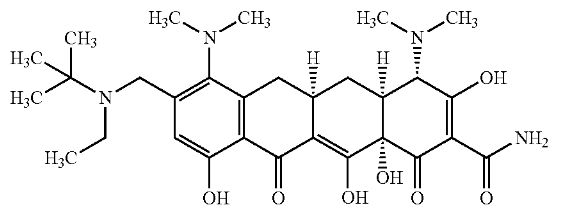

S16-10-124: $^1$H NMR (400 MHz, $CD_3OD$) δ 7.08, 7.04 (s, 1 H, total), 4.79, 4.76, 4.54, 4.51 (s, 1 H, total), 4.48, 4.45, 4.24, 4.21 (s, 1 H, total), 4.60, 4.16 (s, 1 H, total), 3.27-2.86 (m, 17 H), 2.54-2.47 (m, 1 H), 2.33-2.30 (m, 1 H), 1.73-1.66 (m, 1 H), 1.60-1.58 (m, 9 H), 1.22-1.20 (m, 3 H); MS (ESI) m/z 571.1 (M+H).

S16-10-125

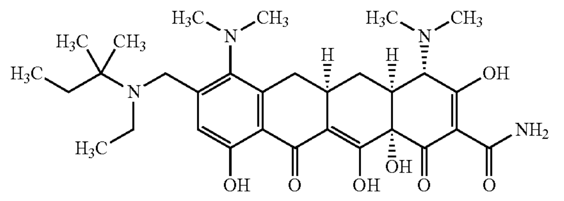

S16-10-125: $^{1}$H NMR (400 MHz, $CD_3OD$) δ 7.10, 7.08 (s, 1 H, total), 4.85, 4.81, 4.26, 4.23 (s, 1 H, total), 4.54 (s, 1 H), 4.18 (s, 1 H), 3.59-3.54 (m, 1 H), 3.29-3.27 (m, 1 H), 3.18-2.89 (m, 15 H), 2.54-2.42 (m, 1 H), 2.36-2.34 (m, 1 H), 2.08-2.04 (m, 1 H), 1.98-1.92 (m, 1 H), 1.70-1.61 (m, 1 H), 1.58-1.56 (m, 6 H), 1.24-1.19 (m, 6 H); MS (ESI) m/z 585.4 (M+H).

S16-10-126

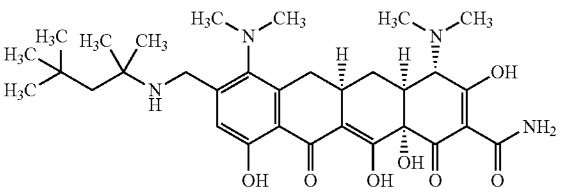

S16-10-126: $^{1}$H NMR (400 MHz, $CD_3OD$) δ 7.02 (s, 1 H), 4.36 (d, J=13.2 Hz, 1 H), 4.15-4.11 (d, J=13.2 Hz, 1 H), 4.11 (s, 1 H), 3.06-2.84 (m, 16 H), 2.49-4.41 (m, 1 H), 2.35-2.27 (m, 1 H), 1.82 (d, J=7.2 Hz, 2 H), 1.68-1.63 (m, 1 H), 1.57 (s, 6 H), 1.12 (s, 9 H); MS (ESI) m/z 599.6 (M+H).

S16-10-127

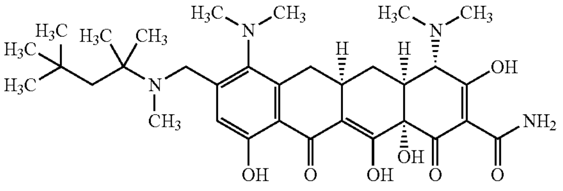

S16-10-127: $^{1}$H NMR (400 MHz, $CD_3OD$) δ 7.00, 6.98 (s, 1 H, total), 4.87, 4.83, 4.62, 4.59 (s, 1 H, total), 4.16 (s, 1 H), 4.24, 4.21, 3.99, 3.96 (s, 1 H, total), 3.14-2.71 (m, 18 H), 2.52-2.41 (m, 1 H), 2.33-2.30 (m, 1 H), 2.01 (s, 1 H), 1.90-1.81 (m, 1 H), 1.70 (s, 3 H), 1.68-1.66 (m, 1 H), 1.65 (s, 3 H), 1.17 (s, 9 H); MS (ESI) m/z 613.1 (M+H).

S16-10-128

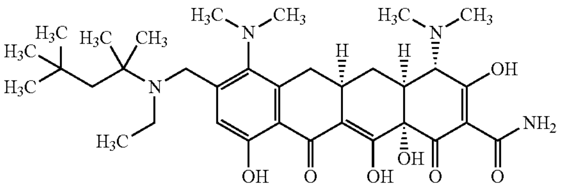

S16-10-128: $^{1}$H NMR (400 MHz, $CD_3OD$) δ 7.04, 7.01 (s, 1 H, total), 4.78, 4.74 (s, 1 H, total), 4.45 (s, 1 H), 4.15, 4.10 (s, 1 H, total), 3.58-3.51 (m, 1 H), 3.19-2.87 (m, 16 H), 2.53-2.46 (m, 1 H), 2.28-2.21 (m, 1 H), 1.94-1.90 (m, 1 H), 1.88-1.83 (m, 1 H), 1.69-1.63 (m, 7 H), 1.12 (s, 12 H); MS (ESI) m/z 627.1 (M+H).

S16-10-129

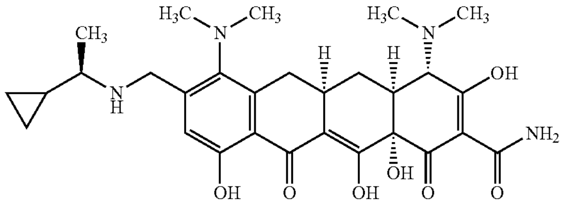

S16-10-129: $^{1}$H NMR (400 MHz, $CD_3OD$) δ 7.00 (s, 1 H), 4.43, 4.39 (s, 1 H, total), 4.34, 4.31 (s, 1 H, total), 4.14 (s, 1 H), 3.13-2.77 (m, 16 H), 2.49-2.40 (m, 1 H), 2.31-2.28 (m, 1 H), 1.67-1.65 (m, 1 H), 1.51, 1.49 (s, 3 H, total), 1.13-1.05 (m, 1 H), 0.82-0.76 (m, 2 H), 0.61-0.55 (m, 1 H), 0.41-0.37 (m, 1 H); MS (ESI) m/z 555.0 (M+H).

S16-10-130

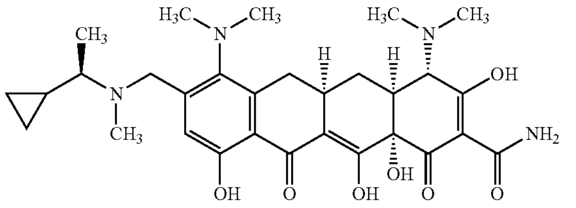

S16-10-130: $^{1}$H NMR (400 MHz, $CD_3OD$) δ 6.87, 6.85 (s, 1 H, total), 4.70, 4.67, 4.41, 4.37 (s, 1 H, total), 4.27, 4.23, 3.97, 3.94 (s, 1 H, total), 4.01 (s, 1 H), 2.94-2.67 (m, 19 H), 2.41-2.32 (m, 1 H), 2.19-2.13 (m, 1 H), 1.58-1.53 (m, 1 H), 1.42-1.37 (m, 3 H), 1.21-1.09 (m, 1 H), 0.75-0.68 (m, 2 H), 0.63-0.60 (m, 1 H), 0.38-0.33 (m, 1 H); MS (ESI) m/z 569.3 (M+H).

S16-10-131

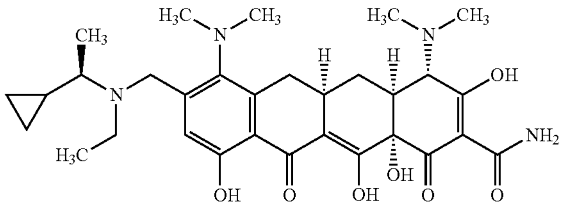

S16-10-131: $^{1}$H NMR (400 MHz, $CD_3OD$) δ 6.87, 6.84 (s, 1 H, total), 4.75, 4.71, 4.48, 4.44 (s, 1 H, total), 4.31, 4.28, 4.04, 4.01 (s, 1 H, total), 4.02 (s, 1 H), 2.94-2.75 (m, 18 H), 2.48-2.38 (m, 1 H), 2.20-2.15 (m, 1 H), 1.58-1.53 (m, 1 H), 1.37 (d, J=6.8 Hz, 3 H), 1.35-1.27 (m, 1 H), 1.13 (t, J=6.4 Hz, 3 H), 0.79-0.70 (m, 2 H), 0.51-0.40 (m, 2 H); MS (ESI) m/z 583.2 (M+H).

S16-10-132

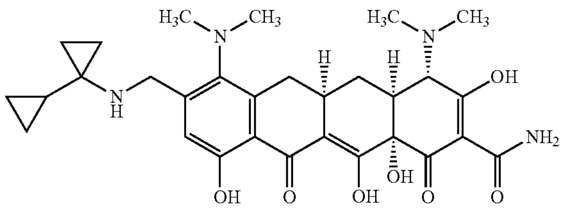

S16-10-132: $^{1}$H NMR (400 MHz, $CD_3OD$) δ 6.97 (s, 1 H), 4.64 (d, J=13.2 Hz, 1 H), 4.37 (d, J=13.2 Hz, 1 H), 4.09 (s, 1

H), 3.12-2.81 (m, 15 H), 2.46-2.42 (m, 1 H), 2.28-2.24 (m, 1 H), 1.67-1.55 (m, 2 H), 1.05-1.04 (m, 2 H), 0.84-0.82 (m, 2 H), 0.75-0.73 (m, 2 H), 0.42-0.39 (m, 2 H); MS (ESI) m/z 567.0 (M+H).

S16-10-133

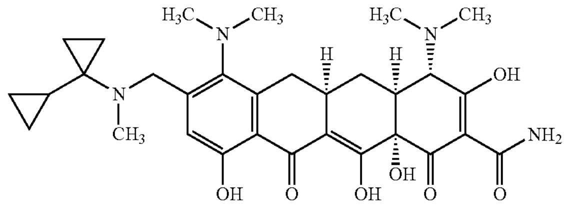

S16-10-133: $^{1}$H NMR (400 MHz, $CD_3OD$) δ 7.00 (s, 1 H), 4.74, 4.71 (s, 1 H, total) 4.54, 4.51 (s, 1 H, total), 4.10 (s, 1 H), 3.09-2.83 (m, 18 H), 2.55-2.46 (m, 1 H), 2.29-2.26 (m, 1 H), 1.67-1.64 (m, 2 H), 1.15-1.00 (m, 2 H), 0.97-0.83 (m, 2 H), 0.79-0.77 (m, 2 H), 0.42-10.37 (m, 2 H); MS (ESI) m/z 581.1 (M+H).

S16-10-134

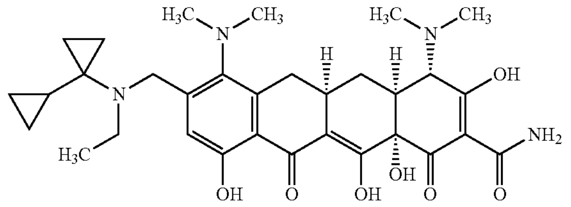

S16-10-134: $^{1}$H NMR (400 MHz, $CD_3OD$) δ 7.07, 7.04 (s, 1 H, total), 4.94, 4.91, 4.87, 4.84 (s, 1 H, total), 4.67, 4.64, 4.55, 4.52 (s, 1 H, total), 4.16 (s, 1 H), 3.05-2.88 (m, 17 H), 2.60-2.52 (m, 1 H), 2.35-2.31 (m, 1 H), 1.72-1.65 (m, 2 H), 1.44 (t, J=14.4, 7.2 Hz, 3 H), 1.11-0.75 (m, 6 H), 0.51-0.33 (m, 2 H); MS (ESI) m/z 595.2 (M+H).

S16-10-135

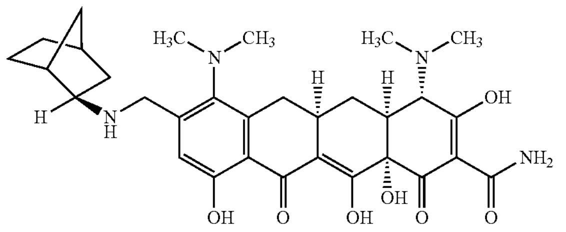

S16-10-135: $^{1}$H NMR (400 MHz, $CD_3OD$) δ 6.98 (d, J=7.6 Hz, 1 H), 4.36-4.32 (m, 1 H), 4.17-4.12 (m, 2 H), 3.11-2.82 (m, 16 H), 2.67-2.63 (m, 1 H), 2.48-2.26 (m, 3 H), 2.18-2.11 (m, 1 H), 1.87-1.42 (m, 7 H), 1.21-1.13 (m, 1 H); MS (ESI) m/z 581.4 (M+H).

S16-10-136

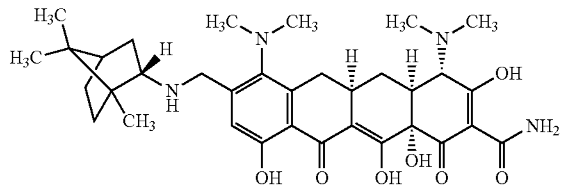

S16-10-136: $^{1}$H NMR (400 MHz, $CD_3OD$) δ 6.98 (s, 1 H), 4.44, 4.41 (s, 1 H, total), 4.25, 4.21 (s, 1 H, total), 4.13 (s, 1 H), 3.47-3.41 (m, 1 H), 3.12-2.83 (m, 15 H), 2.50-2.47 (m, 2 H), 2.32-2.25 (m, 1 H), 1.95-1.81 (m, 2 H), 1.66-1.60 (m, 3 H), 1.45-1.41 (m, 1 H), 1.32-1.29 (m, 1 H), 1.04 (s, 3 H), 0.95, 0.92 (s, 6 H, total); MS (ESI) m/z 623.1 (M+H).

S16-10-137

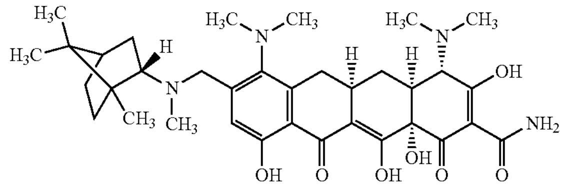

S16-10-137: $^{1}$H NMR (400 MHz, $CD_3OD$) δ 6.84 (s, 1 H), 4.74, 4.71, 4.54, 4.50 (s, 1 H, total), 4.13, 4.09, 3.97, 3.94 (s, 1 H, total), 4.00 (s, 1 H), 3.55-3.52 (m, 1 H), 3.01-2.55 (m, 18 H), 2.55-2.41 (m, 2 H), 2.18-2.13 (m, 1 H), 1.92-1.85 (m, 1 H), 1.75-1.68 (m, 2 H), 1.61-1.50 (m, 2 H), 1.39-1.25 (m, 2 H), 1.17, 0.95 (s, 3 H, total), 0.88 (d, J=5.6 Hz, 6 H); MS (ESI) m/z 637.3 (M+H).

S16-10-138

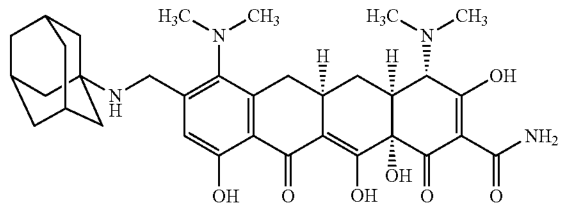

S16-10-138: $^{1}$H NMR (400 MHz, $CD_3OD$) δ 7.00 (s, 1 H), 4.36 (d, J=12.8 Hz, 1 H), 4.13-4.10 (m, 2 H), 3.06-2.82 (m, 15 H), 2.50-2.38 (m, 1 H), 2.29-2.26 (m, 4 H), 2.02-1.94 (m, 6 H), 1.86-1.72 (m, 6 H), 1.68-1.58 (m, 1 H); MS (ESI) m/z 621.2 (M+H).

S16-10-139

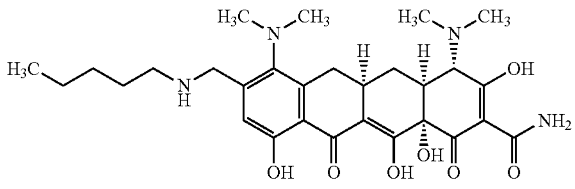

S16-10-139: $^{1}$H NMR (400 MHz, $CD_3OD$) δ 6.86 (s, 1 H), 4.32-4.29 (m, 1 H), 4.09-4.05 (m, 2 H)□3.02-2.73 (m, 17 H), 2.39-2.32 (m, 1H), 2.21-2.18 (m, 1H), 1.69-1.52 (m, 3H)□1.33-1.32 (m, 4H), 0.89-0.86 (m, 3 H); MS (ESI) m/z 557.1 (M+H)

S16-10-140

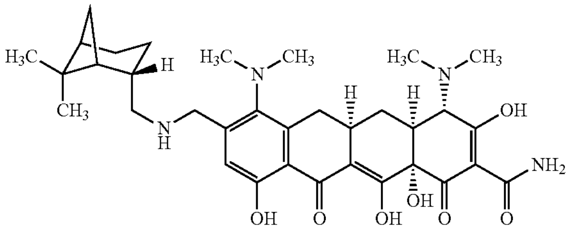

S16-10-140: $^1$H NMR (400 MHz, $CD_3OD$) δ 6.94 (s, 1 H), 4.41, 4.38 (s, 1 H, total), 4.18, 4.15 (s, 1 H, total), 4.12 (s, 1H), 3.11-2.81 (m, 17 H), 2.51-2.44 (m, 2 H), 2.30-2.23 (m, 1 H), 2.12-1.95 (m, 5 H), 1.70-1.55 (m, 2 H), 1.33 (d, J=6.8 Hz, 1 H), 1.25 (s, 3 H), 1.05 (s, 1 H), 1.02 (s, 3 H); MS (ESI) m/z 623.2 (M+H).

S16-10-141

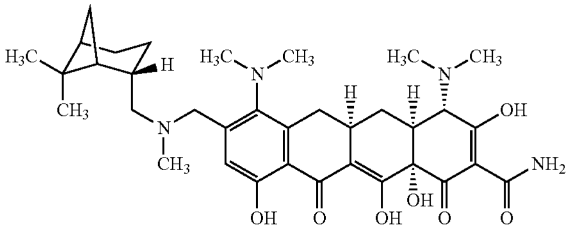

S16-10-141: $^1$H NMR (400 MHz, $CD_3OD$) δ 6.99 (s, 1 H), 4.70, 4.67 (s, 1 H, total), 4.41, 4.14, 4.11 (s, 1 H, total), 4.11 (s, 1H), 3.19-2.81 (m, 20 H), 2.50-2.45 (m, 2 H), 2.29-2.25 (m, 1 H), 2.19-2.11 (m, 1 H), 2.01-1.92 (m, 5 H), 1.70-1.51 (m, 2 H), 1.26-1.18 (m, 3 H), 1.09-1.02 (m, 2 H), 0.91 (s, 1H), 0.80 (s, 1H); MS (ESI) m/z 637.1 (M+H).

S16-10-142

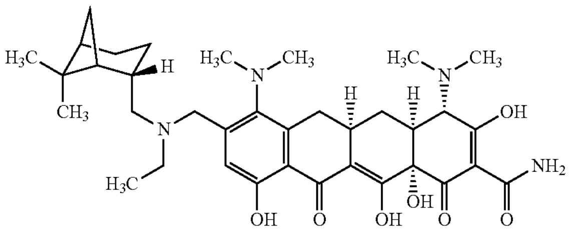

S16-10-142: $^1$H NMR (400 MHz, $CD_3OD$) δ 6.98, 6.96 (s, 1 H, total), 4.64, 4.60, 4.55, 4.51 (s, 1 H, total), 4.29, 4.46, 4.35, 4.22 (s, 1 H, total), 4.11 (s, 1H), 3.25-2.82 (m, 19 H), 2.59-2.53 (m, 1 H), 2.52-2.43 (m, 2 H), 2.30-2.23 (m, 1 H), 2.19-2.10 (m, 1 H), 2.08-1.92 (m, 5 H), 1.69-1.50 (m, 2 H), 1.29-1.18 (m, 4 H), 1.09-1.01 (m, 3 H), 0.91 (s, 1H), 0.85 (s, 1H); MS (ESI) m/z 651.2 (M+H).

S16-10-143

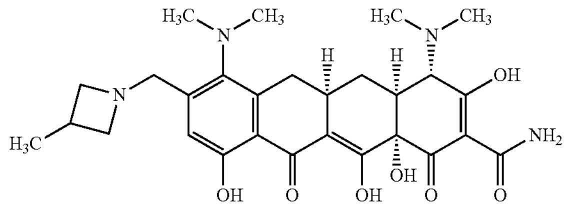

S16-10-143: $^1$H NMR (400 MHz, $CD_3OD$) δ 6.95-6.85 (m, 1 H), 4.65-4.15 (m, 4 H), 4.10 (s, 1 H), 4.04-3.96 (m, 1 H), 3.87-3.80 (m, 1 H), 3.05-2.81 (m, 15 H), 2.47-2.39 (m, 1 H), 2.28-2.25 (m, 1 H), 1.69-1.63 (m, 1 H), 1.35-1.34 (m, 2 H), 1.28-1.26 (m, 2 H), 1.21-1.18 (m, 1 H); MS (ESI) m/z 541.5 (M+H).

S16-10-144

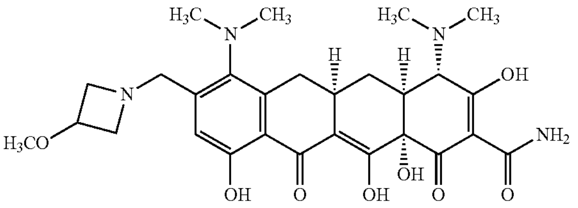

S16-10-144: $^1$H NMR (400 MHz, $CD_3OD$) δ 6.86 (d, J=14.4 Hz, 1 H), 4.69-4.53 (m, 2 H), 4.40-4.24 (m, 4 H), 4.12 (s, 1 H), 4.04-3.98 (m, 2 H), 3.36 (s, 3 H), 3.09-2.82 (m, 15 H), 2.48-2.25 (m, 2 H), 1.64 (ddd, J=13.6, 11.2, 13.2 Hz, 1 H); MS (ESI) m/z 557.0 (M+H).

S16-10-145

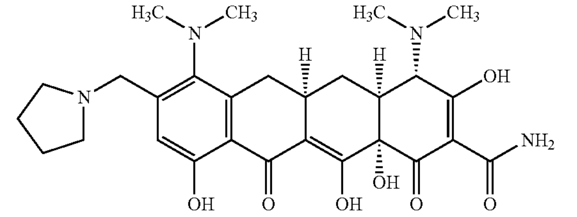

S16-10-145: $^1$H NMR (400 MHz, $CD_3OD$) δ 7.04 (s, 1 H), 4.62-4.59 (m, 1 H), 4.36-4.31 (m, 1 H), 4.14 (s, 1 H), 3.68-3.63 (m, 2 H), 3.23-3.17 (m, 2 H), 3.14-2.99 (m, 9 H), 2.89-2.83 (m, 6 H), 2.54-2.44 (m, 1 H), 2.37-2.28 (m, 1 H), 2.23-2.18 (m, 2 H), 2.13-2.07 (m, 2 H), 1.71-1.62 (m, 1 H); MS (ESI) m/z 541.3 (M+H).

S16-10-146

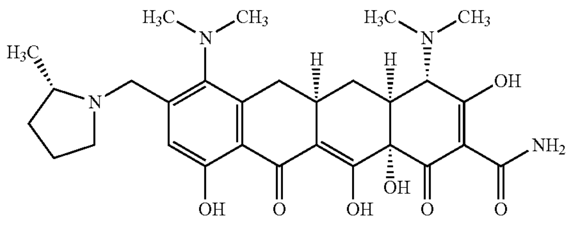

S16-10-146: $^1$H NMR (400 MHz, $CD_3OD$) δ 6.94 (s, 1 H), 4.38-4.35 (m, 2 H), 4.03 (s, 1 H), 3.59-3.52 (m, 1 H), 3.47-3.40 (m, 2 H), 3.05-2.74 (m, 16 H), 2.45-2.32 (m, 1 H), 2.34-2.28 (m, 1 H), 2.21-2.17 (m, 1 H), 2.09-2.05 (m, 1 H), 2.00-1.95 (m, 1 H), 1.78-1.70 (m, 1 H), 1.60-1.57 (m, 1 H), 1.43, 1.42 (s, 3 H, total); MS (ESI) m/z 555.0 (M+H).

S16-10-147

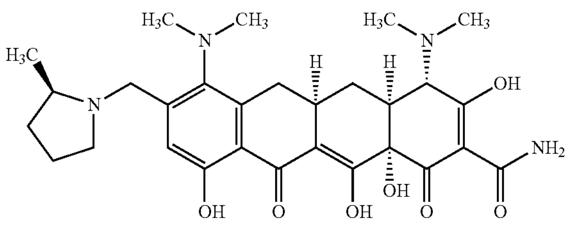

S16-10-147: $^1$H NMR (400 MHz, $CD_3OD$) δ 6.98 (s, 1 H), 4.74, 4.71, 4.12, 4.09 (s, 1 H, total), 4.10 (s, 1 H), 3.65-3.53 (m, 2 H), 3.08-2.81 (m, 17 H), 2.52-2.40 (m, 1 H), 2.41-2.35 (m, 1 H), 2.28-2.23 (m, 1 H), 2.18-2.10 (m, 1 H), 2.08-2.03 (m, 1 H), 1.74-1.68 (m, 1 H), 1.68-1.60 (m, 1 H), 1.49 (d, J=6.4 Hz, 3 H); MS (ESI) m/z 555.1 (M+H).

S16-10-148

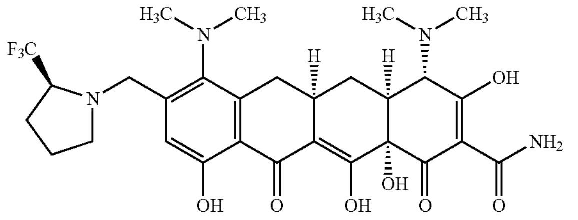

S16-10-148: $^1$H NMR (400 MHz, $CD_3OD$) δ 6.97 (s, 1 H), 4.72, 4.68 (s, 1 H, total), 4.21 (s, 1 H), 4.12, 4.09 (s, 1 H, total), 3.87-3.80 (m, 1 H), 3.45-3.41 (m, 7 H), 3.16-3.01 (m, 10 H), 2.75-2.69 (m, 2 H), 2.49-2.44 (m, 1 H), 2.40-2.38 (m, 1 H), 2.18-2.07 (m, 2 H), 1.73-1.65 (m, 1 H); MS (ESI) m/z 609.0 (M+H).

S16-10-149

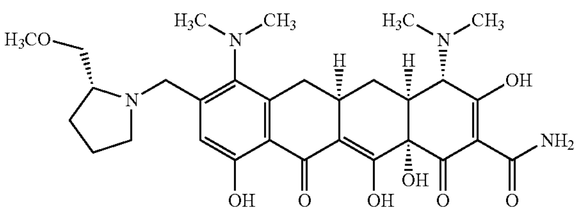

S16-10-149: $^1$H NMR (400 MHz, $CD_3OD$) δ 6.86 (s, 1 H), 4.48 (d, J=12.8 Hz, 1H), 4.28 (d, J=13.2 Hz, 1 H), 4.02 (s, 1 H), 3.77-3.42 (m, 5 H), 3.36 (s, 3 H), 3.13-2.70 (m, 15 H), 2.39-2.32 (m, 1 H)□2.24-2.19 (m, 2 H), 2.16-2.07 (m, 1 H), 2.05-1.87 (m, 2 H), 1.61-1.49 (m, 1H); MS (ESI) m/z 585.0 (M+H).

S16-10-150

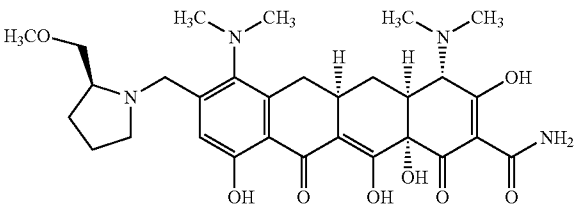

S16-10-150: $^1$H NMR (400 MHz, $CD_3OD$) δ 6.83 (s, 1 H), 4.03 (s, 2 H), 3.83-3.64 (m, 2 H), 3.63-3.53 (m, 2 H), 3.51-3.46 (m, 1 H), 3.43 (s, 3 H), 3.41-3.35 (m, 1 H), 3.12-2.63 (m, 15 H), 2.50-2.35 (m, 1 H), 2.34-2.14 (m, 2 H), 2.13-1.83 (m, 3 H), 1.68-1.43 (m, 1H); MS (ESI) m/z 585.0 (M+H).

S16-10-151

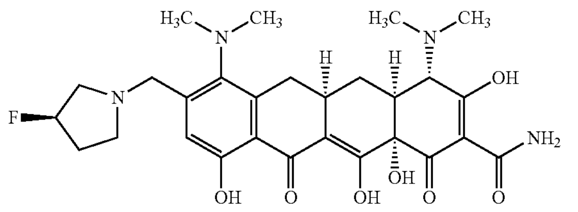

S16-10-151: $^1$H NMR (400 MHz, $CD_3OD$) δ 6.93 (s, 1 H), 5.46, 5.33 (s, 1 H, total), 4.58 (d, J=14.2 Hz, 1 H), 4.34 (d, J=14.2 Hz, 1 H), 4.04 (s, 1 H), 3.85-3.61 (m, 2 H), 3.40-3.39 (m, 1 H), 3.01-2.75 (m, 16 H), 2.43-2.18 (m, 4 H), 1.59-1.56 (m, 1 H); MS (ESI) m/z 559.3 (M+H).

S16-10-152

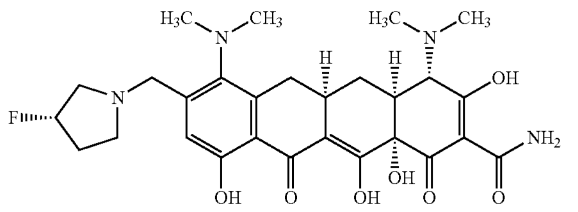

S16-10-152: $^1$H NMR (400 MHz, $CD_3OD$) δ 7.00 (s, 1 H), 5.55, 5.40 (s, 1 H, total), 4.63, 4.60 (s, 1 H, total), 4.39-4.31 (m, 1 H), 4.10 (s, 1 H), 3.89-3.76 (m, 2 H), 3.08-2.82 (m, 17 H), 2.51-2.35 (m, 3 H), 2.32-2.23 (m, 1 H), 1.69-1.57 (m, 1 H); MS (ESI) m/z 559.2 (M+H)

S16-10-153

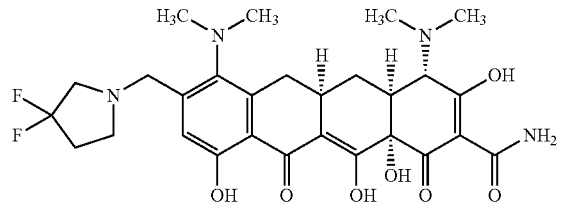

S16-10-153: $^1$H NMR (400 MHz, $CD_3OD$) δ 6.99 (s, 1 H), 4.64, 4.61 (s, 1 H, total), 4.29, 4.26 (s, 1 H, total), 4.13 (s, 1 H), 3.7 (t, J=23.2, 11.6 Hz, 2 H), 3.59-3.51 (m, 2 H), 3.15-2.96 (m, 15 H), 2.69-2.60 (m, 2 H), 2.55-2.42 (m, 1 H), 2.33-2.30 (m, 1 H), 1.66-1.63 (m, 1 H); MS (ESI) m/z 577.0 (M+H).

S16-10-154

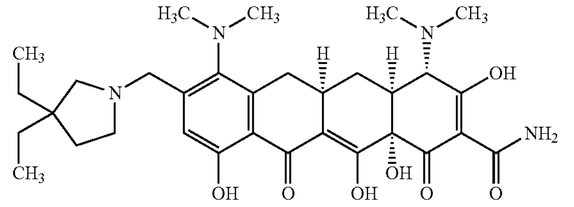

S16-10-154: $^1$H NMR (400 MHz, $CD_3OD$) δ 7.03, 7.02 (s, 1 H, total), 4.63-4.55 (m, 1 H), 4.33 (t, J=28.8, 14.4 Hz, 1 H), 4.12 (s, 1 H), 3.69-3.66 (m, 1 H), 3.42-3.39 (m, 1 H), 3.05-2.83 (m, 17 H), 2.51-2.40 (m, 1 H), 2.29-2.26 (m, 1 H), 2.05-2.01 (m, 1 H), 1.99-1.92 (m, 1 H), 1.66-1.56 (m, 5 H), 0.92-0.86 (m, 6 H); MS (ESI) m/z 597.1 (M+H).

S16-10-155

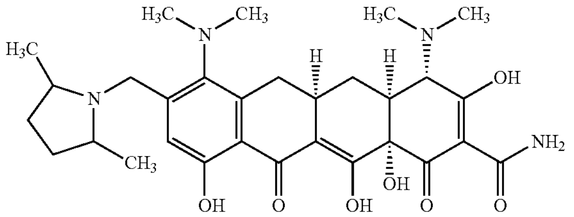

S16-10-155: $^1$H NMR (400 MHz, $CD_3OD$) δ 7.00 (s, 1 H), 4.63, 4.60 (s, 1 H, total), 4.32, 4.29 (s, 1 H, total), 4.11 (s, 1 H), 3.74-3.71 (m, 2 H), 3.06-2.86 (m, 15 H), 2.49-3.38 (m, 1 H), 2.32-2.26 (m, 3 H), 1.83-1.81 (m, 2 H), 1.69-1.60 (m, 1 H), 1.39, 1.38 (s, 3 H, total), 1.31, 1.30 (s, 3 H, total); MS (ESI) m/z 569.1 (M+H).

S16-10-156

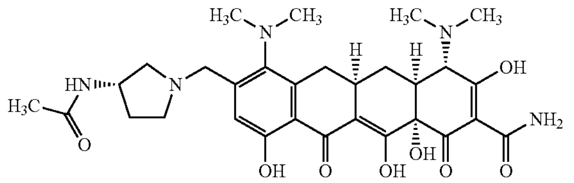

S16-10-156: $^1$H NMR (400 MHz, $CD_3OD$) δ 6.97 (s, 1 H), 4.48-4.22 (m, 2 H), 4.11 (s, 1 H), 3.92-3.81 (m, 1 H), 3.52-3.42 (m, 1 H), 3.22-2.68 (m, 17 H), 2.63-2.51 (m, 1 H), 2.50-2.41 (m, 1 H), 2.31-2.22 (m, 1 H), 2.21-2.10 (m, 1 H), 1.94 (s, 3 H), 1.64-1.58 (m, 1 H); MS (ESI) m/z 598.2 (M+H).

S16-10-157

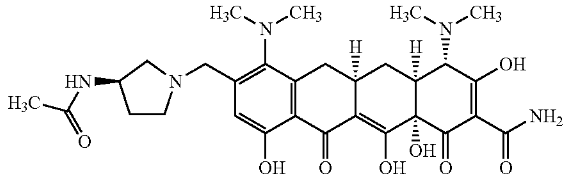

S16-10-157: $^1$H NMR (400 MHz, $CD_3OD$) δ 6.91 (s, 1 H), 4.73-4.69 (m, 1 H), 4.22 (s, 1 H), 4.10 (s, 1 H), 3.79-3.74 (m, 1 H), 3.50-3.40 (m, 1 H), 3.20-2.88 (m, 17 H), 2.61-2.41 (m, 2 H), 2.31-2.22 (m, 1 H), 2.19-2.08 (m, 1 H), 1.95 (s, 3 H), 1.66-1.57 (m, 1 H); MS (ESI) m/z 598.2 (M+H).

S16-10-158

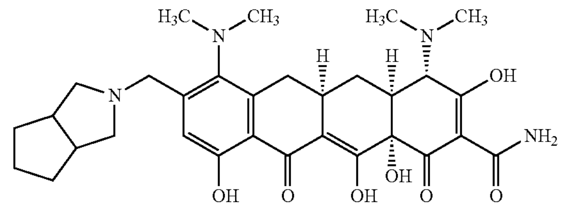

S16-10-158: $^1$H NMR (400 MHz, $CD_3OD$) δ 7.02, 7.00 (s, 1 H, total), 4.55 (t, J=22.8, 13.2 Hz, 1 H), 4.32, 4.29, 4.24, 4.21 (s, 1H, total), 4.12 (s, 1 H), 3.45-3.41 (m, 1 H), 3.20-3.15 (m, 1 H), 3.10-2.75 (m, 19 H), 2.49-2.41 (m, 1 H), 2.28-2.23 (m, 1 H), 1.85-1.53 (m, 7 H); MS (ESI) m/z 581.1 (M+H).

S16-10-159

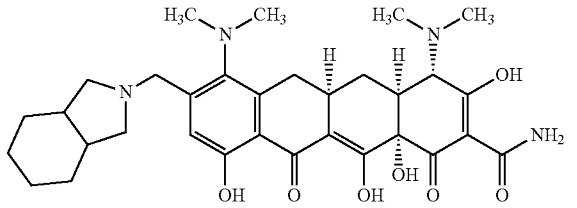

S16-10-159: $^1$H NMR (400 MHz, $CD_3OD$) δ 6.95 (s, 1 H), 4.58-4.53 (m, 1 H), 4.32-4.29 (m, 1 H), 4.03 (s, 1 H), 3.58-3.39 (m, 3 H), 3.12-2.75 (m, 16 H), 2.57-2.33 (m, 3 H), 2.20-2.17 (m, 1 H), 1.65-1.33 (m, 9 H); MS (ESI) m/z 595.2 (M+H).

S16-10-160

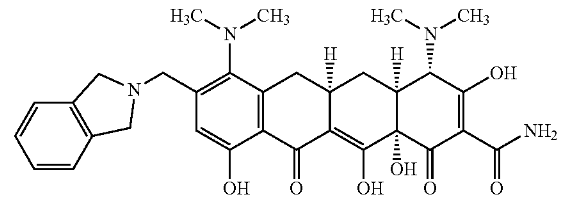

S16-10-160: $^1$H NMR (400 MHz, $CD_3OD$) δ 7.32 (s, 4 H), 6.98 (s, 1 H), 4.76-4.43 (m, 6 H), 4.05 (s, 1 H), 3.01-2.73 (m, 15 H), 2.44-2.36 (m, 1 H), 2.21-2.18 (m, 1 H), 1.62-1.53 (m, 1 H); MS (ESI) m/z 589.0 (M+H).

S16-10-161

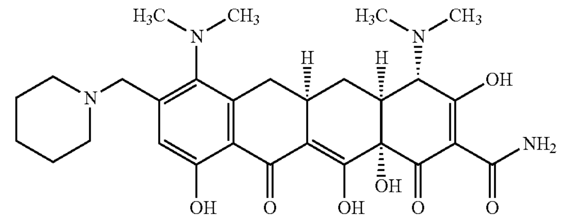

S16-10-161: $^1$H NMR (400 MHz, $CD_3OD$) δ 7.06 (s, 1 H), 4.54-4.47 (m, 1 H), 4.29-4.26 (m, 1 H), 4.14 (s, 1 H), 3.51-

3.44 (m, 2 H), 3.10-2.98 (m, 11 H), 2.89-2.83 (m, 6 H), 2.51-2.43 (m, 1 H), 2.31-2.27 (m, 1 H), 1.97-1.92 (m, 2 H), 1.88-1.81 (m, 3 H), 1.69-1.52 (m, 2 H); MS (ESI) m/z 555.2 (M+H).

S16-10-162

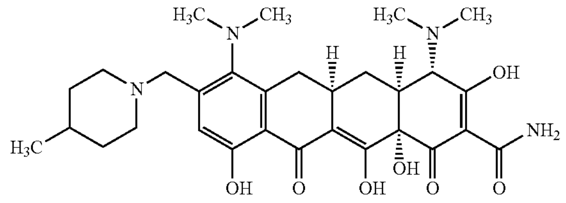

S16-10-162: $^1$H NMR (400 MHz, $CD_3OD$) δ 7.04, 7.03 (s, 1 H, total), 4.50 (d, J=13.2 Hz, 1 H), 4.25 (d, J=13.2 Hz, 1 H), 4.11 (s, 1 H), 3.51-3.42 (m, 2 H), 3.20-2.81 (m, 17 H), 2.49-2.41 (m, 1 H), 2.29-2.25 (m, 1 H), 1.93-1.90 (m, 2 H), 1.73-1.62 (m, 2 H), 1.60-1.42 (m, 2 H), 1.01 (d, J=6.4 Hz, 3 H); MS (ESI) m/z 569.0 (M+H)

S16-10-163

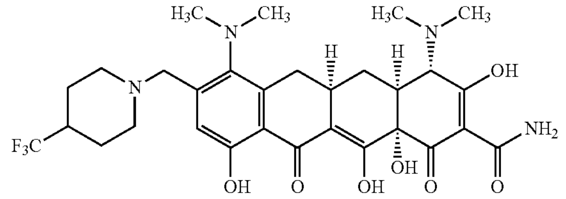

S16-10-163: $^1$H NMR (400 MHz, $CD_3OD$) δ 6.94, 6.93 (s, 1 H, total), 4.40 (d, J=12.8 Hz, 1 H), 4.16 (d, J=13.2 Hz, 1 H), 3.98 (s, 1 H), 3.52-3.49 (m, 1 H), 3.42-3.39 (m, 1 H), 3.07-2.67 (m, 18 H), 2.36-2.28 (m, 1 H), 2.15-2.12 (m, 1 H), 2.02 (m, 2 H), 1.77-1.74 (m, 2 H), 1.55-1.49 (m, 1 H); MS (ESI) m/z 623.0 (M+H).

S16-10-164

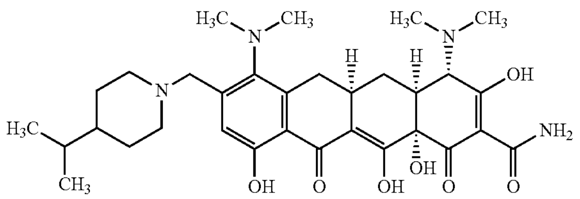

S16-10-164: $^1$H NMR (400 MHz, $CD_3OD$) δ 7.04 (s, 1 H), 4.49 (d, J=13.2 Hz, 1 H), 4.24 (d, J=13.2 Hz, 1 H), 4.12 (s, 1 H), 3.54-3.47 (m, 2 H), 3.05-2.80 (m, 17 H), 2.43-2.38 (m, 1 H), 2.28-2.25 (m, 1 H), 2.01-1.96 (m, 2 H), 1.67-1.64 (m, 1 H), 1.55-1.41 (m, 4 H), 0.99 (d, J=6.8 Hz, 6 H); MS (ESI) m/z 597.3 (M+H).

S16-10-165

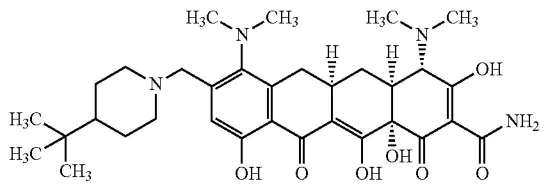

S16-10-165: $^1$H NMR (400 MHz, $CD_3OD$) δ 7.06 (s, 1 H), 4.52, 4.49 (s, 1 H, total), 4.28, 4.24 (s, 1 H, total), 4.13 (s, 1 H), 3.59-3.49 (m, 2 H), 3.41-3.35 (m, 1 H), 3.07-2.82 (m, 16 H), 2.50-2.41 (m, 1 H), 2.30-2.27 (m, 1 H), 2.02-1.98 (m, 2 H), 1.68-1.60 (m, 3 H), 1.46-1.40 (m, 1 H), 0.98 (s, 9 H); MS (ESI) m/z 611.1 (M+H).

S16-10-166

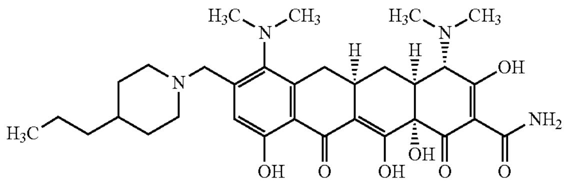

S16-10-166: $^1$H NMR (400 MHz, $CD_3OD$) δ 6.95 (s, 1 H), 4.42 (d, J=13.2 Hz, 1 H), 4.19 (d, J=14.0 Hz, 1 H), 4.03 (s, 1 H), 3.45-3.35 (m, 2 H), 3.05-2.70 (m, 17 H), 2.40-2.29 (m, 1 H), 2.20-2.13 (m, 1 H), 1.93-1.85 (m, 2 H), 1.59-1.50 (m, 2 H), 1.39-1.18 (m, 6 H), 0.88-0.79 (m, 3 H); MS (ESI) m/z 597.1 (M+H).

S16-10-167

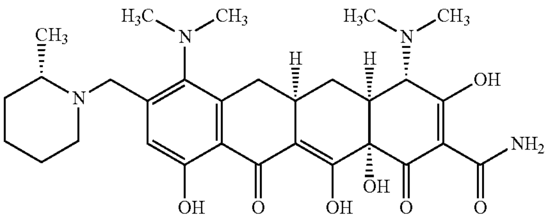

S16-10-167: $^1$H NMR (400 MHz, $CD_3OD$) δ 6.93, 6.89 (s, 1 H, total), 4.52, 4.48, 4.46, 4.41 (s, 1 H, total), 4.27, 4.24, 4.18, 4.14 (s, 1 H, total), 4.01 (s, 1 H), 2.98-2.70 (m, 18 H), 2.43-2.38 (m, 1 H), 2.18-2.13 (m, 1 H), 1.95-1.93 (m, 1 H), 1.80-1.74 (m, 2 H), 1.65-1.58 (m, 4 H), 1.45 (d, J=6.4 Hz, 2 H), 1.39 (d, J=6.8 Hz, 1 H); MS (ESI) m/z 569.1 (M+H).

S16-10-168

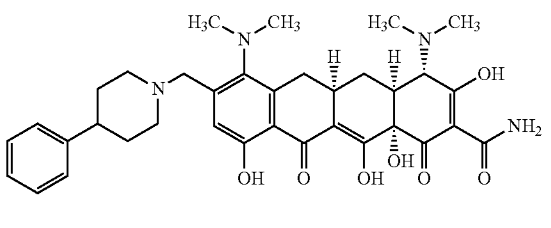

S16-10-168: $^1$H NMR (400 MHz, $CD_3OD$) δ 7.23-7.17 (m, 5 H), 7.02 (s, 1 H), 4.51-4.47 (m, 1 H), 4.26-4.22 (m, 1 H), 4.03 (s, 1 H), 3.58-3.47 (m, 2 H), 3.15-2.75 (m, 17 H), 2.59-2.55 (m, 1 H), 2.42-2.35 (m, 1 H), 2.21-2.18 (m, 1 H), 2.01-1.94 (m, 3 H), 1.62-1.52 (m, 1 H), 1.20-1.18 (m, 1 H); MS (ESI) m/z 631.1 (M+H).

S16-10-169

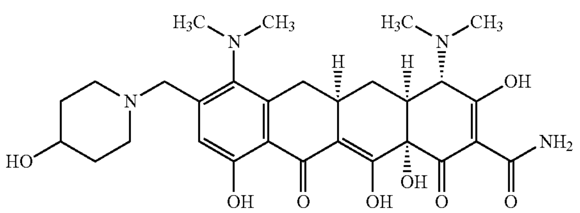

S16-10-169: $^1$H NMR (400 MHz, $CD_3OD$) δ 7.05, 7.04 (s, 1 H, total), 4.56-4.55 (m, 1 H), 4.30-4.23 (m, 1 H), 4.10 (s, 1 H), 4.07, 3.87 (m, 1 H, total), 3.57-3.45 (m, 1 H), 3.38-3.33 (m, 2 H), 3.19-2.81 (m, 15 H), 2.52-2.40 (m, 1 H), 2.29-2.23 (m, 1 H), 2.19-2.13 (m, 1 H), 2.07-2.85 (m, 2 H), 1.79-1.57 (m, 2 H); MS (ESI) m/z 571.0 (M+H).

S16-10-170

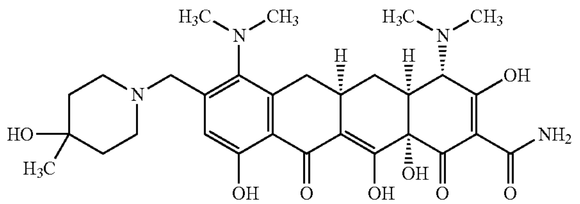

S16-10-170: $^1$H NMR (400 MHz, $CD_3OD$) δ 7.05, 7.03 (s, 1 H total), 4.53 (d, J=13.2 Hz, 1 H), 4.28 (d, J=13.2 Hz, 1 H), 4.11 (s, 1 H), 3.40-3.37 (m, 2 H), 3.16-2.81 (m, 17 H), 2.51-2.43 (m, 1 H), 2.28-2.25 (m, 1 H), 1.90-1.79 (m, 4 H), 1.71-1.61 (m, 1 H), 1.29 (s, 3 H); MS (ESI) m/z 585.1 (M+H).

S16-10-171

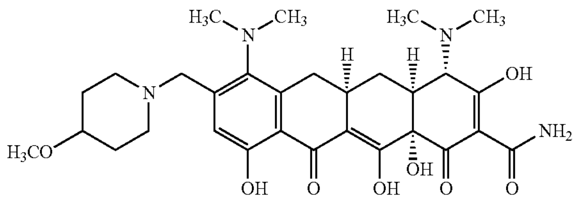

S16-10-171: $^1$H NMR (400 MHz, $CD_3OD$) δ 7.09 (s, 1 H), 4.55-4.51 (m, 1 H), 4.36-4.28 (m, 1 H), 4.14 (s, 1 H), 3.64 (s, 1 H), 3.58-3.51 (m, 1 H), 3.38 (s, 3 H), 3.18-2.84 (m, 15 H), 2.51-2.42 (m, 1 H), 2.31-2.28 (m, 2 H), 2.18-2.13 (m, 1 H), 2.05-1.95 (m, 2 H), 1.78-1.62 (m, 2 H); MS (ESI) m/z 585.1 (M+H).

S16-10-172

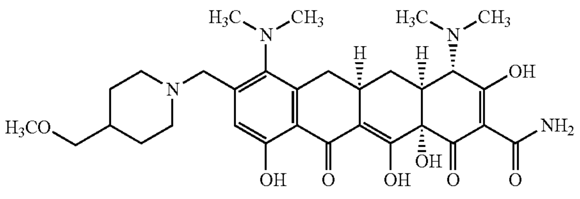

S16-10-172: $^1$H NMR (400 MHz, $CD_3OD$) δ 6.95 (s, 1 H), 4.44-4.40 (m, 1 H), 4.19-4.15 (m, 1 H), 4.03 (s, 1 H), 3.47-3.34 (m, 2 H), 3.23 (s, 3 H), 3.01-2.71 (m, 19 H), 2.41-2.33 (m, 1 H), 2.20-2.17 (m, 1 H), 1.92-1.81 (m, 3 H), 1.61-1.44 (m, 3 H); MS (ESI) m/z 599.3 (M+H).

S16-10-180

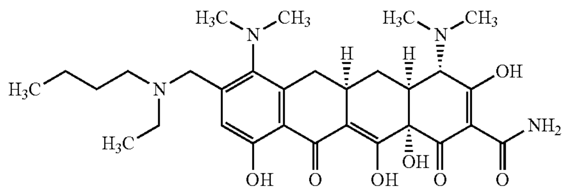

S16-10-180: $^1$H NMR (400 MHz, $CD_3OD$) δ 6.93 (s, 1 H), 4.60 (d, J=13.6 Hz, 1 H), 4.22 (d, J=13.6 Hz, 1 H), 4.09 (s, 1 H), 3.24-2.86 (m, 19 H), 2.52-2.42 (m, 1 H), 2.30-2.20 (m, 1 H), 1.71-1.55 (m, 4 H), 1.41-1.31 (m, 3 H), 1.03-0.99 (m, 6 H); MS (ESI) m/z 571.2 (M+H).

S16-10-174

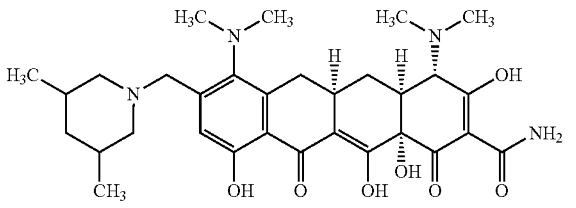

S16-10-174: $^1$H NMR (400 MHz, $CD_3OD$) δ 7.03 (s, 1 H), 4.51 (d, J=13.2 Hz, 1 H), 4.25 (d, J=13.2 Hz, 1 H), 4.11 (s, 1 H), 3.40-3.37 (m, 2 H), 3.05-2.80 (m, 17 H), 2.68-2.57 (m, 2 H), 2.47-2.43 (m, 1 H), 2.28-2.25 (m, 1 H), 1.89-1.85 (m, 2 H), 1.71-1.61 (m, 1 H), 0.99 (d, J=3.6 Hz, 3 H), 0.98 (d, J=3.6 Hz, 3 H); MS (ESI) m/z 583.3 (M+H).

S16-10-175

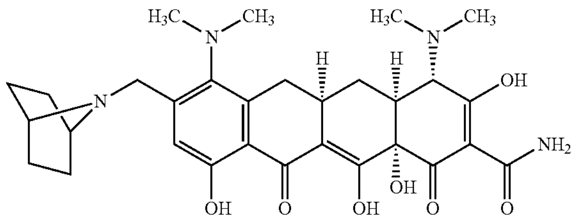

S16-10-175: $^1$H NMR (400 MHz, $CD_3OD$) δ 7.06 (s, 1 H), 4.87 (d, J=20.0 Hz, 1 H), 4.17 (d, J=13.6 Hz, 1 H), 4.13-4.11 (m, 2 H), 4.09 (s, 1 H), 3.09-2.80 (m, 15 H), 2.51-2.40 (m, 1 H), 2.31-2.23 (m, 3 H), 2.18-2.10 (m, 2 H), 1.92-1.85 (m, 4 H), 1.58-1.53 (m, 1 H); MS (ESI) m/z 567.1 (M+H).

S16-10-176

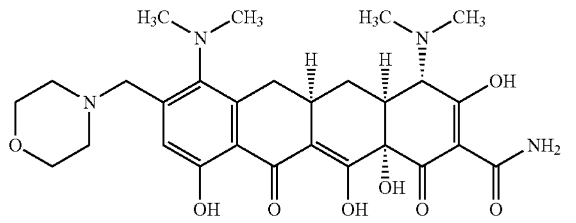

S16-10-176: $^{1}$H NMR (400 MHz, $CD_3OD$) δ 7.07 (s, 1 H), 4.56 (d, J=13.2 Hz, 1 H), 4.30 (d, J=13.2 Hz, 1 H), 4.11 (s, 1 H), 4.05-4.00 (m, 2 H), 3.90-3.76 (m, 2 H), 3.42-3.30 (m, 2 H), 3.24-3.16 (m, 2 H), 3.07-2.84 (m, 15 H), 2.52-2.41 (m, 1 H), 2.29-2.25 (m, 1 H), 1.68-1.58 (m, 1 H); MS (ESI) m/z 557.1 (M+H).

S16-10-177

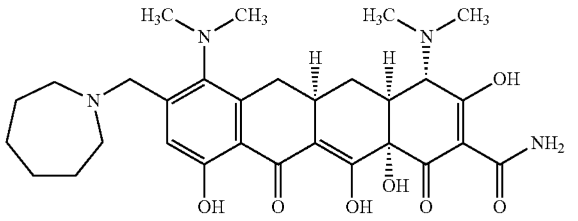

S16-10-177: $^{1}$H NMR (400 MHz, $CD_3OD$) δ 7.03 (s, 1 H), 4.61, 4.58 (s, 1 H, total), 4.33, 4.30 (s, 1 H, total), 4.13 (s, 1 H), 3.53-3.49 (m, 2 H), 3.29-3.26 (m, 2 H), 3.09-2.85 (m, 15 H), 2.49-2.41 (m, 1 H), 2.32-2.27 (m, 1 H), 2.09-1.95 (m, 2 H), 1.95-1.83 (m, 2 H)□ 1.68-1.65 (m, 4 H), 1.65-1.60 (m, 1 H); MS (ESI) m/z 569 (M+H).

S16-10-178

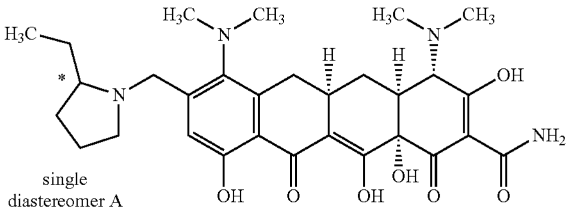

single diastereomer A

S16-10-178: $^{1}$H NMR (400 MHz, $CD_3OD$) δ 6.97 (s, 1 H), 4.73-4.70 (m, 2 H), 4.10 (s, 1 H), 3.52-3.43 (m, 2 H), 3.09-2.72 (m, 16 H), 2.47-2.33 (m, 2 H), 2.29-2.21 (m, 1 H), 2.17-1.98 (m, 3 H), 1.86-1.75 (m, 1 H), 1.63-1.49 (m, 2 H), 1.05 (t, J=7.2 Hz, 3 H); MS (ESI) m/z 569.1 (M+H).

S16-10-179

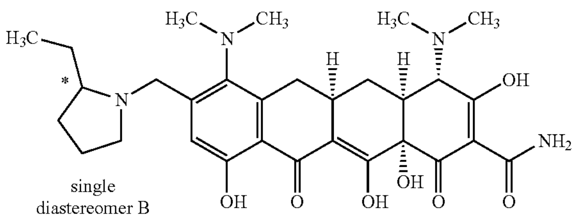

single diastereomer B

S16-10-179: $^{1}$H NMR (400 MHz, $CD_3OD$) δ 7.02 (s, 1 H), 4.51, 4.49 (s, 1 H, total), 4.44, 4.41 (s, 1 H, total), 4.13 (s, 1 H), 3.55-3.49 (m, 2 H), 3.06-2.81 (m, 16 H), 2.46-2.41 (m, 2 H), 2.30-2.25 (m, 1 H), 2.19-2.01 (m, 3 H), 1.85-1.79 (m, 1 H), 1.70-1.6 (m, 1 H), 1.02 (t, J=7.2 Hz, 3H); MS (ESI) m/z 569.1 (M+H).

EXAMPLE 17

Synthesis of Compounds Via Scheme 17

Scheme 17

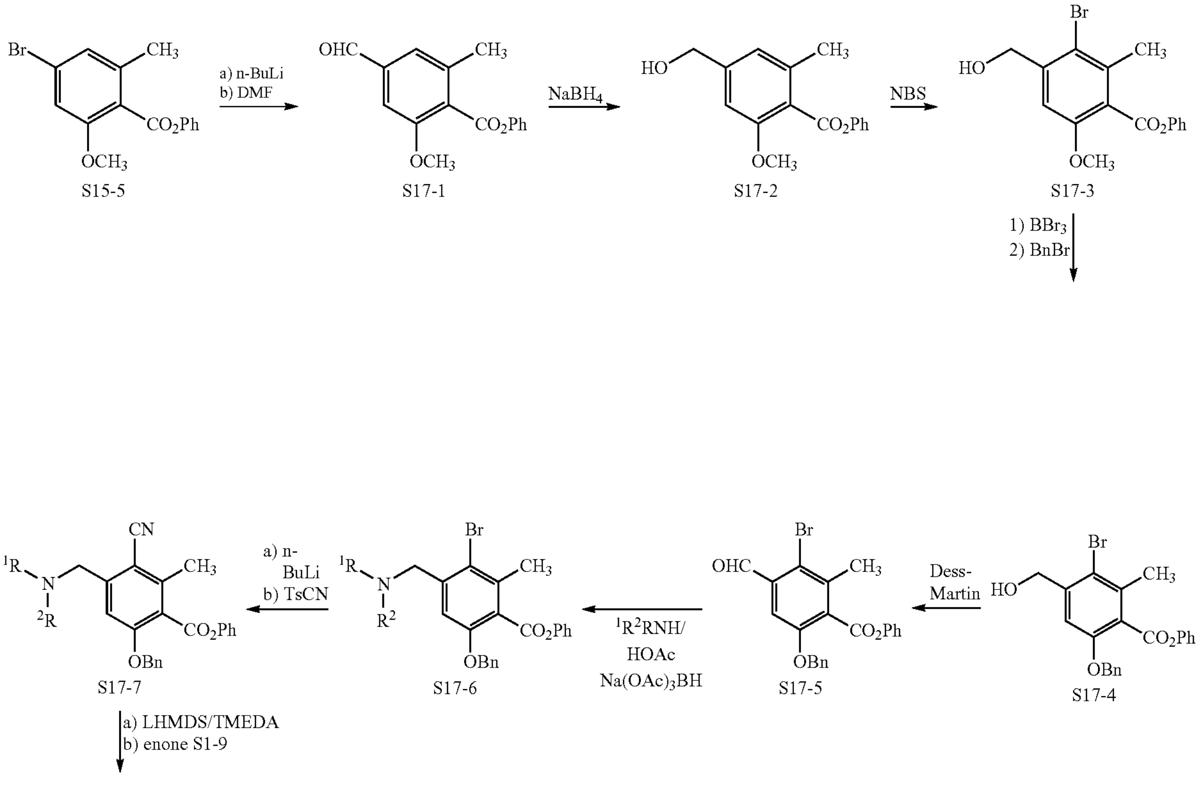

-continued

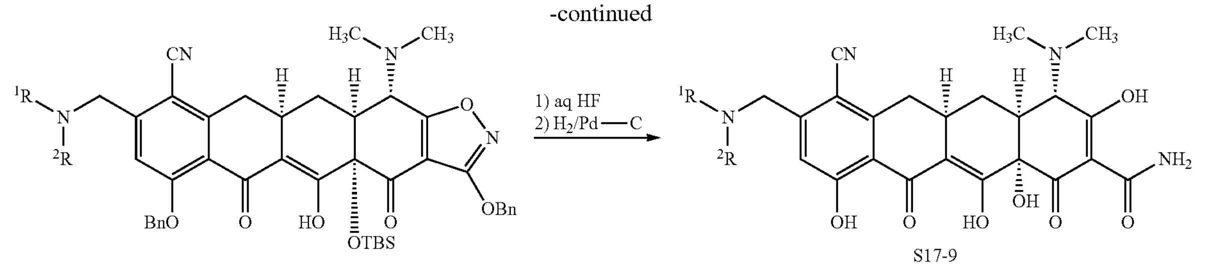

S17-8

S17-9

The following compounds were prepared according to Scheme 17.

S17-1

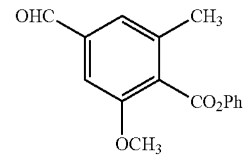

n-BuLi (5.0 mL, 1.62 M/hexanes, 8.12 mmol, 1.3 equiv) was added dropwise to a THF solution (30 mL) of S15-5 (2.0 g, 6.24 mmol, 1.0 equiv) at −100° C. The reaction was stirred at −100° C. for 1 min. DMF (2.0 mL, 25.00 mmol, 4.0 equiv) was added. The reaction was allowed to warm to −78° C. and stirred at −78° C. for 1 h. The reaction mixture was further warmed to 0° C. and quenched by saturated aqueous $NH_4Cl$. The resulting mixture was extracted with EtOAc. The combined EtOAc extracts were dried (sodium sulfate) and concentrated to give crude S17-1.

S17-2

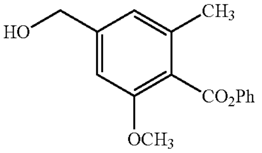

$NaBH_4$ (0.28 g, 7.40 mmol, 1.2 equiv) was added to a solution of crude S17-1 (6.24 mmol, 1.0 equiv) in MeOH (15 mL) at 0° C. The reaction was stirred at 0° C. for 30 min and quenched by $H_2O$. The resulting mixture was extracted with EtOAc. The combined EtOAc extracts were dried (sodium sulfate) and concentrated to give crude S17-2.

S17-3

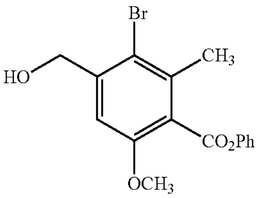

N-Bromosuccinimide (1.32 g, 7.44 mmol, 1.2 equiv) was added to a solution of crude S17-2 (6.24 mmol, 1.0 equiv) in dichloromethane (20 mL). The reaction was stirred at 25° C. for 2 hrs. Saturated aqueous $Na_2SO_3$ was added to the reaction. The resulting mixture was extracted with dichloromethane. The combined dichloromethane extracts were dried (sodium sulfate) and concentrated to give the crude S17-3.

S17-4

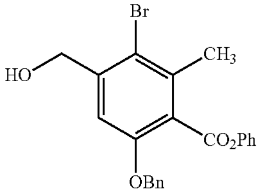

$BBr_3$ (13.4 mL, 1.0 M/dichloromethane, 13.40 mmol, 2.0 equiv) was added to a solution of S17-3 dichloromethane (20 mL) at −78° C. The reaction was stirred from −78° C. to 25° C. for 1.5 hrs, quenched by saturated aqueous $NaHCO_3$ and concentrated under reduced pressure to remove most of the dichloromethane. EtOAc and $H_2O$ were added to the residue. The aqueous layer was extracted with EtOAc. The combined EtOAc extracts were dried (sodium sulfate) and concentrated to yield crude phenol.

Potassium carbonate (1.7 g, 12.40 mmol, 2.0 equiv) and benzylbromide (1.5 mL, 12.40 mmol, 2.0 equiv) were added to a solution of the above crude phenol in acetone at 25° C. The reaction was stirred at 25° C. for 12 hrs. The reaction mixture was concentrated and the residue was redissolved in $H_2O$ and EtOAc. The aqueous layer was extracted with EtOAc. The combined organic layers were dried (sodium sulfate) and concentrated to give crude S17-4. Flash chromatography on silica gel (10:1 to 3:1 hexanes/EtOAc) yielded 1.97 g of compound S-17-4 (72% for 5 steps).

S17-5

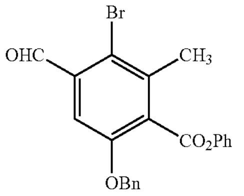

Dess-Martin periodinane (0.18 g, 0.42 mmol, 1.2 equiv) was added to a solution of S17-4 (0.15 g, 0.35 mmol, 1.0 equiv) in dichloromethane (2 mL) at 25° C. The reaction was stirred at 25° C. for 30 min and diluted with $H_2O$. The resulting mixture was extracted with dichloromethane. The combined dichloromethane extracts were dried (sodium sulfate) and concentrated to give crude S17-5.

S17-6-1

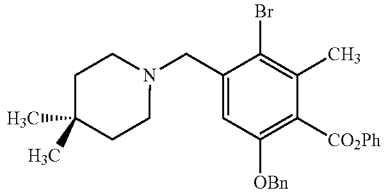

4,4-Dimethylpiperidine hydrochloride (0.11 g, 0.70 mmol, 2.0 equiv) and $Et_3N$ (96 μL, 0.70 mmol, 2.0 equiv) were added to a solution of crude S17-5 (0.35 mmol, 1.0 equiv) in dichloromethane at 25° C. The reaction was stirred at 25° C. for 15 min. $Na(OAc)_3BH$ (0.22 g, 1.05 mmol, 3.0 equiv) and HOAc (0.1 mL) were added to the reaction. The reaction was stirred at 25° C. for 1 h and quenched by $H_2O$. The resulting mixture was extracted with dichloromethane. The combined dichloromethane extracts were dried (sodium sulfate) and concentrated under reduced pressure. Flash chromatography on silica gel (10:1 to 4:1 hexanes/EtOAc) yielded 95 mg of compound S17-6-1 (52% for 2 steps).

S17-7-1

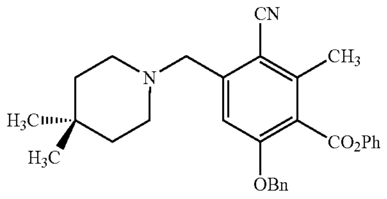

n-BuLi (0.55 mL, 1.6 M/hexanes, 0.88 mmol, 1.4 equiv) was added dropwise to a solution of S17-6-1 (0.33 g, 0.63 mmol, 1.0 equiv) in THF (2 mL) at −100° C. The reaction was stirred at −100° C. for 1 min. TsCN (0.36 g, 1.89 mmol, 3.0 equiv) was added to the reaction mixture. The reaction was allowed to warm to −78° C. and stirred at −78° C. for 1 h. The reaction mixture was further warmed to 0° C. and quenched by saturated aqueous $NH_4Cl$. The resulting mixture was extracted with EtOAc. The combined EtOAc extracts were dried (sodium sulfate) and concentrated under reduced pressure. Flash chromatography on silica gel (4:1 hexanes/EtOAc) yielded 28 mg of compound S17-7-1 (10%).

S17-8-1

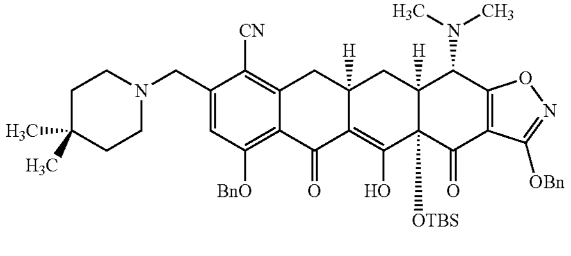

LHMDS (0.24 mL, 1.0 M/THF, 0.24 mmol, 4.0 equiv) was added to a solution of S17-7-1 (28 mg, 0.060 mmol, 1.2 equiv), TMEDA (54 μL, 0.36 mmol, 7.2 equiv) and enone S1-9 (23 mg, 0.050 mmol, 1.0 equiv) in THF (1 mL) at −78° C. The reaction was stirred at −78° C. for 30 min, allowed to warm to 25° C. over 1 h, quenched by saturated $NH_4Cl$ solution, and extracted with EtOAc. The combined EtOAc extracts were dried (sodium sulfate) and concentrated under reduced pressure. The crude product was purified by preparative reverse phase HPLC on a Waters Autopurification system using a Sunfire Prep C18 OBD column [5 μm, 19×50 mm; flow rate, 20 mL/min; Solvent A: $H_2O$ with 0.1% $HCO_2H$; Solvent B: $CH_3CN$ with 0.1% $HCO_2H$; injection volume: 4.0 mL ($CH_3CN$); gradient: 50→100% B over 15 min; mass-directed fraction collection]. Fractions containing the desired product were collected and concentrated at 25° C. to remove most of the acetonitrile. The resulting aqueous solution was extracted with EtOAc. The combined EtOAc extracts were dried (sodium sulfate) and concentrated to give 8 mg of S17-8-1 (16%).

S17-9-1

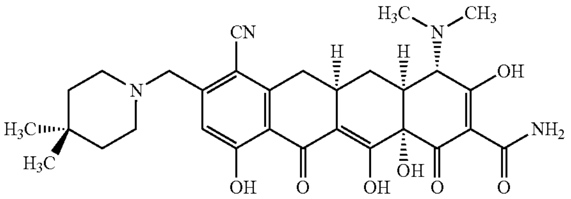

Aqueous HF (0.3 mL, 48-50%) was added to a solution of S17-8-1 (8 mg, 0.0093 mmol) in acetonitrile (2 mL) in a polypropylene tube at 25° C. The reaction was stirred at 25° C. for 18 hrs. The resulting mixture was poured into an aqueous solution of $K_2HPO_4$ (2 g, dissolved in 15 mL water) and extracted with EtOAc. The combined EtOAc extracts were dried (sodium sulfate) and concentrated to yield the crude desilylated intermediate.

Pd—C (8 mg, 10 wt %) was added to a solution of the above crude product in HCl/MeOH (2 mL, 0.5 N). The reaction was purged with hydrogen and stirred under $H_2$ (balloon) at 25° C. for 4 hrs. The reaction mixture was filtered through a small Celite plug. The filtrate was concentrated to yield the crude product, which was Purified by preparative reverse phase HPLC on a Waters Autopurification system using a Phenomenex Polymerx 10μ RP-γ 100A column [10 μm, 150×21.20 mm; flow rate, 20 mL/min; Solvent A: 0.05 N HCl/water; Solvent B: $CH_3CN$; injection volume: 4.0 mL (0.05 N HCl/water); gradient: 0→70% B over 7 min, 70→100% over 3 min, and 100% over 5 min; mass-directed fraction collection]. Fractions containing the desired product were collected and freeze-dried to yield 1 mg of compound S17-9-1: $^1H$ NMR (400 MHz, $CD_3OD$) δ 7.28 (s, 1 H), 4.52 (s, 2 H), 4.12 (s, 1 H), 3.52-3.40 (m, 2 H), 3.20-2.93 (m, 5 H), 3.04 (s, 3 H), 2.95 (s, 3 H), 2.78-2.67 (m, 1 H), 2.30-2.23 (m, 1 H), 1.80-1.58 (m, 5 H), 1.11 (s, 3 H), 1.04 (s, 3 H); MS (ESI) m/z 565.23 (M+H).

The following compound was prepared similarly to S17-9-1.

S17-9-2
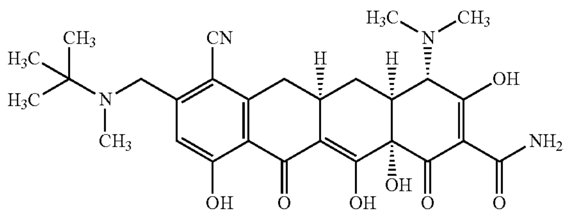
S17-9-2: $^1H$ NMR (400 MHz, $CD_3OD$) δ7.28 (s, 1 H), 4.16 (s, 1 H), 4.13 (s, 1 H), 3.24-2.90 (m, 3 H), 3.05 (s, 3 H), 2.96 (m, 3 H), 2.78 (m, 3 H), 2.83-2.66 (m, 1 H), 2.32-2.24 (m, 1 H), 1.74-1.60 (m, 1 H), 1.58 (s, 9 H); MS (ESI) m/z 539.25 (M+H).
EXAMPLE 18
Synthesis of Compounds Via Scheme 18
Scheme 18
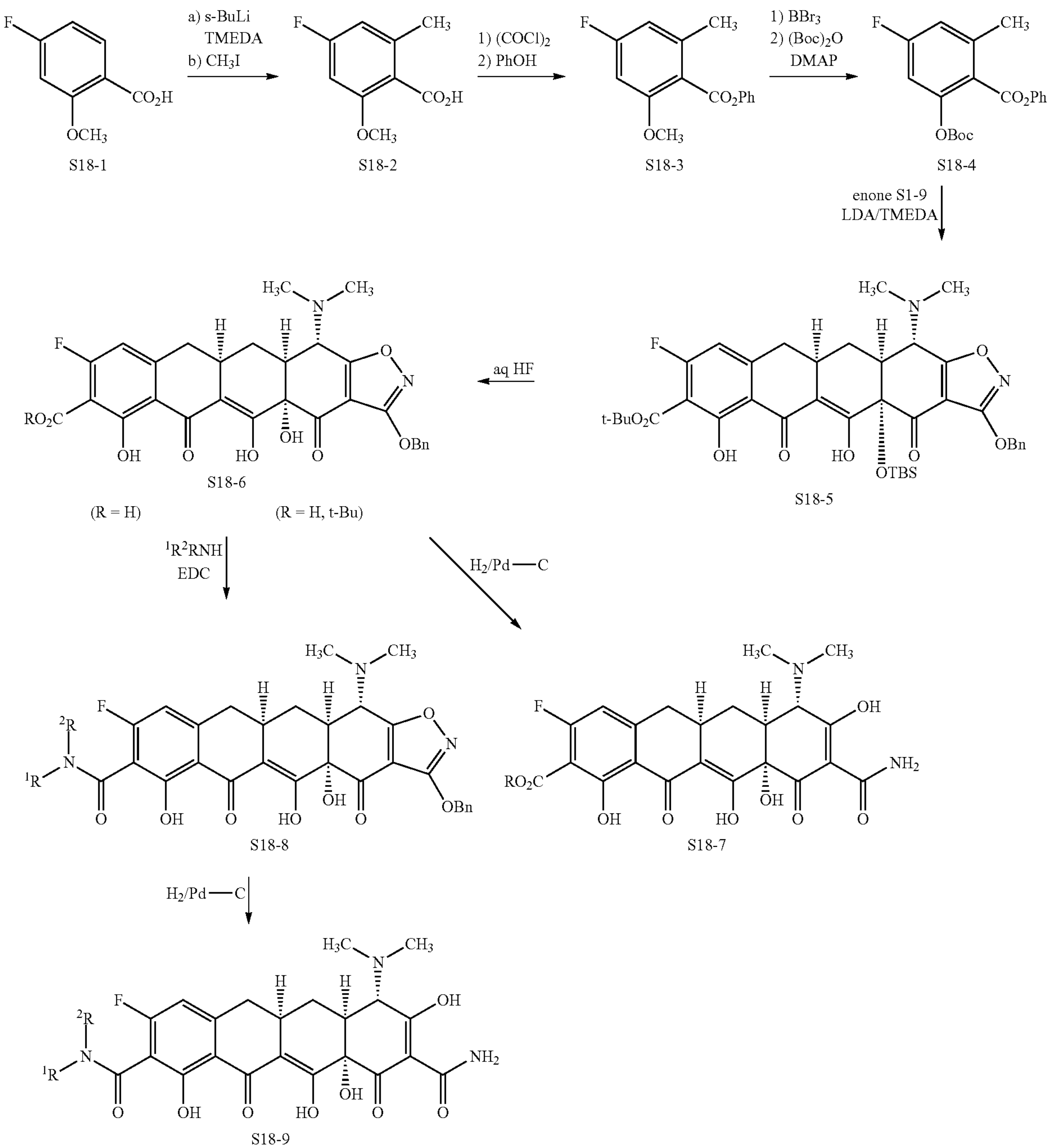

The following compounds were prepared according to Scheme 18.

S18-2

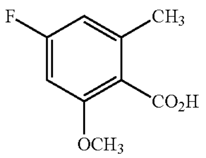

A solution of benzoic acid S18-1 (17.51 g, 102.90 mmol, 1.0 equiv) in THF (150 mL) was added dropwise to a solution of s-BuLi (161.70 mL, 1.4 M/cyclohexane, 226.40 mmol, 2.2 equiv) and TMEDA (34.00 mL, 226.40 mmol, 2.2 equiv) in THF (150 mL) at −78° C. via a cannula over 1 h 30 min. The resulting orange reaction mixture was stirred at −78° C. for 2 hrs. Iodomethane (8.38 mL, 134.30 mmol, 5.0 equiv) was added at −78° C. while manually shaking the reaction mixture. The dry-ice/acetone bath was removed, and the resulting white suspension was then stirred at rt for 30 min. Water (150 mL) was added. The resulting purple mixture was concentrated to remove most of the THF and other organic volatiles. Aqueous NaOH (6 M, 100 mL) was added. The mixture was extracted with methyl t-butyl ether (2×200 mL). The aqueous layer was acidified with aqueous HCl (170 mL, 6 N) to pH 1, and extracted with EtOAc (150 mL, then 2×80 mL). The combined organic phase was dried over magnesium sulfate, filtered and concentrated to afford the crude product as an orange solid (15.03 g, containing the desired product S18-2, the regioisomer (i.e. 2-methoxy-3-methyl-4-fluoro benzoic acid) and starting material S18-1 at a ratio of 1.7:3:0.9 as indicated by $^1$H NMR analysis).

S18-3

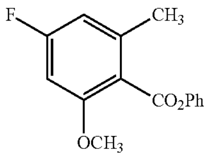

The above crude product was dissolved in dichloromethane (50 mL). Oxalyl chloride (2.66 mL, 30.44 mmol, 1.1 equiv) was added at rt followed by a couple of drops of DMF. The mixture was stirred at rt for 1 h and the solvent was evaporated. The residue was dried under high vacuum. The resulting orange oil was re-dissolved in dichloromethane (50 mL). Phenol (2.86 g, 30.44 mmol, 1.1 equiv), triethylamine (7.70 mL, 55.35 mmol, 2.0 equiv), and DMAP (catalytic amount) were added. The reaction mixture was stirred at rt for 1 h. Solvents were evaporated and the residue was dissolved in EtOAc (150 mL) and water (50 mL). The organic layer was washed with aqueous HCl (50 mL, 1 N), 1 N aqueous NaOH (2×30 mL) and brine (50 mL), dried over anhydrous magnesium sulfate, filtered and concentrated. The residue was purified by flash column chromatography (1-4% EtOAc/hexanes) to afford the desired product S18-3 as a yellow solid (2.73 g, 41% over five steps): $^1$H NMR (400 MHz, $CDCl_3$) δ 7.45-7.41 (m, 2 H), 7.29-7.22 (m, 3 H), 6.59-6.53 (m, 2 H), 3.87 (s, 3 H), 2.43 (s, 3 H); MS (ESI) m/z 259.15 (M+H).

S18-4

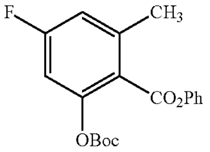

A solution of $BBr_3$ in dichloromethane (10.49 mL, 1.0 M, 10.49 mmol, 1.0 equiv) was added slowly to a solution of the above compound S18-3 (2.73 g, 10.49 mmol, 1.0 equiv) in dichloromethane (50 mL) at −78° C. The resulting orange solution was stirred at −78° C. for 10 min and then at 0° C. for 15 min. Saturated aqueous $NaHCO_3$ (30 mL) was added slowly. The resulting mixture was stirred at rt for 5 min and the dichloromethane was evaporated. The residue was extracted with EtOAc (80 mL, then 30 mL). The organic extracts were combined, dried over anhydrous magnesium sulfate, filtered, and concentrated to afford an orange solid, which was used directly in the next reaction.

Di-t-butyl dicarbonate (2.40 g, 11.01 mmol, 1.05 equiv) and N,N-dimethylaminopyridine (catalytic amount) were added to a solution of the above product in dichloromethane (50 mL). The reaction was stirred for 40 min at rt (monitored by LC-MS and TLC (product is slightly more polar)), and concentrated. The residue was purified by flash column chromatography (1-5% EtOAc/hexanes containing 10% dichloromethane) to afford product S18-4 as a white solid (3.45 g, 95% for two steps): $^1$H NMR (400 MHz, $CDCl_3$) δ 7.46-7.42 (m, 2 H), 7.31-7.24 (m, 3 H), 6.94-6.88 (m, 2 H), 2.54 (s, 3 H), 1.45 (s, 9 H); MS (ESI) m/z 345.25 (M+H).

S18-5

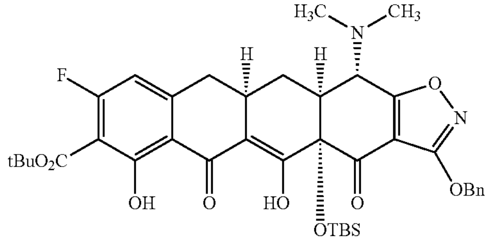

A solution of ester S18-4 (0.50 g, 1.45 mmol, 1.0 equiv) in THF (2.5 mL) was added to a solution of LDA (1.87 mL, 1.55 M/THF/heptane/ethylbenzene, 2.90 mmol, 2.0 equiv) and TMEDA (0.44 mL, 2.90 mmol, 2.0 equiv) in THF (20 mL) via a cannula. The reaction mixture was stirred at −78° C. for 15 min. A solution of enone S1-9 (0.49 g, 1.01 mmol, 0.7 equiv) in THF (2.5 mL) was added to the reaction mixture via a cannula. The reaction mixture was then allowed to warm to 0° C. over 1 h, quenched by saturated aqueous $NH_4Cl$, and extracted with EtOAc (70 mL). The combined organic extracts were dried (sodium sulfate), filtered and concentrated. The residue was purified by flash column chromatography (5-10% EtOAc/hexanes) to yield the desired product S18-5 (0.28 g, 37%): $^1$H NMR (400 MHz, $CDCl_3$) δ 13.97 (br s, 1 H), 7.49-7.47 (m, 2 H), 7.39-7.32 (m, 3 H), 6.44 (d, J=9.2 Hz, 1 H), 5.35 (s, 2 H), 3.86 (d, J=10.4 Hz, 1 H), 3.08-3.00 (m, 1 H), 2.94-2.90 (m, 1 H), 2.81-2.73 (m, 1 H), 2.46-2.41 (m, 9 H), 1.56 (s, 9 H), 0.83 (s, 9 H), 0.27 (s, 3 H), 0.12 (s, 3 H); MS (ESI) m/z 735.41 (M+H). Some unreacted enone S1-9 (0.17 g) was also recovered.

S18-6-1

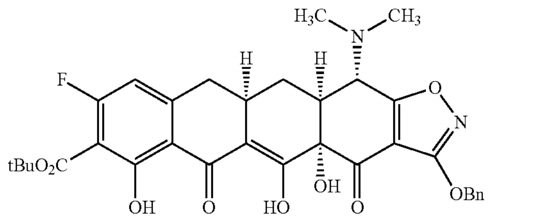

S18-6-2

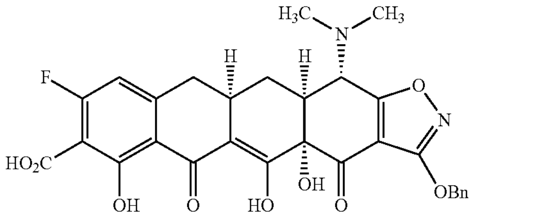

Aqueous HF (48-50%, 0.4 mL) was added to a solution of compound S18-5 (0.28 g, 0.37 mmol) in acetonitrile (1.2 mL) in a polypropylene reaction vessel at 23° C. The resulting mixture was stirred vigorously at 23° C. overnight and poured into aqueous $K_2HPO_4$ (4.8 g dissolved in 30 mL water). The mixture was extracted with 5% MeOH in EtOAc (4×60 mL). The combined organic extracts were dried over anhydrous sodium sulfate, filtered, and concentrated. The residue was purified by preparative reverse phase HPLC on a Waters Autopurification system using a Sunfire Prep C18 OBD column [5 μm, 19×50 mm; flow rate, 20 mL/min; Solvent A: $H_2O$ with 0.1% $HCO_2H$; Solvent B: $CH_3CN$ with 0.1% $HCO_2H$; injection volume: 3.0 mL ($CH_3CN$); gradient: 0→100% B in A over 10 min; mass-directed fraction collection] to yield S18-6-1 and S18-6-2.

S18-6-1 (54 mg, 23%): $^1H$ NMR (400 MHz, $CD_3OD$) δ 14.49 (br s, 1 H), 12.45 (br s, 1 H), 7.46-7.41 (m, 2 H), 7.38-7.30 (m, 3 H), 6.37 (d, J=9.2 Hz, 1 H), 5.34 (s, 2 H), 3.78 (br s, 1 H), 2.96-2.93 (m, 2 H), 2.72-2.67 (m, 1 H), 2.61-2.46 (m, 7 H), 2.05-2.02 (m, 1 H), 1.56 (s, 9 H); MS (ESI) m/z 621.19 (M+H).

S18-6-2 (0.16 g, 77%): $^1H$ NMR (400 MHz, $CD_3OD$) δ 7.40-7.38 (m, 2 H), 7.32-7.26 (m, 3 H), 6.53 (d, J=9.6 Hz, 1 H), 5.32, 5.28 (Abq, J=11.9 Hz, 2 H), 3.35-3.31 (m, 1 H), 3.25-2.98 (m, 9 H), 2.76-2.71 (m, 1 H), 2.44 (t, J=14.6 Hz, 1 H), 2.06-2.02 (m, 1 H); MS (ESI) m/z 565.18 (M+H).

S18-7-1

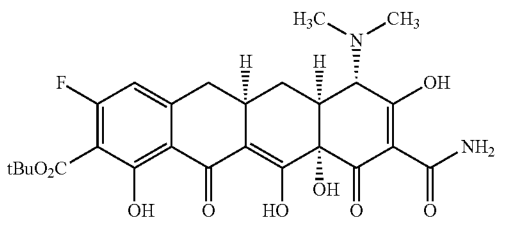

Pd—C (10 wt %, 15 mg) was added in one portion into a solution of compound S18-6-1 (54 mg, 0.087 mmol) in a mixture of MeOH (3 mL) and dioxane (0.5 mL) at 23° C. The reaction vessel was sealed and purged with hydrogen by briefly evacuating the flask followed by flushing with hydrogen gas (1 atm). The resulting mixture was stirred at 23° C. for 50 min. The reaction mixture was then filtered through a small Celite pad. The filtrate was concentrated. The residue was purified by preparative reverse phase HPLC on a Waters Autopurification system using a Phenomenex Polymerx 10μ RP-γ 100A column [10 μm, 150×21.20 mm; flow rate, 20 mL/min; Solvent A: 0.05 N HCl/water; Solvent B: $CH_3CN$; injection volume: 3.0 mL (0.05 N HCl/water); gradient: 20→80% B over 10 min; mass-directed fraction collection]. Fractions containing the desired product, eluting at 6.7-7.6 min, were collected and freeze-dried to yield compound S18-7-1 (29 mg, 59%): $^1H$ NMR (400 MHz, $CD_3OD$) δ 6.62 (d, J=9.6 Hz, 1 H), 4.09 (s, 1 H), 3.07-2.94 (m, 8 H), 2.90-2.85 (m, 1 H), 2.57 (t, J=14.6 Hz, 1 H), 2.21-2.16 (m, 1 H), 1.61-1.57 (m, 1 H), 1.57 (s, 9 H); MS (ESI) m/z 533.25 (M+H).

Compound S18-7-2 was prepared similarly.

S18-7-2

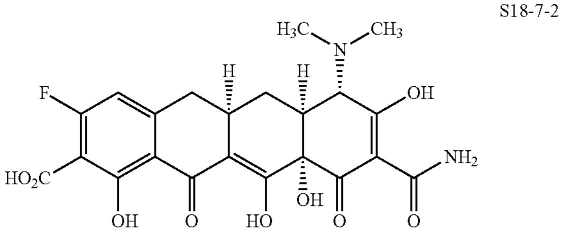 [SMILES: CN(C)[C@@H]1C(O)=C(C(N)=O)C(=O)[C@@]2(O)C(O)=C3C(=O)c4c(cc(F)c(C(=O)O)c4O)C[C@H]3C[C@@H]12]

S18-7-2: $^1H$ NMR (400 MHz, $CD_3OD$) δ 6.65 (d, J=10.1 Hz, 1 H), 4.09 (s, 1 H), 3.10-2.94 (m, 8 H), 2.89 (dd, J=4.1, 15.6 Hz, 1 H), 2.58 (t, J=14.6 Hz, 1 H), 2.22-2.17 (m, 1 H), 1.63-1.54 (m, 1 H); MS (ESI) m/z 477.16 (M+H).

S18-8-1

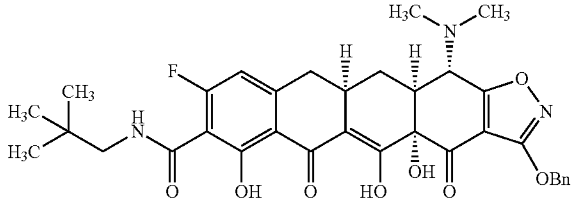

A mixture of compound S18-6-2 (27 mg, 0.048 mmol, 1.0 equiv), EDC (18 mg, 0.095 mmol, 2.0 equiv) and HOBt (3 mg, 0.024 mmol, 0.5 equiv) were dissolved in DMF (0.5 mL). Neopentylamine (11 μL, 0.095 mmol, 2.0 equiv) was added. The reaction mixture was stirred at rt overnight and filtered through a cotton plug. The cotton plug was washed with acetonitrile (1 mL). The filtrate was purified by preparative reverse phase HPLC on a Waters Autopurification system using a Sunfire Prep C18 OBD column [5 μm, 19×50 mm; flow rate, 20 mL/min; Solvent A: $H_2O$ with 0.1% $HCO_2H$; Solvent B: $CH_3CN$ with 0.1% $HCO_2H$; injection volume: 3.0 mL ($CH_3CN$); gradient: 0→60% B in A over 10 min; mass-directed fraction collection]. Fractions containing the desired product, eluting at 7.8-8.7 min, were collected and freeze-dried to yield compound S18-8-1 (14 mg, 46%): $^1H$ NMR (400 MHz, $CDCl_3$) δ 7.50-7.47 (m, 2 H), 7.42-7.36 (m, 3 H), 6.62 (d, J=9.6 Hz, 1 H), 5.42, 5.38 (Abq, J=11.9 Hz, 2 H), 4.82 (d, J=1.4 Hz, 1 H), 3.41-3.38 (m, 1 H), 3.20-3.16 (m, 2 H), 3.16 (s, 3 H), 3.09-3.01 (m, 1 H), 2.83 (dd, J=4.1, 15.6 Hz, 1 H), 2.54 (t, J=14.6 Hz, 1 H), 2.13-2.08 (m, 1 H), 1.42-1.32 (m, 1 H), 0.98 (s, 9 H); MS (ESI) m/z 634.26 (M+H).

S18-9-1

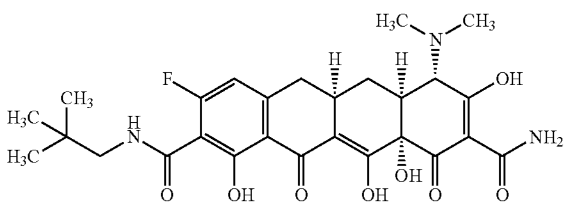

Pd—C (10 wt %, 5 mg) was added in one portion into a solution of compound S18-8-1 (14 mg, 0.022 mmol) in MeOH (3 mL) at 23° C. The reaction vessel was sealed and purged with hydrogen by briefly evacuating the flask followed by flushing with hydrogen gas (1 atm). The reaction mixture was stirred at 23° C. for 30 min. The reaction mixture was then filtered through a small Celite pad. The filtrate was concentrated. The residue was purified by preparative reverse phase HPLC on a Waters Autopurification system using a Phenomenex Polymerx 10μ RP-γ 100A column [10 μm, 150×21.20 mm; flow rate, 20 mL/min; Solvent A: 0.05 N HCl/water; Solvent B: $CH_3CN$; injection volume: 3.0 mL (0.05 N HCl/water); gradient: 15→70% B over 10 min; mass-directed fraction collection]. Fractions containing the desired product, eluting at 7.1-8.8 min, were collected and freeze-dried to yield compound S18-9-1 (8 mg, 64%): $^1H$ NMR (400 MHz, $CD_3OD$) δ 6.64 (d, J=9.2 Hz, 1 H), 4.08 (s, 1 H), 3.18 (s, 2 H), 3.10-2.95 (m, 8 H), 2.91-2.86 (m, 1 H), 2.57 (t, J=14.6 Hz, 1 H), 2.20-2.17 (m, 1 H), 1.63-1.54 (m, 1 H), 0.98 (s, 9 H); MS (ESI) m/z 546.23 (M+H).

The following compounds were prepared similarly to S18-8-1 or S18-9-1.

S18-8-2

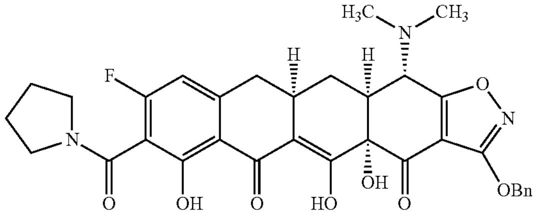

S18-8-2: $^1H$ NMR (400 MHz, $CDCl_3$) δ 7.49-7.47 (m, 2 H), 7.42-7.36 (m, 3 H), 6.66 (d, J=9.6 Hz, 1 H), 5.42, 5.38 (Abq, J=11.9 Hz, 2 H), 4.81 (d, J=1.4 Hz, 1 H), 3.60 (t, J=6.9 Hz, 2 H), 3.41-3.32 (m, 3 H), 3.16 (s, 6 H), 3.11-3.02 (m, 1 H), 2.83 (dd, J=4.1, 15.6 Hz, 1 H), 2.56 (t, J=15.1 Hz, 1 H), 2.11-2.07 (m, 1 H), 2.03-1.90 (m, 4 H), 1.43-1.33 (m, 1 H); MS (ESI) m/z 618.26 (M+H).

S18-9-2

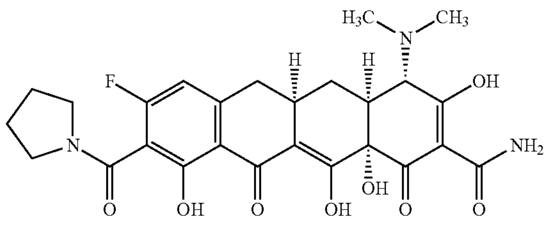

S18-9-2: $^1H$ NMR (400 MHz, $CD_3OD$) δ 6.69 (d, J=9.2 Hz, 1 H), 4.10 (s, 1 H), 3.60 (t, J=6.6 Hz, 2 H), 3.47-3.30 (m, 2 H), 3.12-2.89 (m, 2.58 (t, J=14.6 Hz, 1 H), 2.22-2.18 (m, 1 H), 2.02-1.93 (m, 4 H), 1.63-1.54 (m, 1 H); MS (ESI) m/z 530.20 (M+H).

S18-8-3

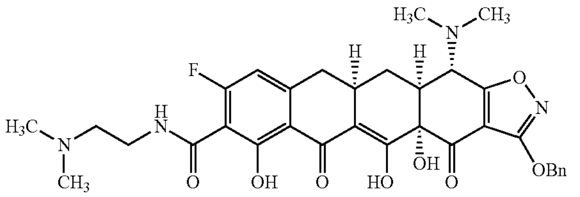

S18-8-3: $^1H$ NMR (400 MHz, $CDCl_3$) δ 7.46-7.44 (m, 2 H), 7.38-7.32 (m, 3 H), 6.43 (d, J=9.8 Hz, 1 H), 5.33 (s, 2 H), 4.20 (br s, 1 H), 3.81-3.80 (m, 2 H), 3.30-3.29 (m, 2 H), 3.09-3.06 (m, 2 H), 2.85-2.82 (m, 16 H), 2.71-2.68 (m, 1 H), 2.48-2.44 (m, 1 H), 2.14-2.10 (m, 1 H), 1.34-1.28 (m, 1 H); MS (ESI) m/z 635.27 (M+H).

S18-9-3

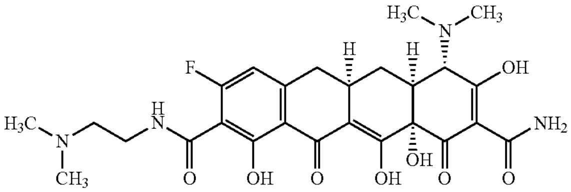

S18-9-3: $^1H$ NMR (400 MHz, $CD_3OD$) δ 6.68 (d, J=9.6 Hz, 1 H), 4.10 (s, 1 H), 3.77 (t, J=6.0 Hz, 2 H), 3.40 (t, J=6.0 Hz, 2 H), 3.10-2.88 (m, 19 H), 2.58 (t, J=14.2 Hz, 1 H), 2.21-2.18 (m, 1 H), 1.63-1.54 (m, 1 H); MS (ESI) m/z 547.23 (M+H).

S18-8-4

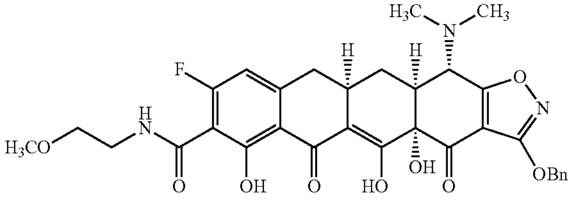

S18-8-4: $^1H$ NMR (400 MHz, $CDCl_3$) δ 7.49-7.47 (m, 2 H), 7.41-7.35 (m, 3 H), 6.61 (d, J=9.6 Hz, 1 H), 5.41, 5.37 (Abq, J=11.9 Hz, 2 H), 4.80 (d, J=0.92 Hz, 1 H), 3.55-3.52 (m, 4 H), 3.40-3.36 (m, 1 H), 3.36 (s, 3 H), 3.15 (s, 6 H), 3.08-2.99 (m, 1 H), 2.81 (dd, J=4.6, 15.6 Hz, 1 H), 2.53 (t, J=14.6 Hz, 1 H), 2.12-2.09 (m, 1 H), 1.41-1.32 (m, 1 H); MS (ESI) m/z 622.27 (M+H).

S18-9-4

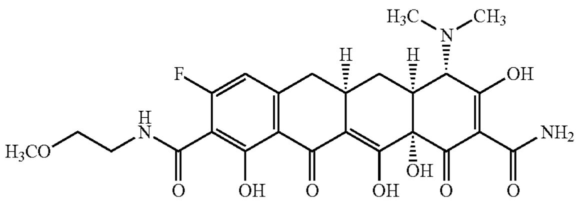

S18-9-4: $^1$H NMR (400 MHz, $CD_3OD$) δ 6.63 (d, J=9.6 Hz, 1 H), 4.07 (s, 1 H), 3.56-3.52 (m, 4 H), 3.37 (s, 3 H), 3.10-2.93 (m, 8 H), 2.90-2.86 (m, 1 H), 2.57 (t, J=14.2 Hz, 1 H), 2.19-2.16 (m, 1 H), 1.63-1.54 (m, 1 H); MS (ESI) m/z 534.19 (M+H).

EXAMPLE 19

Synthesis of Compounds Via Scheme 19

The following compounds were prepared according to Scheme 19.

S19-1

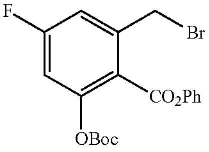

NBS (0.79 g, 4.44 mmol, 1.2 equiv) and AIBN (61 mg, 0.37 mmol, 0.10 equiv) were added to a suspension of compound S18-4 (1.28 g, 3.70 mmol, 1.0 equiv) in carbon tetrachloride (37 mL) at rt. The resulting mixture was stirred at 80° C. for 16 hrs, cooled to rt, and diluted with dichloromethane (40 mL). The resulting mixture was washed with saturated aqueous $NaHCO_3$ and brine (1:1, 40 mL). The aqueous layer was further extracted with dichloromethane (2×15 mL). The com- Scheme 19

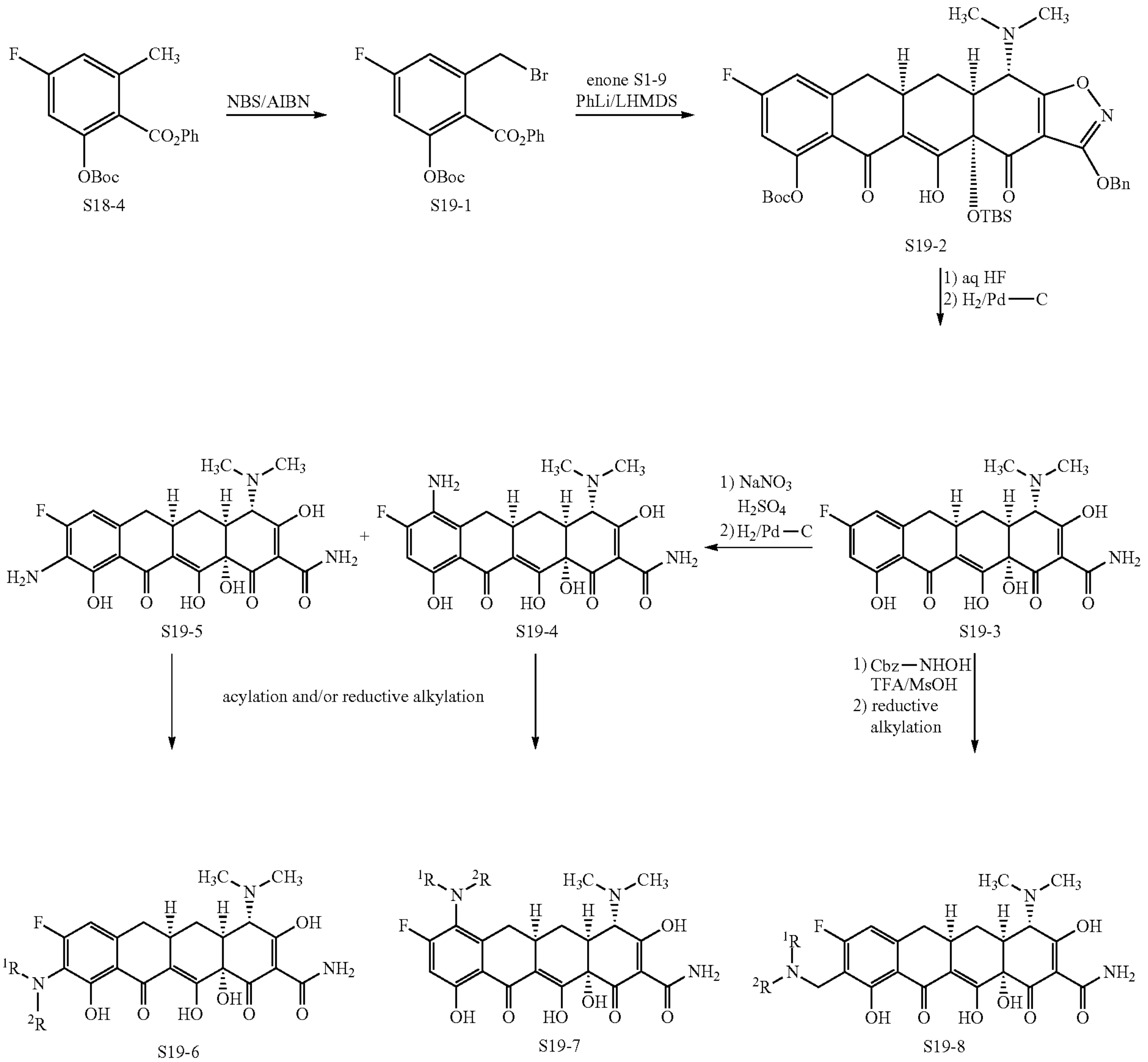

S18-4 S19-1 S19-2 S19-5 S19-4 S19-3 S19-6 S19-7 S19-8 bined organic phase was dried over anhydrous magnesium sulfate, filtered, and concentrated. The residue was purified by flash column chromatography (0-5% EtOAc/hexanes) to afford the desired product S19-1 as a white solid (1.04 g, 66%): $^1$H NMR (400 MHz, $CDCl_3$) δ 7.45-7.41 (m, 2 H), 7.30-7.27 (m, 3 H), 7.10 (dd, J=2.8, 8.7 Hz, 1 H), 7.01 (dd, J=2.8, 8.7 Hz, 1 H), 4.70 (s, 2 H), 1.44 (s, 9 H); MS (ESI) m/z 423.16, 425.13 (M−H).

S19-2

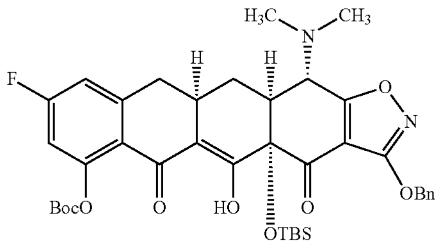

A solution of phenyllithium in di-n-butyl ether (1.22 mL, 1.8 M, 2.20 mmol, 3.0 equiv) was added dropwise via a syringe to a solution of S19-1 (0.94 g, 2.20 mmol, 3.0 equiv) and enone S1-9 (0.35 g, 0.73 mmol, 1.0 equiv) in THF (37 mL) at −100° C. The orange reaction mixture was allowed to warm to −78° C. over 10 min. Then a solution of LHMDS in hexanes (0.73 mL, 1.0 M/THF, 0.73 mmol, 1.0 equiv) was added dropwise at −78° C. The reaction mixture was allowed to warm slowly to −10° C. over 50 min, and then partitioned between aqueous potassium phosphate buffer solution (pH 7, 0.2 M, 50 mL) and EtOAc (120 mL). The phases were separated and the organic phase was dried over anhydrous sodium sulfate, filtered, and concentrated. The residue was purified by preparative reverse phase HPLC on a Waters Autopurification system using a Sunfire Prep C18 OBD column [5 μm, 19×50 mm; flow rate, 20 mL/min; Solvent A: $H_2O$ with 0.1% $HCO_2H$; Solvent B: $CH_3CN$ with 0.1% $HCO_2H$; injection volume: 3.0 mL ($CH_3CN$); gradient: 80→100% B in A over 10 min; mass-directed fraction collection]. Fractions containing the desired product, eluting at 4.3-6.8 min, were collected and concentrated to yield compound S19-2 (0.49 g, 90%): $^1$H NMR (400 MHz, $CDCl_3$) δ 15.69 (s, 1 H), 7.49-7.47 (m, 2 H), 7.38-7.32 (m, 3 H), 6.84 (d, J=7.9 Hz, 1 H), 6.80 (d, J=8.5 Hz, 1 H), 5.34 (s, 2 H), 3.92 (d, J=10.4 Hz, 1 H), 3.10-3.03 (m, 1 H), 2.94-2.78 (m, 2 H), 2.52-2.40 (m, 8 H), 2.07 (d, J=14.6 Hz, 1 H), 1.98 (s, 9 H), 1.53 (s, 9 H), 0.26 (s, 3 H), 0.11 (s, 3 H); MS (ESI) m/z 735.35 (M+H).

S19-3

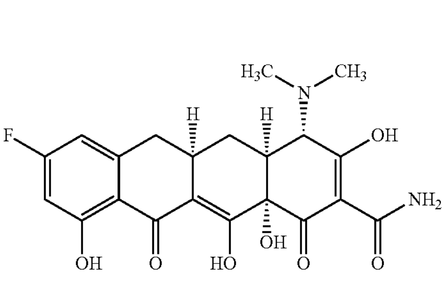

Aqueous HF (48-50%, 0.5 mL) was added to a solution of compound S19-2 (0.49 g, 0.66 mmol) in acetonitrile (1.0 mL) in a polypropylene reaction vessel at 23° C. The mixture was stirred vigorously at 23° C. overnight, poured into aqueous $K_2HPO_4$ (6 g dissolved in 40 mL water), and extracted with EtOAc (100 mL, then 2×20 mL). The combined organic extracts were dried over anhydrous sodium sulfate, filtered, and concentrated. The residue was used directly in the next step.

Pd—C (10 wt %, 10 mg) was added in one portion into a solution of the above product in a mixture of MeOH (2 mL) and dioxane (0.5 mL) at 23° C. The reaction vessel was sealed and purged with hydrogen by briefly evacuating the flask followed by flushing with hydrogen gas (1 atm). The reaction was stirred at 23° C. for 30 min. The reaction mixture was then filtered through a small Celite pad. The filtrate was concentrated. The residue was purified by preparative reverse phase HPLC on a Waters Autopurification system using a Phenomenex Polymerx 10μ RP-γ 100A column [10 μm, 150×21.20 mm; flow rate, 20 mL/min; Solvent A: 0.05 N HCl/water; Solvent B: $CH_3CN$; injection volume: 3.0 mL (0.05 N HCl/water); gradient: 15→60% B over 10 min; mass-directed fraction collection]. Fractions containing the desired product were collected and freeze-dried to yield compound S19-3 (0.22 g, 66% over 2 steps): $^1$H NMR (400 MHz, $CD_3OD$) δ 6.65-6.52 (m, 2 H), 4.08 (s, 1 H), 3.06-2.93 (m, 8 H), 2.86 (dd, J=4.1, 15.1 Hz, 1 H), 2.54 (t, J=14.6 Hz, 1 H), 2.21-2.16 (m, 1 H), 1.62-1.53 (m, 1 H); MS (ESI) m/z 433.19 (M+H).

S19-4

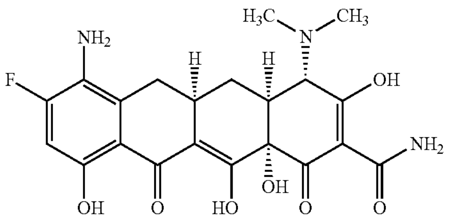

S19-5

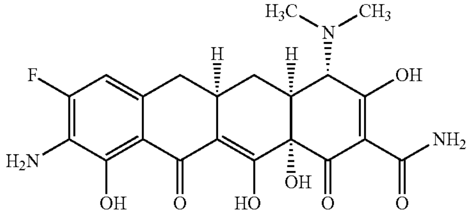

Compound S19-3 (0.15 g, 0.31 mmol, 1.0 equiv) was dissolved in concentrated sulfuric acid (1 mL) at 0° C., forming a red solution. $NaNO_3$ (39 mg, 0.46 mmol, 1.5 equiv) was then added in one portion at 0° C. The resulting orange reaction mixture was stirred at 0° C. for 30 min, and was then added dropwise to vigorously stirring diethyl ether (100 mL). The precipitates were collected onto a small Celite pad, washed with more ether, and eluted with MeOH (20 mL). The MeOH solution was concentrated. The residue was used directly in the next step.

Pd—C (10 wt %, 50 mg) was added in one portion into a solution of the above products in MeOH (5 mL) at 23° C. The reaction vessel was sealed and purged with hydrogen by briefly evacuating the flask followed by flushing with hydrogen gas (1 atm). The mixture was stirred at 23° C. for 1 h. The reaction mixture was then filtered through a small Celite pad. The filtrate was concentrated. The residue was purified by preparative reverse phase HPLC on a Waters Autopurification system using a Phenomenex Polymerx 10μ RP-γ 100A column [10 μm, 150×21.20 mm; flow rate, 20 mL/min; Solvent A: 0.05 N HCl/water; Solvent B: $CH_3CN$; injection volume: 3.0 mL (0.05 N HCl/water); gradient: 5→30% B over 24 min; mass-directed fraction collection] to yield compound S19-4 and S19-5.

Compound S19-4 (18 mg): $^1$H NMR (400 MHz, $CD_3OD$) δ 6.88 (d, J=11.9 Hz, 1 H), 4.15 (s, 1 H), 3.20-2.95 (m, 9 H), 2.45 (t, J=15.6 Hz, 1 H), 2.34-2.29 (m, 1 H), 1.69-1.59 (m, 1 H); MS (ESI) m/z 448.18 (M+H).

Compound S19-5 (68 mg, 72% over 2 steps): $^1$H NMR (400 MHz, $CD_3OD$) δ 6.87 (d, J=9.2 Hz, 1 H), 4.16 (s, 1 H), 3.16-2.94 (m, 9 H), 2.60 (t, J=14.6 Hz, 1 H), 2.28-2.24 (m, 1 H), 1.64-1.55 (m, 1 H); MS (ESI) m/z 448.18 (M+H).

S19-7-1

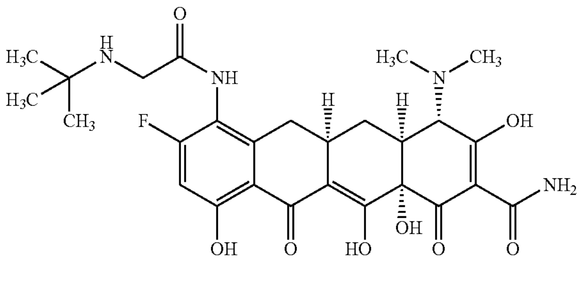

2-t-Butylaminoacetyl chloride hydrochloride (4 mg, 0.020 mmol, 2.0 equiv) was added to a solution of compound S19-4 (5 mg, 0.010 mmol, 1.0 equiv) in DMF (0.3 mL) at rt. The resulting orange reaction mixture was stirred at rt for 15 min and quenched by aqueous HCl (0.5 N, 2 mL). The resulting mixture was purified by preparative reverse phase HPLC on a Waters Autopurification system using a Phenomenex Polymerx 10μ RP-γ 100A column [10 μm, 150×21.20 mm; flow rate, 20 mL/min; Solvent A: 0.05 N HCl/water; Solvent B: $CH_3CN$; injection volume: 3.0 mL (0.05 N HCl/water); gradient: 0→30% B over 20 min; mass-directed fraction collection]. Fractions containing the desired product, eluting at 12.4-13.6 min, were collected and freeze-dried to yield compound S19-7-1 (4 mg, 56%): $^1$H NMR (400 MHz, $CD_3OD$) δ 6.71 (d, J=11.4 Hz, 1 H), 4.11 (s, 1 H), 4.06 (s, 2 H), 3.12-3.08 (m, 1 H), 3.07-2.96 (m, 8 H), 2.31-2.24 (m, 2 H), 1.62-1.52 (m, 1 H), 1.41 (s, 9 H); MS (ESI) m/z 561.39 (M+H).

S19-6-1

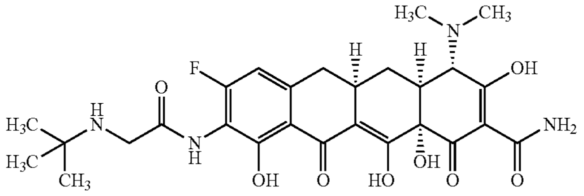

Compound S19-6-1 was prepared from S19-5 with the same procedure: $^1$H NMR (400 MHz, $CD_3OD$) δ 6.70 (d, J=9.6 Hz, 1 H), 4.10 (s, 1 H), 4.05 (s, 2 H), 3.09-2.93 (m, 8 H), 2.92-2.87 (m, 1 H), 2.57 (t, J=14.2 Hz, 1 H), 2.29-2.19 (m, 1 H), 1.64-1.54 (m, 1 H), 1.41 (s, 9 H); MS (ESI) m/z 561.30 (M+H).

S19-7-2

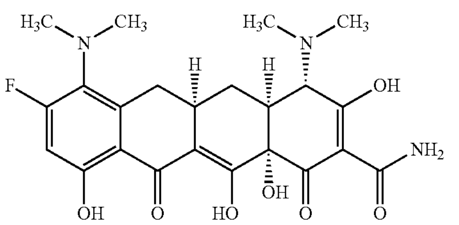

Pd—C (10 wt %, 6 mg) and formaldehyde in water (37%, 9 μL, 0.12 mmol, 5.0 equiv) were added to a solution of compound S19-4 (12 mg, 0.024 mmol, 1.0 equiv) in MeOH (1 mL) at 23° C. The reaction vessel was sealed and purged with hydrogen by briefly evacuating the flask followed by flushing with hydrogen gas (1 atm). The resulting mixture was stirred at 23° C. for 4 hrs. The reaction mixture was then filtered through a small Celite pad. The filtrate was concentrated. The residue was purified by preparative reverse phase HPLC on a Waters Autopurification system using a Phenomenex Polymerx 10μ RP-γ 100A column [10 μm, 150×21.20 mm; flow rate, 20 mL/min; Solvent A: 0.05 N HCl/water; Solvent B: $CH_3CN$; injection volume: 3.0 mL (0.05 N HCl/water); gradient: 15→60% B over 10 min; mass-directed fraction collection]. Fractions containing the desired product, eluting at 4.9-6.1 min, were collected and freeze-dried to yield compound S19-7-2 (9 mg, 68%): $^1$H NMR (400 MHz, $CD_3OD$) δ 6.86 (d, J=14.2 Hz, 1 H), 4.16 (s, 1 H), 3.49 (dd, J=4.1, 15.6 Hz, 1 H), 3.24 (br s, 6 H), 3.12-3.02 (m, 2 H), 3.06 (s, 3 H), 2.97 (s, 3 H), 2.48 (t, J=14.6 Hz, 1 H), 2.33-2.30 (m, 1 H), 1.70-1.61 (m, 1 H); MS (ESI) m/z 476.24 (M+H).

S19-8-1

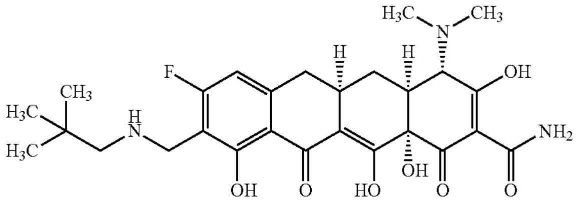

Benzyl N-(hydroxymethyl)carbamate (10 mg, 0.057 mmol, 1.1 equiv) was added to a solution of compound S19-3 (24 mg, 0.052 mmol, 1.0 equiv) in a mixture of TFA (0.2 mL) and methanesulfonic acid (0.1 mL) at rt. The reaction mixture was stirred at rt for 14 hrs. More benzyl N-(hydroxymethyl) carbamate (5 mg, 0.026 mmol, 0.5 equiv) was added. The reaction mixture was stirred at rt for another hour, quenched by 0.05 N HCl/water (1 mL), filtered through a cotton plug, and the cotton plug was washed with 0.05 N HCl/water. The filtrate was purified by preparative reverse phase HPLC on a Waters Autopurification system using a Phenomenex Polymerx 10μ RP-γ 100A column [10 μm, 150×21.20 mm; flow rate, 20 mL/min; Solvent A: 0.05 N HCl/water; Solvent B: $CH_3CN$; injection volume: 3.0 mL (0.05 N HCl/water); gradient: 0→20% B over 22 min; mass-directed fraction collection]. Fractions containing the desired product, eluting at 12.2-15.2 min, were collected and freeze-dried to yield the aminomethylated intermediates as a mixture of regioisomers (~3:2, 10 mg, 36%): $^1$H NMR (400 MHz, $CD_3OD$) δ 6.73-6.71 (m, 1 H), 4.19 (s, 1 H), 4.15 (s, 0.4 H), 4.11 (s, 0.6 H), 3.27-3.22 (m, 0.4 H), 3.14-2.90 (m, 9.6 H), 2.58 (t, J=14.6 Hz, 0.6 H), 2.45 (t, J=14.2 Hz, 0.4 H), 2.34-2.31 (m, 0.4 H), 2.24-2.20 (m, 0.6 H), 1.64-1.54 (m, 1 H); MS (ESI) m/z 462.22 (M+H).

A solution of pivalaldehyde (2 μL, 0.021 mmol, 1.1 equiv) in DMF (0.2 mL) was added to the above aminomethylated intermediates. Triethylamine (5 μL, 0.038 mmol, 2.0 equiv) was added. The reaction mixture was stirred at rt for 50 min. $Na(OAc)_3BH$ (8 mg, 0.038 mmol, 2.0 equiv) was added. After 35 min, more pivalaldehyde (0.5 μL, 0.0050 mmol, 0.25 equiv) was added. The reaction mixture was stirred at rt for another 40 min, diluted with 0.05 N HCl/water, and purified by preparative reverse phase HPLC on a Waters Autopurification system using a Phenomenex Polymerx 10 μ RP-γ 100A column [10 μm, 150×21.20 mm; flow rate, 20 mL/min; Solvent A: 0.05 N HCl/water; Solvent B: $CH_3CN$; injection volume: 3.0 mL (0.05 N HCl/water); gradient: 0→20% B over 20 min, and then kept at 20% B for 5 min; mass-directed fraction collection]. Fractions containing the desired product, eluting at 21.0-21.5 min, were collected and freeze-dried to yield product S19-8-1 (1 mg, 10%): $^1H$ NMR (400 MHz, $CD_3OD$) δ 6.77 (d, J=10.1 Hz, 1 H), 4.34 (s, 2 H), 4.09 (s, 1 H), 3.04 (s, 2 H), 2.98-2.92 (m, 9 H), 2.62 (t, J=14.6 Hz, 1 H), 2.23-2.17 (m, 1 H), 1.66-1.56 (m, 1 H), 1.09 (s, 9 H); MS (ESI) m/z 532.36 (M+H).

EXAMPLE 20

Synthesis of Compounds Via Scheme 20

Scheme 20

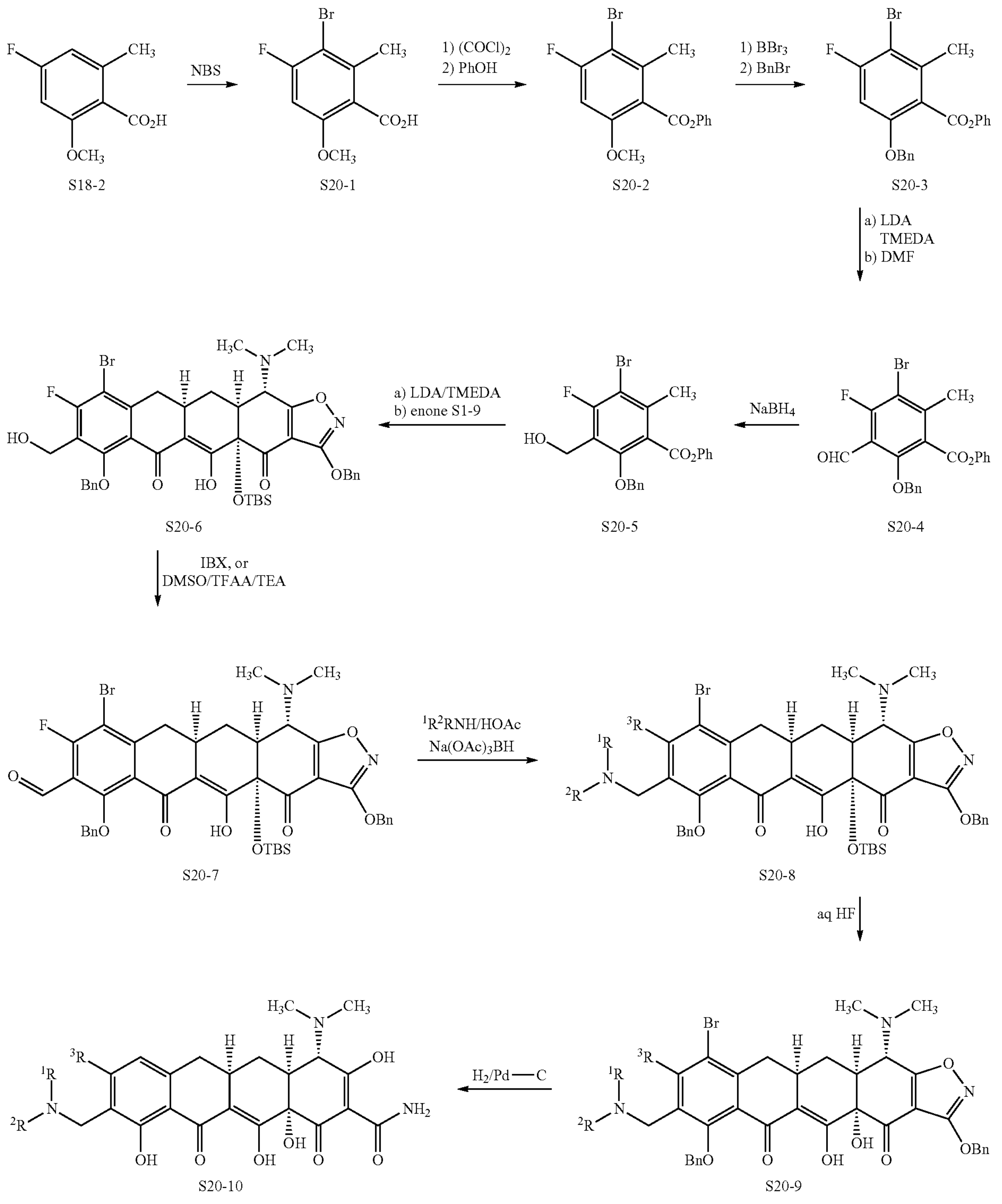

S18-2

S20-1

S20-2

S20-3

S20-4

S20-5

S20-6

S20-7

S20-8

S20-9

S20-10

The following compounds were prepared according to Scheme 20.

S20-1

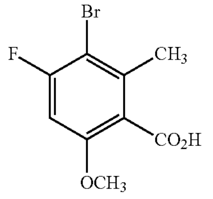

Crude S18-2 (9.4 g, ~51 mmol, 1.0 equiv) was dissolved in TFA (50 mL) and cooled to 0° C. NBS (9.54 g, 53.60 mmol, 1.05 equiv) was added in one portion. The reaction mixture was stirred at 0° C. for 1 h. Volatiles were evaporated, and the mixture was poured onto ice-water (300 mL). The resulting mixture was extracted with EtOAc (300 mL). The combined organic phases were washed with brine (100 mL), dried over anhydrous magnesium sulfate, filtered, concentrated, and further dried under high vacuum to give crude S20-1, which was used in the next reaction without further purification.

S20-2

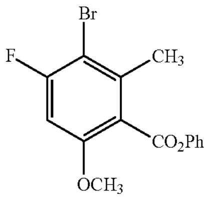

The above crude product S20-1 was dissolved in dichloromethane (100 mL). Oxalyl chloride (5.78 mL, 66.30 mmol, 1.3 equiv) was added at rt (bubbling vigorously). Additional amounts of oxalyl chloride [3×(5.78 mL, 66.30 mmol, 1.3 equiv)] were added, followed by a few drops of DMF. The mixture was stirred at rt for 1 h. Volatiles were evaporated, and the residue was further dried under high vacuum to afford the crude acid chloride. The crude acid chloride was redissolved in dichloromethane (100 mL). Phenol (5.76 g, 61.20 mmol, 1.2 equiv), triethylamine (21.30 mL, 153.00 mmol, 3.0 equiv), and DMAP (catalytic amount) were added. The reaction mixture was stirred overnight at rt. Volatiles were evaporated. The residue was dissolved in EtOAc (300 mL) and water (100 mL). The organic layer was separated and washed with 1 N aqueous HCl (70 mL), brine (50 mL), 1 N aqueous NaOH (70 mL) and brine (50 mL), dried over anhydrous magnesium sulfate, filtered, and concentrated. The residue was purified by hydrolysis of the byproducts as following.

The above crude product was dissolved in 2-methyltetrahydrofuran (25 mL). Water (25 mL) was added, followed by 50 wt % aqueous NaOH (~19N, 2.70 mL). The reaction mixture was stirred vigorously at 75° C. for 3 hrs (monitored by LC-MS). The reaction mixture was cooled to rt diluted with EtOAc (200 mL). The organic phase was washed with 2 N aqueous NaOH (2×45 mL) and brine (50 mL), dried over anhydrous magnesium sulfate, filtered, and concentrated to afford the desired product S20-2 (10.00 g): $^1H$ NMR (400 MHz, $CDCl_3$) δ 7.46-7.42 (m, 2 H), 7.31-7.29 (m, 1 H), 7.26-7.22 (m, 2 H), 6.67 (d, J=10.4 Hz, 1 H), 3.88 (s, 3 H), 2.52 (s, 3 H); MS (ESI) m/z 337.15, 339.12 (M−H).

S20-3

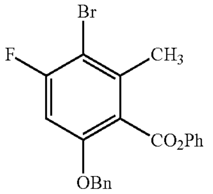

A solution of $BBr_3$ in dichloromethane (29.48 mL, 1.0 M, 29.48 mmol, 1.0 equiv) was added slowly to a solution of the above compound S20-2 in dichloromethane (100 mL) at −78° C. The resulting red solution was allowed to warm to 0° C. in 25 min and kept at that temperature for 10 min (monitored by LC-MS or TLC (product is slightly less polar)). The reaction mixture was poured into saturated $NaHCO_3$ solution (100 mL), stirred at rt for 5 min, and concentrated under reduced pressure. The residue was extracted with EtOAc (180 mL, then 30 mL). The organic extracts were combined and dried over anhydrous magnesium sulfate, filtered, and concentrated to afford the crude phenol, which was used directly in the next reaction: $^1H$ NMR (400 MHz, $CDCl_3$) δ 11.01 (d, J=1.2 Hz, 1 H), 7.48-7.44 (m, 2 H), 7.34-7.30 (m, 1 H), 7.19-7.17 (m, 2 H), 6.72 (d, J=9.2 Hz, 1 H), 2.85 (s, 3 H); MS (ESI) m/z 323, 325 (M−H).

Benzylbromide (3.67 mL, 30.95 mmol, 1.05 equiv) and $Cs_2CO_3$ powder (11.50 g, 35.38 mmol, 1.2 equiv) were added to a solution of the above crude phenol (10.00 g, 29.48 mmol, 1.0 equiv) in acetone (60 mL). The mixture was stirred at it overnight. Solvents were evaporated and the residue was dissolved in a mixture of EtOAc (250 mL), water and brine (1:1, 150 mL). The organic layer was separated, and the aqueous layer was extracted with EtOAc (50 mL). The combined organic phase was dried over anhydrous magnesium sulfate, filtered, and concentrated. The residue was purified by flash column chromatography (1% EtOAc/hexanes), followed by re-crystallization from EtOAc/hexanes to afford the desired product S20-3 as a white solid (6.30 g, 24% five steps): $^1H$ NMR (400 MHz, $CDCl_3$) δ 7.42-7.33 (m, 7 H), 7.26-7.22 (m, 1 H), 7.08-7.05 (m, 2 H), 6.70 (d, J=9.8 Hz, 1 H), 5.12 (s, 2 H), 2.51 (s, 3 H); MS (ESI) m/z 413.27, 415.22 (M−H).

S20-4

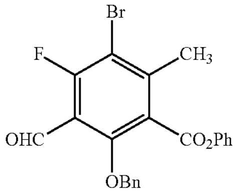

To a solution of S20-3 (1.33 g, 3.19 mmol, 1.0 equiv) and TMEDA (0.96 mL, 6.39 mmol, 2.0 equiv) in THF (50 mL) was added dropwise a solution of LDA (5.32 mL, 1.2 M/THF/heptane/ethylbenzene, 6.39 mmol, 2.0 equiv) at −78° C. The resulting red solution was stirred at that temperature for 15 min, and DMF (0.74 mL, 9.58 mmol, 3.0 equiv) was added. The reaction mixture was stirred at −78° C. for 1 h (monitored by LC-MS and TLC). Saturated aqueous $NH_4Cl$ (10 mL) was added at −78° C. dropwise. The resulting mixture was warmed up to rt, diluted with water (50 mL) and extracted with EtOAc (200 mL). The organic phase was dried over anhydrous magnesium sulfate, filtered, and concentrated. The residue was purified by flash column chromatography (3-6% EtOAc/hexanes) to afford the desired compound S20-4 as an off-white solid (0.53 g): $^1$H NMR (400 MHz, $CDCl_3$) δ 10.27 (s, 1 H), 7.45-7.42 (m, 2 H), 7.38-7.34 (m, 5 H), 7.27-7.24 (m, 1 H), 7.03-7.01 (m, 2 H), 5.12 (s, 2 H), 2.60 (s, 3 H); MS (ESI) m/z 441.20, 443.25 (M−H).

S20-5

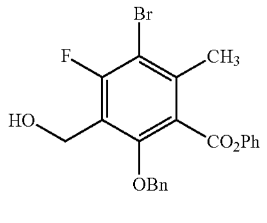

To a solution of S20-4 (0.53 g, 1.20 mmol, 1.0 equiv) in EtOH (3 mL) and dichloromethane (2 mL) was added $NaBH_4$ (45 mg, 1.20 mmol, 1.0 equiv) at rt in one portion (exothermic). After 1 min, TLC showed the reaction was complete. The reaction mixture was then cooled to 0° C., and 1 N aqueous HCl solution (1 mL) was added dropwise (gas evolution). Aqueous saturated $NaHCO_3$ was added to neutralize the aqueous layer to pH 7. The resulting mixture was extracted with dichloromethane (50 mL). The organic phase was dried over anhydrous magnesium sulfate, filtered, and concentrated. The residue was purified by flash column chromatography (10% EtOAc/hexanes) to afford the desired compound S20-5 as a white solid (0.62 g, 43% over two steps): $^1$H NMR (400 MHz, $CDCl_3$) δ 7.43-7.35 (m, 7 H), 7.28-7.24 (m, 1 H), 7.09-7.08 (m, 2 H), 5.14 (s, 2 H), 4.73 (dd, J=1.8, 6.7 Hz, 2 H), 2.55 (s, 3 H), 1.92 (t, J=6.7 Hz, 1 H); MS (ESI) m/z 443.10, 445.09 (M−H).

S20-6

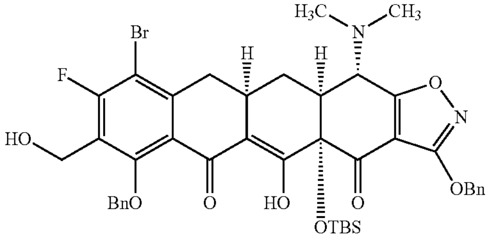

A solution of n-butyllithium in hexanes (1.36 mL, 1.6 M, 2.18 mmol, 2.2 equiv) was added to a solution of diisopropylamine (0.31 mL, 2.18 mmol, 2.2 equiv) and TMEDA (0.33 mL, 2.18 mmol, 2.2 equiv) in THF (20 mL) at −78° C. After stirring at −78° C. for 30 min, a solution of compound S20-5 (0.44 g, 0.99 mmol, 1.0 equiv) in THF (4 mL) was added dropwise via a cannula. The resulting red reaction mixture was then stirred at −78° C. for 10 min, and cooled to −100° C. A solution of enone S1-9 (0.38 g, 0.79 mmol, 0.8 equiv) in THF (4 mL) was added to the reaction mixture via a cannula. The resulting reaction mixture was allowed to warm to −30° C. over 1.5 hrs, quenched by saturated aqueous $NH_4Cl$ (40 mL), and extracted with EtOAc (100 mL). The organic phase were dried (sodium sulfate), filtered and concentrated. The residue was purified by a preparative reverse phase HPLC on a Waters Autopurification system using a Sunfire Prep C18 OBD column [5 μm, 19×50 mm; flow rate, 20 mL/min; Solvent A: $H_2O$ with 0.1% $HCO_2H$; Solvent B: $CH_3CN$ with 0.1% $HCO_2H$; injection volume: 3.0 mL ($CH_3CN$); gradient: 80→100% B in A over 10 min; mass-directed fraction collection]. Fractions containing the desired product were collected and concentrated to yield compound S20-6 (0.36 g, 54%): $^1$H NMR (400 MHz, $CDCl_3$) δ 15.79 (br s, 1 H), 7.51-7.48 (m, 2 H), 7.40-7.33 (m, 8 H), 5.36 (s, 2 H), 5.13 (d, J=11.0 Hz, 1 H), 4.18 (d, J=10.4 Hz, 1 H), 4.64 (dd, J=1.2, 12.2 Hz, 1 H), 4.53 (dd, J=1.2, 12.2 Hz, 1 H), 3.93 (d, J=10.4 Hz, 1 H), 3.40 (dd, J=10.7, 16.5 Hz, 1 H), 3.06-2.99 (m, 1 H), 2.61-2.57 (m, 1 H), 2.54-2.47 (m, 2 H), 2.50 (s, 6 H), 2.19 (d, J=14.6 Hz, 1 H), 1.86 (br s, 1 H), 0.83 (s, 9 H), 0.29 (s, 3 H), 0.14 (s, 3 H); MS (ESI) m/z 833.41, 835.38 (M+H).

S20-7

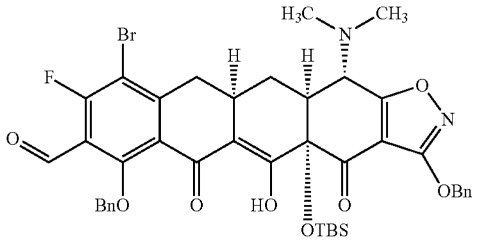

Trifluoroacetic anhydride (0.17 mL, 1.34 mmol, 2.5 equiv) was added dropwise to a solution of compound S20-6 (0.45 g, 0.54 mmol, 1.0 equiv) and DMSO (0.19 mL, 2.68 mmol, 5.0 equiv) in THF (25 mL) at −20° C. The resulting orange reaction mixture was stirred at −20° C. for 25 min. triethylamine (0.37 mL, 2.68 mmol, 5.0 equiv) was added. After stirring for 25 min, saturated aqueous $NaHCO_3$ (20 mL) was added at −20° C. The resulting mixture was extracted with EtOAc (80 mL). The organic phase were dried (sodium sulfate), filtered and concentrated. The residue was purified by a preparative reverse phase HPLC on a Waters Autopurification system using a Sunfire Prep C18 OBD column [5 μm, 19×50 mm; flow rate, 20 mL/min; Solvent A: $H_2O$ with 0.1% $HCO_2H$; Solvent B: $CH_3CN$ with 0.1% $HCO_2H$; injection volume: 3.0 mL ($CH_3CN$); gradient: 80→100% B in A over 10 min; mass-directed fraction collection]. Fractions containing the desired product were collected and concentrated to yield compound S20-7 (0.30 g, 67%): $^1$H NMR (400 MHz, $CDCl_3$) δ 15.69 (s, 1 H), 10.12 (d, J=1.2 Hz, 1 H), 7.51-7.49 (m, 2 H), 7.40-7.32 (m, 8 H), 5.37 (s, 2 H), 5.14 (d, J=11.0 Hz, 1 H), 4.93 (d, J=10.4 Hz, 1 H), 3.91 (d, J=11.0 Hz, 1 H), 3.48-3.44 (m, 1 H), 3.07-3.02 (m, 1 H), 3.61-3.46 (m, 3 H), 2.51 (s, 6 H), 2.20 (d, J=14.7 Hz, 1 H), 1.86 (br s, 1 H), 0.83 (s, 9 H), 0.29 (s, 3 H), 0.15 (s, 3 H); MS (ESI) m/z 831.53, 833.54 (M+H).

S20-8-1

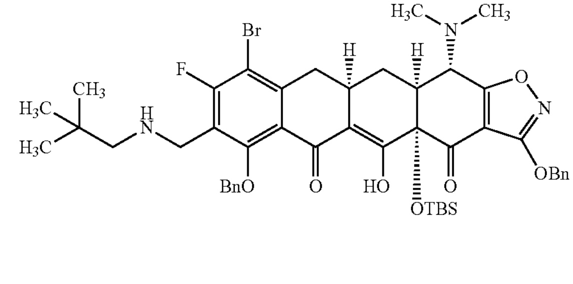

Neopentylamine (46 μL, 0.42 mmol, 2.0 equiv), acetic acid (36 μL, 0.63 mmol, 3.0 equiv) and sodium triacetoxyborohydride (67 mg, 0.32 mmol, 1.5 equiv) were added sequentially to a solution of compound S20-7 (0.18 g, 0.21 mmol, 1.0 equiv) in 1,2-dichloroethane (5 mL) at 23° C. After stirring for 1 h, the reaction mixture was quenched by the addition of saturated aqueous sodium bicarbonate and pH 7 phosphate buffer (1:1, 30 mL) and extracted with dichloromethane (50 mL, then 10 mL). The combined organic extracts were dried over anhydrous sodium sulfate, filtered, and concentrated. The residue was used directly in the next reaction: $^1$H NMR (400 MHz, $CDCl_3$) δ 7.50-7.48 (m, 2 H), 7.39-7.31 (m, 8 H), 5.36 (s, 2 H), 5.08 (d, J=10.4 Hz, 1 H), 4.84 (d, J=10.4 Hz, 1 H), 3.94 (d, J=11.0 Hz, 1 H), 3.83, 3.77 (ABq, J=12.2 Hz, 2 H), 3.43-3.38 (m, 1 H), 3.04-2.99 (m, 1 H), 2.60-2.44 (m, 3 H), 2.50 (s, 6 H), 2.29-2.16 (m, 3 H), 0.82 (s, 9 H), 0.28 (s, 3 H), 0.14 (s, 3 H); MS (ESI) m/z 902.51, 904.51 (M+H).

S19-8-1

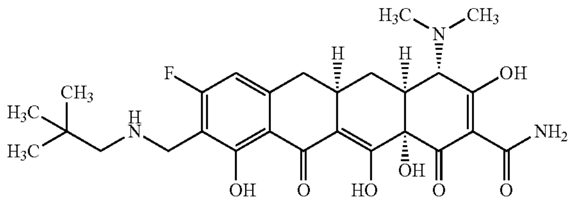

Aqueous HF (48-50%, 0.6 mL) was added to a solution of the above crude product S20-8-1 in acetonitrile (1.2 mL) in a polypropylene reaction vessel at 23° C. The resulting mixture was stirred vigorously at 23° C. overnight and poured into aqueous $K_2HPO_4$ (7.2 g dissolved in 30 mL water). The resulting mixture was extracted with EtOAc (50 mL, then 20 mL). The combined organic extracts were dried over anhydrous sodium sulfate, filtered, and concentrated. The residue was dissolved in MeOH containing HCl/MeOH (0.5 N, 84 μL, 0.42 mmol, 2.0 equiv), concentrated, and dried under high vacuum. The residue was used directly in the next step without further purification.

The above crude product was dissolved in MeOH (5 mL). Pd—C (10 wt %, 58 mg) was added in one portion at 23° C. The reaction vessel was sealed and purged with hydrogen by briefly evacuating the flask followed by flushing with hydrogen gas (1 atm). After stirring at 23° C. for 4.5 hrs, more Pd—C (10 wt %, 10 mg) was added. The resulting mixture was stirred for 1 h 20 min and filtered through a small Celite pad. The filtrate was concentrated. The residue was purified by a preparative reverse phase HPLC on a Waters Autopurification system using a Phenomenex Polymerx 10μ RP-γ 100A column [10 μm, 150×21.20 mm; flow rate, 20 mL/min; Solvent A: 0.05 N HCl/water; Solvent B: $CH_3CN$; injection volume: 3.0 mL (0.05 N HCl/water); gradient: 20→80% B over 10 min; mass-directed fraction collection]. Fractions containing the desired product, eluting at 6.4-7.2 min, were collected and freeze-dried to yield compound S19-8-1 (59 mg, 46% for 3 steps).

The following compounds were prepared similarly to S19-8-1 and S20-8-1.

S20-8-2

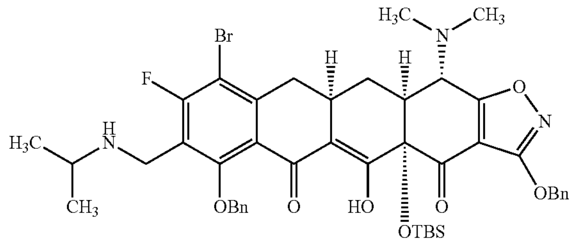

S20-8-2: $^1$H NMR (400 MHz, $CDCl_3$) δ 7.50-7.48 (m, 2 H), 7.39-7.32 (m, 8 H), 5.36 (s, 2 H), 5.11 (d, J=10.4 Hz, 1 H), 4.77 (d, J=11.0 Hz, 1 H), 3.93 (d, J=11.0 Hz, 1 H), 3.79, 3.68 (ABq, J=12.8 Hz, 2 H), 3.39 (dd, J=10.7, 16.5 Hz, 1 H), 3.04-2.98 (m, 1 H), 2.70-2.67 (m, 1 H), 2.60-2.56 (m, 1 H), 2.53-2.44 (m, 2 H), 2.50 (s, 6 H), 2.18 (d, J=14.0 Hz, 1 H), 0.99 (d, J=6.1 Hz, 6 H), 0.82 (s, 9 H), 0.28 (s, 3 H), 0.13 (s, 3 H); MS (ESI) m/z 874.36, 876.39 (M+H).

S20-8-3

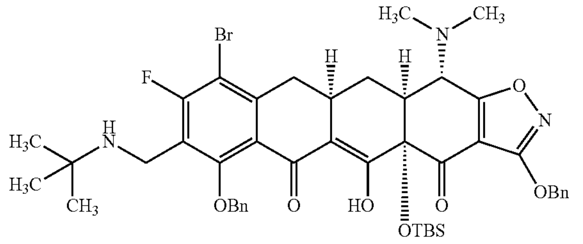

S20-8-3: $^1$H NMR (400 MHz, $CDCl_3$) δ 7.50-7.48 (m, 2 H), 7.39-7.32 (m, 8 H), 5.36 (s, 2 H), 5.12 (d, J=11.0 Hz, 1 H), 4.77 (d, J=10.4 Hz, 1 H), 3.94 (d, J=10.4 Hz, 1 H), 3.70, 3.60 (ABq, J=11.6 Hz, 2 H), 3.38 (dd, J=4.3, 15.9 Hz, 1 H), 3.01-2.94 (m, 1 H), 2.59-2.45 (m, 3 H), 2.50 (s, 6 H), 2.17 (d, J=14.6 Hz, 1 H), 0.03 (s, 9 H), 0.82 (s, 9 H), 0.28 (s, 3 H), 0.12 (s, 3 H); MS (ESI) m/z 888.40, 890.40 (M+H).

S20-10-4

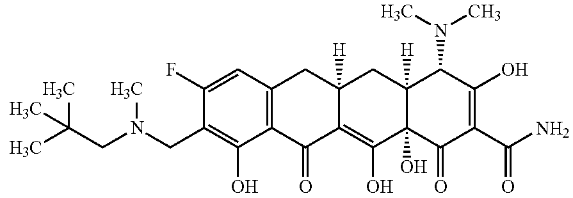

S20-10-4: $^1$H NMR (400 MHz, CD3OD) δ 6.80 (d, J=10.1 Hz, 1 H), 4.54 (dd, J=3.7, 13.3 Hz, 1 H), 4.41 (d, J=13.3 Hz, 1 H), 4.10 (s, 1 H), 3.37-3.32 (m, 1 H), 3.19-2.91 (m, 13 H), 2.62 (t, J=14.6 Hz, 1 H), 2.24-2.19 (m, 1 H), 1.65-1.56 (m, 1 H), 1.15 (d, J=3.2 Hz, 9 H); MS (ESI) m/z 546.35 (M+H).

S20-10-2

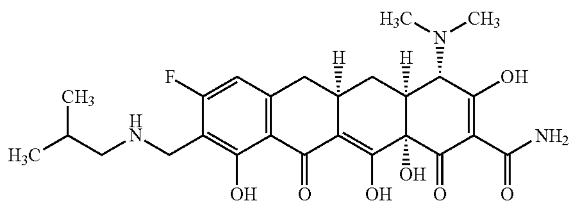

S20-10-2: $^1$H NMR (400 MHz, CD3OD) δ 6.76 (d, J=9.6 Hz, 1 H), 4.29 (s, 2 H), 4.10 (s, 1 H), 3.16-2.89 (m, 11 H), 2.61 (t, J=14.4 Hz, 1 H), 2.24-2.19 (m, 1 H), 2.09 (hept, J=6.4 Hz, 1 H), 1.66-1.56 (m, 1 H), 1.06 (d, J=6.4 Hz, 6 H); MS (ESI) m/z 518.35 (M+H).

S20-10-5

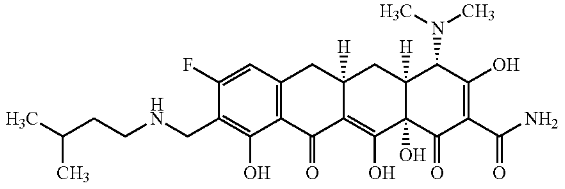

S20-10-5: $^1$H NMR (400 MHz, CD3OD) δ 6.76 (d, J=9.6 Hz, 1 H), 4.28 (s, 2 H), 4.11 (s, 1 H) 3.15-2.92 (m, 11 H), 2.61 (t, J=14.6 Hz, 1 H), 2.24-2.20 (m, 1 H), 1.72-1.56 (m, 4 H), 0.98 (d, J=6.4 Hz, 6 H); MS (ESI) m/z 532.30 (M+H).

S20-10-6

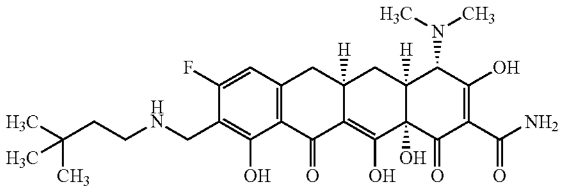

S20-10-6: $^1$H NMR (400 MHz, CD3OD) δ 6.76 (d, J=10.1 Hz, 1 H), 4.29 (s, 2 H), 4.10 (s, 1 H), 3.15-2.92 (m, 11 H), 2.61 (t, J=14.6 Hz, 1 H), 2.24-2.19 (m, 1 H), 1.67-1.56 (m, 3 H), 0.98 (s, 9 H); MS (ESI) m/z 546.37 (M+H).

S20-10-7

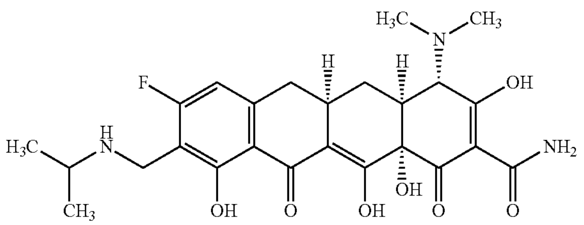

S20-10-7: $^1$H NMR (400 MHz, CD3OD) δ 6.75 (d, J=10.1 Hz, 1 H), 4.26 (s, 2 H), 4.09 (s, 1 H), 3.53-3.47 (m, 1 H), 3.12-2.91 (m, 9 H), 2.60 (t, J=14.6 Hz, 1 H), 2.22-2.18 (m, 1 H), 1.65-1.56 (m, 1 H), 1.41 (d, J=6.4 Hz, 6 H); MS (ESI) m/z 504.39 (M+H).

S20-10-8

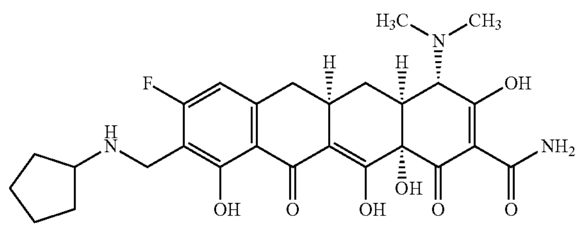

S20-10-8: $^1$H NMR (400 MHz, CD3OD) δ 6.75 (d, J=9.6 Hz, 1 H), 4.26 (s, 2 H), 4.10 (s, 1 H), 3.68-3.63 (m, 1 H), 3.16-2.88 (m, 9 H), 2.59 (t, J=14.6 Hz, 1 H), 2.23-2.14 (m, 3 H), 1.87-1.68 (m, 6 H), 1.64-1.55 (m, 1 H); MS (ESI) m/z 530.36 (M+H).

S20-10-3

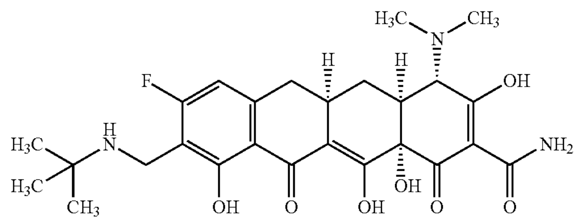

S20-10-3: $^1$H NMR (400 MHz, CD3OD) δ 6.75 (d, J=9.6 Hz, 1 H), 4.23 (s, 2 H), 4.10 (s, 1 H), 3.11-2.92 (m, 9 H), 2.60 (t, J=14.2 Hz, 1 H), 2.22-2.19 (m, 1 H), 1.64-1.55 (m, 1 H), 1.48 (s, 9 H); MS (ESI) m/z 518.42 (M+H).

S20-8-9

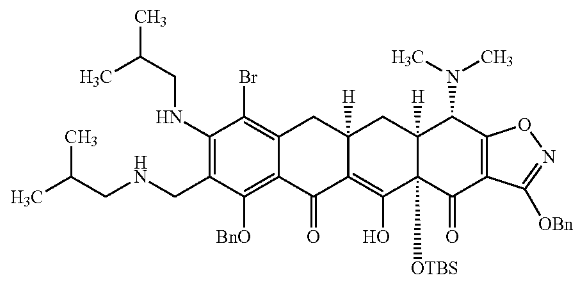

Isobutylamine (13 μL, 0.12 mmol, 5.0 equiv), acetic acid (7 μL, 0.12 mmol, 5.0 equiv) and sodium triacetoxyborohydride (11 mg, 0.050 mmol, 2.0 equiv) were added sequentially to a solution of compound S20-7 (21 mg, 0.025 mmol, 1.0 equiv) in 1,2-dichloroethane (0.5 mL) at 23° C. After stirring overnight, the reaction mixture was quenched by the addition of saturated aqueous sodium bicarbonate and pH 7 phosphate buffer (1:1, 20 mL) and extracted with dichloromethane (3×15 mL). The combined organic extracts were dried over anhydrous sodium sulfate, filtered, and concentrated. The residue was purified by a preparative reverse phase HPLC on a Waters Autopurification system using a Sunfire Prep C18 OBD column [5 μm, 19×50 mm; flow rate, 20 mL/min; Solvent A: H2O with 0.1% HCO2H; Solvent B: CH3CN with 0.1% HCO2H; injection volume: 3.0 mL (CH3CN); gradient: 20→100% B in A over 10 min; mass-directed fraction collection]. Fractions containing the desired product were collected and concentrated to yield compound S20-8-9 (5 mg, 19%): $^1$H NMR (400 MHz, CDCl3) δ 16.03 (br s, 1 H), 7.49-7.48 (m, 2 H), 7.38-7.30 (m, 8 H), 5.35 (s, 2 H), 5.00 (d, J=11.0 Hz, 1 H), 4.68 (d, J=11.0 Hz, 1 H), 3.98 (d, J=10.4 Hz, 1 H), 3.70-3.61 (m, 2 H), 3.38 (dd, J=4.9, 16.5 Hz, 1 H), 3.23 (br s, 2 H), 3.02-2.97 (m, 1 H), 2.57-2.44 (m, 3 H), 2.50 (s, 6 H), 2.26-2.23 (m, 2 H), 2.15 (d, J=14.6 Hz, 1 H), 1.80-1.74 (m, 1 H), 1.65-1.52 (m, 1 H), 0.98-0.93 (m, 6 H), 0.83-0.80 (m, 15 H), 0.28 (s, 3 H), 0.13 (s, 3 H); MS (ESI) m/z 941.50, 943.50 (M+H).

S20-10-9

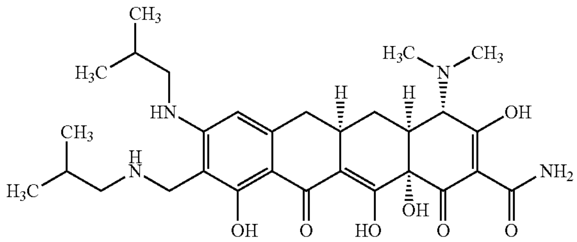

Aqueous HF (48-50%, 0.3 mL) was added to a solution of compound S20-8-9 in acetonitrile (0.8 mL) in a polypropylene reaction vessel at 23° C. The resulting mixture was stirred vigorously at 23° C. overnight and poured into aqueous $K_2HPO_4$ (3.6 g dissolved in 20 mL water). The resulting mixture was extracted with EtOAc (30 mL, then 10 mL). The combined organic extracts were dried over anhydrous sodium sulfate, filtered, and concentrated. The residue was dissolved in MeOH containing HCl/MeOH (0.5 N, 28 μL, 0.014 mmol, 3.0 equiv), concentrated and dried under high vacuum. The residue was used directly in the next step without further purification.

The above crude product was dissolved in MeOH (1 mL). Pd—C (10 wt %, 2 mg) was added in one portion at 23° C. The reaction vessel was sealed and purged with hydrogen by briefly evacuating the flask followed by flushing with hydrogen gas (1 atm). After stirring at 23° C. for 30 min, more Pd—C (10 wt %, 3 mg) was added. The resulting mixture was stirred for 30 min, filtered through a small Celite pad, and the filtrate was concentrated. The residue was purified by a preparative reverse phase HPLC on a Waters Autopurification system using a Phenomenex Polymerx 10μ RP-γ 100A column [10 μm, 150×21.20 mm; flow rate, 20 mL/min; Solvent A: 0.05 N HCl/water; Solvent B: $CH_3CN$; injection volume: 3.0 mL (0.05 N HCl/water); gradient: 15→50% B over 15 min, then 100% B for 5 min; mass-directed fraction collection]. Fractions containing the desired product, eluting at 18.2-19.0 min, were collected and freeze-dried to yield compound S20-20-9 (1 mg, 40% for 2 steps): $^1$H NMR (400 MHz, CD3OD) δ 6.19 (s, 1 H), 4.23 (s, 2 H), 4.05 (s, 1 H), 3.13-2.77 (m, 13 H), 2.47 (t, J=14.2 Hz, 1 H), 2.17-1.95 (m, 3 H), 1.60-1.51 (m, 1 H), 1.05 (d, J=6.4 Hz, 6 H), 1.00 (d, J=6.4 Hz, 6 H); MS (ESI) m/z 571.50 (M+H).

EXAMPLE 21

Synthesis of Compounds Via Scheme 21

Scheme 21

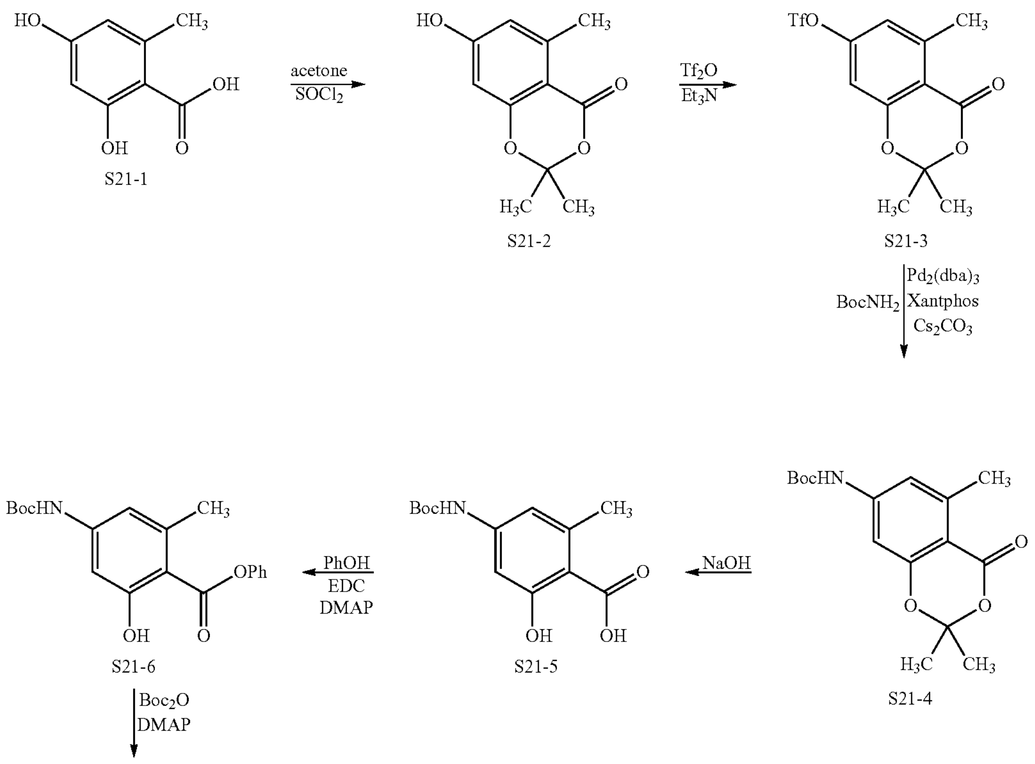

S21-1
S21-2
S21-3
S21-4
S21-5
S21-6

-continued

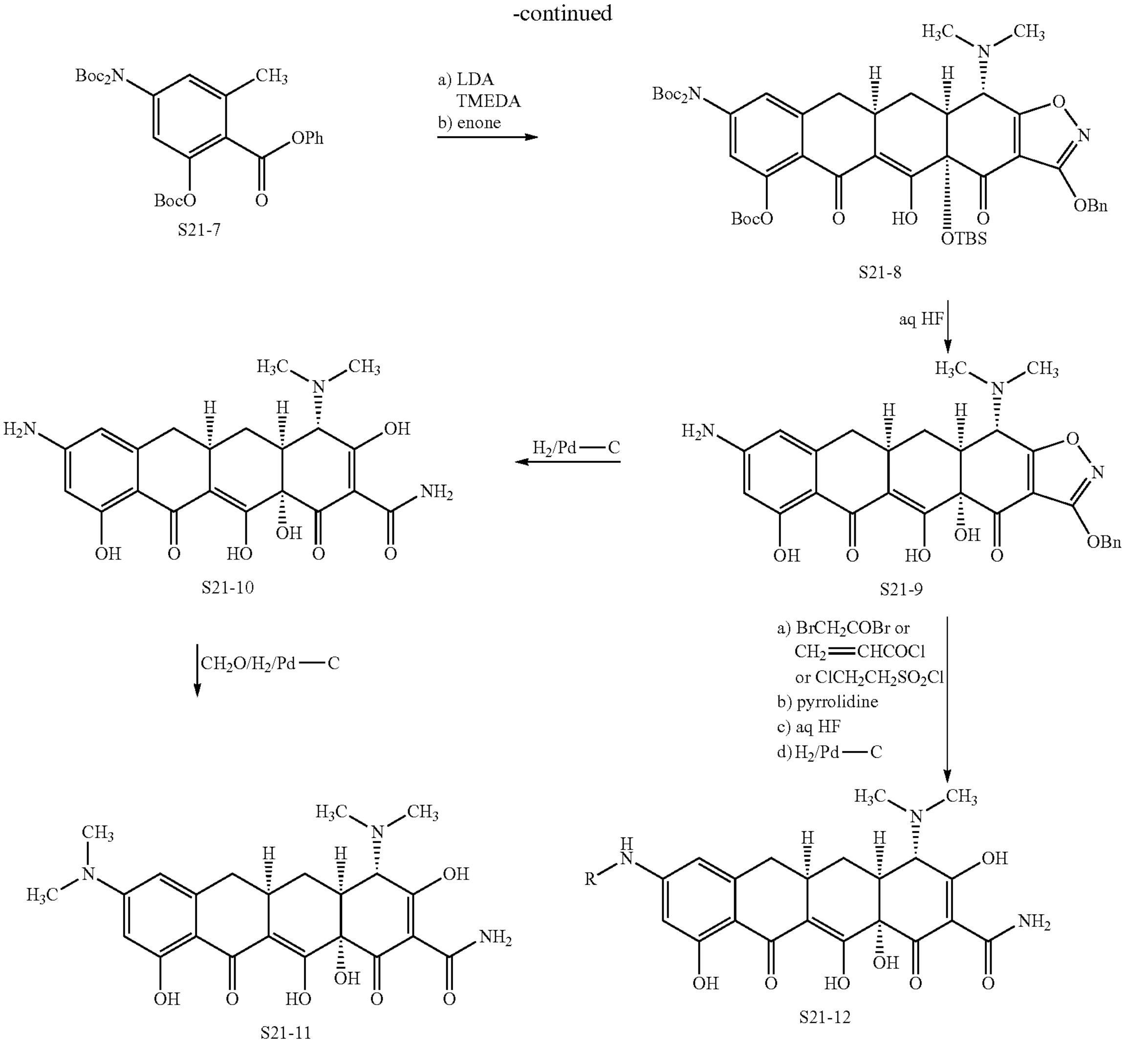

The following compounds were prepared according to Scheme 21.

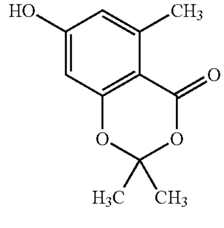

S21-2

To a white suspension of S21-1 (4.27 g, 25.40 mmol, 1.0 equiv), anhydrous acetone (4.20 mL, 57.20 mmol, 2.25 equiv), and DMAP (0.17 mg, 1.38 mmol, 0.05 equiv) in DME (60 mL) at 0° C. was added $SOCl_2$ (5.03 mL, 69.00 mmol, 2.70 equiv) dropwise. The resulting clear solution was stirred from 0° C. to rt for 2 hrs, and slowly added into saturated aqueous $NaHCO_3$ (300 mL). The mixture was extracted with EtOAc (100 mL×3). The combined extracts were dried over sodium sulfate and concentrated under reduced pressure to yield crude S21-2 as a yellow solid: $R_f$ 0.45 (40% EtOAc/hexanes); $^1$H NMR (400 MHz, $CDCl_3$) δ 6.38 (d, J=1.84 Hz, 1 H), 6.25 (d, J=2.44 Hz, 1 H), 2.61 (s, 3 H), 1.67 (s, 6 H).

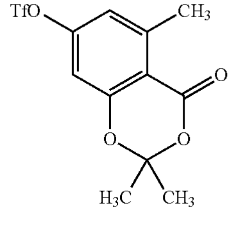

S21-3

To compound S21-2 (25.40 mmol, 1.0 equiv) and triethylamine (4.25 mL, 30.50 mmol, 1.2 equiv) in dry dichloromethane (70 mL) at 0° C. was added $Tf_2O$ (4.49 mL, 26.69 mmol, 1.05 equiv) dropwise. The reaction was stirred at 0° C. for 1 hr, quenched by saturated aqueous ammonium chloride (250 mL), and extracted with dichloromethane (100 mL×3). The dichloromethane extracts were dried over sodium sulfate and concentrated under reduced pressure. Flash column chromatography on silica gel with 0%-5% EtOAc/hexanes yielded the desired compound S21-3 as a pale solid after standing in a refrigerator overnight (7.23 g, 84% 2 steps): $R_f$ 0.33 (10% EtOAc/hexanes); $^1$H NMR (400 MHz, $CDCl_3$) δ 6.82 (d, J=1.84 Hz, 1 H), 6.77 (d, J=2.44 Hz, 1 H), 2.71 (s, 3 H), 1.71 (s, 6 H).

S21-4

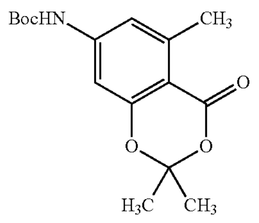

To compound S21-3 (3.40 g, 10.00 mmol, 1.0 equiv), t-butylcarbamate (1.76 g, 15.00 mmol, 1.5 equiv), cesium carbonate (5.86 g, 18.00 mmol, 1.8 equiv), and Xantphos (0.69 g, 1.20 mmol, 0.12 equiv) in dry dioxane (50 mL) at room temperature was added $Pd_2(dba)_3$ (0.18 g, 0.20 mmol, 0.04 equiv Pd). The mixture was purged by bubbling with dry nitrogen gas for 5 min with gentle stirring. The reaction vessel was then heated under nitrogen at 80° C. for 5 hrs with rapid stirring. The resulting light-green mixture was cooled to rt, diluted with water (200 mL), and extracted with EtOAc (200 mL×1, 50 mL×2). The EtOAc extracts were dried over sodium sulfate and concentrated under reduced pressure. Flash column chromatography on silica gel with 0%-20% EtOAc/hexanes afforded the desired product S21-4 as a pale solid (quantitative): $R_f$ 0.45 (20% EtOAc/hexanes); $^1$H NMR (400 MHz, $CDCl_3$) δ 7.06 (d, J=1.80 Hz, 1 H), 6.72 (d, J=1.80 Hz, 1 H), 6.56 (br s, 1 H), 2.61 (s, 3 H), 1.66 (s, 6 H), 1.50 (s, 9 H).

S21-5

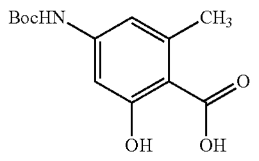

Compound S21-4 (10.00 mmol, 1.0 equiv) was dissolved in dioxane (50 mL). Water (50 mL) and 6 N aqueous NaOH (8.30 mL, 50.00 mmol, 5.0 equiv) were added. The pale suspension was heated at 70° C. with stirring for 20 hrs. The resulting clear yellow solution was cooled to 0° C., carefully acidified with 0.5 N aqueous HCl to pH 5-6, and extracted with EtOAc (200 mL×1, 50 mL×5). The EtOAc extracts were dried over sodium sulfate and concentrated under reduced pressure to yield crude S21-5 as a pale solid (quantitative): $R_f$ 0.10 (20% EtOAc/hexanes); $^1$H NMR (400 MHz, $CDCl_3$ with 2 drops of $CD_3OD$) δ 6.85 (br s, 1 H), 6.76 (br s, 1 H), 2.51 (s, 3 H), 1.48 (s, 9 H).

S21-6

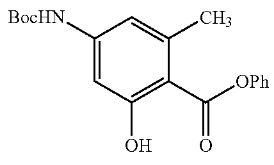

To compound S21-5 (10.00 mmol, 1.0 equiv) in dry dichloromethane was added phenol (1.88 g, 20.00 mmol, 2.0 equiv), DMAP (1.34 g, 11.00 mmol, 1.1 equiv), and EDC (4.79 g, 25.00 mmol, 2.5 equiv). The light-yellow solution was stirred at rt for 20 hrs, diluted with EtOAc (300 mL), washed with saturated aqueous ammonium chloride (100 mL×2), saturated aqueous sodium bicarbonate (100 mL×2), and brine (100 mL×1). The EtOAc solution was dried over sodium sulfate and concentrated under reduced pressure to yield crude S21-6 as a light brown oil (quantitative).

S21-7

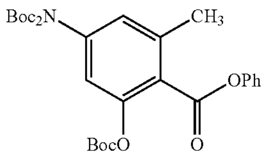

Compound S21-6 (10.00 mmol, 1.0 equiv) was dissolved in dry DMF (25 mL). Di-t-butyl dicarbonate (6.55 g, 30.00 mmol, 3.0 equiv), DIEA (6.97 mL, 40.00 mmol, 4.0 equiv), and DMAP (61 mg, 0.50 mmol, 0.05 equiv) were added. The solution was stirred at rt for 20 hrs, diluted with EtOAc (200 mL), and washed with water (250 mL×1), saturated aqueous sodium bicarbonate (100 mL×2), and brine (100 mL×1). The EtOAc solution was dried over sodium sulfate and concentrated under reduced pressure. Flash column chromatography on silica gel with 0%-15% EtOAc/hexanes yielded the desired product S21-7 as a white solid (3.48 g, 64% 4 steps): $R_f$ 0.50 (20% EtOAc/hexanes); $^1$H NMR (400 MHz, $CDCl_3$) δ 7.39-7.43 (m, 2 H), 7.22-7.26 (m, 3 H), 6.96 (br s, 1 H), 6.93 (d, J=1.84 Hz, 1 H), 2.51 (s, 3 H), 1.43 (s, 18 H), 1.43 (s, 9 H).

S21-8

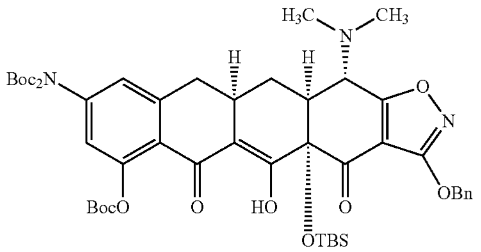

To diisopropylamine (28 μL, 0.20 mmol, 2.0 equiv) in anhydrous THF (4 mL) at −78° C. was added n-BuLi (0.13 mL, 1.6 M/hexanes, 0.20 mmol, 2.0 equiv). The solution was stirred at 0° C. for 10 min and cooled to −78° C. TMEDA (33 μL, 0.22 mmol, 2.2 equiv) was added, followed by dropwise addition of compound S21-7 (0.11 g, 0.20 mmol, 2.0 equiv) in anhydrous THF (4 mL) over a period of 5 min. Additional LDA (0.17 mL, 1.2 M/heptane/THF/ethylbenzene, 0.20 mmol, 2.0 equiv) was added. The resulting deep-red solution was stirred at −78° C. for 15 min. Enone (48 mg, 0.10 mmol, 1.0 equiv) in anhydrous THF (4 mL) was added. The resulting red-brown solution was slowly warmed to −10° C. over a period of 1 hr, quenched by pH 7 phosphate buffer (40 mL), and extracted with EtOAc (20 mL×3). The EtOAc extracts were combined, dried over sodium sulfate, and concentrated under reduced pressure. Flash column chromatography on silica gel with 0%-10% EtOAc/hexanes yielded the desired product S21-8 as a yellow foam (85 mg, 91%): $R_f$ 0.45 (20% EtOAc/hexanes); $^1$H NMR (400 MHz, $CDCl_3$) δ 15.72 (s, 1

H), 7.30-7.50 (m, 5 H), 6.94 (d, J=1.8 Hz, 1 H), 6.86 (d, J=1.8 Hz, 1 H), 5.34 (s. 2 H), 3.94 (d, J=10.4 Hz, 1 H), 2.80-3.20 (m, 2 H), 2.45-2.55 (m, 10 H), 1.52 (s, 9 H), 1.43 (s, 18 H), 0.82 (s, 9 H), 0.25 (s, 3 H), 0.11 (s, 3 H); MS (ESI) m/z 932.3 (M+H), calcd for $C_{49}H_{65}N_3O_{13}Si$ 931.4.

S21-9

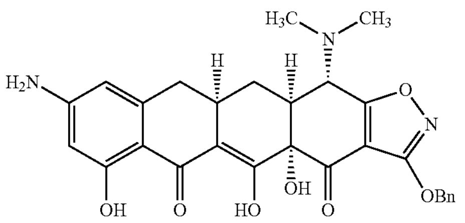

To compound S21-8 (82 mg, 0.088 mmol) in THF (1.5 mL) was added 50% aqueous HF (0.5 mL, 48-50%). The bright yellow solution was stirred at rt overnight, diluted with aqueous $K_2HPO_4$ (7.5 g in 30 mL water), and extracted with EtOAc (20 mL×3). The EtOAc extracts were combined, dried over sodium sulfate, and concentrated under reduced pressure to yield crude S21-9 as a yellow solid (37 mg, 81%): MS (ESI) m/z 518.3 (M+H), calcd for $C_{28}H_{27}N_3O_7$ 517.2.

S21-10

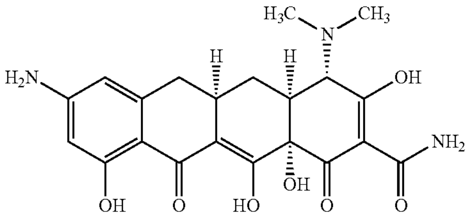

To compound S21-9 (37 mg, 0.071 mmol, 1.0 equiv) in MeOH (7 mL) and dioxane (1 mL) was added 0.5 N HCl/MeOH (2 mL) and 10% Pd—C (30 mg, 0.014 mmol, 0.20 equiv). The mixture was purged with hydrogen and stirred under 1 atm hydrogen atmosphere at rt for 1 h. The catalyst was filtered off with a small Celite pad, and the Celite pad was washed with MeOH (5 mL×3). The yellow MeOH solution was concentrated under reduced pressure. One half of the crude product was purified by reverse phase HPLC using similar conditions for S2-4-1 to give the desired product S21-10 as an orange solid (9 mg, 24%, bis-HCl salt): $^1H$ NMR (400 MHz, $CD_3OD$) δ 6.17 (s, 1 H), 6.12 (s, 1 H), 4.03 (s, 1 H), 3.03 (s, 3 H), 2.97 (s, 3 H), 2.75-3.20 (m, 2 H), 2.72 (dd, J=5.9, 14.8 Hz, 1 H), 2.45 (t, J=14.3 Hz, 1 H), 2.08-2.16 (m, 1 H), 1.40-1.60 (m, 1 H); MS (ESI) m/z 430.2 (M+H), calcd for $C_{21}H_{23}N_3O_7$ 429.2.

S21-11

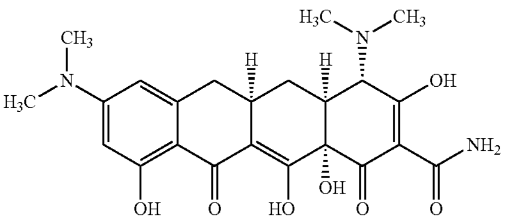

To compound S21-10 (7 mg, 0.014 mmol, 1.0 equiv) in MeOH (2 mL) was added HCl/MeOH (0.5 mL, 0.5 N) and 10% Pd—C (5 mg, 0.0020 mmol, 0.16 equiv). The mixture was purged with hydrogen and stirred under 1 atm hydrogen atmosphere at rt for 3 hrs. The catalyst was filtered off with a small Celite pad, and the Celite pad was washed with MeOH (2 mL×3). The yellow MeOH solution was concentrated under reduced pressure. HPLC purification using similar conditions for S2-4-1 yielded the desired product S21-11 as a bright yellow solid (4 mg, 47%, bis-HCl salt): $^1H$ NMR (400 MHz, $CD_3OD$) δ 4.06 (s, 1 H), 3.13 (s, 6 H), 3.03 (s, 3 H), 2.97 (s, 3 H), 2.90-3.20 (m, 2 H), 2.83 (dd, J=4.9, 14.6 Hz, 1 H), 2.50 (t, J=14.3 Hz, 1 H), 2.12-2.20 (m, 1 H), 1.49-1.60 (m, 1 H); MS (ESI) m/z 458.3 (M+H), calcd for $C_{23}H_{27}N_3O_7$ 457.2.

S21-12-1

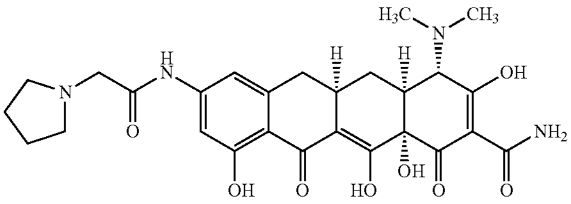

Bromoacetyl bromide (5 μL, 0.057 mmol. 1.1 equiv) was added to compound S21-9 (36 mg, 0.051 mmol, 1.0 equiv) in THF (2 mL) at rt. The bright yellow solution was stirred at rt for 1 h. Pyrrolidine (0.021 mL, 0.25 mmol, 5.0 equiv) was added. The reaction was stirred at rt for another hour and concentrated under reduced pressure to yield the crude intermediate: MS (ESI) m/z 743.4 (M+H), calcd for $C_{40}H_{50}N_4O_8Si$ 742.3.

To the above crude intermediate (0.051 mmol) in THF (1.5 mL) was added 50% aqueous HF (0.5 mL, 48-50%). The bright yellow solution was stirred at rt for 4 hrs, diluted with aqueous $K_2HPO_4$ (7.5 g in 30 mL water), and extracted with EtOAc (30 mL×3). The EtOAc extracts were combined, dried over sodium sulfate, and concentrated under reduced pressure to yield the crude desilylated product as a yellow solid: MS (ESI) m/z 629.3 (M+H), calcd for $C_{34}H_{36}N_4O_8$ 628.2.

To the above crude desilylated product (0.051 mmol, 1.0 equiv) in MeOH (4 mL) was added HCl (1 mL, 0.5 N/MeOH) and 10% Pd—C (22 mg, 0.010 mmol, 0.2 equiv). The mixture was purged with hydrogen and stirred under 1 atm hydrogen atmosphere at rt for 1 h. The catalyst was filtered off with a small Celite pad, and the Celite pad was washed with MeOH (5 mL×3). The yellow MeOH solution was concentrated under reduced pressure. HPLC purification using similar conditions for S2-4-1 yielded the desired product S21-12-1 as a bright yellow solid (17 mg, 55% 3 steps, bis-HCl salt): $^1H$ NMR (400 MHz, $CD_3OD$) δ 7.24 (s, 1 H), 6.96 (s, 1 H), 4.29 (s, 2 H), 4.09 (s, 1 H), 3.75-3.85 (m, 2 H), 3.15-3.28 (m, 2 H), 3.05 (s, 3 H), 2.98 (s, 3 H), 2.90-3.20 (m, 2 H), 2.83 (dd, J=5.2, 15.5 Hz, 1 H), 2.54 (t, J=14.3 Hz, 1 H), 2.00-2.22 (m, 5 H), 1.50-1.65 (m, 1 H); MS (ESI) m/z 541.3 (M+H), calcd for $C_{27}H_{32}N_4O_8$ 540.2.

S21-12-2

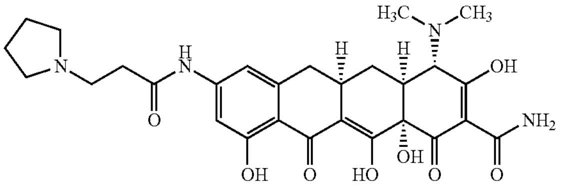

Acryloyl chloride (9 μL, 0.11 mmol, 2.0 equiv) was added to compound S21-9 (36 mg, 0.051 mmol, 1.0 equiv) in THF (2 mL) at rt. The yellow solution was stirred at rt overnight. Pyrrolidine (0.021 mL, 0.25 mmol, 5.0 equiv) was added. The reaction was stirred at rt for another hour and concentrated under reduced pressure to yield the crude intermediate: MS (ESI) m/z 757.4 (M+H), calcd for $C_{41}H_{52}N_4O_8Si$ 756.4.

The crude intermediate was treated with aqueous HF followed by hydrogenation under similar conditions to that in the preparation of compound S21-12-1 to yield the desired product S21-12-2 as a bright-yellow solid (17 mg, 53% 3 steps, bis-HCl salt): $^1H$ NMR (400 MHz, $CD_3OD$) δ 7.24 (s, 1 H), 6.95 (s, 1 H), 4.06 (s, 1 H), 3.65-3.75 (m, 2 H), 3.54 (t, J=8.0 Hz, 2 H), 3.10-3.20 (m, 2 H), 2.80-3.20 (m, 10 H), 2.80 (dd, J=5.3, 18.7 Hz, 1 H), 2.53 (t, J=14.0 Hz, 1 H), 2.10-2.22 (m, 3 H), 2.00-2.10 (m, 2 H), 1.50-1.63 (m, 1 H); MS (ESI) m/z 555.3 (M+H), calcd for $C_{28}H_{34}N_4O_8$ 554.2.

S21-12-3

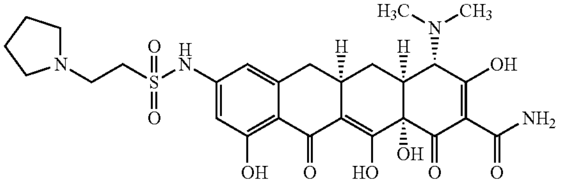

N-Methyl morpholine (0.028 mL, 0.25 mmol, 15 equiv), chloroethanesulfonyl chloride (0.027 mL, 0.25 mmol, 15 equiv), and DMAP (2 mg, 0.017 mmol, 1.0 equiv) were added to compound S21-9 (12 mg, 0.017 mmol, 1.0 equiv) in THF (2 mL) at rt. The reaction was stirred at rt for 72 hrs. Pyrrolidine (0.071 mL, 0.85 mmol, 50 equiv) was added. The reaction was stirred at rt for 30 min. Aqueous HF (2 mL, 48-50%) was added. The reaction was stirred at rt overnight. The yellow solution was diluted with aqueous $K_2HPO_4$ (20 g in 80 mL water) and extracted with EtOAc (30 mL×3). The EtOAc extracts were combined, dried over sodium sulfate, and concentrated under reduced pressure to yield the crude deisilylated sulfonamide: MS (ESI) m/z 679.3 (M+H), calcd for $C_{34}H_{38}N_4O_9S$ 678.2.

The above crude product (0.017 mmol, 1.0 equiv) was dissolved in MeOH (3 mL) and dioxane (1 mL). HCl/MeOH (1 mL, 0.5 N) and 10% Pd—C were added. The mixture was purged with hydrogen and stirred under 1 atm hydrogen atmosphere at rt for 3 hrs. The catalyst was filtered off with a small Celite pad, and the Celite pad was washed with MeOH (2 mL×3). The MeOH filtrate was concentrated under reduced pressure. HPLC purification using similar conditions for S2-4-1 yielded the desired product S21-12-3 as a bright-yellow solid (3 mg, 27% 3 steps, bis-HCl salt): $^1H$ NMR (400 MHz, $CD_3OD$) δ 6.03 (s, 1 H), 5.92 (s, 1 H), 4.02 (s, 1 H), 3.63 (t, J=7.0 Hz, 2 H), 2.80-3.40 (m, 8 H), 3.02 (s, 3 H), 2.96 (s, 3 H), 2.70 (dd, J=4.9, 14.7 Hz, 1 H), 2.41 (t, J=13.7 Hz, 1 H), 1.85-1.95 (m, 4 H), 1.45-1.60 (m, 1 H); MS (ESI) m/z 591.3 (M+H), calcd for $C_{27}H_{34}N_4O_9S$ 590.2.

S21-12-4

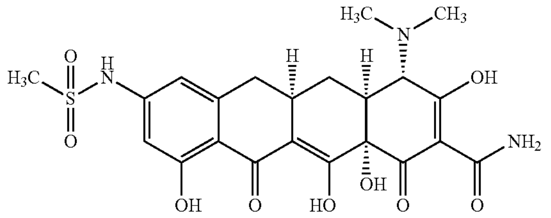

To a suspension of S21-9 (35 mg, 0.056 mmol, 1.0 equiv) in dichloromethane (0.22 mL) was added pyridine (14 μL, 0.17 mmol, 3.0 equiv) and methanesulfonyl chloride (5 μL, 0.061 mmol, 1.1 equiv). The heterogeneous mixture was stirred at room temperature for 21 hrs, and was concentrated under reduced pressure to remove solvent and excess pyridine. This crude mixture was then dissolved in dioxane (1.2 mL) in a plastic vial. Aqueous HF (0.3 mL, 48-50%) was then added and the reaction was stirred at room temperature for 19 hrs. The reaction mixture was poured into an aqueous solution of $K_2HPO_4$ (3.6 g in 30 mL) and was extracted with EtOAc (2×25 mL). The combined organic layers were dried over sodium sulfate, were filtered, and were concentrated under reduced pressure to provide an orange oil. This oil was dissolved in MeOH/dioxane (1 mL, 1:1) and Pd—C (10 mg, 10 wt %) was added. The reaction was purged with hydrogen and stirred under hydrogen (balloon) at room temperature for 22 hrs. The reaction mixture was filtered through a small Celite plug and the filtrate was concentrated under reduced pressure. The crude product was purified via preparative reverse phase HPLC on a Waters Autopurification system using a Phenomenex Polymerx μ RP-γ 100A column [10 μm, 150×21.20 mm; flow rate, 20 mL/min; Solvent A: 0.05 N HCl/water; Solvent B: $CH_3CN$; injection volume: 2.2 mL (0.05 N HCl/water); gradient: 0→70% B over 15 min; mass-directed fraction collection]. Fractions containing the desired product, eluting at 8.9-9.7 min, were collected and freeze-dried to yield 3 mg of compound S21-12-4 as a yellow solid (12% for 3 steps): $^1H$ NMR (400 MHz, $CD_3OD$) δ 6.63-6.61 (m, 1 H), 6.58 (br s, 1 H), 4.04 (s, 1 H), 3.10-2.89 (m, 8 H), 2.79 (dd, J=15.3, 4.3 Hz, 1 H), 2.52 (t, J=14.7 Hz, 1 H), 2.19-2.09 (m, 1 H), 1.63-1.48 (m, 1 H); MS (ESI) m/z 508.24 (M+H).

S21-12-5

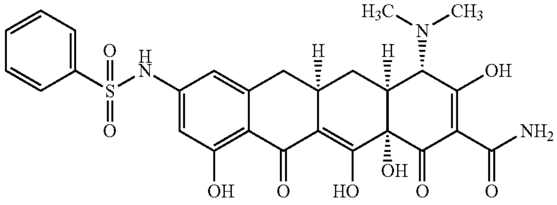

To a suspension of S21-9 (35 mg, 0.056 mmol, 1.0 equiv) in dichloromethane (0.22 mL) was added pyridine (14 μL, 0.17 mmol, 3.0 equiv) and benzenesulfonyl chloride (8 μL, 0.061 mmol, 1.1 equiv). The heterogeneous mixture was stirred at room temperature for 21 hrs and was concentrated under reduced pressure to remove solvent and excess pyridine. This crude mixture was then dissolved in dioxane (1 mL) in a plastic vial. Aqueous HF (0.25 mL, 48-50%) was added and the reaction mixture was stirred at room temperature for 3 hrs. The reaction mixture was poured into an aqueous solution of $K_2HPO_4$ (3.0 g in 25 mL) and was extracted with EtOAc (2x25 mL). The combined organic layers were dried over sodium sulfate, were filtered, and were concentrated under reduced pressure to provide an orange oil. This oil was dissolved in MeOH/dioxane (1 mL, 1:1) and Pd—C (10 mg, 10 wt %) was added. The reaction was purged with hydrogen and stirred under hydrogen (balloon) at room temperature for 17 hrs. The reaction mixture was filtered through a small Celite plug and the filtrate was concentrated under reduced pressure. The crude product was purified via preparative reverse phase HPLC on a Waters Autopurification system using a Phenomenex Polymerx μ RP-γ 100A column [10 μm, 150x21.20 mm; flow rate, 20 mL/min; Solvent A: 0.05 N HCl/water; Solvent B: $CH_3CN$; injection volume: 3.8 mL (0.05 N HCl/water); gradient: 20→70% B over 15 min; mass-directed fraction collection]. Fractions containing the desired product, eluting at 9.0-10.1 min, were collected and freeze-dried to yield 4 mg of compound S21-12-5 as a yellow solid (13% for 3 steps): $^1$H NMR (400 MHz, $CD_3OD$) δ 7.90-785 (m, 2 H), 7.63-7.57 (m, 1 H), 7.56-7.49 (m, 2 H), 6.56-6.53 (m, 1 H), 6.48 (br s, 1 H), 3.99 (s, 1 H), 3.01-2.83 (m, 8 H), 2.69 (dd, J=15.3, 4.3 Hz, 1 H), 2.43 (t, J=14.6 Hz, 1 H), 2.15-2.06 (m, 1 H), 1.59-1.46 (m, 1 H); MS (ESI) m/z 570.25 (M+H).

S21-12-6

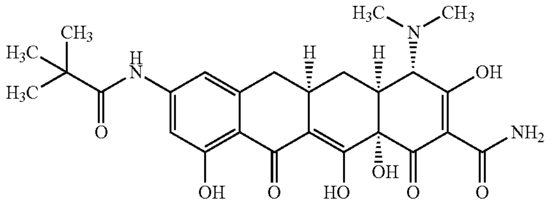

To a suspension of S21-9 (34 mg, 0.053 mmol, 1.0 equiv) in dichloromethane (0.22 mL) was added trimethylacetylchloride (7 μL, 0.058 mmol, 1.1 equiv). The mixture was heterogeneous after 2 hrs and the reaction was complete after 4 hrs. The reaction mixture was concentrated under reduced pressure. The residue was redissolved in dioxane (1.2 mL) in a plastic vial. Aqueous HF (0.25 mL, 48-50%) was added and the reaction mixture was stirred at room temperature for 13 hrs. The reaction mixture was poured into an aqueous solution of $K_2HPO_4$ (3.1 g in 25 mL) and was extracted with EtOAc (2x25 mL). The combined organic layers were dried over sodium sulfate, were filtered, and were concentrated under reduced pressure to provide an orange oil. This oil was dissolved MeOH/dioxane (1 mL, 1:1) and Pd—C (10 mg, 10 wt %) was added. The reaction was purged with hydrogen and stirred under hydrogen (balloon) at room temperature for 2 hrs. The reaction mixture was filtered through a small Celite plug and the filtrate was concentrated under reduced pressure. The crude product was purified via preparative reverse phase HPLC on a Waters Autopurification system using a Phenomenex Polymerx μ RP-γ 100A column [10 μm, 150x21.20 mm; flow rate, 20 mL/min; Solvent A: 0.05 N HCl/water; Solvent B: $CH_3CN$; injection volume: 2.2 mL (0.05 N HCl/water); gradient: 20→70% B over 15 min; mass-directed fraction collection]. Fractions containing the desired product, eluting at 8.0-9.5 min, were collected and freeze-dried to yield 15 mg of compound S21-12-6 as a yellow solid (53% for 3 steps): $^1$H NMR (400 MHz, $CD_3OD$) δ 7.18 (d, J=1.93, 1 H), 7.04 (br s, 1 H), 4.06 (s, 1 H), 3.11-2.88 (m, 8 H), 2.76 (dd, J=15.3, 4.2 Hz, 1 H), 2.51 (t, J=14.0 Hz, 1 H), 2.20-2.12 (m, 1 H), 1.62-1.49 (m, 1 H), 1.27 (s, 9 H); MS (ESI) m/z 514.32 (M+H).

EXAMPLE 22

Synthesis of Compounds Via Scheme 22

Scheme 22

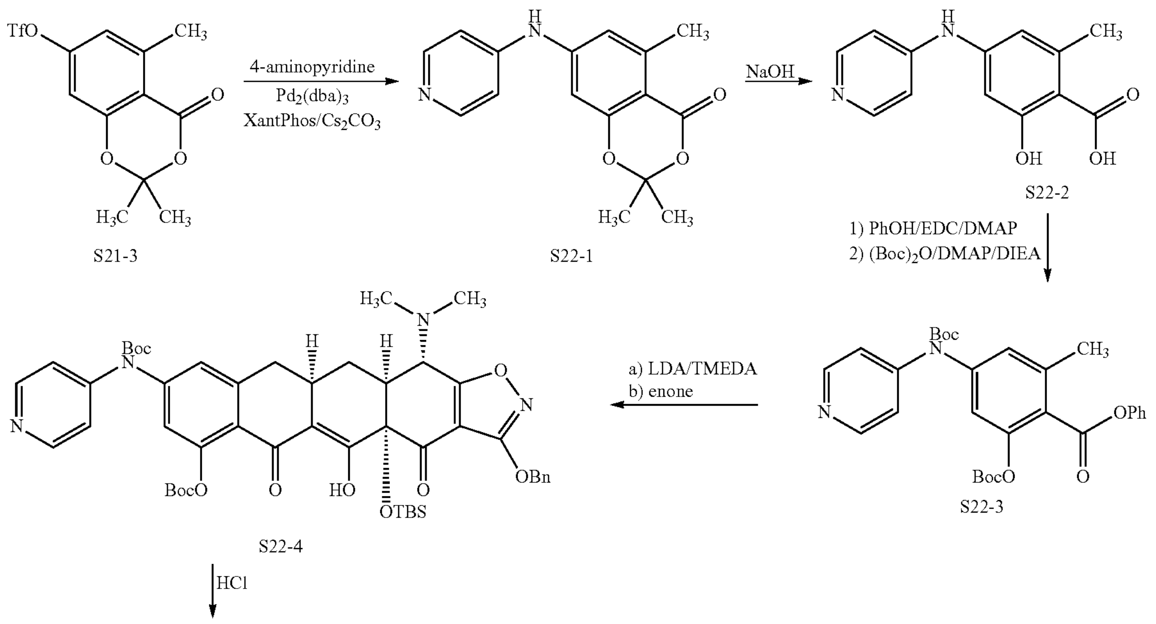

S21-3

S22-1

S22-2

S22-3

S22-4

-continued

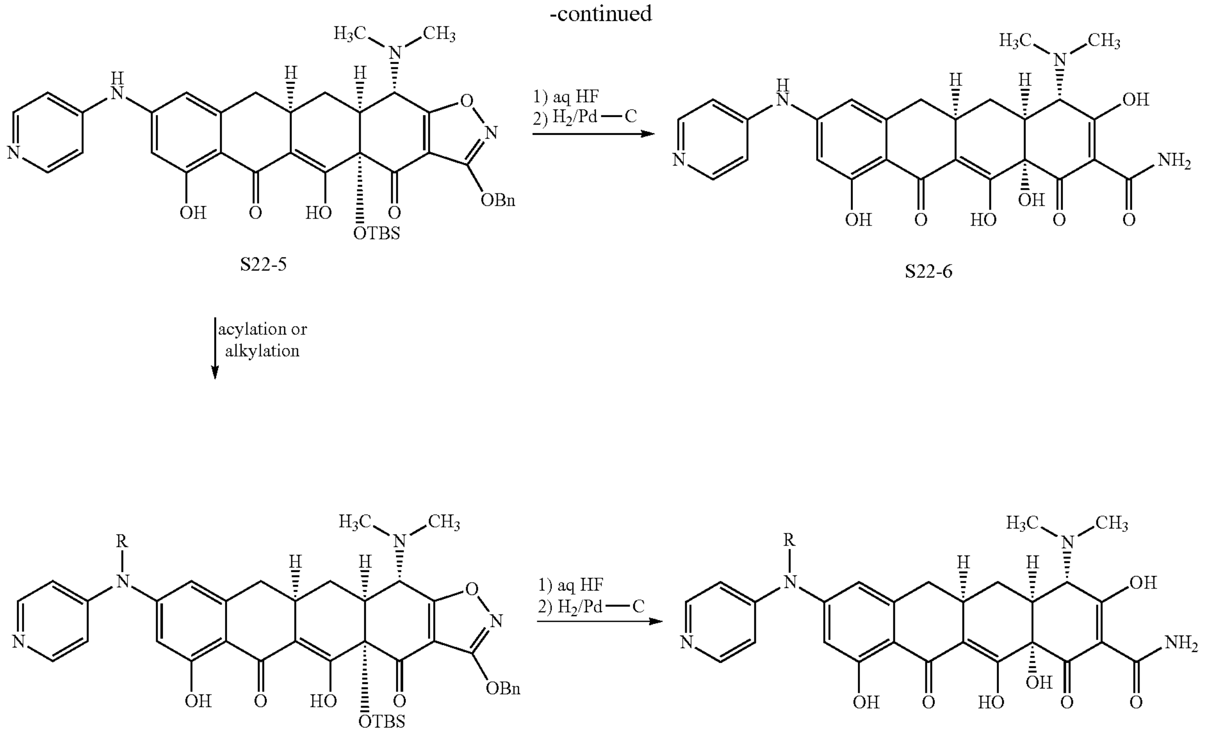

S22-5 S22-6 S22-7 S22-8

The following compounds were prepared according to Scheme 22.

S22-1

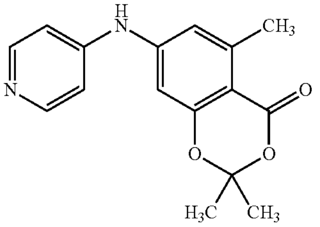

Compound S21-3 (1.02 g, 3.00 mmol, 1.0 equiv) was dissolved in dry 1,4-dioxane (20 mL). 4-Aminopyridine (0.42 g, 4.50 mmol, 1.5 equiv), cesium carbonate (1.76 g, 5.40 mmol, 1.8 equiv), Xantphos (0.21 g, 0.36 mmol, 0.12 equiv), and $Pd_2(dba)_3$ (55 mg, 0.060 mmol, 0.02 equiv) were added. The mixture was purged with dry nitrogen, heated at 80° C. with vigorous stirring for 2 hrs, cooled to rt, diluted with water (100 mL), and extracted with EtOAc (100 mL×1, 20 mL×2). The EtOAc extracts were combined, dried over sodium sulfate, and concentrated under reduced pressure. Flash column chromatography on silica gel with 50% EtOAc/hexanes, 100% EtOAc/hexanes, and 10% MeOH/dichloromethane yielded the desired product S22-1 as a pale solid (0.613 g, 72%): $R_f$=0.17 10% MeOH/dichloromethane; $^1$H NMR (400 MHz, $CD_3OD$) δ 8.30 (d, J=6.7 Hz, 2 H), 6.98 (d, J=6.7 Hz, 2 H), 6.58 (s, 2 H), 2.60 (s, 3 H), 1.66 (s, 6 H); MS (ESI) m/z 285.0 (M+H), calcd for $C_{16}H_{16}N_2O_3$ 284.1.

S22-2

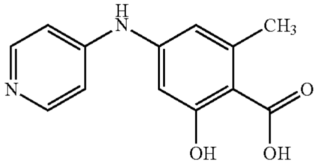

Compound S22-1 (0.55 g, 1.93 mmol, 1.0 equiv) was dissolved in dioxane (9 mL) and water (7.4 mL). Aqueous NaOH (1.61 mL, 6 N, 9.66 mmol, 5.0 equiv) was added. The suspension was heated at 70° C. with stirring overnight, cooled to rt, neutralized with 6 N aqueous HCl to pH 6-7. The precipitates were collected, washed with water (2 mL×3) and ethanol (2 mL×3), and dried under reduced pressure to yield the desired compound S22-2 as a pale solid (quantitative): $^1$H NMR (400 MHz, $CD_3OD$) δ 8.15 (d, J=7.3 Hz, 2 H), 7.15 (d, J=7.3 Hz, 2 H), 6.59 (d, J=1.8 Hz, 1 H), 6.53 (d, J=1.8 Hz, 1 H), 2.61 (s, 3 H); MS (ESI) m/z 245.0 (M+H), calcd for $C_{13}H_{12}N_2O_3$ 244.1.

S22-3

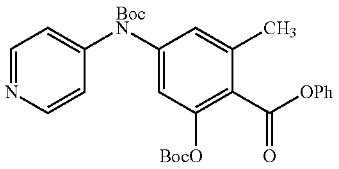

Compound S22-2 (0.57 g, 2.34 mmol, 1.0 equiv) was dissolved in dichloromethane (50 mL). Phenol (0.44 g, 4.68 mmol, 2.0 equiv), DMAP (0.32 g, 2.58 mmol, 1.1 equiv), DIEA (1.22 mL, 7.00 mmol, 3.0 equiv), and EDC (1.12 g, 5.84 mmol, 2.5 equiv) were added. The solution was stirred at rt for 48 hrs. Most of the dichloromethane was removed under reduced pressure. The residue was re-dissolved in EtOAc (100 mL), washed with water (100 mL×2), saturated aqueous sodium bicarbonate (50 mL×2) and brine (50 mL×1), dried over sodium sulfate, and concentrated under reduced pressure to yield the crude phenyl ester as a pale foam.

The above crude phenyl ester was dissolved in dry DMF (10 mL). Di-t-butyl dicarbonate (1.66 g, 7.61 mmol, 3.0 equiv), DIEA (1.77 mL, 10.16 mmol, 4.0 equiv), and DMAP (16 mg, 0.13 mmol, 0.05 equiv) were added. The reaction was stirred at rt for 24 hrs. More di-t-butyl dicarbonate (0.60 g) and DIEA (0.60 mL) were added. Stirring was continued at rt for another 24 hrs. The deep red reaction solution was diluted with EtOAc (100 mL), washed with water (200 mL×1), saturated aqueous sodium bicarbonate (100 mL×2) and brine (100 mL×1), dried over sodium sulfate, and concentrated under reduced pressure. Flash column chromatography on silica gel with 0% to 5% MeOH/dichloromethane yielded the desired product S22-3 as a light-yellow foam (0.18 g, 13%): $R_f$=0.80 (10% MeOH/dichloromethane); $^1$H NMR (400 MHz, $CDCl_3$) δ 8.49 (d, J=6.1 Hz, 2 H), 7.40-7.45 (m, 2 H), 7.20-7.30 (m, 3 H), 7.15 (d, J=6.1 Hz, 2 H), 6.95 (s, 1 H), 6.90 (s, 1 H), 2.49 (s, 3 H), 1.46 (s, 9 H), 1.42 (s, 9 H); MS (ESI) m/z 521.3 (M+H), calcd for $C_{29}H_{32}N_2O_7$ 520.2.

S22-4

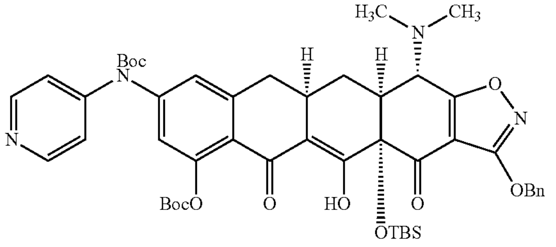

To diisopropylamine (0.053 mL, 0.37 mmol, 2.2 equiv) in anhydrous THF (5 mL) at −78° C. was added n-BuLi (0.24 mL, 1.6 M/hexanes, 0.38 mmol, 2.2 equiv). The pale solution was stirred at 0° C. for 10 min and cooled to −78° C. TMEDA (0.062 mL, 0.41 mmol, 2.4 equiv) was added, followed by dropwise addition of a solution of compound S22-3 (0.18 g, 0.34 mmol, 2.0 equiv) in THF (4 mL) over a period of 10 min. Additional LDA (0.38 mmol, 2.2 equiv) was added. The deep red solution was stirred at −78° C. for 15 min. Enone S1-9 (82 mg, 0.017 mmol, 1.0 equiv) in THF (5 mL) was added dropwise over a period of 5 min. The red solution was slowly warmed to −10° C. over a period of 1 h, quenched by pH 7 phosphate buffer (1 M, 50 mL), and extracted with EtOAc (20 mL×3). The EtOAc extracts were combined, dried over sodium sulfate, and concentrated under reduced pressure. Flash column chromatography on silica gel with 0% to 2% MeOH/dichloromethane yielded the desired product S22-4 as a yellow oil (0.20 g, ~80% pure): MS (ESI) m/z 909.3 (M+H), calcd for $C_{49}H_{60}N_4O_{11}Si$ 908.4.

S22-5

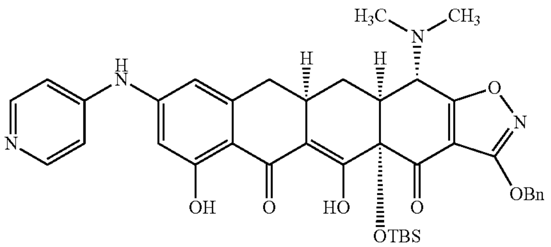

Compound S22-4 (0.17 mmol) in dioxane (5 mL) was added with 4 N HCl/dioxane (5 mL). The reaction was stirred at rt overnight and concentrated under reduced pressure. The residue was partitioned between aqueous sodium bicarbonate (50 mL) and EtOAc (50 mL). The aqueous layer was extracted with more EtOAc (20 mL×3). The combined organic layers were dried over sodium sulfate and concentrated under reduced pressure. Flash column chromatography on silica gel with 0% to 10% MeOH/dichloromethane yielded the desired product S22-5 as a yellow solid (62 mg, 51% 2 steps): $^1$H NMR (400 MHz, $CDCl_3$) δ 14.06 (br s, 1 H), 12.03 (s, 1 H), 11.43 (s, 1 H), 7.17-7.50 (m, 8 H), 6.95-7.05 (m, 3 H), 5.35 (s, 2 H), 3.89 (d, J=9.8 Hz, 1 H), 3.00-3.10 (m, 1 H), 2.7-2.95 (m, 2 H), 2.40-2.55 (m, 2 H), 2.46 (s, 6 H), 2.00-2.10 (m, 1 H), 0.84 (s, 9 H), 0.28 (s, 3 H), 0.14 (s, 3 H); MS (ESI) m/z 709.4 (M+H), calcd for $C_{39}H_{44}N_4O_7Si$ 708.3.

S22-6

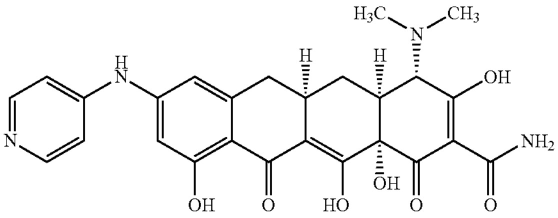

Compound S22-5 (15 mg, 0.021 mmol) was treated with aqueous HF followed by hydrogenation under similar conditions to that in the preparation of compound S21-12-1 to yield the desired product S22-6 as a bright-yellow solid (6 mg, 46% 2 steps, tris-HCl salt): $^1$H NMR (400 MHz, $CD_3OD$) δ 8.30 (d, J=7.3 Hz, 2 H), 7.38 (d, J=7.3 Hz, 2 H), 6.80 (s, 1 H), 6.76 (s, 1 H), 4.10 (s, 1 H), 2.85-3.50 (m, 3 H), 3.05 (s, 3 H), 2.98 (s, 3 H), 2.55-2.65 (m, 1 H), 2.15-2.25 (m, 1 H), 1.55-1.65 (m, 1 H); MS (ESI) m/z 507.1 (M+H), calcd for $C_{26}H_{26}N_4O_7$ 506.2.

S22-7-1

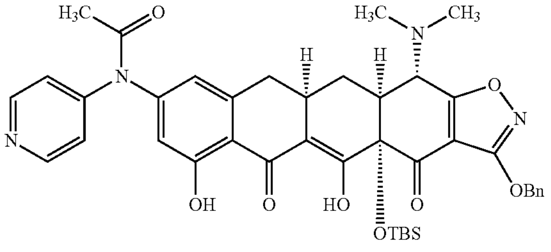

Compound S22-5 (15 mg, 0.021 mmol, 1.0 equiv) was dissolved in dichloromethane. DIEA (0.030 mL, 0.17 mmol, 8.0 equiv) and acetic anhydride (7μ, 0.069 mmol, 3.5 equiv) were added in three equal portions over a period of 4 days at rt. MeOH (1 mL) was added. The yellow solution was concentrated under reduced pressure. HPLC purification using similar conditions for S2-4-1 yielded the desired product S22-7-1 as a yellow solid (7 mg, 44%): $^1H$ NMR (400 MHz, $CDCl_3$) δ 15.82 (br s, 1 H), 8.32 (br d, J=5.5 Hz, 2 H), 7.40-7.50 (m, 2 H), 7.30-7.40 (m, 3 H), 7.05 (br d, J=5.5 Hz, 2 H), 6.90 (s, 1 H), 6.76 (s, 1 H), 5.34 (s, 2 H), 3.89 (d, J=10.4 Hz, 1 H), 3.00-3.10 (m, 1 H), 2.75-2.95 (m, 2 H), 2.35-2.55 (m, 2 H), 2.45 (s, 6 H), 2.30 (s, 3 H), 2.00-2.10 (m, 1 H), 0.83 (s, 9 H), 0.26 (s, 3 H), 0.12 (s, 3 H); MS (ESI) m/z 751.4 (M+H), calcd for $C_{41}H_{46}N_4O_8Si$ 750.3.

S22-8-1

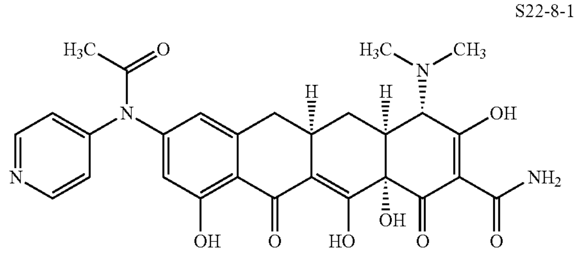 [SMILES: CC(=O)N(c1ccncc1)c1cc(O)c2c(c1)C[C@H]1C[C@H]3[C@H](N(C)C)C(O)=C(C(N)=O)C(=O)[C@@]3(O)C(O)=C1C2=O]

Compound S22-7-1 (7 mg, 0.0090 mmol) was treated with aqueous HF followed by hydrogenation under similar conditions to that in the preparation of compound S21-12-1 to yield the desired product S22-8-1 as a yellow solid (3 mg, 54% 2 steps, bis-HCl salt): $^1H$ NMR (400 MHz, $CD_3OD$) δ 8.31 (d, J=7.4 Hz, 2 H), 7.40 (d, J=7.3 Hz, 2 H), 6.80 (s, 1 H), 6.78 (s, 1 H), 4.37 (s, 1 H), 2.70-3.50 (m, 9 H), 2.55-2.65 (m, 1 H), 2.30-2.40 (m, 1 H), 2.11 (s, 3 H), 1.75-1.80 (m, 1 H); MS (ESI) m/z 549.1 (M+H), calcd for $C_{28}H_{28}N_4O_8$ 548.2.

EXAMPLE 23

Synthesis of Compounds Via Scheme 23

Scheme 23

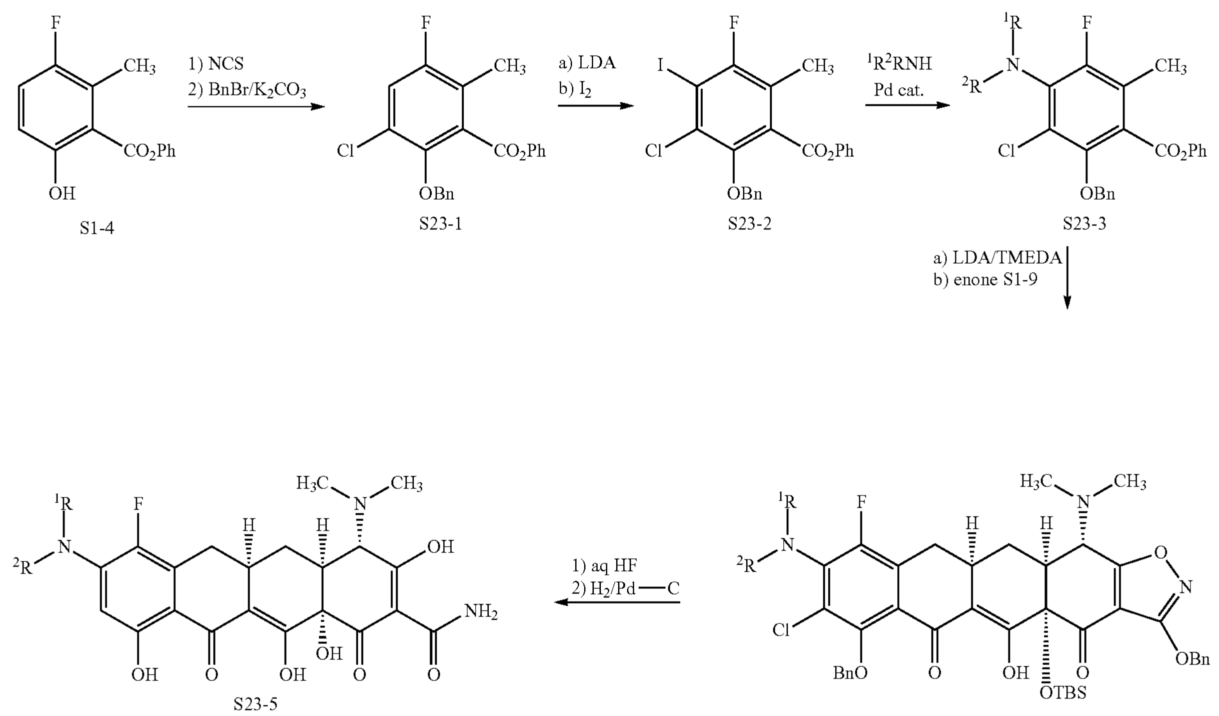

S1-4, S23-1, S23-2, S23-3, S23-4, S23-5

The following compounds were prepared according to Scheme 23.

S23-1

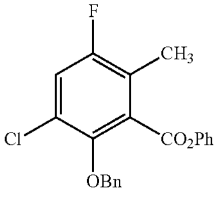

To a solution of S1-4 (8.40 g, 34.10 mmol, 1.0 equiv) in acetonitrile (41 mL) in a vial was added N-chlorosuccinimide (5.05 g, 37.80 mmol, 1.1 equiv). The vial was sealed and heated to 80° C. for 2 h. The reaction mixture was concentrated under reduced pressure, then diluted with water (25 mL) and extracted with EtOAc (2×75 mL). The combined organic layers were washed sequentially with saturated aqueous sodium bicarbonate solution (2×20 mL), water (20 mL), and brine (20 mL). The combined organic layers were then dried over sodium sulfate, filtered, and concentrated under reduced pressure. The resulting crude oil was dissolved in acetone (70 mL). To this solution was added potassium carbonate (9.448 g, 68.40 mmol, 2.0 equiv) and benzyl bromide (4.89 mL, 40.90 mmol, 1.2 equiv). The reaction was stirred at room temperature for 17 hrs. The resulting slurry was filtered through Celite, concentrated under reduced pressure, and purified by flash column chromatography (Biotage 340 g column, 2% to 10% EtOAc in hexanes gradient) to provide S23-1 as a colorless oil (7.31 g, 58%): $^1$H NMR (400 MHz, $CDCl_3$) δ7.49-7.44 (m, 2 H), 7.40-7.32 (m, 5 H), 7.29-7.21 (m, 2 H), 7.06-7.00 (3, 2 H), 5.10 (s, 2 H), 2.34 (d, J=1.8 Hz, 3 H); MS (ESI) m/z 369.13 (M−H).

S23-2

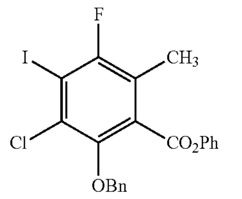

LDA/THF was prepared by adding n-BuLi (1.6 M, 1.31 mL, 2.10 mmol, 1.5 equiv) to diisopropylamine (0.30 mL, 2.10 mmol) in THF (5 mL) at −78° C. The reaction mixture was warmed to −20° C. and stirred for 10 min. After the LDA solution was cooled to −78° C., compound S23-1 (0.52 g, 1.40 mmol) in THF (2 mL) was added dropwise, forming an orange-red solution. After 10 min, a solution of iodine (0.76 g, 2.97 mmol, 2.1 equiv) in THF (2 mL) was added dropwise to the above reaction mixture. The reaction solution was allowed to warm to −15° C. in 1 h and quenched by saturated aqueous $NH_4Cl$. LC/MS indicated that the starting material was all consumed. The reaction mixture was diluted with EtOAc (100 mL), washed with a 5% sodium thiosulfate solution (2×30 mL), water and brine, dried over sodium sulfate, filtered, and concentrated under reduced pressure. The resulting crude oil was purified by flash column chromatography (Silicycle 12 g column, 1% to 5% EtOAc in hexanes gradient), to provide S23-2 (0.56 g, 80%): $^1$H NMR (400 MHz, $CDCl_3$) δ 7.48-7.43 (m, 2 H), 7.39-7.32 (m, 5 H), 7.28-7.22 (m, 1 H), 7.05-6.99 (m, 2 H), 5.08 (s, 2 H), 2.39 (d, J=2.4 Hz, 3 H); MS (ESI) m/z 495.03 (M−H).

S23-3-1

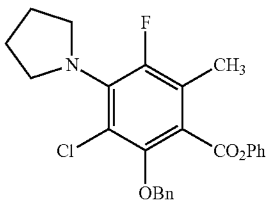

A vial charged with S23-2 (47 mg, 0.095 mmol, 1.0 equiv), tris-(dibenzylideneacetone)dipalladium(0) (4 mg, 0.0047 mmol, 0.05 equiv), Xantphos (11 mg, 0.018 mmol, 0.19 equiv), and cesium carbonate (95 mg, 0.029 mmol, 3.0 equiv) was fitted with a septum, and evacuated and back-filled with nitrogen three times. Dioxane (0.50 mL) and pyrrolidine (0.040 mL, 0.48 mmol, 5.0 equiv) were added and the mixture was degassed by bubbling nitrogen through the heterogeneous solution for two minutes. The mixture was heated at 80° C. with stirring for 2 hrs. The reaction mixture was cooled to rt, filtered through Celite, and concentrated under reduced pressure. The resulting oil was purified by flash column chromatography (Silicycle 4 g column, 1% to 5% EtOAc in hexanes gradient), to provide compound S23-3-1 (23 mg, 55%): $^1$H NMR (400 MHz, $CDCl_3$) δ 7.52-7.46 (m, 2 H), 7.40-7.30 (m, 5 H), 7.27-7.22 (m, 1 H), 7.08-7.03 (m, 2 H), 5.10 (s, 2 H), 3.50-3.41 (m, 4 H), 2.34 (d, J=2.4 Hz, 3 H), 2.00-1.90 (m, 4 H); MS (ESI) m/z 440.15 (M+H).

S23-4-1

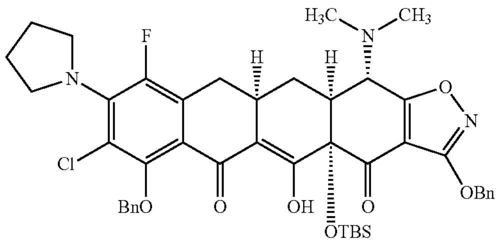

To a solution of LDA (20.053 mL, 2.0 M/THF/heptane/ethylbenzene, 0.10 mmol, 2.5 equiv) in THF (1 mL) at −70° C. was added TMEDA (0.016 mL, 0.10 mmol, 2.5 equiv). A solution of compound S23-3-1 (23 mg, 0.052 mmol, 1.25 equiv) in THF (0.5 mL) was added dropwise. The reaction was stirred at −70° C. for 1 h. A solution of enone S1-9 (21 mg, 0.043 mmol, 1.0 equiv) in THF (0.5 mL) was added dropwise to the reaction mixture. The reaction was stirred from −70° C. to −20° C. over 50 minutes, quenched by saturated aqueous $NH_4Cl$, and extracted with EtOAc (2×30 mL). The combined organic extracts were dried over sodium sulfate and concentrated under reduced pressure. The crude product was purified by preparative reverse phase HPLC on a Waters Autopurification system using a Sunfire Prep C18 OBD column [5 μm, 19×50 mm; flow rate, 20 mL/min; Solvent A: $H_2O$ with 0.1% $HCO_2H$; Solvent B: $CH_3CN$ with 0.1% $HCO_2H$; gradient: 90→100% B over 20 min; mass-directed fraction collection]. Fractions containing the desired product, eluting at 8.0-8.75 min, were collected and freeze-dried to give 10 mg of pure compound S23-4-1 (24%): $^1$H NMR (400 MHz, $CDCl_3$) δ 16.2 (s, 1 H), 7.59-7.54 (m, 2 H), 7.51-7.46 (m, 2 H), 7.40-7.29 (m, 6 H), 5.35 (s, 2 H), 4.94 (d, J=9.8 Hz, 1 H), 4.89 (d, J=9.8 Hz, 1 H), 3.95 (d, J=10.4 Hz, 1 H), 3.75-3.65 (m, 2 H), 3.59-3.50 (m, 2 H), 3.23-3.15 (m, 1 H), 3.00-2.88 (m, 1 H), 2.55-2.30 (m, 9 H), 2.14-2.07 (m, 1 H), 1.99-1.83 (m, 4 H), 0.81 (s, 9 H), 0.26 (s, 3 H), 0.11 (s, 3 H); MS (ESI) m/z 828.30 (M+H).

S23-5-1

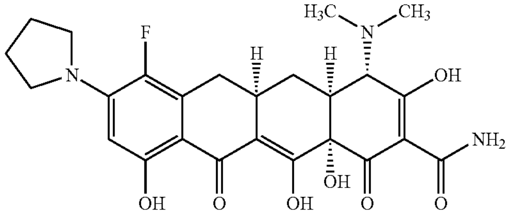

A solution of compound S23-4-1 (10 mg, 0.012 mmol) in 1,4-dioxane (1.3 mL) was treated with HF (0.20 mL, 48-50% aqueous solution). After stirring overnight, the mixture was poured into a solution of $K_2HPO_4$ (2.4 g) in water (25 mL) and extracted with EtOAc (2×30 mL). The combined extracts were dried over sodium sulfate, filtered, and concentrated under reduced pressure.

The above crude material was dissolved in MeOH (0.3 mL), 1,4-dioxane (0.5 mL), and 0.5 N HCl/MeOH (0.2 mL). 10% Pd—C (Degussa, 5 mg) was added, and an atmosphere of hydrogen was introduced. After 17 hrs, the reaction mixture was filtered through Celite and concentrated under reduced pressure. The crude product was purified by preparative reverse phase HPLC on a Waters Autopurification system using a Polymerx 10μ RP-γ 100 R column [30×21.20 mm, 10 micron, solvent A: 0.05 N HCl, solvent B: $CH_3CN$, gradient elution with 15→80% B over 10 min, then 80-100% over 2 min, held at 100% for 2 min; mass-directed fraction collection]. Fractions containing the desired product, eluting at 9.9-11.2 min, were collected and freeze-dried to yield 1 mg of compound S23-5-1 (27%): $^1H$ NMR (400 MHz, $CD_3OD$) δ 5.94 (d, J=7.3 Hz, 1 H), 4.03 (s, 1 H), 3.56-3.49 (m, 4 H), 3.13-2.84 (m, 9 H), 2.20-2.09 (m, 2 H), 2.03-1.91 (m, 4 H), 1.63-1.50 (m, 1 H); MS (ESI) m/z 502.24 (M+H).

EXAMPLE 24

Synthesis of Compounds Via Scheme 24

Scheme 24

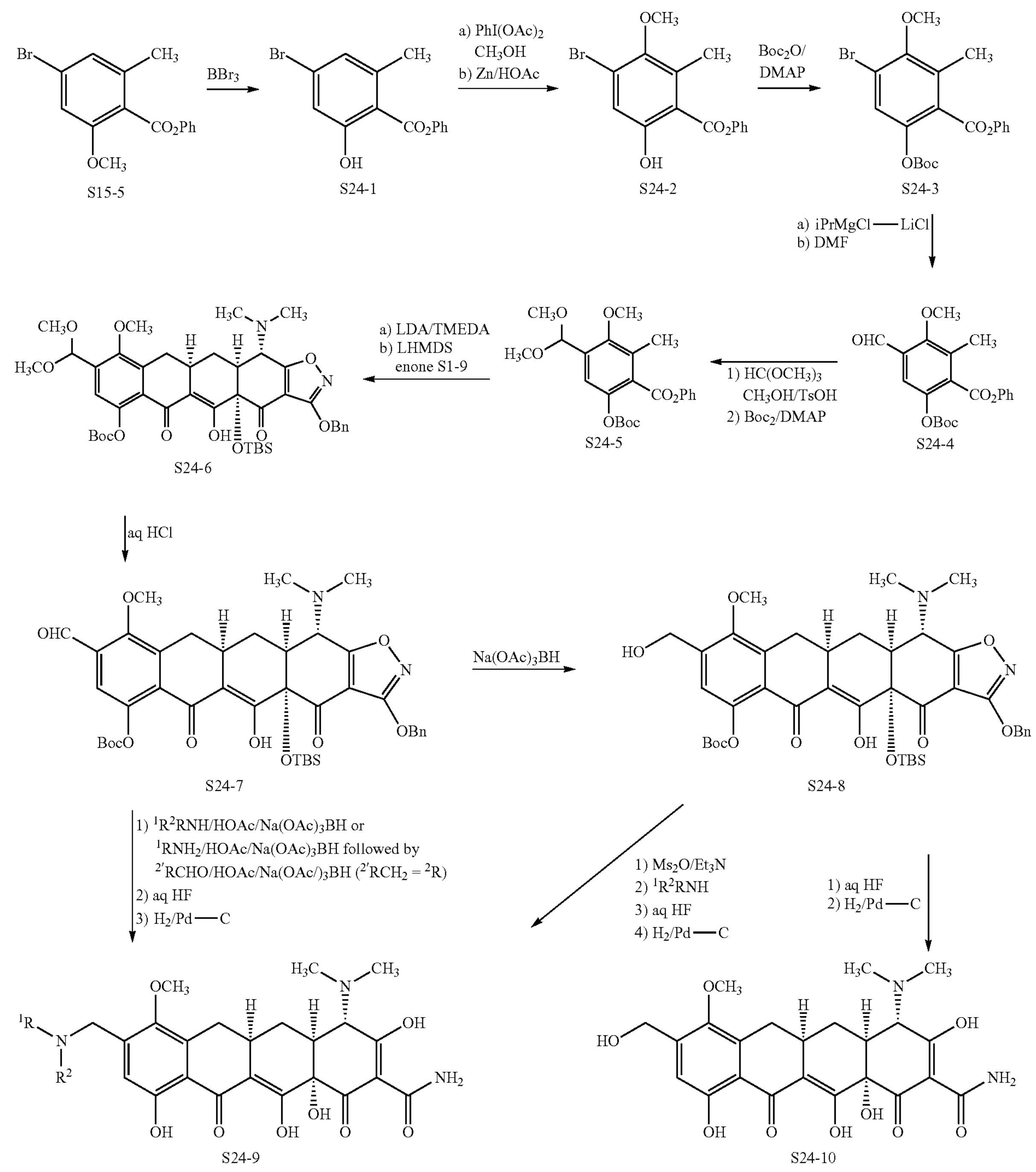

The following compounds were prepared according to Scheme 24.

S24-1

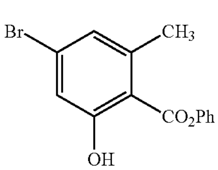

$BBr_3$ solution in DCM (1.0 M, 27.96 mL, 27.96 mmol, 1.0 equiv) was added to a solution of the above phenyl ester S15-5 (8.98 g, 27.96 mmol, 1.0 equiv) in DCM (100 mL) at −78° C. The resulting reaction mixture was stirred at that temperature for 20 min and at 0° C. for 15 min. Saturated $NaHCO_3$ solution (120 mL) was added slowly. The resulting mixture was stirred at rt for 20 min and DCM was evaporated. The residue was extracted with ethyl acetate (250 mL). The organic was separated and dried over anhydrous $MgSO_4$. The dried solution was filtered, and the filtrate was concentrated to afford an off-white solid. The residue was purified by recrystallization from EtOAc/Hexanes to give the desired product S24-1 as a white solid (6.76 g), and the mother liquor was concentrated and purified by flash-column chromatography (2-10% ethyl acetate-hexanes) to afford additional product (973 mg) (90% yield totally). $^1H$ NMR (400 MHz, $CDCl_3$) δ 11.13 (s, 1 H), 7.47-7.43 (m, 2 H), 7.33-7.29 (m, 1 H), 7.19-7.16 (m, 2 H), 7.08 (d, J=1.8 Hz, 1 H), 6.96 (d, J=1.8 Hz, 1 H), 2.66 (s, 3 H); MS (ESI) m/z 305.05, 307.05 (M−H).

S24-2

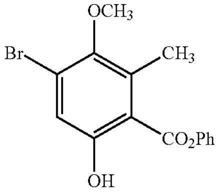

A solution of $PhI(OAc)_2$ (3.77 g, 11.72 mmol, 2.1 equiv) in MeOH (20 mL) was added slowly to a solution of S24-1 (1.71 g, 5.58 mmol, 1.0 equiv) in a mixture of MeOH (30 mL) and dioxane (10 mL) at 0° C. The reaction mixture was then stirred at rt for 17 h. HOAc (6 mL) was added to the reaction mixture. Then Zn dust (1.09 g, 16.74 mmol, 3.0 equiv) was added (slightly exothermic). The resulting reaction mixture was stirred at rt for 20 min, and filtered through a pad of Celite. The cake was washed with EtOAc (100 mL) thoroughly. The filtrate was concentrated. The residue was partitioned between EtOAc (120 mL) and sat. $NaHCO_3$/brine solution. (The aqueous layer pH was adjusted to 7). The organic layer was separated and dried ($MgSO_4$). The dried solution was filtered, and the filtrate was concentrated. The residue was purified by flash-column chromatography (0-4% ethyl acetate-hexanes) to afford the desired product S24-2 (763 mg, 41%). $^1H$ NMR (400 MHz, $CDCl_3$) δ 10.70 (s, 1 H), 7.47-7.43 (m, 2 H), 7.33-7.30 (m, 1 H), 7.20-7.17 (m, 2 H), 7.16 (s, 1 H), 3.75 (s, 3 H), 2.67 (s, 3 H); MS (ESI) m/z 335.11, 337.14 (M−H).

S24-3

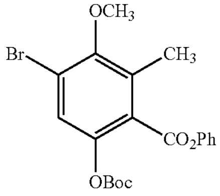

Di-tert-butyl dicarbonate (543 mg, 2.49 mmol, 1.1 equiv) and N,N-dimethylaminopyridine (28 mg, 0.226 mmol, 0.1 equiv) were added to a solution of phenol S24-2 (763 mg, 2.26 mmol, 1.0 equiv) in methylene chloride (20 mL). The resulting mixture was stirred for 20 min at rt (monitored by LC-MS and TLC (product is slightly more polar)), and concentrated. The residue was purified by flash-column chromatography (0-5% ethyl acetate-hexanes) to afford the Boc protection product S24-3 as a white solid (783 mg, 79%). $^1H$ NMR (400 MHz, $CDCl_3$) δ 7.45-7.41 (m, 2 H), 7.38 (s, 1 H), 7.30-7.26 (m, 1 H), 7.24-7.22 (m, 2 H), 3.81 (s, 3 H), 2.47 (s, 3 H), 1.43 (s, 9 H); MS (ESI) m/z 435.14, 437.15 (M−H).

S24-4

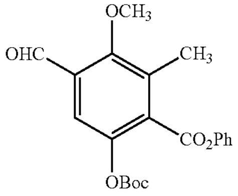

A solution of $^iPrMgCl.LiCl$ in THF (1.2 M, 547 μL, 0.657 mmol, 2.0 equiv) was added dropwise to a solution of compound S24-3 (143.6 mg, 0.328 mmol, 1.0 equiv) in THF (3.3 mL) at 0° C. The resulting yellow reaction mixture was then stirred at that temperature for 1 h. Then DMF (127 μL, 1.64 mmol, 5.0 equiv) was added at 0° C. The resulting mixture was stirred at 0° C. for 10 min and then at rt for 20 min. Sat. $NH_4Cl$ and brine were added. The resulting mixture was extracted with EtOAc (50 mL). The organic layer was separated and dried ($MgSO_4$). The dried solution was filtered, and the filtrate was concentrated. The crude product S24-4 was used directly for the next step. $^1H$ NMR (400 MHz, $CDCl_3$) δ 10.38 (s, 1 H), 7.61 (s, 1 H), 7.46-7.42 (m, 2 H), 7.32-7.28 (m, 1 H), 7.26-7.24 (m, 2 H), 3.91 (s, 3 H), 2.46 (s, 3 H), 1.45 (s, 9 H); MS (ESI) m/z 385.24 (M−H).

S24-5

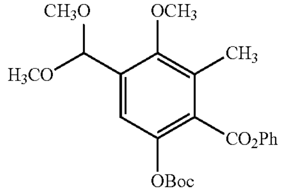

Trimethyl orthoformate (180 μL, 1.64 mmol, 5.0 equiv) and p-TSA (3.1 mg, 0.016 mmol, 0.05 equiv) were added to a solution of the above crude product S24-4 in MeOH (1 mL). The resulting reaction mixture was heated at reflux for 1 h, and cooled to rt. The solvent was evaporated and the residue was diluted with EtOAc (40 mL) and sat. $NaHCO_3$/brine solution (1:1, 20 mL). The organic phase was separated and dried ($MgSO_4$). The dried solution was filtered, and the filtrate was concentrated to afford an organe oil. The crude $^1H$ NMR ($CDCl_3$) showed desired product 6 and deBoc product (~3:1). The crude products were used directly for the next step.

The above crude material was dissolved in DCM (1 mL). Di-tert-butyl dicarbonate (26.8 mg, 0.123 mmol) and N,N-dimethylaminopyridine (1 mg, 0.08 mmol) were added. The resulting mixture was stirred for 40 min at rt and concentrated. The residue was purified by flash-column chromatography (2-10% ethyl acetate-hexanes) to afford the desired product S24-5 as a colorless oil (124.2 mg, 87% over 3 steps). $^1H$ NMR (400 MHz, $CDCl_3$) δ 7.45-7.41 (m, 2 H), 7.33 (s, 1 H), 7.30-7.24 (m, 3 H), 5.65 (s, 1 H), 3.79 (s, 3 H), 3.36 (s, 6 H), 2.43 (s, 3 H), 1.43 (s, 9 H); MS (ESI) m/z 431.29 (M−H).

S24-6

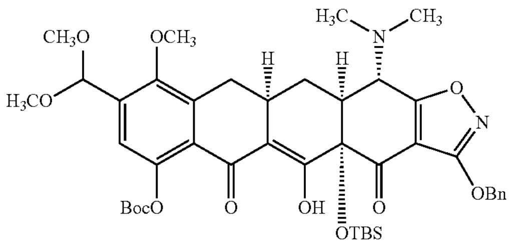

$^n$BuLi solution (2.5 M in hexanes, 138 μL, 0.345 mmol, 1.2 equiv) was added dropwise to a solution of diisopropylamine (49 μL, 0.345 mmol, 1.2 equiv) and TMEDA (103 μL, 0.689 mmol, 2.4 equiv) in THF (2.5 mL) at −78° C. The resulting reaction solution was stirred at −78° C. for 30 min. A solution of ester S24-5 (124.2 mg, 0.287 mmol, 1.0 equiv) in THF (1.5 mL) was added via cannula. The resulting dark red solution was then stirred at −78° C. for 30 min, and cooled to −100° C. using a EtOH/liquid $N_2$ bath. A solution of enone (125 mg, 0.258 mmol, 0.9 equiv) in THF (1.5 mL) was added to the reaction mixture via cannula. The resulting reaction mixture was allowed to warm up to −78° C. over 30 min. LHMDS solution (1.0 M, 287 μL, 0.287 mmol, 1.0 equiv) was added. Then the reaction mixture was warmed up to −10° C. naturally over 40 min, quenched with saturated $NH_4Cl$ and pH=7 buffer (1:1, 30 mL), and extracted with EtOAc (40 mL). The organic phase was separated, dried ($Na_2SO_4$), filtered and concentrated. The residue was purified by flash-column chromatography (5-30% ethyl acetate-hexanes) to afford the desired product S24-6 as a pale yellow solid (201.6 mg, 95%). $^1H$ NMR (400 MHz, $CDCl_3$) δ 15.67 (s, 1 H), 7.49-7.46 (m, 2 H), 7.38-7.29 (m, 3 H), 5.59 (s, 1 H), 5.35, 5.32 (ABq, J=12.2 Hz, 2 H), 3.97 (d, J=10.4 Hz, 1 H), 3.73 (s, 3 H), 3.37 (s, 3 H), 3.31 (s, 3 H), 3.28 (dd, J=4.9, 15.9 Hz, 1 H), 3.02-2.95 (m, 1 H), 2.55-2.42 (m, 9 H), 2.13 (d, J=12.0 Hz, 1 H), 1.51 (s, 9 H), 0.82 (s, 9 H), 0.25 (s, 3 H), 0.11 (s, 3 H); MS (ESI) m/z 821.51 (M+H).

S24-7

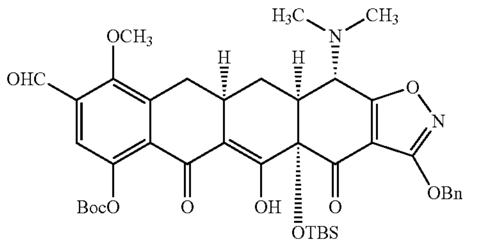

Compound S24-6 (201.6 mg, 0.246 mmol, 1.0 equiv) was dissolved in a premixed solution of 6 N HCl (0.34 mL) and THF (3.66 mL). The resulting reaction solution was stirred at rt for 40 min, and diluted with EtOAc (40 mL). The resulting mixture was washed with sat. $NaHCO_3$ (10 mL), and then brine (10 mL). The organic phase was then dried over $Na_2SO_4$. The dried solution was filtered and concentrated to give the desired product S24-7 as a yellow foamy solid (204.2 mg). $^1H$ NMR (400 MHz, $CDCl_3$) δ 15.55 (s, 1 H), 10.33 (s, 1 H), 7.50-7.47 (m, 3 H), 7.38-7.31 (m, 3 H), 5.36, 5.32 (ABq, J=12.2 Hz, 2 H), 3.94 (d, J=11.0 Hz, 1 H), 3.86 (s, 3 H), 3.33 (dd, J=4.9, 15.9 Hz, 1 H), 3.07-2.99 (m, 1 H), 2.59-2.44 (m, 9 H), 2.16 (d, J=14.6 Hz, 1 H), 1.51 (s, 9 H), 0.82 (s, 9 H), 0.25 (s, 3 H), 0.11 (s, 3 H); MS (ESI) m/z 775.44 (M+H).

S24-9-1

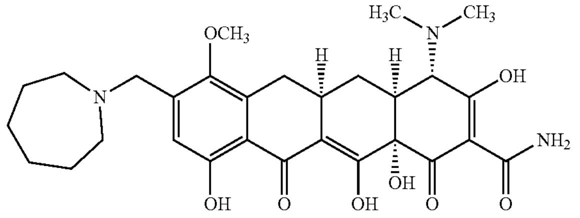

Hexamethyleneimine (8.5 μL, 0.072 mmol, 3.0 equiv), acetic acid (4 μL, 0.072 mmol, 3.0 equiv) and sodium triacetoxyborohydride (10 mg, 0.048 mmol, 2.0 equiv) were added sequentially to a solution of compound S24-7 (one tenth of the above crude product, 0.024 mmol, 1.0 equiv) in 1,2-dichloroethane (1 mL) at 23° C. After stirring for 2 h, the reaction mixture was quenched by the addition of saturated aqueous sodium bicarbonate and brine (1:1, 20 mL) and extracted with dichloromethane (2×20 mL). The combined organic extracts were dried over anhydrous sodium sulfate, filtered, and concentrated. The crude reductive amination product was used directly for the deprotection steps.

Aqueous HF (48-50%, 0.3 mL) was added to a solution of the compound in THF (0.6 mL) in a polypropylene reaction vessel at 23° C. The mixture was stirred vigorously at 23° C. overnight and poured into aqueous $K_2HPO_4$ (3.6 g dissolved in 30 mL water). The mixture was extracted with EtOAc (50 mL). The organic phase was dried over anhydrous sodium sulfate, filtered, and concentrated. The residue was used directly in the next step without further purification.

Pd—C (10 wt %, 6.7 mg) was added in one portion into the yellow solution of the above crude product in a mixture of HCl/MeOH (0.5 N, 96 μL, 2.0 equiv) and MeOH (1 mL) at 23° C. The reaction vessel was sealed and purged with hydrogen by briefly evacuating the flask followed by flushing with hydrogen gas (1 atm). The resulting mixture was stirred at 23° C. for 30 min. The reaction mixture was then filtered through a small Celite pad. The filtrate was concentrated. The residue was purified by preparative reverse phase HPLC on a Waters Autopurification system using a Phenomenex Polymerx 10μ RP-γ 100A column [10 μm, 150×21.20 mm; flow rate, 20 mL/min; Solvent A: 0.05 N HCl/water; Solvent B: $CH_3CN$; injection volume: 3.0 mL (0.05 N HCl/water); gradient: 5→60% B over 10 min; mass-directed fraction collection]. Fractions containing the desired product, eluting at 7.1-8.4 min, were collected and freeze-dried to yield compound S24-9-1 (10.89 mg, 72% for 3 steps). $^1$H NMR (400 MHz, $CD_3OD$, hydrochloride) δ 7.07 (s, 1 H), 4.43 (d, J=12.8 Hz, 1 H), 4.29 (d, J=13.3 Hz, 1 H), 4.12 (s, 1 H), 3.73 (s, 3 H), 3.47-3.41 (m, 2 H), 3.26-3.20 (m, 3 H), 3.05-2.97 (m, 8 H), 2.38 (t, J=14.6 Hz, 1 H), 2.28-2.25 (m, 1 H), 2.00-1.82 (m, 4 H), 1.73 (s, 4 H), 1.70-1.60 (m, 1 H); MS (ESI) m/z 556.33 (M+H).

S24-8

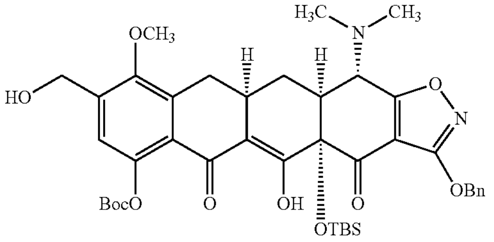

Sodium triacetoxyborohydride (60 mg, 0.284 mmol, 2.0 equiv) was added to a solution of compound S24-7 (110 mg, 0.142 mmol, 1.0 equiv) in 1,2-dichloroethane (1 mL) at 23° C. After stirring overnight, more sodium triacetoxyborohydride (60 mg, 0.284 mmol, 2.0 equiv) was added. The resulting reaction mixture was stirred at rt overnight, quenched by the addition of saturated aqueous sodium bicarbonate and brine (1:1, 40 mL) and extracted with dichloromethane (3×20 mL). The combined organic extracts were dried over anhydrous sodium sulfate, filtered, and concentrated. The residue was purified by flash-column chromatography (8-66% ethyl acetate-hexanes) to afford the desired product S24-8 (70.2 mg, 64%). $^1$H NMR (400 MHz, $CDCl_3$) δ 15.69 (s, 1 H), 7.48-7.47 (m, 2 H), 7.38-7.29 (m, 3 H), 7.16 (s, 1 H), 5.34 (s, 2 H), 4.79, 4.69 (dABq, J=4.9, 14.0 Hz, 2 H), 3.97 (d, J=10.4 Hz, 1 H), 3.71 (s, 3 H), 3.27 (dd, J=4.9, 15.3 Hz, 1 H), 3.01-2.94 (m, 1 H), 2.55-2.42 (m, 9 H), 2.15-2.11 (m, 2 H), 1.53 (s, 9 H), 0.82 (s, 9 H), 0.25 (s, 3 H), 0.11 (s, 3 H); MS (ESI) m/z 777.50 (M+H).

S24-10

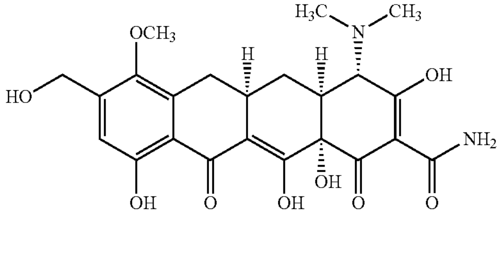

Compound S24-10 was prepared from compound S24-8 by following the general HF deprotection procedure and Pd/C hydrogenation procedure: $^1$H NMR (400 MHz, $CD_3OD$, hydrochloride) δ 6.92 (s, 1 H), 4.66 (s, 2 H), 4.08 (s, 1 H), 3.64 (s, 3 H), 3.33 (s, 1 H), 3.18 (dd, J=4.6, 15.6 Hz, 1 H), 3.03-2.92 (m, 8 H), 2.28 (t, J=14.6 Hz, 1 H), 2.24-2.19 (m, 1 H), 1.67-1.57 (m, 1 H); MS (ESI) m/z 475.24 (M+H).

S24-9-2

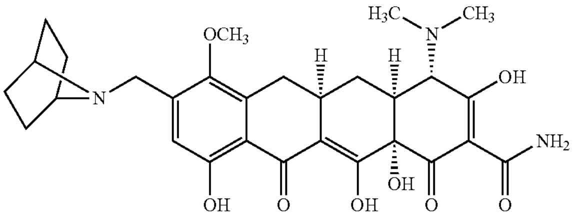

$Ms_2O$ (13 mg, 0.075 mmol, 2.0 equiv) was added to a solution of alcohol S24-8 (29 mg, 0.037 mmol, 1.0 equiv) in THF (0.5 mL). Then TEA (10.4 μL, 0.075 mmol, 2.0 equiv) was added. To another reaction flask charged with a suspension of 7-azabicyclo[2,2,1]heptane.HCl (15 mg, 0.112 mmol, 3.0 equiv) in THF (0.5 mL) was added TEA (16 μL, 0.112 mmol, 3.0 equiv) and aqueous NaOH solution (8 N, 18 μL). The reaction mixtures were stirred for 30 min and mixed. The resulting reaction mixture was stirred at rt for 3 overnights, and diluted with EtOAc (50 mL), washed with pH=7 phosphate buffer solution. The organic phase was separated, dried over anhydrous sodium sulfate. The dried solution was filtered and concentrated. The crude product was used directly for the deprotection reactions. MS (ESI) m/z 856.69 (M+H).

Aqueous HF (48-50%, 0.3 mL) was added to a solution of the above compound in THF (0.6 mL) in a polypropylene reaction vessel at 23° C. The mixture was stirred vigorously at 23° C. overnight and poured into aqueous $K_2HPO_4$ (3.6 g dissolved in 30 mL water). The mixture was extracted with EtOAc (50 mL). The organic phase was dried over anhydrous sodium sulfate, filtered, and concentrated. The residue was used directly in the next step without further purification.

Pd—C (10 wt %, 15 mg) was added in one portion into the yellow solution of the above crude product in a mixture of HCl/MeOH (0.5 N, 148 μL, 2.0 equiv) and MeOH (1 mL) at 23° C. The reaction vessel was sealed and purged with hydrogen by briefly evacuating the flask followed by flushing with hydrogen gas (1 atm). The resulting mixture was stirred at 23° C. for 40 min. The reaction mixture was then filtered through a small Celite pad. The filtrate was concentrated. The residue was purified by preparative reverse phase HPLC on a Waters Autopurification system using a Phenomenex Polymerx 10μ RP-γ 100A column [10 μm, 150×21.20 mm; flow rate, 20 mL/min; Solvent A: 0.05 N HCl/water; Solvent B: $CH_3CN$; injection volume: 3.0 mL (0.05 N HCl/water); gradient: 20→100% B over 10 min; mass-directed fraction collection]. Fractions containing the desired product, eluting at 7.05-7.88 min, were collected and concentrated to yield compound S24-9-2 (2.66 mg, 11% for 3 steps). $^1$H NMR (400 MHz, $CD_3OD$, hydrochloride) δ 7.05 (s, 1 H), 4.31, 4.19 (ABq, J=12.8 Hz, 2 H), 4.09-4.07 (m, 3 H), 3.72 (s, 3 H), 3.23-3.20 (m, 1 H), 3.04-2.96 (m, 8 H), 2.39-2.23 (m, 4 H), 2.03-2.01 (m, 2 H), 1.89-1.78 (m, 4 H), 1.70-1.60 (m, 1 H); MS (ESI) m/z 554.47 (M+H).

S24-9-3

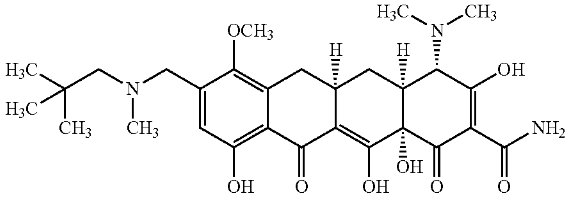

Neopentylamine (5.6 μL, 0.048 mmol, 2.0 equiv), acetic acid (2.7 μL, 0.048 mmol, 2.0 equiv) and sodium triacetoxyborohydride (7.6 mg, 0.036 mmol, 1.5 equiv) were added sequentially to a solution of compound S24-7 (one tenth of the above crude product, 0.024 mmol, 1.0 equiv) in 1,2-dichloroethane (1 mL) at 23° C. After stirring for 3 h, formyladehyde (11 μL, 0.14 mmol, 6.0 equiv), acetic acid (4.1 μL, 0.072 mmol, 3.0 equiv), and sodium triacetoxyborohydride (20 mg, 0.096 mmol, 4.0 equiv) were added. The resulting reaction mixture was stirred at rt for 1 h, and quenched by the addition of saturated aqueous sodium bicarbonate and brine (1:1, 20 mL) and extracted with dichloromethane (2×20 mL). The combined organic extracts were dried over anhydrous sodium sulfate, filtered, and concentrated. The crude product was used directly for the deprotection steps (see procedure for S24-9-1) to give the desired product S24-9-3 (10.97 mg, 72% for four steps). $^1$H NMR (400 MHz, $CD_3OD$, hydrochloride, a mixture of isomers) δ 7.08 (s, 0.6 H), 7.06 (s, 0.4 H), 4.59 (d, J=12.8 Hz, 0.6 H), 4.43, 4.39 (ABq, J=12.8 Hz, 0.8 H), 4.22 (d, J=12.8 Hz, 0.6 H), 4.13 (s, 1 H), 3.78 (s, 1.2 H), 3.73 (s, 1.8 H), 3.26-2.95 (m, 14 H), 2.46-2.35 (m, 1 H), 2.30-2.26 (m, 1 H), 1.71-1.61 (m, 1 H), 1.04 (s, 5.4 H), 1.02 (s, 3.6 H); MS (ESI) m/z 558.36 (M+H).

The following compounds were prepared similarly to S24-9-1, S24-9-2 or S24-9-3 by using the corresponding amines and aldehydes.

S24-9-4

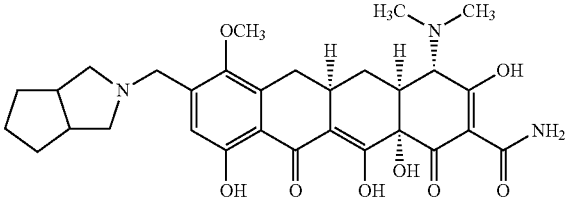

$^1$H NMR (400 MHz, $CD_3OD$, hydrochloride) δ 7.01 (s, 1 H), 4.48 (d, J=12.8 Hz, 1 H), 4.31 (d, J=12.8 Hz, 1 H), 4.12 (s, 1 H), 3.76-3.66 (m, 5 H), 3.22 (dd, J=4.1, 15.6 Hz, 1 H), 3.12-2.98 (m, 9 H), 2.86-2.75 (m, 3 H), 2.39 (t, J=14.2 Hz, 1 H), 2.29-2.25 (m, 1 H), 1.87-1.52 (m, 7 H); MS (ESI) m/z 568.34 (M+H).

S24-9-5

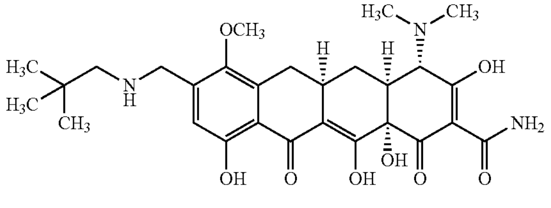

$^1$H NMR (400 MHz, $CD_3OD$, hydrochloride) δ 7.01 (s, 1 H), 4.38 (d, J=13.7 Hz, 1 H), 4.23 (d, J=13.7 Hz, 1 H), 4.13 (s, 1 H), 3.76 (s, 3 H), 123 (dd, J=4.1, 15.6 Hz, 1 H), 3.08-2.98 (m, 8 H), 2.86 (s, 2 H), 2.39 (t, J=14.2 Hz, 1 H), 2.30-2.25 (m, 1 H), 1.71-1.61 (m, 1 H), 1.04 (s, 9 H); MS (ESI) m/z 544.34 (M+H).

S24-9-6

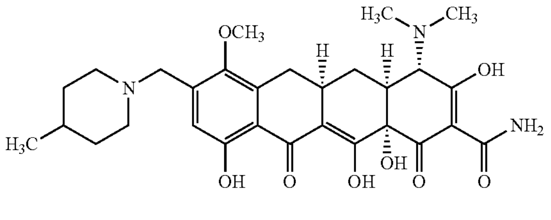

$^1$H NMR (400 MHz, $CD_3OD$, hydrochloride) δ 7.05 (s, 1 H), 4.37 (d, J=13.3 Hz, 1 H), 4.24 (d, J=12.8 Hz, 1 H), 4.12 (s, 1 H), 3.72 (s, 3 H), 3.51-3.43 (m, 2 H), 3.22 (dd, J=4.6, 15.6 Hz, 1 H), 3.10-2.98 (m, 10 H), 2.40 (t, J=14.2 Hz, 1 H), 2.28-2.25 (m, 1 H), 1.90-1.87 (m, 2 H), 1.71-1.61 (m, 2 H), 1.52-1.42 (m, 2 H), 0.99 (d, J=6.4 Hz, 3 H); MS (ESI) m/z 556.34 (M+H).

S24-9-7

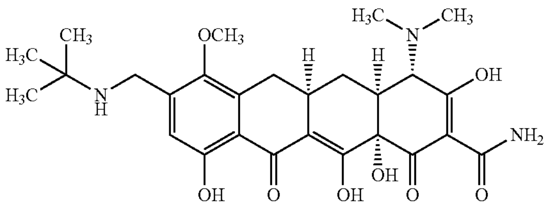

$^1$H NMR (400 MHz, $CD_3OD$, hydrochloride) δ 7.00 (s, 1 H), 4.23 (d, J=12.8 Hz, 1 H), 4.12 (s, 1 H), 4.09 (d, J=12.8 Hz, 1 H), 3.75 (s, 3 H), 3.24 (dd, J=4.6, 15.6 Hz, 1 H), 3.06-2.98 (m, 8 H), 2.39 (t, J=14.2 Hz, 1 H), 2.28-2.24 (m, 1 H), 1.71-1.61 (m, 1 H), 1.47 (s, 9 H); MS (ESI) m/z 530.35 (M+H).

S24-9-8

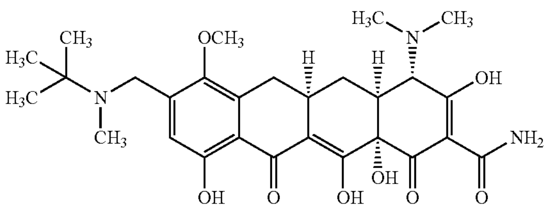

$^1$H NMR (400 MHz, $CD_3OD$, hydrochloride, a mixture of isomers) δ 7.01, 6.99 (s, 1 H), 4.92 (d, J=12.8 Hz, 0.6 H), 4.60 (d, J=13.3 Hz, 0.4 H), 4.13, 4.12 (s, 1 H), 3.96 (d, J=12.8 Hz, 0.4 H), 3.80 (d, J=12.8 Hz, 0.6 H), 3.77, 3.73 (s, 3 H), 3.24 (dd, J=4.6, 15.6 Hz, 1 H), 3.27-3.20 (m, 1 H), 3.06-2.98 (m, 8 H), 2.69 (s, 3 H), 2.47-2.40 (m, 1 H), 2.28-2.26 (m, 1 H), 1.71-1.64 (m, 1 H), 1.55 (s, 9 H); MS (ESI) m/z 544.32 (M+H).

S24-9-9

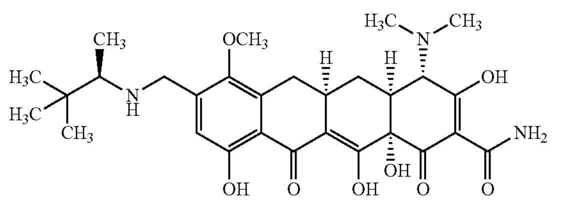

$^1$H NMR (400 MHz, $CD_3OD$, hydrochloride) δ 7.02 (s, 1 H), 4.36, 4.30 (ABq, J=13.3 Hz, 1 H), 4.10 (s, 1 H), 3.77 (s, 3 H), 3.24 (dd, J=3.7, 15.6 Hz, 1 H), 3.05-2.94 (m, 9 H), 2.40 (t, J=14.6 Hz, 1 H), 2.27-2.24 (m, 1 H), 1.71-1.61 (m, 1 H), 1.34 (d, J=6.9 Hz, 3 H), 1.00 (s, 9 H); MS (ESI) m/z 558.34 (M+H).

S24-9-10

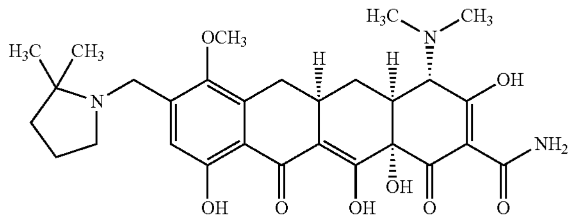

$^1$H NMR (400 MHz, $CD_3OD$, hydrochloride, a mixture of isomers) δ 7.02 (s, 1 H), 4.54 (d, J=12.4 Hz, 0.6 H), 4.43 (d, J=12.8 Hz, 0.4 H), 4.11, 4.10 (s, 1 H), 4.02 (d, J=12.8 Hz, 0.4 H), 3.88 (d, J=12.4 Hz, 0.6 H), 3.78 (s, 1.2 H), 3.74 (s, 1.8 H), 3.44-3.39 (m, 2 H), 3.26-3.18 (m, 1 H), 3.05-2.97 (m, 8 H), 2.46-2.35 (m, 1 H), 2.29-2.24 (m, 1 H), 2.12-2.07 (m, 2 H), 2.02-1.97 (m, 2 H), 1.71-1.58 (m, 4 H), 1.44, 1.43 (s, 3 H); MS (ESI) m/z 556.36 (M+H).

S24-9-11

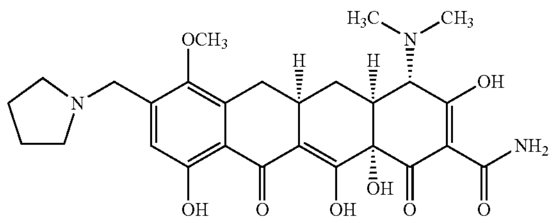

$^1$H NMR (400 MHz, $CD_3OD$, hydrochloride) δ 7.02 (s, 1 H), 4.50 (d, J=12.8 Hz, 1 H), 4.32 (d, J=13.3 Hz, 1 H), 4.12 (s, 1 H), 3.74 (s, 3 H), 3.55-3.50 (m, 2 H), 3.25-3.20 (m, 3 H), 3.05-2.97 (m, 8 H), 2.39 (t, J=14.6 Hz, 1 H), 2.28-2.24 (m, 1 H), 2.17-2.03 (m, 4 H), 1.70-1.60 (m, 1 H); MS (ESI) m/z 528.30 (M+H).

S24-9-12

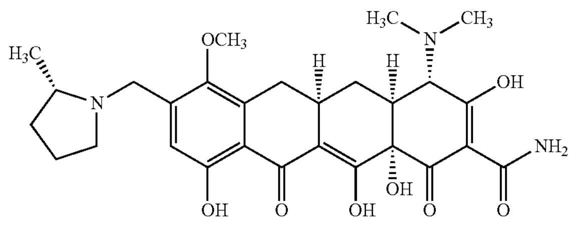

$^1$H NMR (400 MHz, $CD_3OD$, hydrochloride) δ 7.03 (s, 1 H), 4.64 (d, J=13.3 Hz, 1 H), 4.13 (s, 1 H), 4.08 (d, J=12.8 Hz, 1 H), 3.75 (s, 3 H), 3.66-3.60 (m, 1 H), 3.43-3.37 (m, 1 H), 3.27-3.21 (m, 2 H), 3.06-2.98 (m, 8 H), 2.44-2.34 (m, 2 H), 2.28-2.25 (m, 1 H), 2.13-2.07 (m, 1 H), 2.03-1.97 (m, 1 H), 1.81-1.61 (m, 2 H), 1.49 (d, J=6.4 Hz, 3 H); MS (ESI) m/z 542.36 (M+H).

S24-9-13

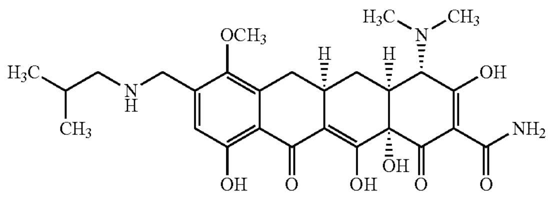

$^1$H NMR (400 MHz, $CD_3OD$, hydrochloride) δ 7.00 (s, 1 H), 4.32 (d, J=13.7 Hz, 1 H), 4.18 (d, J=13.7 Hz, 1 H), 4.12 (s, 1 H), 3.74 (s, 3 H), 3.23 (dd, J=4.6, 15.6 Hz, 1 H), 3.08-2.97 (m, 8 H), 2.91 (d, J=7.3 Hz, 2 H), 2.38 (t, J=14.6 Hz, 1 H), 2.29-2.24 (m, 1 H), 2.11-2.04 (m, 1 H), 1.71-1.61 (m, 1 H), 1.04 (dd, J=0.9, 6.9 Hz, 6 H); MS (ESI) m/z 530.39 (M+H).

S24-9-14

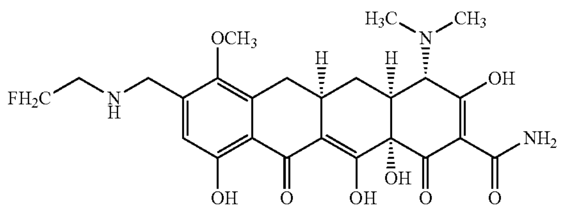

$^1$H NMR (400 MHz, $CD_3OD$, hydrochloride) δ 6.98 (s, 1 H), 4.78 (dt, J=47.2, 4.6 Hz, 2 H), 4.38 (d, J=13.7 Hz, 1 H), 4.25 (d, J=13.7 Hz, 1 H), 4.12 (s, 1 H), 3.74 (s, 3 H), 3.45 (dt, J=26.6, 4.6 Hz, 2 H), 3.22 (dd, J=4.6, 15.6 Hz, 1 H), 3.07-2.97 (m, 8 H), 2.38 (t, J=14.2 Hz, 1 H), 2.28-2.24 (m, 1 H), 1.70-1.60 (m, 1 H); MS (ESI) m/z 520.31 (M+H).

S24-9-15

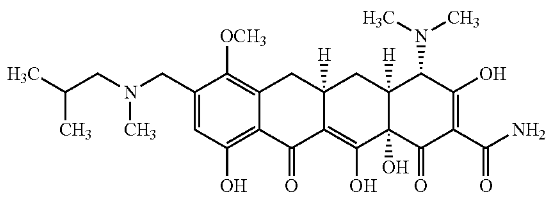

$^1$H NMR (400 MHz, $CD_3OD$, hydrochloride, a mixture of isomers) δ 7.01 (s, 1 H), 4.62 (d, J=12.8 Hz, 0.6 H), 4.43 (d, J=13.3 Hz, 0.4 H), 4.29 (d, J=12.8 Hz, 0.4 H), 4.12 (s, 1 H), 4.04 (d, J=12.8 Hz, 0.6 H), 3.76, 3.74 (s, 3 H), 3.26-3.18 (m, 1 H), 3.15-2.98 (m, 10 H), 2.83 (s, 1.2 H), 2.78 (s, 1.8 H), 2.46-2.35 (m, 1 H), 2.29-2.19 (m, 2 H), 1.71-1.60 (m, 1 H), 1.11-1.01 (m, 6 H); MS (ESI) m/z 544.36 (M+H).

S24-9-16

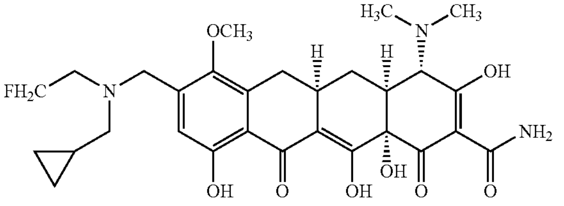

$^1$H NMR (400 MHz, $CD_3OD$, hydrochloride, a mixture of isomers) δ 7.03 (s, 1 H), 4.96-4.83 (m, 2 H), 4.73 (d, J=13.3 Hz, 0.5 H), 4.60 (d, J=13.3 Hz, 0.5 H), 4.50 (d, J=13.3 Hz, 0.5 H), 4.38 (d, J=13.3 Hz, 0.5 H), 4.12 (s, 1 H), 3.76 (s, 3 H), 3.72-3.57 (m, 2 H), 3.25-3.16 (m, 3 H), 3.05-2.97 (m, 8 H), 2.40 (t, J=14.6 Hz, 1 H), 2.28-2.25 (m, 1 H), 1.70-1.60 (m, 1 H), 1.22-1.20 (m, 1 H), 0.82-0.78 (m, 2 H), 0.48-0.46 (m, 2 H); MS (ESI) m/z 574.36 (M+H).

S24-9-17

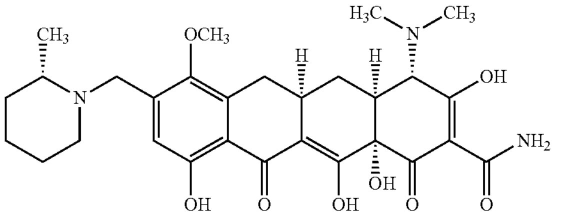

$^1$H NMR (400 MHz, $CD_3OD$, hydrochloride, a mixture of isomers) δ 7.04, 7.00 (s, 1 H), 4.76 (d, J=13.3 Hz, 0.8 H), 4.30 (s, 0.4 H), 4.11 (s, 1 H), 3.98 (d, J=12.8 Hz, 0.8 H), 3.76, 3.74 (s, 3 H), 3.37-3.30 (m, 1 H), 3.22 (dd, J=4.1, 15.6 Hz, 1 H), 3.05-2.91 (m, 10 H), 2.41 (t, J=13.7 Hz, 1 H), 2.27-2.24 (m, 1 H), 2.02-1.98 (m, 2 H), 1.86-1.82 (m, 2 H), 1.72-1.61 (m, 6.4 H), 1.46 (d, J=6.9 Hz, 0.6 H); MS (ESI) m/z 556.41 (M+H).

S24-9-18

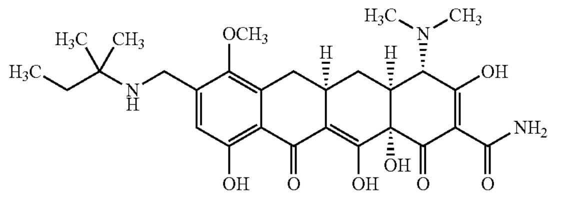

$^1$H NMR (400 MHz, $CD_3OD$, hydrochloride) δ 7.00 (s, 1 H), 4.21 (d, J=12.8 Hz, 1 H), 4.11 (s, 1 H), 4.07 (d, J=12.8 Hz, 1 H), 3.74 (s, 3 H), 3.24 (dd, J=4.6, 15.6 Hz, 1 H), 3.07-2.97 (m, 8 H), 2.38 (t, J=14.6 Hz, 1 H), 2.28-2.24 (m, 1 H), 1.81 (q, J=7.8 Hz, 2 H), 1.70-1.61 (m, 1 H), 1.41 (s, 6 H), 1.04 (t, J=7.3 Hz, 3 H); MS (ESI) m/z 544.36 (M+H).

S24-9-19

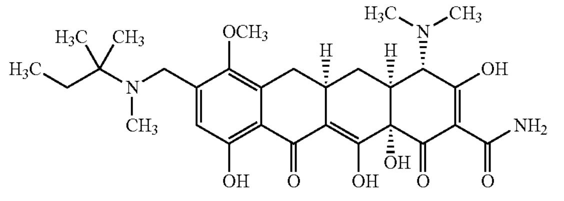

$^1$H NMR (400 MHz, $CD_3OD$, hydrochloride, a mixture of isomers) δ 7.01 (s, 1 H), 4.72 (d, J=12.8 Hz, 0.7 H), 4.60 (d, J=12.8 Hz, 0.3 H), 4.12, 4.11 (s, 1 H), 3.96 (d, J=12.8 Hz, 0.3 H), 3.81 (d, J=12.8 Hz, 0.7 H), 3.77, 3.73 (s, 3 H), 3.26-3.19 (m, 1 H), 3.05-2.98 (m, 8 H), 2.68 (s, 3 H), 2.48-2.32 (m, 1 H), 2.28-2.24 (m, 1 H), 1.94 (q, J=7.3 Hz, 2 H), 1.72-1.62 (m, 1 H), 1.50, 1.48 (s, 6 H), 1.11-1.07 (m, 3 H); MS (ESI) m/z 558.39 (M+H).

S24-9-20

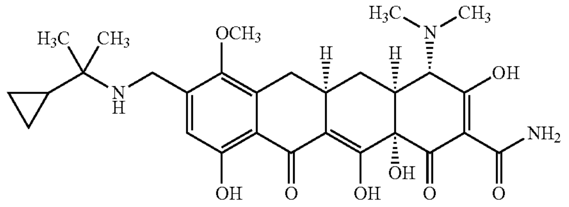

$^1$H NMR (400 MHz, $CD_3OD$, hydrochloride) δ 7.02 (s, 1 H), 4.34 (d, J=12.8 Hz, 1 H), 4.20 (d, J=12.8 Hz, 1 H), 4.12 (s, 1 H), 3.75 (s, 3 H), 3.24 (dd, J=4.1, 15.6 Hz, 1 H), 3.05-2.97 (m, 8 H), 2.38 (t, J=14.6 Hz, 1 H), 2.29-2.24 (m, 1 H), 1.70-1.61 (m, 1 H), 1.32 (s, 3 H), 1.31 (s, 3 H), 1.24-1.18 (m, 1 H), 0.73-0.68 (m, 2 H), 0.62-0.58 (m, 2 H); MS (ESI) m/z 556.39 (M+H).

S24-9-21

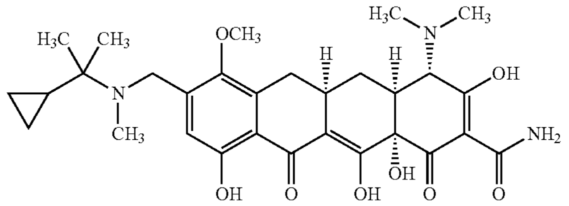

$^1$H NMR (400 MHz, $CD_3OD$, hydrochloride, a mixture of isomers) δ 7.03 (s, 1 H), 4.92-4.85 (m, 0.6 H), 4.76 (d, J=12.8 Hz, 0.4 H), 4.13, 4.12 (s, 1 H), 4.04 (d, J=12.8 Hz, 0.4 H), 3.88 (d, J=12.8 Hz, 0.6 H), 3.77 (s, 1.2 H), 3.74 (s, 1.8 H), 3.28-3.20 (m, 1 H), 3.06-2.98 (m, 8 H), 2.76 (s, 3 H), 2.48-2.33 (m, 1 H), 2.29-2.26 (m, 1 H), 1.72-1.62 (m, 1 H), 1.42 (s, 3 H), 1.37 (s, 3 H), 1.32-1.29 (m, 1 H), 0.83-0.74 (m, 2 H), 0.69-0.66 (m, 2 H); MS (ESI) m/z 570.39 (M+H).

S24-9-22

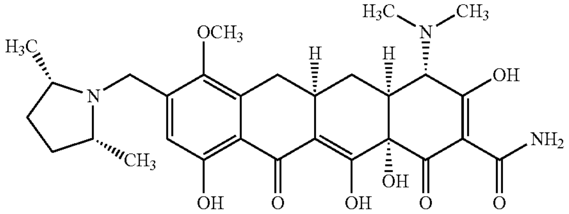

$^1$H NMR (400 MHz, $CD_3OD$, hydrochloride) δ 7.04 (s, 1 H), 4.53 (d, J=13.7 Hz, 1 H), 4.32 (d, J=13.7 Hz, 1 H), 4.13 (s, 1 H), 3.75 (s, 3 H), 3.73-3.69 (m, 2 H), 3.23 (dd, J=4.6, 16.0 Hz, 1 H), 3.08-2.97 (m, 8 H), 2.40 (t, J=14.6 Hz, 1 H), 2.31-2.23 (m, 3 H), 1.79-1.73 (m, 2 H), 1.71-1.61 (m, 1 H), 1.38 (d, J=6.9 Hz, 3 H), 1.32 (d, J=6.4 Hz, 3 H); MS (ESI) m/z 556.43 (M+H).

S24-9-23

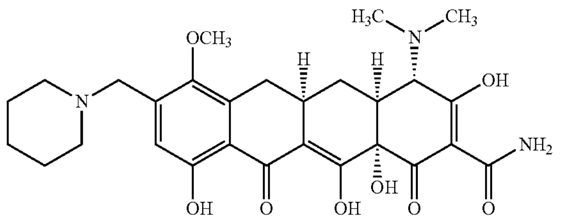

$^1$H NMR (400 MHz, $CD_3OD$, hydrochloride) δ 7.05 (s, 1 H), 4.37, 4.24 (ABq, J=13.3 Hz, 2 H), 4.12 (s, 1 H), 3.72 (s, 3 H), 3.45 (br t, J=13.7 Hz, 2 H), 3.22 (dd, J=4.1, 15.1 Hz, 1 H), 3.07-2.97 (m, 10 H), 2.39 (t, J=14.6 Hz, 1 H), 2.27-2.24 (m, 1 H), 1.93-1.90 (m, 2 H), 1.82-1.75 (m, 3 H), 1.70-1.61 (m, 1 H), 1.56-1.50 (m, 1 H); MS (ESI) m/z 542.41 (M+H).

S24-9-24

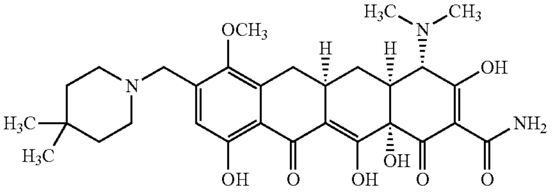

$^1$H NMR (400 MHz, $CD_3OD$, hydrochloride) δ 7.06 (s, 1 H), 4.42 (d, J=12.8 Hz, 1 H), 4.28 (d, J=12.8 Hz, 1 H), 4.12 (s, 1 H), 3.73 (s, 3 H), 3.38-3.30 (m, 2 H), 3.25-3.17 (m, 3 H), 3.05-2.98 (m, 8 H), 2.39 (t, J=14.6 Hz, 1 H), 2.27-2.25 (m, 1 H), 1.76-1.60 (m, 5 H), 1.09 (s, 3 H), 1.03 (s, 3 H); MS (ESI) m/z 570.39 (M+H).

S24-9-25

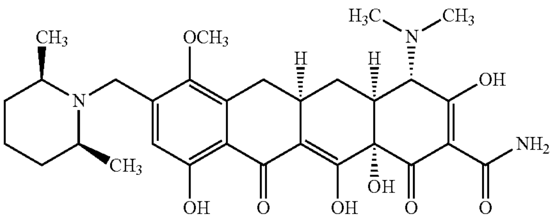

$^1$H NMR (400 MHz, $CD_3OD$, hydrochloride, a mixture of isomers) δ 7.01, 6.99 (s, 1 H), 4.66, 4.58 (ABq, J=15.1 Hz, 0.67 H), 4.43, 4.31 (ABq, J=15.1 Hz, 1.33 H), 4.12 (s, 1 H), 3.74, 3.70 (s, 3 H), 3.59-3.55 (m, 1.33 H), 3.46-3.40 (m, 0.67 H), 3.24-3.20 (m, 1 H), 3.04-2.97 (m, 8 H), 2.39 (t, J=14.2 Hz, 1 H), 2.27-2.24 (m, 1 H), 1.98-1.76 (m, 4 H), 1.70-1.58 (m, 3 H), 1.50 (d, J=6.0 Hz, 1 H), 1.46 (d, J=6.0 Hz, 1 H), 1.32 (d, J=6.4 Hz, 2 H), 1.24 (d, J=6.4 Hz, 2 H); MS (ESI) m/z 570.52 (M+H).

S24-9-26

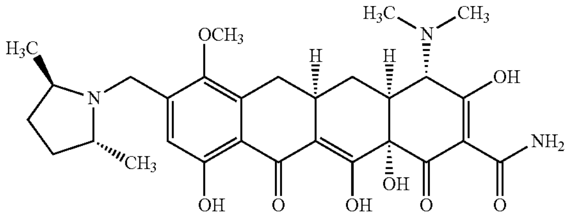

$^1$H NMR (400 MHz, $CD_3OD$, hydrochloride, a mixture of isomers) δ 7.07-7.01 (m, 1 H), 4.54-4.24 (m, 2 H), 4.11 (s, 1 H), 3.92-3.89 (m, 1 H), 3.75 (s, 3 H), 3.77-3.67 (m, 1 H), 3.26-3.21 (m, 1 H), 3.07-2.97 (m, 8 H), 2.44-2.37 (m, 2 H), 2.26-2.22 (m, 2 H), 1.92-1.65 (m, 3 H), 1.43-1.30 (m, 6 H); MS (ESI) m/z 556.49 (M+H).

S24-9-27

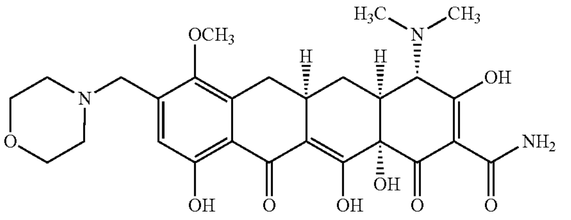

$^1$H NMR (400 MHz, $CD_3OD$) δ 7.10 (s, 1 H), 4.46 (d, J=13.2 Hz, 1 H), 4.33 (d, J=12.8 Hz, 1 H), 4.13 (s, 1 H), 4.04-4.01 (m, 2 H), 3.84-3.74 (m, 2 H), 3.72 (s, 3 H), 3.41 (t, J=13.2 Hz, 2 H), 3.27-2.97 (m, 11 H), 2.40 (dd, J=14.8, 14.4 Hz, 1 H), 2.28 (ddd, J=13.6, 5.6, 2.8 Hz, 1 H), 1.65 (ddd, J=13.2, 13.2, 13.2 Hz, 1 H); MS (ESI) m/z 544.3 (M+H).

S24-9-28

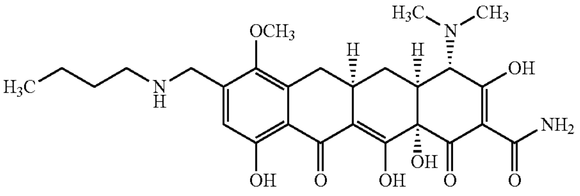

$^1$H NMR (400 MHz, $CD_3OD$) δ 6.99 (s, 1 H), 4.31 (d, J=13.6 Hz, 1 H), 4.17 (d, J=13.6 Hz, 1 H), 4.14 (s, 1 H), 3.74 (s, 3 H), 3.26-2.98 (m, 11 H), 2.37 (dd, J=14.8, 14.4 Hz, 1 H), 2.28 (ddd, J=13.2, 5.6, 2.8 Hz, 1 H), 1.76-1.63 (m, 3 H), 1.47-1.38 (m, 2 H), 0.98 (t, J=7.2 Hz, 3 H); MS (ESI) m/z 530.0 (M+H).

S24-9-29

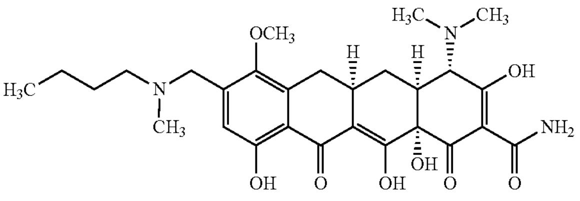

$^1$H NMR (400 MHz, $CD_3OD$) δ 6.99 (s, 1 H), 4.55, 4.08 (d, J=12.8 Hz, 1H total), 4.31 (dd, J=12.8, 12.8 Hz, 1 H), 4.11 (s, 1 H), 3.72 (s, 3 H), 3.28-2.96 (m, 11 H), 2.79, 2.76 (s, 3H total), 2.39-2.23 (m, 2 H), 1.80-1.60 (m, 3 H), 1.44-1.30 (m, 2 H), 0.99-0.91 (m, 3 H); MS (ESI) m/z 544.1 (M+H).

S24-9-30

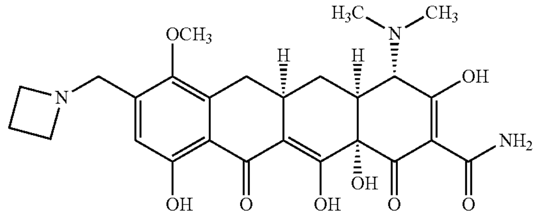

$^1H$ NMR (400 MHz, $CD_3OD$) δ 6.94 (s, 1 H), 4.52 (d, J=13.2 Hz, 1 H), 4.34 (d, J=13.2 Hz, 1 H), 4.25-4.13 (m, 5 H), 3.74 (s, 3 H), 3.24-2.98 (m, 9 H), 2.61-2.58 (m, 1 H), 2.44-2.25 (m, 3 H), 1.65 (ddd, J=13.6, 13.6, 13.6 Hz, 1 H), MS (ESI) m/z 514.0 (M+H).

S24-9-31

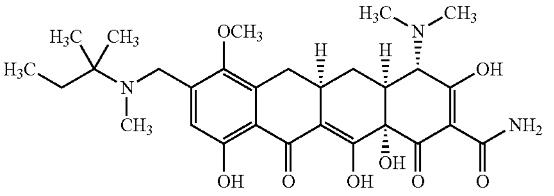

$^1H$ NMR (400 MHz, $CD_3OD$) δ 7.06 (s, 1 H), 4.72, 4.60 (d, J=12.8 Hz, 1H total), 3.98, 3.82 (d, J=12.8 Hz, 1H total), 4.14-4.13 (m, 1 H), 3.74, 3.73 (s, 3H total), 3.28-2.99 (m, 9 H), 2.69 (s, 3 H), 2.41 (dd, J=14.8, 14.8 Hz, 1 H), 2.29 (ddd, J=11.2, 4.8, 2.4 Hz, 1 H), 1.97-1.92 (m, 2 H), 1.72-1.60 (m, 1 H), 1.48 (d, J=7.2 Hz, 6 H), 1.09 (t, J=7.2 Hz, 3 H); MS (ESI) m/z 558.1 (M+H).

S24-9-32

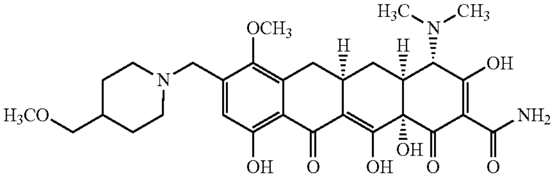

$^1H$ NMR (400 MHz, $CD_3OD$) δ 7.06 (s, 1 H), 4.38 (d, J=12.8 Hz, 1 H), 4.25 (d, J=13.2 Hz, 1 H), 4.13 (s, 1 H), 3.72 (s, 3 H), 3.55-5.43 (m, 2 H), 3.31 (s, 3 H), 3.27-2.98 (m, 13 H), 2.39 (dd, J=14.4, 14.4 Hz, 1H), 2.27 (ddd, J=13.6, 5.6, 2.8 Hz, 1 H), 1.97-1.90 (m, 3 H), 1.71-1.50 (m, 3 H); MS (ESI) m/z 586.1 (M+H).

S24-9-33

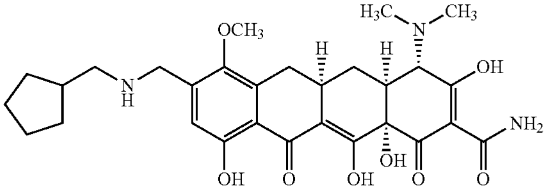

$^1H$ NMR (400 MHz, $CD_3OD$) δ 7.07, 6.99 (s, 1H total), 4.34-4.31 (m, 1 H), 4.21-4.17 (m, 1 H), 4.12 (s, 1 H), 3.77, 3.73 (s, 3H total), 3.26-2.98 (m, 11 H), 2.38 (dd, J=15.2, 14.0 Hz, 1H), 2.29-2.10 (m, 2 H), 1.96-1.90 (m, 2 H), 1.73-1.66 (m, 5 H), 1.32-1.22 (m, 2 H); MS (ESI) m/z 556.3 (M+H).

S24-9-34

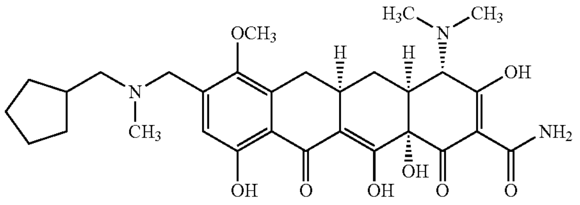

$^1H$ NMR (400 MHz, $CD_3OD$) δ 7.09, 7.01 (s,1H total), 4.66-4.63 (m, 1 H), 4.43-4.33 (m, 1 H), 4.13-4.06 (m, 1 H), 3.79-3.73 (m, 3 H), 3.27-2.98 (m, 14 H), 2.84-2.14 (m, 3 H), 1.98-1.94 (m, 2 H), 1.74-1.65 (m, 5 H), 1.33-1.12 (m, 2 H); MS (ESI) m/z 570.1 (M+H).

S24-9-35

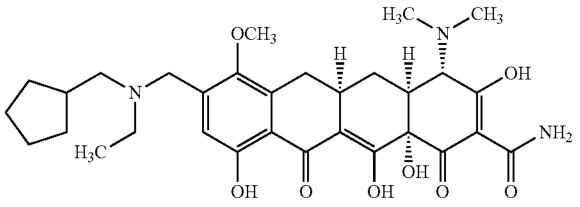

$^1H$ NMR (400 MHz, $CD_3OD$) δ 7.02 (s,1 H), 4.52, 4.32 (d, J=13.2 Hz, 1H total), 4.45, 4.22 (d, J=13.2 Hz, 1H total), 4.12 (s, 1 H), 3.76, 3.75 (s, 3H total), 3.25-2.98 (m, 13 H), 2.42-2.25 (m, 3 H), 1.95-1.91 (m, 2 H), 1.72-1.62 (m, 5 H), 1.41-1.35 (m, 3H), 1.29-1.19 (m, 2H); MS (ESI) m/z 584.1 (M+H).

S24-9-36

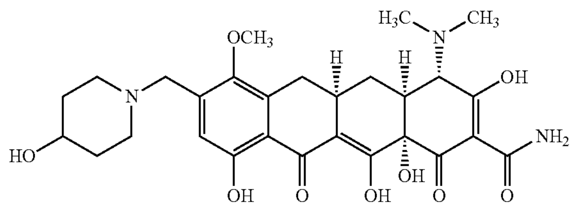

$^1H$ NMR (400 MHz, $CD_3OD$) δ 7.06, 7.04 (s, 1H total), 4.39 (dd, J=13.2, 5.2 Hz, 1 H), 4.27 (d, J=13.2 Hz, 1 H), 4.12 (s, 1 H), 4.05 (s, 1 H), 3.72 (s, 3 H), 3.54-3.47 (m, 1 H), 3.34-3.31 (m, 2 H), 3.24-2.98 (m, 10 H), 2.40 (dd, J=14.4, 14.4 Hz, 1 H), 2.25 (ddd, J=14.4, 5.2, 2.8 Hz, 1 H), 2.14-2.10 (m, 1 H), 1.98-1.88 (m, 2 H), 1.71-1.61 (m, 2 H); MS (ESI) m/z 558.2 (M+H).

S24-9-37

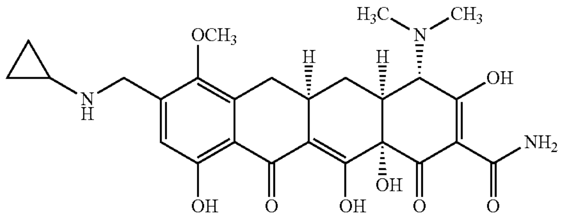

$^1$H NMR (400 MHz, $CD_3OD$) δ 6.98 (s, 1 H), 4.41 (d, J=13.6 Hz, 1 H), 4.27 (d, J=13.2 Hz, 1 H), 4.13 (s, 1 H), 3.75 (s, 3 H), 3.24-2.97 (m, 9 H), 2.81-2.79 (m, 1 H), 2.37 (dd, J=14.4, 14.4 Hz, 1 H), 2.27 (ddd, J=12.8, 5.2, 2.8 Hz, 1 H), 1.65 (ddd, J=12.8, 12.8, 12.8 Hz, 1 H), 0.91 (d, J=5.2 Hz, 4 H); MS (ESI) m/z 514.3 (M+H).

S24-9-38

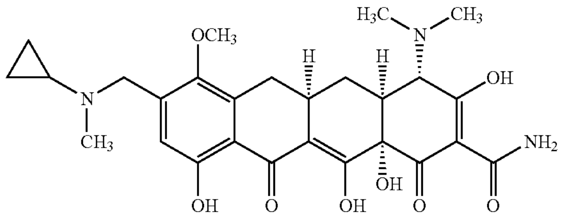

$^1$H NMR (400 MHz, $CD_3OD$) δ 7.04 (s, 1 H), 4.64-4.53 (m, 1 H), 4.72-4.34 (m, 1 H), 4.13 (s, 1 H), 3.76 (s, 3 H), 3.25-2.94 (m, 13 H), 2.40 (dd, J=14.0, 14.0 Hz, 1 H), 2.27 (ddd, J=13.2, 5.2, 2.8 Hz, 1 H), 1.66 (ddd, J=11.2, 11.2, 11.2 Hz, 1 H), 1.02-0.80 (m, 4 H); MS (ESI) m/z 528.1 (M+H).

S24-9-39

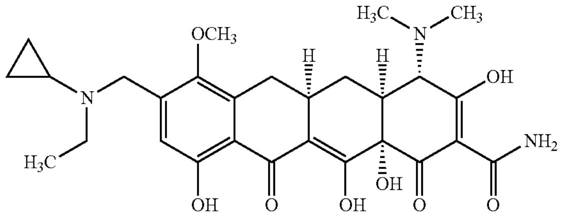

$^1$H NMR (400 MHz, $CD_3OD$) δ 7.05, 7.03 (s, 1H total), 4.61, 4.42 (d, J=12.8 Hz, 1H total), 4.51, 4.35 (d, J=13.2 Hz, 1H total), 4.12 (s, 1 H), 3.75 (s, 3 H), 3.39-3.33 (m, 2 H), 3.25-2.90 (m, 9 H), 2.89-2.85 (m, 1 H), 2.40 (dd, J=14.8, 14.4 Hz, 1 H), 2.26 (ddd, J=13.6, 4.8, 2.8 Hz, 1 H), 1.67 (ddd, J=11.2, 11.2, 11.2 Hz, 1 H), 1.46 (t, J=7.2 Hz, 3 H), 1.04-0.67 (m, 4 H); MS (ESI) m/z 542.1 (M+H).

S24-9-40

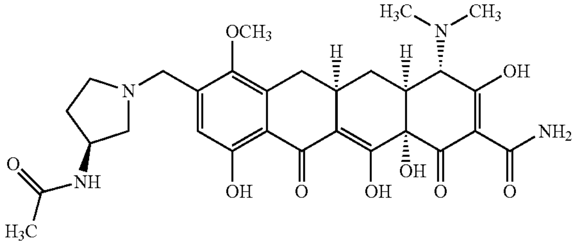

$^1$H NMR (400 MHz, $CD_3OD$) δ 7.06, 7.05 (s, 1H total), 4.59-4.52 (m, 1 H), 4.50-4.40 (m, 2 H), 4.15 (s, 1 H), 3.81-3.74 (m, 4 H), 3.59-3.48 (m, 2 H), 3.24-2.98 (m, 10 H), 2.60-2.50 (m, 1 H), 2.38 (dd, J=13.2, 12.8 Hz, 1 H), 2.28 (ddd, J=12.4, 5.2, 2.8 Hz, 1 H), 2.14-2.07 (m, 1 H), 1.98, 1.95 (s, 3H total), 1.70-1.61 (m, 1 H); MS (ESI) m/z 585.1 (M+H).

S24-9-41

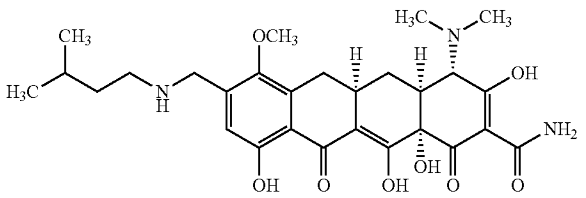

$^1$H NMR (400 MHz, $CD_3OD$) δ 6.99 (s, 1 H), 4.31 (d, J=13.6 Hz, 1 H), 4.18 (d, J=13.6 Hz, 1 H), 4.13 (s, 1 H), 3.74 (s, 3 H), 3.26-2.98 (m, 11 H), 2.38 (dd, J=14.8, 14.4 Hz, 1 H), 2.27 (ddd, J=13.2, 5.2, 2.8 Hz, 1 H), 1.72-1.60 (m, 4 H), 0.97 (d, J=6.4 Hz, 6 H); MS (ESI) m/z 544.0 (M+H).

S24-9-42

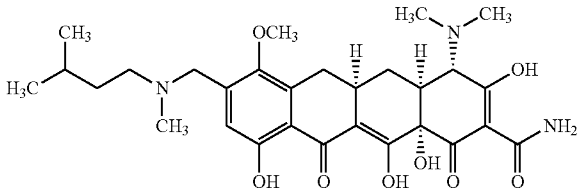

$^1$H NMR (400 MHz, $CD_3OD$) δ 7.02, 7.01 (s, 1H total), 4.58, 4.09 (d, J=12.8 Hz, 1H total), 4.36 (dd, J=12.8 Hz, 1 H), 4.13 (s, 1 H), 3.75 (s, 3 H), 3.25-2.98 (m, 11 H), 2.81, 2.79 (s, 3H total), 2.40 (dd, J=14.0, 13.6 Hz, 1 H), 2.28 (ddd, J=12.4, 5.2, 2.8 Hz, 1 H), 1.71-1.61 (m, 4 H), 0.96 (d, J=6.0 Hz, 6 H); MS (ESI) m/z 558.1 (M+H).

S24-9-43

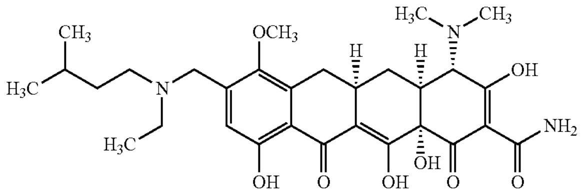

$^1$H NMR (400 MHz, $CD_3OD$) δ 7.03 (s, 1 H), 4.46 (d, J=13.2 Hz, 1 H), 4.26 (d, J=12.4 Hz, 1 H), 4.13 (s, 1 H), 3.75 (s, 3 H), 3.26-2.98 (m, 13 H), 2.44-2.36 (m, 1 H), 2.30-2.26 (m, 1 H), 1.71-1.60 (m, 4 H), 1.37 (dd, J=7.2, 7.2 Hz, 3 H), 0.97-0.95 (m, 6 H); MS (ESI) m/z 572.1 (M+H).

S24-9-44

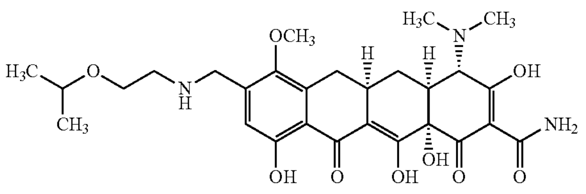

$^{1}$H NMR (400 MHz, $CD_3OD$) δ 6.96 (s, 1 H), 4.35 (d, J=13.6 Hz, 1 H), 4.21 (d, J=14.0 Hz, 1 H), 4.12 (s, 1 H), 3.74 (s, 3 H), 3.72-3.65 (m, 3 H), 3.25-2.97 (m, 11 H), 2.37 (dd, J=14.8, 14.4 Hz, 1 H), 2.26 (ddd, J=13.6, 5.2, 2.8 Hz, 1 H), 1.64 (ddd, J=13.2, 13.2, 13.2 Hz, 1 H), 1.19 (d, J=6.0 Hz, 6 H); MS (ESI) m/z 560.2 (M+H).

S24-9-45

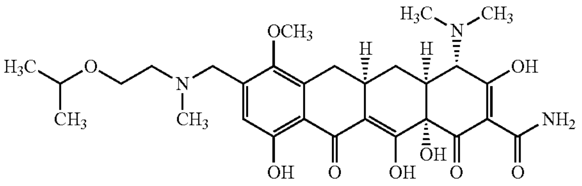

$^{1}$H NMR (400 MHz, $CD_3OD$) δ 7.00 (s, 1 H), 4.65, 4.37 (d, J=13.2, Hz, 1 H total), 4.47, 4.19 (d, J=13.2 Hz, 1 H total), 4.12 (s, 1 H), 3.82-3.79 (m, 2 H), 3.75, 3.74(s, 3 H total), 3.71-3.67 (m, 1 H), 3.42-3.33 (m, 2 H), 3.24-2.97 (m, 9 H), 2.87, 2.83 (s, 3 H total), 2.39 (dd, J=14.8, 14.4 Hz, 1 H), 2.27 (ddd, J=12.0, 5.2, 2.8 Hz, 1 H), 1.65 (ddd, J=13.2, 13.2, 13.2 Hz, 1 H), 1.12 (d, J=6.0 Hz, 6 H); MS (ESI) m/z 574.1 (M+H).

S24-9-46

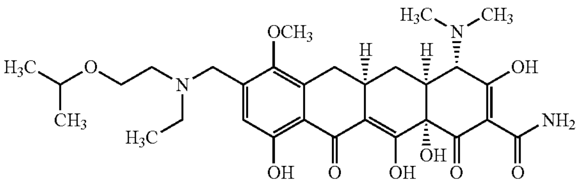

$^{1}$H NMR (400 MHz, $CD_3OD$) δ 7.03 (s, 1 H), 4.59, 4.40 (d, J=13.6 Hz, 1 H total), 4.52, 4.33 (d, J=13.6 Hz, 1 H total), 4.13 (s, 1 H), 3.78-3.76 (m, 5 H), 3.71-3.66 (m, 1 H), 3.45-3.34 (m, 2 H), 3.25-2.98 (m, 11 H), 2.40 (dd, J=13.6, 13.6 Hz, 1 H), 2.27 (ddd, J=12.0, 5.2, 2.8 Hz, 1 H), 1.66 (ddd, J=13.2, 13.2, 13.2 Hz, 1 H), 1.42-1.34 (m, 3 H), 1.21-1.19 (m, 6 H); MS (ESI) m/z 588.1 (M+H).

S24-9-47

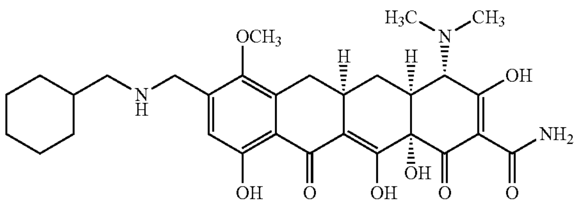

$^{1}$H NMR (400 MHz, $CD_3OD$) δ 6.99 (s, 1 H), 4.31 (d, J=13.6 Hz, 1 H), 4.17 (d, J=13.6, Hz, 1 H), 4.13 (s, 1 H), 3.74 (s, 3 H), 3.25-2.90 (m, 11 H), 2.38 (dd, J=14.4, 14.4 Hz, 1 H), 2.29-2.26 (m, 1 H), 1.83-1.64 (m, 7 H), 1.37-1.20 (m, 3 H), 1.06-0.95 (m, 2 H); MS (ESI) m/z 570.3 (M+H).

S24-9-48

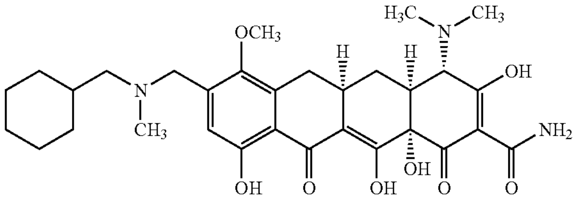

$^{1}$H NMR (400 MHz, $CD_3OD$) δ 7.09-7.00 (m, 1 H), 4.63, 4.30 (d, J=12.8 Hz, 1 H total), 4.43, 4.04 (d, J=13.2 Hz, 1 H total), 4.14 (s, 1 H), 3.81-3.74 (m, 3 H), 3.25-2.79 (m, 14 H), 2.40 (dd, J=15.6, 14.8 Hz, 1 H), 2.30-2.27 (m, 1 H), 1.95-1.64 (m, 7 H), 1.36-1.28 (m, 3 H), 1.06-0.95 (m, 2 H); MS (ESI) m/z 584.1 (M+H).

S24-9-49

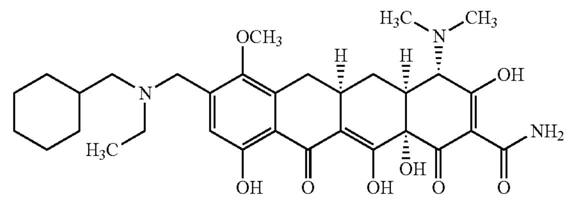

$^{1}$H NMR (400 MHz, $CD_3OD$) δ 7.01 (s, 1 H), 4.50, 4.30 (d, J=13.2 Hz, 1 H total), 4.43, 4.19 (d, J=13.6 Hz, 1 H total), 4.11 (s, 1 H), 3.76, 3.75 (s, 3 H total), 3.25-2.98(m, 13 H), 2.45-2.36 (m, 1 H), 2.28-2.25 (m, 1 H), 1.92-1.62 (m, 7 H), 1.41-1.14 (m, 6 H), 1.06-0.95 (m, 2 H); MS (ESI) m/z 598.1 (M+H).

S24-9-50

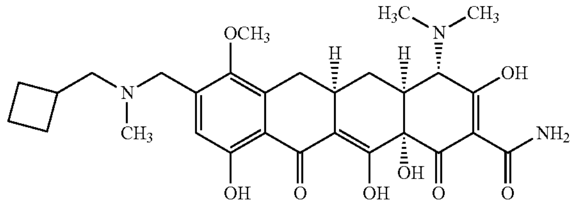

$^{1}$H NMR (400 MHz, $CD_3OD$) δ 7.01 (s, 1 H), 4.50, 4.08 (d, J=12.8 Hz, 1 H total), 4.34, 4.30 (d, J=13.6 Hz, 1 H total), 4.14 (s, 1 H), 3.80, 3.75 (s, 3 H total), 3.27-2.74 (m, 15 H), 2.44-2.12 (m, 4 H), 2.05-1.80 (m, 4 H), 1.65 (ddd, J=13.2, 13.2, 13.2 Hz, 1 H); MS (ESI) m/z 556.1 (M+H).

S24-9-51

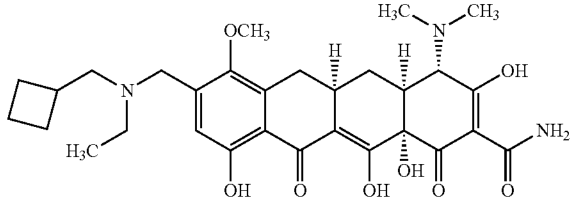

$^{1}$H NMR (400 MHz, $CD_3OD$) δ 7.00 (s, 1 H), 4.40 (t, J=13.2 Hz, 1 H), 4.20 (d, J=12.8 Hz, 1 H), 4.13 (s, 1 H), 3.75

(s, 3 H), 3.23-2.83 (m, 14 H), 2.40 (dd, J=14.8, 13.6 Hz, 1 H), 2.28 (ddd, J=12.4, 5.2, 2.8 Hz, 1 H), 2.20-2.14 (m, 2 H), 2.04-1.97 (m, 1 H), 1.92-1.84 (m, 3 H), 1.66 (ddd, J=13.2, 13.2, 13.2 Hz, 1 H), 1.39-1.30 (m, 3 H); MS (ESI) m/z 570.1 (M+H).

S24-9-52

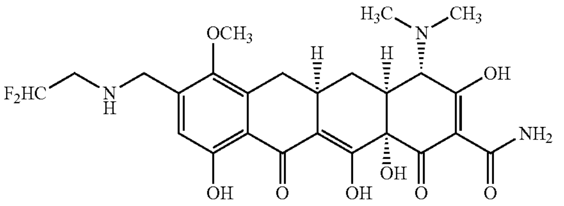

[1] H NMR (400 MHz, $CD_3OD$) δ 7.00 (s, 1 H), 6.34 (t, J=53.6 Hz, 1 H ), 4.43 (d, J=13.6 Hz, 1 H), 4.30 (d, J=13.2 Hz, 1 H), 4.12 (s, 1 H), 3.75 (s, 3 H), 3.63 (ddd, J=13.6, 13.6, 13.6, 2 H), 3.25-2.98 (m, 9 H), 2.39 (dd, J=14.4, 14.8 Hz, 1 H), 2.27 (ddd, J=12.4, 5.2, 2.8 Hz, 1 H), 1.65 J=13.2, 13.2, 13.2 Hz, 1 H); MS (ESI) m/z 538.1 (M+H).

S24-9-53

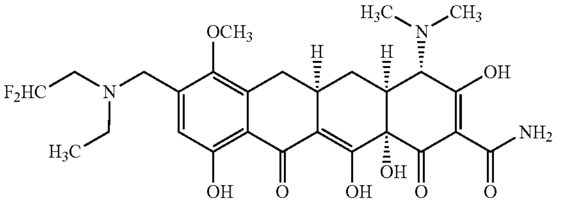

[1] H NMR (400 MHz, $CD_3OD$) δ 7.04 (s, 1 H), 6.46 (t, J=53.6 Hz, 1 H ), 4.60 (d, J=13.2 Hz, 1 H), 4.41 (d, J=13.2 Hz, 1 H), 4.12 (s, 1 H), 3.78-3.72 (m, 5 H), 3.36-3.34 (m, 2 H), 3.25-2.98 (m, 9 H), 2.41 (dd, J=14.4, 14.4 Hz, 1 H), 2.27 (ddd, J=12.0, 5.2, 2.8 Hz, 1 H), 1.66 (ddd, J=12.4, 12.4, 12.4 Hz, 1 H), 1.41 (t, J=7.2 Hz, 3 H); MS (ESI) m/z 565.9 (M+H).

S24-9-54

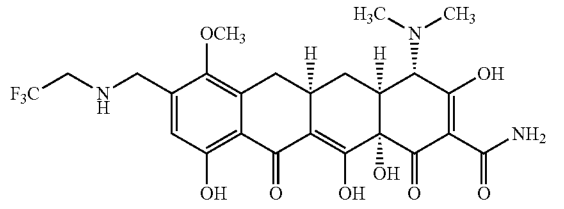

[1] H NMR (400 MHz, $CD_3OD$) δ 7.00 (s, 1 H), 4.45 (d, J=13.2 Hz, 1 H), 4.33 (d, J=13.2 Hz, 1 H), 4.11 (s, 1 H), 4.06 (t, J=8.8 Hz, 2 H), 3.75 (s, 3 H), 3.26-2.97 (m, 9 H), 2.39 (dd, J=14.4, 14.4 Hz, 1 H), 2.26 (ddd, J=13.2, 5.2, 2.8 Hz, 1 H), 1.66 (ddd, J=14.0, 14.0, 14.0 Hz, 1 H); MS (ESI) m/z 556.0 (M+H).

S24-9-55

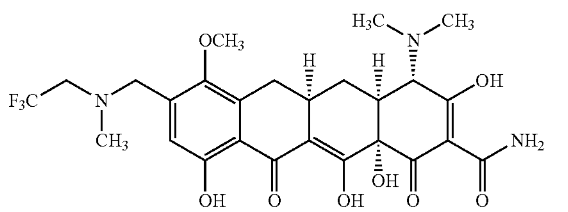

[1] H NMR (400 MHz, $CD_3OD$) δ 7.03 (s, 1 H), 4.52 (d, J=13.2 Hz, 1 H), 4.35 (d, J=12.8 Hz, 1 H), 4.20-4.12 (m, 3 H), 3.74 (s, 3 H), 3.26-2.92 (m, 12 H), 2.40 (dd, J=14.8, 14.8 Hz, 1 H), 2.27 (ddd, J=15.2, 5.2, 2.8 Hz, 1 H), 1.66 (ddd, J=13.2, 13.2, 13.2 Hz, 1 H); MS (ESI) m/z 570.0 (M+H).

S24-9-56

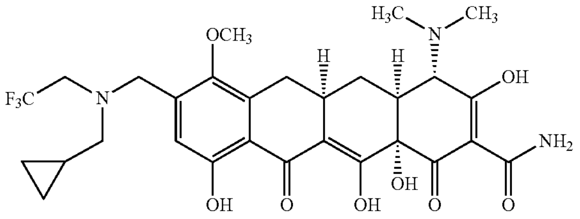

[1] H NMR (400 MHz, $CD_3OD$) δ 7.04 (s, 1 H), 4.59 (d, J=13.6 Hz, 1 H), 4.43 (d, J=13.6 Hz, 1 H), 4.21-4.12 (m, 3 H), 3.74 (s, 3 H), 3.26-2.98 (m, 11 H), 2.40 (dd, J=14.8, 14.4 Hz, 1 H), 2.27 (ddd, J=13.2, 5.2, 2.8 Hz, 1 H), 1.66 (ddd, J=13.2, 13.2, 13.2 Hz, 1 H); 1.18-1.15 (m, 1 H), 0.78 (d, J=7.6 Hz, 2 H), 0.42 (d, J=4.4 Hz, 2 H); MS (ESI) m/z 610.0 (M+H).

S24-9-57

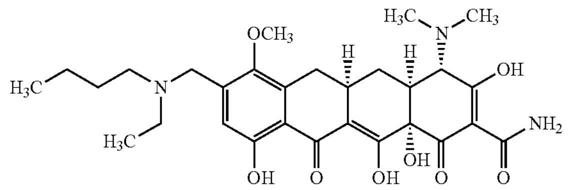

[1] H NMR (400 MHz, $CD_3OD$) δ 7.01 (s, 1 H), 4.43 (dd, J=13.2, 13.2 Hz, 1 H), 4.23 (dd, J=12.8, 12.8 Hz, 1 H), 4.11 (s, 1 H), 3.73 (s, 3 H), 3.28-2.96(m, 13 H), 2.38-2.24 (m, 2 H), 1.76-1.60 (m, 3 H), 1.41-1.31 (m, 5 H), 0.99-0.91 (m, 3 H); MS (ESI) m/z 558.1 (M+H).

S24-9-58

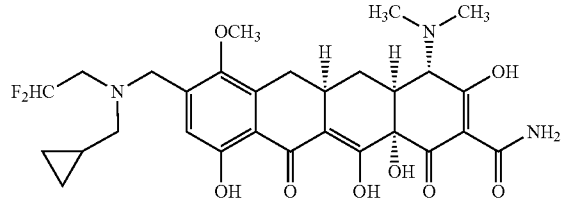

[1] H NMR (400 MHz, $CD_3OD$) δ 7.05 (s, 1 H), 6.49 (t, J=53.2 Hz, 1 H), 4.70 (d, J=13.2 Hz, 1 H), 4.51 (d, J=13.6 Hz,

1 H), 4.13 (s, 1 H), 3.85-3.76 (m, 5 H), 3.25-2.98 (m, 11 H), 2.41 (dd, J=14.8, 14.4 Hz, 1 H), 2.27 (ddd, J=13.2, 5.2, 2.8 Hz, 1 H), 1.66 (ddd, J=13.6, 13.6, 13.6 Hz, 1 H), 1.29-1.24 (m, 1 H), 0.82 (d, J=7.6 Hz, 2 H), 0.48 (d, J=4.8 Hz, 2 H); MS (ESI) m/z 592.0 (M+H).

S24-9-59

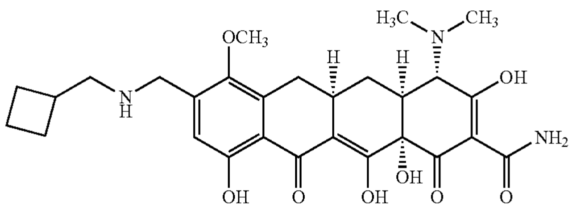

[1] H NMR (400 MHz, $CD_3OD$) δ 6.97 (s, 1 H), 4.28 (d, J=13.6 Hz, 1 H), 4.16-4.12 (m, 2 H), 3.74 (s, 3 H), 3.25-2.98 (m, 11 H), 2.77-2.69 (m, 1 H), 2.37 (dd, J=14.8, 14.4 Hz, 1 H), 2.27 (ddd, J=13.6, 5.2, 2.8 Hz, 1 H), 2.20-2.16 (m, 2 H), 2.03-1.80 (m, 4 H), 1.65 (ddd, J=14.0, 14.0, 14.0 Hz, 1 H); MS (ESI) m/z 542.1 (M+H).

S24-9-60

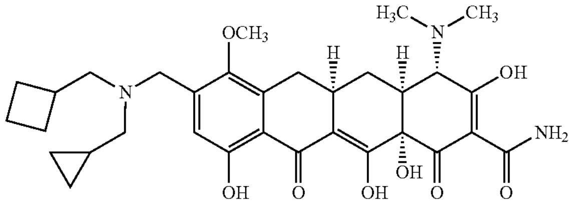

[1] H NMR (400 MHz, $CD_3OD$) δ 7.01 (s, 1 H), 4.63, 4.22 (d, J=13.2 Hz, 1 H total), 4.40 (dd, J=13.6 Hz, 1 H), 4.13 (s, 1 H), 3.76 (s, 3 H), 3.25-2.98 (m, 13 H), 2.88-2.82 (m, 1 H), 2.40 (dd, J=14.4, 14.4 Hz, 1 H), 2.29-2.14 (m, 3 H), 2.03-1.80 (m, 4 H), 1.65 (ddd, J=14.0, 14.0, 14.0 Hz, 1 H), 1.22-1.12 (m, 1 H), 0.83-0.76 (m, 2 H), 0.48-0.40 (m, 2 H); MS (ESI) m/z 596.1 (M+H).

S24-9-61

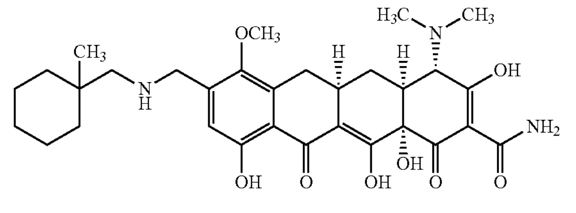

[1] H NMR (400 MHz, $CD_3OD$) δ 7.00 (s, 1 H), 4.62, 4.28 (d, J=13.2 Hz, 1 H total), 4.43, 4.03 (d, J=13.2 Hz, 1 H total), 4.12 (s, 1 H), 3.77, 3.74 (s, 3 H total), 3.26-2.98 (m, 11 H), 2.83, 2.79 (s, 3 H total), 2.40 (dd, J=14.8, 14.8 Hz, 1 H), 2.27 (ddd, J=13.6, 5.2, 2.8 Hz, 1 H), 1.99-1.92 (m, 1 H), 1.80-1.62 (m, 5 H), 1.42-1.20 (m, 3 H), 1.10-0.90 (m, 2 H); MS (ESI) m/z 584.1 (M+H).

S24-9-62

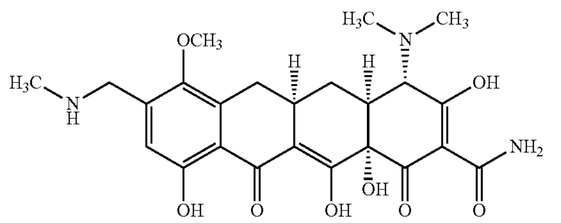

[1] H NMR (400 MHz, $CD_3OD$) δ 6.94 (s, 1 H), 4.31 (d, J=13.6 Hz, 1 H), 4.15 (d, J=14.4 Hz, 1 H), 4.11 (s, 1 H), 3.74 (s, 3 H), 3.25-2.97 (m, 9 H), 2.74 (s, 3 H), 2.38 (dd, J=14.4, 14.8 Hz, 1 H), 2.26 (ddd, J=13.6, 5.2, 2.8 Hz, 1 H), 1.66 (ddd, J=13.6, 13.6, 13.6 Hz, 1 H), MS (ESI) m/z 488.0 (M+H).

S24-9-63

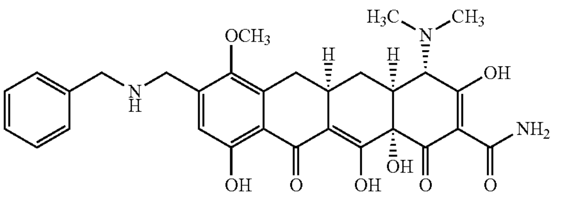

[1] H NMR (400 MHz, $CD_3OD$) δ 7.53-7.47 (m, 5 H), 6.93 (s, 1 H), 4.32-4.25 (m, 3 H), 4.14 (d, J=13.2 Hz, 1 H), 4.11 (s, 1 H), 3.59 (s, 3 H), 3.22-2.97 (m, 9 H), 2.36 (dd, J=14.8, 14.4 Hz, 1 H), 2.25 (ddd, J=14.0, 5.2, 2.8 Hz, 1 H), 1.64 (ddd, J=13.2, 13.2, 13.2 Hz, 1 H); MS (ESI) m/z 564.1 (M+H).

S24-9-64

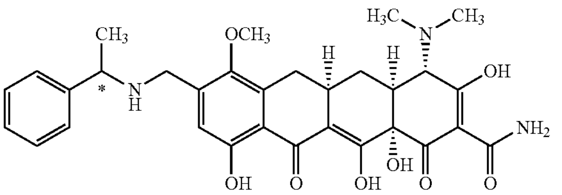

single diastereomer A

[1] H NMR (400 MHz, $CD_3OD$) δ 7.53-7.49 (m, 5 H), 6.88 (s, 1 H), 4.51-4.48 (m, 1 H), 4.15-4.11 (m, 2 H), 3.91 (d, J=13.2 Hz, 1 H), 3.47 (s, 3 H), 3.17-2.97 (m, 9 H), 2.36-2.23 (m, 2 H), 1.73 (d, J=6.8 Hz, 3 H), 1.68-1.58 (m, 1 H); MS (ESI) m/z 578.1 (M+H).

S24-9-65

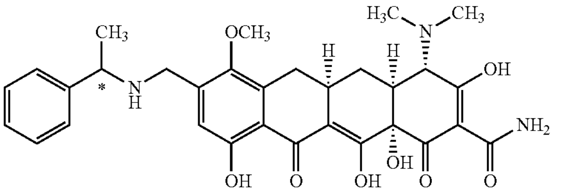

single diastereomer B

[1] H NMR (400 MHz, $CD_3OD$) δ 7.54-7.48 (m, 5 H), 6.90 (s, 1 H), 4.49-4.46 (m, 1 H), 4.11 (s, 1 H), 3.98 (dd, J=13.2, 12.8 Hz, 2 H), 3.39 (s, 3 H), 3.21-2.97 (m, 9 H), 2.36-2.23 (m, 2 H), 1.71 (d, J=6.4 Hz, 3 H), 1.68-1.59 (m, 1 H); MS (ESI) m/z 578.1 (M+H).

S24-9-66

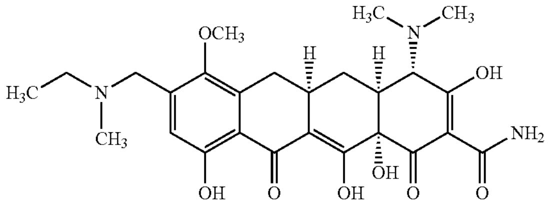

[1] H NMR (400 MHz, $CD_3OD$) δ 7.01 (s, 1 H), 4.55, 4.10 (d, J=13.2 Hz, 1 H total), 4.35 (dd, J=13.2, 13.2 Hz, 1 H), 4.12 (s, 1 H), 3.75 (s, 3 H), 3.34-2.98 (m, 11 H), 2.81, 2.78 (s, 3 H total), 2.45-2.35 (m, 1 H), 2.29-2.25 (m, 1 H), 1.66 (ddd, J=12.8, 12.8, 12.8 Hz, 1 H), 1.43-1.35 (m, 3 H); MS (ESI) m/z 516.1 (M+H).

S24-9-67

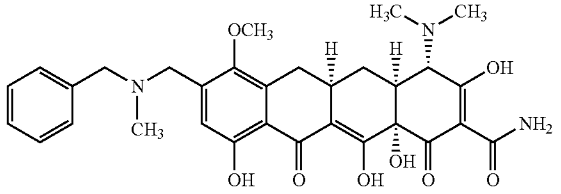

[1] H NMR (400 MHz, $CD_3OD$) δ 7.60-7.53 (m, 5 H), 6.98, 6.95 (s, 1 H total), 4.53, 4.03 (d, J=12.8 Hz, 1 H), 4.42-4.25 (m, 3 H), 4.13 (s, 1 H), 3.52, 3.32 (s, 3 H total), 3.18-2.97 (m, 9 H), 2.83, 2.81 (s, 3 H total), 2.37-2.24 (m, 2 H), 1.63 (ddd, J=12.4, 12.4, 12.4 Hz, 1 H); MS (ESI) m/z 578.1 (M+H).

S24-9-68

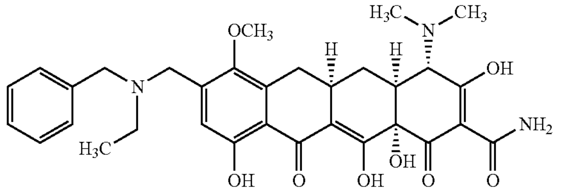

[1] H NMR (400 MHz, $CD_3OD$) δ 7.57-7.49 (m, 5 H), 6.95, 6.85 (s, 1 H total), 4.54-4.10 (m, 5 H), 3.55, 3.34 (s, 3 H total), 3.26-2.97 (m, 11 H), 2.38-2.22 (m, 2 H), 1.64 (ddd, J=13.2, 13.2, 13.2 Hz, 1 H), 1.46-1.41 (m, 3 H); MS (ESI) m/z 592.1 (M+H).

S24-9-69

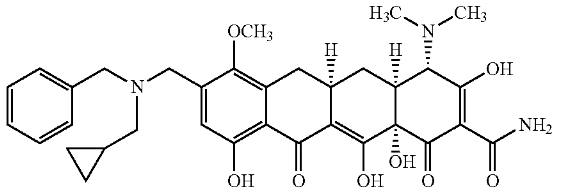

[1] H NMR (400 MHz, $CD_3OD$) δ 7.59-7.48 (m, 5 H), 6.97, 6.86 (s, 1 H total), 4.68, 4.28 (d, J=12.8 Hz, 1 H total), 4.59 (dd, J=12.8, 12.8 Hz, 1 H), 4.42-4.33 (m, 2 H), 4.13, 4.12 (s, 1 H total), 3.57, 3.35 (s, 3 H total), 3.17-2.98 (m, 11 H), 2.37-2.25 (m, 2 H), 1.64 (ddd, J=12.8, 12.8, 12.8 Hz, 1 H), 1.29-1.26 (m, 1 H), 0.82-0.80 (m, 2 H), 0.44-0.42 (m, 2 H); MS (ESI) m/z 618.1 (M+H).

S24-9-70

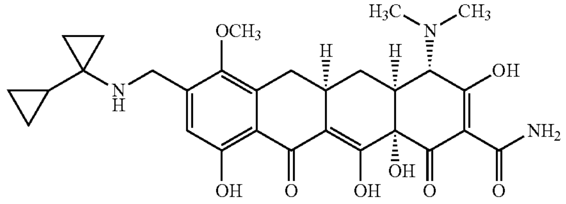

[1] H NMR (400 MHz, $CD_3OD$) δ 7.00 (s, 1 H), 4.54 (d, J=13.2 Hz, 1 H), 4.36 (d, J=12.8 Hz, 1 H), 4.12 (s, 1 H), 3.78 (s, 3 H), 3.26-2.98 (m, 9 H), 2.39 (dd, J=14.4, 14.4 Hz, 1 H), 2.28-2.25 (m, 1 H), 1.71-1.57 (m, 2 H), 1.03-1.01 (m, 2 H), 0.81-0.79 (m, 2 H), 0.75-0.71 (m, 2 H), 0.43-0.40 (m, 2 H); MS (ESI) m/z 554.0 (M+H).

S24-9-71

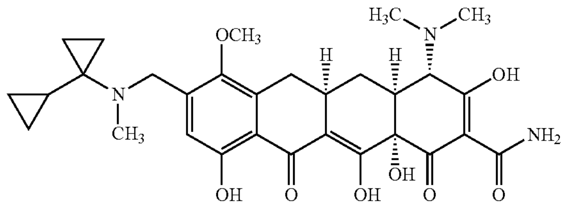

[1] H NMR (400 MHz, $CD_3OD$) δ 7.06 (s, 1 H), 4.70, 4.46 (d, J=12.8 Hz, 1 H total), 4.61 (s, 1 H), 4.13, 4.12 (s, 1 H total), 3.80, 3.76 (s, 3 H total), 3.25-2.94 (m, 12 H), 2.46-2.25 (m, 2 H), 1.70-1.61 (m, 2 H), 1.14-1.10 (m, 2 H), 0.96-0.70 (m, 4 H), 0.40-0.31 (m, 2 H); MS (ESI) m/z 568.2 (M+H).

S24-9-72

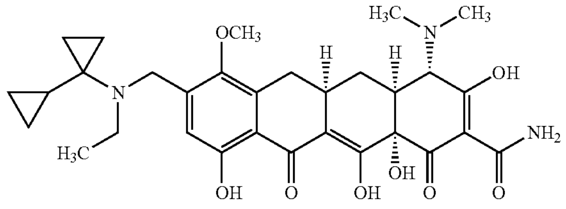

[1] H NMR (400 MHz, $CD_3OD$) δ 7.07 (s, 1 H), 4.67 (dd, J=14.4, 14.0 Hz, 1 H), 4.52 (dd, J=12.4, 12.4 Hz, 1 H), 4.13 (s, 1 H), 3.77, 3.75 (s, 3 H total), 3.69-3.61 (m, 1 H), 3.48-3.43 (m, 1 H), 3.26-2.98 (m, 9 H), 2.40 (dd, J=13.6, 13.6 Hz, 1 H), 2.29-2.25 (m, 1 H), 1.71-1.61 (m, 2 H), 1.39-1.36 (m, 3 H), 1.29-1.22 (m, 1 H), 0.96-0.70 (m, 5 H), 0.42-0.31 (m, 2 H); MS (ESI) m/z 582.0 (M+H).

S24-9-73

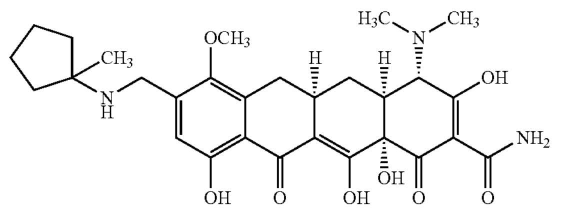

[1] H NMR (400 MHz, $CD_3OD$) δ 7.00 (s, 1 H), 4.24 (d, J=12.8 Hz, 1 H), 4.14-4.10 (m, 2 H), 3.76 (s, 3 H), 3.27-2.98 (m, 9 H), 2.39 (dd, J=14.8, 14.4 Hz, 1 H), 2.27 (ddd, J=13.6, 4.8, 2.8 Hz, 1 H), 1.98-1.80 (m, 8 H), 1.66 (ddd, J=13.6, 13.6, 13.6 Hz, 1 H), 1.50 (s, 3 H); MS (ESI) m/z 556.0 (M+H).

S24-9-74

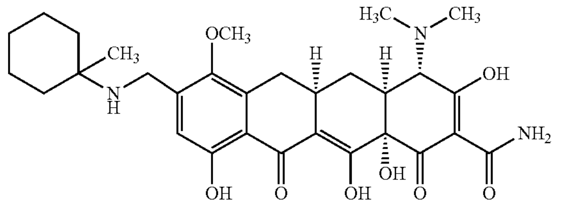

[1] H NMR (400 MHz, $CD_3OD$) δ 7.01 (s, 1 H), 4.24 (d, J=12.8 Hz, 1 H), 4.13-4.18 (m, 2 H), 3.75 (s, 3 H), 3.27-2.97 (m, 9 H), 2.39 (dd, J=14.8, 14.8 Hz, 1 H), 2.27 (ddd, J=13.6, 4.8, 2.4 Hz, 1 H), 1.97-1.91 (m, 2 H), 1.80-1.53 (m, 8 H), 1.50 (s, 3 H), 1.32-1.25 (m, 1 H); MS (ESI) m/z 570.0 (M+H).

S24-9-75

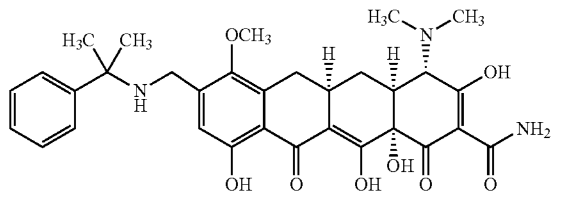

[1] H NMR (400 MHz, $CD_3OD$) δ 7.70-7.67 (m, 2 H), 7.57-7.47 (m, 3 H), 6.87 (s, 1 H), 4.13 (s, 1 H), 3.81 (dd, J=12.8 Hz, 2 H), 3.34 (s, 3 H), 3.19-2.98 (m, 9 H), 2.35-2.23 (m, 2 H), 1.88 (d, J=6.8 Hz, 6 H), 1.63 (ddd, J=13.6, 13.6, 13.6 Hz, 1 H); MS (ESI) m/z 592.0 (M+H).

S24-9-76

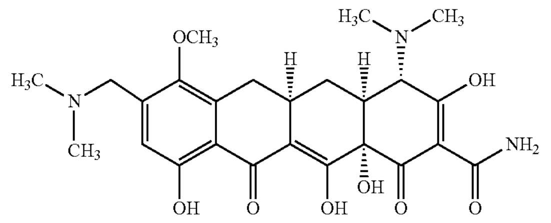

[1] H NMR (400 MHz, $CD_3OD$) δ 6.99 (s, 1 H), 4.45 (d, J=12.8 Hz, 1 H), 4.25 (d, J=13.2 Hz, 1 H), 4.11 (s, 1 H), 3.75 (s, 3 H), 3.25-2.98 (m, 9 H), 2.90 (s, 3 H), 2.85 (s, 3 H), 2.40 (dd, J=14.8, 14.4 Hz, 1 H), 2.27-2.24 (m, 1 H), 1.66 (ddd, J=13.2, 13.2, 13.2 Hz, 1 H); MS (ESI) m/z 502.0 (M+H).

S24-9-77

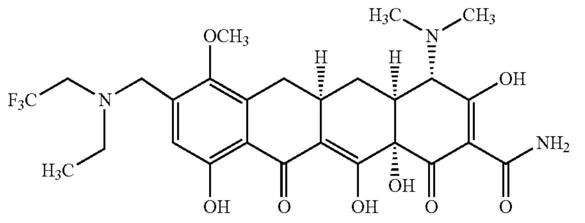

[1] H NMR (400 MHz, $CD_3OD$) δ 7.02 (s, 1 H), 4.43 (d, J=13.6 Hz, 1 H), 4.29 (d, J=13.6 Hz, 1 H), 4.11 (s, 1 H), 4.06-3.99 (m, 2 H), 3.72 (s, 3 H), 3.26-2.97 (m, 11 H), 2.39 (dd, J=14.8, 14.4 Hz, 1 H), 2.26 (ddd, J=13.6, 4.8, 2.8 Hz, 1 H), 1.66 (ddd, J=13.6, 13.6, 13.6 Hz, 1 H), 1.36 (t, J=7.2 Hz, 3 H); MS (ESI) m/z 584.1 (M+H).

S24-9-78

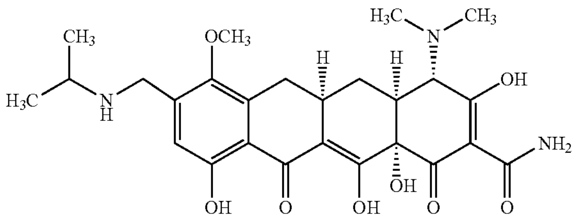

[1] H NMR (400 MHz, $CD_3OD$) δ 7.00 (s, 1 H), 4.29 (d, J=13.2 Hz, 1 H), 4.15 (d, J=13.6 Hz, 1 H), 4.13 (s, 1 H), 3.75 (s, 3 H), 3.50-3.44 (m, 1 H), 3.26-2.98 (m, 9 H), 2.38 (dd, J=14.8, 14.4 Hz, 1 H), 2.29-2.25 (m, 1 H), 1.66 (ddd, J=13.6, 13.6, 13.6 Hz, 1 H), 1.40 (d, J=6.4 Hz, 6 H); MS (ESI) m/z 516.3 (M+H).

S24-9-79

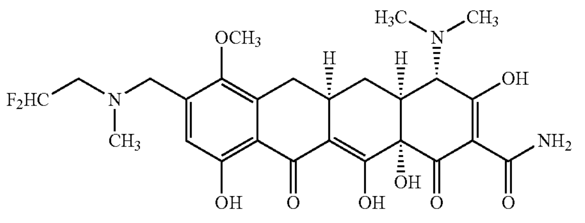

[1] H NMR (400 MHz, $CD_3OD$) δ 7.03 (s, 1 H), 6.46 (t, J=53.2 Hz, 1 H), 4.60 (d, J=13.2 Hz, 1 H), 4.39 (d, J=13.6 Hz, 1 H), 4.11 (s, 1 H), 3.82-3.74 (m, 5 H), 3.26-2.95 (m, 12 H), 2.42 (dd, J=14.8, 14.8 Hz, 1 H), 2.28-2.24 (m, 1 H), 1.67 (ddd, J=13.2, 13.2, 13.2 Hz, 1 H); MS (ESI) m/z 552.1 (M+H).

S24-9-80

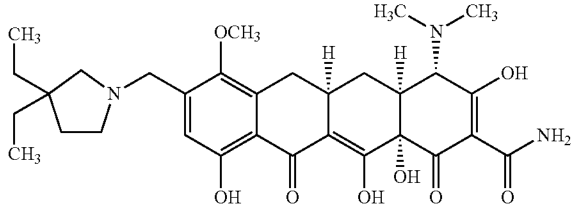

$^1$ H NMR (400 MHz, $CD_3OD$) δ 7.00, 6.99 (s, 1 H total), 4.41 (d, J=12.8 Hz, 1 H), 4.27 (d, J=13.2 Hz, 1 H), 4.06 (s, 1 H), 3.65 (s, 3 H), 3.51-3.47 (m, 1 H), 3.28-3.25 (m, 2 H), 3.17-3.12 (m, 1 H), 2.98-2.90 (m, 9 H), 2.30 (dd, J=14.4, 14.4 Hz, 1 H), 2.21-2.17 (m, 1 H), 1.93-1.88 (m, 1 H), 1.80-1.73 (m, 1 H), 1.62-1.40 (m, 5 H), 0.82-0.73 (m, 6 H); MS (ESI) m/z 584.1 (M+H).

S24-9-81

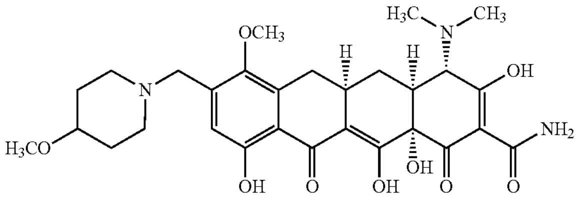

$^1$ H NMR (400 MHz, $CD_3OD$) δ 6.99 (s, 1 H), 4.34-4.29 (m, 1 H), 4.22-4.15 (m, 1 H), 4.03 (s, 1 H), 3.64 (s, 3 H), 3.51-3.41 (m, 2 H), 3.27 (s, 3 H), 3.17-2.90 (m, 12 H), 2.30 (dd, J=14.4, 14.4 Hz, 1 H), 2.19-2.14 (m, 2 H), 2.03-1.99 (m, 1 H), 1.92-1.80 (m, 1 H), 1.61-1.52 (m, 2 H); MS (ESI) m/z 572.0 (M+H).

S24-9-82

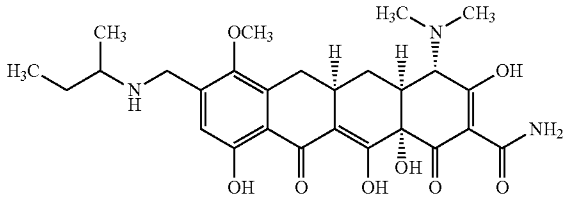

$^1$ H NMR (400 MHz, $CD_3OD$) δ 6.90 (s, 1 H), 4.20 (dd, J=13.6, 5.2 Hz, 1 H), 4.09-4.02 (m, 2 H), 3.66 (s, 3 H), 3.16-2.88 (m, 10 H), 2.29 (dd, J=14.4, 14.4 Hz, 1 H), 2.19-2.16 (m, 1 H), 1.85-1.80 (m, 1 H), 1.58-1.51 (m, 2 H), 1.29 (d, J=6.4 Hz, 3 H), 0.94 (t, J=7.6 Hz, 3 H); MS (ESI) m/z 530.0 (M+H).

S24-9-83

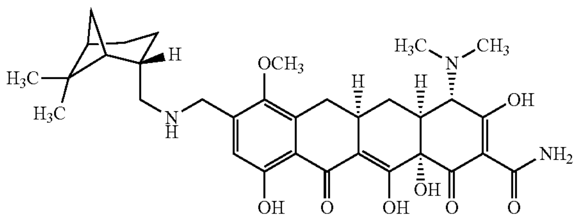

$^1$ H NMR (400 MHz, $CD_3OD$) δ 7.00 (s, 1 H), 4.33 (d, J=13.2 Hz, 1 H), 4.19-4.14 (m, 2 H), 3.74 (s, 3 H), 3.24-2.98 (m, 11 H), 2.45-2.38 (m, 3 H), 2.29-2.26 (m, 1 H), 2.03-1.93 (m, 5 H), 1.67-1.54 (m, 2 H), 1.34-1.32 (m, 1 H), 1.24-1.20 (m, 3 H), 1.02-0.97 (m, 3 H); MS (ESI) m/z 610.4 (M+H).

S24-9-84

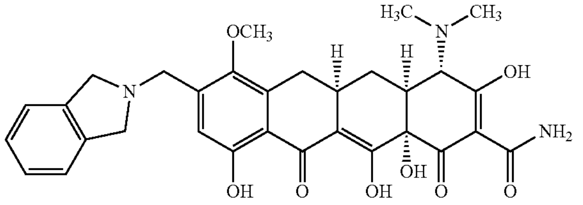

$^1$ H NMR (400 MHz, $CD_3OD$) δ 7.30 (s, 4 H), 6.98 (s, 1 H), 4.67-4.62 (m, 5 H), 4.48 (d, J=13.2 Hz, 1 H), 4.03 (s, 1 H), 3.66 (s, 3 H), 3.19-3.15 (m, 1 H), 2.97-2.80 (m, 8 H), 2.32 (dd, J=14.4, 14.4 Hz, 1 H), 2.17 (ddd, J=14.4, 5.2, 2.8 Hz, 1 H), 1.58 (ddd, J=13.2, 13.2, 13.2 Hz, 1 H); MS (ESI) m/z 576.1 (M+H).

S24-9-85

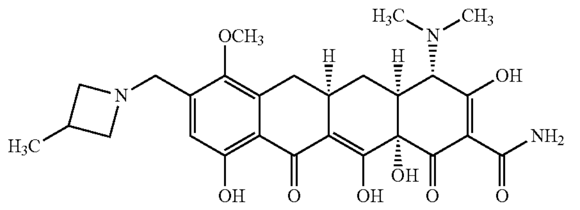

$^1$ H NMR (400 MHz, $CD_3OD$) δ 6.94 (s, 1 H), 4.53-4.47 (m, 1 H), 4.40-4.32 (m, 1 H), 4.28-4.19 (m, 1 H), 4.12 (s, 1 H), 3.89-3.85 (m, 2 H), 3.73 (s, 3 H), 3.24-2.98 (m, 11 H), 2.38 (dd, J=14.8, 14.8 Hz, 1 H), 2.27-2.24 (m, 1 H), 1.70-1.61 (m, 1 H), 1.32, 1.25 (d, J=7.2, 7.2 Hz, 3 H total); MS (ESI) m/z 528.4 (M+H).

S24-9-86

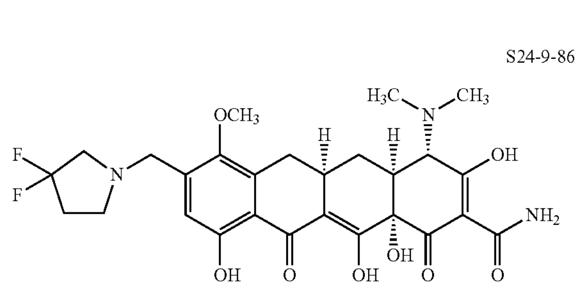 [SMILES: COc1c(CN2CCC(F)(F)C2)cc(O)c2c1C[C@H]1C[C@H]3[C@H](N(C)C)C(O)=C(C(N)=O)C(=O)[C@@]3(O)C(O)=C1C2=O]

$^1$ H NMR (400 MHz, $CD_3OD$) δ 7.07 (s, 1 H), 4.63 (d, J=13.2 Hz, 1 H), 4.47 (d, J=13.2 Hz, 1 H), 4.14 (s, 1 H), 3.96-3.91 (m, 2 H), 3.80-3.72 (m, 5 H), 3.26-2.98 (m, 9 H), 2.70-2.66 (m, 2 H), 2.39 (dd, J=14.4, 14.4 Hz, 1 H), 2.30-2.26 (m, 1 H), 1.66 (ddd, J=13.2, 13.2, 13.2 Hz, 1 H); MS (ESI) m/z 563.9 (M+H).

S24-9-87

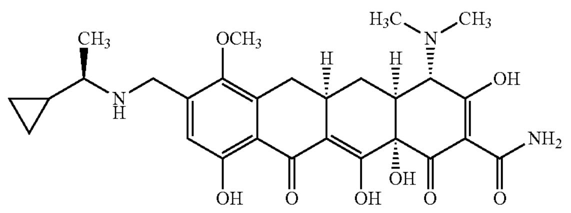

[1] H NMR (400 MHz, $CD_3OD$) δ 6.92 (s, 1 H), 4.36 (d, J=13.2 Hz, 1 H), 4.11 (d, J=13.2 Hz, 1 H), 4.03 (s, 1 H), 3.68 (s, 3 H), 3.18-2.90 (m, 9 H), 2.63 (dd, J=6.4, 6.4 Hz, 1 H), 2.31 (dd, J=14.4, 14.4 Hz, 1 H), 2.20-2.16 (m, 1 H), 1.58 (ddd, J=13.2, 13.2, 13.2 Hz, 1 H), 1.39 (d, J=6.8 Hz, 3 H), 1.01-0.99 (m, 1 H), 0.72-0.62 (m, 2 H), 0.51-0.47 (m, 1 H), 0.32-0.27 (m, 1 H); MS (ESI) m/z 542.1 (M+H).

S24-9-88

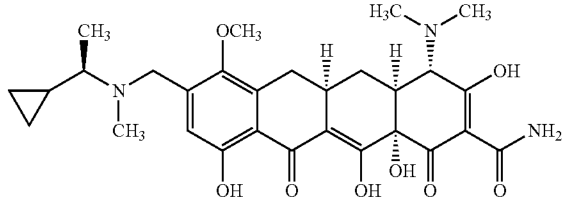

[1] H NMR (400 MHz, $CD_3OD$) δ 6.95 (s, 1 H), 4.59-4.50 (m, 1 H), 4.04-3.98 (m, 2 H), 3.71, 3.67 (s, 3 H total), 3.14-2.60 (m, 13 H), 2.34-2.29 (m, 1 H), 2.19-2.16 (m, 1 H), 1.60-1.52 (m, 1 H), 1.48-1.42 (m, 3 H), 1.14-1.08 (m, 1 H), 0.78-0.60 (m, 2 H), 0.42-0.31 (m, 2 H); MS (ESI) m/z 556.0 (M+H).

S24-9-89

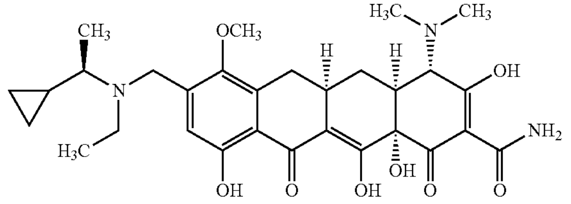

[1] H NMR (400 MHz, $CD_3OD$) δ 6.96, 6.95 (s, 1 H total), 4.62-4.49 (m, 1 H), 4.24-4.14 (m, 1 H), 4.02 (s, 1 H), 3.73-3.67 (m, 3 H), 3.18-2.81 (m, 12 H), 2.34-2.31 (m, 1 H), 2.21-2.18 (m, 1 H), 1.63-1.54 (m, 1 H), 1.44-1.39 (m, 3 H), 1.26-1.12 (m, 4 H), 0.80-0.60 (m, 2 H), 0.48-0.30 (m, 2 H); MS (ESI) m/z 570.0 (M+H).

S24-9-90

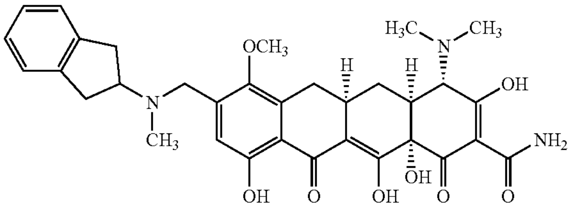

[1] H NMR (400 MHz, $CD_3OD$) δ 7.30-7.22 (m, 4 H), 7.07, 7.05 (s, 1 H total), 4.57-4.47 (m, 1 H), 4.33-4.30 (m, 2 H), 4.13 (s, 1 H), 3.78-3.75 (m, 3 H), 3.59-3.52 (m, 1 H), 3.50-3.40 (m, 3 H), 3.26-2.98 (m, 9 H), 2.79, 2.78 (s, 3 H total), 2.45-2.38 (m, 1 H), 2.30-2.26 (m, 1 H), 1.70-1.61 (m, 1 H); MS (ESI) m/z 604.0 (M+H).

S24-9-91

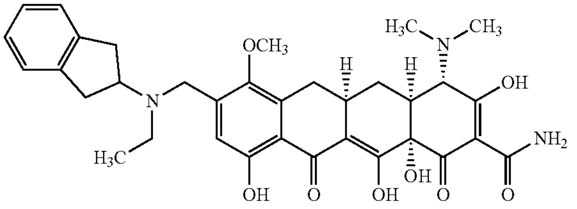

[1] H NMR (400 MHz, $CD_3OD$) δ 7.30-7.22 (m, 4 H), 7.06, 7.04 (s, 1 H total), 4.47-4.24 (m, 3 H), 4.13 (s, 1 H), 3.75 (s, 3 H), 3.57-3.41 (m, 4 H), 3.26-2.98 (m, 11 H), 2.41-2.36 (m, 1 H), 2.30-2.26 (m, 1 H), 1.70-1.61 (m, 1 H), 1.40-1.36 (m, 3 H); MS (ESI) m/z 618.0 (M+H).

S24-9-92

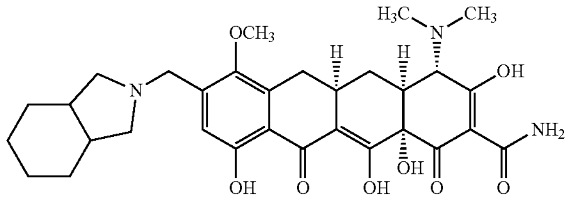

[1] H NMR (400 MHz, $CD_3OD$) δ 7.09, 7.06 (s, 1 H total), 4.56-4.49 (m, 1 H), 4.40-4.35 (m, 1 H), 4.12 (s, 1 H), 3.78, 3.75 (s, 3 H total), 3.56-3.55 (m, 1 H), 3.43-3.34 (m, 2 H), 3.24-2.89 (m, 10 H), 2.56-2.54 (m, 1 H), 2.42-2.36 (m, 2 H), 2.39-2.25 (m, 1 H), 1.74-1.38 (m, 9 H); MS (ESI) m/z 582.3 (M+H)

S24-9-93

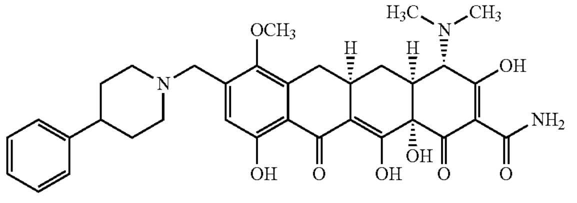

[1] H NMR (400 MHz, $CD_3OD$) δ 7.38-7.20 (m, 5 H), 7.10 (s, 1 H), 4.45 (d, J=13.2 Hz, 1 H), 4.32 (d, J=12.8 Hz, 1 H), 4.12 (s, 1 H), 3.75, 3.74 (s, 3 H total), 3.65-3.58 (m, 2 H), 3.29-3.22 (m, 3 H), 3.05-2.89 (m, 9 H), 2.45-2.42 (m, 1 H), 2.28-2.23 (m, 1 H), 2.08-1.95 (m, 4 H), 1.72-1.66 (m, 1 H); MS (ESI) m/z 618.1 (M+H).

S24-9-94

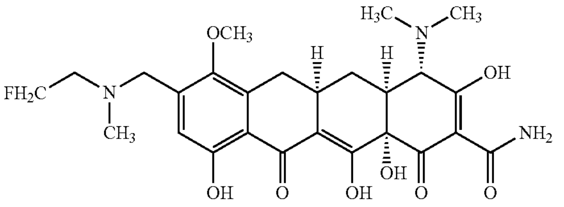

$^1$H NMR (400 MHz, $CD_3OD$) δ 7.01 (s, 1 H), 4.64, 4.20 (d, J=12.4 Hz, 1 H total), 4.45-4.43 (m, 1 H), 4.11 (s, 1 H), 3.74 (s, 3 H), 3.23-2.88 (m, 16 H), 2.44-2.40 (m, 1 H), 2.27-2.23 (m, 1 H), 1.69-1.60 (m, 1 H); MS (ESI) m/z 534.1 (M+H).

S24-9-95

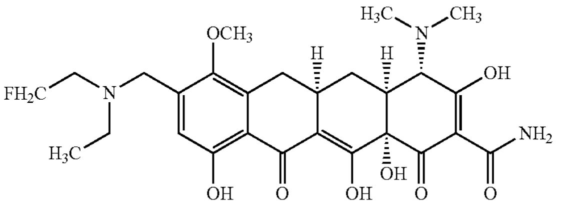

$^1$H NMR (400 MHz, $CD_3OD$) δ 7.02 (s, 1 H), 4.54 (d, J=12.8 Hz, 1 H), 4.34 (d, J=13.6 Hz, 1 H), 4.10 (s, 1 H), 3.74 (s, 3 H), 3.61-3.54 (m, 2 H), 3.04-2.96 (m, 13 H), 2.43-2.36 (m, 1 H), 2.26-2.23 (m, 1 H), 1.70-1.60 (m, 1H), 1.41-1.35 (m, 3 H); MS (ESI) m/z 548.1 (M+H).

S24-9-96

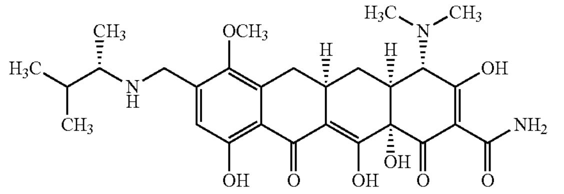

$^1$H NMR (400 MHz, $CD_3OD$) δ 7.02 (s, 1 H), 4.32 (d, J=13.2 Hz, 1 H), 4.19 (d, J=13.6 Hz, 1 H), 4.13 (s, 1 H), 3.76 (s, 3 H), 3.25-2.98 (m, 10 H), 2.42-2.35 (m, 1 H), 2.29-2.26 (m, 1 H), 2.19-2.13 (m, 1 H), 1.70-1.61 (m, 1H), 1.31 (d, J=6.8 Hz, 3 H), 1.04 (d, J=7.2 Hz, 3 H), 0.94 (d, J=7.2 Hz, 3 H); MS (ESI) m/z 544.4 (M+H).

S24-9-97

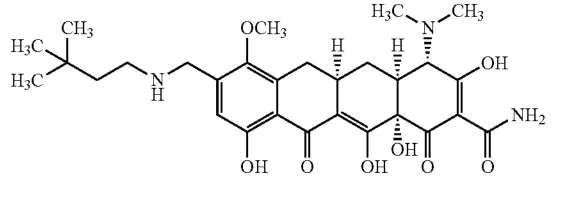

$^1$H NMR (400 MHz, $CD_3OD$) δ 7.02 (s, 1 H), 4.35 (d, J=13.2 Hz, 1 H), 4.22 (d, J=13.6 Hz, 1 H), 4.15 (s, 1 H), 3.77 (s, 3 H), 3.28-3.01 (m, 11 H), 2.41 (dd, J=14.4, 14.8 Hz, 1 H), 2.32-2.28 (m, 1 H), 1.70-1.66 (m, 3 H), 1.00 (s, 9 H); MS (ESI) m/z 558.1 (M+H).

S24-9-98

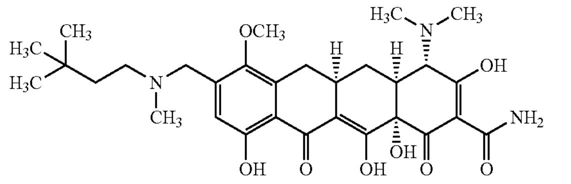

$^1$H NMR (400 MHz, $CD_3OD$) δ 7.03-6.69 (m, 1 H), 4.58, 4.19 (d, J=13.6 Hz, 1 H total), 4.43-4.31 (m, 1 H), 4.13 (s, 1 H), 3.75, 3.74 (s, 3 H total), 3.26-2.98 (m, 11 H), 2.81, 2.80 (s, 3 H total), 2.45-2.39 (m, 1 H), 2.35-2.26 (m, 1 H), 1.77-1.65 (m, 3 H), 1.02-0.96 (m, 9 H); MS (ESI) m/z 572.2 (M+H).

S24-9-99

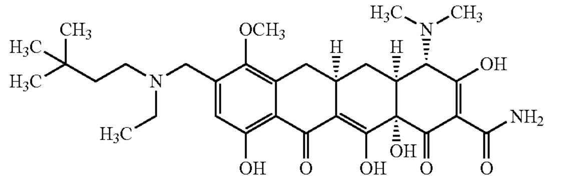

$^1$H NMR (400 MHz, $CD_3OD$) δ 6.94 (s, 1 H), 4.37 (dd, J=13.2, 7.6 Hz, 1 H), 4.18 (dd, J=13.6, 4.0 Hz, 1 H), 4.02 (s, 1 H), 3.66 (s, 3 H), 3.17-2.88 (m, 13 H), 2.36-2.27 (m, 1 H), 2.18-2.15 (m, 1 H), 1.62-1.53 (m, 3 H), 1.28 (q, J=7.6 Hz, 3 H), 0.86 (d, J=5.2 Hz, 9 H); MS (ESI) m/z 586.4 (M+H).

S24-9-100

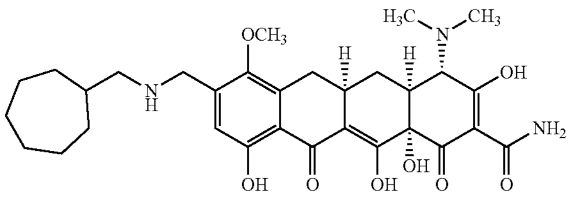

$^1$H NMR (400 MHz, $CD_3OD$) δ 6.89 (s, 1 H), 4.21 (d, J=13.6 Hz, 1 H), 4.07 (d, J=13.6 Hz, 1 H), 4.02 (s, 1 H), 3.64 (s, 3 H), 3.21-2.82 (m, 11 H), 2.29 (dd, J=14.4, 14.8 Hz, 1 H), 2.20-2.15 (m, 1 H), 1.90-1.80 (m, 1 H), 1.70-1.43 (m, 11 H), 1.23-1.18 (m, 2 H); MS (ESI) m/z 584.3 (M+H).

S24-9-101

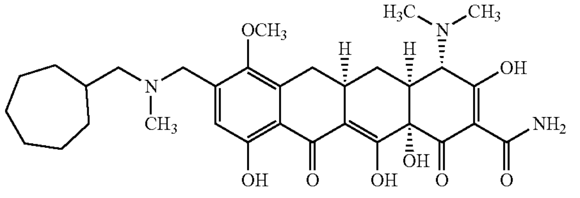

$^1$H NMR (400 MHz, $CD_3OD$) δ 7.02 (d, J=6.4 Hz, 1 H), 4.44, 4.33 (d, J=13.2 Hz, 1 H total), 4.21-4.06 (m, 2 H), 4.08 (d, J=12.0 Hz, 3 H), 3.32-2.82 (m, 14 H), 2.42 (dd, J=14.8, 14.8 Hz, 1 H), 2.31-2.28 (m, 1 H), 2.14-1.55 (m, 12 H), 1.32-1.20 (m, 2 H); MS (ESI) m/z 598.0 (M+H).

S24-9-102

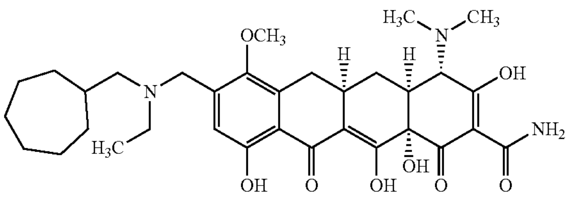

[1] H NMR (400 MHz, $CD_3OD$) δ 6.93 (s, 1 H), 4.39 (dd, J=13.6, 13.6 Hz, 1 H), 4.20, 4.12 (d, J=13.2 Hz, 1 H total), 4.02 (s, 1 H), 3.69, 3.67 (s, 3 H total), 3.18-2.89 (m, 13 H), 2.38-2.28 (m, 1 H), 2.19-2.16 (m, 1 H), 1.90-1.50 (m, 12 H), 1.46-1.38 (m, 3 H), 1.34-1.20 (m, 2 H); MS (ESI) m/z 612.1 (M+H).

S24-9-103

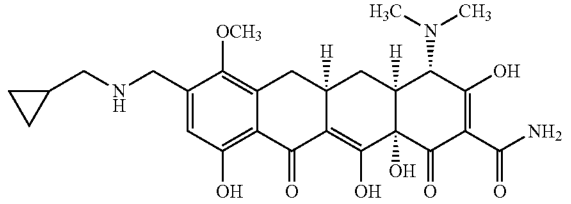

[1] H NMR (400 MHz, $CD_3OD$) δ 7.01 (s, 1 H), 4.39-4.28 (m, 1 H), 4.25-4.22 (m, 1 H), 4.13 (s, 1 H), 3.78 (s, 3 H), 3.29-3.00 (m, 11 H), 2.46-2.39 (m, 1 H), 2.30-2.27 (m, 1 H), 1.74-1.65 (m, 1 H), 1.20-1.15 (m, 1 H), 0.77 (d, J=6.8 Hz, 2 H), 0.46 (d, J=5.6 Hz, 2 H); MS (ESI) m/z 528.1 (M+H).

S24-9-104

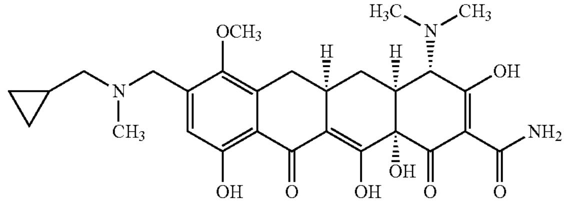

[1] H NMR (400 MHz, $CD_3OD$) δ 7.05, 7.04 (s, 1 H total), 4.53 (d, J=12.8 Hz, 1 H), 4.34 (d, J=12.8 Hz, 1 H), 4.16 (s, 1 H), 3.78, 3.77 (s, 3 H total), 3.28-3.01 (m, 11 H), 2.88, 2.83 (s, 3 H total), 2.42 (dd, J=13.2, 13.2 Hz, 1 H), 2.32-2.29 (m, 1 H), 1.73-1.64 (m, 1 H), 1.30-1.25 (m, 1 H), 0.83 (t, J=8.8 Hz, 2 H), 0.52-0.45 (m, 2 H); MS (ESI) m/z 542.1 (M+H).

S24-9-105

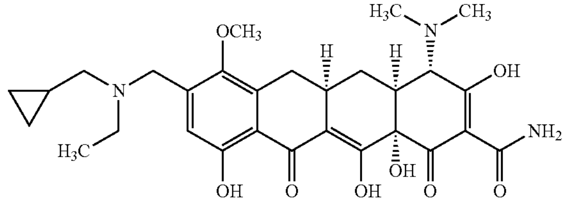

[1] H NMR (400 MHz, $CD_3OD$) δ 7.06 (m, 1 H), 4.67, 4.29 (d, J=13.6 Hz, 1 H total), 4.47 (dd, J=13.2, 13.2 Hz, 1 H), 4.17 (s, 1 H), 3.80 (s, 3 H), 3.29-3.02 (m, 13 H), 2.48-2.33 (m, 2 H), 1.75-1.65 (m, 1 H), 1.44-1.36 (m, 3 H), 1.28-1.21 (m, 1 H), 0.88-0.81 (m, 2 H), 1.50-0.47 (m, 2 H); MS (ESI) m/z 556.1 (M+H)

S24-9-106

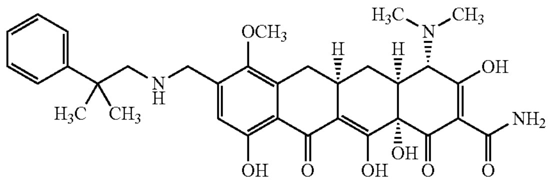

[1] H NMR (400 MHz, $CD_3OD$) δ 7.43-7.38 (m, 5 H), 6.88 (s, 1 H), 4.28 (d, J=13.6 Hz, 1 H), 4.16-4.11 (m, 2 H), 3.62 (s, 3 H), 3.30-3.03 (m, 11 H), 2.41-2.28 (m, 2 H), 1.74-1.64 (m, 1 H), 1.48 (s, 6 H); MS (ESI) m/z 606.0 (M+H).

S24-9-107

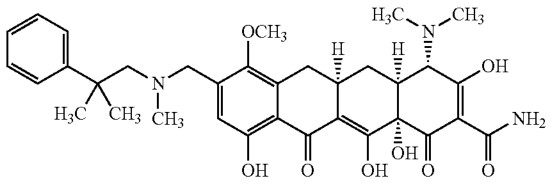

[1] H NMR (400 MHz, $CD_3OD$) δ 7.51 (m, 5 H), 6.88-6.85 (m, 1 H), 4.30 (d, J=12.8 Hz, 1 H), 4.20-4.15 (m, 1 H), 3.93-3.89 (m, 1 H), 3.81-3.60 (m, 6 H), 3.25-3.01 (m, 11 H), 2.45-2.18 (m, 2 H), 1.73-1.64 (m, 1 H), 1.57-1.46 (m, 6 H); MS (ESI) m/z 620.0 (M+H).

S24-9-108

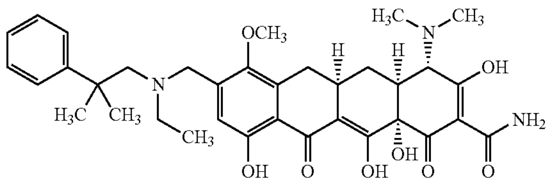

[1] H NMR (400 MHz, $CD_3OD$) δ 7.53 (t, J=8.0 Hz, 2 H), 7.44 (d, J=6.4 Hz, 2 H), 7.38-7.32 (m, 1 H), 6.90, 6.80 (s, 1 H total), 4.35-4.01 (m, 3 H), 3.64 (s, 3 H), 3.54-3.50 (m, 1 H), 3.24-3.01 (m, 12 H), 2.43-2.30 (m, 2 H), 1.72-1.64 (m, 1 H), 1.54 (d, J=12.4 Hz, 3 H), 1.45 (d, J=13.2 Hz, 3 H), 1.30 (d, J=6.4 Hz, 3 H); MS (ESI) m/z 634.0 (M+H)

S24-9-109

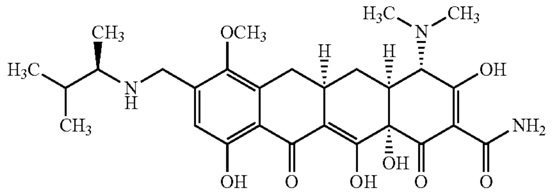

$^{1}$H NMR (400 MHz, $CD_3OD$) δ 7.06 (s, 1 H), 4.36 (d, J=13.2 Hz, 1 H), 4.22 J=13.2 Hz, 1 H), 4.16 (s, 1 H), 3.70 (s, 3 H), 3.31-3.02 (m, 10 H), 2.43 (dd, J=14.8, 14.4 Hz, 1 H), 2.33-2.29 (m, 1 H), 2.24-2.19 (m, 1 H), 1.70 (dd, J=13.6, 13.6 Hz, 1 H), 1.35 (d, J=6.8 Hz, 3 H), 1.06 (dd, J=6.8, 6.8 Hz, 6 H); MS (ESI) m/z 544.0 (M+H).

S24-9-110

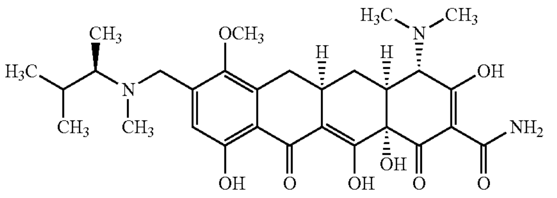

$^{1}$H NMR (400 MHz, $CD_3OD$) δ 7.07, 7.05 (s, 1 H total), 4.67 (d, J=12.8 Hz, 1 H), 4.23-4.11 (m, 2 H), 3.84-3.80 (m, 3 H), 3.31-3.03 (m, 13 H), 2.49-2.20 (m, 3 H), 1.75-1.69 (m, 1 H), 1.48-1.40 (m, 3 H), 1.20-1.13 (m, 6 H); MS (ESI) m/z 558.0 (M+H).

S24-9-111

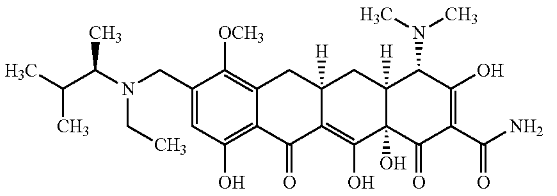

$^{1}$H NMR (400 MHz, $CD_3OD$) δ 7.09, 7.06 (s, 1 H total), 4.62, 4.22 (d, J=13.6 Hz, 1 H total), 4.44 (dd, J=13.6, 13.6 Hz, 1 H), 4.18 (s, 1 H), 3.83, 3.82 (s, 3 H total), 3.30-3.03 (m, 12 H), 2.48-2.25 (m, 3 H), 1.75-1.66 (m, 1 H), 1.45-1.31 (m, 6 H), 1.17-1.02 (m, 6 H); MS (ESI) m/z 572.0 (M+H).

S24-9-112

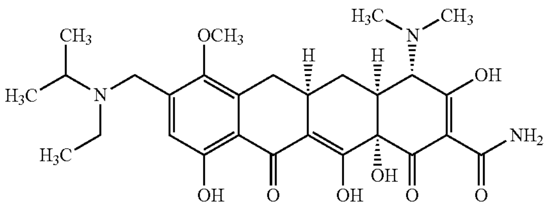

$^{1}$H NMR (400 MHz, $CD_3OD$) δ 7.09, 7.08 (s, 1 H total), 4.58 (d, J=13.6 Hz, 1 H), 4.39 (dd, J=13.6, 13.6 Hz, 1 H), 4.18 (s, 1 H), 3.84, 3.82 (s, 3 H total), 3.33-3.06 (m, 12 H), 2.53-2.43 (m, 1 H), 2.34 (m, 1 H), 1.78-1.69 (m, 1 H), 1.56-1.46 (m, 6 H), 1.40-1.35 (m, 3 H); MS (ESI) m/z 544.1 (M+H).

S24-9-113

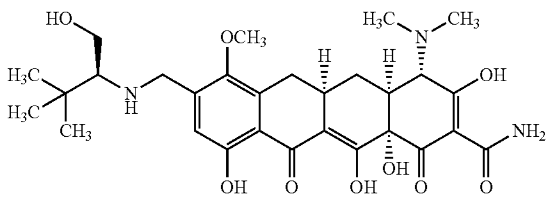

$^{1}$H NMR (400 MHz, $CD_3OD$) δ 7.15, 7.08 (s, 1 H total), 4.52-4.51 (m, 2 H), 4.06-4.03 (m, 1 H), 3.94-4.82 (m, 4 H), 3.28-3.05 (m, 10 H), 2.45 (dd, J=14.4, 14.4 Hz, 1 H), 2.35-2.32 (m, 1 H), 2.25-2.19 (m, 1 H), 1.77-1.68 (m, 1 H), 1.12 (s, 9 H); MS (ESI) m/z 574.0 (M+H).

S24-9-114

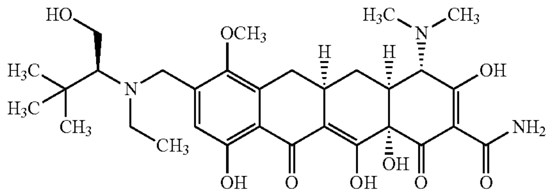

$^{1}$H NMR (400 MHz, $CD_3OD$) δ 7.09, 7.05 (s, 1 H total), 4.80 (s, 2 H), 4.20-4.15 (m, 3 H), 3.93 (s, 3 H), 3.84-3.55 (m, 2 H), 3.28-3.05 (m, 10 H), 2.46-2.39 (m, 2 H), 1.76-1.67 (m, 1 H), 1.57 (t, J=7.2 Hz, 2 H), 1.46 (t, J=7.2 Hz, 1 H), 1.28 (s, 3 H), 1.03 (s, 6 H); MS (ESI) m/z 602.1 (M+H).

S24-9-115

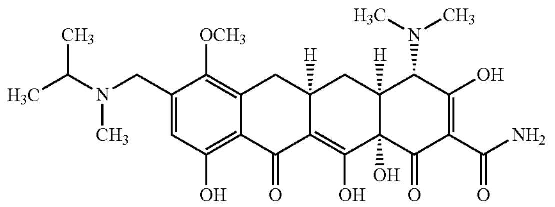

$^{1}$H NMR (400 MHz, $CD_3OD$) δ 7.05 (s, 1 H), 4.57, 4.19 (d, J=13.2 Hz, 1 H total), 4.44, 3.99 (d, J=13.2 Hz, 1 H total), 4.14 (s, 1 H), 3.80, 3.77 (s, 3 H total), 3.70-3.62 (m, 1 H), 3.28-3.00 (m, 9 H), 2.73 (s, 3 H), 2.49-2.27 (m, 2 H), 1.74-1.63 (m, 1 H), 1.52-1.40 (m, 6 H); MS (ESI) m/z 530.0 (M+H).

S24-9-116

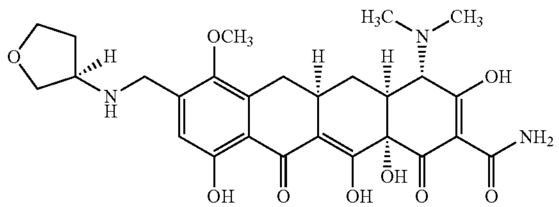

$^{1}$H NMR (400 MHz, $CD_3OD$) δ 7.05 (s, 1 H), 4.36 (d, J=13.6 Hz, 1 H), 4.26 (d, J=12.8 Hz, 1 H), 4.17-4.04 (m, 5 H), 3.92-3.82 (m, 5 H), 3.28-3.04 (m, 10 H), 2.50-2.40 (m, 2 H), 1.78-1.68 (m, 1 H); MS (ESI) m/z 544.0 (M+H).

S24-9-117

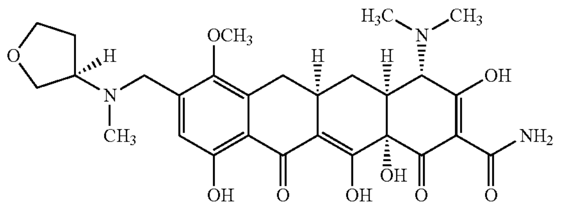

[1] H NMR (400 MHz, $CD_3OD$) δ 7.10 (s, 1 H), 4.53 (d, J=13.6 Hz, 1 H), 4.32 (d, J=14.4 Hz, 1 H), 4.22-4.17 (m, 4 H), 3.92-3.88 (m, 1 H), 3.82 (s, 3 H), 3.27-3.05 (m, 10 H), 2.85 (s, 3 H), 2.53-2.31 (m, 4 H), 1.78-1.68 (m, 1 H); MS (ESI) m/z 557.9 (M+H).

S24-9-118

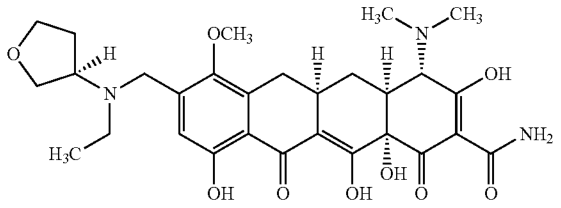

[1] H NMR (400 MHz, $CD_3OD$) δ 7.08 (s, 1 H), 4.43-4.38 (m, 2 H), 4.27-4.21 (m, 2 H), 4.16-4.14 (m, 1 H), 3.91-3.89 (m, 1 H), 3.77-3.75 (m, 3 H), 3.68-3.63 (m, 1 H), 3.31-3.04 (m, 12 H), 2.51-2.45 (m, 2 H), 2.36-2.30 (m, 2 H), 1.77-1.68 (m, 1 H), 1.53-1.40 (m, 3 H); MS (ESI) m/z 572.0 (M+H).

S24-9-119

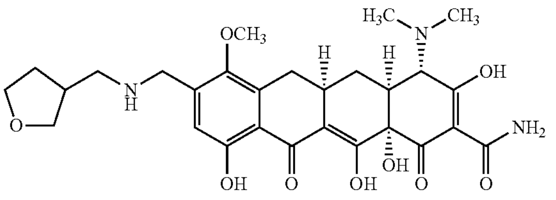

[1] H NMR (400 MHz, $CD_3OD$) δ 7.00 (s, 1 H), 4.35 (d, J=14.0 Hz, 1 H), 4.21 (d, J=13.6 Hz, 1 H), 4.10 (s, 1 H), 3.90-3.86 (m, 2 H), 3.75 (s, 3 H), 3.55-3.52 (m, 1 H), 3.25-2.97 (m, 11 H), 2.68-2.62 (m, 2 H), 2.39 (dd, J=14.4, 14.4 Hz, 1 H), 2.27-2.18 (m, 2 H), 1.71-1.65 (m, 2 H); MS (ESI) m/z 558.0 (M+H).

S24-9-120

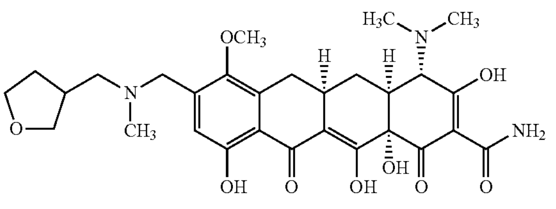

[1] H NMR (400 MHz, $CD_3OD$) δ 7.02 (s, 1 H), 4.66-4.62 (m, 1 H), 4.47-4.36 (m, 1 H), 4.11 (s, 1 H), 3.93-3.84 (m, 2 H), 3.77 (s, 3 H), 3.58-3.43 (m, 2 H), 3.26-2.98 (m, 11 H), 2.88-2.84 (m, 4 H), 2.42 (dd, J=13.6, 13.6 Hz, 1 H), 2.27-2.24 (m, 2 H), 1.72-1.63 (m, 2 H); MS (ESI) m/z 572.0 (M+H).

S24-9-121

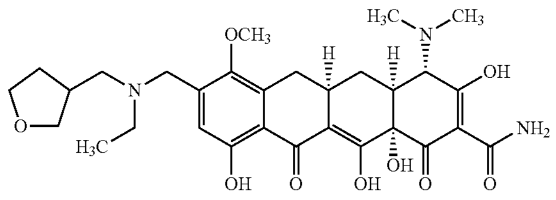

[1] H NMR (400 MHz, $CD_3OD$) δ 7.04, 7.03 (s, 1 H total), 4.52-4.48 (m, 1 H), 4.34-4.25 (m, 1 H), 4.11 (s, 1 H), 3.93-3.87 (m, 2 H), 3.77 (m, 3 H), 3.53-3.37 (m, 2 H), 3.27-2.98 (m, 13 H), 2.79-2.70 (m, 1 H), 2.47-2.38 (m, 1 H), 2.27-2.21 (m, 2 H), 1.72-1.55 (m, 2 H), 1.43-1.38 (m, 3 H); MS (ESI) m/z 586.0 (M+H).

S24-9-122

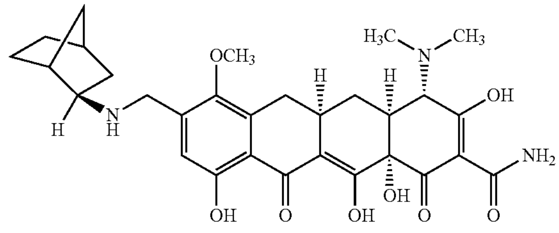

[1] H NMR (400 MHz, $CD_3OD$) δ 7.03, 6.98 (s, 1 H total), 4.31-4.13 (m, 2 H), 3.80-3.76 (m, 1 H), 3.69 (s, 3 H), 3.26-3.01 (m, 10 H), 2.69 (s, 2 H), 2.43-2.02 (m, 5 H), 1.71-1.55 (m, 2 H), 1.50-1.33 (m, 4 H); MS (ESI) m/z 568.1 (M+H).

S24-9-123

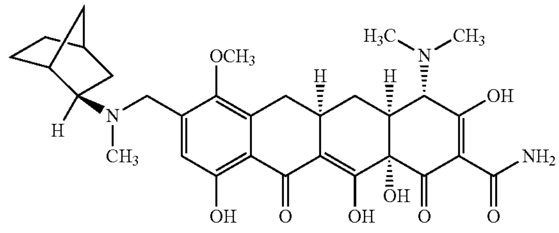

[1] H NMR (400 MHz, $CD_3OD$) δ 7.02, 6.95 (s, 1 H total), 4.15 (d, J=13.2 Hz, 1 H), 3.97-3.91 (m, 1 H), 3.82-3.67 (m, 4 H), 3.24-3.00 (m, 13 H), 2.71, 2.68 (s, 3 H total), 2.40-2.28 (m, 3 H), 2.16-2.06 (m, 1 H), 1.78-1.53 (m, 5 H), 1.37-1.31 (m, 1 H); MS (ESI) m/z 582.1 (M+H).

S24-9-124

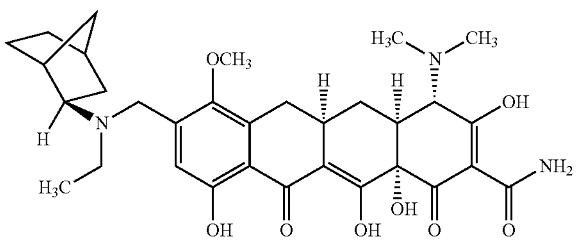

[1] H NMR (400 MHz, $CD_3OD$) δ 7.04-6.97 (m, 1 H), 4.57-4.12 (m, 3 H), 3.79-3.68 (m, 4 H), 3.25-2.92 (m, 12 H), 2.41-2.10 (m, 4 H), 1.74-1.45 (m, 6 H), 1.40-1.32 (m, 5 H); MS (ESI) m/z 596.1 (M+H).

S24-9-125

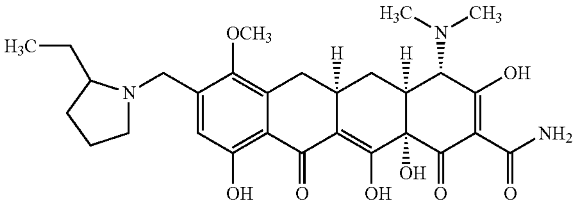

[1] H NMR (400 MHz, $CD_3OD$) δ 7.03, 7.02 (s, 1 H total), 4.66, 4.47 (d, J=13.2 Hz, 1 H total), 4.31, 4.10 (d, J=13.2 Hz, 1 H total), 4.12 (s, 1 H), 3.75, 3.74 (s, 3 H total), 3.48-3.47 (m, 2 H), 3.29-3.25 (m, 1 H), 3.05-2.89 (m, 9 H), 2.41-2.32 (m, 2 H), 2.29-2.22 (m, 1 H), 2.13-2.09 (m, 1 H), 2.01-1.95 (m, 2 H), 1.79-1.70 (m, 1 H), 1.69-1.59 (m, 2 H), 1.07-1.00 (m, 3 H); MS (ESI) m/z 556.1 (M+H).

S24-9-126

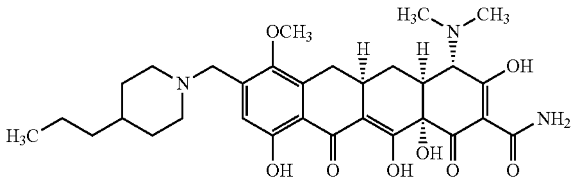

[1] H NMR (400 MHz, $CD_3OD$) δ 7.08 (s, 1 H), 4.39 (d, J=12.0 Hz, 1 H), 4.25 (d, J=14.4 Hz, 1 H), 4.15 (s, 1 H), 3.73 (s, 3 H), 3.50 (t, J=14.4 Hz, 2 H), 3.26-3.23 (m, 2 H), 3.07-2.91 (m, 9 H), 2.40 (dd, J=14.4, 14.4 Hz, 1 H), 2.32-2.28 (m, 1 H), 1.96-1.93 (m, 2 H), 1.75-1.55 (m, 2 H), 1.48-1.26 (m, 6 H), 0.97-0.90 (m, 3 H); MS (ESI) m/z 584.1 (M+H).

S24-9-127

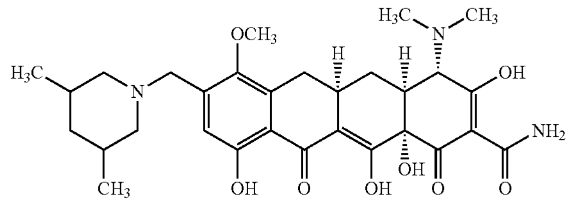

[1] H NMR (400 MHz, $CD_3OD$) δ 7.06 (s, 1 H), 4.40-4.36 (m, 1 H), 4.25 (d, J=12.8 Hz, 1 H), 4.11 (s, 1 H), 3.76-3.71 (m, 3 H total), 3.38-3.33 (m, 2 H), 3.28-3.21 (m, 2 H), 3.07-2.89 (m, 9 H), 2.63-2.58 (m, 1 H), 2.39 (dd, J=14.4, 14.4 Hz, 1 H), 2.28-2.25 (m, 1 H), 1.97-1.94 (m, 1 H), 1.87-1.81 (m, 1 H), 1.67-1.61 (m, 1 H), 1.17-1.13 (m, 1 H), 0.99-0.92 (m, 6 H); MS (ESI) m/z 570.2 (M+H).

S24-9-128

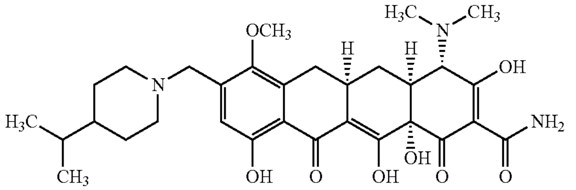

[1] H NMR (400 MHz, $CD_3OD$) δ 7.07 (s, 1 H), 4.37 (d, J=13.2 Hz, 1 H), 4.24 (d, J=12.8 Hz, 1 H), 4.14 (s, 1 H), 3.76 (s, 3 H), 3.55-3.48 (m, 2 H), 3.28-2.99 (m, 11 H), 2.39 (dd, J=14.8, 14.4 Hz, 1 H), 2.30-2.26 (m, 1 H), 1.96-1.92 (m, 2 H), 1.87-1.32 (m, 5 H), 0.92 (d, J=7.2 Hz, 6 H); MS (ESI) m/z 584.3 (M+H).

S24-9-129

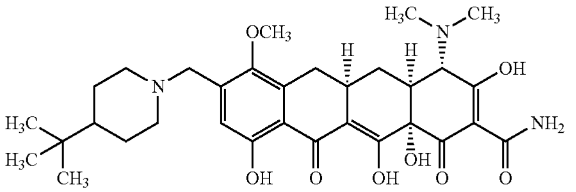

[1] H NMR (400 MHz, $CD_3OD$) δ 7.07 (s, 1 H), 4.37 (d, J=12.8 Hz, 1 H), 4.25 (d, J=12.8 Hz, 1 H), 4.14 (s, 1 H), 3.72 (s, 3 H), 3.57-3.49 (m, 2 H), 3.26-2.98 (m, 11 H), 2.39 (dd, J=14.8, 14.4 Hz, 1 H), 2.29-2.26 (m, 1 H), 1.95-1.93 (m, 2 H), 1.70-1.57 (m, 3 H), 1.41-1.32 (m, 1 H), 0.92 (s, 9 H)); MS (ESI) m/z 598.4 (M+H).

S24-9-130

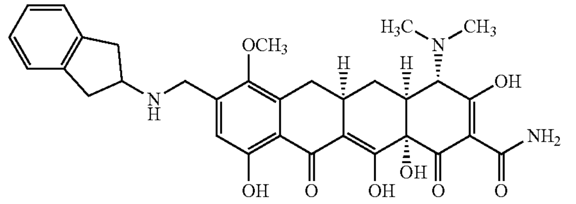

[1] H NMR (400 MHz, $CD_3OD$) δ 7.29-7.21 (m, 4 H), 7.02 (s, 1 H), 4.37 (d, J=13.2 Hz, 1 H), 4.24 (d, J=13.2, Hz, 1 H), 4.17-4.12 (m, 2 H), 3.77 (s, 3 H), 3.48 (dd, J=7.6, 7.6 Hz, 2 H), 3.26-2.97 (m, 11 H), 2.38 (dd, J=14.8, 14.4 Hz, 1 H), 2.28-2.25 (m, 1 H), 1.67-1.61 (m, 1 H); MS (ESI) m/z 590.1 (M+H).

S24-9-131

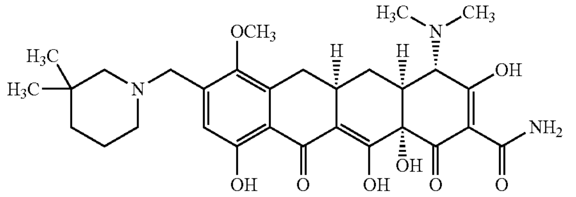

$^{1}$H NMR (400 MHz, $CD_3OD$) δ 7.11, 7.09 (s, 1 H total), 4.41 (dd, J=13.2, 13.2 Hz, 1 H), 4.28 (dd, J=13.2, 4.8 Hz, 1 H), 4.14 (s, 1 H), 3.79-3.72 (m, 3 H), 3.56-3.48 (m, 2 H), 3.28-2.80 (m, 11 H), 2.40 (dd, J=14.4, 14.0 Hz, 1 H), 2.30-2.27 (m, 1 H), 2.06-1.93 (m, 1 H), 1.88-1.80 (m, 1 H), 1.68-1.52 (m, 2 H), 1.48-1.40 (m, 1 H), 1.10 (d, J=7.2 Hz, 3 H), 0.98 (s, 3 H); MS (ESI) m/z 570.2 (M+H).

S24-9-132

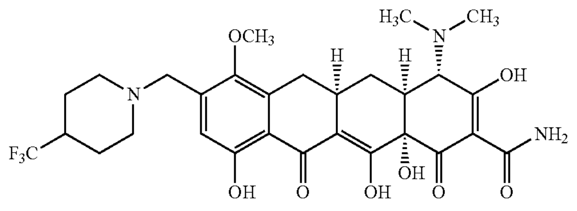

$^{1}$H NMR (400 MHz, $CD_3OD$) δ 7.09 (s, 1 H), 4.44 (d, J=13.2 Hz, 1 H), 4.32 (d, J=12.8 Hz, 1 H), 4.14 (s, 1 H), 3.76 (s, 3 H), 3.67-3.60 (m, 2 H), 3.28-3.00 (m, 11 H), 2.68-2.60 (m, 1 H), 2.42 (dd, J=14.8, 14.4 Hz, 1 H), 2.30-2.27 (m, 1 H), 2.20-2.10 (m, 2 H), 1.97-1.91 (m, 2 H), 1.73-1.64 (m, 1 H); MS (ESI) m/z 610.3 (M+H).

S24-9-133

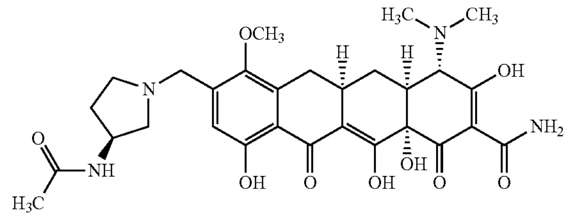

$^{1}$H NMR (400 MHz, $CD_3OD$) δ 7.04 (s, 1 H), 4.57 (d, J=11.6 Hz, 1 H), 4.39-4.30 (m, 2 H), 4.13 (s, 1 H), 3.75 (s, 3 H), 3.52-3.45 (m, 1 H), 3.25-2.98 (m, 11 H), 2.67-2.60 (m, 1 H), 2.42-2.25 (m, 2 H), 2.17-2.02 (m, 2 H), 1.97, 1.95 (s, 3 H total), 1.67-1.60 (m, 1 H); MS (ESI) m/z 585.4 (M+H).

S24-9-134

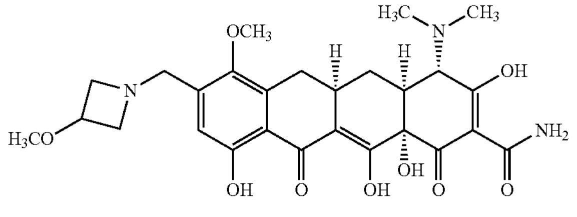

$^{1}$H NMR (400 MHz, $CD_3OD$) δ 6.96, 4.94 (s, 1 H total), 4.56-4.50 (m, 1 H), 4.45-4.35 (m, 3 H), 4.12-4.00 (m, 4 H), 3.75-3.73 (m, 3 H), 3.49-3.46 (m, 3 H), 3.21-2.98 (m, 9 H), 2.42-2.36 (m, 1 H), 1.68-1.60 (m, 1 H); MS (ESI) m/z 544.2 (M+H).

S24-9-135

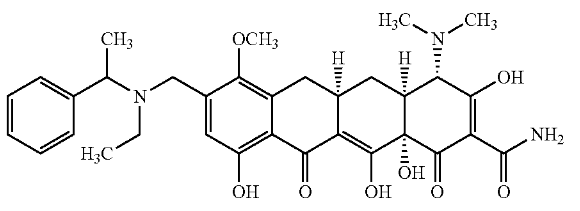

S24-9-135: MS (ESI) m/z 606.4 (M + H).

S24-9-136

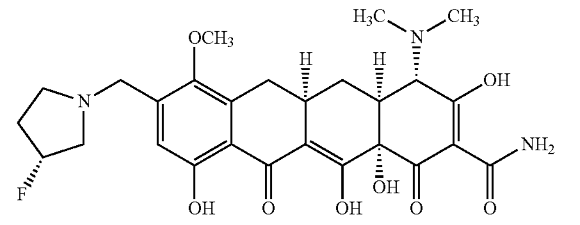

$^{1}$H NMR (400 MHz, $CD_3OD$) δ 7.06 (s, 1 H), 5.45 (d, J=52.8 Hz, 1 H), 4.61-4.56 (m, 1 H), 4.41-4.38 (m, 1 H), 4.13 (s, 1 H), 3.74 (s, 3 H), 3.50-3.47 (m, 2 H), 3.26-2.98 (m, 11 H), 2.43-2.26 (m, 4 H), 1.67-1.60 (m, 1 H); MS (ESI) m/z 546.2 (M+H).

S24-9-137

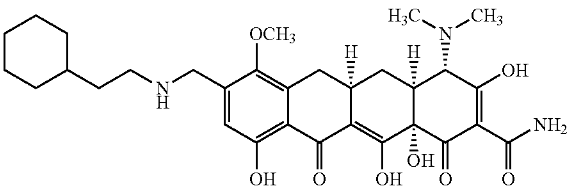

$^{1}$H NMR (400 MHz, $CD_3OD$) δ 6.89 (s, 1 H), 4.21 (d, J=13.2 Hz, 1 H), 4.09-4.03 (m, 2 H), 3.65 (s, 3 H), 3.27-2.88 (m, 11 H), 2.32-2.25 (m, 1 H), 2.19-2.16 (m, 1 H), 1.66-1.52 (m, 8 H), 1.21-1.12 (m, 4 H), 0.91-0.88 (m, 2 H); MS (ESI) m/z 584.3 (M+H).

S24-9-138

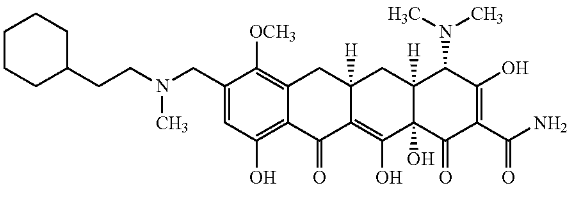

$^{1}$H NMR (400 MHz, $CD_3OD$) δ 7.02, 7.01 (s, 1 H total), 4.57 (d, J=12.8 Hz, 1 H), 4.40-4.30 (m, 1 H), 4.13 (s, 1 H), 3.75, 3.74 (s, 3 H total), 3.25-2.98 (m, 11 H), 2.81, 2.79 (s, 3 H total), 2.45-2.38 (m, 1 H), 2.29-2.26 (m, 1 H), 1.71-1.65 (m, 9 H), 1.40-1.20 (m, 4 H), 1.02-0.96 (m, 1 H); MS (ESI) m/z 598.4 (M+H).

S24-9-139

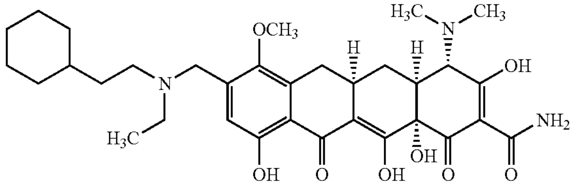

$^1$H NMR (400 MHz, $CD_3OD$) δ 6.93 (s, 1 H), 4.36 (d, J=13.2 Hz, 1 H), 4.16 (d, J=13.2 Hz, 1 H), 4.14 (s, 1 H), 3.66 (s, 3 H), 3.16-2.88 (m, 13 H), 2.34-2.27 (m, 1 H), 2.20-2.17 (m, 1 H), 1.62-1.53 (m, 8 H), 1.28-1.14 (m, 7 H), 0.91-0.86 (m, 2 H); MS (ESI) m/z 612.4 (M+H).

S24-9-140

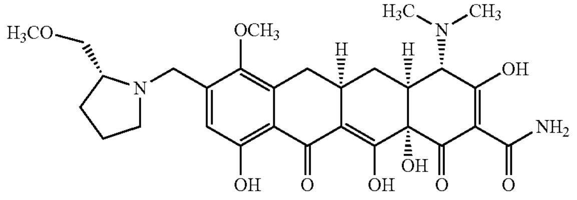

$^1$H NMR (400 MHz, $CD_3OD$) δ 7.01 (s, 1 H), 4.78 (d, J=12.8 Hz, 1 H), 4.17 (d, J=13.2 Hz, 1 H), 4.14 (s, 1 H), 3.88-2.86 (m, 1 H), 3.75 (s, 3 H), 3.70-3.67 (m, 2 H), 3.45 (s, 3 H), 3.41-3.37 (m, 2 H), 3.27-2.98 (m, 9 H), 2.44-2.37 (m, 1 H), 2.30-2.27 (m, 2 H), 2.14-2.11 (m, 1 H), 2.02-1.87 (m, 2 H), 1.70-1.62 (m, 1 H); MS (ESI) m/z 572.2 (M+H).

S24-9-141

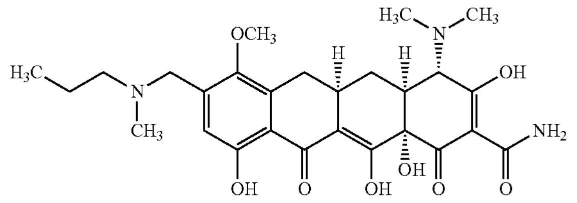

$^1$H NMR (400 MHz, $CD_3OD$) δ 7.02, 7.01 (s, 1 H total), 4.58 (d, J=13.2 Hz, 1 H), 4.38-4.30 (m, 1 H), 4.14 (s, 1 H), 3.75, 3.74 (s, 3 H total), 3.25-2.98 (m, 11 H), 2.81, 2.79 (s, 3 H total), 2.44-2.37 (m, 1 H), 2.29-2.26 (m, 1 H), 1.89-1.81 (m, 2 H), 1.71-16 (m, 1 H), 1.05-1.00 (m, 3 H); MS (ESI) m/z 530.3 (M+H).

S24-9-142

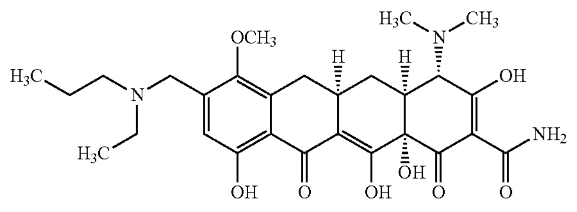

$^1$H NMR (400 MHz, $CD_3OD$) δ 7.01 (s, 1 H), 4.46 (dd, J=13.6, 7.2 Hz, 1 H), 4.25 (dd, J=13.2, 10.8 Hz, 1 H), 4.13 (s, 1 H), 3.75 (s, 3 H), 3.25-2.98 (m, 13 H), 2.44-2.37 (m, 1 H), 2.30-2.26 (m, 1 H), 1.82-1.79 (m, 2 H), 1.71-1.61 (m, 1 H), 1.40-1.33 (m, 3 H), 1.03-0.99 (m, 3 H); MS (ESI) m/z 544.4 (M+H).

S24-9-143

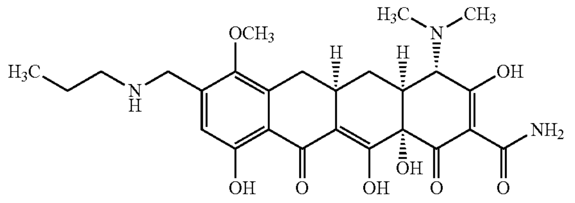

$^1$H NMR (400 MHz, $CD_3OD$) δ 6.98 (s, 1 H), 4.31 (d, J=13.6 Hz, 1 H), 4.17 (d, J=13.6 Hz, 1 H), 4.13 (s, 1 H), 3.74 (s, 3 H), 3.26-2.98 (m, 11 H), 2.38 (dd, J=14.8, 14.4 Hz, 1 H), 2.29-2.25 (m, 1 H), 1.80-1.73 (m, 2 H), 1.67-1.64 (m, 1 H), 1.02 (t, J=7.2 Hz, 3 H); MS (ESI) m/z 516.1 (M+H).

S24-9-144

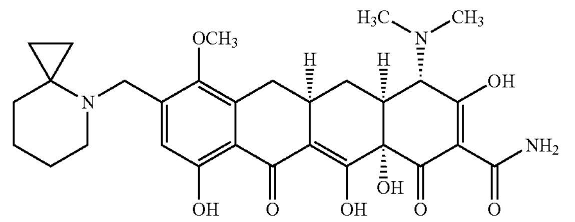

$^1$H NMR (400 MHz, $CD_3OD$) δ 7.04, 7.02 (s, 1 H total), 4.73, 4.60 (d, J=12.8 Hz, 1 H total), 4.51, 4.44 (d, J=13.2 Hz, 1 H total), 4.11 (s, 1 H), 3.78, 3.76 (s, 3 H total), 3.24-2.98 (m, 11 H), 2.52-2.44 (m, 1 H), 2.41-2.30 (m, 1 H), 2.27-2.20 (m, 2 H), 1.98-1.94 (m, 1 H), 1.88-1.82 (m, 1 H), 1.80-1.60 (m, 2 H), 1.31-1.29 (m, 1 H), 1.22-1.18 (m, 1 H), 1.12-1.08 (m, 1 H), 1.00-0.92 (m, 1 H), 0.90-0.83 (m, 1 H); MS (ESI) m/z 568.3 (M+H).

S24-9-145

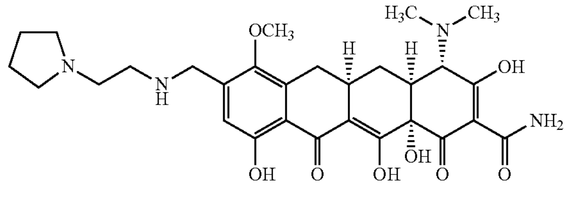

$^1$H NMR (400 MHz, $CD_3OD$) δ 7.04 (s, 1 H), 4.41 (d, J=13.6 Hz, 1 H), 4.28 (d, J=13.6, Hz, 1 H), 4.09 (s, 1 H), 3.74 (s, 3 H), 3.63-3.58 (m, 4 H), 3.24-2.96 (m, 13 H), 2.38 (dd, J=14.8, 14.0 Hz, 1 H), 2.25-2.20 (m, 1 H), 2.18-2.10 (m, 4 H), 1.66-1.60 (m, 1 H); MS (ESI) m/z 571.3 (M+H).

S24-9-146

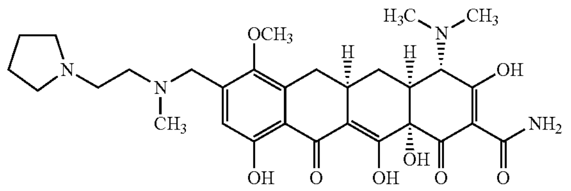

[1] H NMR (400 MHz, $CD_3OD$) δ 7.12 (s, 1 H), 4.60-4.53 (m, 1 H), 4.42-4.37 (m, 1 H), 4.11 (s, 1 H), 3.78-3.62 (m, 9 H), 3.24-2.90 (m, 14 H), 2.39 (dd, J=14.8, 14.0 Hz, 1 H), 2.27-2.23 (m, 1 H), 2.20-2.11 (m, 4 H), 1.69-1.60 (m, 1 H); MS (ESI) m/z 585.4 (M+H).

S24-9-147

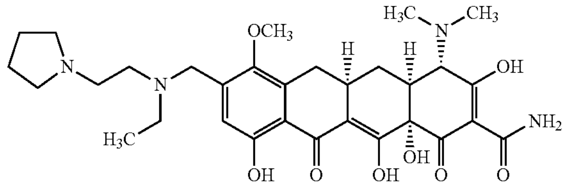

[1] H NMR (400 MHz, $CD_3OD$) δ 7.14 (s, 1 H), 4.58-4.52 (m, 1 H), 4.41-4.38 (m, 1 H), 4.12 (s, 1 H), 3.76-3.64 (m, 9 H), 3.26-2.97 (m, 13 H), 2.39 (dd, J=14.8, 14.4 Hz, 1 H), 2.27-2.24 (m, 1 H), 2.20-2.11 (m, 4 H), 1.69-1.60 (m, 1 H), 1.43 (t, J=6.8 Hz, 3 H); MS (ESI) m/z 599.4 (M+H).

S24-9-148

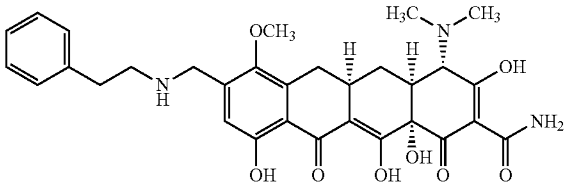

[1] H NMR (400 MHz, $CD_3OD$) δ 7.36-7.28 (m, 5 H), 7.05, 6.98 (s, 1 H total), 4.39-4.34 (m, 1 H), 4.26-4.20 (m, 1 H), 4.11 (s, 1 H), 3.78, 3.73 (s, 3 H total), 3.25-2.98 (m, 13 H), 2.39 (dd, J=15.2, 14.4 Hz, 1 H), 2.27-2.24 (m, 1 H), 1.72-1.62 (m, 1 H); MS (ESI) m/z 578.3 (M+H).

S24-9-149

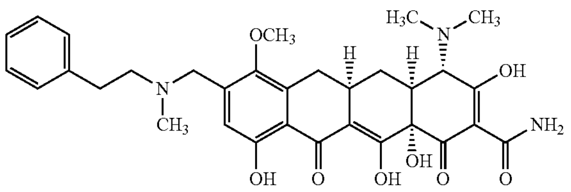

[1] H NMR (400 MHz, $CD_3OD$) δ 7.30-7.26 (m, 5 H), 7.04 (s, 1 H), 4.66, 4.16 (d, J=12.8 Hz, 1 H total), 4.45-4.38 (m, 1 H), 4.13 (s, 1 H), 3.74, 3.72 (s, 3 H total), 3.45-3.34 (m, 2 H), 3.20-2.97 (m, 11 H), 2.89, 2.86 (s, 3 H total), 2.42-2.33 (m, 1 H), 2.29-2.19 (m, 1 H), 1.65-1.58 (m, 1 H); MS (ESI) m/z 592.3 (M+H).

S24-9-150

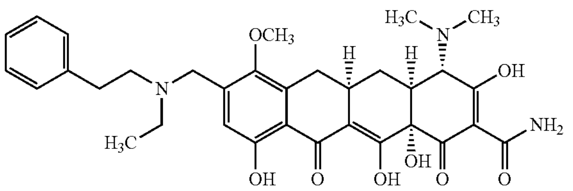

[1] H NMR (400 MHz, $CD_3OD$) δ 7.33-7.24 (m, 5 H), 7.06 (s, 1 H), 4.59-4.54 (m, 1 H), 4.36 (d, J=13.6 Hz, 1 H), 4.13 (s, 1 H), 3.77-3.74 (m, 3 H), 3.36-3.34 (m, 2 H), 3.22-2.98 (m, 13 H), 2.45-2.38 (m, 1 H), 2.30-2.15 (m, 1 H), 1.71-1.59 (m, 1 H), 1.43-1.40 (m, 3 H); MS (ESI) m/z 606.3 (M+H).

S24-9-151

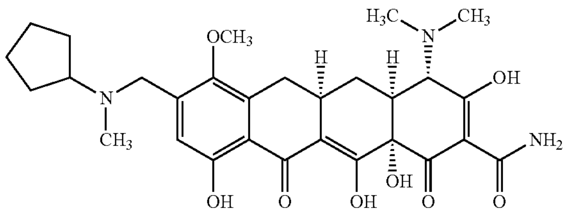

[1] H NMR (400 MHz, $CD_3OD$) δ 7.02, 7.01 (s, 1 H total), 4.58, 4.21 (d, J=13.2 Hz, 1 H total), 4.45, 4.02 (d, J=12.8 Hz, 1 H total), 4.12 (s, 1 H), 3.74-3.73 (m, 3 H), 3.24-2.97 (m, 10 H), 2.73 (s, 3 H), 2.45-2.37 (m, 1 H), 2.33-2.24 (m, 2 H), 2.15-2.13 (m, 1 H), 1.88-1.82 (m, 4 H), 1.74-1.61 (m, 3 H); MS (ESI) m/z 556.3 (M+H).

S24-9-152

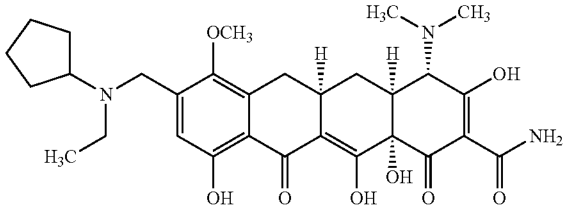

[1] H NMR (400 MHz, $CD_3OD$) δ 7.10-7.01 (m, 1 H), 4.48-4.19 (m, 2 H), 4.12 (s, 1 H), 3.80-3.74 (m, 3 H), 3.26-2.97 (m, 12 H), 2.45-2.35 (m, 1 H), 2.29-2.20 (m, 2 H), 2.15-2.10 (m, 1 H), 1.87-1.80 (m, 4 H), 1.73-1.64 (m, 3 H), 1.34 (t, J=7.2 Hz, 3 H); MS (ESI) m/z 570.2 (M+H).

S24-9-153

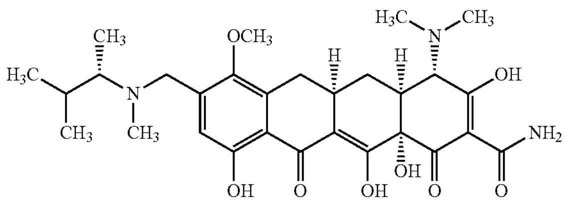

[1] H NMR (400 MHz, $CD_3OD$) δ 7.07-7.00 (m, 1 H), 4.56-4.35 (m, 2 H), 4.12 (s, 1 H), 3.93-3.84 (m, 1 H), 3.79, 3.73 (s, 3 H total), 3.16-2.61 (m, 13 H), 2.46-2.31 (m, 1 H), 2.25-2.12 (m, 1 H), 1.68-1.64 (m, 1 H), 1.43-0.96 (m, 9 H); MS (ESI) m/z 558.2 (M+H).

S24-9-154

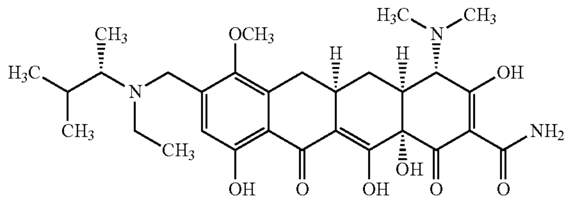

[1] H NMR (400 MHz, $CD_3OD$) δ 7.08, 7.00 (s, 1 H total), 4.63, 4.55 (dd, J=13.6 Hz, 1 H total), 4.39-4.33 (m, 1 H), 4.12 (s, 1 H), 3.85-3.73 (m, 3 H), 3.36-3.33 (m, 1 H), 3.22-2.96 (m, 11 H), 2.46-2.38 (m, 1 H), 2.25-2.15 (m, 2 H), 1.70-1.61 (m, 1 H), 1.46-0.94 (m, 12 H); MS (ESI) m/z 572.3 (M+H).

S24-9-155

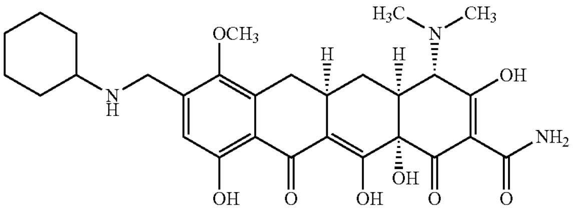

[1] H NMR (400 MHz, $CD_3OD$) δ 7.06, 7.99 (s, 1 H total), 4.31 (d, J=12.8 Hz, 1 H), 4.18 (d, J=13.6 Hz, 1 H), 4.13 (s, 1 H), 3.80, 3.75 (s, 3 H total), 3.27-2.99 (m, 10 H), 2.42-2.35 (m, 1 H), 2.30-2.27 (m, 1 H), 2.20-2.16 (m, 2 H), 1.92-1.89 (m, 2 H), 1.74-1.65 (m, 2 H), 1.43-1.36 (m, 4 H), 1.29-1.24 (m, 1 H); MS (ESI) m/z 556.2 (M+H).

S24-9-156

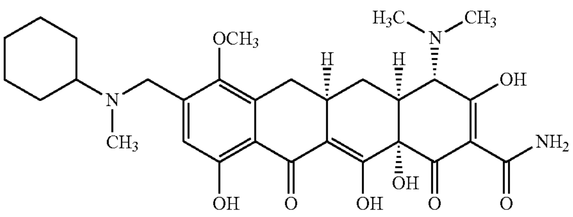

[1] H NMR (400 MHz, $CD_3OD$) δ 7.02, 7.01 (s, 1 H total), 4.61, 4.47 (d, J=12.8 Hz, 1 H total), 4.13 (s, 1 H), 3.96 (d, J=12.8 Hz, 1 H), 3.77, 3.74 (s, 3 H total), 3.24-2.98 (m, 10 H), 2.74 (s, 3 H), 2.46-2.37 (m, 1 H), 2.32-2.29 (m, 1 H), 2.18-2.10 (m, 2 H), 2.00-1.96 (m, 2 H), 1.74-1.51 (m, 4 H), 1.43-1.32 (m, 3 H); MS (ESI) m/z 570.2 (M+H).

S24-9-157

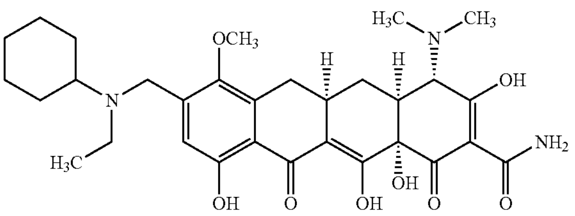

[1] H NMR (400 MHz, $CD_3OD$) δ 7.07, 7.01 (s, 1 H total), 4.59, 4.43 (d, J=13.6 Hz, 1 H total), 4.29, 4.09 (d, J=13.6 Hz, 1 H total), 4.14 (s, 1 H), 3.77, 3.75 (s, 3 H total), 3.28-2.99 (m, 12 H), 2.46-2.40 (m, 1 H), 2.36-2.31 (m, 1 H), 2.16-2.10 (m, 2 H), 1.99-1.96 (m, 2 H), 1.74-1.58 (m, 4 H), 1.41-1.23 (m, 6 H); MS (ESI) m/z 584.3 (M+H).

S24-9-158

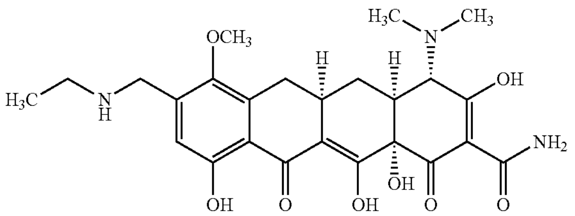

[1] H NMR (400 MHz, $CD_3OD$) δ 6.98 (s, 1 H), 4.31 (d, J=13.6 Hz, 1 H), 4.18 (d, J=13.2 Hz, 1 H), 4.12 (s, 1 H), 3.75 (s, 3 H), 3.27-2.99 (m, 1.1 H), 2.40 (dd, J=15.2, 14.8 Hz, 1 H), 2.28-2.25 (m, 1 H), 1.72-1.63 (m, 1 H), 1.36 (t, J=7.2 Hz, 3 H); MS (ESI) m/z 502.2 (M+H).

S24-9-159

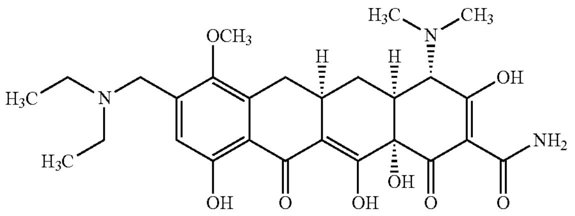

[1] H NMR (400 MHz, $CD_3OD$) δ 7.01 (s, 1 H), 4.44 (d, J=13.6 Hz, 1 H), 4.24 (d, J=13.2 Hz, 1 H), 4.11 (s, 1 H), 3.75 (s, 3 H), 3.25-2.97 (m, 13 H), 2.41 (dd, J=15.2, 14.8 Hz, 1 H), 2.26 (ddd, J=13.6, 4.8, 2.8 Hz, 1 H), 1.68 (ddd, J=13.6, 116, 13.6 Hz, 1 H), 1.39-1.36 (m, 6 H); MS (ESI) m/z 530.2 (M+H).

S24-9-160

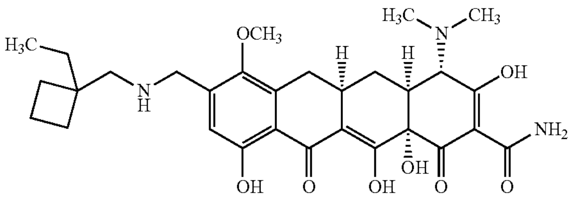

[1] H NMR (400 MHz, $CD_3OD$) δ 7.06, 6.99 (s, 1 H total), 4.35 (d, J=13.2 Hz, 1 H), 4.25-4.18 (m, 1 H), 4.09 (s, 1 H), 3.79, 3.74 (s, 3 H total), 3.23-2.95 (m, 11 H), 2.38 (dd, J=14.8, 14.4 Hz, 1 H), 2.26-2.14 (m, 1 H), 1.90-1.80 (m, 6 H), 1.65-1.56 (m, 3 H), 0.79 (t, J=7.2 Hz, 3 H); MS (ESI) m/z 570.3 (M+H).

S24-9-161

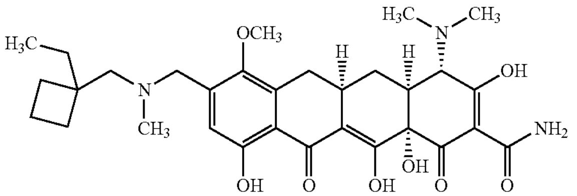

[1] H NMR (400 MHz, $CD_3OD$) δ 7.01 (s, 1 H), 4.47, 4.10 (d, J=12.8 Hz, 1 H total), 4.33 (dd, J=12.8, 12.8 Hz, 1 H), 4.10 (s, 1 H), 3.75, 3.71 (s, 3 H total), 3.24-2.95 (m, 11 H), 2.83, 2.80 (m, 3 H total), 2.40 (dd, J=14.8, 14.8 Hz, 1 H), 2.25-2.23 (m, 1 H), 2.03-1.83 (m, 6 H), 1.80-1.70 (m, 2 H), 1.69-1.59 (m, 1 H), 0.88-0.80 (m, 3 H); MS (ESI) m/z 584.3 (M+H).

S24-9-162

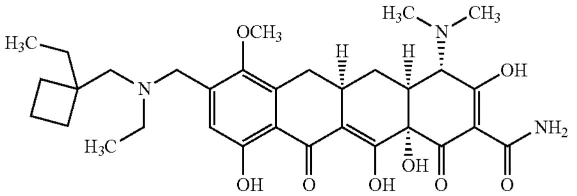

[1] H NMR (400 MHz, $CD_3OD$) δ 7.00 (s, 1 H), 4.42, 4.35 (d, J=13.2 Hz, 1 H total), 4.20 (d, J=13.2 Hz, 1 H), 4.09 (s, 1 H), 3.74, 3.70 (s, 3 H total), 3.23-2.94 (m, 13 H), 2.37 (dd, J=14.4, 13.2 Hz, 1 H), 2.25-2.22 (m, 1 H), 1.84-1.85 (m, 6 H), 1.75-1.71 (m, 2 H), 1.69-1.58 (m, 1 H), 1.43-1.37 (m, 3 H), 0.88-0.80 (m, 3 H); MS (ESI) m/z 598.3 (M+H).

S24-9-163

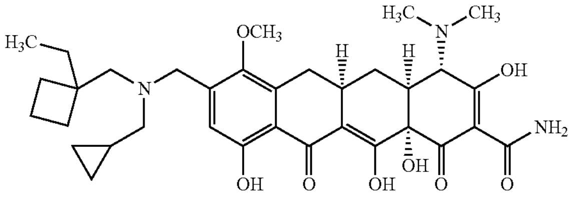

[1] H NMR (400 MHz, $CD_3OD$) δ 7.00 (s, 1 H), 4.67, 4.25 (d, J=13.2 Hz, 1 H total), 4.40 (dd, J=14.0, 14.0 Hz, 1 H), 4.09 (s, 1 H), 3.76, 3.72 (s, 3 H total), 3.46-3.41 (m, 1 H), 3.21-2.93 (m, 12 H), 2.38 (dd, J=14.4, 14.4 Hz, 1 H), 2.25-2.22 (m, 1 H), 1.98-1.82 (m, 6 H), 1.76-1.71 (m, 2 H), 1.69-1.61 (m, 1 H), 1.30-1.20 (m, 1 H), 0.86-0.75 (m, 5 H), 0.44 (dd, J=16.0, 4.4 Hz, 2 H); MS (ESI) m/z 624.3 (M+H).

S24-9-164

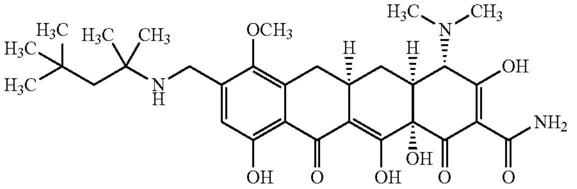

[1] H NMR (400 MHz, $CD_3OD$) δ 7.04, 6.97 (s, 1 H total), 4.22 (d, J=12.4 Hz, 1 H), 4.10-4.04 (m, 2 H), 3.77, 3.72 (s, 3 H total), 3.23-2.94 (m, 9 H), 2.35 (dd, J=14.8, 14.8 Hz, 1 H), 2.25-2.22 (m, 1 H), 1.78 (s, 2 H), 1.67-1.58 (m, 1 H), 1.52 (s, 6 H), 1.08 (s, 9 H); MS (ESI) m/z 586.3 (M+H).

S24-9-165

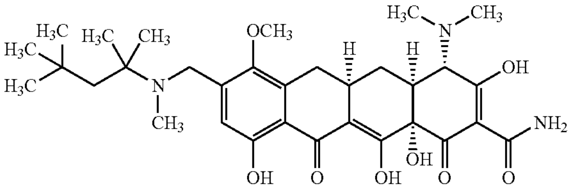

[1] H NMR (400 MHz, $CD_3OD$) δ 7.05, 6.98 (s, 1 H total), 4.71, 4.60 (d, J=12.8 Hz, 1 H total), 4.10 (m, 1 H), 3.93-3.87 (m, 1 H), 3.77-3.71 (m, 3 H), 3.21-2.95 (m, 9 H), 2.66 (s, 3 H), 2.41 (dd, J=14.4, 14.4 Hz, 1 H), 2.33-2.23 (m, 1 H), 2.00-1.94 (m, 1 H), 1.81 (d, J=14.0 Hz, 1 H), 1.66-1.57 (m, 7 H), 1.12 (s, 9 H); MS (ESI) m/z 600.4 (M+H).

S24-9-166

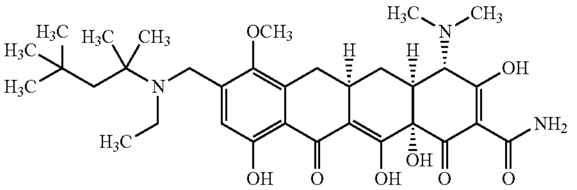

[1] H NMR (400 MHz, $CD_3OD$) δ 7.09, 7.08 (s, 1 H total), 4.70, 4.55 (d, J=13.2 Hz, 1 H total), 4.28, 4.13 (d, J=13.2 Hz, t, J=6.4 Hz, 2 H total), 3.77, 3.76 (s, 3 H total), 3.54-3.47 (m, 1 H), 3.27-2.99 (m, 10 H), 2.42 (dd, J=14.4, 14.4 Hz, 1 H), 2.30-2.27 (m, 1 H), 2.00-1.88 (m, 2 H), 1.72-1.66 (m, 7 H), 1.15 (s, 9 H), 1.08 (t, J=7.2 Hz, 3 H); MS (ESI) m/z 614.3 (M+H).

S24-9-167

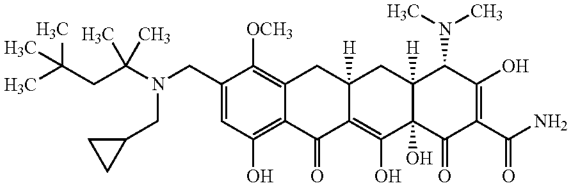

[1] H NMR (400 MHz, $CD_3OD$) δ 7.10, 7.06 (s, 1 H total), 4.70, 4.55 (d, J=13.2 Hz, 1 H total), 4.28, 4.13 (d, J=13.2 Hz, t, J=6.4 Hz, 2 H total), 3.77, 3.76 (s, 3 H total), 3.54-3.47 (m, 1 H), 3.27-2.99 (m, 10 H), 2.42 (dd, J=14.4, 14.4 Hz, 1 H), 2.30-2.27 (m, 1 H), 2.00-1.88 (m, 2 H), 1.72-1.66 (m, 7 H), 1.15 (s, 9 H), 1.08 (t, J=7.2 Hz, 3 H); MS (ESI) m/z 640.4 (M+H).

S24-9-168

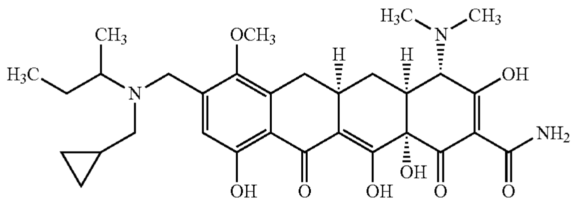

[1] H NMR (400 MHz, $CD_3OD$) δ 7.01, 6.99 (s, 1 H total), 4.57-4.36 (m, 1 H), 433-4.12 (m, 1 H), 4.15, 4.13 (s, 1 H total), 3.77, 3.73 (s, 3 H total), 3.58-3.40 (m, 1 H), 3.24-2.96 (m, 11 H), 2.44-2.37 (m, 1 H), 2.28-2.24 (m, 1 H), 2.04-1.84 (m, 2 H), 1.70-1.60 (m, 1 H), 1.47-1.36 (m, 3 H), 1.06-0.96 (m, 4 H), 0.76-0.68 (m, 2 H), 0.42-0.31 (m, 2 H); MS (ESI) m/z 584.3 (M+H).

S24-9-169

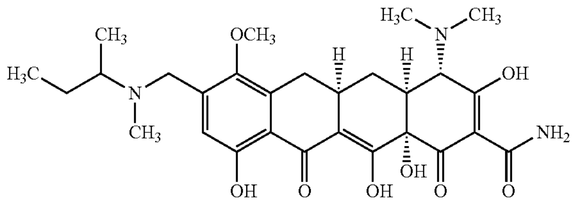

[1] H NMR (400 MHz, $CD_3OD$) δ 7.02, 7.01 (s, 1 H total), 4.56-4.39 (m, 1 H), 4.12 (s, 1 H), 4.02-3.93 (m, 1 H), 3.78-3.74 (m, 3 H), 3.35-3.32 (m, 1 H), 3.26-2.98 (m, 9 H), 2.74, 2.73 (s, 3 H total), 2.46-2.33 (m, 1 H), 2.28-2.25 (m, 1 H), 1.99-1.92 (m, 2 H), 1.82-1.60 (m, 1 H), 1.47-1.40 (m, 3 H), 1.09-1.00 (m, 3 H); MS (ESI) m/z 544.2 (M+H).

S24-9-170

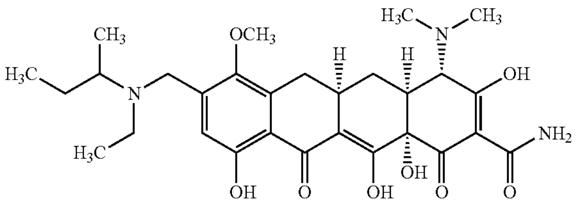

[1] H NMR (400 MHz, $CD_3OD$) δ 7.03-7.00 (m, 1 H), 4.53-4.49 (m, 1 H), 4.37-4.34 (m, 1 H), 4.12 (s, 1 H), 3.77-3.73 (m, 3 H), 3.42-3.34 (m, 1 H), 3.26-2.97 (m, 11 H), 2.42 (dd, J=14.4, 14.4 Hz, 1 H), 2.28-2.25 (m, 1 H), 1.97-1.92 (m, 1 H), 1.72-1.61 (m, 2 H), 1.48-1.46 (m, 6 H), 1.08-0.98 (m, 3 H); MS (ESI) m/z 558.1 (M+H).

S24-9-171

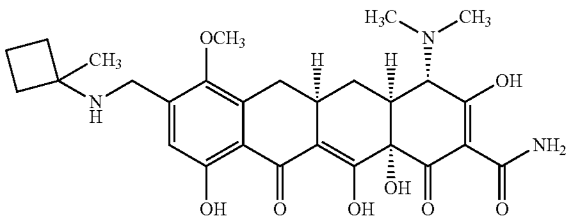

[1] H NMR (400 MHz, $CD_3OD$) δ 6.97 (s, 1 H), 4.12-4.09 (m, 2 H), 3.85 (d, J=13.2 Hz, 1 H), 3.74 (s, 3 H), 3.25-2.96 (m, 9 H), 2.46-4.38 (m, 3 H), 2.27-2.24 (m, 1 H), 2.12-1.93 (m, 4 H), 1.69-1.60 (m, 4 H); MS (ESI) m/z 542.2 (M+H).

S24-9-172

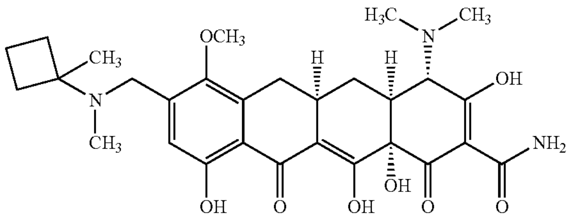

[1] H NMR (400 MHz, $CD_3OD$) δ 7.03 (s, 1 H), 4.31, 4.03 (d, J=12.4 Hz, 1 H total), 4.21, 3.88 (d, J=13.2 Hz, 1 H total), 4.13 (s, 1 H), 3.78, 3.73 (s, 3 H total), 3.25-2.98 (m, 9 H), 2.66-2.61 (m, 3 H), 2.56-2.29 (m, 2 H), 2.26-2.17 (m, 2 H), 2.05-2.00 (m, 1 H), 1.94-1.88 (m, 2 H), 1.71-1.60 (m, 4 H); MS (ESI) m/z 556.2 (M+H).

S24-9-173

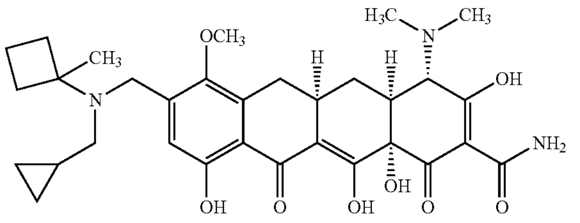

[1] H NMR (400 MHz, $CD_3OD$) δ 7.07, 7.06 (s, 1 H total), 4.50, 4.16 (d, J=13.6 Hz, 1 H total), 4.31-4.29 (m, 1 H), 4.12 (s, 1 H), 3.76, 3.75 (s, 3 H total), 3.26-2.96 (m, 11 H), 2.61-2.56 (m, 1 H), 2.43-2.25 (m, 3 H), 2.09-2.04 (m, 1 H), 1.95-1.70 (m, 3 H), 1.70-1.61 (m, 4 H), 0.93-0.90 (m, 1 H), 0.71-0.67 (m, 2 H), 0.37-0.34 (m, 2 H); MS (ESI) m/z 596.3 (M+H).

S24-9-174

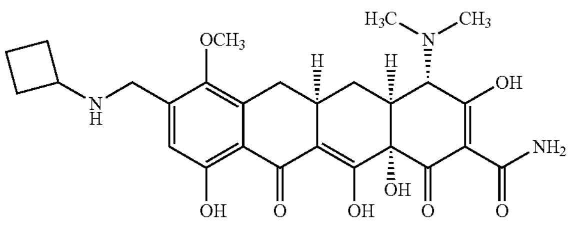

[1] H NMR (400 MHz, $CD_3OD$) δ 6.96 (s, 1 H), 4.20-4.12 (m, 2 H), 4.06 (d, J=13.6 Hz, 1 H), 3.82-3.79 (m, 1 H), 3.74 (s, 3 H), 3.26-2.98 (m, 9 H), 2.42-2.20 (m, 6 H), 1.96-1.89 (m, 2 H), 1.71-1.62 (m, 1 H); MS (ESI) m/z 528.1 (M+H).

S24-9-175

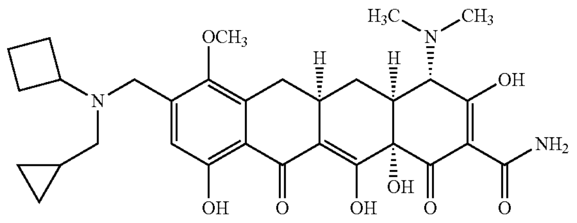

[1] H NMR (400 MHz, $CD_3OD$) δ 7.04, 7.03 (s, 1 H total), 4.36-4.32 (m, 1 H), 4.16-4.13 (m, 1 H), 4.02-3.98 (m, 1 H), 3.81, 3.76 (s, 3 H total), 3.26-2.98 (m, 12 H), 2.66-2.02 (m, 6 H), 1.84-1.60 (m, 3 H), 1.16-1.14 (m, 1 H), 0.80-0.77 (m, 2 H), 0.41-0.38 (m, 2 H); MS (ESI) m/z 582.1 (M+H).

S24-9-176

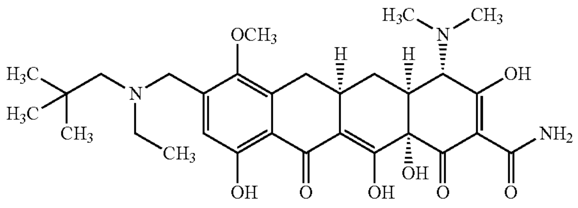

[1] H NMR (400 MHz, $CD_3OD$) δ 7.14, 7.06 (s, 1 H total), 4.55-4.78 (m, 1 H), 4.33-4.29 (m, 1 H), 4.12, 3.98 (s, 1 H total), 3.82-3.74 (m, 3 H), 3.24-2.98 (m, 13 H), 2.38 (dd, J=12.8, 12.8 Hz, 1 H), 2.29-2.26 (m, 1 H), 2.18-2.15 (m, 1 H), 1.72-1.62 (m, 1 H), 1.46-1.42 (m, 3 H), 1.06-1.02 (m, 9 H); MS (ESI) m/z 572.2 (M+H).

S24-9-177

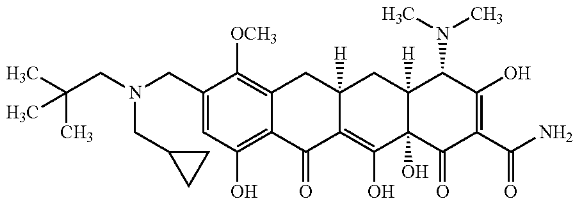

[1] H NMR (400 MHz, $CD_3OD$) δ 7.14-7.06 (m, 1 H), 4.76, 4.32 (d, J=13.6 Hz, 1 H total), 4.61-4.47 (m, 1 H), 4.12, 3.89 (s, 1 H total), 3.82-3.78 (m, 3 H), 3.25-2.98 (m, 13 H), 2.42-2.15 (m, 2 H), 1.72-1.63 (m, 1 H), 1.32-2.28 (m, 1 H), 1.04, 1.00 (s, 9 H total), 0.87-0.82 (m, 2 H), 0.53-0.48 (m, 2 H); MS (ESI) m/z 598.3 (M+H).

S24-9-178

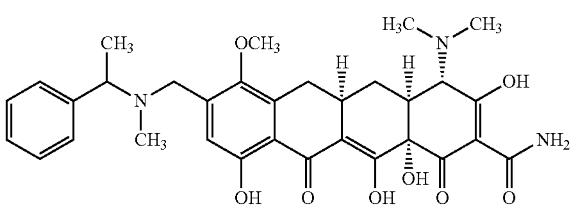

[1] H NMR (400 MHz, $CD_3OD$) δ 7.70-7.51 (m, 5 H), 6.98-6.86 (m, 1 H), 4.62-4.35 (m, 2 H), 4.13 (s, 1 H), 4.10-3.78 (m, 1 H), 3.51-3.57 (m, 3 H), 3.22-2.87 (m, 9 H), 2.80, 2.79, 2.68, 2.67 (s, 3 H total), 2.40-2.23 (m, 2 H), 1.88-1.80 (m, 3 H), 1.68-1.58 (m, 1 H); MS (ESI) m/z 592.0 (M+H).

S24-9-179

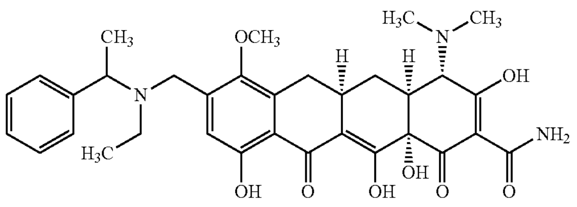

[1] H NMR (400 MHz, $CD_3OD$) δ 7.67-7.52 (m, 5 H), 6.95, 6.90, 6.81, 6.74 (s, 1 H total), 4.68-4.61 (m, 1 H), 4.48-4.17 (m, 1.5 H), 4.13, 4.11 (s, 1 H total), 4.10-4.00 (m, 0.5 H), 3.48, 3.45, 3.41, 3.39 (s, 3 H total), 3.21-2.88 (m, 11 H), 2.39-2.22 (m, 2 H), 1.85-1.76 (m, 3 H), 1.68-1.58 (m, 1 H), 1.45-1.34 (m, 3 H); MS (ESI) m/z 606.1 (M+H).

S24-9-180

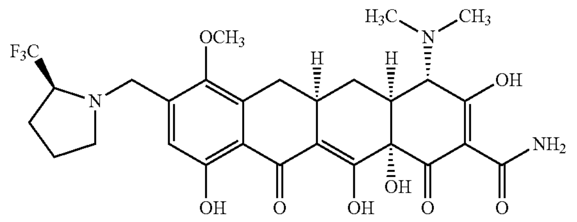

[1] H NMR (400 MHz, $CD_3OD$) δ 7.02 (s, 1 H), 4.67-4.39 (m, 3 H), 4.12 (s, 1 H), 3.72 (s, 3 H), 3.26-3.20 (m, 2 H), 3.05-2.89 (m, 9 H), 2.49-2.40 (m, 1 H), 2.38-2.32 (m, 1 H), 2.29-2.22 (m, 1 H), 2.17-2.11 (m, 2 H), 2.07-2.00 (m, 1 H), 1.70-1.60 (m, 1 H); MS (ESI) m/z 596.1 (M+H).

S24-9-181

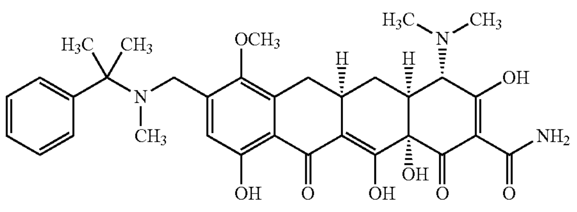

[1] H NMR (400 MHz, $CD_3OD$) δ 7.82-755 (m, 5 H), 6.89 (s, 1 H), 4.22, 3.95 (d, J=12.4 Hz, total 1 H), 4.13 (s, 1 H), 3.11-3.00 (m, 11 H), 2.83, 2.80 (s, total 3 H), 2.37-2.25 (m, 2H), 1.98-1.88 (m, 6 H), 1.69-1.60 (m, 1 H); MS (ESI) m/z 606.1 (M+H).
S24-9-182
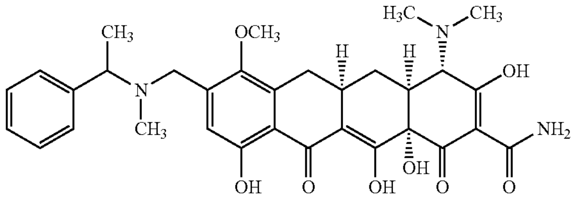
S24-9-182: MS (ESI) m/z 592.3 (M + H).
EXAMPLE 25
Synthesis of Compounds Via Scheme 25

Scheme 25
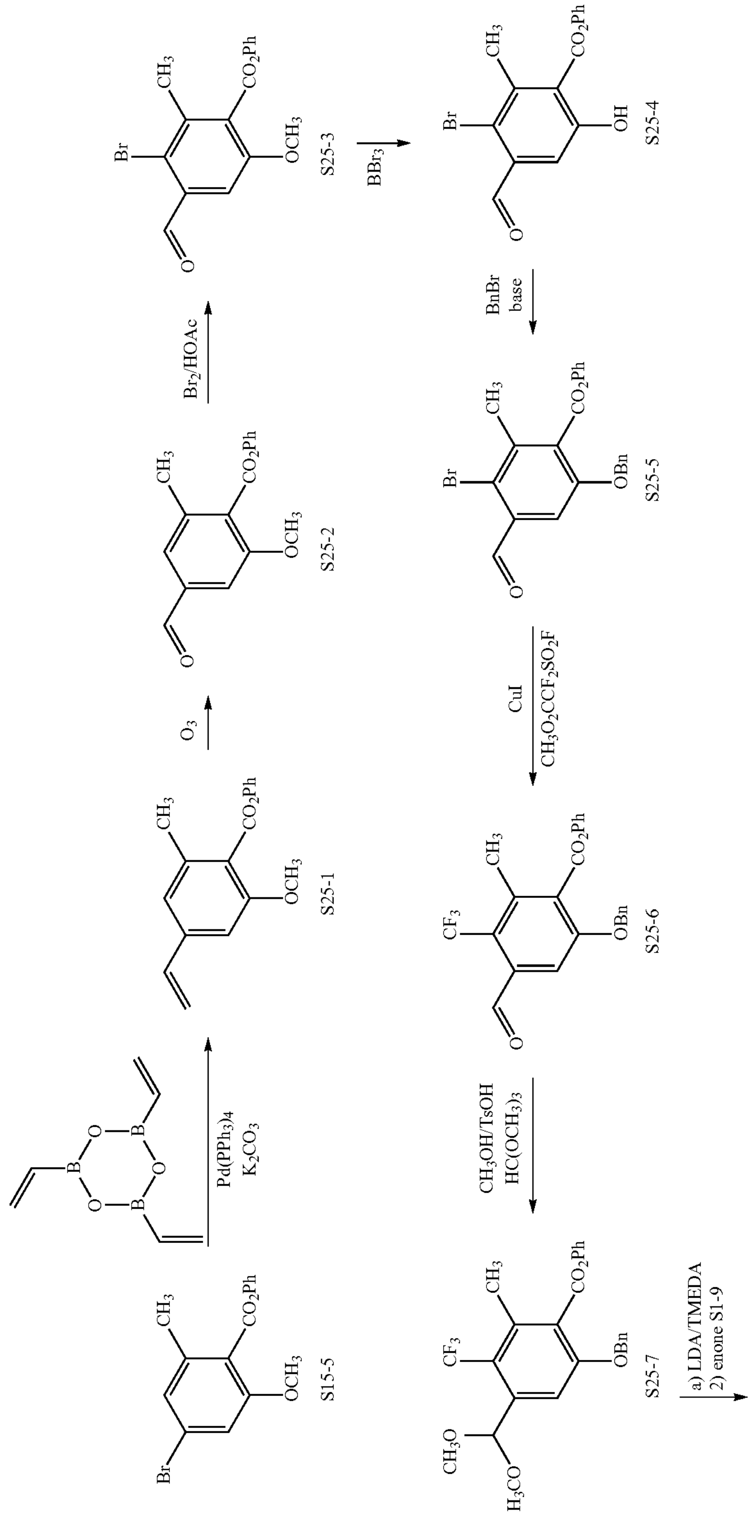

-continued
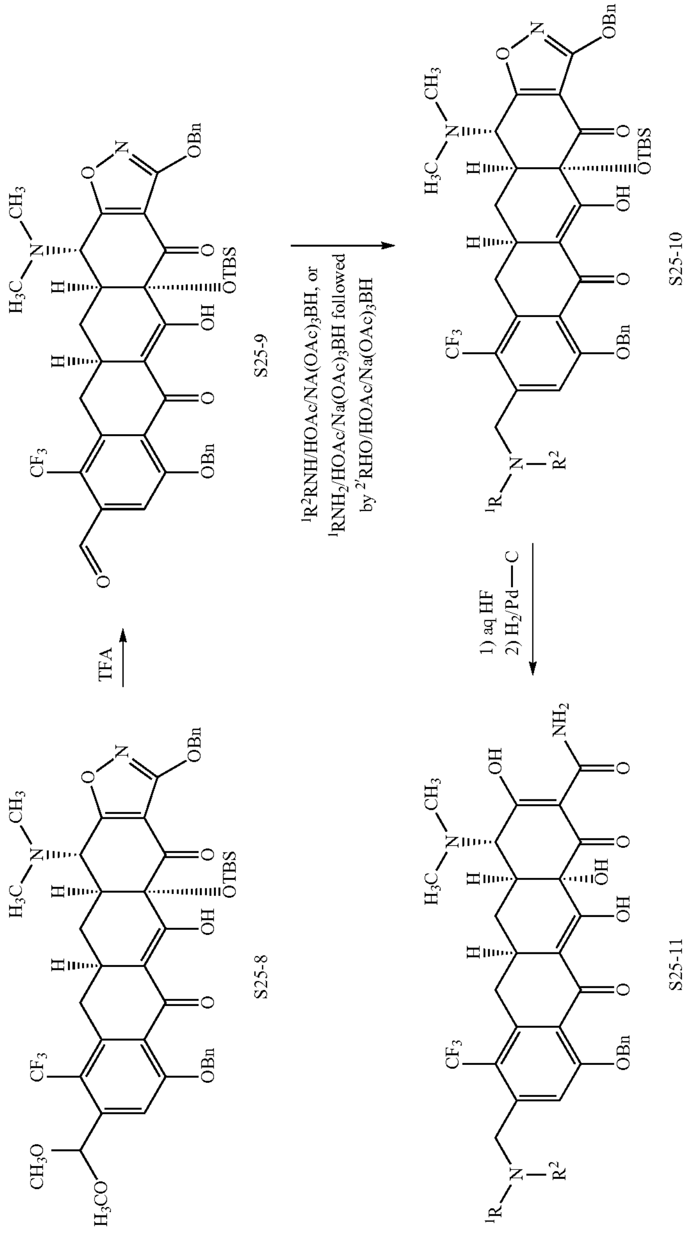
S25-8
S25-9
S25-10
S25-11

The following compounds were prepared according to Scheme 25.

S25-1

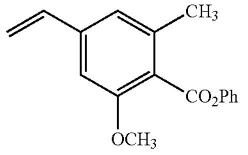

Compound S15-5 (20 g, 62.5 mmol, 1.0 equiv), 2, 4, 6 Trivinylcyclotriboroxane-pyridine complex (7.8 g, 31.25 mmol, 0.50 equiv), $Pd(PPh_3)_4$ (2.2 g, 1.88 mmol, 0.030 equiv) and $K_2CO_3$ (17.25 g, 125 mmol, 2.0 equiv) was added to vessel in 1.4 dioxane:$H_2O$ (3:1, V:V). The mixture was bubbled with $N_2$ to remove $O_2$ for 6 times. The mixture was heated to reflux for 19 h. The mixture was concentrated. The residue partitioned between EA and water. The organic layer was dried over $Na_2SO_4$ and evaporated to dryness. The crude compound was purified by column chromatography on silica gel elute with (PE:EA=200:1→100:1→50:1). yielded (88.3%) 14.8 g compound S25-1 as a light yellow solid. $^1$H NMR (400 MHz, $CDCl_3$) δ 7.38-7.34 (m, 2 H), 7.27-7.16 (m, 3 H), 6.83-6.76 (m, 2 H), 6.65-6.60 (m, 1 H), 5.72 (d, J=17.6 Hz, 1 H), 5.25 (d, J=11.2 Hz, 1 H), 3.83 (s, 3 H), 2.38 (s, 3 H); MS (ESI) m/z 269.1 (M+H).

S25-2

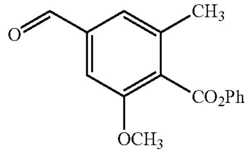

An ozone-enriched steam of oxygen was bubbled through a cold (−78 C) solution of compound S25-1 (21 g, 78.3 mmol, 1.0 equiv) in anhydrous $CH_2Cl_2$ until it turned light blue. The reaction was followed by TLC. The solution was purged with argon at −78 C for 10 min to remove the excess $O_3$. $CH_3SCH_3$ (50 mL) was added into the reaction mixture and stirred for 5 hour from −78 C to 25 C. The reaction was concentrated. he crude compound was purified by column chromatography on silica gel elute with (PE:EA=100:1→50:→30:1) to yield (61.6%) 13 g compound S25-2 as a light yellow solid. $^1$H NMR (400 MHz, $CDCl_3$) δ 9.97 (s, 1 H), 7.46-7.41 (m, 2 H), 7.36-7.22 (m, 5 H), 3.92 (s, 3 H), 2.51 (s, 3 H); MS (ESI) m/z 271.1 (M+H).

S25-3

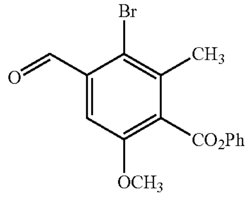

Compound S25-3 (1.8 g, 6.62 mmol, 1 equiv) was dissolved in HOAc. Bromine (1.6 mL, 26.5 mmol, 4 equiv) was added dropwise into the solution. The reaction mixture was stirred for 1 hour at rt. The mixture was concentrated. The residue was extracted with EA and a saturated $NaHCO_3$. The organic layer was washed with brine and water in return, dried over $Na_2SO_4$ and concentrated to dryness. To afford 1.9 g compound S25-3 as a light yellow solid.

S25-4

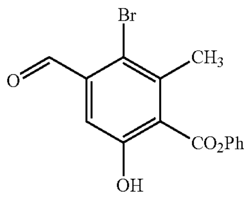

$BBr_3$ (4.9 g, 1.9 mL, 19.5 mmol, 1.5 equiv) was added to a $CH_2Cl_2$ solution (30 mL) of S25-3 (3.5 g, 13.0 mmol, 1.0 equiv) at −78 C. The reaction was stirred from −78° C. to 25° C. for 1.5 h, quenched with saturated $NaHCO_3$ and the reaction mixture was extracted with EtOAc. The combined EtOAc extracts were dried ($Na_2SO_4$) and concentrated to yield 3.3 g of crude S25-4.

S25-5

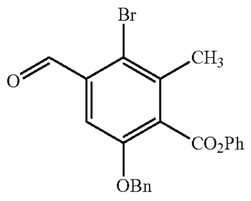

$K_2CO_3$ (3.6 g, 26.0 mmol, 2.0 equiv) and BnBr (4.2 g, 26.0 mmol, 2.0 equiv) were added to a solution of compound S25-4 (3.3 g, 13.0 mmol, 1.0 equiv) in DMF (15 mL). The reaction mixture was stirred at rt for 2 h. The reaction mixture was filtered and washed with EtOAc. Water (150 mL) was added into it and extracted with EtOAc. The organic layer was dried over $Na_2SO_4$ and concentrated. The crude compound was purified by column chromatography on silica gel elute with (PE:EA=100:1→50:1). yielded (61.7% for 3 steps) 3.5 g compound S25-5 as a light yellow solid. $^1$H NMR (400 MHz, $CDCl_3$) δ 10.43 (s, 1 H), 7.46-7.30 (m, 9 H), 7.08-7.05 (m, 2 H), 5.17 (s, 2 H), 2.52 (s, 3 H); MS (ESI) m/z 425.1 (M+H).

S25-6

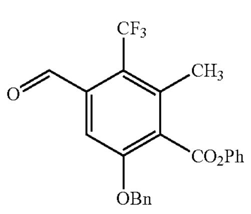

Compound S25-5 (5 g, 11.8 mmol, 1.0 equiv) in anhydrous DMF was added $CH_3O_2CCF_2SO_2F$ (11.3 g, 59 mmol, 5.0 equiv) and CuI (4.5 g, 23.6 mmol, 2.0 equiv) in obturator. The reaction was heated to 100 C for 20 h. The mixture was filtered and washed with EA. The solution was concentrated and extracted with EA and water. The organic layer was dried over $Na_2SO_4$ and concentrated to the crude compound S25-6 as brown oil (7 g), $^1$H NMR (400 MHz, $CDCl_3$) δ 10.35-10.32 (m, 1 H), 7.40-7.28 (m, 9 H), 7.02-6.83 (m, 2 H), 5.17 (s, 2 H), 2.55-2.51 (m, 3 H); MS (ESI) m/z 415.1 (M+H).

S25-7

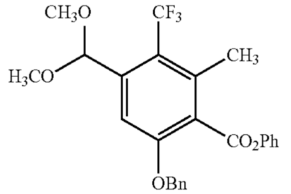

Compound S25-6 (7 g crude, 11.8 mmol, 1.0 equiv) in MeOH was added $HC(OMe)_3$ (3.6 g, 35.4 mmol, 3.0 equiv) and TsOH (0.23 g, 1.18 mmol, 0.1 equiv). The reaction was heated to reflux for 18 h. The mixture was concentrated. The residue was extracted with EA and water. The organic layer was dried over $Na_2SO_4$ and concentrated. The crude compound was purified by column chromatography on silica gel elute with (PE:EA=100:1→50:1) to yield (90.6% for 2 steps) 4.9 g compound S25-7 as a light yellow oil. $^1$H NMR (400 MHz, $CDCl_3$) δ 7.45-7.30 (m, 9 H), 7.08-6.90 (m, 2 H), 5.60 (s, 1 H), 5.20 (s, 2 H), 3.73 (s, 6 H), 2.56-2.51 (m, 3 H); MS (ESI) m/z 461.1 (M+H).

S25-8

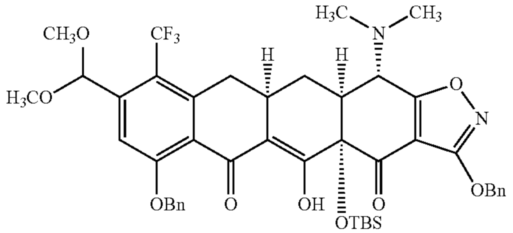

To diisopropylamine (0.414 mL, 2.5 mmol, 5.0 equiv) in THF at −78° C. was added nBuLi (1.04 mL, 2.50 M/hexane, 2.5 mmol, 5.0 equiv) and TMEDA (1.04 mL, 2.5 mmol, 5.0 equiv) at −78° C. dropwise. The reaction was stirred at −78° C. for 30 min. Compound S25-7 (460 mg, 1.25 mmol, 2.5 equiv) in THF was added to the reaction mixture dropwise at −78 C. The resulting deep-red solution was stirred at −78° C. 15 min and added with the enone (240 mg 0.50 mmol, 1.0 equiv) in THF. The deep-red solution was gradually warmed up with stirring from −78° C. to 0° C. over a period of 30 min. and quenched with aqueous saturated ammonium chloride (100 mL). The yellow-green mixture was extracted with EtOAc two times. The combined EtOAc extracts were dried ($Na_2SO_4$) and concentrated to yield the crude product. Flash column chromatography on silica gel with 0%, 5%, 10%, and 20% EtOAc/hexane sequentially yielded the desired product S25-8 as a light-yellow solid (380 mg, 89%). $^1$H NMR (400 MHz, $CDCl_3$) δ 15.65 (s, 1 H), 7.46-7.22 (m, 11 H), 5.49 (s, 1 H), 5.30 (s, 2 H), 5.25 (s, 2 H), 3.91 (d, J=10.8 Hz, 1 H), 3.29 (s, 3 H), 3.20 (s, 3 H), 2.85-2.62 (m, 2 H), 2.53-2.35 (m, 9 H), 2.10-2.04 (m, 1 H), 0.88 (s, 9 H), 0.20 (s, 3 H), 0.09 (s, 3 H); MS (ESI) m/z 849.1 (M+H).

S25-9

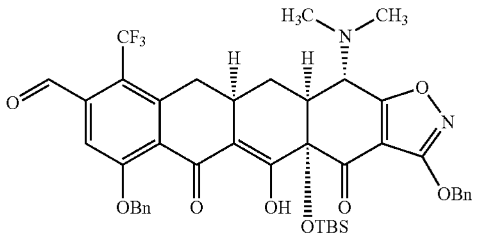

Compound S25-8 (0.3 g, 0.354 mmol) was dissolved in DCM (3 mL) and aqueous TFA (3 mL) was added dropwise. The yellow solution was stirred at rt for 1 h. The reaction was followed by LC-MS. The solution was concentrated. The residue was extracted with EA and water. The combined EtOAc extracts were dried ($Na_2SO_4$) and concentrated to yield the crude product S25-9.

S25-10-1

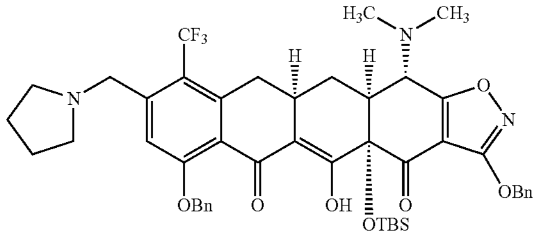

Compound S25-9 (50 mg crude, 0.059 mmol, 1.0 equiv) was dissolved in 1,2-dichloroethane (1.0 mL). Pyrroliding (0.295 mmol, 5.0 equiv) and acetic acid (20 μL, 0.36 mmol, 6.0 equiv) were added. After stirring at rt for 1 h, sodium triacetoxyborohydride (37 mg, 0.177 mmol, 3.0 equiv) was added. Stirring was continued overnight. The reaction mixture was poured into saturated aqueous $NaHCO_3$ and extracted three times with dichloromethane. The combined organic extracts were washed with brine, dried over sodium sulfate, and concentrated to give the crude intermediate S25-10-1, which was used directly in the next step without further purification.

S25-11-1

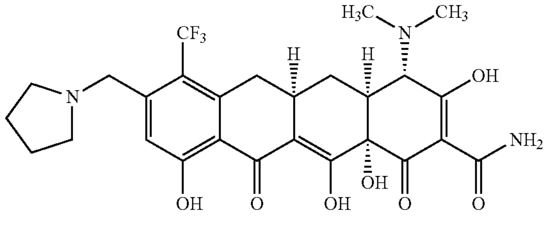

Compound S25-10-1 (50 mg, crude, 0.059 mmol, 1 equiv) was dissolved in THF (10 mL) and aqueous HF (40%, 10 mL) was added dropwise. The yellow solution was stirred at rt for 1 h. The resulting deep-red solution was slowly added into an aqueous $K_2HPO_4$ solution with stirring. The pH of the mixture was adjusted by aqueous $K_2HPO_4$ solution to about 8. The yellow mixture was extracted with EtOAc two times. The combined EtOAc extracts were dried ($Na_2SO_4$) and concentrated to yield the crude intermediate.

The above crude intermediate (50 mg, crude, 0.059 mmol, 1 equiv) was dissolved in HPLC grade MeOH (10 mL). HCl/MeOH (1.0 mL, 4N) and 10% Pd—C (50 mg, 0.046 mmol, 0.78 equiv) were added. The mixture was purged with hydrogen by bubbling hydrogen through with gentle stirring for 5 min. The reaction was then vigorously stirred under hydrogen balloon at rt for 1 hr. LC-MS analysis indicated complete reaction. The catalyst was filtered and concentrated to yield the crude product as a deep-yellow solid. The crude compound was purified by prep-HPLC on a Polymerx column to yield the desired product S25-11-1 as a yellow solid after freeze-drying (7 mg, 21%). $^{1}H$ NMR (400 MHz, $CD_3OD$) δ 7.26 (s, 1 H), 4.71 (d, J=14.0 Hz, 1 H), 4.49 (d, J=14.0 Hz, 1 H), 4.14 (s, 1 H), 3.74-3.59 (m, 2 H), 3.30-2.96 (m, 11 H), 2.69-2.57 (m, 1 H), 2.26-2.01 (m, 5 H), 1.69-1.59 (m, 1 H); MS (ESI) m/z 566.1 (M+H).

The following final compounds were prepared from S25-9 by reductive amination with various amines, followed by aqueous HF treatment and hydrogenation under similar conditions described for S25-11-1.

S25-11-2

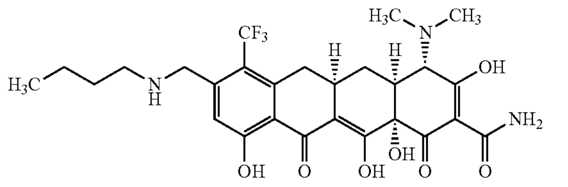

S25-11-2 $^{1}H$ NMR (400 MHz, $CD_3OD$) δ 7.17 (s, 1 H), 4.43 (d, J=14.0 Hz, 1 H), 4.32 (d, J=14.0 Hz, 1 H), 4.13 (s, 1 H), 3.16 (t, J=8.4 Hz, 2 H), 3.09-2.96 (m, 9 H), 2.65-2.62 (m, 1 H), 2.26-2.22 (m, 1 H), 1.77-1.63 (m, 3 H), 1.49-1.43 (m, 2 H), 1.02 (t, J=7.2 Hz, 3 H); MS (ESI) m/z 568.2 (M+H).

S25-11-3

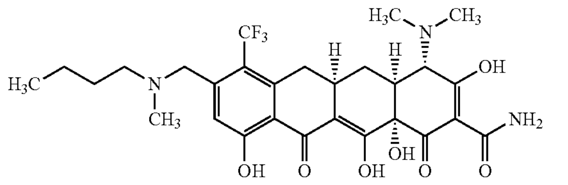

S25-11-3: $^{1}H$ NMR (400 MHz, $CD_3OD$) δ 7.25 (s, 1 H), 4.79-4.67 (m, 1 H), 4.45-4.29 (m, 1 H), 4.15 (s, 1 H), 3.26-2.97 (m, 11 H), 2.90-2.81 (m, 3 H), 2.69-2.57 (m, 1 H), 2.28-2.24 (m, 1 H), 1.83-1.75 (m, 2 H), 1.69-1.60 (m, 1 H), 1.47-1.38 (m, 2 H), 1.00 (t, J=7.2 Hz, 3 H); MS (ESI) m/z 582.1 (M+H).

S25-11-4

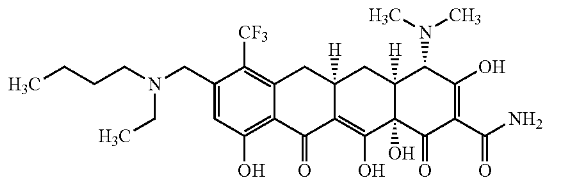

S25-11-4: $^{1}H$ NMR (400 MHz, $CD_3OD$) δ 7.21 (s, 1 H), 4.65-4.55 (m, 1 H), 4.53-4.45 (m, 1 H), 4.12 (s, 1 H), 3.37-3.33 (m, 2 H), 3.26-2.95 (m, 11 H), 2.68-2.57 (m, 1 H), 2.26-2.20 (m, 1 H), 1.82-1.60 (m, 3 H), 1.44-1.35 (m, 5 H), 1.01 (t, J=7.2 Hz, 3 H); MS (ESI) m/z 596.3 (M+H).

S25-11-5

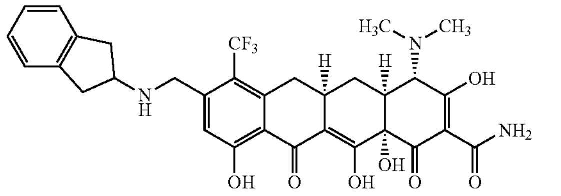

S25-11-5: $^{1}H$ NMR (400 MHz, $CD_3OD$) δ 7.30-7.21 (m, 5 H), 4.51 (d, J=13.6 Hz, 1 H), 4.40 (d, J=14.0 Hz, 1 H), 4.27-4.24 (m, 1 H), 4.12 (s, 1 H), 3.66-3.47 (m, 2 H), 3.24-2.95 (m, 11 H), 2.65-2.61 (m, 1 H), 2.25-2.22 (m, 1 H), 1.65-1.60 (m, 1 H); MS (ESI) m/z 628.2 (M+H).

S25-11-6

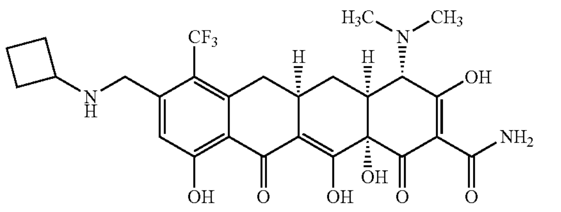

S25-11-6: $^{1}H$ NMR (400 MHz, $CD_3OD$) δ 7.14 (s, 1 H), 4.29 (d, J=14.0 Hz, 1 H), 4.17 (d, J=14.8 Hz, 1 H), 4.13 (s, 1 H), 3.93-3.89 (m, 1 H), 3.09-2.95 (m, 9 H), 2.65-2.60 (m, 1 H), 2.42-2.22 (m, 5 H), 1.98-1.89 (m, 2 H), 1.65-1.60 (m, 1 H); MS (ESI) m/z 566.2 (M+H).

S25-11-7

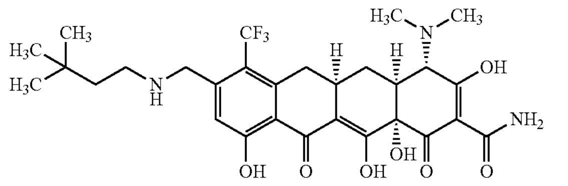

S25-11-7: $^{1}H$ NMR (400 MHz, $CD_3OD$) δ 7.16 (s, 1 H), 4.44 (d, J=14.0 Hz, 1 H), 4.35 (d, J=14.0 Hz, 1 H), 4.12 (s, 1 H), 3.23-2.96 (m, 11 H), 2.66-2.62 (m, 1 H), 2.25-2.21 (m, 1 H), 1.70-1.62 (m, 3 H), 1.05 (s, 9 H); MS (ESI) m/z 596.0 (M+H).

S25-11-8

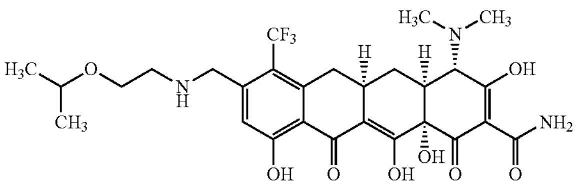

S25-11-8: $^{1}H$ NMR (400 MHz, $CD_3OD$) δ 7.16 (s, 1 H), 4.50 (d, J=15.2 Hz, 1 H), 4.38 (d, J=15.2 Hz, 1 H), 4.13 (s, 1

H), 3.78-3.68 (m, 3 H), 3.37-3.31 (m, 2 H), 3.26-3.25 (m, 1 H), 3.10-2.92 (m, 8 H), 2.66-2.61 (m, 1 H), 2.26-2.22 (m, 1 H), 1.69-1.63 (m, 1 H), 1.21 (d, J=6.4 Hz, 6 H); MS (ESI) m/z 598.1 (M+H).

S25-11-9

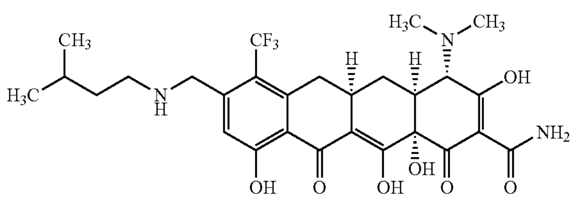

S25-11-9: [1] H NMR (400 MHz, $CD_3OD$) δ 7.08 (s, 1 H), 4.35 (d, J=14.4 Hz, 1 H), 4.23 (d, J=13.6 Hz, 1 H), 4.03 (s, 1 H), 3.09 (t, J=8.4 Hz, 2 H), 2.95-2.86 (m, 9 H), 2.52-2.48 (m, 1 H), 2.16-2.13 (m, 1 H), 1.64-1.44 (m, 4 H), 0.90 (d, J=6.4 Hz, 6 H); MS (ESI) m/z 582.1 (M+H).

S25-11-10

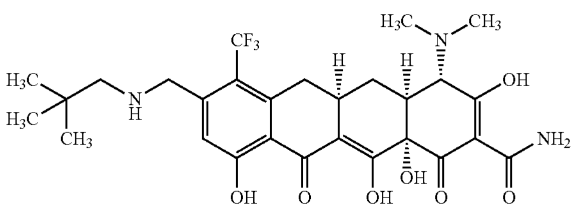

S25-11-10: [1] H NMR (400 MHz, $CD_3OD$) δ 7.15 (s, 1 H), 4.36-4.29 (m, 2 H), 4.04 (s, 1 H), 3.03-2.86 (m, 11 H), 2.56-2.49 (m, 1 H), 2.17-2.12 (m, 1 H), 1.60-1.50 (m, 1 H), 1.00 (s, 9 H); MS (ESI) m/z 582.2 (M+H).

S25-11-11

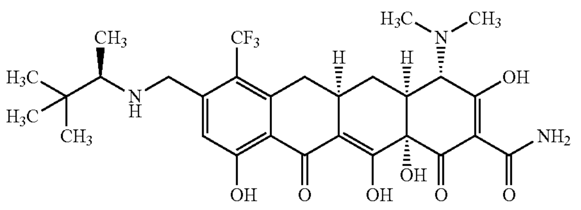

S25-11-11: [1] H NMR (400 MHz, $CD_3OD$) δ 7.25 (s, 1 H), 4.56 (d, J=14.0 Hz, 1 H), 4.39 (d, J=14.0 Hz, 1 H), 4.13 (s, 1 H), 3.19-2.90 (m, 10 H), 2.69-2.59 (m, 1 H), 2.25-2.22 (m, 1 H), 1.69-1.59 (m, 1 H), 1.39 (d, J=8.8 Hz, 3 H), 1.05 (s, 9 H); MS (ESI) m/z 596.2 (M+H).

S25-11-12

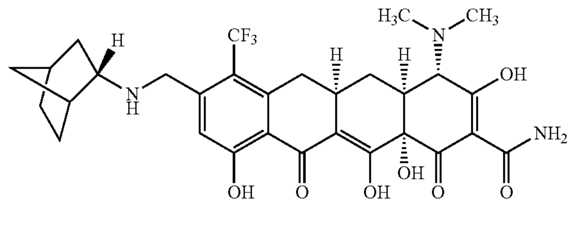

S25-11-12: [1] H NMR (400 MHz, CD3OD) δ 7.22, 720 (s, 1 H total), 4.43-4.26 (m, 2 H), 4.13 (s, 1 H), 3.64-3.62 (m, 1 H), 3.25-2.95 (m, 9 H), 2.67-2.57 (m, 2 H), 2.35-2.11 (m, 3 H), 1.68-1.43 (m, 7 H), 1.18-1.12 (m, 1 H); MS (ESI) m/z 606.3 (M+H).

S25-11-13

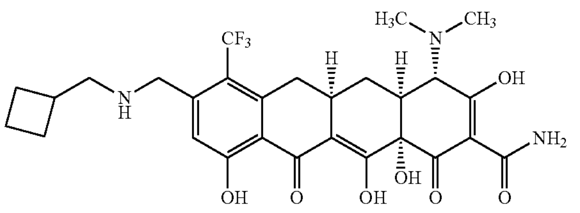

S25-11-13: [1] H NMR (400 MHz, $CD_3OD$) δ 7.18 (s, 1 H), 4.40 (d, J=14.0 Hz, 1 H), 4.31 (d, J=14.0 Hz, 1 H), 4.14 (s, 1 H), 3.25-2.98 (m, 11 H), 2.78-2.55 (m, 2 H), 2.26-2.18 (m, 3 H), 2.08-1.85 (m, 4 H), 1.70-1.58 (m, 1 H); MS (ESI) m/z 580.3 (M+H).

S25-11-14

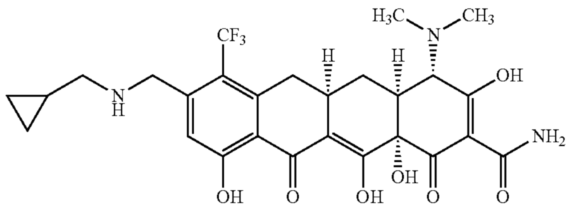

S25-11-14: [1] H NMR (400 MHz, $CD_3OD$) δ 7.05 (s, 1 H), 4.32 (d, J=14.0 Hz, 1 H), 4.20 (d, J=14.4 Hz, 1 H), 4.00 (s, 1 H), 3.15-2.82 (m, 11 H), 2.51-2.43 (m, 1 H), 2.13-2.09 (m, 1 H), 1.55-1.45 (m, 1 H), 1.10-0.99 (m, 1 H), 0.65-0.58 (m, 2 H), 0.35-0.27 (m, 2 H); MS (ESI) m/z 566.1 (M+H).

S25-11-15

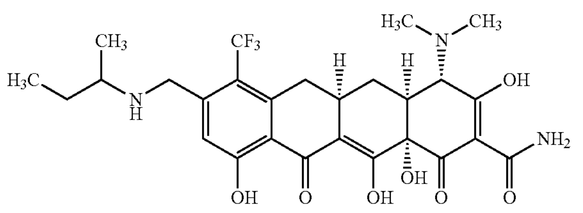

S25-11-15: [1] H NMR (400 MHz, $CD_3OD$) δ 7.19 (s, 1 H), 4.42-4.29 (m, 2 H), 4.13 (s, 1 H), 3.17-2.95 (m, 10 H), 2.65-2.58 (m, 1 H), 2.26-2.22 (m, 1 H), 1.96-1.90 (m, 1 H), 1.68-1.58 (m, 2 H), 1.42-1.37 (m, 3 H), 1.02 (t, J=7.2 Hz, 3 H); MS (ESI) m/z 568.2 (M+H).

S25-11-16

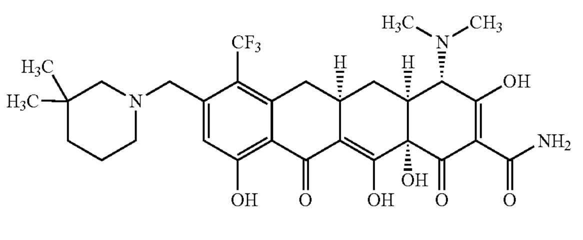

S25-11-16: [1] H NMR (400 MHz, $CD_3OD$) δ 7.33, 7.26 (s, 1 H total), 4.57-4.29 (m, 2 H), 4.13 (s, 1 H), 3.62-3.50 (m, 1

H), 3.22-2.84 (m, 12 H), 2.68-2.55 (m, 1 H), 2.26-2.22 (m, 1 H), 2.07-1.83 (m, 2 H), 1.68-1.44 (m, 3 H), 1.12, 1.11 (s, 3 H total), 1.04, 1.02 (s, 3 H total); MS (ESI) m/z 608.3 (M+H).

S25-11-17

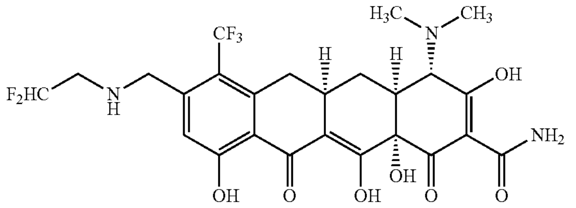

S25-11-17: $^1$H NMR (400 MHz, $CD_3OD$) δ 7.20 (s, 1 H), 6.38 (tt, J=6.4, 54.0 Hz, 1 H), 4.56 (dd, J=1.6, 14.0 Hz, 1 H), 4.46 (dd, J=1.6, 14.8 Hz, 1 H), 4.14 (s, 1 H), 3.77-3.67 (m, 2 H), 3.21-2.98 (m, 9 H), 2.66-2.58 (m, 1 H), 2.27-2.21 (m, 1 H), 1.69-1.59 (m, 1 H); MS (ESI) m/z 575.9 (M+H).

S25-11-18

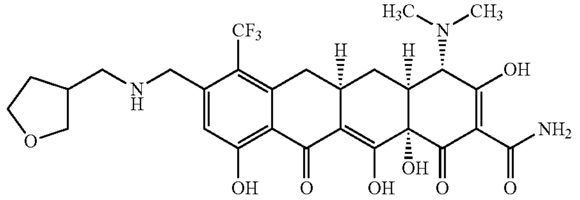

S25-11-18: $^1$H NMR (400 MHz, $CD_3OD$) δ 7.21 (s, 1 H), 4.48-4.32 (m, 2 H), 4.13 (s, 1 H), 3.94-3.88 (m, 2 H), 3.79-3.75 (m, 1 H), 3.59-3.55 (m, 1 H), 3.25-2.96 (m, 11 H), 2.70-2.58 (m, 2 H), 2.27-2.21 (m, 2 H), 1.75-1.63 (m, 2 H); MS (ESI) m/z 596.0 (M+H).

S25-11-19

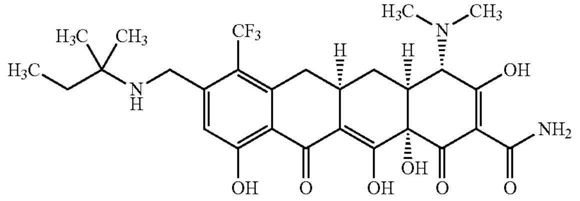

S25-11-19: $^1$H NMR (400 MHz, $CD_3OD$) δ 7.23 (s, 1 H), 4.41 (d, J=14.4 Hz, 1 H), 4.26 (d, J=14.8 Hz, 1 H), 4.13 (s, 1 H), 3.25-2.95 (m, 9 H), 2.69-2.58 (m, 1 H), 2.27-2.22 (m, 1 H), 1.87-1.77 (m, 2 H), 1.69-1.59 (m, 1 H), 1.42 (s, 6 H), 1.03 (t, J=7.2 Hz, 3 H); MS (ESI) m/z 582.0 (M+H).

S25-11-20

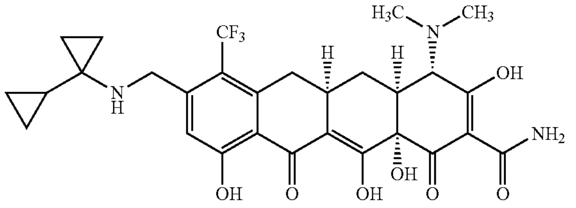

S25-11-20: $^1$H NMR (400 MHz, $CD_3OD$) δ 7.21 (s, 1 H), 4.69 (d, J=14.8 Hz, 1 H), 4.56 (d, J=14.8 Hz, 1 H), 4.14 (s, 1 H), 3.23-2.96 (m, 9 H), 2.69-2.57 (m, 1 H), 2.28-2.22 (m, 1 H), 1.69-1.54 (m, 2 H), 1.11-1.05 (m, 2 H), 0.83-0.76 (m, 2 H), 0.74-0.69 (m, 2 H), 0.41-0.35 (m, 2 H); MS (ESI) m/z 592.0 (M+H).

S25-11-21

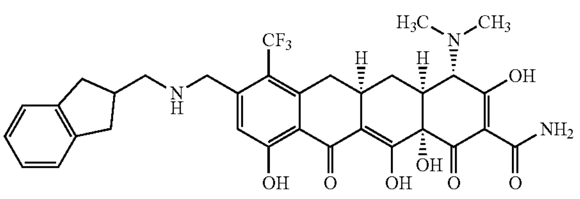

S25-11-21: $^1$H NMR (400 MHz, $CD_3OD$) δ 7.41 (s, 4 H), 7.32 (s, 1 H), 4.78-4.67 (m, 6 H), 4.13 (s, 1 H), 3.22-2.95 (m, 9 H), 2.67-2.58 (m, 1 H), 2.25-2.22 (m, 1 H), 1.68-1.59 (m, 1 H); MS (ESI) m/z 614.0 (M+H).

S25-11-22

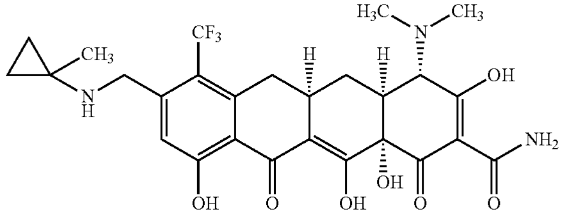

S25-11-22: $^1$H NMR (400 MHz, $CD_3OD$) δ 7.18 (s, 1 H), 4.51 (d, J=13.6 Hz, 1 H), 4.40 (d, J=13.2 Hz, 1 H), 4.13 (s, 1 H), 3.23-2.95 (m, 9 H), 2.67-2.55 (m, 1 H), 2.25-2.22 (m, 1 H), 1.67-1.53 (m, 1 H), 1.52 (s, 3 H), 1.18-1.12 (m, 2 H), 0.88-0.82 (m, 2 H); MS (ESI) m/z 566.0 (M+H).

S25-11-23

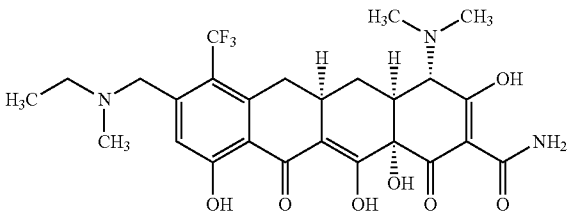

S25-11-23: $^1$H NMR (400 MHz, $CD_3OD$) δ 7.24 (s, 1 H), 4.75-4.63 (m, 1 H), 4.44-4.27 (m, 1 H), 4.14 (s, 1 H), 3.46-3.34 (m, 2 H), 3.20-2.95 (m, 9 H), 2.85 (d, J=14.8 Hz, 3 H), 2.68-2.55 (m, 1 H), 2.26-2.22 (m, 1 H), 1.68-1.59 (m, 1 H), 1.41 (t, J=7.2 Hz, 3 H); MS (ESI) m/z 554.0 (M+H).

S25-11-24

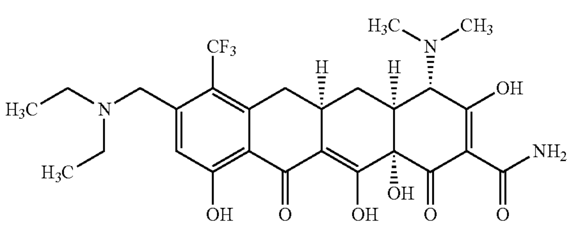

S25-11-24: $^{1}$H NMR (400 MHz, $CD_3OD$) δ 7.21 (s, 1 H), 4.59 (d, J=14.0 Hz, 1 H), 4.45 (d, J=14.4 Hz, 1 H), 4.13 (s, 1 H), 3.35-3.32 (m, 2 H), 3.25-2.95 (m, 11 H), 2.66-2.60 (m, 1 H), 2.26-2.20 (m, 1 H), 1.68-1.58 (m, 1 H), 1.39-1.32 (m, 6 H); MS (ESI) m/z 568.0 (M+H).

S25-11-25

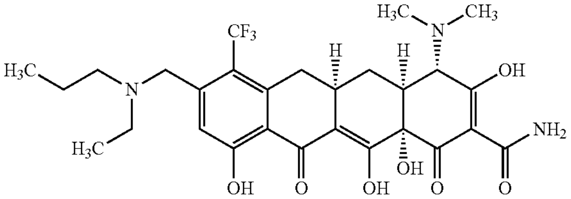

S25-11-25: $^{1}$H NMR (400 MHz, $CD_3OD$) δ 7.20 (s, 1 H), 4.64-4.59 (m, 1 H), 4.51-4.45 (m, 1 H), 4.12 (s, 1 H), 3.35-3.32 (m, 2 H), 3.20-2.95 (m, 11 H), 2.69-2.59 (m, 1 H), 2.25-2.22 (m, 1 H), 1.82-1.60 (m, 3 H), 1.40-1.33 (m, 3 H), 1.05-0.96 (m, 3 H); MS (ESI) m/z 582.2 (M+H).

S25-11-26

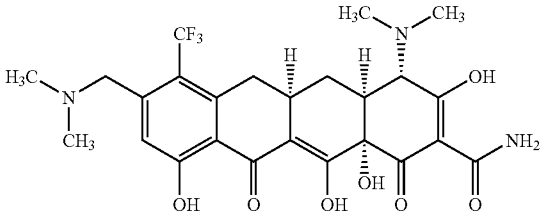

S25-11-26: $^{1}$H NMR (400 MHz, $CD_3OD$) δ 7.23 (s, 1 H), 4.61 (d, J=14.0 Hz, 1 H), 4.45 (d, J=13.6 Hz, 1 H), 4.14 (s, 1 H), 3.18-2.93 (m, 15 H), 2.69-2.58 (m, 1 H), 2.27-2.23 (m, 1 H), 1.67-1.58 (m, 1 H); MS (ESI) m/z 540.1 (M+H).

S25-11-27

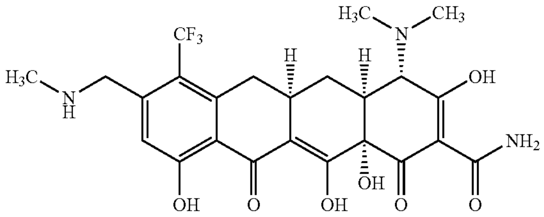

S25-11-27: $^{1}$H NMR (400 MHz, $CD_3OD$) δ 7.14 (s, 1 H), 4.43 (d, J=14.4 Hz, 1 H), 4.32 (d, J=14.4 Hz, 1 H), 4.14 (s, 1 H), 3.20-2.91 (m, 9 H), 2.84 (s, 3 H), 2.69-2.57 (m, 1 H), 2.27-2.23 (m, 1 H), 1.68-1.57 (m, 1 H); MS (ESI) m/z 526.0 (M+H).

S25-11-28

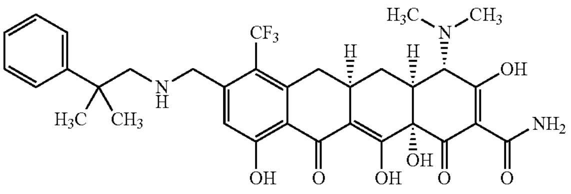

S25-11-18: $^{1}$H NMR (400 MHz, $CD_3OD$) δ 7.48-7.30 (m, 5 H), 7.08 (s, 1 H), 4.35-4.24 (m, 2 H), 4.15 (s, 1 H), 3.45 (s, 2 H), 3.21-2.96 (m, 9 H), 2.69-2.53 (m, 1 H), 2.26-2.22 (m, 1 H), 1.67-1.57 (m, 1 H), 1.48 (d, J=2.4 Hz, 6 H); MS (ESI) m/z 644.1 (M+H).

S25-11-29

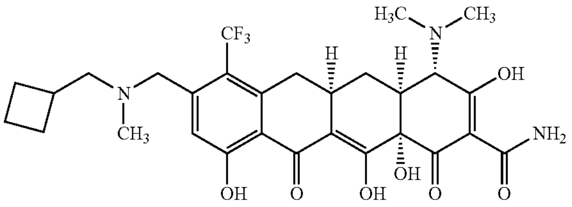

S25-11-29: $^{1}$H NMR (400 MHz, $CD_3OD$) δ 7.23 (s, 1 H), 4.71-4.61 (m, 1 H), 4.41-4.24 (m, 1 H), 4.15 (s, 1 H), 3.25-2.98 (m, 11 H), 2.96-2.81 (m, 4 H), 2.69-2.59 (m, 1 H), 2.26-2.20 (m, 3 H), 2.10-2.01 (m, 1 H), 1.99-1.90 (m, 1 H), 1.69-1.59 (m, 1 H); MS (ESI) m/z 594.0 (M+H).

S25-11-30

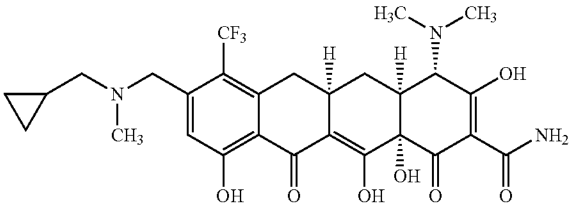

S25-11-30: $^{1}$H NMR (400 MHz, $CD_3OD$) δ 7.22 (s, 1 H), 4.80-4.75 (m, 1 H), 4.42-4.24 (m, 1 H), 4.12 (s, 1 H), 3.22-2.89 (m, 14 H), 2.68-2.60 (m, 1 H), 2.25-2.21 (m, 1 H), 1.69-1.62 (m, 1 H), 1.27-1.10 (m, 1 H), 0.83-0.80 (m, 2 H), 0.50-0.47 (m, 2 H); MS (ESI) m/z 580.1 (M+H).

S25-11-31

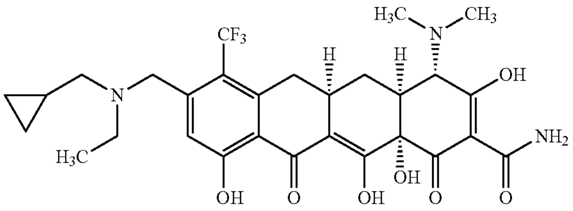

S25-11-31: $^{1}$H NMR (400 MHz, $CD_3OD$) δ 7.21 (s, 1 H), 4.62-4.43 (m, 2 H), 4.11 (s, 1 H), 3.20-2.87 (m, 13 H), 2.69-2.59 (m, 1 H), 2.25-2.20 (m, 1 H), 1.69-1.60 (m, 1 H), 1.41-1.33 (m, 3 H), 1.28-1.10 (m, 1 H), 0.83-0.75 (m, 2 H), 0.46-0.38 (m, 2 H); MS (ESI) m/z 594.1 (M+H).

S25-11-32

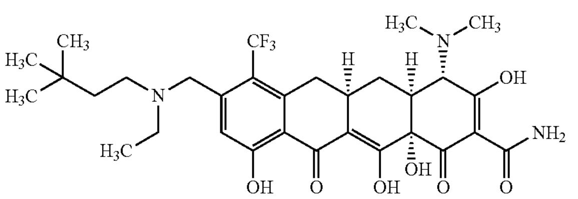

S25-11-32: [1] H NMR (400 MHz, $CD_3OD$) δ 7.23, 7.22 (s, 1 H total), 4.63 (d, J=14.4 Hz, 1 H), 4.51-4.49 (m, 1 H), 4.13 (s, 1 H), 3.22-2.87 (m, 13 H), 2.69-2.59 (m, 1 H), 2.26-2.23 (m, 1 H), 1.71-1.60 (m, 3 H), 1.41-1.33 (m, 3 H), 099, 0.97 (s, 9 H total); MS (ESI) m/z 624.1 (M+H).

S25-11-33

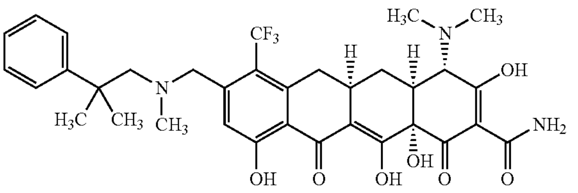

S25-11-33: [1] H NMR (400 MHz, $CD_3OD$) δ 7.50-7.28 (m, 5 H), 7.07, 7.02 (s, 1 H total), 4.46-4.43 (m, 1 H), 4.33-4.19 (m, 1 H), 4.13 (s, 1 H), 3.78-3.51 (m, 2 H), 3.22-2.86 (m, 9 H), 2.66-2.57 (m, 4 H), 2.24-2.21 (m, 1 H), 1.66-1.47 (m, 1 H), 1.45 (s, 6 H); MS (ESI) m/z 658.0 (M+H).

S25-11-34

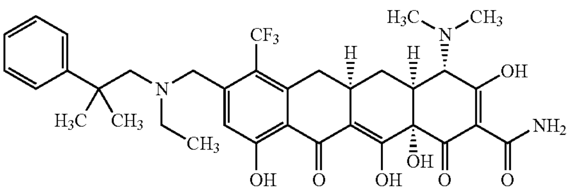

S25-11-34: [1] H NMR (400 MHz, $CD_3OD$) δ 7.51-7.24 (m, 5 H), 7.09, 6.94 (s, 1 H total), 4.43-4.24 (m, 2 H), 4.13 (s, 1 H), 3.75-3.70 (m, 1 H), 3.51-3.44 (m, 1 H), 3.21-2.94 (m, 11 H), 2.67-2.58 (m, 1 H), 2.24-2.21 (m, 1 H), 1.60-1.52 (m, 1 H), 1.44 (t, J=7.2 Hz, 6 H), 1.26-1.22 (m, 3 H); MS (ESI) m/z 672.1 (M+H).

S25-11-35

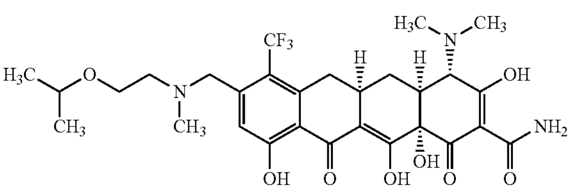

S25-11-35: [1] H NMR (400 MHz, $CD_3OD$) δ 7.23 (s, 1 H), 4.77-4.70 (m, 1 H), 4.50, 38 (d, J=14.4 Hz, 1 H, total), 4.13 (s, 1 H), 3.89-3.68 (m, 3 H), 3.52-3.40 (m, 2 H), 3.21-2.88 (m, 12 H), 2.64-2.61 (m, 1 H), 2.26-2.22 (m, 1 H), 1.67-1.58 (m, 1 H), 1.20 (d, J=6.0 Hz, 6 H); MS (ESI) m/z 612.4 (M+H).

S25-11-36

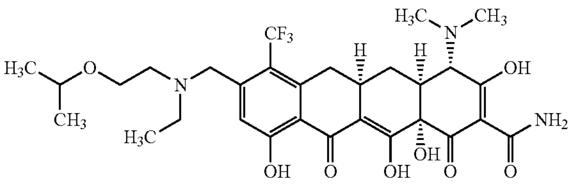

S25-11-36: [1] H NMR (400 MHz, $CD_3OD$) δ 7.30, 7.26 (s, 1 H total), 4.83-4.66 (m, 2 H), 4.13 (s, 1 H), 3.84-3.80 (m, 2 H), 3.70-3.67 (m, 1 H), 3.53-3.40 (m, 4 H), 3.20-2.96 (m, 9 H), 2.66-2.62 (m, 1 H), 2.27-2.22 (m, 1 H), 1.67-1.62 (m, 1 H), 1.42-1.35 (m, 3 H), 1.29-1.21 (m, 6 H); MS (ESI) m/z 626.3 (M+H).

S25-11-37

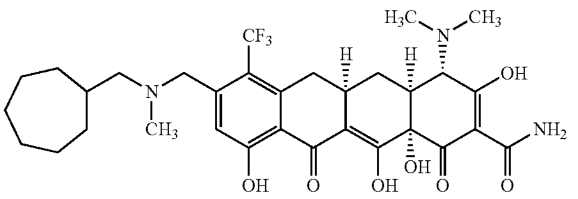

S25-11-37: [1] H NMR (400 MHz, $CD_3OD$) δ 7.25 (s, 1 H), 4.87-4.73 (m, 1 H), 4.46-4.27 (m, 1 H), 4.16 (s, 1 H), 3.30-2.79 (m, 14 H), 2.69-2.56 (m, 1 H), 2.28-2.25 (m, 1 H), 2.18-2.01 (m, 1 H), 1.80-1.55 (m, 11 H), 1.31-1.22 (m, 2 H); MS (ESI) m/z 636.1 (M+H).

S25-11-38

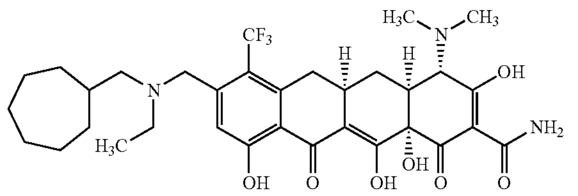

S25-11-38: [1] H NMR (400 MHz, $CD_3OD$) δ 7.24, 7.20 (s, 1 H total), 4.61-4.40 (m, 2 H), 4.12 (s, 1 H), 3.36-3.32 (m, 1 H), 3.28-2.86 (m, 12 H), 2.67-2.58 (m, 1 H), 2.25-2.21 (m, 1 H), 2.16-2.09 (m, 1 H), 1.89-1.41 (m, 12 H), 1.40-1.14 (m, 4 H); MS (ESI) m/z 650.1 (M+H).

S25-11-39

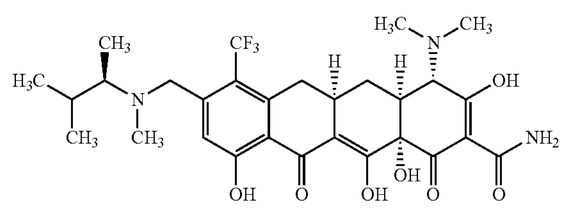

S25-11-39: [1] H NMR (400 MHz, $CD_3OD$) δ 7.31, 7.24 (s, 1 H total), 4.76 (d, J=14.0 Hz, 1 H), 4.48-4.29 (m, 1 H), 4.16 (s, 1 H), 3.44-3.34 (m, 1 H), 3.25-2.97 (m, 9 H), 2.84 (d, J=9.2 Hz, 3 H), 2.66-2.59 (m, 1 H), 2.30-2.12 (m, 2 H), 1.69-1.63

(m, 1 H), 1.43, 1.35 (d, J=6.8 Hz, 3 H total), 1.16-1.01 (m, 6 H); MS (ESI) m/z 596.6 (M+H).

S25-11-40

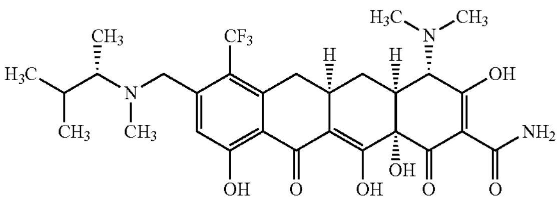

S25-11-40: [1] H NMR (400 MHz, $CD_3OD$) δ 7.16 (s, 1 H), 4.65 (t, J=15.2 Hz, 1 H), 4.26 (t, J=16.0 Hz, 1 H), 4.07 (s, 1 H), 3.35-3.30 (m, 1 H), 3.18-2.82 (m, 9 H), 2.74 (s, 3 H), 2.69-2.52 (m, 1 H), 2.18-2.02 (m, 2 H), 1.60-1.51 (m, 1 H), 1.32 (d, J=6.4 Hz, 3 H), 1.01, 0.97 (d, J=6.4 Hz, 6 H total); MS (ESI) m/z 596.3 (M+H).

S25-11-41

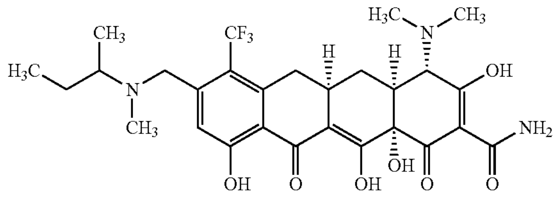

S25-11-41: [1] H NMR (400 MHz, $CD_3OD$) δ 7.25 (s, 1 H), 4.70 (d, J=13.2 Hz, 1 H), 4.36-4.24 (m, 1 H), 4.15 (s, 1 H), 3.54-3.42 (m, 1 H), 3.23-2.96 (m, 9 H), 2.79 (s, 3 H), 2.69-2.59 (m, 1 H), 2.28-2.22 (m, 1 H), 1.97-1.92 (m, 1 H), 1.71-1.60 (m, 2 H), 1.45-1.43 (m, 3 H), 1.10-1.03 (m, 3 H); MS (ESI) m/z 582.0 (M+H).

S25-11-42

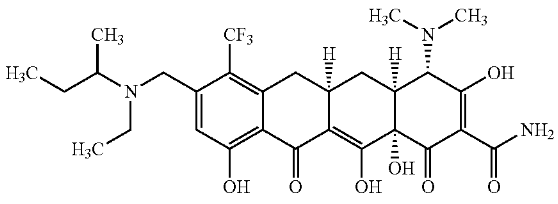

S25-11-42: [1] H NMR (400 MHz, $CD_3OD$) δ 7.27, 7.25, 7.24 (s, 1 H total), 4.75-4.63 (m, 1 H), 4.51-4.28 (m, 1 H), 4.14 (s, 1 H), 3.61-3.42 (m, 2 H), 3.28-2.96 (m, 10 H), 2.67-2.58 (m, 1 H), 2.27-2.23 (m, 1 H), 1.97-1.88 (m, 1 H), 1.81-1.60 (m, 2 H), 1.50-1.35 (m, 3 H), 1.33-1.26 (m, 3 H), 1.08-1.00 (m, 3 H); MS (ESI) m/z 596.0 (M+H).

S25-11-43

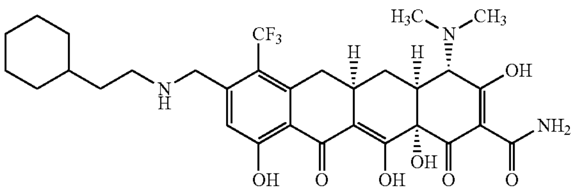

S25-11-43: [1] H NMR (400 MHz, $CD_3OD$) δ 7.07 (s, 1 H), 4.39-4.32 (m, 1 H), 4.24-4.20 (m, 1 H), 4.04 (s, 1 H), 3.11-2.78 (m, 11 H), 2.58-2.48 (m, 1 H), 2.16-2.08 (m, 1 H), 1.68-1.50 (m, 8 H), 1.35-1.08 (m, 4 H), 0.98-0.81 (m, 2 H); MS (ESI) m/z 622.3 (M+H).

S25-11-44

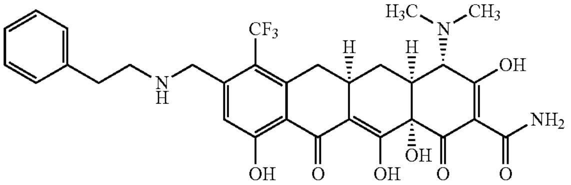

S25-11-44: [1] H NMR (400 MHz, $CD_3OD$) δ 7.48-7.21 (m, 5 H), 7.13 (s, 1 H), 4.53-4.45 (m, 1 H), 4.37-4.30 (m, 1 H), 4.12 (s, 1 H), 3.46-3.36 (m, 2 H), 3.19-2.89 (m, 11 H), 2.71-2.56 (m, 1 H), 2.24-2.17 (m, 1 H), 1.73-1.57 (m, 1 H); MS (ESI) m/z 616.2 (M+H).

S25-11-45

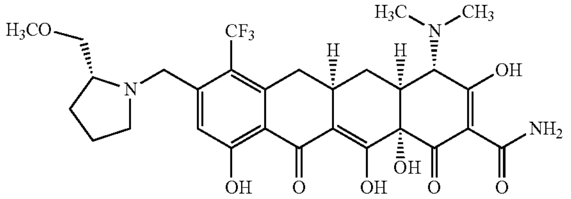

S25-11-45: [1] H NMR (400 MHz, $CD_3OD$) δ 7.23 (s, 1 H), 4.42 (d, J=13.6 Hz, 2 H), 4.13 (s, 1 H), 3.92-3.81 (m, 2 H), 3.68-3.59 (m, 2 H), 3.58-3.46 (m, 1 H), 3.38 (s, 3 H), 3.20-2.96 (m, 9 H), 2.65-2.54 (m, 1 H), 2.38-2.12 (m, 3 H), 2.09-1.93 (m, 2 H), 1.69-1.59 (m, 1 H); MS (ESI) m/z 610.2 (M+H).

S25-11-46

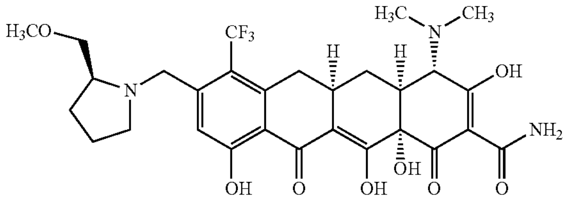

S25-11-46: [1] H NMR (400 MHz, $CD_3OD$) δ 7.14 (s, 1 H), 4.90 (d, J=13.2 Hz, 1 H), 4.20 (d, J=13.2 Hz, 1 H), 4.04 (s, 1 H), 3.88-3.78 (m, 1 H), 3.72-3.63 (m, 1 H), 3.61-3.56 (m, 1 H), 3.43-3.28 (m, 5 H), 3.19-2.82 (m, 9 H), 2.64-2.50 (m, 1 H), 2.24-2.06 (m, 3 H), 1.93-1.84 (m, 2 H), 1.56-1.50 (m, 1H); MS (ESI) m/z 610.0 (M+H).

S25-11-47

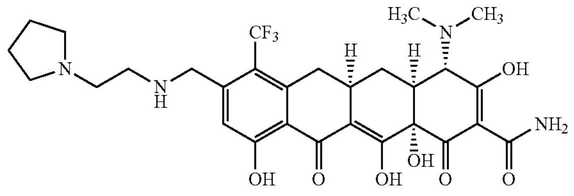

S25-11-47: [1] H NMR (400 MHz, $CD_3OD$) δ 7.28 (s, 1 H), 4.58-4.44 (m, 2 H), 4.12 (s, 1 H), 3.92-3.62 (m, 6 H), 3.24-2.95 (m, 11 H), 2.68-2.58 (m, 1 H), 2.29-1.98 (m, 5 H), 1.68-1.59 (m, 1 H); MS (ESI) m/z 609.0 (M+H).

S25-11-48

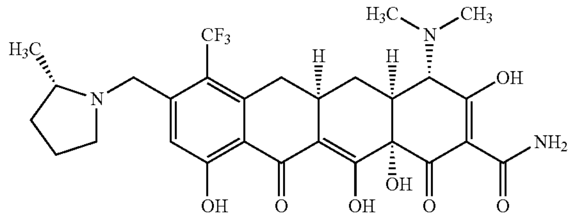

S25-11-48: [1] H NMR (400 MHz, $CD_3OD$) δ 7.23 (s, 1 H), 4.30 (d, J=14.0 Hz, 1 H), 4.11 (s, 1 H), 3.69-3.62 (m, 1 H), 3.53-3.41 (m, 1 H), 3.40-3.32 (m, 2 H), 3.22-2.88 (m, 9 H), 2.63-2.52 (m, 1 H), 2.42-2.32 (m, 1 H), 2.29-2.00 (m, 3 H), 1.82-1.77 (m, 1 H), 1.71-1.58(m, 1 H), 1.43 (d, J=6.4 Hz, 3 H); MS (ESI) m/z 579.9 (M+H).

S25-11-49

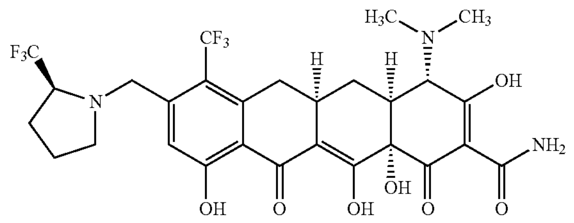

S25-11-49: [1] H NMR (400 MHz, $CD_3OD$) δ 7.40 (s, 1 H), 4.24 (d, J=13.6 Hz, 1 H), 4.09 (s, 1 H), 4.01 (d, J=14.0 Hz, 1 H), 3.59-3.43 (m, 1 H), 3.22-2.94 (m, 11 H), 2.61-2.54 (m, 1 H), 2.39-2.35 (m, 1 H), 2.20-2.13 (m, 2 H), 2.00-1.84 (m, 2 H), 1.67-1.57 (m, 1 H); MS (ESI) m/z 634.1 (M+H).

S25-11-50

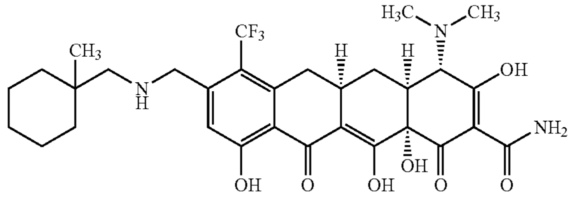

S25-11-50: [1] H NMR (400 MHz, $CD_3OD$) δ 7.16 (s, 1 H), 4.32-4.29 (m, 2 H), 4.05 (s, 1 H), 3.11-2.86 (m, 11 H), 2.60-2.52 (m, 1 H), 2.17-2.14 (m, 1 H), 1.59-1.23 (m, 11 H), 1.00 (s, 3 H); MS (ESI) m/z 622.3 (M+H).

S25-11-51

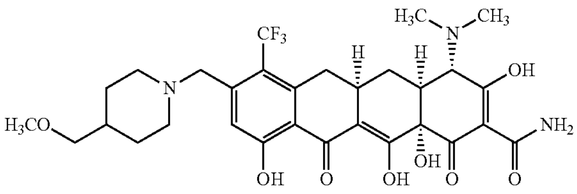

S25-11-51: [1] H NMR (400 MHz, $CD_3OD$) δ 7.18 (s, 1 H), 4.49 (d, J=14.0 Hz, 1 H), 4.31 (d, J=13.6 Hz, 1 H), 4.04 (s, 1 H), 3.54-3.47 (m, 2 H), 3.22 (s, 3 H), 3.12-2.86 (m, 13 H), 2.60-2.48 (m, 1 H), 2.16-2.13 (m, 1 H), 1.89-1.86 (m, 3 H), 1.56-1.46 (m, 3 H); MS (ESI) m/z 624.1 (M+H).

S25-11-52

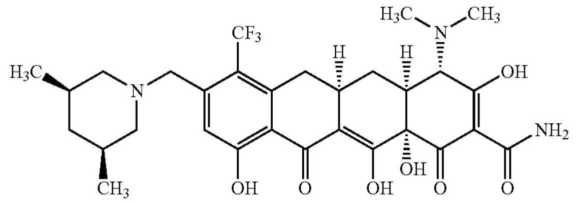

S25-11-52: [1] H NMR (400 MHz, $CD_3OD$) δ 7.30 (s,1 H), 4.60 (d, J=13.6 Hz, 1 H), 4.42 (d, J=14.0 Hz, 1 H), 4.14 (s, 1 H), 3.47-3.35 (m, 2 H), 3.26-2.97 (m, 9 H), 2.78-2.60 (m, 3 H), 2.27-2.23 (m, 1 H), 2.02-1.94 (m, 2 H), 1.89-1.82 (m, 1 H), 1.66 (ddd, J=13.6, 13.6, 13.6 Hz, 1 H), 1.02-1.88 (m, 7; MS (ESI) m/z 608.1 (M+H).

S25-11-53

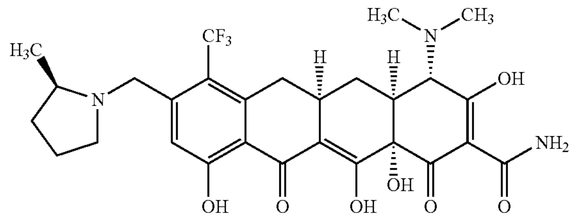

S25-11-53: [1] H NMR (400 MHz, $CD_3OD$) δ 7.12 (s, 1 H), 4.71 (d, J=13.2 Hz, 1 H), 4.07 (d, J=13.2 Hz, 1 H), 4.00 (s, 1 H), 3.57-3.51 (m, 1 H), 3.37-3.22 (m, 2 H), 3.08-2.78 (m, 9 H), 2.54-2.45 (m, 1 H), 2.29-2.24 (m, 1 H), 2.12-1.89 (m, 3 H), 1.69-1.61 (m, 1 H), 1.54-1.41 (m, 1 H), 1.38 (d, J=6.0 Hz, 3 H); MS (ESI) m/z 580.1 (M+H).

S25-11-54

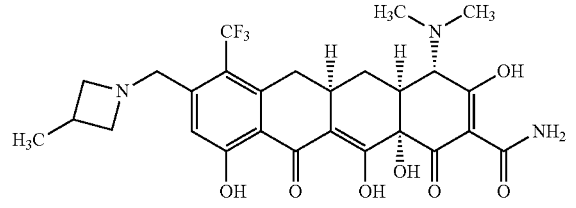

S25-11-54: [1] H NMR (400 MHz, $CD_3OD$) δ 7.05, 6.95, 6.87 (s, 1 H total), 4.58-4.41 (m, 1 H), 4.41-4.32 (m, 1 H), 4.21-4.14 (m, 2 H), 3.99 (s, 1 H), 3.93-3.72 (m, 2 H), 3.61-3.49 (m, 1 H), 2.91-2.81 (m, 9 H), 2.55-2.41 (m, 1 H), 2.12-2.08 (m, 1 H), 1.54-1.44 (m, 1 H), 1.22-1.04 (m, 3 H); MS (ESI) m/z 565.9 (M+H).

S25-11-55

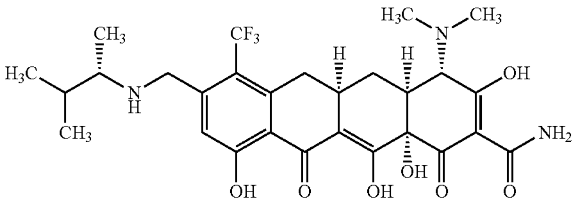

S25-11-55: $^{1}$H NMR (400 MHz, $CD_3OD$) δ 7.25 (s, 1 H), 4.38 (s, 2 H), 4.14 (s, 1 H), 3.37-3.34 (m, 1 H), 3.25-2.96 (m, 9 H), 2.66-2.58 (m, 1 H), 2.27-2.16 (m, 2 H), 1.69-1.59 (m, 1 H), 1.33 (d, J=6.8 Hz, 3 H), 1.07 (d, J=6.8 Hz, 3 H), 1.00 (d, J=6.8 Hz, 3 H); MS (ESI) m/z 582.1 (M+H).

S25-11-56

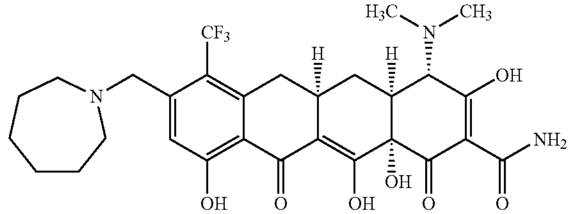

S25-11-56: $^{1}$H NMR (400 MHz, $CD_3OD$) δ 7.28 (s, 1 H), 4.59 (d, J=14.4 Hz, 1 H), 4.48 (d, J=14.0 H, 1 H), 4.12 (s, 1 H), 3.58-3.53 (m, 1 H), 3.46-3.41 (m, 1 H), 3.35-3.33 (m, 1 H), 3.28-2.94 (m, 10 H), 2.60-2.54 (m, 1 H), 2.25-2.20 (m, 1 H), 2.01-1.83 (m, 4 H), 1.74 (s, 4 H), 1.68-1.53 (m, 1 H); MS (ESI) m/z 594.0 (M+H).

S25-11-57

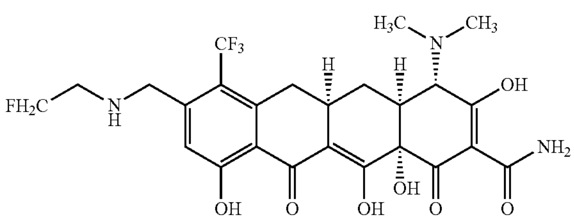

S25-11-57: $^{1}$H NMR (400 MHz, $CD_3OD$) δ 7.19 (s, 1 H), 4.98 (t, J=8.8 Hz, 1 H), 4.75 (t, J=8.8 Hz, 1 H), 4.52-4.51 (m, 1 H), 4.41-4.37 (m, 1 H), 4.13 (s, 1 H), 3.55 (dt, J=31.6, 9.2 Hz, 2 H), 3.21-3.08 (m, 9 H), 2.64-2.55 (m, 1 H), 2.25-2.21 (m, 1 H), 1.67-1.57 (m, 1 H); MS (ESI) m/z 558.1 (M+H).

S25-11-58

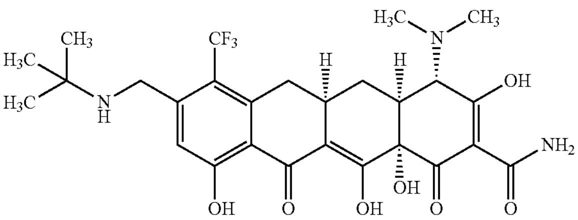

S25-11-58: $^{1}$H NMR (400 MHz, $CD_3OD$) δ 7.24 (s, 1 H), 4.42-4.38 (m, 1 H), 4.27-4.21 (m, 1 H), 4.13 (s, 1 H), 3.23-2.92 (m, 9 H), 2.62-2.58 (m, 1 H), 2.27-2.22 (m, 1 H), 1.69-1.62 (m, 1 H), 1.47 (s, 9 H); MS (ESI) m/z 568.0 (M+H).

S25-11-59

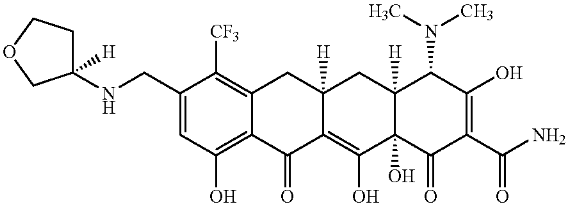

S25-11-59: $^{1}$H NMR (400 MHz, $CD_3OD$) δ 7.21 (s, 1 H), 4.48-4.47 (m, 1 H), 4.44-4.37 (m, 1 H), 4.13 (s, 1 H), 4.13-4.07 (m, 3 H), 3.90-3.85 (m, 1 H), 3.76-3.73 (m, 1 H), 3.25-2.96 (m, 9 H), 2.70-2.60 (m, 1 H), 2.49-2.44 (m, 1 H), 2.27-2.22 (m, 1 H), 2.14-2.11 (m, 1 H), 1.69-1.61 (m, 1 H); MS (ESI) m/z 582.1 (M+H).

S25-11-60

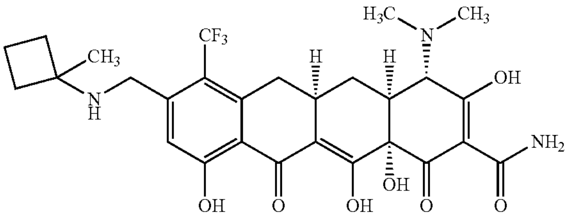

S25-11-60: $^{1}$H NMR (400 MHz, $CD_3OD$) δ 7.19 (s, 1 H), 4.27 (d, J=13.6 Hz, 1 H), 4.16 (d, J=14.8 Hz, 1 H), 4.12 (s, 1 H), 3.24-2.94 (m, 9 H), 2.67-2.56 (m, 1 H), 2.46-2.44 (m, 2 H), 2.24-2.22 (m, 1 H), 2.10-1.97 (m, 4 H), 1.67-1.62 (m, 4 H); MS (ESI) m/z 579.9 (M+H).

S25-11-61

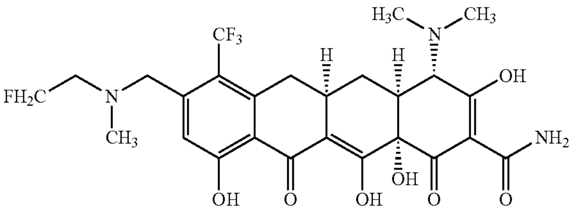

S25-11-61: $^{1}$H NMR (400 MHz, $CD_3OD$) δ 7.22 (s, 1 H), 4.95-4.94 (m, 1 H), 4.82-4.76 (m, 1 H), 4.11 (s, 1 H), 3.69 (dt,

J=30.8, 8.8 Hz, 2 H), 3.20-2.94 (m, 14 H), 2.67-2.57 (m, 1 H), 2.24-2.21 (m, 1 H), 1.67-1.58 (m, 1 H); MS (ESI) m/z 572.0 (M+H).

S25-11-62

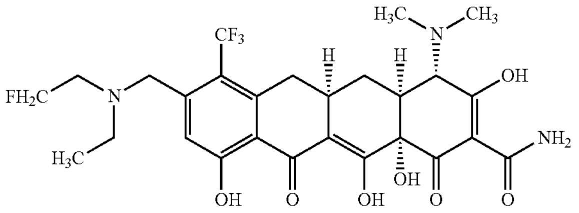

S25-11-62: [1] H NMR (400 MHz, $CD_3OD$) δ 7.22 (s, 1 H), 4.70 (d, J=13.6 Hz, 1 H), 4.55 (d, J=13.6 Hz, 1 H), 4.11 (s, 1 H), 3.68-3.63 (m, 2 H), 3.48-3.41 (m, 2 H), 3.20-2.94 (m, 11 H), 2.66-2.58 (m, 1 H), 2.24-2.21 (m, 1 H), 1.69-1.59 (m, 1 H), 1.40 (t, J=7.2 Hz, 3 H); MS (ESI) m/z 586.0 (M+H).

S25-11-63

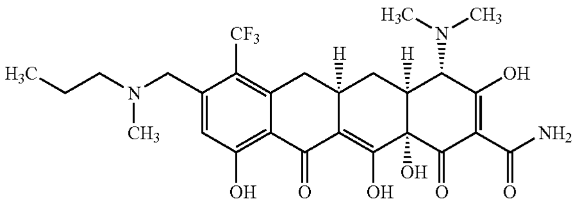

S25-11-63: [1] H NMR (400 MHz, $CD_3OD$) δ 7.24 (s, 1 H), 4.72-4.65 (m, 1 H), 4.44-4.27 (m, 1 H), 4.13 (s, 1 H), 3.03-2.94 (m, 11 H), 2.85 (d, J=13.6 Hz, 3 H), 2.60-2.57 (m, 1 H), 2.25-2.22 (m, 1 H), 1.84-1.81 (m, 2 H), 1.67-1.57 (m, 1 H), 1.02-1.00 (t, J=7.2 Hz, 3 H); MS (ESI) m/z 568.0 (M+H).

S25-11-64

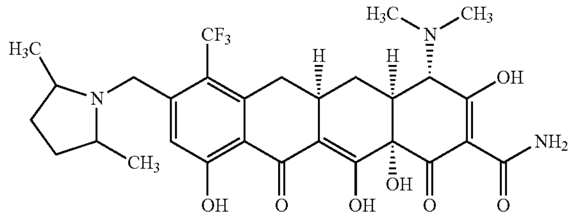

S25-11-64: [1] H NMR (400 MHz, $CD_3OD$) δ 7.34 (s, 1 H), 4.72 (d, J=13.6 Hz, 1 H), 4.59 (d, J=14.0 Hz, 1 H), 4.15 (s, 1 H), 3.85-3.79 (m, 2 H), 3.04-2.95 (m, 9 H), 2.63-2.61 (m, 1 H), 2.35-2.23 (m, 3 H), 1.84-1.81 (m, 2 H), 1.66-1.64 (m, 1 H), 1.36 (d, J=6.4 Hz, 3 H), 1.22 (d, J=6.8 Hz, 3 H); MS (ESI) m/z 594.1 (M+H).

S25-11-65

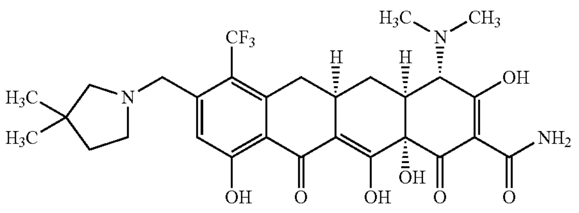

S25-11-65: [1] H NMR (400 MHz, $CD_3OD$) δ 7.28 (s, 1 H), 4.73-4.70 (m, 1 H), 4.58-4.48 (m, 1 H), 4.14 (s, 1 H), 3.79-3.66 (m, 1 H), 3.53-3.50 (m, 1 H), 3.21-2.96 (m, 11 H), 2.69-2.58 (m, 1 H), 2.28-2.23 (m, 1 H), 2.05-1.95 (m, 2 H), 1.66-1.62 (m, 1 H), 1.28, 1.22 (s, 6 H total); MS (ESI) m/z 594.0 (M+H).

S25-11-66

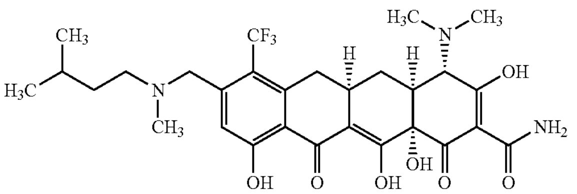

S25-11-66: [1] H NMR (400 MHz, $CD_3OD$) δ 7.23 (s, 1 H), 4.75-4.68 (m, 1 H), 4.44-4.41 (m, 1 H), 4.30-4.27 (m, 1 H), 4.13 (s, 1 H), 3.08-2.95 (m, 11 H), 2.87 (d, J=14.0 Hz, 1 H), 2.68-2.58 (m, 1 H), 2.26-2.23 (m, 1 H), 1.69-1.66 (m, 4 H), 1.00 (d, J=5.2 Hz, 6 H); MS (ESI) m/z 596.0 (M+H).

S25-11-67

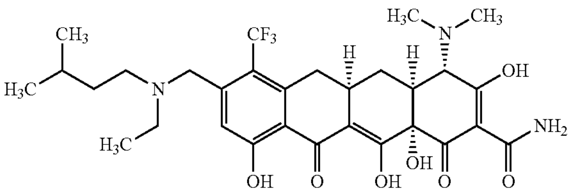

S25-11-67: [1] H NMR (400 MHz, $CD_3OD$) δ 7.22 (s, 1 H), 4.64-4.60 (m, 1 H), 4.52-4.48 (m, 1 H), 4.13 (s, 1 H), 3.41-3.35 (m, 2 H), 3.19-2.96 (m, 11 H), 2.64-2.52 (m, 1 H), 2.27-2.23 (m, 1 H), 1.66-1.63 (m, 4 H), 1.41-1.33 (m, 3 H), 0.97 (d, J=5.2 Hz, 6 H); MS (ESI) m/z 610.0 (M+H).

S25-11-68

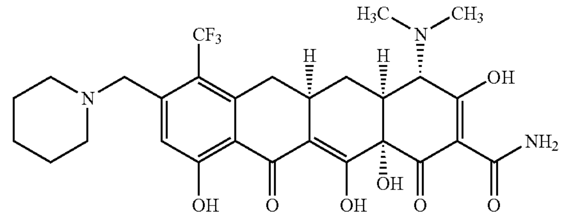

S25-11-68: [1] H NMR (400 MHz, $CD_3OD$) δ 7.35 (s, 1 H), 4.58-4.55 (m, 1 H), 4.45-4.42 (m, 1 H), 4.18 (s, 1 H), 3.59-3.49 (m, 2 H), 3.28-2.97 (m, 11 H), 2.63-2.55 (m, 1 H), 2.29-2.26 (m, 1 H), 1.94-1.82 (m, 5 H), 1.66-1.58 (m, 2 H); MS (ESI) m/z 580.0 (M+H).

S25-11-69

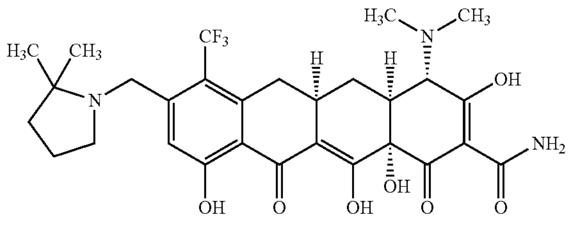

S25-11-69: [1] H NMR (400 MHz, $CD_3OD$) δ 7.27 (s, 1 H), 4.82-4.76 (m, 1 H), 4.14 (s, 1 H), 4.05-4.02 (m, 1 H), 3.60-3.47 (m, 2 H), 3.11-2.95 (m, 9 H), 2.60-2.55 (m, 1 H), 2.22-1.95 (m, 5 H), 1.71-1.62 (m, 1 H), 1.63 (s, 3 H), 1.42 (s, 3 H); MS (ESI) m/z 594.0 (M+H).

S25-11-70

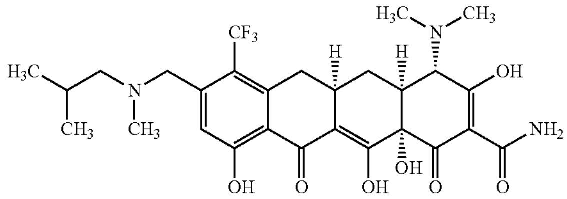

S25-11-70: [1] H NMR (400 MHz, $CD_3OD$) δ 7.24 (s, 1 H), 4.80-4.77 (m, 1 H), 4.44-4.25 (m, 1 H), 4.14 (s, 1 H), 3.19-2.96 (m, 11 H), 2.90 (d, J=7.6 Hz, 3 H), 2.64-2.60 (m, 1 H), 2.27-2.22 (m, 2 H), 1.69-1.60 (m, 1 H), 1.09-1.01 (m, 6 H); MS (ESI) m/z 582.0 (M+H).

S25-11-71

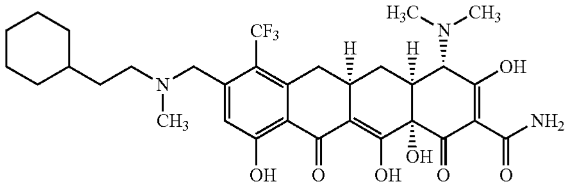

S25-11-71: [1] H NMR (400 MHz, $CD_3OD$) δ 7.24 (s, 1 H), 4.75-4.67 (m, 2 H), 4.45-4.42 (m, 1 H), 4.31-4.27 (m, 1 H), 4.14 (s, 1 H), 3.18-2.96 (m, 9 H), 2.87 (d, J=15.2 Hz, 3 H), 2.63-2.60 (m, 1 H), 2.27-2.23 (m, 1 H), 1.78-1.62 (m, 8 H), 1.31-1.25 (m, 4 H), 1.04-1.02 (m, 2 H); MS (ESI) m/z 636.1 (M+H).

S25-11-72

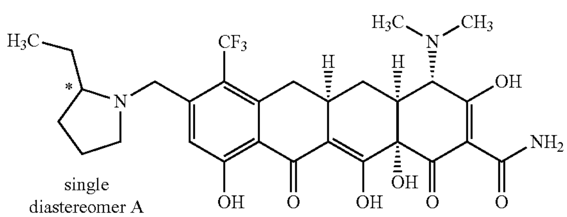

single diastereomer A

S25-11-72: [1] H NMR (400 MHz, $CD_3OD$) δ 7.26 (s, 1 H), 4.24-4.20 (m, 1 H), 4.13 (s, 1 H), 3.53-3.43 (m, 4 H), 3.09-2.95 (m, 9 H), 2.69-2.62 (m, 1 H), 2.48-2.41 (m, 1 H), 2.31-2.02 (m, 4 H), 1.88-1.79 (m, 1 H), 1.69-1.52 (m, 2 H), 1.06 (t, J=7.2 Hz, 3 H); MS (ESI) m/z 594.1 (M+H).

S25-11-73

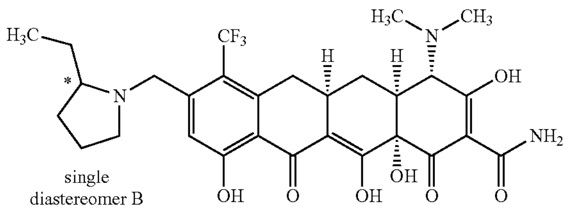

single diastereomer B

S25-11-73: [1] H NMR (400 MHz, $CD_3OD$) δ 7.25 (s, 1 H), 4.75-4.72 (m, 1 H), 4.36-4.33 (m, 1 H), 4.12 (s, 1 H), 3.52-3.48 (m, 3 H), 3.09-2.95 (m, 9 H), 2.63-2.59 (m, 1 H), 2.48-2.41 (m, 1 H), 2.25-2.16 (m, 2 H), 2.05-1.95 (m, 2 H), 1.88-1.79 (m, 1 H), 1.66-1.60 (m, 2 H), 1.02 (t, J=7.2 Hz, 3 H); MS (ESI) m/z 594.0 (M+H).

S25-11-74

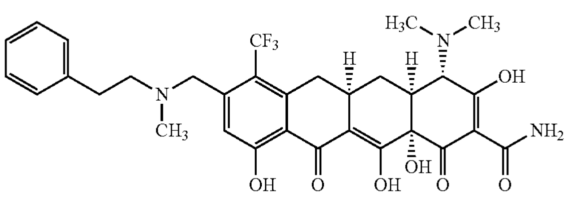

S25-11-74: [1] H NMR (400 MHz, $CD_3OD$) δ 7.33-7.25 (m, 6 H), 4.74-4.71 (m, 1 H), 4.52-4.35 (m, 1 H), 4.12 (s, 1 H), 3.52-3.48 (m, 2 H), 3.14-2.92 (m, 14 H), 2.67-2.61 (m, 1 H), 2.25-2.21 (m, 1 H), 1.67-1.58 (m, 1 H); MS (ESI) m/z 630.1 (M+H).

S25-11-75

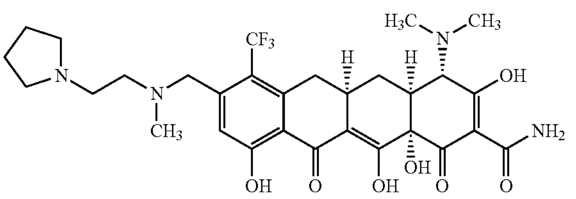

S25-11-75: [1] H NMR (400 MHz, $CD_3OD$) δ 7.39 (s, 1 H), 4.56-4.45 (m, 2 H), 4.12 (s, 1 H), 3.74-3.60 (m, 6 H), 3.04-2.95 (m, 11 H), 2.81 (s, 3 H), 2.61-2.57 (m, 1 H), 2.23-2.20 (m, 1 H), 2.12-2.02 (m, 4 H), 1.68-1.59 (m, 1 H); MS (ESI) m/z 623.1 (M+H).

S25-11-76

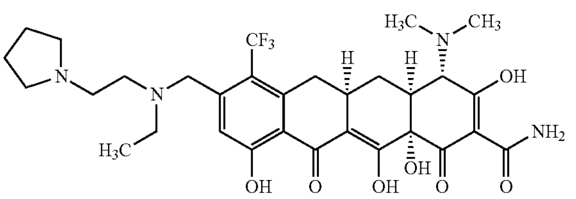

S25-11-76: [1] H NMR (400 MHz, $CD_3OD$) δ 7.41 (s, 1 H), 4.59-4.48 (m, 2 H), 4.12 (s, 1 H), 3.74-3.58 (m, 6 H), 3.20-

2.95 (m, 13 H), 2.61-2.57 (m, 1 H), 2.24-2.11 (m, 5 H), 1.68-1.58 (m, 1 H), 1.35 (t, J=7.2 Hz, 3 H); MS (ESI) m/z 637.1 (M+H).

S25-11-77

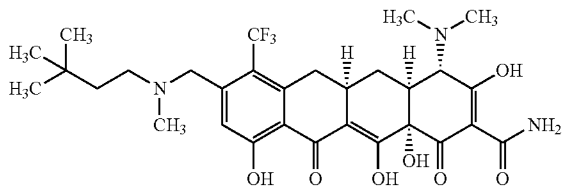

S25-11-77: $^1$H NMR (400 MHz, $CD_3OD$) δ 7.23 (s, 1 H), 4.80-4.69 (m, 1 H), 4.43-4.26 (m, 1 H), 4.13 (s, 1 H), 3.41-3.35 (m, 2 H), 3.03-2.94 (m, 9 H), 2.85 (d, J=14.8 Hz, 3 H), 2.61-2.57 (m, 1 H), 2.25-2.21 (m, 1 H), 1.74-1.61 (m, 3 H), 0.99, 0.97 (s, 9 H total); MS (ESI) m/z 610.1 (M+H).

S25-11-78

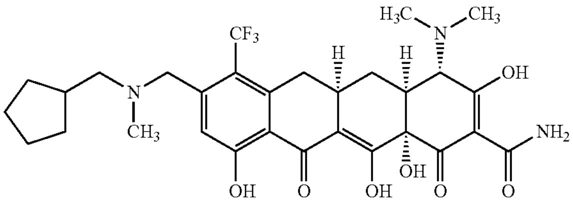

S25-11-78: $^1$H NMR (400 MHz, $CD_3OD$) δ 7.25 (s, 1 H), 4.78-4.74 (m, 1 H), 4.44-4.26 (m, 1 H), 4.14 (s, 1 H), 3.30-2.96 (m, 11 H), 2.90 (d, J=9.6 Hz, 3 H) 2.63-2.59 (m, 1 H), 2.40-2.37 (m, 1 H), 2.27-2.23 (m, 1 H), 1.97-1.91 (m, 2 H), 1.73-1.63 (m, 5 H), 1.33-1.27 (m, 2 H); MS (ESI) m/z 608.2 (M+H).

S25-11-79

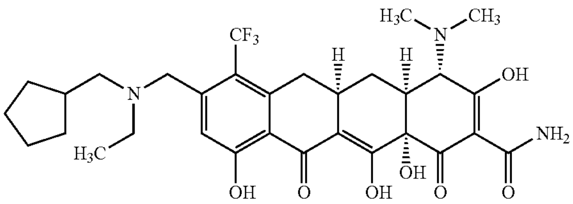

S25-11-79: $^1$H NMR (400 MHz, $CD_3OD$) δ 7.24, 7.21 (s, 1 H total), 4.69-4.42 (m, 2 H), 4.13 (s, 1 H), 3.09-2.96 (m, 13 H), 2.65-2.58 (m, 1 H), 2.31-2.22 (m, 2 H), 1.68-1.52 (m, 7 H), 1.40 (t, J=7.2 Hz, 3 H), 1.28-1.21 (m, 2 H); MS (ESI) m/z 622.4 (M+H).

S25-11-80

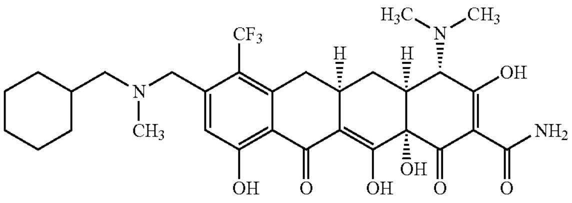

S25-11-80: $^1$H NMR (400 MHz, $CD_3OD$) δ 7.16, 7.14 (s, 1 H total), 4.69-4.66 (m, 1 H), 4.35-4.17 (m, 1 H), 4.05 (s, 1 H), 3.20-2.87 (m, 11 H), 2.80 (d, J=11.2 Hz, 3 H), 2.56-2.49 (m, 1 H), 2.17-2.14 (m, 1 H), 1.78-1.56 (m, 7 H), 1.27-1.00 (m, 3 H), 0.97-0.92 (m, 2 H); MS (ESI) m/z 622.0 (M+H).

S25-11-81

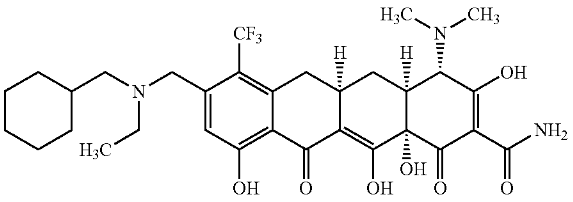

S25-11-81: $^1$H NMR (400 MHz, $CD_3OD$) δ 7.23, 7.19 (s, 1 H total), 4.65-4.40 (m, 2 H), 4.11 (s, 1 H), 3.10-2.86 (m, 13 H), 2.67-2.64 (m, 1 H), 2.24-2.21 (m, 1 H), 1.82-1.64 (m, 7 H), 1.39-1.18 (m, 6 H), 1.01-0.98 (m, 2 H); MS (ESI) m/z 636.1 (M+H).

S25-11-82

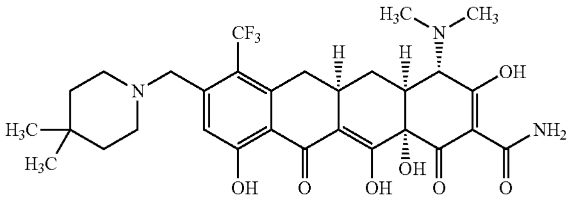

S25-11-82: $^1$H NMR (400 MHz, $CD_3OD$) δ 7.26 (s, 1 H), 4.58 (d, J=14.4 Hz, 1 H), 4.45 (d, J=14.4 Hz, 1 H), 4.13 (s, 1 H), 3.47-3.41 (m, 2 H), 3.12-2.95 (m, 11 H), 2.69-2.58 (m, 1 H), 2.26-2.22 (m, 1 H), 1.78-1.62 (m, 5 H), 1.12 (s, 3 H), 1.04 (s, 3 H); MS (ESI) m/z 608.3 (M+H).

S25-11-83

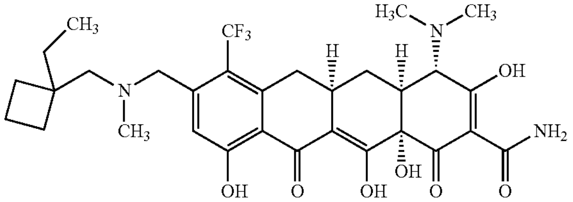

S25-11-83: $^1$H NMR (400 MHz, $CD_3OD$) δ 7.35, 7.26 (s, 1 H total), 4.70-4.67 (m, 1 H), 4.54-4.34 (m, 1 H), 4.15 (s, 1 H), 3.42-3.38 (m, 1 H), 3.21-2.86 (m, 13 H), 2.69-2.63 (m, 1 H), 2.24-2.17 (m, 2 H), 2.02-1.69 (m, 8 H), 0.93, 0.84 (t, J=6.8 Hz, 3 H total); MS (ESI) m/z 622.4 (M+H).

S25-11-84

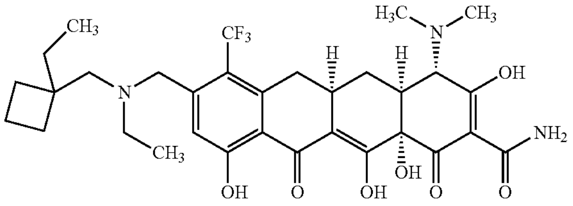

S25-11-84: $^1$H NMR (400 MHz, $CD_3OD$) δ 7.37, 7.36, 7.31, 7.30 (s, 1 H total), 4.65-4.50 (m, 2 H), 4.15 (s, 1 H), 3.48-3.38 (m, 2 H), 3.25-2.96 (m, 11 H), 2.68-2.53 (m, 1 H), 2.27-2.24 (m, 1 H), 2.05-1.63 (m, 8 H), 1.47-1.44 (m, 3 H), 0.91, 0.79 (t, J=7.2 Hz, 3 H total); MS (ESI) m/z 636.6 (M+H).

S25-11-85

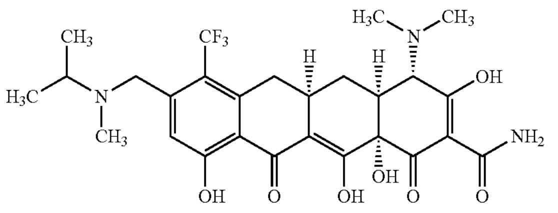

S25-11-85: [1] H NMR (400 MHz, $CD_3OD$) δ 7.23 (s, 1 H), 4.71-4.68 (m, 1 H), 4.31-4.22 (m, 1 H), 4.12 (s, 1 H), 3.81-3.73 (m, 1 H), 3.18-2.95 (m, 9 H), 2.77 (s, 3 H), 2.67-2.59 (m, 1 H), 2.25-2.21 (m, 1 H), 1.68-1.59 (m, 1 H), 1.42 (d, J=5.6 Hz, 6 H); MS (ESI) m/z 568.0 (M+H).

S25-11-86

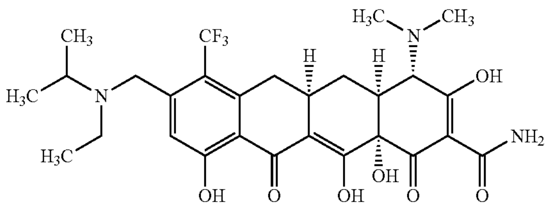

S25-11-86: [1] H NMR (400 MHz, $CD_3OD$) δ 7.26, 7.24 (s, 1 H total), 4.74-4.62 (m, 1 H), 4.48-4.28 (m, 1 H), 4.14 (s, 1 H), 3.88-3.72 (m, 1 H), 3.28-2.91 (m, 11 H), 2.62-2.59 (m, 1 H), 2.26-2.23 (m, 1 H), 1.66-1.63 (m, 1 H), 1.51-1.39 (m, 6 H), 1.33, 1.27 (t, J=7.2 Hz, 3 H total); MS (ESI) m/z 582.1 (M+H).

S25-11-87

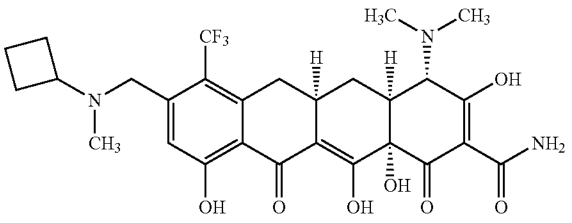

S25-11-87: [1] H NMR (400 MHz, $CD_3OD$) δ 7.26 (s, 1 H), 4.67-4.59 (m, 1 H), 4.31-4.28 (m, 0.5 H), 4.19-4.15 (m, 0.5 H), 4.14 (s, 1 H), 3.95-3.91 (m, 1 H), 3.18-2.96 (m, 9 H), 2.73 (d, J=7.2 Hz, 3 H), 2.69-2.59 (m, 1 H), 2.41-2.38 (m, 3 H), 2.27-2.24 (m, 2 H), 1.91-1.81 (m, 2 H), 1.69-1.59 (m, 1 H); MS (ESI) m/z 580.0 (M+H).

S25-11-88

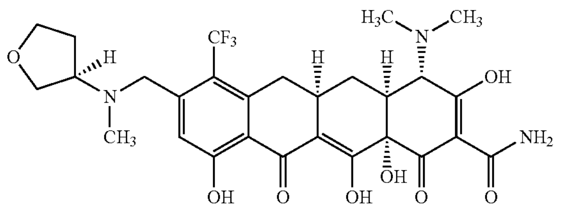

S25-11-88: [1] H NMR (400 MHz, $CD_3OD$) δ 7.29 (s, 1 H), 4.32-4.21 (m, 3 H), 4.18-4.16 (m, 1 H), 4.15 (s, 1 H), 3.83-3.72 (m, 2 H), 3.11-2.96 (m, 10 H), 2.82 (s, 3 H), 2.65-2.61 (m, 1 H), 2.46-2.35 (m, 2 H), 2.26-2.23 (m, 1 H), 1.69-1.63 (m, 1 H); MS (ESI) m/z 596.0 (M+H).

S25-11-89

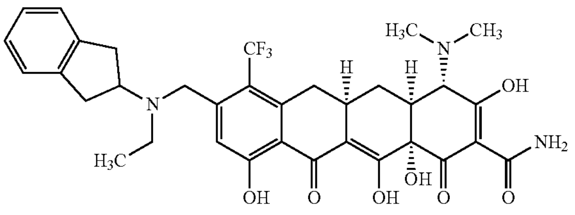

S25-11-89: [1] H NMR (400 MHz, $CD_3OD$) δ 7.30-7.22 (m, 5 H), 4.76-4.45 (m, 4 H), 4.14 (s, 1 H), 3.51-3.45 (m, 4 H), 3.19-2.96 (m, 10 H), 2.65-2.61 (m, 1 H), 2.26-2.23 (m, 1 H), 1.67-1.60 (m, 1 H), 1.40-1.35 (m, 3 H); MS (ESI) m/z 656.0 (M+H).

S25-11-90

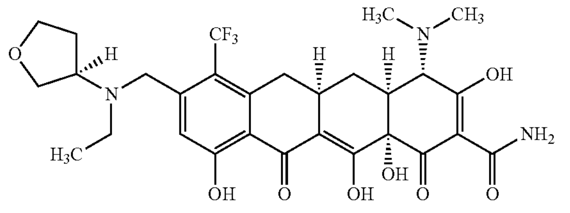

S25-11-90: [1] H NMR (400 MHz, $CD_3OD$) δ 7.22 (s, 1 H), 4.72-4.61 (m, 1 H), 4.51-4.42 (m, 1 H), 4.33-4.10 (m, 4 H), 3.90-3.60 (m, 3 H), 3.12-2.89 (m, 10 H), 2.69-2.58 (m, 1 H), 2.41-2.20 (m, 3 H), 1.65-1.62 (m, 1 H), 1.37-1.27 (m, 3 H); MS (ESI) m/z 610.2 (M+H).

S25-11-91

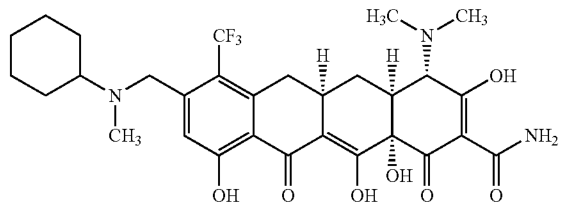

S25-11-91: [1] H NMR (400 MHz, $CD_3OD$) δ 7.24, 7.22 (s, 1 H total), 4.78-4.74 (m, 1 H), 4.31-4.20 (m, 1 H), 4.13 (s, 1 H), 3.47-3.37 (m, 1 H), 3.21-2.92 (m, 9 H), 2.79 (d, J=5.2 Hz, 3 H), 2.66-2.59 (m, 1 H), 2.25-2.22 (m, 1 H), 2.12-2.09 (m, 2 H), 2.01-1.92 (m, 2 H), 1.74-1.60 (m, 4 H), 1.46-1.40 (m, 2 H), 1.32-1.22 (m, 1 H); MS (ESI) m/z 608.3 (M+H).

S25-11-92

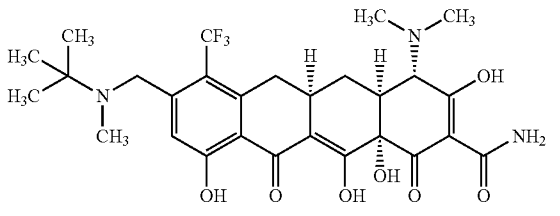

S25-11-92: [1] H NMR (400 MHz, $CD_3OD$) δ 7.25, 7.24 (s, 1 H total), 4.83-4.82 (m, 1 H), 4.22-4.10 (m, 1 H), 4.12 (s, 1

H), 3.20-2.90 (m, 9 H), 2.70 (d, J=10.8 Hz, 3 H), 2.65-2.57 (m, 1 H), 2.24-2.21 (m, 1 H), 1.67-1.61 (m, 1 H), 1.53 (s, 9 H); MS (ESI) m/z 582.1 (M+H).

S25-11-93

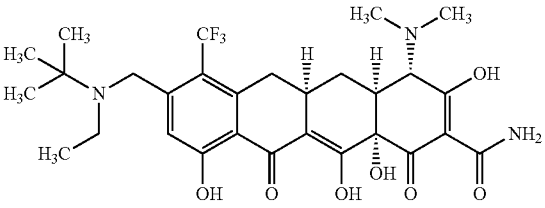

S25-11-93: [1] H NMR (400 MHz, $CD_3OD$) δ 7.35, 7.30 (s, 1 H total), 4.76-4.73 (m, 1 H), 4.49-4.38 (m, 1 H), 4.11 (s, 1 H), 3.53-3.47 (m, 1 H), 3.18-2.91 (m, 10 H), 2.66-2.59 (m, 1 H), 2.23-2.20 (m, 1 H), 1.67-1.61 (m, 1 H), 1.56, 1.53 (s, 9 H total), 1.13, 1.03 (t, J=7.2 Hz, 3 H total); MS (ESI) m/z 596.1 (M+H).

S25-11-94

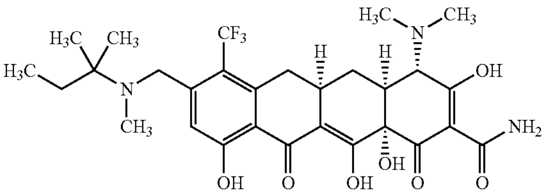

S25-11-94: [1] H NMR (400 MHz, $CD_3OD$) δ 7.23, 7.22 (s, 1 H total), 4.82-4.73 (m, 1 H), 4.26-4.14 (m, 1 H), 4.11 (s, 1 H), 3.22-2.92 (m, 9 H), 2.71, 2.68 (s, 3 H total), 2.65-2.58 (m, 1 H), 2.24-2.21 (m, 1 H), 1.95-1.87 (m, 2 H), 1.67-1.58 (m, 1 H), 1.50, 1.48 (s, 6 H total), 1.06 (t, J=7.2 Hz, 3 H); MS (ESI) m/z 596.0 (M+H).

S25-11-95

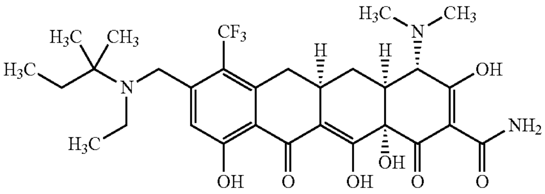

S25-11-95: [1] H NMR (400 MHz, $CD_3OD$) δ 7.37, 7.32 (s, 1 H total), 4.79-4.75 (m, 1 H), 4.52-4.41 (m, 1 H), 4.12 (s, 1 H), 3.58-3.52 (m, 1 H), 3.20-2.92 (m, 10 H), 2.68-2.60 (m, 1 H), 2.25-2.21 (m, 1 H), 1.96-1.90 (m, 2 H), 1.69-1.59 (m, 1 H), 1.53-1.50 (m, 6 H), 1.07-1.01 (m, 6 H); MS (ESI) m/z 610.1 (M+H).

S25-11-96

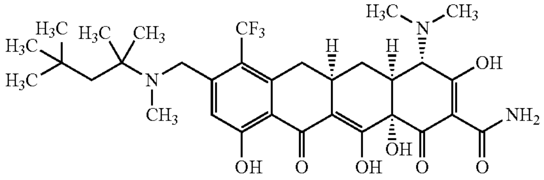

S25-11-96: [1] H NMR (400 MHz, $CD_3OD$) δ 7.26, 7.24 (s, 1 H total), 4.79-4.73 (m, 1 H), 4.26-4.15 (m, 1 H), 4.13 (s, 1

H), 3.21-2.92 (m, 9 H), 2.70, 2.68 (s, 3 H total), 2.70-2.58 (m, 1 H), 2.25-2.21 (m, 1 H), 1.96-1.93 (m, 1 H), 1.82-1.79 (m, 1 H), 1.67-1.63 (m, 7 H), 1.13 (s, 9 H); MS (ESI) m/z 638.1 (M+H).

S25-11-97

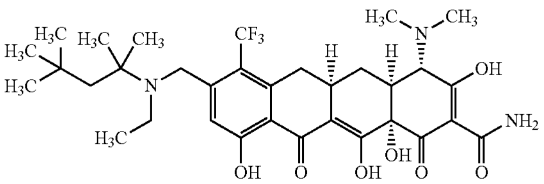

S25-11-97: [1] H NMR (400 MHz, $CD_3OD$) δ 7.40, 7.35 (s, 1 H total), 4.78-4.75 (m, 1 H), 4.52-4.41 (m, 1 H), 4.12 (s, 1 H), 3.63-3.55 (m, 1 H), 3.07-2.95 (m, 10 H), 2.67-2.60 (m, 1 H), 2.25-2.22 (m, 1 H), 1.94-1.86 (m, 2 H), 1.82-1.79 (m, 7 H), 1.13, 1.11 (s, 9 H total), 0.98 (t, J=7.2 Hz, 3 H); MS (ESI) m/z 652.1 (M+H).

S25-11-98

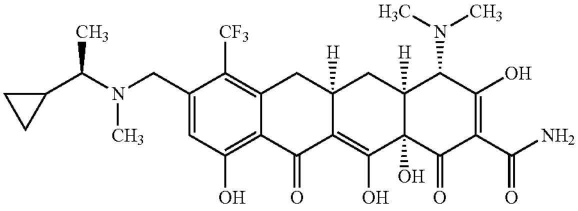

S25-11-98: [1] H NMR (400 MHz, $CD_3OD$) δ 7.28 (s, 1 H), 4.80-4.76 (m, 1 H), 4.41-4.30 (m, 1 H), 4.15 (s, 1 H), 3.21-2.95 (m, 10 H), 2.84, 2.89 (s, 3 H total), 2.67-2.58 (m, 1 H), 2.28-2.25 (m, 1 H), 1.69-1.60 (m, 1 H), 1.54-1.49 (m, 3 H), 1.23-1.20 (m, 1 H), 0.85-0.71 (m, 3 H), 0.52-0.41 (m, 1 H); MS (ESI) m/z 594.2 (M+H).

S25-11-99

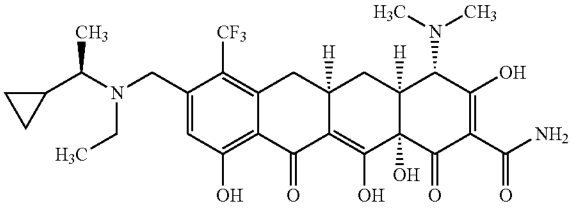

S25-11-99: [1] H NMR (400 MHz, $CD_3OD$) δ 7.27, 7.26 (s, 1 H total), 4.97-4.94 (m, 1 H), 4.80-4.44 (m, 1 H), 4.62-4.58 (m, 0.4 H), 4.32-4.29 (m, 0.6 H), 4.14 (s, 1 H), 3.21-2.92 (m, 11 H), 2.68-2.61 (m, 1 H), 2.27-2.23 (m, 1 H), 1.70-1.60 (m, 1 H), 1.51-1.47 (m, 3 H), 1.37, 1.24 (t, J=7.2 Hz, 3 H total), 1.35-1.31 (m, 1 H), 0.85-0.82 (m, 2 H), 0.64-0.39 (m, 2 H); MS (ESI) m/z 608.2 (M+H).

S25-11-100

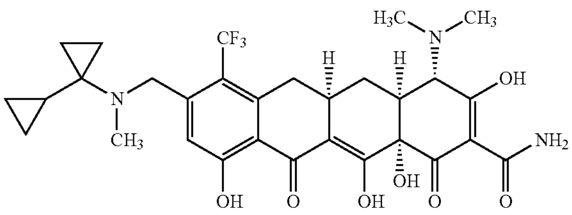

S25-11-100: [1] H NMR (400 MHz, $CD_3OD$) δ 7.30 (s, 1 H), 4.77-4.73 (m, 2 H), 4.13 (s, 1 H), 3.24-2.92 (m, 12 H), 2.65-2.57 (m, 1 H), 2.25-2.22 (m, 1 H), 1.64-1.61 (m, 2 H), 1.19-1.14 (m, 2 H), 0.92-0.81 (m, 2 H), 0.77-0.75 (m, 2 H), 0.40-0.32 (m, 2 H); MS (ESI) m/z 606.0 (M+H).

S25-11-101

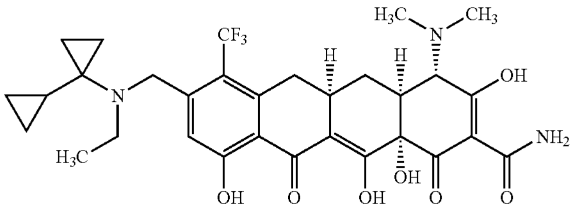

S25-11-101: [1] H NMR (400 MHz, $CD_3OD$) δ 7.30 (s, 1 H), 4.82-4.75 (m, 2 H), 4.12 (s, 1 H), 3.70-3.62 (m, 1 H), 3.21-2.92 (m, 10 H), 2.65-2.57 (m, 1 H), 2.24-2.21 (m, 1 H), 1.64-1.62 (m, 2 H), 1.41-1.37 (m, 4 H), 1.00-0.68 (m, 5 H), 0.51-0.24 (m, 2 H); MS (ESI) m/z 620.1 (M+H).

S25-11-102

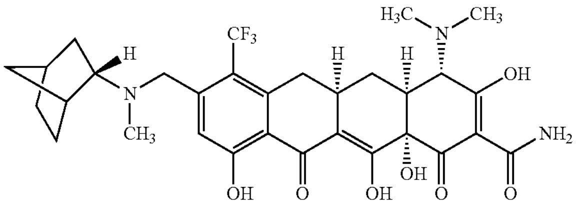

S25-11-102: [1] H NMR (400 MHz, $CD_3OD$) δ 7.26, 7.21 (s, 1 H total), 4.75-4.72 (m, 1 H), 4.34-4.28 (m, 1 H), 4.13 (s, 1 H), 3.71-3.62 (m, 1 H), 3.11-2.92 (m, 9 H), 2.85-2.78 (m, 3 H), 2.65-2.58 (m, 1 H), 2.39-2.35 (m, 1 H), 2.25-2.22 (m, 1 H), 2.18-2.12 (m, 1 H), 1.73-1.53 (m, 8 H), 1.43-1.28 (m, 1 H); MS (ESI) m/z 620.0 (M+H).

S25-11-103

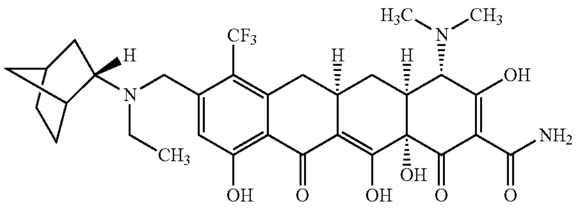

S25-11-103: [1] H NMR (400 MHz, $CD_3OD$) δ 7.30, 7.28, 7.25 (s, 1 H total), 4.79-4.75 (m, 1 H), 4.66-4.48 (m, 1 H), 4.13 (s, 1 H), 3.82-3.78 (m, 1 H), 3.22-2.92 (m, 11 H), 2.69-2.60 (m, 2 H), 2.40-2.38 (m, 1 H), 2.26-2.23 (m, 1 H), 2.13-2.07 (m, 1 H), 1.68-1.41 (m, 8 H), 1.29, 1.23 (t, J=7.2 Hz, 3 H total); MS (ESI) m/z 634.1 (M+H).

S25-11-104

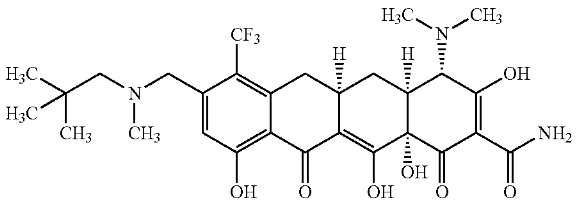

S25-11-104: [1] H NMR (400 MHz, $CD_3OD$) δ 7.37, 7.30 (s, 1 H total), 4.79-4.76 (m, 1 H), 4.60-4.42 (m, 1 H), 4.15 (s, 1 H), 3.29-2.98 (m, 14 H), 2.64-2.60 (m, 1 H), 2.28-2.25 (m, 1 H), 1.72-1.65 (m, 1 H), 1.15, 1.07 (s, 9 H total); MS (ESI) m/z 596.2 (M+H).

S25-11-105

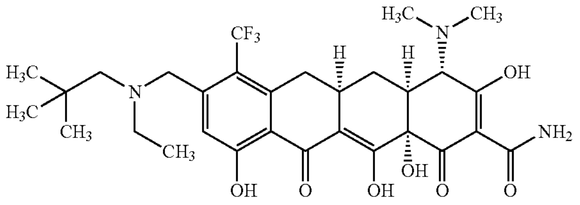

S25-11-105: [1] H NMR (400 MHz, $CD_3OD$) δ 7.38, 7.31 (s, 1 H total), 4.69-4.62 (m, 2 H), 4.14 (s, 1 H), 3.52-3.41 (m, 2 H), 3.28-2.88 (m, 11 H), 2.70-2.61 (m, 1 H), 2.28-2.24 (m, 1 H), 1.71-1.61 (m, 1 H), 1.51-1.44 (m, 3 H), 1.09, 0.99 (s, 9 H total); MS (ESI) m/z 610.0 (M+H).

S25-11-106

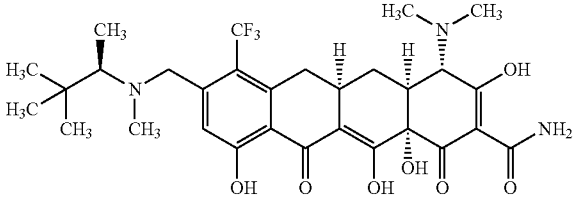

S25-11-106: [1] H NMR (400 MHz, $CD_3OD$) δ 7.42 (s, 1 H), 4.76-4.72 (m, 1 H), 4.57-4.53 (m, 1 H), 4.13 (s, 1 H), 3.20-2.92 (m, 13 H), 2.61-2.58 (m, 1 H), 2.26-2.23 (m, 1 H), 1.69-1.60 (m, 1 H), 1.39, 1.38 (s, 3 H total), 0.97 (s, 9 H); MS (ESI) m/z 610.0 (M+H).

S25-11-106

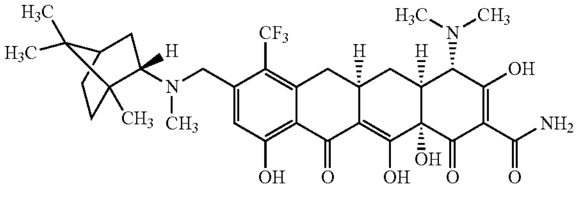

S25-11-106: [1] H NMR (400 MHz, $CD_3OD$) δ 7.29 (s, 1 H), 4.97-4.94 (m, 1 H), 4.43-4.28 (m, 1 H), 4.14 (s, 1 H), 3.94-3.63 (m, 1 H), 3.21-2.98 (m, 9 H), 2.85, 2.74 (s, 3 H total), 2.67-2.59 (m, 1 H), 2.50-2.42 (m, 1 H), 2.27-2.24 (m, 1 H), 1.94-1.93 (m, 1 H), 1.82-1.52 (m, 6 H), 1.25, 1.18 (s, 3 H total), 0.98-0.93 (m, 6 H); MS (ESI) m/z 662.0 (M+H).

S25-11-107

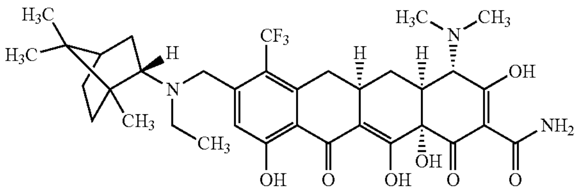

S25-11-107: $^1$H NMR (400 MHz, $CD_3OD$) δ 7.38 (s, 1 H), 4.95-4.92 (m, 1 H), 4.43-4.40 (m, 1 H), 4.14 (s, 1 H), 3.79-3.76 (m, 1 H), 3.21-2.91 (m, 11 H), 2.69-2.62 (m, 1 H), 2.47-2.41 (m, 1 H), 2.27-2.24 (m, 1 H), 1.82-1.58 (m, 6 H), 1.47-1.44 (m, 1 H), 1.26-1.21 (m, 6 H), 1.00-0.98 (m, 5 H), 0.93 (s, 1 H); MS (ESI) m/z 676.1 (M+H).

S25-11-108

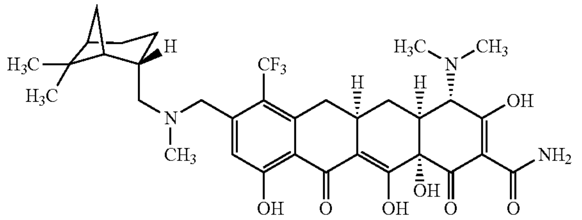

S25-11-108: $^1$H NMR (400 MHz, $CD_3OD$) δ 7.28, 7.25 (s, 1 H total), 4.76-4.72 (m, 1 H), 4.50-4.32 (m, 1 H), 4.14 (s, 1 H), 3.28-2.95 (m, 11 H), 2.91 (s, 3 H), 2.66-2.60 (m, 2 H), 2.46-2.44 (m, 1 H), 2.27-2.15 (m, 2 H), 2.02-1.94 (m, 5 H), 1.66-1.60 (m, 1 H), 1.22 (s, 3 H), 1.08-1.06 (m, 1 H), 0.94, 0.91 (s, 3 H total); MS (ESI) m/z 662.1 (M+H).

S25-11-109

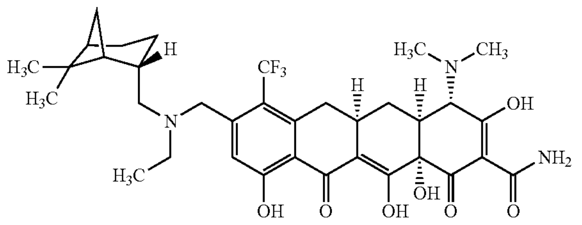

S25-11-109 $^1$H NMR (400 MHz, $CD_3OD$) δ 7.28, 7.26, 7.25 (s, 1 H total), 4.67-4.61 (m, 1 H), 4.57-4.50 (m, 1 H), 4.42-4.36 (m, 1 H), 4.14 (s, 1 H), 3.38-3.37 (m, 1 H), 3.28-2.88 (m, 11 H), 2.67-2.45 (m, 3 H), 2.28-2.05 (m, 2 H), 2.00-1.91 (m, 5 H), 1.67-1.61 (m, 1 H), 1.41 (t, J=5.6 Hz, 3 H), 1.26-1.17 (m, 3 H), 1.06-1.04 (m, 2 H), 0.88-0.83 (m, 2 H); MS (ESI) m/z 676.1 (M+H).

S25-11-110

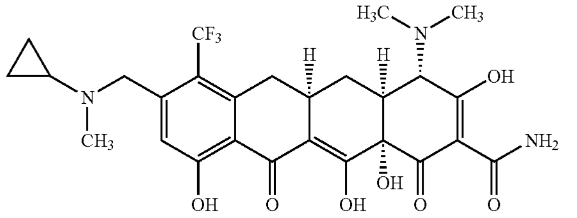

S25-11-110: $^1$H NMR (400 MHz, $CD_3OD$) δ 7.25 (s, 1 H), 4.72-4.58 (m, 2 H), 4.12 (s, 1 H), 3.05-2.96 (m, 13 H), 2.70-2.59 (m, 1 H), 2.25-2.22 (m,1 H), 1.70-1.61 (m, 1 H), 1.01-0.93 (m, 4 H); MS (ESI) m/z 566.0 (M+H).

S25-11-111

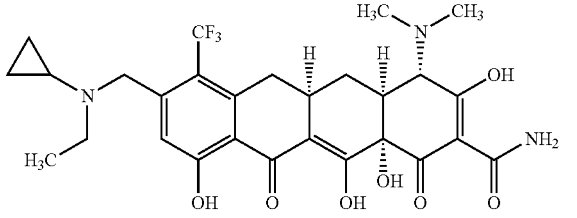

S25-11-111: $^1$H NMR (400 MHz, $CD_3OD$) δ 7.27 (s, 1 H), 4.72-4.64 (m, 2 H), 4.14 (s, 1 H), 3.50-3.44 (m, 1 H), 3.21-2.82 (m, 11 H), 2.62-2.59 (m,1 H), 2.26-2.23 (m, 1 H), 1.70-1.60 (m, 1 H), 1.51-1.43 (m, 3 H), 1.10-0.80 (m, 3 H), 0.70-0.32 (m, 1 H); MS (ESI) m/z 580.0 (M+H).

S25-11-112

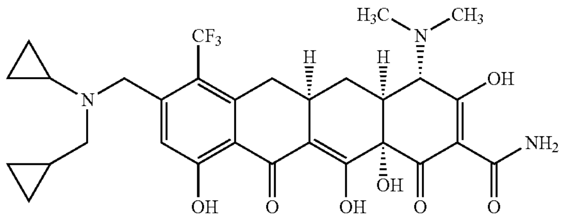

S25-11-112: $^1$H NMR (400 MHz, $CD_3OD$) δ 7.28 (s, 1 H), 4.76-4.67 (m, 2 H), 4.12 (s, 1 H), 3.45-3.39 (m, 1 H), 3.18-2.91(m, 11 H), 2.67-2.57 (m,1 H), 2.25-2.22 (m, 1 H), 1.68-1.58 (m, 1 H), 1.31-1.25 (m, 2 H), 1.08-0.92 (m, 1 H), 0.84-0.82 (m, 3 H), 0.52-0.47 (m, 3 H); MS (ESI) m/z 606.0 (M+H).

S25-11-113

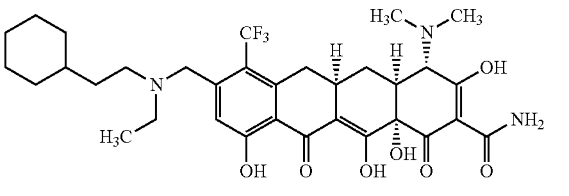

S25-11-113: $^1$H NMR (400 MHz, $CD_3OD$) δ 7.21 (s, 1 H), 4.63-4.59 (m, 1 H), 4.49-4.46 (m, 1 H), 4.12 (s, 1 H), 3.24-

2.92 (m, 13 H), 2.68-2.58 (m, 1 H), 2.25-2.22 (m,1 H), 1.74-1.63 (m, 8 H), 1.43-1.38 (m, 1 H), 1.36-1.24 (m, 6 H), 1.02-0.97 (m, 2 H); MS (ESI) m/z 650.2 (M+H).

S25-11-114

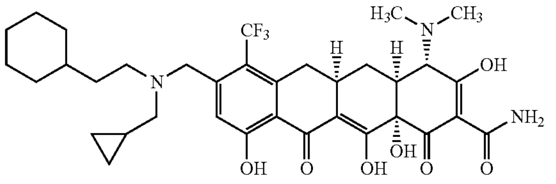

S25-11-114: $^1$H NMR (400 MHz, $CD_3OD$) δ 7.24 (s, 1 H), 4.82-4.58 (m, 2 H), 4.13 (s, 1 H), 3.28-2.92 (m, 13 H), 2.68-2.59 (m, 1 H), 2.26-2.23 (m, 1 H), 1.73-1.63 (m, 8 H), 1.28-1.17 (m, 5 H), 1.02-0.97 (m, 2 H), 0.81-0.77 (m, 2 H), 0.47-0.41 (m, 2 H); MS (ESI) m/z 676.2 (M+H).

S25-11-115

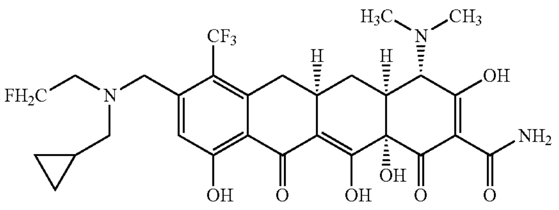

S25-11-115: $^1$H NMR (400 MHz, $CD_3OD$) δ 7.25 (s, 1 H), 4.97 (m, 1 H), 4.64 (m, 1 H), 4.68-4.62 (m, 1 H), 4.12 (s, 1 H), 3.85-3.58 (m, 1 H), 3.25-2.90 (m, 13 H), 2.64-2.57 (m, 1 H), 2.24-2.21 (m, 1 H), 1.68-1.58 (m, 1 H), 1.22-1.15 (m, 1 H), 0.81-0.79 (m, 2 H), 0.48-0.44 (m, 2 H); MS (ESI) m/z 612.1 (M+H).

S25-11-116

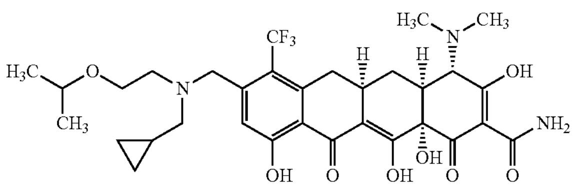

S25-11-116: $^1$H NMR (400 MHz, $CD_3OD$) δ 7.28, 7.24 (s, 1 H total), 4.78-4.74 (m, 1 H), 4.65-4.62 (m, 1 H), 4.08 (s, 1 H), 3.78-3.72 (m, 2 H), 3.66-3.63 (m, 1 H), 3.52-3.43 (m, 1 H), 3.20-2.82 (m, 12 H), 2.64-2.55 (m, 1 H), 2.20-2.17 (m, 1 H), 1.65-1.56 (m, 1 H), 1.17-1.16 (m, 7 H), 0.76-0.72 (m, 2 H), 1.43-0.39 (m, 2 H); MS (ESI) m/z 652.1 (M+H).

S25-11-117

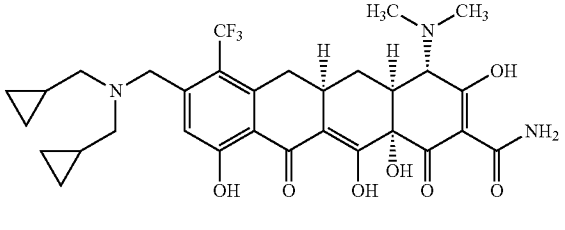

S25-11-117: $^1$H NMR (400 MHz, $CD_3OD$) δ 7.21 (s, 1 H), 4.81-4.77 (m, 1 H), 4.62-4.58 (m, 1 H), 4.10 (s, 1 H), 3.36-3.33 (m, 1 H), 3.22-2.91 (m, 12 H), 2.64-2.55 (m, 1 H), 2.21-2.18 (m,1 H), 1.65-1.55 (m, 1 H), 1.17-1.11 (m, 2 H), 0.76-0.73 (m, 4 H), 0.43-0.32 (m, 4 H); MS (ESI) m/z 620.0 (M+H).

S25-11-118

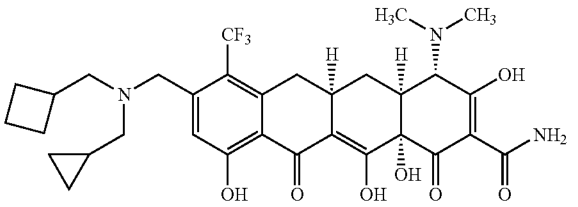

S25-11-118: $^1$H NMR (400 MHz, $CD_3OD$) δ 7.18 (s, 1 H), 4.75-4.72 (m, 0.5 H), 4.55 (m, 1 H), 4.46-4.42 (m, 0.5 H), 4.10 (s, 1 H), 3.42-3.40 (m, 1 H), 3.12-2.85 (m, 13 H), 2.65-2.55 (m, 1 H), 2.21-2.10 (m, 4 H), 1.99-1.97 (m, 1 H), 1.91-1.81 (m, 4 H), 1.65-1.56 (m, 1 H), 1.15-1.09 (m, 1 H), 0.77-0.73 (m, 2 H), 0.42-0.36 (m, 2 H); MS (ESI) m/z 634.0 (M+H).

S25-11-119

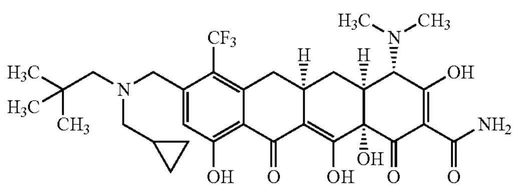

S25-11-119: $^1$H NMR (400 MHz, $CD_3OD$) δ 7.42, 7.38 (s, 1 H total), 4.82-4.71 (m, 2 H), 4.13 (s, 1 H), 3.48-3.38 (m, 2 H), 3.28-2.83 (m, 11 H), 2.68-2.60 (m, 1 H), 2.26-2.23 (m, 1 H), 1.69-1.60 (m, 1 H), 1.34-1.28 (m, 1 H), 1.05, 0.95 (s, 9 H total), 0.88-0.84 (m, 2 H), 0.53-0.48 (m, 2 H); MS (ESI) m/z 636.1 (M+H).

S25-11-120

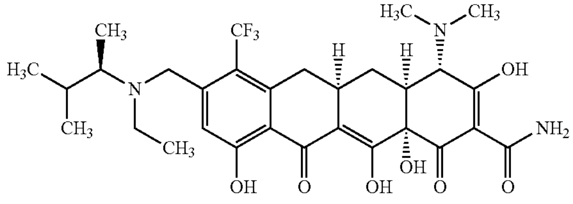

S25-11-120: $^1$H NMR (400 MHz, $CD_3OD$) δ 7.43, 7.31 (s, 1 H total), 4.89-4.82 (m, 0.5 H), 4.71-4.67 (m, 1 H), 4.32-4.29 (m, 0.5 H), 4.14 (s, 1 H), 3.50-3.47 (m, 2 H), 3.22-2.96 (m, 10 H), 2.67-2.64 (m, 1 H), 2.27-2.23 (m, 2 H), 1.66-1.60 (m, 1 H), 1.44-1.28 (m, 6 H), 1.15-0.99 (m, 6 H); MS (ESI) m/z 610.0 (M+H).

S25-11-121

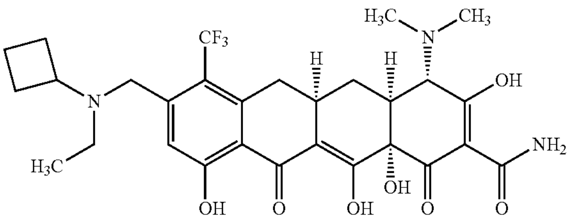

S25-11-121: $^1$H NMR (400 MHz, $CD_3OD$) δ 7.27 (s, 1 H), 4.62-4.38 (m, 2 H), 4.14 (s, 1 H), 4.01 (s, 1 H), 3.25-2.88 (m, 11 H), 2.69-2.57 (m, 1 H), 2.45-2.33 (m, 2 H), 2.27-2.05 (m, 2 H), 2.02-1.71 (m, 3 H), 1.69-1.58 (m, 1 H), 1.48-1.37 (m, 3 H); MS (ESI) m/z 594.2 (M+H).

S25-11-122

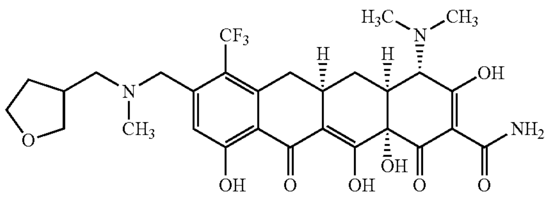

S25-11-122: $^1$H NMR (400 MHz, $CD_3OD$) δ 7.28 (s, 1 H), 4.82-4.75 (m, 1 H), 4.50-4.31 (m, 1 H), 4.15 (s, 1 H), 3.99-3.75 (m, 3 H), 3.52-3.35 (m, 3 H), 3.25-2.82 (m, 13 H), 2.69-2.63 (m, 1 H), 2.27-2.24 (m, 2 H), 1.70-1.60 (m, 2 H); MS (ESI) m/z 610.2 (M+H).

S25-11-123

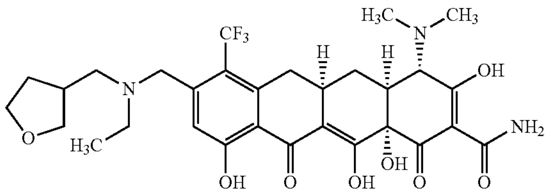

S25-11-123: $^1$H NMR (400 MHz, $CD_3OD$) δ 7.24 (s, 1 H), 4.73-4.49 (m, 2 H), 4.13 (s, 1 H), 3.95-3.75 (m, 3 H), 3.48-3.30 (m, 3 H), 3.25-2.70 (m, 12 H), 2.69-2.60 (m, 1 H), 2.26-2.23 (m, 2 H), 1.72-1.60 (m, 2 H), 1.40 (t, J=7.2 Hz, 3 H); MS (ESI) m/z 624.2 (M+H).

S25-11-124

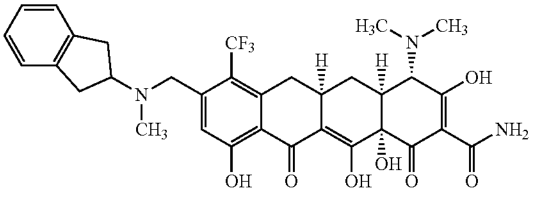

S25-11-124: $^1$H NMR (400 MHz, $CD_3OD$) δ 7.31-7.21 (m, 5 H), 4.40-4.36 (m, 2 H), 4.14 (s, 1 H), 3.60-3.33 (m, 5 H), 3.25-2.82 (m, 9 H), 2.79 (s, 3 H), 2.68-2.61 (m, 1 H), 2.26-2.23 (m, 1 H), 1.69-1.59 (m, 1 H); MS (ESI) m/z 642.1 (M+H).

S25-11-125

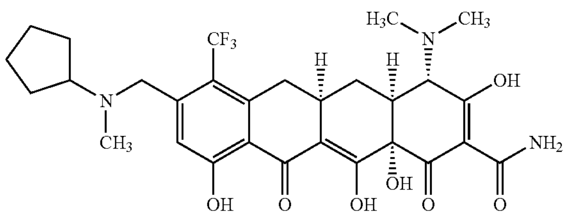

S25-11-125: $^1$H NMR (400 MHz, $CD_3OD$) δ 7.26 (s, 1 H), 4.81-4.71 (m, 1 H), 4.44-4.26 (m, 1 H), 4.15 (s, 1 H), 3.84-3.82 (m, 1 H), 3.21-2.87 (m, 9 H), 2.78 (s, 3 H), 2.69-2.55 (m, 1 H), 2.35-2.17 (m, 3 H), 1.95-1.73 (m, 4 H), 1.69-1.59 (m, 3 H); MS (ESI) m/z 594.1 (M+H).

S25-11-126

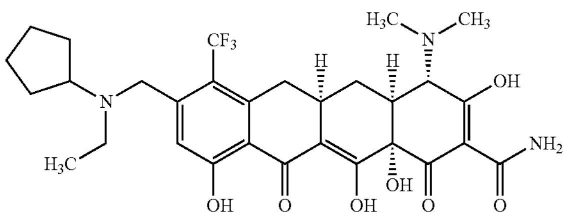

S25-11-126: $^1$H NMR (400 MHz, $CD_3OD$) δ 7.26, 7.24 (s, 1 H total), 4.75-4.71 (m, 0.6 H), 4.61-4.59 (m, 1 H), 4.52-4.48 (m, 0.5 H), 4.14 (s, 1 H), 3.89-3.82 (m, 1 H), 3.25-2.95 (m, 11 H), 2.65-2.62 (m, 1 H), 2.26-2.14 (m, 3 H), 1.95-1.84 (m, 4 H), 1.72-1.62 (m, 3 H), 1.35, 1.28 (t, J=7.2 Hz, 3 H total); MS (ESI) m/z 608.2 (M+H).

S25-11-127

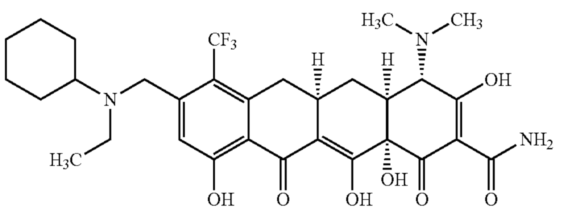

S25-11-127: $^1$H NMR (400 MHz, $CD_3OD$) δ 7.21, 7.20 (s, 1 H total), 4.80-4.68 (m, 1 H), 4.44-4.40 (m, 0.5 H), 4.28-4.25 (m, 0.5 H), 4.11 (s, 1 H), 3.59-3.42 (m, 2 H), 3.24-2.85 (m, 10 H), 2.67-2.56 (m, 1 H), 2.23-1.90 (m, 5 H), 1.83-1.58 (m, 4 H), 1.45-1.24 (m, 6 H); MS (ESI) m/z 622.3 (M+H).

S25-11-128

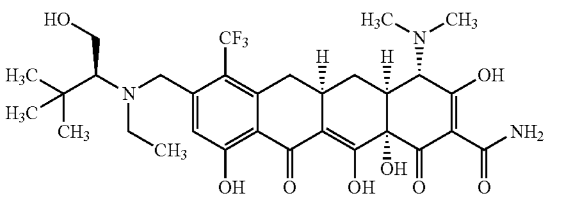

S25-11-128: $^1$H NMR (400 MHz, $CD_3OD$) δ 7.33, 7.24 (s, 1 H total), 5.03-4.96 (m, 2 H), 4.14-4.10 (m, 3 H), 3.87-3.62

(m, 2 H), 3.48-3.38 (m, 1 H), 3.25-2.89 (m, 9 H), 2.70-2.63 (m, 1 H), 2.27-2.24 (m, 1 H), 1.71-1.55 (m, 3 H), 1.35-1.19 (m, 4 H), 0.98 (s, 6 H); MS (ESI) m/z 640.0 (M+H).

S25-11-129

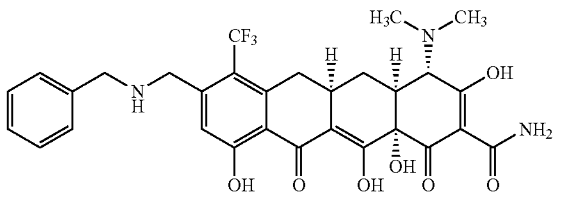

S25-11-129: [1] H NMR (400 MHz, $CD_3OD$) δ 7.69-7.49 (m, 5 H), 7.13 (s, 1 H), 4.49-4.32 (m, 4 H), 4.13 (s, 1 H), 3.23-2.88 (m, 9 H), 2.70-2.56 (m, 1 H), 2.29-2.22 (m, 1 H), 1.68-1.59 (m, 1 H); MS (ESI) m/z 602.1 (M+H).

S25-11-130

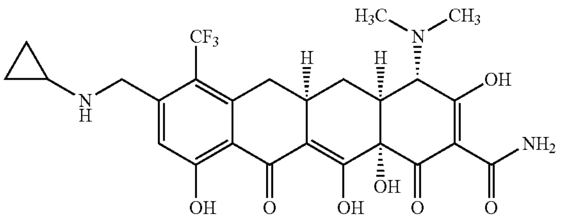

S25-11-130: [1] H NMR (400 MHz, $CD_3OD$) δ 7.15 (s, 1 H), 4.53 (d, J=14.0 Hz, 1 H), 4.43 (d, J=12.4 Hz, 1 H), 4.12 (s, 1 H), 3.23-2.86 (m, 10 H), 2.67-2.55 (m, 1 H), 2.25-2.21 (m, 1 H), 1.67-1.57 (m, 1 H), 0.96-0.95 (m, 4 H); MS (ESI) m/z 552.1 (M+H).

S25-11-131

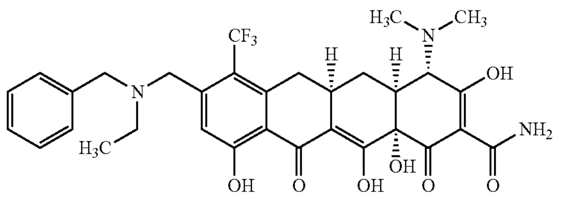

S25-11-131: [1] H NMR (400 MHz, $CD_3OD$) δ 7.53-7.49 (m, 5 H), 7.31, 7.16 (s, 1 H total), 4.63-4.23 (m, 4 H), 4.13 (s, 1 H), 3.22-2.89 (m, 11 H), 2.70-2.56 (m, 1 H), 2.26-2.22 (m, 1 H), 1.69-1.59 (m, 1 H), 1.48 (t, J=7.2 Hz, 3 H); MS (ESI) m/z 630.1 (M+H).

S25-11-132

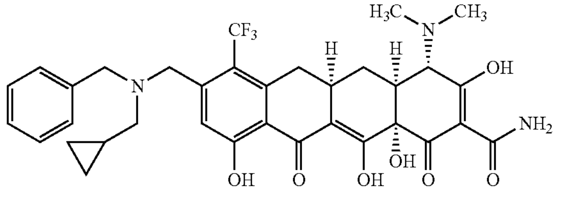

S25-11-132: [1] H NMR (400 MHz, $CD_3OD$) δ 7.67-7.46 (m, 5 H), 7.23, 7.18 (s, 1 H total), 4.63-4.39 (m, 4 H), 4.12 (s, 1 H), 3.22-2.81 (m, 11 H), 2.68-2.53 (m, 1 H), 2.23-2.20 (m, 1 H), 1.66-1.58 (m, 1 H), 1.36-1.31 (m, 1 H), 0.85-0.78 (m, 2 H), 0.47-0.42 (m, 2 H); MS (ESI) m/z 656.2 (M+H).

S25-11-133

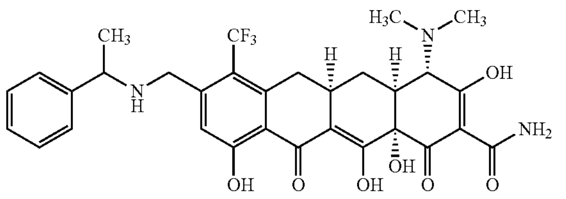

S25-11-133: [1] H NMR (400 MHz, $CD_3OD$) δ 7.55-7.52 (m, 5 H), 7.14, 6.99 (s, 1 H total), 4.62-4.55 (m, 0.4 H), 4.40-4.25 (m, 1 H), 4.13-3.98 (m, 1.5 H), 3.22-2.88 (m, 10 H), 2.71-2.56 (m, 1 H), 2.24-2.21 (m, 1 H), 1.80-1.1.78 (m, 3 H), 1.66-1.59 (m, 1 H); MS (ESI) m/z 616.2 (M+H).

S25-11-134

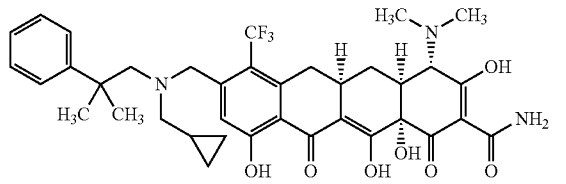

S25-11-134: [1] H NMR (400 MHz, $CD_3OD$) δ 7.21-6.99 (m, 5 H), 6.89, 6.79 (s, 1 H total), 4.72-4.62 (m, 1. H), 3.86 (s, 1 H), 3.62-3.52 (m, 1 H), 3.32-3.10 (m, 2 H), 3.00-2.55 (m, 11 H), 2.40-2.39 (m, 1 H), 2.02-1.95 (m, 1 H), 1.42-1.33 (m, 1 H), 1.29-1.09 (m, 6 H), 0.93-0.80 (m, 1 H), 0.52-0.42 (m, 2 H), 0.10-0.01 (m, 2 H); MS (ESI) m/z 698.1 (M+H).

S25-11-135

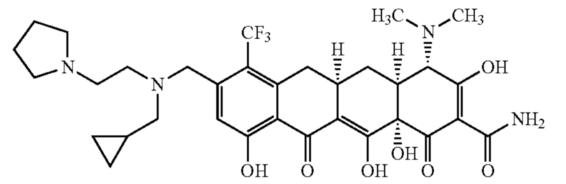

S25-11-135: [1] H NMR (400 MHz, $CD_3OD$) δ 7.48 (s, 1 H), 4.83-4.62 (m, 2 H), 4.13 (s, 1 H), 3.85-3.63 (m, 6 H), 3.23-2.87 (m, 13 H), 2.68-2.58 (m, 1 H), 2.28-2.00 (m, 5 H), 1.68-1.59 (m, 1 H), 1.29-1.18 (m, 1 H), 0.86-0.78 (m, 2 H), 0.52-0.42 (m, 2 H); MS (ESI) m/z 663.3 (M+H).

S25-11-136

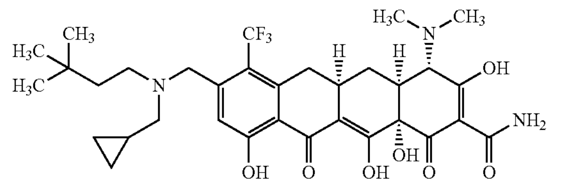

S25-11-136: [1] H NMR (400 MHz, $CD_3OD$) δ 7.32, 7.24, 7.23 (s, 1 H total), 4.78-4.50 (m, 2 H), 4.12, 3.87 (s, 1 H total), 3.25-2.95 (m, 13 H), 2.68-2.62 (m, 1 H), 2.25-2.11 (m, 1 H), 1.78-1.54 (m, 3 H), 1.20-1.10 (m, 1 H), 1.00, 0.97, 0.94 (s, 9 H total), 0.86-0.75 (m, 2 H), 0.51-0.41 (m, 2 H); MS (ESI) m/z 650.1 (M+H).

S25-11-137

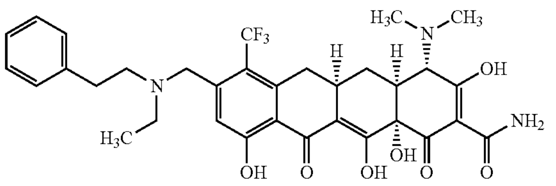

S25-11-137: $^{1}$H NMR (400 MHz, $CD_3OD$) δ 7.52-7.19 (m, 6 H), 4.76-4.57 (m, 2 H), 4.14 (s, 1 H), 3.52-3.36 (m, 4 H), 3.22-2.90 (m, 11 H), 2.67-2.60 (m, 1 H), 2.27-2.23 (m, 1 H), 1.71-1.61 (m, 1 H), 1.47 (t, J=14.0 Hz, 3 H); MS (ESI) m/z 644.5 (M+H).

S25-11-138

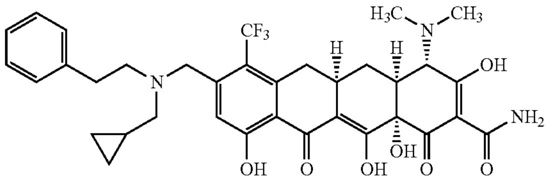

S25-11-138: $^{1}$H NMR (400 MHz, $CD_3OD$) δ 7.53-7.28 (m, 6 H), 4.76-4.57 (m, 2 H), 4.16 (s, 1 H), 3.68-3.40 (m, 3 H), 3.23-2.91 (m, 12 H), 2.71-2.61 (m, 1 H), 2.28-2.25 (m, 1 H), 1.71-1.65 (m, 1 H), 1.32-1.18 (m, 1 H), 0.89-0.78 (m, 2 H), 0.55-0.45 (m, 2 H); MS (ESI) m/z 670.1 (M+H).

S25-11-139

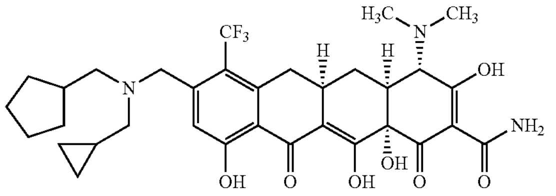

S25-11-139: $^{1}$H NMR (400 MHz, $CD_3OD$) δ 7.29, 7.28 (s, 1 H total), 4.83-4.75 (m, 1 H), 4.71-4.65 (m, 1 H), 4.15 (s, 1 H), 3.54-3.36 (m, 1 H), 3.23-2.98 (m, 12 H), 2.69-2.61 (m, 1 H), 2.42-2.25 (m, 2 H), 2.02-1.97 (m, 2 H), 1.74-1.62 (m, 5 H), 1.35-1.16 (m, 3 H), 0.87-0.78 (m, 2 H), 0.54-0.44 (m, 2 H); MS (ESI) m/z 648.1 (M+H).

S25-11-140

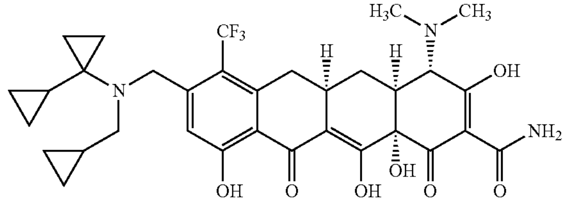

S25-11-140: $^{1}$H NMR (400 MHz, $CD_3OD$) δ 7.34 (s, 1 H), 5.12-5.03 (m, 2 H), 4.16 (s, 1 H), 3.75-3.73 (m, 1 H), 3.25-2.96 (m, 10 H), 2.69-2.62 (m, 1 H), 2.31-2.25 (m, 1 H), 1.76-1.65 (m, 2 H), 1.61-1.41 (m, 1 H), 1.28-1.16 (m, 1 H), 1.04-0.95 (m, 1 H), 0.94-0.73 (m, 6 H), 0.55-0.30 (m, 4 H); MS (ESI) m/z 646.1 (M+H)

S25-11-141

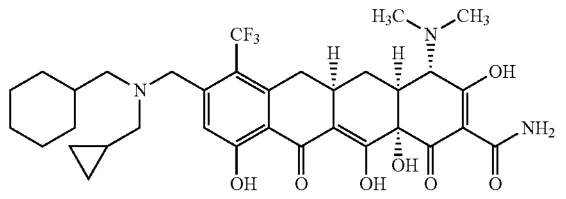

S25-11-141: $^{1}$H NMR (400 MHz, $CD_3OD$) δ 7.33, 7.32, 7.29 (s, 1 H total), 4.85-4.61 (m, 2 H), 4.15 (s, 1 H), 3.21-2.90 (m, 13 H), 2.70-2.60 (m, 1 H), 2.29-2.25 (m, 1 H), 1.91-1.60 (m, 7 H), 1.41-1.15 (m, 4 H), 1.12-0.75 (m, 4 H), 0.54-0.40 (m, 2 H); MS (ESI) m/z 662.1 (M+H)

S25-11-142

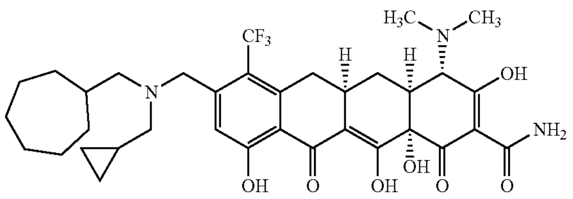

S25-11-142: $^{1}$H NMR (400 MHz, $CD_3OD$) δ 7.35, 7.30 (s, 1 H total), 4.83-4.59 (m, 2 H), 4.15 (s, 1 H), 3.40-3.35 (m, 1 H), 3.24-2.93 (m, 12 H), 2.68-2.61 (m, 1 H), 2.29-2.25 (m, 1 H), 2.08-1.92 (m, 1 H), 1.85-1.42 (m, 11 H), 1.35-1.16 (m, 3 H), 0.86-0.78 (m, 2 H), 0.54-0.41 (m, 2 H); MS (ESI) m/z 676.1 (M+H)

S25-11-143

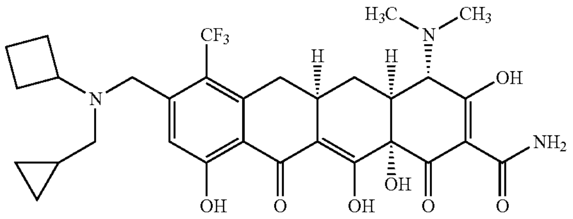

S25-11-143: $^{1}$H NMR (400 MHz, $CD_3OD$) δ 7.31 (s, 1 H), 4.82-4.71 (m, 1 H), 4.58-4.42 (m, 1 H), 4.14 (s, 1 H), 4.11-4.01 (m, 1 H), 3.21-2.97 (m, 11 H), 2.68-2.59 (m, 1 H), 2.48-2.33 (m, 2 H), 2.28-2.20 (m, 1 H), 2.18-1.60 (m, 5 H), 1.21-1.10 (m, 1 H), 0.85-0.74 (m, 2 H), 0.48-0.35 (m, 2 H); MS (ESI) m/z 620.1 (M+H).

S25-11-144

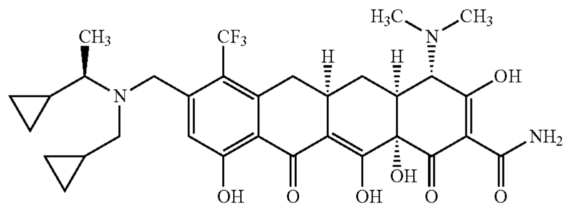

S25-11-144: $^{1}$H NMR (400 MHz, $CD_3OD$) δ 7.29, 7.25 (s, 1 H total), 4.68-4.62 (m, 1 H), 4.36-4.30 (m, 1 H), 4.12 (s, 1 H), 3.15-2.93 (m, 12 H), 2.70-2.60 (m, 1 H), 2.28-2.22 (m, 1 H), 1.70-1.60 (m, 1 H), 1.51 (d, J=6.4 Hz, 3 H), 097-0.73 (m, 6 H), 0.67-0.38 (m, 6 H); MS (ESI) m/z 634.1 (M+H)

S25-11-145

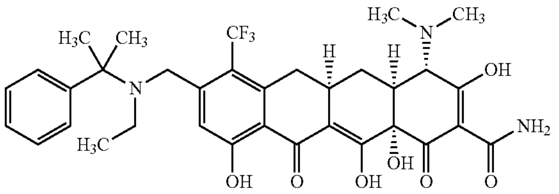

S25-11-145: $^{1}$H NMR (400 MHz, $CD_3OD$) δ 7.86-7.72 (m, 2 H), 7.57-7.43 (m, 3 H), 7.22, 7.08 (s, 1 H total), 4.64-4.36 (m, 2 H), 4.12 (s, 1 H), 3.73-3.61 (m, 1 H), 3.23-2.89 (m, 10 H), 2.66-2.48 (m, 1 H), 2.30-2.20 (m, 1 H), 2.04-1.99 (m, 6 H), 1.65-1.56 (m, 1 H), 1.19, 0.98 (t, J=7.2 Hz, 3 H total); MS (ESI) m/z 658.1 (M+H).

S25-11-146

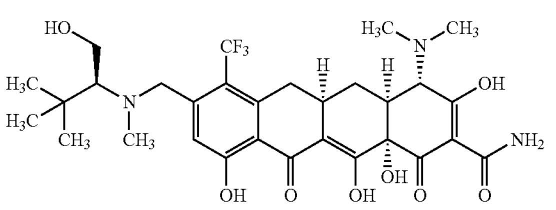

S25-11-146: $^{1}$H NMR (400 MHz, $CD_3OD$) δ 7.37 (s, 1 H), 5.10 (d, J=14.0 Hz, 1 H), 4.75 (d, J=14.0 Hz, 1 H), 4.15 (s, 1 H), 4.10-4.08 (m, 2 H), 3.30-2.96 (m, 13 H), 2.69-2.58 (m, 1 H), 2.27-2.23 (m, 1 H), 1.69-1.60 (m, 1 H), 1.02 (s, 9 H); MS (ESI) m/z 626.1 (M+H).

S25-11-147

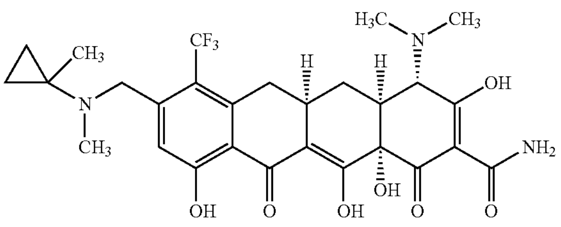

S25-11-147: $^{1}$H NMR (400 MHz, $CD_3OD$) δ 7.27 (s, 1 H), 4.60-4.42 (m, 2 H), 4.14 (s, 1 H), 3.22-2.90 (m, 12 H), 2.70-2.62 (m, 1 H), 2.27-2.23 (m, 1 H), 1.70-1.60 (m, 1 H), 1.59 (s, 3 H), 1.31-1.22 (m, 2 H), 1.08-0.87 (m, 2 H); MS (ESI) m/z 580.1 (M+H).

S25-11-148

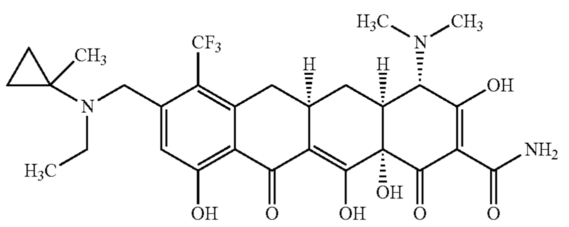

S25-11-148: $^{1}$H NMR (400 MHz, $CD_3OD$) δ 7.26 (s, 1 H), 4.83-4.66 (m, 2 H), 4.13 (s, 1 H), 3.51-3.40 (m, 2 H), 3.21-2.96 (m, 9 H), 2.69-2.58 (m, 1 H), 2.26-2.22 (m, 1 H), 1.69-1.60 (m, 1 H), 1.59 (s, 3 H), 1.48-1.35 (m, 4 H), 1.05-0.76 (m, 3 H); MS (ESI) m/z 594.1 (M+H).

S25-11-149

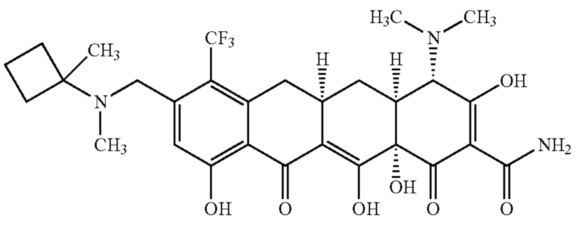

S25-11-149: $^{1}$H NMR (400 MHz, $CD_3OD$) δ 7.26 (s, 1 H), 4.56-4.52 (m, 1 H), 4.18-4.13 (m, 2 H), 3.21-2.97 (m, 9 H), 2.66 (s, 3 H), 2.65-2.45 (m, 3 H), 2.29-2.17 (m, 2 H), 2.11-2.02 (m, 1 H), 1.96-1.90 (m, 2 H), 1.69-1.60 (m, 4 H); MS (ESI) m/z 594.1 (M+H).

S25-11-150

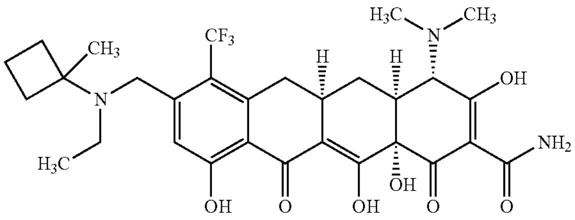

S-25-11-149: $^{1}$H NMR (400 MHz, $CD_3OD$) δ 7.36, 7.35 (s, 1 H total), 4.53-4.36 (m, 2 H), 4.14 (s, 1 H), 3.21-2.96 (m, 11 H), 2.76-2.47 (m, 3 H), 2.36-2.22 (m, 1 H), 2.13-2.02 (m, 2 H), 2.01-1.88 (m, 2 H), 1.68-1.63 (m, 4 H), 1.23, 1.12 (t, J=7.2 Hz, 3 H total); MS (ESI) m/z 608.1 (M+H).

S25-11-151

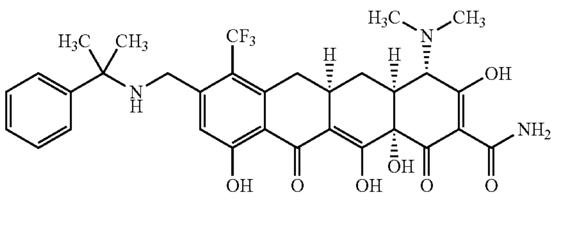

S25-11-151: $^{1}$H NMR (400 MHz, $CD_3OD$) δ 7.67-7.27 (m, 5 H), 6.88 (s, 1 H), 4.11 (s, 1 H), 4.05 (d, J=13.6 Hz, 1 H), 3.96 (d, J=14.0 Hz, 1 H), 3.21-2.85 (m, 9 H), 2.57-2.50 (m, 1 H), 2.23-2.13 (m, 1 H), 1.90 (m, 6 H), 1.64-1.54 (m, 1 H); MS (ESI) m/z 630.1 (M+H).

S25-11-152

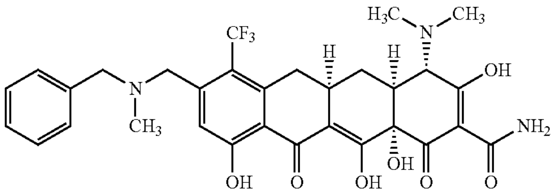

S25-11-152: $^1$H NMR (400 MHz, $CD_3OD$) δ 7.53 (s, 5 H), 7.21 (s, 1 H), 4.75-4.62 (m, 1 H), 4.53-4.27 (m, 3 H), 4.13 (s, 1 H), 3.20-2.85 (m, 9 H), 2.79 (s, 3 H), 2.69-2.57 (m, 1 H), 2.25-2.14 (m, 1 H), 1.68-1.58 (m, 1 H); MS (ESI) m/z 616.1 (M+H).

S25-11-153

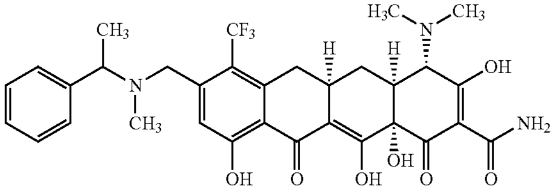

S25-11-153: $^1$H NMR (400 MHz, $CD_3OD$) δ 7.73-7.54 (m, 5 H), 7.23, 7.18, 7.13 (s, 1 H total), 4.87-4.73 (m, 2 H), 4.13-4.02 (m, 2 H), 3.21-2.88 (m, 9 H), 2.79, 2.72 (s, 3 H total), 2.66-2.52 (m, 1 H), 2.30-2.21 (m, 1 H), 1.86 (d, J=4.4 Hz, 3 H), 1.67-1.58 (m, 1 H); MS (ESI) m/z 630.0 (M+H).

S25-11-154

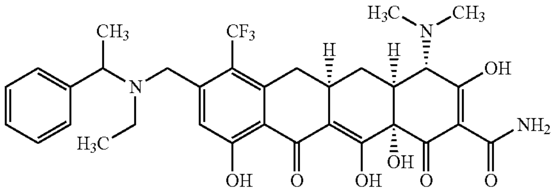

S25-11-154: $^1$H NMR (400 MHz, $CD_3OD$) δ 7.64-7.50 (m, 5 H), 7.16, 7.08 (s, 1 H total), 5.02-4.98 (m, 1 H), 4.68-4.23 (m, 2 H), 4.13 (s, 1 H), 3.47-3.35 (m, 1 H), 3.21-2.88 (m, 10 H), 2.69-2.54 (m, 1 H), 2.26-2.20 (m, 1 H), 1.88-1.83 (m, 3 H), 1.66-1.57 (m, 1 H), 1.44-1.33 (m, 3 H); MS (ESI) m/z 644.2 (M+H).

S25-11-155

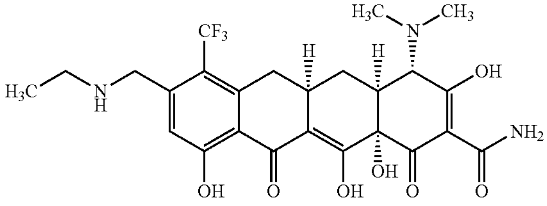

S25-11-155: $^1$H NMR (400 MHz, $CD_3OD$) δ 7.17 (s, 1 H), 4.21 (d, J=14.4 Hz, 1 H), 4.31 (d, J=14.0 Hz, 1 H), 4.14 (s, 1 H), 3.22-2.88 (m, 11 H), 2.69-2.57 (m, 1 H), 2.26-2.23 (m, 1 H), 1.68-1.59 (m, 1 H), 1.38 (t, J=7.2 Hz, 3 H); MS (ESI) m/z 540.1 (M+H).

S25-11-156

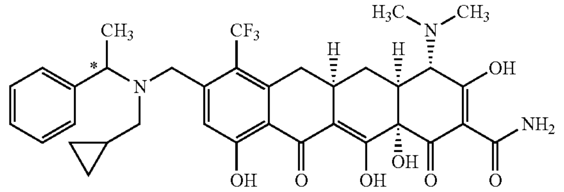

single diastereomer A

S25-11-156: $^1$H NMR (400 MHz, $CD_3OD$) δ 7.60-7.45 (m, 5 H), 7.21, 7.18 (s, 1 H total), 5.10-4.93 (m, 1 H), 4.72-4.64 (m, 1 H), 4.49-4.45 (1 H), 4.12 (s, 1 H), 3.22-2.87 (m, 11 H), 2.66-2.55 (m, 1 H), 2.26-2.18 (m, 1 H), 1.95-1.85 (m, 3 H), 1.68-1.58 (m, 1 H), 1.15-1.08 (m, 1 H), 0.90-0.66 (m, 2 H), 0.50-0.35 (m, 2 H); MS (ESI) m/z 670.1 (M+H).

S25-11-157

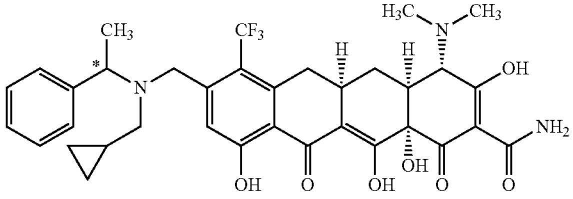

single diastereomer B

S25-11-157: $^1$H NMR (400 MHz, $CD_3OD$) δ 7.65-7.48 (m, 5 H), 7.26, 7.10 (s, 1 H total), 5.35-5.25 (m, 0.5 H), 4.76-4.65 (m, 1.5 H), 4.49-4.35 (m, 1 H), 4.11 (s, 1 H), 3.21-2.95 (m, 11 H), 2.66-2.54 (m, 1 H), 2.26-2.19 (m, 1 H), 1.95-1.82 (m, 3 H), 1.68-1.59 (m, 1 H), 1.20-1.01 (m, 1 H), 0.91-0.68 (m, 2 H), 0.48-0.33 (m, 2 H); MS (ESI) m/z 670.1 (M+H).

S25-11-158

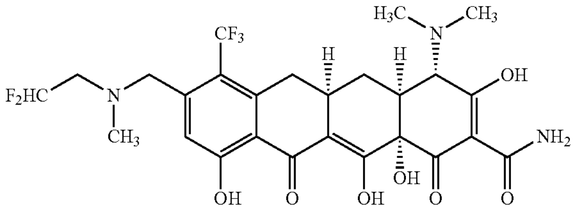

S25-11-158: $^1$H NMR (400 MHz, $CD_3OD$) δ 7.27 (s, 1 H), 6.39 (t, J=54.0 Hz, 1 H), 4.57 (d, J=13.6 Hz, 1 H), 4.46 (d, J=13.2 Hz, 1 H), 4.14 (s, 1 H), 3.67 (t, J=14.4 Hz, 2 H), 3.15-2.98 (m, 9 H), 2.89 (s, 3 H), 2.68-2.60 (m, 1 H), 2.28-2.23 (m, 1 H), 1.69-1.62 (m, 1 H); MS (ESI) m/z 590.1 (M+H).

S25-11-159

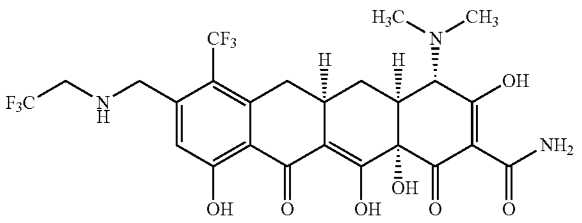

S25-11-159: $^{1}H$ NMR (400 MHz, $CD_3OD$) δ 7.24 (s, 1 H), 4.52 (d, J=14.4 Hz, 1 H), 4.43 (d, J=14.4 Hz, 1 H), 4.14 (s, 1 H), 4.11-4.04 (m, 2 H), 3.15-2.90 (m, 9 H), 2.68-2.60 (m, 1 H), 2.27-2.24 (m, 1 H), 1.68-1.62 (m, 1 H); MS (ESI) m/z 594.1 (M+H).

S25-11-160

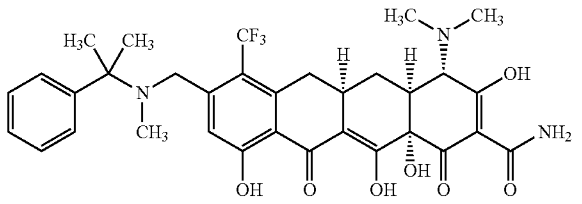

S25-11-160: $^{1}H$ NMR (400 MHz, $CD_3OD$) δ 7.80-7.78 (m, 2 H), 7.64-7.29 (m, 3 H), 7.01, 6.93 (s, 1 H total), 4.52-4.41 (m, 1 H), 4.15 (s, 1 H), 4.13-4.08 (m, 1 H), 3.23-2.87 (m, 9 H), 2.77 (s, 3 H), 2.61-2.48 (m, 1 H), 2.25-2.20 (m, 1 H), 2.05 (m, 6 H), 1.66-1.57 (m, 1 H); MS (ESI) m/z 644.1 (M+H).

S25-11-161

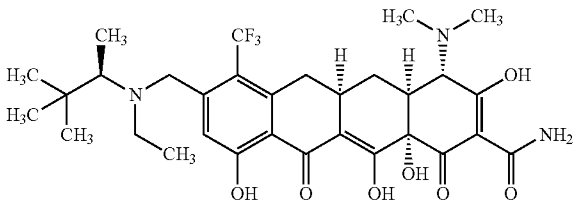

S25-11-161: $^{1}H$ NMR (400 MHz, $CD_3OD$) δ 7.41, 7.38, 7.23 (s, 1 H total), 4.76-4.45 (m, 2 H), 4.16, 4.15 (s, 1 H total), 3.62-3.35 (m, 2 H), 3.26-2.96 (m, 10 H), 2.70-2.64 (m, 1 H), 2.28-2.24 (m, 1 H), 1.67-1.55 (m, 3 H), 1.48-1.38 (m, 3 H), 1.38-1.28 (m, 1 H), 1.24 (s, 3 H), 0.92 (s, 6 H); MS (ESI) m/z 624.1 (M+H).

S25-11-162

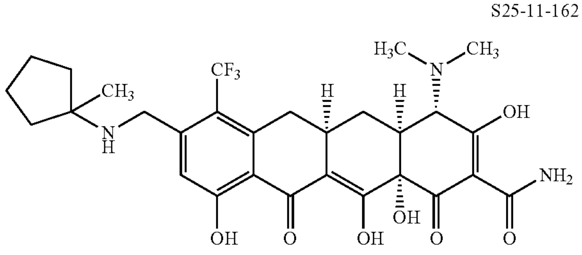 [SMILES: CN(C)[C@@H]1C(O)=C(C(N)=O)C(=O)[C@@]2(O)C(O)=C3C(=O)c4c(O)cc(CNC5(C)CCCC5)c(C(F)(F)F)c4C[C@H]3C[C@@H]12]

S25-11-162: $^{1}H$ NMR (400 MHz, $CD_3OD$) δ 7.24, 7.23 (s, 1 H total), 4.43 (d, J=13.2 Hz, 1 H), 4.30 (d, J=13.6 Hz, 1 H), 4.14 (s, 1 H), 3.21-2.88 (m, 9 H), 2.69-2.58 (m, 1 H), 2.27-2.23 (m, 1 H), 2.03-1.69 (m, 8 H), 1.69-1.61 (m, 1 H), 1.49 (s, 3 H); MS (ESI) m/z 594.1 (M+H).

S25-11-163

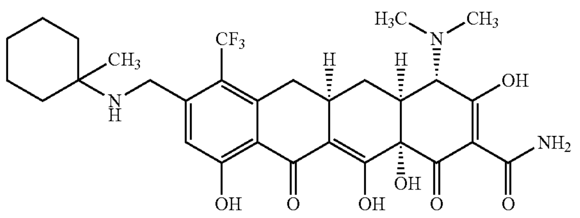

S25-11-163: $^{1}H$ NMR (400 MHz, $CD_3OD$) δ 7.25 (s, 1 H), 4.43 (d, J=13.6 Hz, 1 H), 4.28 (d, J=12.8 Hz, 1 H), 4.14 (s, 1 H), 3.11-2.96 (m, 9 H), 2.66-2.58 (m, 1 H), 2.26-2.23 (m, 1 H), 2.01-1.94 (m, 2 H), 1.78-1.53 (m, 9 H), 1.50 (s, 3 H); MS (ESI) m/z 608.1 (M+H).

S25-11-164

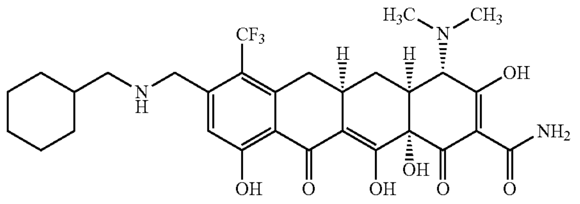

S25-11-164: $^{1}H$ NMR (400 MHz, $CD_3OD$) δ 7.19 (s, 1 H), 4.43 (d, J=14.0 Hz, 1 H), 4.33 (d, J=14.8 Hz, 1 H), 4.10 (s, 1 H), 3.03-2.95 (m, 11 H), 2.69-2.57 (m, 1 H), 2.26-2.22 (m, 1 H), 1.83-1.76 (m, 6 H), 1.39-1.25 (m, 4 H), 1.11-1.05 (m, 2 H); MS (ESI) m/z 608.1 (M+H).

S25-11-165

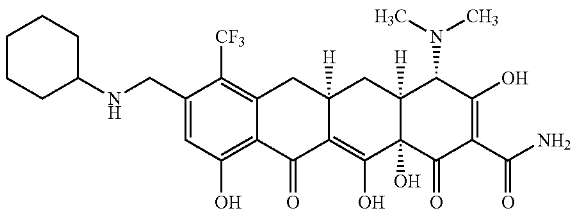

S25-11-165: $^{1}H$ NMR (400 MHz, $CD_3OD$) δ 7.19 (s, 1 H), 4.45-4.28 (m, 2 H), 4.13 (s, 1 H), 3.21-2.96 (m, 10 H), 2.66-2.60 (m, 1 H), 2.26-2.15 (m, 2 H), 1.95-1.84 (m, 3 H), 1.78-1.60 (m, 3 H), 1.45-1.21 (m, 6 H); MS (ESI) m/z 594.1 (M+H).

S25-11-166

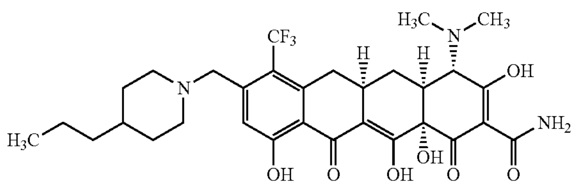

S25-11-166: $^{1}H$ NMR (400 MHz, $CD_3OD$) δ 7.17 (s, 1 H), 4.48 (d, J=14.4 Hz, 1 H), 4.30 (d, J=14.0 Hz, 1 H), 4.04 (s, 1 H), 3.48 (t, J=12.4 Hz, 2 H), 3.17-2.86 (m, 11 H), 2.60-2.50

(m, 1 H), 2.17-2.13 (m, 1 H), 1.92-1.85 (m, 2 H), 1.60-1.51 (m, 2 H), 1.43-1.15 (m, 6 H), 0.82 (t, J=7.2 Hz, 3 H); MS (ESI) m/z 622.2 (M+H).

S25-11-167

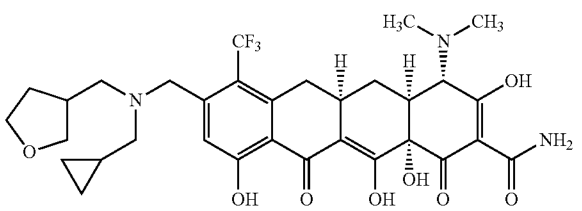

S25-11-211: MS (ESI) m/z 650.1 (M + H).

S25-11-168

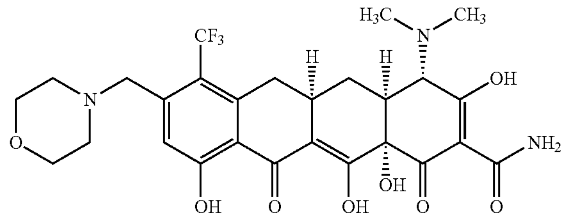

S25-11-168: [1] H NMR (400 MHz, $CD_3OD$) δ 7.28 (s, 1 H), 4.64 (d, J=14.4 Hz, 1 H), 4.49 (d, J=13.6 Hz, 1 H), 4.13 (s, 1 H), 4.05-3.75 (m, 4 H), 3.51-3.40 (m, 4 H), 3.15-2.96 (m, 9 H), 2.69-2.60 (m, 1 H), 2.26-2.22 (m, 1 H), 1.68-1.62 (m, 1 H); MS (ESI) m/z 582.2 (M+H).

S25-11-169

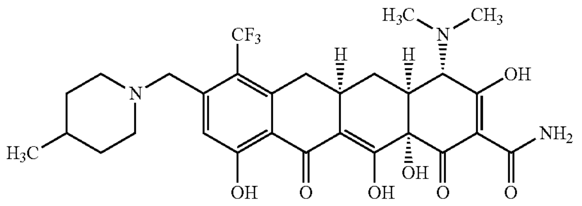

S25-11-169: [1] H NMR (400 MHz, $CD_3OD$) δ 7.26 (s, 1 H), 4.57 (d, J=13.6 Hz, 1 H), 4.39 (d, J=13.6 Hz, 1 H), 4.13 (s, 1 H), 3.56 (t, J=14.4 Hz, 2 H), 3.23-2.95 (m, 11 H), 2.66-2.59 (m, 1 H), 2.26-2.23 (m, 1 H), 1.98-1.90 (m, 3 H), 1.70-1.60 (m, 3 H), 1.55-1.45 (m, 2 H), 1.01 (d, J=6.4 Hz, 3 H); MS (ESI) m/z 594.2 (M+H).

S25-11-170

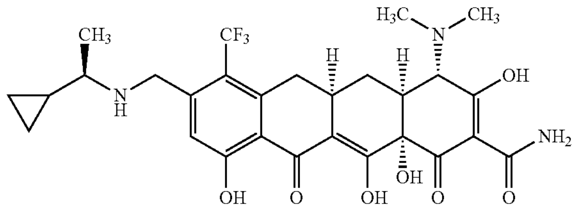

S25-11-170: [1] H NMR (400 MHz, $CD_3OD$) δ 7.23 (s, 1 H), 4.44 (q, J=14 Hz, 2 H), 4.15 (s, 1 H), 3.05-2.96 (m, 9 H), 2.81-2.79 (m, 1 H), 2.64-2.60 (m, 1 H), 2.27-2.23 (m, 1 H), 1.63 (q, J=13.2 Hz, 1 H), 1.49 (d, J=6.4 Hz, 3 H), 1.11-1.05 (m, 1 H), 0.83-0.81 (m, 2 H), 0.62-0.59 (m, 1 H), 0.39-0.35 (m, 1 H); MS (ESI) m/z 580.2 (M+H).

S25-11-171

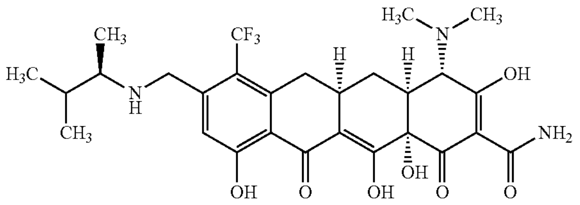

S25-11-171: [1] H NMR (400 MHz, $CD_3OD$) δ 7.24 (s, 1 H), 4.46 (d, J=14 Hz, 1 H), 4.34 (d, J=13.2 Hz, 1 H), 4.15 (s, 1 H), 3.36-3.37 (m, 1 H), 3.05-2.96 (m, 9 H), 2.65-2.56 (m, 1 H), 2.27-2.21 (m, 2 H), 1.68-1.59 (m, 1 H), 1.32 (d, J=6.8 Hz, 3 H), 1.05 (d, J=6.8 Hz, 3 H), 1.01 (d, J=6.8 Hz, 3 H); MS (ESI) m/z 582.3 (M+H).

S25-11-172

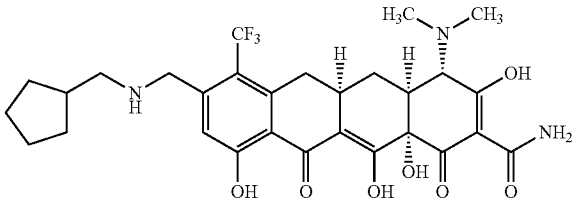

S25-11-172: [1] H NMR (400 MHz, $CD_3OD$) δ 7.19 (s, 1 H), 4.43 (d, J=14.4 Hz, 1 H), 4.33 (d, J=14 Hz, 1 H), 4.13 (s, 1 H), 3.15-2.96 (m, 10 H), 2.65-2.61 (m, 2H), 1.96-1.93 (m,2H), 1.74-1.63 (m, 5 H), 1.31-1.29 (m,2 H); MS (ESI) m/z 594.5 (M+H).

S25-11-173

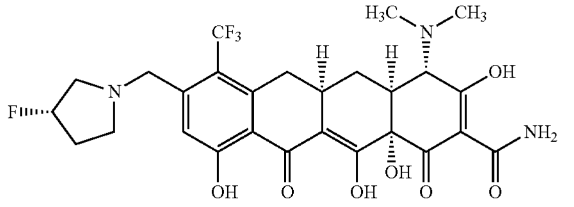

S25-11-173: [1] H NMR (400 MHz, $CD_3OD$) δ 7.27 (s, 1 H), 5.49 (d, J=52.8 Hz, 1 H), 4.55 (m, 1 H), 4.12 (s, 1 H), 3.95-2.43 (m , 4 H), 3.04-2.96 (m, 9 H), 2.69-2.61 (m, 3 H), 2.41-2.23 (m, 1H), 2.25-2.22 (m, 1 H), 1.69-1.58 (m, 1 H); MS (ESI) m/z 584.3 (M+H).

S25-11-174

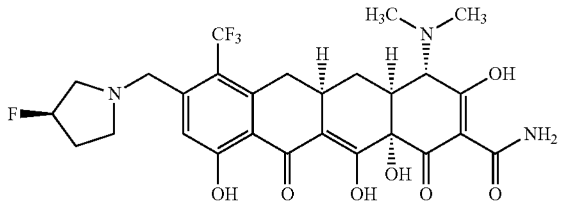

S25-11-174: [1] H NMR (400 MHz, $CD_3OD$) δ 7.26 (s, 1 H), 5.49 (d, J=52.8 Hz, 1 H), 4.59 (d, J=13.6 Hz, 1 H), 4.13 (s, 1

H), 3.83-2.79 (m , 4 H), 3.04-2.96 (m, 9H), 2.65-2.62 (m, 3 H), 2.44-2.43 (m,1H), 2.26-2.22 (m, 1 H), 1.69-1.59 (m, 1 H); MS (ESI) m/z 584.2 (M+H).

S25-11-175

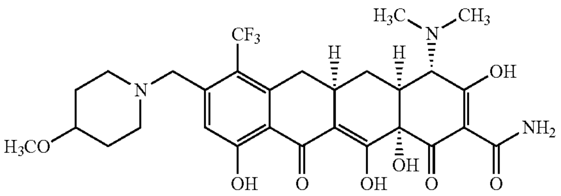

S25-11-175: $^{1}$H NMR (400 MHz, $CD_3OD$) δ 7.25 (s, 1 H), 4.54 (d, J=13.2 Hz, 1 H), 4.59 (d, J=13.2 Hz, 1 H), 4.11 (s, 1 H), 3.61-3.53 (m, 2 H), 3.39-3.34 (m, 6 H), 3.28-2.81 (m, 9 H), 2.67-2.57 (m, 1 H), 2.24-1.92 (m, 5H), 1.68-1.58 (m, 1 H); MS (ESI) m/z 610.0 (M+H).

S25-11-176

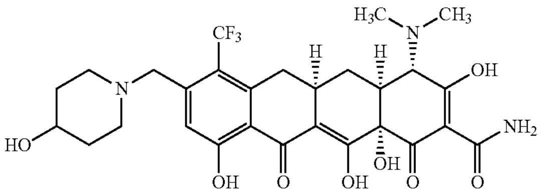

S25-11-176: $^{1}$H NMR (400 MHz, $CD_3OD$) δ 7.25 (s, 1 H), 4.56 (d, J=14.4 Hz, 1 H), 4.42 (d, J=14.4 Hz, 1 H), 4.12 (s, 1 H), 3.89-3.38 (m, 4 H), 3.25-2.91 (m, 9 H), 2.65-2.57 (m, 1 H), 2.24-2.21 (m, 1H), 2.12-1.74(m, 5 H), 1.68-1.58(m, 1 H); MS (ESI) m/z 596.0 (M+H).

S25-11-177

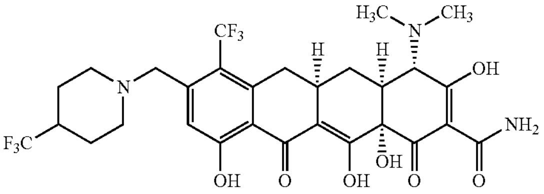

S25-11-177: $^{1}$H NMR (400 MHz, $CD_3OD$) δ 7.29 (s, 1 H), 4.61 (d, J=13.6 Hz, 1 H), 4.42 (d, J=13.6 Hz, 1 H), 4.13 (s, 1 H), 3.74-3.61 (m, 2 H), 3.29-3.15 (m, 2 H), 3.04-2.95 (m, 9 H), 2.69-2.59 (m, 3 H), 2.25-2.15 (m, 4 H), 1.69-1.59 (m, 1 H); MS (ESI) m/z 648.0 (M+H).

S25-11-178

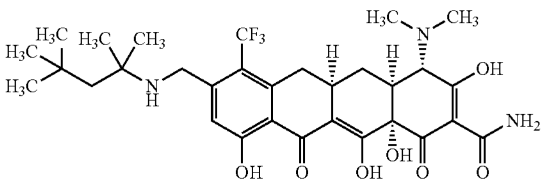

S25-11-178: $^{1}$H NMR (400 MHz, $CD_3OD$) δ 7.25 (s, 1 H), 4.41 (d, J=13.6 Hz, 1 H), 4.26 (d, J=13.6 Hz, 1 H), 4.14 (s, 1 H), 3.09-2.96 (m, 9 H), 2.69-2.58 (m, 1 H), 2.25-2.22 (m, 1 H),1.81 (s, 2 H), 1.68-1.59 (m, 1 H), 1.57 (s, 6 H), 1.11(s, 9 H); MS (ESI) m/z 624.1 (M+H).

S25-11-179

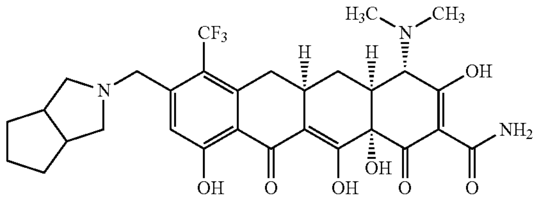

S25-11-179: $^{1}$H NMR (400 MHz, $CD_3OD$) δ 7.14 (s, 1 H), 4.60 (d, J=13.6 Hz, 1 H), 4.36 (d, J=13.2 Hz, 1 H), 4.05 (s, 1 H), 3.77-3.70 (m, 2 H), 3.22-2.79 (m, 13 H), 2.59-2.49 (m, 1 H), 2.17-2.14 (m, 1 H), 1.85-1.50 (m, 7 H); MS (ESI) m/z 606.0 (M+H)

S25-11-180

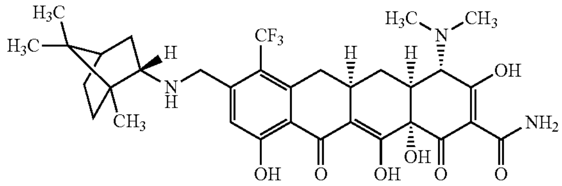

S25-11-180: $^{1}$H NMR (400 MHz, $CD_3OD$) δ 7.29 (s, 1 H), 4.41-4.38 (m, 2 H), 4.13 (s, 1 H), 3.51-3.49 (m, 1 H), 3.23-2.91 (m, 9 H), 2.69-2.63 (m, 1 H), 2.44-2.40 (m, 1 H), 2.27-2.23 (m, 1 H), 1.94-1.82 (m, 2 H), 1.69-1.53 (m, 3 H), 1.50-1.45 (m, 2 H), 1.28 (s, 3 H), 0.97 (s, 6 H); MS (ESI) m/z 648.3 (M+H).

S25-11-181

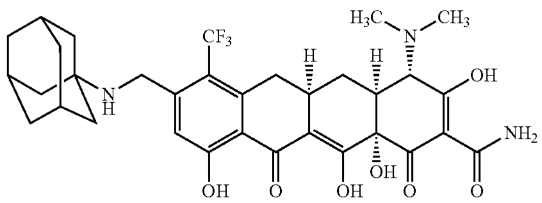

S25-11-181: $^{1}$H NMR (400 MHz, $CD_3OD$) δ 7.26-7.10 (s, 1 H total), 4.46 (d, J=13.2 Hz, 1 H), 4.33 (d, J=14.0 Hz, 1 H), 4.11 (s, 1 H), 3.55 (s, 1 H), 3.24-2.87 (m, 9 H), 2.69-2.59 (m, 1 H), 2.31-2.21 (m, 3 H), 2.02-1.76 (m, 17 H), 1.70-1.60 (m, 1 H); MS (ESI) m/z 646.1.0 (M+H).

S25-11-182

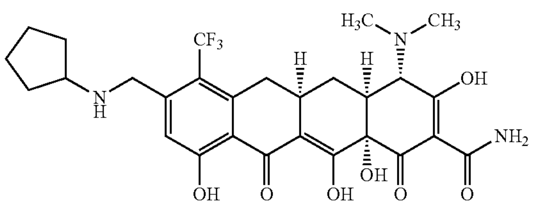

S25-11-182: $^{1}$H NMR (400 MHz, $CD_3OD$) δ 7.11 (s, 1 H), 4.34 (d, J=14.8 Hz, 1 H), 4.23 (d, J=14.8 Hz, 1 H), 4.05 (s, 1 H), 3.63-3.60 (m, 1 H), 3.18-2.88 (s, 9 H), 2.60-2.50 (m, 1 H), 2.17-2.05 (m, 3 H), 1.80-1.71 (m, 2 H), 1.69-1.61 (m, 4 H), 1.59-1.52 (m, 1 H); MS (ESI) m/z 580.0 (M+H).

S25-11-183

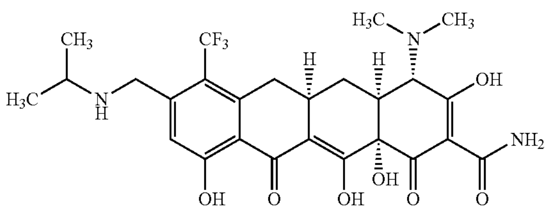

S25-11-183: $^{1}$H NMR (400 MHz, $CD_3OD$) δ 7.12, 7.10 (s, 1 H total), 4.33 (d, J=14.0 Hz, 1 H), 4.22 (d, J=14.4 Hz, 1 H), 4.05, 4.04 (s, 1 H total), 3.52-3.46 (m, 1 H), 3.20-2.88 (s, 9 H), 2.61-2.52 (m, 1 H), 2.27-2.22 (m, 1 H), 1.61-1.52 (m, 1 H), 1.35 (d. J=6.4 Hz, 6 H); MS (ESI) m/z 554.0 (M+H).

S25-11-184

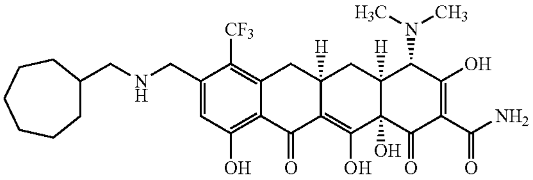

S25-11-184: $^{1}$H NMR (400 MHz, $CD_3OD$) δ 7.19 (s, 1 H), 4.43-4.39 (m, 1 H), 4.33-4.29 (m, 1 H), 4.12 (s, 1 H), 3.23-2.90 (s, 11 H), 2.68-2.55 (m, 1 H), 2.25-2.22 (m, 1 H), 2.02-1.91 (m, 1 H), 1.87-1.78 (m, 2 H), 1.75-1.47 (m, 9 H), 1.36-1.28 (m, 2 H); MS (ESI) m/z 622.0 (M+H).

S25-11-185

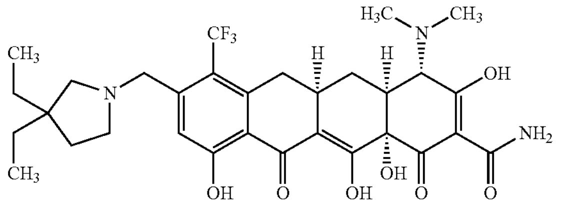

S25-11-185: $^{1}$H NMR (400 MHz, $CD_3OD$) δ 7.26 (s, 1 H), 4.75-4.65 (m, 1 H), 4.58-4.42 (m, 1 H), 4.12 (s, 1 H), 3.72-3.58 (m, 1 H), 3.55-3.36 (m, 2 H), 3.25-2.95 (s, 10 H), 2.67-2.55 (m, 1 H), 2.26-2.21 (m, 1 H), 2.06-1.98 (m, 1 H), 1.90-1.82 (m, 1 H), 1.62-1.51 (m, 5 H), 0.93-0.84 (m, 6 H); MS (ESI) m/z 622.0 (M+H).

S25-11-186

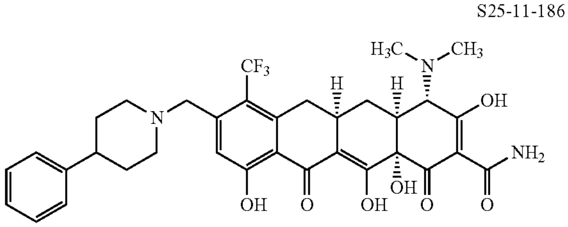 [SMILES: CN(C)[C@@H]1C(O)=C(C(N)=O)C(=O)[C@@]2(O)C(O)=C3C(=O)c4c(O)cc(CN5CCC(c6ccccc6)CC5)c(C(F)(F)F)c4C[C@H]3C[C@@H]12]

S25-11-186: $^{1}$H NMR (400 MHz, $CD_3OD$) δ 7.27-7.14 (m, 6 H), 4.57 (d, J=14.4 Hz, 1 H), 4.40 (d, J=14.4 Hz, 1 H), 4.07 (s, 1 H), 3.66-3.57 (m, 2 H), 3.35-3.29 (m, 2 H), 3.17-2.91 (s, 10 H), 2.61-2.51 (m, 1 H), 2.20-2.16 (m, 1 H), 2.06-1.98 (m, 4 H), 1.62-1.52 (m, 1 H); MS (ESI) m/z 656.3 (M+H).

S25-11-187

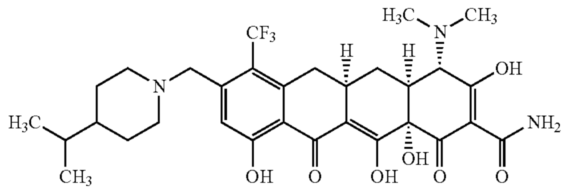

S25-11-187: $^{1}$H NMR (400 MHz, $CD_3OD$) δ 7.18 (s, 1 H), 4.48 (d, J=14.0 Hz, 1 H), 4.30 (d, J=14.0 Hz, 1 H), 4.05 (s, 1 H), 3.56-3.49 (m, 2 H), 3.23-2.88 (s, 11 H), 2.62-2.52 (m, 1 H), 2.18-2.14 (m, 1 H), 1.92-1.85 (m, 2 H), 1.59-1.39 (m, 5 H), 0.85 (d, J=6.8 Hz, 6 H); MS (ESI) m/z 622.1 (M+H).

S25-11-188

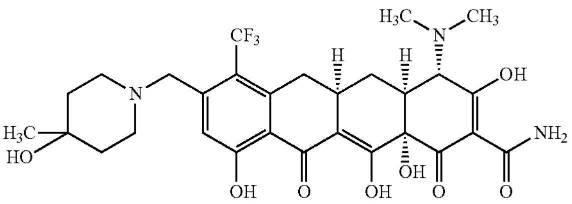

S25-11-188: $^{1}$H NMR (400 MHz, $CD_3OD$) δ 7.22 (s, 1 H), 4.54 (d, J=13.2 Hz, 1 H), 4.38 (d, J=14.4 Hz, 1 H), 4.07 (s, 1 H), 3.47-3.35 (m, 4 H), 3.13-2.90 (s, 9 H), 2.63-2.55 (m, 1 H), 2.21-2.15 (m, 1 H), 1.88-1.75 (m, 4 H), 1.63-1.55 (m, 1 H), 1.23 (s, 3 H); MS (ESI) m/z 610.1 (M+H).

S25-11-189

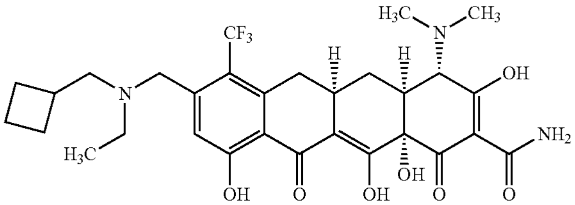

S25-11-189: $^{1}$H NMR (400 MHz, $CD_3OD$) δ 7.18 (s, 1 H), 4.55 (d, J=12.4 Hz, 1 H), 4.44 (d, J=16.0 Hz, 1 H), 4.12 (s, 1 H), 3.22-2.80 (m, 13 H), 2.67-2.56 (m, 1 H), 2.25-2.12 (m, 4 H), 2.06-1.83 (m, 5 H), 1.69-1.59 (m, 1 H), 1.40-1.30 (m, 3 H); MS (ESI) m/z 608.2 (M+H).

S25-11-190

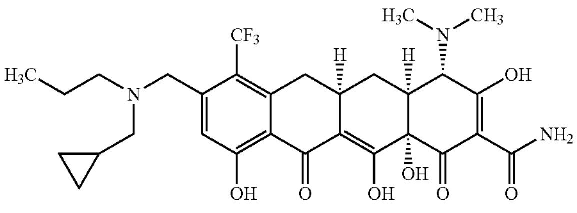

S25-11-190: $^1H$ NMR (400 MHz, $CD_3OD$) δ 7.24 (s, 1 H), 4.80-4.49 (m, 2 H), 4.14 (s, 1 H), 3.25-2.95 (m, 13 H), 2.67-2.57 (m, 1 H), 2.27-2.22 (m, 1 H), 1.88-1.60 (m, 3 H), 1.25-1.12 (m, 1 H), 1.02-0.95 (m, 3 H), 0.85-0.75 (m, 2 H), 0.48-0.37 (m, 2 H); MS (ESI) m/z 608.1 (M+H).

S25-11-191

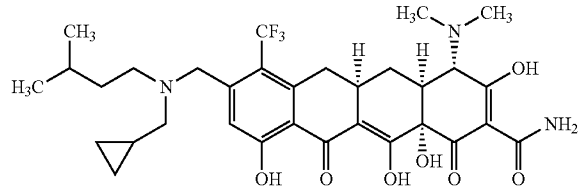

S25-11-191: $^1H$ NMR (400 MHz, $CD_3OD$) δ 7.25 (s, 1 H), 4.81-4.50 (m, 2 H), 4.14 (s, 1 H), 3.41-3.35 (m, 1 H), 3.21-2.96 (m, 12 H), 2.68-2.58 (m, 1 H), 2.27-2.22 (m, 1 H), 1.83-1.56 (m, 3 H), 1.21-1.10 (m, 1 H), 1.02-0.93 (m, 7 H), 0.85-0.75 (m, 2 H), 0.52-0.39 (m, 2 H); MS (ESI) m/z 636.1 (M+H).

S25-11-192

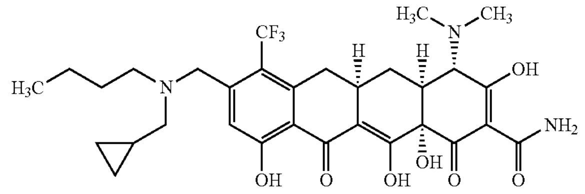

S25-11-192: $^1H$ NMR (400 MHz, $CD_3OD$) δ 7.23 (s, 1 H), 4.81-4.49 (m, 2 H), 4.13 (s, 1 H), 3.39-3.35 (m, 1 H), 3.23-2.98 (m, 12 H), 2.69-2.59 (m, 1 H), 2.26-2.21 (m, 1 H), 1.85-1.60 (m, 3 H), 1.45-1.35 (m, 2 H), 1.23-1.10 (m, 1 H), 0.98 (d, J=7.2 Hz, 3 H), 0.85-0.75 (m, 2 H), 0.49-0.39 (m, 2 H); MS (ESI) m/z 622.1 (M+H).

S25-11-193

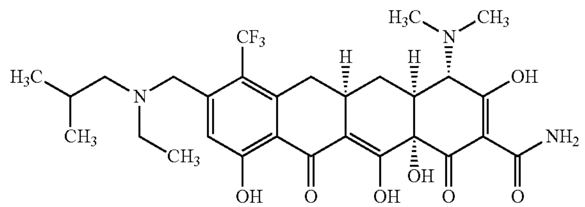

S25-11-193: $^1H$ NMR (400 MHz, $CD_3OD$) δ 7.24, 7.21 (s, 1H total), 4.60-4.44 (m, 2 H), 4.13 (s, 1 H), 3.22-2.91 (m, 13 H), 2.69-2.59 (m, 1 H), 2.29-2.09 (m, 2 H), 1.69-1.60 (m, 1 H), 1.45-1.35 (m, 3 H), 1.09-0.95 (m, 6 H); MS (ESI) m/z 596.1 (M+H).

S25-11-194

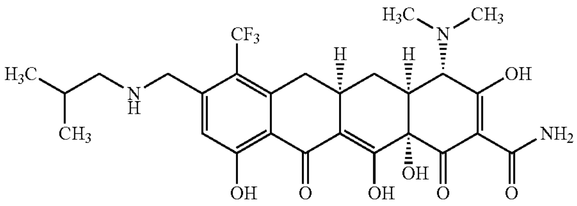

S25-11-194: $^1H$ NMR (400 MHz, $CD_3OD$) δ 7.21 (s, 1 H), 4.43 (d, J=13.8 Hz, 1 H), 4.36 (d, J=14.0 Hz, 1 H), 4.14 (s, 1 H), 3.12-2.88 (m, 11 H), 2.69-2.55 (m, 1 H), 2.28-2.22 (m, 1 H), 2.16-2.05 (m, 1 H), 1.69-1.58 (m, 1 H), 1.09 (d, J=6.8 Hz, 6 H); MS (ESI) m/z 568.0 (M+H).

S25-11-195

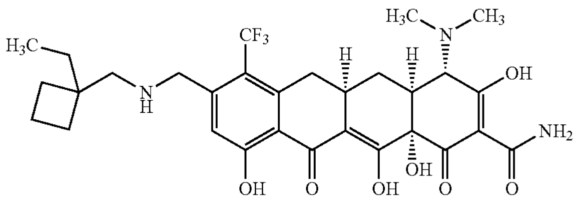

S25-11-195: $^1H$ NMR (400 MHz, $CD_3OD$) δ 7.25 (s, 1 H), 4.47-4.37 (m, 2 H), 4.13 (s, 1 H), 3.28-2.94 (s, 11 H), 2.67-2.57 (m, 1 H), 2.27-2.22 (m, 1 H), 2.00-1.89 (m, 6 H), 1.67-1.61 (m, 3 H), 0.91 (t, J=7.4 Hz, 3 H); MS (ESI) m/z 608.0 (M+H).

S25-11-196

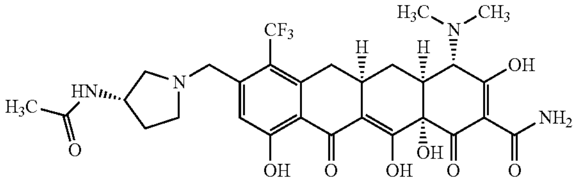

S25-11-196: $^1H$ NMR (400 MHz, $CD_3OD$) δ 7.27 (s, 1 H), 4.68-4.61 (m, 2 H), 4.59-4.51 (m, 1 H), 4.41-4.39 (m, 1 H), 4.15 (s, 1 H), 3.99-3.87 (m, 1 H), 3.58-3.52 (m, 2 H), 3.22-2.97 (m, 9 H), 2.67-2.60 (m, 2 H), 2.27-2.24 (m, 1 H), 2.16-2.11 (m, 2 H), 2.01-1.95 (m, 3 H), 1.71-1.61 (m, 1 H); MS (ESI) m/z 623.0 (M+H).

S25-11-197

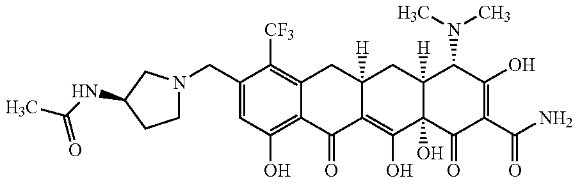

S25-11-197: $^1H$ NMR (400 MHz, $CD_3OD$) δ 7.26 (s, 1 H), 4.56-4.51 (m, 2 H), 4.47-4.32 (m, 2 H), 4.14 (s, 1 H), 3.94-3.72 (m, 2 H), 3.65-3.52 (m, 2 H), 3.22-2.97 (m, 9 H), 2.67-

2.62 (m, 2 H), 2.27-2.24 (m, 1 H), 2.01-1.98 (m, 4 H), 1.71-1.61 (m, 1 H); MS (ESI) m/z 623.0 (M+H).

S25-11-198

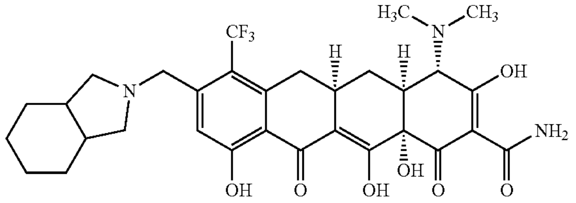

S25-11-198: $^1$H NMR (400 MHz, $CD_3OD$) δ 7.30 (s, 1 H), 4.67-4.62 (m, 1 H), 4.49-4.42 (m, 1 H), 4.05 (s, 1 H), 3.56-3.52 (m, 1 H), 3.44-3.31 (m, 1 H), 3.05-2.88 (m, 9 H), 2.58-2.45 (m, 2 H), 2.35-2.31 (m, 1 H), 2.18-2.15 (m, 1 H), 1.69-1.21 (m, 11 H); MS (ESI) m/z 620.0 (M+H).

S25-11-199

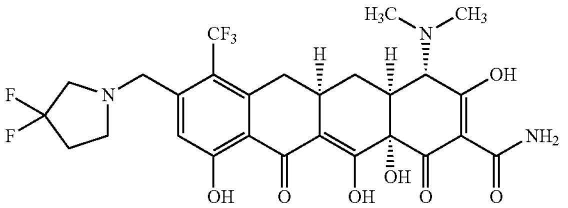

S25-11-199: $^1$H NMR (400 MHz, $CD_3OD$) δ 7.19 (s, 1 H), 4.67-4.63 (m, 1 H), 4.50-4.46 (m, 1 H), 4.06 (s, 1 H), 3.89-3.82 (m, 2 H), 3.68-3.62 (m, 2 H), 3.16-2.80 (m, 9 H), 2.69-2.48 (m, 3 H), 2.18-2.11 (m, 1 H), 1.60-1.50 (m, 1 H); MS (ESI) m/z 601.9 (M+H).

S25-11-200

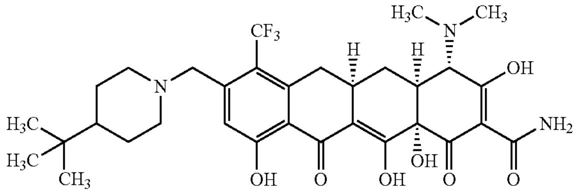

S25-11-200: $^1$H NMR (400 MHz, $CD_3OD$) δ 7.28 (s, 1 H), 4.61-4.56 (m, 1 H), 4.41-4.38 (m, 1 H), 4.14 (s, 1 H), 3.66-3.61 (m, 2 H), 3.19-2.99 (m, 11 H), 2.67-2.60 (m, 1 H), 2.28-2.24 (m, 1 H), 2.03-1.95 (m, 2 H), 1.71-1.61 (m, 3 H), 1.48-1.41 (m, 1 H), 0.93 (s, 9 H); MS (ESI) m/z 636.1 (M+H).

S25-11-201

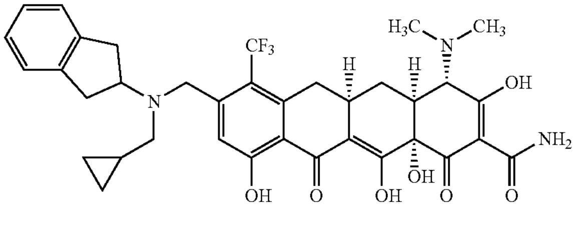

S25-11-201: $^1$H NMR (400 MHz, $CD_3OD$) δ 7.47-7.26 (m, 5 H), 4.68-4.58 (m, 3 H), 4.18 (s, 1 H), 3.56-3.45 (m, 4 H), 3.29-2.99 (m, 11 H), 2.69-2.61 (m, 1 H), 2.30-2.27 (m, 1 H), 1.72-1.63 (m, 1 H), 1.21-1.11 (m, 1 H), 0.82-0.77 (m, 2 H), 0.43-0.38 (m, 2 H); MS (ESI) m/z 682.3 (M+H).

S25-11-202

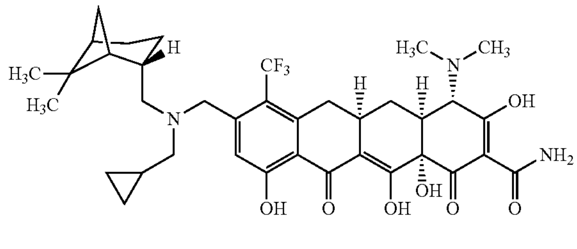

S25-11-202: $^1$H NMR (400 MHz, $CD_3OD$) δ 7.36 (s, 1 H), 4.70-4.63 (m, 2 H), 4.18 (s, 1 H), 3.53-3.48 (m, 1 H), 3.31-2.94 (m, 12 H), 2.69-2.57 (m, 2 H), 2.48-2.45 (m, 2 H), 2.32-2.25 (m, 1 H), 2.05-1.98 (m, 6 H), 1.70-1.67 (m, 1 H), 1.26-1.22 (m, 2 H), 1.18-1.14 (m, 1 H), 1.10-1.04 (m, 2 H), 0.88=0.84 (m, 3 H), 0.72-0.70 (m, 1 H), 0.54-0.49 (m, 2 H); MS (ESI) m/z 702.3 (M+H).

S25-11-203

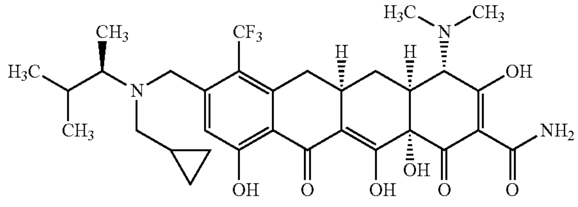

S25-11-203: $^1$H NMR (400 MHz, $CD_3OD$) δ 7.39, 7.29 (s, 1H total), 4.78-4.65 (m, 1 H), 4.36-4.34 (m, 1 H), 3.91-3.85 (m, 1 H), 3.46-3.40 (m, 1 H), 4.18 (s, 1 H), 3.31-2.98 (m, 11 H), 2.68-2.63 (m, 1 H), 2.32-2.25 (m, 1 H), 1.72-1.65 (m, 1 H), 1.46-1.41 (m, 3 H), 1.21-1.15 (m, 3 H), 1.08-1.02 (m, 4 H), 0.91-0.71 (m, 2 H), 0.60-0.40 (m, 2 H); MS (ESI) m/z 636.0 (M+H).

S25-11-204

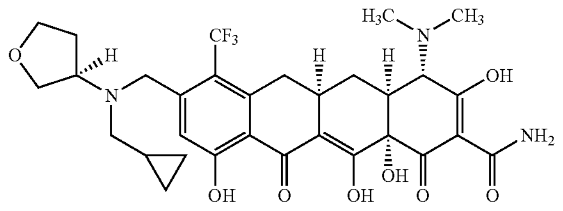

S25-11-204: $^1$H NMR (400 MHz, $CD_3OD$) δ 7.27 (s, 1 H), 4.69-4.50 (m, 2 H), 4.41-4.38 (m, 1 H), 4.24-4.10 (m, 3 H), 3.84-3.68 (m, 3 H), 3.21-2.96 (m, 10 H), 2.66-2.59 (m, 1 H), 2.42-2.33 (m, 2 H), 2.27-2.24 (m, 1 H), 1.69-1.63 (m, 1 H), 1.21-1.08 (m, 1 H), 0.87-0.73 (m, 2 H), 0.48-0.36 (m, 2 H); MS (ESI) m/z 636.2 (M+H).

S25-11-205

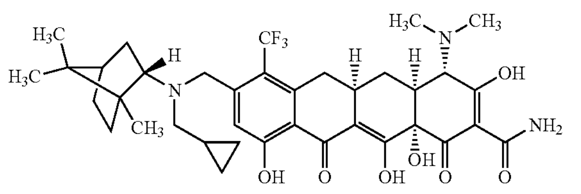

S25-11-205: $^1$H NMR (400 MHz, $CD_3OD$) δ 7.53 (s, 1 H), 5.07-5.03 (m, 1 H), 4.61-4.58 (m, 1 H), 4.17 (s, 1 H), 4.07-4.03 (m, 1 H), 3.21-2.69 (m, 11 H), 2.49-2.42 (m, 1 H), 2.31-2.27 (m, 1 H), 2.02-1.62 (m, 8 H), 1.33-1.28 (m, 3 H), 1.07-0.99 (m, 7 H), 0.97-0.91 (m, 2 H), 0.79-0.68 (m, 2 H); MS (ESI) m/z 702.4 (M+H).

S25-11-206

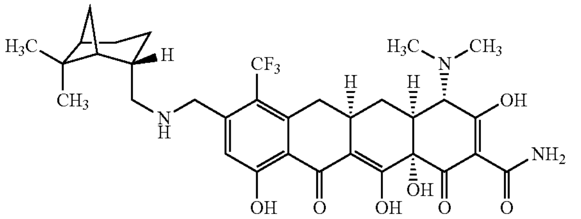

S25-11-206: $^1$H NMR (400 MHz, $CD_3OD$) δ 7.22 (s, 1 H), 4.46-4.43 (m, 1 H), 4.37-4.34 (m, 1 H), 4.15 (s, 1 H), 3.24-2.99 (m, 11 H), 2.67-2.46 (m, 3 H), 2.28-2.25 (m, 1 H), 2.18-1.98 (m, 6 H), 1.69-1.62 (m, 2 H), 1.28 (s, 3 H), 1.07 (s, 3 H); MS (ESI) m/z 648.3 (M+H).

S25-11-207

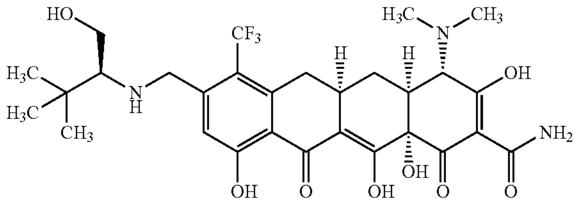

S25-11-207: $^1$H NMR (400 MHz, $CD_3OD$) δ 7.26 (s, 1 H), 4.73-4.69 (m, 1 H), 4.58-4.55 (m, 1 H), 4.16 (s, 1 H), 4.01-3.89 (m, 2 H), 3.20-2.98 (m, 10 H), 2.67-2.57 (m, 1 H), 2.28-2.25 (m, 1 H), 1.69-1.62 (m, 1 H), 1.11 (s, 9 H); MS (ESI) m/z 612.3 (M+H).

S25-11-208

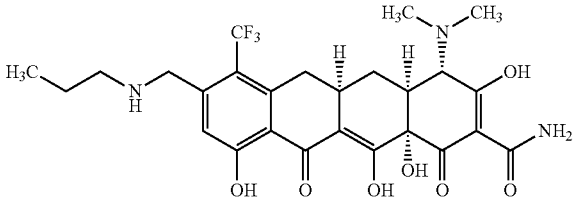

S25-11-208: $^1$H NMR (400 MHz, $CD_3OD$) δ 7.18 (s, 1 H), 4.48 (d, J=12.0 Hz, 1 H), 4.33 (d, J=14.0 Hz, 1 H), 4.14 (s, 1 H), 3.22-2.89 (m, 11 H), 2.70-2.59 (m, 1 H), 2.26-2.20 (m, 1 H), 1.85-1.75 (m, 3 H), 1.72-1.60 (m, 2 H), 1.11 (t, J=7.2 Hz, 3 H); MS (ESI) m/z 554.1 (M+H).

S25-11-209

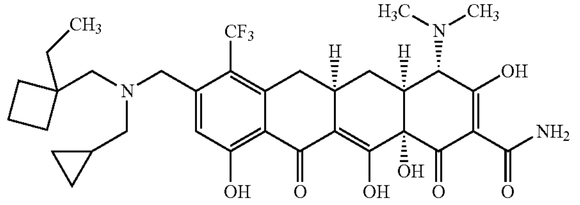

S25-11-209: $^1$H NMR (400 MHz, $CD_3OD$) δ 7.43, 7.39 (s, 1H total), 4.85-4.80 (m, 0.5 H), 4.71-4.65 (m, 1.5 H), 4.16 (s, 1 H), 3.24-2.97 (m, 13 H), 2.67-2.61 (m, 1 H), 2.31-2.25 (m, 1 H), 2.15-1.62 (m, 8 H), 1.40-1.15 (m, 1 H), 0.93-0.75 (m, 6 H), 0.58-0.45 (m, 2 H); MS (ESI) m/z 662.1 (M+H).

S25-11-210

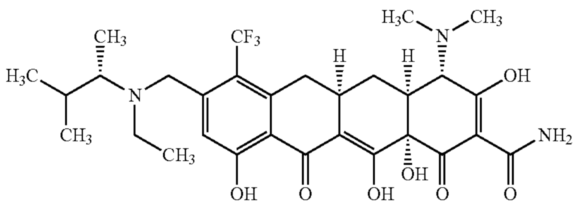

S25-11-210: $^1$H NMR (400 MHz, $CD_3OD$) δ 7.24 (s, 1 H), 4.76-4.64 (m, 1 H), 4.46-4.38 (m, 1 H), 4.12 (s, 1 H), 3.45-3.42 (m, 1 H), 3.18-2.94 (m, 11 H), 2.65-2.58 (m, 1 H), 2.33-2.19 (m, 2 H), 1.67-1.57 (m, 1 H), 1.36-1.22 (m, 6 H), 1.10-1.07 (m, 6 H); MS (ESI) m/z 610.1 (M+H).

EXAMPLE 26

Synthesis of Compounds Via Scheme 26

Scheme 26

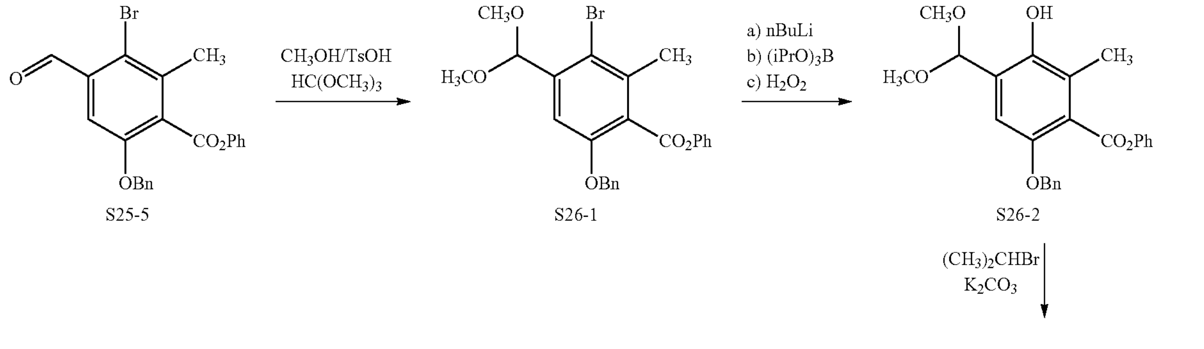

-continued

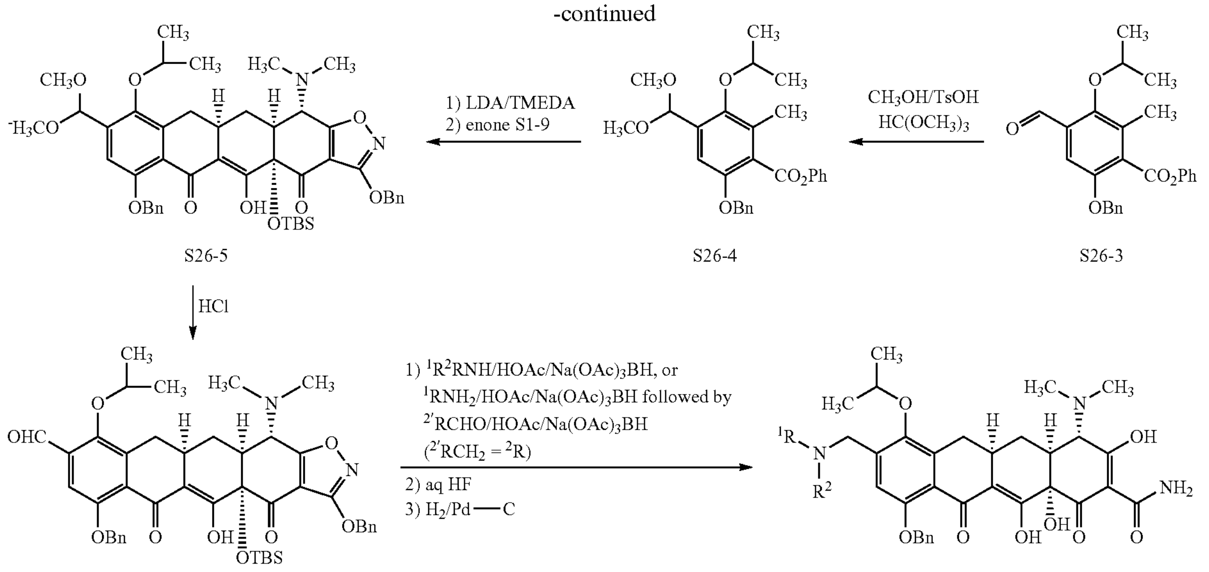

S26-5 S26-4 S26-3

S26-6 S26-7

The following compounds were prepared according to Scheme 25.

S26-1

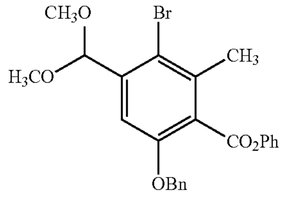

To a solution of compound. S25-5 (3.0 g, 7.06 mmol, 1.0 eq.) in MeOH (50 mL), was added trimethyl orthoformate (3.74 g, 7.06 mmol, 5.0 eq.) and p-TSA (67 mg, 0.353 mmol, 0.05 eq.). The resulting mixture was refluxed overnight. The solvent was evaporated, the residue was diluted with EtOAc (50 mL), the resulting solution was washed with sat. aq. $NaHCO_3$/brine (1:1, 50 mL). The organic phase was dried over $NaSO_4$, filtered and concentrated. The residue was purified with flash chromatography (200~300 mesh, PE/EA=100:1~50:1) to give the desired product S26-1 (3.3 g, 99%) as a white solid: $^1H$ NMR (400 MHz, $CDCl_3$): δ7.43 (d, J=6.8 Hz, 2 H), 7.37-7.30 (m, 6 H), 7.25-7.19 (m, 1 H), 7.07 (d, J=6.8 Hz, 2 H), 5.58 (s, 1 H), 5.18 (s, 2 H), 3.36 (s, 6 H), 2.51 (s, 3 H).

S26-2

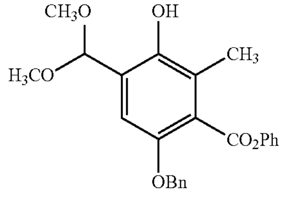

To a solution of S26-1 (471 mg, 1 mmol, 1.0 eq.) in anhydrous THF (5 mL) was added n-BuLi (2.5 M in hexane, 0.44 mL, 1.1 mmol, 1.1 eq.) slowly at −78° C. After stirred at −78° C. for 30 min, triisopropyl borate (0.46 ml, 2.0 mmol, 2.0 eq.) was added. After stirred at −78° C. for 4 h, acetic acid (0.165 mL, 3 mmol, 3.0 eq.) was added. while the resulting mixture was warmed up to 0° C., 30% $H_2O_2$ (0.27 mL, 2 mmol, 2.0 eq.) was added. The resulting mixture was stirred at rt overnight and then quenched with saturated aqueous $NaHSO_3$ solution (caution: till the starch iodide was negative). The resulting solution was extracted with EtOAc (50 mL). The organic phase was washed with saturated aqueous $NaHCO_3$ (30 mL), $H_2O$ (30 mL), brine (30 mL) and dried over $NaSO_4$ and filtered and then concentrated to give the crude product S26-2, which was used for next step directly.

S26-3

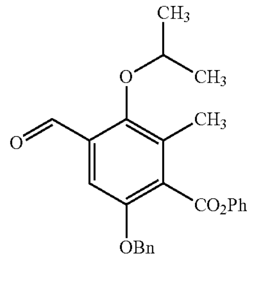

To a solution of S26-2 (1.0 mmol, 1.0 eq.) and $K_2CO_3$ (276 g, 2 mmol, 2.0 eq.) in MeCN (10 mL) was added 2-iodopropane (0.615 g, 5 mmol, 5.0 eq.). The resulting mixture was stirred at 80° C. overnight. The reaction mixture was filtered, the filtrate was concentrated. The residue was diluted with EtOAc (50 mL) and $H_2O$ (20 mL). The organic phase was separated, dried over $Na_2SO_4$, filtered and concentrated. The residue was purified with flash chromatography (200~300 mesh, PE/EA=100:1~50:1) to give the desired product S27-3 (140 mg, 34.6%) as a pale yellow solid. $^1H$ NMR (400 MHz, $CDCl_3$): δ10.30 (s, 1 H), 7.38-7.36 (m, 2 H), 7.33-7.27 (m, 6 H), 7.20-7.17 (m, 1 H), 7.02-7.00 (m, 2 H), 5.10 (s, 2 H), 4.12-4.08 (m, 1 H), 2.34 (s, 3 H), 1.29 (d, J=6.4 Hz, 6 H).

S26-4

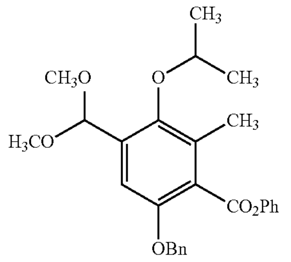

To a solution of compound S26-3 (0.25 g, 0.62 mmol, 1.0 eq.) in MeOH (20 mL), was added trimethyl orthoformate (0.33 g, 3.11 mmol, 5.0 eq.) and p-TSA (6 mg, 0.031 mmol, 0.05 eq.). The resulting mixture was refluxed overnight. The solvent was evaporated, the residue was diluted with EtOAc (50 mL) and saturated $NaHCO_3$/brine (1:1, 20 mL). The organic phase was separated, dried over $Na_2SO_4$, filtered and concentrated. The residue was purified by Prep-TLC to give the desired product S26-4 (200 mg, 72%) as a colorless oil: $^1H$ NMR (400 MHz, $CD_3OD$): δ7.45 (d, J=7.2 Hz, 2 H), 7.37-7.22 (m, 6 H), 7.11 (s, 1 H), 7.05 (d, J=7.6 Hz, 2 H), 5.54 (s, 1 H), 5.15 (s, 2 H), 4.27-4.21 (m, 1 H), 3.32 (s, 6 H), 2.33 (s, 3 H), 1.29 (d, J=6.0 Hz, 6 H).

S26-5

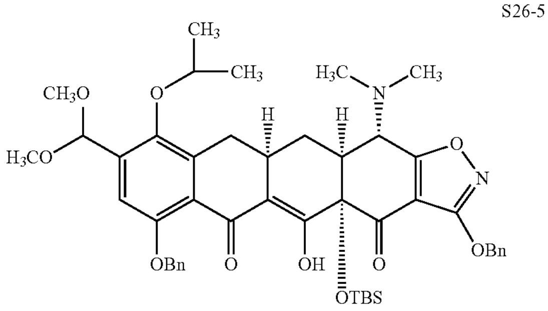

To a solution of diisopropylamine (0.17 mL, 1.2 mmol, 3.0 eq.) and TMEDA (0.3 mL, 2.0 mmol, 5.0 eq.) in THF (3 mL) was added n-BuLi in hexane (2.5 M, 0.48 mL, 1.2 mmol, 3.0 eq.) dropwise at −78° C. After stirred at −78° C. for 30 min, A solution of S26-4 (180 mg, 0.4 mmol, 1.0 eq.) in THF (2.0 mL) was added. The resulting dark red solution was then stirred at −78° C. for 30 min and then cooled to −100° C., A solution of enone (173 mg, 0.36 mmol, 0.9 eq.) in THF (2.0 mL) was added. The resulting reaction mixture was warmed up to −10° C. naturally over 30 min. The reaction mixture was quenched with saturated $NH_4Cl$ (50 mL) and then extracted with EtOAc (50 mL). The organic phase was separated, dried over $Na_2SO_4$, filtered and concentrated. The residue was purified by Prep-TLC to afford the desired product S26-5 (120 mg, 36%) as a pale yellow solid. $^1H$ NMR (400 MHz, $CDCl_3$): δ7.37-7.33 (m, 4 H), 7.26-7.17 (m, 5 H), 7.13-7.10 (m, 1 H), 6.97 (s, 1 H), 5.34 (s, 1 H), 5.22 (s, 2 H), 5.07 (dd, J=12.8, 12.4 Hz, 2 H), 4.02-3.94 (m, 2 H), 3.88 (d, J=10.8 Hz, 1 H), 3.21 (s, 3 H), 3.13 (s, 3 H), 0.72-2.70 (m, 1 H), 2.41-2.32 (m, 9 H), 2.00-1.96 (m, 1 H), 1.16 (dd, J=6.0, 6.0 Hz, 6 H), 0.68 (s, 9 H), 0.12 (s, 3 H), 0.09 (s, 3 H).

S26-6

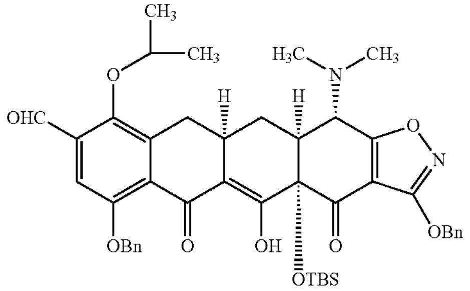

To a solution of compound S26-5 (120 mg, 0.143 mmol, 1.0 eq.) in THF (2 mL) was added 6N HCl (0.17 mL). The resulting reaction solution was stirred at rt for 1 h. The reaction mixture was diluted with EtOAc (40 mL). The resulting mixture was washed with saturated $NaHCO_3$ (10 mL), and then brine (10 mL). The organic phase was dried over $Na_2SO_4$, filtered and concentrated to give the desired crude product S26-6 as a yellow oil.

S26-7-1

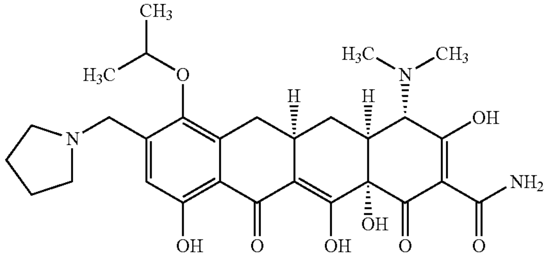

To a solution of crude compound S26-6 (0.0715 mmol, 1.0 eq.) in 1,2-dichloroethane (5 mL) were added pyrrolidine (25 μL; 0.286 mmol, 4.0 eq.) and acetic acid (13 μL, 0.215 mmol, 3.0 eq.). After stirring for 2 h at r.t., sodium triacetoxyborohydride (30 mg, 0.0.143 mmol, 2.0 eq.) was added. The resulting reaction mixture was still stirred at r.t. for 2 h. The reaction was quenched with saturated aqueous $NaHCO_3$ and brine (1:1, 20 mL) and then extracted with EtOAc (40 mL). The organic phase were dried over anhydrous $Na_2SO_4$, filtered and concentrated to give the crude product, which was used for the next step directly.

To the crude product in THF (8 mL) solution was added Aqueous HF (40%, 4 mL) in a polypropylene reaction vessel at 23° C. The reaction mixture was stirred vigorously at 23° C. overnight and poured into saturated aqueous $K_2HPO_4$ (150 mL). The reaction mixture was extracted with EtOAc (2×20 mL). The combined organic phases were dried over anhydrous $Na_2SO_4$, filtered and concentrated. The residue was used in the next step directly without further purification.

To the crude product in HCl/MeOH (4 N, 1 mL) and MeOH (5 mL) was added Pd/C (10 wt %, 50 mg) in one portion at 23° C. The reaction vessel was sealed and purged with $H_2$ gas (1 atm) for 1 h. The reaction mixture was then filtered through a small Celite pad. The filtrate was concentrated. The residue was purified by preparative HPLC to yield compound S26-7-1 (13.35 mg, 33.6% for 3 steps) as a yellow solid: $^1H$ NMR (400 MHz, $CD_3OD$) δ 7.06 (s, 1 H), 4.50 (d, J=12.8 Hz, 1 H), 4.33 (d, J=12.8 Hz, 1 H), 4.16-4.12 (m, 2 H), 3.54-3.45 (m, 2 H), 3.26-2.98 (m, 11 H), 2.36 (dd, J=14.4, 14.0 Hz, 1 H), 2.27-2.24 (m, 1 H), 2.16-2.10 (m, 2 H), 2.09-2.01 (m, 2 H), 1.65 (ddd, J=13.2, 13.2, 13.2 Hz, 1 H), 1.37 (d, J=6.0 Hz, 3 H), 1.20 (d, J=6.0 Hz, 3 H); MS (ESI) m/z 556.1 (M+H).

The following compounds were prepared similarly to S26-7-1.

S26-7-2

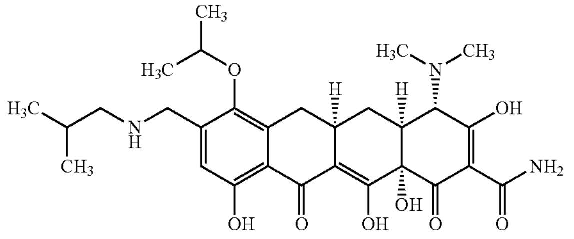

$^1$H NMR (400 MHz, $CD_3OD$) δ 7.01 (s, 1 H), 4.35 (d, J=14.0 Hz, 1 H), 4.18-4.09 (m, 3 H), 3.20-2.88 (m, 11 H), 2.36 (dd, J=14.4, 14.4 Hz, 1 H), 2.24 (ddd, J=13.6, 5.2, 2.8 Hz, 1 H), 2.09-2.02 (m, 1 H), 1.65 (ddd, J=14.0, 14.0, 14.0 Hz, 1 H), 1.35 (d, J=6.0 Hz, 3 H), 1.20 (d, J=6.0 Hz, 3 H), 1.03 (d, J=4.4 Hz, 6 H); MS (ESI)-m/z 558.1 (M+H).

S26-7-3

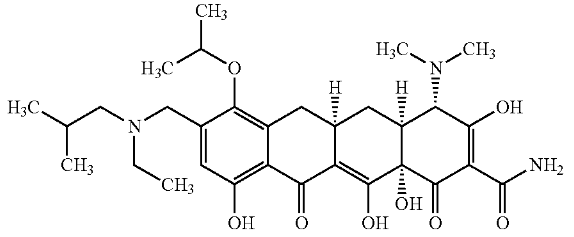

$^1$H NMR (400 MHz, $CD_3OD$) δ 7.04 (s, 1 H), 4.53, 4.32 (d, J=13.2 Hz, 1H total), 4.46, 4.21 (d, J=13.2 Hz, 1H total), 4.18-4.12 (m, 1 H), 4.10 (s, 1 H), 3.25-2.97 (m, 13 H), 2.44-2.35 (m, 1 H), 2.26-2.23 (m, 1 H), 2.17-2.06 (m, 1 H), 1.65 (ddd, J=13.2, 13.2, 13.2 Hz, 1 H), 1.39-1.35 (m, 6 H), 1.20 (t, J=7.2 Hz, 3 H), 1.03 (d, J=4.4 Hz, 3 H), 1.00-0.94 (m, 3 H); MS (ESI) m/z 586.1 (M+H).

S26-7-4

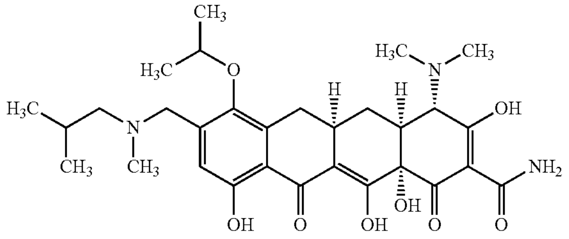

$^1$H NMR (400 MHz, $CD_3OD$) δ 7.05 (s, 1 H), 4.64, 4.08 (d, J=12.8 Hz, 1H total), 4.43, 4.35 (d, J=12.8 Hz, 1H total), 4.18-4.13 (m, 2 H), 3.19-2.99 (m, 11 H), 2.80 (s, 3 H), 2.39 (dd, J=14.4, 15.2 Hz, 1 H), 2.29-2.19 (m, 2 H), 1.66 (ddd, J=12.4, 12.0, 12.0 Hz, 1 H), 1.41-1.36 (m, 3 H), 1.23-1.17 (m, 3 H), 1.10-1.00 (m, 7 H); MS (ESI) m/z 572.1 (M+H).

EXAMPLE 27

Synthesis of Compounds Via Scheme 27

Scheme 27

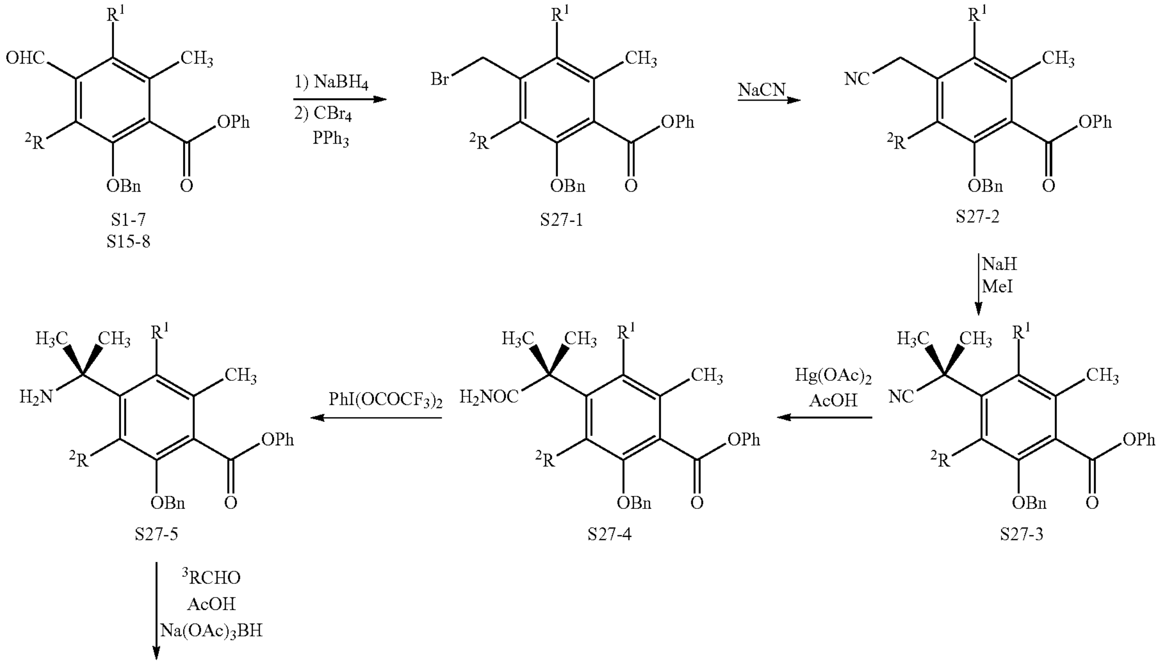

-continued

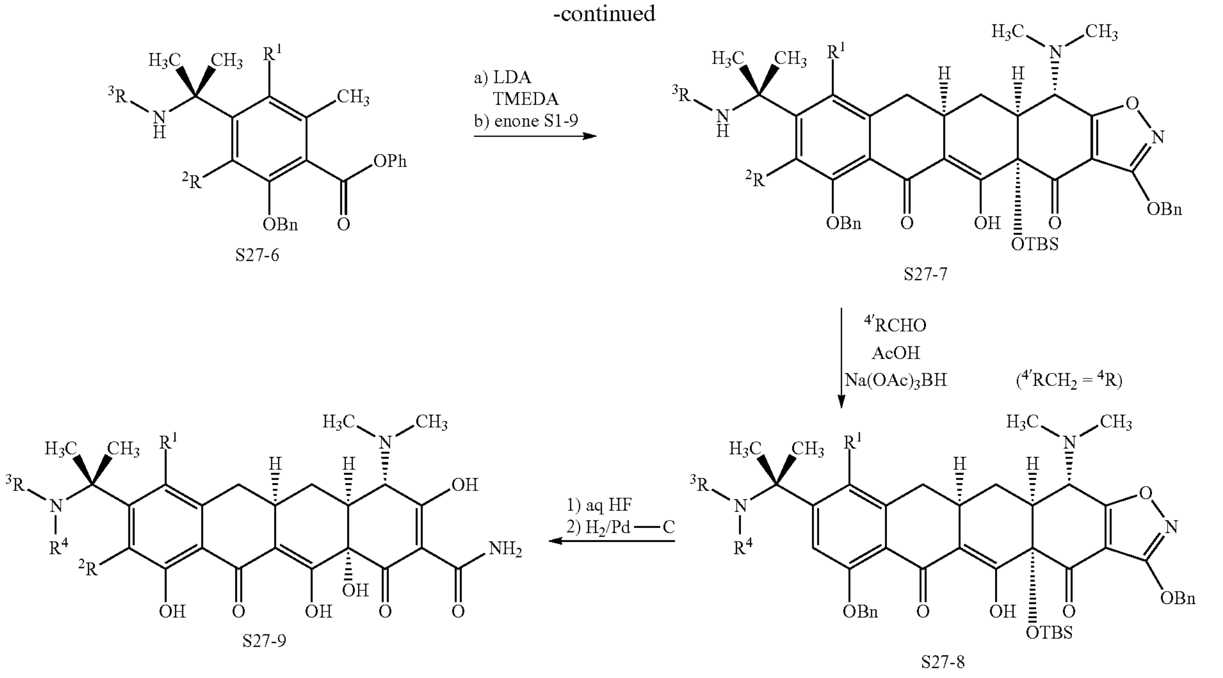

S27-6

S27-7

S27-8

S27-9

The following compounds were prepared according to Scheme 27.

S27-1-1

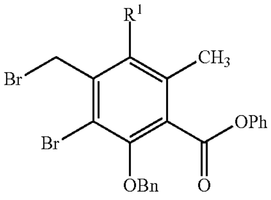

Sodium borohydride (0.387 g, 10.2 mmol) was added to a suspension of S1-7 (3.02 g, 6.81 mmol) in MeOH (30 mL). After bubbling ceased and complete solution was achieved, the reaction was quenched with $NaHCO_3$ (saturated, aqueous solution) and was extracted with EtOAc (3×). The combined EtOAc extracts were dried over sodium sulfate and concentrated. The material was dissolved in $CH_2Cl_2$ (20 mL) and triphenylphosphine (2.14 g, 8.17 mmol) was added. A solution of carbontetrabromide (2.71 g, 8.17 mmol) in $CH_2Cl_2$ (5 mL) was added dropwise. After stirring overnight, ~50% conversion was observed. Additional triphenylphosphine (2.14 g, 8.17 mmol) and carbontetrabromide (2.71 g, 8.17 mmol) were added. After 1 h, the reaction mixture was concentrated, and the residue was triturated with toluene (5 times). The combined toluene fractions were concentrated, and the material was purified by column chromatography (Biotage 100 g column, 2 to 20% EtOAc in Hexanes gradient). This gave 2.71 g (71%) of the product: $R_f$ 0.41 (10% EtOAc/hexanes); $^1$H NMR (400 MHz, $CDCl_3$) δ 7.50-7.46 (m, 2 H), 7.40-7.32 (m, 5 H), 7.29-7.22 (m, 1 H), 7.04 (d, J=8.7 Hz, 2 H), 5.11 (s, 2 H), 4.67 (d, J=2.3 Hz, 2 H), 2.35 (d, J=2.3 Hz, 3 H); MS (ESI) m/z 528.95, 530.95, 532.95 (M+Na).

S27-2-1

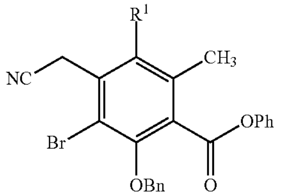

Sodium cyanide (0.104 g, 3.12 mmol) was added to a solution of S27-1-1 (1.08 g, 2.12 mmol) in DMF (5 mL) and water (1 mL). The reaction mixture was heated to 70° C. overnight. Upon cooling to rt, the reaction mixture was diluted with EtOAc and was washed with $NaHCO_3$ (saturated, aqueous solution, 2 times) water (2 times), and brine (1 time). The organics were dried over sodium sulfate, filtered and concentrated. The material was purified by column chromatography (Biotage 50 g column, 5 to 40% EtOAc in Hexanes gradient). This gave 0.82 g (85%) of the product as a white solid: $R_f$ 0.33 (20% EtOAc/hexanes); MS (ESI) m/z 476.05, 478.04 (M+Na).

S27-3-1

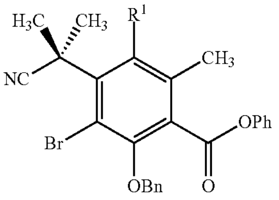

A solution of S27-2-1 (0.817 g, 1.80 mmol) was added to a suspension of sodium hydride (60% dispersion in mineral oil, 0.158 g, 3.96 mmol) in DMF (5 mL). After bubbling ceased (~5 min), iodomethane (0.247 mL, 3.96 mmol) was added. After 45 min, the reaction mixture was quenched with $NH_4Cl$ (saturated, aqueous solution) and was diluted with EtOAc. The layers were separated, and washed with water (3 times) and brine (1 time). The organics were dried over $Na_2SO_4$, filtered, and concentrated under reduced pressure. The material was purified by column chromatography (Biotage 50 g column, 5 to 40% EtOAc in Hexanes gradient). This gave 0.34 g (39%) of the product: $R_f$ 0.53 (20% EtOAc/hexanes); $^1H$ NMR (400 MHz, $CDCl_3$) δ 7.50-7.44 (m, 2 H), 7.40-7.30 (m, 5 H), 7.29-7.22 (m, 1 H), 7.03 (d, J=8.2 Hz, 2 H), 5.10 (s, 2 H), 2.33 (d, J=2.8 Hz, 3 H), 2.02 (d, J=4.1 Hz, 6 H); MS (ESI) m/z 504.06, 506.06 (M+Na).

S27-4-1

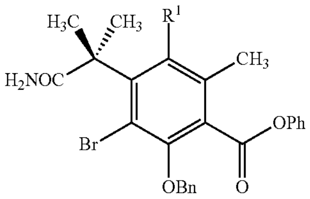

Compound S27-3-1 (0.927 g, 1.92 mmol) and mercury(II) acetate (609 mg, 1.92 mmol) were heated to 100° C. in acetic acid (25 mL). After heating overnight, the reaction mixture was heated to 120° C. After 8 h, heating continued overnight at 100° C. Upon cooling to rt, the reaction mixture was poured into ice water (100 mL). The resulting solid was collected by filtration and was washed with water (3 times). The solid was dissolved in $CH_2Cl_2$ and was dried over $Na_2SO_4$, filtered, and concentrated under reduced pressure. This gave 930 mg (97%) of the crude product as a white solid: $^1H$ NMR (400 MHz, $CDCl_3$) δ 7.50-7.42 (m, 2 H), 7.40-7.32 (m, 5 H), 7.28-7.24 (m, 1 H), 7.03 (d, J=8.2 Hz, 2 H), 5.55-5.35 (br s, 2 H), 5.08 (s, 2 H), 2.33 (d, J=2.7 Hz, 3 H), 1.79 (d, J=5.0 Hz, 6 H); MS (ESI) m/z 522.19, 524.19 (M+Na).

S27-5-1

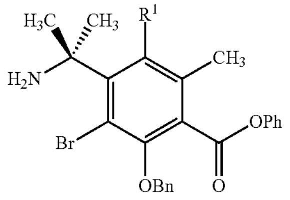

Bis-(trifluoroacetoxy)iodobenzene (178 mg, 0.414 mmol) was added to a solution of S27-4-1 (207 mg, 0.414 mmol) in acetonitrile (0.5 mL) and water (0.5 mL). After stirring overnight, the reaction mixture was diluted with water (5 mL) and was stirred for 30 min. The reaction mixture was diluted with $NaHCO_3$ (saturated, aqueous solution) and was extracted with EtOAc (3 times). The combined extracts were dried over $Na_2SO_4$, filtered, and concentrated under reduced pressure, yielding S27-5-1 which was used in the next step without purification: $^1H$ NMR (400 MHz, $CDCl_3$) δ 7.52-7.48 (m, 2 H), 7.40-7.30 (m, 5 H), 7.28-7.24 (m, 1 H), 7.06-7.02 (m, 2 H), 5.08 (s, 2 H), 2.31 (d, J=3.2 Hz, 3 H), 1.74 (d, J=4.6 Hz, 6 H); MS (ESI) m/z 472.19, 474.19 (M+H).

S27-5-2

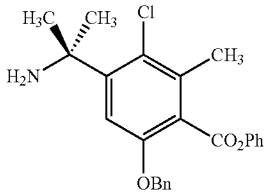

Prepared according to the methods of compound S27-5-1, starting from compound S15-8: $^1H$ NMR (400 MHz, $CDCl_3$) δ 7.46-7.40 (m, 2 H), 7.40-7.30 (m, 5 H), 7.28-7.20 (m, 2 H), 7.12-7.08 (m, 2 H), 5.16 (s, 2 H), 2.48 (s, 3 H), 2.04 (br s, 2 H), 1.61 (s, 6 H); MS (ESI) m/z 410.39 (M+H).

S27-6-1

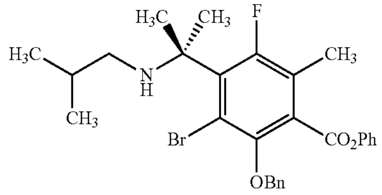

Isobutyraldehyde (0.029 mL, 0.32 mmol), acetic acid (0.036 mL, 0.64 mmol) and S27-5-1 (100 mg, 0.212 mmol) were stirred in 1,2-dichloroethane (2 mL). After 1 h, sodium triacetoxyborohydride (67.4 mg, 0.318 mmol) was added. After 1 h, the reaction mixture was diluted with $NaHCO_3$ (saturated, aqueous solution) and was extracted with $CH_2Cl_2$. The combined extracts were dried over $Na_2SO_4$, filtered, and concentrated under reduced pressure. The material was purified by column chromatography (Biotage 10 g column, 0 to 4% MeOH in $CH_2Cl_2$ gradient). This gave 77.8 mg (69%) of the product (~85% pure): $R_f$ 0.38 (5% MeOH/$CH_2Cl_2$); $^1H$ NMR (400 MHz, $CDCl_3$) δ 7.3-7.7 (m, 2 H), 7.40-7.32 (m, 5 H), 7.26-7.20 (m, 1 H), 7.03 (d, J=7.8 Hz, 2 H), 5.08 (s, 2 H), 2.31 (d, J=3.2 Hz, 3 H), 2.00 (d, J=6.9 Hz, 2 H), 1.69 (d, J=6.4 Hz, 6 H), 1.68-1.58 (m, 1 H), 0.86 (d, J=6.4 Hz, 6 H); MS (ESI) m/z 528.26, 530.26 (M+H).

S27-7-1

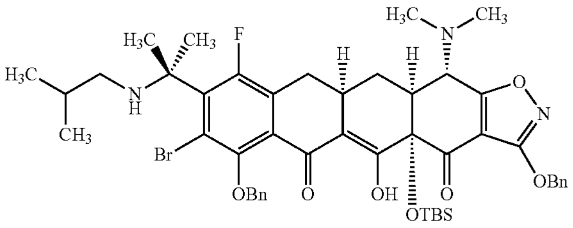

n-Butyllithium (0.127 mL, 2.2 M/hexanes, 0.279 mmol) was added to diisopropylamine (0.0395 mL, 0.279 mmol) in THF (5 mL) at −40° C. The reaction mixture was cooled to −78° C., and TMEDA (0.073 mL, 0.48 mmol) was added. A solution of compound S27-6-1 (77 mg, 0.15 mmol) in THF (1 mL) was added dropwise. Initially an orange colored solution formed, but the color faded as the solution was added. Additional lithium diisopropylamide (1.8 M solution, 0.155 mL, 0.279 mmol) was added, giving an orange color. The reaction was stirred at −78° C. for 5 min. A solution of enone S1-9 (58.4 mg, 0.121 mmol) in THF (0.5 mL) was added dropwise to the reaction mixture. The reaction was stirred from −78° C. to −20° C. for 45 minutes, quenched by saturated aqueous $NH_4Cl$, and extracted with EtOAc (3 times). The combined EtOAc extracts were dried (sodium sulfate) and concentrated to yield the crude product, which was purified by preparative reverse phase HPLC on a Waters Autopurification system using a Sunfire Prep C18 OBD column [5 μm, 19×50 mm; flow rate, 20 mL/min; Solvent A: $H_2O$ with 0.1% $HCO_2H$; Solvent B: MeOH with 0.1% $HCO_2H$; gradient: 80→100% B over 20 min; mass-directed fraction collection]. Fractions containing the desired product were collected and concentrated to give 14 mg of compound S27-7-1 (13%): $^1$H NMR (400 MHz, $CDCl_3$) δ 16.0-15.8 (br s, 1 H), 7.58-7.45 (m, 4 H), 7.40-7.20 (m, 6 H), 5.36 (s, 2 H), 5.00-4.85 (m, 2 H), 3.93 (d, J=10.4 Hz, 1 H), 3.26-3.18 (m, 1 H), 3.07-2.96 (m, 1 H), 2.60-2.34 (m, 9 H), 2.19-2.10 (br m, 1 H), 2.01 (d, J=4.9 Hz, 2 H), 1.76-1.62 (m, 7 H), 0.94-0.74 (m, 15 H), 0.27 (s, 3 H), 0.13 (s, 3 H); MS (ESI) m/z 916.49, 918.47 (M+H).

S27-9-1

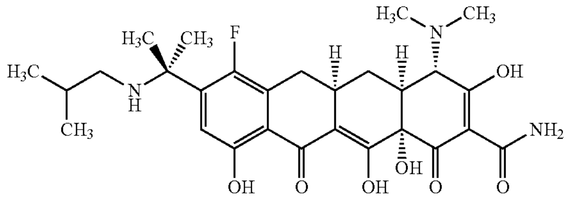

A solution of compound S27-7-1 (14.2 mg, 0.0155 mmol) in 1,4-dioxane (1 mL) was treated with HF (0.40 mL, 48-50% aqueous solution). After stirring overnight, the mixture was poured into a solution of $K_2HPO_4$ (4.8 g) in water (20 mL). This mixture was extracted with EtOAc (3 times). The combined extracts were dried over sodium sulfate, filtered, and concentrated under reduced pressure. The material was dissolved in MeOH (1 mL), 1,4-dioxane (1 mL), and 0.5 N HCl/MeOH (0.2 mL). 10% Pd—C (Degussa, 5 mg) was added, and an atmosphere of hydrogen was introduced. After 5 hrs, the reaction mixture was filtered through Celite and concentrated under reduced pressure. The crude product was purified by preparative reverse phase HPLC on a Waters Autopurification system using a Polymerx 10μ RP-γ100 R column [30×21.20 mm, 10 micron, solvent A: 0.05 N HCl, solvent B: MeOH, gradient elution with 0→100% B over 20 min; mass-directed fraction collection]. Fractions containing the desired product were concentrated to remove MeOH and were freeze-dried from 0.05N HCl in water/$CH_3CN$ to yield 2.4 mg (25%) of compound S27-9-1: $^1$H NMR (400 MHz, $CD_3OD$) δ 6.92 (d, J=6.4 Hz, 1 H), 4.15 (s, 1 H), 3.26-2.96 (m, 9 H), 2.68-2.56 (m, 2 H), 2.40-2.24 (m, 2 H), 2.02-1.94 (m, 1 H), 1.83 (s, 6 H), 1.68-1.58 (m, 1 H), 0.99 (dd, J=6.9, 3.7 Hz, 6 H); MS (ESI) m/z 546.21 (M+H).

The following compounds were prepared according to the methods of preparing S27-9-1.

S27-9-2

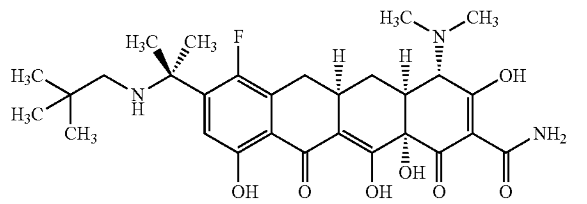

S27-9-2: $^1$H NMR (400 MHz, $CD_3OD$) δ 6.96 (d, J=6.4 Hz, 1 H), 4.16 (s, 1 H), 3.26-2.96 (m, 9 H), 2.61 (dd, J=18.4, 5.5 Hz, 2 H), 2.40-2.26 (m, 2 H), 1.87 (s, 6 H), 1.70-1.58 (m, 1 H), 1.01 (s, 9 H); MS (ESI) m/z 560.26 (M+H).

S27-8-1

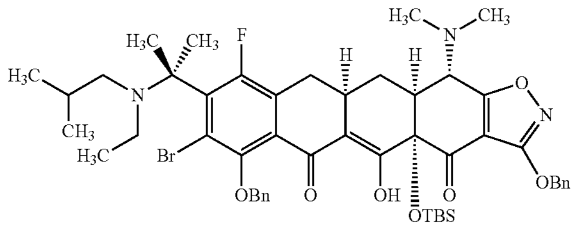

Acetaldehyde (0.25 mL, 4.46 mmol) and sodium triacetoxyborohydride (60 mg, 0.28 mmol) were added to a solution of S27-9-1 (78.5 mg, 93.7 mmol) in acetic acid (0.5 mL) and $CH_2Cl_2$ (5 mL). After stirring overnight, additional acetaldehyde (0.25 mL, 4.46 mmol) and sodium triacetoxyborohydride (120 mg, 0.56 mmol) were added. After 3 h, the reaction mixture was diluted with pH 7.0 phosphate buffer and was extracted with $CH_2Cl_2$ (3 times). The combined extracts were dried over sodium sulfate, filtered, and concentrated under reduced pressure. The material was used directly in the next step: MS (ESI) m/z 866.78 (M+H).

S27-9-3

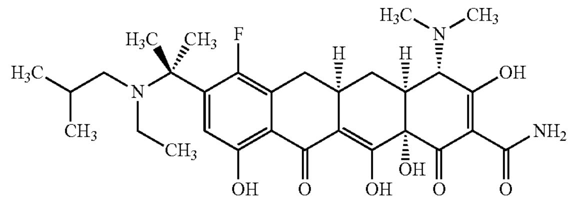

A solution of compound S27-8-1 (81 mg, 0.094 mmol) in 1,4-dioxane (1 mL) was treated with HF (0.40 mL, 48-50% aqueous solution). After 30 min, the mixture was poured into a solution of $K_2HPO_4$ (4.8 g) in water (20 mL). This mixture was extracted with EtOAc (2 times). The combined extracts were dried over sodium sulfate, filtered, and concentrated under reduced pressure. The material was dissolved in MeOH (2 mL), 1,4-dioxane (2 mL), and 0.5 N HCl/MeOH (0.2 mL). 10% Pd—C (Degussa, 5 mg) was added, and an atmosphere of hydrogen was introduced. After 2 hrs, the reaction mixture was filtered through Celite and concentrated under reduced pressure. The crude product was purified by preparative reverse phase HPLC on a Waters Autopurification system using a Polymerx 10μ RP-γ100 R column [30×21.20 mm, 10 micron, solvent A: 0.05 N HCl, solvent B: MeOH, gradient elution with 20→100% B over 20 min; mass-directed fraction collection]. Fractions containing the desired product were concentrated to remove MeOH and were freeze-dried from 0.05N HCl in water/$CH_3CN$ to yield 7.7 mg (13%) of compound S27-9-3: $^1$H NMR (400 MHz, $CD_3OD$) δ 7.13 (d, J=2.8 Hz, 1 H), 4.16 (s, 1 H), 3.64-3.52 (m, 1 H), 3.42-3.30 (m, 1 H), 3.28-2.94 (m, 11 H), 2.42-2.27 (m, 2 H), 2.04-1.85 (m, 7 H), 1.70-1.59 (m, 1 H), 1.43 (dd, J=15.1, 7.3 Hz, 3 H), 0.99 (dd, J=6.4, 5.9 Hz, 3 H), 0.86 (dd, J=16.0, 6.0 Hz, 3 H); MS (ESI) m/z 574.33 (M+H).

The following compounds were prepared according to the methods of preparing S27-9-3.

S27-9-4

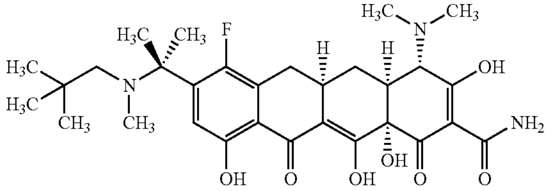

S27-9-4: $^1$H NMR (400 MHz, $CD_3OD$) δ 7.12 (d, J=4.6 Hz, 1 H), 4.16 (s, 1 H), 3.26-2.88 (m, 16 H), 2.42-2.24 (m, 2 H), 1.92 (s, 3 H), 1.88 (s, 1 H), 1.70-1.58 (m, 1 H), 1.00-0.94 (m, 9 H); MS (ESI) m/z 574.32 (M+H).

S27-9-5

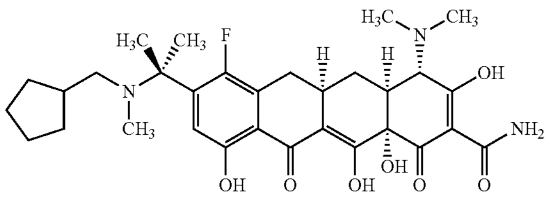

S27-9-5: $^1$H NMR (400 MHz, $CD_3OD$) δ 7.07 (d, J=4.6 Hz, 1 H), 4.17 (s, 1 H), 3.26-2.95 (m, 12 H), 2.84-2.72 (m, 1 H), 2.43-2.16 (m, 3 H), 1.98-1.80 (m, 9 H), 1.74-1.44 (m, 5 H), 1.20-1.06 (m, 1 H), 1.00-0.84 (m, 1 H); MS (ESI) m/z 586.33 (M+H).

S27-9-6

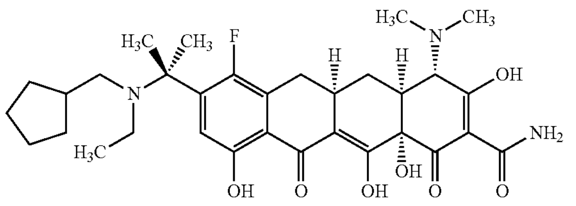

SX-9-6: $^1$H NMR (400 MHz, $CD_3OD$) δ 7.13 (d, J=6.4 Hz, 1 H), 4.17 (s, 1 H), 3.64-3.52 (m, 1 H), 3.45-3.32 (m, 1 H), 3.30-2.95 (m, 9 H), 2.43-2.26 (m, 2 H), 2.26-2.10 (m, 1 H), 1.98-1.76 (m, 9 H), 1.74-1.54 (m, 6 H), 1.50-1.40 (m, 3 H), 1.28-1.16 (m, 1 H), 1.00-0.84 (m, 1 H); MS (ESI) m/z 600.40 (M+H).

S27-9-7

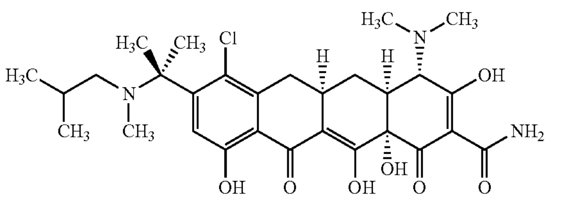

S27-9-7: $^1$H NMR (400 MHz, $CD_3OD$) δ 7.23 (s, 1 H), 4.20 (s, 1 H), 3.50-3.40 (m, 1 H), 3.26-2.95 (m, 12 H), 2.70-2.52 (m, 1 H), 2.48-2.30 (m, 2 H), 2.22-2.08 (m, 1 H), 2.06-1.90 (m, 6 H), 1.72-1.58 (m, 1 H), 1.08-0.99 (m, 6 H); MS (ESI) m/z 576.33 (M+H).

EXAMPLE 28

Synthesis of Compounds Via Scheme 28

Scheme 28

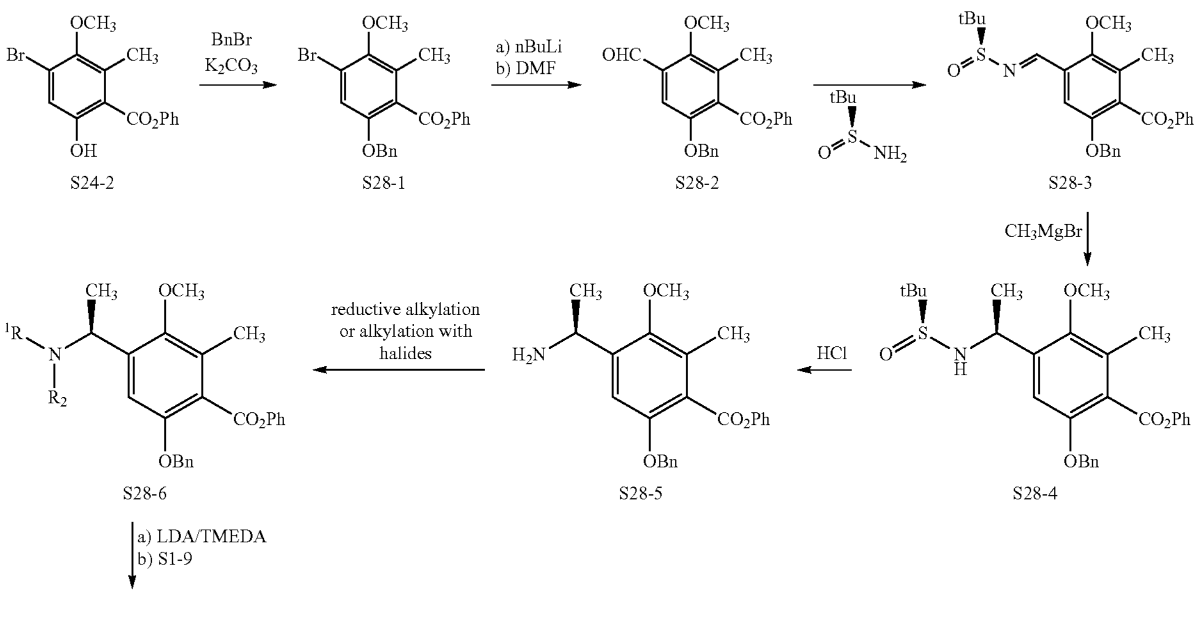

S24-2 S28-1 S28-2 S28-3 S28-4 S28-5 S28-6

-continued

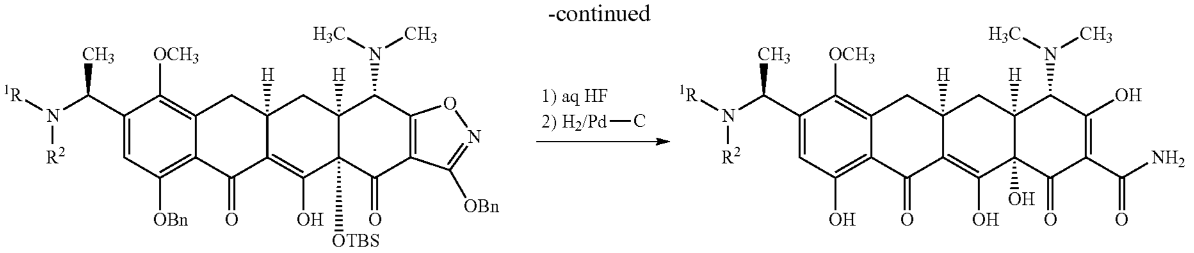

S28-7 S28-8

The following compounds were prepared according to Scheme 28.

S28-1

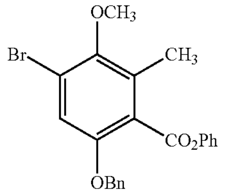

Benzylbromide (0.687 mL, 5.78 mmol, 1.1 equiv) and $K_2CO_3$ powder (1.09 g, 7.88 mmol, 1.5 equiv) were added to a solution of compound S24-2 (1.772 g, 5.25 mmol, 1.0 equiv) in acetone (10 mL). The mixture was stirred at rt overnight. The reaction mixture was filter through celite pad to remove most of the solid. Solvents were evaporated and the residue was dissolved in a mixture of EtOAc (40 mL) and water (1:1). The organic layer was separated, and the aqueous layer was extracted with EtOAc (10 mL×2). The combined organic phase was dried over anhydrous magnesium sulfate, filtered, and concentrated. The residue was purified by flash column chromatography (5% to 20% EtOAc/hexanes) to afford the desired product S28-1 as white solid (2.213 g, 98%): $^1$H NMR (400 MHz, $CDCl_3$) δ 7.49-7.33 (m, 7 H), 7.26-7.22 (m, 1 H), 7.15-7.04 (m, 3 H), 5.10 (s, 2 H), 3.79 (s, 3 H), 2.42 (s, 3 H); MS (ESI) m/z 449.13 (M+Na).

S28-2

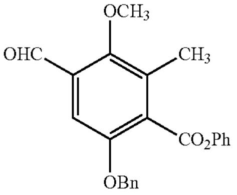

A solution of n-BuLi in hexanes (15.64 mL, 2.5 M, 39.1 mmol, 1.1 equiv) was added dropwise to a solution of compound S28-1 (15.18 g, 35.54 mmol, 1.0 equiv) in THF (100 mL) at −100° C. under a $N_2$ atmosphere. The resulting red solution was stirred at −100° C. for 5 min and then DMF (6.85 mL, 88.9 mmol, 2.5 equiv.) was added dropwise, slowly warmed to 0° C. in 1 hr. Saturated aqueous $NH_4Cl$ was added. The resulting mixture was extracted three times with EtOAc (50 mL×3). The combined EtOAc extracts were washed with brine, dried (sodium sulfate), and concentrated. Purification of the residue by flash chromatography gave compound S28-2 (9.50 g, 71%) as white solid: $^1$H NMR (400 MHz, $CDCl_3$) δ 10.38 (d, J=2.3 Hz, 1 H), 7.46-7.41 (m, 2 H), 7.41-7.31 (m, 5 H), 7.29-7.24 (m, 2 H), 7.11-7.06 (m, 2 H), 5.17 (d, J=1.4 Hz, 2 H), 3.88 (d, J=2.3 Hz, 3 H), 2.42 (d, J=1.8 Hz, 3 H); MS (ESI) m/z 399.22 (M+Na).

S28-3

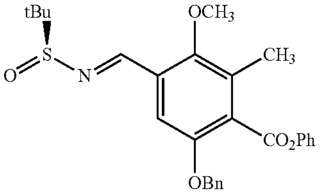

The compound S28-2 (595.6 mg, 1.583 mmol, 1.0 eq.) was dissolved in THF (8 mL), and (S)-(−)-2-methyl-2-propane-sulfinamide (217.5 mg, 1.793 mmol, 1.1 eq.) was added. $Ti(OEt)_4$ (0.371 mL, 1.793 mmol, 1.1 eq.) was added slowly. After stirring overnight, the reaction mixture was poured into brine (10 mL) with stirring and was then filtered through a Celite pad. The resulting solution was extracted twice with ethyl acetate (10 mL). The combined organic extracts were washed with brine, dried over sodium sulfate, and concentrated to give the crude intermediate. Purification of the residue by flash chromatography gave compound S28-3 (647 mg, 85.2%) as an orange oil: $^1$H NMR (400 MHz, $CDCl_3$) δ 8.90 (s, 1 H), 7.47-7.40 (m, 3 H), 7.39-7.28 (m, 4 H), 7.27-7.21 (m, 1 H), 7.18-7.13 (m, 1 H), 7.12-7.07 (m, 2 H), 5.09 (d, J=3.1 Hz, 2 H), 3.78 (s, 3 H), 2.40 (s, 3 H), 1.24 (s, 9 H); MS (ESI) m/z 480.33 (M+H).

S28-4

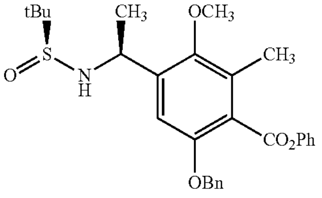

Methylmagnesium bromide (3.0M solution in $Et_2O$, 0.367 mL, 1.10 mmol) was added to a −48° C. solution of S28-3 (264 mg, 0.550 mmol) in $CH_2Cl_2$ (3.5 mL). After 2 h, the solution was allowed to slowly warm to rt and stir overnight. The reaction was quenched with $NH_4Cl$ (saturated, aqueous solution) and was extracted with EtOAc (1 time). The EtOAc extracts were washed with brine (1 time), dried over sodium sulfate, filtered and concentrated. The material was purified by column chromatography (Biotage 10 g column, 50 to 100% EtOAc in Hexanes gradient). This gave 179 mg (66%)

of product S28-4 as a white solid: $R_f$ 0.14 (70% EtOAc/hexanes); $^1$H NMR (400 MHz, $CDCl_3$) δ 7.43-7.28 (m, 7 H), 7.26-7.20 (m, 1 H), 7.10-7.05 (m, 2 H), 6.86 (s, 1 H), 5.13-4.92 (m, 3 H), 3.77 (s, 3 H), 3.31 (d, J=2.8 Hz, 1 H), 2.38 (s, 3 H), 1.43 (d, J=6.9 Hz, 3 H), 1.18 (s, 9 H); MS (ESI) m/z 496.34 (M+H).

S28-5

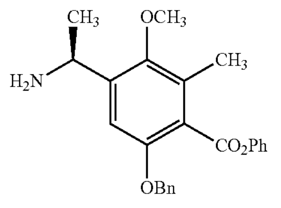

Compound S28-4 (179 mg, 0.361 mmol) was treated with 0.5M HCl in MeOH (5 mL). After 1 h, the reaction mixture was concentrated under reduced pressure. The material was used directly in the next step as the hydrochloride salt: MS (ESI) m/z 392.30 (M+H).

S28-6-1

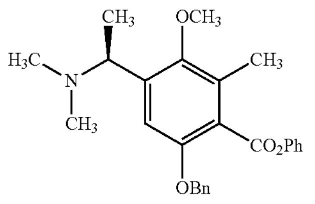

Sodium triacetoxyborohydride (76 mg, 0.36 mmol) was added to a solution of S28-5 (47 mg, 0.12 mmol) and formaldehyde (37% aqueous solution, 0.5 mL) in AcOH (0.5 mL) and $CH_2Cl_2$ (3 mL). After 30 min, the solution was diluted with EtOAc and was washed with $NaHCO_3$ (saturated, aqueous solution, 2 times) and brine (1 time). The organics were dried over sodium sulfate, filtered and concentrated. The material was purified by column chromatography (Biotage 10 g column, 0 to 10% MeOH in $CH_2Cl_2$ gradient). This gave 36.8 mg (73%) of product S28-6-1 as a thick oil: $R_f$ 0.40 (10% MeOH/$CH_2Cl_2$); $^1$H NMR (400 MHz, $CDCl_3$) δ 7.47-7.43 (m, 2 H), 7.39-7.28 (m, 5 H), 7.28-7.22 (m, 1 H), 7.12-7.06 (m, 2 H), 7.06 (s, 1 H), 5.14 (dd, J=11.4, 2.8 Hz, 2 H), 3.71 (s, 3 H), 3.64-3.56 (m, 1 H), 2.39 (s, 3 H), 2.24 (s, 6H), 1.32 (d, J=6.4 Hz, 3 H); MS (ESI) m/z 420.33 (M+H).

S28-6-2

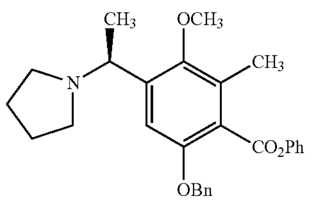

1,4-Dibromobutane (0.0285 mL, 0.240 mmol) was added to a solution of S28-5 (94 mg, 0.24 mmol) and triethylamine (0.134 mL, 0.960 mmol) in $CH_3CN$ (3 mL), and the reaction mixture was heated to 130° C. (sealed). After 30 min, additional 1,4-dibromobutane (0.028 mL, 0.24 mmol) was added and heating was continued at 130° C. After 15 min, additional 1,4-dibromobutane (0.20 mL, 1.7 mmol) was added and heating was continued at 130° C. After 20 min, the reaction mixture was diluted with EtOAc and was washed with $NaHCO_3$ (saturated, aqueous solution, 2 times) and brine (1 time). The organics were dried over sodium sulfate, filtered and concentrated. The material was purified by column chromatography (Biotage 10 g column, 0 to 10% MeOH in $CH_2Cl_2$ gradient). This gave 48.7 mg (46%) of product S28-6-2 as a thick oil: $^1$H NMR (400 MHz, $CDCl_3$) δ 7.48-7.39 (m, 2 H), 7.37-7.26 (m, 5 H), 7.26-7.18 (m, 1 H), 7.12-7.04 (m, 3 H), 5.13 (s, 2 H), 3.38 (s, 3 H), 3.66-3.56 (m, 1 H), 2.57-2.47 (m, 2 H), 2.44-2.34 (m, 5 H), 1.80-1.68 (m, 4 H), 1.38-1.30 (m, 3 H); MS (ESI) m/z 446.73 (M+H).

S28-7-1

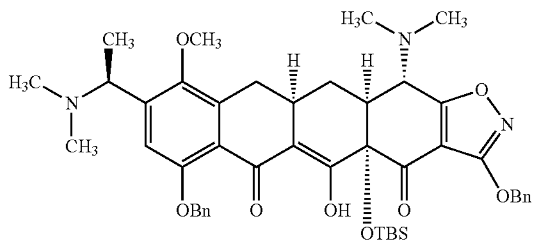

n-Butyllithium (2.5 M/hexanes, 0.876 mL, 0.219 mmol) was added to diisopropylamine (0.310 mL, 0.219 mmol) in THF (3 mL) at −40° C. The reaction mixture was cooled to −78° C., and TMEDA (0.048 mL, 0.32 mmol) was added. A solution of compound S28-6-1 (36.8 mg, 0.0877 mmol) in THF (0.5 mL) was added dropwise. The reaction was stirred at −78° C. for 15 min. A solution of enone S1-9 (38.5 mg, 0.0800 mmol) in THF (0.5 mL) was added dropwise to the reaction mixture. The reaction was stirred from −78° C. to −20° C. for 1 h, quenched by saturated aqueous $NH_4Cl$, and extracted with EtOAc (1 time). The combined EtOAc extracts were washed with water (2 times) and brine (1 time), dried (sodium sulfate) and concentrated. The material was purified by column chromatography (Biotage 10 g column, 0 to 10% MeOH in $CH_2Cl_2$ gradient). This gave 31.4 mg (49%) of product S28-7-1 as a yellow solid: $^1$H NMR (400 MHz, $CDCl_3$) δ 16.2 (s, 1 H), 7.53-7.45 (m, 4 H), 7.40-7.28 (m, 5 H), 7.27-7.22 (m, 1 H), 7.09 (s, 1 H), 5.35 (s, 2 H), 5.19 (q, J=12.8 Hz, 2 H), 4.02 (d, J=10.4 Hz, 1 H), 3.66 (s, 3 H), 3.52-3.46 (m, 1 H), 3.26 (dd, J=15.9, 4.9 Hz, 1 H), 2.99-2.89 (m, 1 H), 2.55-2.42 (m, 9 H), 2.22-2.10 (m, 7 H), 1.34-1.20 (m, 3 H), 0.83 (s, 9 H), 0.27 (s, 3 H), 0.13 (s, 3 H); MS (ESI) m/z 808.55 (M+H).

S28-8-1

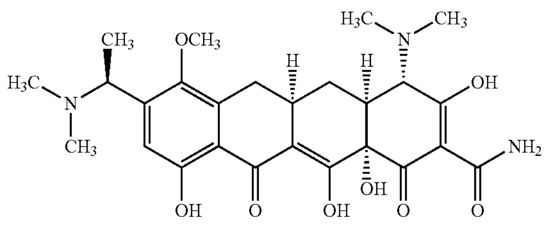

A solution of compound S28-7-1 (31.4 mg, 0.0389 mmol) in 1,4-dioxane (1 mL) was treated with HF (0.40 mL, 48-50% aqueous solution). After stirring overnight, the mixture was poured into a solution of $K_2HPO_4$ (4.8 g) in water (20 mL).

This mixture was extracted with EtOAc (2 times). The combined extracts were dried over sodium sulfate, filtered, and concentrated under reduced pressure. The material was dissolved in MeOH and 0.5 M HCl in MeOH (2 mL) and was concentrated under reduced pressure. The material was dissolved in MeOH (2 mL) and 1,4-dioxane (2 mL). 10% Pd—C (Degussa, 5 mg) was added, and an atmosphere of hydrogen was introduced. After 1 h, the reaction mixture was filtered through Celite and concentrated under reduced pressure. The crude product was purified by preparative reverse phase HPLC on a Waters Autopurification system using a Polymerx 10μ RP-γ 100 R column [30×21.20 mm, 10 micron, solvent A: 0.05 N HCl, solvent B: $CH_3CN$, gradient elution with 0→100% B over 20 min; mass-directed fraction collection]. Fractions containing the desired product were freeze-dried to yield 18 mg (79%) of compound SX-6-1: $^1H$ NMR (400 MHz, $CD_3OD$) 7.01 (s, 1 H), 4.67 (q, J=6.9 Hz, 1 H), 4.13 (s, 1 H), 3.80 (s, 3 H), 3.24-2.94 (m, 12 H), 2.75 (s, 3 H), 2.44-2.34 (m, 1 H), 2.33-2.24 (m, 1 H), 1.76-1.59 (m, 4 H); MS (ESI) m/z 516.13 (M+H).

S28-8-2

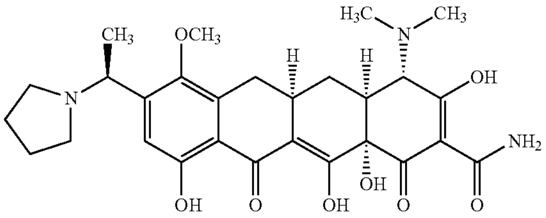

Prepared from S28-7-2 according to the methods of compound S28-8-1: $^1H$ NMR (400 MHz, $CD_3OD$) δ 7.07 (s, 1 H), 4.65 (q, J=6.9 Hz, 1 H), 4.13 (s, 1 H), 3.89-3.81 (m, 1 H), 3.77 (s, 3 H), 3.40-3.31 (m, 1 H), 3.29-2.88 (m, 12 H), 2.44-2.32 (m, 1 H), 2.31-2.03 (m, 3 H), 2.02-1.92 (m, 1 H), 1.76-1.58 (m, 4 H); MS (ESI) m/z 542.1 (M+H).

EXAMPLE 29

Synthesis of Compounds Via Scheme 29

Scheme 29

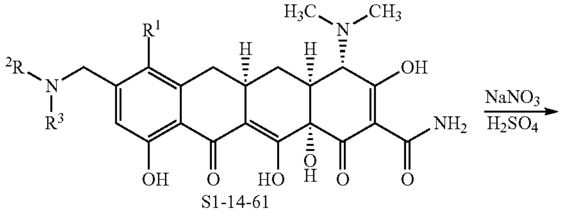

S1-14-61
S2-4-14
S2-4-28
S2-4-50

-continued

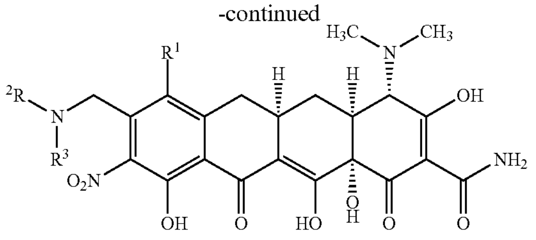

S29-1

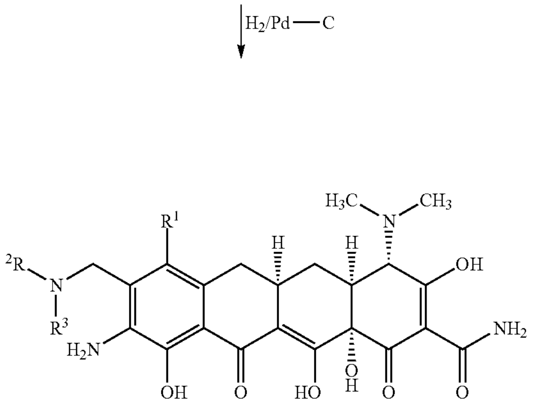

S29-2

The following compounds were prepared according to Scheme 29.

S29-2-1

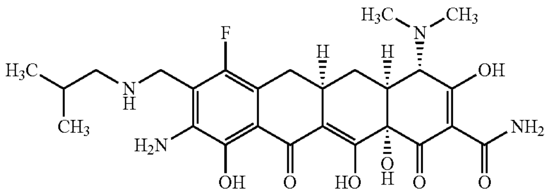

To a solution of S2-4-14 (18 mg, 0.03 mmol) in concentrated $H_2SO_4$ (1 mL) was added sodium nitrate solution (0.07 mL of 0.5 M concentrated $H_2SO_4$ solution, 0.04 mmol) at 0° C. The mixture was stirred for 20 min and then transferred dropwise to a stirring diethyl ether solution (100 mL). The yellow precipitation was filtered with celite and washed with ether (30 mL). The precipitation was then flashed with methanol (30 mL) and concentrated.

To the residue in MeOH/dioxane solution (4:1, 5 mL) was added palladium on carbon (8 mg, 10 wt %) and HCl in MeOH (0.5 N, 0.1 mL). The reaction was stirred under $H_2$ (balloon) at 25° C. for 60 min. The mixture was filtered through a small Celite plug and flashed with MeOH. The filtrate was concentrated to yield the crude product. Preparative reverse phase HPLC purification on a Waters Autopurification system using a Phenomenex Polymerx 10μ RP-$_1$ 100A column [10 μm, 150×21.20 mm; flow rate, 20 mL/min; Solvent A: 0.05 N HCl/water; Solvent B: MeOH; injection volume: 2.9 mL (0.05 N HCl/Water); gradient: 0→100% B over 25 min; mass-directed fraction collection]. Fractions with the desired MW, eluting at 13.6-15.5 min, were collected and freeze-dried to yield 10.0 mg of S29-2-1: $^1H$ NMR (400 MHz, $CD_3OD$) δ 4.30 (s, 2 H), 4.07 (s, 1 H), 3.04 (s, 3 H), 2.97

(s, 3 H), 3.15-2.94 (comp, 5 H), 2.28-2.03 (comp, 3 H), 1.68-1.57 (m, 1 H), 1.05 (d, J=6.7 Hz, 6 H); MS (ESI) m/z 533.29 (M+H).

S29-2-2

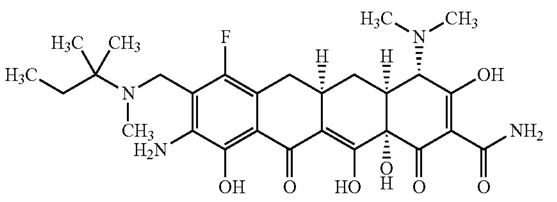

S29-2-2 was prepared from S2-4-28 according to the procedure for preparation of S29-2-1: $^1$H NMR (400 MHz, $CD_3OD$) δ 4.68-4.60 (m, 1 H), 4.20-4.12 (m, 1 H), 4.07 (s, 1 H), 3.03 (s, 3 H), 2.96 (s, 3 H), 3.13-2.93 (comp, 3 H), 2.76 (s, 3 H), 2.28-2.16 (m, 2 H), 2.00-1.86 (m, 2 H), 1.68-1.55 (m, 1 H), 1.49 (s, 3 H), 1.47 (s, 3 H), 1.07 (t, J=7.3 Hz, 3 H); MS (ESI) m/z 561.36 (M+H).

S29-2-3

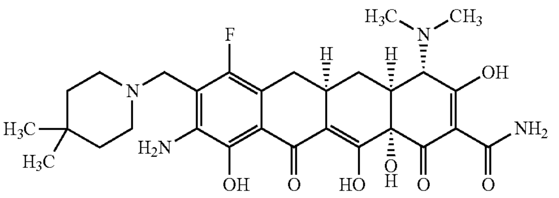

S29-2-3 was prepared from S2-4-50 according to the procedure for preparation of S29-2-1: $^1$H NMR (400 MHz, $CD_3OD$) δ 4.40 (s, 2 H), 4.08 (s, 1 H), 3.49-3.20 (m, 4 H), 3.04 (s, 3 H), 2.96 (s, 3 H), 3.14-2.94 (comp, 3 H), 2.27-2.17 (comp, 2 H), 1.78-1.56 (comp, 5 H), 1.11 (s, 3 H), 1.04 (s, 3 H); MS (ESI) m/z 573.35 (M+H).

S29-2-4

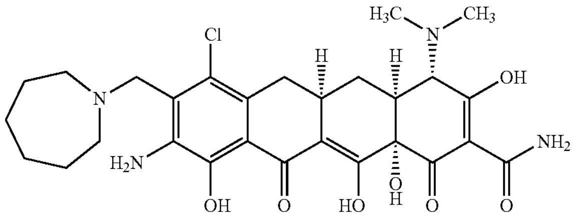

S29-2-4 was prepared from S1-14-61 according to the procedure for preparation of S29-2-1: $^1$H NMR (400 MHz, $CD_3OD$) δ 4.61 (d, J=14.0 Hz, 1 H), 4.57 (d, J=14.0 Hz, 1 H), 4.09 (s, 1 H), 3.55-3.36 (m, 4 H), 3.03 (s, 3 H), 2.95 (s, 3 H), 3.13-2.94 (comp, 3 H), 2.35-2.26 (m, 1 H), 2.26-2.17 (m, 1 H), 2.08-1.58 (comp, 9 H); MS (ESI) m/z 575.30 (M+H).

EXAMPLE 30

Synthesis of Compounds Via Scheme 30

Scheme 30

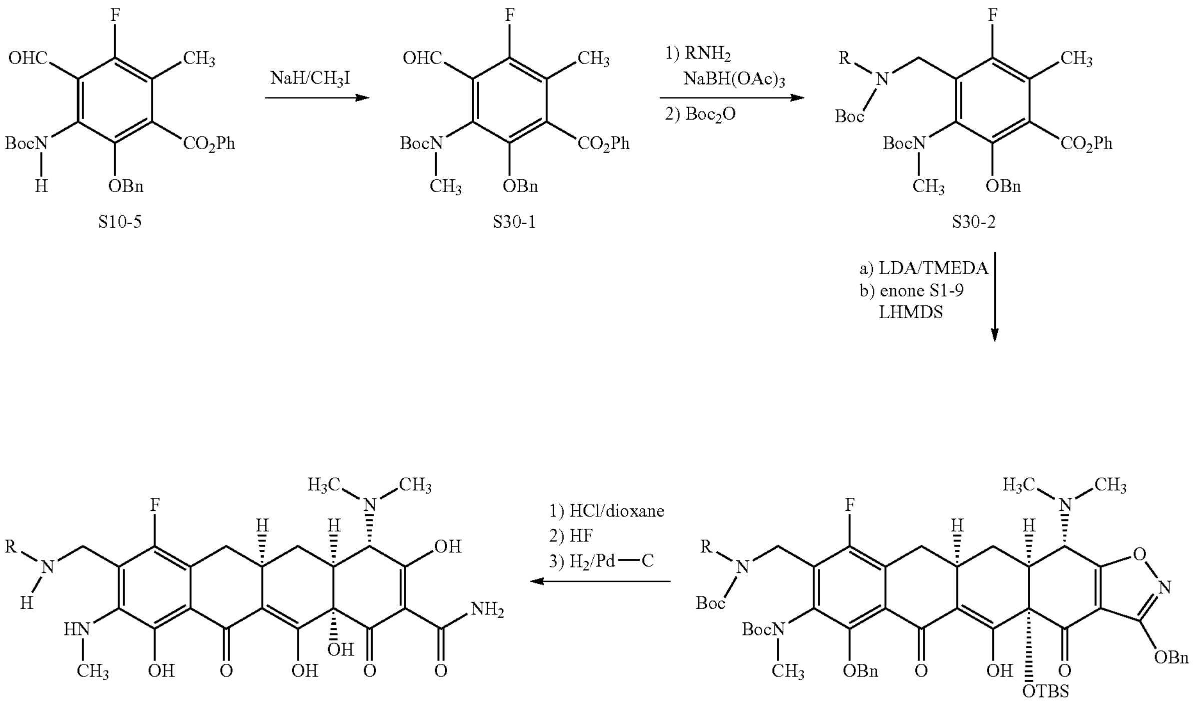

S10-5

S30-1

S30-2

S30-4

S30-3

The following compounds were prepared according to Scheme 30.

S30-1

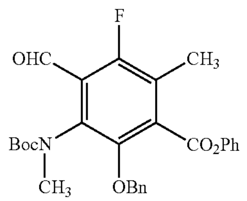

To a solution of aldehyde S10-5 (1.0 g, 2.09 mmol) in DMF (10 mL) was added NaH (167 mg, 4.18 mmol) and methyl iodide (390 μL, 6.27 mmol). The mixture was stirred at room temperature for 1 h and then quenched with water (2 mL). The solution was diluted with EtOAc (150 mL), washed with brine (50 mL×4), dried ($Na_2SO_4$), and concentrated. The residue was purified by flash chromatography on silica gel, eluting with hexanes/EtOAc (1:0 to 5:1) to afford imidazole S30-1 (310 mg, 30% yield); $^1$H NMR (400 MHz, $CDCl_3$) δ 10.30 (s, 1 H), 7.40-7.24 (comp, 8 H), 7.04-6.99 (comp, 2 H), 5.00-4.80 (m, 2 H), 3.19 (s, 1.9 H), 3.15 (s, 1.1 H), 2.40 (d, J=2.4 Hz, 1.9 H), 2.38 (d, J=2.4 Hz, 1.1 H), 1.50 (s, 3.3 H), 1.35 (s, 5.7 H); MS (ESI) m/z 516.44 (M+Na).

S30-2-1

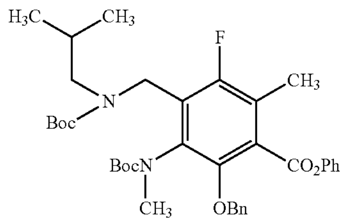

To a solution of aldehyde S30-1 (200 mg, 0.41 mmol) in 1,2-dichloroethane (3 mL) was added isobutylamine (119 μL, 1.23 mmol) and acetic acid (92 μL, 1.64 mmol). The mixture was stirred at room temperature for 4 h. $NaBH(OAc)_3$ (254 mg, 1.20 mmol) was added. The reaction was stirred at room temperature for 15 h. The mixture was diluted with EtOAc (20 mL), washed with brine (5 mL×3), dried ($Na_2SO_4$) and concentrated. The residue was purified by flash chromatography on silica gel, eluting with hexanes/EtOAc (1:1) to give amine (126 mg, 56% yield); MS (ESI) m/z 551.47 (M+H).

To the amine (126 mg, 0.23 mmol) in DCM (4 mL) was added $Boc_2O$ (150 mg, 0.69 mmol) and $Et_3N$ (96 μL, 0.69 mmol). The reaction was stirred at room temperature for 4 h and then concentrated. The residue was purified by flash chromatography on silica gel, eluting with hexanes/EtOAc (7:1) to afford 148 mg of S30-2-1; MS (ESI) m/z 673.68 (M+Na).

S30-3-1

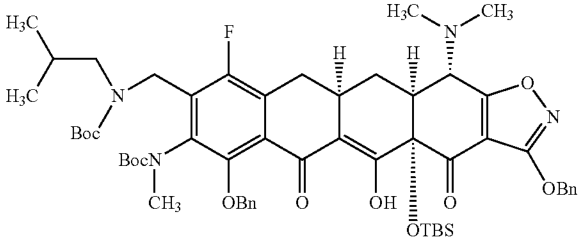

To a solution of i-$Pr_2NH$ (88 μL, 0.63 mmol) in THF (2 mL) was added a solution of n-BuLi (0.38 mL of a 1.70 M solution in hexanes, 0.63 mmol) dropwise at −78° C. The reaction was allowed to warm to 0° C. by removal of cooling bath, and then cooled to −78° C. TMEDA (93 μL, 0.63 mmol) was added, and the mixture was stirred at −78° C. for 5 min. A solution of amine S30-2-1 (148 mg, 0.23 mmol) in THF (0.5 mL) was added dropwise to the LDA solution over 5 min. Once addition was complete, the reaction mixture was stirred at −78° C. for 20 min. A solution of enone (100 mg, 0.21 mmol) in THF (0.5 mL) was added dropwise over 5 min. The mixture was slowly warmed to −20° C. over 45 min. The mixture was quenched with saturated ammonium chloride solution (5 mL), diluted with EtOAc (50 mL), washed with brine (10 mL×3), dried ($Na_2SO_4$), and concentrated. The residue was purified by flash chromatography on silica gel, eluting with hexanes/EtOAc (1:0 to 10:1) to afford 60 mg of compound S30-3-1 (28%): MS (ESI) m/z 1040.00 (M+H).

S30-4-1

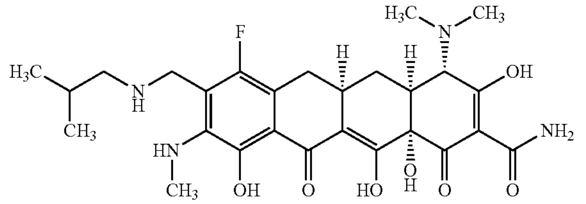

To a solution of S30-3-1 (60 mg, 0.06 mmol) in 1,4-dioxane (2 mL) was added hydrochloric acid (2 mL of 4 M solution) at room temperature. The mixture was stirred for 8 h. The mixture was diluted with EtOAc (20 mL), washed two times with potassium phosphate dibasic solution (prepared from 2 g $K_2HPO_4$ and 5 mL water), dried ($Na_2SO_4$) and concentrated to give a crude methyl aniline.

To a solution of methyl aniline in 1,4-dioxane (3 mL) was added HF (0.3 mL of 48% solution in water). The mixture was stirred at room temperature for 5 h. The mixture was quenched with potassium phosphate dibasic solution (prepared from 2 g $K_2HPO_4$ and 5 mL water). The aqueous layer was extracted with EtOAc (10 mL×3). All organic layers were combined, dried ($Na_2SO_4$) and concentrated. The residue was dissolved in ethyl acetate (5 mL), and hydrochloric acid (1 mL, 0.5 N in methanol) was added. The mixture was concentrated to give the HCl complex.

To the HCl complex in MeOH/dioxane solution (4:1, 5 mL) was added palladium on carbon (50 mg, 10 wt %). The reaction was stirred under $H_2$ (balloon) for overnight. The mixture was filtered through a small Celite plug and flashed with MeOH. The filtrate was concentrated to yield the crude product. Preparative reverse phase HPLC purification on a Waters Autopurification system using a Phenomenex Polymerx 10μ RP-$_1$ 100A column [10 μm, 150×21.20 mm; flow rate, 20 mL/min; Solvent A: 0.05 N HCl/water; Solvent B: MeOH; injection volume: 3.2 mL (0.05 N HCl/water); gradient: 0→100% B over 25 min; mass-directed fraction collection]. Fractions with the desired MW, eluting at 13.3-15.1 min, were collected and freeze-dried to yield 19.1 mg of S30-4-1: $^1$H NMR (400 MHz, $CD_3OD$) δ 4.52 (s, 2 H), 4.12 (s, 1 H), 3.76-3.56 (m, 1 H), 3.05 (s, 3 H), 3.04 (s, 3 H), 2.97 (s, 3 H), 3.24-2.94 (comp, 4 H), 2.46-2.37 (m, 1 H), 2.32-2.24 (m, 1 H), 2.20-2.09 (m, 1 H), 1.73-1.63 (m, 1 H), 1.09 (d, J=6.7 Hz, 6 H); MS (ESI) m/z 547.34 (M+H).

S30-4-2
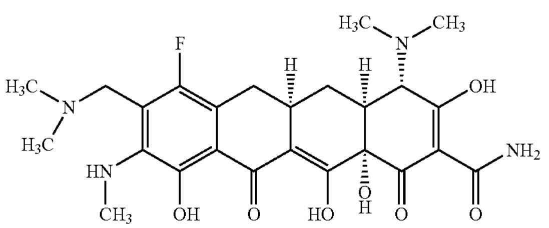
S30-4-2 was prepared according to the procedure for preparation of S30-4-1: $^{1}H$ NMR (400 MHz, $CD_3OD$) δ 4.66 (s, 2 H), 4.12 (s, 1 H), 3.05 (s, 3 H), 3.01 (s, 3 H), 3.01 (s, 3 H), 3.00 (s, 3 H), 2.97 (s, 3 H), 3.22-2.94 (comp, 3 H), 2.44-2.10 (m, 2 H), 1.72-1.60 (m, 1 H); MS (ESI) m/z 519.30 (M+H).
EXAMPLE 31
Synthesis of Compounds Via Scheme 31
Scheme 31
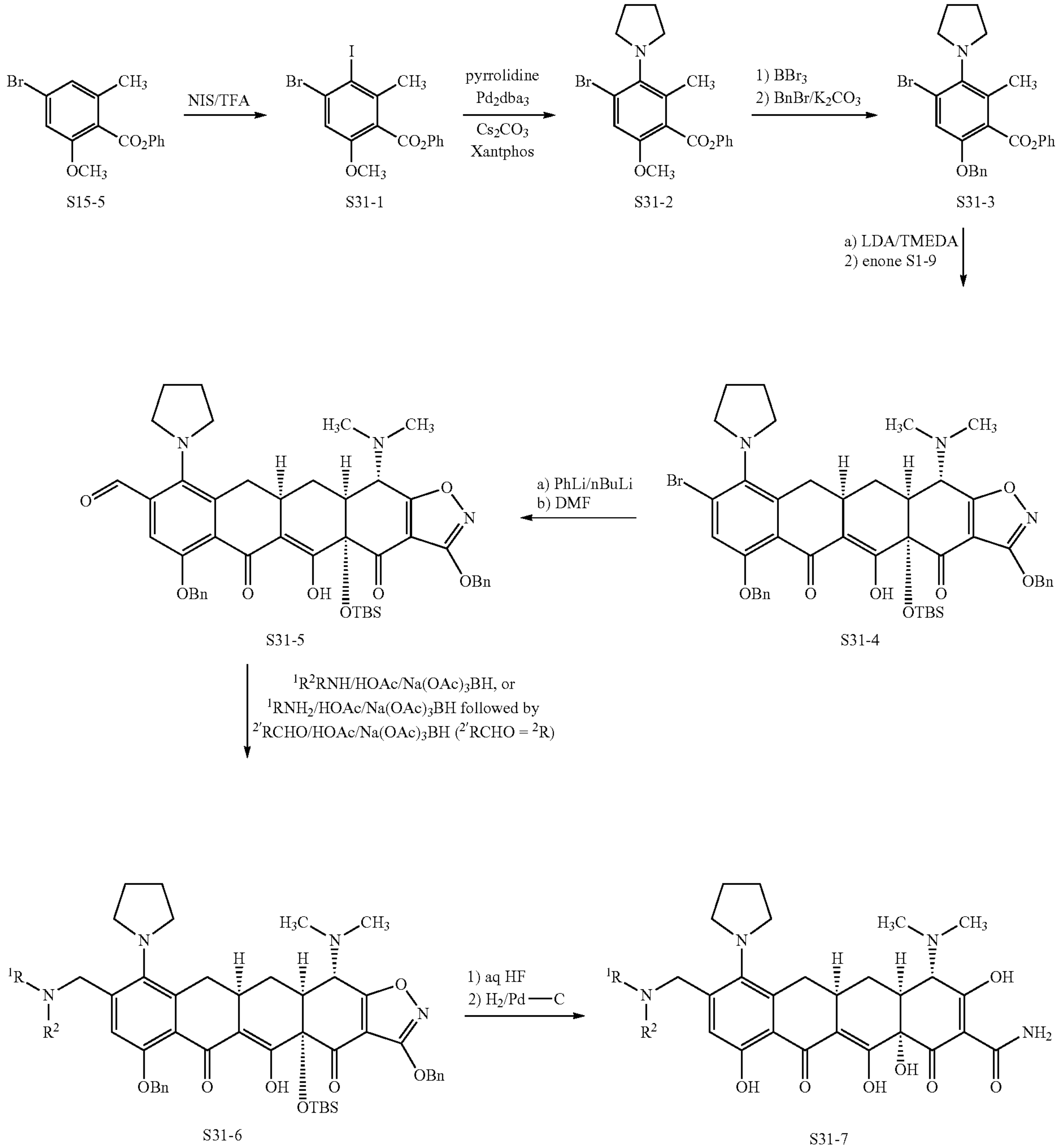
S15-5, S31-1, S31-2, S31-3, S31-4, S31-5, S31-6, S31-7

The following compounds were prepared according to Scheme 31.

S31-1

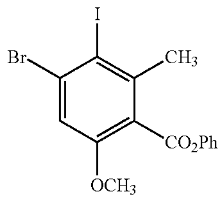

To a mixture of S15-5 (3.12 g, 9.71 mmol, 1.0 equiv) and NIS (2.40 g, 10.68 mmol, 1.1 equiv) was added MeCN (20 mL) and TFA (224 μL, 2.91 mmol, 0.3 equiv). The resulting reaction mixture was stirred at reflux overnight. More NIS (874 mg, 3.88 mmol, 0.4 equiv) and TFA (75 μL, 0.97 mmol, 0.1 equiv) were added. The resulting reaction mixture was stirred at reflux overnight, and cooled to rt. The reaction mixture was diluted with EtOAc (200 mL), washed with saturated $NaHCO_3$ solution (70 mL), and sodium thiosulfate solution (2M, 70 mL), and brine (50 mL). The resulting organic phase was dried over anhydrous sodium sulfate, filtered, and concentrated to afford an orange solid, which was recrystallized from EtOAc/MeOH to give the product as a white solid (2.74 g). The mother liquor was concentrated, and the residue was purified by flash-column chromatography (0-15% ethyl acetate-hexanes) to afford the desired product S31-1 as a white solid (1.03 g, total yield: 87%): $^1H$ NMR (400 MHz, $CDCl_3$) δ 7.46-7.42 (m, 2 H), 7.31-7.26 (m, 1 H), 7.24-7.22 (m, 2 H), 7.18 (s, 1 H), 3.89 (s, 3 H), 2.64 (s, 3 H); MS (ESI) m/z 444.93, 446.95 (M−H).

S31-2

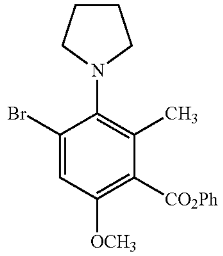

To compound S31-1 (447 mg, 1.00 mmol, 1.0 equiv), pyrrolidine (0.165 mL, 2.00 mmol, 2.0 equiv), cesium carbonate (489 mg, 1.5 mmol, 1.5 equiv), and Xantphos (31.8 mg, 0.055 equiv) in dry dioxane (5 mL) at room temperature was added $Pd_2(dba)_3$ (22.8 mg, 0.05 equiv Pd). The mixture was purged by bubbling with dry nitrogen gas for 5 min with gentle stirring. The reaction vessel was then heated under nitrogen at 100° C. for 5 hrs with rapid stirring. The resulting mixture was cooled to rt, diluted with water (20 mL), and extracted with EtOAc (10 mL×3). The EtOAc extracts were dried over sodium sulfate and concentrated under reduced pressure. Flash column chromatography on silica gel with 5%-30% EtOAc/hexanes afforded the desired product S31-2 (156 mg, 40%) as a pale colorless oil; MS (ESI) m/z 390.30 (M+H).

S31-3

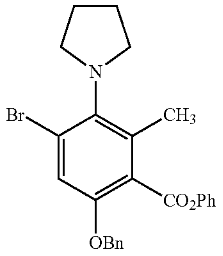

A solution of $BBr_3$ in dichloromethane (0.6 mL, 1.0 M, 0.6 mmol, 1.5 equiv) was added slowly to a solution of the above compound S31-2 in dichloromethane (5 mL) at −78° C. The resulting light yellow solution was allowed to warm to 0° C. in 30 min and kept at that temperature for 10 min (monitored by LC-MS). The reaction mixture was poured into saturated $NaHCO_3$ solution (10 mL), stirred at rt for 5 min, and extracted with dichloromethane (10 mL×2). The organic extracts were combined and dried over anhydrous magnesium sulfate, filtered, and concentrated to afford the crude phenol, which was used directly in the next reaction; MS (ESI) m/z 376.27 (M+H).

Benzylbromide (59.3 μL, mmol, 1.25 equiv) and $K_2CO_3$ powder (110 mg, 0.8 mmol, 2 equiv) were added to a solution of the above crude phenol (0.4 mmol, 1.0 equiv) in acetonitrile (10 mL). The mixture was stirred at rt overnight. Solvents were evaporated and the residue was dissolved in a mixture of EtOAc (20 mL) and water (1:1). The organic layer was separated, and the aqueous layer was extracted with EtOAc (10 mL×2). The combined organic phase was dried over anhydrous magnesium sulfate, filtered, and concentrated. The residue was purified by flash column chromatography (5% to 25% EtOAc/hexanes) to afford the desired product S31-3 as a colorless oil (151 mg, 81% two steps): $^1H$ NMR (400 MHz, $CDCl_3$) δ 7.44-7.35 (m, 7 H), 7.26-7.22 (m, 1 H), 7.09-7.07 (m, 3 H), 5.10 (s, 2 H), 3.50-3.41 (m, 4 H), 2.34 (d, J=2.4 Hz, 3 H), 2.00-1.90 (m, 4 H); MS (ESI) m/z 466.34 (M+H).

S31-4

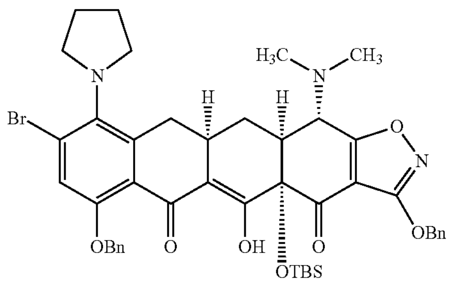

A solution of n-butyllithium in hexanes (0.30 mL, 1.6 M, 0.48 mmol, 1.5 equiv) was added to a solution of diisopropylamine (67.3 μL, 0.48 mmol, 1.5 equiv) and TMEDA (71.9 μL, 0.48 mmol, 1.5 equiv) in THF (2 mL) at −78° C. The reaction solution was warmed to −20° C. and then re-cooled to −78° C. A solution of compound S31-3 (149 mg, 0.32 mmol, 1.0 equiv) in THF (1.5 mL) was added dropwise via a cannula. The resulting red reaction mixture was then stirred at −78° C. for 10 min, and cooled to −100° C. A solution of enone S1-9 (154 mg, 0.32 mmol, 1.0 equiv) in THF (1 mL) was added to the reaction mixture via a cannula, followed by LHMDS solution (0.4 mL, 1.0 M, 1.2 eq.). The resulting reaction mixture was allowed to warm to −30° C. over 1.5 hrs, quenched by saturated aqueous $NH_4Cl$ (10 mL), and extracted with EtOAc (10 mL×3). The organic phase was dried over sodium sulfate, filtered and concentrated. The residue was purified by a preparative reverse phase HPLC on a Waters Autopurification system using a Sunfire Prep C18 OBD column [5 μm, 19×50 mm; flow rate, 20 mL/min; Solvent A: $H_2O$ with 0.1% $HCO_2H$; Solvent B: $CH_3CN$ with 0.1% $HCO_2H$; injection volume: 3.0 mL ($CH_3CN$); gradient: 80→100% B in A over 10 min; mass-directed fraction collection]. Fractions containing the desired product were collected and concentrated to yield compound S31-4 (40.1 mg, 14.7%): $^1H$ NMR (400 MHz, $CDCl_3$) δ 16.00 (br s, 1 H), 7.50-7.46 (m, 4 H), 7.39-7.27 (m, 6 H), 7.10 (s, 1 H), 5.36 (s, 2 H), 5.18, 5.12 (ABq, J=12.8 Hz, 2 H), 4.10 (d, J=10.4 Hz, 1 H), 3.75-3.65 (m, 2 H), 3.59-3.50 (m, 2 H), 3.37 (dd, J=4.3, 15.9 Hz, 1 H), 2.88-2.74 (m, 1 H), 2.55-2.40 (m, 9 H), 2.12 (d, J=14.0 Hz, 1 H), 1.99-1.83 (m, 4 H), 0.84 (s, 9 H), 0.28 (s, 3 H), 0.14 (s, 3 H); MS (ESI) m/z 854.72 (M+H).

S31-6-1

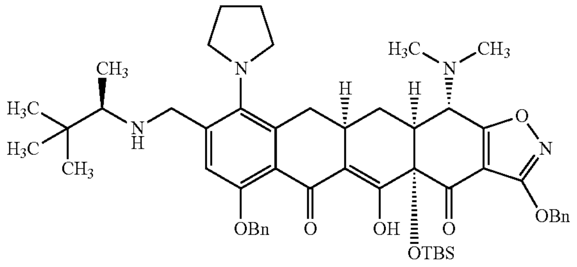

A solution of phenyllithium in di-n-butyl ether (39 μL, 1.8 M, 0.07 mmol, 1.5 equiv) was added dropwise to a solution of compound S31-4 (40 mg, 0.047 mmol, 1.0 equiv) in THF (1.5 mL) at −78° C., forming an orange solution. After 5 min, a solution of n-butyllithium in hexanes (35.3 μL, 1.6 M, 0.056 mmol, 1.2 equiv) was added dropwise at −78° C., followed 2 min later by the addition of N,N-dimethylformamide (18.1 μL, 5.0 equiv). The resulting dark red reaction mixture was stirred at −78° C. for 1 hour. The reaction mixture was allowed to warm to −40° C. LCMS indicate only about 30% product present in reaction mixture. Saturated aqueous ammonium chloride (5 mL) was added dropwise at −40° C. The reaction mixture was allowed to warm to 23° C., diluted with saturated aqueous ammonium chloride (~10 mL), and extracted with EtOAc (2×15 mL). The organic extracts were combined, dried over anhydrous sodium sulfate, filtered, and concentrated, affording compound S31-5 as orange oil, which was used directly in the next reactions: MS (ESI) m/z 804.73 (M+H).

(R)-2,3,3-trimethyl-butylamine (3.8 μL, 0.03 mmol, 2.0 equiv), acetic acid (4.5 μL, 0.045 mmol, 3.0 equiv) and sodium triacetoxyborohydride (6.4 mg, 0.03 mmol, 2.0 equiv) were added sequentially to a solution of compound S31-5 (crude product, 0.014 mmol, 1.0 equiv) in 1,2-dichloroethane (2 mL) at 23° C. After stirring for overnight, the reaction mixture was quenched by the addition of saturated aqueous sodium bicarbonate (5 mL) and extracted with dichloromethane (2×10 mL). The combined organic extracts were dried over anhydrous sodium sulfate, filtered, and concentrated. The residue was purified by preparative reverse phase HPLC on a Waters Autopurification system using a Sunfire Prep C18 OBD column [5 μm, 19×50 mm; flow rate, 20 mL/min; Solvent A: $H_2O$ with 0.1% $HCO_2H$; Solvent B: $CH_3CN$ with 0.1% $HCO_2H$; injection volume: 3.0 mL ($CH_3CN$); gradient: 20→100% B in A over 10 min; mass-directed fraction collection]. Fractions containing the desired product, eluting at 5.6-6.5 min, were collected and freeze-dried to yield compound S31-6-1 (7.5 mg, 18% for 2 steps): MS (ESI) m/z 889.83 (M+H).

S31-7-1

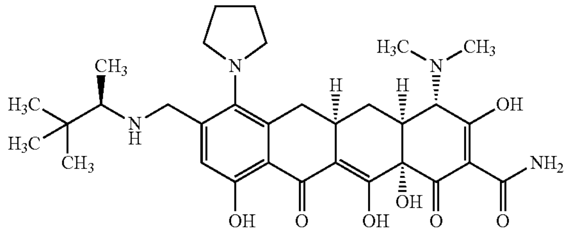

Aqueous HF (48-50%, 0.2 mL) was added to a solution of compound S31-6-1 (7.5 mg, 0.0084 mmol, 1.0 equiv) in acetonitrile (1.0 mL) in a polypropylene reaction vessel at 23° C. The mixture was stirred vigorously at 23° C. overnight and poured into aqueous $K_2HPO_4$ (2.0 g dissolved in 10 mL water). The mixture was extracted with EtOAc (3×10 mL). The combined organic extracts were dried over anhydrous sodium sulfate, filtered, and concentrated. The residue was used directly in the next step without further purification.

Pd—C (10 wt %, 5 mg) was added in one portion into the yellow solution of the above crude product in a mixture of HCl/MeOH (0.5 N, 0.25 mL) and MeOH (2 mL) at 23° C. The reaction vessel was sealed and purged with hydrogen by briefly evacuating the flask followed by flushing with hydrogen gas (1 atm). The resulting mixture was stirred at 23° C. for 60 min. The reaction mixture was then filtered through a small Celite pad. The filtrate was concentrated. The residue was purified by preparative reverse phase HPLC on a Waters Autopurification system using a Phenomenex Polymerx 10μ RP-γ 100A column [10 μm, 150×21.20 mm; flow rate, 20 mL/min; Solvent A: 0.05 N HCl/water; Solvent B: $CH_3CN$; injection volume: 3.0 mL (0.05 N HCl/water); gradient: 15→60% B over 10 min; mass-directed fraction collection]. Fractions containing the desired product, eluting at 5.8-8.0 min, were collected and freeze-dried to yield compound S31-7-1 (2.77 mg, 54% for 2 steps): $^1H$ NMR (400 MHz, $CD_3OD$) δ 7.01 (s, 1 H), 4.36 (d, J=12.8 Hz, 1 H), 4.14 (d, J=12.8 Hz, 1 H), 4.12 (s, 1 H), 3.56-3.49 (m, 4 H), 3.13-2.84 (m, 10 H), 2.39-2.12 (m, 2 H), 2.03-1.91 (m, 4 H), 1.70-1.60 (m, 1 H), 1.47 (s, 9 H), 1.35 (d, J=6.9 Hz, 3 H), 1.00 (s, 9 H); MS (ESI) m/z 597.25 (M+H).

EXAMPLE 32
Synthesis of Compounds Via Scheme 32
Scheme 32
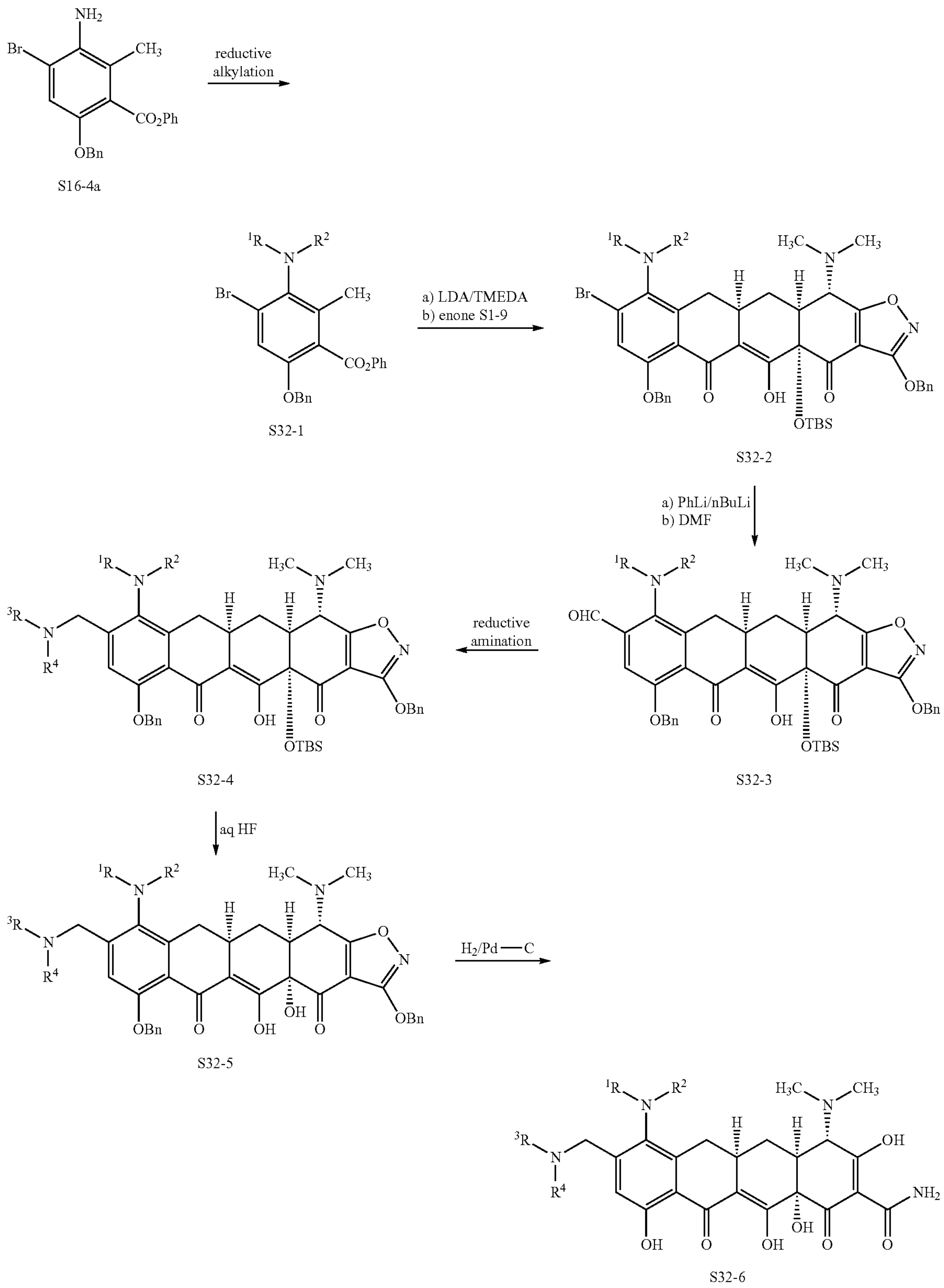

The following compounds were prepared according to Scheme 32.

S32-1-1

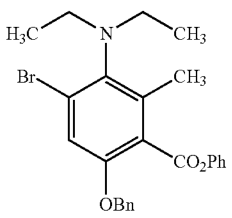

Compound S16-4a (1.61 g, 3.57 mmol, 1.0 equiv) was dissolved in 1,2-dichloroethane (20 mL). Acetaldehyde (1.2 mL, 21.42 mmol, 6.0 equiv) and acetic acid (0.62 mL, 10.71 mmol, 3.0 equiv) were added. After stirring at rt for 1 h, sodium triacetoxyborohydride (2.27 g, 10.71 mmol, 3.0 equiv) was added. Stirring was continued for 1 hr. The reaction mixture was poured into saturated aqueous $NaHCO_3$ and extracted three times with dichloromethane. The combined organic extracts were washed with brine, dried over sodium sulfate, and concentrated to give the crude intermediate. Purification of the residue by flash chromatography gave compound S32-1-1 (1.52 g, 91%) as a white solid: $^1H$ NMR (400 MHz, $CDCl_3$) δ 7.45-7.40 (m, 2 H), 7.39-7.30 (m, 5 H), 7.25-7.20 (m, 1 H), 7.09 (s, 1 H), 7.07-7.03 (m, 2 H), 5.08 (s, 2 H), 3.23-3.05 (m, 4 H), 2.42 (s, 3 H), 1.00 (t, J=7.1 Hz, 6 H); MS (ESI) m/z 468.39 (M+H).

S32-1-2

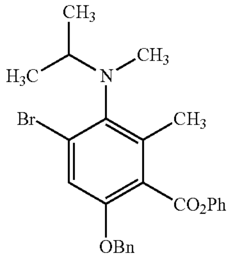

Compound S16-4a (1.61 g, 3.57 mmol, 1.0 equiv) was dissolved in 1,2-dichloroethane (20 mL). Acetone (0.786 mL, 10.71 mmol, 3.0 equiv) and acetic acid (0.62 mL, 10.71 mmol, 3.0 equiv) were added. After stirring at rt for 1 h, sodium triacetoxyborohydride (1.14 g, 5.35 mmol, 1.5 equiv) was added. Stirring was continued for overnight. The reaction mixture was poured into saturated aqueous $NaHCO_3$ and extracted three times with dichloromethane. The combined organic extracts were washed with brine, dried over sodium sulfate, and concentrated to give the crude intermediate. Purification of the residue by flash chromatography gave compound (970 mg, 2.14 mmol, 60%) as a white solid: MS (ESI) m/z 454.36 (M+H).

The compound was redissolved in 1,2-dichloroethane (20 mL), followed by acetic acid (0.367 mL, 6.41 mmol, 3.0 equiv) and formaldehyde (0.478 mL, 37%, 6.41 mmol, 3.0 eq.). After stirring at rt for 1 h, sodium triacetoxyborohydride (0.907 mg, 4.28 mmol, 2.0 equiv) was added. Stirring was continued for overnight. The reaction mixture was poured into saturated aqueous $NaHCO_3$ and extracted three times with dichloromethane. The combined organic extracts were washed with brine, dried over sodium sulfate, and concentrated to give the crude intermediate. Purification of the residue by flash chromatography gave compound S32-1-2 (1.08 g, 66% for two steps) as a white solid: $^1H$ NMR (400 MHz, $CDCl_3$) δ 7.45-7.31 (m, 7 H), 7.27-7.22 (m, 1 H), 7.09 (s, 1 H), 7.08-7.04 (m, 2 H), 5.09 (s, 2 H), 3.60-3.50 (m, 1 H), 2.76 (s, 3 H), 2.41 (s, 3 H), 1.15 (d, J=6.4 Hz, 3 H), 0.94 (d, J=6.4 Hz, 3 H); MS (ESI) m/z 468.36 (M+H).

S32-2-1

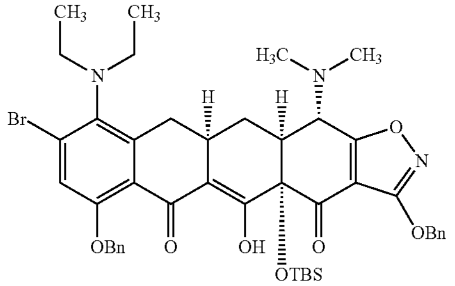

A solution of n-BuLi in hexanes (1.05 mL, 1.6 M, 1.68 mmol, 1.4 equiv) was added dropwise to a solution of i-$Pr_2$NH (0.235 mL, 1.68 mmol, 1.4 equiv) in THF (5 mL) at −78° C. under a $N_2$ atmosphere. The resulting solution was stirred at −78° C. for 20 min and −20° C. for 5 min, and then re-cooled to −78° C. N,N,N',N'-Tetramethylethylenediamine (TMEDA, 0.252 mL, 1.68 mmol, 1.4 equiv) was added, followed by dropwise addition of compound S32-1-1 (620 mg, 1.32 mmol, 1.1 equiv) in THF (3 mL) via syringe. After complete addition, the resulting dark-red mixture was stirred for another 15 min at −78° C. A solution of enone S1-9 (580 mg, 1.20 mmol, 1.0 equiv) in THF (2 mL) was added dropwise via syringe. LHMDS (1.44 mL, 1.0 M/THF, 1.44 mmol, 1.2 equiv) was then added and the reaction was slowly warmed to −20° C. Saturated aqueous $NH_4Cl$ was added. The resulting mixture was extracted three times with EtOAc. The combined EtOAc extracts were washed with brine, dried (sodium sulfate), and concentrated. Purification of the residue by flash chromatography gave compound S32-2-1 (627 mg, 62%) as light yellow foam: $^1H$ NMR (400 MHz, $CDCl_3$) δ 16.0 (s, 1 H), 7.52-7.45 (m, 4 H), 7.42-7.27 (m, 6 H), 7.12 (s, 1 H), 5.35 (s, 2 H), 5.22-5.09 (m, 2 H), 4.00 (d, J=9.8 Hz, 1 H), 3.62-3.52 (m, 1 H), 3.30-3.09 (m, 3 H), 3.04-2.93 (m, 1 H), 2.87-2.75 (m, 1 H), 2.58-2.30 (m, 9 H), 2.10 (d, J=14.0 Hz, 1 H), 1.03 (t, J=7.1 Hz, 3 H), 0.91 (t, J=7.1 Hz, 3 H), 0.82 (s, 9 H), 0.26 (s, 3 H), 0.13 (s, 3 H); MS (ESI) m/z 856.50 (M+H).

S32-3-1

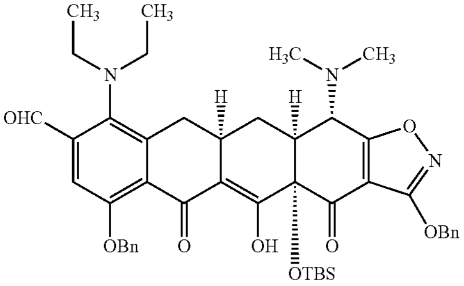

A solution of phenyllithium in di-n-butyl ether (0.345 mL, 1.8 M, 0.620 mmol, 1.5 equiv) was added dropwise to a solution of compound S32-2-1 (352 mg, 0.414 mmol, 1.0 equiv) in THF (10 mL) at −78° C., forming an orange solution. After 5 min, a solution of n-butyllithium in hexanes (0.311 mL, 1.6 M, 0.497 mmol, 1.2 equiv) was added dropwise at −78° C., followed 2 min later by the addition of N,N-dimethylformamide (0.160 mL, 2.07 mmol, 5.0 equiv). The resulting dark red reaction mixture was stirred at −78° C. for 10 min then warm up to −40° C. in 30 min. Saturated aqueous ammonium chloride (10 mL) was added dropwise at −78° C. The reaction mixture was allowed to warm to 23° C., diluted with saturated aqueous ammonium chloride (~20 mL), and extracted with EtOAc (2×25 mL). The organic extracts were combined, dried over anhydrous sodium sulfate, filtered, and concentrated, affording compound S32-3-1 as an orange oil (419 mg, with reduced by-product), which was used directly in the next reactions: $^1$H NMR (400 MHz, $CDCl_3$) δ 15.9 (s, 1 H), 10.31 (s, 1 H), 7.50-7.46 (m, 4 H), 7.39-7.26 (m, 7 H), 5.36 (s, 2 H), 5.30-5.13 (m, 2 H), 4.01 (d, J=11.0 Hz, 1 H), 3.62-3.52 (m, 1 H), 3.30-3.09 (m, 3 H), 3.04-2.93 (m, 1 H), 2.87-2.75 (m, 1 H), 2.58-2.30 (m, 9 H), 2.15 (d, J=14M Hz, 1 H), 1.03 (t, J=7.1 Hz, 3 H), 0.91 (t, J=7.1 Hz, 3 H), 0.82 (s, 9 H), 0.27 (s, 3 H), 0.14 (s, 3 H); MS (ESI) m/z 806.76 (M+H).

S32-6-1-1

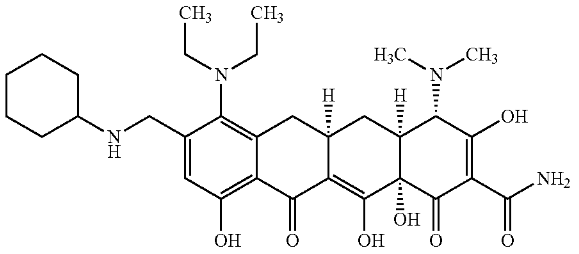

Compound S32-3-1 (100 mg, 0.05 mmol, 1.0 equiv) was dissolved in 1,2-dichloroethane (2.0 mL). Cyclohexylamine (17.2 μL, 0.15 mmol, 3.0 equiv) and acetic acid (11.45 μL, 0.20 mmol, 4.0 equiv) were added. After stirring at rt for 1 h, sodium triacetoxyborohydride (31.8 mg, 0.15 mmol, 3.0 equiv) was added. Stirring was continued overnight. The reaction mixture was poured into saturated aqueous $NaHCO_3$ and extracted three times with dichloromethane. The combined organic extracts were washed with brine, dried over sodium sulfate, and concentrated to give the crude intermediate S32-4-1-1 (27.5 mg), which was used directly in the next step without further purification: MS (ESI) m/z 889.85 (M+H).

In a plastic vial, the above amine intermediate was dissolved in $CH_3CN$ (1 mL). Aqueous HF (48-50%, 0.25 mL) was added. After stirring at rt for 16 hrs, the reaction mixture was poured into aqueous solution (10 mL) of $K_2HPO_4$ (2.0 g) and extracted three times with dichloromethane. The combined organic phases were washed with brine, dried, and concentrated to yield the crude intermediate: MS (ESI) m/z 775.72 (M+H).

The above crude intermediate was dissolved in MeOH (2 mL) with 0.5 N HCl/MeOH (0.20 mL). Pd—C (10 wt %, 5 mg) was added. The reaction flask was briefly evacuated and re-filled with hydrogen. The reaction mixture was stirred at rt and monitored by LC-MS. After the reaction was complete, the mixture was filtered through a small pad of Celite. The filtrate was concentrated to give the crude product, which was purified by HPLC on a Waters Autopurification system using a Phenomenex Polymerx 10μ RP-γ 100 R column [30×21.20 mm, 10 micron; flow rate, 20 mL/min; Solvent A: 0.05 N HCl/water; Solvent B: MeOH; injection volume: 4.0 mL (0.05 N HCl/water); gradient: 20→100% B over 10 min; mass-directed fraction collection]. Fractions containing the desired product were collected and freeze-dried to give the desired product as a yellow solid S32-6-1-1 (4.35 mg, 7.4% for four steps): $^1$H NMR (400 MHz, $CD_3OD$) δ 7.00 (s, 1 H), 4.49, 4.32 (ABq, J=14.7 Hz, 2 H), 4.08 (s, 1 H), 3.22-2.90 (m, 13 H), 2.39-2.28 (m, 1 H), 2.27-2.14 (m, 3 H), 1.97-1.86 (m, 2 H), 1.79-1.70 (m, 1 H), 1.69-1.57 (m, 1 H), 1.50-1.35 (m, 4 H), 1.35-1.19 (m, 2 H), 1.08 (t, J=6.9 Hz, 3 H), 0.99 (t, J=6.9 Hz, 3 H); MS (ESI) m/z 597.30 (M+H).

The following compounds were prepared according to the methods for S32-6-1-1, substituting the appropriate amine for cyclohexylamine.

S32-6-1-2

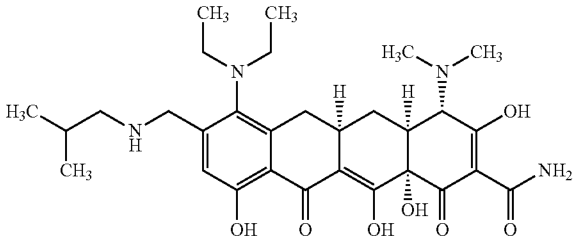

S32-6-1-2: $^1$H NMR (400 MHz, $CD_3OD$) δ 6.98 (s, 1 H), 4.48, 4.32 (ABq, J=15.7 Hz, 2 H), 4.06 (s, 1 H), 3.18-2.89 (m, 15 H), 2.40-2.28 (m, 1 H), 2.24-2.14 (m, 1 H), 2.15-2.05 (m, 1 H), 1.70-1.58 (m, 1 H), 1.07 (d, J=6.4 Hz, 6 H), 0.99 (t, J=6.9 Hz, 6 H); MS (ESI) m/z 571.29 (M+H).

S32-6-1-3

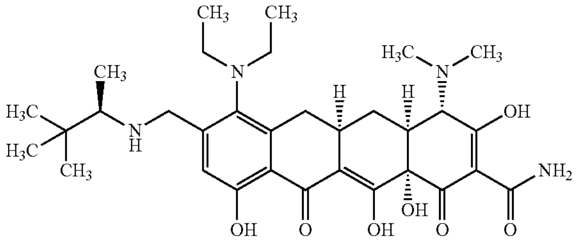

S32-6-1-3: $^1$H NMR (400 MHz, $CD_3OD$) δ 7.05 (s, 1 H), 4.49 (s, 2 H), 4.09 (s, 1 H), 3.17-2.93 (m, 14 H), 2.40-2.30 (m, 1 H), 2.23-2.17 (m, 1 H), 1.70-1.57 (m, 1 H), 1.38 (d, J=6.4 Hz, 3 H), 1.13 (t, J=6.9 Hz, 3 H), 1.08 (s, 9 H), 0.99 (t, J=6.9 Hz, 3 H); MS (ESI) m/z 599.39 (M+H).

S32-6-1-4

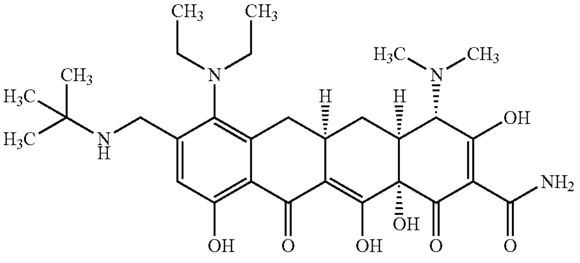

S32-6-1-4: $^1$H NMR (400 MHz, $CD_3OD$) δ 7.05 (s, 1 H), 4.50, 4.28 (ABq, J=14.7 Hz, 2 H), 4.08 (s, 1 H), 3.17-2.92 (m, 14 H), 2.39-2.30 (m, 1 H), 2.24-2.16 (m, 1 H), 1.70-1.57 (m, 1 H), 1.48 (s, 9 H), 1.09 (t, J=6.9 Hz, 3 H), 1.00 (t, J=6.9 Hz, 3 H); MS (ESI) m/z 571.29 (M+H).

S32-6-1-5

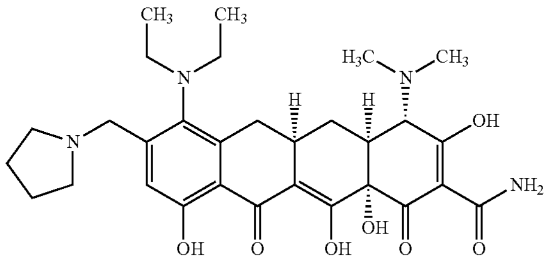

S32-6-1-5: $^1$H NMR (400 MHz, $CD_3OD$) δ 7.04 (s, 1 H), 4.68, 4.52 (ABq, J=14.7 Hz, 2 H), 4.08 (s, 1 H), 3.73-3.59 (m, 2 H), 3.17-2.92 (m, 15 H), 2.39-2.30 (m, 1 H), 2.28-2.01 (m, 5 H), 1.70-1.57 (m, 1 H), 1.08 (t, J=6.9 Hz, 3 H), 1.00 (t, J=6.9 Hz, 3 H); MS (ESI) m/z 569.29 (M+H).

S32-6-1-6

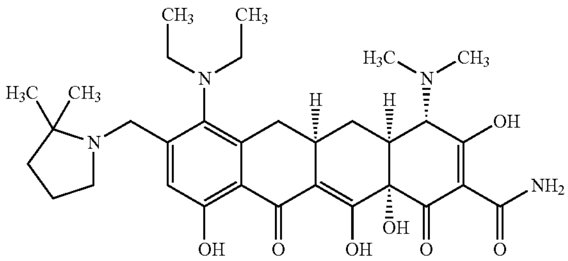

S32-6-1-6: $^1$H NMR (400 MHz, $CD_3OD$) δ 7.10 (s, 0.5 H), 7.07 (s, 0.5 H), 4.65 (d, J=12.8 Hz, 0.5 H), 4.58 (d, J=12.8 Hz, 0.5 H), 4.43 (d, J=12.8 Hz, 0.5 H), 4.30 (d, J=12.8 Hz, 0.5 H), 4.10 (s, 1 H), 3.24-2.81 (m, 15 H), 2.43-2.33 (m, 1 H), 2.27-1.99 (m, 5 H), 1.71-1.58 (m, 1 H), 1.64 (s, 3 H), 1.45 (s, 3 H), 1.12-1.00 (m, 6 H); MS (ESI) m/z 597.30 (M+H).

S32-6-1-7

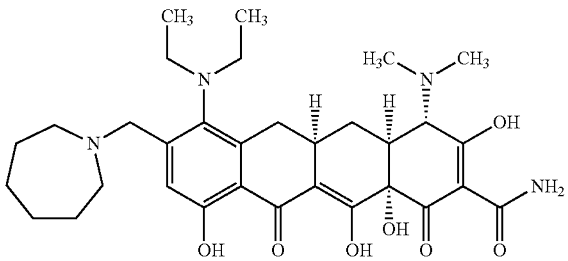

S32-6-1-7: $^1$H NMR (400 MHz, $CD_3OD$) δ 7.09 (s, 1 H), 4.68, 4.47 (ABq, J=14.7 Hz, 2 H), 4.08 (s, 1 H), 3.57-3.40 (m, 2 H), 3.24-2.90 (m, 15 H), 2.41-2.31 (m, 1 H), 2.23-1.97 (m, 5 H), 2.07-1.84 (m, 4 H), 1.83-1.70 (m, 4 H), 1.69-1.58 (m, 1 H), 1.08 (t, J=6.9 Hz, 3 H), 1.02 (t, J=6.9 Hz, 3 H); MS (ESI) m/z 597.37 (M+H).

S32-6-2-1

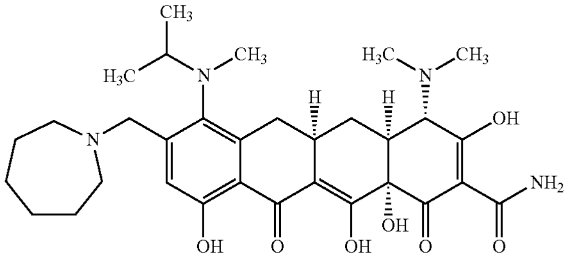

Compound S32-6-2-1 to S32-6-2-3 was prepared similarly from S32-1-2: $^1$H NMR (400 MHz, $CD_3OD$) δ 7.05 (s, 0.4 H), 7.04 (s, 0.6 H), 4.80-4.64 (m, 0.8 H), 4.43-4.20 (m, 1.2 H), 4.08 (s, 0.4 H), 4.07 (s, 0.6 H), 3.67-3.53 (m, 2 H), 3.20-2.78 (m, 15 H), 2.52-2.30 (m, 1 H), 2.26-2.17 (m, 1 H), 2.05-1.58 (m, 9 H), 1.26 (d, J=6.4 Hz, 1.8 H), 1.21 (d, J=6.4 Hz, 1.2 H), 0.94 (d, J=6.4 Hz, 1.8 H), 0.79 (d, J=6.4 Hz, 1.2 H); MS (ESI) m/z 597.35 (M+H).

S32-6-2-2

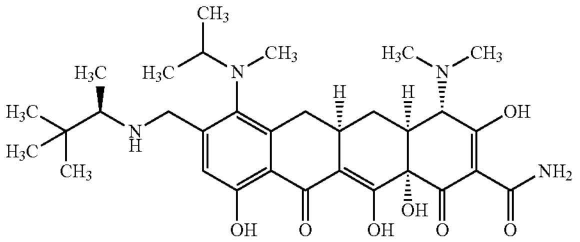

$^1$H NMR (400 MHz, $CD_3OD$) δ 7.06 (s, 0.4 H), 7.03 (s, 0.6 H), 4.70-4.64 (m, 0.8 H), 4.40-4.20 (m, 1.2 H), 4.08 (s, 0.6 H), 4.07 (s, 0.4 H), 3.18-2.79 (m, 14 H), 2.49-2.30 (m, 1 H), 2.26-2.17 (m, 1 H), 1.71-1.58 (m, 1 H), 1.41-1.20 (m, 6 H), 1.08 (s, 4 H), 1.05 (s, 5 H), 0.98-0.79 (m, 3 H); MS (ESI) m/z 599.38 (M+H).

S32-6-2-3

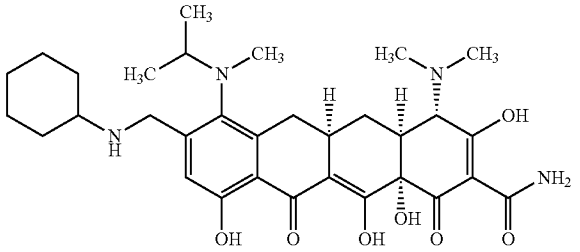

$^1$H NMR (400 MHz, $CD_3OD$) δ 6.98 (s, 0.5 H), 6.97 (s, 0.5 H), 4.58 (d, J=12.8 Hz, 0.5 H), 4.45 (d, J=12.8 Hz, 0.5 H), 4.31 (d, J=12.8 Hz, 0.5 H), 4.15 (d, J=12.8 Hz, 0.5 H), 4.09 (s, 0.5 H), 4.08 (s, 0.5 H), 3.17-2.90 (m, 11 H), 2.86 (s, 1.5 H), 2.75 (s, 1.5 H), 2.46-2.28 (m, 1 H), 2.27-2.13 (m, 3 H), 1.97-1.85 (m, 2 H), 1.70-1.58 (m, 1 H), 1.50-1.34 (m, 5 H), 1.33-1.16 (m, 4 H), 0.95 (d, J=6.4 Hz, 1.5 H), 0.81 (d, J=6.4 Hz, 1.5 H); MS (ESI) m/z 597.37 (M+H).

EXAMPLE 33
Synthesis of Compounds Via Scheme 33
Scheme 33
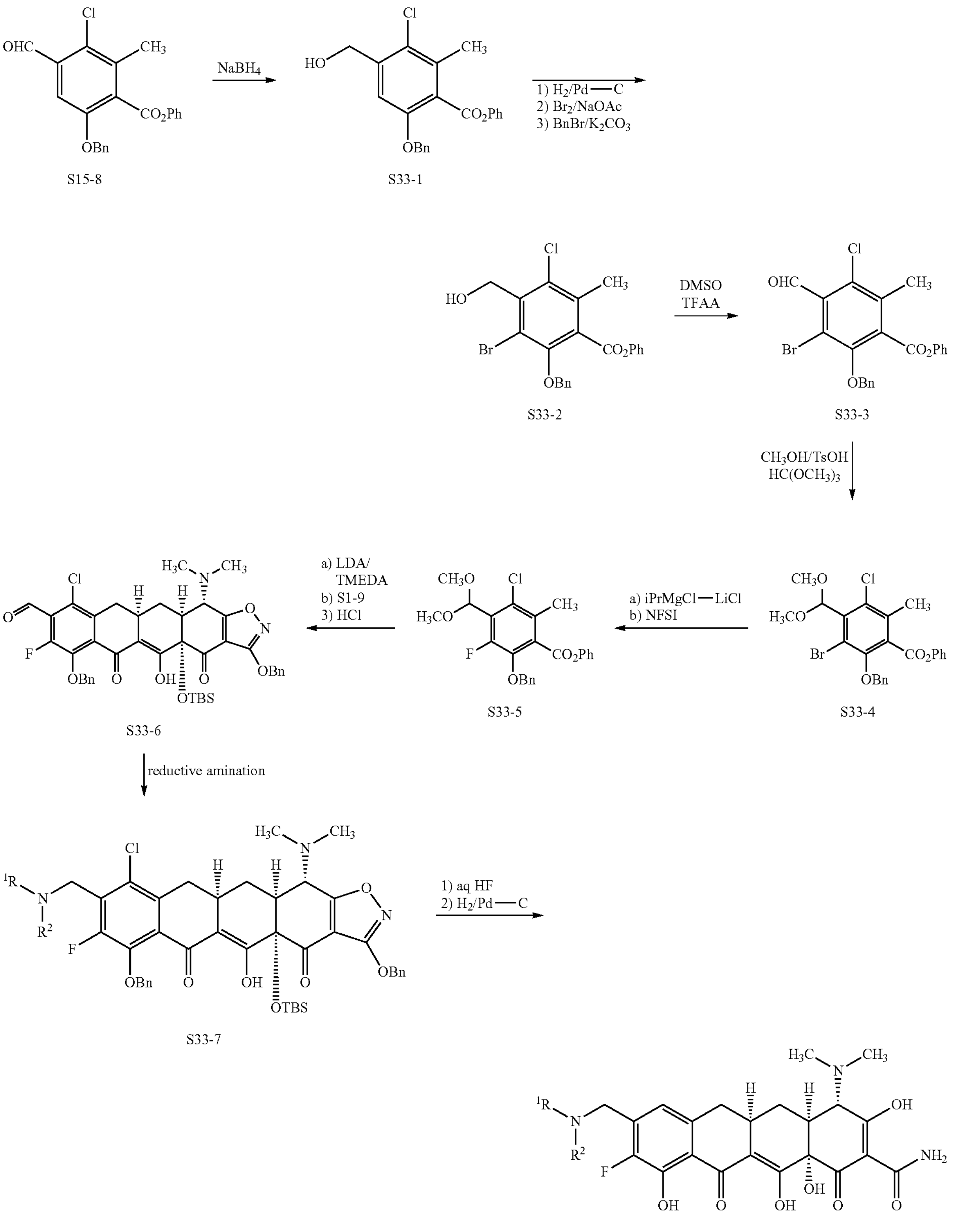
S15-8, S33-1, S33-2, S33-3, S33-4, S33-5, S33-6, S33-7, S33-8

The following compounds were prepared according to Scheme 33.

S33-1

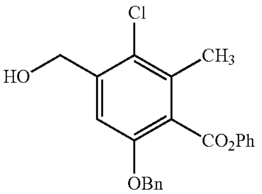

Compound S15-8 (2.51 g, 6.59 mmol) was suspended in methanol (25 mL) and sodium borohydride (373 mg, 9.88 mmol) was added in several portions. After gas evolution ceased and complete solution was achieved, the reaction mixture was quenched with $NaHCO_3$ (saturated, aqueous solution) and was extracted with EtOAc (3×). The organics were dried over $Na_2SO_4$, filtered, and concentrated under reduced pressure. This gave 2.49 g (99%) of S33-1 as a white solid. NMR (400 MHz, $CDCl_3$) δ 7.46-7.32 (m, 7 H), 7.27-7.21 (m, 1 H), 7.13 (s, 1 H), 7.07 (d, J=8.7 Hz, 2 H), 5.16 (s, 2 H), 4.77 (d, J=6.4 Hz, 2 H), 2.46 (s, 3 H), 2.06 (t, J=6.4 Hz, 1 H); MS (ESI) m/z 405.15 (M+H).

S33-2

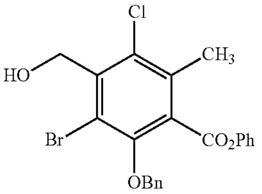

10% Palladium on carbon (Degussa, 50 mg) was added to a solution of compound S33-2 (1.85 g, 4.84 mmol) in EtOAc (10 mL), Methanol (10 mL), and chlorobenzene (1.5 mL) and an atmosphere of hydrogen was introduced. After 5 hours, the reaction mixture was purged with nitrogen and was filtered through Celite. The filtrate was concentrated under reduced pressure, yielding the phenol intermediate as a white solid. The intermediate was dissolved in acetic acid (15 mL) and sodium acetate (0.595 g, 7.26 mmol) was added. Bromine (0.372 mL, 7.26 mmol) was added dropwise over ~3 min. After 10 min, the reaction mixture was quenched with $Na_2S_2O_3$ (5% aqueous solution) and was diluted with EtOAc. The layers were separated, and the EtOAc layer was washed with water (3×) and brine (1×). The organics were dried over $Na_2SO_4$, filtered, and concentrated under reduced pressure. The material was dissolved in acetone (30 mL), and $K_2CO_3$ (1.34 g, 9.68 mmol) and benzylbromide (0.633 mL, 5.32 mmol) were added. The reaction mixture was heated to 50° C. overnight. Upon cooling to it, the reaction mixture was diluted with EtOAc and was washed with water (3×) and brine (1×). The organics were dried over $Na_2SO_4$, filtered, and concentrated under reduced pressure. The material was purified by column chromatography (Biotage 50 g column, 7 to 60% EtOAc in hexane gradient), yielding 2.03 g (91%) of S33-2. $^1H$ NMR (400 MHz, $CDCl_3$) δ 7.51-7.47 (m, 2 H), 7.41-7.31 (m, 5 H), 7.30-7.23 (m, 1 H), 7.03 (d, J=8.2 Hz, 2 H), 5.12-5.05 (m, 4 H), 2.48 (s, 3 H), 2.18 (t, J=7.1 Hz, 1 H); MS (ESI) m/z 482.99, 484.99, 486.99 (M+Na).

S33-3

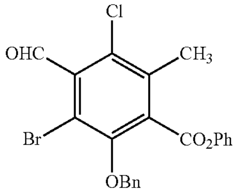

Compound S33-2 (195 mg, 0.423 mmol) was dissolved in dichloromethane (4 mL) and DMSO (60.1 μL, 0.846 mmol, 2.0 eq.) was added dropwise at −30° C. After stirred for 5 minutes, trifluoroacetic anhydride (TFAA, 0.117 mL, 0.846 mmol, 2.0 eq.) was added slowly in 5 min. The reaction mixture was warmed up to −20° C. and stirred another 15 min. Triethylamine (0.173 mL, 1.27 mmol, 3.0 eq.) was added and reaction mixture was allow to warm up to rt. The reaction mixture was quenched with $NH_4Cl$ (saturated, aqueous solution) and was extracted with EtOAc (3×10 mL). The organics were dried over $Na_2SO_4$, filtered, and concentrated under reduced pressure. The material was purified by column chromatography (Biotage 10 g column, 5 to 20% EtOAc in hexane gradient), yielding 150 mg (76%) of S33-3 and recover 37 mg compound S-33-2. $^1H$ NMR (400 MHz, $CDCl_3$) δ 10.34 (s, 1 H), 7.51-7.45 (m, 2 H), 7.43-7.31 (m, 5 H), 7.31-7.23 (m, 1 H), 7.03 (d, J=8.2 Hz, 2 H), 5.13 (s, 2 H), 2.49 (s, 3 H); MS (ESI) m/z 481.02, 483.02 (M+Na).

S33-4

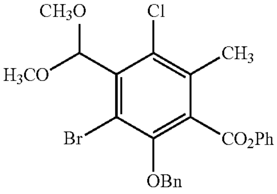

To a solution of aldehyde S33-3 (156 mg, 0.34 mmol, 1.0 equiv) in MeOH (4 mL) was added trimethylorthoformate (231 μL, 2.11 mmol, 5.0 equiv) and TsOH (8 mg, 0.1 equiv). The reaction was heated to 65° C. for overnight. The solvent was evaporated. The residue was redissolved in EtOAc (20 mL), washed with saturated aqueous $NaHCO_3$ and brine, dried Over sodium sulfate, and concentrated. Purification of the residue by flash chromatography gave compound S33-4 (163 mg, 94.5%) as a white solid: $^1H$ NMR (400 MHz, $CDCl_3$) δ 7.44-7.40 (m, 2 H), 7.38-7.30 (m, 5 H), 7.25-7.20 (m, 1 H), 7.09-7.03 (m, 2 H), 5.60 (s, 1 H), 5.16 (s, 2 H), 3.35 (s, 6 H), 2.46 (s, 3 H); MS (ESI) m/z 527.09 (M+Na).

S33-5

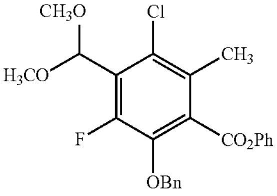

To a solution of compound S33-4 (163 mg, 0.32 mmol, 1.0 equiv) in anhydrous THF (3 mL) was added i-PrMgCl.LiCl (0.536 mL, 1.2 M/THF, 0.643 mmol, 2.0 equiv) dropwise at −78° C. under a $N_2$ atmosphere. After 10 min, the temperature was raised to 0° C. and the reaction was stirred for 1 h at 0° C. The reaction mixture was cooled to −60° C. and N-fluorobenzenesulfonimide (304 mg, 0.964 mmol, 3.0 eq.) in 1 mL THF solution was added slowly. The reaction was warmed to −20° C., stirred for 30 min at rt, and quenched by saturated aqueous $NH_4Cl$. The layers were separated and the aqueous layer was further extracted twice with EtOAc. The combined organic layers were washed with brine, dried over sodium sulfate, filtered, and concentrated. Purification of the residue by flash chromatography gave compound S33-5 (93 mg, 65%) as a white solid: $^1H$ NMR (400 MHz, $CDCl_3$) δ 7.46-7.42 (m, 2 H), 7.40-7.31 (m, 5 H), 7.26-7.22 (m, 1 H), 7.09-7.03 (m, 2 H), 5.62 (s, 1 H), 5.19 (s, 2 H), 3.36 (s, 6 H), 2.48 (s, 3 H); MS (ESI) m/z 467.15 (M+Na).

S33-6

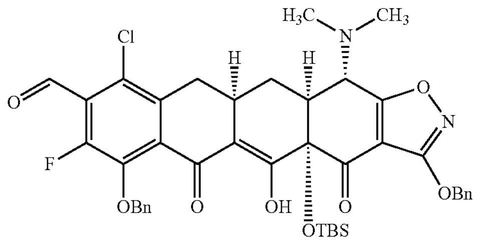

A solution of n-BuLi in hexanes (196 μL, 1.6 M, 0.313 mmol, 1.5 equiv) was added dropwise to a solution of i-$Pr_2NH$ (43.9 μL, 0.313 mmol, 1.5 equiv) in THF (2 mL) at −78° C. under a $N_2$ atmosphere. The resulting solution was stirred at −78° C. for 20 min and −20° C. for 5 min, and then re-cooled to −78° C. N,N,N',N'-Tetramethylethylenediamine (TMEDA, 62.7 μL, 0.418 mmol, 2.0 equiv) was added, followed by dropwise addition of S33-5 (93 mg, 0.209 mmol, 1.0 equiv) in THF (1 mL) via syringe. After complete addition, the resulting dark-red mixture was stirred for another hour at −78° C. and then cooled to −100° C. A solution of enone S1-9 (100.9 mg, 0.209 mmol, 1.0 equiv) in THF (1 mL) was added dropwise via syringe. The resulting red mixture was slowly warmed to −78° C. LHMDS (0.313 mL, 1.0 M/THF, 0.313 mmol, 1.5 equiv) was then added and the reaction was slowly warmed to −20° C. Saturated aqueous $NH_4Cl$ was added. The resulting mixture was extracted three times with EtOAc. The combined EtOAc extracts were washed with brine, dried (sodium sulfate), and concentrated. Purification of the residue by flash chromatography gave the desired product (120 mg, 69%) as light yellow foam: MS (ESI) m/z 833.47 (M+H).

To a solution of the above product (120 mg, 0.144 mmol, 1.0 equiv) in THF (10 mL) was added 6 N HCl (1.5 mL) at rt. The resulting mixture was stirred at rt for 2 hrs, diluted with EtOAc, washed with saturated aqueous $NaHCO_3$ and brine, dried over sodium sulfate, and concentrated. Purification of the residue by flash chromatography gave crude aldehyde S33-6 as a light yellow foam: MS (ESI) m/z 819.40 [(M+MeOH)+H].

S33-8-1

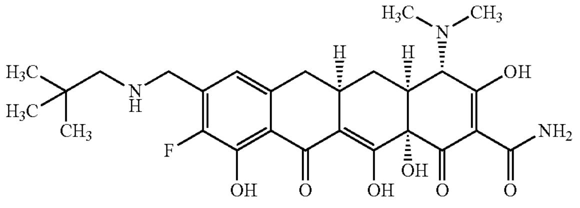

Compound S33-6 (45 mg, 0.057 mmol, 1.0 equiv) was dissolved in 1,2-dichloroethane (3.0 mL). Neopentylamine (20 μL, 0.171 mmol, 3.0 equiv) and acetic acid (13.6 μL, 0.228 mmol, 4.0 equiv) were added. After stirring at rt for 1 h, sodium triacetoxyborohydride (24.1 mg, 0.104 mmol, 2.0 equiv) was added. Stirring was continued overnight. The reaction mixture was poured into saturated aqueous $NaHCO_3$ and extracted three times with dichloromethane. The combined organic extracts were washed with brine, dried over sodium sulfate, and concentrated to give the crude intermediate (20 mg), which was used directly in the next step without further purification: MS (ESI) m/z 858.50 (M+H).

In a plastic vial, the above amine intermediate was dissolved in $CH_3CN$ (1 mL). Aqueous HF (48-50%, 0.25 mL) was added. After stirring at rt for 16 hrs, the reaction mixture was poured into aqueous solution (10 mL) of $K_2HPO_4$ (2.0 g) and extracted three times with dichloromethane. The combined organic phases were washed with brine, dried, and concentrated to yield the crude intermediate: MS (ESI) m/z 744.40 (M+H).

The above crude intermediate was dissolved in MeOH (2 mL) with 0.5 N HCl/MeOH (0.4 mL). Pd—C (10 wt %, 20 mg) was added. The reaction flask was briefly evacuated and re-filled with hydrogen. The reaction mixture was stirred at rt and monitored by LC-MS. After the reaction was complete, the mixture was filtered through a small pad of Celite. The filtrate was concentrated to give the crude product, which was purified by HPLC on a Waters Autopurification system using a Phenomenex Polymerx 10μ RP-γ 100 R column [30×21.20 mm, 10 micron; flow rate, 20 mL/min; Solvent A: 0.05 N HCl/water; Solvent B: MeOH; injection volume: 4.0 mL (0.05 N HCl/water); gradient: 20→100% B over 10 min; mass-directed fraction collection]. Fractions containing the desired product were collected and freeze-dried to give the desired product as a yellow solid S33-8-1 (4.5 mg, 14.9% for three steps): $^1H$ NMR (400 MHz, $CD_3OD$) δ 6.94 (d, J=6.0 Hz, 1 H), 4.34 (s, 2 H), 4.08 (s, 1 H), 3.21-2.92 (m, 3 H), 3.03 (s, 3 H), 2.96 (s, 3 H), 2.92 (s, 2 H), 2.65-2.52 (m, 1 H), 2.25-2.16 (m, 1 H), 1.68-1.55 (m, 1 H), 1.06 (s, 9 H); MS (ESI) m/z 532.25 (M+H).

The following compounds were prepared according to the methods for compound S33-8-1.

S33-8-2

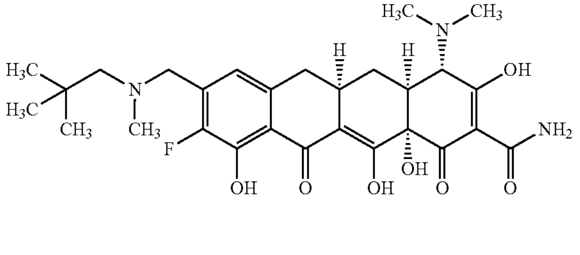

S33-8-2: $^1$H NMR (400 MHz, $CD_3OD$) δ 6.97 (d, J=6.0 Hz, 1 H), 4.63-4.54 (m, 1 H), 4.40-4.32 (m, 1 H), 4.08 (s, 1 H), 3.22-2.86 (m, 13 H), 2.64-2.53 (m, 1 H), 2.24-2.16 (m, 1 H), 1.68-1.58 (m, 1 H), 1.08 (s, 9 H); MS (ESI) m/z 546.28 (M+H).

S33-8-3

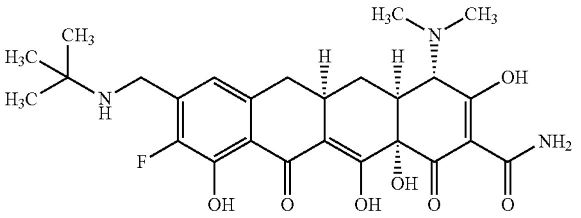

S33-8-3: $^1$H NMR (400 MHz, $CD_3OD/DCl$) δ 6.92 (d, J=5.96 Hz, 1 H), 4.30-4.20 (m, 2 H), 4.08 (s, 1 H), 3.18-2.94 (m, 3 H), 3.04 (s, 3 H), 2.96 (s, 3 H), 2.90 (dd, J=13.1, 4.6 Hz, 1 H), 2.62-2.52 (m, 1 H), 2.25-2.14 (m, 1 H), 1.68-1.56 (m, 1 H), 1.47 (s, 9 H); MS (ESI) m/z 518.24 (M+H).

The compounds of the invention including those described above are set forth in Figures: FIGS. 2A-2K; FIGS. 3A-3EE; FIGS. 4A-4Z; FIGS. 5A-5O; FIGS. 6A-6LLL.

EXAMPLE 34

Antibacterial Activity of Compounds of the Invention

The antibacterial activities for the compounds of the invention were studied according to the following protocols.

Minimum Inhibitory Concentration Assay

Frozen bacterial strains were thawed and subcultured onto Mueller Hinton Broth (MHB) or other appropriate media (*Streptococcus* requires blood and *Haemophilus* requires hemin and NAD). Following incubation overnight, the strains were subcultured onto Mueller Hinton Agar and again incubated overnight. Colonies were observed for appropriate colony morphology and lack of contamination. Isolated colonies were selected to prepare a starting inoculum equivalent to a 0.5 McFarland standard. The starting inoculum was diluted 1:125 using MHB for further use. Test compounds were prepared by dilution in sterile water to a final concentration of 5.128 mg/mL. Antibiotics (stored frozen, thawed and used within 3 hours of thawing) and compounds were further diluted to the desired working concentrations.

The assays were run as follows. Fifty μL of MHB was added to wells 2-12 of a 96-well plate. One hundred μL of appropriately diluted antibiotics was added to well 1. Fifty μL of antibiotics was removed from well 1 and added to well 2 and the contents of well 2 mixed by pipetting up and down five times. Fifty μL of the mixture in well 2 was removed and added to well 3 and mixed as above. Serial dilutions were continued in the same manner through well 12. Fifty μL was removed from well 12 so that all contained 50 μL. Fifty μL of the working inoculum was then added to all test wells. A growth control well was prepared by adding 50 μL of working inoculum and 50 μL of MHB to an empty well. The plates were then incubated at 37° C. overnight, removed from the incubator and each well was read on a plate reading mirror. The lowest concentration (MIC) of test compound that inhibited the growth of the bacteria was recorded.

Example

| | 1 | 2 | 3 | 4 | 5 | 6 | 7 | 8 | 9 | 10 | 11 | 12 |
|---|---|---|---|---|---|---|---|---|---|---|---|---|
| [Abt] | 32 | 16 | 8 | 4 | 2 | 1 | 0.5 | 0.25 | 0.125 | 0.06 | 0.03 | 0.015 |
| Grow | − | − | − | − | − | + | + | + | + | + | + | + |

Interpretation: MIC = 2 μg/mL
[abt] = antibiotic concentration in the well
Grow = bacterial growth (cloudiness)

Protocol for Determining Inoculum Concentration (Viable Count)

Ninety μl of sterile 0.9% NaCl was pipetted into wells 2-6 of a 96-well microtiter plate. Fifty 50 μl of the inoculum was pipetted into well 1. Ten μL, from was removed from well 1 and added it to well 2 followed by mixing. Ten μL was removed from well two and mixed with the contents of well 3 and so on creating serial dilutions through well 6. Ten μL was removed from each well and spotted onto an appropriate agar plate. The plate was placed into a $CO_2$ incubator overnight. The colonies in spots that contain distinct colonies were counted. Viable count was calculated by multiplying the number of colonies by the dilution factor.

| | Spot from Well | | | | | |
|---|---|---|---|---|---|---|
| | 1 | 2 | 3 | 4 | 5 | 6 |
| Dilution Factor | $10^2$ | $10^3$ | $10^4$ | $10^5$ | $10^6$ | $10^7$ |

Bacterial Strains

Fifteen bacterial strains, listed below, were examined in minimum inhibitory concentration (MIC) assays.

| Organism | Strain Designation | Key Properties |
|---|---|---|
| *Staphylococcus aureus* | SA100 | ATCC 13709, MSSA, Smith strain |
| *Staphylococcus aureus* | SA101 | ATCC 29213, CLSI quality control strain, MSSA |
| *Staphylococcus aureus* | SA191 | HA-MRSA, tetracycline-resistant, lung infection model isolate |
| *Staphylococcus aureus* | SA161 | HA-MRSA, tetracycline-resistant, tet(M) |
| *Staphylococcus aureus aaaureusaureus* | SA158 | Tetracycline-resistant tet(K) |

-continued

| Organism | Strain Designation | Key Properties |
|---|---|---|
| *Staphylococcus epidermidis* | SE164 | ATCC 12228, CLSI quality control strain, tetracycline-resistant |
| *Enterococcus faecalis* | EF103 | ATCC 29212, tet-I/R, control strain |
| *Enterococcus faecalis* | EF159 | Tetracycline-resistant, tet(M) |
| *Enterococcus faecalis* | EF327 | Wound isolate (US) tet(M) |
| *Enterococcus faecium* | EF404 | Blood isolate (US) tet(M) |
| *Streptococcus pneumoniae* | SP106 | ATCC 49619, CLSI quality control strain |
| *Streptococcus pneumoniae* | SP160 | Tetracycline-resistant, tet(M) |
| *Streptococcus pyogenes* | SP312 | 2009 clinical isolate, tet(M) |
| *Streptococcus pyogenes* | SP193 | *S. pyogenes* for efficacy models; tetS; sensitive to sulfonamides |
| *Haemophilus influenzae* | HI262 | Tetracycline-resistant, ampicillin-resistant |
| *Moraxella catarrhalis* | MC205 | ATCC 8176, CLSI quality control strain |
| *Escherichia coli* | EC107 | ATCC 25922, CLSI quality control strain |
| *Escherichia coli* | EC155 | Tetracycline-resistant, tet(A) |
| *Escherichia coli* | EC878 | MG1655 tolC::kan |
| *Escherichia coli* | EC880 | lpxA |
| *Escherichia coli* | EC882 | impA |
| *Escherichia coli* | EC200 | MDR uropathogenic; serotype O17:K52:H18; UMN 026; trimeth/sulfa-R; BAA-1161 |
| *Enterobacter cloacae* | EC108 | ATCC 13047, wt |
| *Enterobacter cloacae* | EC603 | Urine isolate (Spain) |
| *Klebsiella pneumoniae* | KP109 | ATCC 13883, wt |
| *Klebsiella pneumoniae* | KP153 | Tetracycline-resistant, tet(A), MDR, ESBL$^+$ |
| *Klebsiella pneumoniae* | KP457 | 2009 ESBL$^+$, CTX-M, OXA |
| *Proteus mirabilis* | PM112 | ATCC 35659 |
| *Proteus mirabilis* | PM385 | Urine ESBL$^+$ isolate |
| *Pseudomonas aeruginosa* | PA111 | ATCC 27853, wt, control strain |
| *Pseudomonas aeruginosa* | PA169 | Wt, parent of PA170-173 |
| *Pseudomonas aeruginosa* | PA173 | PA170 ΔmexX; MexXY- (missing a functional efflux pump) |
| *Pseudomonas aeruginosa* | PA555 | ATCC BAA-47, wild type strain PAO1 |
| *Pseudomonas aeruginosa* | PA556 | Multiple-Mex efflux pump knockout strain |
| *Pseudomonas aeruginosa* | PA689 | Blood isolate (US) |
| *Acinetobacter baumannii* | AB110 | ATCC 19606, wt |
| *Acinetobacter baumannii* | AB250 | Cystic fibrosis isolate, MDR |
| *Stenotrophomonas maltophilia* | SM256 | Cystic fibrosis isolate, MDR |
| *Burkholderia cenocepacia* | BC240 | Cystic fibrosis isolate, MDR |

*MDR, multidrug-resistant; MRSA, methicillin-resistant *S. aureus*; MSSA, methicillin-sensitive *S. aureus*; HA-MRSA, hospital-associated MRSA; tet(K), major gram-positive tetracycline efflux mechanism; tet(M), major gram-positive tetracycline ribosome-protection mechanism; ESBL$^+$, extended spectrum β-lactamase Results Values of minimum inhibition concentration (MIC) for the compounds of the invention are provided in FIGS. 7A-7J; FIGS. 8A-8D; FIGS. 9A-9M; FIGS. 10A-10I; FIGS. 11A-11G.

BIOLOGICAL TESTING

Neutropenic Respiratory Infection Models for *S. pneumoniae*

Compounds were tested in a neutropenic BALB/c murine model of lung infection challenged with tetracycline-resistant tet(M) *S. pneumoniae* strain SP160. Mice were made neutropenic by pre-treatment with cyclophosphamide and infected with SP160 via intranasal administration. Mice were dosed orally with 30 mg/kg compound at 2 and 12 hours post-infection. At 24 hours following initiation of treatment, mice were euthanized and bacterial reduction in the lung was quantified by plating lung homogenates. Data was recorded as $\log_{10}$ reduction in lung colony forming units versus an untreated control group. The results of the testing are shown in Table A.

TABLE A

| COMPOUND NO. | Bacterial Reduction in the Lung ($Log_{10}$ change from 24 hour control) |
|---|---|
| S2-4-28 | −0.06 |
| S15-13-188 | −0.22 |
| S15-13-223 | −0.12 |
| S16-10-79 | −4.31 |
| S24-9-21 | −0.89 |

Neutropenic Respiratory Infection Model for MRSA

Compounds were tested in a neutropenic BALB/c murine model of lung infection challenged with a tetracycline-resistant tet(M) MRSA strain SA191 infected via intranasal administration. At 2 and 12 hours mice were dosed orally with 50 mg/kg compound. At 24 hours following initiation of treatment, mice were euthanized and bacterial reduction in the lung was quantified by plating lung homogenates. Data was recorded as $\log_{10}$ reduction in lung colony forming units versus an untreated control group. The results of the testing are shown in Table B.

TABLE B

| COMPOUND NO. | Bacterial Reduction in the Lung ($Log_{10}$ change from 24 hour control) |
|---|---|
| S29-2-4 | −1.29 |
| S16-10-79 | −1.27 |
| S24-9-21 | −1.98 |

Mouse Systemic Infection Protocol-*S. aureus* Smith Septicemia

Compounds were screened for antibacterial activity in vivo in a mouse systemic infection (septicemia) model. In the model, CD-1 female mice (18-22 grams) were injected IP with a *S. aureus* Smith (ATCC 13709) inoculum that results in 0% survival within 24 to 48 hours. The bacterial dose required to achieve this effect was previously established through virulence studies. At one hour post infection, mice received either 3 mg/ml IV or 30 mg/ml PO. Typically, six mice were treated per dose group. Animal survival was assessed and recorded for 48 hours. Percent survival at 48 hours was recorded and $PD_{50}$ (mg/kg) was determined for each compound tested. The results (% survival or PD50, the dose in mg/kg that prevents 50% of the mice from death) are presented in Table C.

TABLE C

| | SA Smith septicemia survival | | SA Smith septicemia | |
|---|---|---|---|---|
| | IV | PO | PD50 (mg/kg) | |
| Compound | (3 mg/kg) | 30 mg/kg) | IV | PO |
| S1-14-105 | 67% | 0% | | |
| S1-14-128 | 100% | 100% | | |
| S1-14-134 | 50% | 17% | | |
| S1-14-25 | 33% | 17% | | |
| S1-14-28 | 33% | 17% | | |
| S1-14-31 | 0% | 0% | | |
| S1-14-36 | 33% | 0% | | |
| S1-14-4 | 100% | 0% | | |

TABLE C-continued

| Compound | SA Smith septicemia survival IV (3 mg/kg) | SA Smith septicemia survival PO 30 mg/kg) | SA Smith septicemia PD50 (mg/kg) IV | SA Smith septicemia PD50 (mg/kg) PO |
|---|---|---|---|---|
| S1-14-46 | 0% | 0% | | |
| S1-14-73 | 50% | 75% | | |
| S1-14-90 | 33% | 0% | | |
| S1-14-91 | 17% | 60% | | |
| S15-13-117 | 33% | 20% | | |
| S15-13-15 | 100% | 100% | | 3.5 |
| S15-13-16 | 33% | 17% | | |
| S15-13-17 | 100% | 67% | | |
| S15-13-182 | 33% | 67% | | |
| S15-13-184 | 17% | 0% | | |
| S15-13-187 | 100% | 100% | | |
| S15-13-188 | 100% | 100% | | 8.3 |
| S15-13-194 | 100% | 100% | | |
| S15-13-203 | 100% | 100% | | |
| S15-13-215 | 50% | 50% | | |
| S15-13-221 | 33% | 50% | | |
| S15-13-222 | 100% | 100% | | |
| S15-13-223 | 100% | 100% | | |
| S15-13-225 | 100% | 100% | | |
| S15-13-226 | 100% | 83% | | |
| S15-13-227 | 17% | 0% | | |
| S15-13-23 | 83% | 50% | | |
| S15-13-4 | 100% | 100% | | 6.2 |
| S15-13-5 | 50% | 17% | | |
| S15-13-8 | 67% | 50% | | |
| S16-10-107 | 100% | 100% | | |
| S16-10-11 | 100% | 100% | | 10 |
| S16-10-161 | 100% | 100% | | |
| S16-10-177 | 100% | 100% | | |
| S16-10-18 | 17% | 0% | | |
| S16-10-79 | 100% | 100% | | |
| S19-8-1 | 100% | 100% (1) | 0.36 | 12.2 |
| S21-12-1 | 100% | 33 | | |
| S2-4-11 | 0% | 0% | | |
| S2-4-12 | 100% | 100% | 0.69 | 2.1 |
| S2-4-14 | 100% | 100% | 0.84 | 12.2 |
| S2-4-19 | 100% | 83% | 1 | 14.3 |
| S2-4-21 | 16% (2) | 0% | | |
| S2-4-25 | 100% | 100% | 0.35 | 1.4 (2) |
| S2-4-28 | 100% | 100% | 0.62 | 3 |
| S2-4-29 | 100% | 100% | 1 | 3.5 |
| S2-4-30 | 33% | | | >60 |
| S2-4-33 | 67% | 33% | | |
| S2-4-41 | 0% | 0% | | |
| S2-4-50 | 33% | 20% | | |
| S2-4-50 | 100% | 100% | 1 | 10.1 |
| S2-4-57 | 50% | 33% | | |
| S2-4-60 | 17% | 33% | | |
| S2-4-62 | 17% | 25% | | |
| S2-4-65 | 100% | 100% | | 8.4 |
| S2-4-66 | 100% | 100% | | 8.5 |
| S2-4-7 | 67% | 17% | | |
| S24-9-10 | 100% | 100% | | |
| S24-9-17 | 100% | 100% | | |
| S24-9-19 | 100% | 100% | | |
| S24-9-21 | 100% | 100% | | |
| S24-9-23 | 100% | 100% | | |
| S24-9-25 | 100% | 100% | | |
| S24-9-31 | 100% | 100% | | |
| S25-11-1 | 100% | 100% | | |
| S25-11-12 | 0% | 20% | | |
| S25-11-171 | 83% | 17% | | |
| S25-11-48 | 100% | 100% | | |
| S25-11-56 | 67% | 33% | | |
| S25-11-68 | 50% | 83% | | |
| S27-9-5 | 83% | 67% | | |
| S27-9-7 | 17% | 33% | | |
| S29-2-4 | 100% | 83% | | |
| S3-5-5 | 100% | 100% | | |
| S6-4-1 | 100% | 100% | | |

Kidney Infection Models for Uropathogenic *E. coli* EC200 and *K. pneumoniae* ESBL Isolate KP453

Compounds were tested in a BALB/c murine kidney infection model challenged with tetracycline-resistant *E. coli* strain uropathogenic ED200 via intravenous injection. At 12 and 24 hours post infection mice were treated orally with 2 mg/kg of test compound. For IV administration test compound was dosed at 3 mg/kg. Thirty-six hours following initiation of treatment, mice were euthanized and bacterial reduction in the kidney was quantified by plating kidney homogenates. Results are reported in Table D as $log_{10}$ reduction in colony forming units (CFUs) in the kidney versus untreated controls (receiving no test compound).

Compounds were also tested in BALB/c murine kidney infection model challenged with levofloxacin-resistant, $ESBL^+$ strain KP453 via intravenous injection with 2% carageenen. At 9 and 24 hours post infection mice were treated orally with 50 mg/kg of test compound. For IV administration, test compounds were dosed at 20 mg/kg. At 36 hours following initiation of treatment, mice were euthanized and bacterial reduction in the kidney was quantified by plating homogenates. Results are reported in Table D as $log_{10}$ reduction in colony forming units (CFUs) in the kidney versus untreated controls (receiving no test compound).

TABLE D

| Compd. No. | EC200 UTI IV 3 mg/kg | EC200 UTI PO 2 mg/kg | KP453 ESBL UTI IV 20 mg/kg | KP453 ESBL UTI PO 50 mg/kg |
|---|---|---|---|---|
| S2-4-25 | | −3.63 @ 3 mpk; −2.78 A 2 mpk | −1.07, −2.15[a] | |
| S2-4-19 | | −1.91 | | −1.27 |
| S2-4-12 | | −2.51 | | −2.15 |
| S2-4-65 | | −4.61 @ 12 mpk; −3.18 @ 2 mpk | | −2.28 |
| S3-5-5 | | −2.26 | | −1.01, −1.74[a] |
| S15-13-15 | | −2.82 | | −1.45 |
| S15-13-4 | | −3.17 | | −1.69 |
| S15-13-188 | | −3.48 @ 3 mpk | | −1.55 |
| S15-13-187 | | −3.46 @ 3 mpk | | −0.98, −1.99[a] |
| S15-13-194 | | −3.44 | | −2.18 |
| S15-13-122 | | −2.64 | | −1.84 |
| S15-13-223 | | −2.27 | | −1.32 |
| S16-10-161 | @ 5 mpk −3.99 | −1.85, −2.83 | −3.09 | −1.04, −1.07[a] |
| S24-9-17 | | −2.61 | | −2.41 |
| S24-9-23 | @ 5 mpk −4.34 | −2.99 | −2.95 | −2.93 |
| S24-9-21 | @ 5 mpk −4.09 | −2.30 | −2.87 | −2.16 |
| S24-9-25 | | −2.99 | | −1.71 |
| S25-11-1 | | −3.97 | | −1.84 |

[a]Different testing days

Neutropenic Thigh Model

Female CD-1 mice were pre-treated with cyclophosphamide to render the mice neutropenic. Mice were infected with *S. aureus* ATCC 13709 via injection of 0.1 ml into the right thigh muscle of each mouse. One and a half hours post infection mice were treated IV with test compounds in doses ranging from 0.3 to 30 mg/kg or 0.3 to 20 mg/kg. Four mice were treated with each drug concentration. Twenty-four hours post treatment, mice were euthanized by $CO_2$ inhalation. The right thighs of the mice were aseptically removed, weighed, homogenized, serially diluted, and plated on TSA medium. The plates were incubated overnight at 37° C. in 5% $CO_2$. Colony forming units per gram of thigh was calculated by enumerating the plated colonies then adjusting for serial dilutions and the weight of the thigh. Data was recorded as $log_{10}$ reduction in colony forming units versus an untreated control group and is presented in Table E.

TABLE E

| COMPOUND NO. | $log_{10}$ REDUCTION |
|---|---|
| S2-4-14 | 3.68 |
| S2-4-25 | 4.1 |
| 22-4-29 | 4.35 |

Pharmacokinetic Studies in Rats

Test compounds were evaluated in fasted (no food for 18 hours prior to dosing) male Sprague Dawley rats (3 animals per group) by administration of 1 mg/kg intravenously into the jugular vein and 10 mg/jg by oral gavage. Ten plasma samples were drawn for each dosing route up to 24 hours into heparin-coated vacutainer tubes. The plasma concentrations of the test compounds were quantified by LC/MS/MS using an internal standards. WinNONLIN was used to determine PK parameters ±standard deviation (AUC, Cmax, CL, Vss and % oral bioavailabilty (% F) and are set forth in Table F.

TABLE F

| Cmpd. No. | Oral Rat PK 10 mg/kg | IV Rat PK 1 mg/kg |
|---|---|---|
| S2-4-14 | Cmax 543; AUC 6160; 13.7% (% F) | Cmax 667; AUC 4432; Cl 233; Vss 1.4 |
| S2-4-25 | Cmax 76.7; AUC 826; 9.1% (% F) | Cmax 214; AUC 838; Cl 1164; Vss 6.6 12 h urine 11 ug/mL |
| S2-4-28 | Cmax 381; AUC 4381; 44.7% (% F) | Cmax 170; AUC 970; Cl 1056; Vss 5.7; |
| S2-4-29 | Cmax 171; AUC 1597; 25.4% (% F) | Cmax 112; AUC 616; Cl 1589; Vss 9.2 |
| S2-4-19 | Cmax 572; AUC 4981; 14.9% (% F) | Cmax 518; AUC 3321; Cl 300; Vdss 1.6 |
| S2-4-12 | Cmax 117; AUC 1163; 14.6% (% F) | Cmax 126; AUC 754; Cl 1277; Vdss 9.3 |
| S15-13-15 | Cmax 162; AUC 2263; 21.0% (% F) | Cmax 154; AUC 1104; Cl 927; Vdss 6.4 |
| S16-10-161 | Cmax 465; AUC 4442; 31.6% (% F) | Cmax 689; AUC 1307; Cl 768; Vdss 4.96 |
| S24-9-23 | Cmax 310; AUC 2226; 12.2% (% F) | Cmax 795; AUC 1831; Cl 555.6; Vdss 3.9 |

SA MIC90

FIGS. 1A-1C provides the results of testing selected compounds against selected groups isolates as indicated in the figure to determine the minimal inhibitory concentration (MIC) of test compounds for 90% of the isolates ($MIC_{90}$). MICs were performed by microtiter broth dilution in a 96-well format according to Clinical Laboratory Standards Institute (CLSI) guidelines, as described above.

Viable counts were determined by 10-fold serial dilution. Dilutions were prepared in sterile 0.9% NaCl. Ten microliters of the inoculum and of each of 5 dilutions were plated onto blood or Mueller Hinton agar plates, incubated overnight at 37° C. with 5% $CO_2$, and counted. Results are shown in FIGS. 1A-1C.

Monkey PK

Compounds S24-9-23 and S16-10-161 were evaluated in 3 non-naïve cynomolgus monkeys. Each animal received a single IV dose of 1 mg/kg and after a 7-day washout, received a single PO dose of 10 mg/kg. Nine to ten plasma samples were drawn for each dosing route up to 24 hours into heparin-coated vacutainer tubes. Dose formulations were verified with a 5-point calibration curve. The plasma concentration of the compound was quantified by LC/MS/MS using an internal standard. WinNonLin was used to determine individual and mean PK parameters ±standard deviation (% F (oral bioavailability), Cmax, Tmax, CL, Vss, AUC. Results were as follows: For S24-9-23 oral: Cmax=1350 ng/mL; AUC=22767 ng·hr/mL; % F=36.8% and IV: Cmax=1373 ng/mL; AUC=7070 ng·h/mL; Cl=144 mL/hr/kg, Vdss=3.4 L/kg. For S16-10-161 oral: Cmax=982 ng/mL; AUC=26000 ng·hr/mL; % F=42.7% and IV: Cmax=861; AUC=5677 ng·h/mL; C1=183.6 mL/hr; Vdss=4.047.

While this invention has been particularly shown and described with references to example embodiments thereof, it will be understood by those skilled in the art that various changes in form and details may be made therein without departing from the scope of the invention encompassed by the appended claims.

What is claimed is:

1. A compound of Formula (II):

(II)

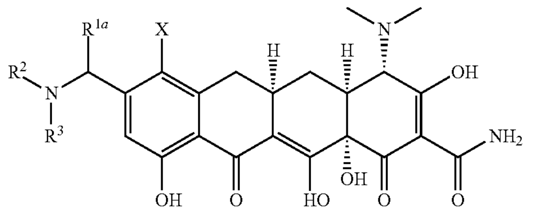

or a pharmaceutically acceptable salt thereof, wherein:

X is selected from bromo, fluoro, chloro, $C_1$-$C_6$ fluoroalkyl, —O—$C_1$-$C_6$ alkyl, —$S(O)_m$—$C_1$-$C_6$ alkyl, $C_3$-$C_7$ cycloalkyl, —O—$C_3$-$C_7$ cycloalkyl, —$S(O)_m$—$C_3$-$C_7$ cycloalkyl, —CN, and —NH—C(O)—($C_1$-$C_6$ alkylene)-N($R^4$)($R^5$), wherein each alkyl, alkylene or cycloalkyl in the group represented by X is optionally substituted with fluoro;

$R^{1a}$ is selected from hydrogen, $C_1$-$C_4$ alkyl, and $C_3$-$C_{10}$ carbocyclyl;

$R^2$ is selected from hydrogen, $C_1$-$C_{12}$ alkyl, —$C_0$-$C_6$ alkylene-$C_3$-$C_{10}$ carbocyclyl, and —$C_0$-$C_6$ alkylene-(4-13 membered) heterocyclyl;

$R^3$ is selected from hydrogen, $C_1$-$C_8$ alkyl, —$C_0$-$C_6$ alkylene-$C_3$-$C_{10}$ carbocyclyl, —$C_0$-$C_6$ alkylene-(4-13 membered) heterocyclyl, —C(O)—$C_1$-$C_6$ alkyl, —$C_0$-$C_6$ alkylene—C(O)N($R^4$)($R^5$), —C(O)—$C_1$-$C_6$ alkylene-N($R^4$)($R^5$), —$C_2$-$C_6$ alkylene—N($R^4$)($R^5$), —$S(O)_m$—$C_1$-$C_6$ alkyl, —$S(O)_m$—$C_3$-$C_{10}$carbocyclyl, and —$S(O)_m$-(4-13 membered) heterocyclyl, wherein each alkyl, carbocyclyl, alkylene or heterocyclyl in the group represented by $R^2$ or $R^3$ is optionally and independently substituted with one or more substituents independently selected from fluoro, chloro, —OH, —O—$C_1$-$C_4$ alkyl, $C_1$-$C_4$ alkyl, fluoro-substituted-$C_1$-$C_4$ alkyl, —N($R^4$)($R^5$), $C_3$-$C_{10}$carbocyclyl or a (4-13 membered) heterocyclyl; or $R^2$ and $R^3$ taken together with the nitrogen atom to which they are bound form a (4-7 membered) monocyclic heterocylic ring, or a (6-13 membered) bicyclic, spirocyclic or bridged heterocylic ring, wherein the (4-7 membered) monocyclic heterocylic ring, or the (6-13 membered) bicyclic, spirocyclic or bridged heterocyclic ring optionally comprises 1 to 4 additional heteroatoms independently selected from N, S and O; and wherein the (4-7 membered) monocyclic heterocylic ring, or the (6-13 membered) bicyclic, spirocyclic or bridged heterocyclic ring is optionally substituted with one or more substituents independently selected from $C_3$-$C_{10}$carbocyclyl, (4-13membered) heterocyclyl, fluoro, chloro, —OH, —$C_1$-$C_4$ fluoroalkyl, —$C_1$-$C_4$ alkyl, —O—$C_3$-$C_{10}$carbocyclyl, —O—(4-13 membered) heterocyclyl, —$C_0$-$C_4$ alkylene-O—$C_1$-$C_4$ alkyl, —$C_0$-$C_4$ alkylene-O—$C_1$-$C_4$ fluoroalkyl, =O, —C(O)—$C_1$-$C_4$ alkyl, —C(O)N($R^4$)($R^5$), —N($R^4$)—C(O)—$C_1$-$C_4$ alkyl, and —$C_0$-$C_4$ alkylene-N($R^4$)($R^5$), and wherein each carbocyclyl or heterocyclyl substituent is optionally substituted with fluoro, chloro, —OH, $C_1$-$C_4$ fluoroalkyl, $C_1$-$C_4$ alkyl, —O—$C_1$-$C_4$ alkyl, —O—$C_1$-$C_4$ fluoroalkyl, —$NH_2$, —NH($C_1$-$C_4$ alkyl), or —N($C_1$-$C_4$ alkyl)$_2$;

each of $R^4$ and $R^5$ is independently selected from hydrogen and $C_1$-$C_4$ alkyl; or $R^4$ and $R^5$ taken together with the nitrogen atom to which they are bound form a (4-7 membered) heterocylic ring optionally comprising one additional heteroatom selected from N, S and O, wherein the (4-7 membered) heterocylic ring is optionally substituted with fluoro, chloro, —OH, fluoro-substituted $C_1$-$C_4$ alkyl, —$C_1$-$C_4$ alkyl, or —$C_1$-$C_4$ alkylene-O—$C_1$-$C_4$ alkyl, and is optionally fused to phenyl;

each m is independently 0, 1 or 2.

2. The compound of claim 1, wherein:

$R^{1a}$ is selected from hydrogen and methyl;

$R^2$ is selected from hydrogen, $C_1$-$C_3$ straight chained alkyl, $C_1$-$C_3$ straight chained fluoroalkyl, cyclopropyl, and —$CH_2$-cyclopropyl;

$R^3$ is selected from hydrogen, $C_1$-$C_8$ alkyl, —$CH_2$—$CHF_2$, —$C_2$-$C_6$ alkylene-O—$C_1$-$C_3$ alkyl, —$C_3$-$C_{10}$ cycloalkyl, —$C_3$-$C_{10}$ cycloalkyl-substituted $C_1$-$C_3$ alkyl, cyclopropyl-substituted cyclopropyl, —$(CH_2)_2$-phenyl, and —$S(O)_2$-phenyl, when $R^2$ is hydrogen or $C_1$-$C_2$ alkyl, $R^3$ is additionally selected from benzyl; or $R^2$ and $R^3$ taken together with the nitrogen atom to which they are bound form a ring selected from pyrrolidine, piperidine, piperazine or morpholine, wherein the ring is optionally substituted with one or more substituents independently selected from —OH, —$C_1$-$C_3$ alkyl and —$C_1$-$C_3$ alkylene-O—$C_1$-$C_3$ alkyl, and wherein the ring is optionally fused to phenyl or spirofused to cyclopropyl.

3. The compound of claim 1, wherein:

$R^{1a}$ is selected from hydrogen and methyl;

$R^2$ is selected from hydrogen, $C_1$-$C_3$ straight chained alkyl and —$CH_2$-cyclopropyl;

$R^3$ is selected from hydrogen, $C_1$-$C_8$ alkyl, —$CH_2$—$CHF_2$, —$C_1$-$C_6$ alkylene-O—$C_1$-$C_3$ alkyl, $C_3$-$C_{10}$cycloalkyl, —$(CH_2)_2$-phenyl and $C_3$-$C_{10}$ cycloalkyl-substituted $C_1$-$C_3$ alkyl, wherein each cycloalkyl in the group represented by $R^3$ is optionally substituted with —$C_1$-$C_3$ alkyl or optionally benzofused and when $R^2$ is hydrogen or —$C_1$-$C_2$ alkyl, $R^3$ is additionally selected from benzyl; or $R^2$ and $R^3$ taken together with the nitrogen atom to which they are bound form a ring selected from pyrrolidine and piperidine, wherein the ring is optionally substituted with one or more substituents independently selected from fluoro —$C_1$-$C_3$ alkyl and —$C_1$-$C_3$ alkylene-O—$C_1$-$C_3$ alkyl, and wherein the ring is optionally fused to phenyl or spirofused to cyclopropyl.

4. The compound of claim 1, wherein X is fluoro or chloro.

5. The compound of claim 4, wherein:

X is fluoro and —CH($R^{1a}$)—$NR^2R^3$ is

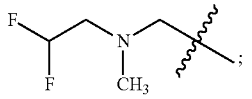

X is fluoro and —CH($R^{1a}$)—$NR^2R^3$ is

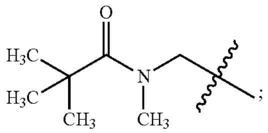

X is fluoro and —CH($R^{1a}$)—$NR^2R^3$ is

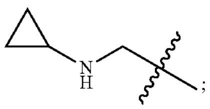

X is fluoro and —CH($R^{1a}$)—$NR^2R^3$ is

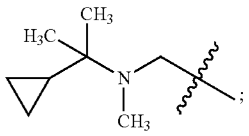

X is fluoro and —CH($R^{1a}$)—$NR^2R^3$ is

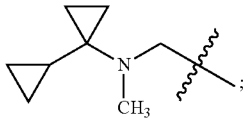 [SMILES: *CN(C)C1(C2CC2)CC1]

X is fluoro and —CH($R^{1a}$)—$NR^2R^3$ is

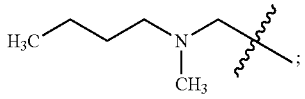 [SMILES: *CN(C)CCCC]

X is fluoro and —CH($R^{1a}$)—$NR^2R^3$ is

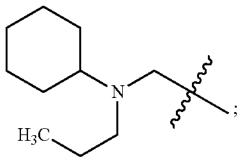 [SMILES: *CN(CCC)C1CCCCC1]

X is fluoro and —CH($R^{1a}$)—$NR^2R^3$ is

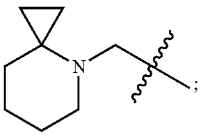 [SMILES: *CN1CCCCC12CC2]

X is fluoro and —CH($R^{1a}$)—$NR^2R^3$ is

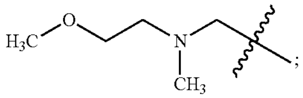 [SMILES: *CN(C)CCOC]

X is fluoro and —CH($R^{1a}$)—$NR^2R^3$ is

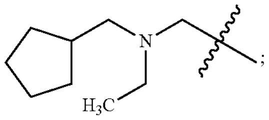 [SMILES: *CN(CC)CC1CCCC1]

X is fluoro and —CH($R^{1a}$)—$NR^2R^3$ is

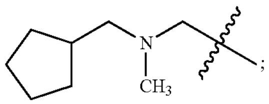 [SMILES: *CN(C)CC1CCCC1]

X is fluoro and —CH($R^{1a}$)—$NR^2R^3$ is

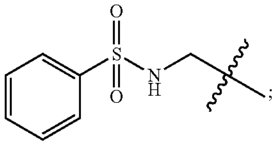 [SMILES: *CNS(=O)(=O)c1ccccc1]

X is fluoro and —CH($R^{1a}$)—$NR^2R^3$ is

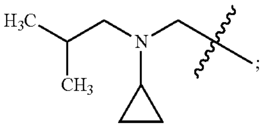 [SMILES: *CN(CC(C)C)C1CC1]

X is fluoro and —CH($R^{1a}$)—$NR^2R^3$ is

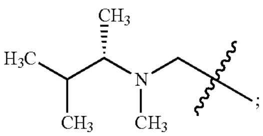

X is fluoro and —CH($R^{1a}$)—$NR^2R^3$ is

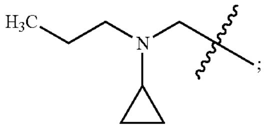 [SMILES: *CN(CCC)C1CC1]

X is fluoro and —CH($R^{1a}$)—$NR^2R^3$ is

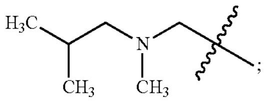

X is fluoro and —CH($R^{1a}$)—$NR^2R^3$ is

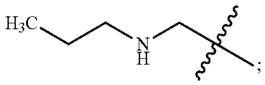 [SMILES: *CNCCC]

X is fluoro and —CH($R^{1a}$)—$NR^2R^3$ is

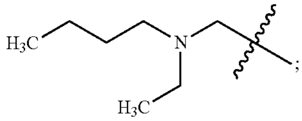 [SMILES: *CN(CC)CCCC]

X is fluoro and —CH($R^{1a}$)—$NR^2R^3$ is

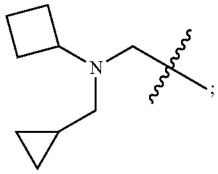 [SMILES: *CN(CC1CC1)C1CCC1]

X is fluoro and —CH($R^{1a}$)—$NR^2R^3$ is

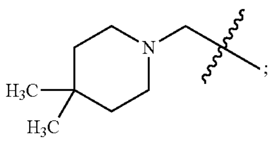

X is fluoro and —CH($R^{1a}$)—$NR^2R^3$ is

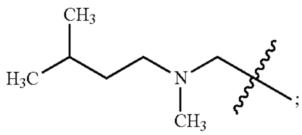 [SMILES: *CN(C)CCC(C)C]

X is fluoro and —CH($R^{1a}$)—$NR^2R^3$ is

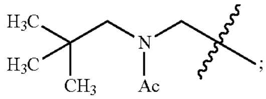
;

X is fluoro and —CH($R^{1a}$)—$NR^2R^3$ is

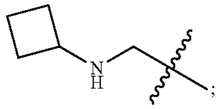 [SMILES: *CNC1CCC1]
;

X is fluoro and —CH($R^{1a}$)—$NR^2R^3$ is

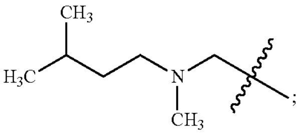
;

X is fluoro and —CH($R^{1a}$)—$NR^2R^3$ is

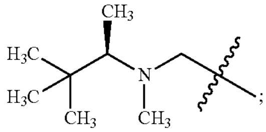 [SMILES: *CN(C)[C@H](C)C(C)(C)C]
;

X is fluoro and —CH($R^{1a}$)—$NR^2R^3$ is

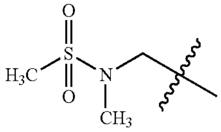
;

X is fluoro and —CH($R^{1a}$)—$NR^2R^3$ is

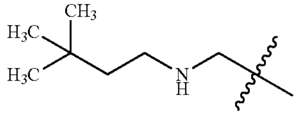
;

X is fluoro and —CH($R^{1a}$)—$NR^2R^3$ is

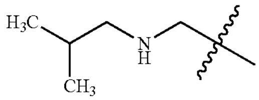
;

X is fluoro and —CH($R^{1a}$)—$NR^2R^3$ is

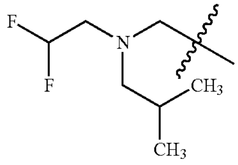
;

X is fluoro and —CH($R^{1a}$)—$NR^2R^3$ is

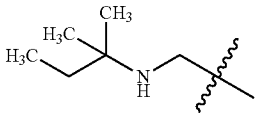
;

X is fluoro and —CH($R^{1a}$)—$NR^2R^3$ is

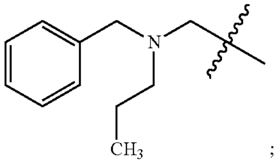 [SMILES: *CN(CCC)Cc1ccccc1]
;

X is fluoro and —CH($R^{1a}$)—$NR^2R^3$ is

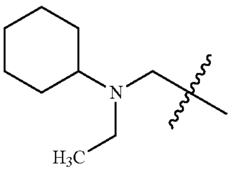
;

X is fluoro and —CH($R^{1a}$)—$NR^2R^3$ is

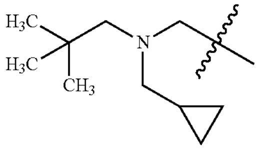
;

X is fluoro and —CH($R^{1a}$)—$NR^2R^3$ is

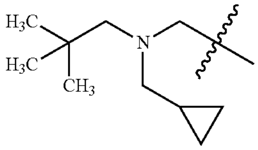
;

X is fluoro and —CH($R^{1a}$)—$NR^2R^3$ is

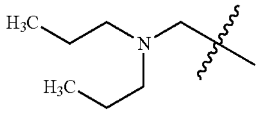

;

X is fluoro and —CH($R^{1a}$)—$NR^2R^3$ is

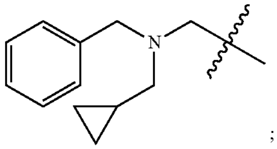 [SMILES: *CN(Cc1ccccc1)CC1CC1]

;

X is fluoro and —CH($R^{1a}$)—$NR^2R^3$ is

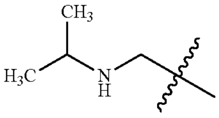

;

X is fluoro and —CH($R^{1a}$)—$NR^2R^3$ is

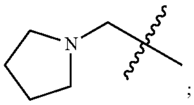 [SMILES: *CN1CCCC1]

;

X is fluoro and —CH($R^{1a}$)—$NR^2R^3$ is

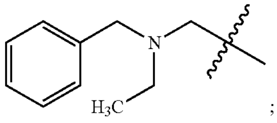

;

X is fluoro and —CH($R^{1a}$)—$NR^2R^3$ is

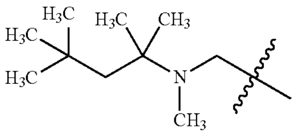

;

X is fluoro and —CH($R^{1a}$)—$NR^2R^3$ is

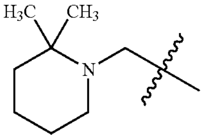

;

X is fluoro and —CH($R^{1a}$)—$NR^2R^3$ is

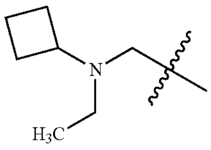

;

X is fluoro and —CH($R^{1a}$)—$NR^2R^3$ is

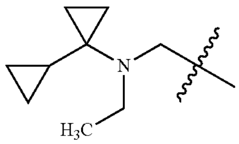

;

X is fluoro and —CH($R^{1a}$)—$NR^2R^3$ is

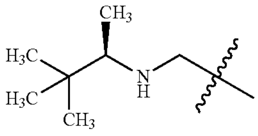

;

X is fluoro and —CH($R^{1a}$)—$NR^2R^3$ is

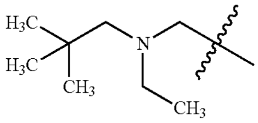

;

X is fluoro and —CH($R^{1a}$)—$NR^2R^3$ is

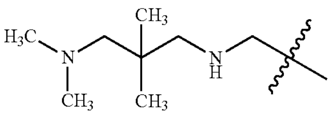

;

X is fluoro and —CH($R^{1a}$)—$NR^2R^3$ is

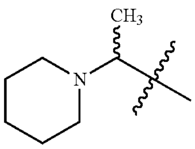

;

X is fluoro and —CH($R^{1a}$)—$NR^2R^3$ is

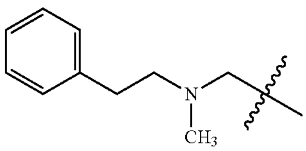

;

X is fluoro and —CH($R^{1a}$)—$NR^2R^3$ is

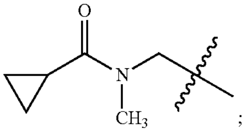 [SMILES: *CN(C)C(=O)C1CC1]

;

X is fluoro and —CH($R^{1a}$)—$NR^2R^3$ is

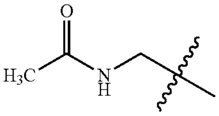

;

X is fluoro and —CH($R^{1a}$)—$NR^2R^3$ is

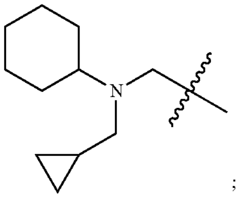 [SMILES: *CN(CC1CC1)C1CCCCC1]

;

X is fluoro and —CH($R^{1a}$)—$NR^2R^3$ is

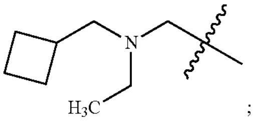 [SMILES: *CN(CC)CC1CCC1]

;

X is fluoro and —CH($R^{1a}$)—$NR^2R^3$ is

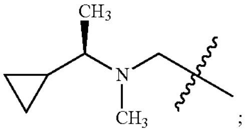 [SMILES: *CN(C)[C@H](C)C1CC1]

;

X is fluoro and —CH($R^{1a}$)—$NR^2R^3$ is

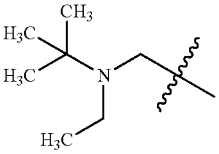

;

X is fluoro and —CH($R^{1a}$)—$NR^2R^3$ is

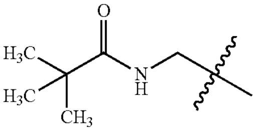

;

X is fluoro and —CH($R^{1a}$)—$NR^2R^3$ is

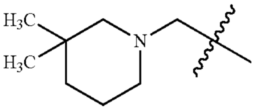

;

X is fluoro and —CH($R^{1a}$)—$NR^2R^3$ is

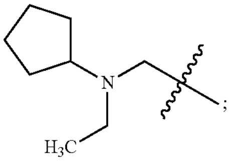 [SMILES: *CN(CC)C1CCCC1]

;

X is fluoro and —CH($R^{1a}$)—$NR^2R^3$ is

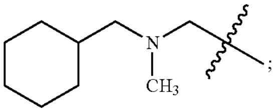 [SMILES: *CN(C)CC1CCCCC1]

;

X is fluoro and —CH($R^{1a}$)—$NR^2R^3$ is

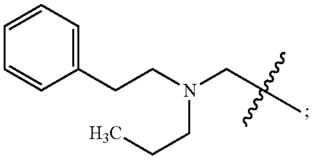 [SMILES: *CN(CCC)CCc1ccccc1]

;

X is fluoro and —CH($R^{1a}$)—$NR^2R^3$ is

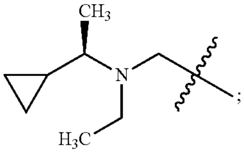 [SMILES: *CN(CC)[C@H](C)C1CC1]

;

X is fluoro and —CH($R^{1a}$)—$NR^2R^3$ is

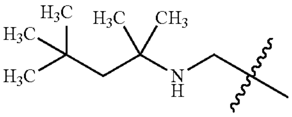

;

X is fluoro and —CH($R^{1a}$)—$NR^2R^3$ is

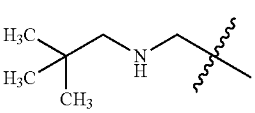

;

X is fluoro and —CH($R^{1a}$)—$NR^2R^3$ is

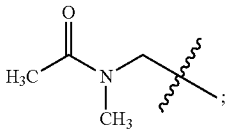 [SMILES: *CN(C)C(C)=O]

X is fluoro and —CH($R^{1a}$)—$NR^2R^3$ is

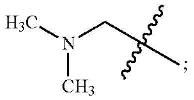

X is fluoro and —CH($R^{1a}$)—$NR^2R^3$ is

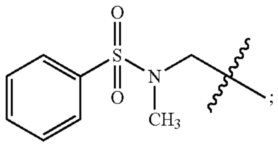 [SMILES: *CN(C)S(=O)(=O)c1ccccc1]

X is fluoro and —CH($R^{1a}$)—$NR^2R^3$ is

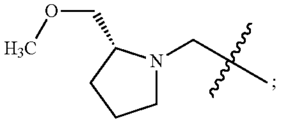 [SMILES: *CN1CCC[C@@H]1COC]

X is fluoro and —CH($R^{1a}$)—$NR^2R^3$ is

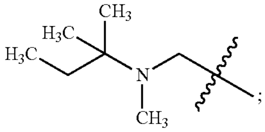 [SMILES: *CN(C)C(C)(C)CC]

X is fluoro and —CH($R^{1a}$)—$NR^2R^3$ is

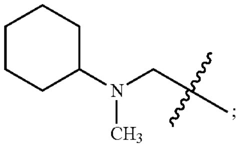 [SMILES: *CN(C)C1CCCCC1]

X is fluoro and —CH($R^{1a}$)—$NR^2R^3$ is

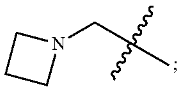 [SMILES: *CN1CCC1]

X is fluoro and —CH($R^{1a}$)—$NR^2R^3$ is

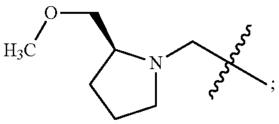 [SMILES: *CN1CCC[C@H]1COC]

X is fluoro and —CH($R^{1a}$)—$NR^2R^3$ is

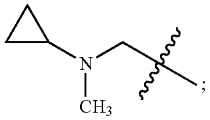

X is fluoro and —CH($R^{1a}$)—$NR^2R^3$ is

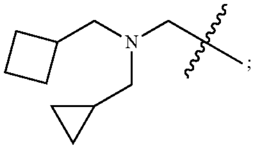 [SMILES: *CN(CC1CCC1)CC1CC1]

X is fluoro and —CH($R^{1a}$)—$NR^2R^3$ is

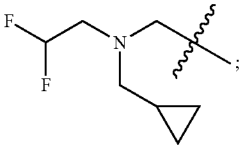 [SMILES: *CN(CC(F)F)CC1CC1]

X is fluoro and —CH($R^{1a}$)—$NR^2R^3$ is

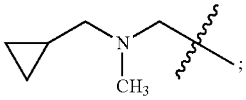

X is fluoro and —CH($R^{1a}$)—$NR^2R^3$ is

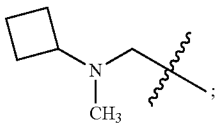 [SMILES: *CN(C)C1CCC1]

X is fluoro and —CH($R^{1a}$)—$NR^2R^3$ is

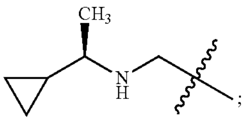

X is fluoro and —CH($R^{1a}$)—$NR^2R^3$ is

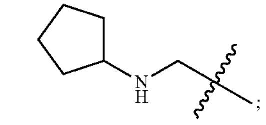 [SMILES: *CNC1CCCC1]

X is fluoro and —CH($R^{1a}$)—$NR^2R^3$ is

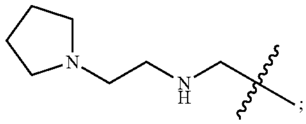 [SMILES: *CNCCN1CCCC1]

X is fluoro and —CH($R^{1a}$)—$NR^2R^3$ is

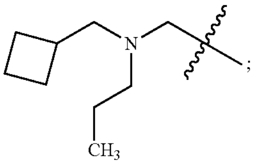 [SMILES: *CN(CCC)CC1CCC1]

X is fluoro and —CH($R^{1a}$)—$NR^2R^3$ is

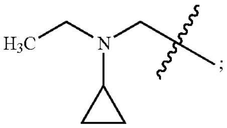 [SMILES: *CN(CC)C1CC1]

X is fluoro and —CH($R^{1a}$)—$NR^2R^3$ is

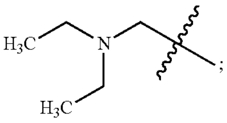 [SMILES: *CN(CC)CC]

X is fluoro and —CH($R^{1a}$)—$NR^2R^3$ is

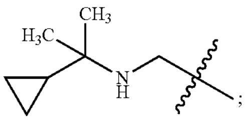 [SMILES: *CNC(C)(C)C1CC1]

X is fluoro and —CH($R^{1a}$)—$NR^2R^3$ is

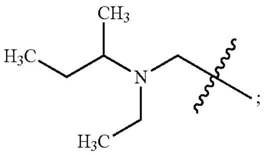

X is fluoro and —CH($R^{1a}$)—$NR^2R^3$ is

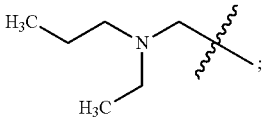 [SMILES: *CN(CC)CCC]

X is fluoro and —CH($R^{1a}$)—$NR^2R^3$ is

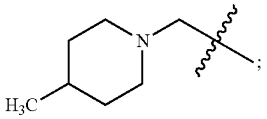 [SMILES: *CN1CCC(C)CC1]

X is fluoro and —CH($R^{1a}$)—$NR^2R^3$ is

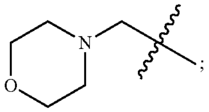 [SMILES: *CN1CCOCC1]

X is fluoro and —CH($R^{1a}$)—$NR^2R^3$ is

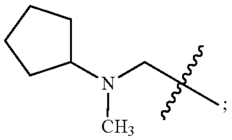

X is fluoro and —CH($R^{1a}$)—$NR^2R^3$ is

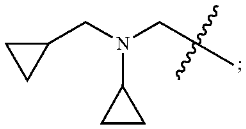 [SMILES: *CN(CC1CC1)C1CC1]

X is fluoro and —CH($R^{1a}$)—$NR^2R^3$ is

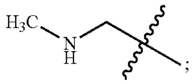 [SMILES: *CNC]

X is fluoro and —CH($R^{1a}$)—$NR^2R^3$ is

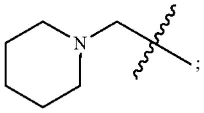 [SMILES: *CN1CCCCC1]

X is fluoro and —CH($R^{1a}$)—$NR^2R^3$ is

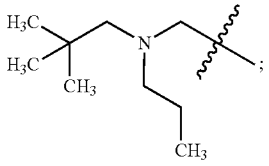 [SMILES: *CN(CCC)CC(C)(C)C]

X is fluoro and —CH($R^{1a}$)—$NR^2R^3$ is

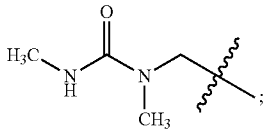

X is fluoro and —CH($R^{1a}$)—$NR^2R^3$ is

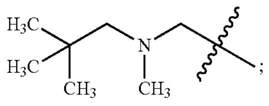

X is fluoro and —CH($R^{1a}$)—$NR^2R^3$ is

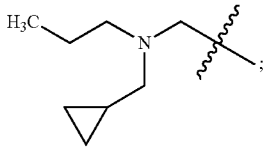 [SMILES: *CN(CCC)CC1CC1]

X is fluoro and —CH($R^{1a}$)—$NR^2R^3$ is

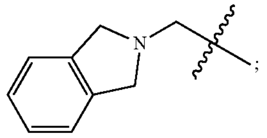 [SMILES: *CN1Cc2ccccc2C1]

X is fluoro and —CH($R^{1a}$)—$NR^2R^3$ is

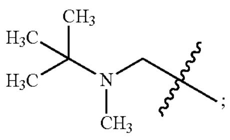 [SMILES: *CN(C)C(C)(C)C]

X is fluoro and —CH($R^{1a}$)—$NR^2R^3$ is

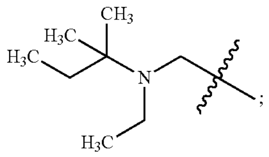 [SMILES: *CN(CC)C(C)(C)CC]

X is fluoro and —CH($R^{1a}$)—$NR^2R^3$ is

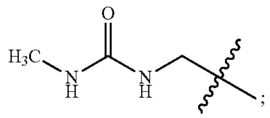 [SMILES: *CNC(=O)NC]

X is fluoro and —CH($R^{1a}$)—$NR^2R^3$ is

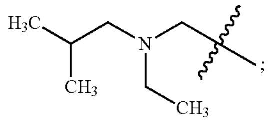

X is fluoro and —CH($R^{1a}$)—$NR^2R^3$ is

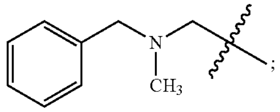 [SMILES: *CN(C)Cc1ccccc1]

X is fluoro and —CH($R^{1a}$)—$NR^2R^3$ is

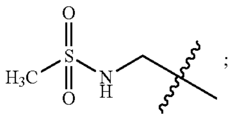 [SMILES: *CNS(C)(=O)=O]

X is fluoro and —CH($R^{1a}$)—$NR^2R^3$ is

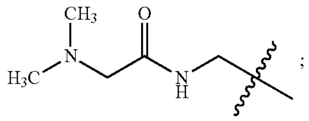 [SMILES: *CNC(=O)CN(C)C]

X is fluoro and —CH($R^{1a}$)—$NR^2R^3$ is

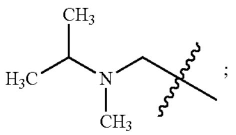

X is fluoro and —CH($R^{1a}$)—$NR^2R^3$ is

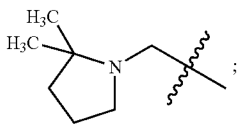 [SMILES: *CN1CCCC1(C)C]

X is fluoro and —CH($R^{1a}$)—$NR^2R^3$ is

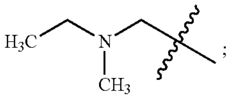

X is fluoro and —CH($R^{1a}$)—$NR^2R^3$ is

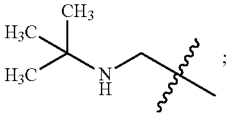 [SMILES: *CNC(C)(C)C]

X is fluoro and —CH($R^{1a}$)—$NR^2R^3$ is

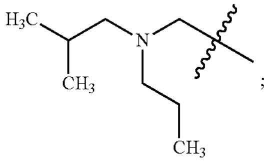 [SMILES: *CN(CCC)CC(C)C]

X is fluoro and —CH($R^{1a}$)—$NR^2R^3$ is

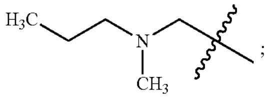

X is fluoro and —CH($R^{1a}$)—$NR^2R^3$ is

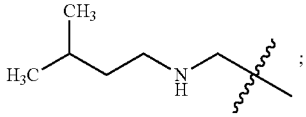 [SMILES: *CNCCC(C)C]

X is fluoro and —CH($R^{1a}$)—$NR^2R^3$ is

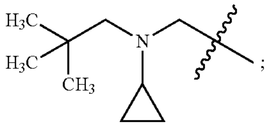 [SMILES: *CN(CC(C)(C)C)C1CC1]

X is fluoro and —CH($R^{1a}$)—$NR^2R^3$ is

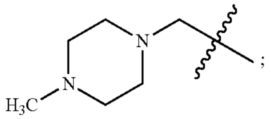

X is fluoro and —CH($R^{1a}$)—$NR^2R^3$ is

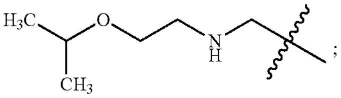

X is fluoro and —CH($R^{1a}$)—$NR^2R^3$ is

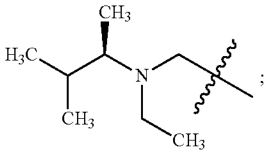 [SMILES: *CN(CC)[C@H](C)C(C)C]

X is fluoro and —CH($R^{1a}$)—$NR^2R^3$ is

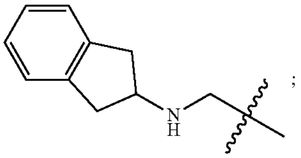 [SMILES: *CNC1Cc2ccccc2C1]

X is fluoro and —CH($R^{1a}$)—$NR^2R^3$ is

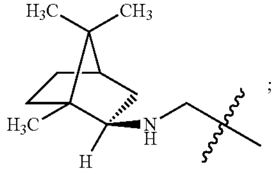 [SMILES: *CN[C@@H]1CC2CCC1(C)C2(C)C]

X is fluoro and —CH($R^{1a}$)—$NR^2R^3$ is

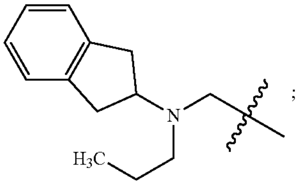 [SMILES: *CN(CCC)C1Cc2ccccc2C1]

X is fluoro and —CH($R^{1a}$)—$NR^2R^3$ is

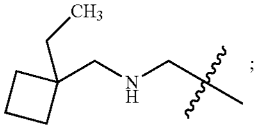 [SMILES: *CNCC1(CC)CCC1]

X is fluoro and —CH($R^{1a}$)—$NR^2R^3$ is

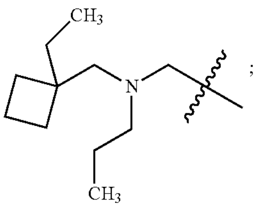 [SMILES: *CN(CCC)CC1(CC)CCC1]

X is fluoro and —CH($R^{1a}$)—$NR^2R^3$ is

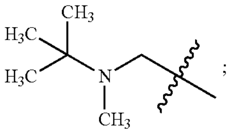

X is chloro and —CH($R^{1a}$)—$NR^2R^3$ is

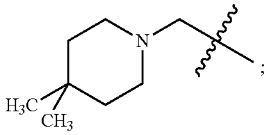 [SMILES: *CN1CCC(C)(C)CC1]

X is chloro and —CH($R^{1a}$)—$NR^2R^3$ is

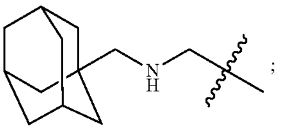 [SMILES: *CNCC12CC3CC(CC(C3)C1)C2]

X is chloro and —CH($R^{1a}$)—$NR^2R^3$ is

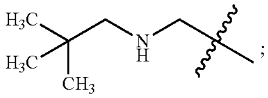

X is chloro and —CH($R^{1a}$)—$NR^2R^3$ is

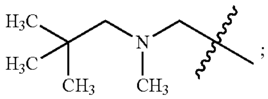

X is chloro and —CH($R^{1a}$)—$NR^2R^3$ is

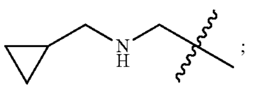 [SMILES: *CNCC1CC1]

X is chloro and —CH($R^{1a}$)—$NR^2R^3$ is

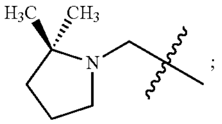

X is chloro and —CH($R^{1a}$)—$NR^2R^3$ is

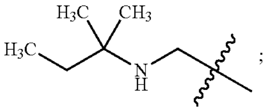 [SMILES: *CNC(C)(C)CC]

X is chloro and —CH($R^{1a}$)—$NR^2R^3$ is

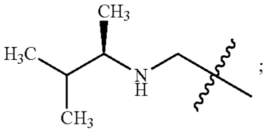

X is chloro and —CH($R^{1a}$)—$NR^2R^3$ is

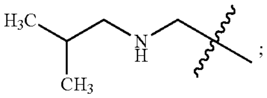

X is chloro and —CH($R^{1a}$)—$NR^2R^3$ is

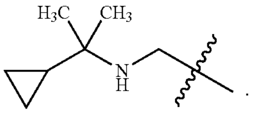 [SMILES: *CNC(C)(C)C1CC1]

6. The compound of claim 1, wherein X is —$OCH_3$, —$CF_3$, Cl, or F.

7. The compound of claim 1, wherein X is selected from fluoro, chloro, and —CN.

8. A pharmaceutical composition comprising a pharmaceutically acceptable carrier or diluent and a compound of claim 1.

9. A method for reducing a bacterial infection in a subject comprising administering to the subject an effective amount of the compound of claim 1.

10. The method of claim 9, wherein the bacterial infection is caused by a Gram-positive organism.

11. The method of claim 9, wherein the bacterial infection is caused by a Gram-negative organism.

12. The method of claim 9, wherein the bacterial infection is caused by an organism selected from the group consisting of rickettsiae, chlamydiae, and *Mycoplasma pneumoniae*.

13. The method of claim 9, wherein the bacterial infection is caused by an organism resistant to tetracycline.

14. The method of claim 9, wherein the bacterial infection is caused by an organism resistant to methicillin.

15. The method of claim 9, wherein the bacterial infection is caused by an organism resistant to vancomycin.

* * * * *